US012599672B2

(12) United States Patent
Ji et al.

(10) Patent No.: US 12,599,672 B2
(45) Date of Patent: Apr. 14, 2026

(54) KRAS PROTEOLYSIS TARGETING CHIMERAS

(71) Applicant: PAQ Therapeutics Inc., Burlington, MA (US)

(72) Inventors: Nan Ji, Arlington, MA (US); Hui Qiu, Acton, MA (US); Ruoxi Lan, Waltham, MA (US)

(73) Assignee: PAQ Therapeutics Inc., Burlington, MA (US)

( * ) Notice: Subject to any disclaimer, the term of this patent is extended or adjusted under 35 U.S.C. 154(b) by 0 days.

(21) Appl. No.: 18/904,330

(22) Filed: Oct. 2, 2024

(65) Prior Publication Data

US 2025/0144225 A1 May 8, 2025

Related U.S. Application Data

(60) Provisional application No. 63/614,141, filed on Dec. 22, 2023, provisional application No. 63/542,251, filed on Oct. 3, 2023.

(51) Int. Cl.
*A61K 47/55* (2017.01)
*A61K 47/54* (2017.01)

(52) U.S. Cl.
CPC ............ *A61K 47/55* (2017.08); *A61K 47/545* (2017.08)

(58) Field of Classification Search
CPC ...................................................... A61K 47/55
See application file for complete search history.

(56) References Cited

U.S. PATENT DOCUMENTS

| | | | |
|---|---|---|---|
| 10,849,982 B2 | 12/2020 | Phillips et al. | |
| 11,352,350 B2 | 6/2022 | Mainolfi et al. | |
| 2020/0140456 A1 | 5/2020 | Phillips et al. | |
| 2020/0377469 A1 | 12/2020 | Mainolfi et al. | |
| 2024/0216516 A1 | 7/2024 | Liu et al. | |
| 2024/0217972 A1 | 7/2024 | Luo et al. | |
| 2024/0246963 A1 | 7/2024 | Lu et al. | |
| 2024/0247000 A1 | 7/2024 | Ji et al. | |

FOREIGN PATENT DOCUMENTS

| | | | |
|---|---|---|---|
| CA | 3095494 A1 | 10/2019 | |
| CN | 116375742 A | 7/2023 | |
| CN | 118496300 A | 8/2024 | |
| WO | WO2019060742 * | 3/2019 | ........... A61K 31/427 |
| WO | WO2021041671 * | 3/2021 | |
| WO | WO-2021041671 A1 * | 3/2021 | ........... A61K 31/519 |
| WO | 2021127278 A1 | 6/2021 | |
| WO | 2021173524 A1 | 9/2021 | |
| WO | WO2021188948 * | 9/2021 | ........... A61K 31/427 |
| WO | 2021249519 A1 | 12/2021 | |
| WO | 2022002102 A1 | 1/2022 | |
| WO | 2022015375 A1 | 1/2022 | |
| WO | 2022031678 A1 | 2/2022 | |
| WO | 2022066646 A1 | 3/2022 | |
| WO | 2022105857 A1 | 5/2022 | |
| WO | 2022105859 A1 | 5/2022 | |
| WO | 2022132200 A1 | 6/2022 | |
| WO | WO2022132200 * | 6/2022 | ........... A61K 31/427 |
| WO | 2022148421 A1 | 7/2022 | |
| WO | 2022194066 A1 | 9/2022 | |
| WO | 2022194191 A1 | 9/2022 | |
| WO | 2022221739 A1 | 10/2022 | |
| WO | 2022256459 A1 | 12/2022 | |
| WO | 2022262838 A1 | 12/2022 | |
| WO | 2023001141 A1 | 1/2023 | |
| WO | 2023283933 A1 | 1/2023 | |
| WO | 2023284537 A1 | 1/2023 | |
| WO | 2023018809 A1 | 2/2023 | |
| WO | 2023018810 A1 | 2/2023 | |
| WO | 2023018812 A1 | 2/2023 | |
| WO | 2023051586 A1 | 4/2023 | |
| WO | 2023072188 A1 | 5/2023 | |
| WO | 2023077441 A1 | 5/2023 | |

(Continued)

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Xie Front. Pharmacol., Nov. 13, 2017 Sec. Experimental Pharmacology and Drug Discovery vol. 8—2017.*

(Continued)

*Primary Examiner* — Nizal S Chandrakumar
(74) *Attorney, Agent, or Firm* — McNeill PLLC

(57) ABSTRACT

Provided herein are KRAS proteolysis targeting chimeras (PROTACs), compositions comprising the KRAS PROTACs, and methods of making and using the KRAS PROTACs, e.g., to promote degradation of KRAS and/or treat KRAS-associated cancers. In an embodiment, the KRAS PROTAC has the following structural formula:

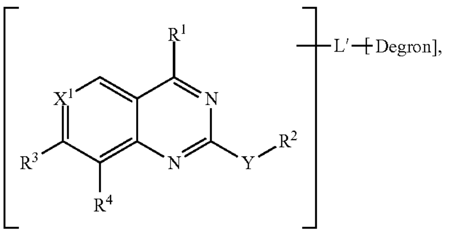

or a pharmaceutically acceptable salt thereof, wherein values for the variables are as described herein.

25 Claims, No Drawings

(56) References Cited

FOREIGN PATENT DOCUMENTS

| | | | | |
|---|---|---|---|---|
| WO | 2023081476 | A1 | 5/2023 | |
| WO | 2023097227 | A1 | 6/2023 | |
| WO | 2023099592 | A1 | 6/2023 | |
| WO | 2023099620 | A1 | 6/2023 | |
| WO | 2023099623 | A1 | 6/2023 | |
| WO | 2023114733 | A1 | 6/2023 | |
| WO | 2023116934 | A1 | 6/2023 | |
| WO | WO2023116934 | * | 6/2023 | ........... A61K 31/427 |
| WO | 2023130012 | A1 | 7/2023 | |
| WO | 2023133183 | A1 | 7/2023 | |
| WO | 2023150284 | A2 | 8/2023 | |
| WO | 2023154766 | A1 | 8/2023 | |
| WO | 2023173016 | A1 | 9/2023 | |
| WO | 2023173017 | A1 | 9/2023 | |
| WO | 2023184178 | A1 | 10/2023 | |
| WO | 2023215906 | A1 | 11/2023 | |
| WO | 2024029613 | A1 | 2/2024 | |
| WO | 2024034593 | A1 | 2/2024 | |
| WO | 2024083256 | A1 | 4/2024 | |
| WO | 2024118960 | A1 | 6/2024 | |
| WO | 2024118966 | A1 | 6/2024 | |
| WO | 2024119278 | A1 | 6/2024 | |
| WO | 2024120424 | A1 | 6/2024 | |
| WO | 2024159164 | A2 | 8/2024 | |
| WO | 2024199266 | A1 | 10/2024 | |
| WO | 2024233838 | A1 | 11/2024 | |
| WO | 2024263586 | A1 | 12/2024 | |
| WO | 2025006753 | A2 | 1/2025 | |
| WO | 2025006783 | A2 | 1/2025 | |
| WO | 2025076044 | | 4/2025 | |

OTHER PUBLICATIONS

Dorwald F. A. Side Reactions in Organic Synthesis, 2005, Wiley: VCH, Weinheim p. IX of Preface p. 1-15.*
Sundaresan, Protein Science (2002), 11:1330-1339. See col. A, Fig. 1.*
Mao, Cell Discovery, 2022, 8(5), 1-14 and Cermakova, Molecules 2018, 23, 1958, 1-26.*
Tinworth, Med. Chem. Commun., 2016, 7, 2206-2216.*
Li, J Clin Invest. 2014;124(2):835-846.*
Feldman, Understanding 'Evergreening' : Making Minor Modifications Of Existing Medications To Extend Protections, Health Affairs Jun. 2022 41:6, 801-804.*
Dwivedi, Evergreening: A deceptive device in patent rights, Technology in Society 32 (2010) 324-330.*
Venkatesh, J. Pharm. Sci. 89, 145-154 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
Tinworth, Med. Chem. Commun., 2016, 7, 2206.*
Collins, Biochemical Journal (2017) 474 1127-1147.*
Troup, Current strategies for the design of PROTAC linkers: a critical review, Explor Target Antitumor Ther. 2020;1:273-312.*
Kim D., et al., Nature vol. 619, 160, Jul. 6, 2023, https://doi.org/10.1038/s41586-023-06123-3.
Mao et al., "KRAS(G12D) can be targeted by potent inhibitors via formation of salt bridge," Cell Discovery, 2022, 8.
Wang, et al., "Identification of MRTX1133, a Noncovalent, Potent, and Selective KRASG12D Inhibitor," J. Med Chem., https://doi.org/10.1021/acs.jmedchem.1c01688.
International Search Report issued in connection with PCT/US2024/049534, dated Feb. 13, 2025, 8 pages.
Kargbo, Robert B., A new frontier in targeted therapies: harnessing PROTACs and advanced delivery systems, ACS Medicinal Chemistry Letter, vol. 15, No. 11, Oct. 15, 2024, pp. 1818-1820.

* cited by examiner

KRAS PROTEOLYSIS TARGETING CHIMERAS

RELATED APPLICATIONS

This application claims the benefit of U.S. Provisional Application No. 63/542,251, filed on Oct. 3, 2023, and U.S. Provisional Application No. 63/614,141, filed on Dec. 22, 2023. The entire teachings of the above applications are incorporated herein by reference.

BACKGROUND

Kirsten rat sarcoma viral oncogene homolog (KRAS) is a group of genes responsible for making K-Ras proteins, which are important for cellular growth and proliferation. KRAS amplifications and various mutations of KRAS have been implicated in many types of carcinomas. For example, KRAS mutations such as G12A/C/D/F/L/R/V/S, G13A/C/D, V14L, L19F, Q22K/E/R, Q25A, D33E, P34L/R, A59E/G/P/S/T/V, Q61H/K/L/R, K117N, and A146V/T, as well as KRAS overexpression, have all been identified in cancer.

Proteolysis targeting chimeras (PROTACs) are bifunctional molecules comprising two active domains, known colloquially as "warheads," covalently attached to one another by a linking moiety (Hodges et. Al., Next-Generation Drugs and Probes for Chromatin Biology: From Targeted Protein Degradation to Phase Separation. *Molecules.* 23 (8), 1958).

There is a need for a PROTAC that is capable of binding to KRAS, or one or more mutants thereof, and inducing degradation of the KRAS.

SUMMARY

Provided herein in one embodiment is a compound of structural formula I:

(I)

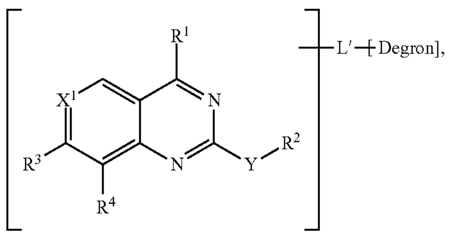

or a pharmaceutically acceptable salt thereof, wherein values for the variables (e.g., $X^1$, Y, $R^1$, $R^2$, $R^3$, $R^4$, L', Degron) are as described herein.

Provided herein in another embodiment is a compound of structural formula III:

(III)

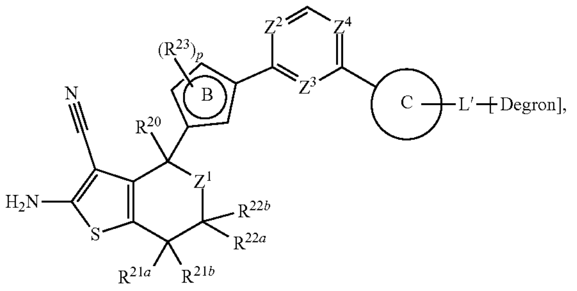

or a pharmaceutically acceptable salt thereof, wherein values for the variables (e.g., Ring B, Ring C, $Z^1$, $Z^2$, $Z^3$, $Z^4$, $R^{20}$, $R^{21a}$, $R^{21b}$, $R^{22a}$, $R^{22b}$, $R^{23}$, p, L', Degron) are as described herein.

Also provided herein is a pharmaceutical composition comprising a compound of the disclosure (e.g., a compound of any of structural formulas I-V, or Table 1 or 2 or 3, or a pharmaceutically acceptable salt thereof) and a pharmaceutically acceptable carrier.

Also provided herein is a pharmaceutical combination comprising a compound of the disclosure (e.g., a compound of any of structural formulas I-V, or Table 1 or 2 or 3, or a pharmaceutically acceptable salt thereof) and at least one additional therapeutic agent.

Also provided herein is a method of reducing a level or activity of a KRAS in a cell expressing the KRAS, comprising contacting the cell with (e.g., an effective amount of) a compound of the disclosure (e.g., a compound of any of structural formulas I-V, or Table 1 or 2 or 3, or a pharmaceutically acceptable salt thereof), e.g., in the form of a pharmaceutical composition.

Also provided herein is a method of reducing a level or activity of a KRAS in a subject in need thereof, comprising administering to the subject an effective amount of a compound of the disclosure (e.g., a compound of any of structural formulas I-V, or Table 1 or 2 or 3, or a pharmaceutically acceptable salt thereof), e.g., in the form of a pharmaceutical composition.

Also provided herein a method for treating a KRAS-associated cancer in a subject in need thereof, comprising administering to the subject a therapeutically effective amount of a compound of the disclosure (e.g., a compound of any of structural formulas I-V, or Table 1 or 2 or 3, or a pharmaceutically acceptable salt thereof), e.g., in the form of a pharmaceutical composition.

Also provided herein is a compound of the disclosure (e.g., a compound of any of structural formulas I-V, or Table 1 or 2 or 3, or a pharmaceutically acceptable salt thereof) or a pharmaceutical composition comprising a compound of the disclosure for a use described herein (e.g., reducing a level or activity of a KRAS; treating a KRAS-associated cancer, e.g., in a subject). Also provided herein is a use of a compound of the disclosure (e.g., a compound of any of structural formulas I-V, or Table 1 or 2 or 3, or a pharmaceutically acceptable salt thereof) for the manufacture of a medicament for a use described herein (e.g., reducing a level or activity of a KRAS; treating a KRAS-associated cancer, e.g., in a subject).

DETAILED DESCRIPTION

A description of example embodiments follows.

Definitions

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the relevant contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version 17.0.0.206, PerkinElmer Informatics, Inc.).

When introducing elements disclosed herein, unless indicated otherwise, e.g., expressly or by context, the articles "a," "an," "the," and "said" are intended to mean that there are one or more of the elements. Further, the one or more elements may be the same or different.

"Aliphatic" refers to a saturated or unsaturated, branched- or straight-chain, hydrocarbon radical having the specified number of carbon atoms. Thus, "($C_1$-$C_5$) aliphatic" refers to a radical having from 1-5 carbon atoms in a branched or linear arrangement. In some embodiments, aliphatic is ($C_1$-$C_{15}$) aliphatic, e.g., ($C_1$-$C_{10}$) aliphatic, ($C_1$-$C_6$) aliphatic, ($C_1$-$C_5$) aliphatic, ($C_1$-$C_4$) aliphatic or ($C_1$-$C_3$) aliphatic. In some embodiments, aliphatic is methylene or ethylene. Examples of aliphatic include alkyl, alkenyl and alkynyl. In some aspects, aliphatic is alkyl or alkynyl. In some aspects, aliphatic is alkyl or alkenyl.

"Alkenyl" refers to a branched- or straight-chain, hydrocarbon radical having the specified number of carbon atoms and at least one carbon-carbon double bond. Thus, "($C_2$-$C_6$) alkenyl" refers to a radical having from 2-6 carbon atoms and at least one carbon-carbon double bond in a branched or linear arrangement. In some embodiments, alkenyl is ($C_2$-$C_{15}$)alkenyl, e.g., ($C_2$-$C_{10}$)alkenyl, ($C_2$-$C_6$)alkenyl, ($C_2$-$C_5$) alkenyl, ($C_2$-$C_4$)alkenyl or ($C_2$-$C_3$)alkenyl. Examples of alkenyl include vinyl and the like.

"Alkoxy" refers to an alkyl attached through an oxygen linking atom, wherein alkyl is as described herein. Examples of alkoxy include, but are not limited to, methoxy, ethoxy, propoxy, isopropoxy, tert-butoxy and the like.

"Alkyl" refers to a saturated, branched- or straight-chain, hydrocarbon radical having the specified number of carbon atoms. Thus, "($C_1$-$C_6$)alkyl" refers to a radical having from 1-6 carbon atoms in a branched or linear arrangement. In some embodiments, alkyl is ($C_1$-$C_{15}$)alkyl, e.g., ($C_1$-$C_{10}$) alkyl, ($C_1$-$C_6$)alkyl, ($C_1$-$C_5$)alkyl, ($C_1$-$C_4$)alkyl or ($C_1$-$C_3$) alkyl. Examples of alkyl include methyl, ethyl, propyl (e.g., n-propyl, isopropyl), butyl(e.g., n-butyl, isobutyl, sec-butyl, t-butyl), pentyl (e.g., n-pentyl, isopentyl, neopentyl, 2-methylpentyl), hexyl (e.g., n-hexyl), and the like.

"Alkylene" refers to a divalent alkyl radical, wherein alkyl is as described herein. Examples of alkylene include methylene, ethylene, propylene, and the like.

"Alkynyl" refers to a branched- or straight-chain, hydrocarbon radical having the specified number of carbon atoms and at least one carbon-carbon triple bond. Thus, "($C_2$-$C_6$) alkynyl" refers to a radical having from 2-6 carbon atoms and at least one carbon-carbon triple bond in a branched or linear arrangement. In some embodiments, alkynyl is ($C_2$-$C_{15}$)alkynyl, e.g., ($C_2$-$C_{10}$)alkynyl, ($C_2$-$C_6$)alkynyl, ($C_2$-$C_5$) alkynyl, ($C_2$-$C_4$)alkynyl or ($C_2$-$C_3$)alkynyl. Examples of alkynyl include propargyl and the like.

"Aryl" refers to a monocyclic or polycyclic (e.g., bicyclic, tricyclic), aromatic, hydrocarbon ring radical having the specified number of ring atoms. Thus, "($C_6$-$C_{14}$)aryl" means an aromatic ring radical having from 6-14 ring atoms. In some embodiments, aryl is ($C_6$-$C_{14}$)aryl, e.g., ($C_6$-$C_{12}$)aryl, ($C_6$-$C_{10}$)aryl or ($C_6$)aryl. Examples of aryl include phenyl, naphthyl, anthracenyl and fluorenyl. In some embodiments, aryl is phenyl. "Aryl" includes bicyclic and tricyclic ring systems consisting of an aromatic ring fused to one or two non-aromatic rings or one non-aromatic ring system consisting of two non-aromatic rings. When the aromatic ring is fused to one non-aromatic ring system, the non-aromatic rings in the ring system may be fused or spirocyclic to one another.

"Arylalkyl" refers to an alkyl wherein one hydrogen of the alkyl is replaced with aryl, and alkyl and aryl are as described herein. Examples of arylalkyl include benzyl, phenethyl and napthylmethyl.

"Cyano" refers to —C≡N.

"Cyanoalkyl" refers to an alkyl wherein one hydrogen of the alkyl is replaced with cyano, and alkyl and cyano are as described herein. Examples of cyanoalkyl include cyanomethyl, cyanoethyl, cyanopropyl, and the like.

"Cycloalkyl" refers to a saturated or partially unsaturated, monocyclic or polycyclic (e.g., bicyclic, tricyclic), hydrocarbon ring radical having the specified number of ring atoms. Thus, "($C_3$-$C_6$) cycloalkyl" refers to a ring radical having from 3-6 ring atoms. A cycloalkyl can be monocyclic, fused bicyclic, bridged bicyclic or polycyclic, but is typically monocyclic. In some embodiments, cycloalkyl is ($C_3$-$C_{12}$) cycloalkyl, e.g., ($C_3$-$C_8$) cycloalkyl or ($C_3$-$C_6$) cycloalkyl. In some embodiments, cycloalkyl is saturated. Examples of cycloalkyl include cyclopropyl, cyclobutyl, cyclopentyl, cyclopentenyl, cyclohexyl, cyclohexenyl, cycloheptyl, cyclooctyl, bicyclo[1.1.1]pentanyl and the like.

The suffix "ene" or "enyl" is used herein to indicate that the group being modified with the suffix has two or more points of attachment (i.e., divalent, trivalent, or polyvalent) within the compound being described. For example, divalent alkyl groups are alkylene groups, divalent heteroalkyl groups are heteroalkylene, divalent aryl groups are arylene groups, divalent heteroaryl groups are heteroarylene groups, and so forth. Substituted groups having a single point of attachment to the compound being described are not referred to using the "ene" designation. Thus, e.g., a trifluoromethyl substituent is not referred to herein as trifluoromethylene.

"Halogen" and "halo" are used interchangeably herein and each refers to fluorine, chlorine, bromine, or iodine. In some embodiments, halogen is fluoro, chloro or bromo. In some embodiments, halogen is fluoro or chloro. In some embodiments, halogen is fluoro.

"Haloalkyl" refers to an alkyl wherein at least one hydrogen of the alkyl is replaced with a halo, and alkyl and halo are as described herein. Haloalkyl includes mono, poly, and perhaloalkyl groups, wherein each halogen is independently selected. In some embodiments, haloalkyl is perhaloalkyl (e.g., perfluoroalkyl). Haloalkyl includes, but is not limited to, fluoromethyl, difluoromethyl, trifluoromethyl, trifluoromethylethyl, pentafluoroethyl and the like.

"Hetero" refers to an atom that is not carbon or hydrogen. Examples of heteroatoms include, but are not limited to, nitrogen, oxygen, sulfur and the like. In some embodiments, hetero is independently selected from nitrogen, oxygen or sulfur. In some embodiments, hetero is independently selected from nitrogen or oxygen.

"Heteroaryl" refers to a monocyclic or polycyclic (e.g., bicyclic, tricyclic), aromatic, hydrocarbon ring radical having the specified number of ring atoms, wherein at least one carbon atom in the ring has been replaced with a heteroatom (e.g., a heteroatom independently selected from N, O or S). Thus, "($C_5$-$C_6$) heteroaryl" refers to an aromatic ring radical having 5 or 6 ring atoms consisting of carbon and one or more independently selected heteroatoms (e.g., selected from N, O or S). In some embodiments, heteroaryl contains 1, 2, 3 or 4 (e.g., 1, 2 or 3; 1 or 2) heteroatoms independently selected from N, S and O. In some embodiments, heteroaryl contains 1, 2, 3 or 4 (e.g., 1, 2 or 3; 1 or 2) independently selected heteroatoms, e.g., independently selected from N and O. In some embodiments, heteroaryl is ($C_5$-$C_{14}$) heteroaryl, e.g., ($C_5$-$C_{10}$) heteroaryl, ($C_5$-$C_6$) heteroaryl, ($C_6$) heteroaryl, ($C_5$) heteroaryl, ($C_9$-$C_{10}$) heteroaryl, ($C_9$) heteroaryl, ($C_{10}$) heteroaryl or ($C_{14}$) heteroaryl. Examples of heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a] imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl (e.g., 1,2,3-oxadiazolyl, 1,2,4-oxadiazolyl, 1,2,5-oxadiazolyl, 1,3,4-oxadiazolyl), oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thianthrenyl, thiazolyl, thienyl, thienothiazolyl, thienooxazolyl, thienoimidazolyl, thiophenyl, triazinyl, triazolyl (e.g., 1,2,3-triazolyl, 1,2,4-triazolyl, 1,2,5-triazolyl, 1,3,4-triazolyl) and xanthenyl. "Heteroaryl" includes bicyclic ring systems consisting of a heteroaromatic ring fused to a non-aromatic ring.

"Heterocyclyl" or "heterocycloalkyl" refers to a saturated, monocyclic or polycyclic (e.g., bicyclic, tricyclic), hydrocarbon ring radical having the specified number of ring atoms, wherein at least one carbon atom in the ring has been replaced with a heteroatom. Thus, "($C_3$-$C_6$) heterocyclyl" means a heterocyclic ring system having from 3-6 ring atoms consisting of carbon and one or more independently selected heteroatoms. A heterocyclyl can be monocyclic, fused bicyclic, bridged bicyclic or polycyclic, but is typically monocyclic. In some embodiments, heterocyclyl contains 1, 2, 3 or 4 (e.g., 1, 2 or 3; 1 or 2) heteroatoms independently selected from N, S and O. In some embodiments, heterocyclyl contains 1, 2, 3 or 4 (e.g., 1, 2 or 3; 1 or 2) heteroatoms independently selected from N and O. When one heteroatom is S, it can be optionally mono- or di-oxygenated (i.e., —S(O)— or —$S(O)_2$). In some embodiments, heterocyclyl is ($C_3$-$C_{15}$) heterocyclyl, e.g., ($C_3$-$C_{12}$) heterocyclyl, ($C_4$-$C_8$) heterocyclyl, ($C_3$-$C_7$) heterocyclyl or ($C_3$-$C_6$) heterocyclyl. Examples of monocyclic heterocyclyls include, but are not limited to, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1-dioxide, morpholinyl, azepanyl, oxazepanyl, azabicyclohexanyl, azabicycloheptanyl, azabicyclooctanyl, azabicyclononanyl (e.g., octahydroindolizinyl), azaspiroheptanyl, dihydro-1H,3H, 5H-oxazolo-[3,4-c] oxazolyl, tetrahydro-1'H,3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyl, oxaazaspirooctanyl, diazaspirononanyl, oxaazabiocycloheptanyl, hexahydropyrrolizinyl 4 (1H)-oxide, tetrahydro-2H-thiopyranyl 1-oxide and tetrahydro-2H-thiopyranyl 1,1-dioxide.

"Hydroxy" refers to —OH.

"Hydroxyalkyl" refers to an alkyl wherein one hydrogen of the alkyl is replaced with hydroxy, and alkyl and hydroxy are as described herein. Examples of hydroxyalkyl include hydroxymethyl, hydroxyethyl, hydroxypropyl, and the like.

"Hydroxyalkynyl" refers to an alkynyl wherein one hydrogen of the alkynyl is replaced with hydroxy, and alkynyl and hydroxy are as described herein.

"Oxo" refers to =O.

The term "substituted" refers to replacement of a hydrogen atom with a suitable substituent. Typically, the suitable substituent replaces a hydrogen atom bound to a carbon atom, but a substituent may also replace a hydrogen bound to a heteroatom, such as a nitrogen atom. When two or more hydrogen atoms are each replaced with an independently selected substituent, the substituents can be the same or different. It will be understood that "substitution" or "substituted with" includes the implicit proviso that such substitution is in accordance with permitted valence of the substituted atom. It is also preferred that the substituent, and the substitution, result in a stable compound, e.g., which does not spontaneously undergo transformation such as by rearrangement, cyclization, elimination, etc.

The term "optionally substituted", as used herein, means that substitution is optional and, therefore, it is possible for the atom or moiety designated as "optionally substituted" to be unsubstituted or substituted. In some embodiments, an optionally substituted group is unsubstituted. In some embodiments, an optionally substituted group is substituted. An "optionally substituted" group is, in some embodiments, substituted with 0-5 (e.g., 1-5, 0-3, 1-3, 0, 1, 2, 3, 4, 5) substituents. Unless otherwise indicated, e.g., as with the terms "substituted" or "optionally substituted," a group designated herein is unsubstituted.

When a bond to a substituent is shown to cross a bond connecting two atoms in a ring (as, for example, the bond to $R^{23}$, $R^{27}$ in the structural formulas depicted herein) or to cross a circle denoting a ring, then such substituent may be bonded to any substitutable atom in the ring. Further, when the ring the bond to the substituent is shown to cross into is polycyclic, the substituent may be bonded to any substitutable atom of the ring or ring system the bond to the substituent is shown to cross into.

When a substituent is listed or depicted without indicating the atom to which such substituent is bonded to the rest of the compound of a given formula, then such substituent may be bonded via any atom in such substituent, so long as the substitution results in a stable compound. Square brackets are used herein to depict a substituent without indicating the atom to which such substituent is bonded to the rest of the compound of a given formula. Thus, for example, in a compound of the following structural formula:

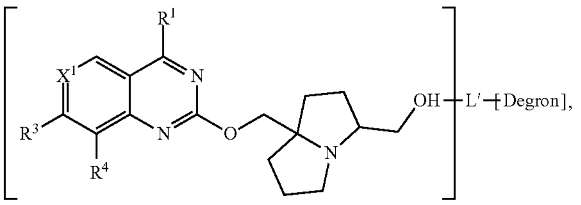

the portion of the compound in square brackets bonded to -L'-[Degron] can be bonded via the oxygen atom of the hydroxyl, so as to result in a compound of structural formula II. Similarly, in a compound of the following structural formula: [KRASi]-L'-[Degron], wherein Degron is

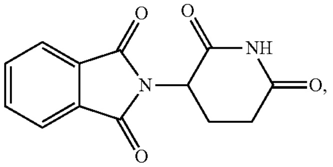 [SMILES: O=C1CCC(N2C(=O)c3ccccc3C2=O)C(=O)N1]

the Degron can be bonded to [KRASi]-L'-via the ortho carbon atom of the phthalimide, as in

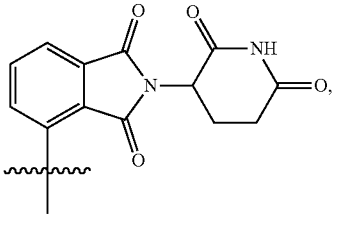 [SMILES: *c1cccc2c1C(=O)N(C1CCC(=O)NC1=O)C2=O]

or via the meta carbon atom of phthalimide, as in

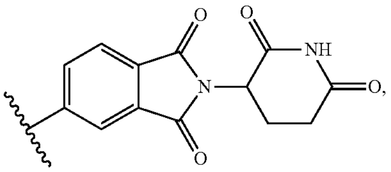 [SMILES: *c1ccc2c(c1)C(=O)N(C1CCC(=O)NC1=O)C2=O]

for examples. These examples are for illustration only, and are given without limitation to other binding sites in the portion of the compound in square brackets bonded to -L'-[Degron] and/or in Degron, all of which are contemplated by this disclosure.

Suitable substituents for use herein include halogen, hydroxyl, carbonyl (such as carboxyl, alkoxycarbonyl, formyl, or acyl), thiocarbonyl (such as thioester, thioacetate, or thioformate), alkyl, alkoxy, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, cycloalkyl, heterocyclyl, aralkyl, aryl or heteroaryl. It will be understood by those skilled in the art that substituents can themselves be substituted, if appropriate. Accordingly, substituents can further include an acetamide, for example.

When a bivalent substituent is listed without indicating directionality of such substituent (as, for example, variable L'), the bivalent substituent can be bonded in either direction. Thus, for example, a compound of structural formula (A): [KRASi]-L'-[Degron], wherein L' is —X—$(CH_2CH_2)$— includes compounds of both the following structural formula: [KRASi]—X—$(CH_2CH_2)$-[Degron], and the following structural formula: [KRASi]—$(CH_2CH_2)$—X-[Degron].

As used herein, the term "compound of the disclosure" refers to a compound of any structural formulas depicted herein (e.g., a compound of Structural Formula I or III or a subformula thereof, such as a compound of Structural Formula II°, II, II', II", II'", III', V, Table 1, Table 2, Table 3), as well as isomers, such as stereoisomers (including diastereoisomers, enantiomers and racemates) and tautomers thereof, isotopologues thereof, and inherently formed moieties (e.g., polymorphs and/or solvates, such as hydrates) thereof. When a moiety is present that is capable of forming a salt, then salts are included as well, in particular, pharmaceutically acceptable salts.

Compounds of the disclosure may have asymmetric centers, chiral axes, and chiral planes (e.g., as described in: E. L. Eliel and S. H. Wiley, Stereo-chemistry of Carbon Compounds, John Wiley & Sons, New York, 1994, pages 1119-1190), and occur as racemic mixtures, individual isomers (e.g., diastereomers, enantiomers, geometrical isomers (including cis and trans double bond isomers), conformational isomers (including rotamers and atropisomers), tautomers and intermediate mixtures, with all possible isomers and mixtures thereof being included, unless otherwise indicated.

Unless indicated otherwise at the point of use herein, when a disclosed compound or moiety is depicted by structure without indicating the stereochemistry, and the compound or moiety has one or more chiral centers, it is to be understood that the structure encompasses one enantiomer or diastereomer of the compound or moiety separated or substantially separated from the corresponding optical isomer(s), a racemic mixture, and mixtures enriched in one enantiomer or diastereomer relative to its corresponding optical isomer(s). Unless indicated otherwise at the point of use herein, when a disclosed compound or moiety is depicted by a structure indicating stereochemistry using solid and/or broken wedges, and the compound or moiety has one or more chiral centers, the stereochemistry indicates absolute configuration of the substituents around the one or more chiral centers. Unless indicated otherwise as the point of use herein, when a disclosed compound or moiety is depicted by a structure indicating stereochemistry using solid and/or broken bolded lines, and the compound or moiety has one or more chiral centers, the stereochemistry indicates relative stereochemistry of unspecified absolute configuration of the substituents around the one or more chiral centers. "R" and "S" can also or alternatively be used to indicate the absolute configuration of substituents around one or more chiral centers (e.g., carbon atoms). D- and L- can also or alternatively be used to designate stereochemistry. Thus, for example, a single stereoisomer with known relative and absolute configuration of two chiral centers can be designated using the conventional RS system (e.g., (1S, 2S)); diastereomers in a racemic mixture can be designated using the RS system with two letters (e.g., (1RS,2RS) as a racemic mixture of (1R,2R) and (1S,2S); (1RS,2SR) as a racemic mixture of (1R,2S) and (1S,2R)).

"Enantiomers" are pairs of stereoisomers that are non-superimposable mirror images of one another, most commonly because they contain an asymmetrically substituted carbon atom that acts as a chiral center.

"Diastereomers" are stereoisomers that are not related as mirror images, most commonly because they contain two or more asymmetrically substituted carbon atoms.

"Racemate" or "racemic mixture," as used herein, refer to a mixture containing equimolar quantities of two enantiomers of a compound. Such mixtures exhibit no optical activity (i.e., they do not rotate a plane of polarized light).

Percent enantiomeric excess (ee) is defined as the absolute difference between the mole fraction of each enantiomer multiplied by 100% and can be represented by the following equation:

$$ee = \left|\frac{R - S}{R + S}\right| \times 100\%,$$

where R and S represent the respective fractions of each enantiomer in a mixture, such that R+S=1. In some embodiments, an enantiomer is present in an ee of at least or about 50%, e.g., at least or about: 60%, 70%, 80%, 90%, 95%, 98%, 99% or 99.9%.

Percent diastereomeric excess (de) is defined as the absolute difference between the mole fraction of each diastereomer multiplied by 100% and can be represented by the following equation:

$$de = \left|\frac{D1 - (D2 + D3 + D4 \ldots)}{D1 + (D2 + D3 + D4 \ldots)}\right| \times 100\%,$$

where D1 and (D2+D3+D4 . . . ) represent the respective fractions of each diastereomer in a mixture, such that D1+(D2+D3+D4 . . . )=1. In some embodiments, a diastereomer is present in a de of at least or about 50%, e.g., at least or about: 60%, 70%, 80%, 90%, 95%, 98%, 99% or 99.9%.

Tautomers are isomers of a compound that differ in the position of one or more hydrogen atoms.

Unless otherwise indicated, all possible isomers and mixtures thereof, including optical isomers, rotamers, tautomers and cis- and trans-isomers, are included in the present invention.

The term "isotopologue" refers to a molecule that differs from a reference molecule only in its isotopic composition.

Certain atoms naturally occur in various isotopic forms. Natural isotopic abundance describes the relative abundance of the various naturally-occurring isotopes of a given atom. Thus, it will be understood that a population of molecules represented by a particular chemical structure will typically contain isotopologues of the particular chemical structure. The relative amount of such isotopologues will depend upon a number of factors, such as relative natural isotopic abundance, the isotopic purity of reagents used to make the compound and the efficiency of incorporation of isotopic atoms in the various synthetic steps used to prepare the compound. In certain embodiments, the amount of such isotopologues in toto will be less than 49.9%, for example, less than 47.5%, less than 40%, less than 32.5%, less than 25%, less than 17.5%, less than 10%, less than 5%, less than 3%, less than 1%, or less than 0.5%.

Structures depicted herein are meant to allow for such natural isotopic abundance, as well as replacement of one or more atoms in a structure with an isotope thereof or an isotopically enriched counterpart, e.g., at a non-natural isotopic abundance. For example, compounds produced by the replacement of a hydrogen with deuterium or tritium, or of a carbon with a $^{13}C$ or $^{14}C$ are within the scope of this disclosure. In some embodiments, a hydrogen atom in a compound of the disclosure is replaced or enriched with D. In some embodiments, a methyl group in a compound of the disclosure is replaced or enriched with $—CD_3$. Isotopologues can be useful, for example, as analytical tools, as probes in biological assays, or as therapeutic agents in accordance with the present disclosure.

The phrase "pharmaceutically acceptable" means that the substance or composition the phrase modifies is, within the scope of sound medical judgment, suitable for use in contact with the tissues of humans and lower animals without undue toxicity, irritation, allergic response and the like, and are commensurate with a reasonable benefit/risk ratio.

As used herein, the term "pharmaceutically acceptable salt" refers to those salts which are, within the scope of sound medical judgment, suitable for use in contact with the tissues of mammals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include pharmaceutically acceptable acid addition salts and pharmaceutically acceptable base addition salts.

Examples of pharmaceutically acceptable acid addition salts are salts of an amino group formed with inorganic acids such as hydrochloric acid, hydrobromic acid, phosphoric acid, sulfuric acid and perchloric acid, or with organic acids, such as acetic acid, oxalic acid, maleic acid, tartaric acid, citric acid, succinic acid or malonic acid or by using other methods used in the art, such as ion exchange. Other pharmaceutically acceptable acid addition salts include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like. Either the mono-, di- or tri-acid salts can be formed, and such salts can exist in either a hydrated, solvated or substantially anhydrous form.

Pharmaceutically acceptable base addition salts include salts formed with inorganic bases, such as alkali metal, alkaline earth metal, and ammonium bases, and salts formed with aliphatic, alicyclic or aromatic organic amines, such as methylamine, trimethylamine and picoline, or $N^+((C_1-C_4)$ alkyl$)_4$ salts. Representative alkali or alkaline earth metal salts include sodium, lithium, potassium, calcium, magnesium, barium and the like. Further pharmaceutically acceptable base addition salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Compounds described herein can also exist as "solvates" or "hydrates." A "hydrate" is a compound that exists in a composition with one or more water molecules. A hydrate can include water in stoichiometric quantities, such as a monohydrate or a dihydrate, or can include water in random amounts. A "solvate" is similar to a hydrate, except that a solvent other than water, such as methanol, ethanol, dimethylformamide, diethyl ether, or the like replaces water. Mixtures of such solvates or hydrates can also be prepared. The source of such solvate or hydrate can be from the solvent of crystallization, inherent in the solvent of preparation or crystallization, or adventitious to such solvent.

"Pharmaceutically acceptable carrier" refers to a non-toxic carrier or excipient that does not destroy the pharmacological activity of the agent with which it is formulated and is nontoxic when administered in doses sufficient to deliver a therapeutic amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

"Treating," as used herein, refers to taking steps to deliver a therapy to a subject, such as a mammal, in need thereof (e.g., as by administering to a subject one or more therapeutic agents). "Treating" includes inhibiting a disease or condition (e.g., as by slowing or stopping its progression or causing regression of the disease or condition), and relieving the symptoms resulting from a disease or condition.

"KRAS" refers to mammalian wild-type KRAS protein or a mutant thereof. Examples of KRAS mutants include KRAS G12A/C/D/F/L/R/V/S, G13A/C/D, V14L, L19F, Q22K/E/R, Q25A, D33E, P34L/R, A59E/G/P/S/T/V, Q61H, K117N, and A146V/T mutants, wherein A, C, F, R, V, S, L, Q, K, E, H, N, and T are alanine, cysteine, phenylalanine, arginine, valine, serine, leucine, glutamine, lysine, glutamic acid, histidine, asparagine, and threonine, respectively.

"KRAS G12D" refers to mammalian KRAS protein containing an aspartic acid substitution for glycine at amino acid position 12. The assignment of amino acid codon and residue positions for human KRAS is based on the amino acid sequence identified by UniProtKB/Swiss-Prot P01116: Variantp.Gly 12Asp. KRAS mutants, including KRAS G12A/C/D/F/L/R/V/S, G13A/C/D, V14L, L19F, Q22K/E/R, Q25A, D33E, P34L/R, A59E/G/P/S/T/V, Q61H/K/L/R, K117N, and A146V/T mutants are similarly identified.

A "KRAS-associated cancer" refers to a cancer associated with (e.g., mediated by) wild-type KRAS or a mutant thereof. KRAS-associated cancers are known to those skilled in the art and described herein.

A "KRAS G12D-associated cancer" refers to a cancer associated with (e.g., mediated by) or having a KRAS G12D mutation. Analogously, a "KRAS G12V-associated cancer" refers to a cancer associated with or having a KRAS G12V mutation. A person skilled in the art will know how to determine whether (e.g., diagnose) a cancer or subject has a KRAS mutation, such as a KRAS G12D mutation, for example, using a kit or assay approved by a regulatory agency, such as U.S. Food and Drug Administration (FDA). Techniques that can be used to determine whether a cancer or subject has a KRAS mutation, such as a KRAS G12D mutation, include next generation sequencing, immunohistochemistry, fluorescence microscopy, break apart FISH analysis, Southern blotting, Western blotting, FACS analysis, Northern blotting and PCR-based amplification (e.g., RT-PCR).

A "binding moiety" is a portion of a compound that binds to an indicated target with measurable affinity. In the context of the instant disclosure, the target is typically a protein as, for example, KRAS in a KRAS binding moiety, ubiquitin E3 ligase in a ubiquitin E3 ligase binding moiety. In the compounds of the disclosure, binding of the compound of the disclosure to an indicated target is typically mediated by a binding moiety for that target. For example, binding to KRAS in the compounds of the disclosure is typically mediated by a KRAS binding moiety. For example, binding to a ubiquitin E3 ligase is typically mediated by a ubiquitin E3 ligase binding moiety.

Binding (of a binding moiety and/or a compound of the disclosure) to a target may result, for example, in inhibition and/or agonism (full or partial) of the target, such as a target protein. Thus, in some embodiments, a binding moiety and/or compound of the disclosure is an inhibitor. In certain embodiments, a binding moiety and/or compound of the disclosure has an $IC_{50}$ against its indicated target and/or binding constant with its indicated target of less than about 50 μM, e.g., less than about 10 μM, less than about 5 μM, less than about 1 μM, less than about 500 nM, less than about 100 nM, less than about 10 nM, or less than about 1 nM. Methods of measuring $IC_{50}$ and binding constants are described herein and/or within the abilities of a person skilled in the art.

Binding (of a binding moiety and/or a compound of the disclosure) to a target may be selective. Binding is "selective," in accordance with the present disclosure, when a binding moiety and/or a compound of the disclosure has an $IC_{50}$ against a first indicated target (e.g., KRAS G12D or KRAS G12V) and/or binding constant with a first indicated target (e.g., KRAS G12D or KRAS G12V) that is at least two-fold less than its $IC_{50}$ against another indicated target (s)(e.g., KRAS G12V or KRAS G12D, respectively) and/or binding constant with another indicated target(s)(e.g., KRAS G12V or KRAS G12D, respectively) In certain embodiments, a binding moiety and/or a compound of the disclosure has an $IC_{50}$ against a first indicated target and/or binding constant with a first indicated target that is at least five-fold less, e.g., at least 10-fold less, at least 20-fold less, at least 30-fold less, at least 40-fold less, or at least 50-fold less, than its $IC_{50}$ against another indicated target(s) and/or binding constant with another indicated target(s).

A KRAS binding moiety and/or a compound of the disclosure may also or alternatively bind to two or more (e.g., three, four, five, etc.) KRAS targets, such as KRAS G12C, KRAS G12D, and KRAS G12V. Such KRAS binding moieties and/or compounds of the disclosure may be referred to herein as "pan-KRAS inhibitors." A KRAS binding moiety and/or compound of the disclosure may be referred to herein as a "pan-KRAS inhibitor" when the KRAS binding moiety and/or compound of the disclosure has an $IC_{50}$ against two or more KRAS targets (e.g., KRAS G12D and KRAS G12V) and/or binding constant with two or more KRAS targets (e.g., KRAS G12D and KRAS G12V) that is less than 10-fold of one another. In certain embodiments, a KRAS binding moiety and/or compound of the disclosure has an $IC_{50}$ against two or more KRAS targets and/or binding constant with two or more KRAS targets that is less than five-fold, e.g., less than two-fold, of one another. In certain embodiments, a KRAS binding moiety and/or compound of the disclosure is a pan inhibitor and has an $IC_{50}$ against two or more KRAS targets and/or binding constant with two or more KRAS targets of less than about 1 μM, e.g., less than about 500 nM, less than about 100 nM, less than about 10 nM, or less than about 1 nM.

An "effective amount" is an amount effective, at dosages and for periods of time necessary, to achieve a desired result (e.g., a desired therapeutic result, a desired in vitro result).

"A therapeutically effective amount" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual. A therapeutically effective amount of an agent to be administered can be determined by a clinician of ordinary skill using the guidance provided herein and other methods known in the art.

As used herein, "subject" includes humans, domestic animals, such as laboratory animals (e.g., dogs, monkeys, pigs, rats, mice, etc.), household pets (e.g., cats, dogs, rabbits, etc.) and livestock (e.g., pigs, cattle, sheep, goats, horses, etc.), and non-domestic animals. In some embodiments, a subject is a human.

Compounds

The compounds described herein are of general formula (A):

[KRASi]-*L*'-[Degron] (A), or a pharmaceutically acceptable salt thereof, wherein:

- KRASi is a binding moiety of KRAS, or one or more mutants thereof, such as G12A/C/D/F/L/R/V/S, G13A/C/D, V14L, L19F, Q22K/E/R, Q25A, D33E, P34L/R, A59E/G/P/S/T/V, Q61H, K117N, and/or A146V/T;
- L' is a bivalent linker connecting KRASi to Degron; and
- Degron is a degron, preferably, a ubiquitin E3 ligase binding moiety.

An embodiment is a compound of the following structural formula:

(I)

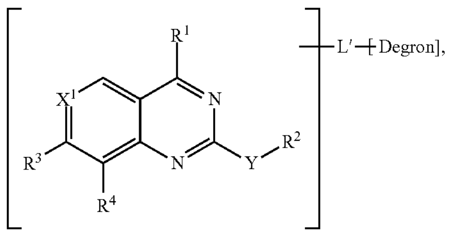

or a pharmaceutically acceptable salt thereof, wherein values for the variables (e.g., $X^1$, Y, $R^1$, $R^2$, $R^3$, $R^4$, L', Degron) are as described herein, e.g., in the following sections.

In a particular embodiment, the compound has the following structural formula:

(II°)

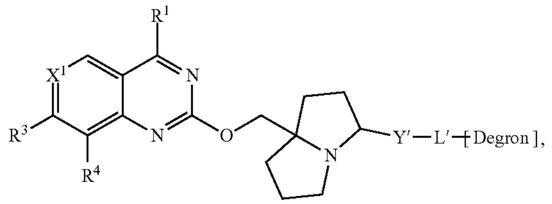

or a pharmaceutically acceptable salt thereof, wherein Y' is —$(C_1$-$C_3)$alkylene-O—#, $(C_1$-$C_3)$alkylene-N(H)—#, or $(C_1$-$C_3)$alkylene-N($(C_1$-$C_3)$alkyl)-#, or is absent, and # indicates point of attachment of Y' to L'. In some aspects, Y' is —$CH_2$—O—#, —$CH_2$—N(H)—#, or —$CH_2$—N($(C_1$-$C_3)$alkyl)-#, or is absent. In further aspects, Y' is —$CH_2$—O—# or —$CH_2$—N(H)—#. Values for the remaining variables (e.g., $X^1$, $R^1$, $R^3$, $R^4$, Y', L', Degron) are as described herein, e.g., in the following sections.

In another particular embodiment, the compound has the following structural formula:

(II)

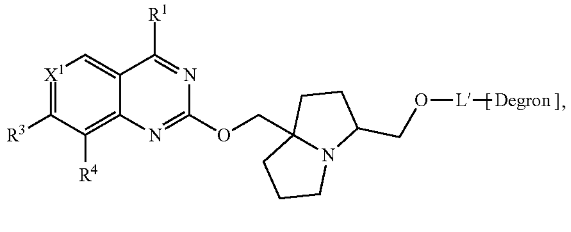

or a pharmaceutically acceptable salt thereof, wherein values for the variables (e.g., $X^1$, $R^1$, $R^3$, $R^4$, L', Degron) are as described herein, e.g., in the following sections.

In a more particular embodiment, the compound has the following structural formula:

(II')

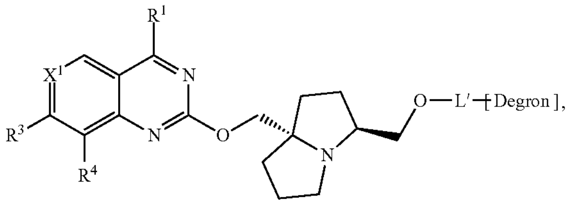

or a pharmaceutically acceptable salt thereof, wherein values for the variables (e.g., $X^1$, $R^1$, $R^3$, $R^4$, L', Degron) are as described herein, e.g., in the following sections.

In another particular embodiment, the compound has the following structural formula:

(II'')

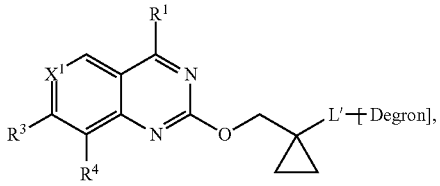

or a pharmaceutically acceptable salt thereof, wherein values for the variables (e.g., $X^1$, $R^1$, $R^3$, $R^4$, L', Degron) are as described herein, e.g., in the following sections.

In another particular embodiment, the compound has the following structural formula:

(II''')

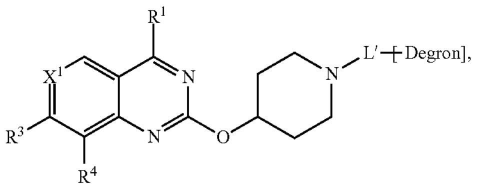

or a pharmaceutically acceptable salt thereof, wherein values for the variables (e.g., $X^1$, $R^1$, $R^3$, $R^4$, L', Degron) are as described herein, e.g., in the following sections.

Another embodiment is a compound of the following structural formula:

(III)

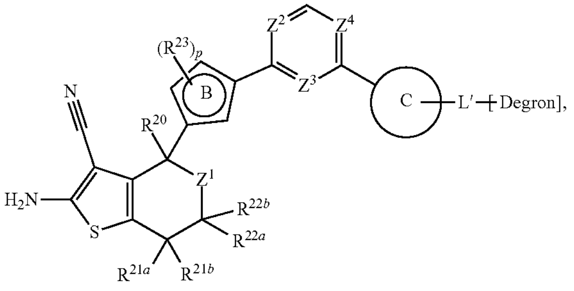

or a pharmaceutically acceptable salt thereof, wherein values for the variables (e.g., Ring B, Ring C, $Z^1$, $Z^2$, $Z^3$, $Z^4$, $R^{20}$, $R^{21a}$, $R^{21b}$, $R^{22a}$, $R^{220}$, $R^{23}$, p, L', Degron) are as described herein, e.g., in the following sections.

In a particular embodiment, the compound has the following structural formula:

(III')

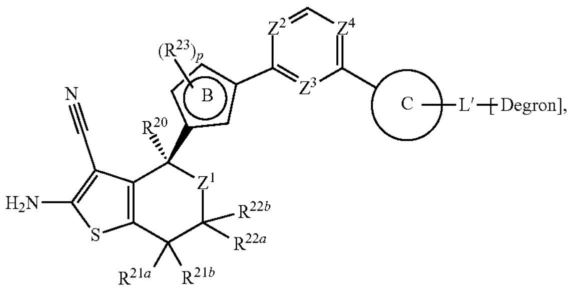

or a pharmaceutically acceptable salt thereof, wherein values for the variables (e.g., Ring B, Ring C, $Z^1$, $Z^2$, $Z^3$, $Z^4$, $R^{20}$, $R^{21a}$, $R^{21b}$, $R^{22a}$, $R^{22b}$, $R^{23}$, p, L', Degron) are as described herein, e.g., in the following sections.

In another particular embodiment, the compound has the following structural formula:

(IV)

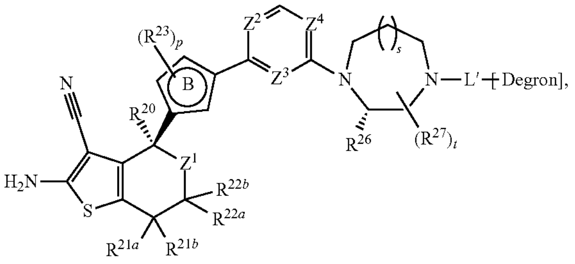

or a pharmaceutically acceptable salt thereof, wherein values for the variables (e.g., Ring B, $Z^1$, $Z^2$, $Z^3$, $Z^4$, $R^{20}$, $R^{21a}$, $R^{21b}$, $R^{22a}$, $R^{22b}$, $R^{23}$, $R^{26}$, $R^{27}$, p, s, t, L', Degron) are as described herein, e.g., in the following sections.

In another particular embodiment, the compound has the following structural formula:

(V)

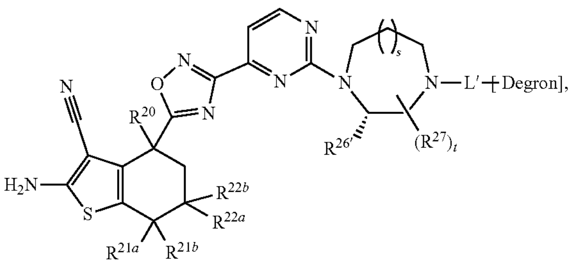

or a pharmaceutically acceptable salt thereof, wherein values for the variables (e.g., $R^{20}$, $R^{21a}$, $R^{21b}$, $R^{22a}$, $R^{22b}$, $R^{26'}$, $R^{27}$, s, t, L', Degron) are as described herein, e.g., in the following sections.

This disclosure contemplates all combinations of the values and alternative values for the variables set forth herein.

KRAS Binding Moieties

In a first embodiment, a KRAS binding moiety has the following structural formula:

(Ia)

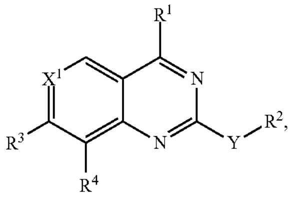

wherein:

$R^1$ is

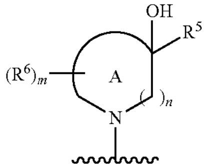

or

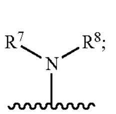

Ring A is $(C_5\text{-}C_{12})$ heterocyclyl;

$R^5$ is hydrogen, $(C_1\text{-}C_6)$alkyl, $(C_1\text{-}C_6)$haloalkyl, $(C_1\text{-}C_6)$ hydroxyalkyl, or $(C_1\text{-}C_6)$ cyanoalkyl;

each $R^6$ is independently halo, cyano, hydroxy, $(C_1\text{-}C_6)$alkyl, $(C_1\text{-}C_6)$haloalkyl, $(C_1\text{-}C_6)$ hydroxyalkyl, or $(C_1\text{-}C_6)$ cyanoalkyl;

$R^7$ is hydrogen or $(C_1\text{-}C_6)$alkyl;

$R^8$ is -L-$(C_5\text{-}C_{12})$ heteroaryl or -L-$(C_6\text{-}C_{12})$aryl substituted with $(R^9)$ p';

$R^9$ is independently halo, cyano, hydroxy, —$N(R^{11})_2$, —$C(O)N(R^{11})_2$, $(C_1\text{-}C_6)$alkyl, $(C_1\text{-}C_6)$haloalkyl, $(C_1\text{-}C_6)$ hydroxyalkyl, $(C_1\text{-}C_6)$ cyanoalkyl, $(C_1\text{-}C_6)$ alkoxy, or $(C_1\text{-}C_6)$haloalkoxy;

L is $(C_1\text{-}C_3)$alkylene optionally substituted with one or more deutero or hydroxy;

n is 1 or 2;

m is 0, 1, 2, or 3;

p' is 0, 1, 2, 3, or 4;

$X^1$ is N or $C(R^{10})$;

$R^{10}$ is hydrogen, halogen, $(C_1\text{-}C_6)$alkyl, $(C_1\text{-}C_6)$haloalkyl, $(C_1\text{-}C_6)$haloalkoxy, $(C_2\text{-}C_6)$alkenyl, $(C_2\text{-}C_6)$ alkynyl, —CN, $(C_1\text{-}C_6)$alkoxy, —S—$(C_1\text{-}C_6)$alkyl or —S—$(C_1\text{-}C_6)$haloalkyl;

Y is O—$(C_1\text{-}C_3)$alkylene optionally substituted with one or more deutero or hydroxy, or O;

$R^2$ is hydrogen, —$N(R^{11})_2$, $(C_3\text{-}C_{12})$ heterocyclyl, $(C_1\text{-}C_6)$alkyl, $(C_6\text{-}C_{14})$aryl, —$(C_5\text{-}C_{14})$ heteroaryl, —$(C_3\text{-}C_{12})$ cycloalkyl, —N(H)C(NH) $NH_2$, —$C(O)N(R^{11})_2$, —$(C_1\text{-}C_6)$haloalkyl, —$OR^{11}$, —$NR^{11}C(O)$—$(C_6\text{-}C_{14})$aryl, —COOH or —C(O)O $(C_1\text{-}C_6)$alkyl, wherein the $(C_3\text{-}C_{12})$ heterocyclyl and the $(C_3\text{-}C_{12})$ cycloalkyl are optionally substituted with one or more $R^{12}$, and the $(C_6\text{-}C_{14})$aryl and $(C_5\text{-}C_{14})$ heteroaryl are optionally substituted with one or more $R^{13}$, $R^3$ is $(C_6\text{-}C_{14})$aryl or $(C_5\text{-}C_{14})$ heteroaryl, wherein the $(C_6\text{-}C_{14})$aryl or $(C_5\text{-}C_{14})$ heteroaryl is optionally substituted with one or more $R^{14}$, $R^4$ is hydrogen, halogen or $(C_1\text{-}C_3)$alkyl;

each $R^{11}$ is independently hydrogen or $(C_1\text{-}C_3)$alkyl;

each $R^{12}$ is independently halogen, hydroxy, $(C_1\text{-}C_3)$ hydroxyalkyl, $(C_1\text{-}C_3)$alkyl, $(C_1\text{-}C_3)$haloalkyl, $(C_1\text{-}C_3)$ alkoxy, cyano, -Q-phenyl, -Q-phenyl-$SO_2F$, —N(H)C(O)-phenyl, —N(H)C(O)-phenyl-$SO_2F$, $(C_1\text{-}C_3)$alkyl-substituted pyrazole, $(C_6\text{-}C_{14})$aryl$(C_1\text{-}C_3)$alkyl, tert-butyldimethylsilyloxy-$CH_2$—, —$N(R^{11})_2$, $(C_1\text{-}C_3)$ alkoxy $(C_1\text{-}C_3)$alkyl, $(C_1\text{-}C_3)$alkyl-C(O)—, oxo, $(C_1\text{-}C_3)$haloalkyl-C(O)—, —$SO_2F$, $(C_1\text{-}C_3)$alkoxy $(C_1\text{-}C_3)$ alkoxy, —$CH_2OC(O)N(R^{11})_2$, —$CH_2N(H)C(O)O$—$(C_1\text{-}C_6)$alkyl, —$CH_2N(H)C(O)N(R^{11})_2$, —$CH_2N(H)C(O)(C_1\text{-}C_6)$alkyl, —$CH_2$ (pyrazolyl), —$CH_2N(H)S(O)_2$ $(C_1\text{-}C_6)$alkyl, —$CH_2OC(O)(C_3\text{-}C_{12})$ heterocyclyl, —$OC(O)N(R^{11})_2$, —OC(O)N(H)$(C_1\text{-}C_3)$alkyl-O—$(C_1\text{-}C_3)$alkyl, —OC(O)N(H)$(C_1\text{-}C_3)$alkyl-O—$(C_1\text{-}C_3)$ alkyl-phenyl-$(C_1\text{-}C_3)$alkyl-$N(CH_3)_2$, —OC(O)N(H) $(C_1\text{-}C_3)$alkyl-O—$(C_1\text{-}C_3)$alkyl-phenyl, —OC(O)$(C_3\text{-}C_{12})$ heterocyclyl or —$CH_2$—$(C_3\text{-}C_{12})$ heterocyclyl, wherein the phenyl of —N(H)C(O)phenyl and —OC(O)N(H)$(C_1\text{-}C_3)$alkyl-O—$(C_1\text{-}C_3)$alkyl-phenyl is optionally substituted with —C(O)H or —OH, and the $(C_3\text{-}C_{12})$ heterocyclyl of —$CH_2$—$(C_3\text{-}C_{12})$ heterocyclyl is optionally substituted with oxo;

Q is a bond or O;

each $R^{13}$ is independently halogen, hydroxy, —C(O)H, $(C_1\text{-}C_4)$alkyl, $(C_1\text{-}C_4)$alkoxy, $(C_1\text{-}C_4)$haloalkyl, $(C_1\text{-}C_4)$ hydroxyalkyl, or —$N(R^{11})_2$; and each $R^{14}$ is independently halogen, cyano, hydroxy, $(C_1\text{-}C_4)$alkyl, —S—$(C_1\text{-}C_3)$alkyl, $(C_2\text{-}C_4)$alkenyl, $(C_2\text{-}C_4)$ alkynyl, $(C_2\text{-}C_4)$ hydroxyalkynyl, $(C_1\text{-}C_3)$ cyanoalkyl, triazolyl, $(C_1\text{-}C_3)$haloalkyl, —O—$(C_1\text{-}C_3)$haloalkyl, —S—$(C_1\text{-}C_3)$haloalkyl, $(C_1\text{-}C_3)$alkoxy, $(C_1\text{-}C_3)$ hydroxyalkyl, —$CH_2C(O)N(R^{11})_2$, $(C_3\text{-}C_4)$alkynyl-N$(R^{11})_2$, $N(R^{11})_2$, deutero $(C_2\text{-}C_4)$alkynyl, $(C_1\text{-}C_3)$ alkoxy $(C_1\text{-}C_3)$haloalkyl, or $(C_3\text{-}C_6)$ cycloalkyl, wherein the $(C_3\text{-}C_6)$ cycloalkyl is optionally substituted with halogen or $(C_1\text{-}C_3)$alkyl.

In a first aspect of the first embodiment, $X^1$ is N. Values for the remaining variables are as described in the first embodiment.

In a second aspect of the first embodiment, $X^1$ is $C(R^{10})$. Values for the remaining variables are as described in the first embodiment, or first aspect thereof.

In a third aspect of the first embodiment, Y is $OCH_2$. Values for the remaining variables are as described in the first embodiment, or first or second aspect thereof.

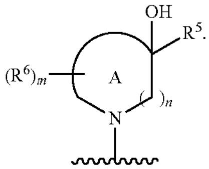

In a fourth aspect of the first embodiment, $R^1$ is Values for the remaining variables (including Rina A, $R^5$, $R^6$, m, n) are as described in the first embodiment, or first through third aspects thereof.

In a fifth aspect of the first embodiment, $R^1$ is selected from:

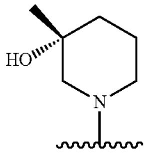, 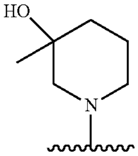, 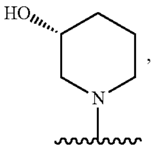,

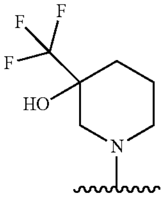, 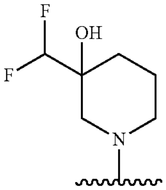, 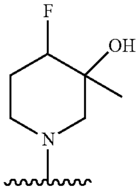,

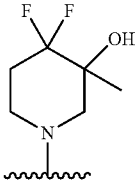, 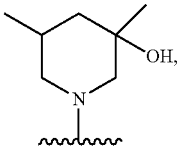 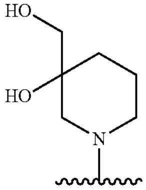,

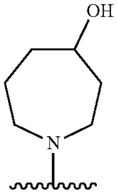, 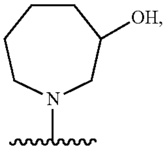 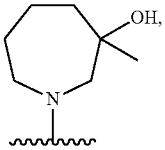

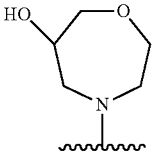 and 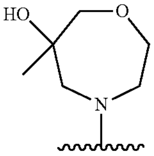.

Values for the remaining variables are as described in the first embodiment, or first through fourth aspects thereof.

In a sixth aspect of the first embodiment, $R^1$ is

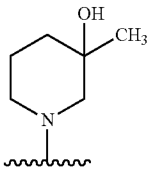 or 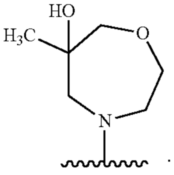.

Values for the remaining variables are as described in the first embodiment, or first through fifth aspects thereof.

In a seventh aspect of the first embodiment, $R^1$ is

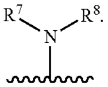

Values for the remaining variables (including $R^7$ and $R^8$) are as described in the first embodiment, or first through sixth aspects thereof.

In an eighth aspect of the first embodiment, Ring A is ($C_5$-$C_8$) monocyclic heterocyclyl. Values for the remaining variables are as described in the first embodiment, or first through seventh aspects thereof.

In a ninth aspect of the first embodiment, Ring A is piperidinyl, azepanyl, oxazepanyl, or thioazepanyl. Values for the remaining variables are as described in the first embodiment, or first through eighth aspects thereof.

In a tenth aspect of the first embodiment, $R^2$ is —($C_3$-$C_{12}$) heterocyclyl or —($C_3$-$C_{12}$) cycloalkyl, optionally substituted with one or more $R^{12}$. Values for the remaining variables (including $R^{12}$) are as described in the first embodiment, or first through ninth aspects thereof.

In an eleventh aspect of the first embodiment, $R^2$ is hexahydro-1H-pyrrolizinylene optionally substituted with one or more $R^{12}$. Values for the remaining variables (including $R^{12}$) are as described in the first embodiment, or first through tenth aspects thereof.

In a twelfth aspect of the first embodiment, Y—$R^2$ is

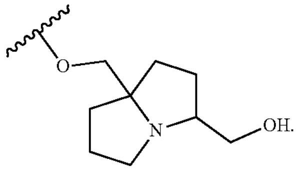 [SMILES: *OCC12CCCN1C(CO)CC2]

Values for the remaining variables are as described in the first embodiment, or first through eleventh aspects thereof.

In a thirteenth aspect of the first embodiment, $R^3$ is ($C_6$-$C_{14}$)aryl(and in further aspects, napthyl or phenyl) optionally substituted with one or more $R^{13}$. Values for the remaining variables (including $R^{13}$) are as described in the first embodiment, or first through twelfth aspects thereof.

In a fourteenth aspect of the first embodiment, $R^3$ is

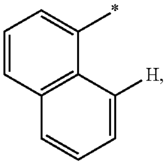, 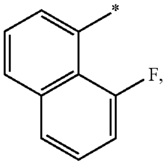, 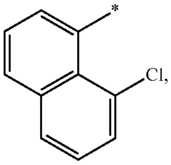,

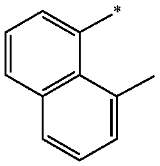, 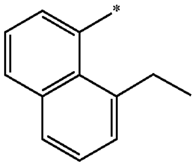,

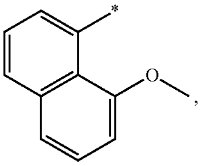, 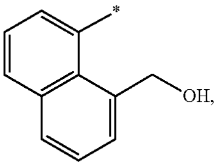,

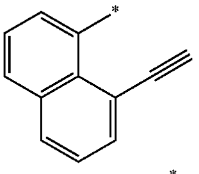, 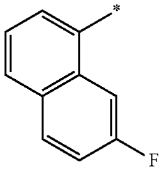, 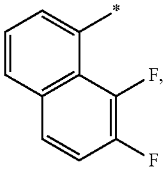,

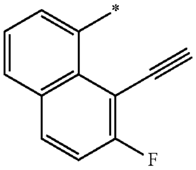, 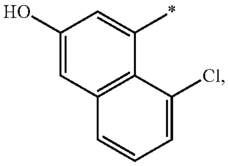,

-continued

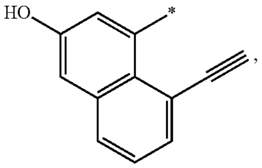,
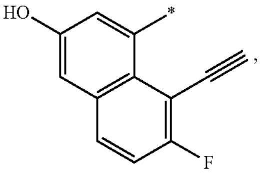,
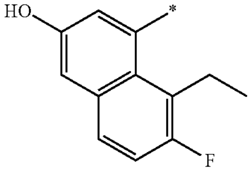
or
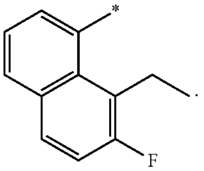.

Values for the remaining variables are as described in the first embodiment, or first through thirteenth aspects thereof.

In a fifteenth aspect of the first embodiment, $R^3$ is

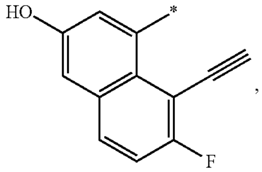,
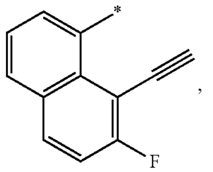,
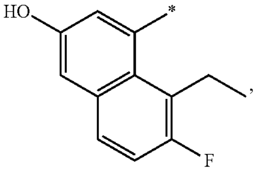,
or
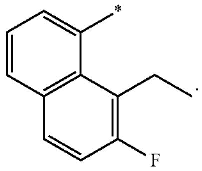.

Values for the remaining variables are as described in the first embodiment, or first through fourteenth aspects thereof.

In a sixteenth aspect of the first embodiment, $R^3$ is

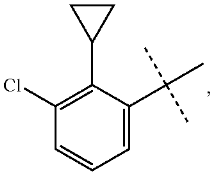,
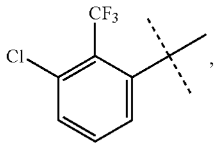,
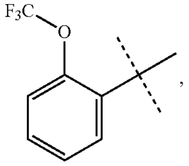,
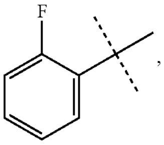,
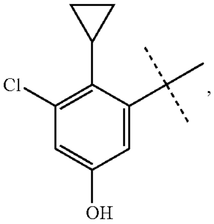,
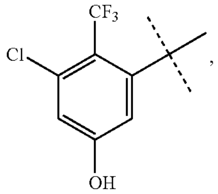,

-continued

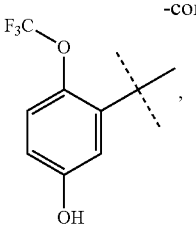,
or
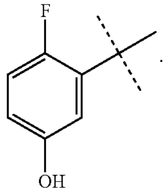.

Values for the remaining variables are as described in the first embodiment, or first through fourteenth aspects thereof.

In a seventeenth aspect of the first embodiment, $R^4$ is halogen. Values for the remaining variables are as described in the first embodiment, or first through sixteenth aspects thereof.

In an eighteenth aspect of the first embodiment, $R^4$ is fluoro. Values for the remaining variables are as described in the first embodiment, or first through seventeenth aspects thereof.

In a nineteenth aspect of the first embodiment, $R^5$ is hydrogen, $CH_3$, $CF_3$, $CHF_2$, or hydroxymethyl. Values for the remaining variables are as described in the first embodiment, or first through eighteenth aspects thereof.

In a twentieth aspect of the first embodiment, $R^7$ is hydrogen. Values for the remaining variables are as described in the first embodiment, or first through nineteenth aspects thereof.

In a twenty-first aspect of the first embodiment, $R^8$ is -L-($C_5$-$C_{12}$) heteroaryl substituted with ($R^9$) p'. Values for the remaining variables (including L, $R^9$, p') are as described in the first embodiment, or first through twentieth aspects thereof.

In a twenty-second aspect of the first embodiment, $R^8$ is -L-($C_5$-$C_{12}$) fused bicyclic heteroaryl substituted with ($R^9$) p'. Values for the remaining variables (including L, $R^9$, p') are as described in the first embodiment, or first through twenty-first aspects thereof.

In a twenty-third aspect of the first embodiment, $R^8$ is -L-benzo[c][1,2,5]oxadiazolyl, -L-imidazo[1,2-a]pyridinyl, or -L-7aH-pyrrolo[2,3-b]pyridinyl, substituted with ($R^9$) p'. Values for the remaining variables (including L, $R^9$, p') are as described in the first embodiment, or first through twenty-second aspects thereof.

In a twenty-fourth aspect of the first embodiment, L is $—CH_2—$. Values for the remaining variables (including L, $R^9$, p') are as described in the first embodiment, or first through twenty-third aspects thereof.

In a twenty-fifth aspect of the first embodiment, each $R^9$ is independently cyano, $—NH_2$, —N(H) $CH_3$, $—N(CH_3)_2$, —C(O) $NH_2$, —C(O)N(H) $CH_3$, $—C(O)N(CH_3)_2$, methyl, or hydroxymethyl. Values for the remaining variables are as described in the first embodiment, or first through twenty-fourth aspects thereof.

In a twenty-sixth aspect of the first embodiment, $R^{10}$ is hydrogen, fluoro, chloro, methyl, $—CF_3$, $—OCF_3$, —CN, —OCH, $—SCH_3$, or $—SCF_3$. Values for the remaining variables are as described in the first embodiment, or first through twenty-fifth aspects thereof.

In a twenty-seventh aspect of the first embodiment, each $R^{11}$ is independently hydrogen or methyl. Values for the remaining variables are as described in the first embodiment, or first through twenty-sixth aspects thereof.

In a twenty-eighth aspect of the first embodiment, each $R^{12}$ is independently halogen, hydroxy, ($C_1$-$C_3$) hydroxyalkyl, ($C_1$-$C_3$)alkyl, ($C_1$-$C_3$)haloalkyl, ($C_1$-$C_3$)alkoxy, or cyano. Values for the remaining variables are as described in the first embodiment, or first through twenty-seventh aspects thereof.

In a twenty-ninth aspect of the first embodiment, each $R^{14}$ is independently halogen, hydroxy, $(C_1-C_4)$alkyl, —S—$(C_1-C_3)$alkyl, $(C_2-C_4)$alkenyl, $(C_2-C_4)$alkynyl, $(C_1-C_3)$alkoxy, $(C_1-C_3)$ hydroxyalkyl, or deutero $(C_2-C_4)$alkynyl. Values for the remaining variables are as described in the first embodiment, or first through twenty-eighth aspects thereof.

In a thirtieth aspect of the first embodiment, n is 1. Values for the remaining variables are as described in the first embodiment, or first through twenty-ninth aspects thereof.

In a thirty-first aspect of the first embodiment, m is 0, 1, or 2. Values for the remaining variables are as described in the first embodiment, or first through thirtieth aspects thereof.

In a thirty-second aspect of the first embodiment, m is 0. Values for the remaining variables are as described in the first embodiment, or first through thirty-first aspects thereof.

In a thirty-third aspect of the first embodiment, p' is 0. Values for the remaining variables are as described in the first embodiment, or first through thirty-second aspects thereof.

In a thirty-fourth aspect of the first embodiment, Y is O—$(C_1-C_3)$alkylene optionally substituted with one or more deutero or hydroxy. Values for the remaining variables are as described in the first embodiment, or first through thirty-third aspects thereof.

In a thirty-fifth aspect of the first embodiment, Y is O. Values for the remaining variables are as described in the first embodiment, or first through thirty-fourth aspects thereof.

In a thirty-sixth aspect of the first embodiment, Y—$R^2$ is

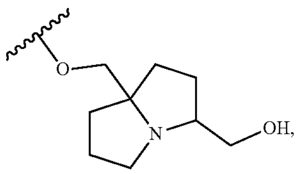
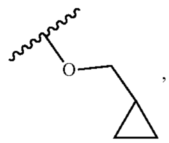
, or
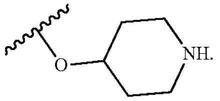

Values for the remaining variables are as described in the first embodiment, or first through thirty-fifth aspects thereof.

In a thirty-seventh aspect of the first embodiment, Ring A is piperidinyl, morpholinyl, azepanyl, oxazepanyl, or thioazepanyl. Values for the remaining variables are as described in the first embodiment, or first through thirty-sixth aspects thereof.

In a thirty-eighth aspect of the first embodiment, $R^3$ is

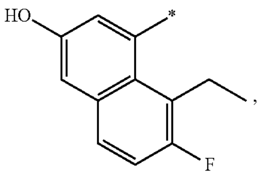
,
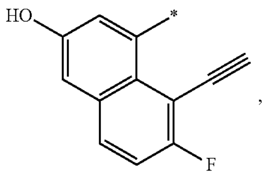
,

-continued

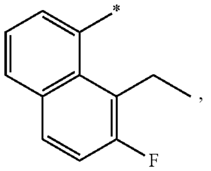
,
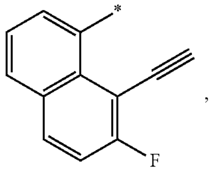
,
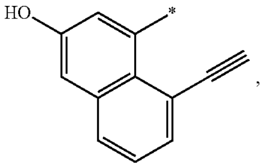
,
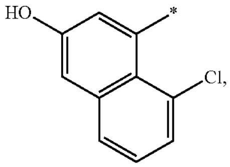
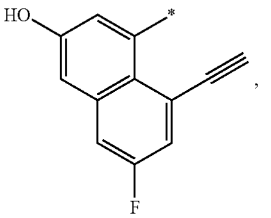
,
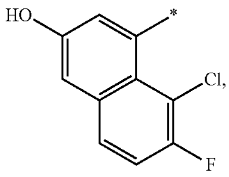
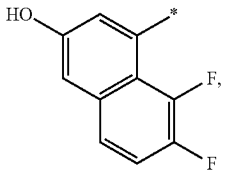
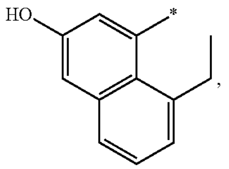
, or
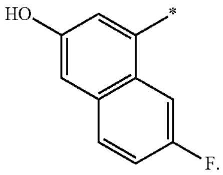

Values for the remaining variables are as described in the first embodiment, or first through thirty-seventh aspects thereof.

In a second embodiment, the KRAS binding moiety has the following structural formula:

(IIa)

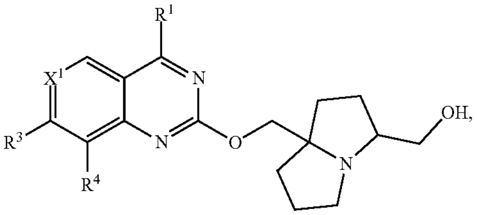

wherein values for the variables (e.g., $X^1$, $R^1$, $R^3$, $R^4$, L', Degron) are as described in the first embodiment, or any aspect thereof.

In a first aspect of the second embodiment, the KRAS binding moiety has the following structural formula:

(II'a)

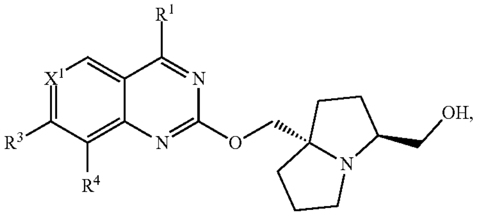

wherein values for the variables (e.g., $X^1$, $R^1$, $R^3$, $R^4$, L', Degron) are as described in the first embodiment, or any aspect thereof.

It will be understood that the moiety which is shown in square brackets in the compounds of structural formulas (I)—(II'), corresponds to the KRAS binding moiety in the compounds of structural formulas (Ia)-(II'a).

In some aspects of any of the aforementioned embodiments or aspects thereof, the KRAS binding moiety is bonded to -L'-[Degron] via an atom of the group corresponding to $R^2$, $R^{12}$, or $R^{13}$ in structural formulas (Ia)-(II'a) as, for example, in structural formula (II) or (II'). In some aspects of any of the aforementioned embodiments or aspects thereof, the KRAS binding moiety is bonded to -L'-[Degron] via an atom of the group corresponding to $R^1$ in structural formulas (Ia)-(II'a).

In a third embodiment, the KRAS binding moiety has the following structural formula:

(IIIa)

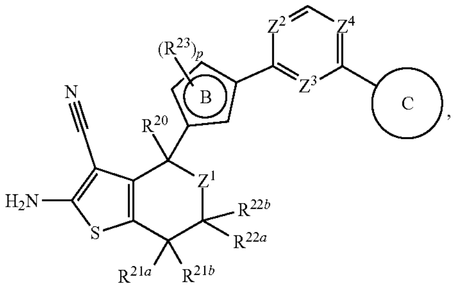

wherein:

Ring B is a five-membered heteroarylene;

Ring C is $(C_3-C_{11})$ heterocyclylene optionally and independently substituted with one or more $(C_1-C_6)$alkyl, cyclopropyl$(C_1-C_6)$alkyl, $(C_1-C_6)$alkoxy, or $(C_5-C_6)$ heterocyclyl;

$Z^1$ is —$(CR^{25a}R^{25b})_q$—;

$Z^2$ is N or C(H);

$Z^3$ is N or C(H);

$Z^4$ is N or $C(R^{24})$;

$R^{20}$ is hydrogen, $(C_1-C_4)$alkyl, $(C_1-C_4)$haloalkyl, $(C_1-C_4)$ cyanoalkyl, $(C_1-C_4)$alkoxy, $(C_1-C_4)$haloalkoxy, halogen, cyano, —OH, —$NH_2$, —N(H)$(C_1-C_4)$alkyl, —N($(C_1-C_4)$alkyl$)_2$, $(C_3-C_5)$ cycloalkyl, or $(C_3-C_5)$ heterocyclyl;

$R^{21a}$ and $R^{21b}$ are each independently hydrogen, $(C_1-C_4)$ alkyl, $(C_1-C_4)$haloalkyl, $(C_1-C_4)$alkoxy, $(C_1-C_4)$haloalkoxy, halogen, —$NH_2$, —N(H)$(C_1-C_4)$alkyl, —N($(C_1-C_4)$alkyl$)_2$, $(C_3-C_5)$ cycloalkyl, or $(C_3-C_5)$ heterocyclyl; and $R^{22a}$ and $R^{22b}$ are each independently hydrogen, $(C_1-C_4)$ alkyl, $(C_1-C_4)$haloalkyl, $(C_1-C_4)$alkoxy, $(C_1-C_4)$haloalkoxy, halogen, —$NH_2$, —N(H)$(C_1-C_4)$alkyl, —N($(C_1-C_4)$alkyl$)_2$, $(C_3-C_5)$ cycloalkyl, or $(C_3-C_5)$ heterocyclyl; or one of $R^{21a}$ and $R^{21b}$ and one of $R^{22a}$ and $R^{22b}$, together with the carbon atoms to which they are attached, form a cyclopropane;

each $R^{23}$ is independently $(C_1-C_4)$alkyl, $(C_1-C_4)$haloalkyl, $(C_1-C_4)$ cyanoalkyl, $(C_1-C_4)$alkoxy, $(C_1-C_4)$haloalkoxy, halogen, cyano, —OH, —$NH_2$, —N(H)$(C_1-C_4)$alkyl, —N($(C_1-C_4)$alkyl$)_2$, $(C_3-C_5)$ cycloalkyl, or $(C_3-C_5)$ heterocyclyl;

$R^{24}$ is hydrogen, halogen, or $(C_1-C_4)$alkoxy;

$R^{25a}$ and $R^{25b}$ are independently hydrogen, $(C_1-C_4)$alkyl, $(C_1-C_4)$haloalkyl, $(C_1-C_4)$alkoxy, $(C_1-C_4)$haloalkoxy, halogen, —$NH_2$, —N(H)$(C_1-C_4)$alkyl, —N($(C_1-C_4)$alkyl$)_2$, $(C_3-C_5)$ cycloalkyl, or $(C_3-C_5)$ heterocyclyl; or $R^{25a}$ and $R^{25b}$, together with the carbon atom to which they are attached, form a cyclopropane; and p is 0, 1, 2, or 3 (for example, in some aspects, 0, 1, or 2);

q is 0, 1, or 2;

In a first aspect of the third embodiment, Ring B is pyrrolylene, furanylene, thiophenylene, imidazolylene, pyrazolylene, oxazolylene, isoxazolylene, thiazolylene, isothiazolylene, oxadiazolylene, thiadiazolylene, or triazolylene. Values for the remaining variables are as described in the third embodiment.

In a second aspect of the third embodiment, Ring B is oxadiazolylene. Values for the remaining variables are as described in the third embodiment, or first aspect thereof.

In a third aspect of the third embodiment, $Z^1$ is $CH_2$. Values for the remaining variables are as described in the third embodiment, or first or second aspect thereof.

In a fourth aspect of the third embodiment, $Z^2$ is C(H). Values for the remaining variables are as described in the third embodiment, or first through third aspects thereof.

In a fifth aspect of the third embodiment, $Z^2$ is N. Values for the remaining variables are as described in the third embodiment, or first through fourth aspects thereof.

In a sixth aspect of the third embodiment, $Z^3$ is C(H). Values for the remaining variables are as described in the third embodiment, or first through fifth aspects thereof.

In a seventh aspect of the third embodiment, $Z^3$ is N. Values for the remaining variables are as described in the third embodiment, or first through sixth aspects thereof.

In an eighth aspect of the third embodiment, $Z^4$ is $C(R^{24})$. Values for the remaining variables are as described in the third embodiment, or first through seventh aspects thereof.

In a ninth aspect of the third embodiment, $Z^4$ is N. Values for the remaining variables are as described in the third embodiment, or first through eighth aspects thereof.

In a tenth aspect of the third embodiment, $Z^2$ is C(H), and $Z^3$ and $Z^4$ are N. Values for the remaining variables are as described in the third embodiment, or first through ninth aspects thereof.

In an eleventh aspect of the third embodiment, $Z^2$ and $Z^3$ are N, and $Z^4$ is C(H). Values for the remaining variables are as described in the third embodiment, or first through tenth aspects thereof.

In a twelfth aspect of the third embodiment, $R^{20}$ is methyl. Values for the remaining variables are as described in the third embodiment, or first through eleventh aspects thereof.

In a thirteenth aspect of the third embodiment, $R^{21a}$ and $R^{21b}$ are each hydrogen. Values for the remaining variables are as described in the third embodiment, or first through twelfth aspects thereof.

In a fourteenth aspect of the third embodiment, $R^{22a}$ and $R^{22b}$ are each hydrogen. Values for the remaining variables are as described in the third embodiment, or first through thirteenth aspects thereof.

In a fifteenth aspect of the third embodiment, $R^{24}$ is hydrogen. Values for the remaining variables are as described in the third embodiment, or first through fourteenth aspects thereof.

In a sixteenth aspect of the third embodiment, $R^{25a}$ and $R^{25b}$ are each hydrogen. Values for the remaining variables are as described in the third embodiment, or first through fifteenth aspects thereof.

In a seventeenth aspect of the third embodiment, p is 0. Values for the remaining variables are as described in the third embodiment, or first through sixteenth aspects thereof.

In an eighteenth aspect of the third embodiment, q is 1. Values for the remaining variables are as described in the third embodiment, or first through seventeenth aspects thereof.

In a nineteenth aspect of the third embodiment, Ring C is piperazinyl optionally and independently substituted with one or more $(C_1-C_6)$alkyl, cyclopropyl$(C_1-C_6)$alkyl, $(C_1-C_6)$alkoxy, or $(C_5-C_6)$ heterocyclyl. Values for the remaining variables are as described in the third embodiment, or first through eighteenth aspects thereof.

In a fourth embodiment, Ring C is

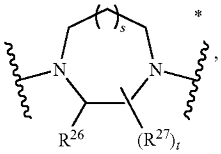

, wherein:

* indicates point of attachment to L';

s is 0, 1, or 2;

t is 0, 1, or 2;

$R^{26}$ is $(C_1-C_3)$alkyl; and each $R^{27}$ is independently $(C_1-C_3)$alkyl.

Values for the remaining variables are as described in the third embodiment, or any aspect thereof.

In a first aspect of the fourth embodiment, s is 1. Values for the remaining variables are as described in the third embodiment, or any aspect thereof, or fourth embodiment.

In a second aspect of the fourth embodiment, t is 0. Values for the remaining variables are as described in the third embodiment, or any aspect thereof, or fourth embodiment, or first aspect thereof.

In a third aspect of the fourth embodiment, $R^{26}$ is methyl. Values for the remaining variables are as described in the third embodiment, or any aspect thereof, or fourth embodiment, or first or second aspect thereof.

In a fourth aspect of the fourth embodiment, each $R^{27}$ is methyl. Values for the remaining variables are as described in the third embodiment, or any aspect thereof, or fourth embodiment, or first through third aspects thereof.

In a fifth aspect of the fourth embodiment, Ring C is

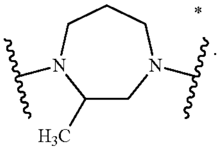 [SMILES: *N1CCCN(*)C(C)C1]

.

Values for the remaining variables are as described in the third embodiment, or any aspect thereof, or fourth embodiment, or first through fourth aspects thereof.

In a fifth embodiment, the KRAS binding moiety has the following structural formula:

(III'a)

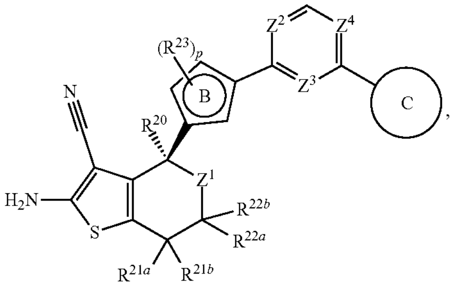

, or a pharmaceutically acceptable salt thereof, wherein values for the variables (e.g., Ring B, Ring C, $Z^1$, $Z^2$, $Z^3$, $Z^4$, $R^{20}$, $R^{21a}$, $R^{21b}$, $R^{22a}$, $R^{22b}$, $R^{23}$, p) are as described in the third or fourth embodiment, or any aspect of the foregoing.

In a sixth embodiment, the KRAS binding moiety has the following structural formula:

(IVa)

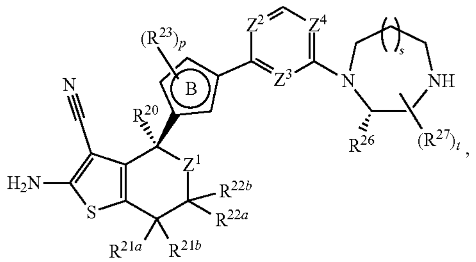

, or a pharmaceutically acceptable salt thereof, wherein values for the variables (e.g., Ring B, $Z^1$, $Z^2$, $Z^3$, $Z^4$, $R^{20}$, $R^{21a}$, $R^{21b}$, $R^{22a}$, $R^{22b}$, $R^{23}$, $R^{26}$, $R^{27}$, p, s, t) are as described in the third embodiment, or any aspect thereof.

In a first aspect of the sixth embodiment, s is 1. Values for the remaining variables are as described in the third embodiment, or any aspect thereof, or sixth embodiment.

In a second aspect of the sixth embodiment, t is 0. Values for the remaining variables are as described in the third embodiment, or any aspect thereof, or sixth embodiment, or first aspect thereof.

In a third aspect of the sixth embodiment, $R^{26}$ is methyl. Values for the remaining variables are as described in the third embodiment, or any aspect thereof, or sixth embodiment, or first or second aspect thereof.

In a fourth aspect of the sixth embodiment, each $R^{27}$ is methyl. Values for the remaining variables are as described in the third embodiment, or any aspect thereof, or sixth embodiment, or first through third aspects thereof.

In a seventh embodiment, the KRAS binding moiety has the following structural formula:

(Va)

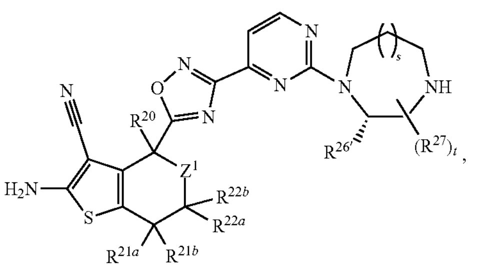

or a pharmaceutically acceptable salt thereof, wherein $R^{26'}$ is $R^{26}$ or H, and values for the remaining variables (e.g., Ring B, $Z^1$, $Z^2$, $Z^3$, $Z^4$, $R^{20}$, $R^{21a}$, $R^{21b}$, $R^{22a}$, $R^{22b}$, $R^{27}$, s, t) are as described in the third through sixth embodiments, or any aspect of the foregoing.

In a first aspect of the seventh embodiment, $R^{26}$ is $R^{26}$. Values for the remaining variables are as described in the third through sixth embodiments, or any aspect of the foregoing, or seventh embodiment.

In a second aspect of the seventh embodiment, s is 0 or 1. Values for the remaining variables are as described in the third through sixth embodiments, or any aspect of the foregoing, or seventh embodiment, or first aspect thereof.

In some aspects of any of the third through seventh embodiments or aspects thereof, the KRAS binding moiety is bonded to -L'-[Degron] via an atom of the group corresponding to Ring C in structural formulas (IIIa) and/or (III'a) as, for example, in structural formulas (III), (III'), (IV), and (V).

In an eighth embodiment, a KRAS binding moiety has structural formula (Ia):

(Ia)

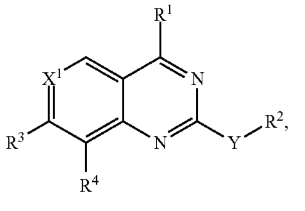

wherein:

$R^1$ is

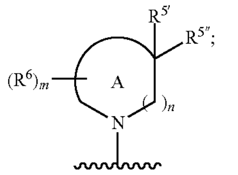

Ring A is $(C_5-C_{12})$ heterocyclyl;

$R^{5'}$ is hydroxy, cyano, fluoro, or hydrogen;

$R^{5''}$ is hydrogen, halo, $(C_1-C_6)$alkyl, $(C_1-C_6)$haloalkyl, $(C_1-C_6)$ hydroxyalkyl, or $(C_1-C_6)$ cyanoalkyl;

each $R^6$ is independently halo, cyano, hydroxy, $(C_1-C_6)$alkyl, $(C_1-C_6)$haloalkyl, $(C_1-C_6)$ hydroxyalkyl, or $(C_1-C_6)$ cyanoalkyl;

n is 1 or 2;

m is 0, 1, 2, or 3;

$X^1$ is N or $C(R^{10})$;

$R^{10}$ is hydrogen, halogen, $(C_1-C_6)$alkyl, $(C_1-C_6)$haloalkyl, $(C_1-C_6)$haloalkoxy, $(C_2-C_6)$alkenyl, $(C_2-C_6)$ alkynyl, —CN, $(C_1-C_6)$alkoxy, —S—$(C_1-C_6)$alkyl or —S—$(C_1-C_6)$haloalkyl;

Y is O—$(C_1-C_3)$alkylene optionally substituted with one or more deutero or hydroxy, or 0;

$R^2$ is hydrogen, —$N(R^{11})_2$, $(C_3-C_{12})$ heterocyclyl, $(C_1-C_6)$alkyl, —$(C_6-C_{14})$aryl, —$(C_5-C_{14})$ heteroaryl, —$(C_3-C_{12})$ cycloalkyl, —N(H)C(NH) $NH_2$, —C(O)$N(R^{11})_2$, —$(C_1-C_6)$haloalkyl, —$OR^{11}$, —$NR^{11}$C(O)—$(C_6-C_{14})$aryl, —COOH or —C(O)O$(C_1-C_6)$alkyl, wherein the $(C_3-C_{12})$ heterocyclyl and the $(C_3-C_{12})$ cycloalkyl are optionally substituted with one or more $R^{12}$, and the $(C_6-C_{14})$aryl and $(C_5-C_{14})$ heteroaryl are optionally substituted with one or more $R^{13}$;

$R^3$ is $(C_6-C_{14})$aryl or $(C_5-C_{14})$ heteroaryl, wherein the $(C_6-C_{14})$aryl or $(C_5-C_{14})$ heteroaryl is optionally substituted with one or more $R^{14}$, $R^4$ is hydrogen, halogen or $(C_1-C_3)$alkyl;

each $R^{11}$ is independently hydrogen or $(C_1-C_3)$alkyl;

each $R^{12}$ is independently halogen, hydroxy, $(C_1-C_3)$ hydroxyalkyl, $(C_1-C_3)$alkyl, $(C_1-C_3)$haloalkyl, $(C_1-C_3)$ alkoxy, cyano, -Q-phenyl, -Q-phenyl-$SO_2F$, —N(H)C(O)-phenyl, —N(H)C(O)-phenyl-$SO_2F$, $(C_1-C_3)$alkyl-substituted pyrazole, $(C_6-C_{14})$aryl$(C_1-C_3)$alkyl, tert-butyldimethylsilyloxy-$CH_2$—, —$N(R^{11})_2$, $(C_1-C_3)$ alkoxy $(C_1-C_3)$alkyl, $(C_1-C_3)$alkyl-C(O)—, oxo, $(C_1-C_3)$haloalkyl-C(O)—, —$SO_2F$, $(C_1-C_3)$alkoxy $(C_1-C_3)$ alkoxy, —$CH_2OC(O)N(R^{11})_2$, —$CH_2N(H)C(O)O$—$(C_1-C_6)$alkyl, —$CH_2N(H)C(O)N(R^{11})_2$, —$CH_2N(H)C(O)(C_1-C_6)$alkyl, —$CH_2$ (pyrazolyl), —$CH_2N(H)S(O)_2$ $(C_1-C_6)$alkyl, —$CH_2OC(O)(C_3-C_{12})$ heterocyclyl, —$OC(O)N(R^{11})_2$, —OC(O)N(H)$(C_1-C_3)$alkyl-O—$(C_1-C_3)$alkyl, —OC(O)N(H)$(C_1-C_3)$alkyl-O—$(C_1-C_3)$ alkyl-phenyl-$(C_1-C_3)$alkyl-$N(CH_3)_2$, —OC(O)N(H)$(C_1-C_3)$alkyl-O—$(C_1-C_3)$alkyl-phenyl, —OC(O)$(C_3-C_{12})$ heterocyclyl or —$CH_2$—$(C_3-C_{12})$ heterocyclyl, wherein the phenyl of —N(H)C(O)phenyl and —OC(O)N(H)$(C_1-C_3)$alkyl-O—$(C_1-C_3)$alkyl-phenyl is optionally substituted with —C(O)H or —OH, and the $(C_3-C_{12})$ heterocyclyl of —$CH_2$—$(C_3-C_{12})$ heterocyclyl is optionally substituted with oxo;

Q is a bond or O;

each $R^{13}$ is independently halogen, hydroxy, —C(O)H, $(C_1-C_4)$alkyl, $(C_1-C_4)$alkoxy, $(C_1-C_4)$haloalkyl, $(C_1-C_4)$ hydroxyalkyl, or —$N(R^{11})_2$; and each $R^{14}$ is independently halogen, cyano, hydroxy, $(C_1-C_4)$alkyl, —S—$(C_1-C_3)$alkyl, $(C_2-C_4)$alkenyl, $(C_2-C_4)$ alkynyl, $(C_2-C_4)$ hydroxyalkynyl, $(C_1-C_3)$ cyanoalkyl, triazolyl, $(C_1-C_3)$haloalkyl, —O—$(C_1-C_3)$haloalkyl, —S—$(C_1-C_3)$haloalkyl, $(C_1-C_3)$alkoxy, $(C_1-C_3)$ hydroxyalkyl, —$CH_2C(O)N(R^{11})_2$, $(C_3-C_4)$alkynyl-$N(R^{11})_2$, $N(R^{11})_2$, deutero $(C_2-C_4)$alkynyl, $(C_1-C_3)$ alkoxy $(C_1-C_3)$haloalkyl, or $(C_3-C_6)$ cycloalkyl, wherein the $(C_3-C_6)$ cycloalkyl is optionally substituted with halogen or $(C_1-C_3)$alkyl.

Alternative values for variables (e.g., $X^1$, Y, $R^1$, $R^2$, $R^3$, $R^4$) in structural formula (Ia) are as described in the first embodiment, or any aspect thereof.

In a first aspect of the eighth embodiment, $R^{5''}$ is hydrogen, fluoro, or $CH_3$. Values for the remaining variables are as described in the first embodiment, or any aspect thereof, or eighth embodiment.

In a second aspect of the eighth embodiment, $R^1$ is

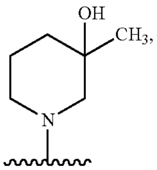, 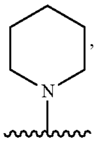, 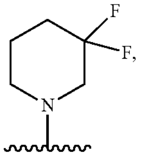, 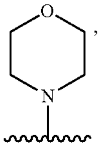, 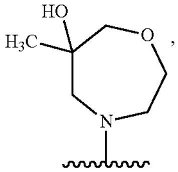, 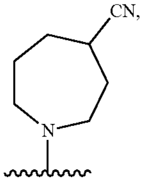, or 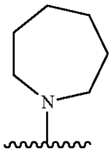.

Values for the remaining variables are as described in the first embodiment, or any aspect thereof, or eighth embodiment, or first aspect thereof.

In a ninth embodiment, the KRAS binding moiety has the following structural formula:

(II''a)

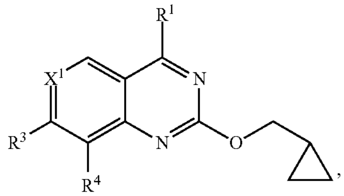

wherein values for the variables (e.g., $X^1$, $R^1$, $R^3$, $R^4$) are as described in the first or eighth embodiment, or any aspect of the foregoing.

In a tenth embodiment, the KRAS binding moiety has the following structural formula:

(II'''a)

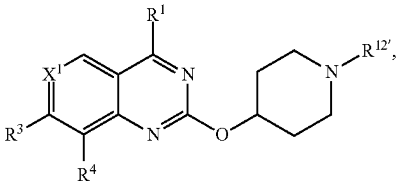

or a pharmaceutically acceptable salt thereof, wherein $R^{12'}$ is $R^{12}$ or hydrogen, and values for the remaining variables (e.g., $X^1$, $R^1$, $R^3$, $R^4$) are as described in the first or eighth embodiment, or any aspect of the foregoing.

In a first aspect of the tenth embodiment, $R^{12'}$ is hydrogen or $(C_1$-$C_3)$alkyl. Values for the remaining variables are as described in the first or eighth embodiment, or any aspect thereof, or tenth embodiment.

In another or alternative aspect of the first, second, eighth, ninth, or tenth embodiment, or any aspect of the foregoing, $R^1$ is

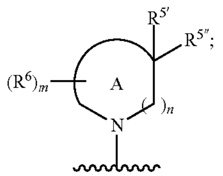

wherein Ring A is $(C_5$-$C_{12})$ heterocyclyl; $R^{5'}$ is hydroxy, —$NH_2$, cyano, fluoro, or hydrogen; $R^{5''}$ is hydrogen, halo, $(C_1$-$C_6)$alkyl, $(C_1$-$C_6)$haloalkyl, $(C_1$-$C_6)$ hydroxyalkyl, or $(C_1$-$C_6)$ cyanoalkyl; each $R^6$ is independently halo, cyano, hydroxy, $(C_1$-$C_6)$alkyl, $(C_1$-$C_6)$haloalkyl, $(C_1$-$C_6)$ hydroxyalkyl, or $(C_1$-$C_6)$ cyanoalkyl; n is 1 or 2; m is 0, 1, 2, or 3. In a first aspect of the further aspect of the first, second, eighth, ninth, or tenth embodiment, or any aspect of the foregoing, $R^1$ is

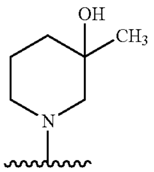, 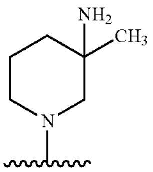 (e.g., 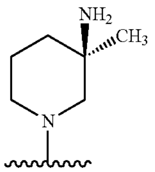 or 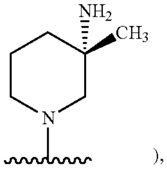), 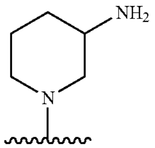 (e.g., 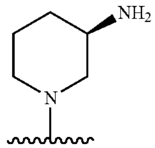 or 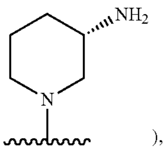), 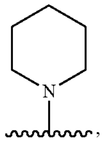, 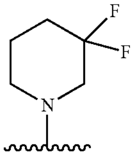, 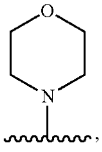, 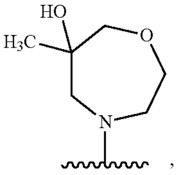, 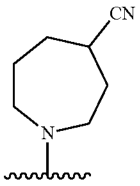, or 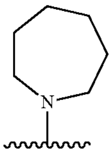.

Values for the remaining variables are as described in the first or eighth embodiment, or any aspect thereof.

In an eleventh embodiment, the KRAS binding moiety has the following structural formula:

(II#)

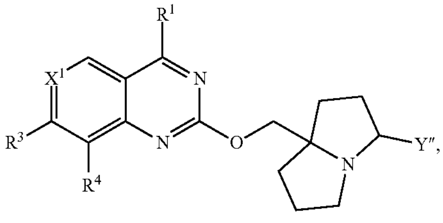

wherein Y" is $(C_1-C_3)$ hydroxyalkyl, $H_2N—(C_1-C_3)$alkyl, or $(C_1-C_3)$alkylN(H)$(C_1-C_3)$alkyl, or is absent. In a first aspect of the eleventh embodiment, Y" is $—CH_2—OH$, $—CH_2—NH_2$, $—CH_2—N(H)(C_1-C_3)$alkyl, or is absent. In a second aspect of the eleventh embodiment, Y" is $—CH_2—OH$ or $—CH_2—NH_2$. In a third aspect of the eleventh embodiment, Y" is absent. Values and alternative values for the remaining variables (e.g., $X^1$, $R^1$, $R^3$, $R^4$) are as described in the first or eighth embodiment, or any aspect thereof.

In some aspects of any of the eighth through eleventh embodiments or any aspect of the foregoing, the KRAS binding moiety is bonded to -L'-[Degron] via an atom of the group corresponding to $R^2$, $R^{12}$, or $R^{13}$ in structural formula (Ia) as, for example, in structural formulas (II") and/or (II"). In some aspects of any of the eighth through eleventh embodiments or any aspect of the foregoing, the KRAS binding moiety is bonded to -L'-[Degron] via an atom of the group corresponding to $R^1$ in structural formulas (II"a) and/or (II'"a).

KRAS binding moieties (e.g., KRAS G12D binding moieties) and methods of making the same are also disclosed in International Publication Nos. WO 2021/041671; WO 2022/031678; WO 2022/066646; and WO 2022/015375, the entire contents of which are incorporated herein by reference. In some embodiments, a KRAS binding moiety is a KRAS inhibitor, e.g., a KRAS inhibitor disclosed in WO 2021/041671; WO 2022/031678; WO 2022/066646; or WO 2022/015375. In some embodiments, a KRAS binding moiety is a KRAS inhibitor disclosed in WO 2021/041671 or WO 2022/015375.

KRAS binding moieties (e.g., KRAS G12D binding moieties) and methods of making the same are also disclosed in Mao et al. "KRAS (G12D) can be targeted by potent inhibitors via formation of salt bridge," Cell Discovery, 2022, 8, the entire content of which is incorporated herein by reference. See, in particular, FIGS. 1 and 2 therein. In some embodiments, a KRAS binding moiety is a KRAS inhibitor disclosed in Mao et al.

KRAS binding moieties (e.g., KRAS G12D binding moieties) and methods of making the same are also disclosed in International Publication No. WO 2022/105857, the entire content of which is incorporated herein by reference. In some embodiments, a KRAS binding moiety is a KRAS inhibitor disclosed in WO 2022/105857.

KRAS binding moieties and methods of making the same are also disclosed in International Publication No. WO 2022/105859, the entire content of which is incorporated herein by reference. In some embodiments, a KRAS G12D binding moiety is a KRAS G12D inhibitor disclosed in WO 2022/105859.

Yet other specific examples of KRAS binding moieties (e.g., KRAS G12D binding moieties) include those disclosed in Wang, et al., "Identification of MRTX1133, a Noncovalent, Potent, and Selective $KRAS^{G12D}$ Inhibitor," *J. Med Chem.*, https://doi.org/10.1021/acs.jmedchem.1c01688, the entire content of which is incorporated herein by reference. In some embodiments, the KRAS binding moiety is a KRAS inhibitor disclosed in Wang et al.

Yet other specific examples of KRAS binding moieties (e.g., KRAS G12D binding moieties) are disclosed in International Publication No. WO 2021/249519, the entire content of which is incorporated herein by reference. In some embodiments, a KRAS binding moiety is a KRAS inhibitor binding moiety (e.g., inhibitor) disclosed in WO 2021/249519.

Yet other specific examples of KRAS binding moieties (e.g., KRAS G12D binding moieties) are disclosed in International Publication No. WO 2022/221739, the entire content of which is incorporated herein by reference. In some embodiments, a KRAS binding moiety is a KRAS inhibitor binding moiety (e.g., inhibitor) disclosed in WO 2022/221739.

Yet other specific examples of KRAS binding moieties (e.g., KRAS G12D binding moieties) are disclosed in International Publication No. WO 2023/018810, the entire content of which is incorporated herein by reference. In some embodiments, a KRAS binding moiety is a KRAS binding moiety (e.g., inhibitor) disclosed in WO 2023/018810.

Yet other specific examples of KRAS binding moieties (e.g., KRAS G12D binding moieties) are disclosed in International Publication No. WO 2022/194191, the entire content of which is incorporated herein by reference. In some embodiments, a KRAS binding moiety is a KRAS binding moiety (e.g., inhibitor) disclosed in WO 2022/194191.

Yet other specific examples of KRAS binding moieties (e.g., KRAS G12D binding moieties) are disclosed in International Publication No. WO 2022/194066, the entire content of which is incorporated herein by reference. In some embodiments, a KRAS binding moiety is a KRAS binding moiety (e.g., inhibitor) disclosed in WO 2022/194066.

Other specific examples of KRAS binding moieties (e.g., KRAS G12D binding moieties) are disclosed in International Publication No. WO 2022/148421, the entire content of which is incorporated herein by reference. In some embodiments, a KRAS binding moiety is a KRAS binding moiety (e.g., inhibitor) disclosed in WO 2022/148421.

Other specific examples of KRAS binding moieties (e.g., KRAS G12D binding moieties) are disclosed in International Publication No. WO 2023/284537, the entire content of which is incorporated herein by reference. In some embodiments, a KRAS binding moiety is a KRAS binding moiety (e.g., inhibitor) disclosed in WO 2023/284537.

Other specific examples of KRAS binding moieties (e.g., KRAS G12D binding moieties) are disclosed in International Publication No. WO 2023/001141, the entire content of which is incorporated herein by reference. In some embodiments, a KRAS binding moiety is a KRAS binding moiety (e.g., inhibitor) disclosed in WO 2023/001141.

Yet other specific examples of KRAS binding moieties (e.g., KRAS G12D binding moieties) are disclosed in International Publication No. WO 2022/262838, the entire content of which is incorporated herein by reference. In some embodiments, a KRAS binding moiety is a KRAS binding moiety (e.g., inhibitor) disclosed in WO 2022/262838.

Other specific examples of KRAS binding moieties (e.g., KRAS G12D binding moieties) are disclosed in International Publication No. WO 2022/002102, the entire content of which is incorporated herein by reference. In some embodiments, a KRAS binding moiety is a KRAS binding moiety (e.g., inhibitor) disclosed in WO 2022/002102.

Other specific examples of KRAS binding moieties (e.g., KRAS G12D binding moieties) are disclosed in International Publication No. WO 2023/283933, the entire content of which is incorporated herein by reference. In some embodiments, a KRAS binding moiety is a KRAS binding moiety (e.g., inhibitor) disclosed in WO 2023/283933.

Other specific examples of KRAS binding moieties (e.g., KRAS G12D binding moieties) are disclosed in International Publication No. WO 2023/097227, the entire content of which is incorporated herein by reference. In some embodiments, a KRAS binding moiety is a KRAS binding moiety (e.g., inhibitor) disclosed in WO 2023/097227.

Other specific examples of KRAS binding moieties (e.g., KRAS G12D binding moieties) are disclosed in International Publication No. WO 2023/051586, the entire content of which is incorporated herein by reference. In some embodiments, a KRAS binding moiety is a KRAS binding moiety (e.g., inhibitor) disclosed in WO 2023/051586.

Other specific examples of KRAS binding moieties, including pan KRAS inhibitors and KRAS G12V binding moieties, are disclosed in Kim D., et al., *Nature* Vol. 619, 160, 6 Jul. 2023 (https://doi.org/10.1038/s41586-023-06123-3), and International Publication Nos. WO 2023/133183; WO 2023/099592; and WO 2022/132200, the entire contents of which are incorporated herein by reference. In some embodiments, a KRAS binding moiety is a KRAS binding moiety (e.g., inhibitor) disclosed in Kim D., et al., *Nature* Vol. 619, 160, 6 Jul. 2023 (https://doi.org/10.1038/s41586-023-06123-3). In some embodiments, a KRAS binding moiety is a KRAS binding moiety (e.g., inhibitor) disclosed in WO 2023/133183. In some embodiments, a KRAS binding moiety is a KRAS binding moiety (e.g., inhibitor) disclosed in WO 2023/099592. In some embodiments, a KRAS binding moiety is a KRAS binding moiety (e.g., inhibitor) disclosed in WO 2022/132200.

Other specific examples of KRAS binding moieties, including pan KRAS inhibitors, are disclosed in International Publication Nos. WO 2023/114733; WO 2022/256459; WO 2023/150284; WO 2023/173017; WO 2023/173016; WO 2023/018809; WO 2023/018812; WO 2023/072188; WO 2023/184178; WO 2022/256459; WO 2023/114733; WO 2023/154766; and WO 2023/099623, the entire contents of which are incorporated herein by reference. In some embodiments, a KRAS binding moiety is a KRAS binding moiety (e.g., inhibitor) disclosed in WO 2023/114733. In some embodiments, a KRAS binding moiety is a KRAS binding moiety (e.g., inhibitor) disclosed in WO 2022/256459. In some embodiments, a KRAS binding moiety is a KRAS binding moiety (e.g., inhibitor) disclosed in WO 2023/150284. In some embodiments, a KRAS binding moiety is a KRAS binding moiety (e.g., inhibitor) disclosed in WO 2023/173017. In some embodiments, a KRAS binding moiety is a KRAS binding moiety (e.g., inhibitor) disclosed in WO 2023/173016. In some embodiments, a KRAS binding moiety is a KRAS binding moiety (e.g., inhibitor) disclosed in WO 2023/018809. In some embodiments, a KRAS binding moiety is a KRAS binding moiety (e.g., inhibitor) disclosed in WO 2023/018812. In some embodiments, a KRAS binding moiety is a KRAS binding moiety (e.g., inhibitor) disclosed in WO 2023/072188. In some embodiments, a KRAS binding moiety is a KRAS binding moiety (e.g., inhibitor) disclosed in WO 2023/184178. In some embodiments, a KRAS binding moiety is a KRAS binding moiety (e.g., inhibitor) disclosed in WO 2022/256459. In some embodiments, a KRAS binding moiety is a KRAS binding moiety (e.g., inhibitor) disclosed in WO 2023/114733. In some embodiments, a KRAS binding moiety is a KRAS binding moiety (e.g., inhibitor) disclosed in WO 2023/154766. In some embodiments, a KRAS binding moiety is a KRAS binding moiety (e.g., inhibitor) disclosed in WO 2023/099623.

Linkers (L')

A linker is a bivalent moiety that connects KRASi to Degron. Linkers are disclosed, for example, in International Publication No. WO 2021/127278, the entire content of which is incorporated herein by reference, and are referred to therein by variable L. See, in particular, paragraphs [00491]-[00501] and Table B therein. In some aspects (e.g., of any of the foregoing embodiments, aspects or combinations of aspects), L' is a linker disclosed in WO 2021/127278. Linkers are also disclosed, for example, in U.S. Pat. No. 11,352,350, the entire content of which is incorporated herein by reference, and are referred to therein by variable L. See, in particular, columns 408-409 and 2573-2574 therein. In some aspects (e.g., of any of the foregoing embodiments, aspects of combinations of aspects, L' is a linker disclosed in U.S. Pat. No. 11,352,350.

Linkers are also disclosed in U.S. Patent Application Publication No. US 2020/0140456, the entire content of which is incorporated herein by reference. See, in particular, paragraphs [0491]-[0508] therein. In some aspects (e.g., of any of the foregoing embodiments, aspects or combinations of aspects), L' is a linker disclosed in US 2020/0140456.

In some aspects (e.g., of any of the foregoing embodiments, aspects or combinations of aspects), L' is a covalent bond or a bivalent, saturated or unsaturated, straight or branched $C_{1-50}$ hydrocarbon chain, wherein 0-10 methylene units of L' are independently replaced by X, wherein:

each X is independently —C(D)(H)—, —$C(D)_2$-, —C(H)(F)—, —$C(F)_2$—, -Cy-, —O—, —N(R)—, —$Si(R)_2$—, —Si(OH)(R)—, —$Si(OH)_2$—, —P(O)(OR)—, —P(O)(R)—, —P(O)($NR^2$)—, —S—, —OC(O)—, —C(O)—, —S(O)—, —$S(O)_2$—, —N(R)$S(O)_2$—, —N(R)C(O)—, —OC(O)N(R)—, —N(R)C(O)N(R)—,

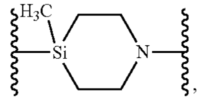,
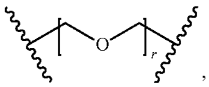,
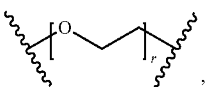, or
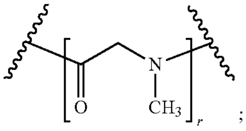;

each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 (and, in some aspects, 1-2) heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur; or two R on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur; and r is 0, 1, 2, 3, 4, 5, 6, 7, 8, 9, or 10.

In some aspects (e.g., of any of the foregoing embodiments, aspects or combinations of aspects), L' is a covalent bond.

In some aspects (e.g., of any of the foregoing embodiments, aspects or combinations of aspects), L' is a bivalent, saturated or unsaturated, straight or branched $C_1$-$C_{50}$ hydrocarbon chain wherein 0-10 methylenes of L' are replaced by X. In further aspects, L' is a bivalent, saturated or unsaturated, straight or branched $C_1$-$C_{25}$ hydrocarbon chain wherein 0-10 methylenes of L' are replaced by X. In yet further aspects, L' is a bivalent, saturated or unsaturated, straight or branched $C_1$-Cis hydrocarbon chain wherein 0-10, e.g., 0-5; 0-3; 1-5; 1-3; 1; 2; 3; 4; or 5, methylenes of L' are replaced by X. In further aspects, L' is a bivalent, saturated or unsaturated, straight or branched $C_1$-$C_{10}$ hydrocarbon chain wherein 0-10, e.g., 0-5; 0-3; 1-5; 1-3; 1; 2; 3; 4; or 5, methylenes of L' are replaced by X. In further aspects, L' is a bivalent, saturated or unsaturated, straight or branched $C_1$-$C_5$ hydrocarbon chain wherein 0-5, e.g., 0-3; 1-5; 1-3; 1; 2; 3; 4; or 5, methylenes of L' are replaced by X.

In some aspects, L' is saturated. In some aspects, L' is straight-chain. In some aspects, L' is saturated and straight-chain.

In some aspects, 0-5 methylenes of L' are replaced by X. In some aspects, 1-5 methylenes of L' are replaced by X. In some aspects, 0-3 methylenes of L' are replaced by X. In some aspects, 1-3 methylenes of L' are replaced by X. In some aspects, 1 or 2 methylene of L' are replaced by X.

In some aspects, 1 or 2 methylenes of L' are replaced by Cy and 1-3 methylenes of L' are replaced by X, wherein each X is independently —C(D)(H)—, —$C(D)_2$-, —C(H)(F)—, —$C(F)_2$—, —O—, —N(R)—, —$Si(R)_2$—, —Si(OH)(R)—, —$Si(OH)_2$—, —P(O)(OR)—, —P(O)(R)—, —P(O)($NR^2$)—, —S—, —OC(O)—, —C(O)—, —S(O)—, —$S(O)_2$—, —N(R) $S(O)_2$—, —N(R)C(O)—, —OC(O)N(R)—, —N(R)C(O)N(R)—,

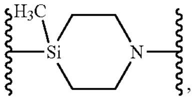,
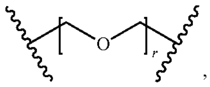,
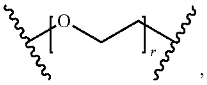, or
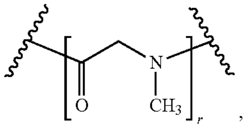, for example, each X is independently —O—, —N(R)—, —S—, —OC(O)—, —C(O)—, —C(H)(F)—, —$C(F)_2$—, —S(O)—, —$S(O)_2$—, —N(R) $S(O)_2$—, —N(R)C(O)—, —OC(O)N(R)—, —N(R)C(O)N(R)—,

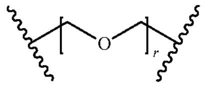 or 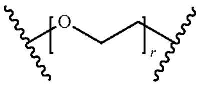;

or each X is independently —O—, —C(O)—, —N(R)—, —S—, —OC(O)—, —N(R)C(O)—, —OC(O)N(R)— or —N(R)C(O)N(R)—. In a particular aspect, each X is independently —O—, —C(O)—, —N(R)—, or —N(R)C(O)—.

In some aspects, 0 or 1 methylene of L' is replaced by Cy and 0-3 (e.g., in some aspects, 0 or 1)methylenes of L' are replaced by X, wherein each X is independently —C(D)(H)—, —$C(D)_2$-, —C(H)(F)—, —$C(F)_2$—, —O—, —N(R)—, —$Si(R)_2$—, —Si(OH)(R)—, —$Si(OH)_2$—, —P(O)(OR)—, —P(O)(R)—, —P(O)($NR^2$)—, —S—, —OC(O)—, —C(O)—, —S(O)—, —$S(O)_2$—, —N(R) $S(O)_2$—, —N(R)C(O)—, —OC(O)N(R)—, —N(R)C(O)N(R)—,

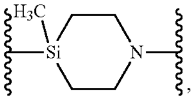,
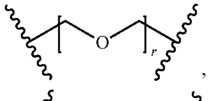,
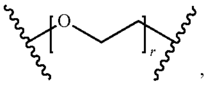, or
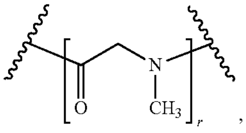, for example, each X is independently —O—, —N(R)—, —S—, —OC(O)—, —C(O)—, —C(H)(F)—, —$C(F)_2$—, —S(O)—, —$S(O)_2$—, —N(R) $S(O)_2$—, —N(R)C(O)—, —OC(O)N(R)—, —N(R)C(O)N(R)—,

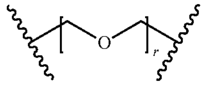 or 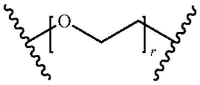;

or each X is independently —O—, —C(O)—, —N(R)—, —S—, —OC(O)—, —N(R)C(O)—, —OC(O)N(R)— or —N(R)C(O)N(R)—. In a particular aspect, each X is independently —N(R)—,

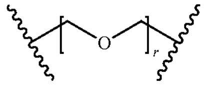 or 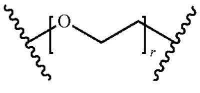.

In a more particular aspect, each X is independently

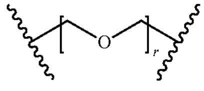 or 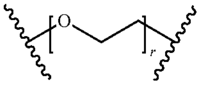.

In some aspects, r is 1, 2, 3, 4, or 5. In some aspects, r is 1, 2 or 3, e.g., 2 or 3; 2; or 3.

In some aspects, each X is independently —O—, —N(R)—, —S—, —OC(O)—, —C(O)—, —C(H)(F)—, —C(F)$_2$—, -Cy-, —S(O)—, —S(O)$_2$—, —N(R) S(O)$_2$—, —N(R)C(O)—, —OC(O)N(R)—, —N(R)C(O)N(R)—,

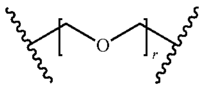
or
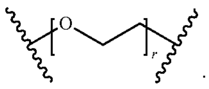
.

In some aspects, each X is independently —O—, —C(O)—, —N(R)—, —S—, —OC(O)—, -Cy-, —N(R)C(O)—, —OC (O)N(R)— or —N(R)C(O)N(R)—. In some aspects, each X is independently —O—, —C(O)—, —N(R)—, -Cy-, or —N(R)C(O)—. In some aspects, each X is independently —O—, —C(O)—, —N(R)—, or —N(R)C(O)—.

In some aspects, each R is independently hydrogen or methyl. In further aspects, each R is hydrogen.

In some aspects, each -Cy- is independently an optionally substituted bivalent ring selected from a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-3 (and, in some aspects, 1-2) heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur. In some aspects, each -Cy- is independently an optionally substituted (e.g., unsubstituted) bivalent ring selected from a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, or an 8-10 membered bicyclic saturated or partially unsaturated heterocyclylenyl having 1-2 heteroatoms independently selected from nitrogen, oxygen, and sulfur. In further aspects, each -Cy- is independently an optionally substituted (e.g., unsubstituted) bivalent 4-7 membered saturated or partially unsaturated (e.g., saturated) heterocyclylenyl having 1-2 heteroatoms independently selected from nitrogen, oxygen, and sulfur, or 4-11 membered saturated or partially unsaturated (e.g., saturated)spiro heterocyclylenyl having 1-3 (and, in some aspects, 1-2) heteroatoms independently selected from nitrogen, oxygen, and sulfur. In yet further aspects, each -Cy- is independently an optionally substituted (e.g., unsubstituted) bivalent 4-7 membered saturated or partially unsaturated (e.g., saturated) heterocyclylenyl having 1-2 heteroatoms independently selected from nitrogen, oxygen, and sulfur.

In some aspects, each -Cy- is independently a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked via a nitrogen atom.

In some aspects, each -Cy- is independently selected from optionally substituted (e.g., unsubstituted)cyclopropylene, cyclobutylene, cyclopentylene, cyclohexylene, 2,3-dihydro-1H-indenylene, piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 2-azaspiro[3.5]nonanylene, 7-azaspiro[3.5]nonanylene, 3-azabicyclo[3.2.1]octanylene, 8-azabicyclo[3.2.1]octanylene, 2-azaspiro[4.5]decanylene, 8-azaspiro[4.5]decanylene, 2,8-diazaspiro[4.5]decanylene, 2,6-diazaspiro[3.5]nonanylene, 1,7-diazaspiro[3.5]nonanylene, 2,7-diazaspiro[3.5]nonanylene, 3,9-diazaspiro[5.5]undecanylene, 2,6-diazaspiro[3.3]heptanylene, 3-azabicyclo[3.1.0]hexanylene, 3-azabicyclo[3.1.1]heptanylene, phenylene (e.g., 1,4-phenylene), or triazinylene. In some aspects, each -Cy- is independently selected from optionally substituted (e.g., unsubstituted)cyclohexylene, piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, 3,9-diazaspiro[5.5]undecanylene, or triazinylene. In some aspects, each -Cy- is independently selected from optionally substituted (e.g., unsubstituted) piperidinylene or piperazinylene.

In some aspects, each -Cy- is independently optionally substituted with halo (e.g., fluoro), alkyl (e.g., methyl) or haloalkyl (e.g., —CF$_3$, —CHF$_2$). In some aspects, each -Cy- is unsubstituted.

In some aspects of L', L' is linked to KRASi via-X-Cy-. In some aspects, when-X-Cy-links L' to KRASi, —X-Cy- is —C(O)-Cy-, wherein Cy is a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 (and, in some aspects, 1) additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked to the —C(O)— via the nitrogen atom, for example, -Cy- is piperidinylene, azetidinylene, pyrrolidinylene, piperazinylene, morpholinylene, 1-oxa-4,9-diazaspiro[5.5]undecanylene, 3-azaspiro[5.5]undecanylene, 2-azaspiro[3.3]heptanylene, 7-azaspiro[3.5]nonanylene, 3-azabicyclo[3.2.1]octanylene, 2,7-diazaspiro[3.5]nonanylene, or 3,9-diazaspiro[5.5]undecanylene. In some further aspects, —X-Cy-, when-X-Cy-links L' to KRASi, is

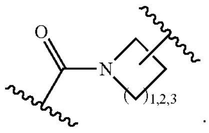
.

In some yet further aspects, —X-Cy-, when-X-Cy-links L' to KRASi, is

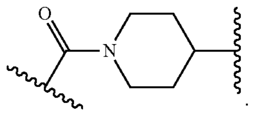 [SMILES: *C(=O)N1CCC(*)CC1]

In some aspects of L', L' comprises $-Cy^1-(CH_2)-Cy^2-$, wherein $Cy^1$ and $Cy^2$ are each independently -Cy- and -Cy- is as described herein. For example, in some aspects, $Cy^1$ is a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 (and, in some aspects, 1) additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked (e.g., to the rest of L' (if present), KRASi or Degron) via a nitrogen atom, for example, $Cy^1$ is piperidinylene or pyrrolidinylene. In some further aspects, $Cy^1$ is

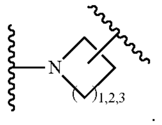

In some yet further aspects, $Cy^1$ is

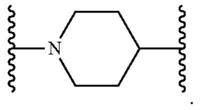

In some preferred aspects, $Cy^1$ represents the terminus of $-Cy^1-(CH_2)-Cy^2-$nearer KRASi in the compounds of the disclosure.

In some further or alternative aspects, $Cy^2$ is a 4-7 membered saturated or partially unsaturated heterocyclylenyl having 1 nitrogen atom and optionally one additional heteroatom selected from nitrogen, oxygen, and sulfur, a 4-11 membered saturated or partially unsaturated spiro heterocyclylenyl having 1 nitrogen atom and optionally 1-2 (and, in some aspects, 1) additional heteroatoms independently selected from nitrogen, oxygen, and sulfur, or an 8-10 membered bicyclic saturated or partially unsaturated heterocyclylenyl having 1 nitrogen atom and optionally 1 additional heteroatom independently selected from nitrogen, oxygen, and sulfur, and is linked (e.g., to the rest of L' (if present), KRASi or Degron) via a nitrogen atom, for example, $Cy^2$ is piperidinylene or pyrrolidinylene. In some preferred aspects, $Cy^2$ represents the terminus of $-Cy^1-(CH_2)-Cy^2-$nearer Degron in the compounds of the disclosure.

In some aspects, $Cy^1$ is linked to KRASi via X, wherein X is as described herein, e.g., —C(O)— or —C(O)O—. In some aspects wherein $Cy^1$ is linked to KRASi via —C(O)— or —C(O)O—, $Cy^1$ is linked to the carbonyl carbon of —C(O)— or —C(O)O— via a nitrogen atom of $Cy^1$.

In some aspects, L' is $-(CH_2)_{0-1}-C(O)-Cy^1-(CH_2)_{0-2}-Cy^2-$ or $-CH_2-Cy^1-(CH_2)_{0-2}-Cy^2-$, wherein $Cy^1$ and $Cy^2$ are each independently -Cy-. In some aspects, L' is $-C(O)-Cy^1-(CH_2)-Cy^2-$ or $-CH_2-Cy^1-(CH_2)-Cy^2-$, wherein $Cy^1$ and $Cy^2$ are each independently -Cy-. In some aspects, L' is $-C(O)-Cy^1-(CH_2)-Cy^2-$. In some aspects, L' is $-CH_2-Cy^1-(CH_2)-Cy^2-$. In some aspects, L' is $-CH_2-C(O)-Cy^1-(CH_2)-Cy^2-$.

In some aspects, L' is

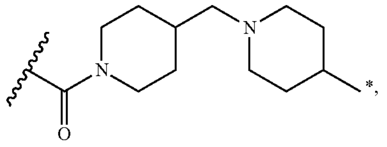

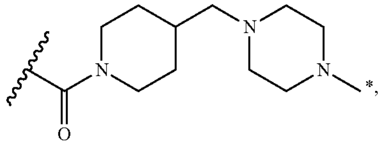

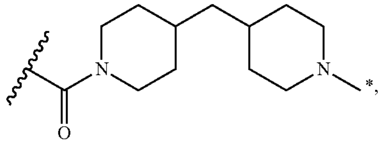

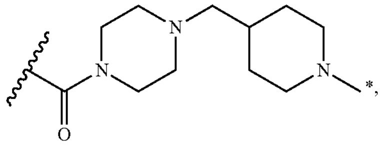

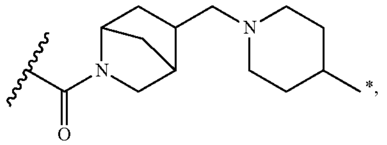

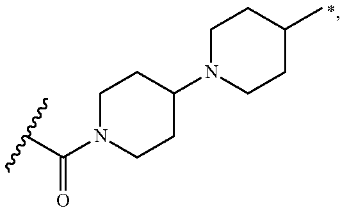

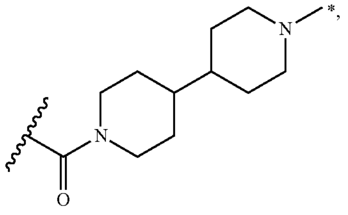

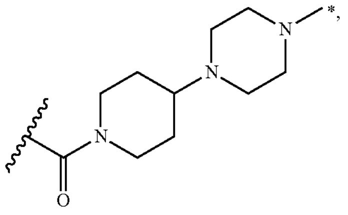

-continued
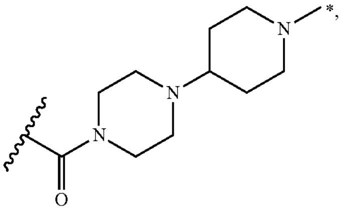
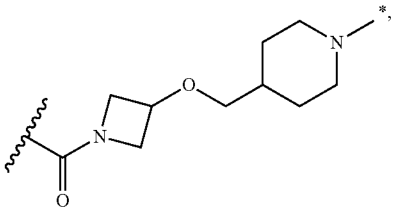
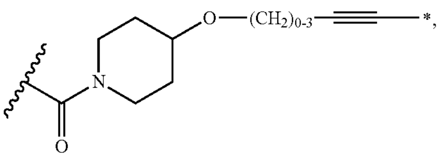
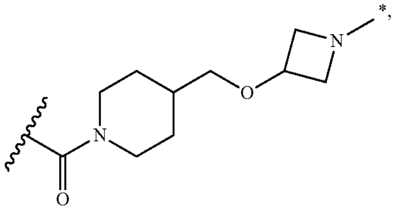
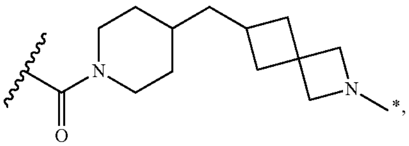
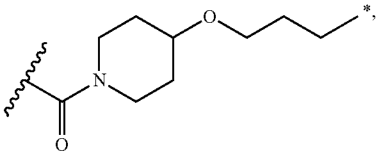
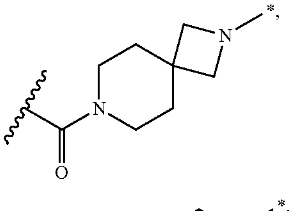
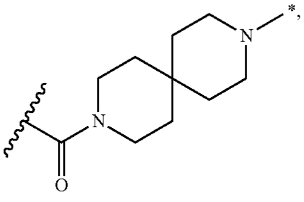
-continued
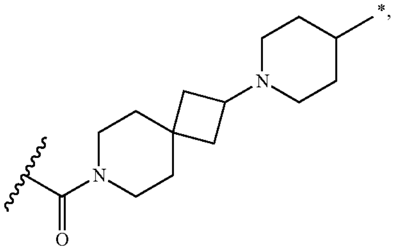
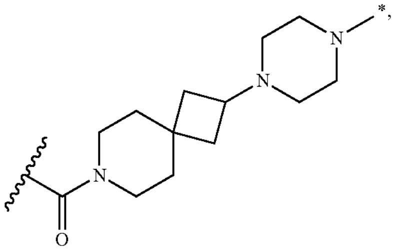
or
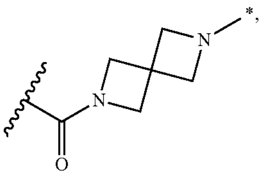 [SMILES: *C(=O)N1CC2(CN(C)C2)C1]
wherein * indicates point of attachment of L' to Degron. Specific examples of L' include
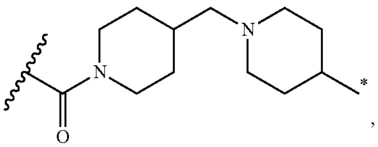
,
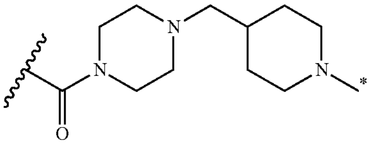
, and
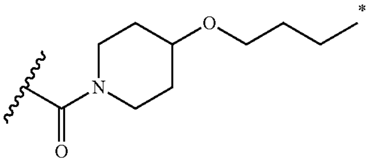
,
wherein * indicates point of attachment of L' to Degron.
In some aspects, L' is
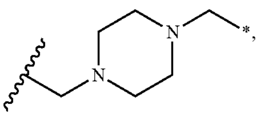
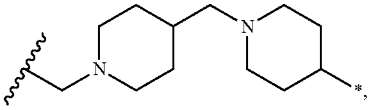

-continued
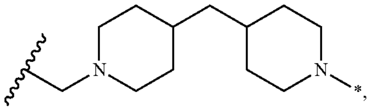
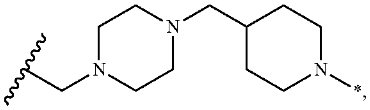
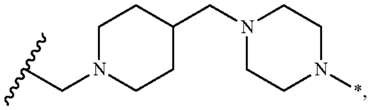
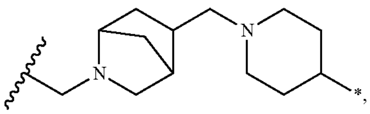
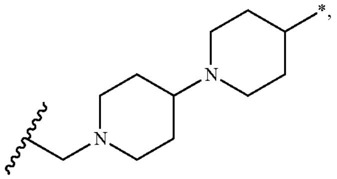
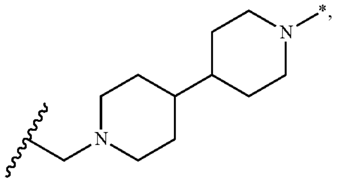
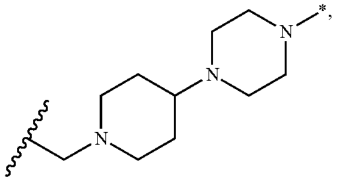
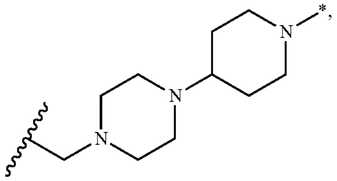
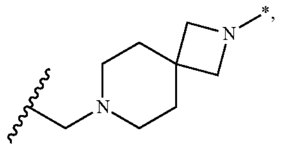
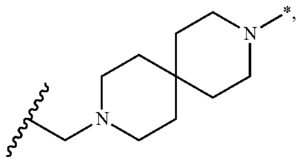
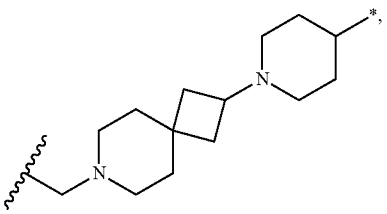
-continued
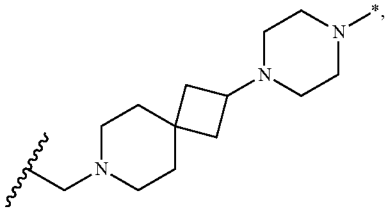
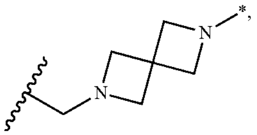
or
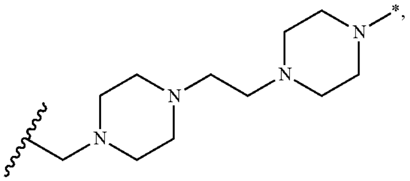
wherein * indicates point of attachment of L' to Degron.
In some aspects, L' is
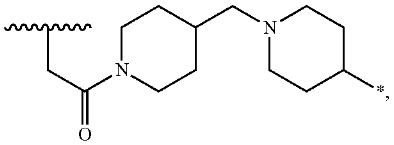
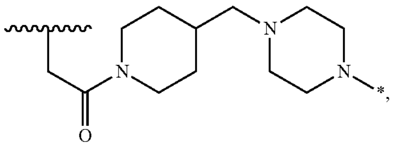
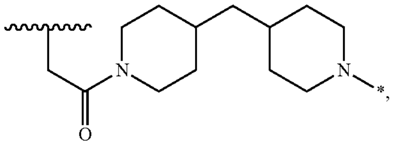
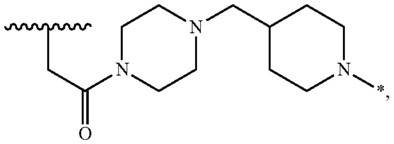
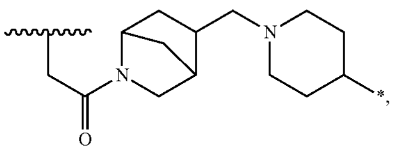
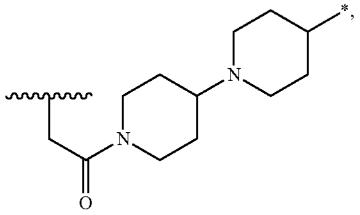

-continued
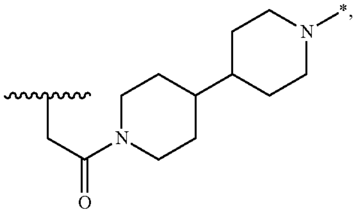
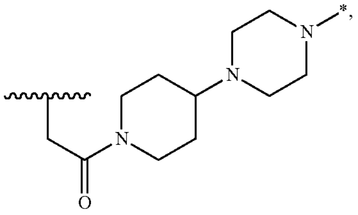
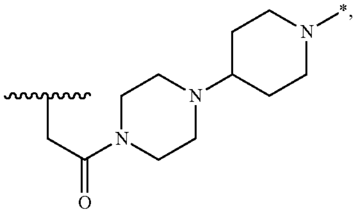
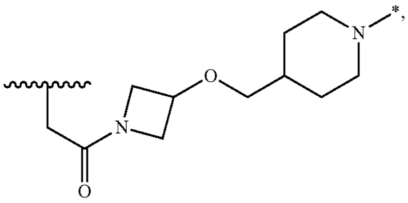
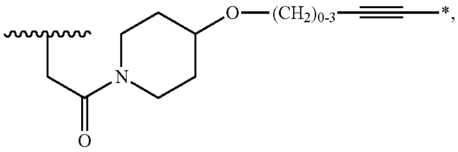
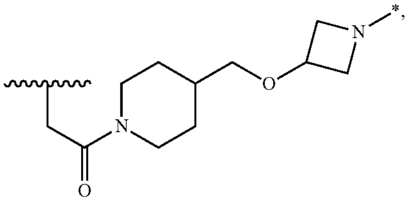
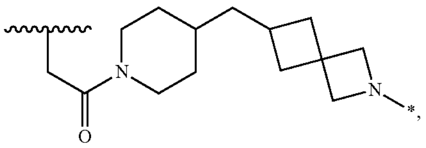
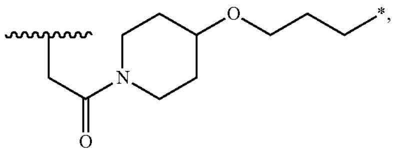
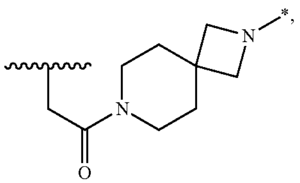
-continued
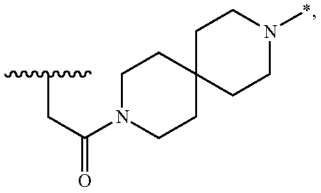
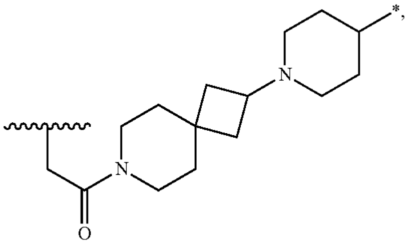
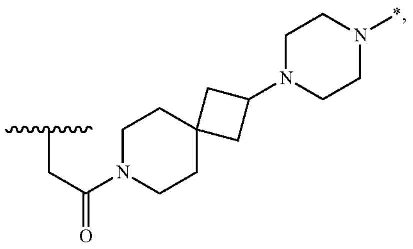
or
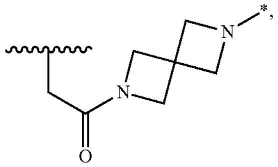
wherein * indicates point of attachment of L' to Degron.
In some aspects, L' is
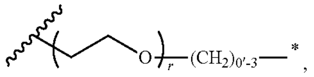
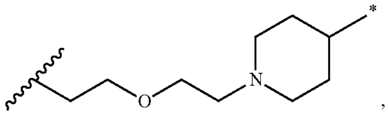
, or
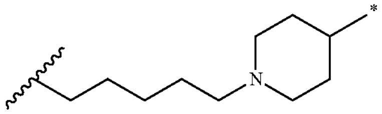
,
wherein * indicates point of attachment of L' to Degron; and r is 1, 2, 3, or 4. In some aspects, L' is
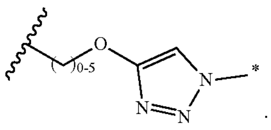
.

In some aspects, L' is
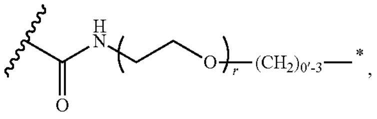
wherein r is 1, 2, 3, or 4; and*indicates point of attachment to Degron.
In some aspects, L' is
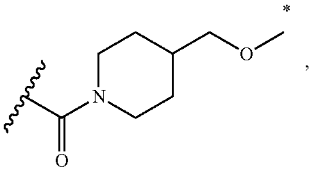
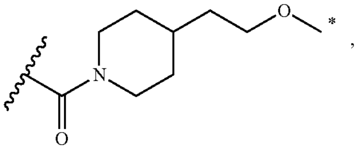
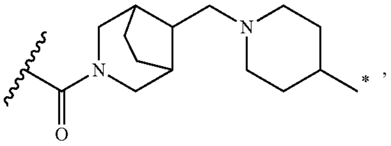
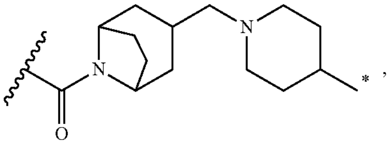
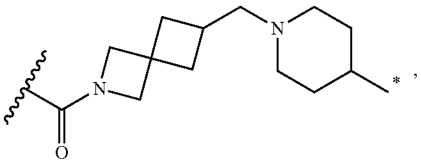
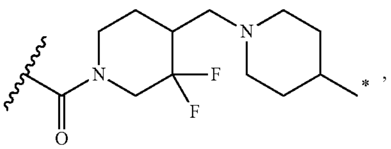
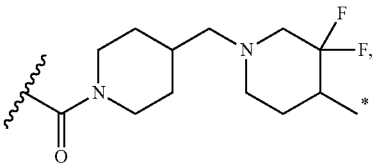
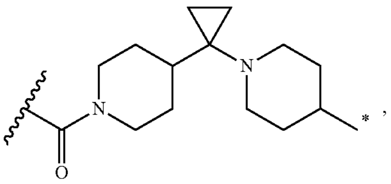
-continued
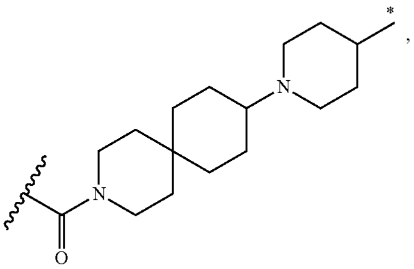
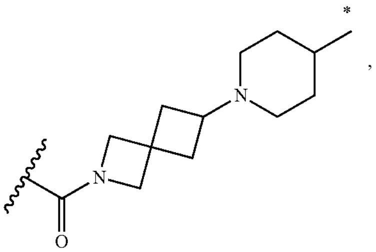
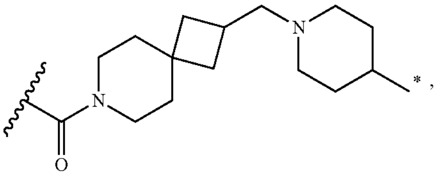
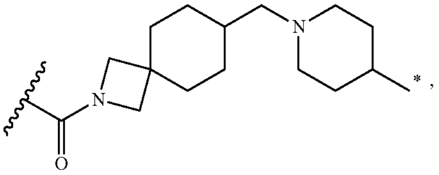
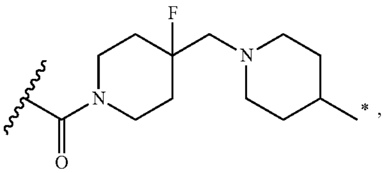
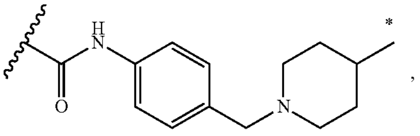
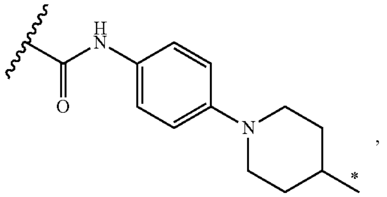
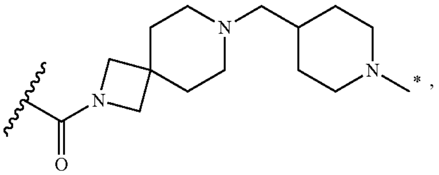
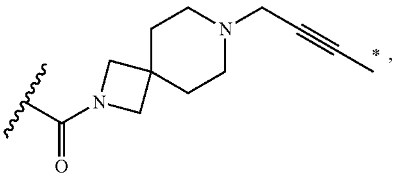

-continued
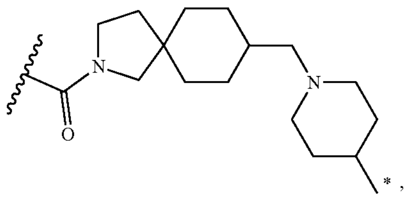
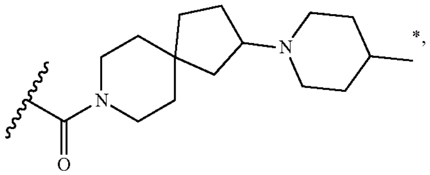
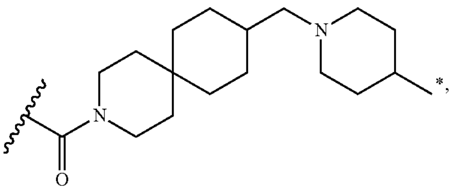
-continued
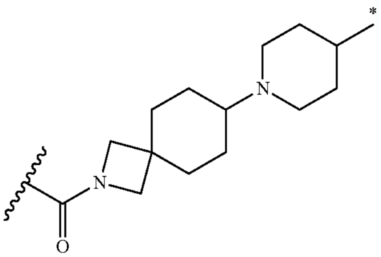
, or
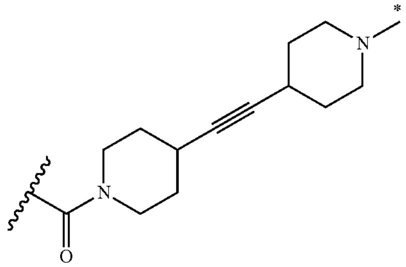
wherein * indicates point of attachment of L' to Degron.
Other specific examples of L' include the linkers depicted in Table A. In some aspects, L' is a linker in Table A.
TABLE A
| Linkers (L') | |
|---|---|
| 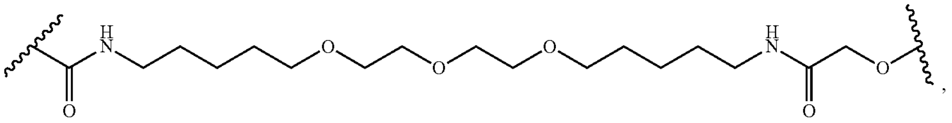 [SMILES: *OCC(=O)NCCCCCOCCOCCOCCCCCNC(*)=O] | (1) |
| 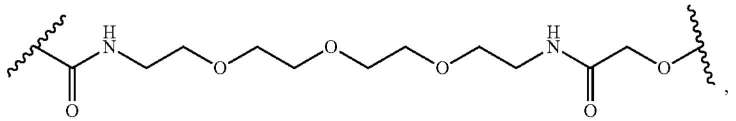 [SMILES: *OCC(=O)NCCOCCOCCOCCNC(*)=O] | (2) |
| 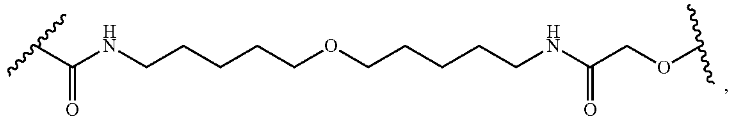 [SMILES: *OCC(=O)NCCCCCOCCCCCNC(*)=O] | (3) |
| 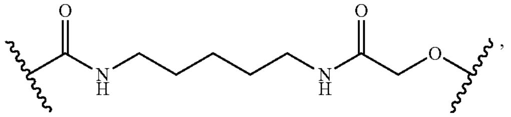 [SMILES: *OCC(=O)NCCCCCNC(*)=O] | (4) |
| 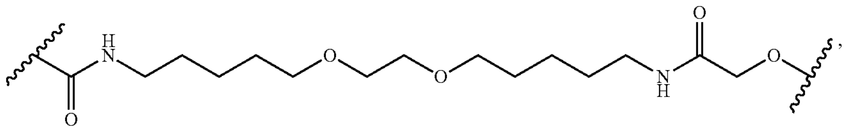 [SMILES: *OCC(=O)NCCCCCOCCOCCCCCNC(*)=O] | (5) |
| 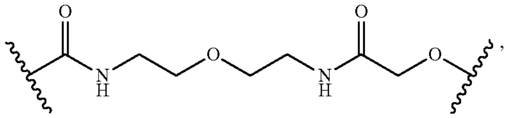 [SMILES: *OCC(=O)NCCOCCNC(*)=O] | (6) |
| 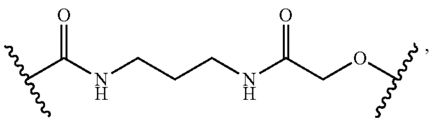 [SMILES: *OCC(=O)NCCCNC(*)=O] | (7) |

TABLE A-continued
Linkers (L')
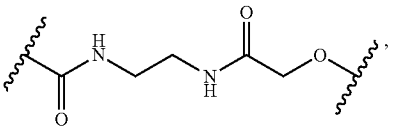 [SMILES: *OCC(=O)NCCNC(*)=O]
(8)
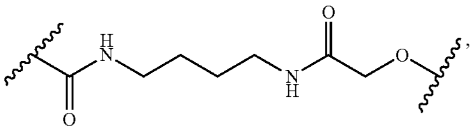 [SMILES: *OCC(=O)NCCCCNC(*)=O]
(9)
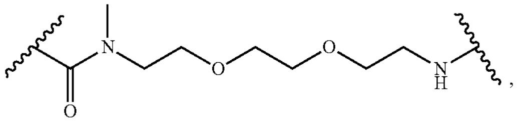 [SMILES: *NCCOCCOCCN(C)C(*)=O]
(10)
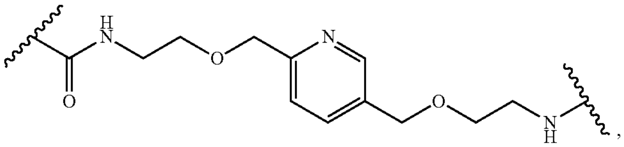 [SMILES: *NCCOCc1ccc(COCCNC(*)=O)nc1]
(11)
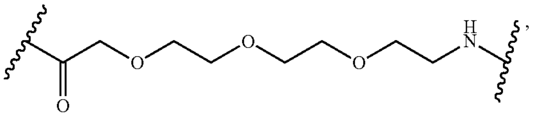 [SMILES: *NCCOCCOCCOCC(*)=O]
(12)
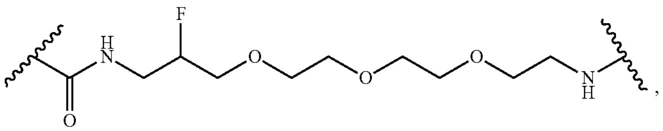 [SMILES: *NCCOCCOCCOCC(F)CNC(*)=O]
(13)
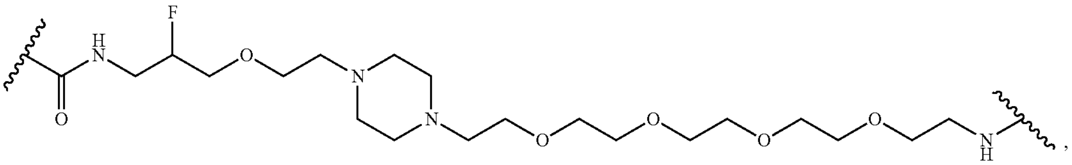 [SMILES: *NCCOCCOCCOCCOCCN1CCN(CCOCC(F)CNC(*)=O)CC1]
(14)
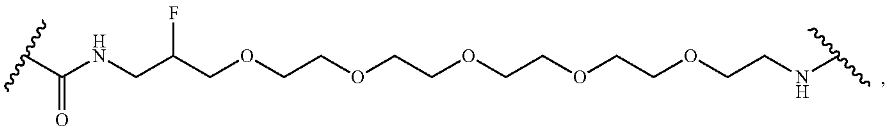 [SMILES: *NCCOCCOCCOCCOCCOCC(F)CNC(*)=O]
(15)
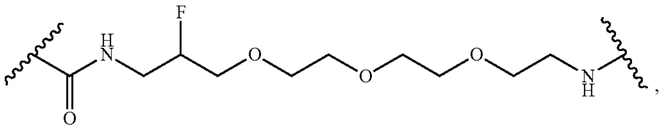 [SMILES: *NCCOCCOCCOCC(F)CNC(*)=O]
(16)
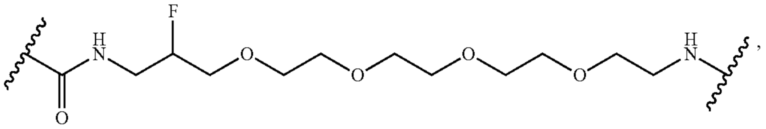 [SMILES: *NCCOCCOCCOCCOCC(F)CNC(*)=O]
(17)

TABLE A-continued
Linkers (L')
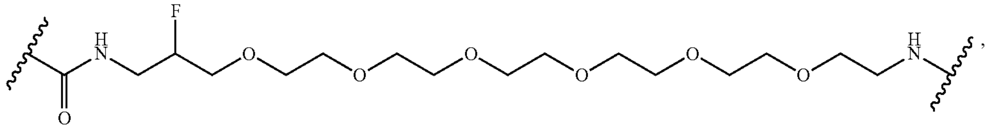 [SMILES: *NCCOCCOCCOCCOCCOCCOCC(F)CNC(*)=O]
(18)
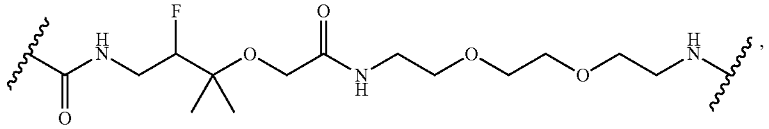 [SMILES: *NCCOCCOCCNC(=O)COC(C)(C)C(F)CNC(*)=O]
(19)
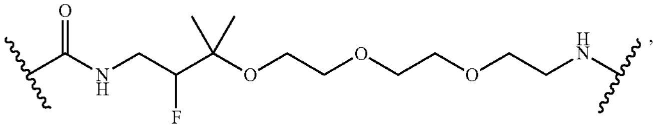 [SMILES: *NCCOCCOCCOC(C)(C)C(F)CNC(*)=O]
(20)
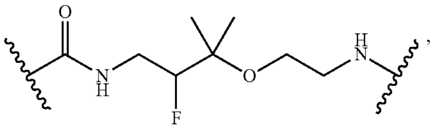 [SMILES: *NCCOC(C)(C)C(F)CNC(*)=O]
(21)
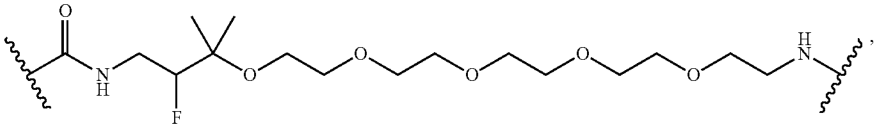 [SMILES: *NCCOCCOCCOCCOCCOC(C)(C)C(F)CNC(*)=O]
(22)
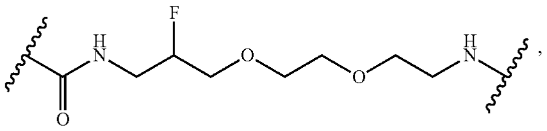 [SMILES: *NCCOCCOCC(F)CNC(*)=O]
(23)
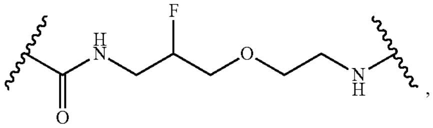 [SMILES: *NCCOCC(F)CNC(*)=O]
(24)
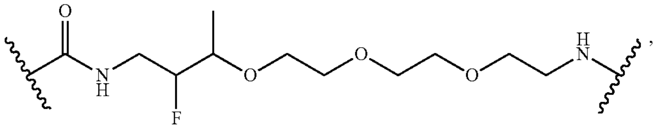 [SMILES: *NCCOCCOCCOC(C)C(F)CNC(*)=O]
(25)
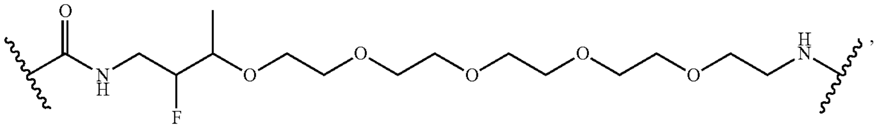 [SMILES: *NCCOCCOCCOCCOCCOC(C)C(F)CNC(*)=O]
(26)
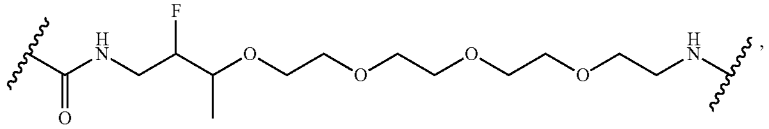 [SMILES: *NCCOCCOCCOCCOC(C)C(F)CNC(*)=O]
(27)
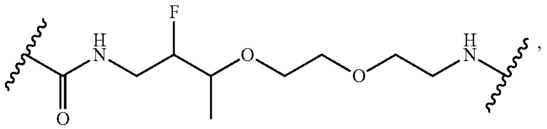 [SMILES: *NCCOCCOC(C)C(F)CNC(*)=O]
(28)

TABLE A-continued
| Linkers (L') |
| --- |
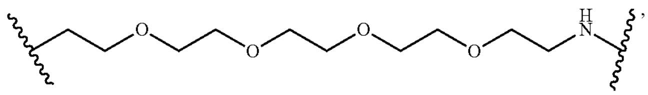 [SMILES: *CCOCCOCCOCCOCCN*]
(29)
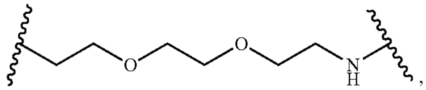 [SMILES: *CCOCCOCCN*]
(30)
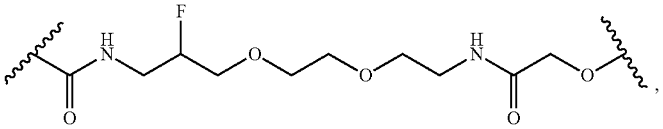 [SMILES: *OCC(=O)NCCOCCOCC(F)CNC(*)=O]
(31)
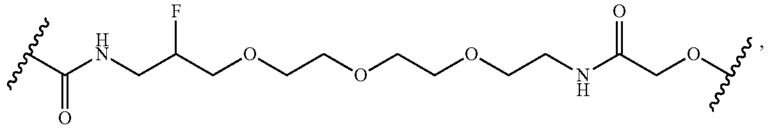 [SMILES: *OCC(=O)NCCOCCOCCOCC(F)CNC(*)=O]
(32)
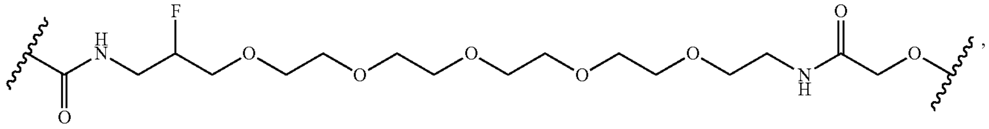 [SMILES: *OCC(=O)NCCOCCOCCOCCOCCOCC(F)CNC(*)=O]
(33)
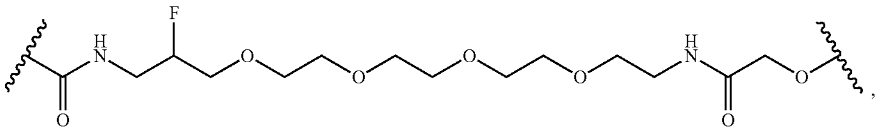 [SMILES: *OCC(=O)NCCOCCOCCOCCOCC(F)CNC(*)=O]
(34)
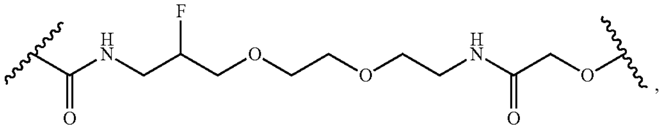 [SMILES: *OCC(=O)NCCOCCOCC(F)CNC(*)=O]
(35)
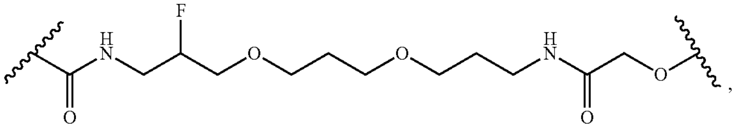 [SMILES: *OCC(=O)NCCCOCCCOCC(F)CNC(*)=O]
(36)
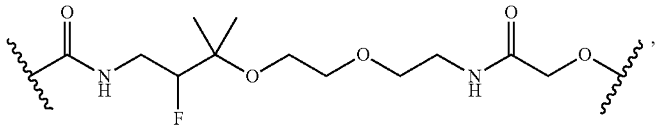 [SMILES: *OCC(=O)NCCOCCOC(C)(C)C(F)CNC(*)=O]
(37)
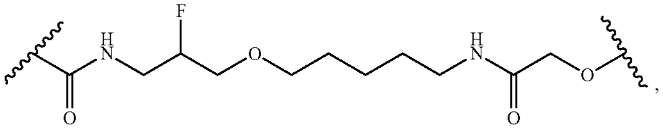 [SMILES: *OCC(=O)NCCCCCOCC(F)CNC(*)=O]
(38)
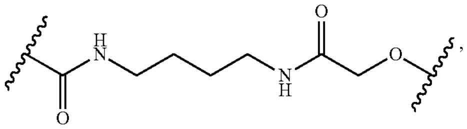 [SMILES: *OCC(=O)NCCCCNC(*)=O]
(39)

TABLE A-continued
| Linkers (L') |
| --- |
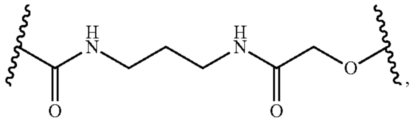 [SMILES: *OCC(=O)NCCCNC(*)=O]
(40)
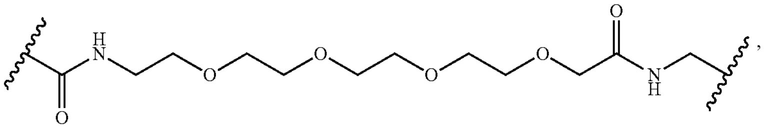 [SMILES: *CNC(=O)COCCOCCOCCOCCNC(*)=O]
(41)
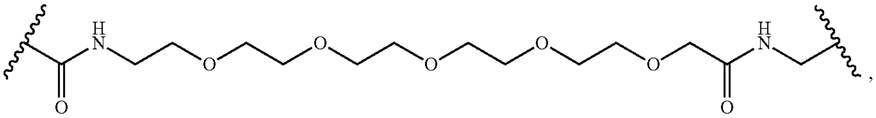 [SMILES: *CNC(=O)COCCOCCOCCOCCOCCNC(*)=O]
(42)
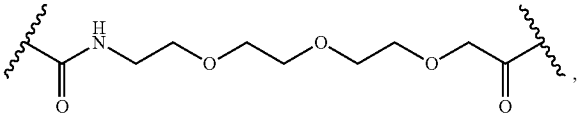 [SMILES: *C(=O)COCCOCCOCCNC(*)=O]
(43)
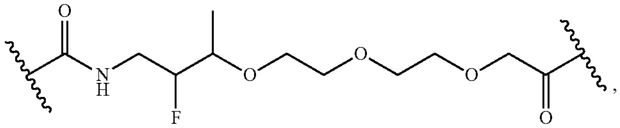 [SMILES: *C(=O)COCCOCCOC(C)C(F)CNC(*)=O]
(44)
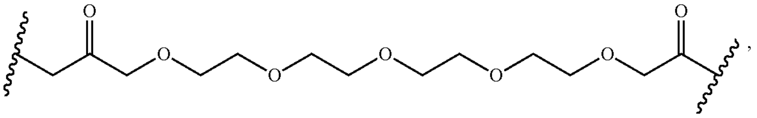 [SMILES: *CC(=O)COCCOCCOCCOCCOCC(*)=O]
(45)
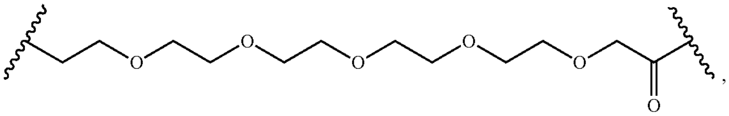 [SMILES: *CCOCCOCCOCCOCCOCC(*)=O]
(46)
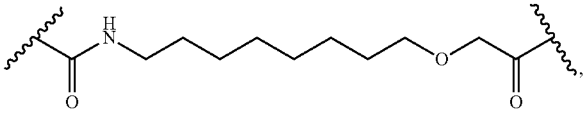 [SMILES: *C(=O)COCCCCCCCCNC(*)=O]
(47)
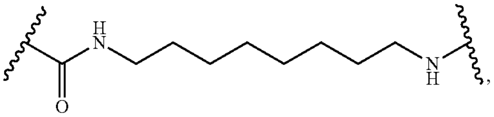 [SMILES: *NCCCCCCCCNC(*)=O]
(49)
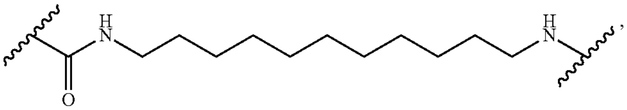 [SMILES: *NCCCCCCCCCCCNC(*)=O]
(50)
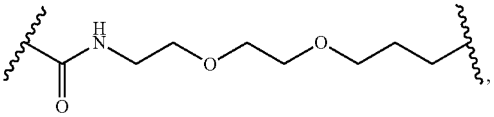 [SMILES: *CCCOCCOCCNC(*)=O]
(51)
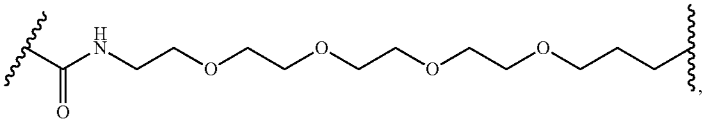 [SMILES: *CCCOCCOCCOCCOCCNC(*)=O]
(52)

TABLE A-continued
Linkers (L')
(53)
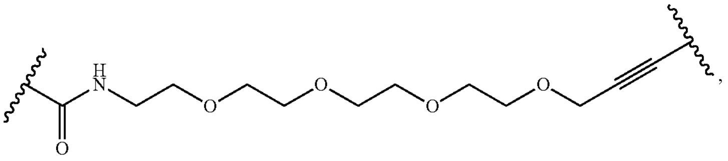 [SMILES: *C#CCOCCOCCOCCOCCNC(*)=O]
(54)
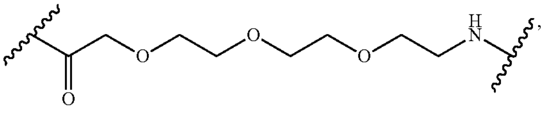 [SMILES: *NCCOCCOCCOCC(*)=O]
(55)
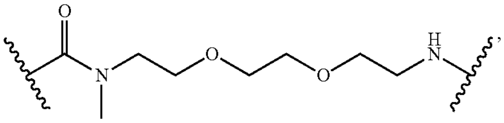 [SMILES: *NCCOCCOCCN(C)C(*)=O]
(56)
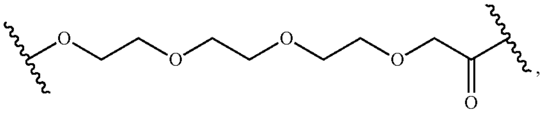 [SMILES: *OCCOCCOCCOCC(*)=O]
(57)
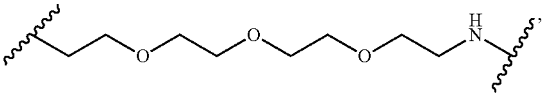 [SMILES: *CCOCCOCCOCCN*]
(58)
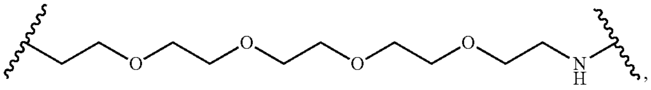 [SMILES: *CCOCCOCCOCCOCCN*]
(59)
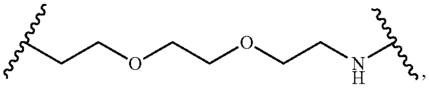 [SMILES: *CCOCCOCCN*]
(60)
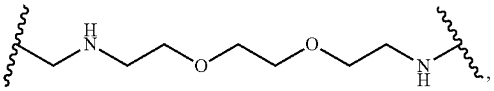 [SMILES: *CNCCOCCOCCN*]
(61)
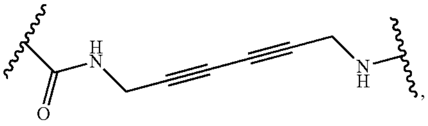 [SMILES: *NCC#CC#CCNC(*)=O]
(62)
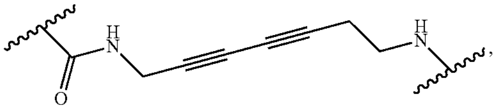 [SMILES: *NCCC#CC#CCNC(*)=O]
(63)
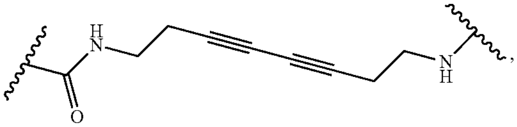 [SMILES: *NCCC#CC#CCCNC(*)=O]
(64)
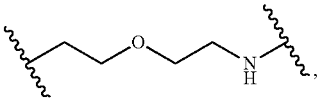 [SMILES: *CCOCCN*]

TABLE A-continued
Linkers (L')
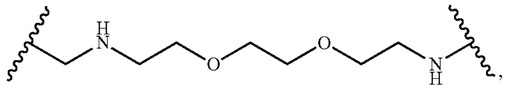 [SMILES: *CNCCOCCOCCN*]
(65)
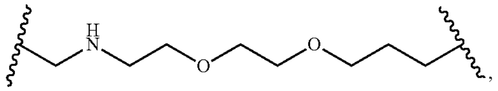 [SMILES: *CCCOCCOCCNC*]
(66)
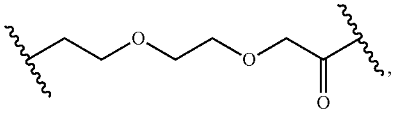 [SMILES: *CCOCCOCC(*)=O]
(67)
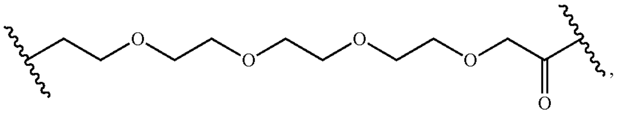 [SMILES: *CCOCCOCCOCCOCC(*)=O]
(68)
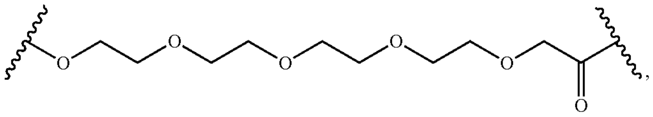 [SMILES: *OCCOCCOCCOCCOCC(*)=O]
(69)
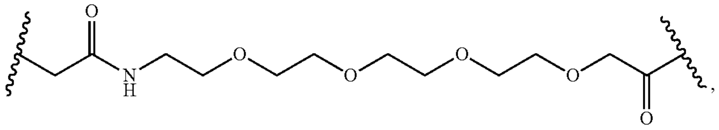 [SMILES: *CC(=O)NCCOCCOCCOCCOCC(*)=O]
(70)
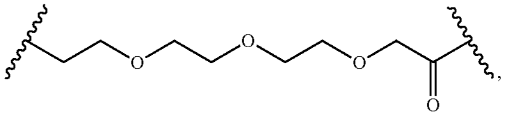 [SMILES: *CCOCCOCCOCC(*)=O]
(71)
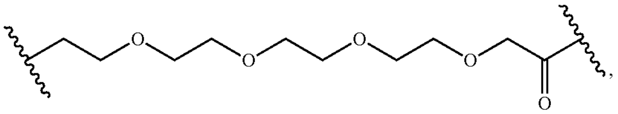 [SMILES: *CCOCCOCCOCCOCC(*)=O]
(72)
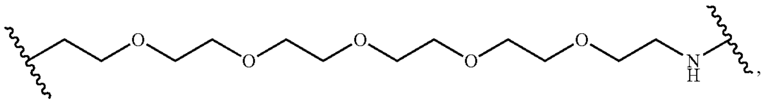 [SMILES: *CCOCCOCCOCCOCCOCCN*]
(73)
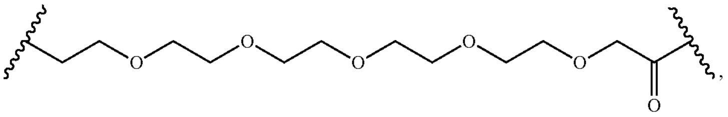 [SMILES: *CCOCCOCCOCCOCCOCC(*)=O]
(74)
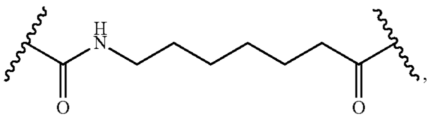 [SMILES: *C(=O)CCCCCCNC(*)=O]
(75)
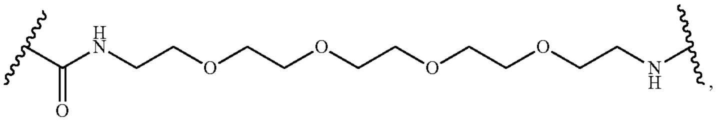 [SMILES: *NCCOCCOCCOCCOCCNC(*)=O]
(76)

TABLE A-continued
Linkers (L')
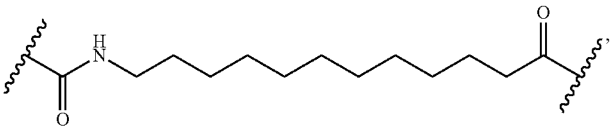 [SMILES: *C(=O)CCCCCCCCCCCNC(*)=O]
(77)
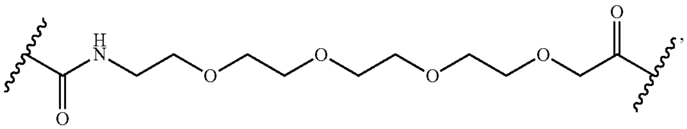 [SMILES: *C(=O)COCCOCCOCCOCCNC(*)=O]
(78)
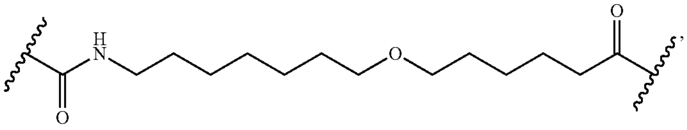 [SMILES: *C(=O)CCCCCOCCCCCCCNC(*)=O]
(79)
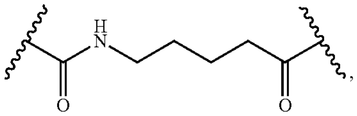 [SMILES: *C(=O)CCCCNC(*)=O]
(80)
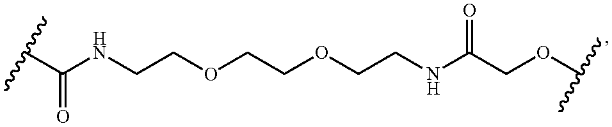 [SMILES: *OCC(=O)NCCOCCOCCNC(*)=O]
(81)
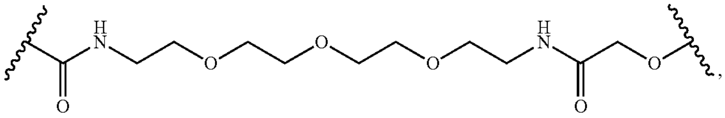 [SMILES: *OCC(=O)NCCOCCOCCOCCNC(*)=O]
(82)
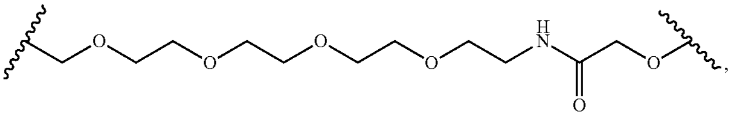 [SMILES: *COCCOCCOCCOCCNC(=O)CO*]
(83)
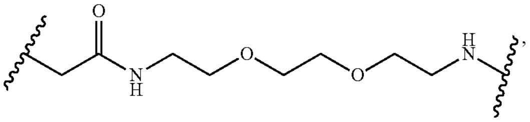 [SMILES: *CC(=O)NCCOCCOCCN*]
(84)
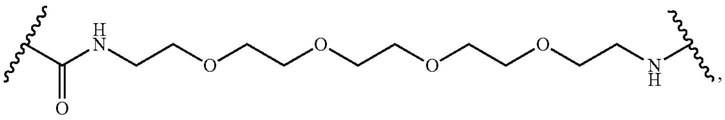 [SMILES: *NCCOCCOCCOCCOCCNC(*)=O]
(85)
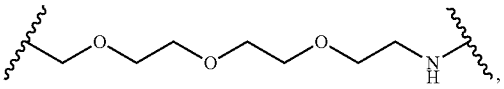 [SMILES: *COCCOCCOCCN*]
(86)
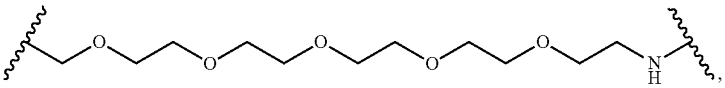 [SMILES: *COCCOCCOCCOCCOCCN*]
(87)
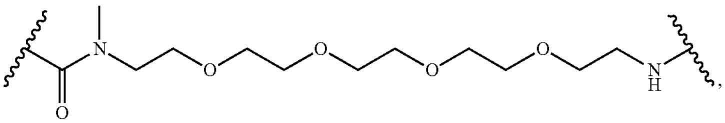 [SMILES: *NCCOCCOCCOCCOCCN(C)C(*)=O]
(88)

TABLE A-continued
| Linkers (L') |
| --- |
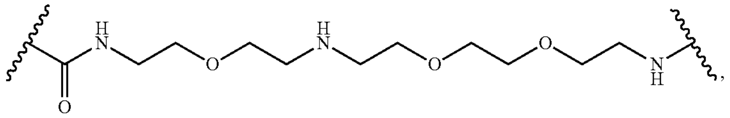 [SMILES: *NCCOCCOCCNCCOCCNC(*)=O]
(89)
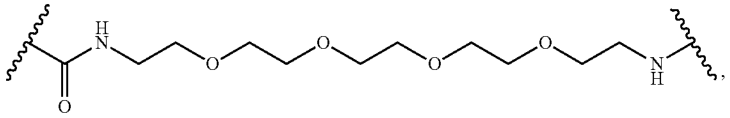 [SMILES: *NCCOCCOCCOCCOCCNC(*)=O]
(90)
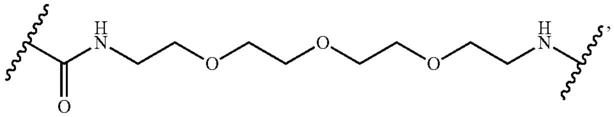 [SMILES: *NCCOCCOCCOCCNC(*)=O]
(91)
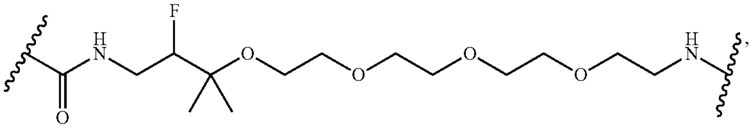 [SMILES: *NCCOCCOCCOCCOC(C)(C)C(F)CNC(*)=O]
(92)
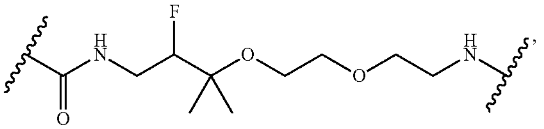 [SMILES: *NCCOCCOC(C)(C)C(F)CNC(*)=O]
(93)
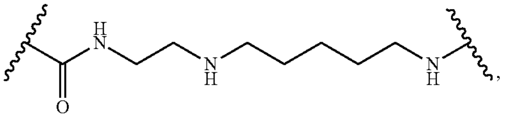 [SMILES: *NCCCCCNCCNC(*)=O]
(94)
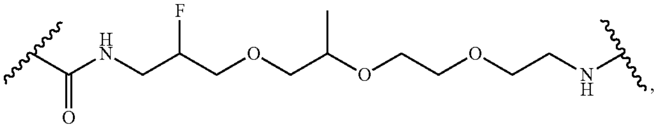 [SMILES: *NCCOCCOC(C)COCC(F)CNC(*)=O]
(95)
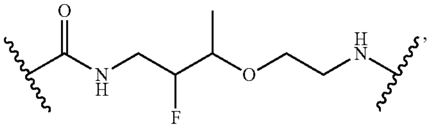 [SMILES: *NCCOC(C)C(F)CNC(*)=O]
(96)
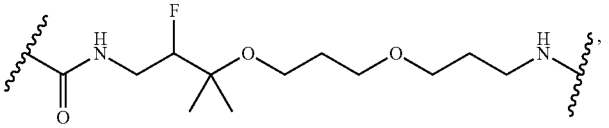 [SMILES: *NCCCOCCCOC(C)(C)C(F)CNC(*)=O]
(97)
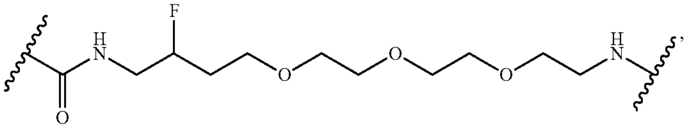 [SMILES: *NCCOCCOCCOCCC(F)CNC(*)=O]
(98)
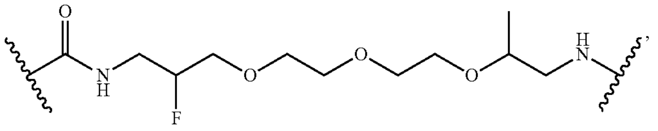 [SMILES: *NCC(C)OCCOCCOCC(F)CNC(*)=O]
(99)

TABLE A-continued
| Linkers (L') | |
|---|---|
| 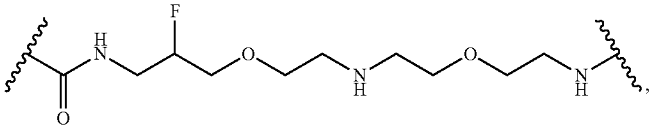 [SMILES: *NCCOCCNCCOCC(F)CNC(*)=O] | (100) |
| 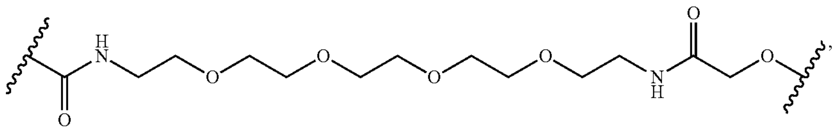 [SMILES: *OCC(=O)NCCOCCOCCOCCOCCNC(*)=O] | (101) |
| 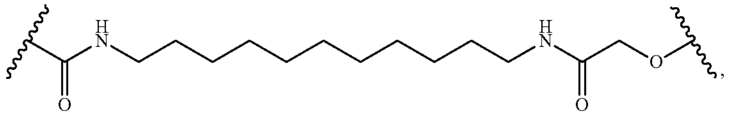 [SMILES: *OCC(=O)NCCCCCCCCCCCNC(*)=O] | (102) |
| 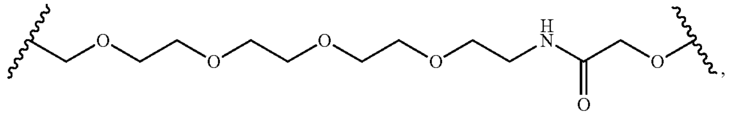 [SMILES: *COCCOCCOCCOCCNC(=O)CO*] | (103) |
| 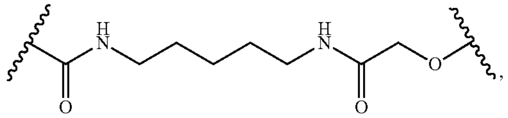 [SMILES: *OCC(=O)NCCCCCNC(*)=O] | (104) |
| 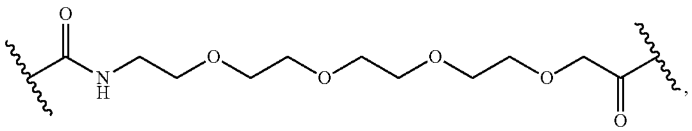 [SMILES: *C(=O)COCCOCCOCCOCCNC(*)=O] | (105) |
| 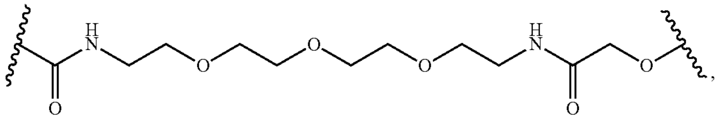 [SMILES: *OCC(=O)NCCOCCOCCOCCNC(*)=O] | (106) |
| 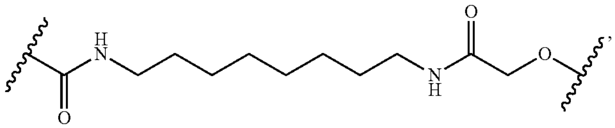 [SMILES: *OCC(=O)NCCCCCCCCNC(*)=O] | (107) |
| 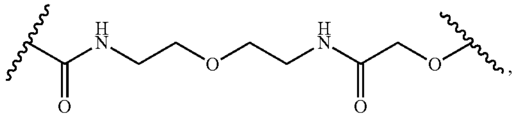 [SMILES: *OCC(=O)NCCOCCNC(*)=O] | (108) |
| 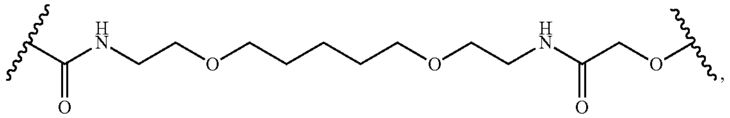 [SMILES: *OCC(=O)NCCOCCCCCOCCNC(*)=O] | (109) |
| 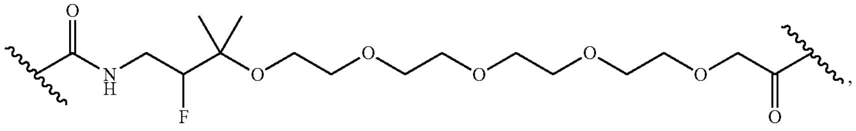 [SMILES: *C(=O)COCCOCCOCCOCCOC(C)(C)C(F)CNC(*)=O] | (110) |

TABLE A-continued
Linkers (L')
(111)
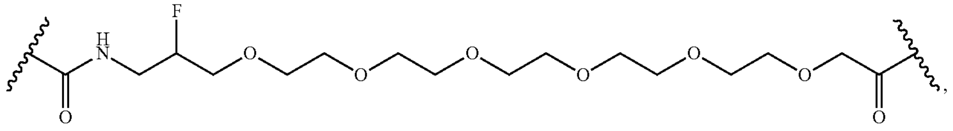 [SMILES: *C(=O)COCCOCCOCCOCCOCCOCC(F)CNC(*)=O]
(112)
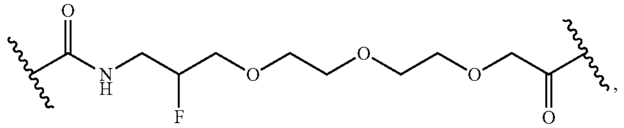 [SMILES: *C(=O)COCCOCCOCC(F)CNC(*)=O]
(113)
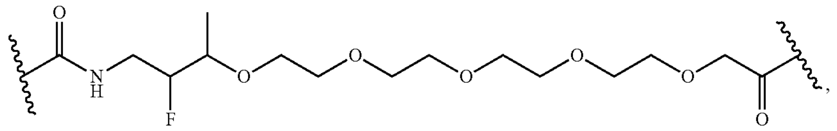 [SMILES: *C(=O)COCCOCCOCCOCCOC(C)C(F)CNC(*)=O]
(114)
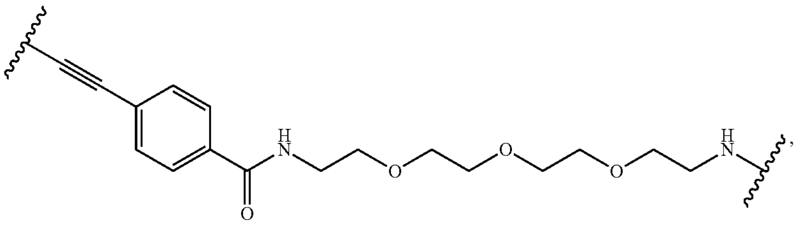 [SMILES: *C#Cc1ccc(C(=O)NCCOCCOCCOCCN*)cc1]
(115)
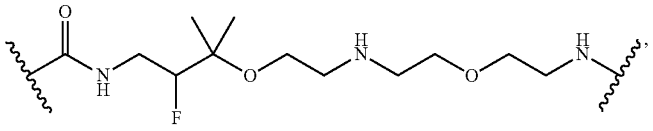 [SMILES: *NCCOCCNCCOC(C)(C)C(F)CNC(*)=O]
(116)
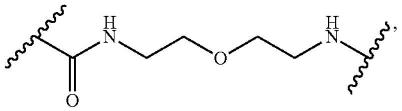 [SMILES: *NCCOCCNC(*)=O]
(117)
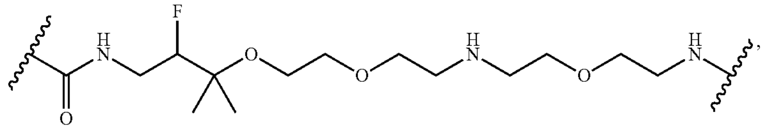 [SMILES: *NCCOCCNCCOCCOC(C)(C)C(F)CNC(*)=O]
(118)
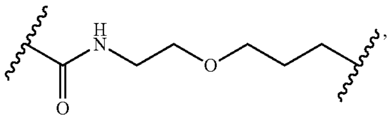 [SMILES: *CCCOCCNC(*)=O]
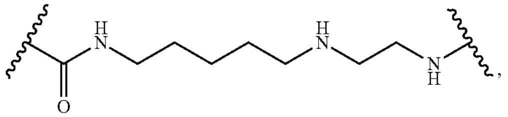 [SMILES: *NCCNCCCCCNC(*)=O]
(119)
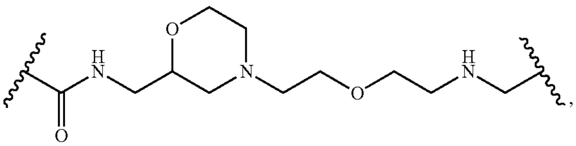 [SMILES: *CNCCOCCN1CCOC(CNC(*)=O)C1]

TABLE A-continued
| Linkers (L') |
| --- |
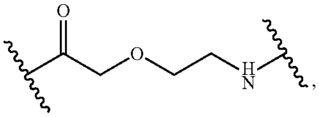 [SMILES: *NCCOCC(*)=O]
,
(120)
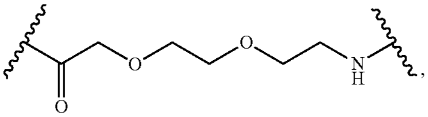 [SMILES: *NCCOCCOCC(*)=O]
,
(121)
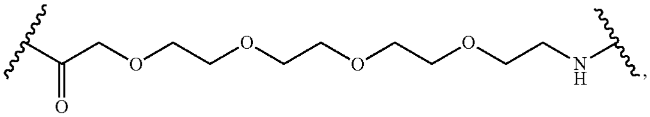 [SMILES: *NCCOCCOCCOCCOCC(*)=O]
,
(122)
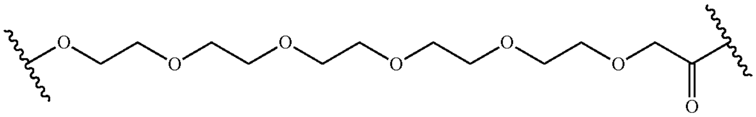
,
(123)
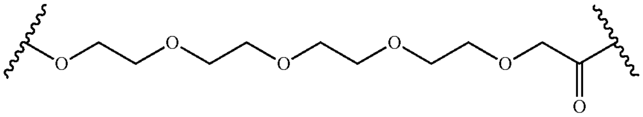
,
(124)
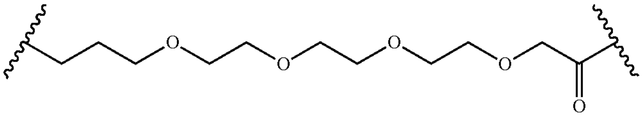
,
(125)
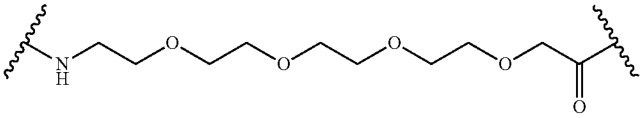
,
(126)
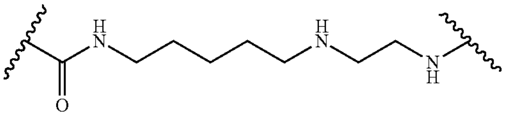
,
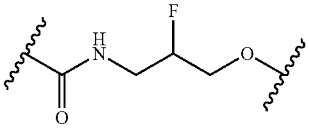
,
(127)
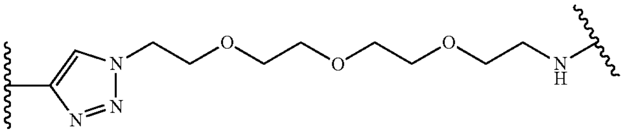
,
(128)
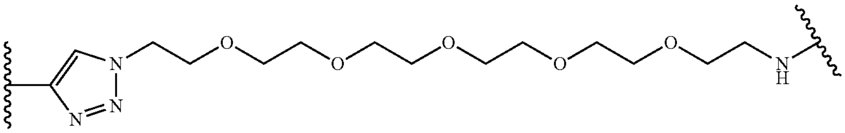
, TABLE A-continued
Linkers (L')
(129)
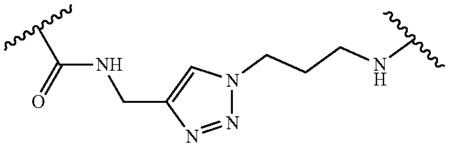
,
(130)
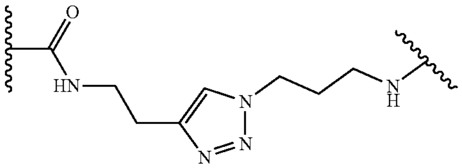
,
(131)
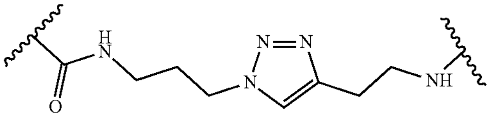
,
(132)
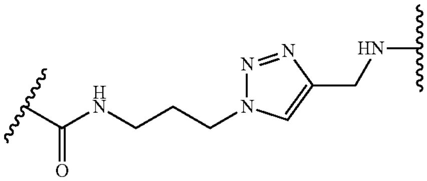
,
(133)
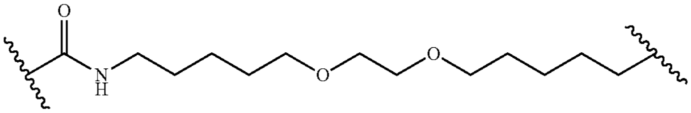
,
(134)
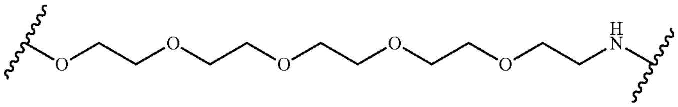
,
(135)
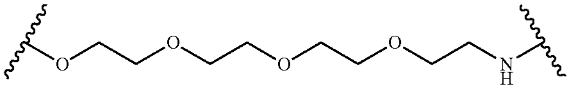
,
(136)
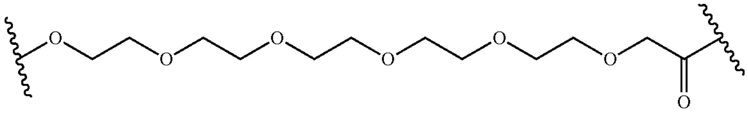
,
(137)
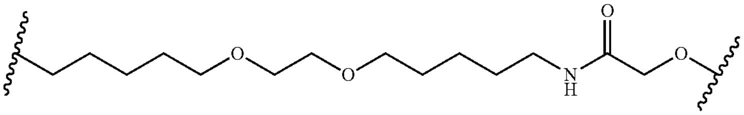
,
(138)
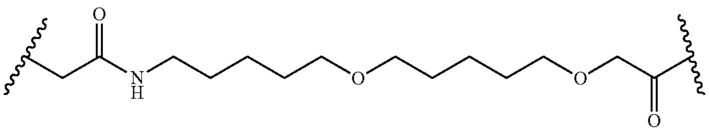
,
(139)
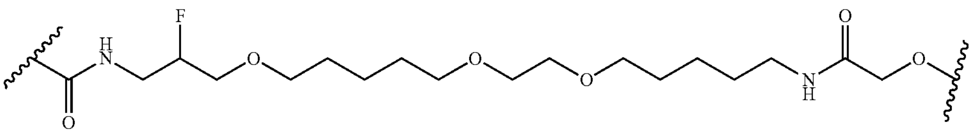
, TABLE A-continued
Linkers (L')
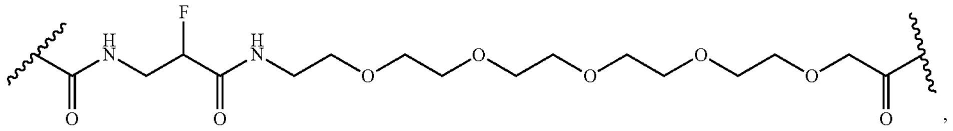 [SMILES: *C(=O)COCCOCCOCCOCCOCCNC(=O)C(F)CNC(*)=O]
(140)
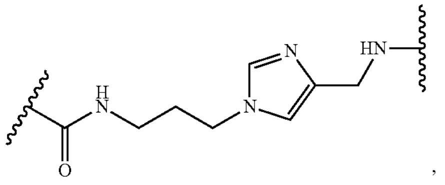 [SMILES: *NCc1cn(CCCNC(*)=O)cn1]
(141)
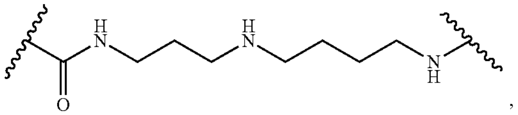 [SMILES: *NCCCCNCCCNC(*)=O]
(142)
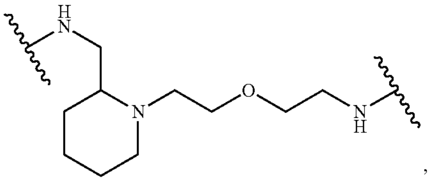 [SMILES: *NCCOCCN1CCCCC1CN*]
(143)
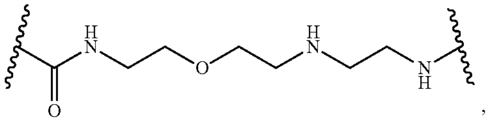 [SMILES: *NCCNCCOCCNC(*)=O]
(144)
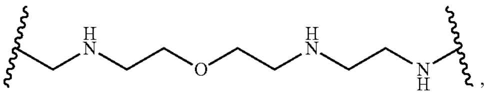 [SMILES: *CNCCOCCNCCN*]
(145)
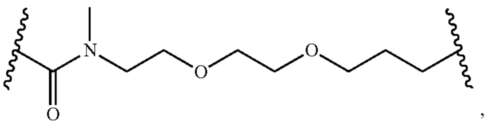 [SMILES: *CCCOCCOCCN(C)C(*)=O]
(146)
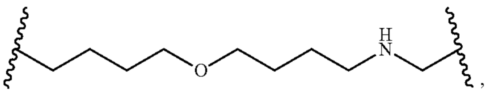 [SMILES: *CCCCOCCCCNC*]
(147)
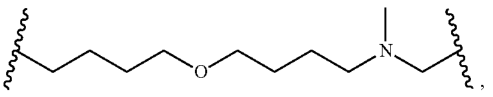 [SMILES: *CCCCOCCCCN(C)C*]
(148)
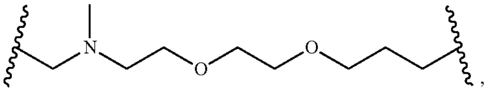 [SMILES: *CCCOCCOCCN(C)C*]
(149)
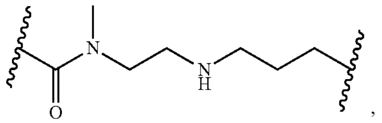 [SMILES: *CCCNCCN(C)C(*)=O]
(150)

TABLE A-continued
Linkers (L')
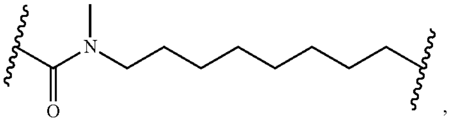 [SMILES: *CCCCCCCCN(C)C(*)=O]
(151)
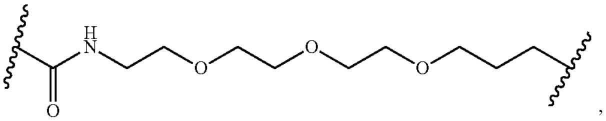 [SMILES: *CCCOCCOCCOCCNC(*)=O]
(152)
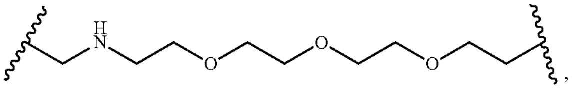 [SMILES: *CCOCCOCCOCCNC*]
(153)
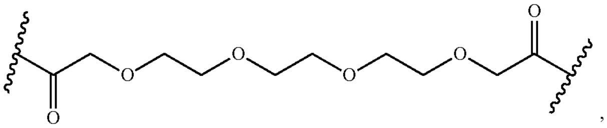 [SMILES: *C(=O)COCCOCCOCCOCC(*)=O]
(154)
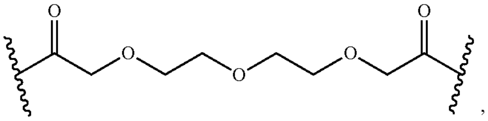 [SMILES: *C(=O)COCCOCCOCC(*)=O]
(155)
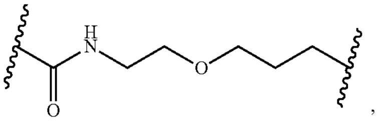 [SMILES: *CCCOCCNC(*)=O]
(156)
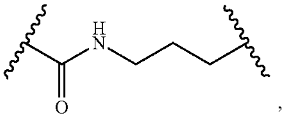 [SMILES: *CCCNC(*)=O]
(157)
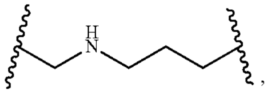 [SMILES: *CCCNC*]
(158)
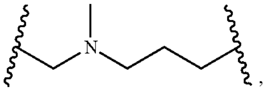 [SMILES: *CCCN(C)C*]
(159)
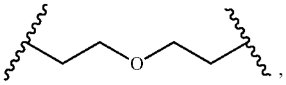 [SMILES: *CCOCC*]
(160)
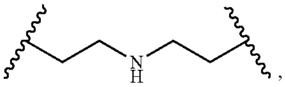 [SMILES: *CCNCC*]
(161)
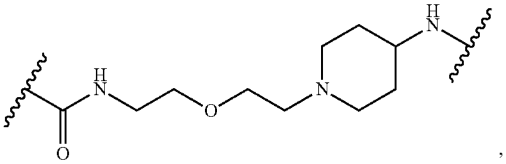 [SMILES: *NC1CCN(CCOCCNC(*)=O)CC1]
(162)

TABLE A-continued
| Linkers (L') |
|---|
| 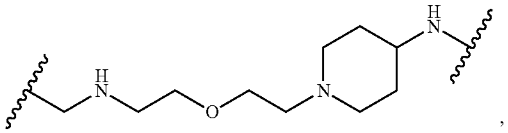 [SMILES: *CNCCOCCN1CCC(N*)CC1] (163) |
| 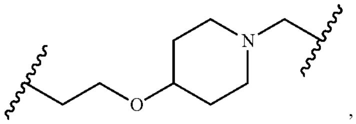 [SMILES: *CCOC1CCN(C*)CC1] (164) |
| 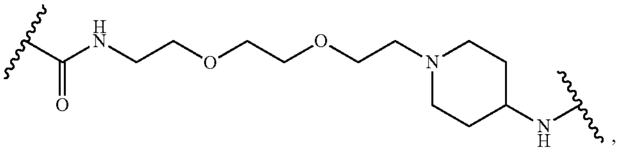 [SMILES: *NC1CCN(CCOCCOCCNC(*)=O)CC1] (165) |
| 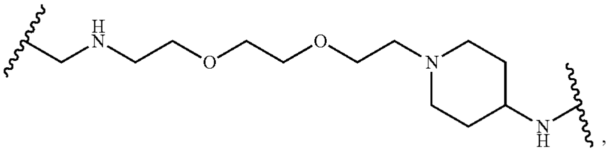 [SMILES: *CNCCOCCOCCN1CCC(N*)CC1] (166) |
| 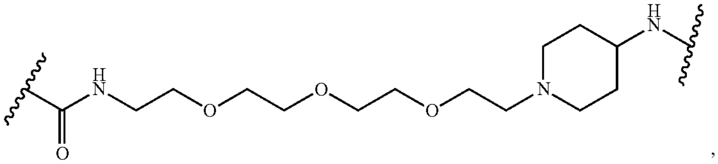 [SMILES: *NC1CCN(CCOCCOCCOCCNC(*)=O)CC1] (167) |
| 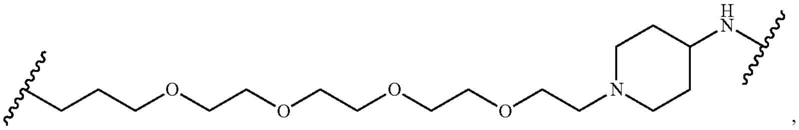 [SMILES: *CCCOCCOCCOCCOCCN1CCC(N*)CC1] (168) |
| 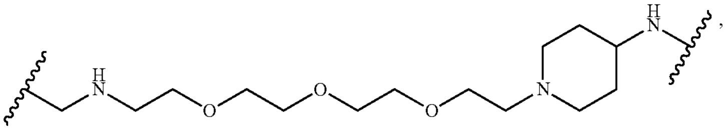 [SMILES: *CNCCOCCOCCOCCN1CCC(N*)CC1] (169) |
| 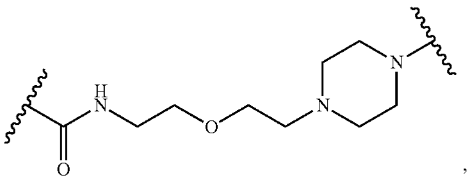 [SMILES: *C(=O)NCCOCCN1CCN(*)CC1] (170) |
| 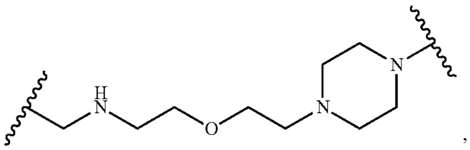 [SMILES: *CNCCOCCN1CCN(*)CC1] (171) |

TABLE A-continued
| Linkers (L') | |
|---|---|
| 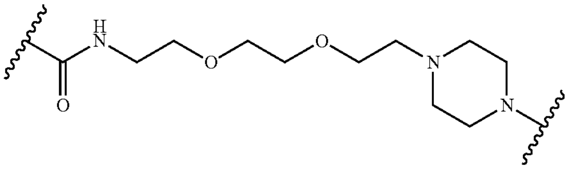, | (172) |
| 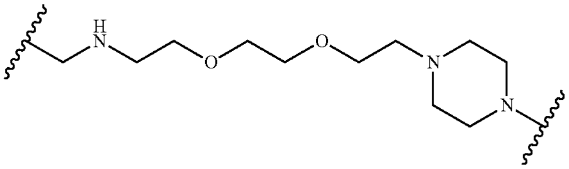, | (173) |
| 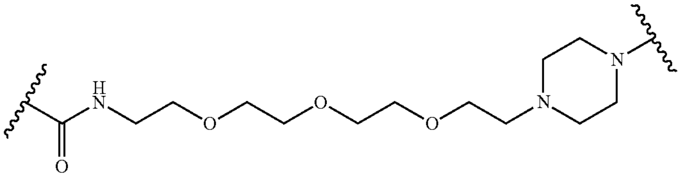, | (174) |
| 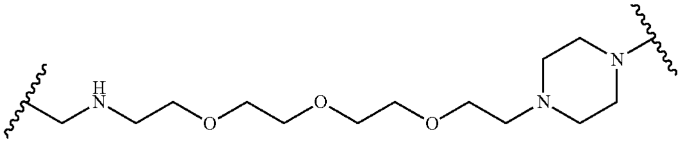, | (175) |
| 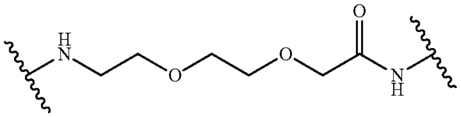, | (176) |
| 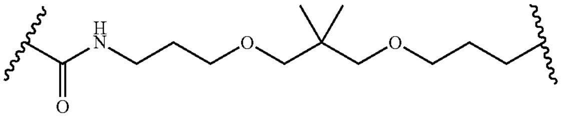, | (177) |
| 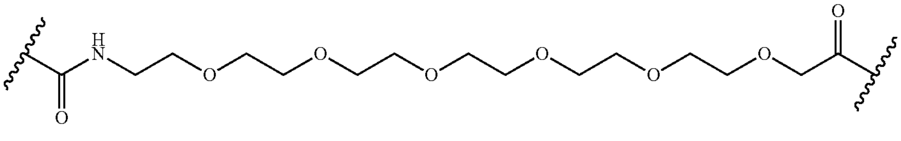, | (178) |
| 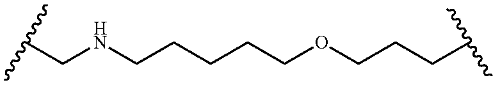, | (179) |
| 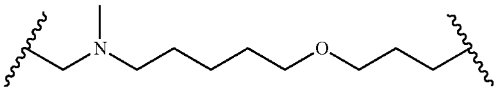, | (180) |
| 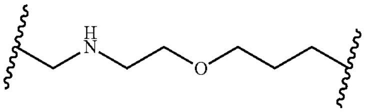, | (181) |
| 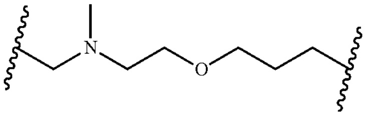, | (182) |

TABLE A-continued
| Linkers (L') |
| --- |
| 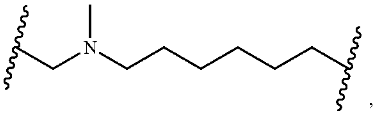 [SMILES: *CCCCCCN(C)C*] (183) |
| 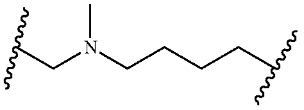 (184) |
| 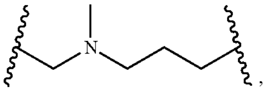 [SMILES: *CCCN(C)C*] (185) |
| 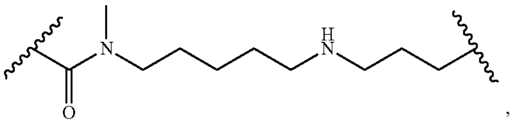 [SMILES: *CCCNCCCCCN(C)C(*)=O] (186) |
| 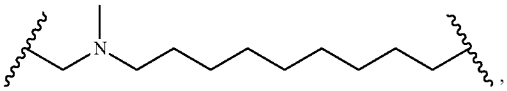 [SMILES: *CCCCCCCCCN(C)C*] (187) |
| 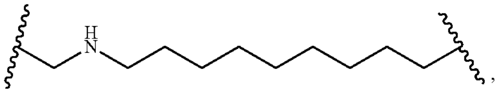 [SMILES: *CCCCCCCCCNC*] (188) |
| 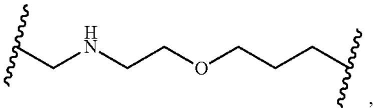 [SMILES: *CCCOCCNC*] (189) |
| 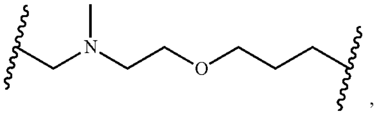 [SMILES: *CCCOCCN(C)C*] (190) |
| 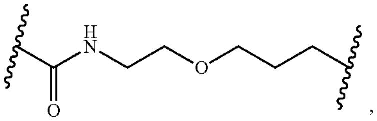 [SMILES: *CCCOCCNC(*)=O] (191) |
| 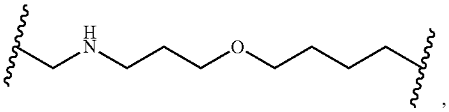 [SMILES: *CCCCOCCCNC*] (192) |
| 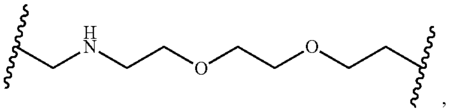 [SMILES: *CCOCCOCCNC*] (193) |
| 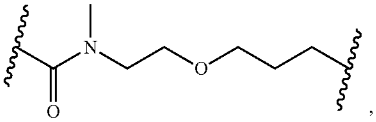 [SMILES: *CCCOCCN(C)C(*)=O] (194) |

TABLE A-continued
Linkers (L')
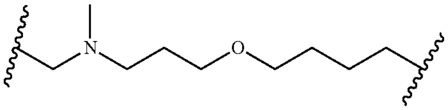,
(195)
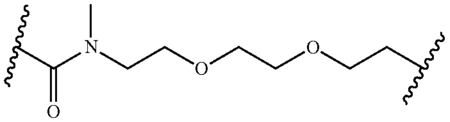,
(196)
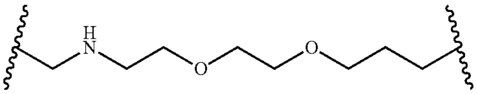,
(197)
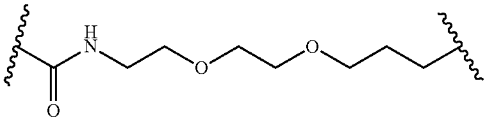,
(198)
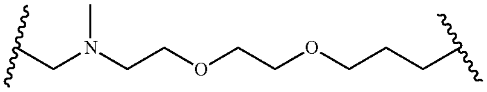,
(199)
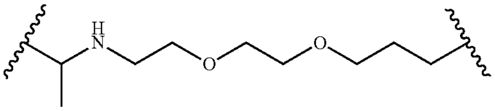,
(200)
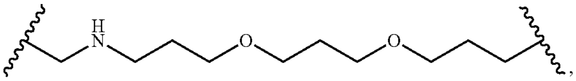 [SMILES: *CCCOCCCOCCCNC*],
(201)
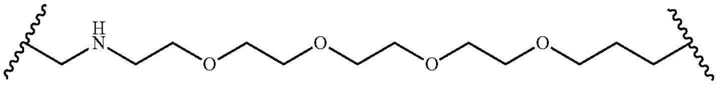,
(202)
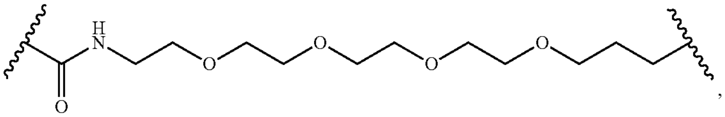 [SMILES: *CCCOCCOCCOCCOCCNC(*)=O],
(203)
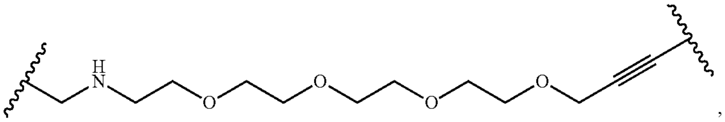 [SMILES: *C#CCOCCOCCOCCOCCNC*],
(204)
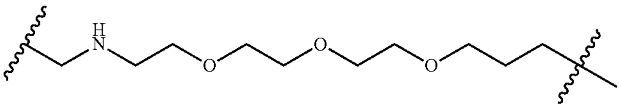,
(205)
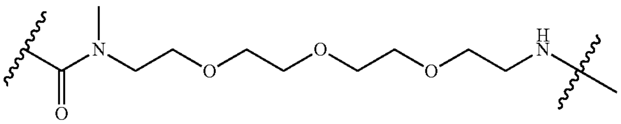,
(206)

TABLE A-continued
| Linkers (L') |
|---|
| 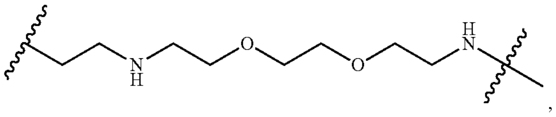 [SMILES: *CCNCCOCCOCCN*] (207) |
| 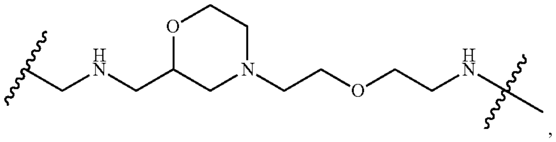 [SMILES: *CNCC1CN(CCOCCN*)CCO1] (208) |
| 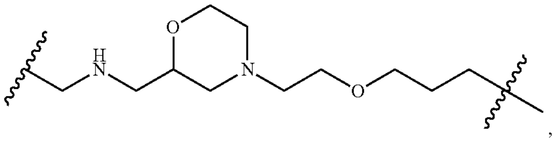 [SMILES: *CCCOCCN1CCOC(CNC*)C1] (209) |
| 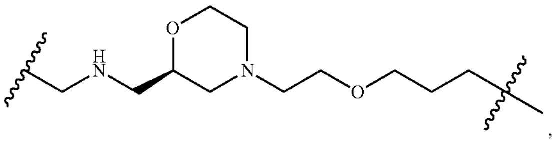 [SMILES: *CCCOCCN1CCO[C@H](CNC*)C1] (210) |
| 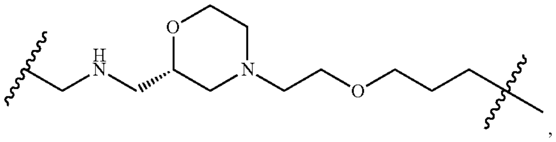 [SMILES: *CCCOCCN1CCO[C@@H](CNC*)C1] (211) |
| 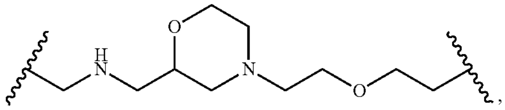 [SMILES: *CCOCCN1CCOC(CNC*)C1] (212) |
| 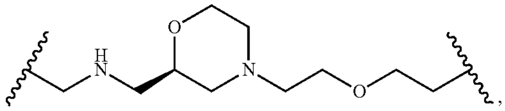 [SMILES: *CCOCCN1CCO[C@H](CNC*)C1] (213) |
| 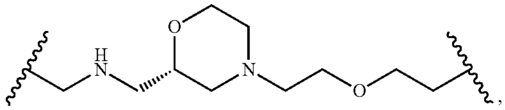 [SMILES: *CCOCCN1CCO[C@@H](CNC*)C1] (214) |
| 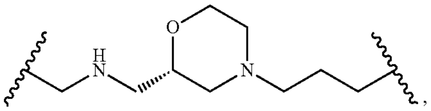 [SMILES: *CCCN1CCO[C@@H](CNC*)C1] (215) |
| 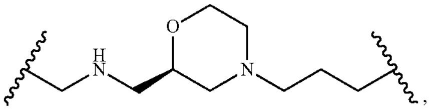 [SMILES: *CCCN1CCO[C@H](CNC*)C1] (216) |
| 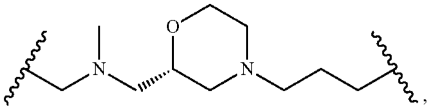 [SMILES: *CCCN1CCO[C@@H](CN(C)C*)C1] (217) |

TABLE A-continued
Linkers (L')
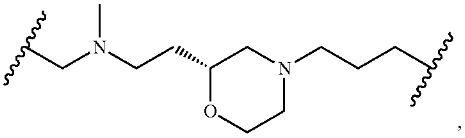 [SMILES: *CCCN1CCO[C@H](CCN(C)C*)C1]
(218)
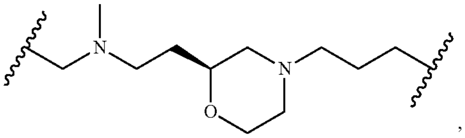 [SMILES: *CCCN1CCO[C@@H](CCN(C)C*)C1]
(219)
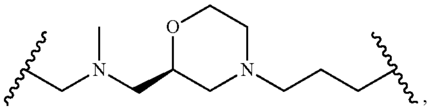 [SMILES: *CCCN1CCO[C@H](CN(C)C*)C1]
(220)
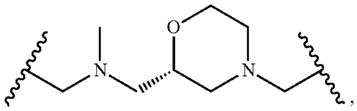 [SMILES: *CN(C)C[C@H]1CN(C*)CCO1]
(221)
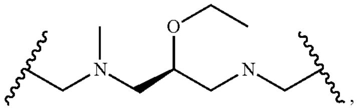 [SMILES: *CNC[C@@H](CN(C)C*)OCC]
(222)
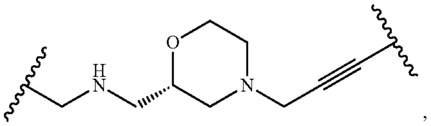 [SMILES: *C#CCN1CCO[C@@H](CNC*)C1]
(223)
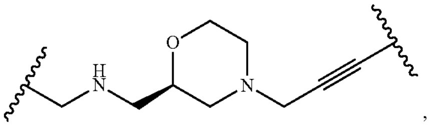 [SMILES: *C#CCN1CCO[C@H](CNC*)C1]
(224)
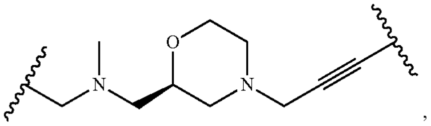 [SMILES: *C#CCN1CCO[C@H](CN(C)C*)C1]
(225)
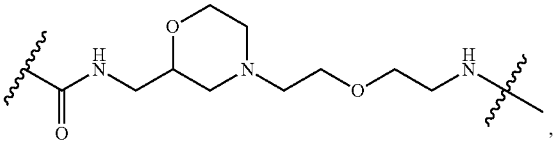 [SMILES: *NCCOCCN1CCOC(CNC(*)=O)C1]
(226)
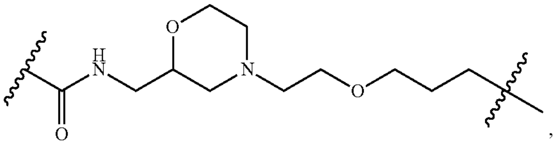 [SMILES: *CCCOCCN1CCOC(CNC(*)=O)C1]
(227)
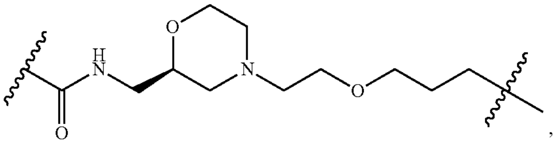 [SMILES: *CCCOCCN1CCO[C@H](CNC(*)=O)C1]
(228)

TABLE A-continued
Linkers (L')
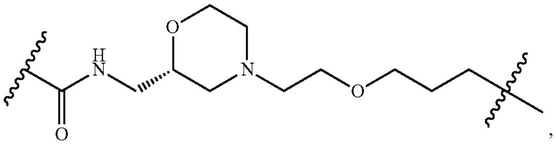 [SMILES: *CCCOCCN1CCO[C@@H](CNC(*)=O)C1]
(229)
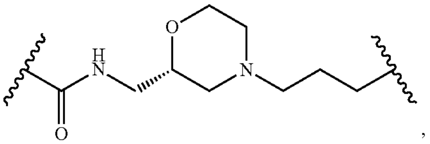 [SMILES: *CCCN1CCO[C@@H](CNC(*)=O)C1]
(230)
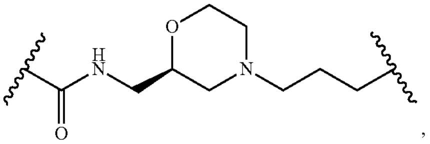 [SMILES: *CCCN1CCO[C@H](CNC(*)=O)C1]
(231)
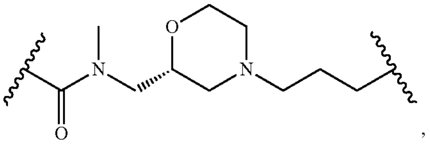 [SMILES: *CCCN1CCO[C@@H](CN(C)C(*)=O)C1]
(232)
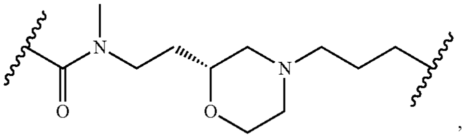 [SMILES: *CCCN1CCO[C@H](CCN(C)C(*)=O)C1]
(233)
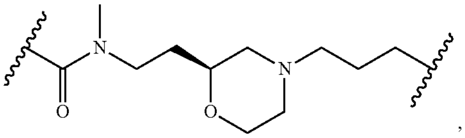 [SMILES: *CCCN1CCO[C@@H](CCN(C)C(*)=O)C1]
(234)
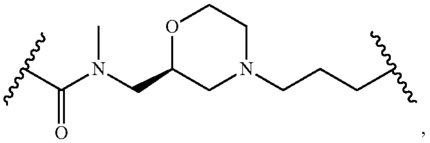 [SMILES: *CCCN1CCO[C@H](CN(C)C(*)=O)C1]
(235)
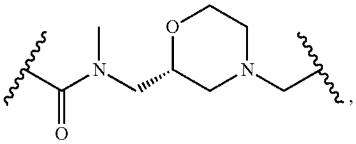 [SMILES: *CN1CCO[C@@H](CN(C)C(*)=O)C1]
(236)
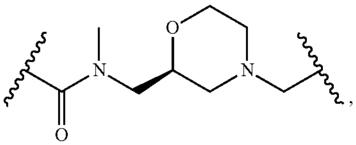 [SMILES: *CN1CCO[C@H](CN(C)C(*)=O)C1]
(237)
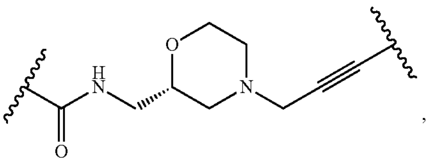 [SMILES: *C#CCN1CCO[C@@H](CNC(*)=O)C1]
(238)

TABLE A-continued
Linkers (L')
(239)
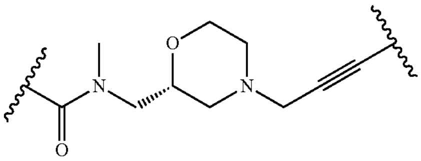
,
(240)
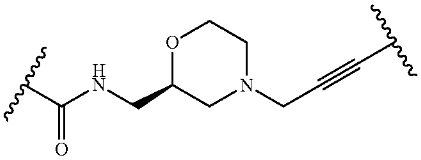
,
(241)
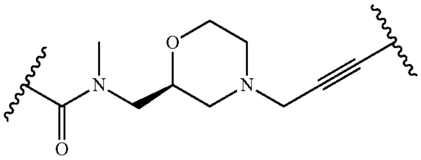
,
(242)
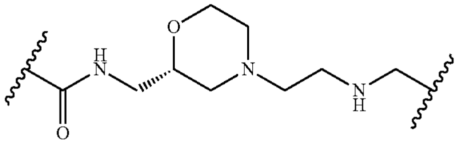
,
(243)
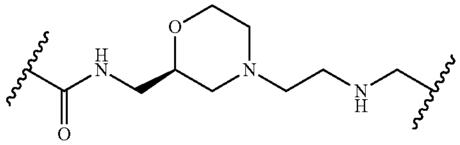
,
(244)
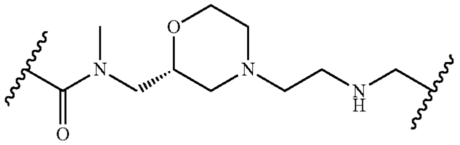
,
(245)
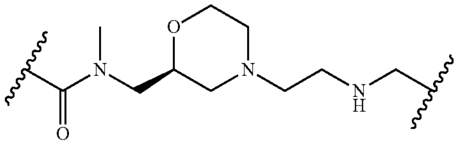
,
(246)
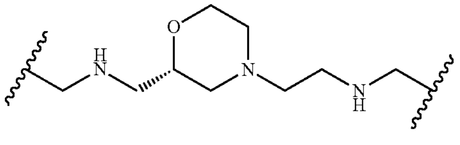
,
(247)
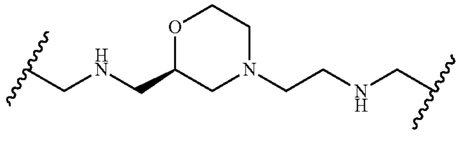
,
(248)
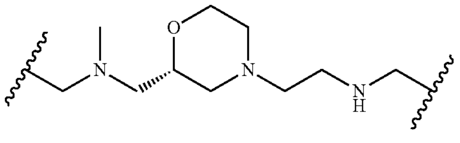
, TABLE A-continued
Linkers (L')
(249)
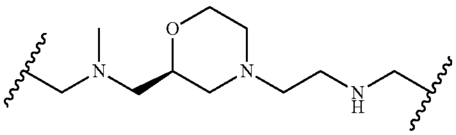
,
(250)
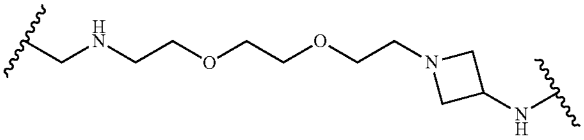
,
(251)
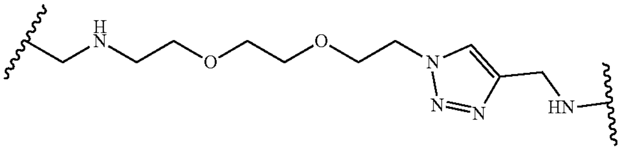
,
(253)
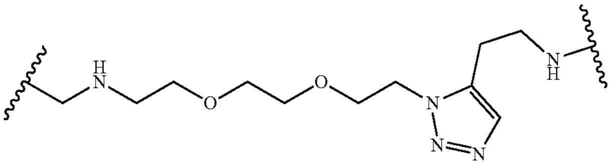
,
(254)
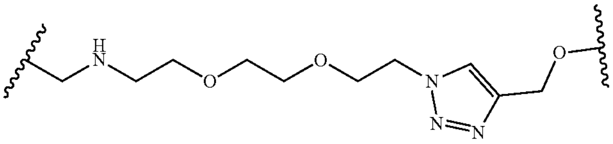
,
(255)
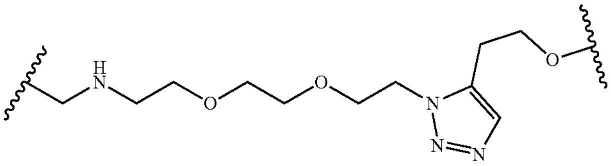
,
(256)
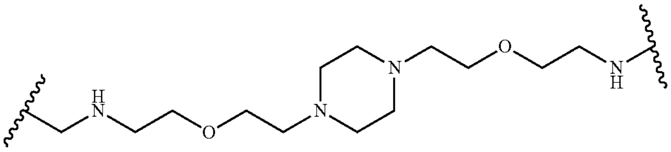
,
(257)
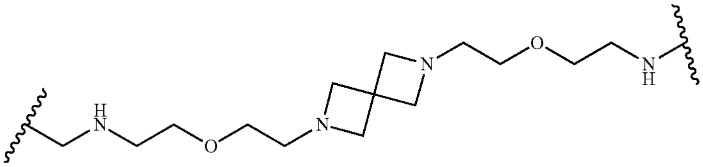
,
(258)
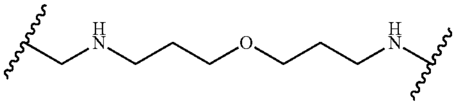
,
(259)
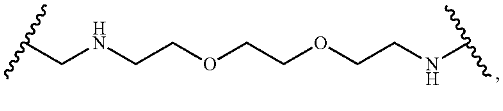 [SMILES: *CNCCOCCOCCN*]
, TABLE A-continued
| Linkers (L') |
|---|
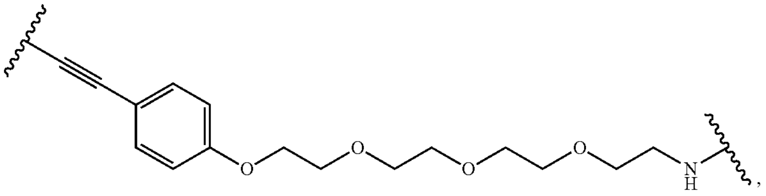 [SMILES: *C#Cc1ccc(OCCOCCOCCOCCN*)cc1]
(260)
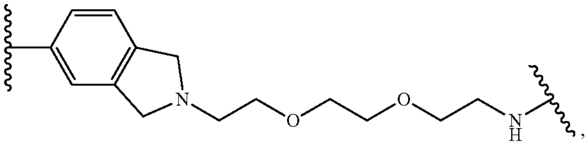 [SMILES: *NCCOCCOCCN1Cc2ccc(*)cc2C1]
(261)
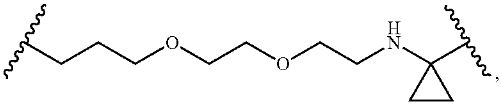 [SMILES: *CCCOCCOCCNC1(*)CC1]
(262)
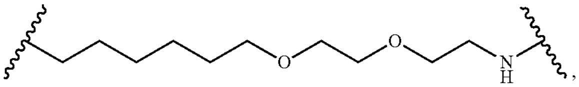 [SMILES: *CCCCCCOCCOCCN*]
(263)
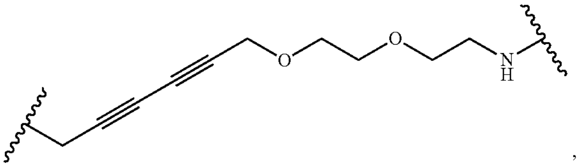 [SMILES: *CC#CC#CCOCCOCCN*]
(264)
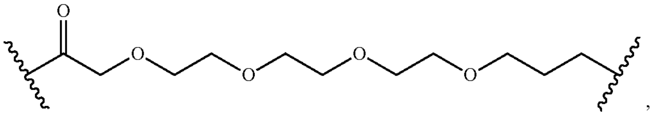 [SMILES: *CCCOCCOCCOCCOCC(*)=O]
(265)
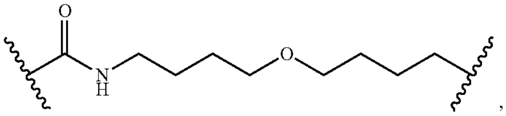 [SMILES: *CCCCOCCCCNC(*)=O]
(266)
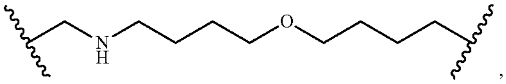 [SMILES: *CCCCOCCCCNC*]
(267)
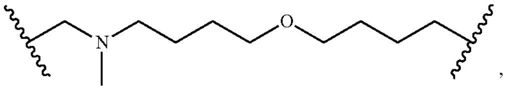 [SMILES: *CCCCOCCCCN(C)C*]
(268)
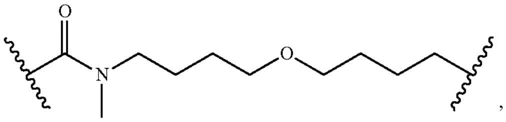 [SMILES: *CCCCOCCCCN(C)C(*)=O]
(269)
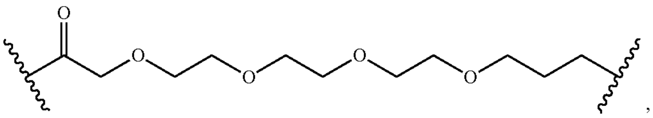 [SMILES: *CCCOCCOCCOCCOCC(*)=O]
(270)

TABLE A-continued
Linkers (L')
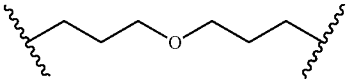
,
(271)
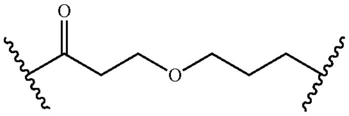
,
(272)
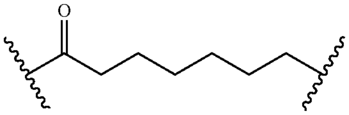
,
(273)
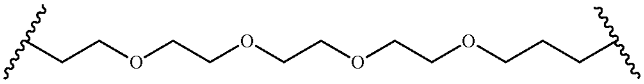
,
(274)
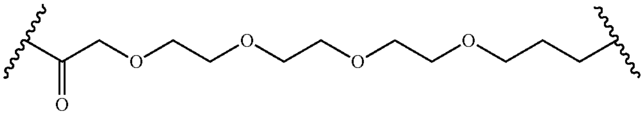
,
(275)
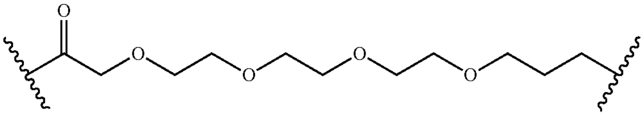
,
(276)
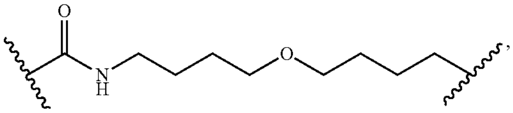 [SMILES: *CCCCOCCCCNC(*)=O]
,
(277)
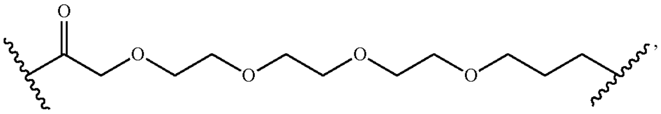 [SMILES: *CCCOCCOCCOCCOCC(*)=O]
,
(278)
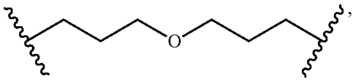 [SMILES: *CCCOCCC*]
,
(279)
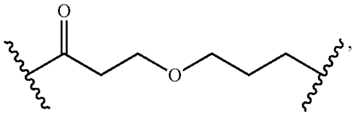 [SMILES: *CCCOCCC(*)=O]
,
(280)
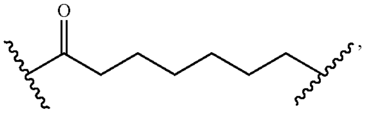 [SMILES: *CCCCCCC(*)=O]
,
(281)
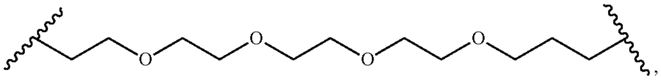 [SMILES: *CCCOCCOCCOCCOCC*]
,
(282)
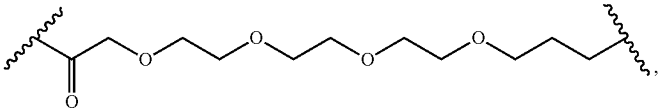 [SMILES: *CCCOCCOCCOCCOCC(*)=O]
,
(283)

TABLE A-continued
Linkers (L')
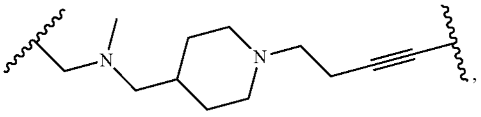 [SMILES: *C#CCCN1CCC(CN(C)C*)CC1]
(284)
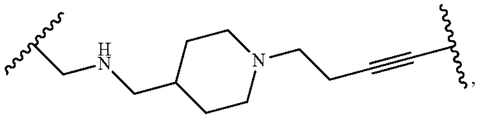 [SMILES: *C#CCCN1CCC(CNC*)CC1]
(285)
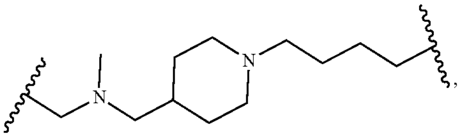 [SMILES: *CCCCN1CCC(CN(C)C*)CC1]
(286)
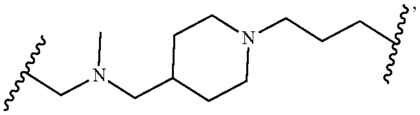 [SMILES: *CCCN1CCC(CN(C)C*)CC1]
(287)
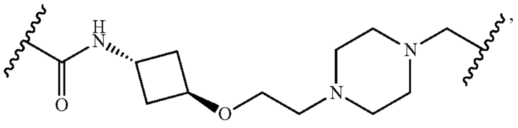 [SMILES: *CN1CCN(CCO[C@H]2C[C@H](NC(*)=O)C2)CC1]
(288)
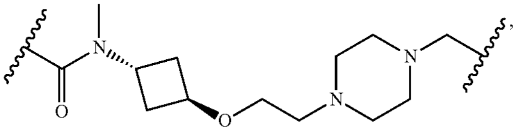 [SMILES: *CN1CCN(CCO[C@H]2C[C@H](N(C)C(*)=O)C2)CC1]
(289)
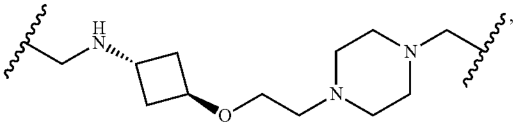 [SMILES: *CN[C@H]1C[C@H](OCCN2CCN(C*)CC2)C1]
(290)
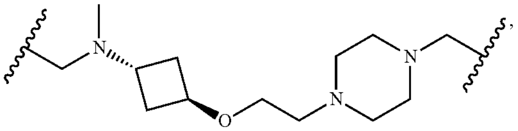 [SMILES: *CN1CCN(CCO[C@H]2C[C@H](N(C)C*)C2)CC1]
(291)
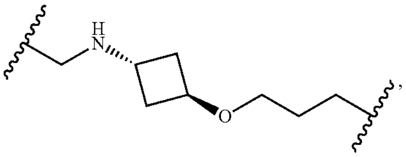 [SMILES: *CCCO[C@H]1C[C@H](NC*)C1]
(292)
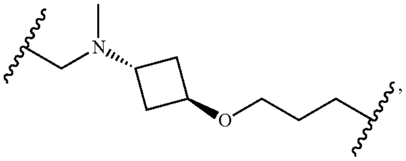 [SMILES: *CCCO[C@H]1C[C@H](N(C)C*)C1]
(293)
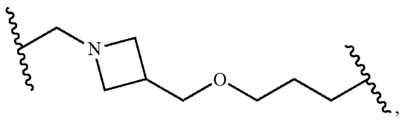 [SMILES: *CCCOCC1CN(C*)C1]
(294)

TABLE A-continued
| Linkers (L') | |
| --- | --- |
| 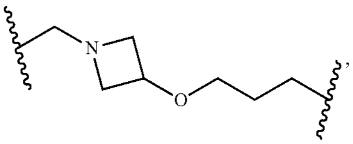 [SMILES: *CCCOC1CN(C*)C1], | (295) |
| 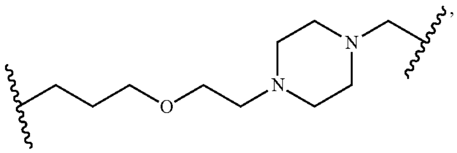 [SMILES: *CCCOCCN1CCN(C*)CC1], | (296) |
| 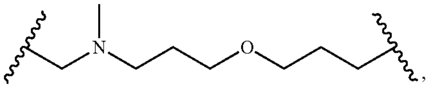 [SMILES: *CCCOCCCN(C)C*], | (297) |
| 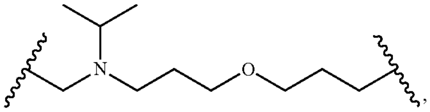 [SMILES: *CCCOCCCN(C*)C(C)C], | (298) |
| 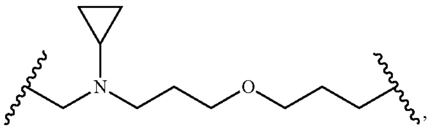 [SMILES: *CCCOCCCN(C*)C1CC1], | (299) |
| 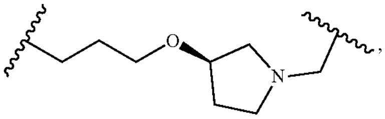 [SMILES: *CCCO[C@@H]1CCN(C*)C1], | (300) |
| 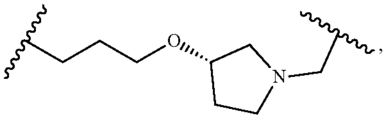 [SMILES: *CCCO[C@H]1CCN(C*)C1], | (301) |
| 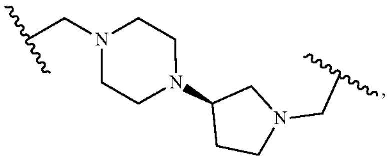 [SMILES: *CN1CCN([C@@H]2CCN(C*)C2)CC1], | (302) |
| 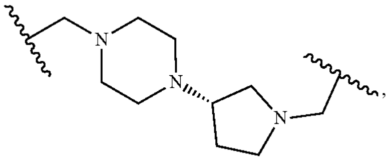 [SMILES: *CN1CCN([C@H]2CCN(C*)C2)CC1], | (303) |
| 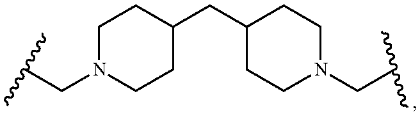 [SMILES: *CN1CCC(CC2CCN(C*)CC2)CC1], | (304) |

TABLE A-continued
Linkers (L')
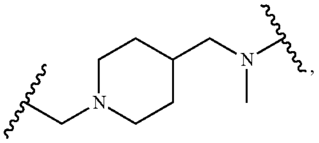 [SMILES: *CN1CCC(CN(*)C)CC1]
(305)
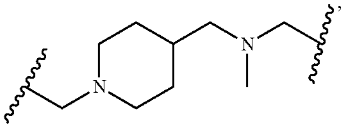 [SMILES: *CN(C)CC1CCN(C*)CC1]
(306)
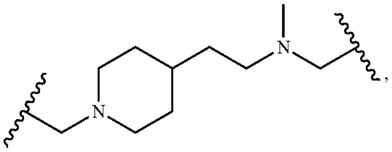 [SMILES: *CN(C)CCC1CCN(C*)CC1]
(307)
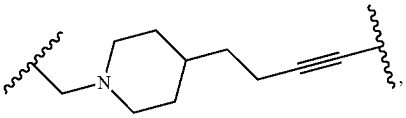 [SMILES: *C#CCCC1CCN(C*)CC1]
(308)
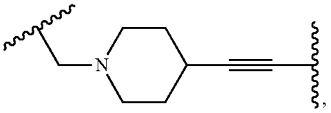 [SMILES: *C#CC1CCN(C*)CC1]
(309)
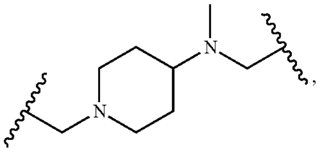 [SMILES: *CN1CCC(N(C)C*)CC1]
(310)
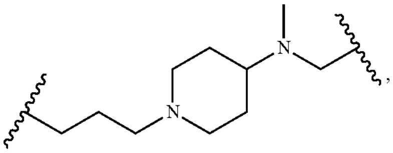 [SMILES: *CCCN1CCC(N(C)C*)CC1]
(311)
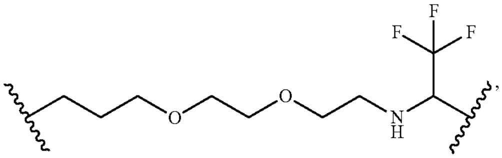 [SMILES: *CCCOCCOCCNC(*)C(F)(F)F]
(312)
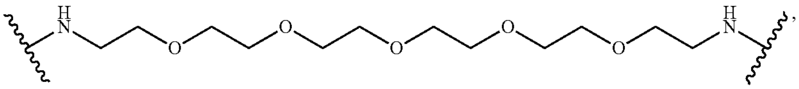 [SMILES: *NCCOCCOCCOCCOCCOCCN*]
(313)
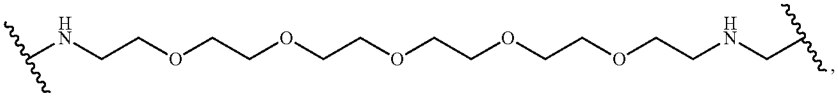 [SMILES: *CNCCOCCOCCOCCOCCOCCN*]
(314)
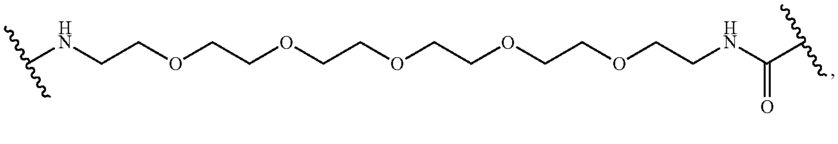 [SMILES: *NCCOCCOCCOCCOCCOCCNC(*)=O]
(315)

TABLE A-continued
Linkers (L')
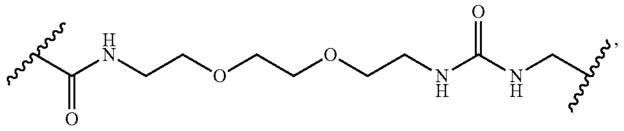 [SMILES: *CNC(=O)NCCOCCOCCNC(*)=O]
(316)
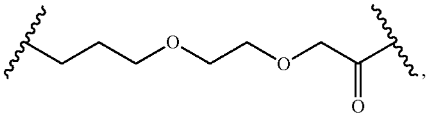 [SMILES: *CCCOCCOCC(*)=O]
(317)
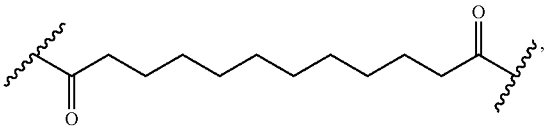 [SMILES: *C(=O)CCCCCCCCCCC(*)=O]
(318)
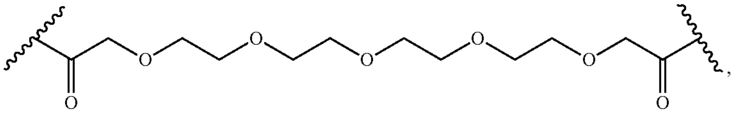 [SMILES: *C(=O)COCCOCCOCCOCCOCC(*)=O]
(319)
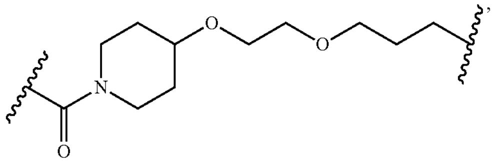 [SMILES: *CCCOCCOC1CCN(C(*)=O)CC1]
(320)
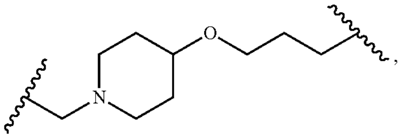 [SMILES: *CCCOC1CCN(C*)CC1]
(321)
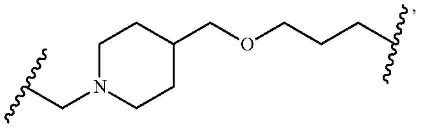 [SMILES: *CCCOCC1CCN(C*)CC1]
(322)
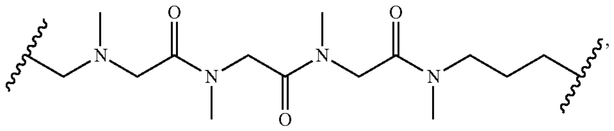 [SMILES: *CCCN(C)C(=O)CN(C)C(=O)CN(C)C(=O)CN(C)C*]
(323)
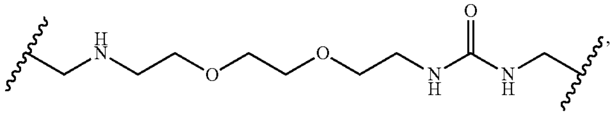 [SMILES: *CNCCOCCOCCNC(=O)NC*]
(324)
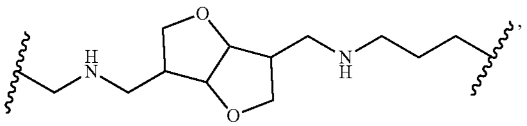 [SMILES: *CCCNCC1COC2C(CNC*)COC12]
(325)
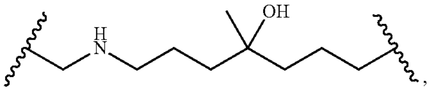 [SMILES: *CCCC(C)(O)CCCNC*]
(326)

TABLE A-continued
Linkers (L')
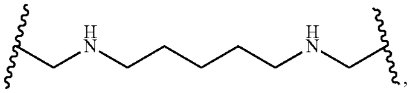 [SMILES: *CNCCCCCNC*]
(327)
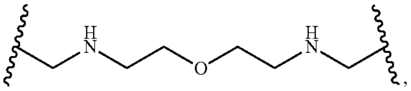 [SMILES: *CNCCOCCNC*]
(328)
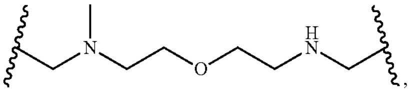 [SMILES: *CNCCOCCN(C)C*]
(329)
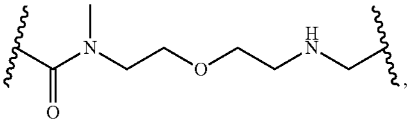 [SMILES: *CNCCOCCN(C)C(*)=O]
(330)
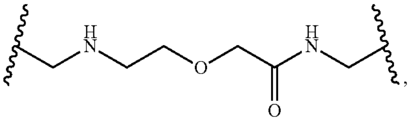 [SMILES: *CNCCOCC(=O)NC*]
(331)
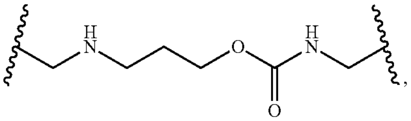 [SMILES: *CNCCCOC(=O)NC*]
(332)
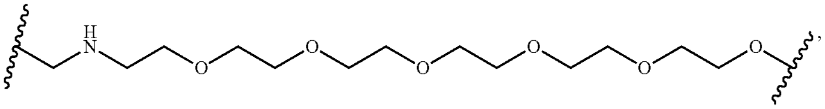 [SMILES: *CNCCOCCOCCOCCOCCOCCO*]
(333)
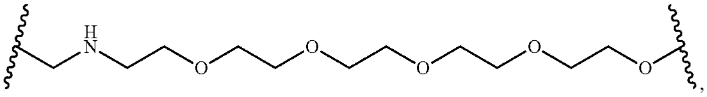 [SMILES: *CNCCOCCOCCOCCOCCO*]
(334)
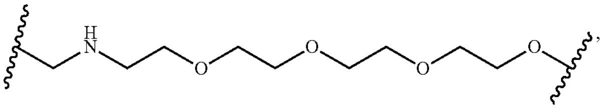 [SMILES: *CNCCOCCOCCOCCO*]
(335)
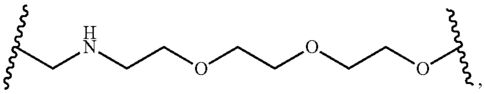 [SMILES: *CNCCOCCOCCO*]
(336)
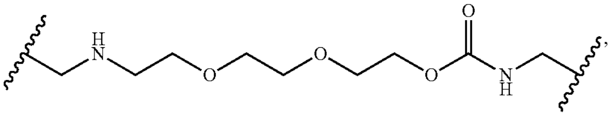 [SMILES: *CNCCOCCOCCOC(=O)NC*]
(337)
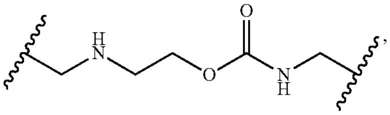 [SMILES: *CNCCOC(=O)NC*]
(338)
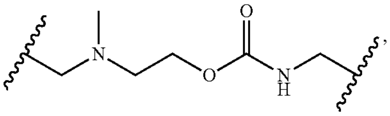 [SMILES: *CNC(=O)OCCN(C)C*]
(339)

TABLE A-continued
| Linkers (L') |
| --- |
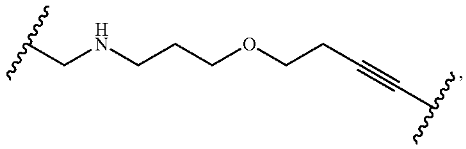 [SMILES: *C#CCCOCCCNC*]
(340)
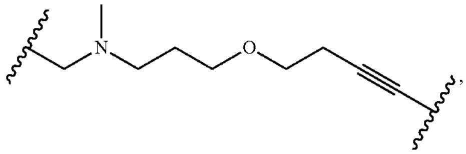 [SMILES: *C#CCCOCCCN(C)C*]
(341)
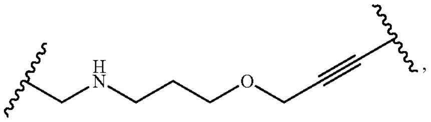 [SMILES: *C#CCOCCCNC*]
(342)
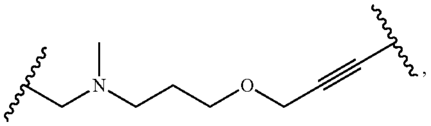 [SMILES: *C#CCOCCCN(C)C*]
(343)
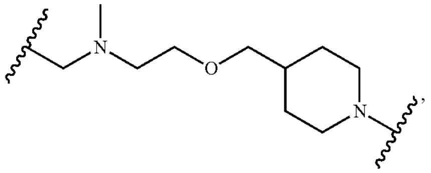 [SMILES: *CN(C)CCOCC1CCN(*)CC1]
(344)
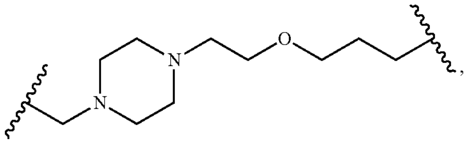 [SMILES: *CCCOCCN1CCN(C*)CC1]
(345)
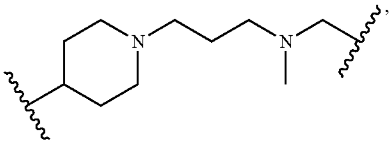 [SMILES: *CN(C)CCCN1CCC(*)CC1]
(346)
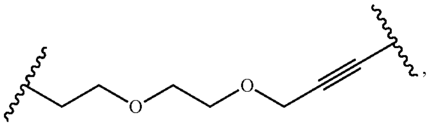 [SMILES: *C#CCOCCOCC*]
(347)
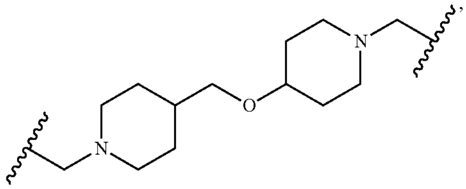 [SMILES: *CN1CCC(COC2CCN(C*)CC2)CC1]
(348)

TABLE A-continued
Linkers (L')
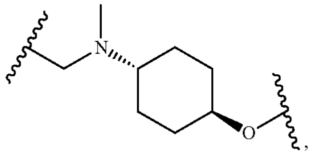 [SMILES: *CN(C)[C@H]1CC[C@H](O*)CC1]
(349)
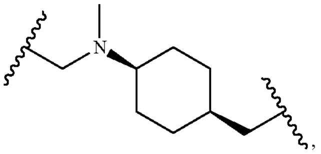 [SMILES: *CN(C)[C@H]1CC[C@@H](C*)CC1]
(350)
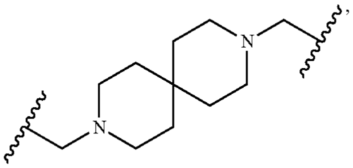 [SMILES: *CN1CCC2(CC1)CCN(C*)CC2]
(351)
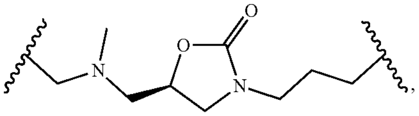 [SMILES: *CCCN1C[C@@H](CN(C)C*)OC1=O]
(352)
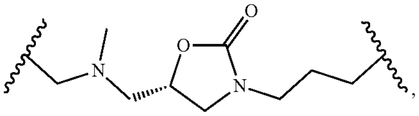 [SMILES: *CCCN1C[C@H](CN(C)C*)OC1=O]
(353)
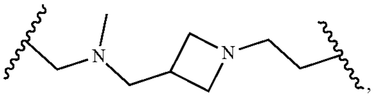 [SMILES: *CCN1CC(CN(C)C*)C1]
(354)
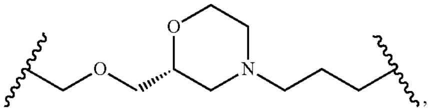 [SMILES: *CCCN1CCO[C@@H](COC*)C1]
(355)
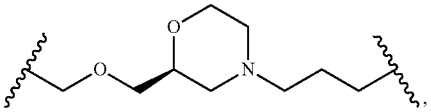 [SMILES: *CCCN1CCO[C@H](COC*)C1]
(356)
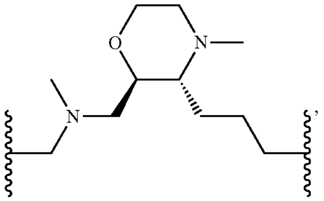 [SMILES: *CCC[C@@H]1[C@@H](CN(C)C*)OCCN1C]
(357)
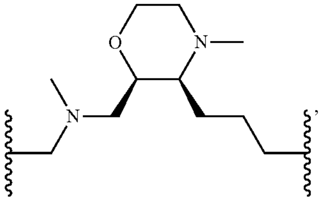 [SMILES: *CCC[C@H]1[C@@H](CN(C)C*)OCCN1C]
(358)

TABLE A-continued
Linkers (L')
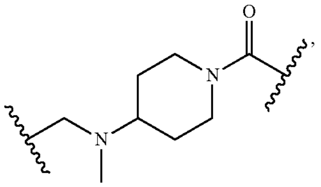 [SMILES: *CN(C)C1CCN(C(*)=O)CC1]
(359)
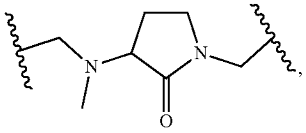 [SMILES: *CN1CCC(N(C)C*)C1=O]
(360)
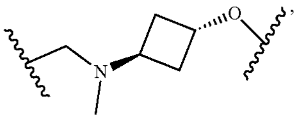 [SMILES: *CN(C)[C@H]1C[C@H](O*)C1]
(361)
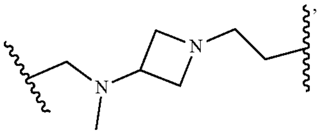 [SMILES: *CCN1CC(N(C)C*)C1]
(362)
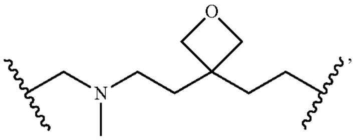 [SMILES: *CCC1(CCN(C)C*)COC1]
(363)
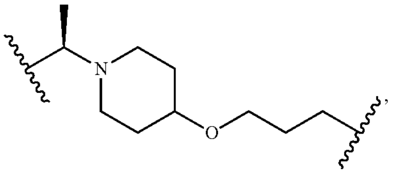 [SMILES: *CCCOC1CCN([C@@H](*)C)CC1]
(364)
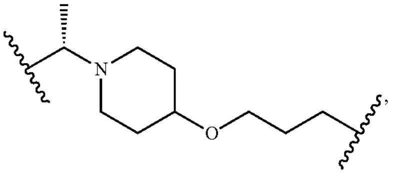 [SMILES: *CCCOC1CCN([C@H](*)C)CC1]
(365)
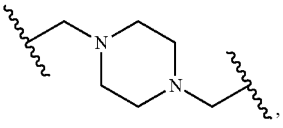 [SMILES: *CN1CCN(C*)CC1]
(366)
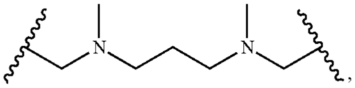 [SMILES: *CN(C)CCCN(C)C*]
(367)
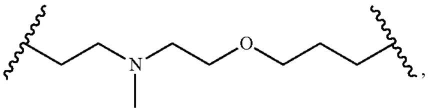 [SMILES: *CCCOCCN(C)CC*]
(368)

TABLE A-continued
Linkers (L')
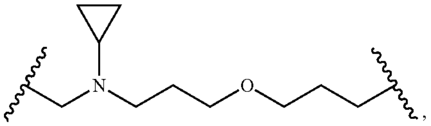 [SMILES: *CCCOCCCN(C*)C1CC1]
(369)
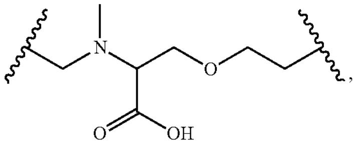 [SMILES: *CCOCC(C(=O)O)N(C)C*]
(370)
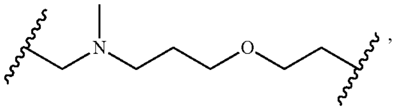 [SMILES: *CCOCCCN(C)C*]
(371)
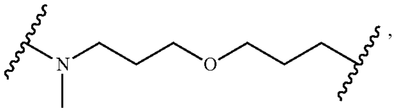 [SMILES: *CCCOCCCN(*)C]
(372)
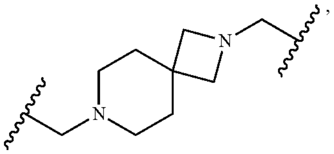 [SMILES: *CN1CCC2(CC1)CN(C*)C2]
(373)
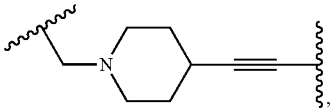
(374)
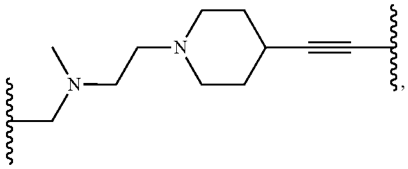 [SMILES: *C#CC1CCN(CCN(C)C*)CC1]
(375)
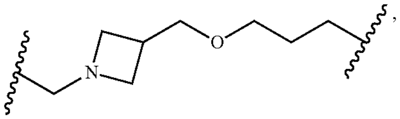 [SMILES: *CCCOCC1CN(C*)C1]
(376)
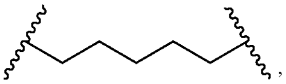 [SMILES: *CCCCC*]
(377)
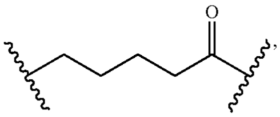
(378)
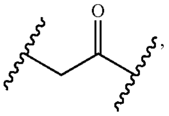 [SMILES: *CC(*)=O]
(379)

TABLE A-continued
| Linkers (L') |
| --- |
| 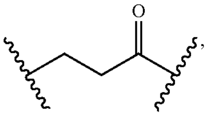 [SMILES: *CCC(*)=O] (380) |
| 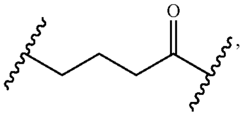 [SMILES: *CCCC(*)=O] (381) |
| 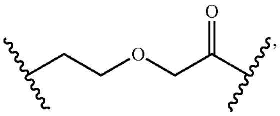 [SMILES: *CCOCC(*)=O] (382) |
| 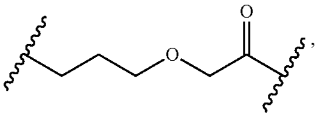 [SMILES: *CCCOCC(*)=O] (383) |
| 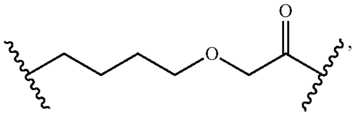 [SMILES: *CCCCOCC(*)=O] (384) |
| 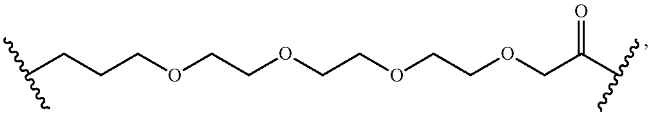 [SMILES: *CCCOCCOCCOCCOCC(*)=O] (385) |
| 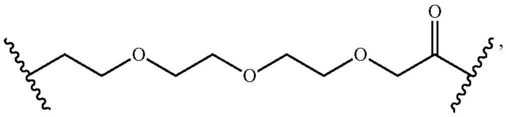 [SMILES: *CCOCCOCCOCC(*)=O] (386) |
| 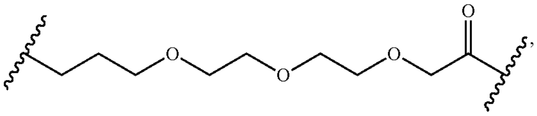 [SMILES: *CCCOCCOCCOCC(*)=O] (387) |
| 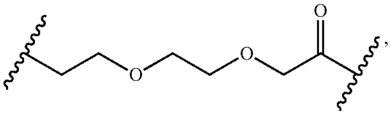 [SMILES: *CCOCCOCC(*)=O] (388) |
| 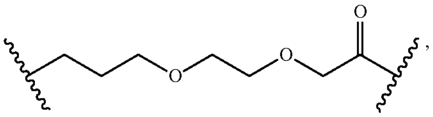 [SMILES: *CCCOCCOCC(*)=O] (389) |
| 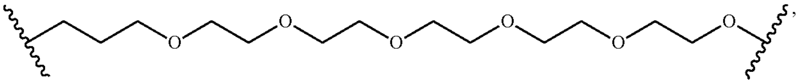 [SMILES: *CCCOCCOCCOCCOCCOCCO*] (390) |
| 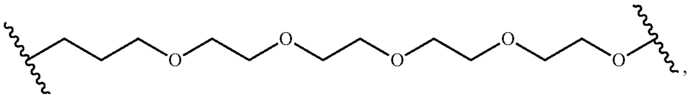 [SMILES: *CCCOCCOCCOCCOCCO*] (391) |

TABLE A-continued
| Linkers (L') | |
|---|---|
| 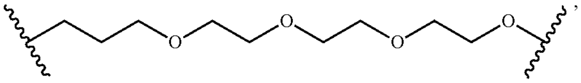 [SMILES: *CCCOCCOCCOCCO*] , | (392) |
| 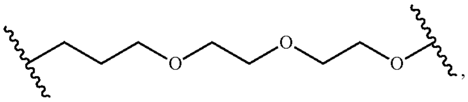 [SMILES: *CCCOCCOCCO*] , | (393) |
| 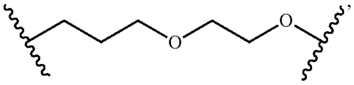 [SMILES: *CCCOCCO*] , | (394) |
| 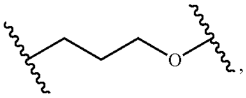 [SMILES: *CCCO*] , | (395) |
| 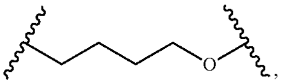 [SMILES: *CCCCO*] , | (396) |
| 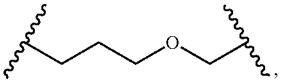 [SMILES: *CCCOC*] , | (397) |
| 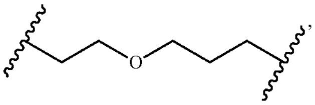 [SMILES: *CCCOCC*] , | (398) |
| 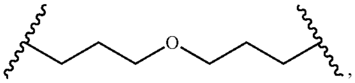 [SMILES: *CCCOCCC*] , | (399) |
| 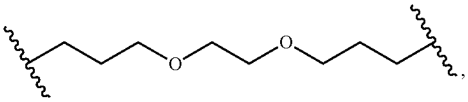 [SMILES: *CCCOCCOCCC*] , | (400) |
| 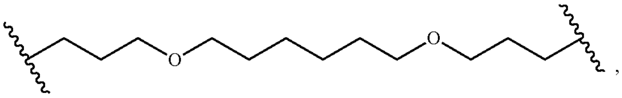 [SMILES: *CCCOCCCCCCOCCC*] , | (401) |
| 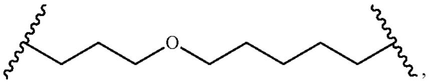 [SMILES: *CCCCCOCCC*] , | (402) |
| 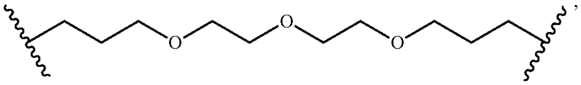 [SMILES: *CCCOCCOCCOCCC*] , | (403) |
| 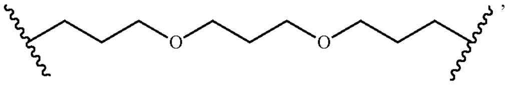 [SMILES: *CCCOCCCOCCC*] , | (404) |
| 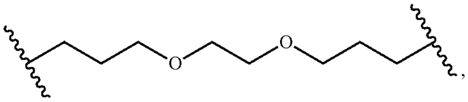 [SMILES: *CCCOCCOCCC*] , | (405) |

TABLE A-continued
Linkers (L')
(406)
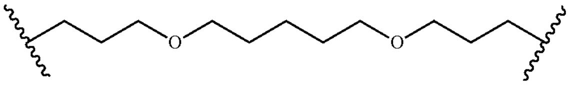,
(407)
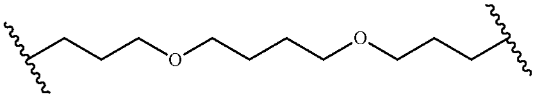,
(408)
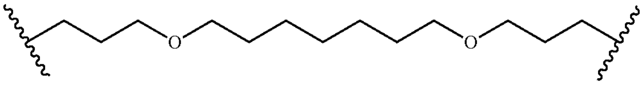,
(409)
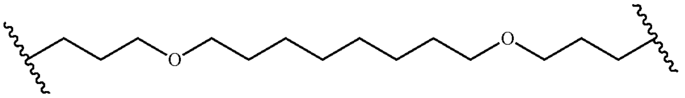,
(410)
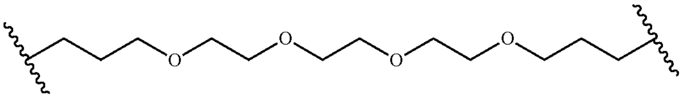,
(411)
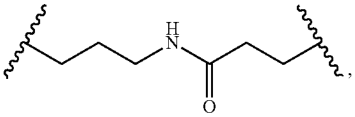 [SMILES: *CCCNC(=O)CC*],
(412)
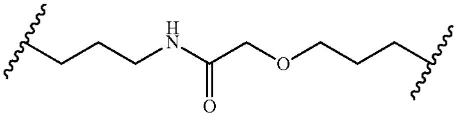,
(413)
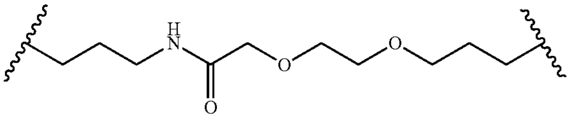,
(414)
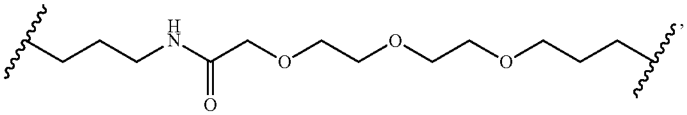 [SMILES: *CCCNC(=O)COCCOCCOCCC*],
(415)
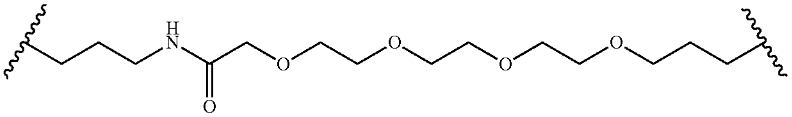,
(416)
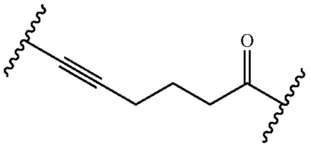,
(417)
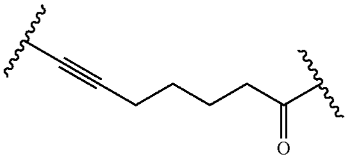, TABLE A-continued
Linkers (L')
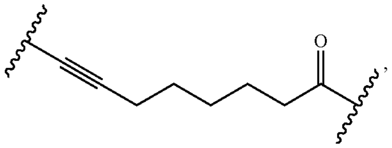 [SMILES: *C#CCCCCCC(*)=O]
(418)
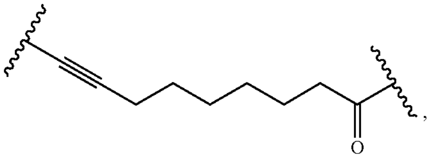 [SMILES: *C#CCCCCCCC(*)=O]
(419)
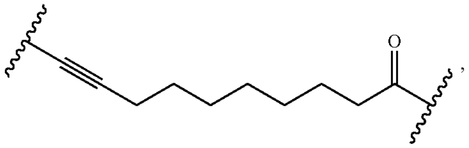 [SMILES: *C#CCCCCCCCC(*)=O]
(420)
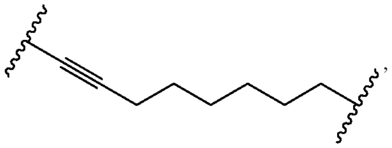 [SMILES: *C#CCCCCCC*]
(421)
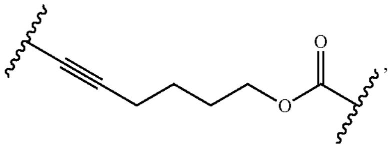 [SMILES: *C#CCCCCOC(*)=O]
(422)
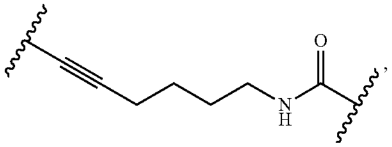 [SMILES: *C#CCCCCNC(*)=O]
(423)
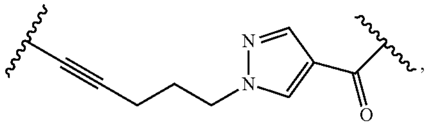 [SMILES: *C#CCCCn1cc(C(*)=O)cn1]
(424)
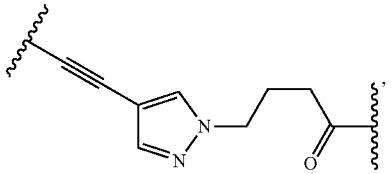 [SMILES: *C#Cc1cnn(CCCC(*)=O)c1]
(425)
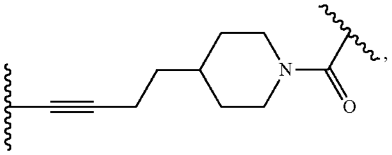 [SMILES: *C#CCCC1CCN(C(*)=O)CC1]
(426)
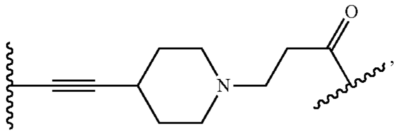 [SMILES: *C#CC1CCN(CCC(*)=O)CC1]
(427)

TABLE A-continued
| Linkers (L') | |
|---|---|
| 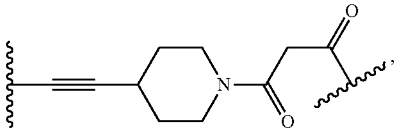 [SMILES: *C#CC1CCN(C(=O)CC(*)=O)CC1] | (428) |
| 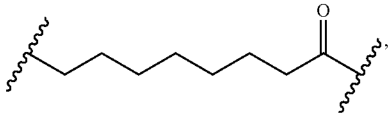 [SMILES: *CCCCCCCC(*)=O] | (429) |
| 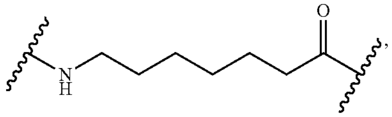 [SMILES: *NCCCCCCC(*)=O] | (430) |
| 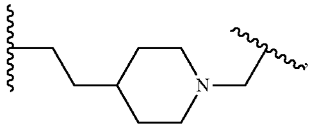 [SMILES: *CCC1CCN(C*)CC1] | (431) |
| 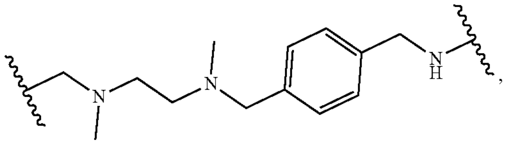 [SMILES: *CN(C)CCN(C)Cc1ccc(CN*)cc1] | (432) |
| 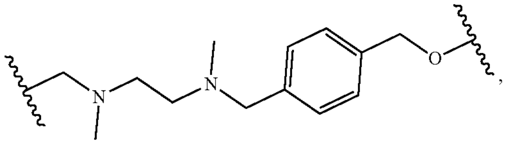 [SMILES: *CN(C)CCN(C)Cc1ccc(CO*)cc1] | (433) |
| 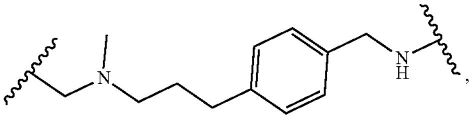 [SMILES: *CN(C)CCCc1ccc(CN*)cc1] | (434) |
| , | (435) |
| 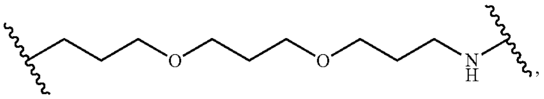 | |
| 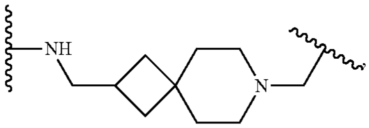 [SMILES: *CN1CCC2(CC1)CC(CN*)C2] | (436) |
| 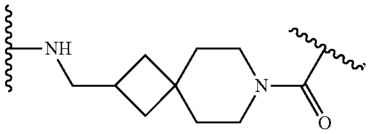 [SMILES: *NCC1CC2(CCN(C(*)=O)CC2)C1] | (437) |

TABLE A-continued
Linkers (L')
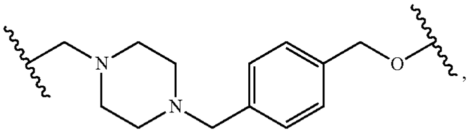 [SMILES: *CN1CCN(Cc2ccc(CO*)cc2)CC1]
(438)
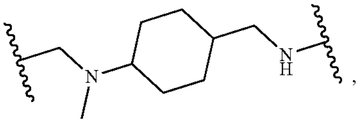 [SMILES: *CN(C)C1CCC(CN*)CC1]
(438)
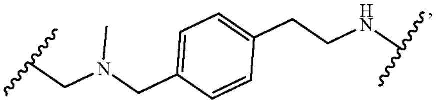 [SMILES: *CN(C)Cc1ccc(CCN*)cc1]
(439)
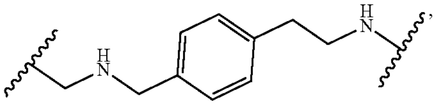 [SMILES: *CNCc1ccc(CCN*)cc1]
(440)
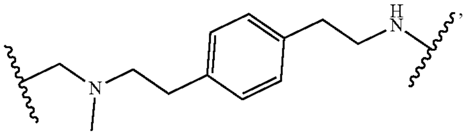 [SMILES: *CN(C)CCc1ccc(CCN*)cc1]
(441)
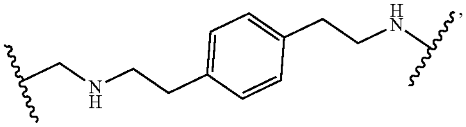 [SMILES: *CNCCc1ccc(CCN*)cc1]
(442)
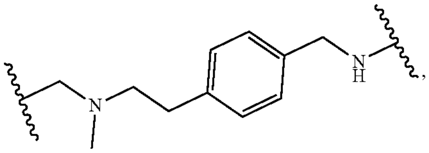 [SMILES: *CN(C)CCc1ccc(CN*)cc1]
(443)
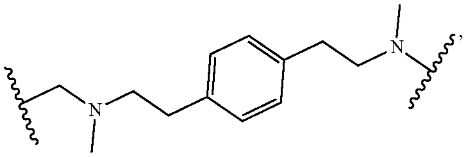 [SMILES: *CN(C)CCc1ccc(CCN(*)C)cc1]
(444)
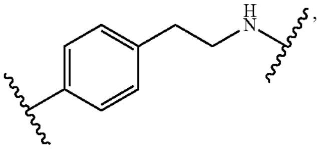 [SMILES: *NCCc1ccc(*)cc1]
(445)
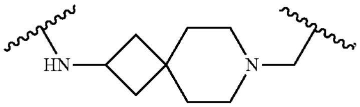 [SMILES: *CN1CCC2(CC1)CC(N*)C2]
(446)
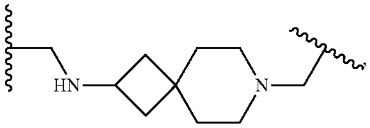 [SMILES: *CNC1CC2(CCN(C*)CC2)C1]
(447)

TABLE A-continued
Linkers (L')
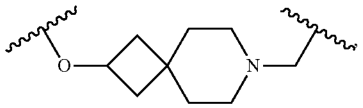 [SMILES: *CN1CCC2(CC1)CC(O*)C2]
(448)
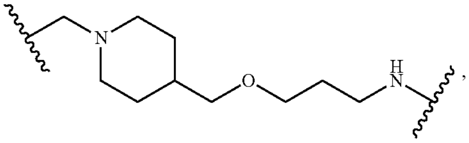 [SMILES: *CN1CCC(COCCCN*)CC1]
(449)
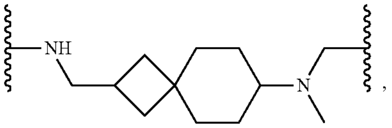 [SMILES: *CN(C)C1CCC2(CC1)CC(CN*)C2]
(450)
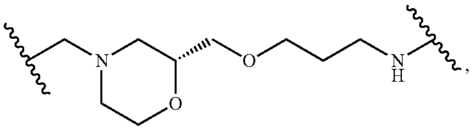 [SMILES: *CN1CCO[C@@H](COCCCN*)C1]
(451)
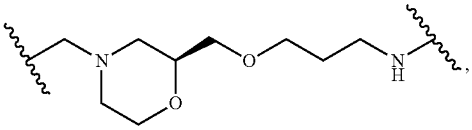 [SMILES: *CN1CCO[C@H](COCCCN*)C1]
(452)
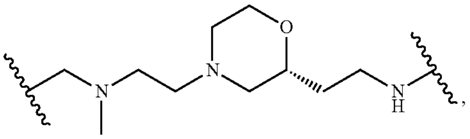 [SMILES: *CN(C)CCN1CCO[C@H](CCN*)C1]
(453)
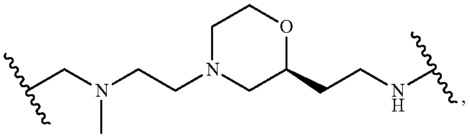 [SMILES: *CN(C)CCN1CCO[C@@H](CCN*)C1]
(454)
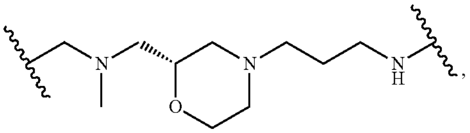 [SMILES: *CN(C)C[C@@H]1CN(CCCN*)CCO1]
(455)
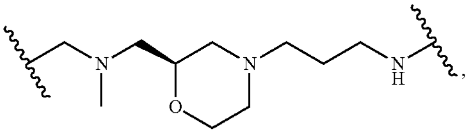 [SMILES: *CN(C)C[C@H]1CN(CCCN*)CCO1]
(456)
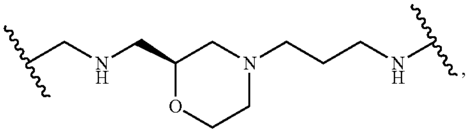 [SMILES: *CNC[C@H]1CN(CCCN*)CCO1]
(457)

TABLE A-continued
| Linkers (L') |
|---|
(458)
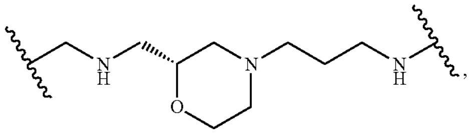 [SMILES: *CNC[C@@H]1CN(CCCN*)CCO1]
,
(459)
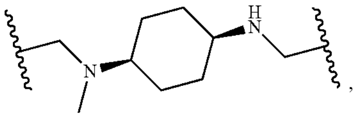 [SMILES: *CN[C@H]1CC[C@@H](N(C)C*)CC1]
,
(460)
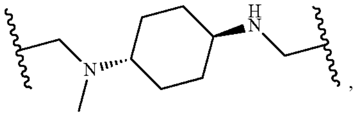 [SMILES: *CN[C@H]1CC[C@H](N(C)C*)CC1]
,
(461)
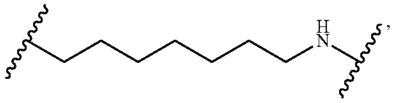 [SMILES: *CCCCCCCN*]
,
(462)
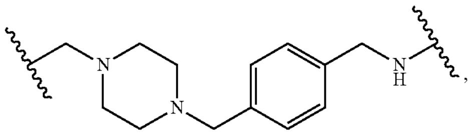 [SMILES: *CN1CCN(Cc2ccc(CN*)cc2)CC1]
,
(463)
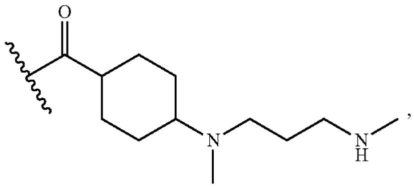 [SMILES: *C(=O)C1CCC(N(C)CCCNC)CC1]
,
(464)
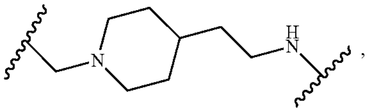 [SMILES: *CN1CCC(CCN*)CC1]
,
(465)
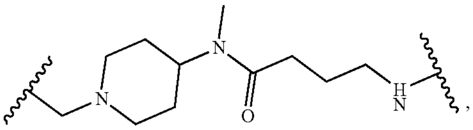 [SMILES: *CN1CCC(N(C)C(=O)CCCN*)CC1]
,
(466)
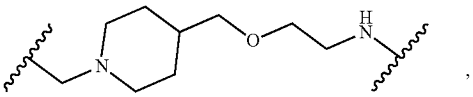 [SMILES: *CN1CCC(COCCN*)CC1]
,
(467)
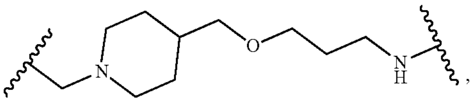 [SMILES: *CN1CCC(COCCCN*)CC1]
,
(468)
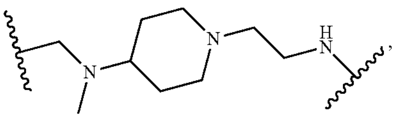 [SMILES: *CN(C)C1CCN(CCN*)CC1]
, TABLE A-continued
Linkers (L')
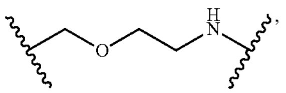 [SMILES: *COCCN*]
(469)
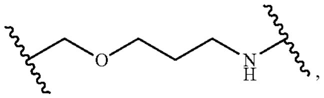 [SMILES: *COCCCN*]
(470)
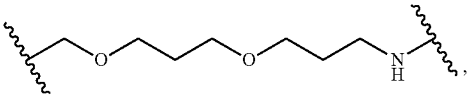 [SMILES: *COCCCOCCCN*]
(471)
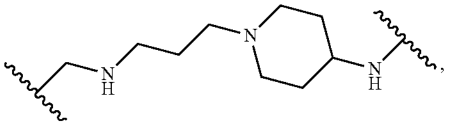 [SMILES: *CNCCCN1CCC(N*)CC1]
(472)
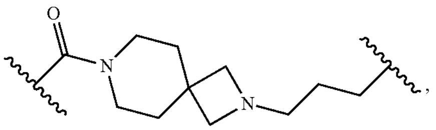 [SMILES: *CCCN1CC2(CCN(C(*)=O)CC2)C1]
(473)
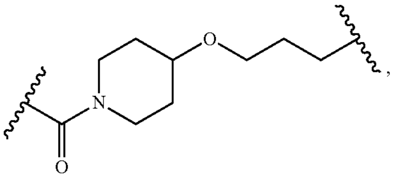 [SMILES: *CCCOC1CCN(C(*)=O)CC1]
(474)
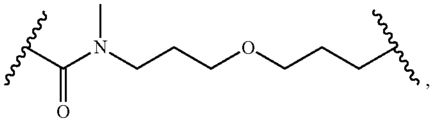 [SMILES: *CCCOCCCN(C)C(*)=O]
(475)
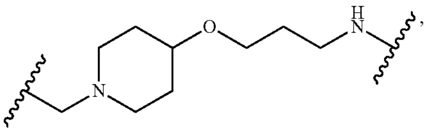 [SMILES: *CN1CCC(OCCCN*)CC1]
(475)
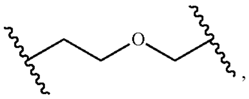 [SMILES: *CCOC*]
(476)
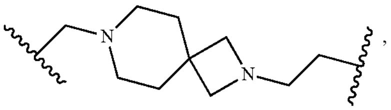 [SMILES: *CCN1CC2(CCN(C*)CC2)C1]
(477)
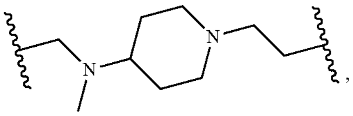 [SMILES: *CCN1CCC(N(C)C*)CC1]
(478)

TABLE A-continued
Linkers (L')
(479)
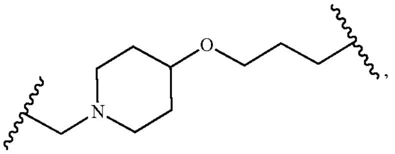 [SMILES: *CCCOC1CCN(C*)CC1]
(480)
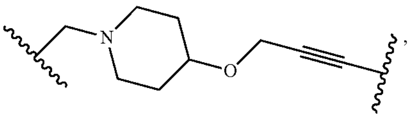 [SMILES: *C#CCOC1CCN(C*)CC1]
(481)
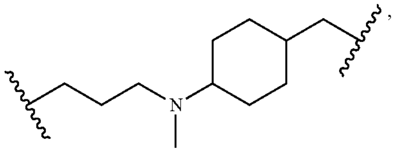 [SMILES: *CCCN(C)C1CCC(C*)CC1]
(482)
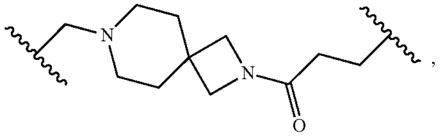 [SMILES: *CCC(=O)N1CC2(CCN(C*)CC2)C1]
(483)
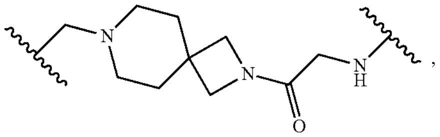 [SMILES: *CN1CCC2(CC1)CN(C(=O)CN*)C2]
(484)
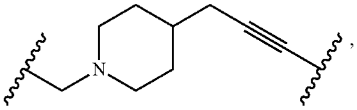 [SMILES: *C#CCC1CCN(C*)CC1]
(485)
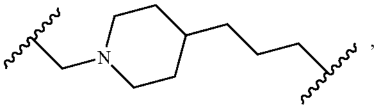 [SMILES: *CCCC1CCN(C*)CC1]
(486)
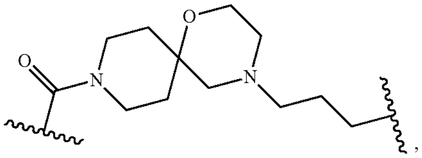 [SMILES: *CCCN1CCOC2(CCN(C(*)=O)CC2)C1]
(487)
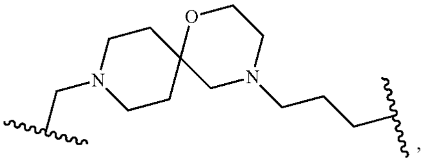 [SMILES: *CCCN1CCOC2(CCN(C*)CC2)C1]
(488)
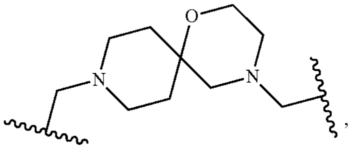 [SMILES: *CN1CCC2(CC1)CN(C*)CCO2]

TABLE A-continued
| Linkers (L') | |
|---|---|
| 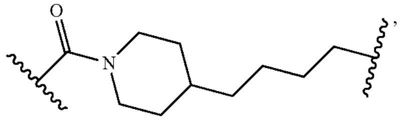 [SMILES: *CCCCC1CCN(C(*)=O)CC1] | (489) |
| 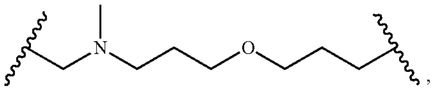 [SMILES: *CCCOCCCN(C)C*] | (490) |
| 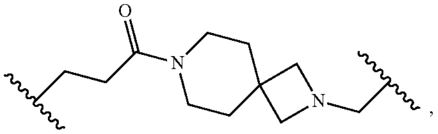 [SMILES: *CCC(=O)N1CCC2(CC1)CN(C*)C2] | (491) |
| 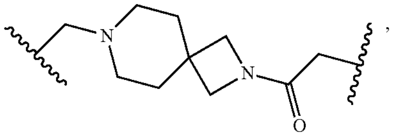 [SMILES: *CC(=O)N1CC2(CCN(C*)CC2)C1] | (492) |
| 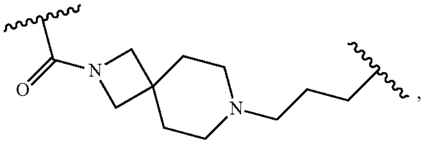 [SMILES: *CCCN1CCC2(CC1)CN(C(*)=O)C2] | (493) |
| 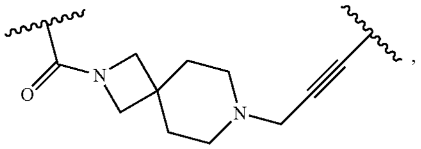 [SMILES: *C#CCN1CCC2(CC1)CN(C(*)=O)C2] | (494) |
| 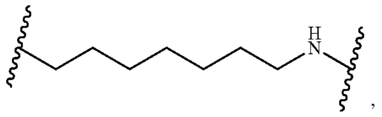 [SMILES: *CCCCCCCN*] | (495) |
| 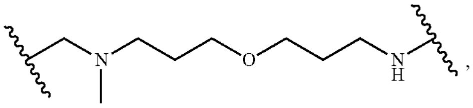 [SMILES: *CN(C)CCCOCCCN*] | (496) |
| 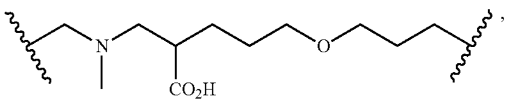 [SMILES: *CCCOCCCC(CN(C)C*)C(=O)O] | (497) |
| 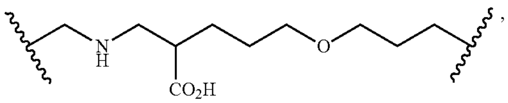 [SMILES: *CCCOCCCC(CNC*)C(=O)O] | (498) |
| 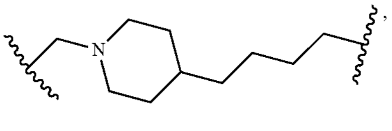 [SMILES: *CCCCC1CCN(C*)CC1] | (499) |

TABLE A-continued
Linkers (L')
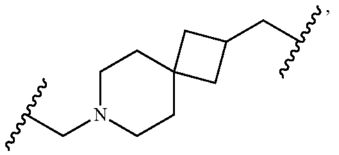 [SMILES: *CC1CC2(CCN(C*)CC2)C1]
(500)
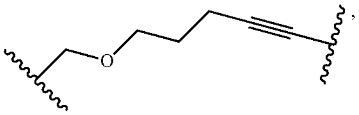 [SMILES: *C#CCCCOC*]
(501)
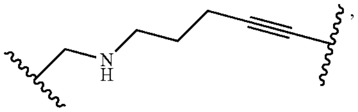 [SMILES: *C#CCCCNC*]
(502)
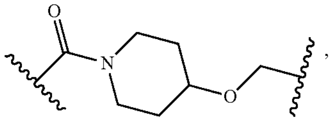 [SMILES: *COC1CCN(C(*)=O)CC1]
(503)
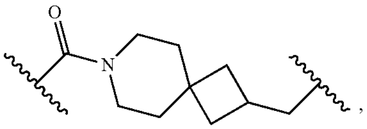 [SMILES: *CC1CC2(CCN(C(*)=O)CC2)C1]
(504)
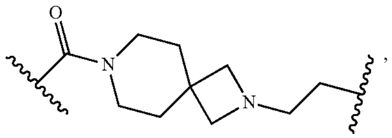 [SMILES: *CCN1CC2(CCN(C(*)=O)CC2)C1]
(505)
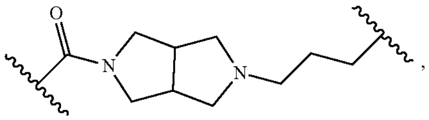 [SMILES: *CCCN1CC2CN(C(*)=O)CC2C1]
(506)
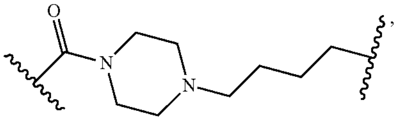 [SMILES: *CCCCN1CCN(C(*)=O)CC1]
(507)
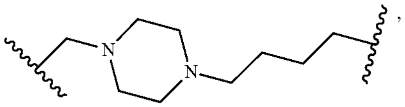 [SMILES: *CCCCN1CCN(C*)CC1]
(508)
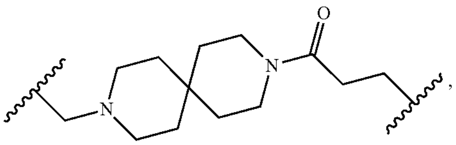 [SMILES: *CCC(=O)N1CCC2(CCN(C*)CC2)CC1]
(509)
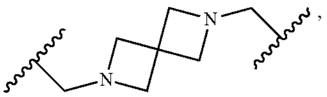 [SMILES: *CN1CC2(C1)CN(C*)C2]
(510)

TABLE A-continued
Linkers (L')
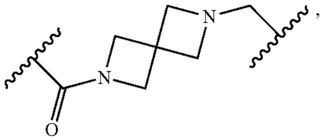 [SMILES: *CN1CC2(C1)CN(C(*)=O)C2]
(511)
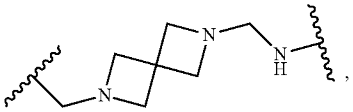 [SMILES: *CN1CC2(C1)CN(CN*)C2]
(512)
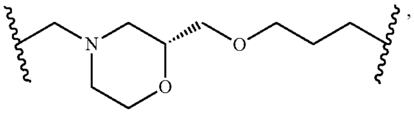 [SMILES: *CCCOC[C@H]1CN(C*)CCO1]
(513)
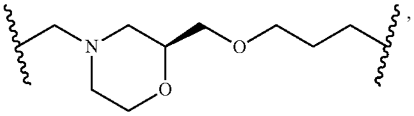 [SMILES: *CCCOC[C@@H]1CN(C*)CCO1]
(514)
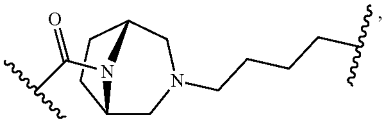 [SMILES: *CCCCN1C[C@H]2CC[C@@H](C1)N2C(*)=O]
(515)
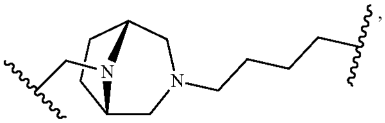 [SMILES: *CCCCN1C[C@H]2CC[C@@H](C1)N2C*]
(516)
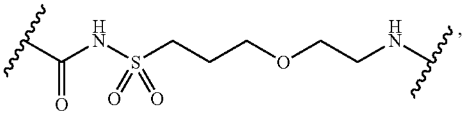 [SMILES: *NCCOCCCS(=O)(=O)NC(*)=O]
(517)
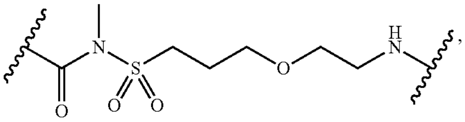 [SMILES: *NCCOCCCS(=O)(=O)N(C)C(*)=O]
(518)
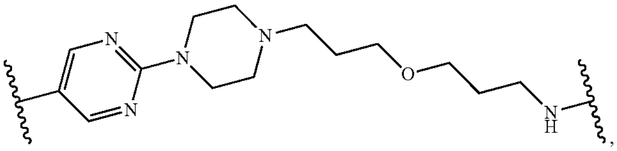 [SMILES: *NCCCOCCCN1CCN(c2ncc(*)cn2)CC1]
(519)
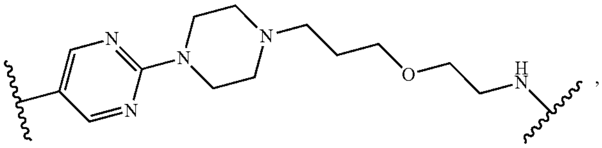 [SMILES: *NCCOCCCN1CCN(c2ncc(*)cn2)CC1]
(520)
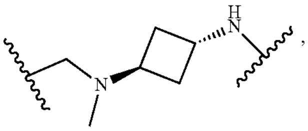 [SMILES: *CN(C)[C@H]1C[C@H](N*)C1]
(521)

TABLE A-continued
| Linkers (L') | |
|---|---|
| 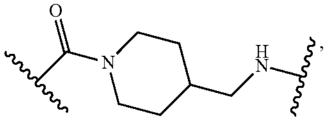 [SMILES: *NCC1CCN(C(*)=O)CC1] | (522) |
| 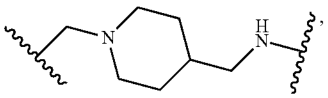 [SMILES: *CN1CCC(CN*)CC1] | (523) |
| 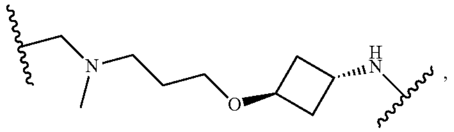 [SMILES: *CN(C)CCCO[C@H]1C[C@H](N*)C1] | (524) |
| 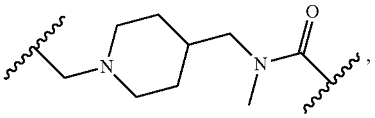 [SMILES: *CN1CCC(CN(C)C(*)=O)CC1] | (525) |
| 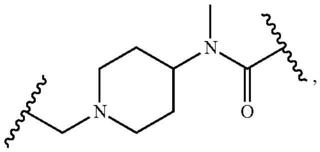 [SMILES: *CN1CCC(N(C)C(*)=O)CC1] | (526) |
| 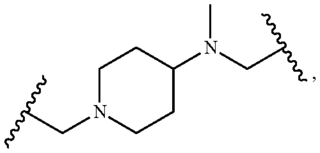 [SMILES: *CN1CCC(N(C)C*)CC1] | (527) |
| 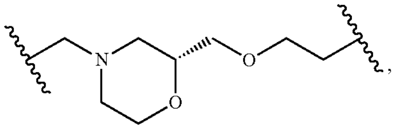 [SMILES: *CCOC[C@H]1CN(C*)CCO1] | (528) |
| 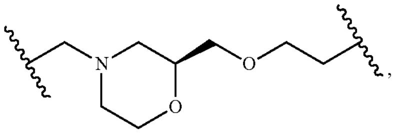 [SMILES: *CCOC[C@@H]1CN(C*)CCO1] | (529) |
| 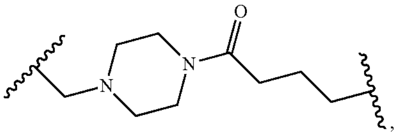 [SMILES: *CCCC(=O)N1CCN(C*)CC1] | (530) |
| 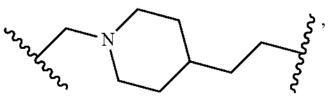 [SMILES: *CCC1CCN(C*)CC1] | (531) |
| 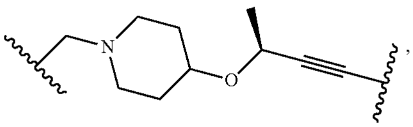 [SMILES: *C#C[C@H](C)OC1CCN(C*)CC1] | (532) |

TABLE A-continued
| Linkers (L') | |
|---|---|
| 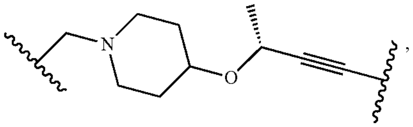 [SMILES: *C#C[C@@H](C)OC1CCN(C*)CC1] | (533) |
| 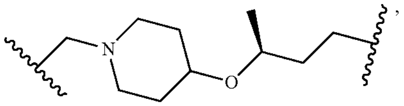 [SMILES: *CC[C@H](C)OC1CCN(C*)CC1] | (534) |
| 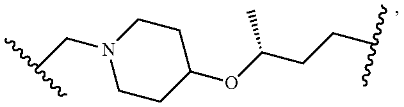 [SMILES: *CC[C@@H](C)OC1CCN(C*)CC1] | (535) |
| 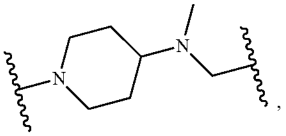 [SMILES: *CN(C)C1CCN(*)CC1] | (536) |
| 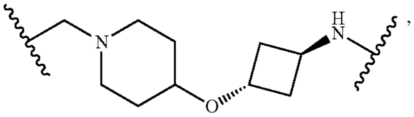 [SMILES: *CN1CCC(O[C@H]2C[C@H](N*)C2)CC1] | (537) |
| 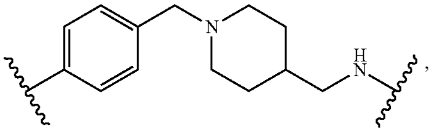 [SMILES: *NCC1CCN(Cc2ccc(*)cc2)CC1] | (538) |
| 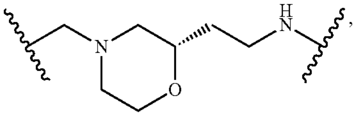 [SMILES: *CN1CCO[C@@H](CCN*)C1] | (539) |
| 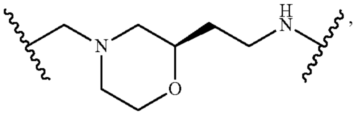 [SMILES: *CN1CCO[C@H](CCN*)C1] | (540) |
| 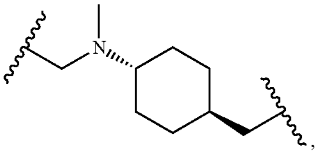 [SMILES: *CN(C)[C@H]1CC[C@H](C*)CC1] | (541) |
| 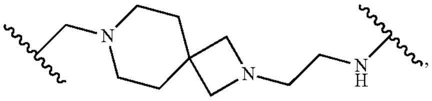 [SMILES: *CN1CCC2(CC1)CN(CCN*)C2] | (542) |
| 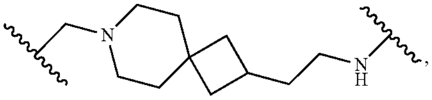 [SMILES: *CN1CCC2(CC1)CC(CCN*)C2] | (543) |

TABLE A-continued
| Linkers (L') | |
|---|---|
| 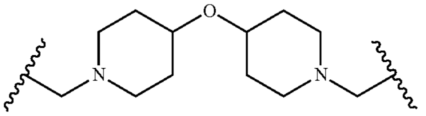, | (544) |
| 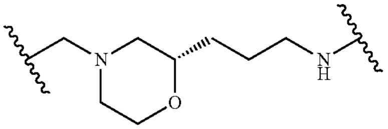, | (545) |
| 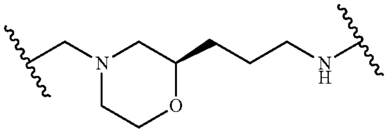, | (546) |
| 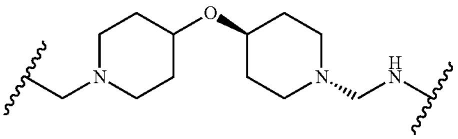, | (547) |
| 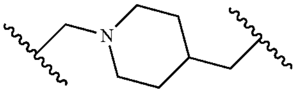, | (548) |
| 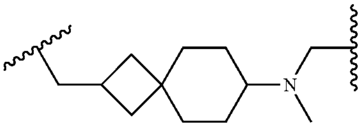, | (549) |
| 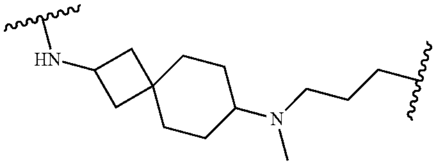, | (550) |
| 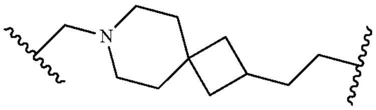, | (551) |
| 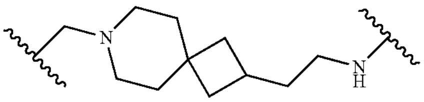, | (552) |
| 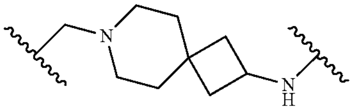 [SMILES: *CN1CCC2(CC1)CC(N*)C2] | (553) |
| 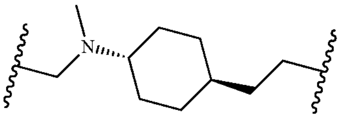, | (554) |

TABLE A-continued
Linkers (L')
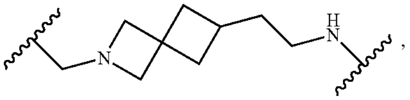 [SMILES: *CN1CC2(CC(CCN*)C2)C1]
(555)
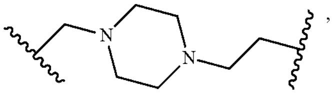 [SMILES: *CCN1CCN(C*)CC1]
(556)
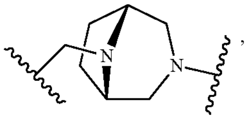 [SMILES: *CN1[C@@H]2CC[C@H]1CN(*)C2]
(557)
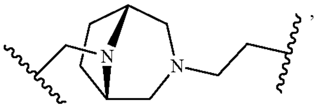 [SMILES: *CCN1C[C@H]2CC[C@@H](C1)N2C*]
(558)
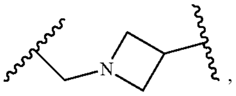 [SMILES: *CN1CC(*)C1]
(559)
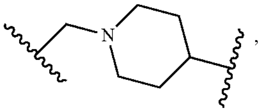 [SMILES: *CN1CCC(*)CC1]
(560)
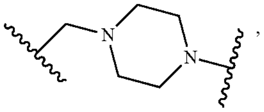 [SMILES: *CN1CCN(*)CC1]
(561)
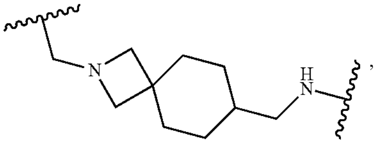 [SMILES: *CN1CC2(CCC(CN*)CC2)C1]
(562)
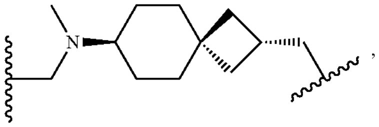
(563)
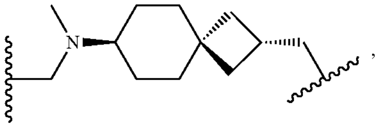
(564)
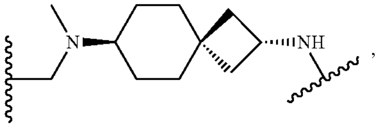
(565)
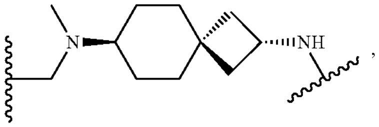
(566)

TABLE A-continued
Linkers (L')
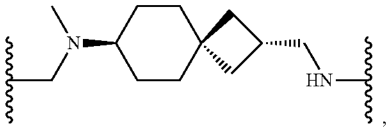
(567)
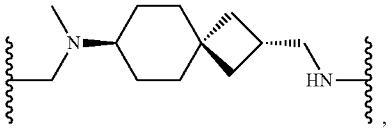
(568)
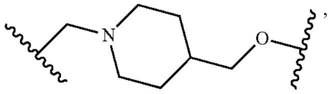 [SMILES: *CN1CCC(CO*)CC1]
(569)
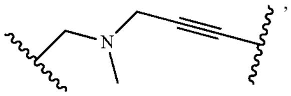 [SMILES: *C#CCN(C)C*]
(570)
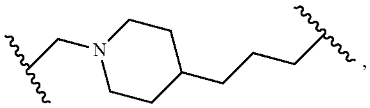 [SMILES: *CCCC1CCN(C*)CC1]
(571)
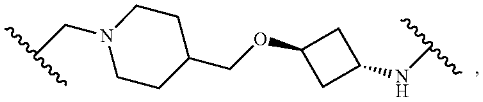 [SMILES: *CN1CCC(CO[C@H]2C[C@H](N*)C2)CC1]
(572)
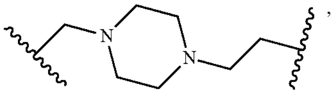 [SMILES: *CCN1CCN(C*)CC1]
(573)
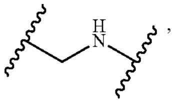
(574)
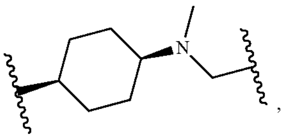 [SMILES: *CN(C)[C@H]1CC[C@@H](*)CC1]
(575)
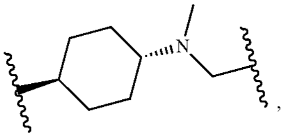 [SMILES: *CN(C)[C@H]1CC[C@H](*)CC1]
(576)
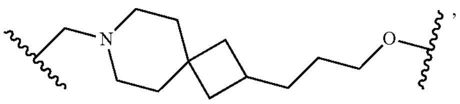 [SMILES: *CN1CCC2(CC1)CC(CCCO*)C2]
(577)
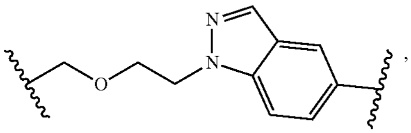 [SMILES: *COCCn1ncc2cc(*)ccc21]
(578)

TABLE A-continued
| Linkers (L') |
|---|
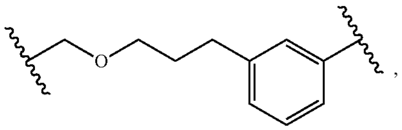 [SMILES: *COCCCc1cccc(*)c1]
(579)
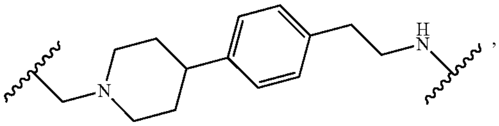 [SMILES: *CN1CCC(c2ccc(CCN*)cc2)CC1]
(580)
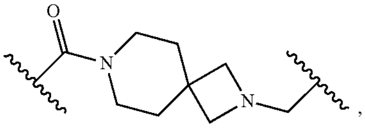 [SMILES: *CN1CC2(CCN(C(*)=O)CC2)C1]
(581)
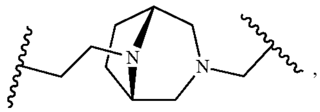 [SMILES: *CCN1[C@@H]2CC[C@H]1CN(C*)C2]
(582)
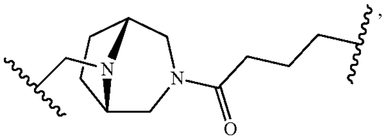 [SMILES: *CCCC(=O)N1C[C@H]2CC[C@@H](C1)N2C*]
(583)
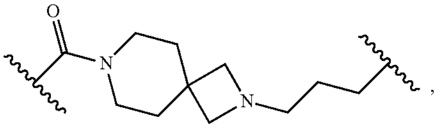 [SMILES: *CCCN1CC2(CCN(C(*)=O)CC2)C1]
(584)
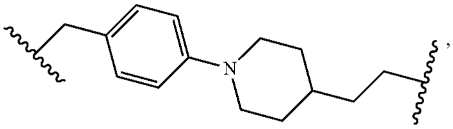 [SMILES: *CCC1CCN(c2ccc(C*)cc2)CC1]
(585)
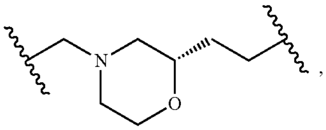 [SMILES: *CC[C@H]1CN(C*)CCO1]
(586)
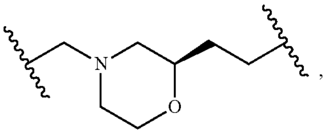 [SMILES: *CC[C@@H]1CN(C*)CCO1]
(587)
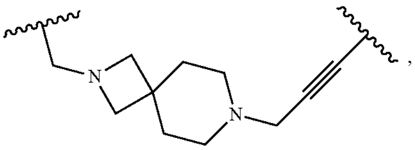 [SMILES: *C#CCN1CCC2(CC1)CN(C*)C2]
(588)

TABLE A-continued
Linkers (L')
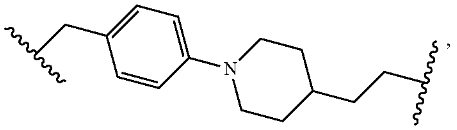 [SMILES: *CCC1CCN(c2ccc(C*)cc2)CC1]
(589)
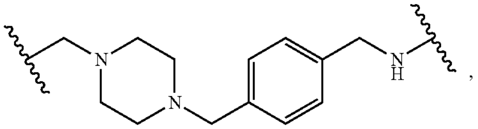 [SMILES: *CN1CCN(Cc2ccc(CN*)cc2)CC1]
(590)
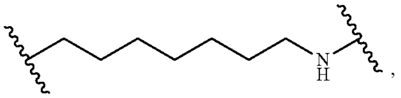 [SMILES: *CCCCCCCN*]
(591)
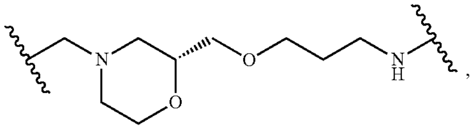 [SMILES: *CN1CCO[C@@H](COCCCN*)C1]
(592)
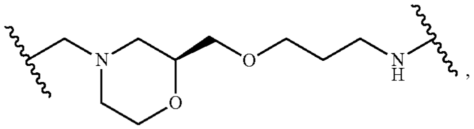 [SMILES: *CN1CCO[C@H](COCCCN*)C1]
(593)
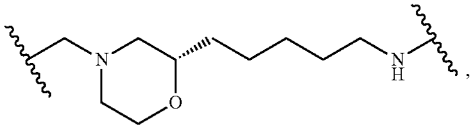 [SMILES: *CN1CCO[C@@H](CCCCCN*)C1]
(594)
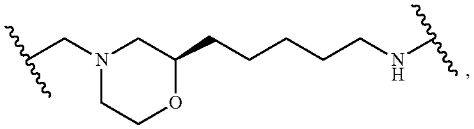 [SMILES: *CN1CCO[C@H](CCCCCN*)C1]
(595)
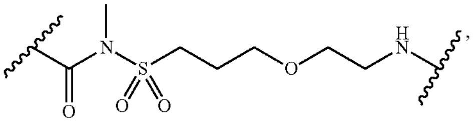 [SMILES: *NCCOCCCS(=O)(=O)N(C)C(*)=O]
(596)
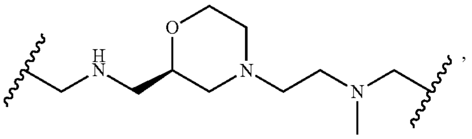 [SMILES: *CNC[C@@H]1CN(CCN(C)C*)CCO1]
(597)
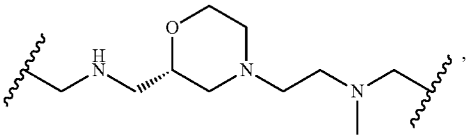 [SMILES: *CNC[C@H]1CN(CCN(C)C*)CCO1]
(598)
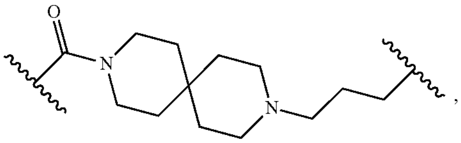 [SMILES: *CCCN1CCC2(CC1)CCN(C(*)=O)CC2]
(599)

TABLE A-continued
Linkers (L')
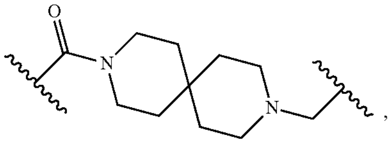 [SMILES: *CN1CCC2(CC1)CCN(C(*)=O)CC2]
(600)
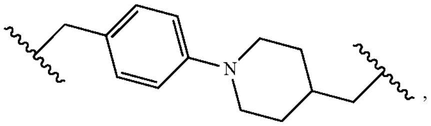 [SMILES: *Cc1ccc(N2CCC(C*)CC2)cc1]
(601)
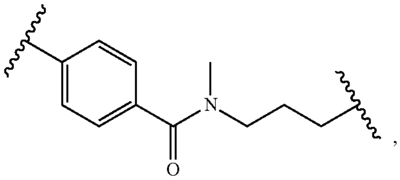 [SMILES: *CCCN(C)C(=O)c1ccc(*)cc1]
(602)
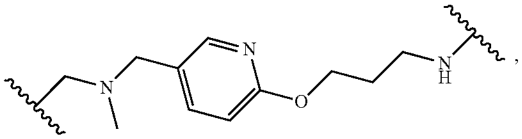 [SMILES: *CN(C)Cc1ccc(OCCCN*)nc1]
(603)
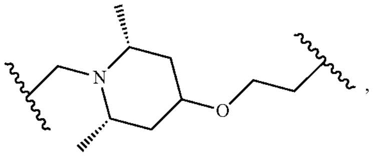 [SMILES: *CCOC1C[C@@H](C)N(C*)[C@@H](C)C1]
(604)
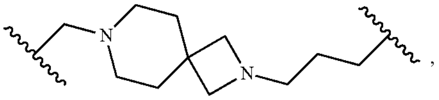 [SMILES: *CCCN1CC2(CCN(C*)CC2)C1]
(605)
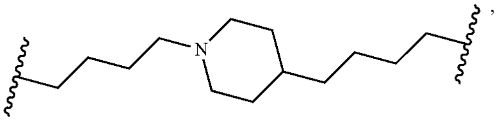 [SMILES: *CCCCC1CCN(CCCC*)CC1]
(606)
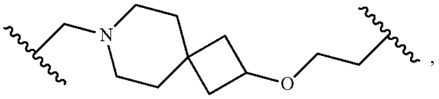 [SMILES: *CCOC1CC2(CCN(C*)CC2)C1]
(607)
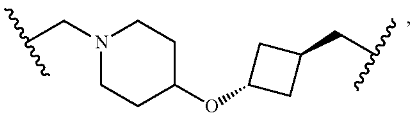 [SMILES: *CN1CCC(O[C@H]2C[C@H](C*)C2)CC1]
(608)
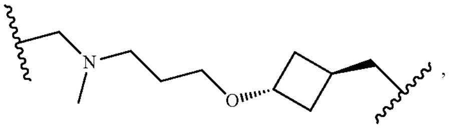 [SMILES: *CN(C)CCCO[C@H]1C[C@H](C*)C1]
(609)
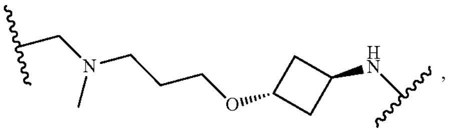 [SMILES: *CN(C)CCCO[C@H]1C[C@H](N*)C1]
(610)

TABLE A-continued

| Linkers (L') | |
|---|---|
| 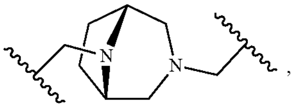 [SMILES: *CN1C[C@H]2CC[C@@H](C1)N2C*] | (611) |
| 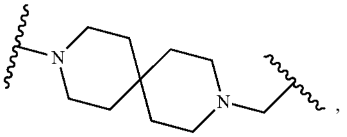 [SMILES: *CN1CCC2(CCN(*)CC2)CC1] | (612) |
| 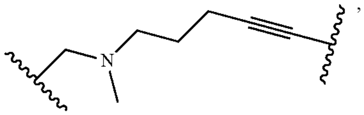 [SMILES: *C#CCCCN(C)C*] | (613) |
| 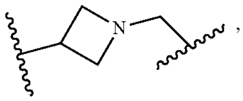 [SMILES: *CN1CC(*)C1] | (614) |
| 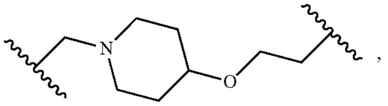 [SMILES: *CCOC1CCN(C*)CC1] | (615) |
| 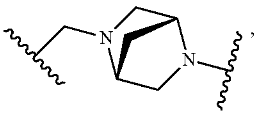 [SMILES: *CN1C[C@H]2C[C@@H]1CN2*] | (616) |
| 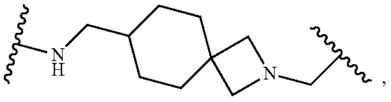 [SMILES: *CN1CC2(CCC(CN*)CC2)C1] | (617) |
| 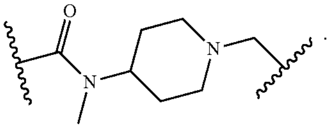 [SMILES: *CN1CCC(N(C)C(*)=O)CC1] | (618) |

From the foregoing, it will be understood that, unless specified, as for example by "*", when a value for L' is asymmetric (e.g., —C(O)N(H)—), the value can be oriented between KRASi and Degron in either direction. Thus, for example, unless specified, —C(O)N(H)— can be oriented so as to produce a compound of either of the following structural formulas: [KRASi]—C(O)N(H)-[Degron] or [KRASi]—N(H)C(O)-[Degron]. Recitation of —C(O)N(H)—*, wherein * indicates the point of attachment of L' to Degron, can be used to describe a compound of the following structural formula: [KRASi]—C(O)N(H)-[Degron].

Degrons

Degrons bring the ligase enzyme into close contact with the target protein, enabling the protein to be labelled with a ubiquitin tag and targeted for degradation by the ubiquitin-proteasome system "Degron," as used herein, refers to a moiety that is capable, under suitable conditions (e.g., in vitro, in vivo), of promoting degradation of a target protein, such as KRAS, via the ubiquitin proteasome pathway (UPP). Typically, in a PROTAC, such as a compound of the disclosure, a degron is capable of binding an ubiquitin E3 ligase, thereby recruiting the ubiquitin E3 ligase into the vicinity of the PROTAC and, by extension, the target protein, which, under suitable conditions, binds to the KRASi in a compound of the disclosure. Formation of the ternary ligase-PROTAC-target protein complex leads to ubiquitination and degradation of the target protein, for example, by the 26S proteasome, a component of the UPP. Examples of degrons therefore include ubiquitin E3 ligase binding moieties, which bind to an ubiquitin E3 ligase. Examples of E3 ligases include cereblon (CRBN), von Hippel-Lindau (VHL), inhibitors of apoptosis proteins (IAP), mouse double minute 2 homolog (MDM2), DDB1- and CUL4-associated factor 16 (DCAF16) and ring finger protein 114 (RNF114). Other examples of degrons include hydrogen atoms and lysine mimetics, both of which are disclosed in International Publication No. WO 2021/127278, the entire content of which is incorporated herein.

In some aspects (e.g., of any of the foregoing embodiments, aspects or combinations of aspects), Degron is a ubiquitin E3 ligase binding moiety (e.g., a cereblon binding moiety). In further aspects, the ubiquitin E3 ligase is CRBN, VHL, IAP, MDM2, DCAF16 or RNF114. In yet further aspects, the ubiquitin E3 ligase is CRBN, as when the ubiquitin E3 ligase binding moiety is a cereblon binding moiety. Thus, in some aspects, Degron is a cereblon binding moiety.

Ubiquitin E3 ligase binding moieties, including cereblon binding moieties, are disclosed in International Publication No. WO 2021/127278. See, for example, Table A therein. In some aspects (e.g., of any of the foregoing embodiments, aspects or combinations of aspects), Degron is a ubiquitin E3 ligase binding moiety (e.g., cereblon binding moiety) disclosed in WO 2021/127278.

Cereblon binding moieties are also disclosed in U.S. Pat. No. 10,849,982; and U.S. Patent Application Publication Nos. US 2020/0140456 and US 2020/0377469. In some aspects (e.g., of any of the foregoing embodiments, aspects or combinations of aspects), Degron is a cereblon binding moiety disclosed in U.S. Pat. No. 10,849,982, or U.S. Patent Application Publication No. US 2020/0140456 or US 2020/0377469.

In some aspects (e.g., of any of the foregoing embodiments, aspects or combinations of aspects), Degron is

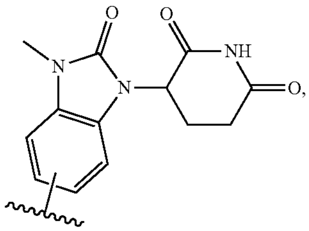
,

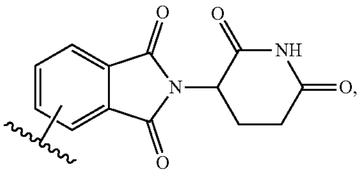
,

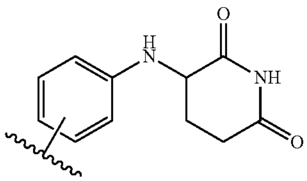

(e.g.,
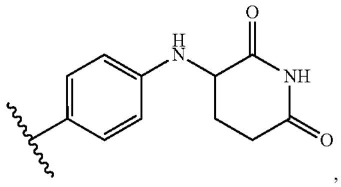
,

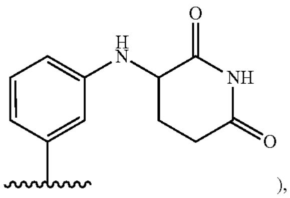
),

-continued

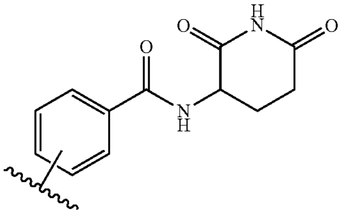

(e.g.,
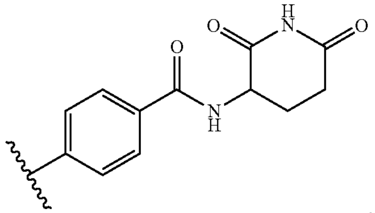
,

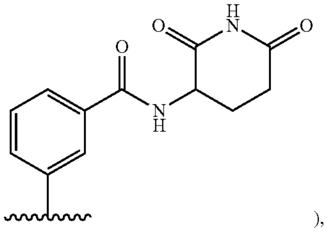
),

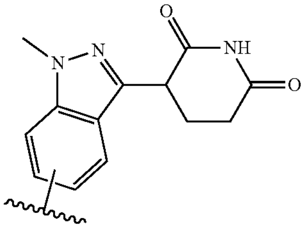

(e.g.,
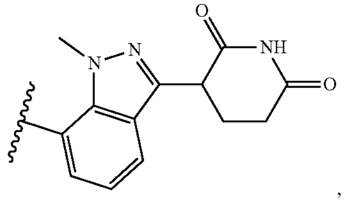
,

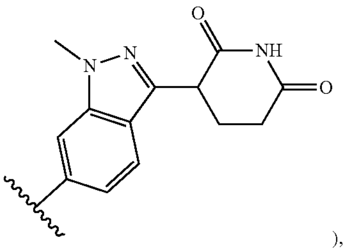
), or

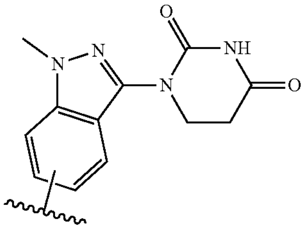

-continued
(e.g., 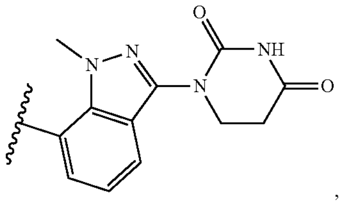 ,
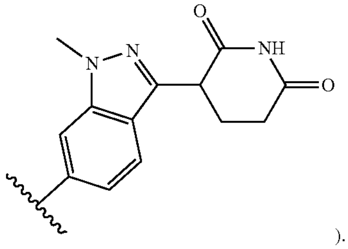 ).
In some aspects (e.g., of any of the foregoing embodiments, aspects or combinations of aspects), Degron is
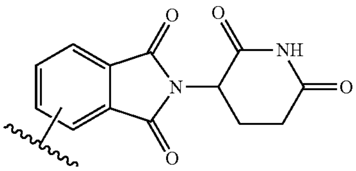 or
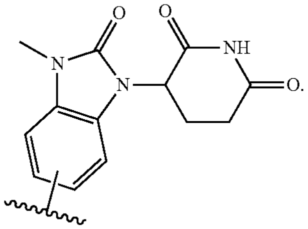
In further aspects, Degron is
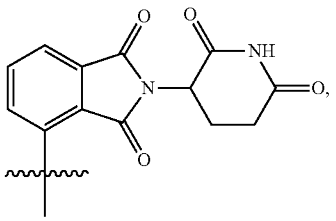
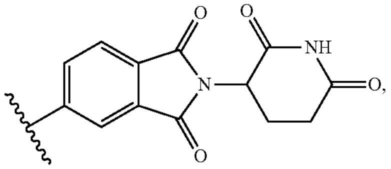
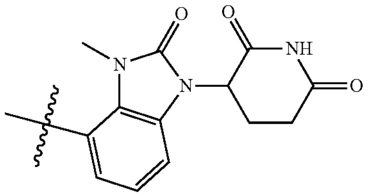 or
-continued
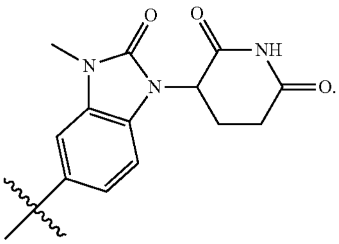
In some aspects (e.g., of any of the foregoing embodiments, aspects or combination of aspects), Degron is
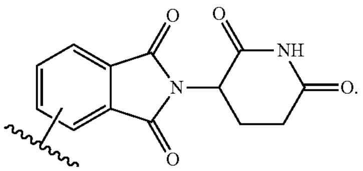
In further aspects, Degron is
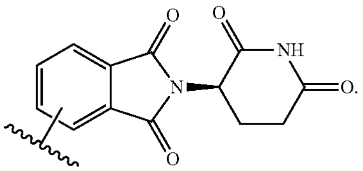
In yet further aspects, Degron is
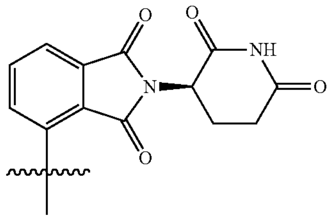 [SMILES: *c1cccc2c1C(=O)N([C@@H]1CCC(=O)NC1=O)C2=O]
or
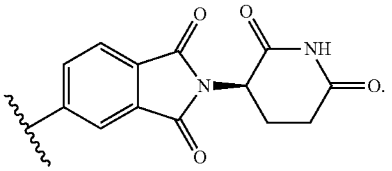 [SMILES: *c1ccc2c(c1)C(=O)N([C@@H]1CCC(=O)NC1=O)C2=O]

In other aspects, Degron is

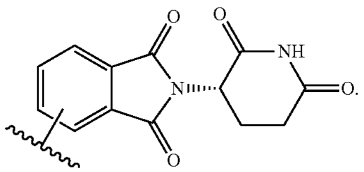

In further aspects, Degron is

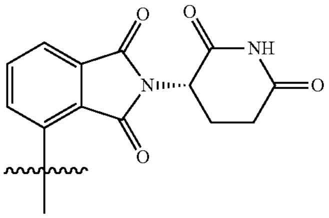

or

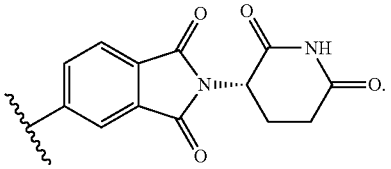

In some aspects (e.g., of any of the foregoing embodiments, aspects or combination of aspects), Degron is

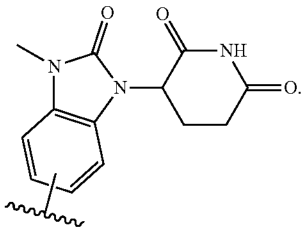

In further aspects, Degron is

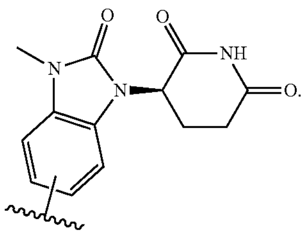

In yet further aspects, Degron is

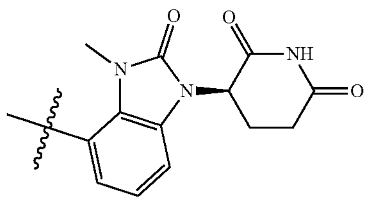

or

-continued

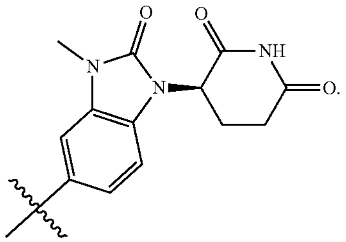

In other aspects, Degron is

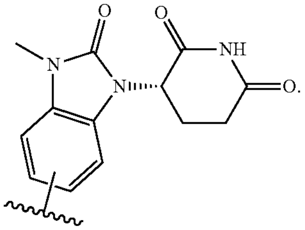

In further aspects, Degron is

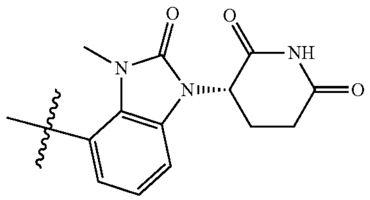

or

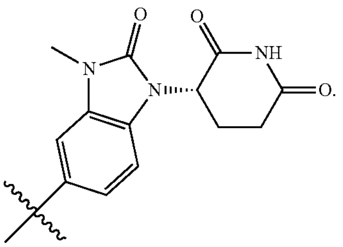

In some aspects (e.g., of any of the foregoing embodiments, aspects or combinations of aspects), Degron is

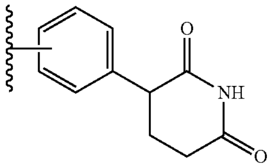

or

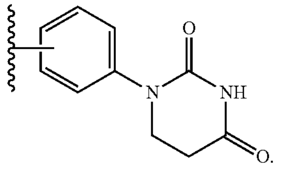

In further aspects, Degron is

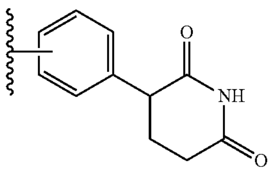

(e.g.,

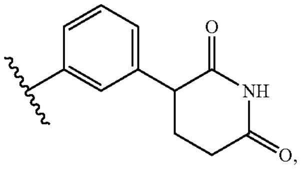

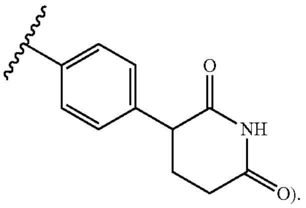

In other aspects, Degron is

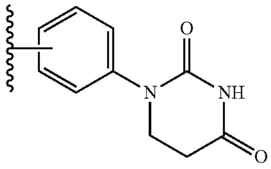

(e.g.,

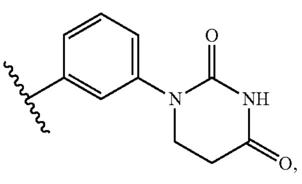

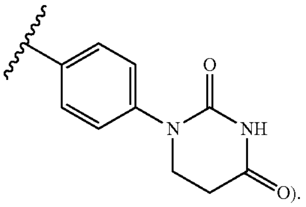

In some aspects (e.g., of any of the foregoing embodiments, aspects or combination of aspects), Degron is

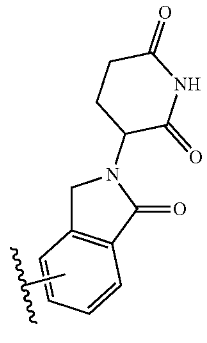

or

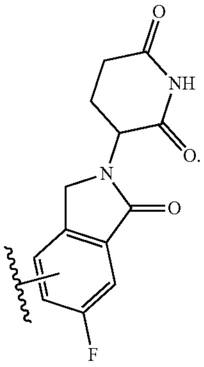

In any of the Degron structures containing a benzene ring (e.g., any of the foregoing Degron structures), it will be appreciated that one or more hydrogen atoms of the benzene ring may be substituted, as, for example, in the following structural formula:

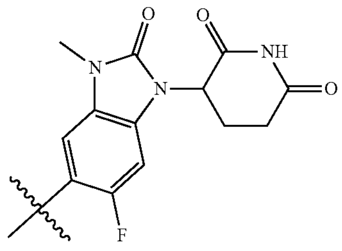

or

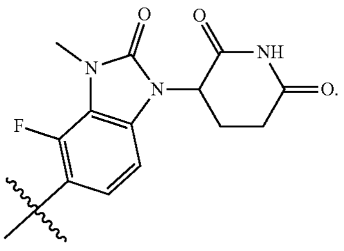

Where indicated, such substitutions are encompassed by this disclosure. Thus, in some aspects, one or more hydrogen atoms (e.g., 1-4; 1-3; 1 or 2) on the benzene ring of Degron is optionally replaced with a fluorine atom. In some aspects, one hydrogen atom on the benzene ring of Degron is replaced with a fluorine atom. In some aspects, two hydrogen atoms on the benzene ring of Degron are replaced with a fluorine atom. In some aspects, three hydrogen atoms on the benzene ring of Degron are replaced with a fluorine atom. In some aspects, the benzene ring of Degron is perfluorinated. In some aspects, the benzene ring of Degron is unsubstituted.

Other specific examples of ubiquitin E3 ligase binding moieties include those depicted in Table B. In some aspects, Degron is a ubiquitin E3 ligase binding moiety in Table B.

TABLE B
| Ubiquitin E3 ligase binding moieties | |
| --- | --- |
| 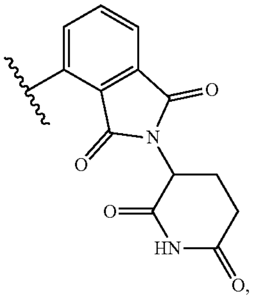 [SMILES: *c1cccc2c1C(=O)N(C1CCC(=O)NC1=O)C2=O] | (a) |
| 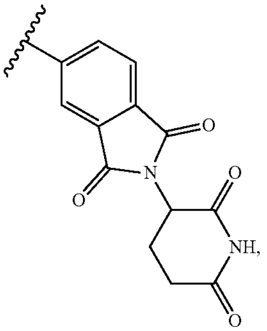 [SMILES: *c1ccc2c(c1)C(=O)N(C1CCC(=O)NC1=O)C2=O] | (b) |
| 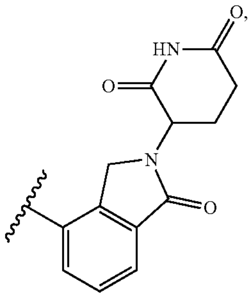 [SMILES: *c1cccc2c1CN(C1CCC(=O)NC1=O)C2=O] | (c) |
| 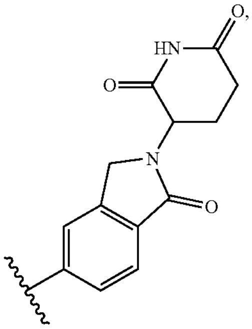 [SMILES: *c1ccc2c(c1)CN(C1CCC(=O)NC1=O)C2=O] | (d) |
| 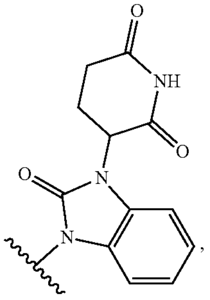 [SMILES: *n1c(=O)n(C2CCC(=O)NC2=O)c2ccccc21] | (e) |

TABLE B-continued
| Ubiquitin E3 ligase binding moieties |
| --- |
| 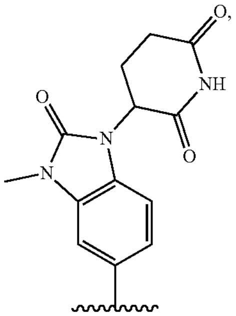 [SMILES: *c1ccc2c(c1)n(C)c(=O)n2C1CCC(=O)NC1=O] (f) |
| 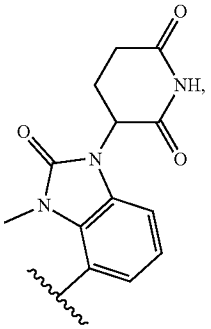 [SMILES: *c1cccc2c1n(C)c(=O)n2C1CCC(=O)NC1=O] (g) |
| 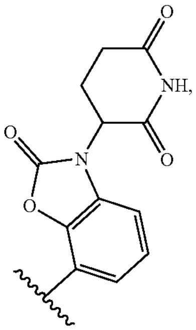 [SMILES: *c1cccc2c1oc(=O)n2C1CCC(=O)NC1=O] (h) |
| 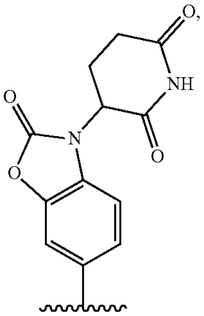 [SMILES: *c1ccc2c(c1)oc(=O)n2C1CCC(=O)NC1=O] (i) |

TABLE B-continued
| Ubiquitin E3 ligase binding moieties | |
| --- | --- |
| 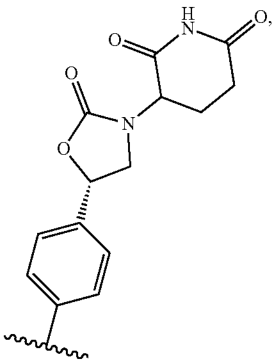 [SMILES: *c1ccc([C@H]2CN(C3CCC(=O)NC3=O)C(=O)O2)cc1] | (j) |
| 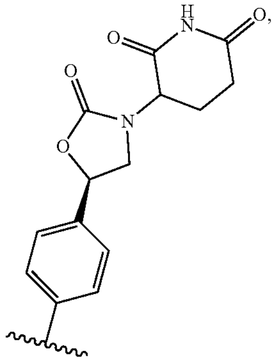 [SMILES: *c1ccc([C@@H]2CN(C3CCC(=O)NC3=O)C(=O)O2)cc1] | (k) |
| 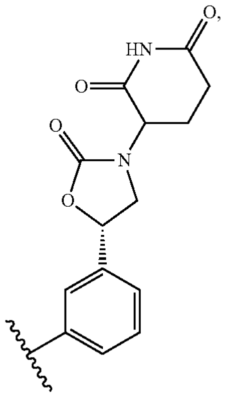 [SMILES: *c1cccc([C@H]2CN(C3CCC(=O)NC3=O)C(=O)O2)c1] | (l) |
| 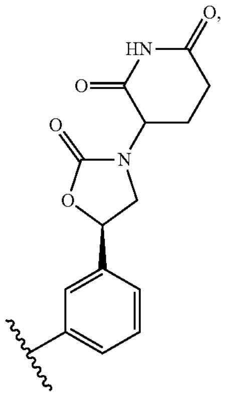 [SMILES: *c1cccc([C@@H]2CN(C3CCC(=O)NC3=O)C(=O)O2)c1] | (m) |

TABLE B-continued
| Ubiquitin E3 ligase binding moieties |
| --- |
| 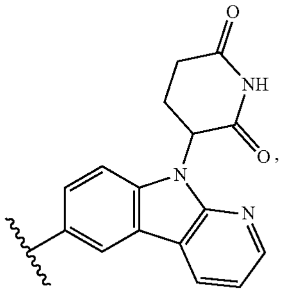 [SMILES: *c1ccc2c(c1)c1cccnc1n2C1CCC(=O)NC1=O] (n) |
| 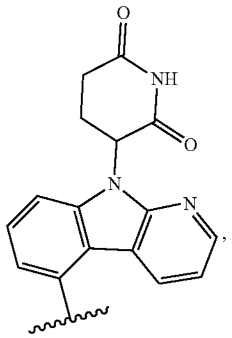 [SMILES: *c1cccc2c1c1cccnc1n2C1CCC(=O)NC1=O] (o) |
| 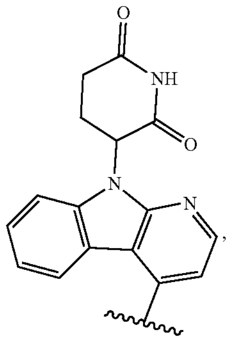 [SMILES: *c1ccnc2c1c1ccccc1n2C1CCC(=O)NC1=O] (p) |
| 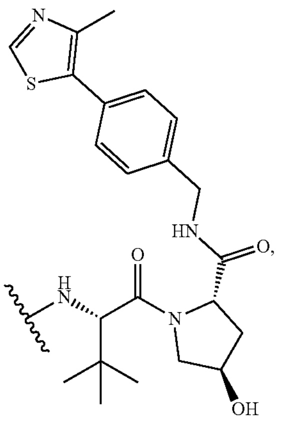 [SMILES: *N[C@H](C(=O)N1C[C@H](O)C[C@H]1C(=O)NCc1ccc(-c2scnc2C)cc1)C(C)(C)C] (q) |

TABLE B-continued
| Ubiquitin E3 ligase binding moieties |
|---|
| 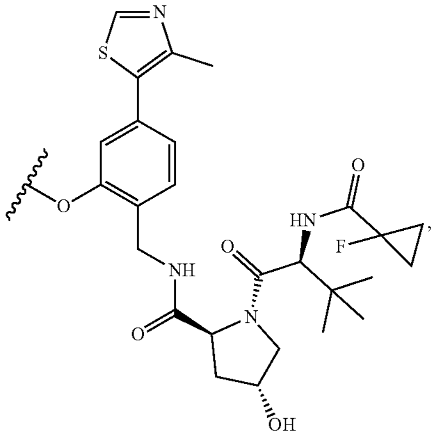 (n) |
| 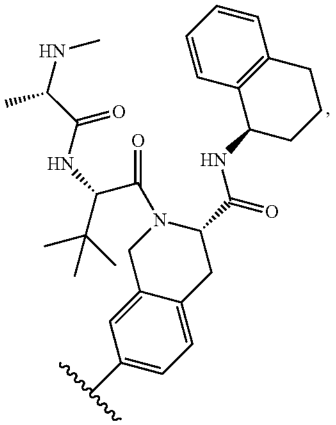 [SMILES: *c1ccc2c(c1)CN(C(=O)[C@@H](NC(=O)[C@H](C)NC)C(C)(C)C)[C@H](C(=O)N[C@@H]1CCCc3ccccc31)C2] (o) |
| 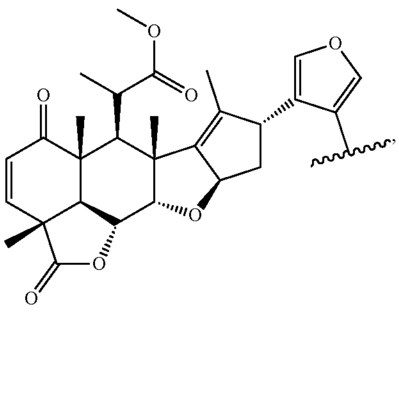 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45] (p) |

TABLE B-continued
| Ubiquitin E3 ligase binding moieties |
| --- |
(q)
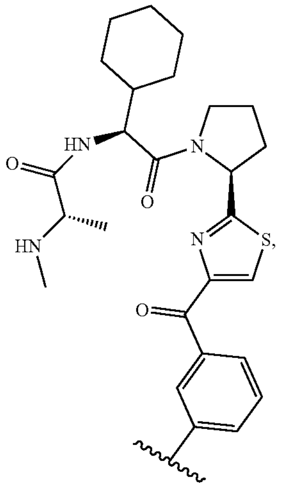 [SMILES: *c1cccc(C(=O)c2csc([C@@H]3CCCN3C(=O)[C@@H](NC(=O)[C@H](C)NC)C3CCCCC3)n2)c1]
(r)
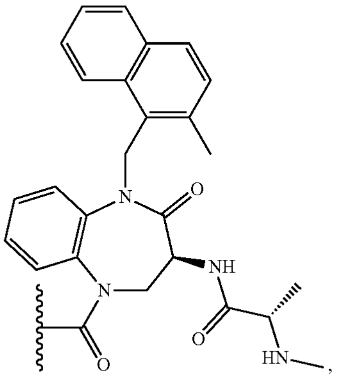 [SMILES: *C(=O)N1C[C@H](NC(=O)[C@H](C)NC)C(=O)N(Cc2c(C)ccc3ccccc23)c2ccccc21]
(s)
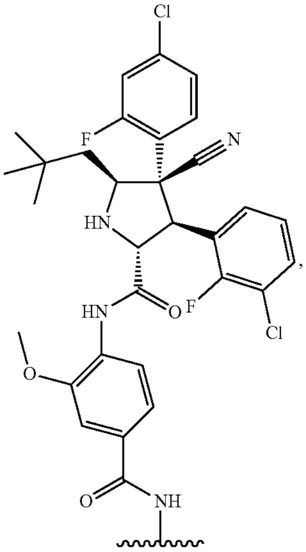 [SMILES: *NC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]

TABLE B-continued
| Ubiquitin E3 ligase binding moieties |
| --- |
| 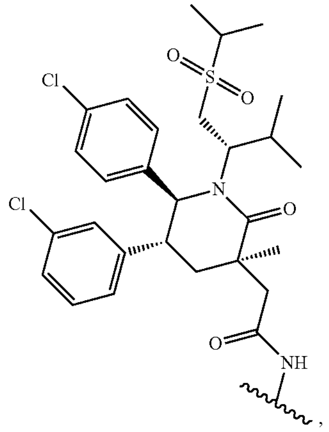 [SMILES: *NC(=O)C[C@@]1(C)C[C@H](c2cccc(Cl)c2)[C@@H](c2ccc(Cl)cc2)N([C@H](CS(=O)(=O)C(C)C)C(C)C)C1=O] (t) |
| 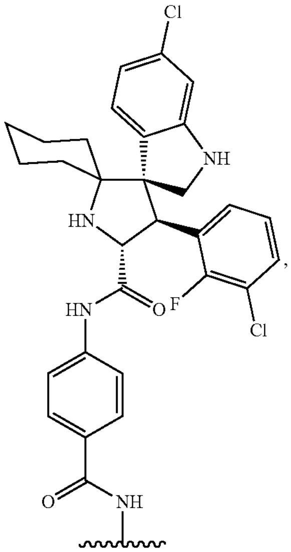 [SMILES: *NC(=O)c1ccc(NC(=O)[C@@H]2NC3(CCCCC3)[C@@]3(CNc4cc(Cl)ccc43)[C@H]2c2cccc(Cl)c2F)cc1] (u) |
| 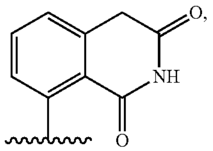 [SMILES: *c1cccc2c1C(=O)NC(=O)C2] (v) |
| 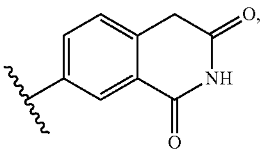 [SMILES: *c1ccc2c(c1)C(=O)NC(=O)C2] (w) |
| 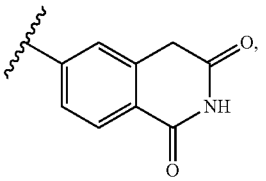 [SMILES: *c1ccc2c(c1)CC(=O)NC2=O] (x) |

TABLE B-continued
| Ubiquitin E3 ligase binding moieties |
| --- |
| 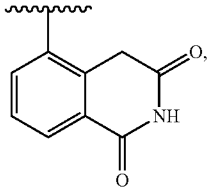 [SMILES: *c1cccc2c1CC(=O)NC2=O] (y) |
| 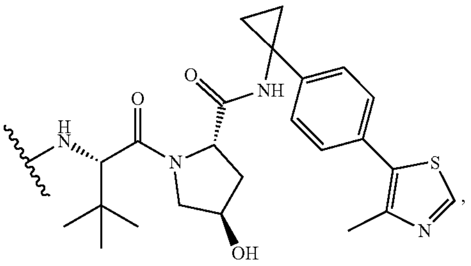 [SMILES: *N[C@H](C(=O)N1C[C@H](O)C[C@H]1C(=O)NC1(c2ccc(-c3scnc3C)cc2)CC1)C(C)(C)C] (z) |
| 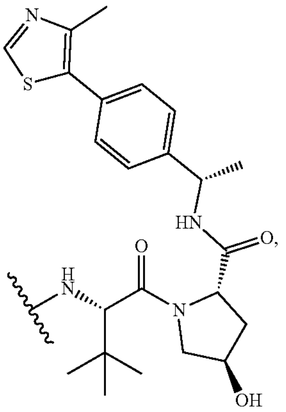 [SMILES: *N[C@H](C(=O)N1C[C@H](O)C[C@H]1C(=O)N[C@@H](C)c1ccc(-c2scnc2C)cc1)C(C)(C)C] (aa) |
| 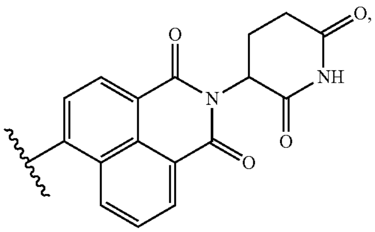 [SMILES: *c1ccc2c3c(cccc13)C(=O)N(C1CCC(=O)NC1=O)C2=O] (bb) |
| 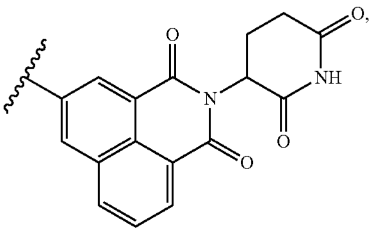 [SMILES: *c1cc2c3c(cccc3c1)C(=O)N(C1CCC(=O)NC1=O)C2=O] (cc) |
| 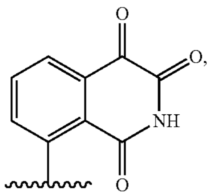 [SMILES: *c1cccc2c1C(=O)NC(=O)C2=O] (dd) |

TABLE B-continued
| Ubiquitin E3 ligase binding moieties |
| --- |
| 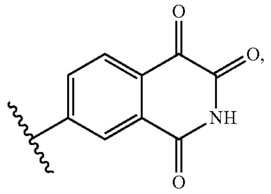 [SMILES: *c1ccc2c(c1)C(=O)NC(=O)C2=O] (ee) |
| 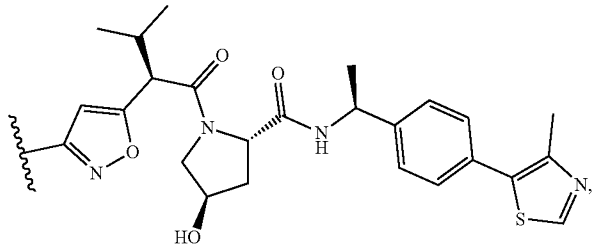 [SMILES: *c1cc([C@H](C(=O)N2C[C@H](O)C[C@H]2C(=O)N[C@@H](C)c2ccc(-c3scnc3C)cc2)C(C)C)on1] (ff) |
| 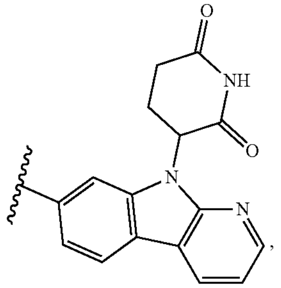 [SMILES: *c1ccc2c3cccnc3n(C3CCC(=O)NC3=O)c2c1] (gg) |
| 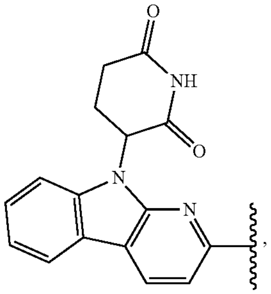 [SMILES: *c1ccc2c3ccccc3n(C3CCC(=O)NC3=O)c2n1] (hh) |
| 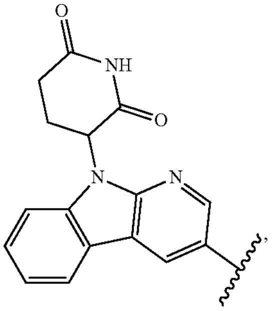 [SMILES: *c1cnc2c(c1)c1ccccc1n2C1CCC(=O)NC1=O] (ii) |

TABLE B-continued
| Ubiquitin E3 ligase binding moieties |
|---|
| 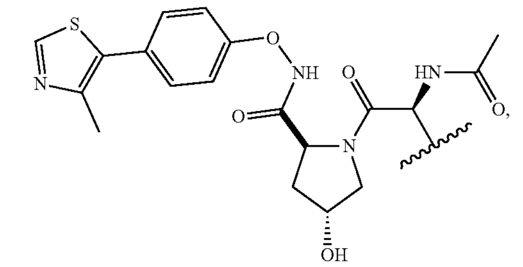 [SMILES: *[C@H](NC(C)=O)C(=O)N1C[C@H](O)C[C@H]1C(=O)NOc1ccc(-c2scnc2C)cc1] (jj) |
| 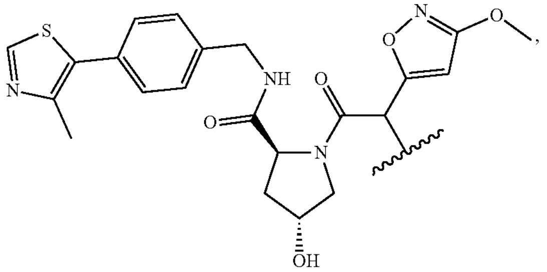 [SMILES: *C(C(=O)N1C[C@H](O)C[C@H]1C(=O)NCc1ccc(-c2scnc2C)cc1)c1cc(OC)no1] (kk) |
| 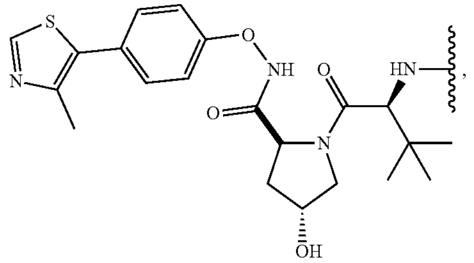 [SMILES: *N[C@H](C(=O)N1C[C@H](O)C[C@H]1C(=O)NOc1ccc(-c2scnc2C)cc1)C(C)(C)C] (ll) |
| 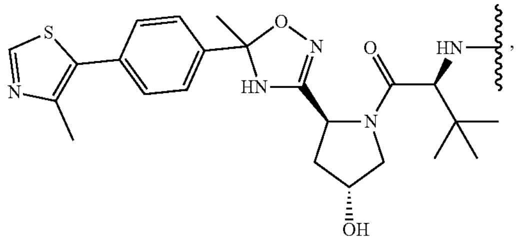 [SMILES: *N[C@H](C(=O)N1C[C@H](O)C[C@H]1C1=NOC(C)(c2ccc(-c3scnc3C)cc2)N1)C(C)(C)C] (mm) |
| 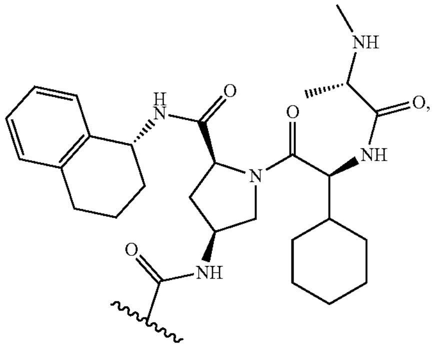 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1] (nn) |

TABLE B-continued
| Ubiquitin E3 ligase binding moieties |
|---|
| 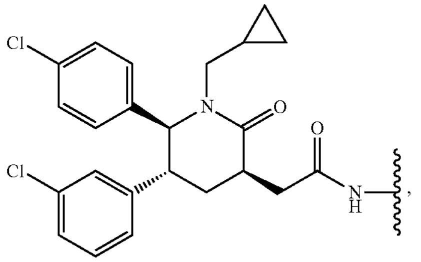 [SMILES: *NC(=O)C[C@H]1C[C@H](c2cccc(Cl)c2)[C@@H](c2ccc(Cl)cc2)N(CC2CC2)C1=O] (oo) |
| 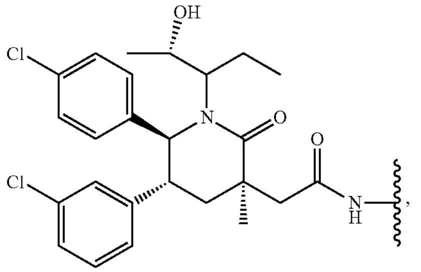 [SMILES: *NC(=O)C[C@@]1(C)C[C@H](c2cccc(Cl)c2)[C@@H](c2ccc(Cl)cc2)N(C(CC)[C@H](C)O)C1=O] (pp) |
| 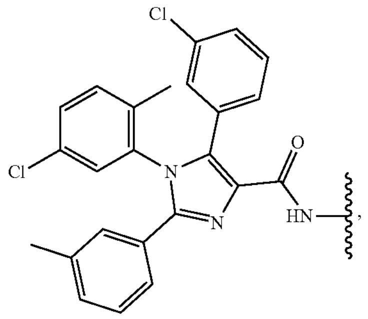 [SMILES: *NC(=O)c1nc(-c2cccc(C)c2)n(-c2cc(Cl)ccc2C)c1-c1cccc(Cl)c1] (qq) |
| 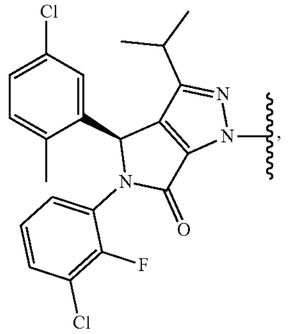 [SMILES: *n1nc(C(C)C)c2c1C(=O)N(c1cccc(Cl)c1F)[C@H]2c1cc(Cl)ccc1C] (rr) |
| 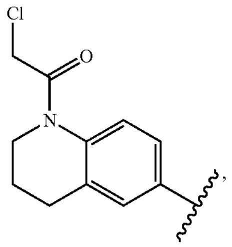 [SMILES: *c1ccc2c(c1)CCCN2C(=O)CCl] (ss) |

TABLE B-continued
| Ubiquitin E3 ligase binding moieties |
|---|
| 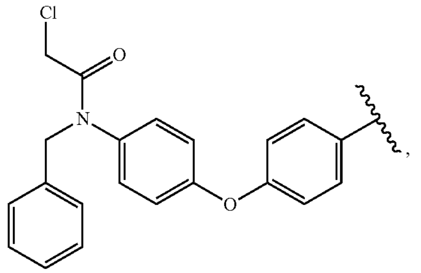 [SMILES: *c1ccc(Oc2ccc(N(Cc3ccccc3)C(=O)CCl)cc2)cc1] (tt) |
| 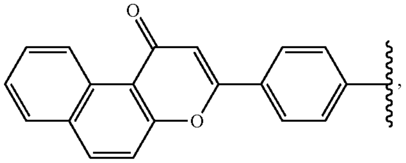 [SMILES: *c1ccc(-c2cc(=O)c3c(ccc4ccccc43)o2)cc1] (uu) |
| 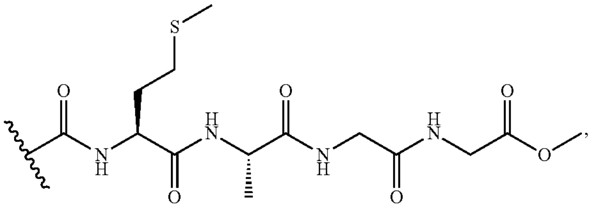 [SMILES: *C(=O)N[C@@H](CCSC)C(=O)N[C@@H](C)C(=O)NCC(=O)NCC(=O)OC] (vv) |
| 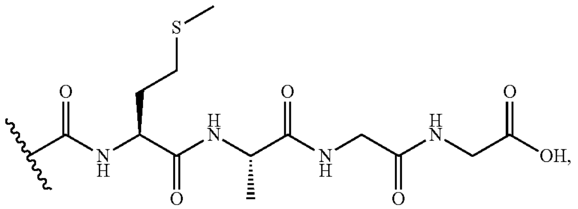 [SMILES: *C(=O)N[C@@H](CCSC)C(=O)N[C@@H](C)C(=O)NCC(=O)NCC(=O)O] (ww) |
| 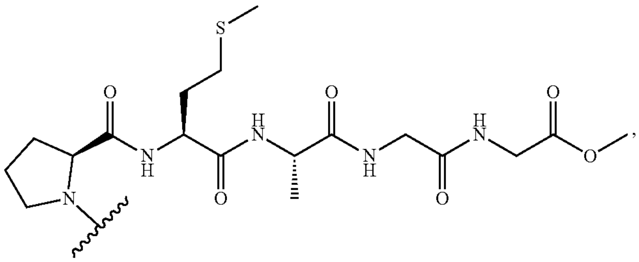 [SMILES: *N1CCC[C@H]1C(=O)N[C@@H](CCSC)C(=O)N[C@@H](C)C(=O)NCC(=O)NCC(=O)OC] (xx) |
| 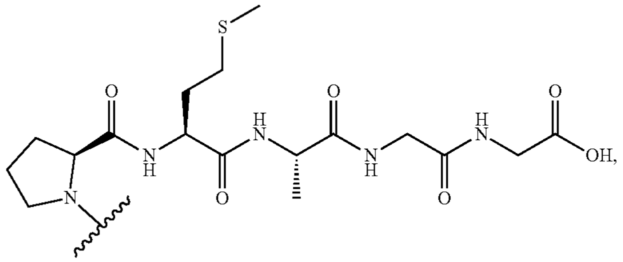 [SMILES: *N1CCC[C@H]1C(=O)N[C@@H](CCSC)C(=O)N[C@@H](C)C(=O)NCC(=O)NCC(=O)O] (yy) |

TABLE B-continued

Ubiquitin E3 ligase binding moieties

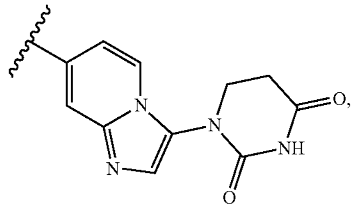 [SMILES: *c1ccn2c(N3CCC(=O)NC3=O)cnc2c1]

(zz)

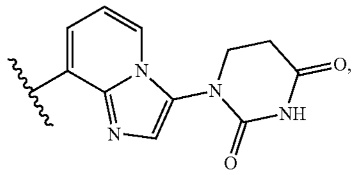 [SMILES: *c1cccn2c(N3CCC(=O)NC3=O)cnc12]

(aaa)

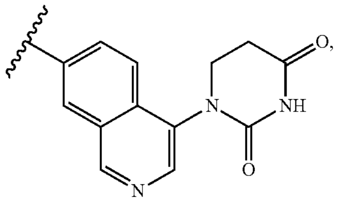 [SMILES: *c1ccc2c(N3CCC(=O)NC3=O)cncc2c1]

(bbb)

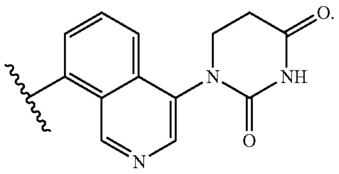 [SMILES: *c1cccc2c(N3CCC(=O)NC3=O)cncc12]

(ccc)

Specific examples of compounds of the disclosure are listed in Tables 1, 2, and 3. One embodiment provides a compound of Table 1, or a pharmaceutically acceptable salt thereof. One embodiment provides a compound of Table 2, or a pharmaceutically acceptable salt thereof. One embodiment provides a compound of Table 3, or a pharmaceutically acceptable salt thereof. One embodiment provides a compound selected from Compound No. 32, 94, 95, 96, 98, 101, 103, 104, 105, 106, 107, 108, 109, 110, 111, 112, 113, 114, 115, 116, 117, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 174, 175, 177, 300, 301, 302, 303, 304, 306, 307, 308, 309, 310, 311, 312, 313, 314, 315, 316, 317, 318, 319, 320, 321, 322, 323, 324, 325, 326, 327, 328, 329, 330, 337, 338, 339, 340, 341, 344, 345, 346, 347, 348, 349, 350, 351, 352, 354, 355, 357, 358, 362, 363, 364, 365, 366, 367, 369, 370, 371, 372, 373, 374, 375, 376, 377, 378, 379, 383, 384, 387, 389, 390, 391, 392, 393, 394, 395, 396, 397, 398, 399, 400, 401, 402, 403, 404, 405, 406, 407, 409, 410, 413, 414, 415, 416, 417, 418, 419, 420, 421, 422, 423, 424, 425,426, 427, 428, 429, 430, 431, 433, 434, 435, 436, 437, 438, 439, 440, 441, 442, 443, 444, 445, 446, 447, 448, 449, 450, 451, 452, 453, 454, 455, 456, 457, 458, 461, 462, 463, 464, 465, 466, 467, 468, 469, 470, 471, 472, 473, 474, 476, 477, 478,479, 484, 485, 486, 487, 489, 490, 491, 492, 493, 494, 495, 496, 497, 499, 500, 501, 502, or 503, or a pharmaceutically acceptable salt thereof. One embodiment provides a compound selected from Compound No. 1, 2, 3, 4, or 5, or a pharmaceutically acceptable salt thereof.

TABLE 1
| Compound No. | Compound Structure |
|---|---|
| | Example Compounds of the Disclosure |
| 1 | 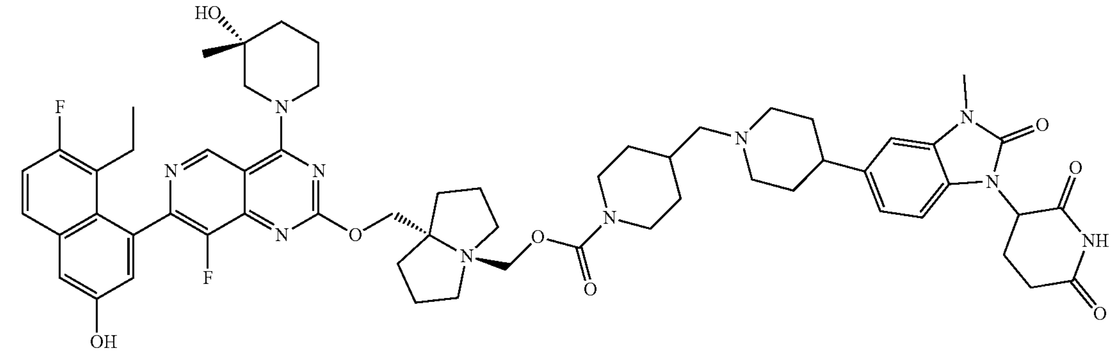 |
| 2 | 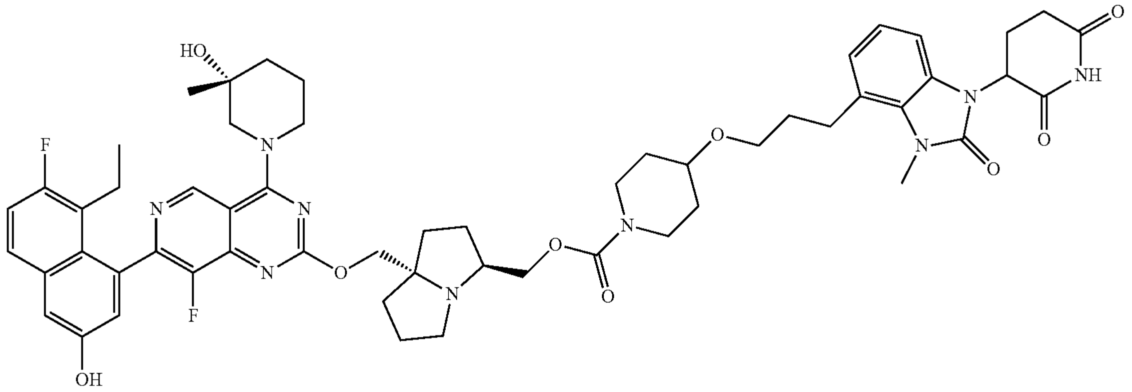 [SMILES: CCc1c(F)ccc2cc(O)cc(-c3ncc4c(N5CCC[C@@](C)(O)C5)nc(OC[C@@]56CCCN5[C@H](COC(=O)N5CCC(OCCCc7cccc8c7n(C)c(=O)n8C7CCC(=O)NC7=O)CC5)CC6)nc4c3F)c12] |
| 3 | 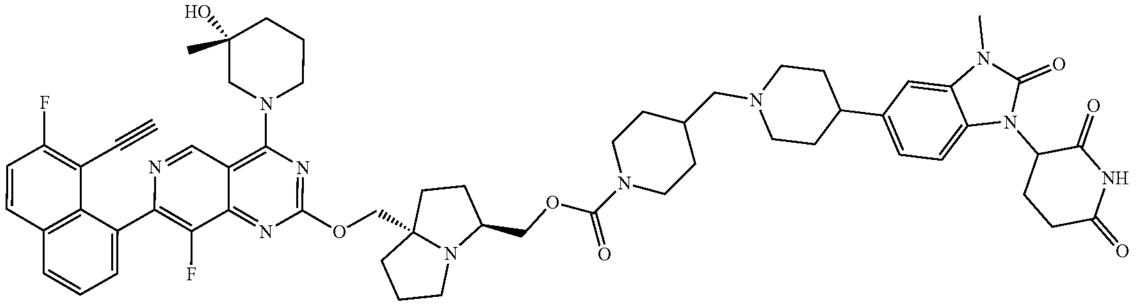 [SMILES: C#Cc1c(F)ccc2cccc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 4 | 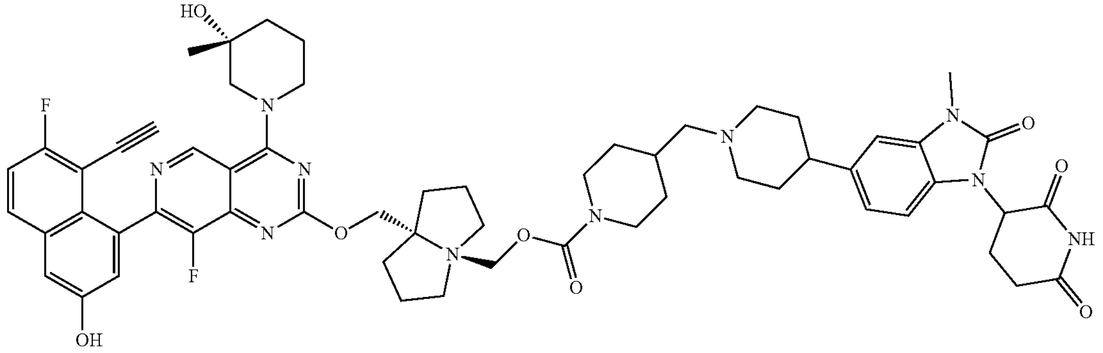 |

TABLE 1-continued
| Example Compounds of the Disclosure | |
|---|---|
| Compound No. | Compound Structure |
| 5 | 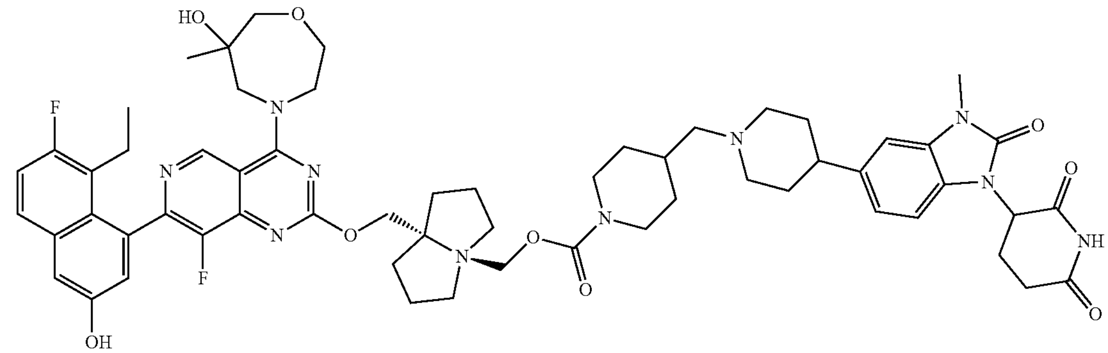 |
| 7 | 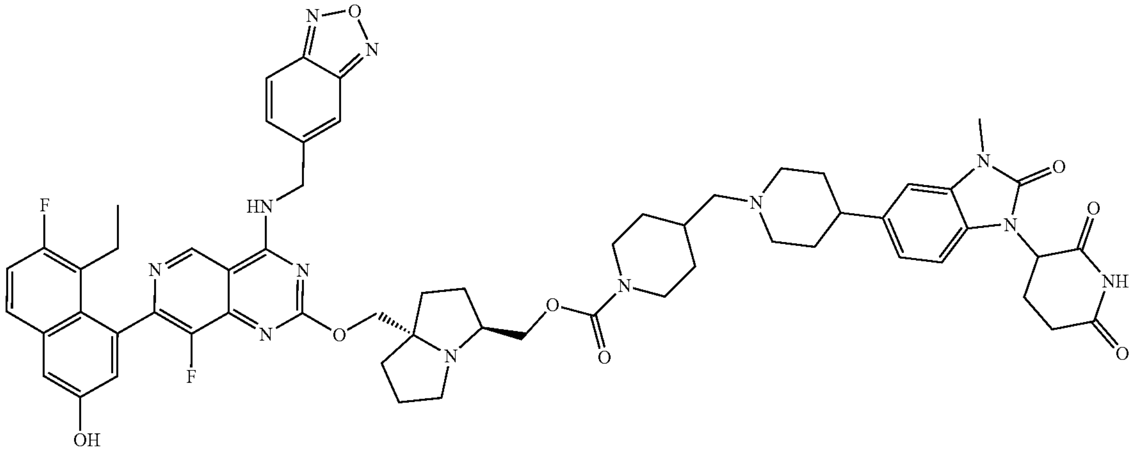 [SMILES: CCc1c(F)ccc2cc(O)cc(-c3ncc4c(NCc5ccc6nonc6c5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 8 | 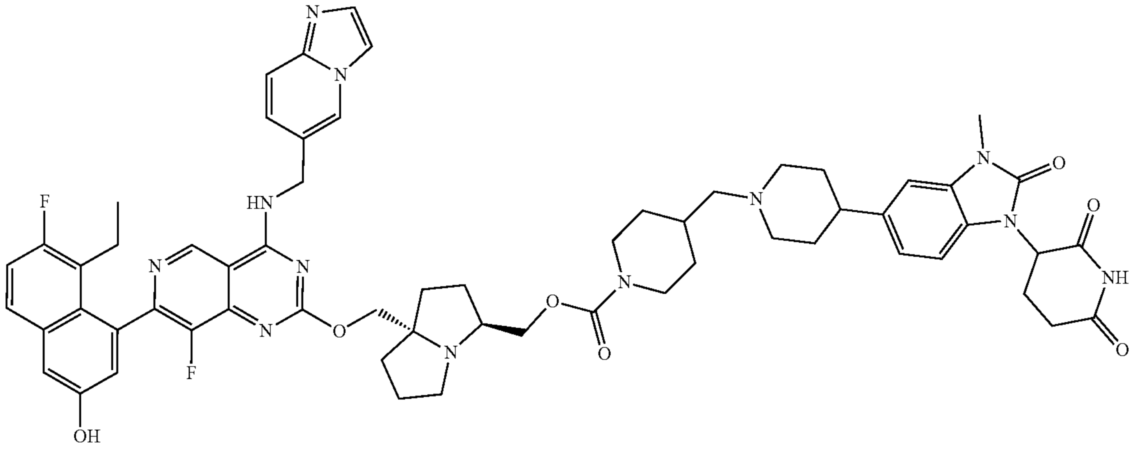 [SMILES: CCc1c(F)ccc2cc(O)cc(-c3ncc4c(NCc5ccc6nccn6c5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |

TABLE 1-continued
| Example Compounds of the Disclosure | |
|---|---|
| Compound No. | Compound Structure |
| 9 | 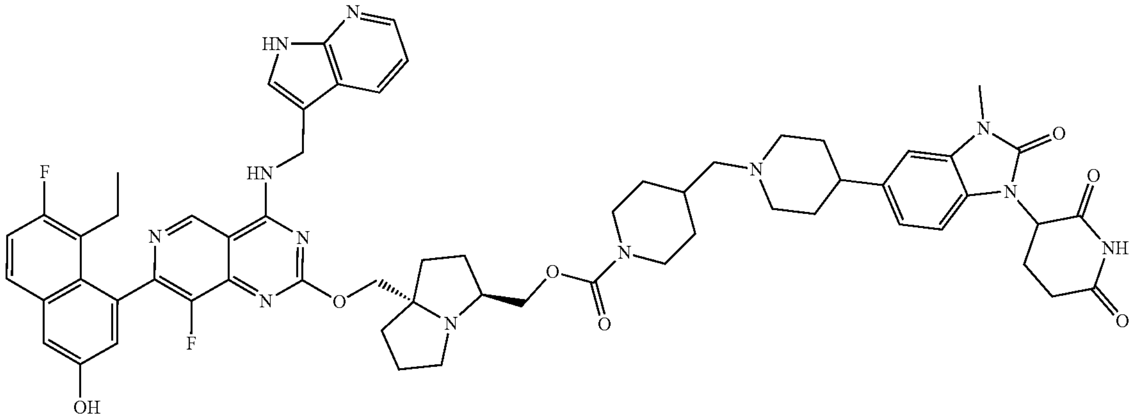 [SMILES: CCc1c(F)ccc2cc(O)cc(-c3ncc4c(NCc5c[nH]c6ncccc56)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 10 | 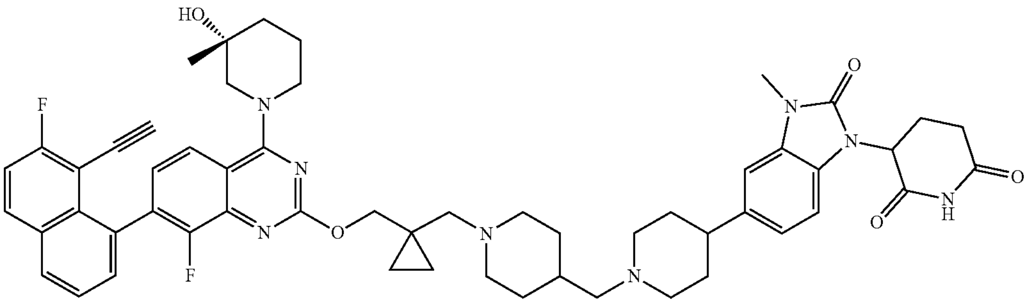 [SMILES: C#Cc1c(F)ccc2cccc(-c3ccc4c(N5CCC[C@@](C)(O)C5)nc(OCC5(CN6CCC(CN7CCC(c8ccc9c(c8)n(C)c(=O)n9C8CCC(=O)NC8=O)CC7)CC6)CC5)nc4c3F)c12] |
| 11 | 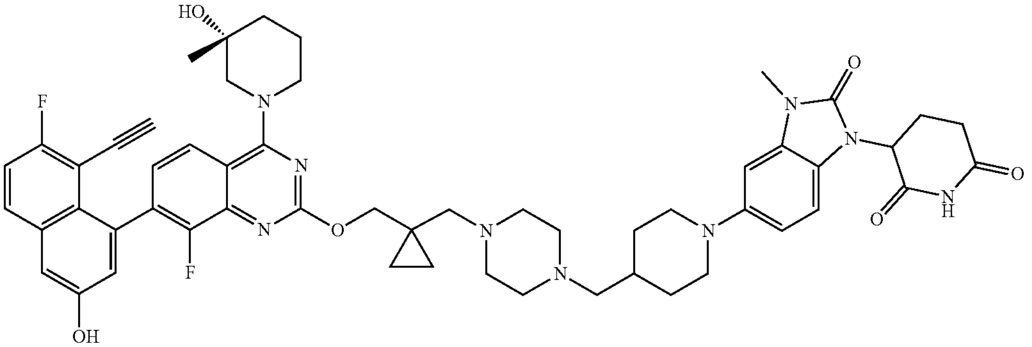 [SMILES: C#Cc1c(F)ccc2cc(O)cc(-c3ccc4c(N5CCC[C@@](C)(O)C5)nc(OCC5(CN6CCN(CC7CCN(c8ccc9c(c8)n(C)c(=O)n9C8CCC(=O)NC8=O)CC7)CC6)CC5)nc4c3F)c12] |
| 12 | 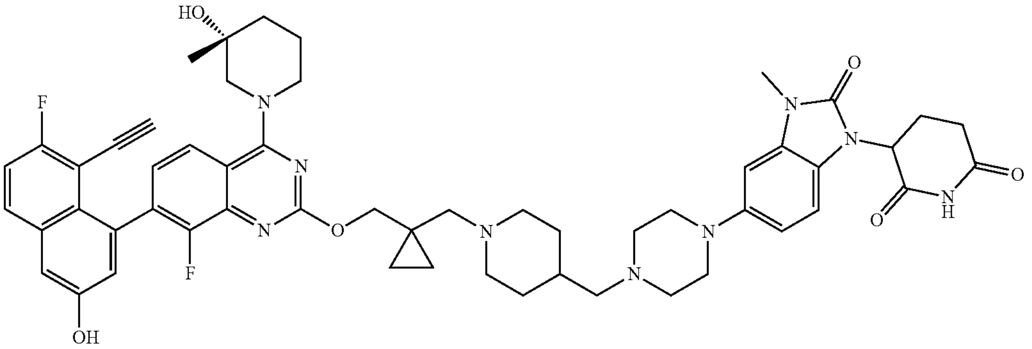 [SMILES: C#Cc1c(F)ccc2cc(O)cc(-c3ccc4c(N5CCC[C@@](C)(O)C5)nc(OCC5(CN6CCC(CN7CCN(c8ccc9c(c8)n(C)c(=O)n9C8CCC(=O)NC8=O)CC7)CC6)CC5)nc4c3F)c12] |

TABLE 1-continued
| Example Compounds of the Disclosure | |
|---|---|
| Compound No. | Compound Structure |
| 13 | 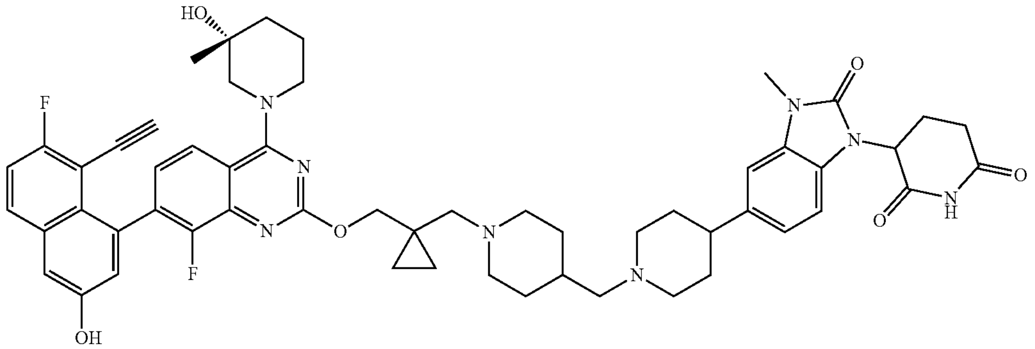 [SMILES: C#Cc1c(F)ccc2cc(O)cc(-c3ccc4c(N5CCC[C@@](C)(O)C5)nc(OCC5(CN6CCC(CN7CCC(c8ccc9c(c8)n(C)c(=O)n9C8CCC(=O)NC8=O)CC7)CC6)CC5)nc4c3F)c12] |
| 14 | 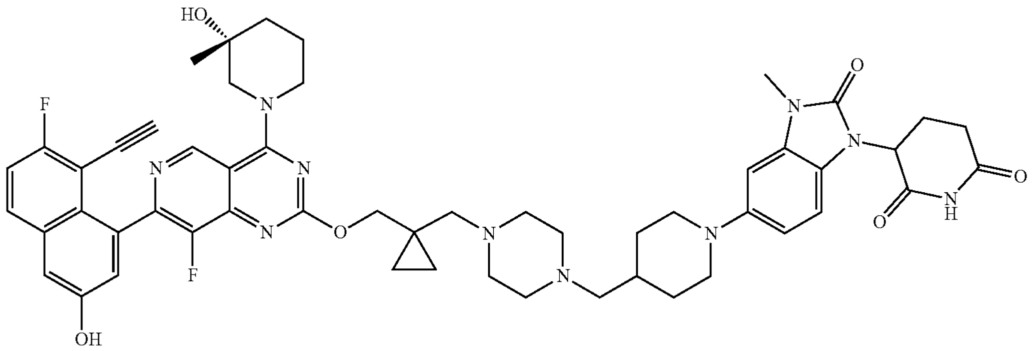 [SMILES: C#Cc1c(F)ccc2cc(O)cc(-c3ncc4c(N5CCC[C@@](C)(O)C5)nc(OCC5(CN6CCN(CC7CCN(c8ccc9c(c8)n(C)c(=O)n9C8CCC(=O)NC8=O)CC7)CC6)CC5)nc4c3F)c12] |
| 15 | 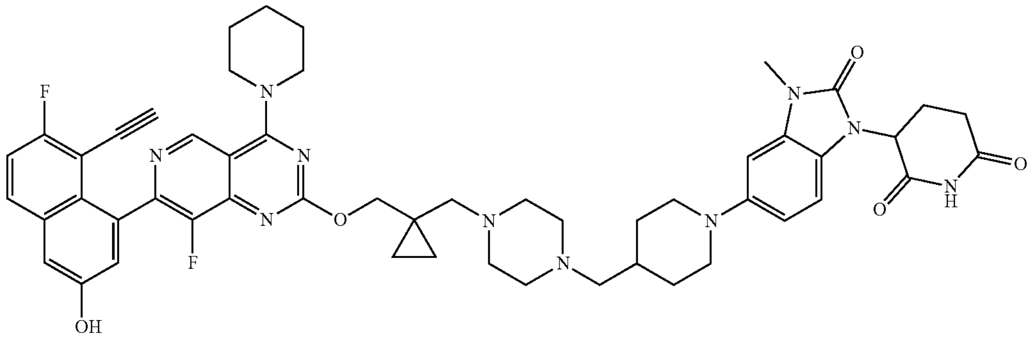 [SMILES: C#Cc1c(F)ccc2cc(O)cc(-c3ncc4c(N5CCCCC5)nc(OCC5(CN6CCN(CC7CCN(c8ccc9c(c8)n(C)c(=O)n9C8CCC(=O)NC8=O)CC7)CC6)CC5)nc4c3F)c12] |
| 16 | 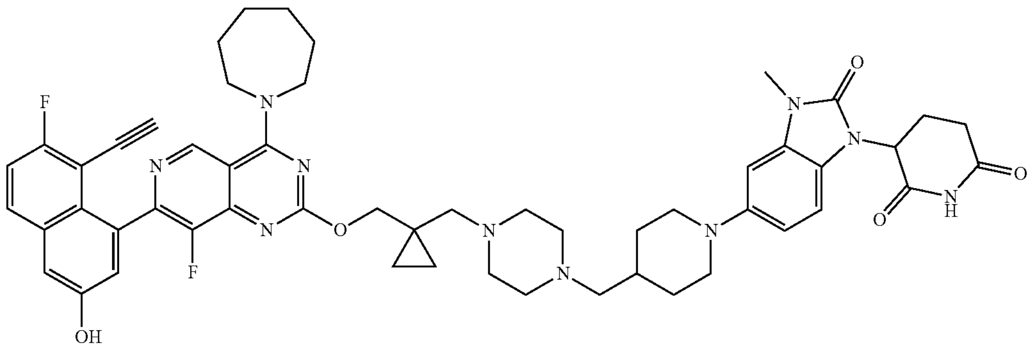 [SMILES: C#Cc1c(F)ccc2cc(O)cc(-c3ncc4c(N5CCCCCC5)nc(OCC5(CN6CCN(CC7CCN(c8ccc9c(c8)n(C)c(=O)n9C8CCC(=O)NC8=O)CC7)CC6)CC5)nc4c3F)c12] |

TABLE 1-continued
| Example Compounds of the Disclosure | |
|---|---|
| Compound No. | Compound Structure |
| 17 | 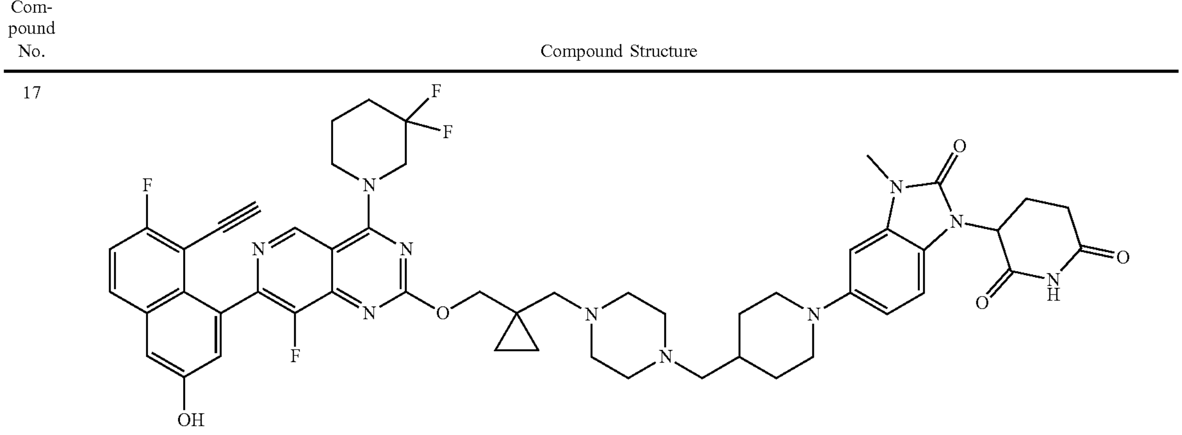 |
| 18 | 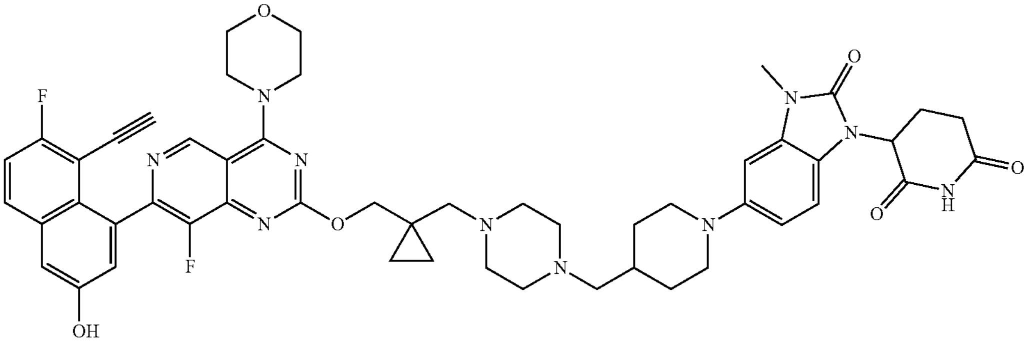 [SMILES: C#Cc1c(F)ccc2cc(O)cc(-c3ncc4c(N5CCOCC5)nc(OCC5(CN6CCN(CC7CCN(c8ccc9c(c8)n(C)c(=O)n9C8CCC(=O)NC8=O)CC7)CC6)CC5)nc4c3F)c12] |
| 19 | 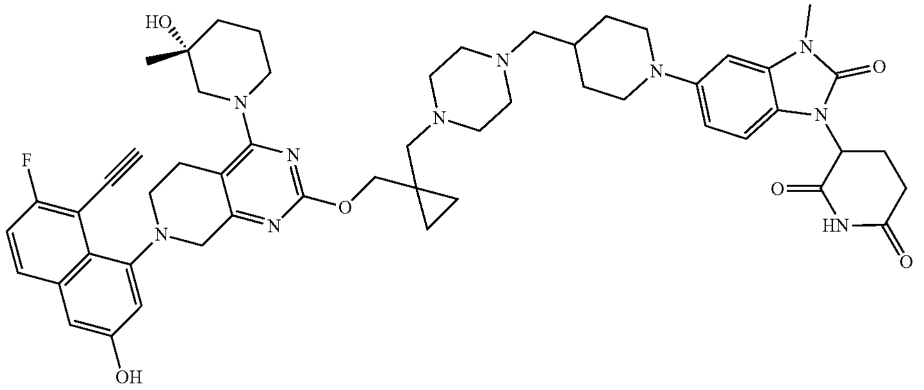 [SMILES: C#Cc1c(F)ccc2cc(O)cc(N3CCc4c(nc(OCC5(CN6CCN(CC7CCN(c8ccc9c(c8)n(C)c(=O)n9C8CCC(=O)NC8=O)CC7)CC6)CC5)nc4N4CCC[C@@](C)(O)C4)C3)c12] |
| 20 | 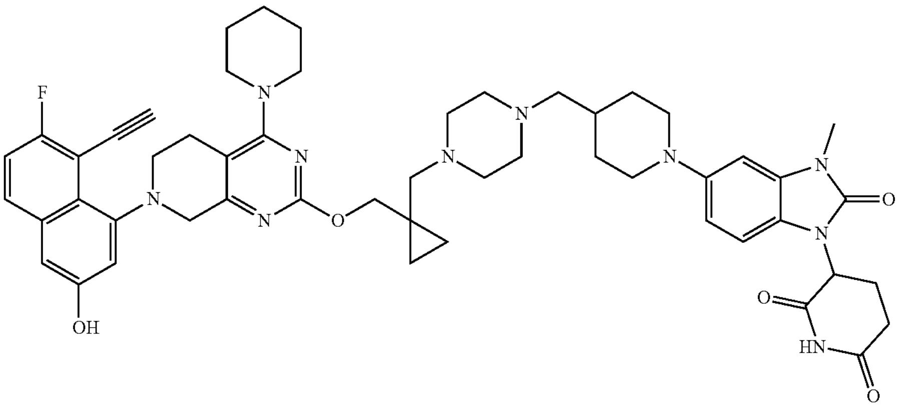 [SMILES: C#Cc1c(F)ccc2cc(O)cc(N3CCc4c(nc(OCC5(CN6CCN(CC7CCN(c8ccc9c(c8)n(C)c(=O)n9C8CCC(=O)NC8=O)CC7)CC6)CC5)nc4N4CCCCC4)C3)c12] |

TABLE 1-continued
| Example Compounds of the Disclosure | |
|---|---|
| Compound No. | Compound Structure |
| 21 | 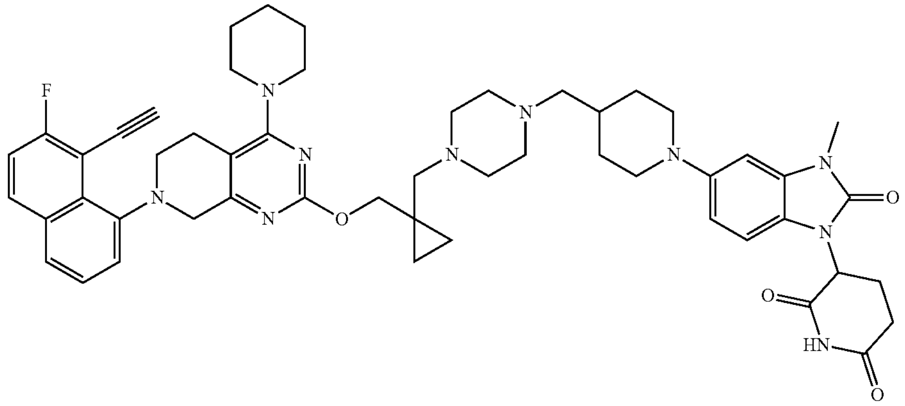 [SMILES: C#Cc1c(F)ccc2cccc(N3CCc4c(nc(OCC5(CN6CCN(CC7CCN(c8ccc9c(c8)n(C)c(=O)n9C8CCC(=O)NC8=O)CC7)CC6)CC5)nc4N4CCCCC4)C3)c12] |
| 22 | 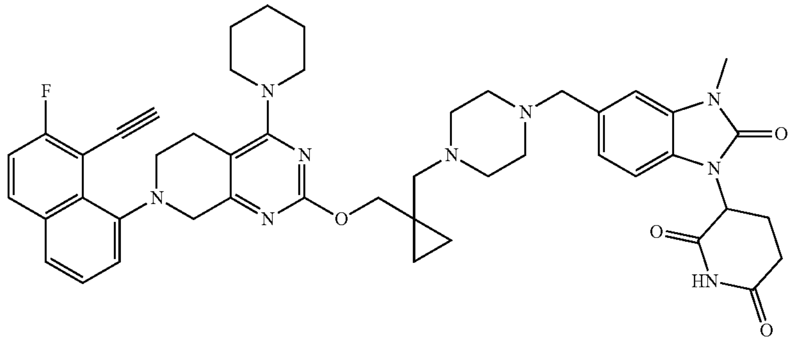 [SMILES: C#Cc1c(F)ccc2cccc(N3CCc4c(nc(OCC5(CN6CCN(Cc7ccc8c(c7)n(C)c(=O)n8C7CCC(=O)NC7=O)CC6)CC5)nc4N4CCCCC4)C3)c12] |
| 24 | 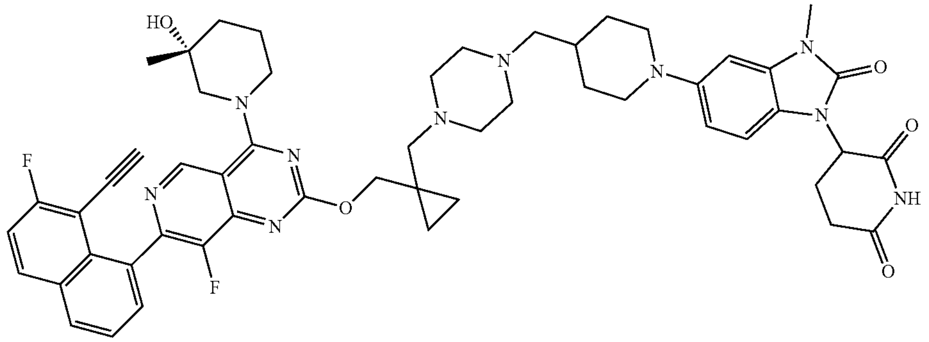 [SMILES: C#Cc1c(F)ccc2cccc(-c3ncc4c(N5CCC[C@@](C)(O)C5)nc(OCC5(CN6CCN(CC7CCN(c8ccc9c(c8)n(C)c(=O)n9C8CCC(=O)NC8=O)CC7)CC6)CC5)nc4c3F)c12] |
| 25 | 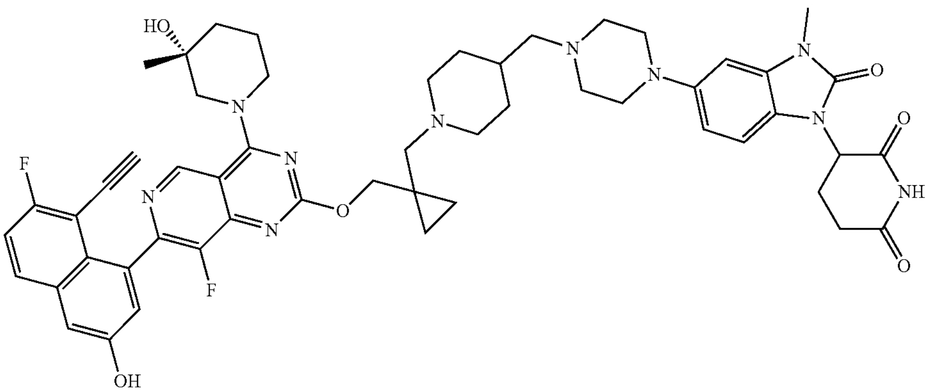 [SMILES: C#Cc1c(F)ccc2cc(O)cc(-c3ncc4c(N5CCC[C@@](C)(O)C5)nc(OCC5(CN6CCC(CN7CCN(c8ccc9c(c8)n(C)c(=O)n9C8CCC(=O)NC8=O)CC7)CC6)CC5)nc4c3F)c12] |

TABLE 1-continued
| Example Compounds of the Disclosure | |
|---|---|
| Compound No. | Compound Structure |
| 26 | 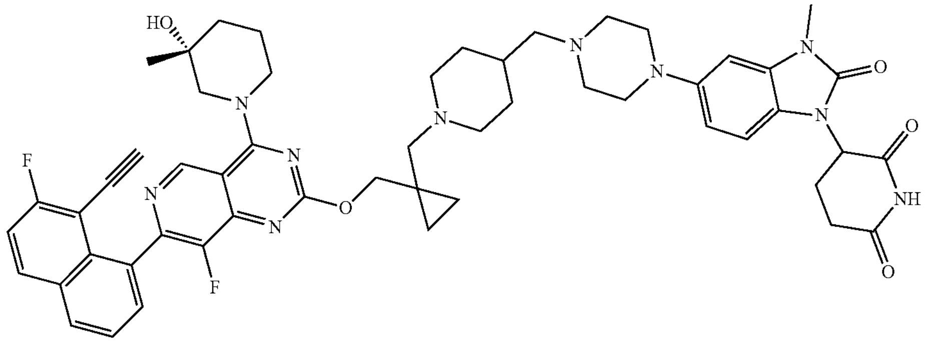 [SMILES: C#Cc1c(F)ccc2cccc(-c3ncc4c(N5CCC[C@@](C)(O)C5)nc(OCC5(CN6CCC(CN7CCN(c8ccc9c(c8)n(C)c(=O)n9C8CCC(=O)NC8=O)CC7)CC6)CC5)nc4c3F)c12] |
| 27 | 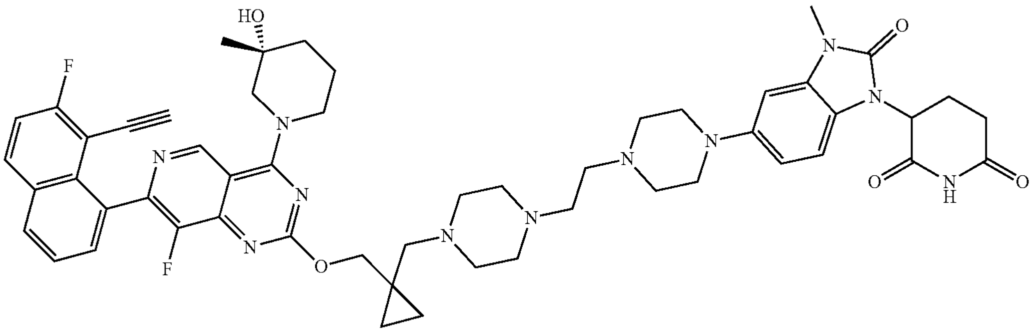 [SMILES: C#Cc1c(F)ccc2cccc(-c3ncc4c(N5CCC[C@@](C)(O)C5)nc(OCC5(CN6CCN(CCN7CCN(c8ccc9c(c8)n(C)c(=O)n9C8CCC(=O)NC8=O)CC7)CC6)CC5)nc4c3F)c12] |
| 28 | 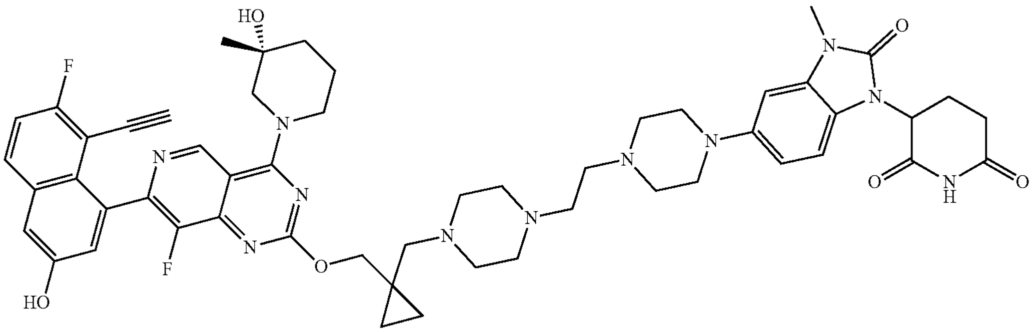 [SMILES: C#Cc1c(F)ccc2cc(O)cc(-c3ncc4c(N5CCC[C@@](C)(O)C5)nc(OCC5(CN6CCN(CCN7CCN(c8ccc9c(c8)n(C)c(=O)n9C8CCC(=O)NC8=O)CC7)CC6)CC5)nc4c3F)c12] |
| 29 | 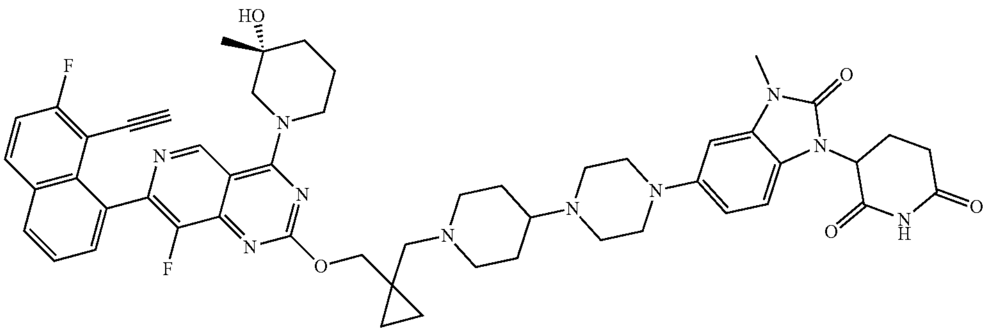 [SMILES: C#Cc1c(F)ccc2cccc(-c3ncc4c(N5CCC[C@@](C)(O)C5)nc(OCC5(CN6CCC(N7CCN(c8ccc9c(c8)n(C)c(=O)n9C8CCC(=O)NC8=O)CC7)CC6)CC5)nc4c3F)c12] |

TABLE 1-continued
| Example Compounds of the Disclosure | |
|---|---|
| Compound No. | Compound Structure |
| 30 | 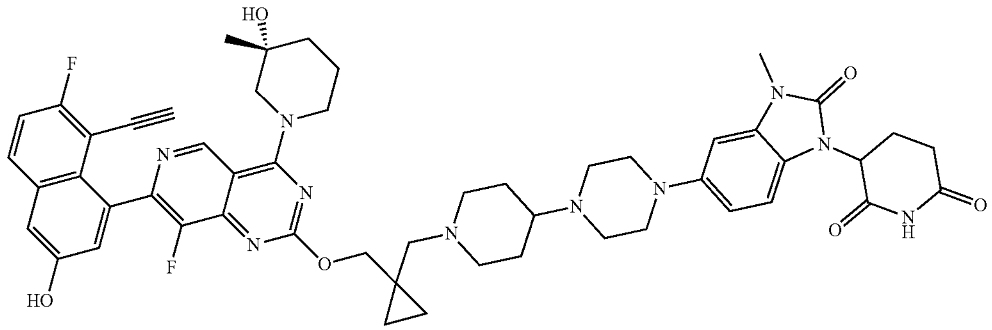 [SMILES: C#Cc1c(F)ccc2cc(O)cc(-c3ncc4c(N5CCC[C@@](C)(O)C5)nc(OCC5(CN6CCC(N7CCN(c8ccc9c(c8)n(C)c(=O)n9C8CCC(=O)NC8=O)CC7)CC6)CC5)nc4c3F)c12] |
| 31 | 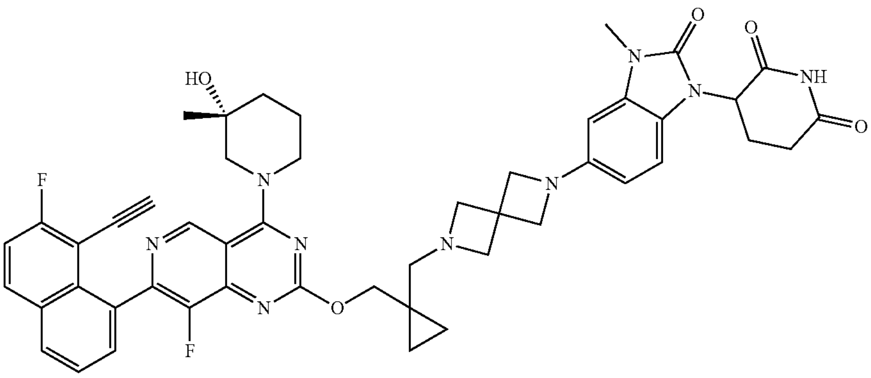 [SMILES: C#Cc1c(F)ccc2cccc(-c3ncc4c(N5CCC[C@@](C)(O)C5)nc(OCC5(CN6CC7(C6)CN(c6ccc8c(c6)n(C)c(=O)n8C6CCC(=O)NC6=O)C7)CC5)nc4c3F)c12] |
| 32 | 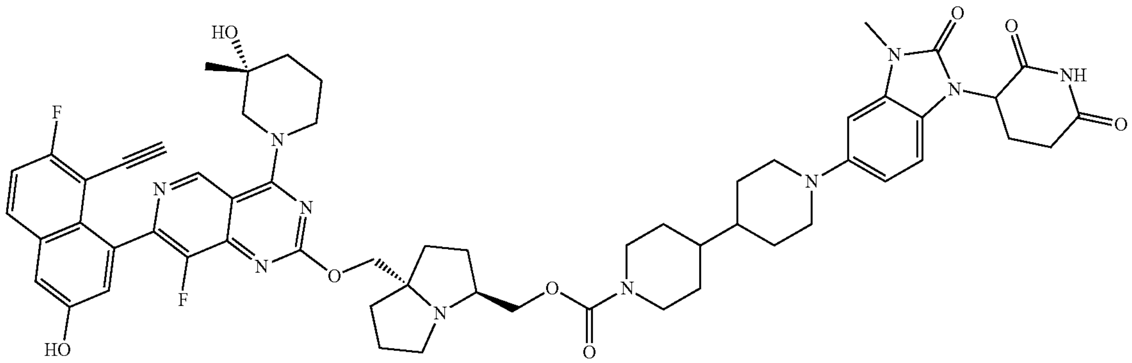 |
| 33 | 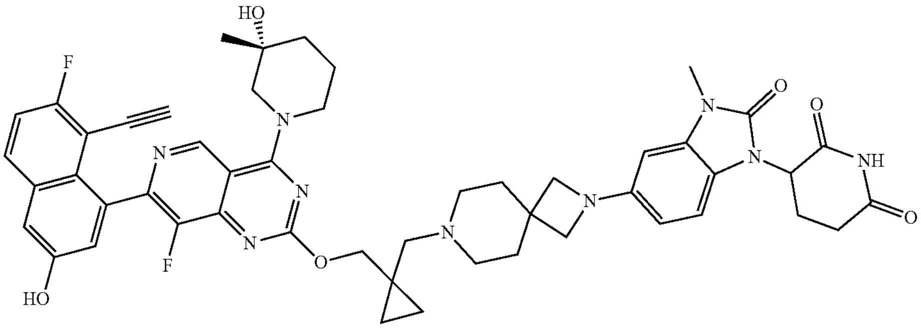 [SMILES: C#Cc1c(F)ccc2cc(O)cc(-c3ncc4c(N5CCC[C@@](C)(O)C5)nc(OCC5(CN6CCC7(CC6)CN(c6ccc8c(c6)n(C)c(=O)n8C6CCC(=O)NC6=O)C7)CC5)nc4c3F)c12] |

TABLE 1-continued
| Compound No. | Compound Structure |
| --- | --- |
| | Example Compounds of the Disclosure |
| 34 | 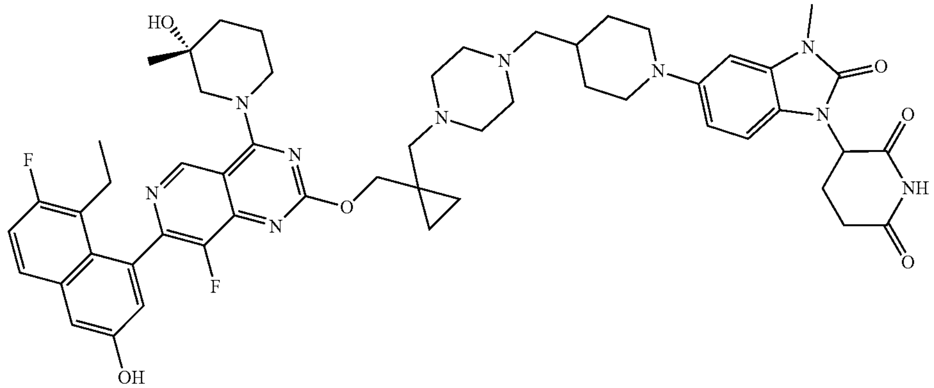 [SMILES: CCc1c(F)ccc2cc(O)cc(-c3ncc4c(N5CCC[C@@](C)(O)C5)nc(OCC5(CN6CCN(CC7CCN(c8ccc9c(c8)n(C)c(=O)n9C8CCC(=O)NC8=O)CC7)CC6)CC5)nc4c3F)c12] |
| 35 | 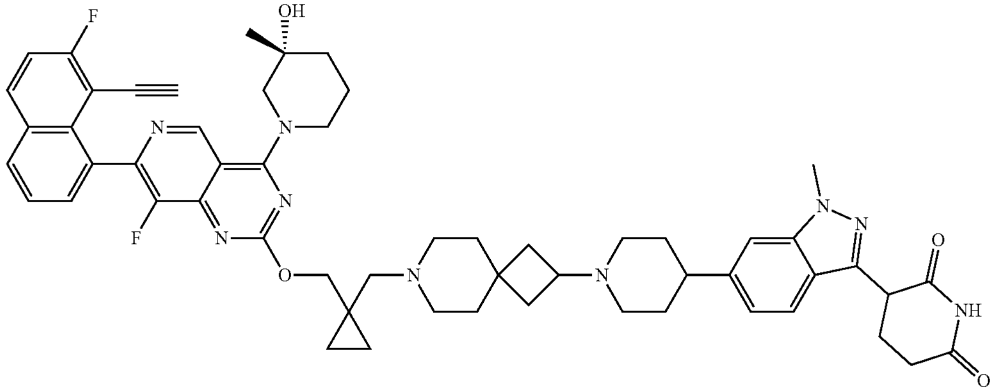 [SMILES: C#Cc1c(F)ccc2cccc(-c3ncc4c(N5CCC[C@@](C)(O)C5)nc(OCC5(CN6CCC7(CC6)CC(N6CCC(c8ccc9c(C%10CCC(=O)NC%10=O)nn(C)c9c8)CC6)C7)CC5)nc4c3F)c12] |
| 36 | 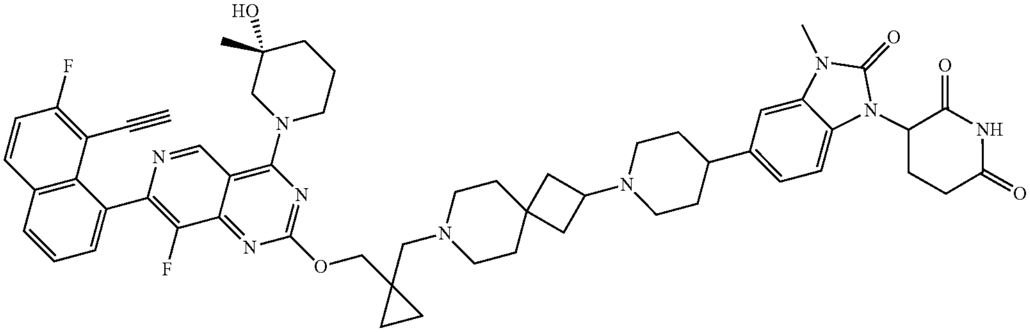 [SMILES: C#Cc1c(F)ccc2cccc(-c3ncc4c(N5CCC[C@@](C)(O)C5)nc(OCC5(CN6CCC7(CC6)CC(N6CCC(c8ccc9c(c8)n(C)c(=O)n9C8CCC(=O)NC8=O)CC6)C7)CC5)nc4c3F)c12] |
| 37 | 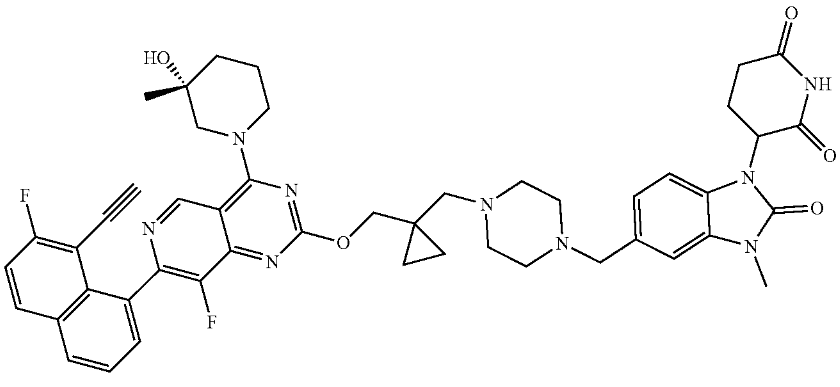 [SMILES: C#Cc1c(F)ccc2cccc(-c3ncc4c(N5CCC[C@@](C)(O)C5)nc(OCC5(CN6CCN(Cc7ccc8c(c7)n(C)c(=O)n8C7CCC(=O)NC7=O)CC6)CC5)nc4c3F)c12] |

TABLE 1-continued
| Example Compounds of the Disclosure | |
|---|---|
| Compound No. | Compound Structure |
| 38 | 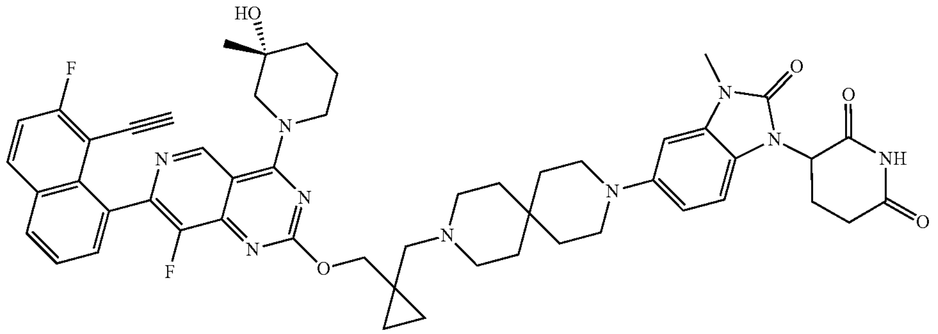 [SMILES: C#Cc1c(F)ccc2cccc(-c3ncc4c(N5CCC[C@@](C)(O)C5)nc(OCC5(CN6CCC7(CC6)CCN(c6ccc8c(c6)n(C)c(=O)n8C6CCC(=O)NC6=O)CC7)CC5)nc4c3F)c12] |
| 39 | 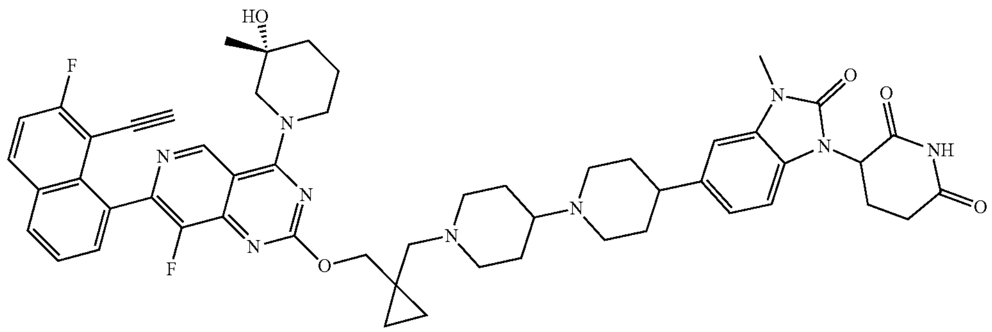 [SMILES: C#Cc1c(F)ccc2cccc(-c3ncc4c(N5CCC[C@@](C)(O)C5)nc(OCC5(CN6CCC(N7CCC(c8ccc9c(c8)n(C)c(=O)n9C8CCC(=O)NC8=O)CC7)CC6)CC5)nc4c3F)c12] |
| 40 | 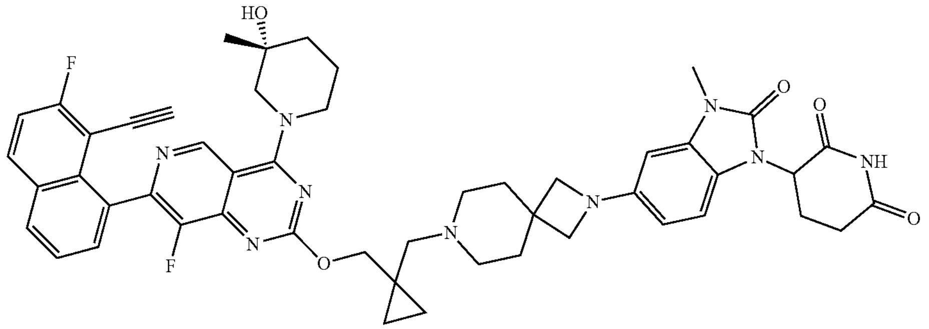 [SMILES: C#Cc1c(F)ccc2cccc(-c3ncc4c(N5CCC[C@@](C)(O)C5)nc(OCC5(CN6CCC7(CC6)CN(c6ccc8c(c6)n(C)c(=O)n8C6CCC(=O)NC6=O)C7)CC5)nc4c3F)c12] |
| 41 | 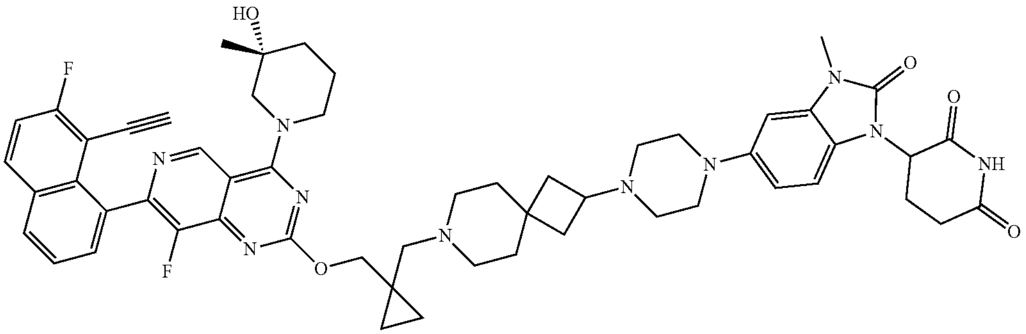 [SMILES: C#Cc1c(F)ccc2cccc(-c3ncc4c(N5CCC[C@@](C)(O)C5)nc(OCC5(CN6CCC7(CC6)CC(N6CCN(c8ccc9c(c8)n(C)c(=O)n9C8CCC(=O)NC8=O)CC6)C7)CC5)nc4c3F)c12] |

TABLE 1-continued
| Example Compounds of the Disclosure | |
|---|---|
| Compound No. | Compound Structure |
| 42 | 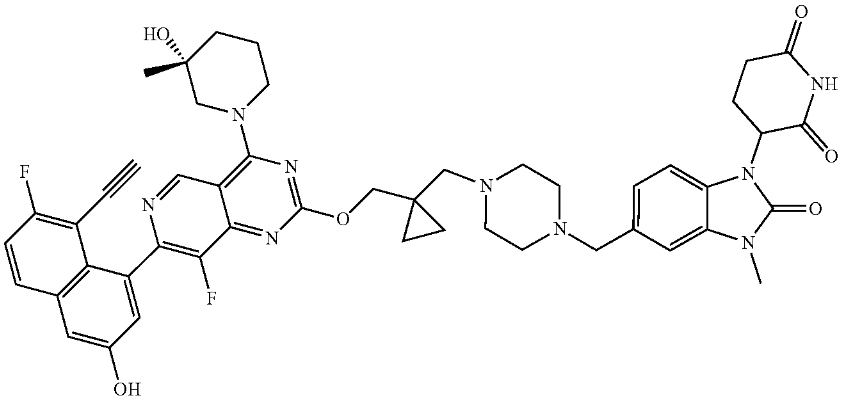 [SMILES: C#Cc1c(F)ccc2cc(O)cc(-c3ncc4c(N5CCC[C@@](C)(O)C5)nc(OCC5(CN6CCN(Cc7ccc8c(c7)n(C)c(=O)n8C7CCC(=O)NC7=O)CC6)CC5)nc4c3F)c12] |
| 43 | 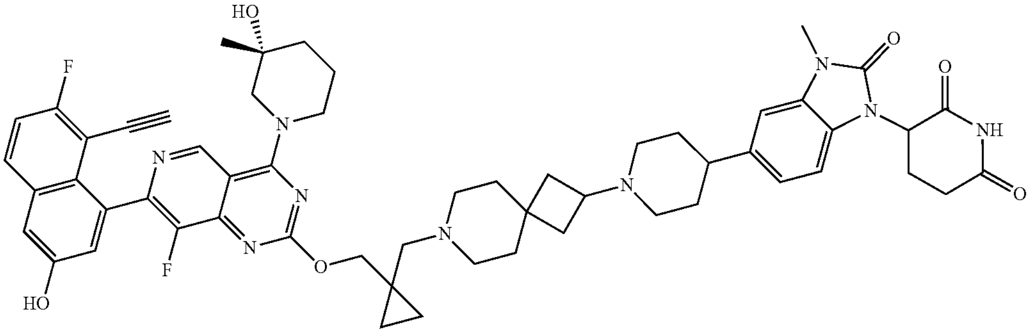 [SMILES: C#Cc1c(F)ccc2cc(O)cc(-c3ncc4c(N5CCC[C@@](C)(O)C5)nc(OCC5(CN6CCC7(CC6)CC(N6CCC(c8ccc9c(c8)n(C)c(=O)n9C8CCC(=O)NC8=O)CC6)C7)CC5)nc4c3F)c12] |
| 44 | 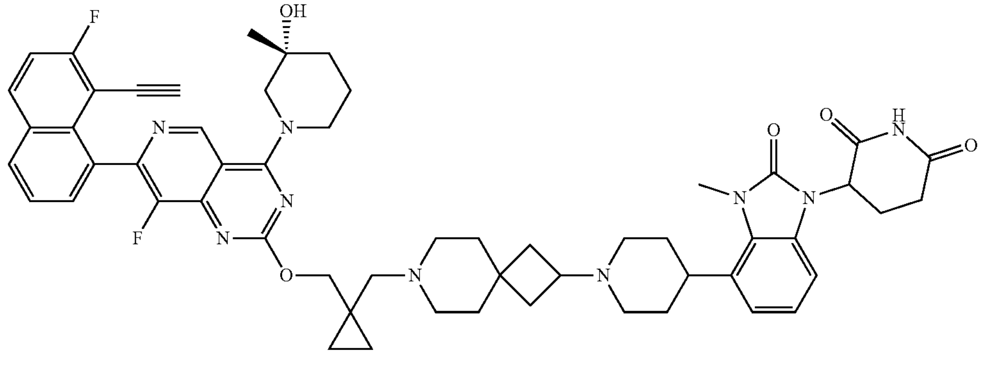 [SMILES: C#Cc1c(F)ccc2cccc(-c3ncc4c(N5CCC[C@@](C)(O)C5)nc(OCC5(CN6CCC7(CC6)CC(N6CCC(c8cccc9c8n(C)c(=O)n9C8CCC(=O)NC8=O)CC6)C7)CC5)nc4c3F)c12] |
| 45 | 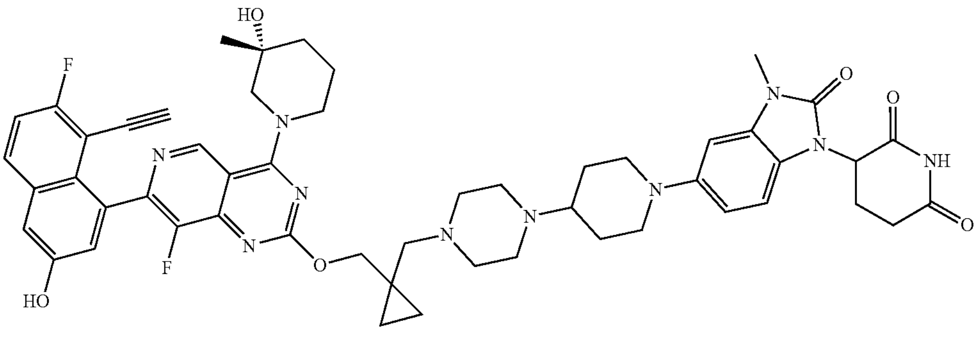 [SMILES: C#Cc1c(F)ccc2cc(O)cc(-c3ncc4c(N5CCC[C@@](C)(O)C5)nc(OCC5(CN6CCN(C7CCN(c8ccc9c(c8)n(C)c(=O)n9C8CCC(=O)NC8=O)CC7)CC6)CC5)nc4c3F)c12] |

TABLE 1-continued
| Example Compounds of the Disclosure | |
|---|---|
| Compound No. | Compound Structure |
| 46 | 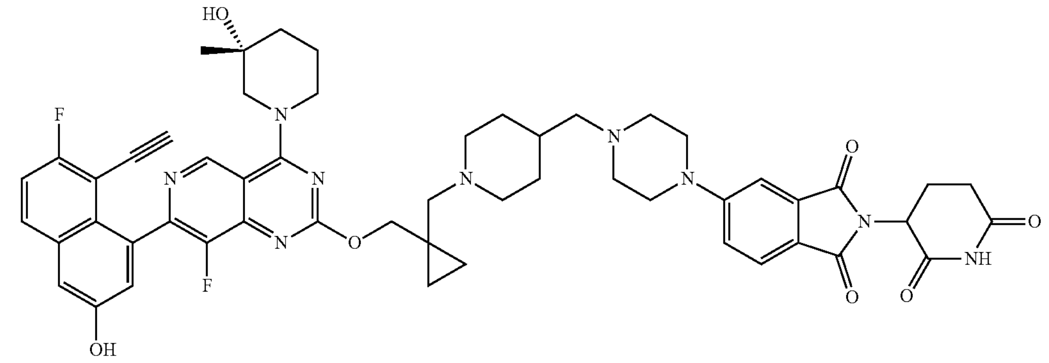 [SMILES: C#Cc1c(F)ccc2cc(O)cc(-c3ncc4c(N5CCC[C@@](C)(O)C5)nc(OCC5(CN6CCC(CN7CCN(c8ccc9c(c8)C(=O)N(C8CCC(=O)NC8=O)C9=O)CC7)CC6)CC5)nc4c3F)c12] |
| 47 | 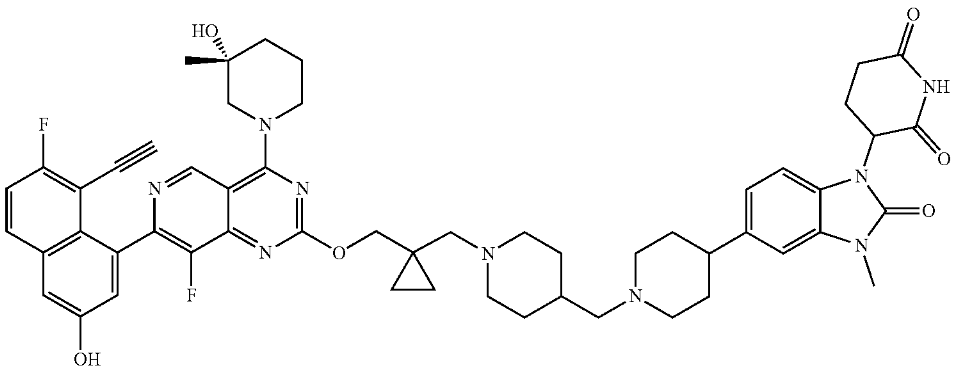 [SMILES: C#Cc1c(F)ccc2cc(O)cc(-c3ncc4c(N5CCC[C@@](C)(O)C5)nc(OCC5(CN6CCC(CN7CCC(c8ccc9c(c8)n(C)c(=O)n9C8CCC(=O)NC8=O)CC7)CC6)CC5)nc4c3F)c12] |
| 48 | 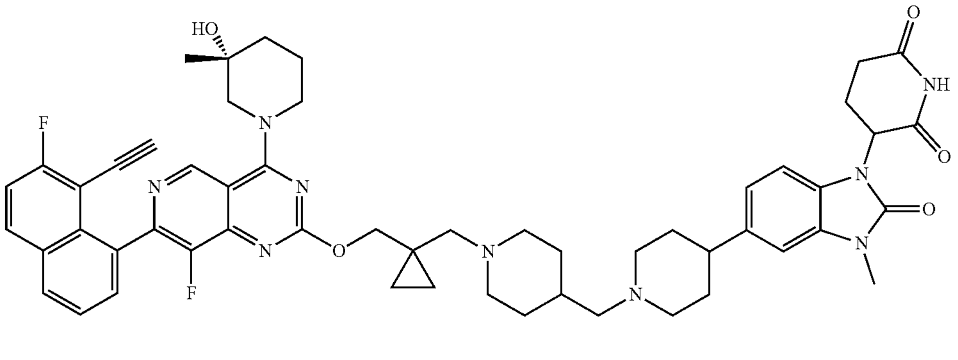 [SMILES: C#Cc1c(F)ccc2cccc(-c3ncc4c(N5CCC[C@@](C)(O)C5)nc(OCC5(CN6CCC(CN7CCC(c8ccc9c(c8)n(C)c(=O)n9C8CCC(=O)NC8=O)CC7)CC6)CC5)nc4c3F)c12] |
| 49 | 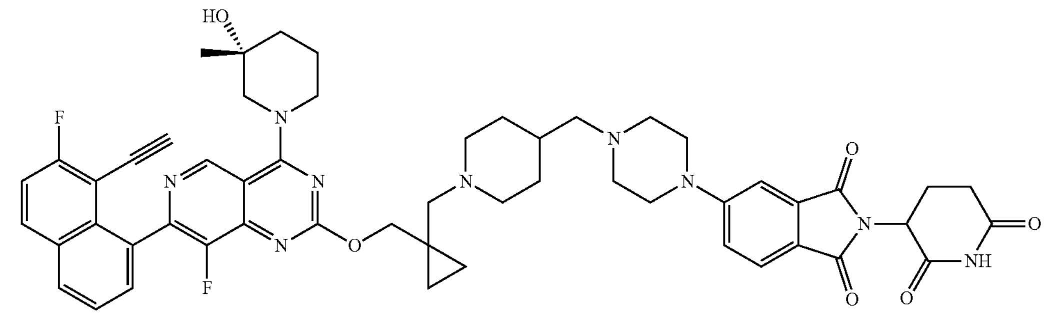 [SMILES: C#Cc1c(F)ccc2cccc(-c3ncc4c(N5CCC[C@@](C)(O)C5)nc(OCC5(CN6CCC(CN7CCN(c8ccc9c(c8)C(=O)N(C8CCC(=O)NC8=O)C9=O)CC7)CC6)CC5)nc4c3F)c12] |

TABLE 1-continued
| Example Compounds of the Disclosure | |
|---|---|
| Compound No. | Compound Structure |
| 50 | 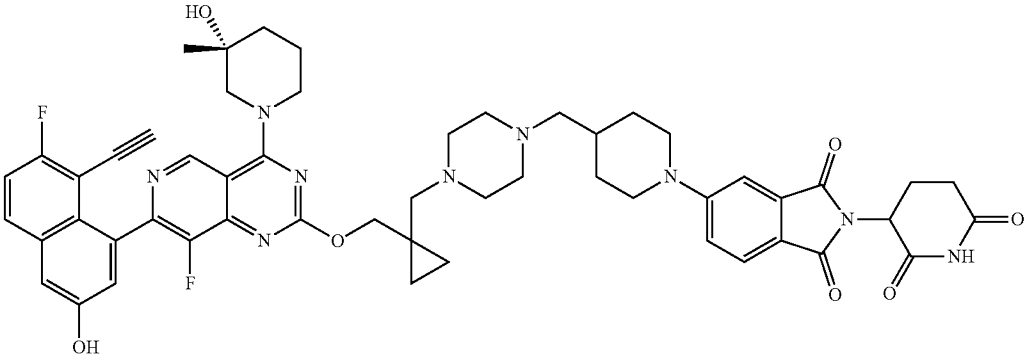 [SMILES: C#Cc1c(F)ccc2cc(O)cc(-c3ncc4c(N5CCC[C@@](C)(O)C5)nc(OCC5(CN6CCN(CC7CCN(c8ccc9c(c8)C(=O)N(C8CCC(=O)NC8=O)C9=O)CC7)CC6)CC5)nc4c3F)c12] |
| 51 | 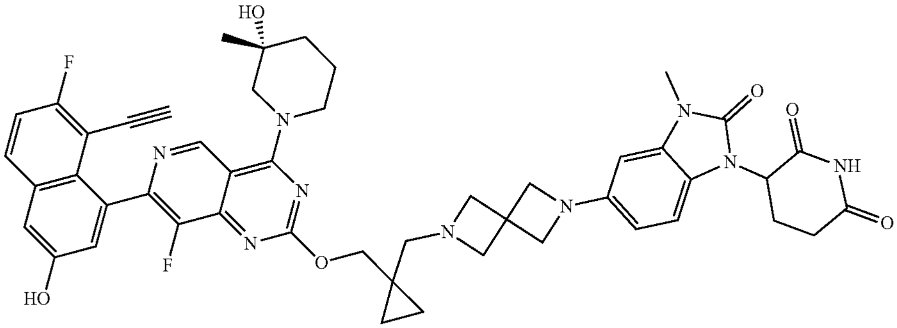 [SMILES: C#Cc1c(F)ccc2cc(O)cc(-c3ncc4c(N5CCC[C@@](C)(O)C5)nc(OCC5(CN6CC7(C6)CN(c6ccc8c(c6)n(C)c(=O)n8C6CCC(=O)NC6=O)C7)CC5)nc4c3F)c12] |
| 52 | 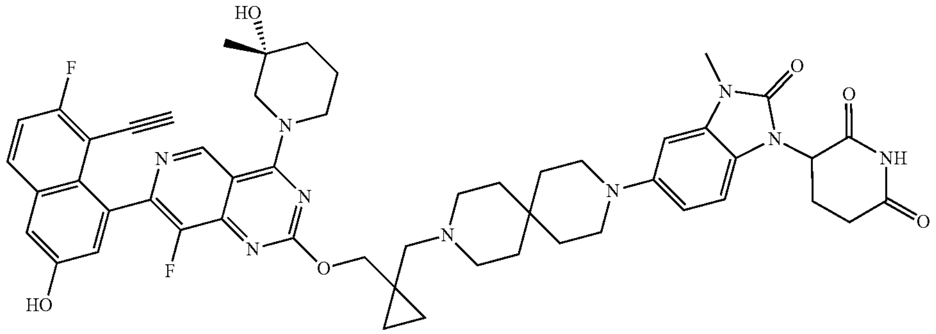 [SMILES: C#Cc1c(F)ccc2cc(O)cc(-c3ncc4c(N5CCC[C@@](C)(O)C5)nc(OCC5(CN6CCC7(CC6)CCN(c6ccc8c(c6)n(C)c(=O)n8C6CCC(=O)NC6=O)CC7)CC5)nc4c3F)c12] |
| 53 | 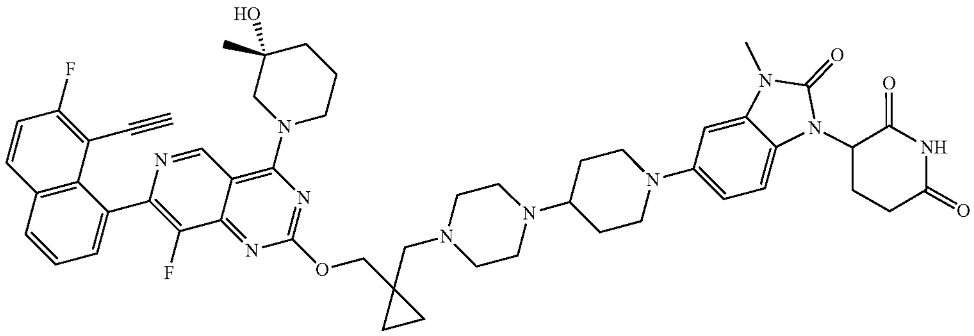 [SMILES: C#Cc1c(F)ccc2cccc(-c3ncc4c(N5CCC[C@@](C)(O)C5)nc(OCC5(CN6CCN(C7CCN(c8ccc9c(c8)n(C)c(=O)n9C8CCC(=O)NC8=O)CC7)CC6)CC5)nc4c3F)c12] |

TABLE 1-continued
| Compound No. | Compound Structure |
|---|---|
| | Example Compounds of the Disclosure |
| 54 | 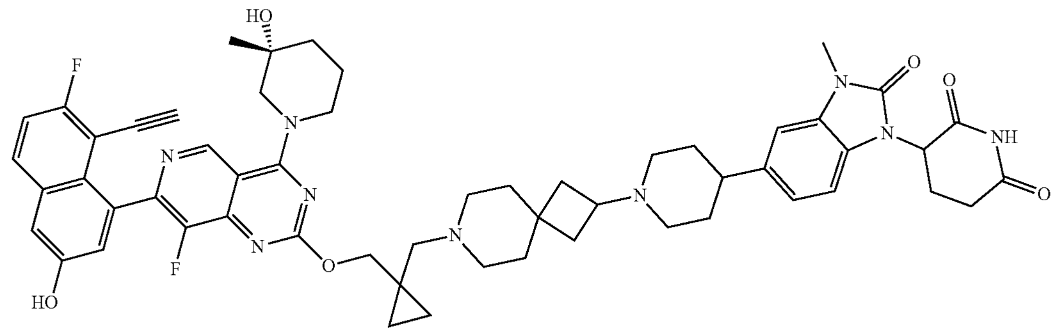 [SMILES: C#Cc1c(F)ccc2cc(O)cc(-c3ncc4c(N5CCC[C@@](C)(O)C5)nc(OCC5(CN6CCC7(CC6)CC(N6CCC(c8ccc9c(c8)n(C)c(=O)n9C8CCC(=O)NC8=O)CC6)C7)CC5)nc4c3F)c12] |
| 55 | 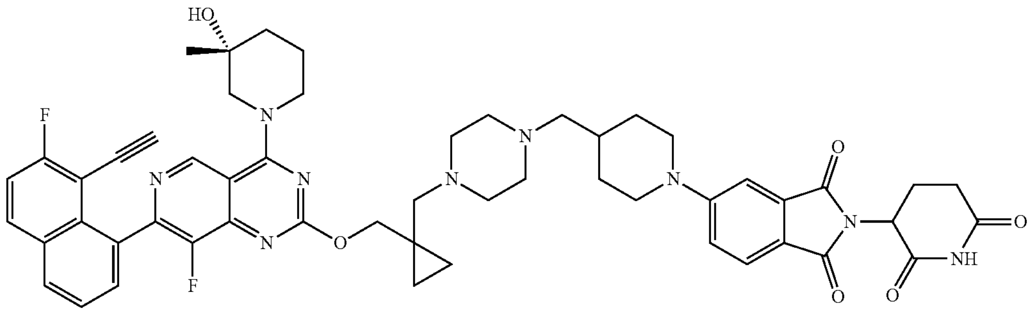 [SMILES: C#Cc1c(F)ccc2cccc(-c3ncc4c(N5CCC[C@@](C)(O)C5)nc(OCC5(CN6CCN(CC7CCN(c8ccc9c(c8)C(=O)N(C8CCC(=O)NC8=O)C9=O)CC7)CC6)CC5)nc4c3F)c12] |
| 56 | 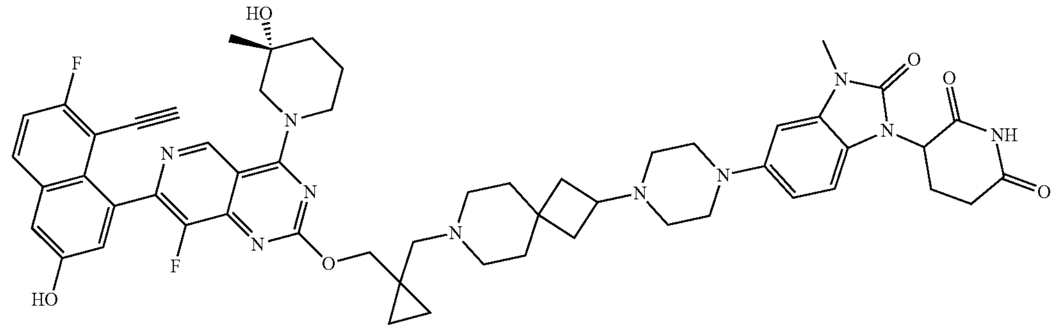 [SMILES: C#Cc1c(F)ccc2cc(O)cc(-c3ncc4c(N5CCC[C@@](C)(O)C5)nc(OCC5(CN6CCC7(CC6)CC(N6CCN(c8ccc9c(c8)n(C)c(=O)n9C8CCC(=O)NC8=O)CC6)C7)CC5)nc4c3F)c12] |
| 57 | 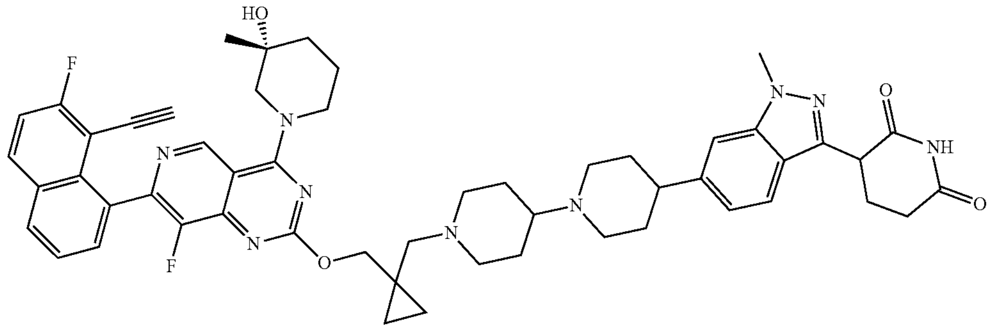 [SMILES: C#Cc1c(F)ccc2cccc(-c3ncc4c(N5CCC[C@@](C)(O)C5)nc(OCC5(CN6CCC(N7CCC(c8ccc9c(C%10CCC(=O)NC%10=O)nn(C)c9c8)CC7)CC6)CC5)nc4c3F)c12] |

TABLE 1-continued
| Example Compounds of the Disclosure | |
|---|---|
| Compound No. | Compound Structure |
| 58 | 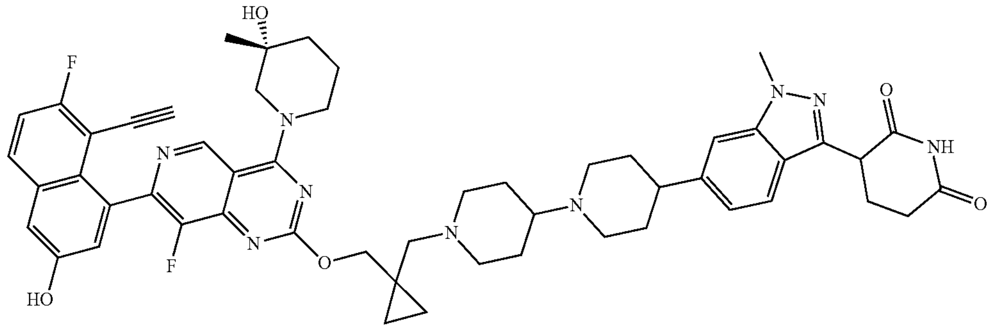 [SMILES: C#Cc1c(F)ccc2cc(O)cc(-c3ncc4c(N5CCC[C@@](C)(O)C5)nc(OCC5(CN6CCC(N7CCC(c8ccc9c(C%10CCC(=O)NC%10=O)nn(C)c9c8)CC7)CC6)CC5)nc4c3F)c12] |
| 59 | 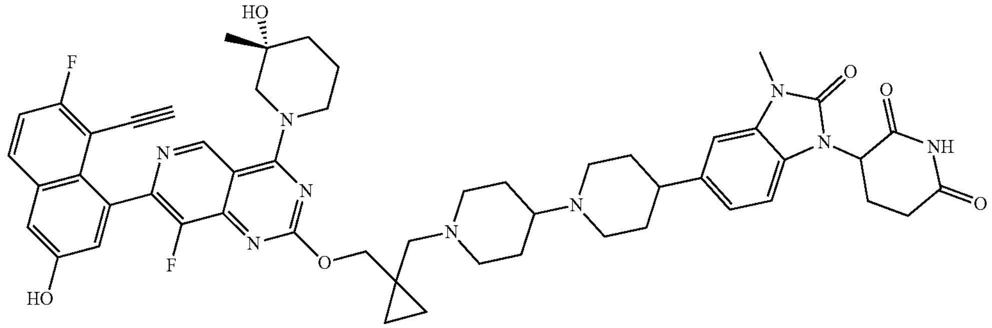 [SMILES: C#Cc1c(F)ccc2cc(O)cc(-c3ncc4c(N5CCC[C@@](C)(O)C5)nc(OCC5(CN6CCC(N7CCC(c8ccc9c(c8)n(C)c(=O)n9C8CCC(=O)NC8=O)CC7)CC6)CC5)nc4c3F)c12] |
| 60 | 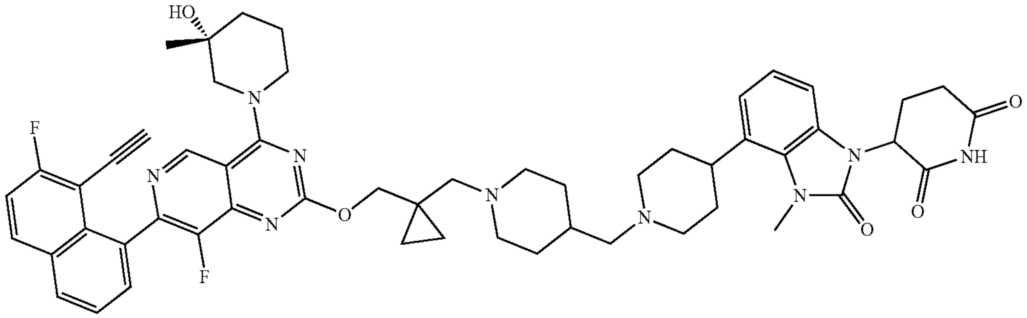 [SMILES: C#Cc1c(F)ccc2cccc(-c3ncc4c(N5CCC[C@@](C)(O)C5)nc(OCC5(CN6CCC(CN7CCC(c8cccc9c8n(C)c(=O)n9C8CCC(=O)NC8=O)CC7)CC6)CC5)nc4c3F)c12] |
| 61 | 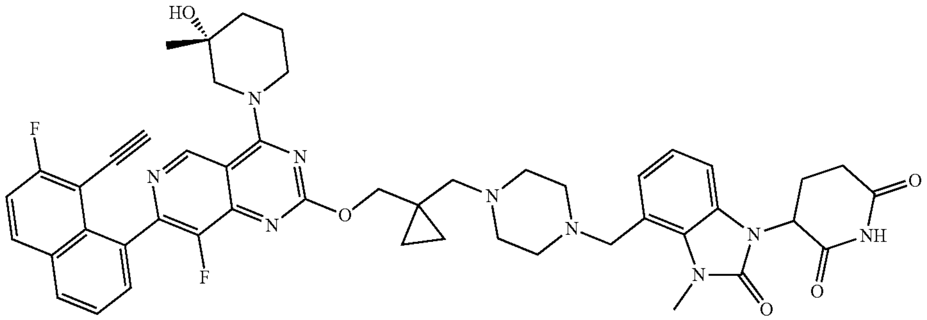 [SMILES: C#Cc1c(F)ccc2cccc(-c3ncc4c(N5CCC[C@@](C)(O)C5)nc(OCC5(CN6CCN(Cc7cccc8c7n(C)c(=O)n8C7CCC(=O)NC7=O)CC6)CC5)nc4c3F)c12] |

TABLE 1-continued
| Example Compounds of the Disclosure | |
|---|---|
| Compound No. | Compound Structure |
| 62 | 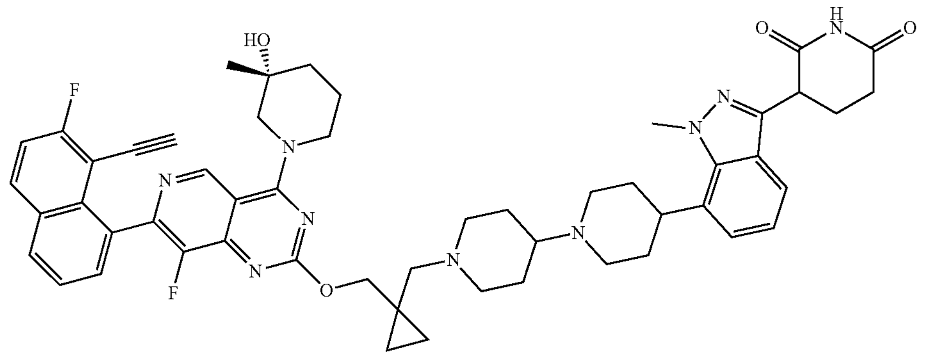 [SMILES: C#Cc1c(F)ccc2cccc(-c3ncc4c(N5CCC[C@@](C)(O)C5)nc(OCC5(CN6CCC(N7CCC(c8cccc9c(C%10CCC(=O)NC%10=O)nn(C)c89)CC7)CC6)CC5)nc4c3F)c12] |
| 63 | 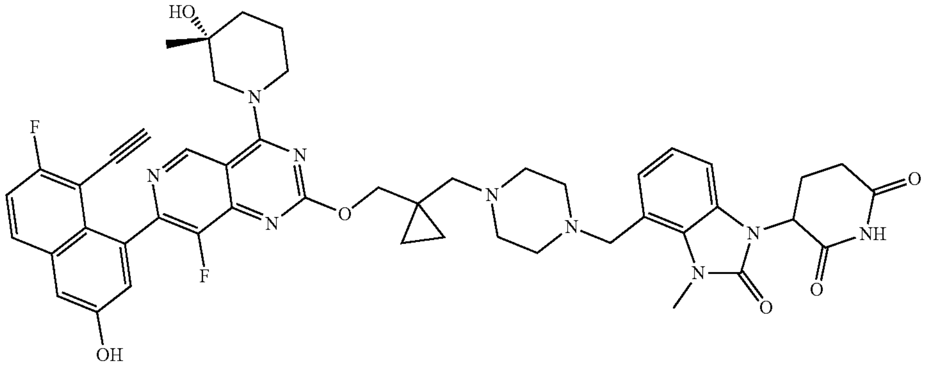 [SMILES: C#Cc1c(F)ccc2cc(O)cc(-c3ncc4c(N5CCC[C@@](C)(O)C5)nc(OCC5(CN6CCN(Cc7cccc8c7n(C)c(=O)n8C7CCC(=O)NC7=O)CC6)CC5)nc4c3F)c12] |
| 64 | 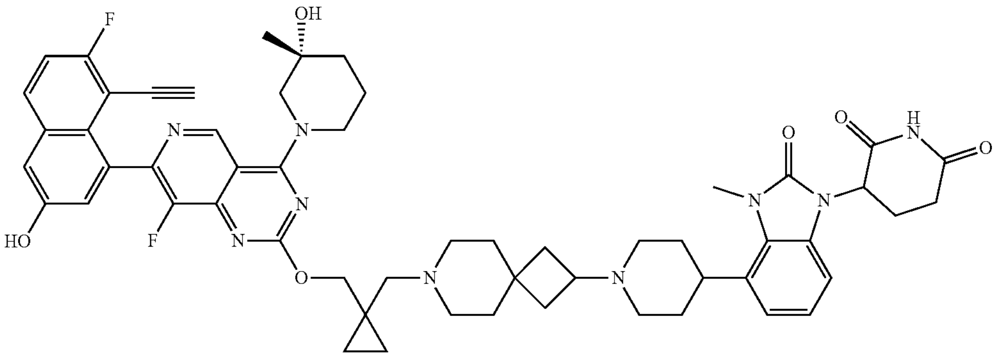 [SMILES: C#Cc1c(F)ccc2cc(O)cc(-c3ncc4c(N5CCC[C@@](C)(O)C5)nc(OCC5(CN6CCC7(CC6)CC(N6CCC(c8cccc9c8n(C)c(=O)n9C8CCC(=O)NC8=O)CC6)C7)CC5)nc4c3F)c12] |
| 65 | 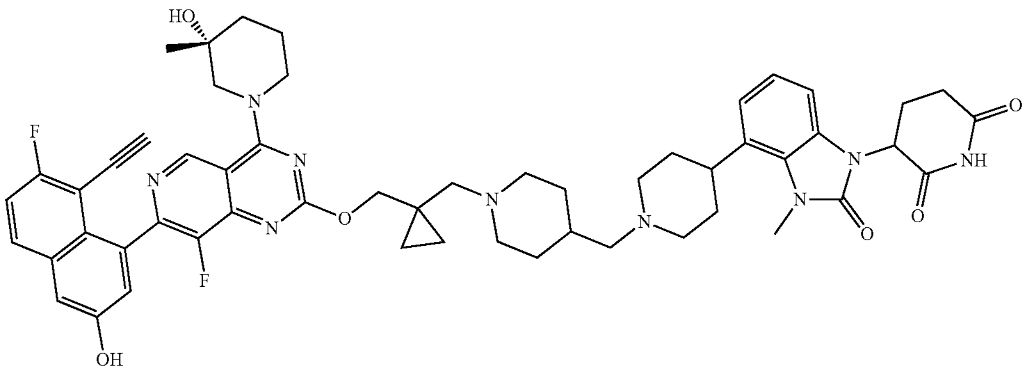 [SMILES: C#Cc1c(F)ccc2cc(O)cc(-c3ncc4c(N5CCC[C@@](C)(O)C5)nc(OCC5(CN6CCC(CN7CCC(c8cccc9c8n(C)c(=O)n9C8CCC(=O)NC8=O)CC7)CC6)CC5)nc4c3F)c12] |

TABLE 1-continued
Example Compounds of the Disclosure
| Compound No. | Compound Structure |
|---|---|
| 66 | 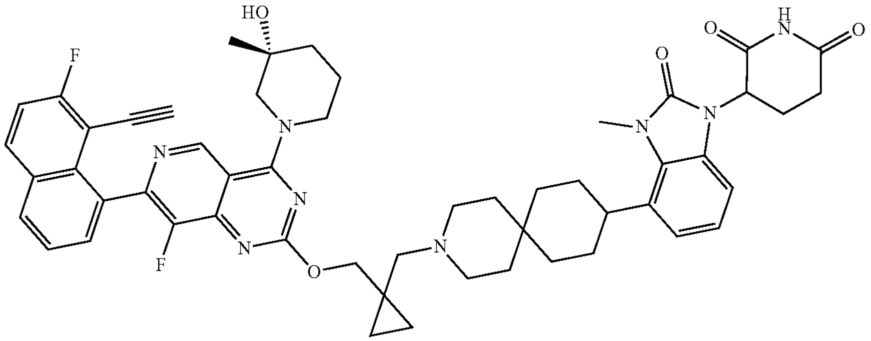 [SMILES: C#Cc1c(F)ccc2cccc(-c3ncc4c(N5CCC[C@@](C)(O)C5)nc(OCC5(CN6CCC7(CCC(c8cccc9c8n(C)c(=O)n9C8CCC(=O)NC8=O)CC7)CC6)CC5)nc4c3F)c12] |
| 67 | 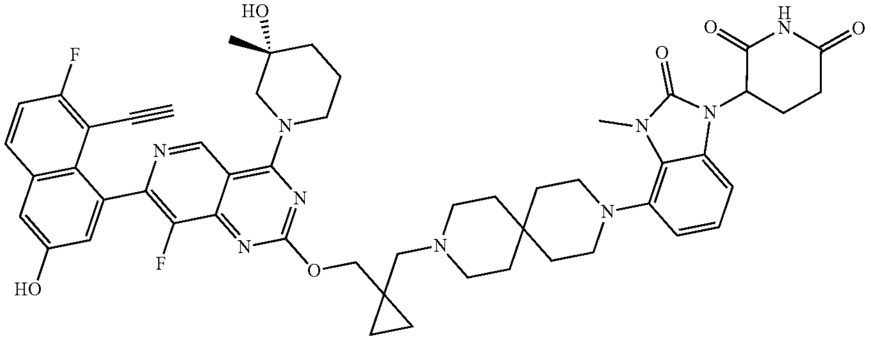 [SMILES: C#Cc1c(F)ccc2cc(O)cc(-c3ncc4c(N5CCC[C@@](C)(O)C5)nc(OCC5(CN6CCC7(CC6)CCN(c6cccc8c6n(C)c(=O)n8C6CCC(=O)NC6=O)CC7)CC5)nc4c3F)c12] |
| 68 | 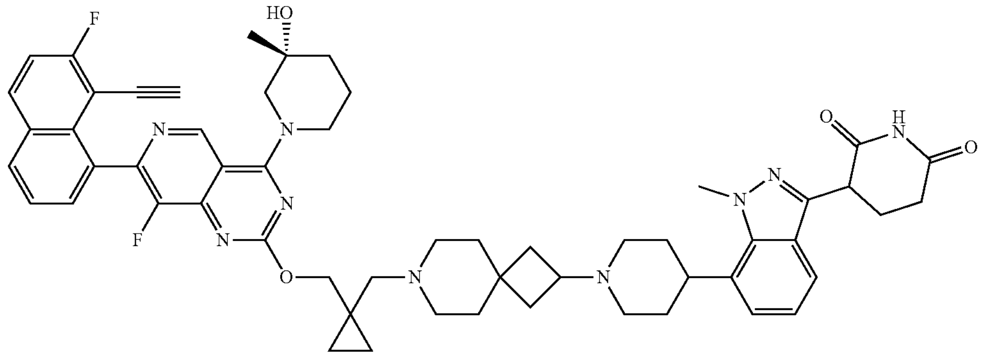 [SMILES: C#Cc1c(F)ccc2cccc(-c3ncc4c(N5CCC[C@@](C)(O)C5)nc(OCC5(CN6CCC7(CC6)CC(N6CCC(c8cccc9c(C%10CCC(=O)NC%10=O)nn(C)c89)CC6)C7)CC5)nc4c3F)c12] |
| 69 | 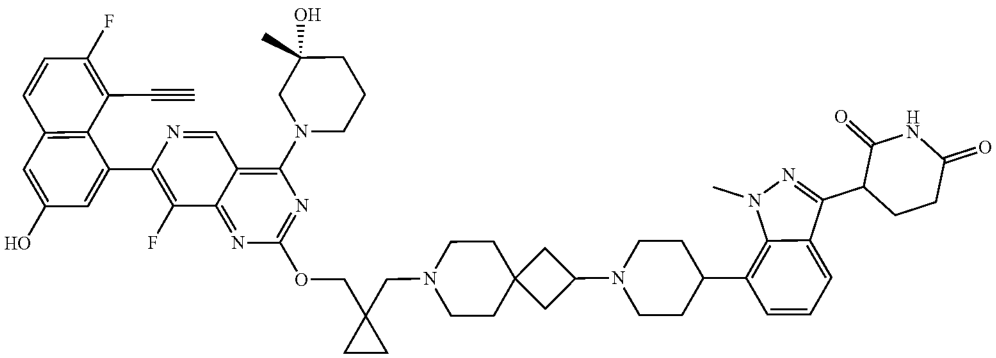 [SMILES: C#Cc1c(F)ccc2cc(O)cc(-c3ncc4c(N5CCC[C@@](C)(O)C5)nc(OCC5(CN6CCC7(CC6)CC(N6CCC(c8cccc9c(C%10CCC(=O)NC%10=O)nn(C)c89)CC6)C7)CC5)nc4c3F)c12] |

TABLE 1-continued
| Compound No. | Compound Structure |
|---|---|
| | Example Compounds of the Disclosure |
| 70 | 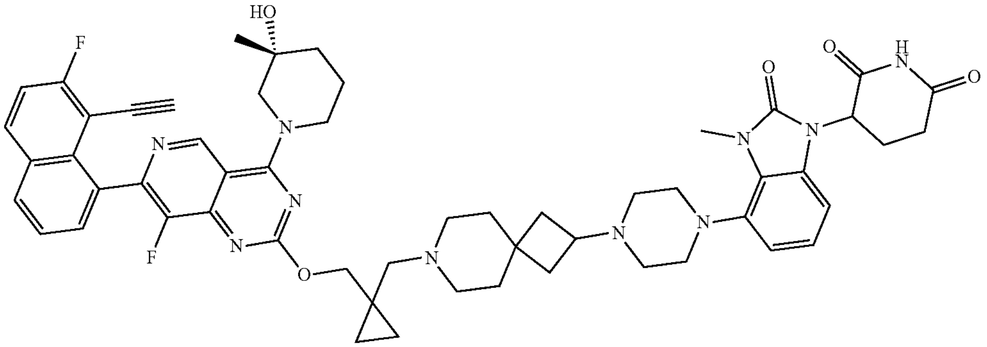 [SMILES: C#Cc1c(F)ccc2cccc(-c3ncc4c(N5CCC[C@@](C)(O)C5)nc(OCC5(CN6CCC7(CC6)CC(N6CCN(c8cccc9c8n(C)c(=O)n9C8CCC(=O)NC8=O)CC6)C7)CC5)nc4c3F)c12] |
| 71 | 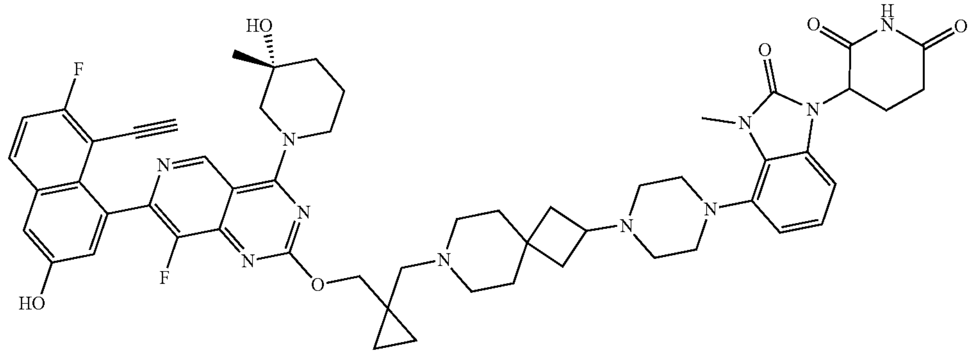 [SMILES: C#Cc1c(F)ccc2cc(O)cc(-c3ncc4c(N5CCC[C@@](C)(O)C5)nc(OCC5(CN6CCC7(CC6)CC(N6CCN(c8cccc9c8n(C)c(=O)n9C8CCC(=O)NC8=O)CC6)C7)CC5)nc4c3F)c12] |
| 72 | 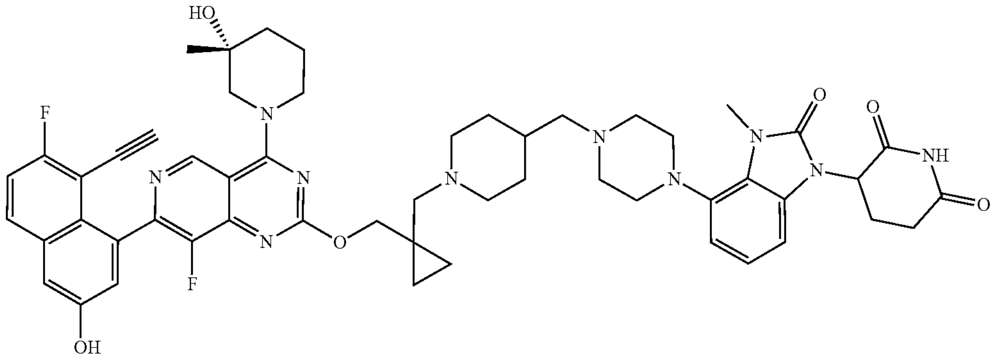 [SMILES: C#Cc1c(F)ccc2cc(O)cc(-c3ncc4c(N5CCC[C@@](C)(O)C5)nc(OCC5(CN6CCC(CN7CCN(c8cccc9c8n(C)c(=O)n9C8CCC(=O)NC8=O)CC7)CC6)CC5)nc4c3F)c12] |
| 73 | 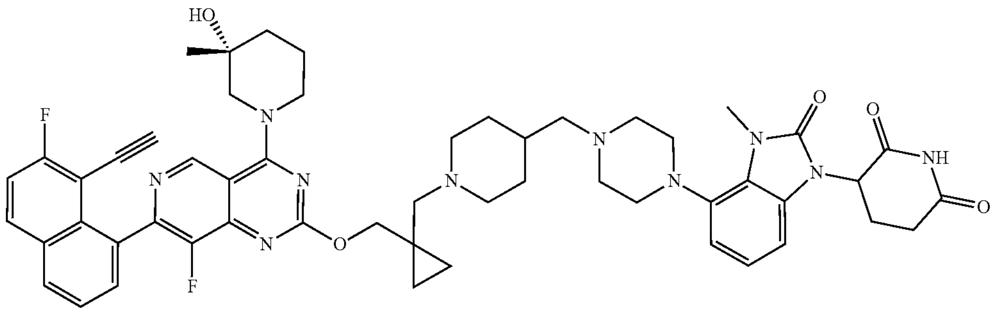 [SMILES: C#Cc1c(F)ccc2cccc(-c3ncc4c(N5CCC[C@@](C)(O)C5)nc(OCC5(CN6CCC(CN7CCN(c8cccc9c8n(C)c(=O)n9C8CCC(=O)NC8=O)CC7)CC6)CC5)nc4c3F)c12] |

TABLE 1-continued
| Example Compounds of the Disclosure | |
|---|---|
| Compound No. | Compound Structure |
| 74 | 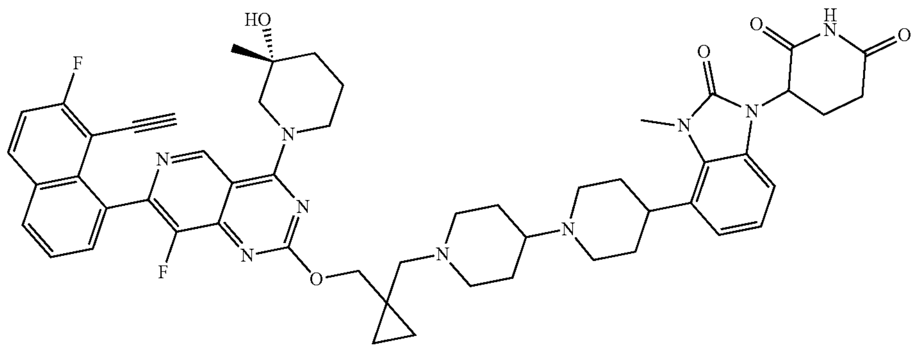 [SMILES: C#Cc1c(F)ccc2cccc(-c3ncc4c(N5CCC[C@@](C)(O)C5)nc(OCC5(CN6CCC(N7CCC(c8cccc9c8n(C)c(=O)n9C8CCC(=O)NC8=O)CC7)CC6)CC5)nc4c3F)c12] |
| 77 | 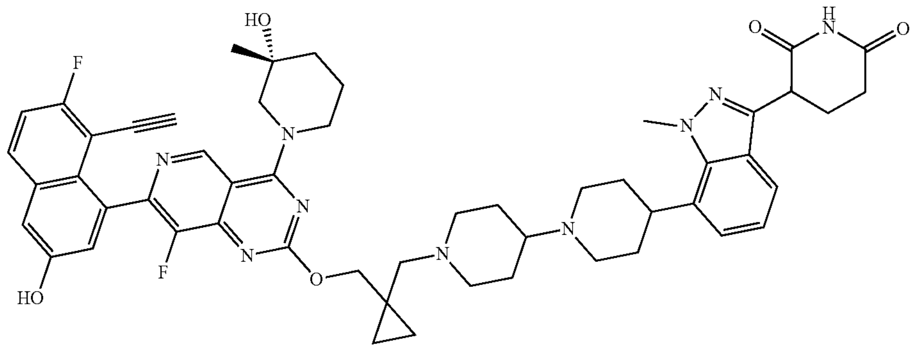 [SMILES: C#Cc1c(F)ccc2cc(O)cc(-c3ncc4c(N5CCC[C@@](C)(O)C5)nc(OCC5(CN6CCC(N7CCC(c8cccc9c(C%10CCC(=O)NC%10=O)nn(C)c89)CC7)CC6)CC5)nc4c3F)c12] |
| 78 | 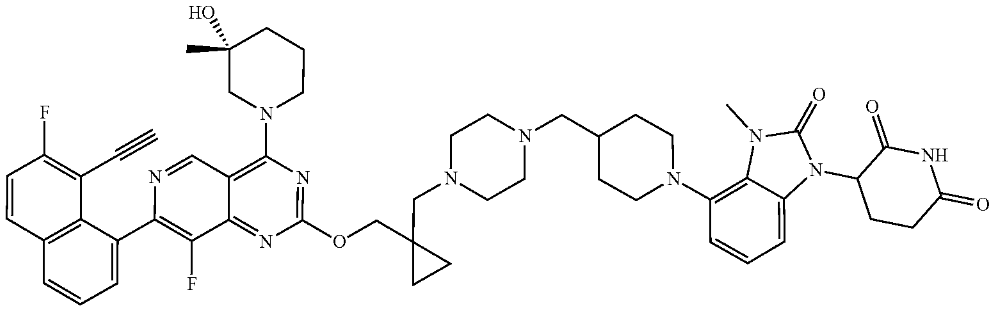 [SMILES: C#Cc1c(F)ccc2cccc(-c3ncc4c(N5CCC[C@@](C)(O)C5)nc(OCC5(CN6CCN(CC7CCN(c8cccc9c8n(C)c(=O)n9C8CCC(=O)NC8=O)CC7)CC6)CC5)nc4c3F)c12] |
| 85 | 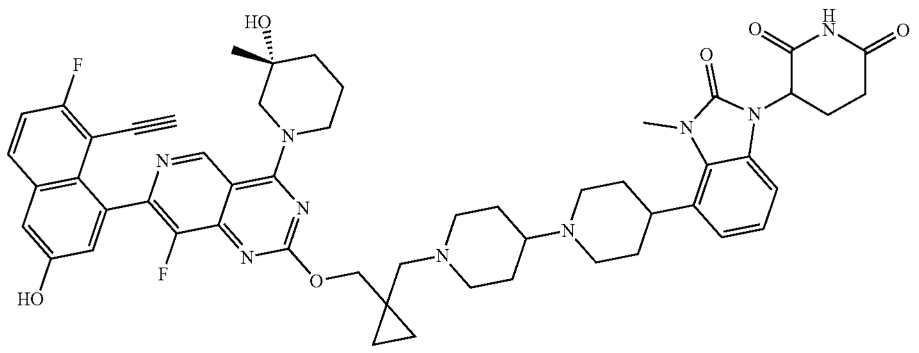 [SMILES: C#Cc1c(F)ccc2cc(O)cc(-c3ncc4c(N5CCC[C@@](C)(O)C5)nc(OCC5(CN6CCC(N7CCC(c8cccc9c8n(C)c(=O)n9C8CCC(=O)NC8=O)CC7)CC6)CC5)nc4c3F)c12] |

TABLE 1-continued
| Compound No. | Compound Structure |
|---|---|
| | Example Compounds of the Disclosure |
| 86 | 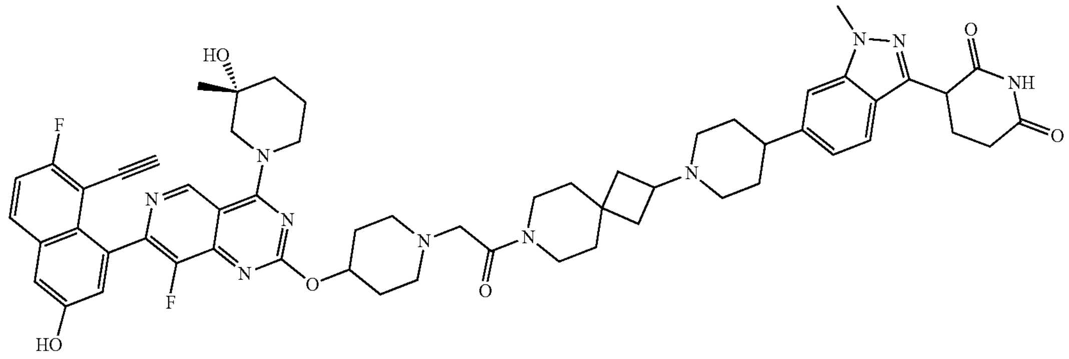 [SMILES: C#Cc1c(F)ccc2cc(O)cc(-c3ncc4c(N5CCC[C@@](C)(O)C5)nc(OC5CCN(CC(=O)N6CCC7(CC6)CC(N6CCC(c8ccc9c(C%10CCC(=O)NC%10=O)nn(C)c9c8)CC6)C7)CC5)nc4c3F)c12] |
| 87 | 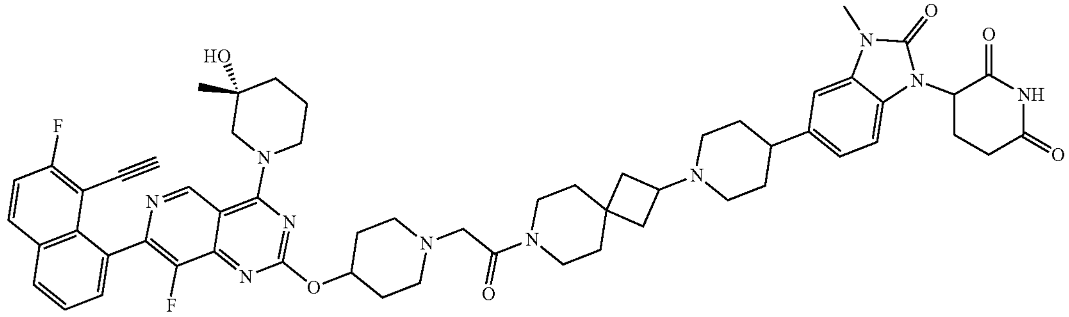 [SMILES: C#Cc1c(F)ccc2cccc(-c3ncc4c(N5CCC[C@@](C)(O)C5)nc(OC5CCN(CC(=O)N6CCC7(CC6)CC(N6CCC(c8ccc9c(c8)n(C)c(=O)n9C8CCC(=O)NC8=O)CC6)C7)CC5)nc4c3F)c12] |
| 88 | 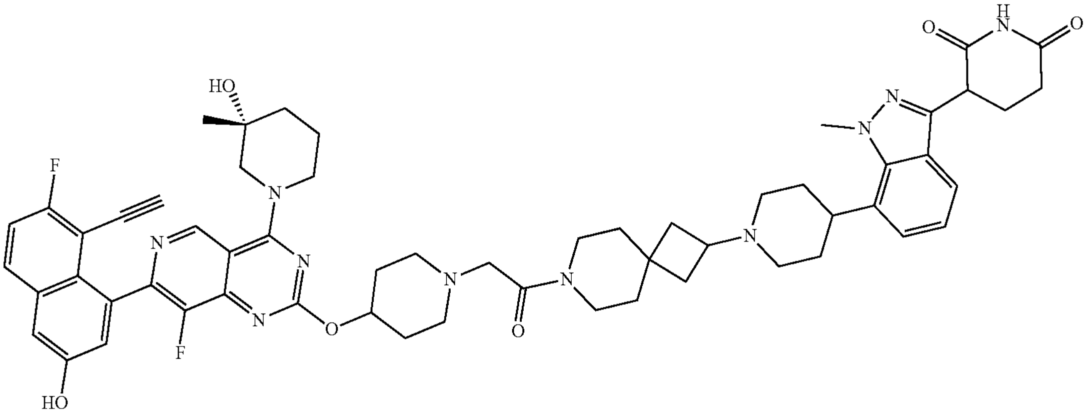 [SMILES: C#Cc1c(F)ccc2cc(O)cc(-c3ncc4c(N5CCC[C@@](C)(O)C5)nc(OC5CCN(CC(=O)N6CCC7(CC6)CC(N6CCC(c8cccc9c(C%10CCC(=O)NC%10=O)nn(C)c89)CC6)C7)CC5)nc4c3F)c12] |
| 89 | 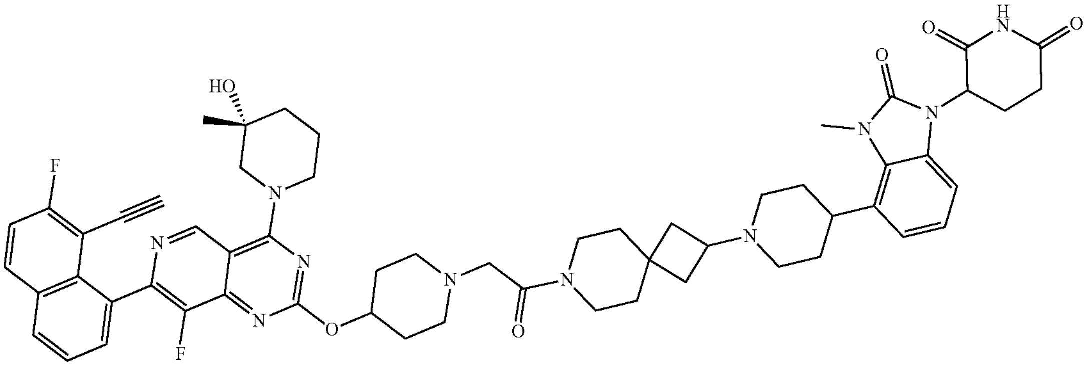 [SMILES: C#Cc1c(F)ccc2cccc(-c3ncc4c(N5CCC[C@@](C)(O)C5)nc(OC5CCN(CC(=O)N6CCC7(CC6)CC(N6CCC(c8cccc9c8n(C)c(=O)n9C8CCC(=O)NC8=O)CC6)C7)CC5)nc4c3F)c12] |

TABLE 1-continued
| Example Compounds of the Disclosure | |
|---|---|
| Compound No. | Compound Structure |
| 94 | 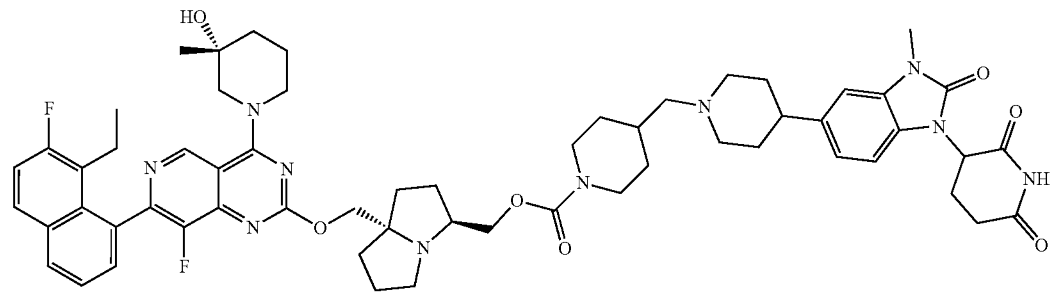 [SMILES: CCc1c(F)ccc2cccc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 95 | 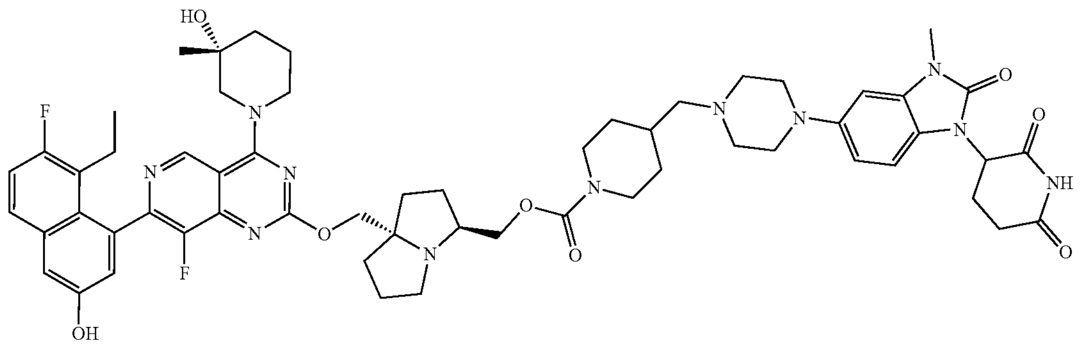 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCN(c8ccc9c(c8)n(C)c(=O)n9C8CCC(=O)NC8=O)CC7)CC5)CC6)nc4c3F)c12] |
| 96 | 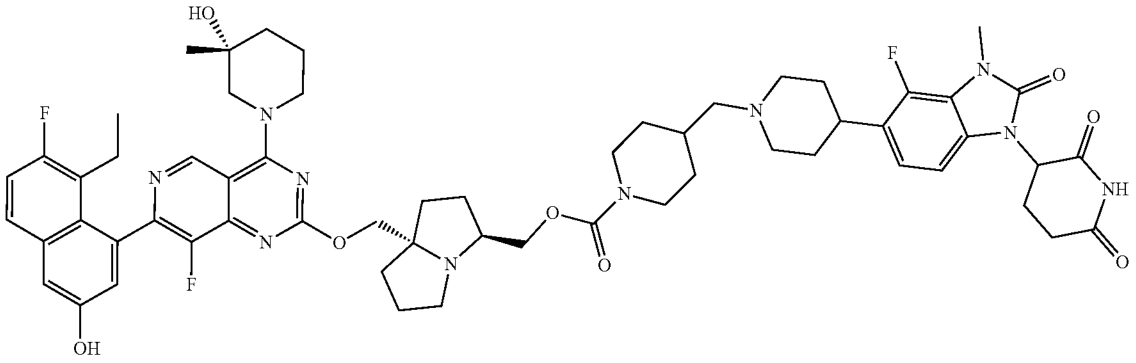 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(c8F)n(C)c(=O)n9C8CCC(=O)NC8=O)CC7)CC5)CC6)nc4c3F)c12] |
| 97 | 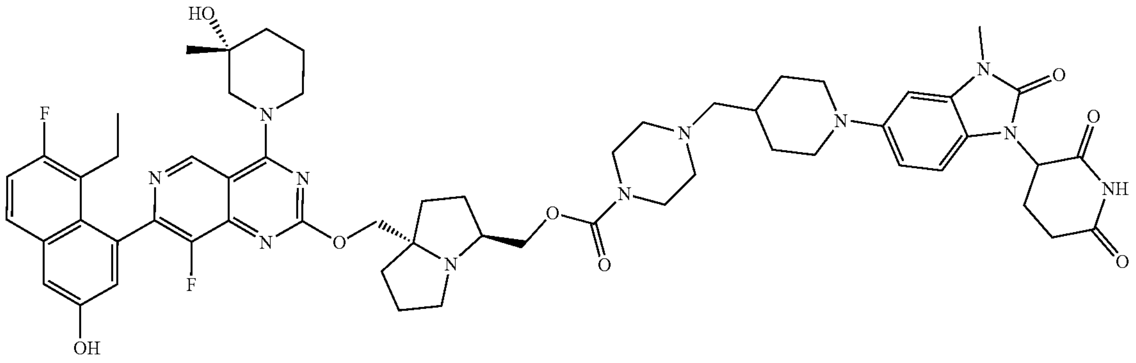 [SMILES: CCc1c(F)ccc2cc(O)cc(-c3ncc4c(N5CCC[C@@](C)(O)C5)nc(OC[C@@]56CCCN5[C@H](COC(=O)N5CCN(CC7CCN(c8ccc9c(c8)n(C)c(=O)n9C8CCC(=O)NC8=O)CC7)CC5)CC6)nc4c3F)c12] |

TABLE 1-continued
Example Compounds of the Disclosure
| Compound No. | Compound Structure |
|---|---|
| 98 | 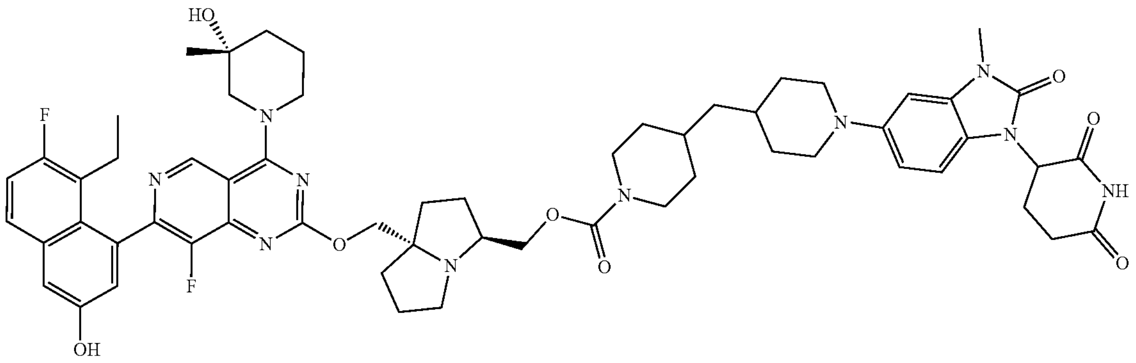 |
| 99 | 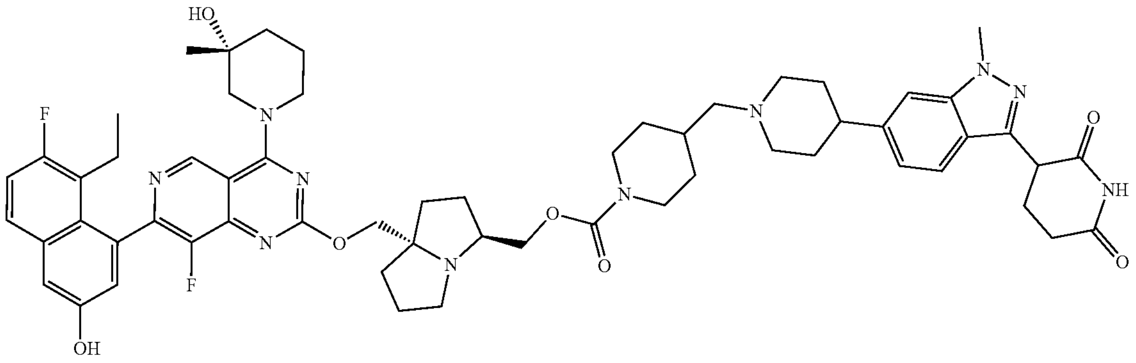 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(C%10CCC(=O)NC%10=O)nn(C)c9c8)CC7)CC5)CC6)nc4c3F)c12] |
| 100 | 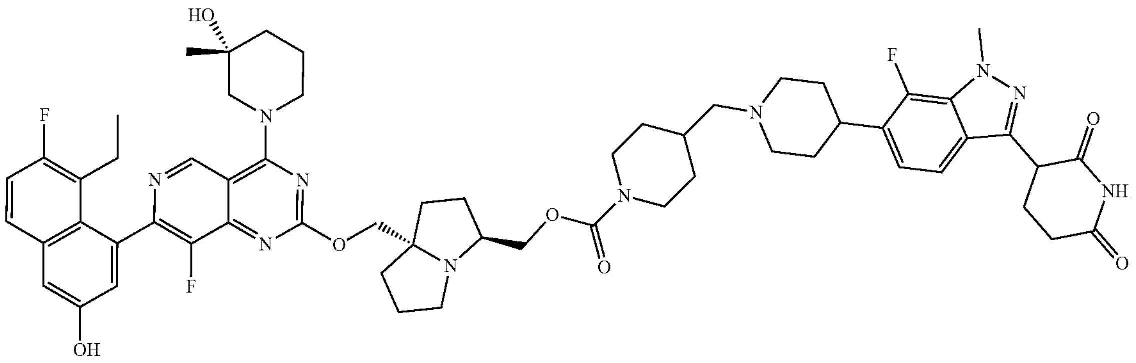 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(C%10CCC(=O)NC%10=O)nn(C)c9c8F)CC7)CC5)CC6)nc4c3F)c12] |
| 101 | 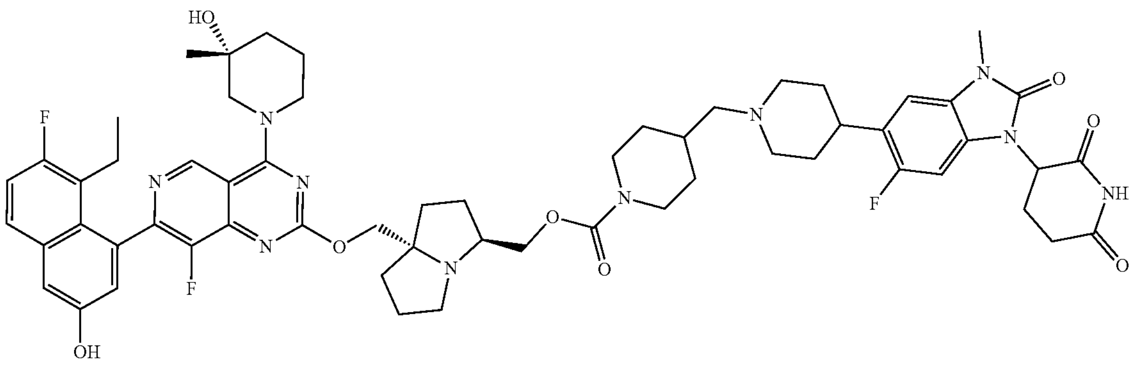 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8cc9c(cc8F)n(C8CCC(=O)NC8=O)c(=O)n9C)CC7)CC5)CC6)nc4c3F)c12] |

TABLE 1-continued
| Example Compounds of the Disclosure | |
|---|---|
| Compound No. | Compound Structure |
| 102 | 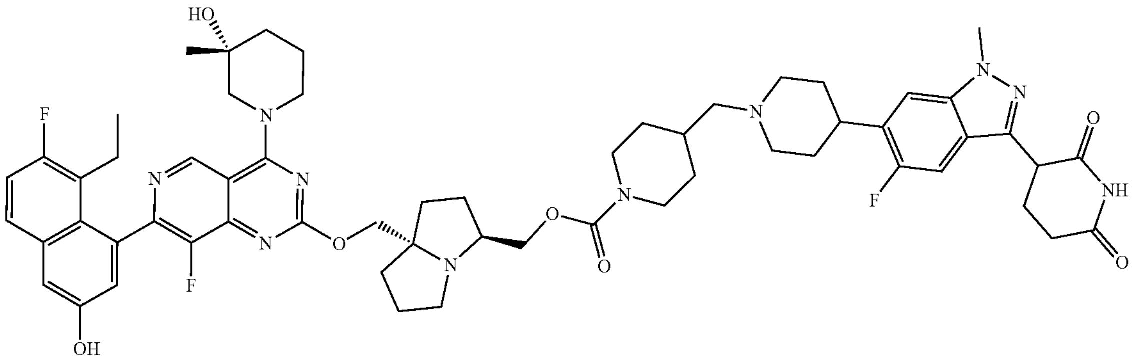 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8cc9c(cc8F)c(C8CCC(=O)NC8=O)nn9C)CC7)CC5)CC6)nc4c3F)c12] |
| 103 | 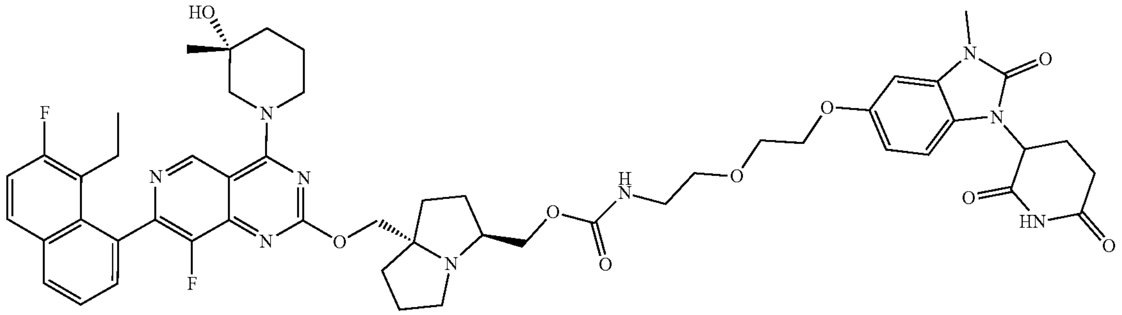 [SMILES: CCc1c(F)ccc2cccc(-c3ncc4c(N5CCC[C@@](C)(O)C5)nc(OC[C@@]56CCCN5[C@H](COC(=O)NCCOCCOc5ccc7c(c5)n(C)c(=O)n7C5CCC(=O)NC5=O)CC6)nc4c3F)c12] |
| 104 | 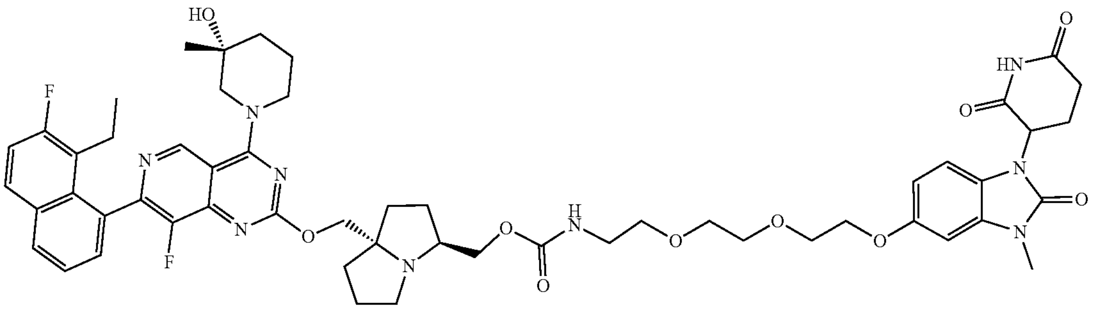 [SMILES: CCc1c(F)ccc2cccc(-c3ncc4c(N5CCC[C@@](C)(O)C5)nc(OC[C@@]56CCCN5[C@H](COC(=O)NCCOCCOCCOc5ccc7c(c5)n(C)c(=O)n7C5CCC(=O)NC5=O)CC6)nc4c3F)c12] |
| 105 | 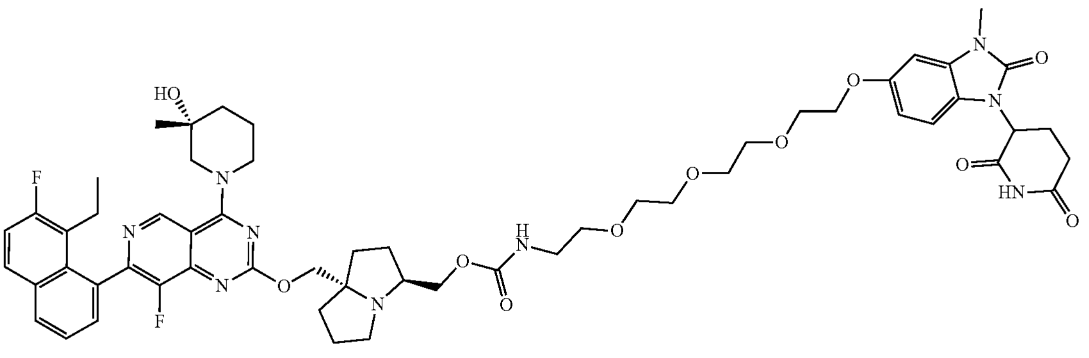 [SMILES: CCc1c(F)ccc2cccc(-c3ncc4c(N5CCC[C@@](C)(O)C5)nc(OC[C@@]56CCCN5[C@H](COC(=O)NCCOCCOCCOCCOc5ccc7c(c5)n(C)c(=O)n7C5CCC(=O)NC5=O)CC6)nc4c3F)c12] |

TABLE 1-continued
| Example Compounds of the Disclosure | |
|---|---|
| Compound No. | Compound Structure |
| 106 | 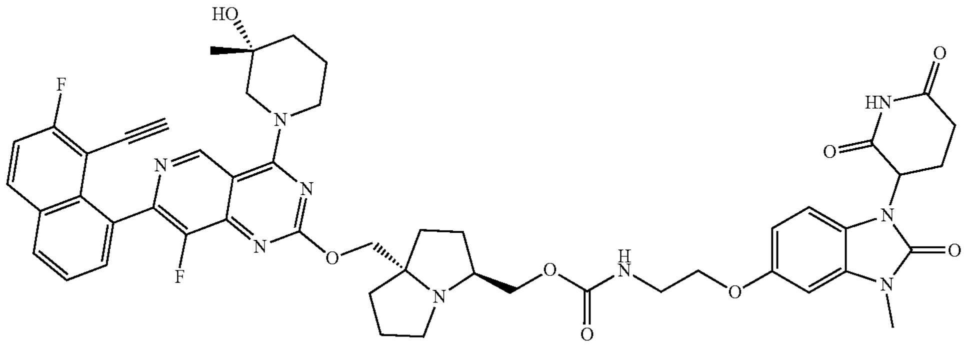 [SMILES: C#Cc1c(F)ccc2cccc(-c3ncc4c(N5CCC[C@@](C)(O)C5)nc(OC[C@@]56CCCN5[C@H](COC(=O)NCCOc5ccc7c(c5)n(C)c(=O)n7C5CCC(=O)NC5=O)CC6)nc4c3F)c12] |
| 107 | 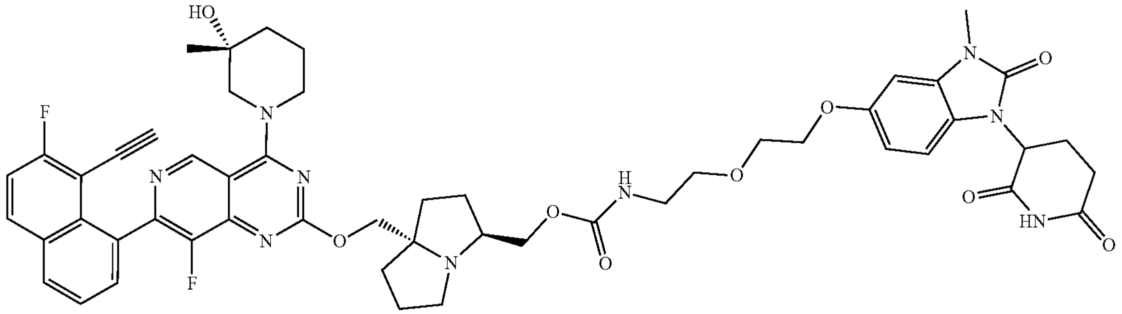 [SMILES: C#Cc1c(F)ccc2cccc(-c3ncc4c(N5CCC[C@@](C)(O)C5)nc(OC[C@@]56CCCN5[C@H](COC(=O)NCCOCCOc5ccc7c(c5)n(C)c(=O)n7C5CCC(=O)NC5=O)CC6)nc4c3F)c12] |
| 108 | 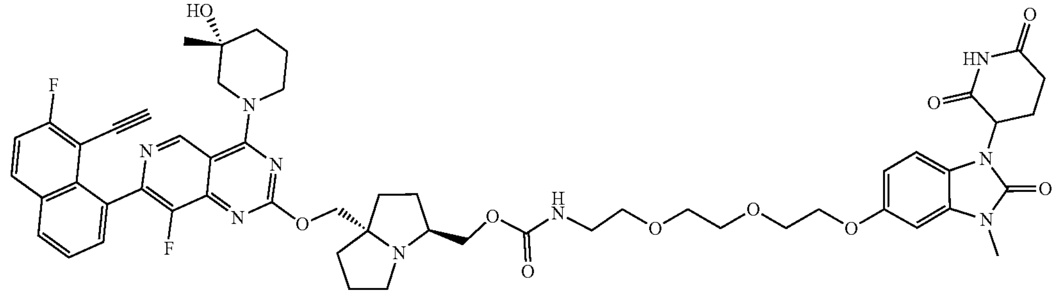 [SMILES: C#Cc1c(F)ccc2cccc(-c3ncc4c(N5CCC[C@@](C)(O)C5)nc(OC[C@@]56CCCN5[C@H](COC(=O)NCCOCCOCCOc5ccc7c(c5)n(C)c(=O)n7C5CCC(=O)NC5=O)CC6)nc4c3F)c12] |
| 109 | 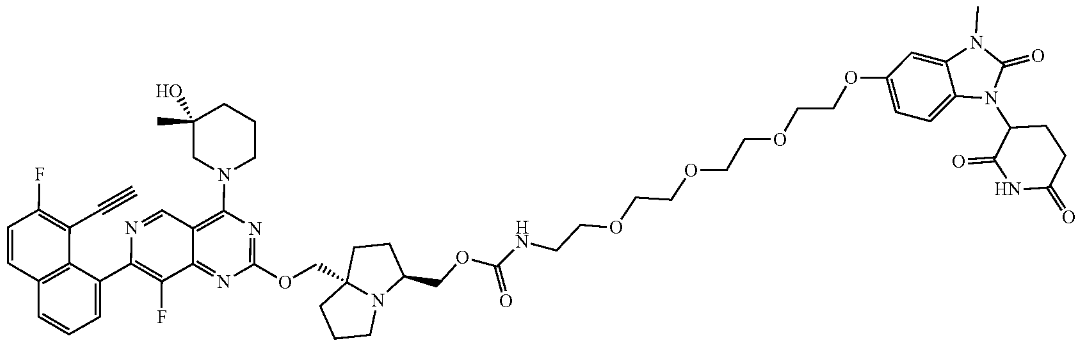 [SMILES: C#Cc1c(F)ccc2cccc(-c3ncc4c(N5CCC[C@@](C)(O)C5)nc(OC[C@@]56CCCN5[C@H](COC(=O)NCCOCCOCCOCCOc5ccc7c(c5)n(C)c(=O)n7C5CCC(=O)NC5=O)CC6)nc4c3F)c12] |

TABLE 1-continued
| Compound No. | Compound Structure |
|---|---|
| 110 | 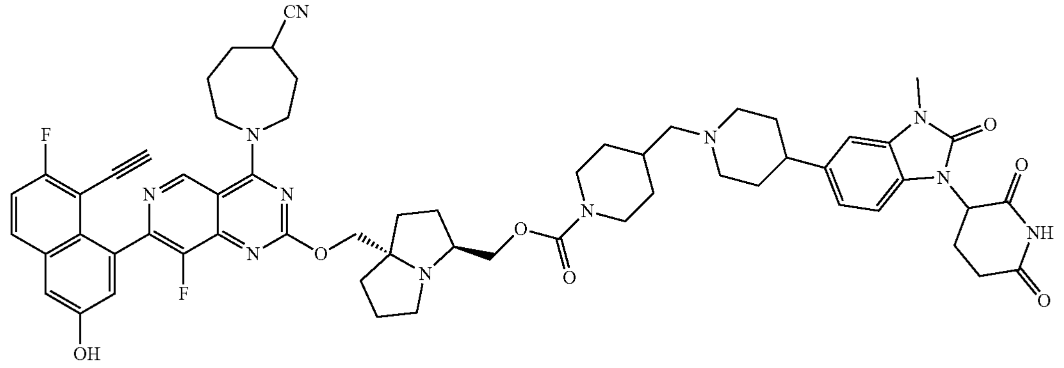 [SMILES: C#Cc1c(F)ccc2cc(O)cc(-c3ncc4c(N5CCCC(C#N)CC5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 111 | 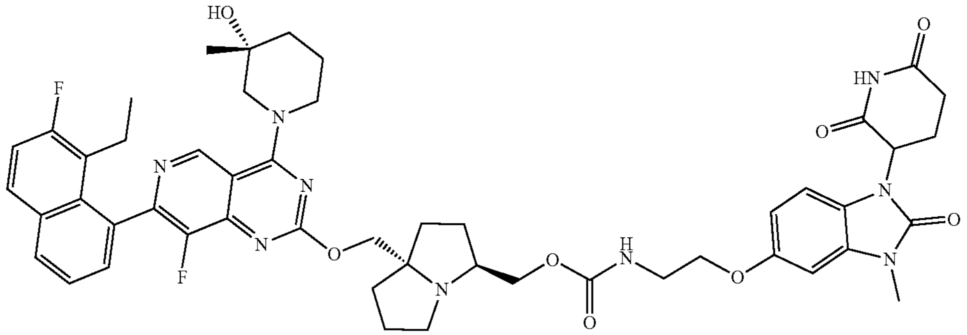 [SMILES: CCc1c(F)ccc2cccc(-c3ncc4c(N5CCC[C@@](C)(O)C5)nc(OC[C@@]56CCCN5[C@H](COC(=O)NCCOc5ccc7c(c5)n(C)c(=O)n7C5CCC(=O)NC5=O)CC6)nc4c3F)c12] |
| 112 | 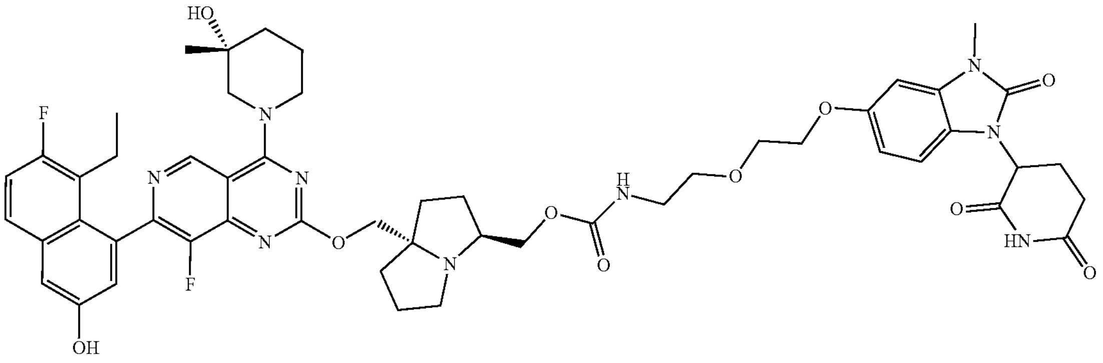 [SMILES: CCc1c(F)ccc2cc(O)cc(-c3ncc4c(N5CCC[C@@](C)(O)C5)nc(OC[C@@]56CCCN5[C@H](COC(=O)NCCOCCOc5ccc7c(c5)n(C)c(=O)n7C5CCC(=O)NC5=O)CC6)nc4c3F)c12] |
| 113 | 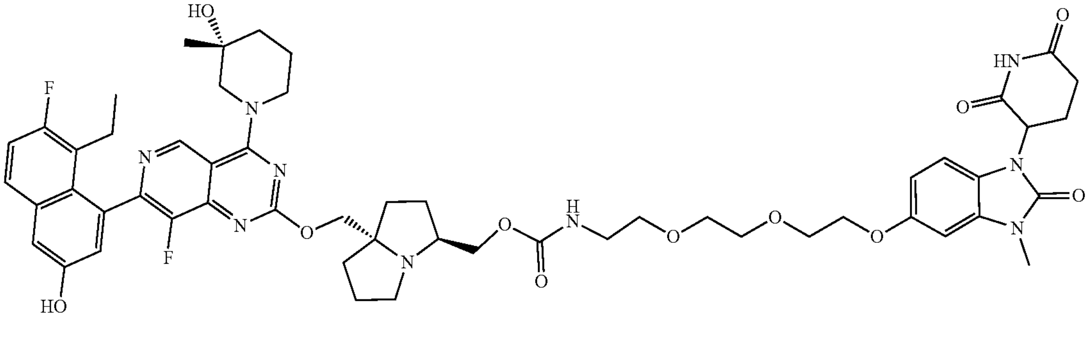 [SMILES: CCc1c(F)ccc2cc(O)cc(-c3ncc4c(N5CCC[C@@](C)(O)C5)nc(OC[C@@]56CCCN5[C@H](COC(=O)NCCOCCOCCOc5ccc7c(c5)n(C)c(=O)n7C5CCC(=O)NC5=O)CC6)nc4c3F)c12] |
Example Compounds of the Disclosure TABLE 1-continued
| Compound No. | Compound Structure |
|---|---|
| | Example Compounds of the Disclosure |
| 114 | 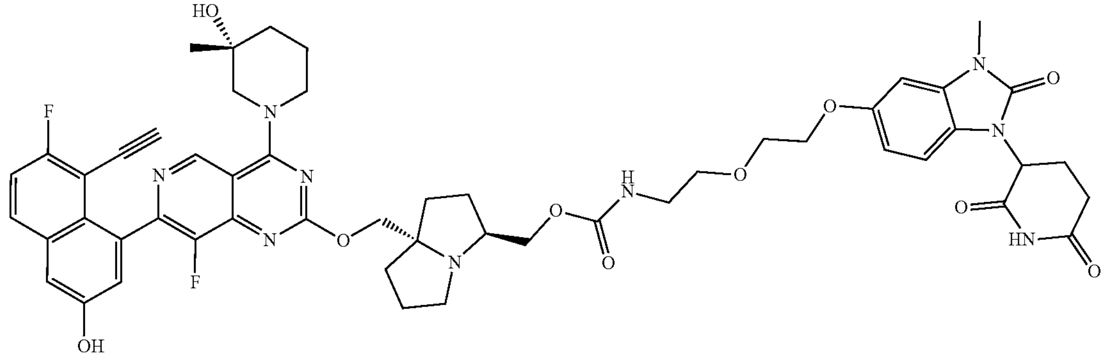 [SMILES: C#Cc1c(F)ccc2cc(O)cc(-c3ncc4c(N5CCC[C@@](C)(O)C5)nc(OC[C@@]56CCCN5[C@H](COC(=O)NCCOCCOc5ccc7c(c5)n(C)c(=O)n7C5CCC(=O)NC5=O)CC6)nc4c3F)c12] |
| 115 | 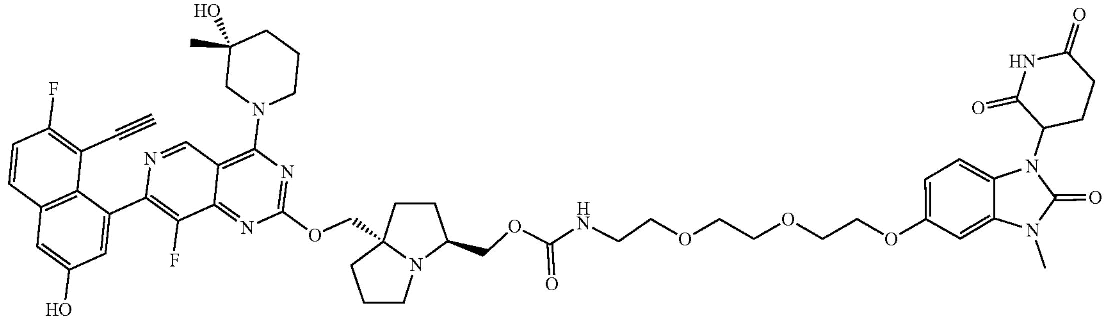 [SMILES: C#Cc1c(F)ccc2cc(O)cc(-c3ncc4c(N5CCC[C@@](C)(O)C5)nc(OC[C@@]56CCCN5[C@H](COC(=O)NCCOCCOCCOc5ccc7c(c5)n(C)c(=O)n7C5CCC(=O)NC5=O)CC6)nc4c3F)c12] |
| 116 | 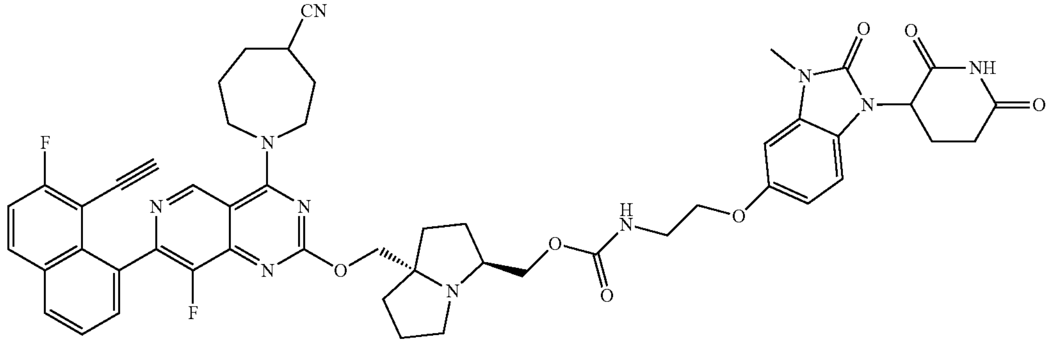 [SMILES: C#Cc1c(F)ccc2cccc(-c3ncc4c(N5CCCC(C#N)CC5)nc(OC[C@@]56CCCN5[C@H](COC(=O)NCCOc5ccc7c(c5)n(C)c(=O)n7C5CCC(=O)NC5=O)CC6)nc4c3F)c12] |
| 117 | 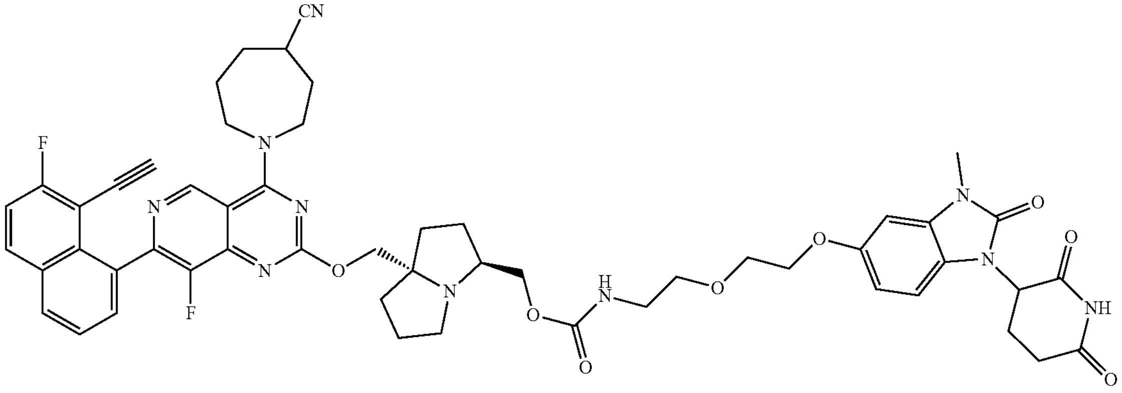 [SMILES: C#Cc1c(F)ccc2cccc(-c3ncc4c(N5CCCC(C#N)CC5)nc(OC[C@@]56CCCN5[C@H](COC(=O)NCCOCCOc5ccc7c(c5)n(C)c(=O)n7C5CCC(=O)NC5=O)CC6)nc4c3F)c12] |

TABLE 1-continued
| Example Compounds of the Disclosure | |
|---|---|
| Compound No. | Compound Structure |
| 120 | 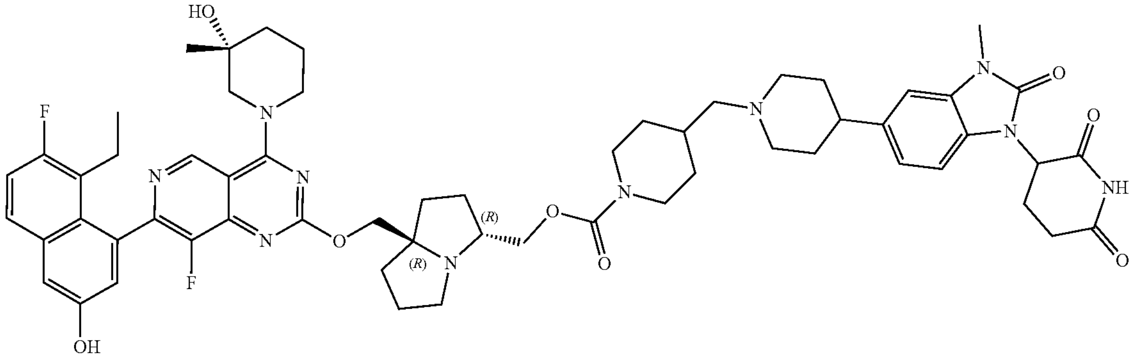 |
| 121 | 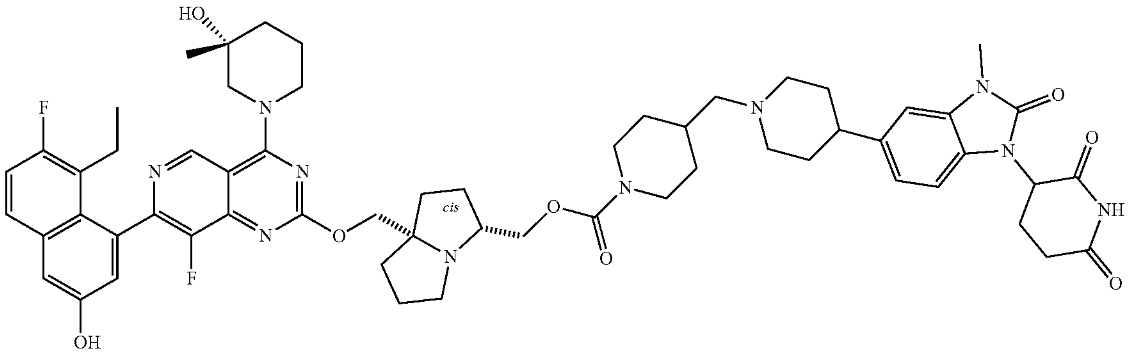 |
| 122 | 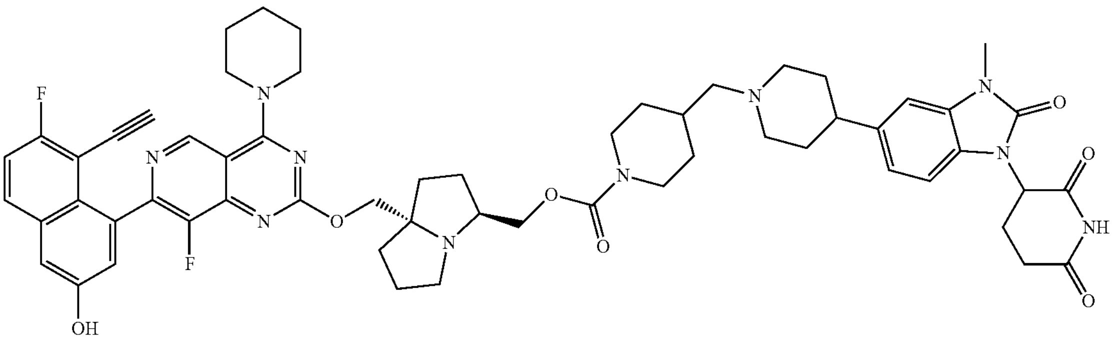 [SMILES: C#Cc1c(F)ccc2cc(O)cc(-c3ncc4c(N5CCCCC5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 123 | 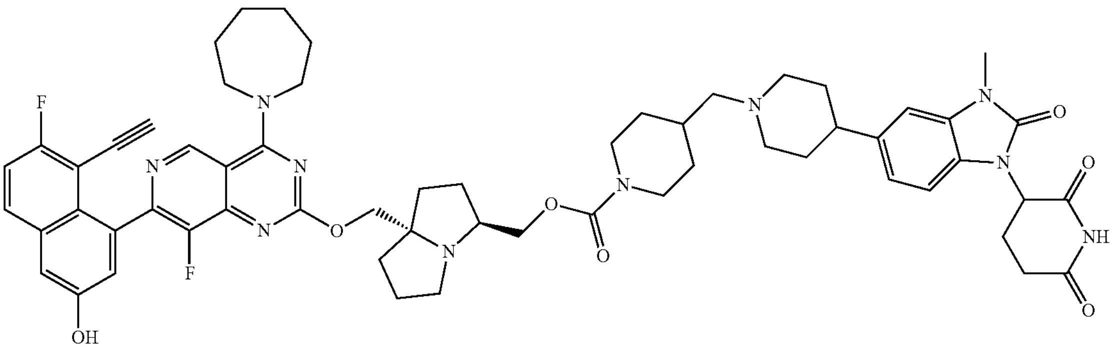 [SMILES: C#Cc1c(F)ccc2cc(O)cc(-c3ncc4c(N5CCCCCC5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |

TABLE 1-continued
| Example Compounds of the Disclosure | |
|---|---|
| Compound No. | Compound Structure |
| 124 | 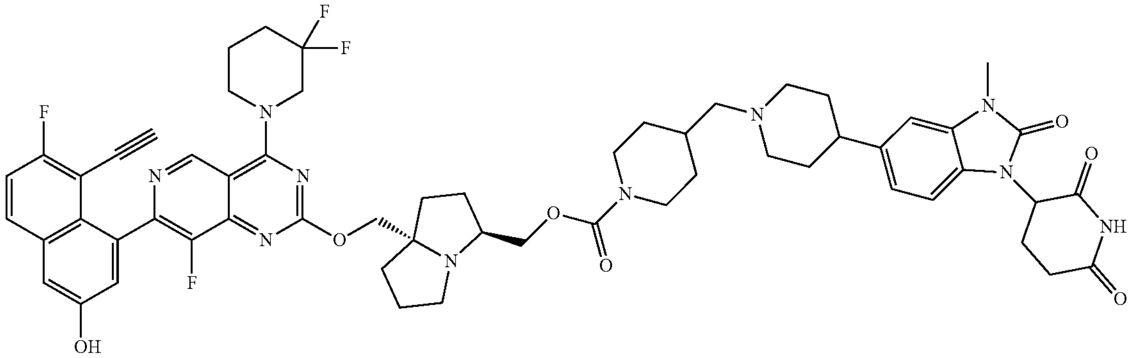 [SMILES: C#Cc1c(F)ccc2cc(O)cc(-c3ncc4c(N5CCCC(F)(F)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 125 | 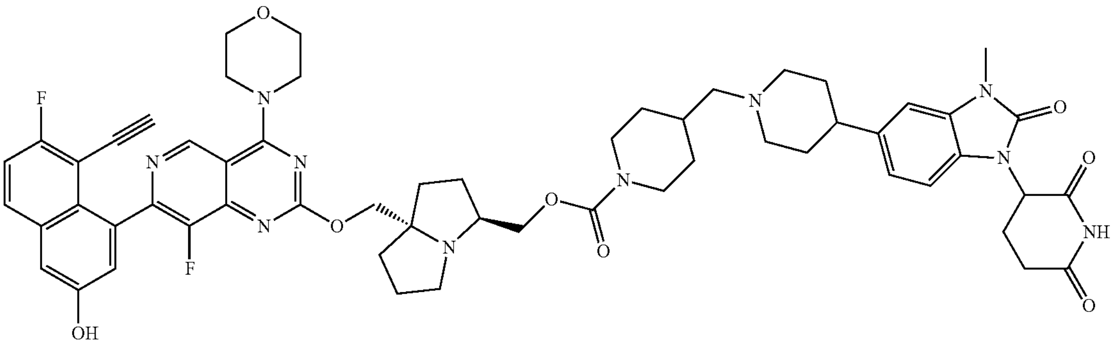 [SMILES: C#Cc1c(F)ccc2cc(O)cc(-c3ncc4c(N5CCOCC5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 126 | 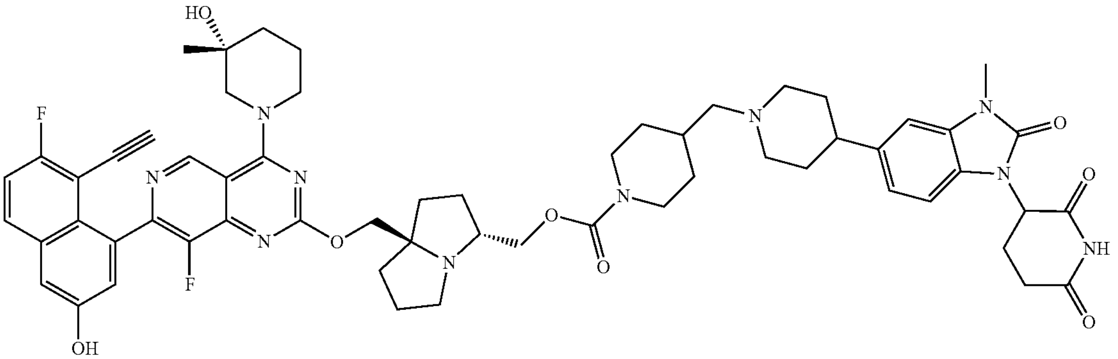 [SMILES: C#Cc1c(F)ccc2cc(O)cc(-c3ncc4c(N5CCC[C@@](C)(O)C5)nc(OC[C@]56CCCN5[C@@H](COC(=O)N5CCC(CN7CCC(c8ccc9c(c8)n(C)c(=O)n9C8CCC(=O)NC8=O)CC7)CC5)CC6)nc4c3F)c12] |
| 127 | 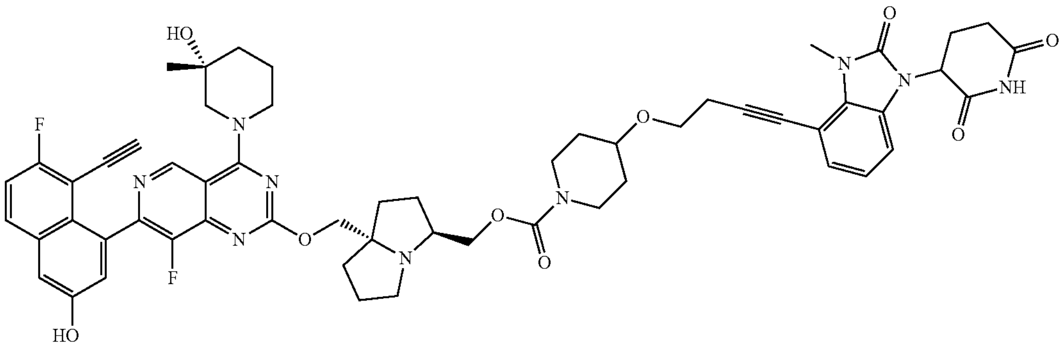 [SMILES: C#Cc1c(F)ccc2cc(O)cc(-c3ncc4c(N5CCC[C@@](C)(O)C5)nc(OC[C@@]56CCCN5[C@H](COC(=O)N5CCC(OCCC#Cc7cccc8c7n(C)c(=O)n8C7CCC(=O)NC7=O)CC5)CC6)nc4c3F)c12] |

TABLE 1-continued
| Example Compounds of the Disclosure | |
|---|---|
| Compound No. | Compound Structure |
| 128 | 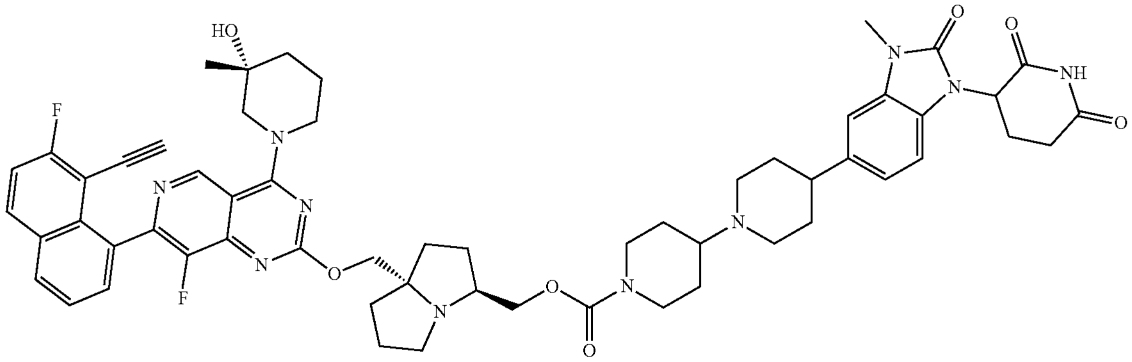 [SMILES: C#Cc1c(F)ccc2cccc(-c3ncc4c(N5CCC[C@@](C)(O)C5)nc(OC[C@@]56CCCN5[C@H](COC(=O)N5CCC(N7CCC(c8ccc9c(c8)n(C)c(=O)n9C8CCC(=O)NC8=O)CC7)CC5)CC6)nc4c3F)c12] |
| 129 | 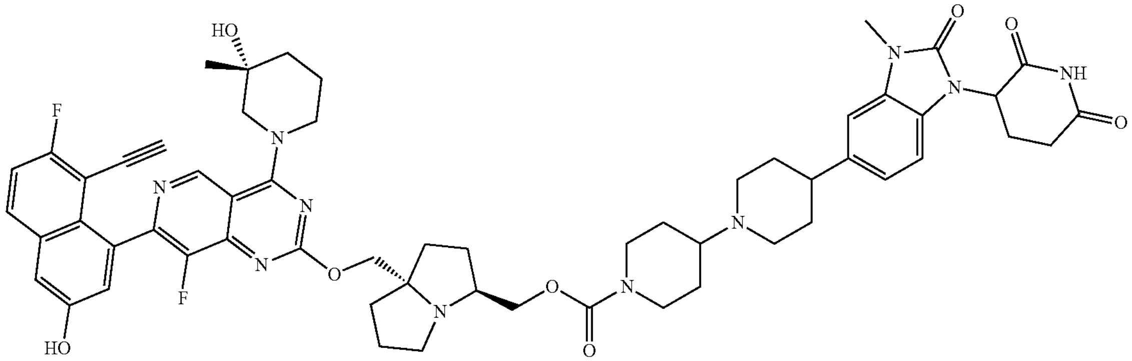 [SMILES: C#Cc1c(F)ccc2cc(O)cc(-c3ncc4c(N5CCC[C@@](C)(O)C5)nc(OC[C@@]56CCCN5[C@H](COC(=O)N5CCC(N7CCC(c8ccc9c(c8)n(C)c(=O)n9C8CCC(=O)NC8=O)CC7)CC5)CC6)nc4c3F)c12] |
| 130 | 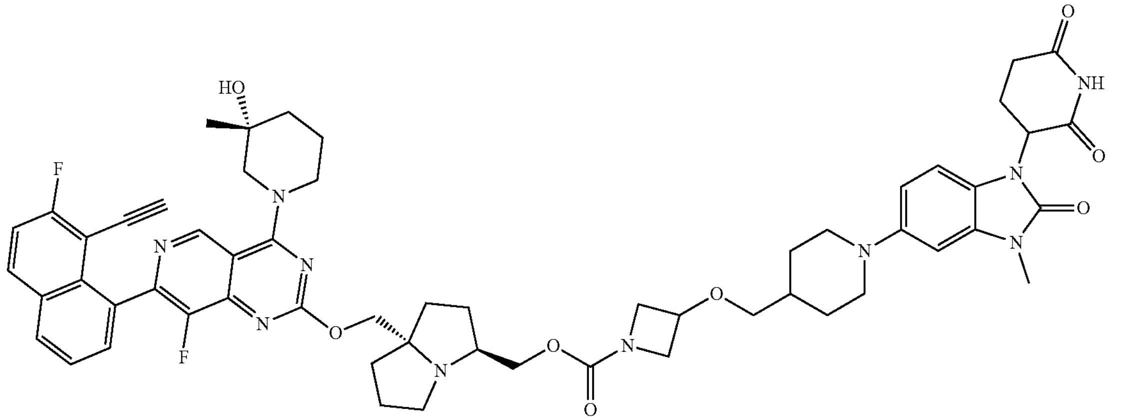 [SMILES: C#Cc1c(F)ccc2cccc(-c3ncc4c(N5CCC[C@@](C)(O)C5)nc(OC[C@@]56CCCN5[C@H](COC(=O)N5CC(OCC7CCN(c8ccc9c(c8)n(C)c(=O)n9C8CCC(=O)NC8=O)CC7)C5)CC6)nc4c3F)c12] |
| 131 | 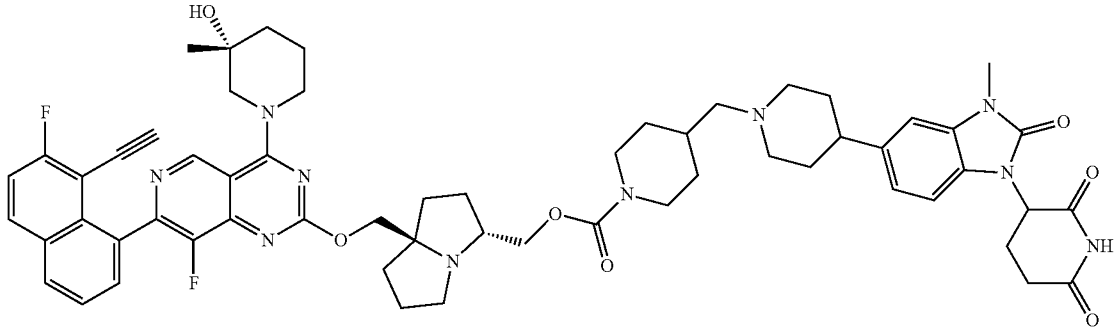 [SMILES: C#Cc1c(F)ccc2cccc(-c3ncc4c(N5CCC[C@@](C)(O)C5)nc(OC[C@]56CCCN5[C@@H](COC(=O)N5CCC(CN7CCC(c8ccc9c(c8)n(C)c(=O)n9C8CCC(=O)NC8=O)CC7)CC5)CC6)nc4c3F)c12] |

TABLE 1-continued
Example Compounds of the Disclosure
| Compound No. | Compound Structure |
|---|---|
| 132 | 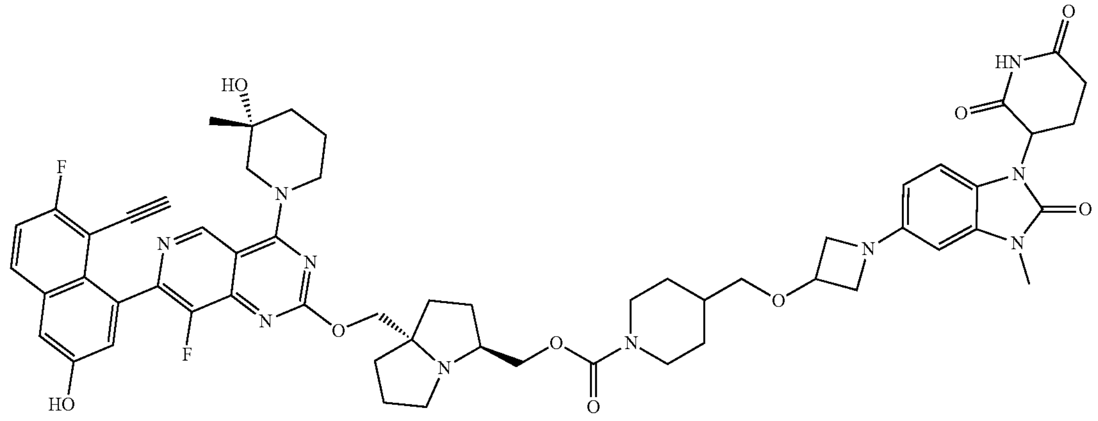 [SMILES: C#Cc1c(F)ccc2cc(O)cc(-c3ncc4c(N5CCC[C@@](C)(O)C5)nc(OC[C@@]56CCCN5[C@H](COC(=O)N5CCC(COC7CN(c8ccc9c(c8)n(C)c(=O)n9C8CCC(=O)NC8=O)C7)CC5)CC6)nc4c3F)c12] |
| 133 | 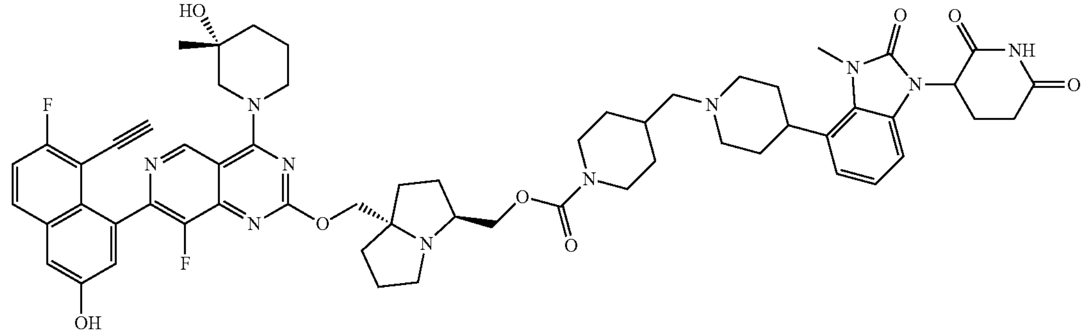 [SMILES: C#Cc1c(F)ccc2cc(O)cc(-c3ncc4c(N5CCC[C@@](C)(O)C5)nc(OC[C@@]56CCCN5[C@H](COC(=O)N5CCC(CN7CCC(c8cccc9c8n(C)c(=O)n9C8CCC(=O)NC8=O)CC7)CC5)CC6)nc4c3F)c12] |
| 134 | 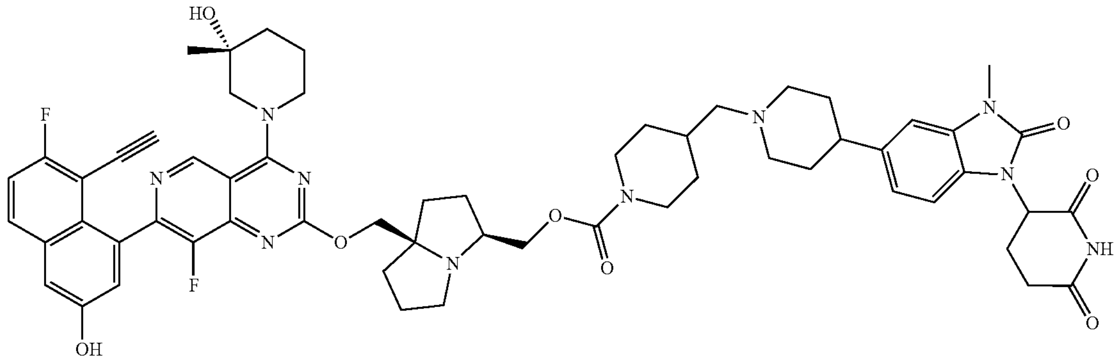 [SMILES: C#Cc1c(F)ccc2cc(O)cc(-c3ncc4c(N5CCC[C@@](C)(O)C5)nc(OC[C@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 135 | 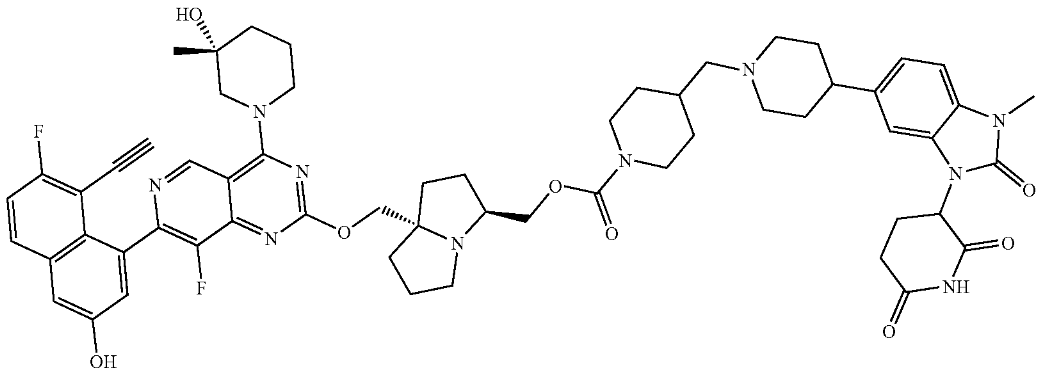 [SMILES: C#Cc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C8CCC(=O)NC8=O)c(=O)n9C)CC7)CC5)CC6)nc4c3F)c12] |

TABLE 1-continued
| Example Compounds of the Disclosure | |
|---|---|
| Compound No. | Compound Structure |
| 136 | 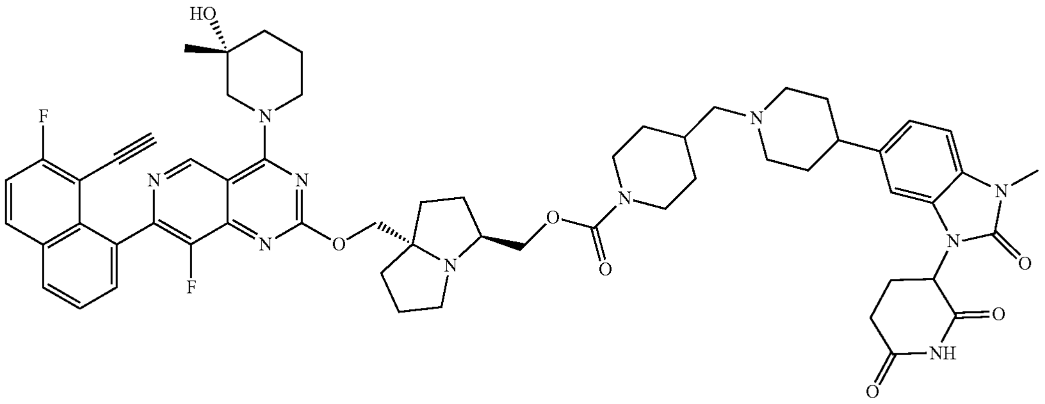 [SMILES: C#Cc1c(F)ccc2cccc(-c3ncc4c(N5CCC[C@@](C)(O)C5)nc(OC[C@@]56CCCN5[C@H](COC(=O)N5CCC(CN7CCC(c8ccc9c(c8)n(C8CCC(=O)NC8=O)c(=O)n9C)CC7)CC5)CC6)nc4c3F)c12] |
| 137 | 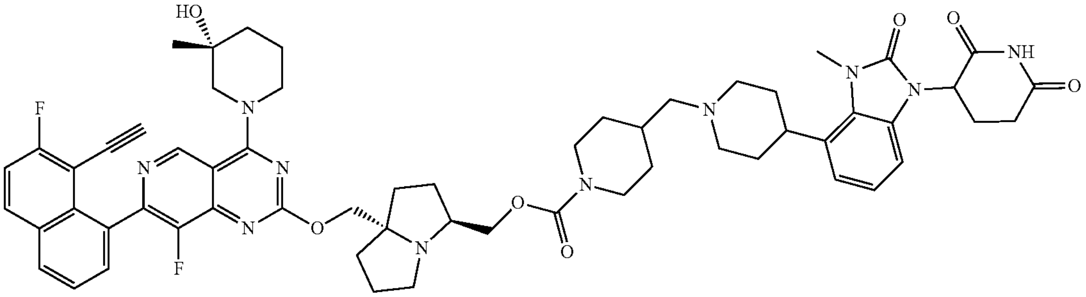 [SMILES: C#Cc1c(F)ccc2cccc(-c3ncc4c(N5CCC[C@@](C)(O)C5)nc(OC[C@@]56CCCN5[C@H](COC(=O)N5CCC(CN7CCC(c8cccc9c8n(C)c(=O)n9C8CCC(=O)NC8=O)CC7)CC5)CC6)nc4c3F)c12] |
| 138 | 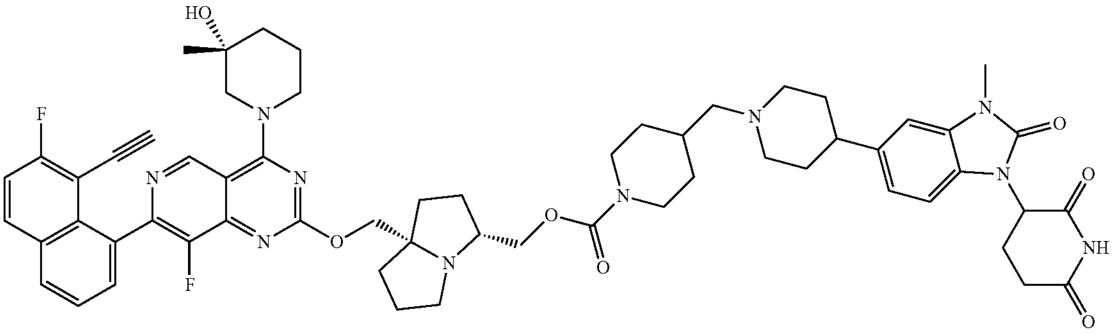 [SMILES: C#Cc1c(F)ccc2cccc(-c3ncc4c(N5CCC[C@@](C)(O)C5)nc(OC[C@@]56CCCN5[C@@H](COC(=O)N5CCC(CN7CCC(c8ccc9c(c8)n(C)c(=O)n9C8CCC(=O)NC8=O)CC7)CC5)CC6)nc4c3F)c12] |
| 139 | 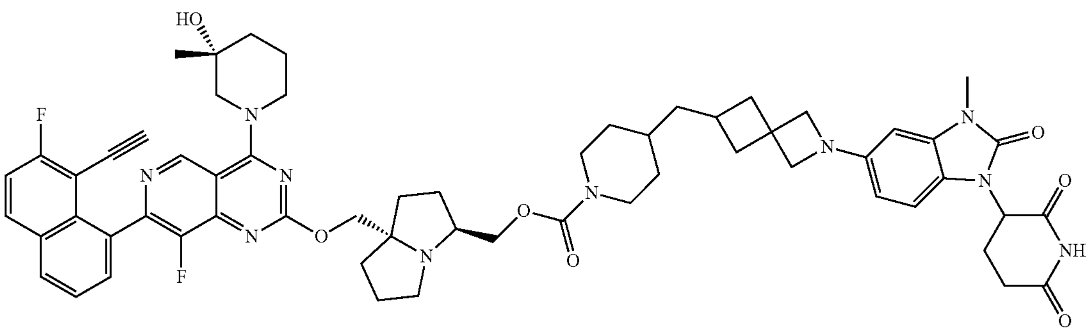 [SMILES: C#Cc1c(F)ccc2cccc(-c3ncc4c(N5CCC[C@@](C)(O)C5)nc(OC[C@@]56CCCN5[C@H](COC(=O)N5CCC(CC7CC8(C7)CN(c7ccc9c(c7)n(C)c(=O)n9C7CCC(=O)NC7=O)C8)CC5)CC6)nc4c3F)c12] |

TABLE 1-continued
| Compound No. | Compound Structure |
| --- | --- |
| | Example Compounds of the Disclosure |
| 140 | 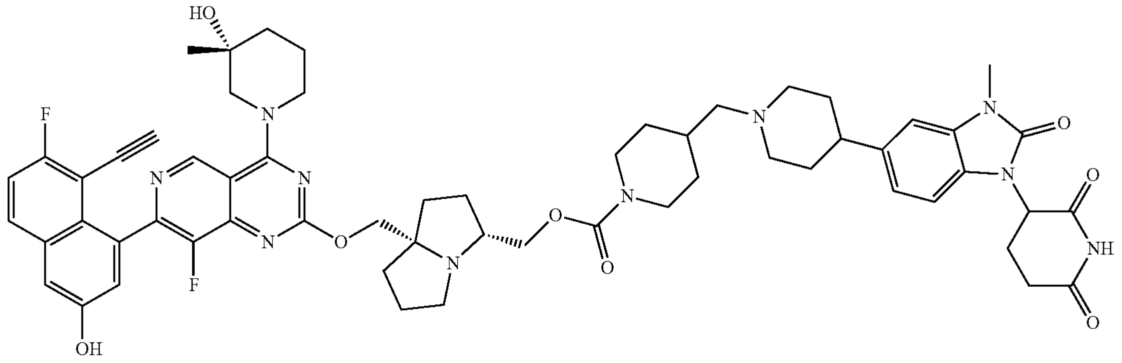 [SMILES: C#Cc1c(F)ccc2cc(O)cc(-c3ncc4c(N5CCC[C@@](C)(O)C5)nc(OC[C@@]56CCCN5[C@@H](COC(=O)N5CCC(CN7CCC(c8ccc9c(c8)n(C)c(=O)n9C8CCC(=O)NC8=O)CC7)CC5)CC6)nc4c3F)c12] |
| 141 | 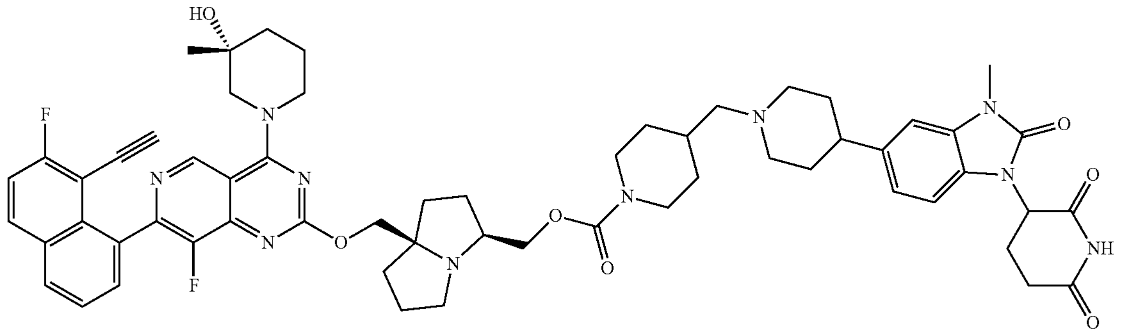 [SMILES: C#Cc1c(F)ccc2cccc(-c3ncc4c(N5CCC[C@@](C)(O)C5)nc(OC[C@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 142 | 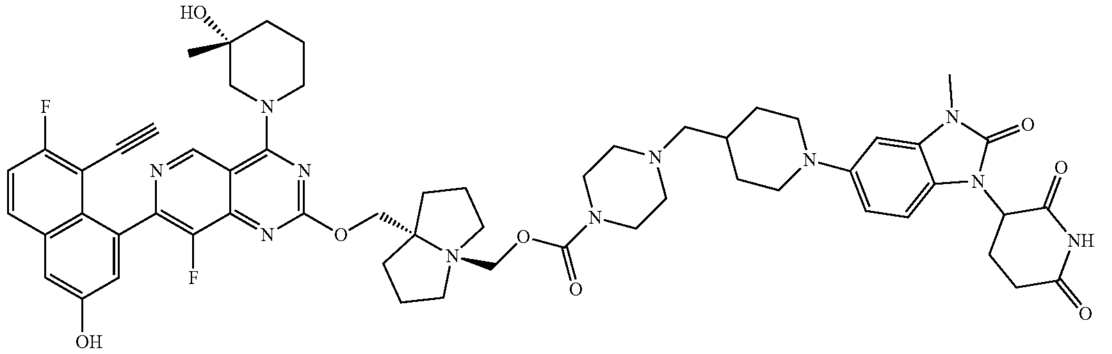 |
| 143 | 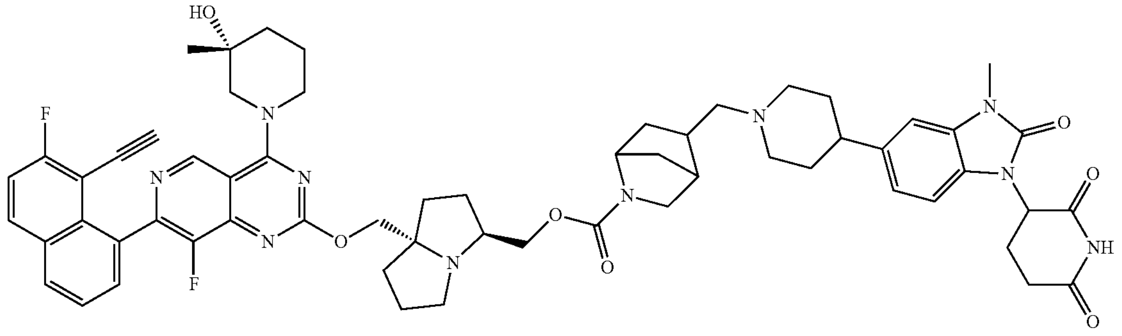 [SMILES: C#Cc1c(F)ccc2cccc(-c3ncc4c(N5CCC[C@@](C)(O)C5)nc(OC[C@@]56CCCN5[C@H](COC(=O)N5CC7CC5CC7CN5CCC(c7ccc8c(c7)n(C)c(=O)n8C7CCC(=O)NC7=O)CC5)CC6)nc4c3F)c12] |

TABLE 1-continued
| Example Compounds of the Disclosure | |
|---|---|
| Compound No. | Compound Structure |
| 144 | 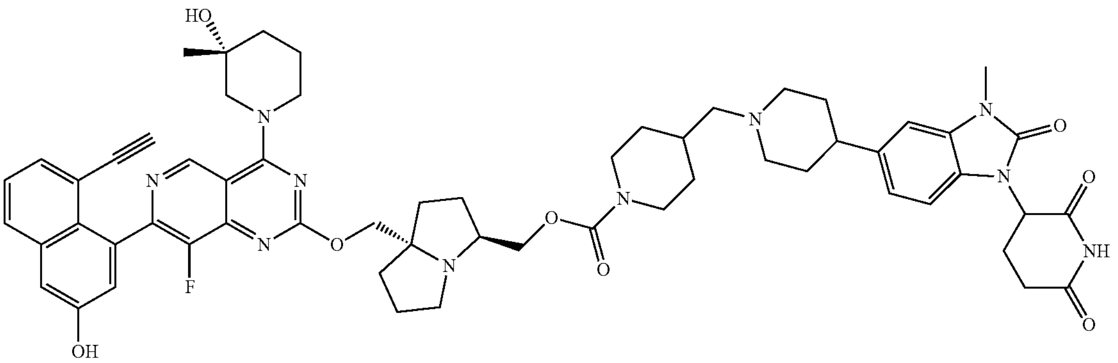 [SMILES: C#Cc1cccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 145 | 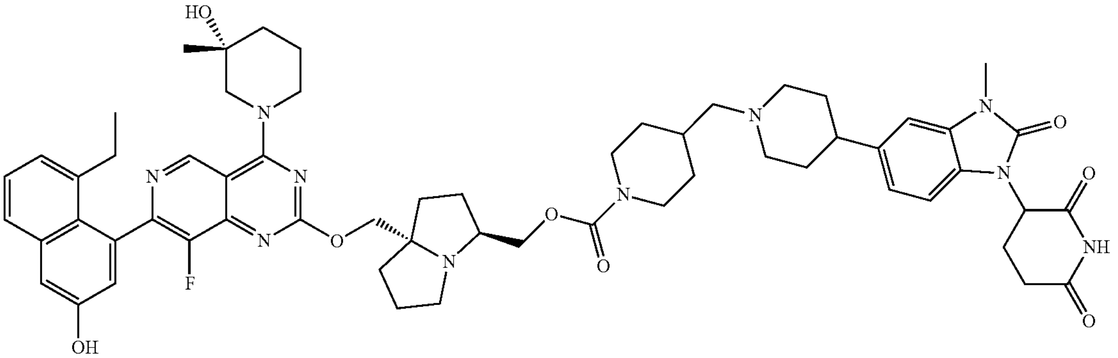 [SMILES: CCc1cccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 146 | 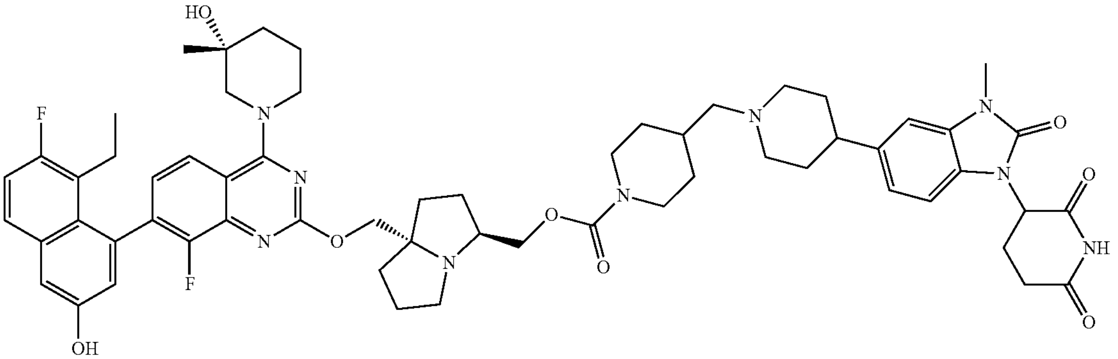 [SMILES: CCc1c(F)ccc2cc(O)cc(-c3ccc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 147 | 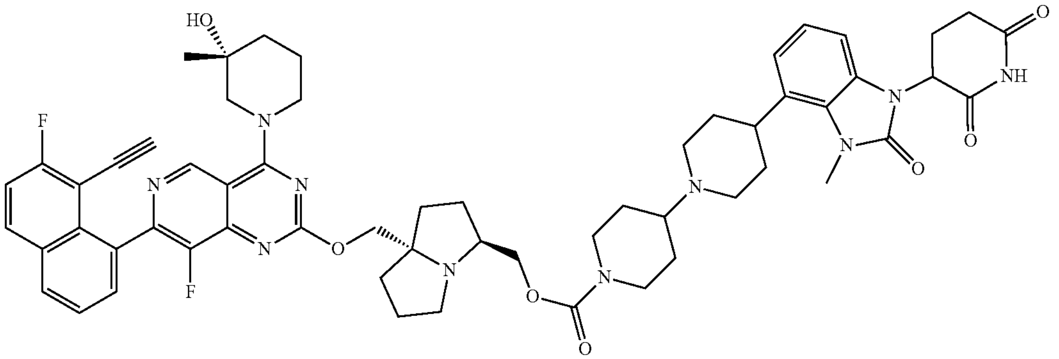 [SMILES: C#Cc1c(F)ccc2cccc(-c3ncc4c(N5CCC[C@@](C)(O)C5)nc(OC[C@@]56CCCN5[C@H](COC(=O)N5CCC(N7CCC(c8cccc9c8n(C)c(=O)n9C8CCC(=O)NC8=O)CC7)CC5)CC6)nc4c3F)c12] |

TABLE 1-continued
| Compound No. | Compound Structure |
| --- | --- |
| | Example Compounds of the Disclosure |
| 148 | 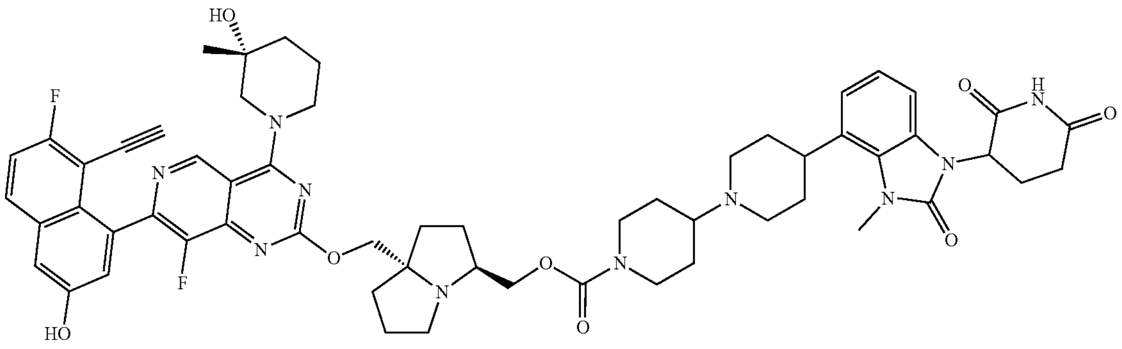 [SMILES: C#Cc1c(F)ccc2cc(O)cc(-c3ncc4c(N5CCC[C@@](C)(O)C5)nc(OC[C@@]56CCCN5[C@H](COC(=O)N5CCC(N7CCC(c8cccc9c8n(C)c(=O)n9C8CCC(=O)NC8=O)CC7)CC5)CC6)nc4c3F)c12] |
| 149 | 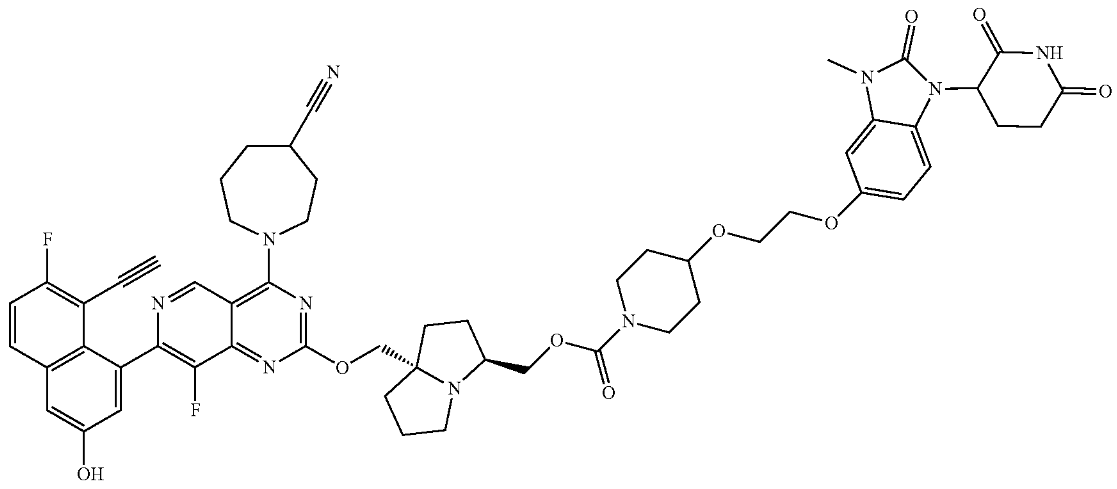 [SMILES: C#Cc1c(F)ccc2cc(O)cc(-c3ncc4c(N5CCCC(C#N)CC5)nc(OC[C@@]56CCCN5[C@H](COC(=O)N5CCC(OCCOc7ccc8c(c7)n(C)c(=O)n8C7CCC(=O)NC7=O)CC5)CC6)nc4c3F)c12] |
| 150 | 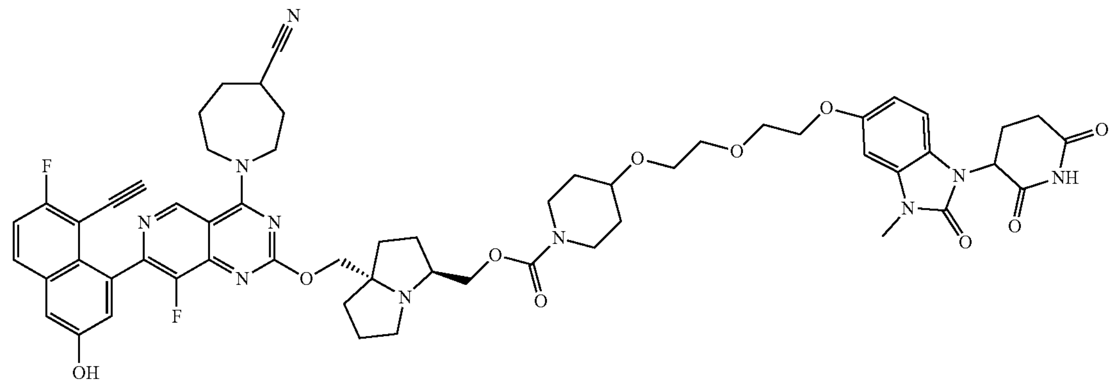 [SMILES: C#Cc1c(F)ccc2cc(O)cc(-c3ncc4c(N5CCCC(C#N)CC5)nc(OC[C@@]56CCCN5[C@H](COC(=O)N5CCC(OCCOCCOc7ccc8c(c7)n(C)c(=O)n8C7CCC(=O)NC7=O)CC5)CC6)nc4c3F)c12] |

TABLE 1-continued
| Example Compounds of the Disclosure | |
|---|---|
| Compound No. | Compound Structure |
| 151 | 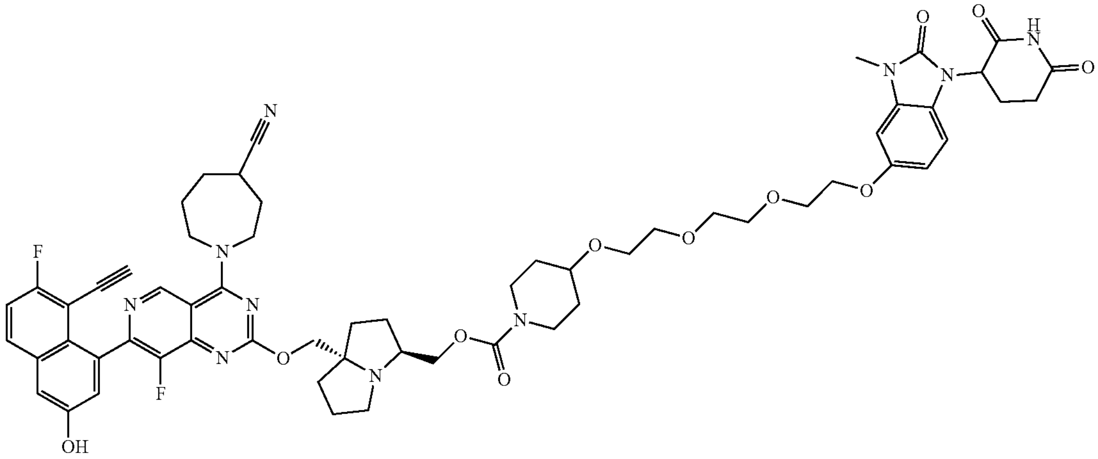 [SMILES: C#Cc1c(F)ccc2cc(O)cc(-c3ncc4c(N5CCCC(C#N)CC5)nc(OC[C@@]56CCCN5[C@H](COC(=O)N5CCC(OCCOCCOCCOc7ccc8c(c7)n(C)c(=O)n8C7CCC(=O)NC7=O)CC5)CC6)nc4c3F)c12] |
| 152 | 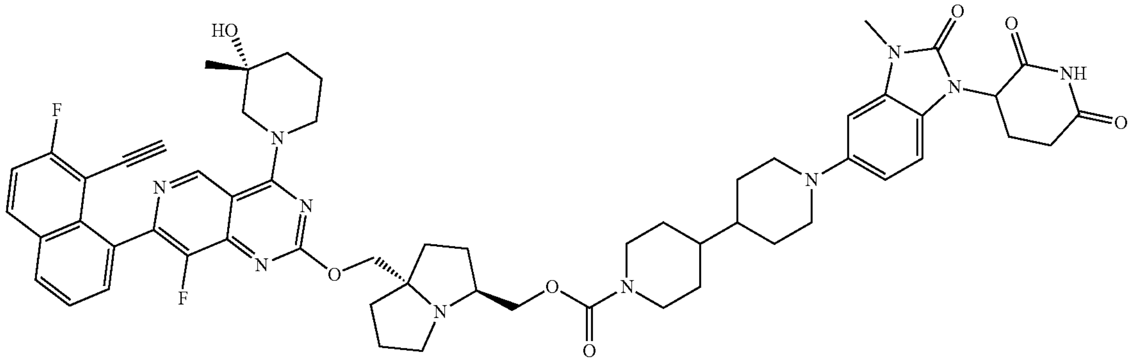 [SMILES: C#Cc1c(F)ccc2cccc(-c3ncc4c(N5CCC[C@@](C)(O)C5)nc(OC[C@@]56CCCN5[C@H](COC(=O)N5CCC(C7CCN(c8ccc9c(c8)n(C)c(=O)n9C8CCC(=O)NC8=O)CC7)CC5)CC6)nc4c3F)c12] |
| 153 | 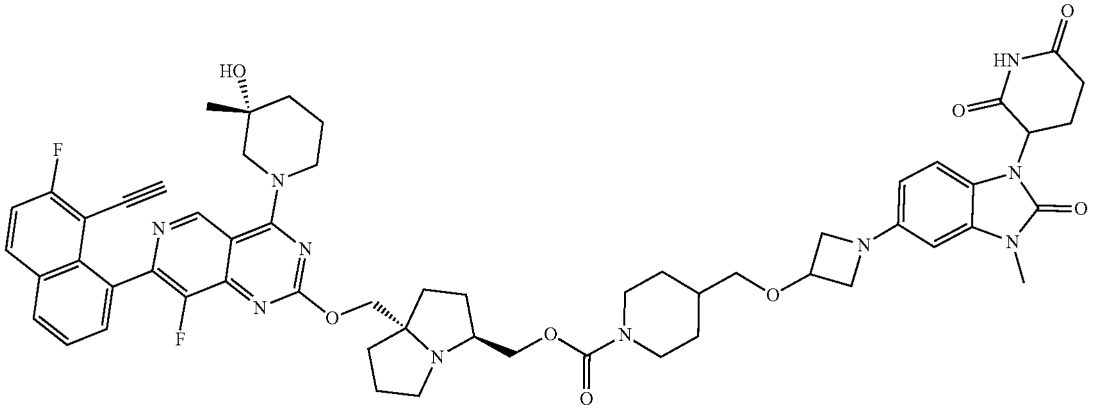 [SMILES: C#Cc1c(F)ccc2cccc(-c3ncc4c(N5CCC[C@@](C)(O)C5)nc(OC[C@@]56CCCN5[C@H](COC(=O)N5CCC(COC7CN(c8ccc9c(c8)n(C)c(=O)n9C8CCC(=O)NC8=O)C7)CC5)CC6)nc4c3F)c12] |

TABLE 1-continued
| Example Compounds of the Disclosure | |
|---|---|
| Compound No. | Compound Structure |
| 154 | 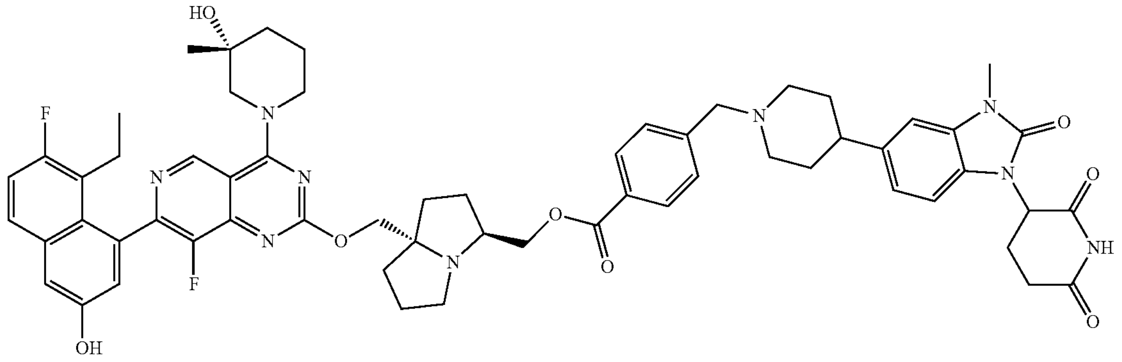 [SMILES: CCc1c(F)ccc2cc(O)cc(-c3ncc4c(N5CCC[C@@](C)(O)C5)nc(OC[C@@]56CCCN5[C@H](COC(=O)c5ccc(CN7CCC(c8ccc9c(c8)n(C)c(=O)n9C8CCC(=O)NC8=O)CC7)cc5)CC6)nc4c3F)c12] |
| 155 | 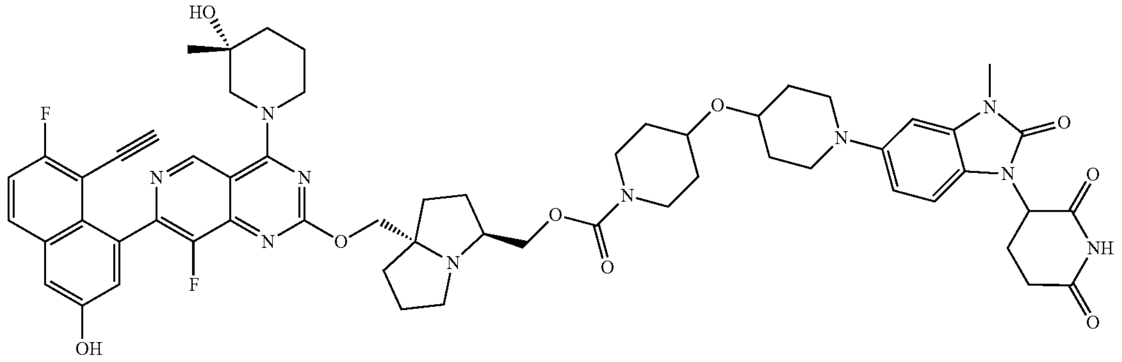 [SMILES: C#Cc1c(F)ccc2cc(O)cc(-c3ncc4c(N5CCC[C@@](C)(O)C5)nc(OC[C@@]56CCCN5[C@H](COC(=O)N5CCC(OC7CCN(c8ccc9c(c8)n(C)c(=O)n9C8CCC(=O)NC8=O)CC7)CC5)CC6)nc4c3F)c12] |
| 156 | 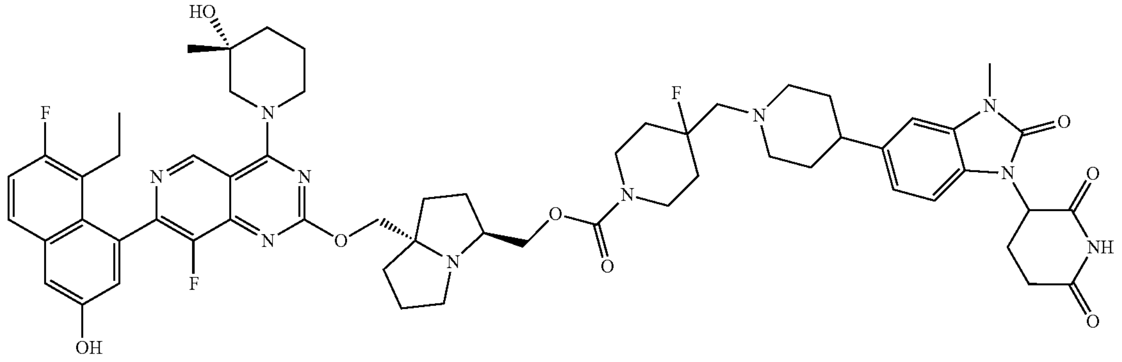 [SMILES: CCc1c(F)ccc2cc(O)cc(-c3ncc4c(N5CCC[C@@](C)(O)C5)nc(OC[C@@]56CCCN5[C@H](COC(=O)N5CCC(F)(CN7CCC(c8ccc9c(c8)n(C)c(=O)n9C8CCC(=O)NC8=O)CC7)CC5)CC6)nc4c3F)c12] |
| 157 | 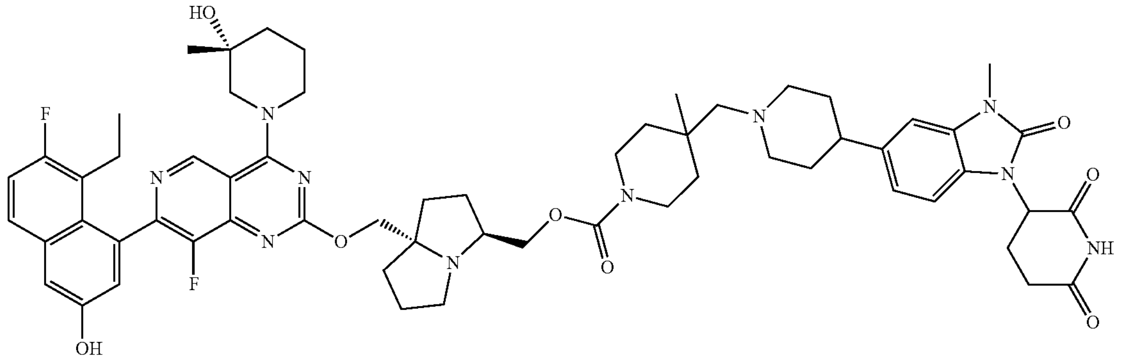 |

TABLE 1-continued
| Example Compounds of the Disclosure | |
|---|---|
| Compound No. | Compound Structure |
| 158 | 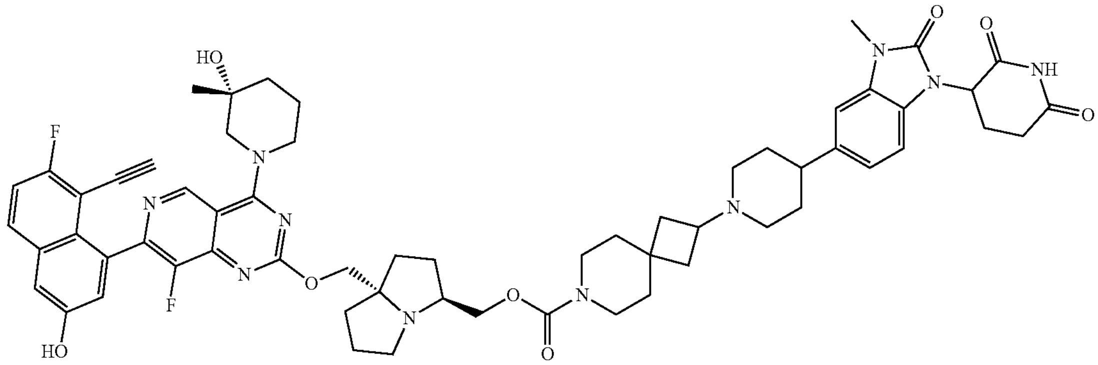 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 159 | 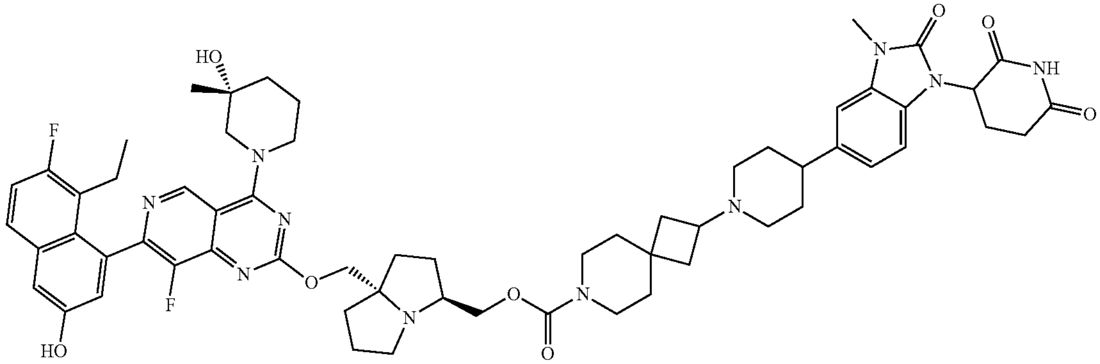 [SMILES: CCc1c(F)ccc2cc(O)cc(-c3ncc4c(N5CCC[C@@](C)(O)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 160 | 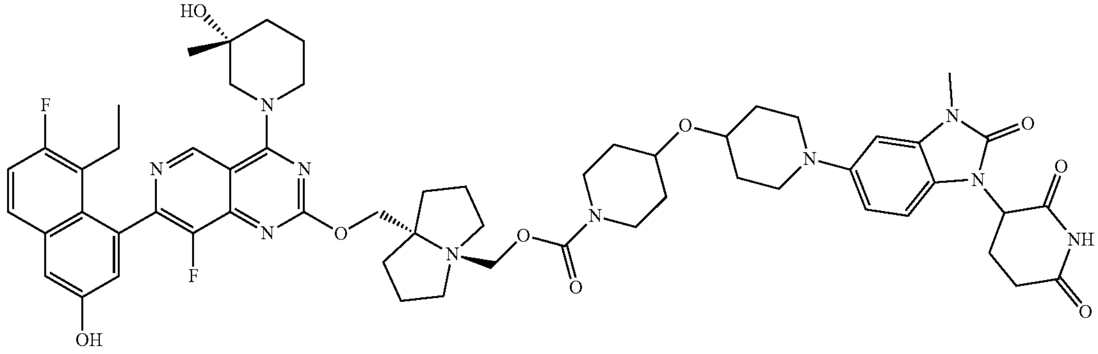 |
| 174 | 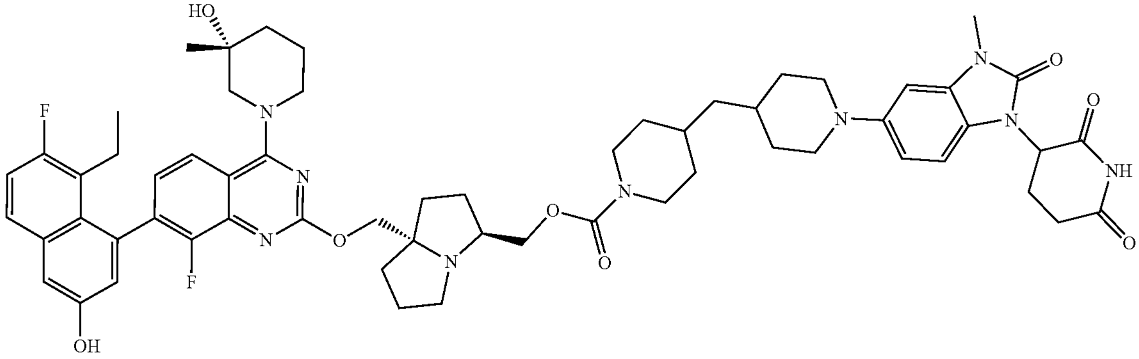 [SMILES: CCc1c(F)ccc2cc(O)cc(-c3ccc4c(N5CCC[C@@](C)(O)C5)nc(OC[C@@]56CCCN5[C@H](COC(=O)N5CCC(CC7CCN(c8ccc9c(c8)n(C)c(=O)n9C8CCC(=O)NC8=O)CC7)CC5)CC6)nc4c3F)c12] |

TABLE 1-continued
| Example Compounds of the Disclosure | |
|---|---|
| Compound No. | Compound Structure |
| 175 | 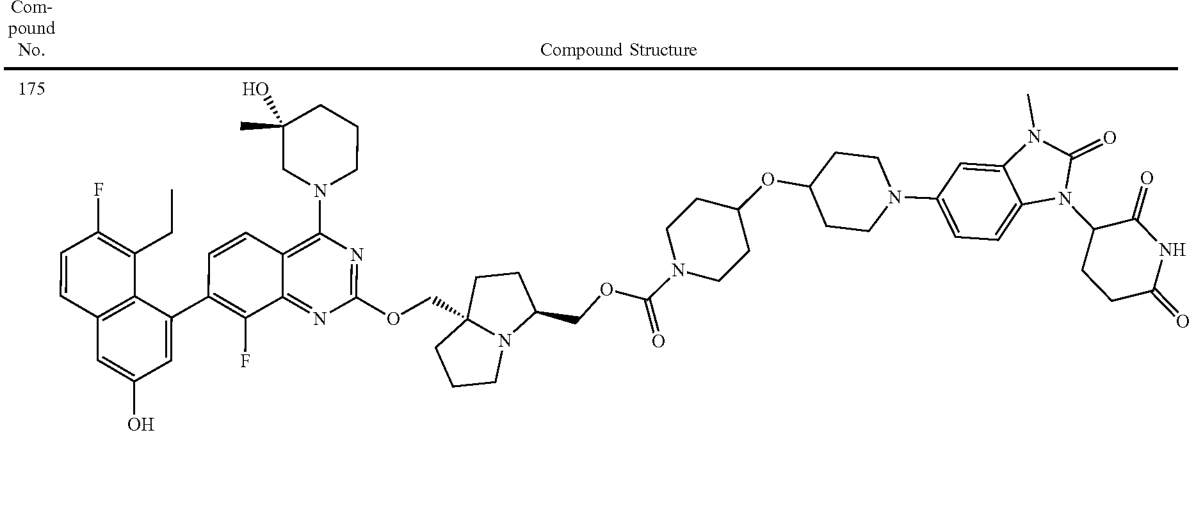 |
| 177 | 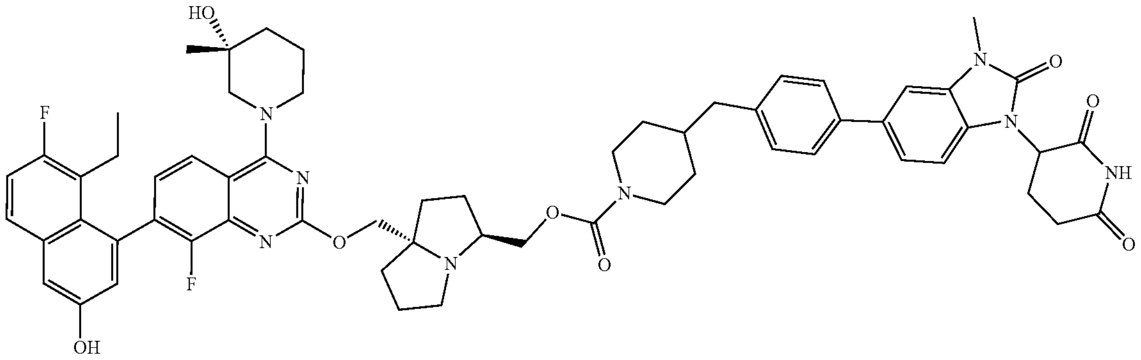 [SMILES: CCc1c(F)ccc2cc(O)cc(-c3ccc4c(N5CCC[C@@](C)(O)C5)nc(OC[C@@]56CCCN5[C@H](COC(=O)N5CCC(Cc7ccc(-c8ccc9c(c8)n(C)c(=O)n9C8CCC(=O)NC8=O)cc7)CC5)CC6)nc4c3F)c12] |
TABLE 2
| Example Compounds of the Disclosure | |
|---|---|
| Compound No. | Compound Structure |
| 200 | 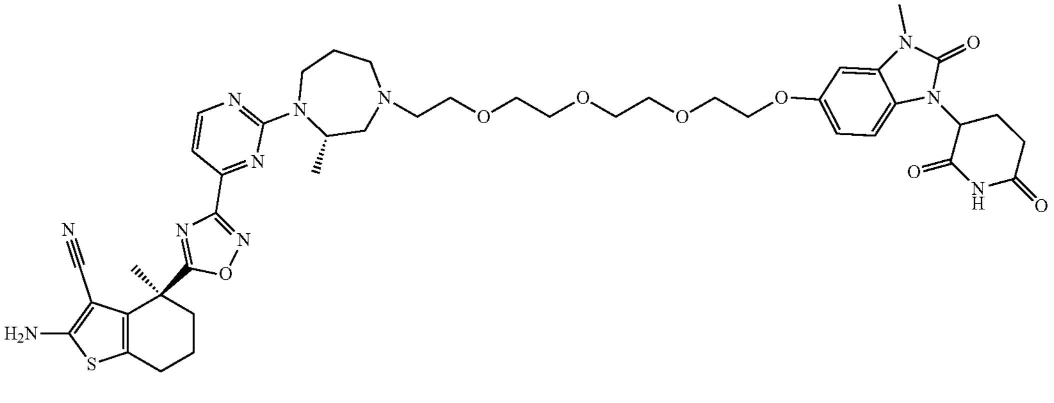 [SMILES: C[C@H]1CN(CCOCCOCCOCCOc2ccc3c(c2)n(C)c(=O)n3C2CCC(=O)NC2=O)CCCN1c1nccc(-c2noc([C@@]3(C)CCCc4sc(N)c(C#N)c43)n2)n1] |

TABLE 2-continued
| Example Compounds of the Disclosure | |
|---|---|
| Compound No. | Compound Structure |
| 201 | 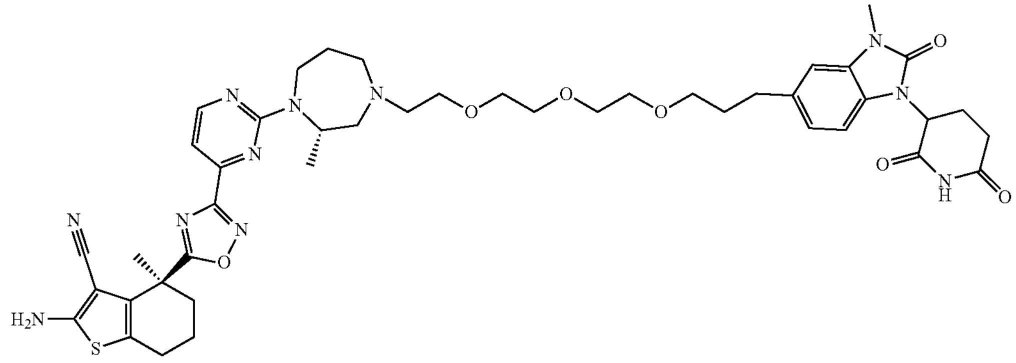 |
| 202 | 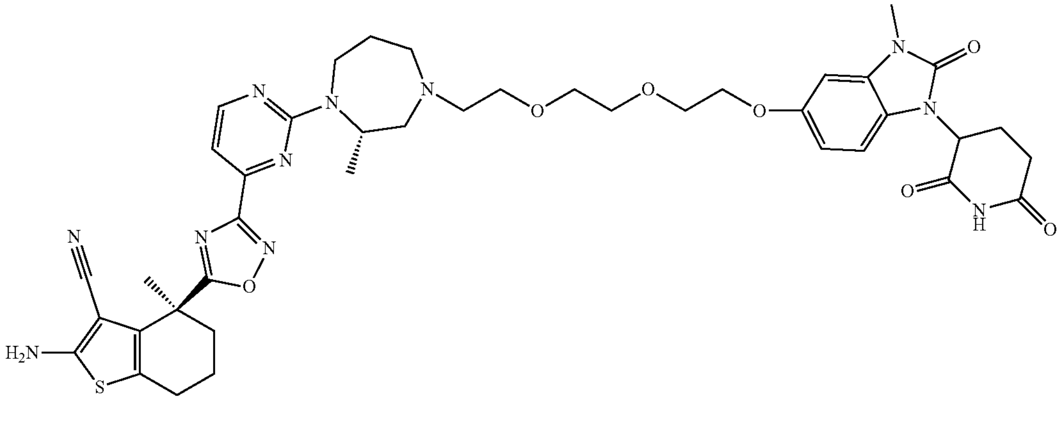 [SMILES: C[C@H]1CN(CCOCCOCCOc2ccc3c(c2)n(C)c(=O)n3C2CCC(=O)NC2=O)CCCN1c1nccc(-c2noc([C@@]3(C)CCCc4sc(N)c(C#N)c43)n2)n1] |
| 203 | 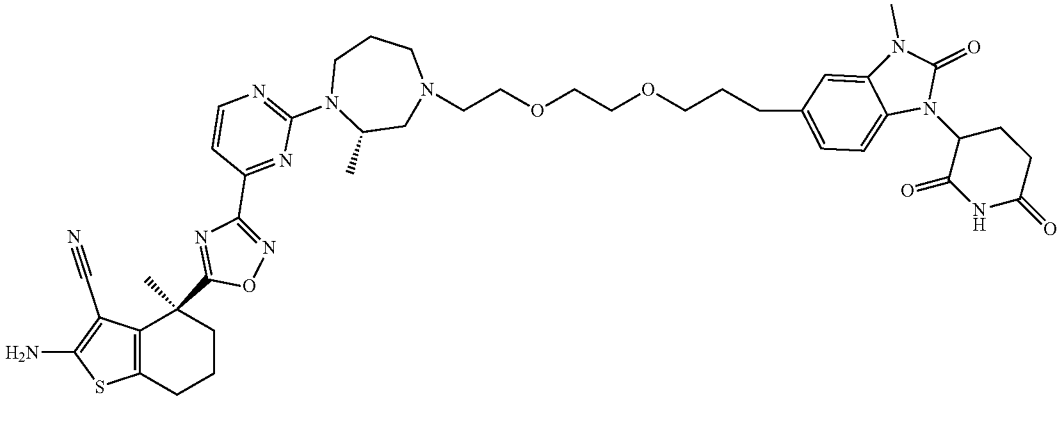 [SMILES: C[C@H]1CN(CCOCCOCCCc2ccc3c(c2)n(C)c(=O)n3C2CCC(=O)NC2=O)CCCN1c1nccc(-c2noc([C@@]3(C)CCCc4sc(N)c(C#N)c43)n2)n1] |

TABLE 2-continued
| Example Compounds of the Disclosure | |
|---|---|
| Compound No. | Compound Structure |
| 204 | 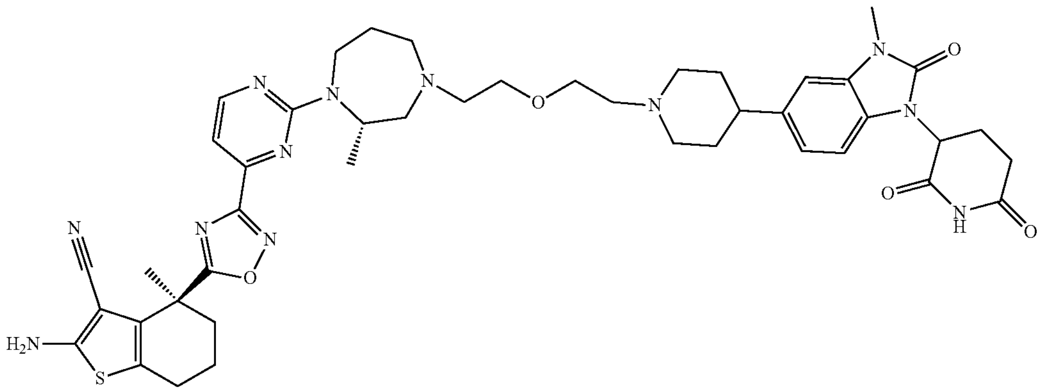 |
| 205 | 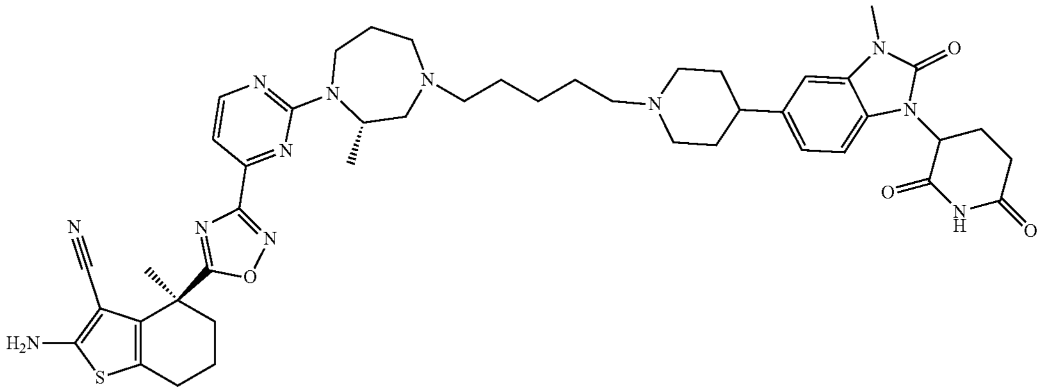 [SMILES: C[C@H]1CN(CCCCCN2CCC(c3ccc4c(c3)n(C)c(=O)n4C3CCC(=O)NC3=O)CC2)CCCN1c1nccc(-c2noc([C@@]3(C)CCCc4sc(N)c(C#N)c43)n2)n1] |
| 206 | 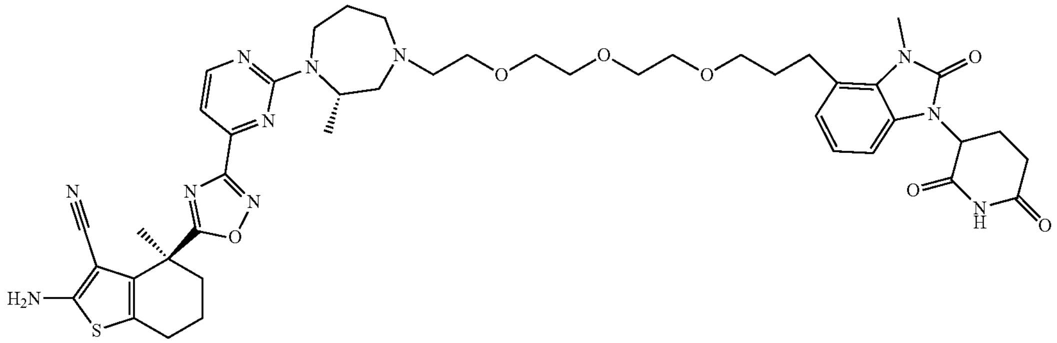 [SMILES: C[C@H]1CN(CCOCCOCCOCCCc2cccc3c2n(C)c(=O)n3C2CCC(=O)NC2=O)CCCN1c1nccc(-c2noc([C@@]3(C)CCCc4sc(N)c(C#N)c43)n2)n1] |
| 207 | 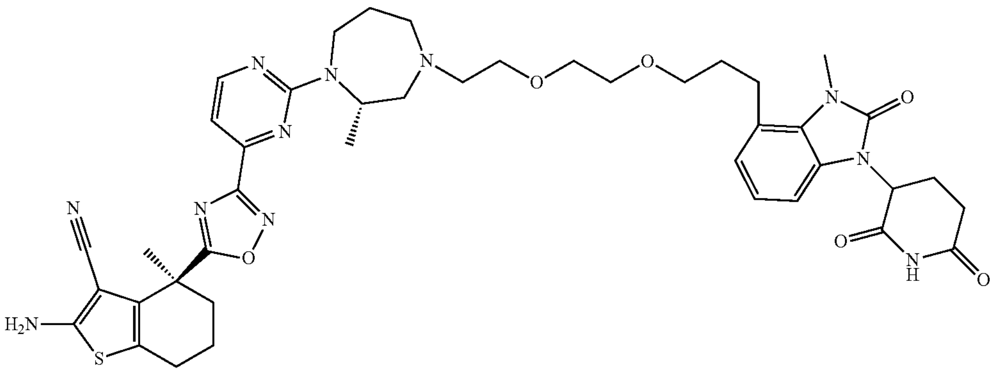 [SMILES: C[C@H]1CN(CCOCCOCCCc2cccc3c2n(C)c(=O)n3C2CCC(=O)NC2=O)CCCN1c1nccc(-c2noc([C@@]3(C)CCCc4sc(N)c(C#N)c43)n2)n1] |

TABLE 2-continued
| Example Compounds of the Disclosure | |
|---|---|
| Compound No. | Compound Structure |
| 208 | 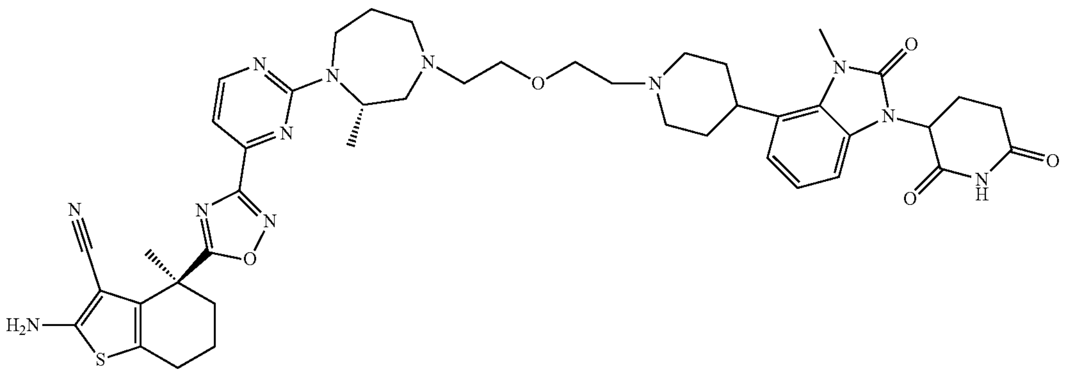 [SMILES: C[C@H]1CN(CCOCCN2CCC(c3cccc4c3n(C)c(=O)n4C3CCC(=O)NC3=O)CC2)CCCN1c1nccc(-c2noc([C@@]3(C)CCCc4sc(N)c(C#N)c43)n2)n1] |
| 209 | 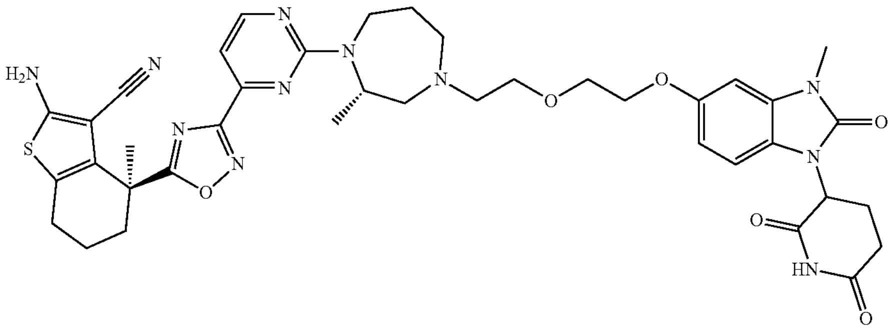 [SMILES: C[C@H]1CN(CCOCCOc2ccc3c(c2)n(C)c(=O)n3C2CCC(=O)NC2=O)CCCN1c1nccc(-c2noc([C@@]3(C)CCCc4sc(N)c(C#N)c43)n2)n1] |
| 210 | 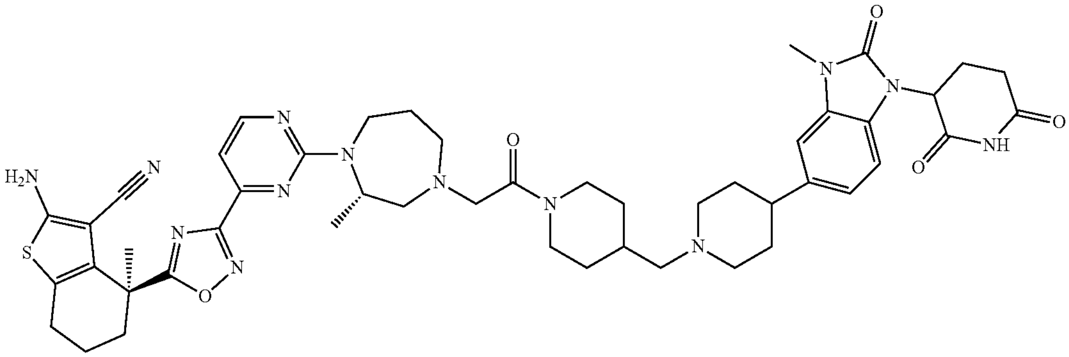 [SMILES: C[C@H]1CN(CC(=O)N2CCC(CN3CCC(c4ccc5c(c4)n(C)c(=O)n5C4CCC(=O)NC4=O)CC3)CC2)CCCN1c1nccc(-c2noc([C@@]3(C)CCCc4sc(N)c(C#N)c43)n2)n1] |
| 211 | 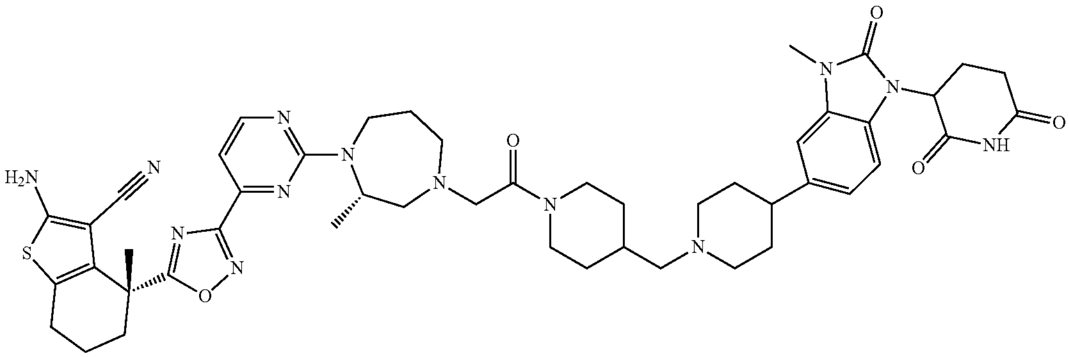 [SMILES: C[C@H]1CN(CC(=O)N2CCC(CN3CCC(c4ccc5c(c4)n(C)c(=O)n5C4CCC(=O)NC4=O)CC3)CC2)CCCN1c1nccc(-c2noc([C@]3(C)CCCc4sc(N)c(C#N)c43)n2)n1] |

TABLE 2-continued
| Example Compounds of the Disclosure | |
|---|---|
| Compound No. | Compound Structure |
| 214 | 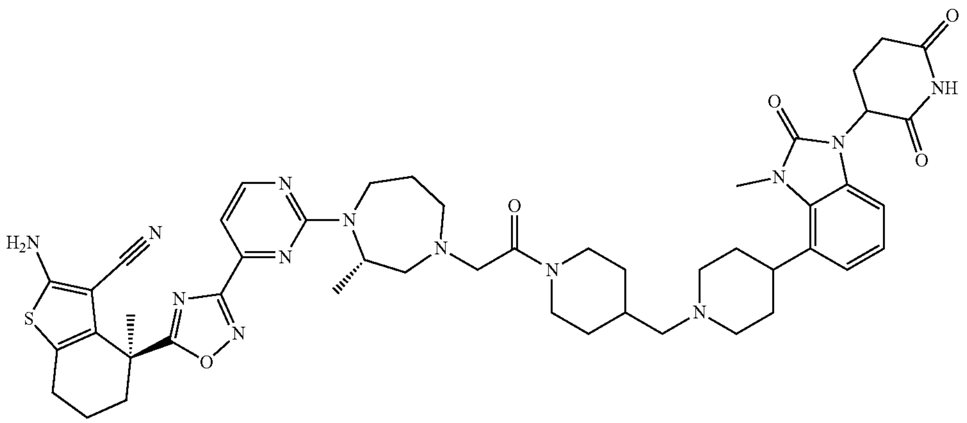 [SMILES: C[C@H]1CN(CC(=O)N2CCC(CN3CCC(c4cccc5c4n(C)c(=O)n5C4CCC(=O)NC4=O)CC3)CC2)CCCN1c1nccc(-c2noc([C@@]3(C)CCCc4sc(N)c(C#N)c43)n2)n1] |
| 215 | 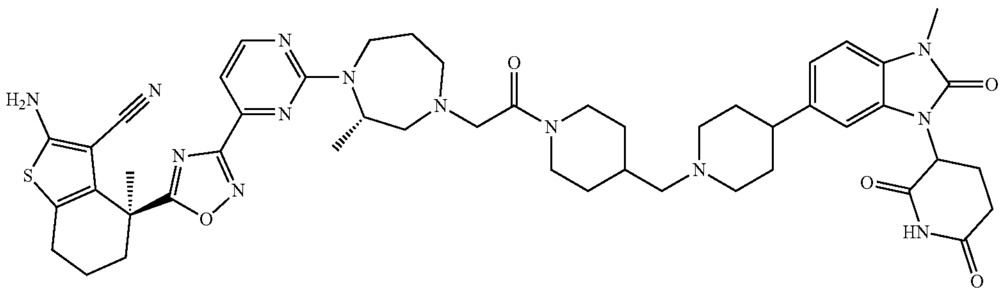 [SMILES: C[C@H]1CN(CC(=O)N2CCC(CN3CCC(c4ccc5c(c4)n(C4CCC(=O)NC4=O)c(=O)n5C)CC3)CC2)CCCN1c1nccc(-c2noc([C@@]3(C)CCCc4sc(N)c(C#N)c43)n2)n1] |
| 216 | 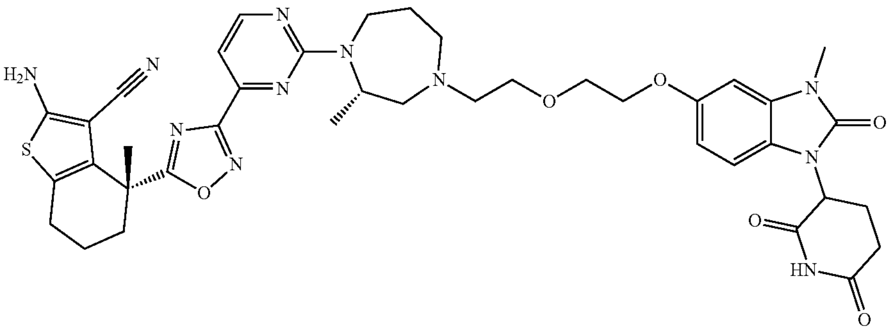 [SMILES: C[C@H]1CN(CCOCCOc2ccc3c(c2)n(C)c(=O)n3C2CCC(=O)NC2=O)CCCN1c1nccc(-c2noc([C@]3(C)CCCc4sc(N)c(C#N)c43)n2)n1] |
| 217 | 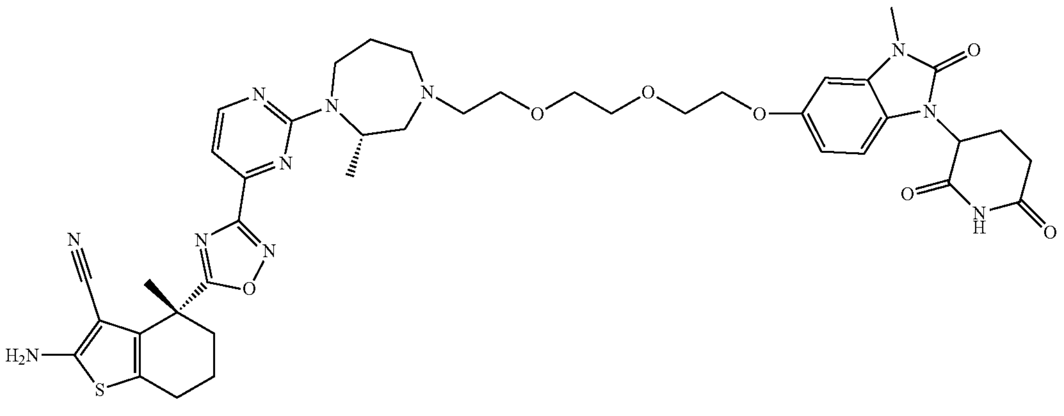 [SMILES: C[C@H]1CN(CCOCCOCCOc2ccc3c(c2)n(C)c(=O)n3C2CCC(=O)NC2=O)CCCN1c1nccc(-c2noc([C@]3(C)CCCc4sc(N)c(C#N)c43)n2)n1] |

TABLE 2-continued
| Example Compounds of the Disclosure | |
|---|---|
| Compound No. | Compound Structure |
| 219 | 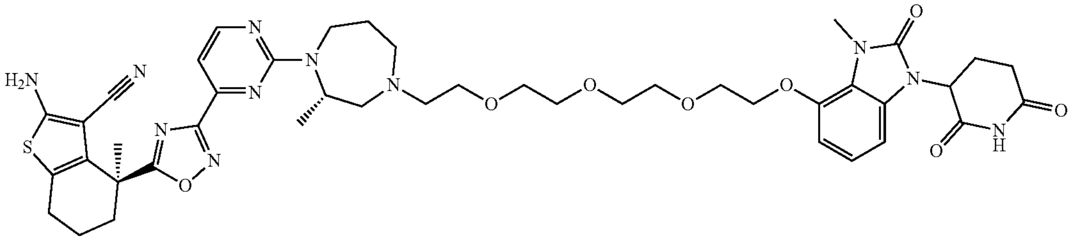 [SMILES: C[C@H]1CN(CCOCCOCCOCCOc2cccc3c2n(C)c(=O)n3C2CCC(=O)NC2=O)CCCN1c1nccc(-c2noc([C@@]3(C)CCCc4sc(N)c(C#N)c43)n2)n1] |
| 220 | 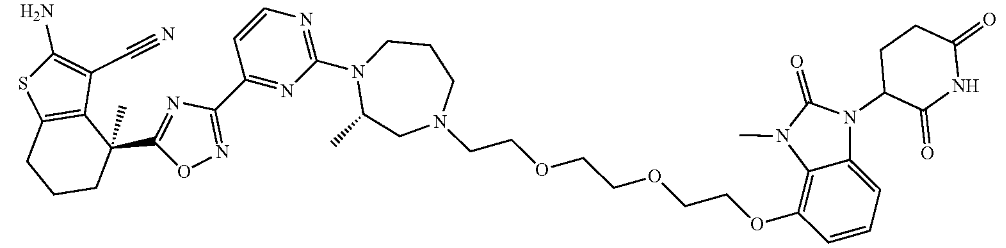 [SMILES: C[C@H]1CN(CCOCCOCCOc2cccc3c2n(C)c(=O)n3C2CCC(=O)NC2=O)CCCN1c1nccc(-c2noc([C@@]3(C)CCCc4sc(N)c(C#N)c43)n2)n1] |
| 221 | 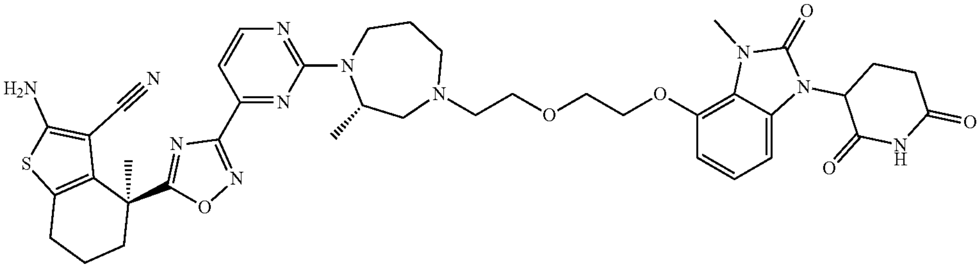 [SMILES: C[C@H]1CN(CCOCCOc2cccc3c2n(C)c(=O)n3C2CCC(=O)NC2=O)CCCN1c1nccc(-c2noc([C@@]3(C)CCCc4sc(N)c(C#N)c43)n2)n1] |
| 222 | 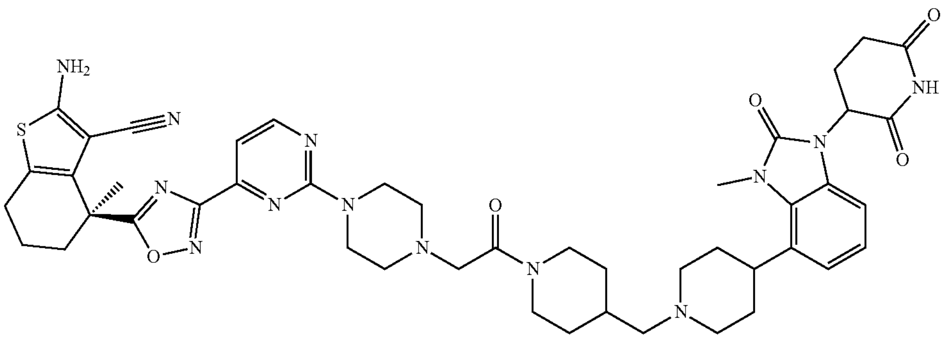 [SMILES: Cn1c(=O)n(C2CCC(=O)NC2=O)c2cccc(C3CCN(CC4CCN(C(=O)CN5CCN(c6nccc(-c7noc([C@@]8(C)CCCc9sc(N)c(C#N)c98)n7)n6)CC5)CC4)CC3)c21] |
| 223 | 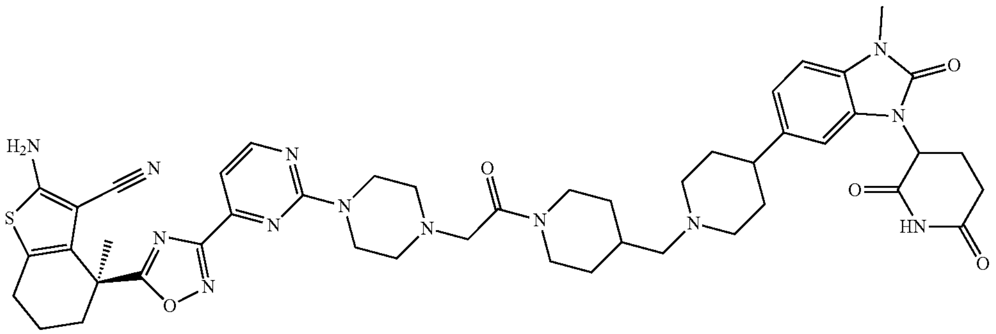 [SMILES: Cn1c(=O)n(C2CCC(=O)NC2=O)c2cc(C3CCN(CC4CCN(C(=O)CN5CCN(c6nccc(-c7noc([C@@]8(C)CCCc9sc(N)c(C#N)c98)n7)n6)CC5)CC4)CC3)ccc21] |

TABLE 2-continued
| Example Compounds of the Disclosure | |
|---|---|
| Compound No. | Compound Structure |
| 224 | 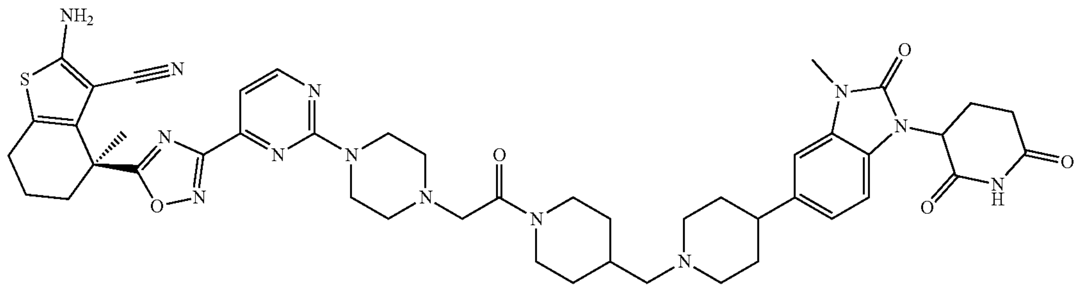 [SMILES: Cn1c(=O)n(C2CCC(=O)NC2=O)c2ccc(C3CCN(CC4CCN(C(=O)CN5CCN(c6nccc(-c7noc([C@@]8(C)CCCc9sc(N)c(C#N)c98)n7)n6)CC5)CC4)CC3)cc21] |
TABLE 3
| Example Compounds of the Disclosure | |
|---|---|
| Compound No. | Compound Structure |
| 300 | 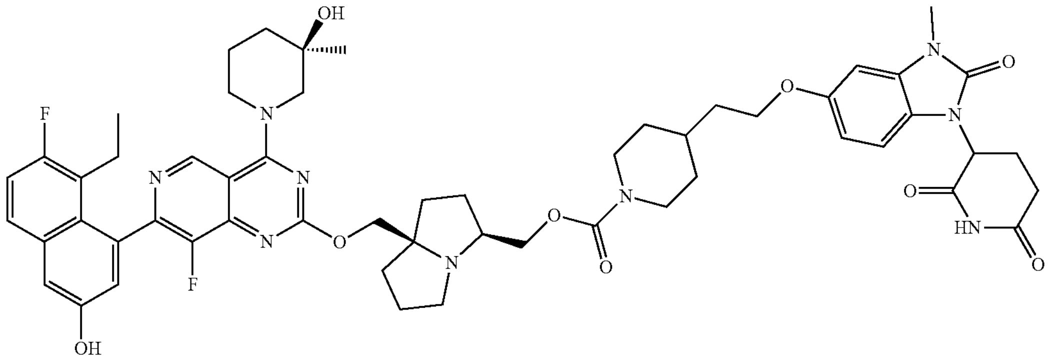 [SMILES: CCc1c(F)ccc2cc(O)cc(-c3ncc4c(N5CCC[C@@](C)(O)C5)nc(OC[C@]56CCCN5[C@H](COC(=O)N5CCC(CCOc7ccc8c(c7)n(C)c(=O)n8C7CCC(=O)NC7=O)CC5)CC6)nc4c3F)c12] |
| 301 | 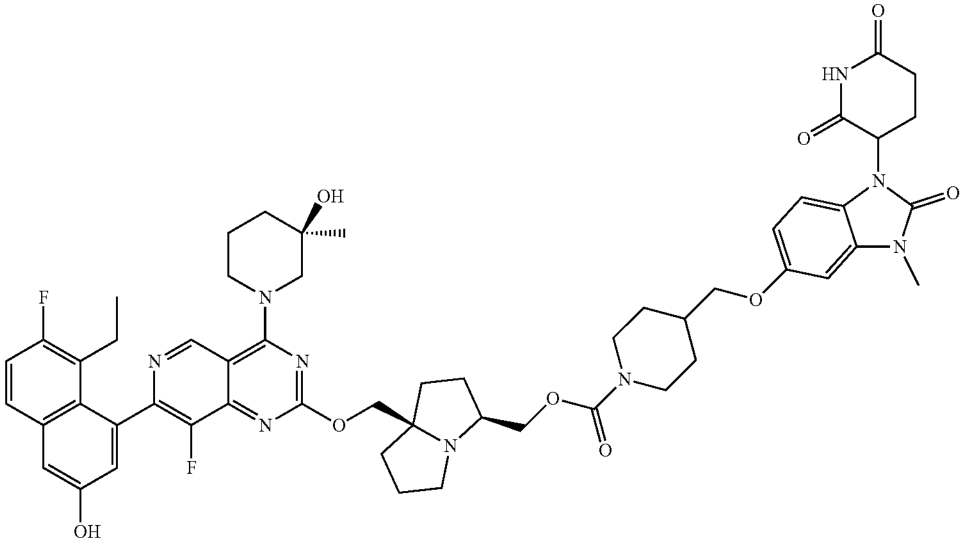 [SMILES: CCc1c(F)ccc2cc(O)cc(-c3ncc4c(N5CCC[C@@](C)(O)C5)nc(OC[C@]56CCCN5[C@H](COC(=O)N5CCC(COc7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 302 | 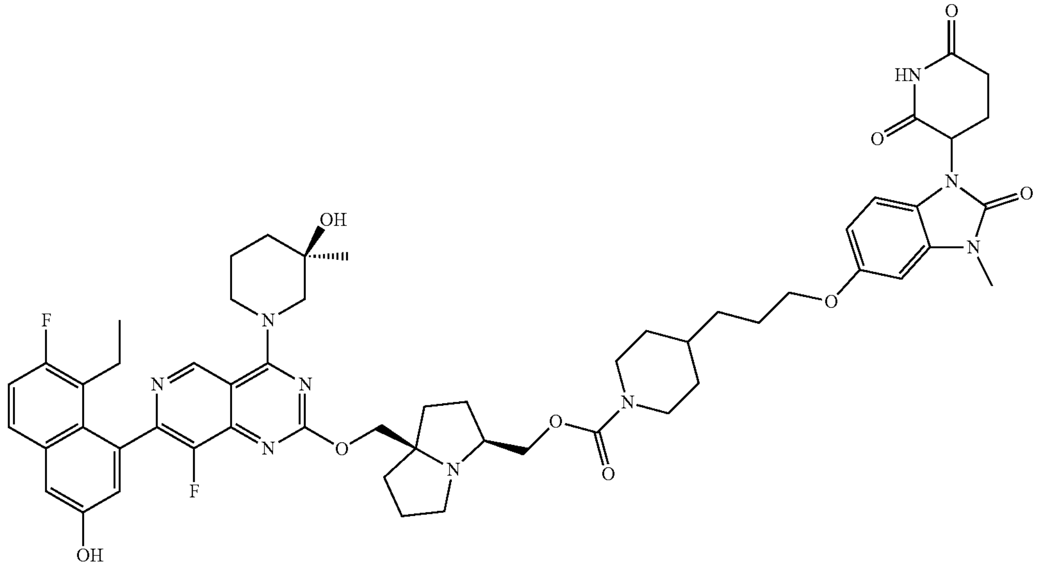 [SMILES: CCc1c(F)ccc2cc(O)cc(-c3ncc4c(N5CCC[C@@](C)(O)C5)nc(OC[C@]56CCCN5[C@H](COC(=O)N5CCC(CCCOc7ccc8c(c7)n(C)c(=O)n8C7CCC(=O)NC7=O)CC5)CC6)nc4c3F)c12] |
| 303 | 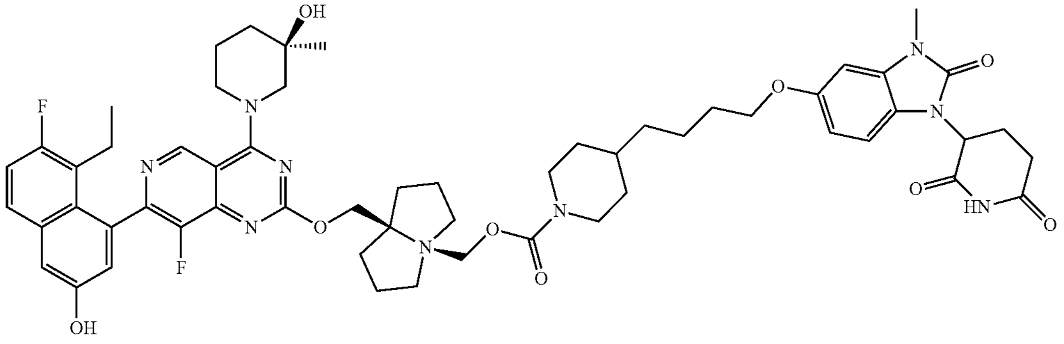 |
| 304 | 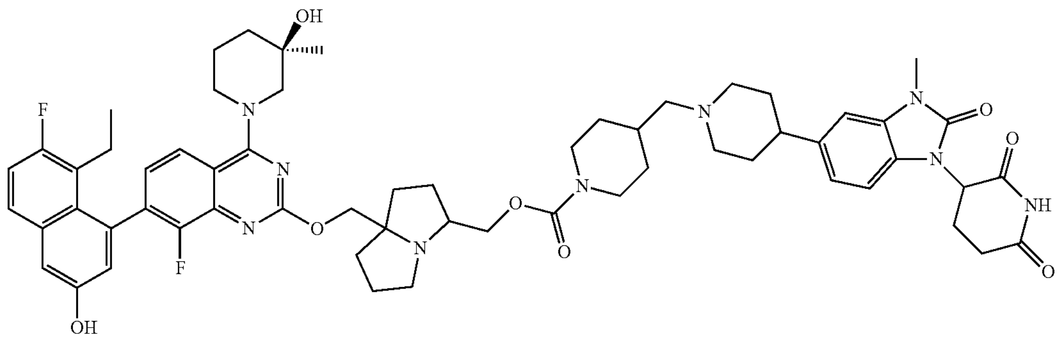 [SMILES: CCc1c(F)ccc2cc(O)cc(-c3ccc4c(N5CCC[C@@](C)(O)C5)nc(OCC56CCCN5C(COC(=O)N5CCC(CN7CCC(c8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 306 | 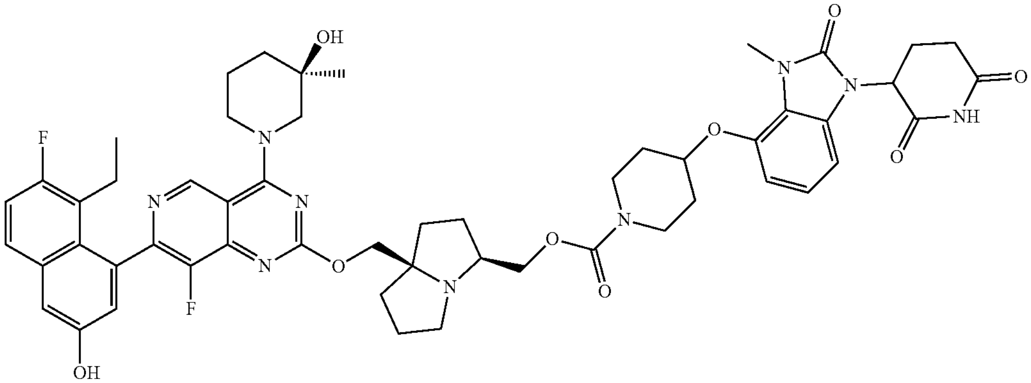 [SMILES: CCc1c(F)ccc2cc(O)cc(-c3ncc4c(N5CCC[C@@](C)(O)C5)nc(OC[C@]56CCCN5[C@H](COC(=O)N5CCC(Oc7cccc8c7n(C)c(=O)n8C7CCC(=O)NC7=O)CC5)CC6)nc4c3F)c12] |
| 307 | 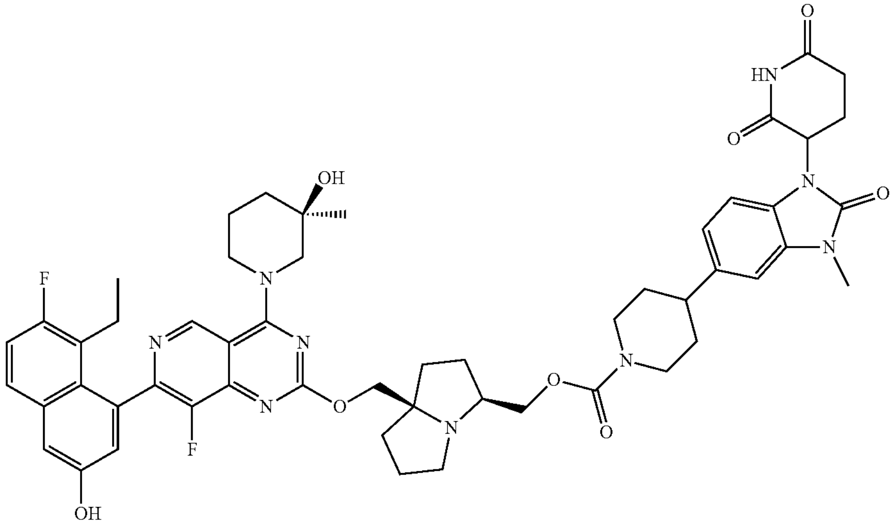 [SMILES: CCc1c(F)ccc2cc(O)cc(-c3ncc4c(N5CCC[C@@](C)(O)C5)nc(OC[C@]56CCCN5[C@H](COC(=O)N5CCC(c7ccc8c(c7)n(C)c(=O)n8C7CCC(=O)NC7=O)CC5)CC6)nc4c3F)c12] |
| 308 | 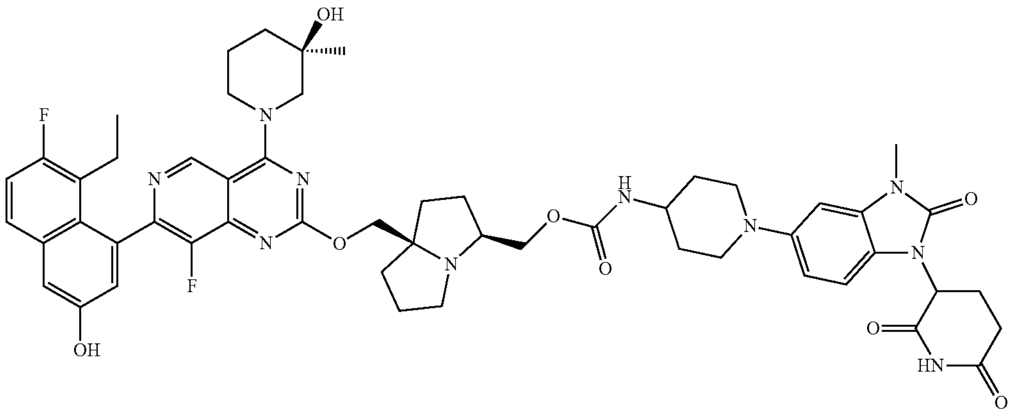 [SMILES: CCc1c(F)ccc2cc(O)cc(-c3ncc4c(N5CCC[C@@](C)(O)C5)nc(OC[C@]56CCCN5[C@H](COC(=O)NC5CCN(c7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 309 | 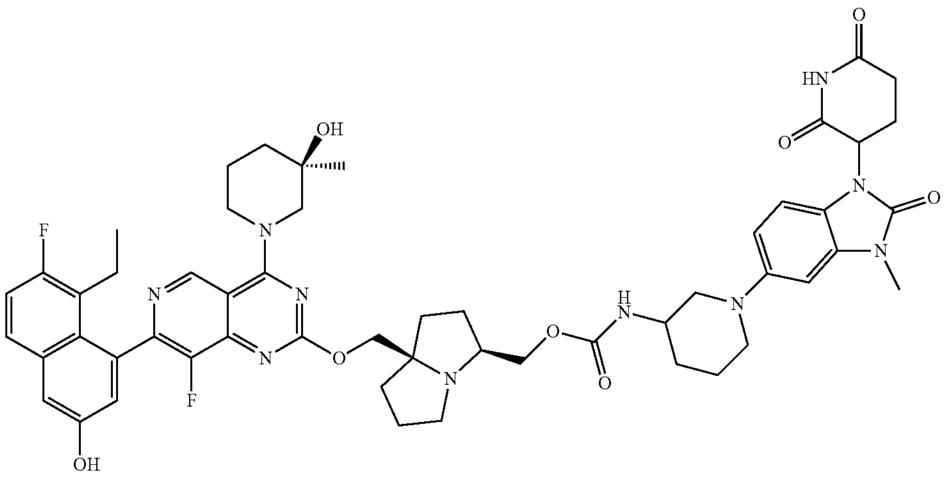 [SMILES: CCc1c(F)ccc2cc(O)cc(-c3ncc4c(N5CCC[C@@](C)(O)C5)nc(OC[C@]56CCCN5[C@H](COC(=O)NC5CCCN(c7ccc8c(c7)n(C)c(=O)n8C7CCC(=O)NC7=O)C5)CC6)nc4c3F)c12] |
| 310 | 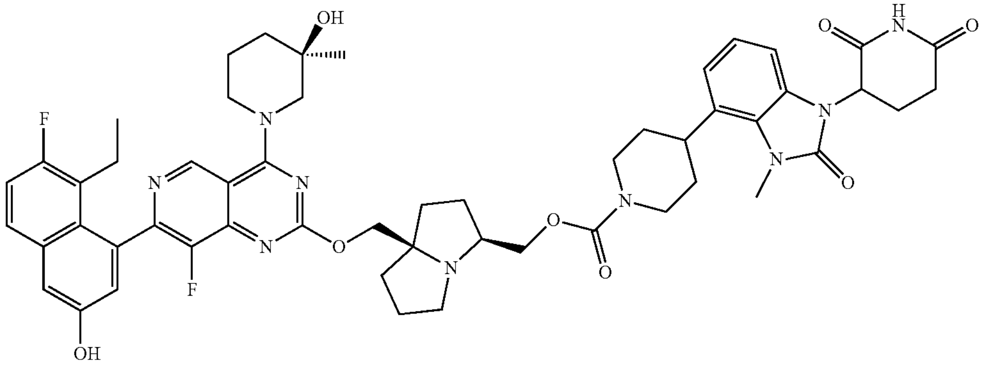 [SMILES: CCc1c(F)ccc2cc(O)cc(-c3ncc4c(N5CCC[C@@](C)(O)C5)nc(OC[C@]56CCCN5[C@H](COC(=O)N5CCC(c7cccc8c7n(C)c(=O)n8C7CCC(=O)NC7=O)CC5)CC6)nc4c3F)c12] |
| 311 | 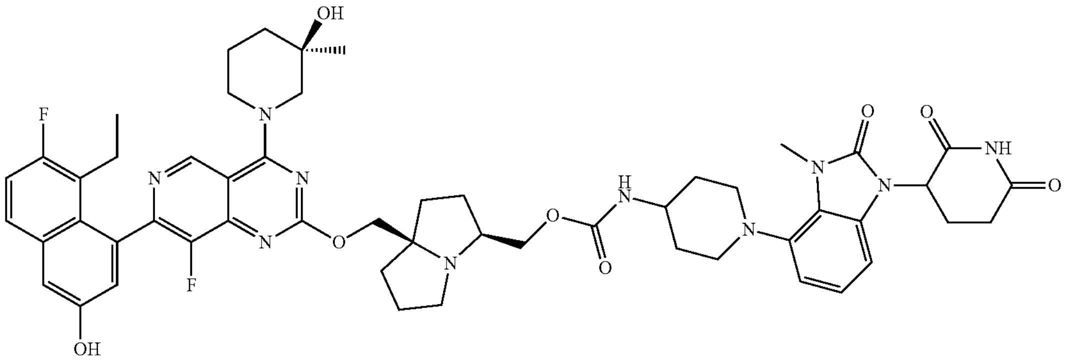 [SMILES: CCc1c(F)ccc2cc(O)cc(-c3ncc4c(N5CCC[C@@](C)(O)C5)nc(OC[C@]56CCCN5[C@H](COC(=O)NC5CCN(c7cccc8c7n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 312 | 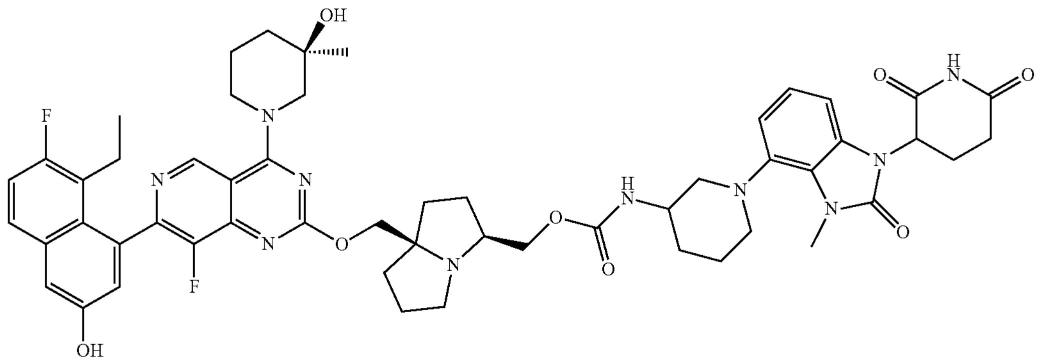 [SMILES: CCc1c(F)ccc2cc(O)cc(-c3ncc4c(N5CCC[C@@](C)(O)C5)nc(OC[C@]56CCCN5[C@H](COC(=O)NC5CCCN(c7cccc8c7n(C)c(=O)n8C7CCC(=O)NC7=O)C5)CC6)nc4c3F)c12] |
| 313 | 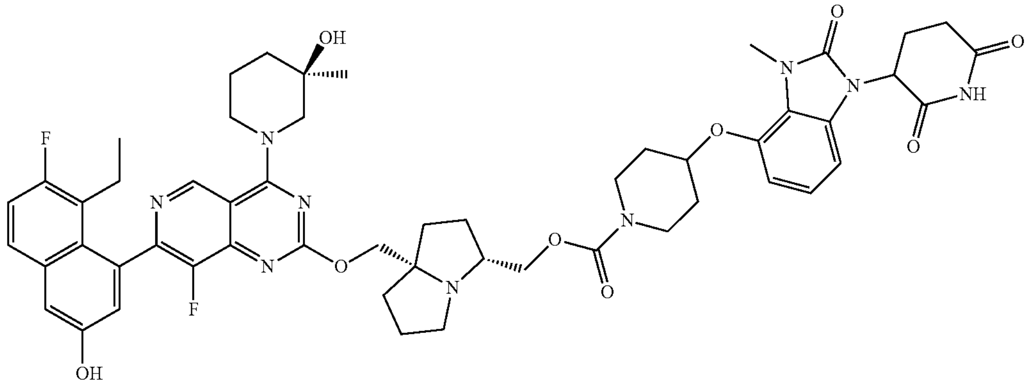 [SMILES: CCc1c(F)ccc2cc(O)cc(-c3ncc4c(N5CCC[C@@](C)(O)C5)nc(OC[C@@]56CCCN5[C@@H](COC(=O)N5CCC(Oc7cccc8c7n(C)c(=O)n8C7CCC(=O)NC7=O)CC5)CC6)nc4c3F)c12] |
| 314 | 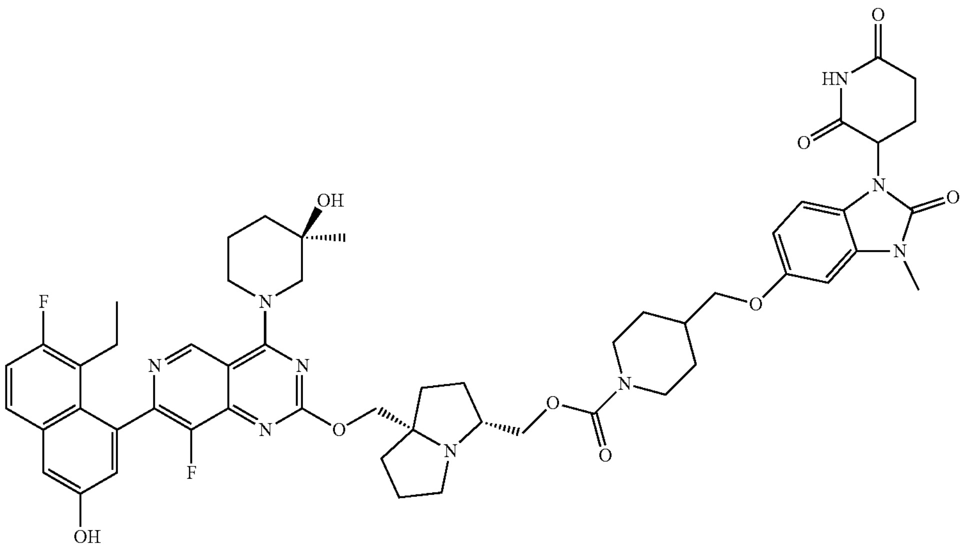 [SMILES: CCc1c(F)ccc2cc(O)cc(-c3ncc4c(N5CCC[C@@](C)(O)C5)nc(OC[C@@]56CCCN5[C@@H](COC(=O)N5CCC(COc7ccc8c(c7)n(C)c(=O)n8C7CCC(=O)NC7=O)CC5)CC6)nc4c3F)c12] |

TABLE 3-continued
| Example Compounds of the Disclosure | |
| --- | --- |
| Compound No. | Compound Structure |
| 315 | 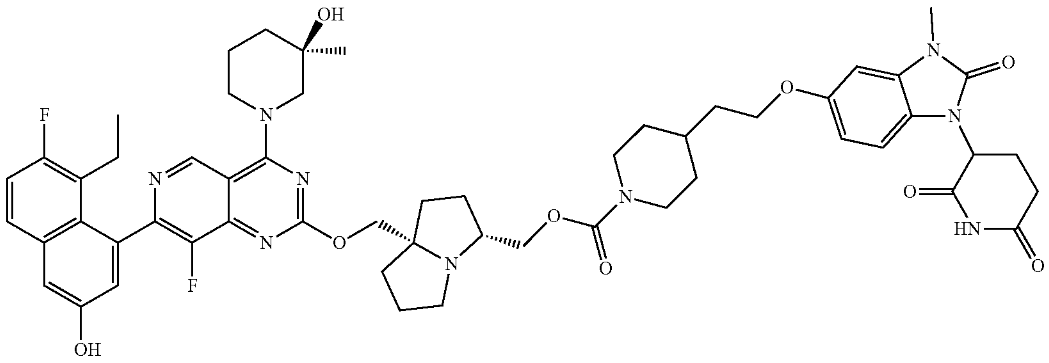 [SMILES: CCc1c(F)ccc2cc(O)cc(-c3ncc4c(N5CCC[C@@](C)(O)C5)nc(OC[C@@]56CCCN5[C@@H](COC(=O)N5CCC(CCOc7ccc8c(c7)n(C)c(=O)n8C7CCC(=O)NC7=O)CC5)CC6)nc4c3F)c12] |
| 316 | 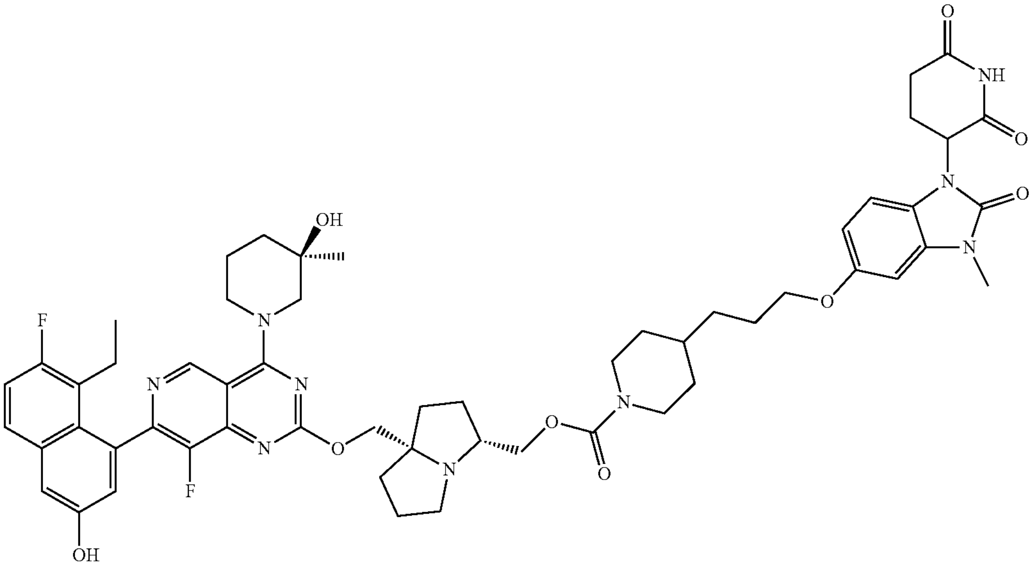 [SMILES: CCc1c(F)ccc2cc(O)cc(-c3ncc4c(N5CCC[C@@](C)(O)C5)nc(OC[C@@]56CCCN5[C@@H](COC(=O)N5CCC(CCCOc7ccc8c(c7)n(C)c(=O)n8C7CCC(=O)NC7=O)CC5)CC6)nc4c3F)c12] |
| 317 | 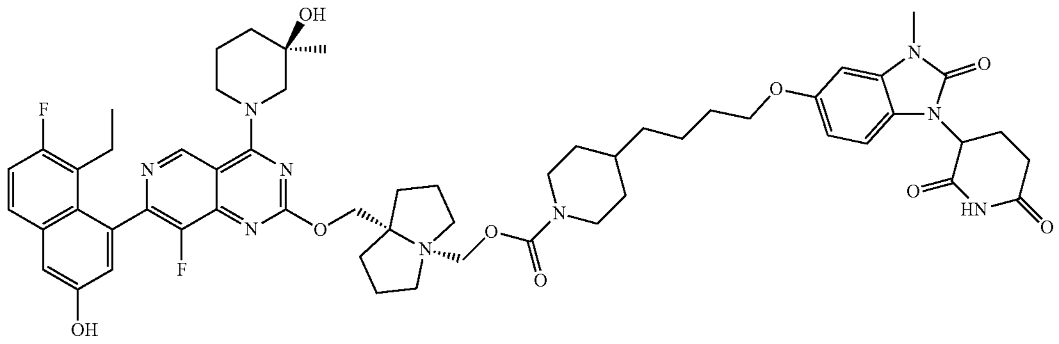 |

TABLE 3-continued
| Example Compounds of the Disclosure | |
|---|---|
| Compound No. | Compound Structure |
| 318 | 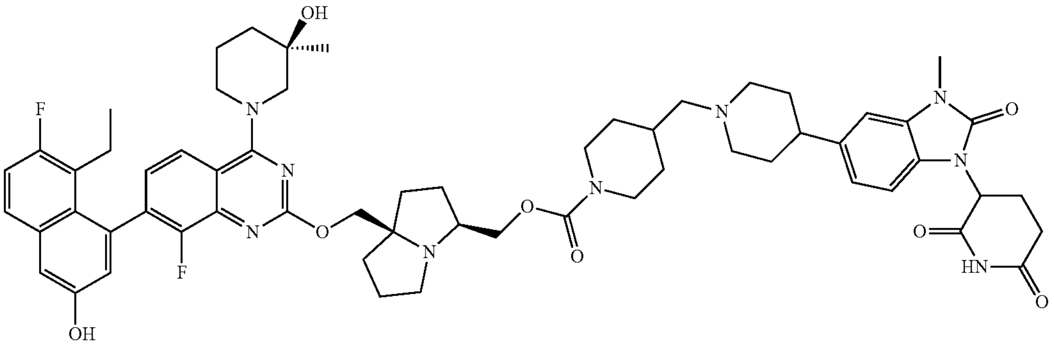 |
| 319 | 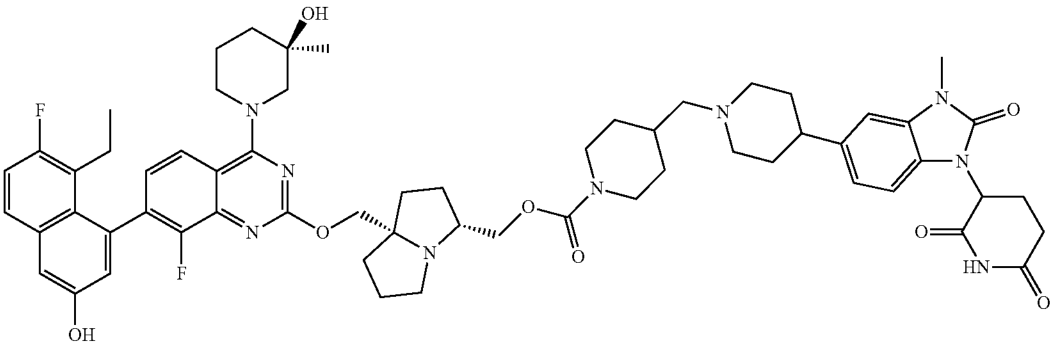 [SMILES: CCc1c(F)ccc2cc(O)cc(-c3ccc4c(N5CCC[C@@](C)(O)C5)nc(OC[C@@]56CCCN5[C@@H](COC(=O)N5CCC(CN7CCC(c8ccc9c(c8)n(C)c(=O)n9C8CCC(=O)NC8=O)CC7)CC5)CC6)nc4c3F)c12] |
| 320 | 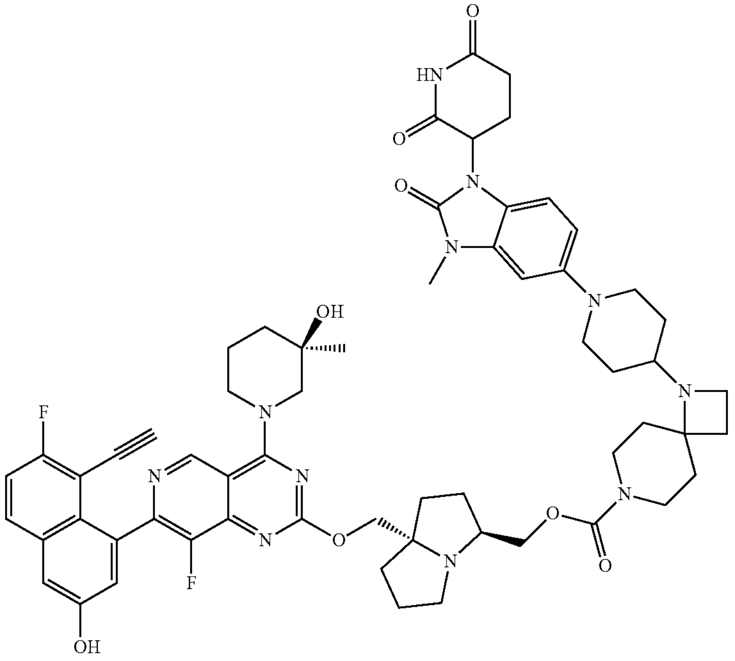 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CC5)CCN7C5CCN(c7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 321 | 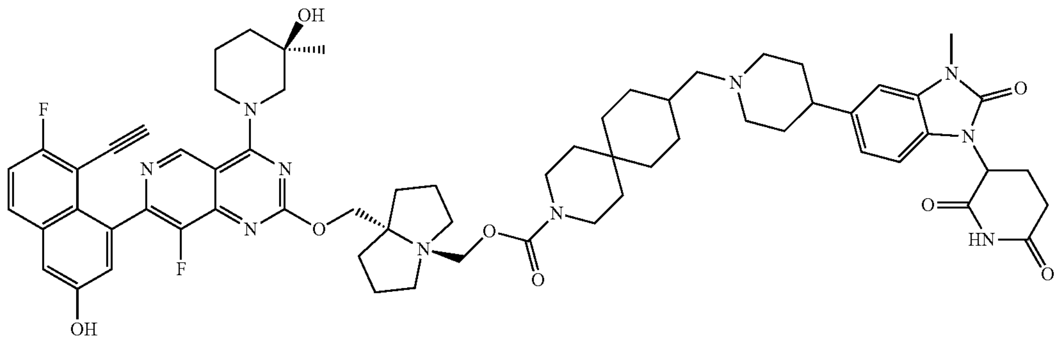 |
| 322 | 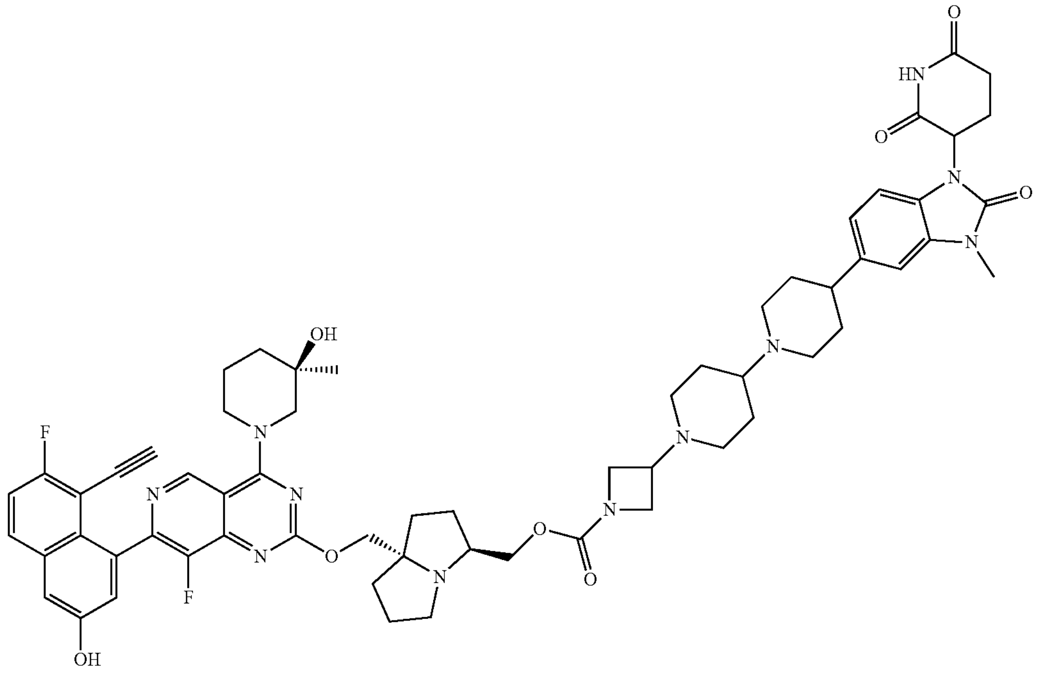 [SMILES: C#Cc1c(F)ccc2cc(O)cc(-c3ncc4c(N5CCC[C@@](C)(O)C5)nc(OC[C@@]56CCCN5[C@H](COC(=O)N5CC(N7CCC(N8CCC(c9ccc%10c(c9)n(C)c(=O)n%10C9CCC(=O)NC9=O)CC8)CC7)C5)CC6)nc4c3F)c12] |
| 323 | 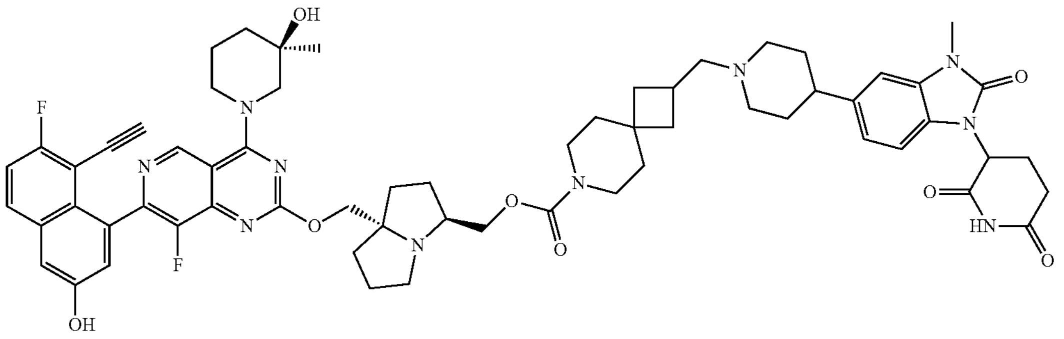 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CC5)CC(CN5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 324 | 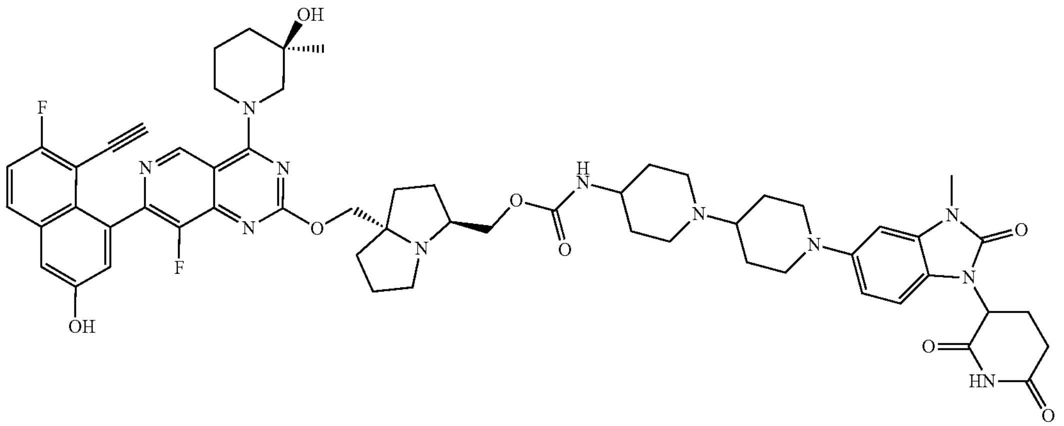 [SMILES: C#Cc1c(F)ccc2cc(O)cc(-c3ncc4c(N5CCC[C@@](C)(O)C5)nc(OC[C@@]56CCCN5[C@H](COC(=O)NC5CCN(C7CCN(c8ccc9c(c8)n(C)c(=O)n9C8CCC(=O)NC8=O)CC7)CC5)CC6)nc4c3F)c12] |
| 325 | 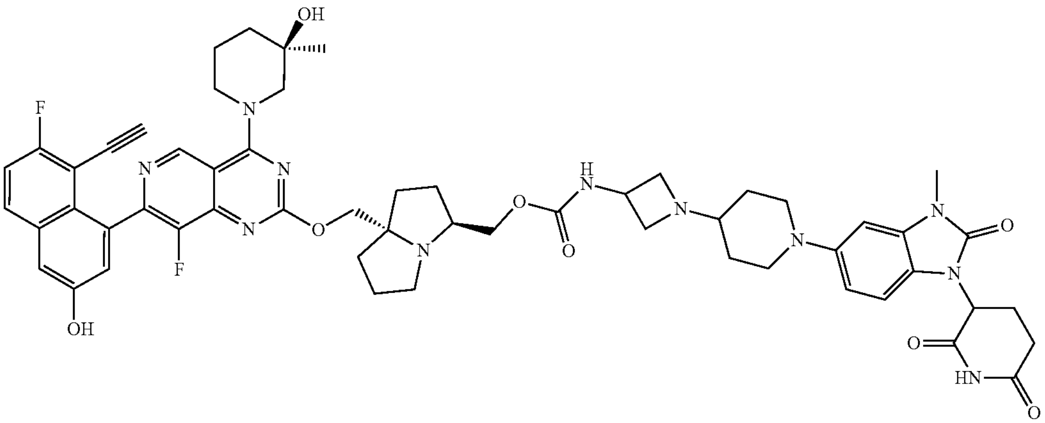 [SMILES: C#Cc1c(F)ccc2cc(O)cc(-c3ncc4c(N5CCC[C@@](C)(O)C5)nc(OC[C@@]56CCCN5[C@H](COC(=O)NC5CN(C7CCN(c8ccc9c(c8)n(C)c(=O)n9C8CCC(=O)NC8=O)CC7)C5)CC6)nc4c3F)c12] |
| 326 | 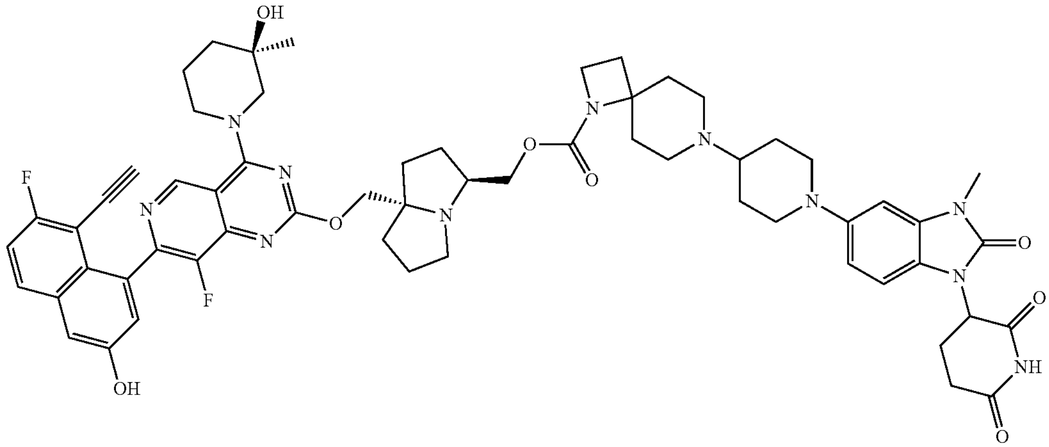 [SMILES: C#Cc1c(F)ccc2cc(O)cc(-c3ncc4c(N5CCC[C@@](C)(O)C5)nc(OC[C@@]56CCCN5[C@H](COC(=O)N5CCC57CCN(C5CCN(c8ccc9c(c8)n(C)c(=O)n9C8CCC(=O)NC8=O)CC5)CC7)CC6)nc4c3F)c12] |

TABLE 3-continued
| Example Compounds of the Disclosure | |
|---|---|
| Compound No. | Compound Structure |
| 327 | 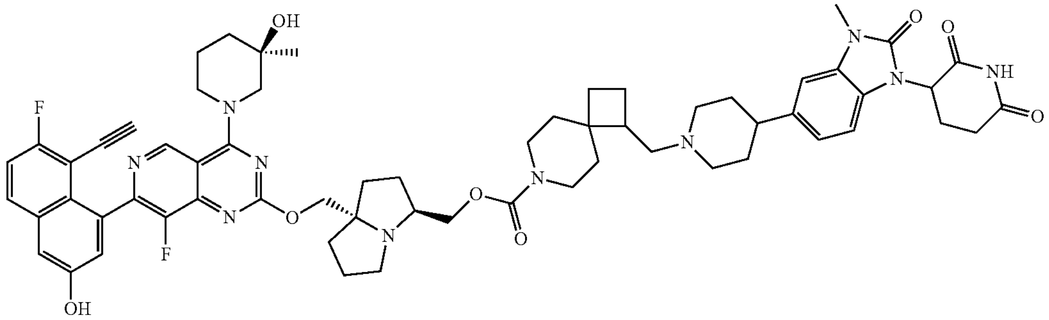 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CCC7CN7CCC(c8ccc9c(c8)n(C)c(=O)n9C8CCC(=O)NC8=O)CC7)CC5)CC6)nc4c3F)c12] |
| 328 | 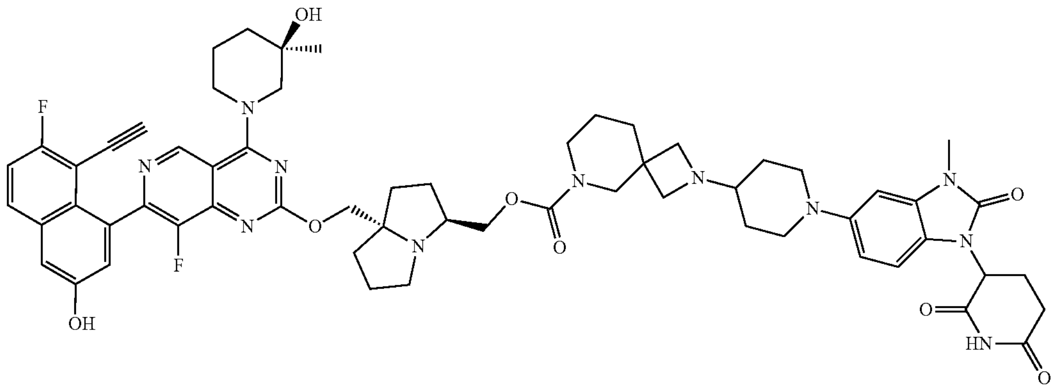 [SMILES: C#Cc1c(F)ccc2cc(O)cc(-c3ncc4c(N5CCC[C@@](C)(O)C5)nc(OC[C@@]56CCCN5[C@H](COC(=O)N5CCCC7(C5)CN(C5CCN(c8ccc9c(c8)n(C)c(=O)n9C8CCC(=O)NC8=O)CC5)C7)CC6)nc4c3F)c12] |
| 329 | 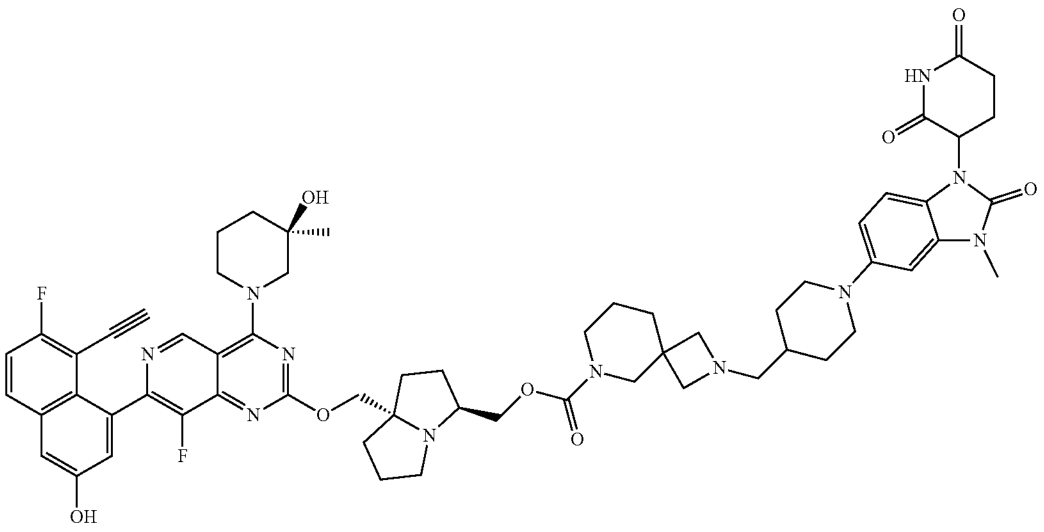 [SMILES: C#Cc1c(F)ccc2cc(O)cc(-c3ncc4c(N5CCC[C@@](C)(O)C5)nc(OC[C@@]56CCCN5[C@H](COC(=O)N5CCCC7(CN(CC8CCN(c9ccc%10c(c9)n(C)c(=O)n%10C9CCC(=O)NC9=O)CC8)C7)C5)CC6)nc4c3F)c12] |

TABLE 3-continued
| Example Compounds of the Disclosure | |
|---|---|
| Compound No. | Compound Structure |
| 330 | 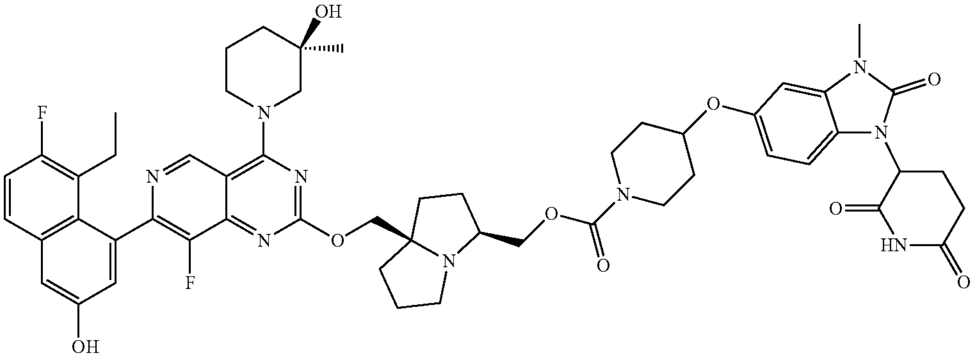 [SMILES: CCc1c(F)ccc2cc(O)cc(-c3ncc4c(N5CCC[C@@](C)(O)C5)nc(OC[C@]56CCCN5[C@H](COC(=O)N5CCC(Oc7ccc8c(c7)n(C)c(=O)n8C7CCC(=O)NC7=O)CC5)CC6)nc4c3F)c12] |
| 337 | 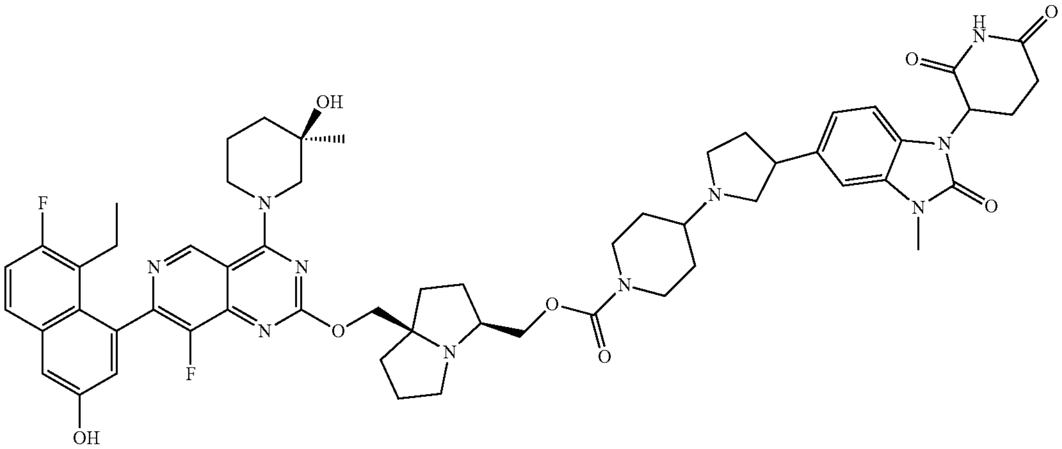 [SMILES: CCc1c(F)ccc2cc(O)cc(-c3ncc4c(N5CCC[C@@](C)(O)C5)nc(OC[C@]56CCCN5[C@H](COC(=O)N5CCC(N7CCC(c8ccc9c(c8)n(C)c(=O)n9C8CCC(=O)NC8=O)C7)CC5)CC6)nc4c3F)c12] |
| 338 | 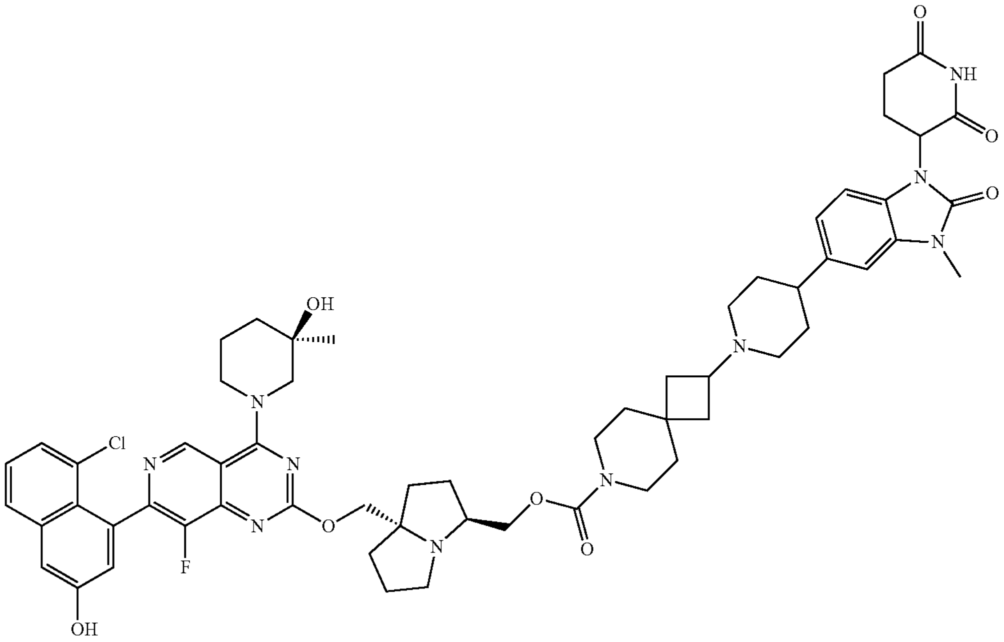 [SMILES: Cn1c(=O)n(C2CCC(=O)NC2=O)c2ccc(C3CCN(C4CC5(CCN(C(=O)OC[C@@H]6CC[C@]7(COc8nc(N9CCC[C@@](C)(O)C9)c9cnc(-c%10cc(O)cc%11cccc(Cl)c%10%11)c(F)c9n8)CCCN67)CC5)C4)CC3)cc21] |

TABLE 3-continued
| Example Compounds of the Disclosure | |
|---|---|
| Compound No. | Compound Structure |
| 339 | 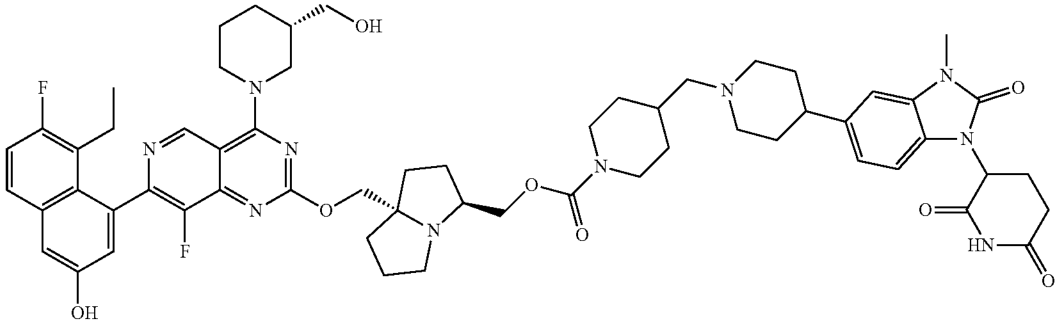 [SMILES: CCc1c(F)ccc2cc(O)cc(-c3ncc4c(N5CCC[C@H](CO)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 340 | 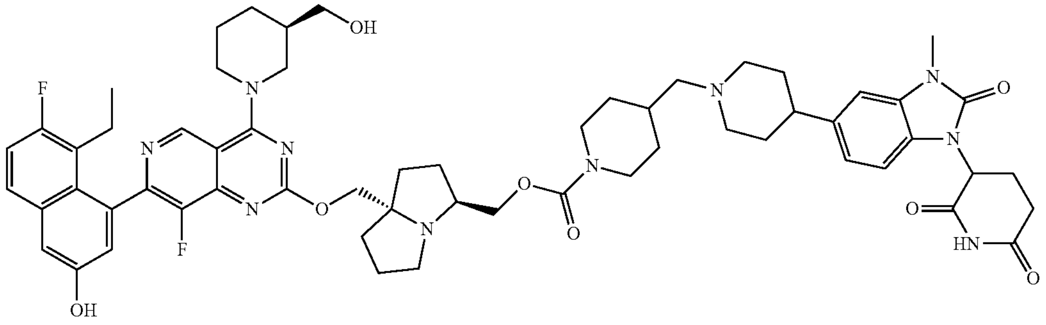 [SMILES: CCc1c(F)ccc2cc(O)cc(-c3ncc4c(N5CCC[C@@H](CO)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 341 | 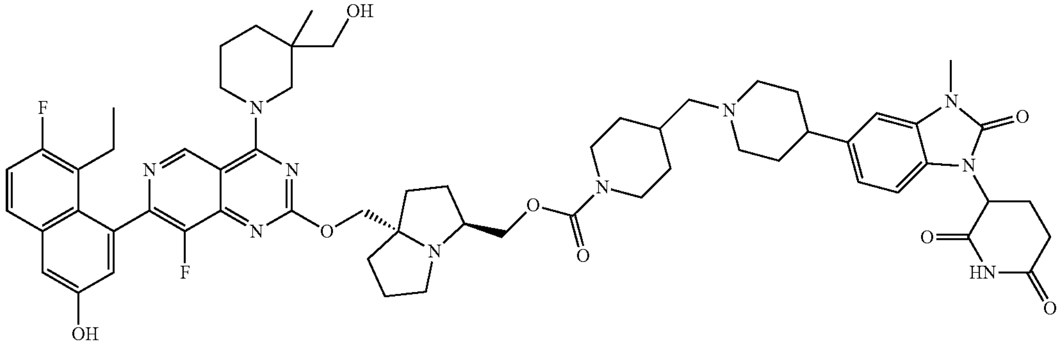 [SMILES: CCc1c(F)ccc2cc(O)cc(-c3ncc4c(N5CCCC(C)(CO)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 344 | 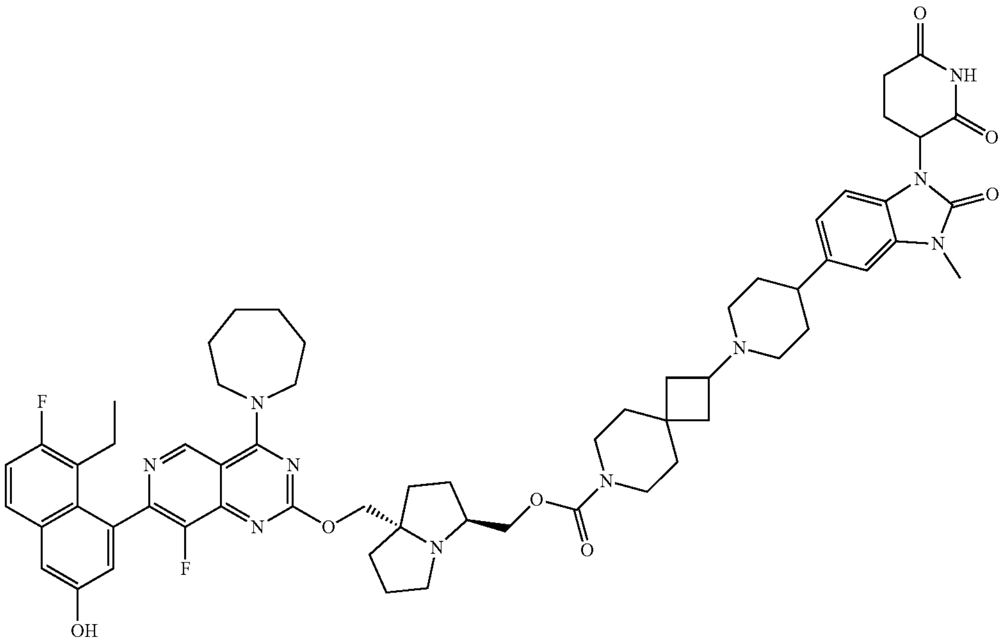 [SMILES: CCc1c(F)ccc2cc(O)cc(-c3ncc4c(N5CCCCCC5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 345 | 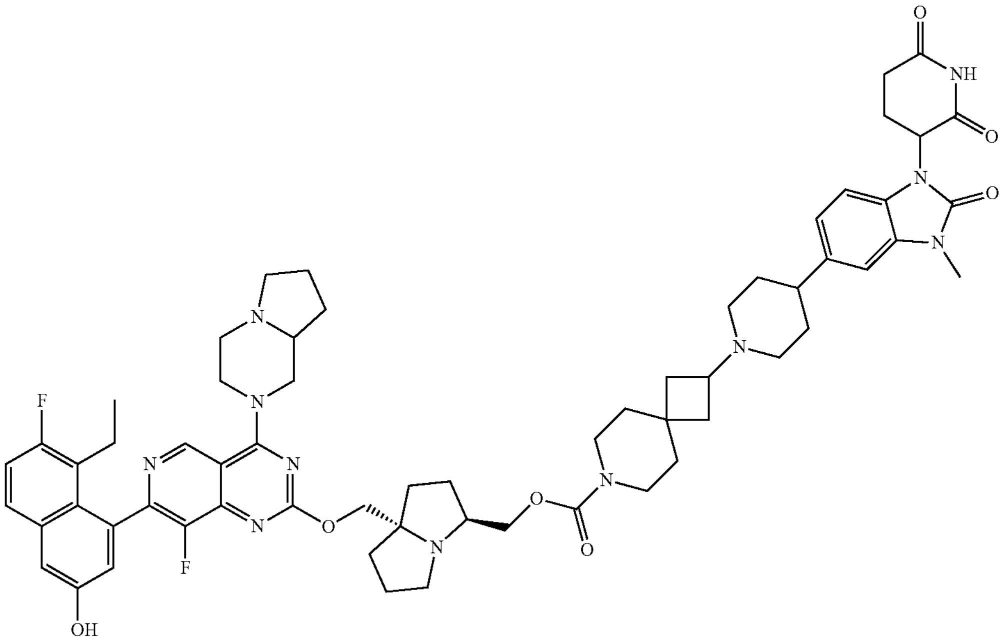 [SMILES: CCc1c(F)ccc2cc(O)cc(-c3ncc4c(N5CCN6CCCC6C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 346 | 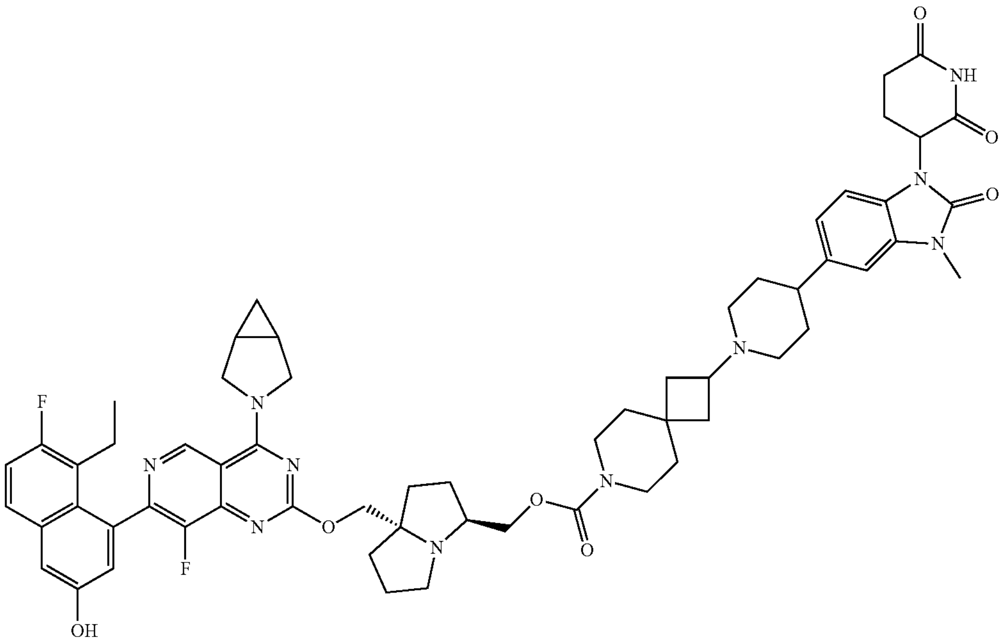 [SMILES: CCc1c(F)ccc2cc(O)cc(-c3ncc4c(N5CC6CC6C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 347 | 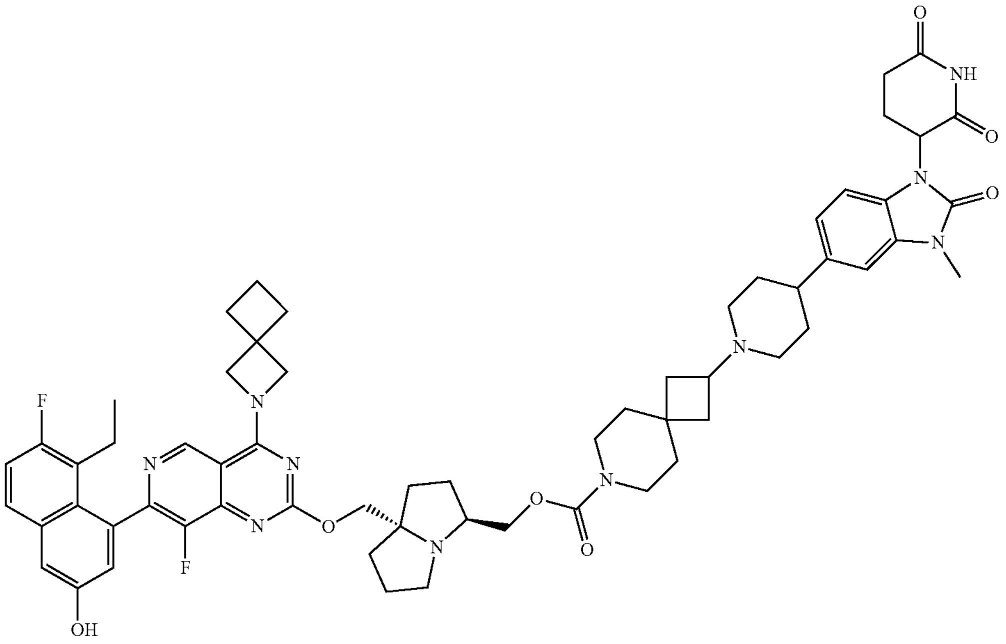 [SMILES: CCc1c(F)ccc2cc(O)cc(-c3ncc4c(N5CC6(CCC6)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 348 | 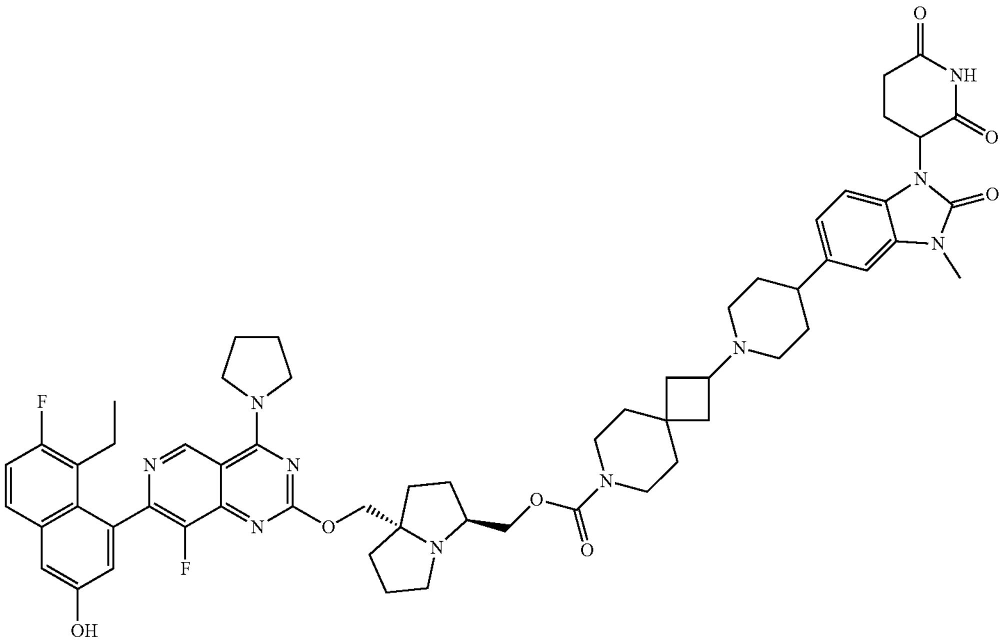 [SMILES: CCc1c(F)ccc2cc(O)cc(-c3ncc4c(N5CCCC5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 349 | 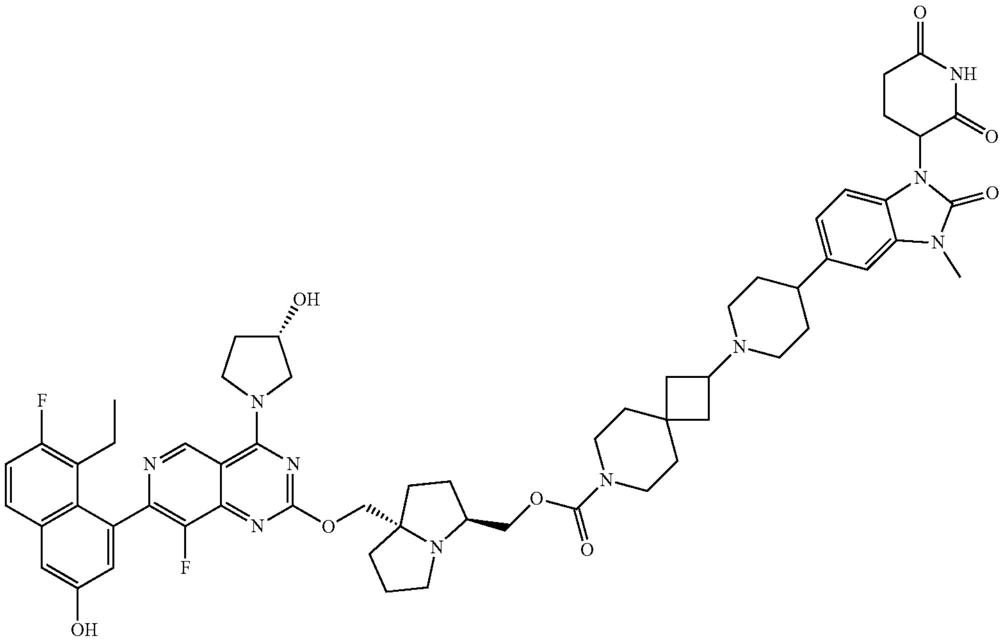 [SMILES: CCc1c(F)ccc2cc(O)cc(-c3ncc4c(N5CC[C@H](O)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 350 | 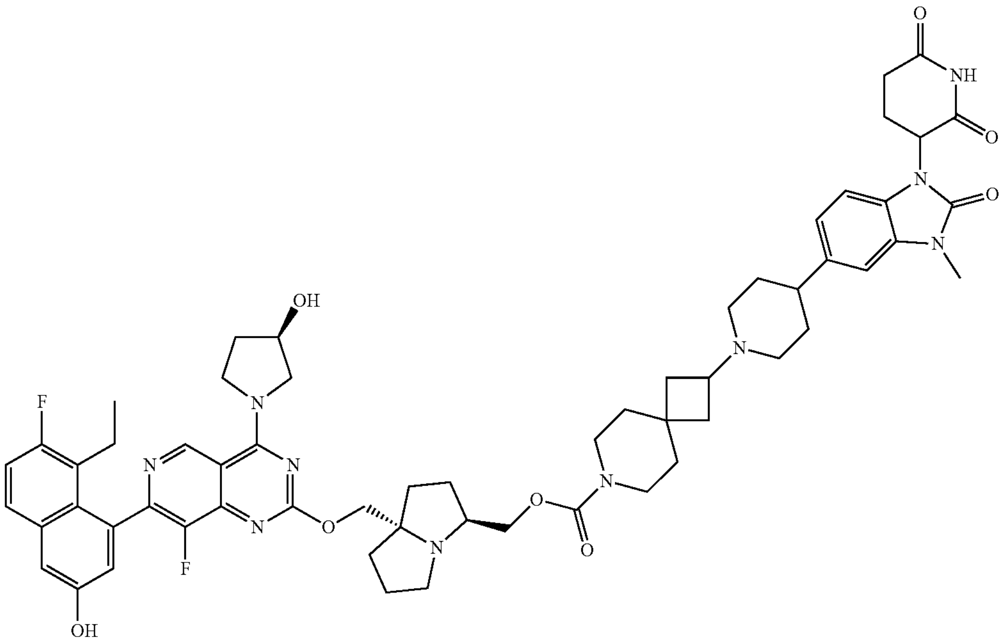 [SMILES: CCc1c(F)ccc2cc(O)cc(-c3ncc4c(N5CC[C@@H](O)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 351 | 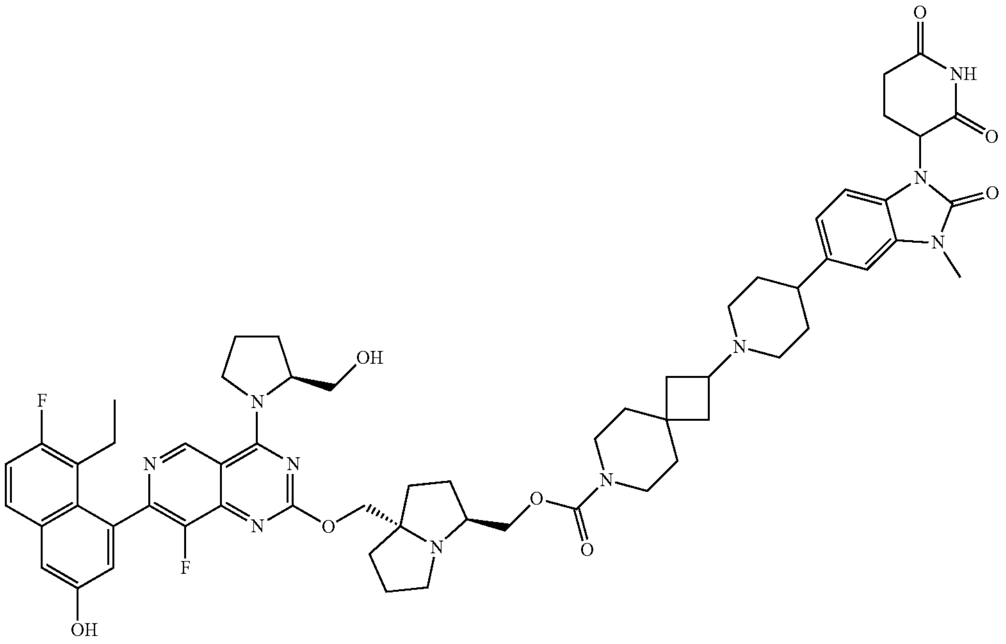 [SMILES: CCc1c(F)ccc2cc(O)cc(-c3ncc4c(N5CCC[C@H]5CO)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Compound No. | Compound Structure |
|---|---|
| | Example Compounds of the Disclosure |
| 352 | 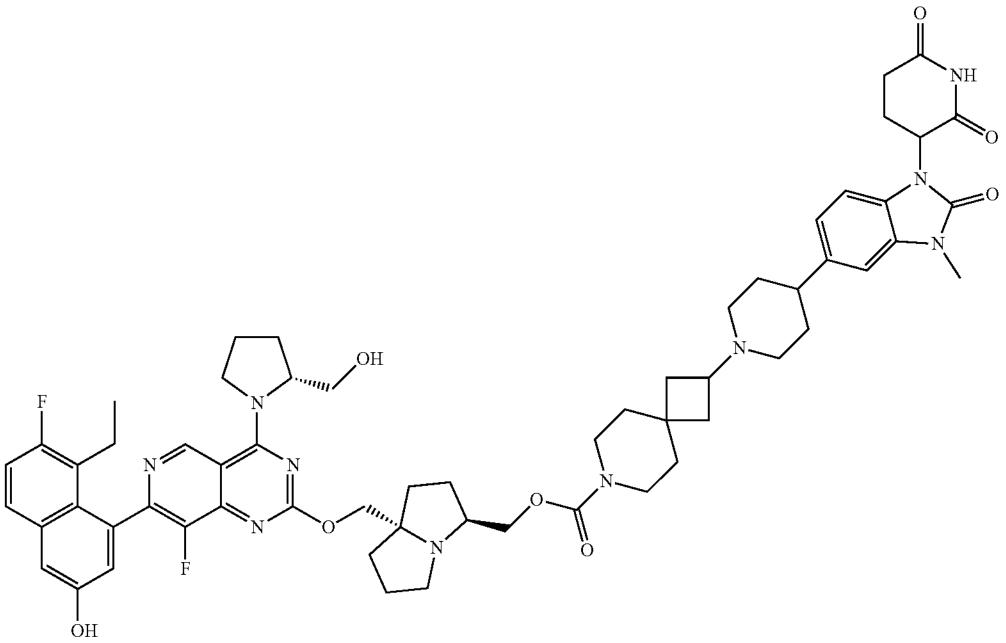 [SMILES: CCc1c(F)ccc2cc(O)cc(-c3ncc4c(N5CCC[C@@H]5CO)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 354 | 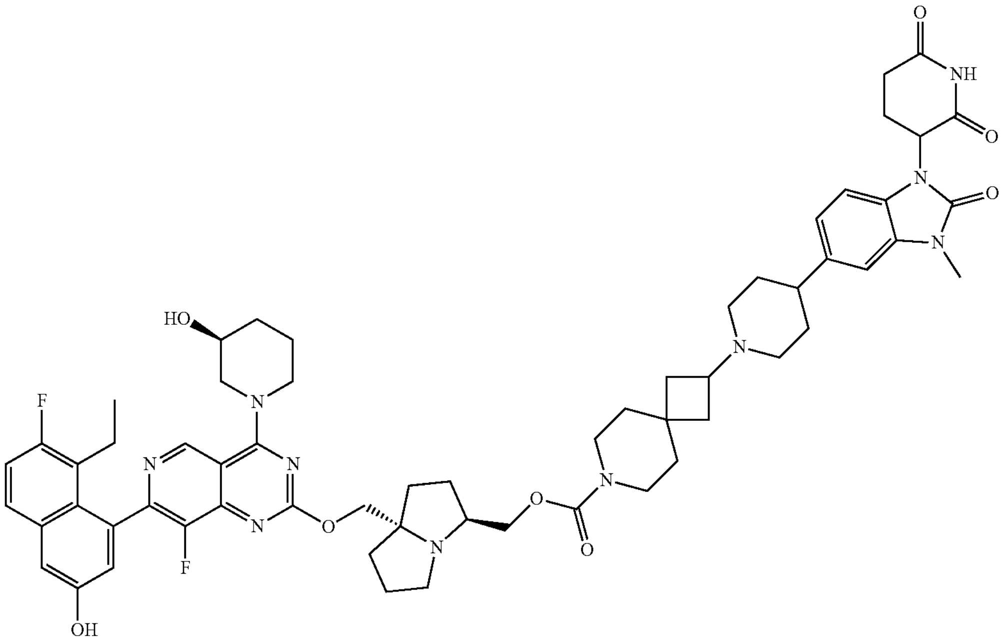 [SMILES: CCc1c(F)ccc2cc(O)cc(-c3ncc4c(N5CCC[C@H](O)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 355 | 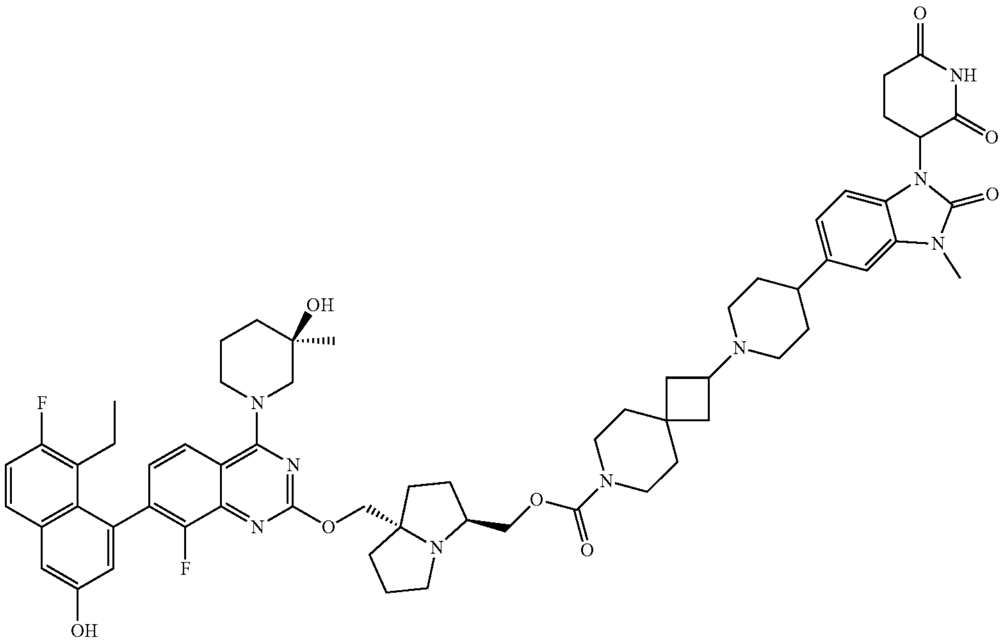 [SMILES: CCc1c(F)ccc2cc(O)cc(-c3ccc4c(N5CCC[C@@](C)(O)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 357 | 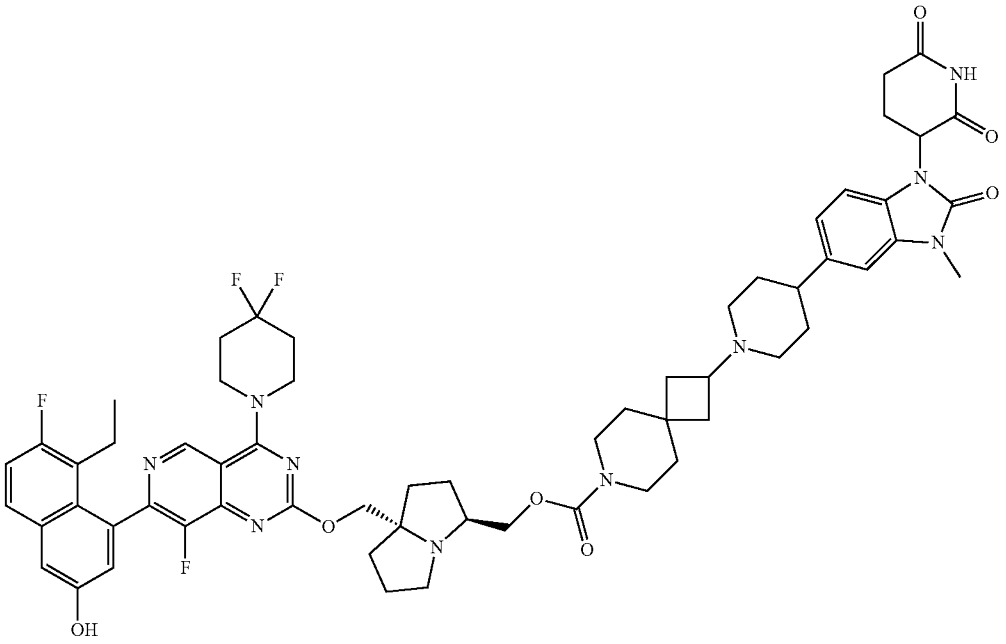 [SMILES: CCc1c(F)ccc2cc(O)cc(-c3ncc4c(N5CCC(F)(F)CC5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 358 | 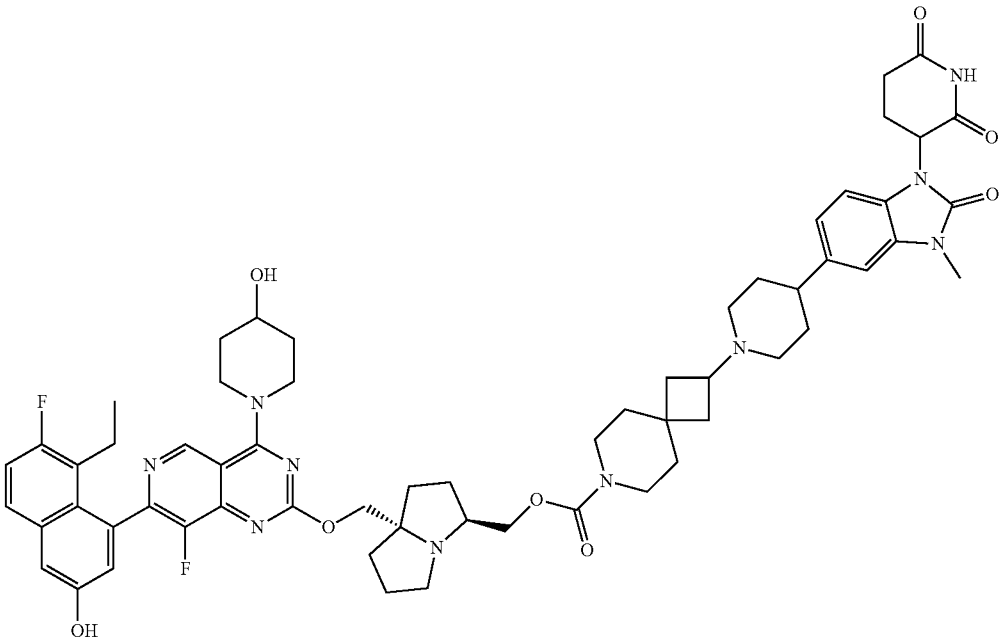 [SMILES: CCc1c(F)ccc2cc(O)cc(-c3ncc4c(N5CCC(O)CC5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 362 | 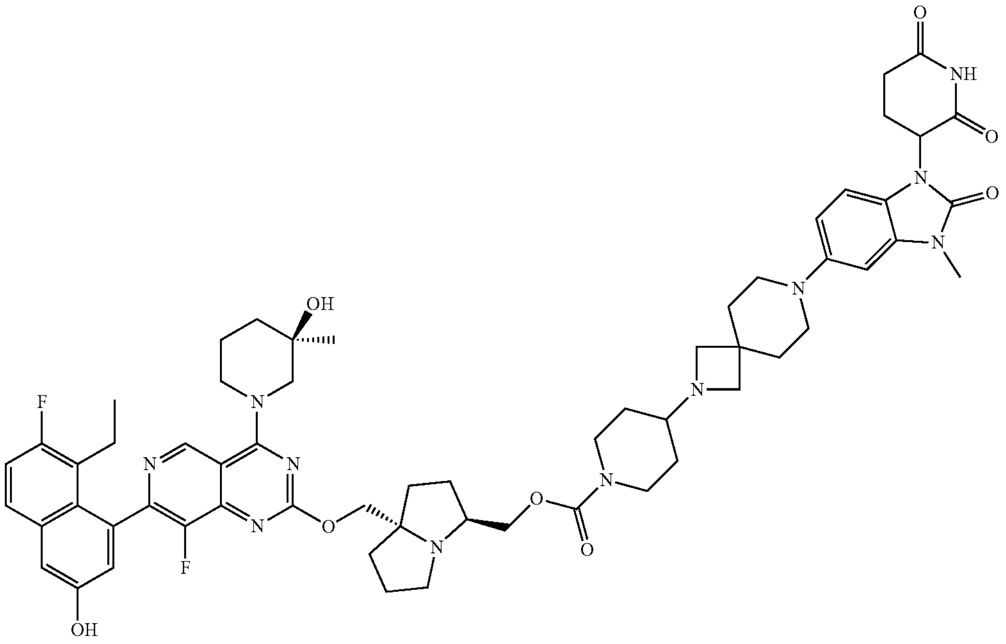 [SMILES: CCc1c(F)ccc2cc(O)cc(-c3ncc4c(N5CCC[C@@](C)(O)C5)nc(OC[C@@]56CCCN5[C@H](COC(=O)N5CCC(N7CC8(CCN(c9ccc%10c(c9)n(C)c(=O)n%10C9CCC(=O)NC9=O)CC8)C7)CC5)CC6)nc4c3F)c12] |

TABLE 3-continued
| Example Compounds of the Disclosure | |
|---|---|
| Compound No. | Compound Structure |
| 363 | 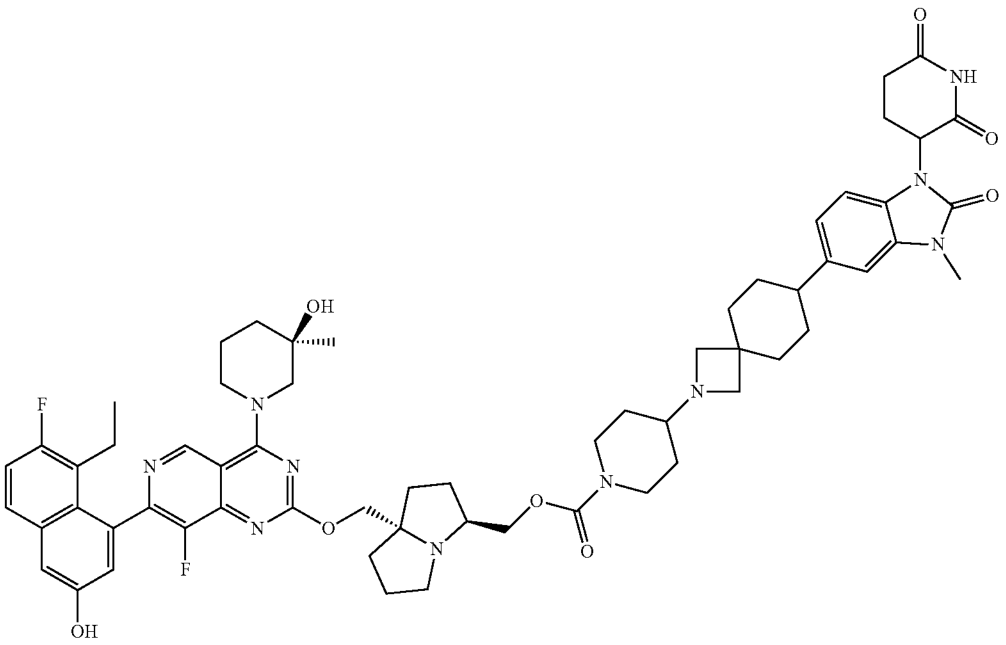 [SMILES: CCc1c(F)ccc2cc(O)cc(-c3ncc4c(N5CCC[C@@](C)(O)C5)nc(OC[C@@]56CCCN5[C@H](COC(=O)N5CCC(N7CC8(CCC(c9ccc%10c(c9)n(C)c(=O)n%10C9CCC(=O)NC9=O)CC8)C7)CC5)CC6)nc4c3F)c12] |
| 364 | 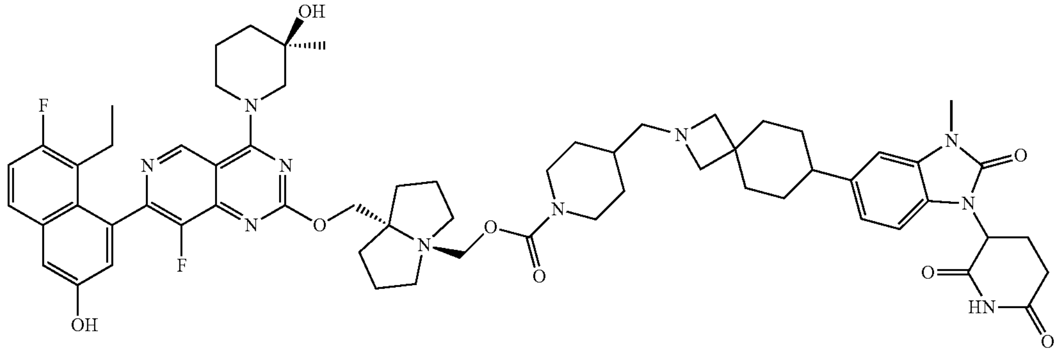 |

TABLE 3-continued
| Example Compounds of the Disclosure | |
|---|---|
| Compound No. | Compound Structure |
| 365 | 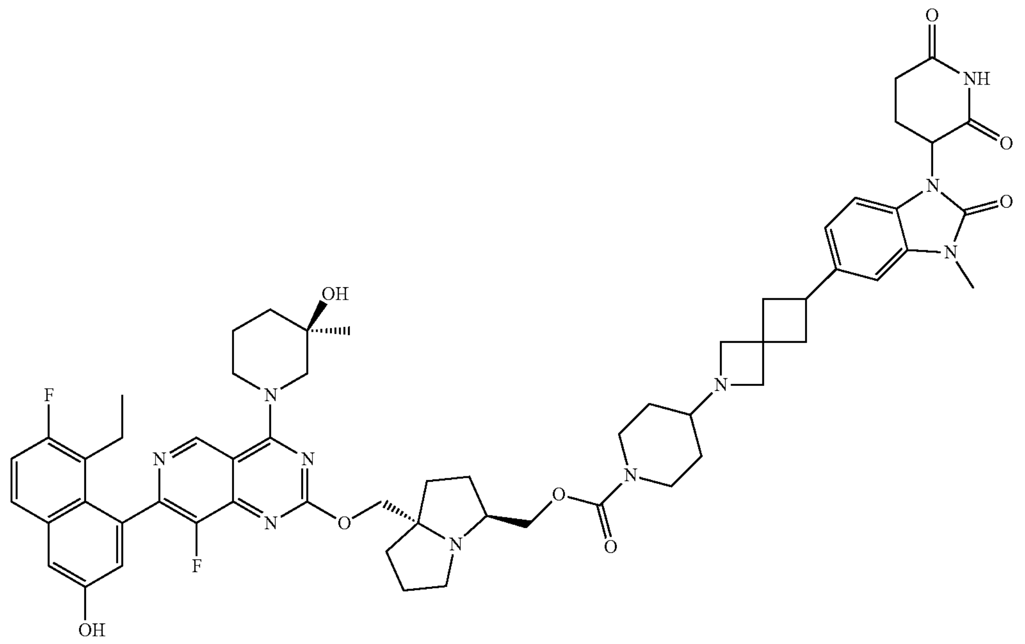 |
| 366 | 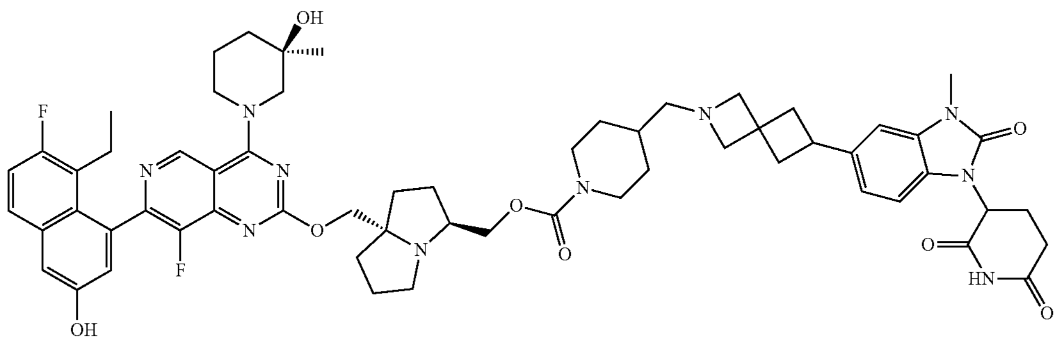 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CC8(CC(c9ccc%10c(c9)n(C)c(=O)n%10C9CCC(=O)NC9=O)C8)C7)CC5)CC6)nc4c3F)c12] |

TABLE 3-continued
| Example Compounds of the Disclosure | |
|---|---|
| Compound No. | Compound Structure |
| 367 | 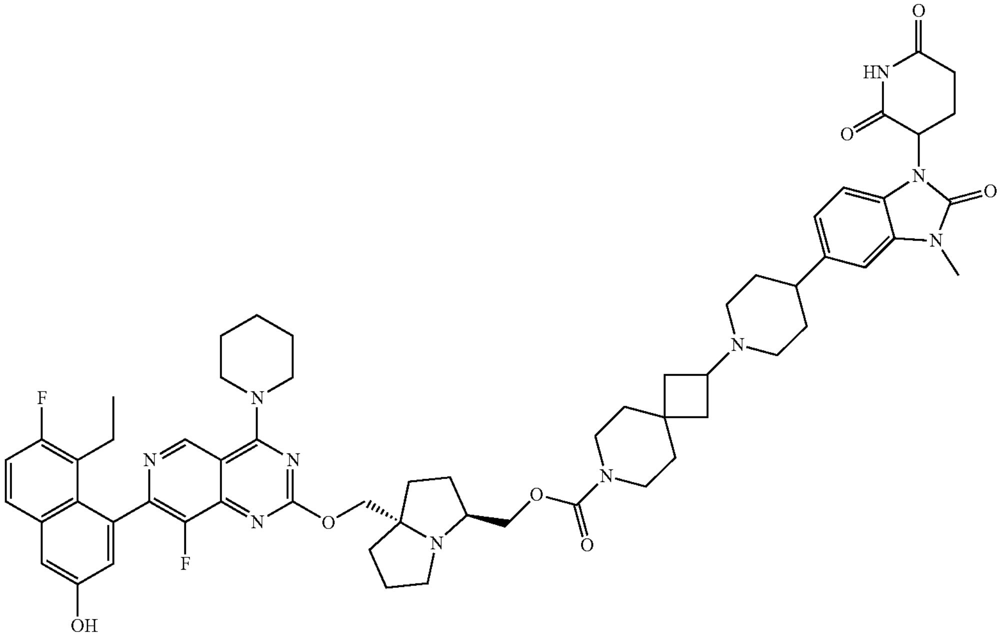 [SMILES: CCc1c(F)ccc2cc(O)cc(-c3ncc4c(N5CCCCC5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 369 | 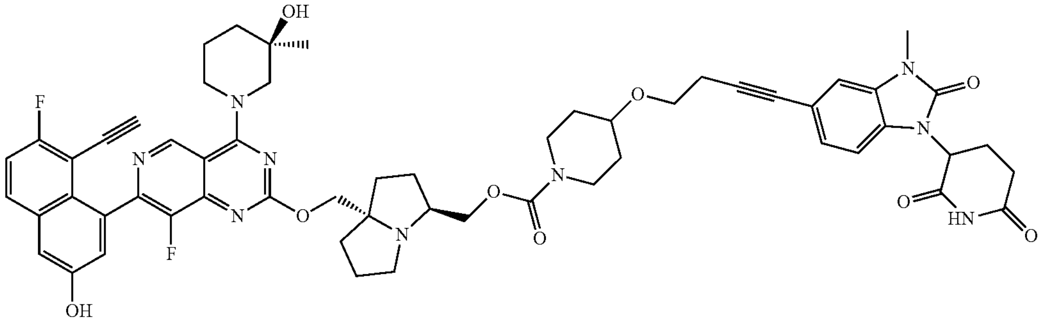 [SMILES: C#Cc1c(F)ccc2cc(O)cc(-c3ncc4c(N5CCC[C@@](C)(O)C5)nc(OC[C@@]56CCCN5[C@H](COC(=O)N5CCC(OCCC#Cc7ccc8c(c7)n(C)c(=O)n8C7CCC(=O)NC7=O)CC5)CC6)nc4c3F)c12] |
| 370 | 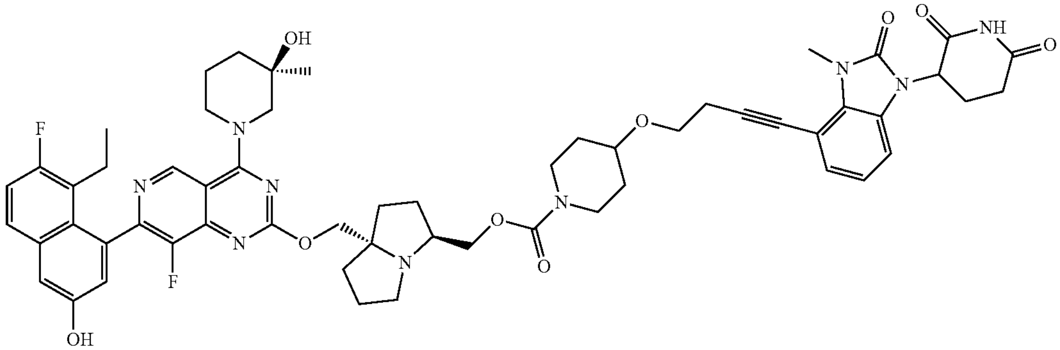 [SMILES: CCc1c(F)ccc2cc(O)cc(-c3ncc4c(N5CCC[C@@](C)(O)C5)nc(OC[C@@]56CCCN5[C@H](COC(=O)N5CCC(OCCC#Cc7cccc8c7n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 371 | 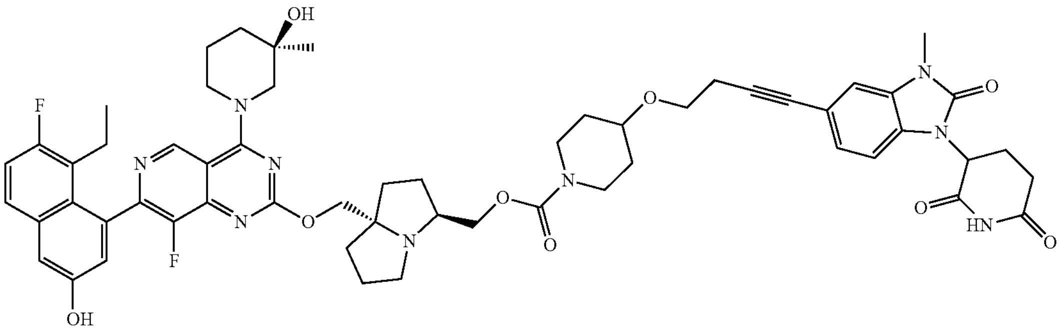 [SMILES: CCc1c(F)ccc2cc(O)cc(-c3ncc4c(N5CCC[C@@](C)(O)C5)nc(OC[C@@]56CCCN5[C@H](COC(=O)N5CCC(OCCC#Cc7ccc8c(c7)n(C)c(=O)n8C7CCC(=O)NC7=O)CC5)CC6)nc4c3F)c12] |
| 372 | 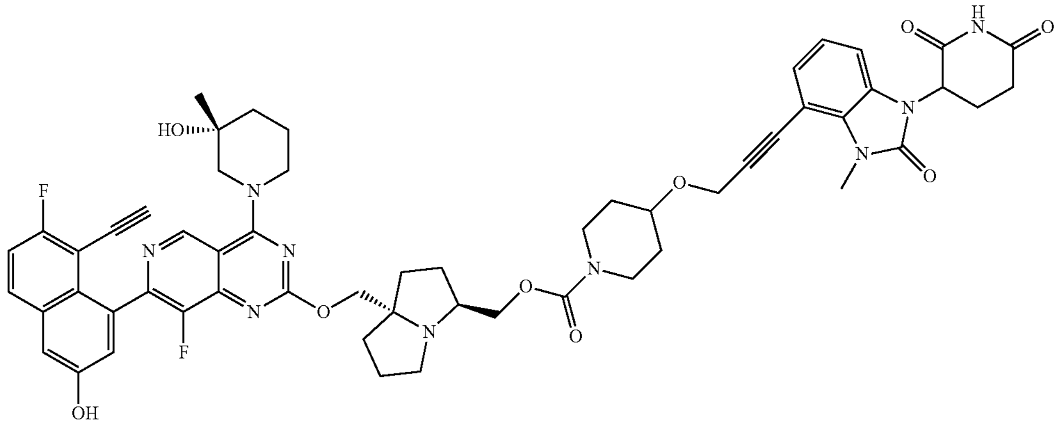 [SMILES: C#Cc1c(F)ccc2cc(O)cc(-c3ncc4c(N5CCC[C@@](C)(O)C5)nc(OC[C@@]56CCCN5[C@H](COC(=O)N5CCC(OCC#Cc7cccc8c7n(C)c(=O)n8C7CCC(=O)NC7=O)CC5)CC6)nc4c3F)c12] |
| 373 | 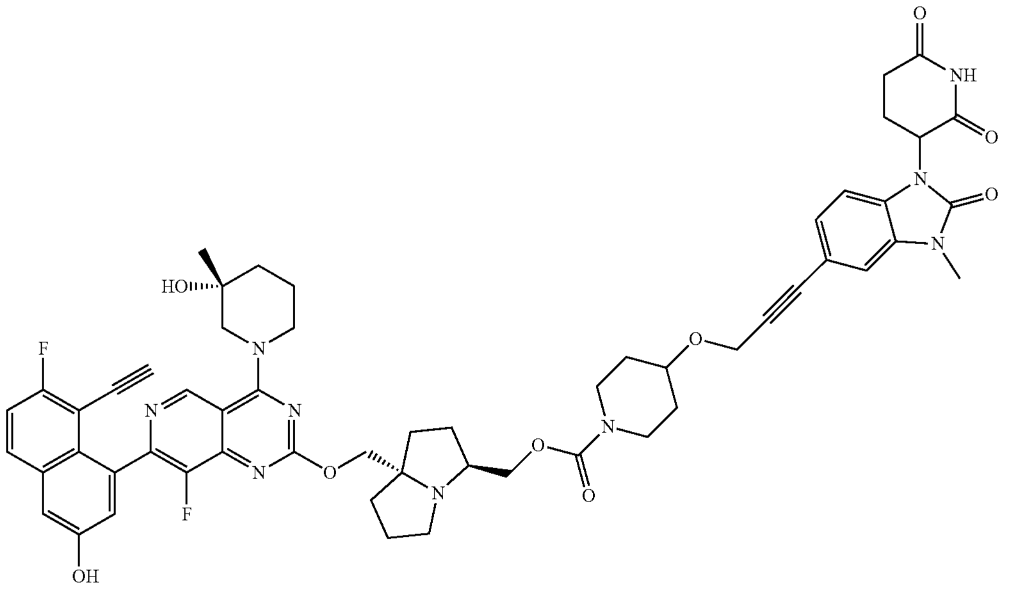 [SMILES: C#Cc1c(F)ccc2cc(O)cc(-c3ncc4c(N5CCC[C@@](C)(O)C5)nc(OC[C@@]56CCCN5[C@H](COC(=O)N5CCC(OCC#Cc7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 374 | 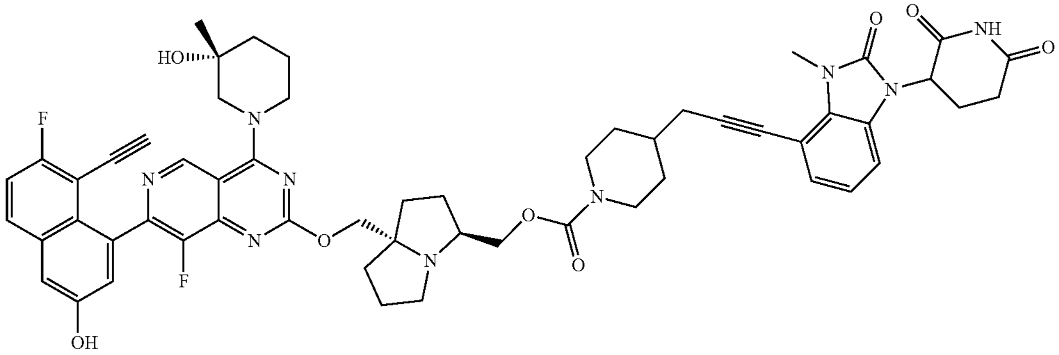 [SMILES: C#Cc1c(F)ccc2cc(O)cc(-c3ncc4c(N5CCC[C@@](C)(O)C5)nc(OC[C@@]56CCCN5[C@H](COC(=O)N5CCC(CC#Cc7cccc8c7n(C)c(=O)n8C7CCC(=O)NC7=O)CC5)CC6)nc4c3F)c12] |
| 375 | 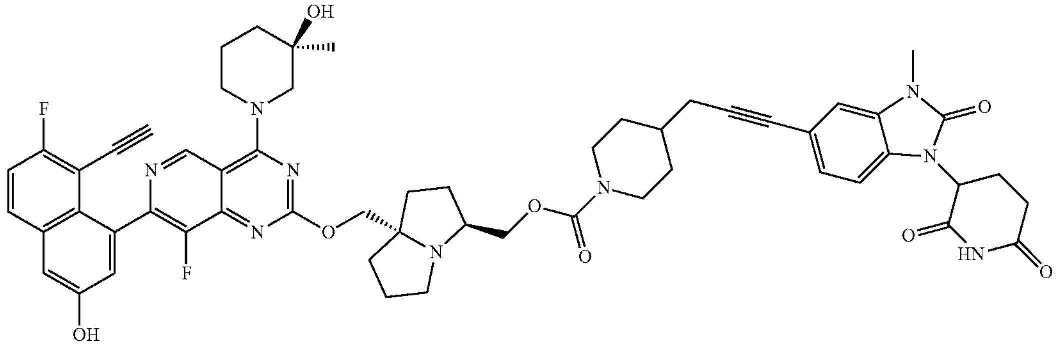 [SMILES: C#Cc1c(F)ccc2cc(O)cc(-c3ncc4c(N5CCC[C@@](C)(O)C5)nc(OC[C@@]56CCCN5[C@H](COC(=O)N5CCC(CC#Cc7ccc8c(c7)n(C)c(=O)n8C7CCC(=O)NC7=O)CC5)CC6)nc4c3F)c12] |
| 376 | 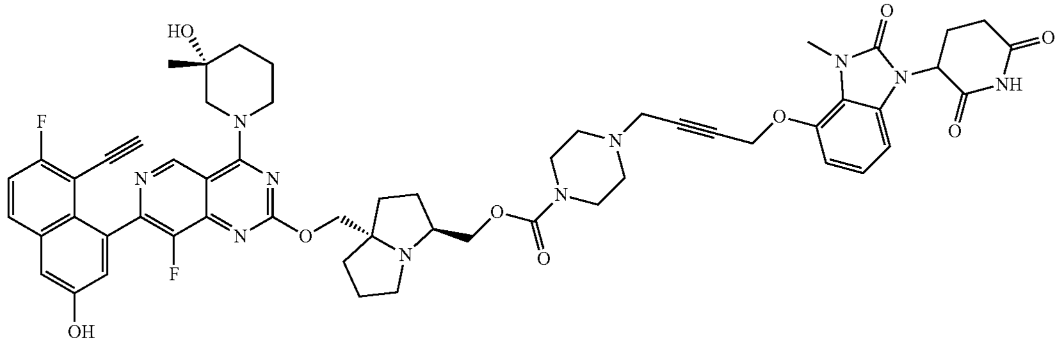 [SMILES: C#Cc1c(F)ccc2cc(O)cc(-c3ncc4c(N5CCC[C@@](C)(O)C5)nc(OC[C@@]56CCCN5[C@H](COC(=O)N5CCN(CC#CCOc7cccc8c7n(C)c(=O)n8C7CCC(=O)NC7=O)CC5)CC6)nc4c3F)c12] |
| 377 | 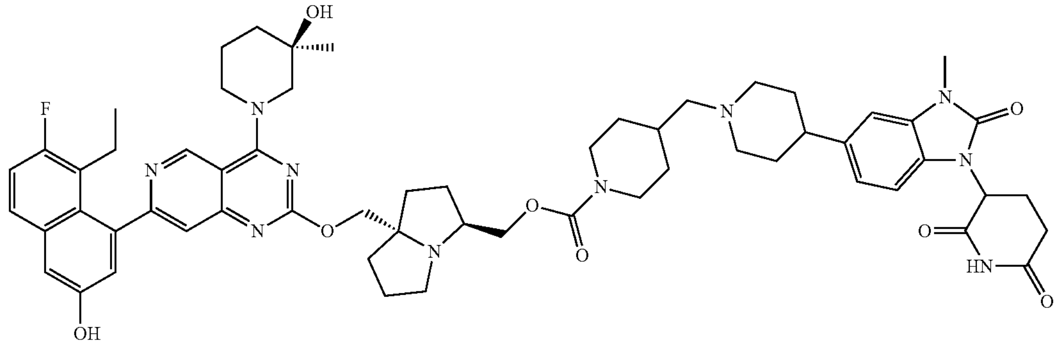 [SMILES: CCc1c(F)ccc2cc(O)cc(-c3cc4nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc(N5CCC[C@@](C)(O)C5)c4cn3)c12] |

TABLE 3-continued
| Example Compounds of the Disclosure | |
|---|---|
| Compound No. | Compound Structure |
| 378 | 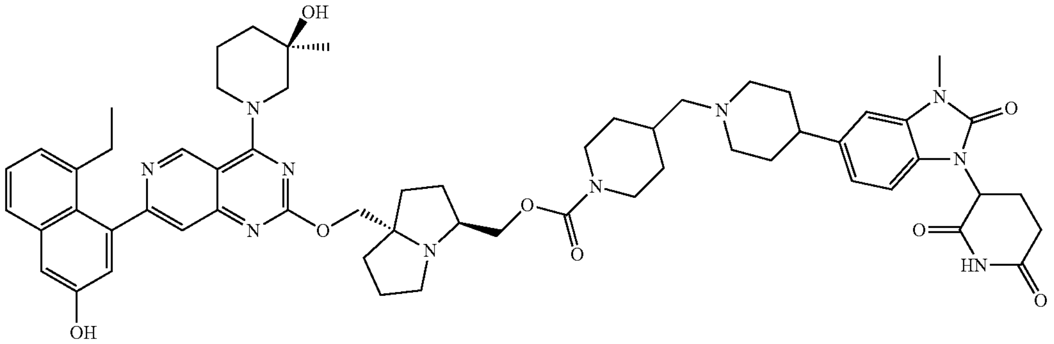 [SMILES: CCc1cccc2cc(O)cc(-c3cc4nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc(N5CCC[C@@](C)(O)C5)c4cn3)c12] |
| 379 | 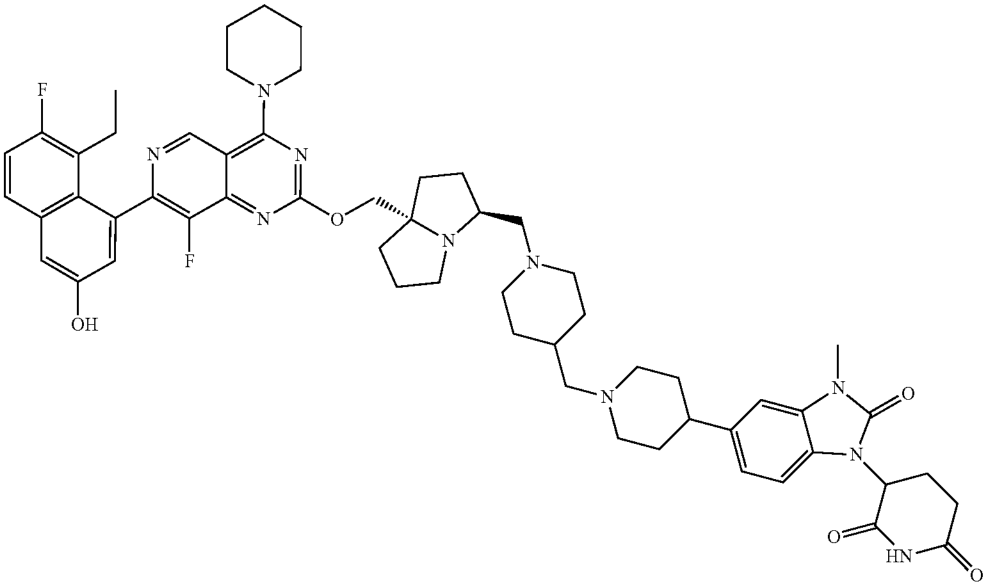 [SMILES: CCc1c(F)ccc2cc(O)cc(-c3ncc4c(N5CCCCC5)nc(OC[C@@]56CCCN5[C@H](CN5CCC(CN7CCC(c8ccc9c(c8)n(C)c(=O)n9C8CCC(=O)NC8=O)CC7)CC5)CC6)nc4c3F)c12] |
| 383 | 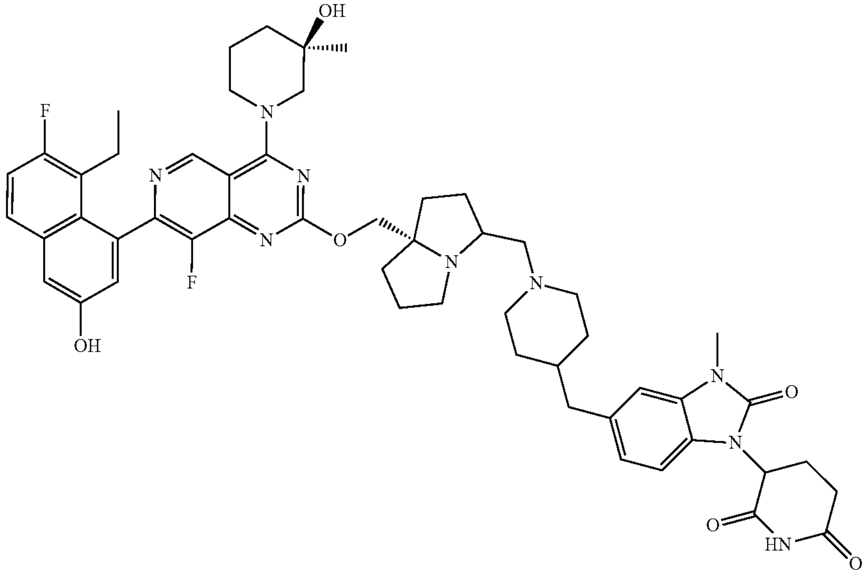 [SMILES: CCc1c(F)ccc2cc(O)cc(-c3ncc4c(N5CCC[C@@](C)(O)C5)nc(OC[C@@]56CCCN5C(CN5CCC(Cc7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 384 | 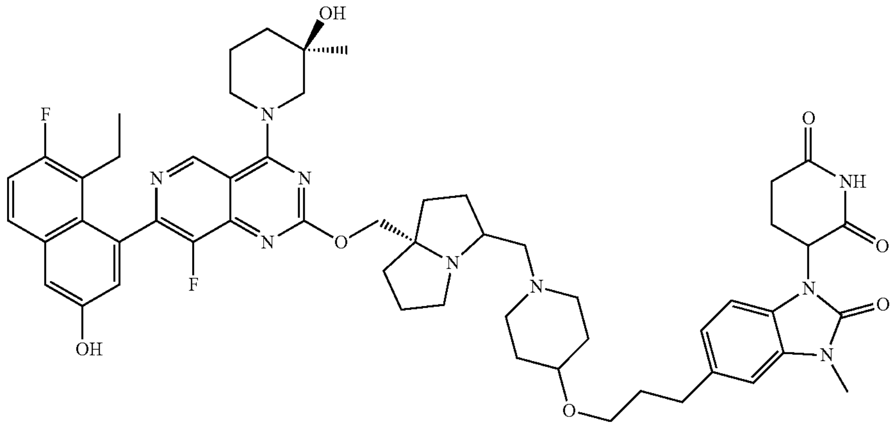 [SMILES: CCc1c(F)ccc2cc(O)cc(-c3ncc4c(N5CCC[C@@](C)(O)C5)nc(OC[C@@]56CCCN5C(CN5CCC(OCCCc7ccc8c(c7)n(C)c(=O)n8C7CCC(=O)NC7=O)CC5)CC6)nc4c3F)c12] |
| 387 | 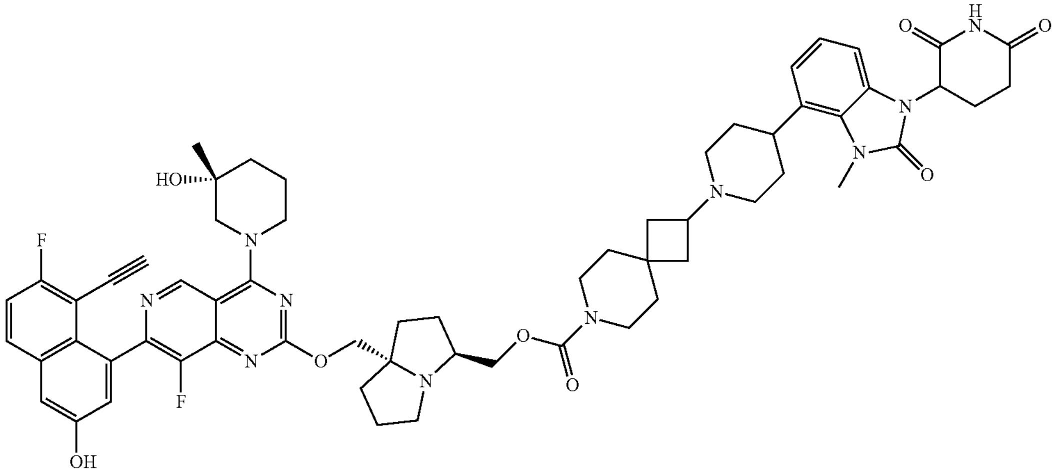 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CC5)CC(N5CCC(c8cccc9c8n(C)c(=O)n9C8CCC(=O)NC8=O)CC5)C7)CC6)nc4c3F)c12] |
| 389 | 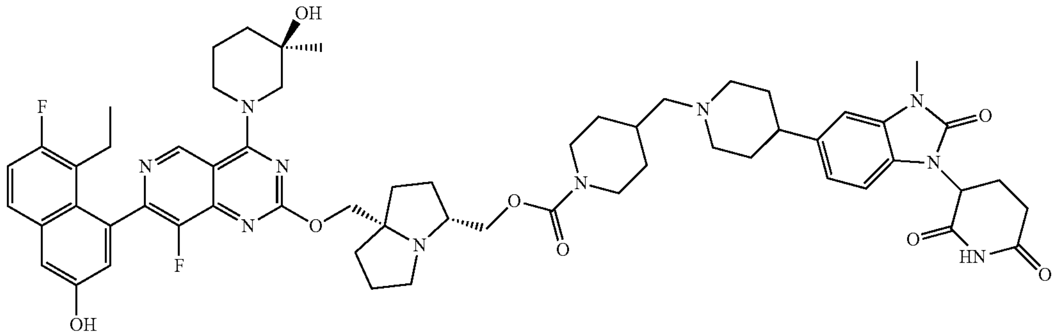 [SMILES: CCc1c(F)ccc2cc(O)cc(-c3ncc4c(N5CCC[C@@](C)(O)C5)nc(OC[C@@]56CCCN5[C@@H](COC(=O)N5CCC(CN7CCC(c8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 390 | 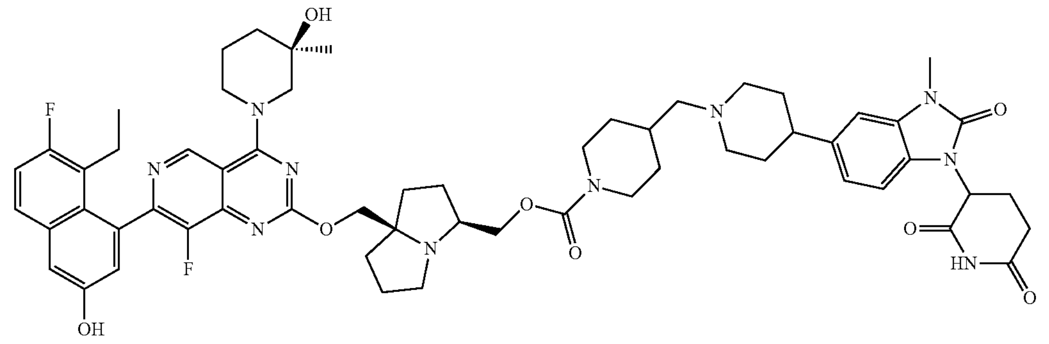 [SMILES: CCc1c(F)ccc2cc(O)cc(-c3ncc4c(N5CCC[C@@](C)(O)C5)nc(OC[C@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 391 | 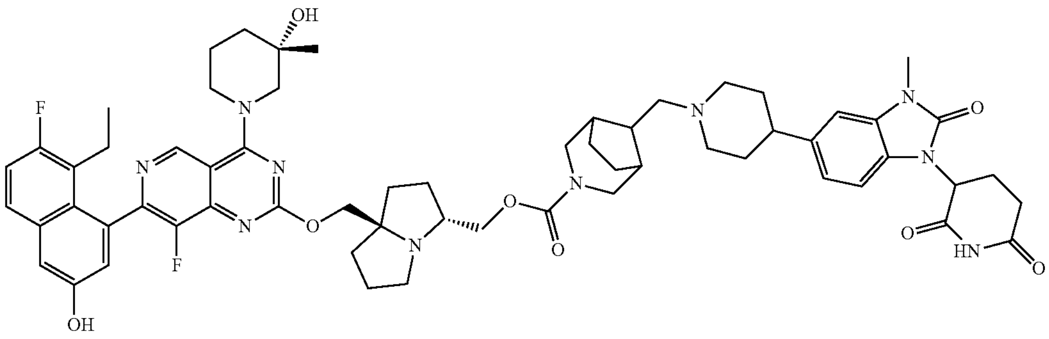 [SMILES: CCc1c(F)ccc2cc(O)cc(-c3ncc4c(N5CCC[C@](C)(O)C5)nc(OC[C@]56CCCN5[C@@H](COC(=O)N5CC7CCC(C5)C7CN5CCC(c7ccc8c(c7)n(C)c(=O)n8C7CCC(=O)NC7=O)CC5)CC6)nc4c3F)c12] |
| 392 | 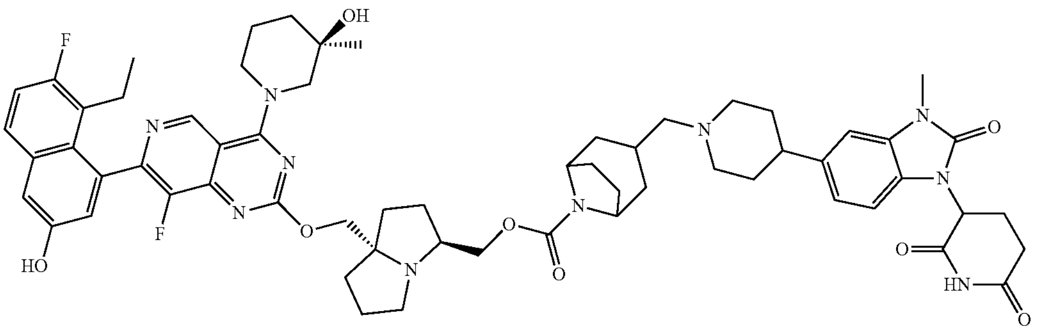 [SMILES: CCc1c(F)ccc2cc(O)cc(-c3ncc4c(N5CCC[C@@](C)(O)C5)nc(OC[C@@]56CCCN5[C@H](COC(=O)N5C7CCC5CC(CN5CCC(c8ccc9c(c8)n(C)c(=O)n9C8CCC(=O)NC8=O)CC5)C7)CC6)nc4c3F)c12] |
| 393 | 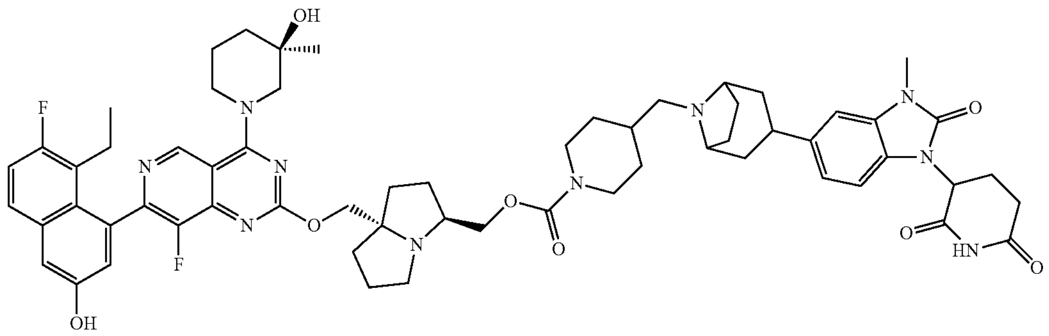 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7C8CCC7CC(c7ccc9c(c7)n(C)c(=O)n9C7CCC(=O)NC7=O)C8)CC5)CC6)nc4c3F)c12] |

TABLE 3-continued
| Example Compounds of the Disclosure | |
|---|---|
| Compound No. | Compound Structure |
| 394 | 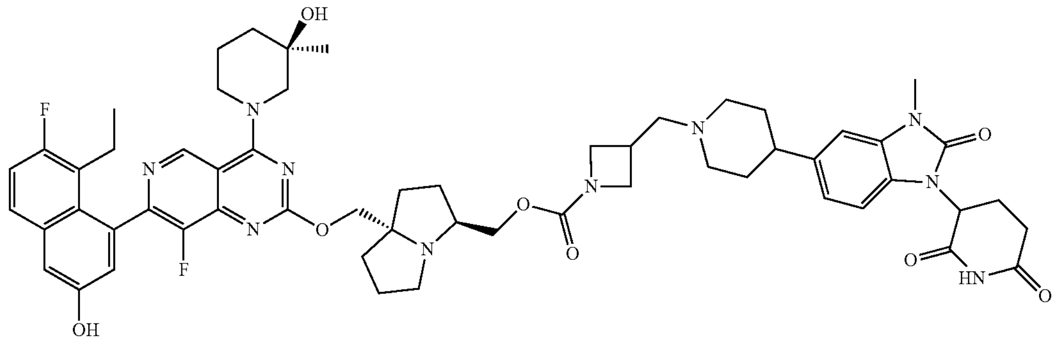 [SMILES: CCc1c(F)ccc2cc(O)cc(-c3ncc4c(N5CCC[C@@](C)(O)C5)nc(OC[C@@]56CCCN5[C@H](COC(=O)N5CC(CN7CCC(c8ccc9c(c8)n(C)c(=O)n9C8CCC(=O)NC8=O)CC7)C5)CC6)nc4c3F)c12] |
| 395 | 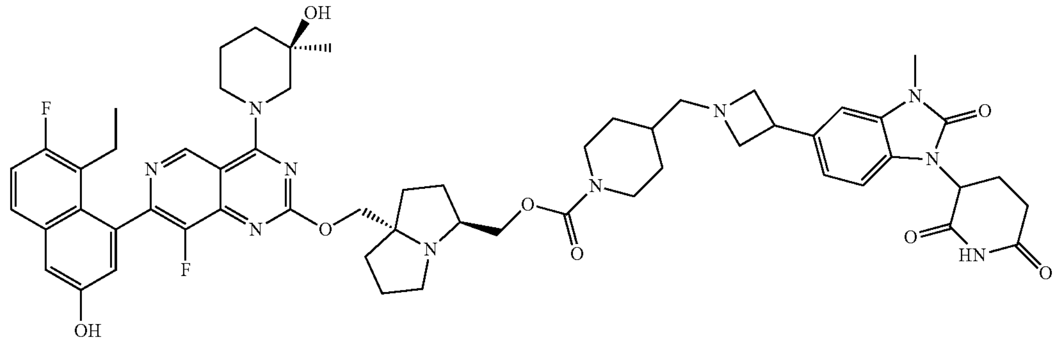 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CC(c8ccc9c(c8)n(C)c(=O)n9C8CCC(=O)NC8=O)C7)CC5)CC6)nc4c3F)c12] |
| 396 | 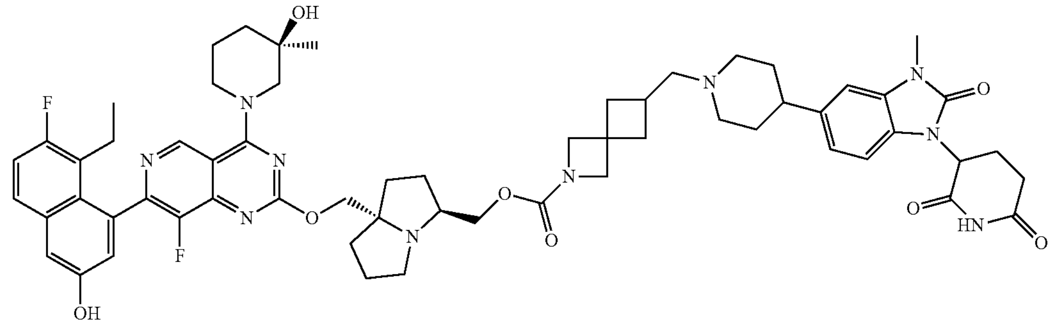 [SMILES: CCc1c(F)ccc2cc(O)cc(-c3ncc4c(N5CCC[C@@](C)(O)C5)nc(OC[C@@]56CCCN5[C@H](COC(=O)N5CC7(CC(CN8CCC(c9ccc%10c(c9)n(C)c(=O)n%10C9CCC(=O)NC9=O)CC8)C7)C5)CC6)nc4c3F)c12] |
| 397 | 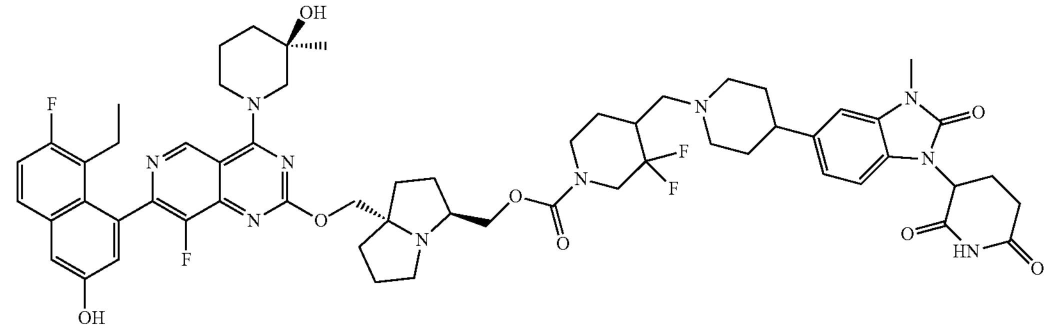 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)C(F)(F)C5)CC6)nc4c3F)c12] |

TABLE 3-continued
| Example Compounds of the Disclosure | |
|---|---|
| Compound No. | Compound Structure |
| 398 | 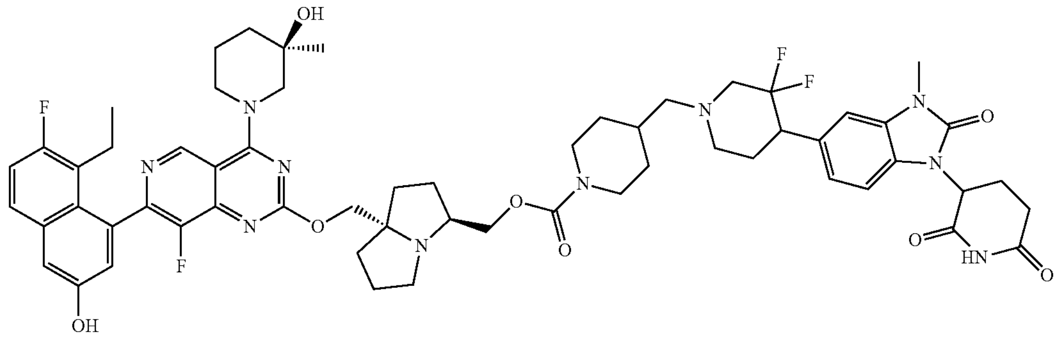 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)C(F)(F)C7)CC5)CC6)nc4c3F)c12] |
| 399 | 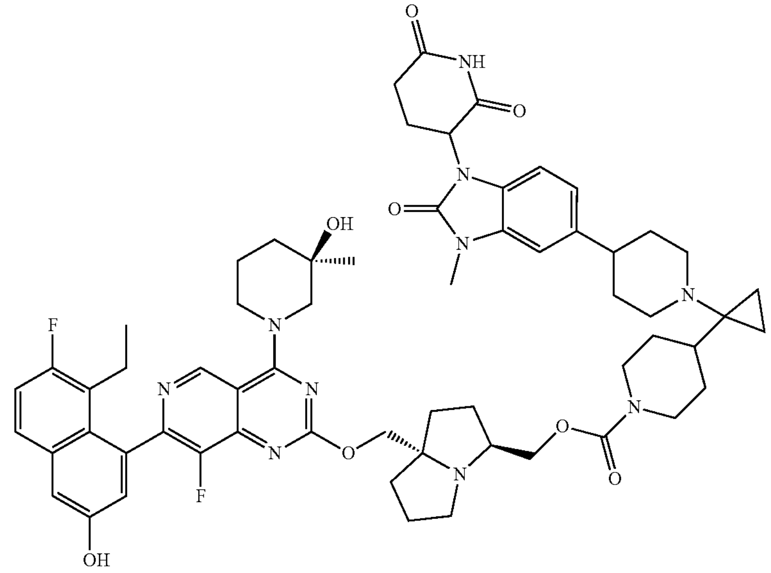 [SMILES: CCc1c(F)ccc2cc(O)cc(-c3ncc4c(N5CCC[C@@](C)(O)C5)nc(OC[C@@]56CCCN5[C@H](COC(=O)N5CCC(C7(N8CCC(c9ccc%10c(c9)n(C)c(=O)n%10C9CCC(=O)NC9=O)CC8)CC7)CC5)CC6)nc4c3F)c12] |
| 400 | 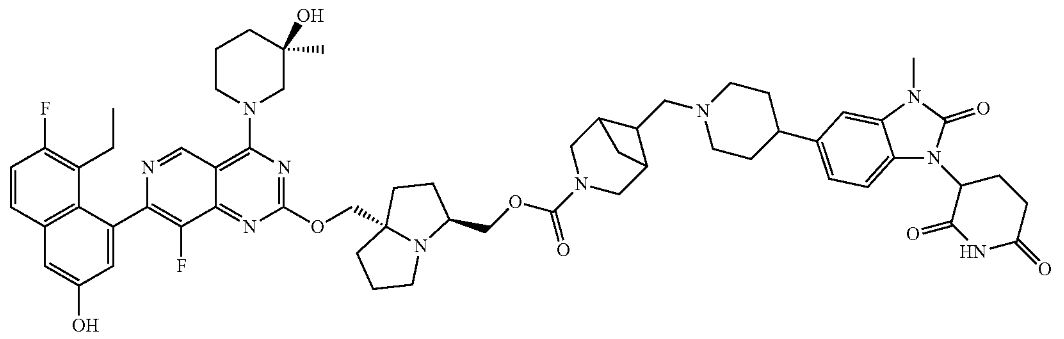 [SMILES: CCc1c(F)ccc2cc(O)cc(-c3ncc4c(N5CCC[C@@](C)(O)C5)nc(OC[C@@]56CCCN5[C@H](COC(=O)N5CC7CC(C5)C7CN5CCC(c7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 401 | 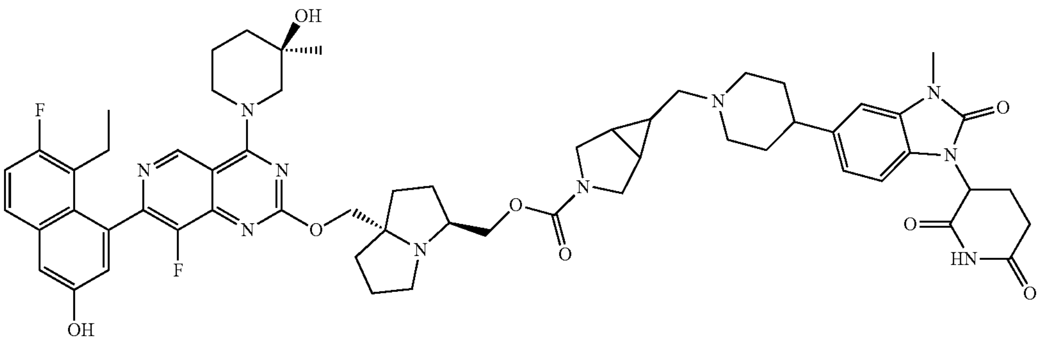 [SMILES: CCc1c(F)ccc2cc(O)cc(-c3ncc4c(N5CCC[C@@](C)(O)C5)nc(OC[C@@]56CCCN5[C@H](COC(=O)N5CC7C(CN8CCC(c9ccc%10c(c9)n(C)c(=O)n%10C9CCC(=O)NC9=O)CC8)C7C5)CC6)nc4c3F)c12] |
| 402 | 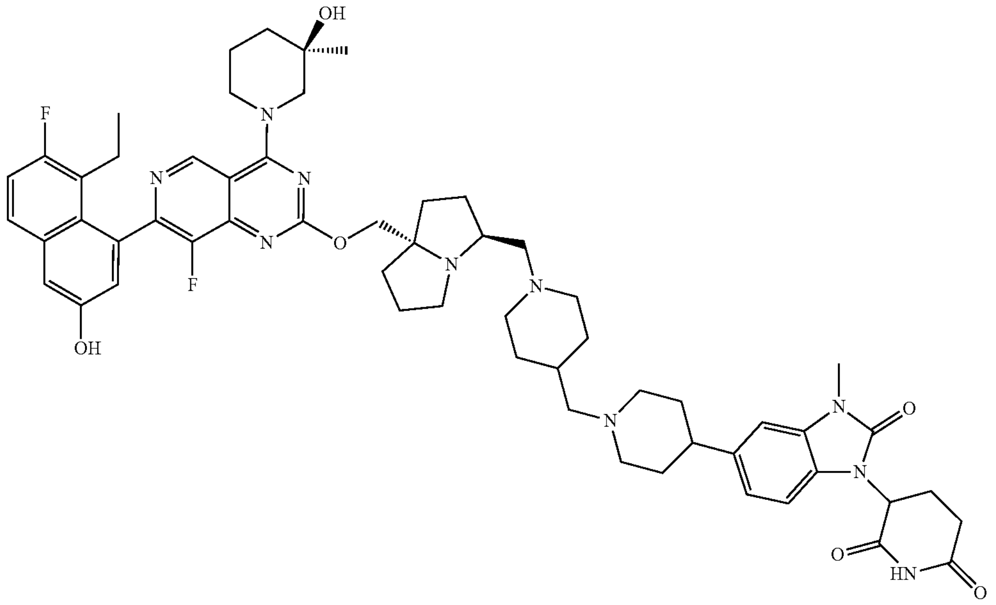 [SMILES: CCc1c(F)ccc2cc(O)cc(-c3ncc4c(N5CCC[C@@](C)(O)C5)nc(OC[C@@]56CCCN5[C@H](CN5CCC(CN7CCC(c8ccc9c(c8)n(C)c(=O)n9C8CCC(=O)NC8=O)CC7)CC5)CC6)nc4c3F)c12] |
| 403 | 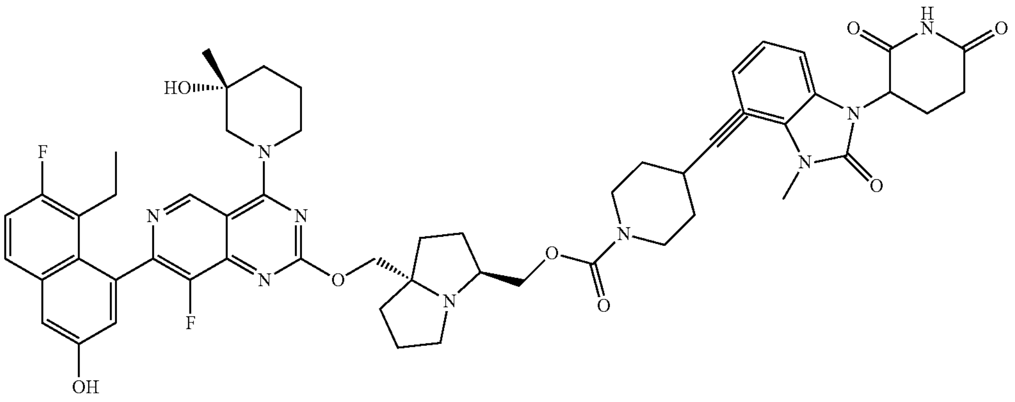 |

TABLE 3-continued
| Example Compounds of the Disclosure | |
|---|---|
| Compound No. | Compound Structure |
| 404 | 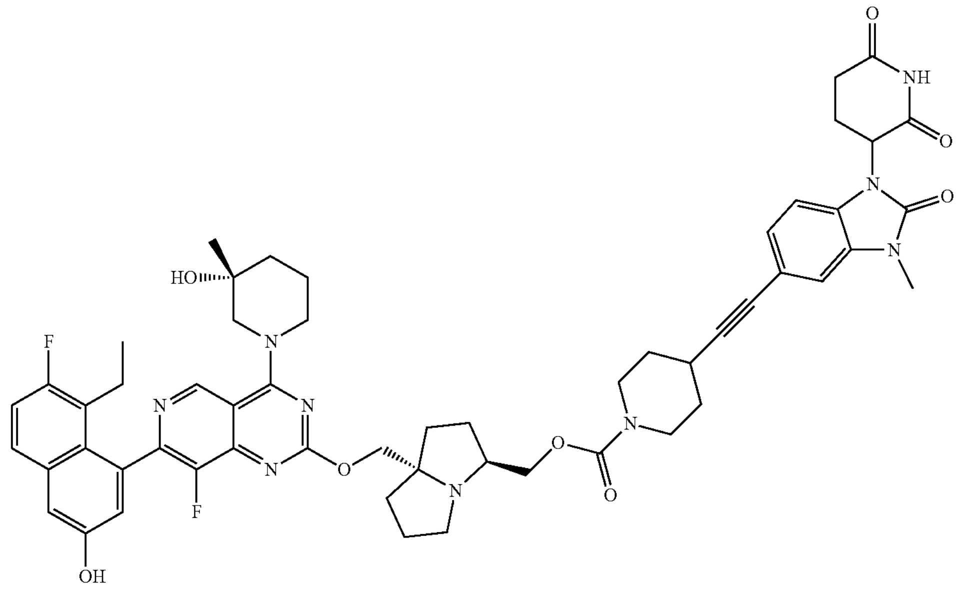 [SMILES: CCc1c(F)ccc2cc(O)cc(-c3ncc4c(N5CCC[C@@](C)(O)C5)nc(OC[C@@]56CCCN5[C@H](COC(=O)N5CCC(C#Cc7ccc8c(c7)n(C)c(=O)n8C7CCC(=O)NC7=O)CC5)CC6)nc4c3F)c12] |
| 405 | 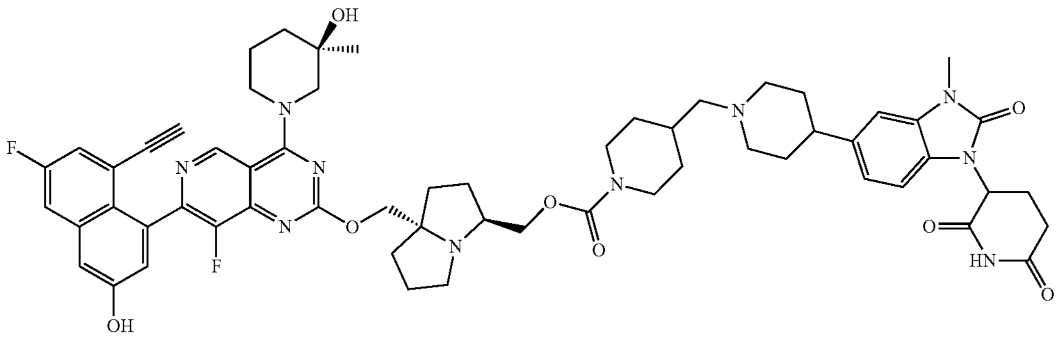 [SMILES: C#Cc1cc(F)cc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 406 | 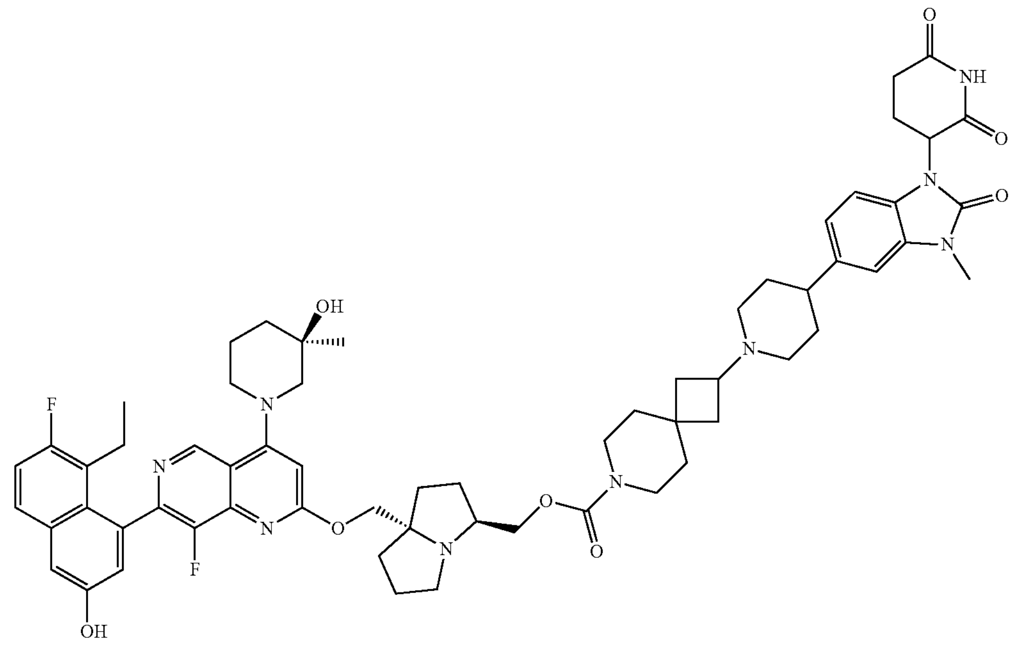 [SMILES: CCc1c(F)ccc2cc(O)cc(-c3ncc4c(N5CCC[C@@](C)(O)C5)cc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 407 | 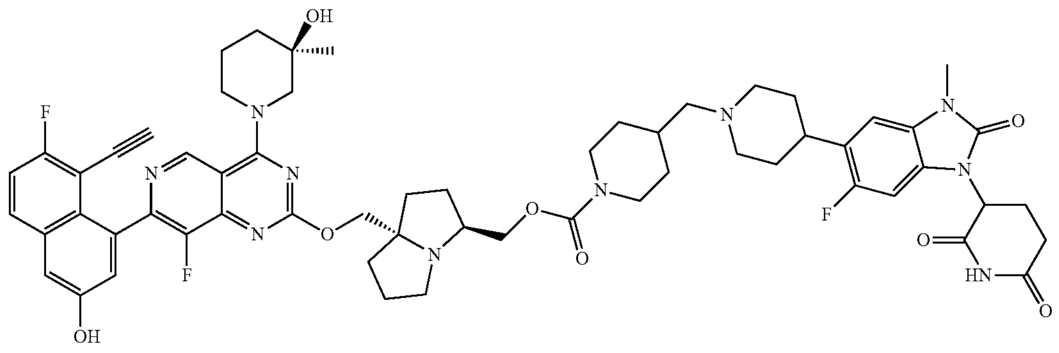 [SMILES: C#Cc1c(F)ccc2cc(O)cc(-c3ncc4c(N5CCC[C@@](C)(O)C5)nc(OC[C@@]56CCCN5[C@H](COC(=O)N5CCC(CN7CCC(c8cc9c(cc8F)n(C8CCC(=O)NC8=O)c(=O)n9C)CC7)CC5)CC6)nc4c3F)c12] |
| 409 | 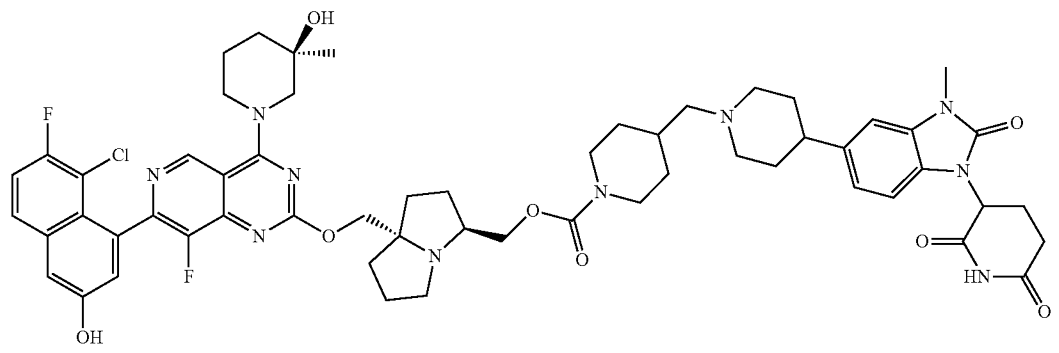 [SMILES: Cn1c(=O)n(C2CCC(=O)NC2=O)c2ccc(C3CCN(CC4CCN(C(=O)OC[C@@H]5CC[C@]6(COc7nc(N8CCC[C@@](C)(O)C8)c8cnc(-c9cc(O)cc%10ccc(F)c(Cl)c9%10)c(F)c8n7)CCCN56)CC4)CC3)cc21] |

TABLE 3-continued
| Example Compounds of the Disclosure | |
|---|---|
| Compound No. | Compound Structure |
| 410 | 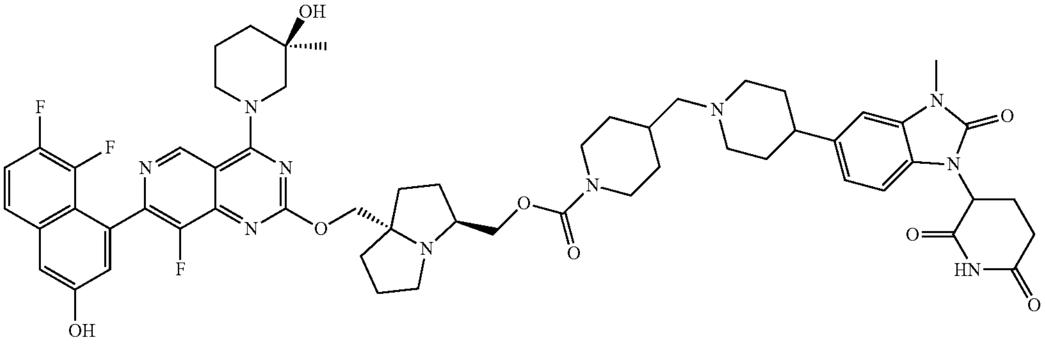 [SMILES: Cn1c(=O)n(C2CCC(=O)NC2=O)c2ccc(C3CCN(CC4CCN(C(=O)OC[C@@H]5CC[C@]6(COc7nc(N8CCC[C@@](C)(O)C8)c8cnc(-c9cc(O)cc%10ccc(F)c(F)c9%10)c(F)c8n7)CCCN56)CC4)CC3)cc21] |
| 413 | 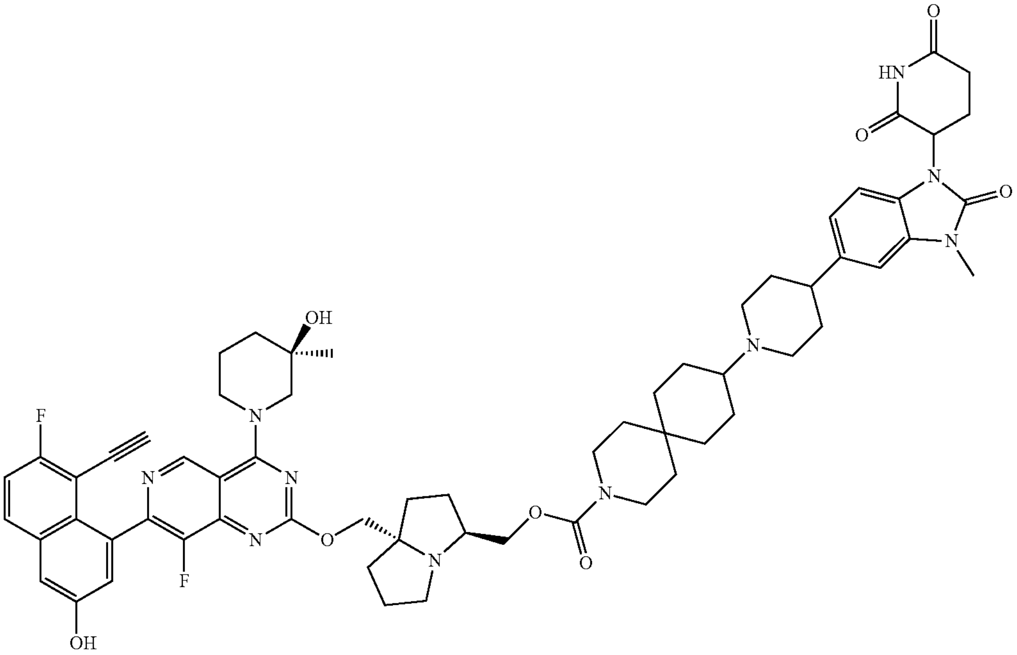 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CCC(N8CCC(c9ccc%10c(c9)n(C)c(=O)n%10C9CCC(=O)NC9=O)CC8)CC7)CC5)CC6)nc4c3F)c12] |

TABLE 3-continued
| Example Compounds of the Disclosure | |
|---|---|
| Compound No. | Compound Structure |
| 414 | 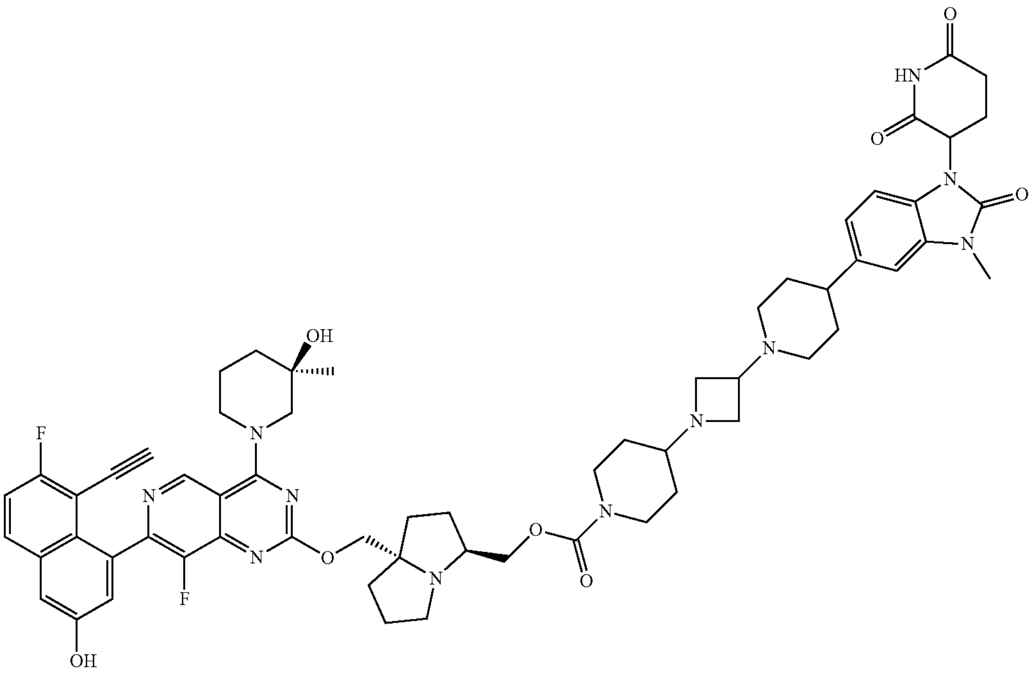 [SMILES: C#Cc1c(F)ccc2cc(O)cc(-c3ncc4c(N5CCC[C@@](C)(O)C5)nc(OC[C@@]56CCCN5[C@H](COC(=O)N5CCC(N7CC(N8CCC(c9ccc%10c(c9)n(C)c(=O)n%10C9CCC(=O)NC9=O)CC8)C7)CC5)CC6)nc4c3F)c12] |
| 415 | 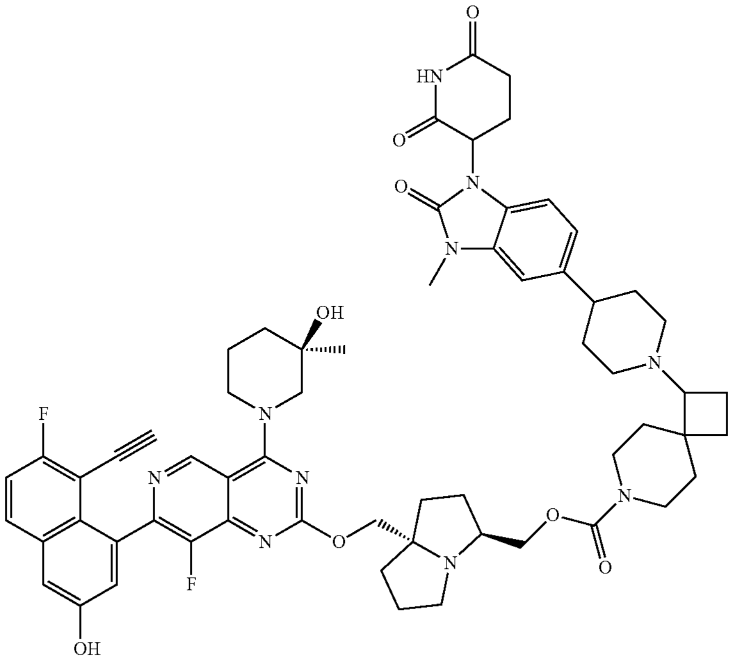 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CCC7N7CCC(c8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 416 | 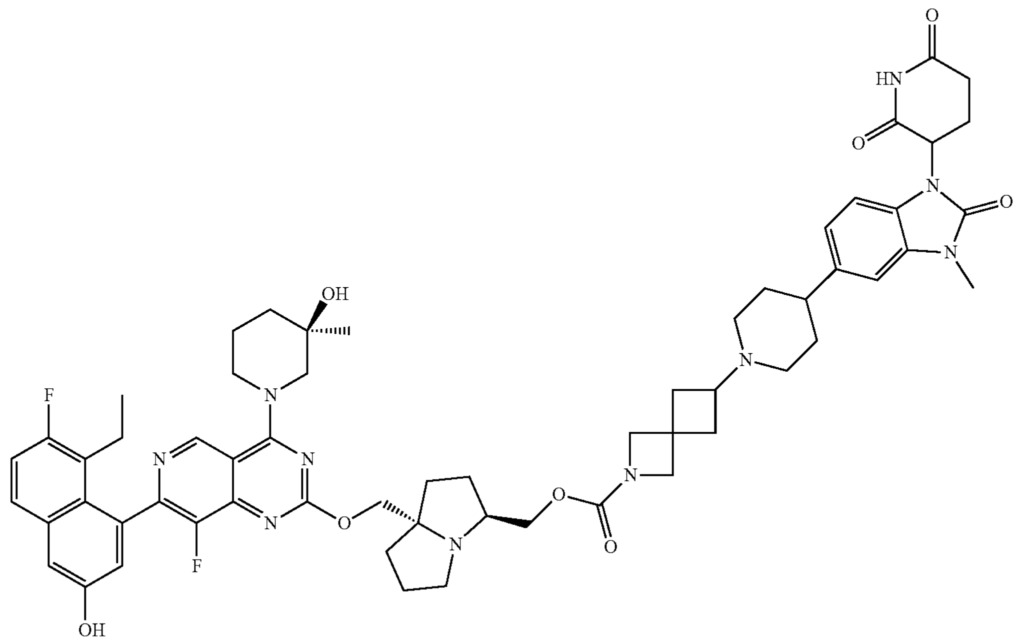 [SMILES: CCc1c(F)ccc2cc(O)cc(-c3ncc4c(N5CCC[C@@](C)(O)C5)nc(OC[C@@]56CCCN5[C@H](COC(=O)N5CC7(CC(N8CCC(c9ccc%10c(c9)n(C)c(=O)n%10C9CCC(=O)NC9=O)CC8)C7)C5)CC6)nc4c3F)c12] |
| 417 | 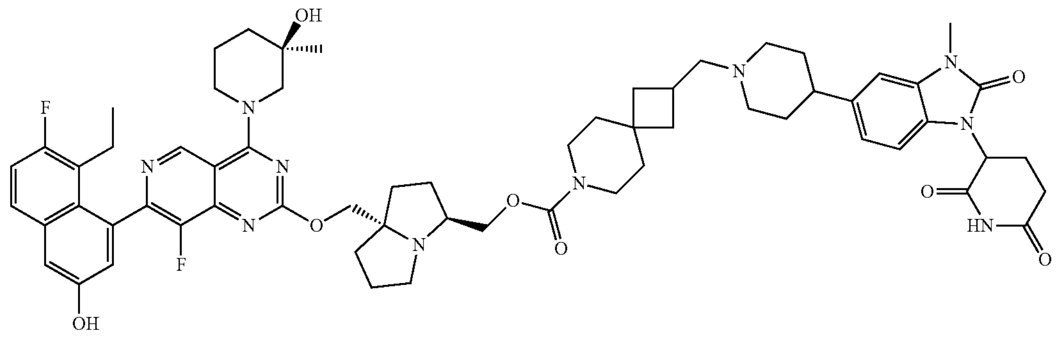 [SMILES: CCc1c(F)ccc2cc(O)cc(-c3ncc4c(N5CCC[C@@](C)(O)C5)nc(OC[C@@]56CCCN5[C@H](COC(=O)N5CCC7(CC5)CC(CN5CCC(c8ccc9c(c8)n(C)c(=O)n9C8CCC(=O)NC8=O)CC5)C7)CC6)nc4c3F)c12] |
| 418 | 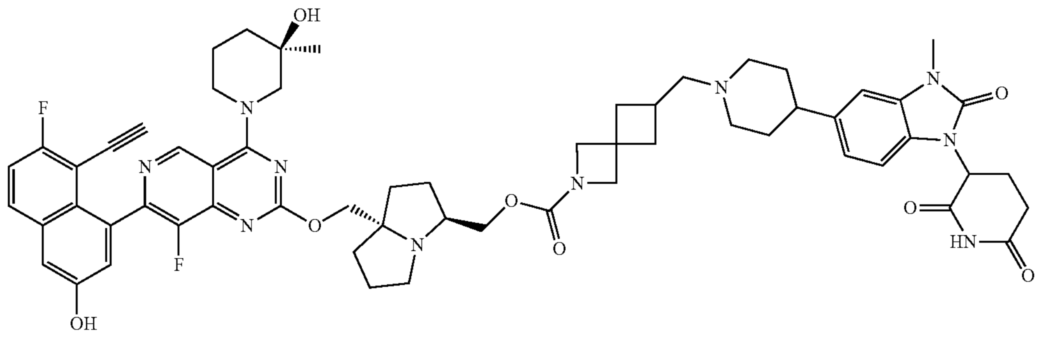 [SMILES: C#Cc1c(F)ccc2cc(O)cc(-c3ncc4c(N5CCC[C@@](C)(O)C5)nc(OC[C@@]56CCCN5[C@H](COC(=O)N5CC7(CC(CN8CCC(c9ccc%10c(c9)n(C)c(=O)n%10C9CCC(=O)NC9=O)CC8)C7)C5)CC6)nc4c3F)c12] |

TABLE 3-continued
| Example Compounds of the Disclosure | |
|---|---|
| Compound No. | Compound Structure |
| 419 | 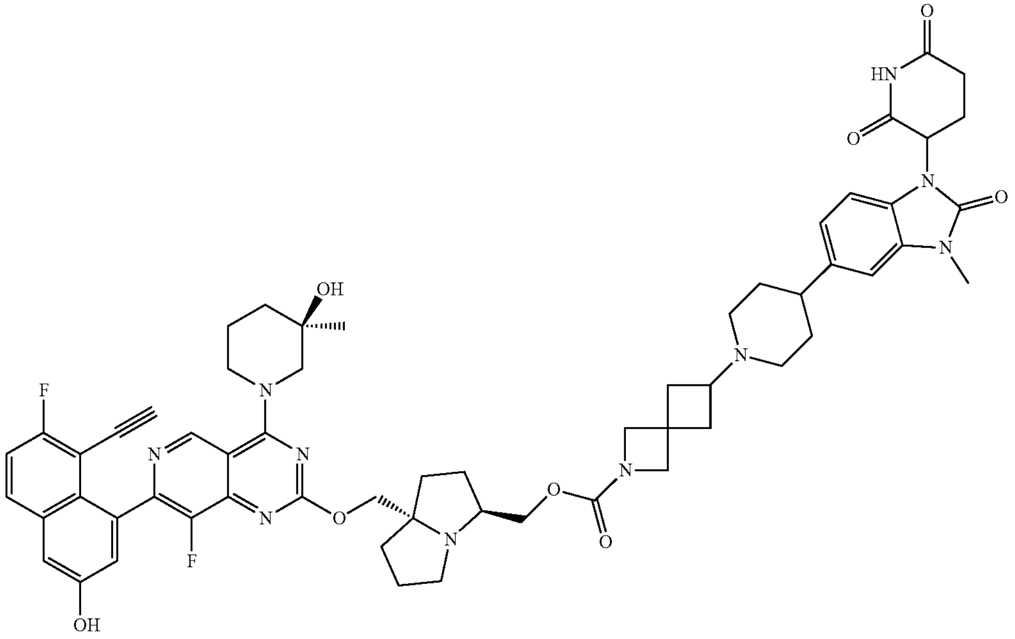 [SMILES: C#Cc1c(F)ccc2cc(O)cc(-c3ncc4c(N5CCC[C@@](C)(O)C5)nc(OC[C@@]56CCCN5[C@H](COC(=O)N5CC7(CC(N8CCC(c9ccc%10c(c9)n(C)c(=O)n%10C9CCC(=O)NC9=O)CC8)C7)C5)CC6)nc4c3F)c12] |
| 420 | 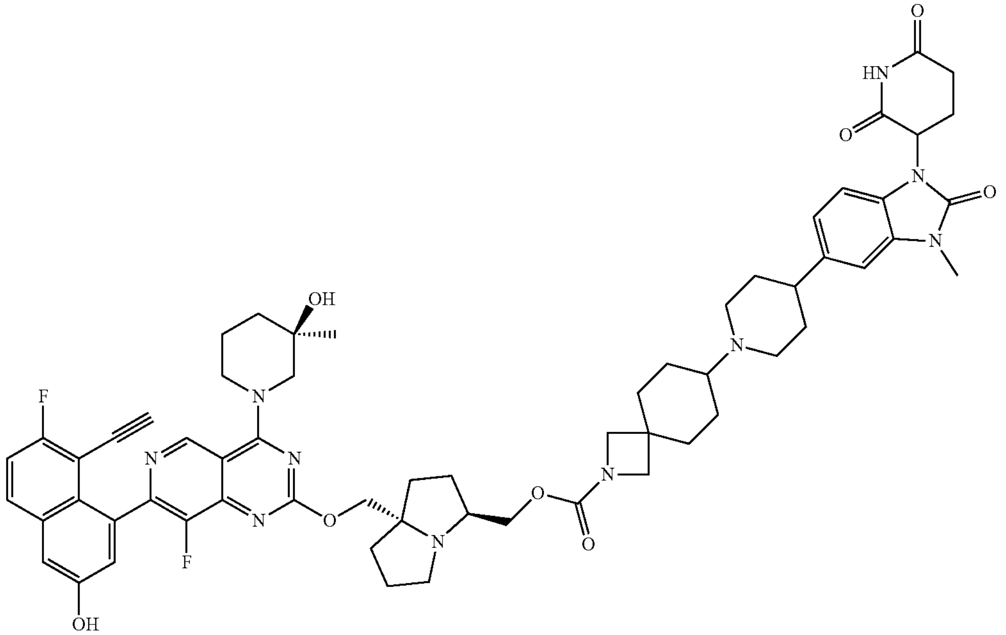 [SMILES: C#Cc1c(F)ccc2cc(O)cc(-c3ncc4c(N5CCC[C@@](C)(O)C5)nc(OC[C@@]56CCCN5[C@H](COC(=O)N5CC7(CCC(N8CCC(c9ccc%10c(c9)n(C)c(=O)n%10C9CCC(=O)NC9=O)CC8)CC7)C5)CC6)nc4c3F)c12] |

TABLE 3-continued
| Example Compounds of the Disclosure | |
|---|---|
| Compound No. | Compound Structure |
| 421 | 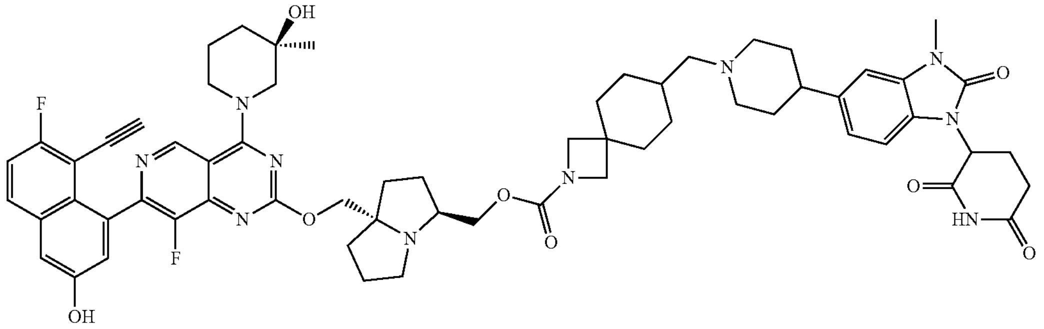 [SMILES: C#Cc1c(F)ccc2cc(O)cc(-c3ncc4c(N5CCC[C@@](C)(O)C5)nc(OC[C@@]56CCCN5[C@H](COC(=O)N5CC7(CCC(CN8CCC(c9ccc%10c(c9)n(C)c(=O)n%10C9CCC(=O)NC9=O)CC8)CC7)C5)CC6)nc4c3F)c12] |
| 422 | 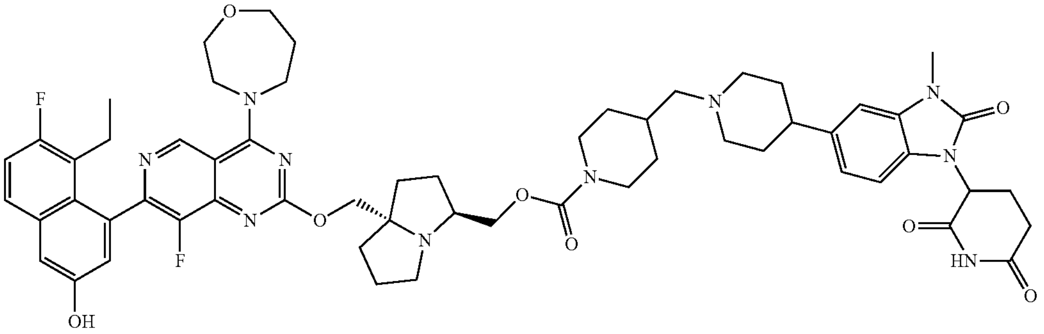 [SMILES: CCc1c(F)ccc2cc(O)cc(-c3ncc4c(N5CCCOCC5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 423 | 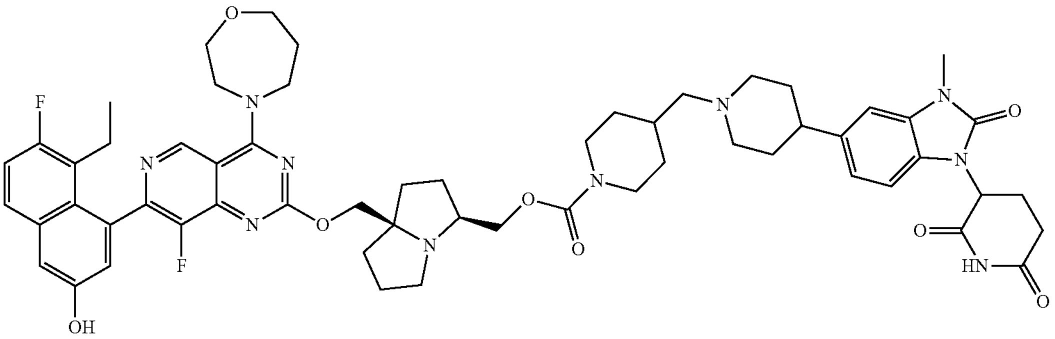 [SMILES: CCc1c(F)ccc2cc(O)cc(-c3ncc4c(N5CCCOCC5)nc(OC[C@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 424 | 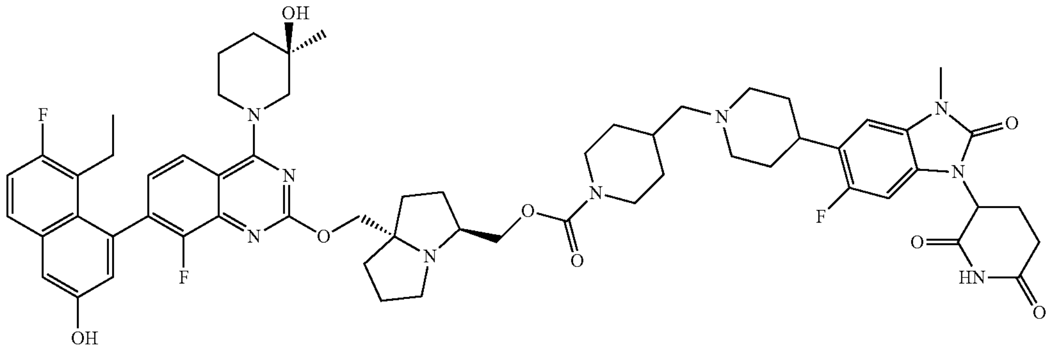 [SMILES: CCc1c(F)ccc2cc(O)cc(-c3ccc4c(N5CCC[C@@](C)(O)C5)nc(OC[C@@]56CCCN5[C@H](COC(=O)N5CCC(CN7CCC(c8cc9c(cc8F)n(C8CCC(=O)NC8=O)c(=O)n9C)CC7)CC5)CC6)nc4c3F)c12] |

TABLE 3-continued
| Example Compounds of the Disclosure | |
|---|---|
| Compound No. | Compound Structure |
| 425 | 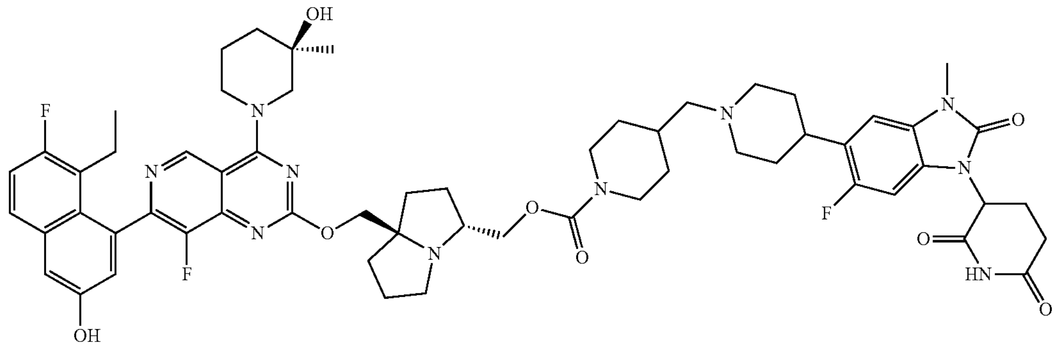 [SMILES: CCc1c(F)ccc2cc(O)cc(-c3ncc4c(N5CCC[C@@](C)(O)C5)nc(OC[C@]56CCCN5[C@@H](COC(=O)N5CCC(CN7CCC(c8cc9c(cc8F)n(C8CCC(=O)NC8=O)c(=O)n9C)CC7)CC5)CC6)nc4c3F)c12] |
| 426 | 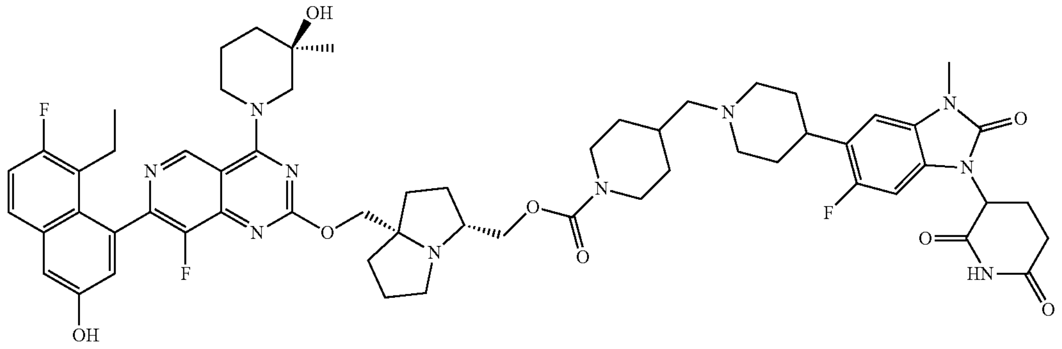 [SMILES: CCc1c(F)ccc2cc(O)cc(-c3ncc4c(N5CCC[C@@](C)(O)C5)nc(OC[C@@]56CCCN5[C@@H](COC(=O)N5CCC(CN7CCC(c8cc9c(cc8F)n(C8CCC(=O)NC8=O)c(=O)n9C)CC7)CC5)CC6)nc4c3F)c12] |
| 427 | 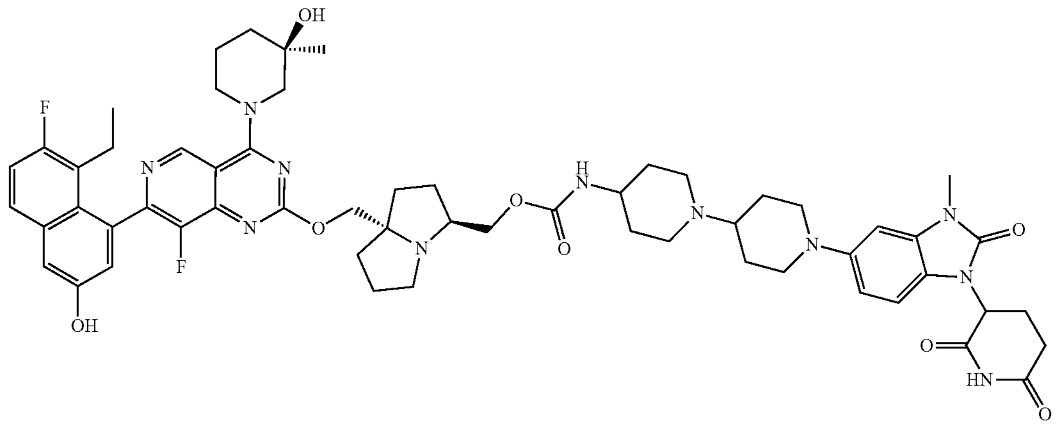 [SMILES: CCc1c(F)ccc2cc(O)cc(-c3ncc4c(N5CCC[C@@](C)(O)C5)nc(OC[C@@]56CCCN5[C@H](COC(=O)NC5CCN(C7CCN(c8ccc9c(c8)n(C)c(=O)n9C8CCC(=O)NC8=O)CC7)CC5)CC6)nc4c3F)c12] |

TABLE 3-continued
Example Compounds of the Disclosure
| Compound No. | Compound Structure |
| --- | --- |
| 428 | 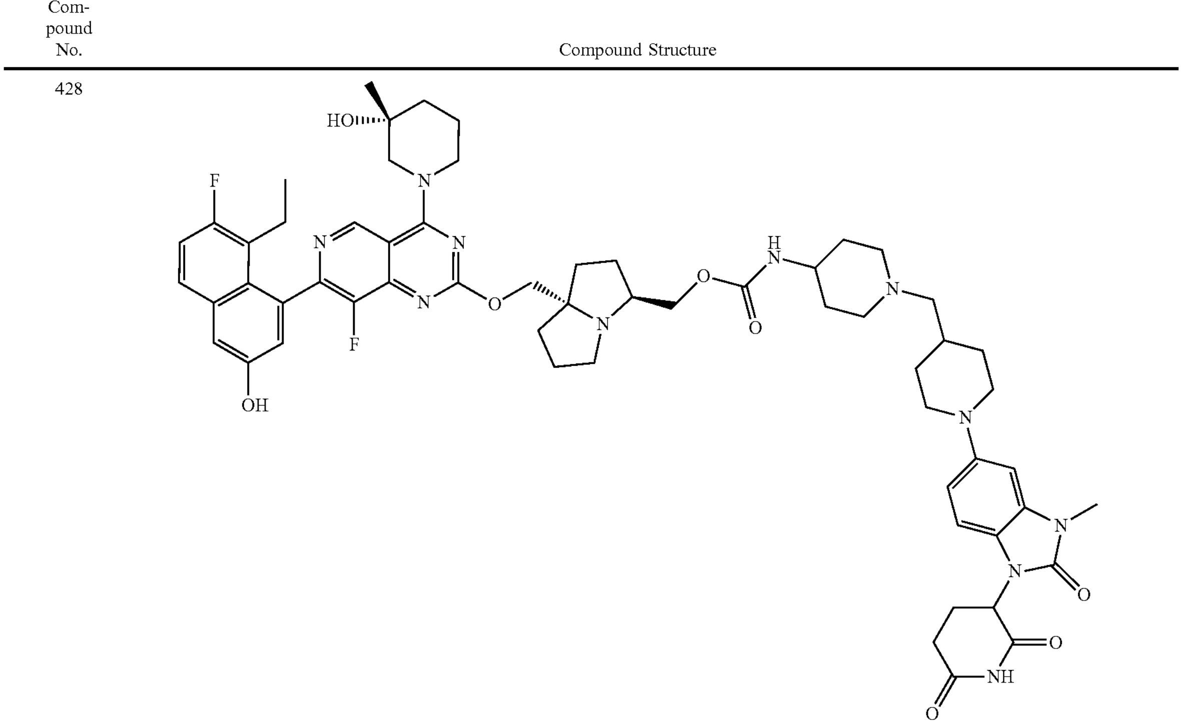 |
| 429 | 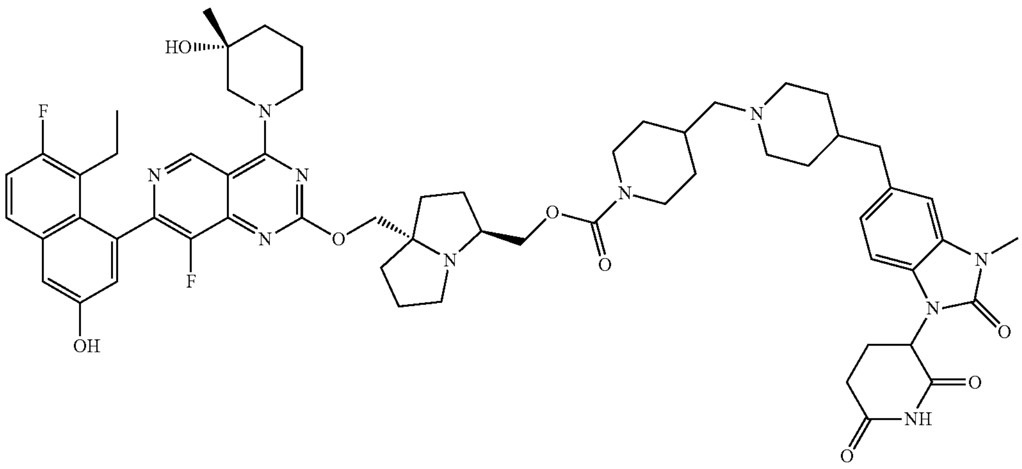 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(Cc8ccc9c(c8)n(C)c(=O)n9C8CCC(=O)NC8=O)CC7)CC5)CC6)nc4c3F)c12] |
| 430 | 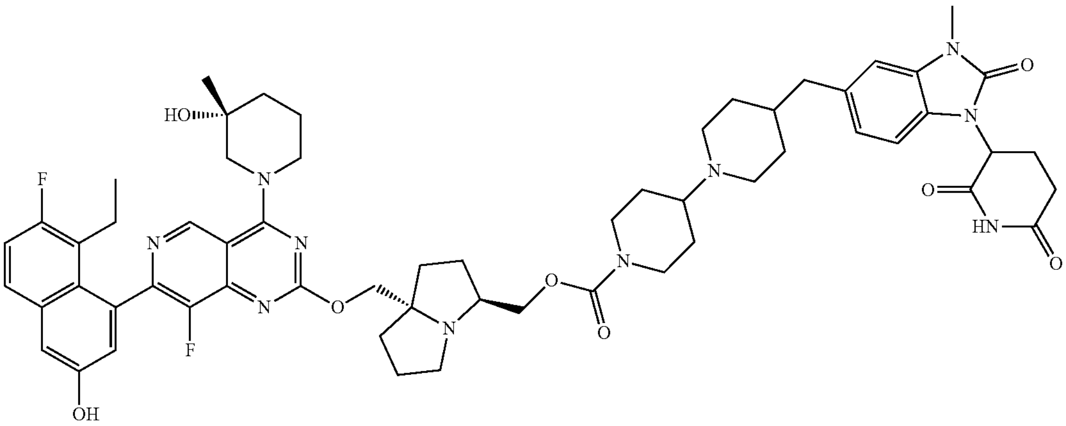 [SMILES: CCc1c(F)ccc2cc(O)cc(-c3ncc4c(N5CCC[C@@](C)(O)C5)nc(OC[C@@]56CCCN5[C@H](COC(=O)N5CCC(N7CCC(Cc8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 431 | 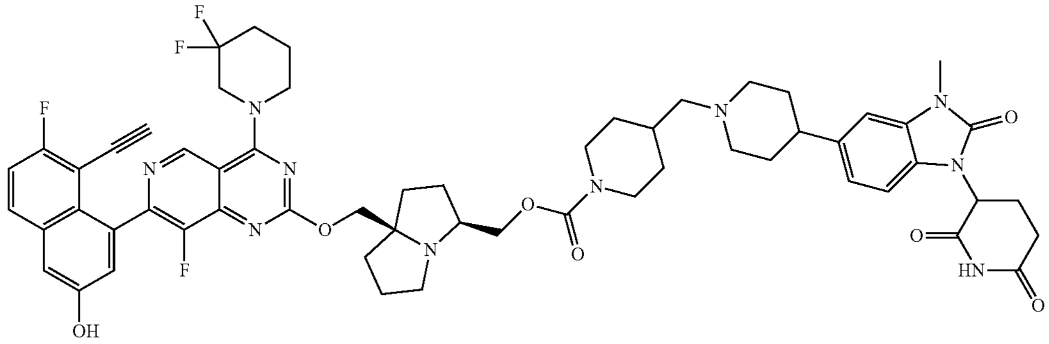 [SMILES: C#Cc1c(F)ccc2cc(O)cc(-c3ncc4c(N5CCCC(F)(F)C5)nc(OC[C@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 433 | 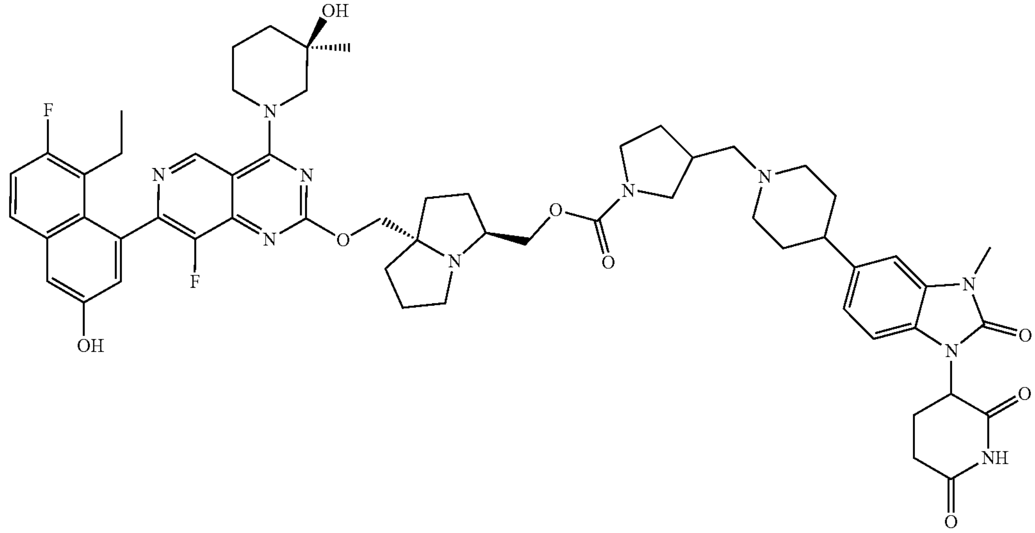 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)C5)CC6)nc4c3F)c12] |
| 434 | 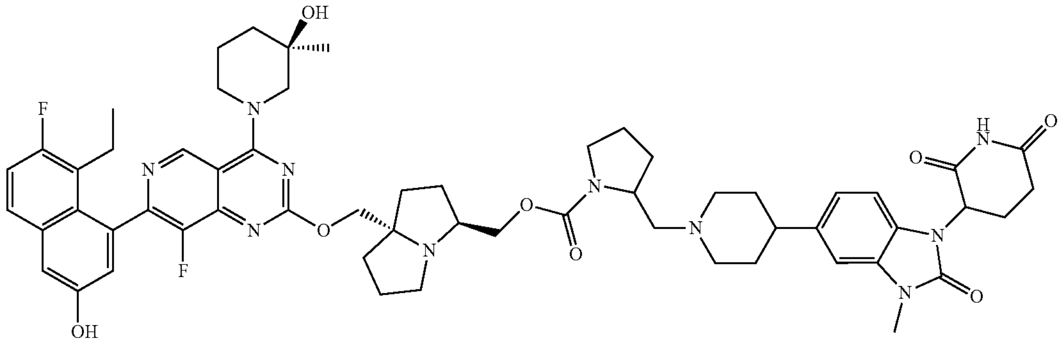 [SMILES: CCc1c(F)ccc2cc(O)cc(-c3ncc4c(N5CCC[C@@](C)(O)C5)nc(OC[C@@]56CCCN5[C@H](COC(=O)N5CCCC5CN5CCC(c7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 435 | 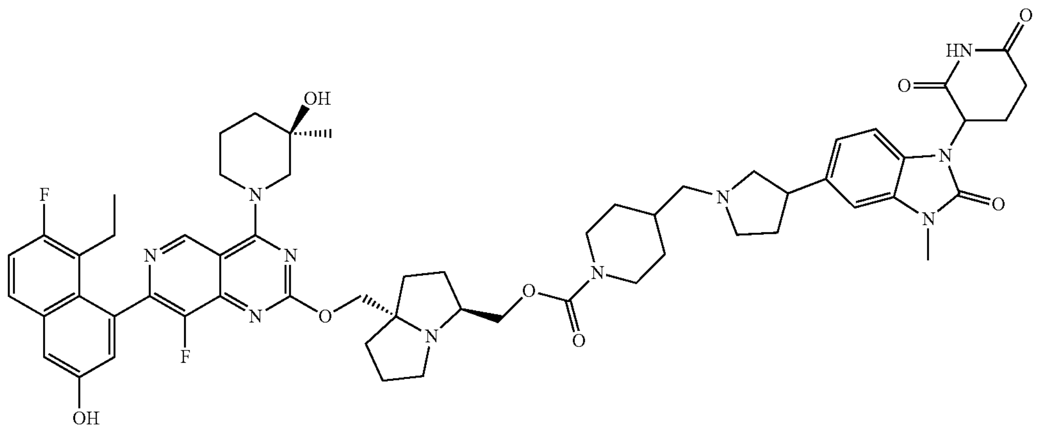 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)C7)CC5)CC6)nc4c3F)c12] |
| 436 | 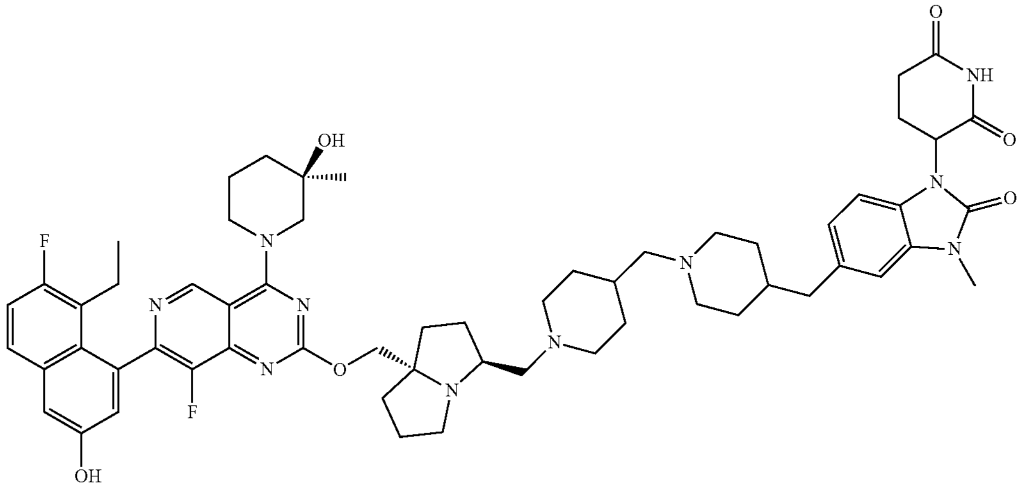 [SMILES: CCc1c(F)ccc2cc(O)cc(-c3ncc4c(N5CCC[C@@](C)(O)C5)nc(OC[C@@]56CCCN5[C@H](CN5CCC(CN7CCC(Cc8ccc9c(c8)n(C)c(=O)n9C8CCC(=O)NC8=O)CC7)CC5)CC6)nc4c3F)c12] |
| 437 | 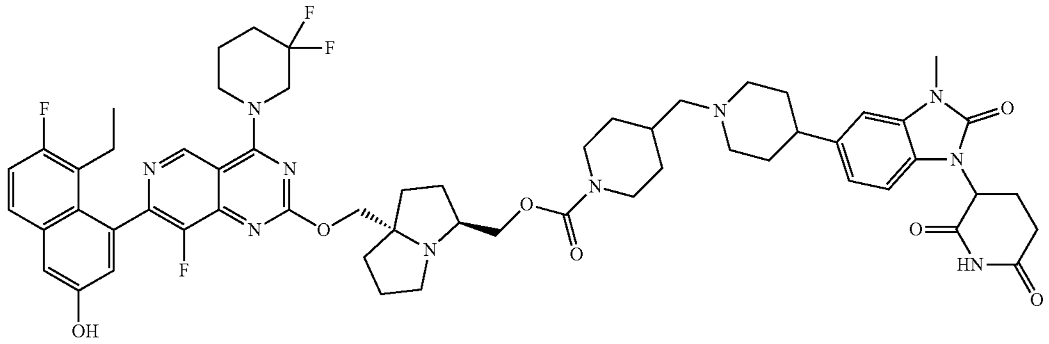 [SMILES: CCc1c(F)ccc2cc(O)cc(-c3ncc4c(N5CCCC(F)(F)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 438 | 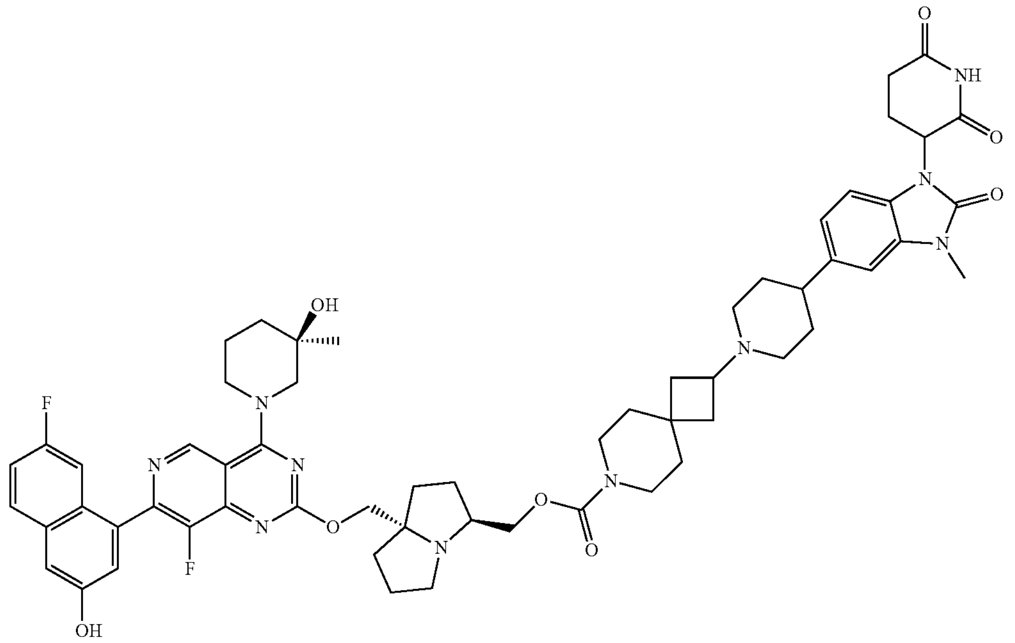 [SMILES: Cn1c(=O)n(C2CCC(=O)NC2=O)c2ccc(C3CCN(C4CC5(CCN(C(=O)OC[C@@H]6CC[C@]7(COc8nc(N9CCC[C@@](C)(O)C9)c9cnc(-c%10cc(O)cc%11ccc(F)cc%10%11)c(F)c9n8)CCCN67)CC5)C4)CC3)cc21] |
| 439 | 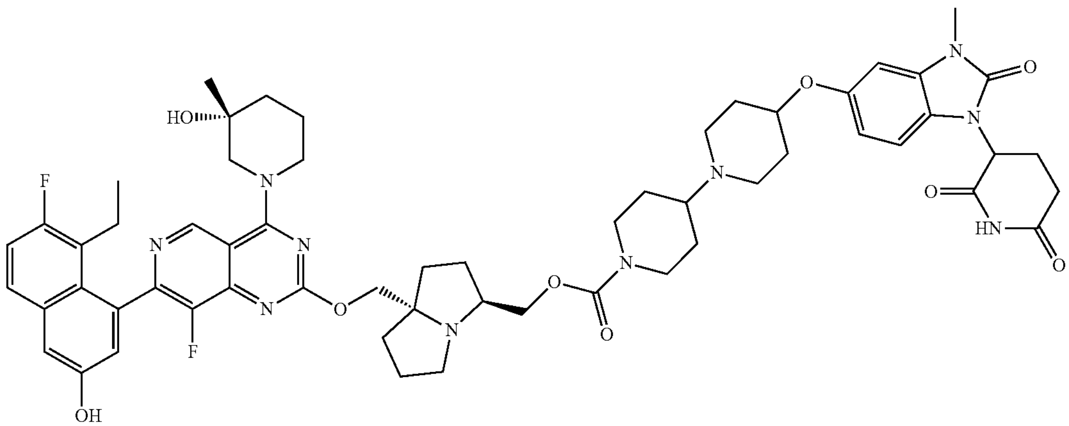 [SMILES: CCc1c(F)ccc2cc(O)cc(-c3ncc4c(N5CCC[C@@](C)(O)C5)nc(OC[C@@]56CCCN5[C@H](COC(=O)N5CCC(N7CCC(Oc8ccc9c(c8)n(C)c(=O)n9C8CCC(=O)NC8=O)CC7)CC5)CC6)nc4c3F)c12] |
| 440 | 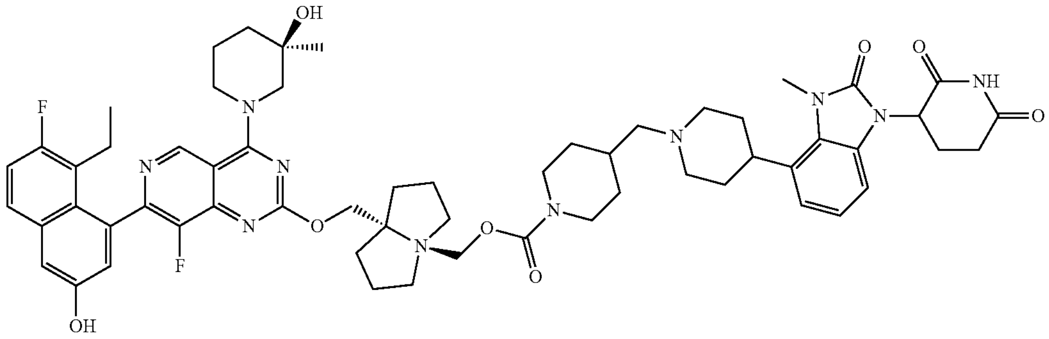 |

TABLE 3-continued
| Example Compounds of the Disclosure | |
|---|---|
| Compound No. | Compound Structure |
| 441 | 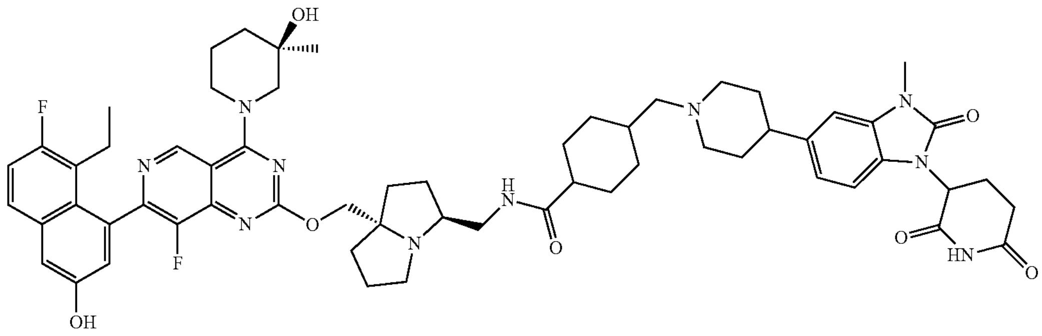 [SMILES: CCc1c(F)ccc2cc(O)cc(-c3ncc4c(N5CCC[C@@](C)(O)C5)nc(OC[C@@]56CCCN5[C@H](CNC(=O)C5CCC(CN7CCC(c8ccc9c(c8)n(C)c(=O)n9C8CCC(=O)NC8=O)CC7)CC5)CC6)nc4c3F)c12] |
| 442 | 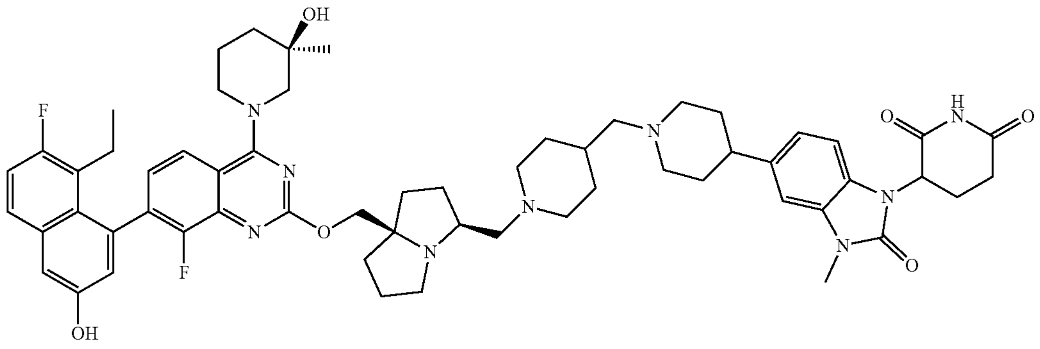 [SMILES: CCc1c(F)ccc2cc(O)cc(-c3ccc4c(N5CCC[C@@](C)(O)C5)nc(OC[C@]56CCCN5[C@H](CN5CCC(CN7CCC(c8ccc9c(c8)n(C)c(=O)n9C8CCC(=O)NC8=O)CC7)CC5)CC6)nc4c3F)c12] |
| 443 | 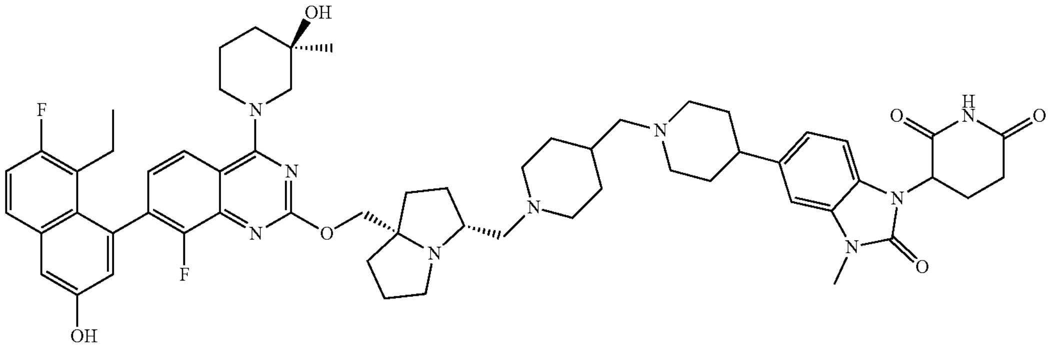 [SMILES: CCc1c(F)ccc2cc(O)cc(-c3ccc4c(N5CCC[C@@](C)(O)C5)nc(OC[C@@]56CCCN5[C@@H](CN5CCC(CN7CCC(c8ccc9c(c8)n(C)c(=O)n9C8CCC(=O)NC8=O)CC7)CC5)CC6)nc4c3F)c12] |

TABLE 3-continued
| Example Compounds of the Disclosure | |
|---|---|
| Compound No. | Compound Structure |
| 444 | 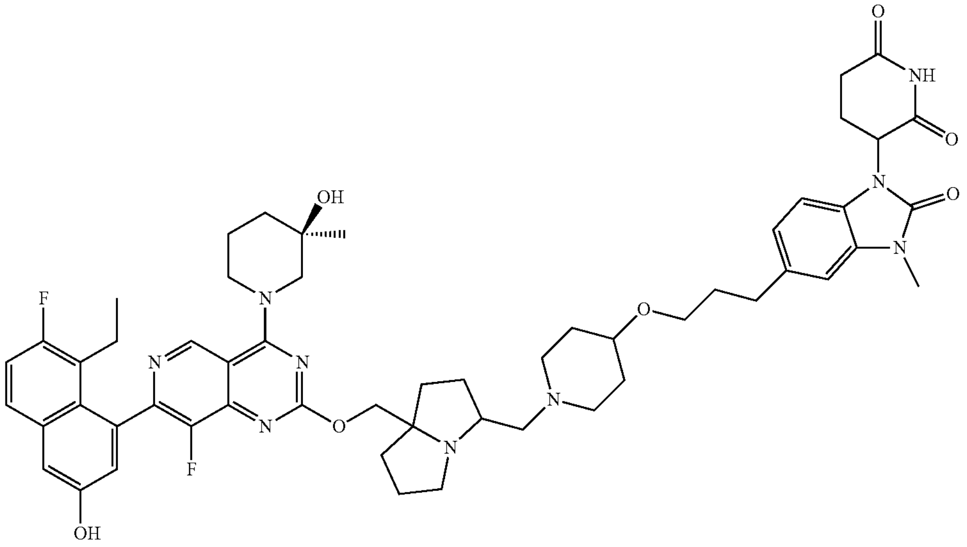 [SMILES: CCc1c(F)ccc2cc(O)cc(-c3ncc4c(N5CCC[C@@](C)(O)C5)nc(OCC56CCCN5C(CN5CCC(OCCCc7ccc8c(c7)n(C)c(=O)n8C7CCC(=O)NC7=O)CC5)CC6)nc4c3F)c12] |
| 445 | 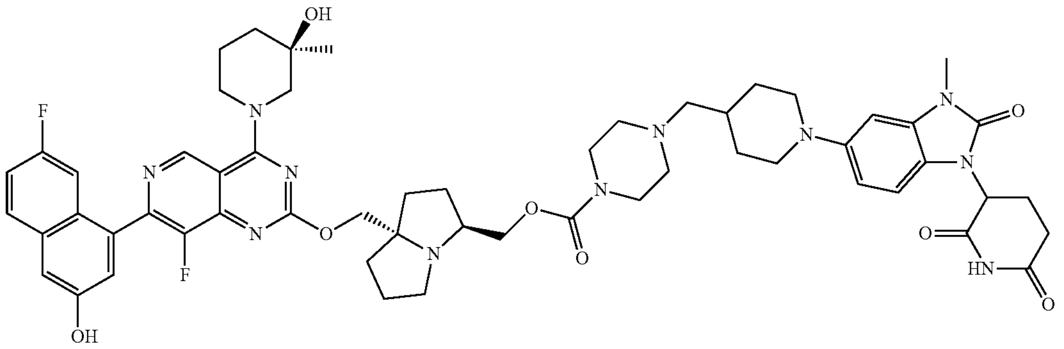 [SMILES: Cn1c(=O)n(C2CCC(=O)NC2=O)c2ccc(N3CCC(CN4CCN(C(=O)OC[C@@H]5CC[C@]6(COc7nc(N8CCC[C@@](C)(O)C8)c8cnc(-c9cc(O)cc%10ccc(F)cc9%10)c(F)c8n7)CCCN56)CC4)CC3)cc21] |
| 446 | 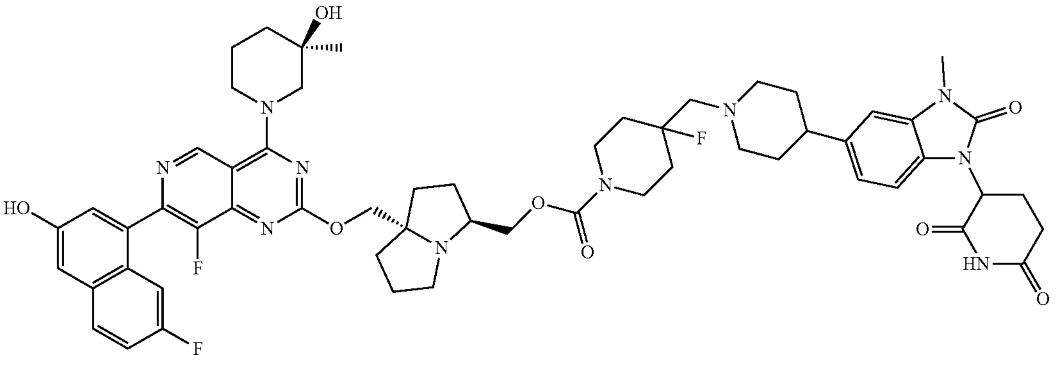 [SMILES: Cn1c(=O)n(C2CCC(=O)NC2=O)c2ccc(C3CCN(CC4(F)CCN(C(=O)OC[C@@H]5CC[C@]6(COc7nc(N8CCC[C@@](C)(O)C8)c8cnc(-c9cc(O)cc%10ccc(F)cc9%10)c(F)c8n7)CCCN56)CC4)CC3)cc21] |

TABLE 3-continued
| Example Compounds of the Disclosure | |
|---|---|
| Compound No. | Compound Structure |
| 447 | 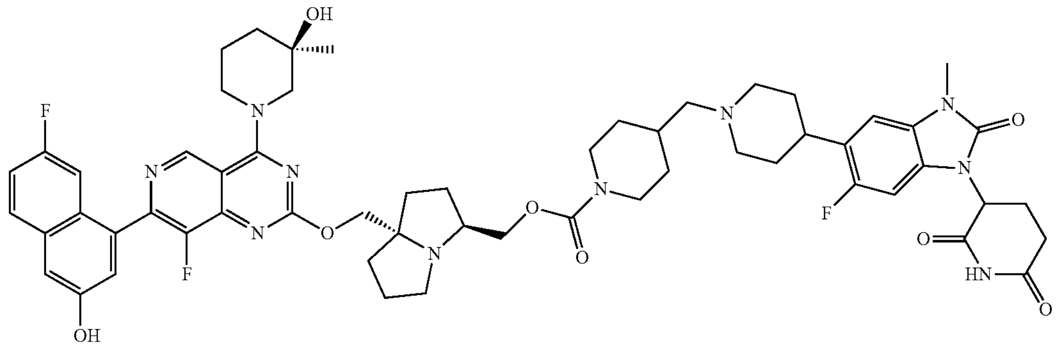 [SMILES: Cn1c(=O)n(C2CCC(=O)NC2=O)c2cc(F)c(C3CCN(CC4CCN(C(=O)OC[C@@H]5CC[C@]6(COc7nc(N8CCC[C@@](C)(O)C8)c8cnc(-c9cc(O)cc%10ccc(F)cc9%10)c(F)c8n7)CCCN56)CC4)CC3)cc21] |
| 448 | 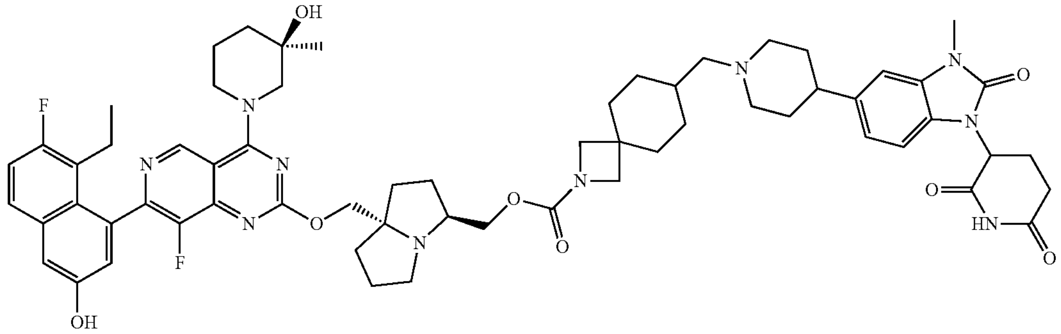 [SMILES: CCc1c(F)ccc2cc(O)cc(-c3ncc4c(N5CCC[C@@](C)(O)C5)nc(OC[C@@]56CCCN5[C@H](COC(=O)N5CC7(CCC(CN8CCC(c9ccc%10c(c9)n(C)c(=O)n%10C9CCC(=O)NC9=O)CC8)CC7)C5)CC6)nc4c3F)c12] |
| 449 | 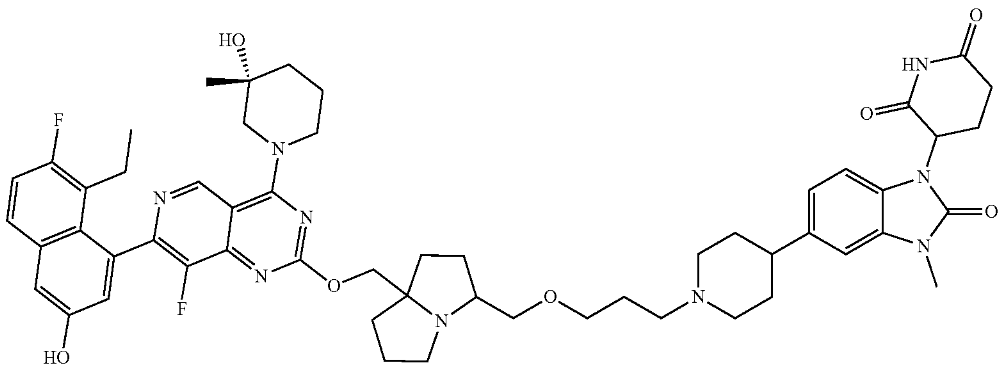 |

TABLE 3-continued
| Example Compounds of the Disclosure | |
|---|---|
| Compound No. | Compound Structure |
| 450 | 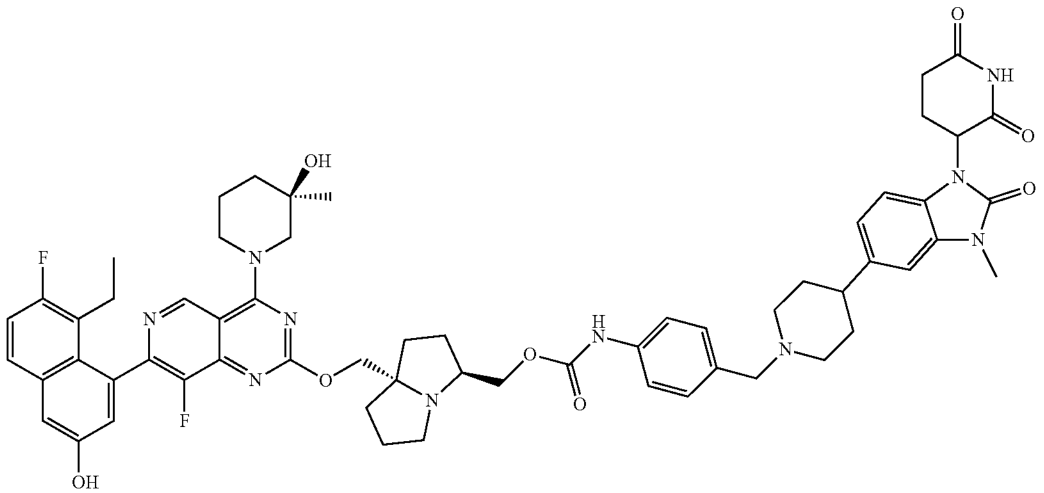 [SMILES: CCc1c(F)ccc2cc(O)cc(-c3ncc4c(N5CCC[C@@](C)(O)C5)nc(OC[C@@]56CCCN5[C@H](COC(=O)Nc5ccc(CN7CCC(c8ccc9c(c8)n(C)c(=O)n9C8CCC(=O)NC8=O)CC7)cc5)CC6)nc4c3F)c12] |
| 451 | 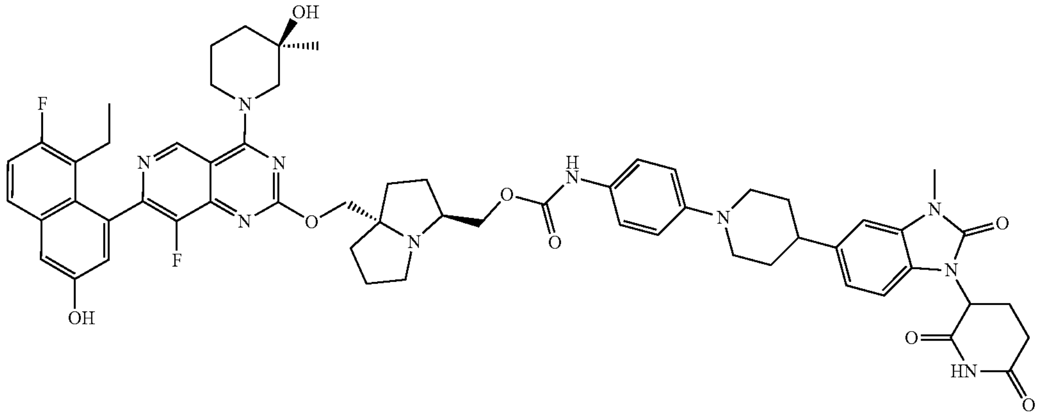 [SMILES: CCc1c(F)ccc2cc(O)cc(-c3ncc4c(N5CCC[C@@](C)(O)C5)nc(OC[C@@]56CCCN5[C@H](COC(=O)Nc5ccc(N7CCC(c8ccc9c(c8)n(C)c(=O)n9C8CCC(=O)NC8=O)CC7)cc5)CC6)nc4c3F)c12] |
| 452 | 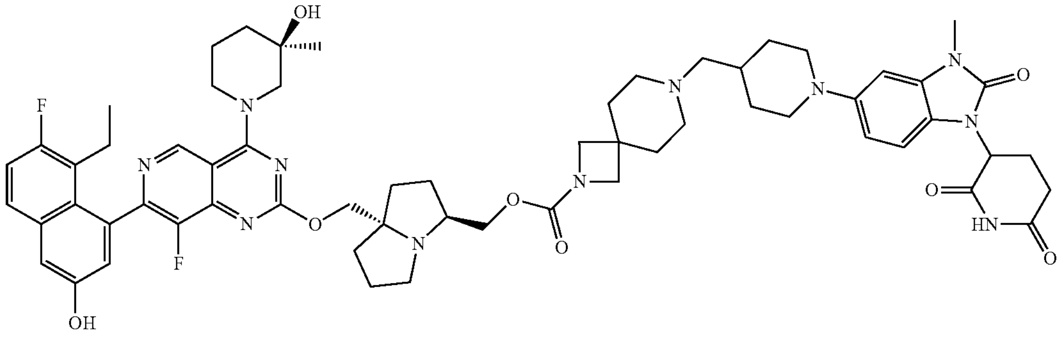 [SMILES: CCc1c(F)ccc2cc(O)cc(-c3ncc4c(N5CCC[C@@](C)(O)C5)nc(OC[C@@]56CCCN5[C@H](COC(=O)N5CC7(CCN(CC8CCN(c9ccc%10c(c9)n(C)c(=O)n%10C9CCC(=O)NC9=O)CC8)CC7)C5)CC6)nc4c3F)c12] |

TABLE 3-continued
| Example Compounds of the Disclosure | |
|---|---|
| Compound No. | Compound Structure |
| 453 | 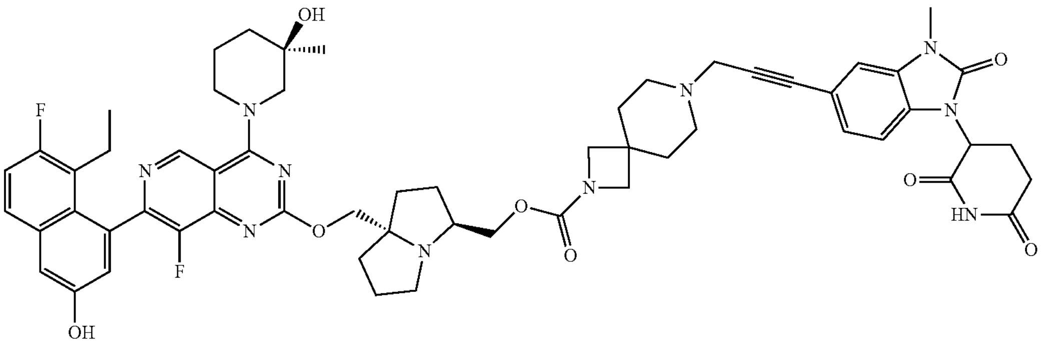 [SMILES: CCc1c(F)ccc2cc(O)cc(-c3ncc4c(N5CCC[C@@](C)(O)C5)nc(OC[C@@]56CCCN5[C@H](COC(=O)N5CC7(CCN(CC#Cc8ccc9c(c8)n(C)c(=O)n9C8CCC(=O)NC8=O)CC7)C5)CC6)nc4c3F)c12] |
| 454 | 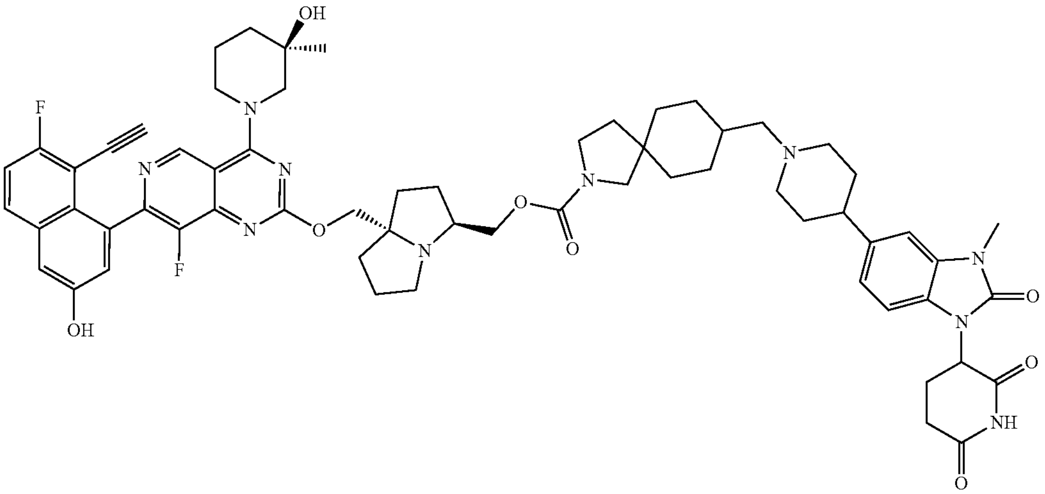 [SMILES: C#Cc1c(F)ccc2cc(O)cc(-c3ncc4c(N5CCC[C@@](C)(O)C5)nc(OC[C@@]56CCCN5[C@H](COC(=O)N5CCC7(CCC(CN8CCC(c9ccc%10c(c9)n(C)c(=O)n%10C9CCC(=O)NC9=O)CC8)CC7)C5)CC6)nc4c3F)c12] |
| 455 | 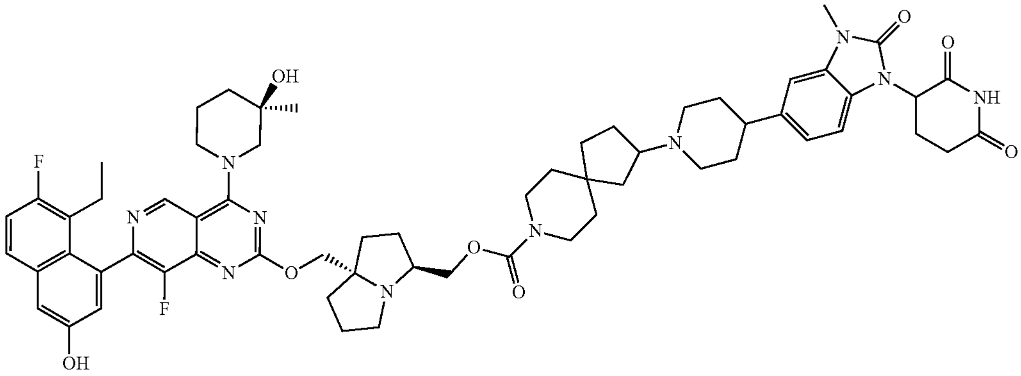 [SMILES: CCc1c(F)ccc2cc(O)cc(-c3ncc4c(N5CCC[C@@](C)(O)C5)nc(OC[C@@]56CCCN5[C@H](COC(=O)N5CCC7(CC5)CCN(C5CCN(c8ccc9c(c8)n(C)c(=O)n9C8CCC(=O)NC8=O)CC5)C7)CC6)nc4c3F)c12] |

TABLE 3-continued
| Com-pound No. | Compound Structure |
|---|---|
| 456 | 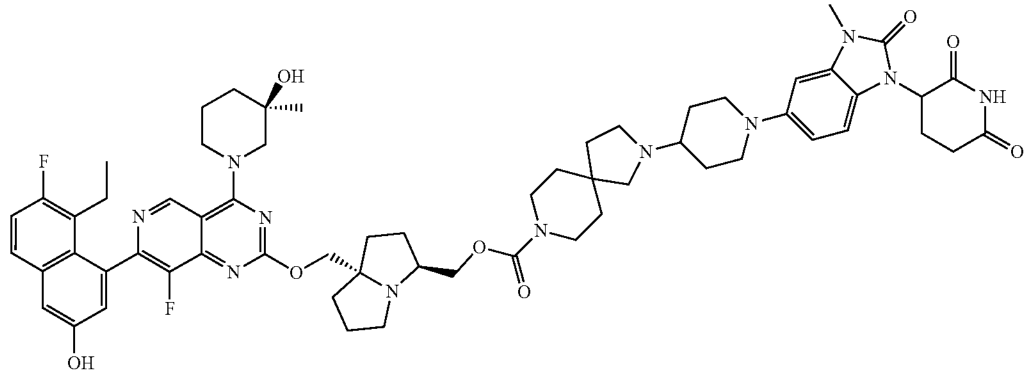 |
| 457 | 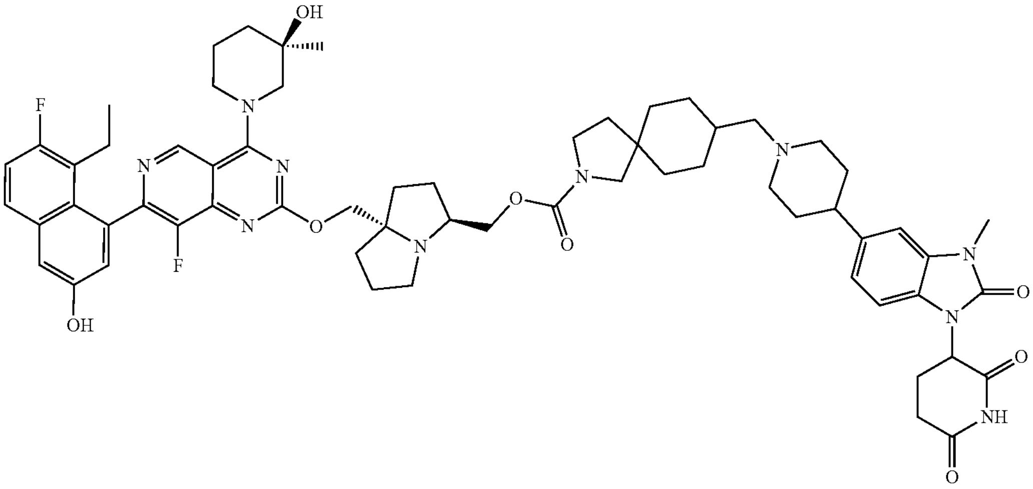 [SMILES: CCc1c(F)ccc2cc(O)cc(-c3ncc4c(N5CCC[C@@](C)(O)C5)nc(OC[C@@]56CCCN5[C@H](COC(=O)N5CCC7(CCC(CN8CCC(c9ccc%10c(c9)n(C)c(=O)n%10C9CCC(=O)NC9=O)CC8)CC7)C5)CC6)nc4c3F)c12] |
| 458 | 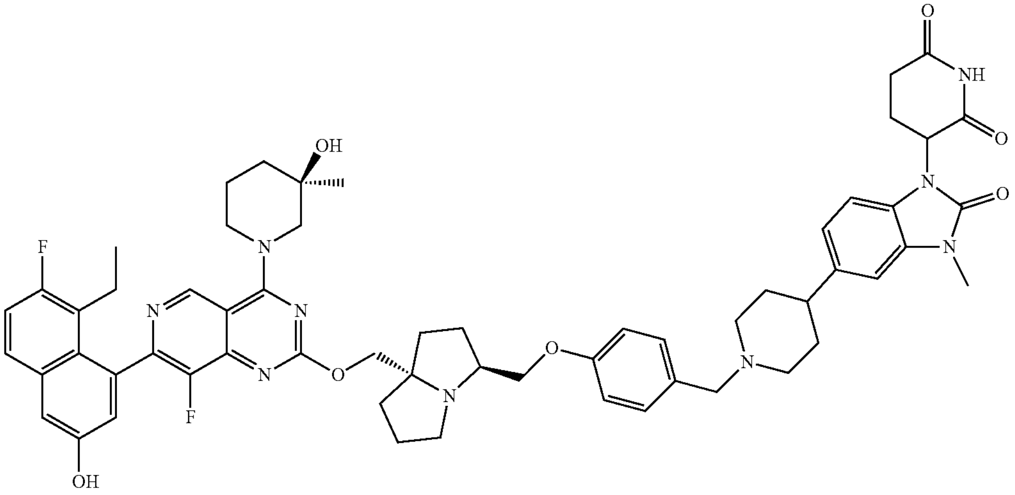 [SMILES: CCc1c(F)ccc2cc(O)cc(-c3ncc4c(N5CCC[C@@](C)(O)C5)nc(OC[C@@]56CCCN5[C@H](COc5ccc(CN7CCC(c8ccc9c(c8)n(C)c(=O)n9C8CCC(=O)NC8=O)CC7)cc5)CC6)nc4c3F)c12] |

TABLE 3-continued
| Example Compounds of the Disclosure | |
|---|---|
| Compound No. | Compound Structure |
| 461 | 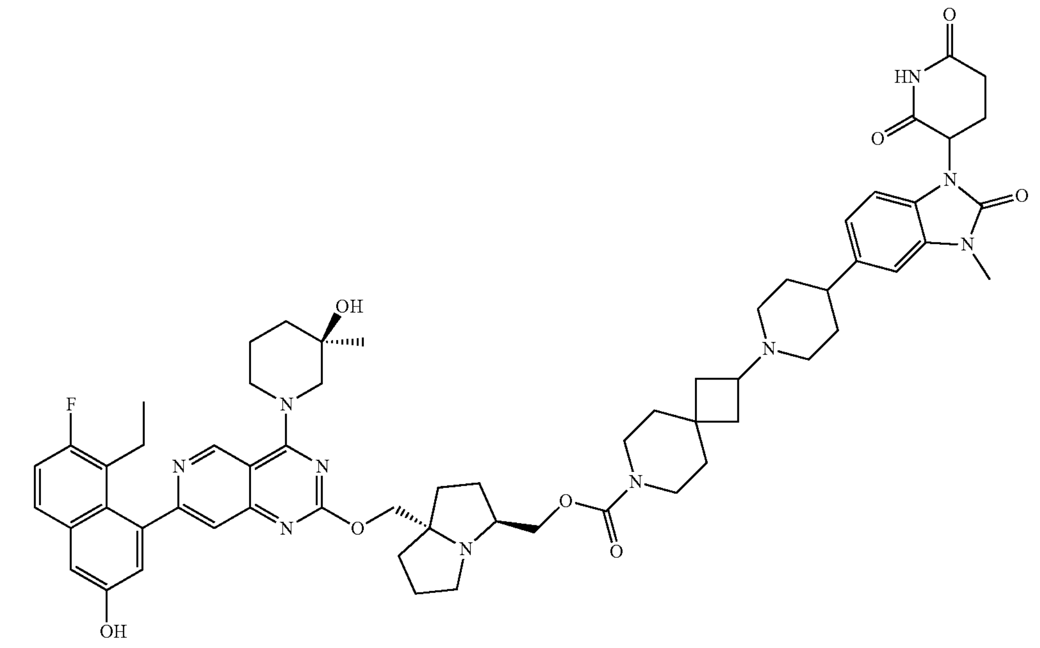 [SMILES: CCc1c(F)ccc2cc(O)cc(-c3cc4nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc(N5CCC[C@@](C)(O)C5)c4cn3)c12] |
| 462 | 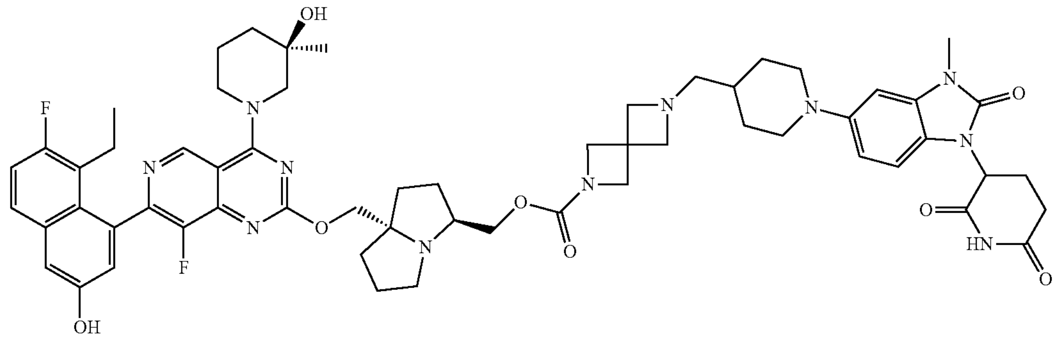 [SMILES: CCc1c(F)ccc2cc(O)cc(-c3ncc4c(N5CCC[C@@](C)(O)C5)nc(OC[C@@]56CCCN5[C@H](COC(=O)N5CC7(CN(CC8CCN(c9ccc%10c(c9)n(C)c(=O)n%10C9CCC(=O)NC9=O)CC8)C7)C5)CC6)nc4c3F)c12] |

TABLE 3-continued
| Example Compounds of the Disclosure | |
|---|---|
| Compound No. | Compound Structure |
| 463 | 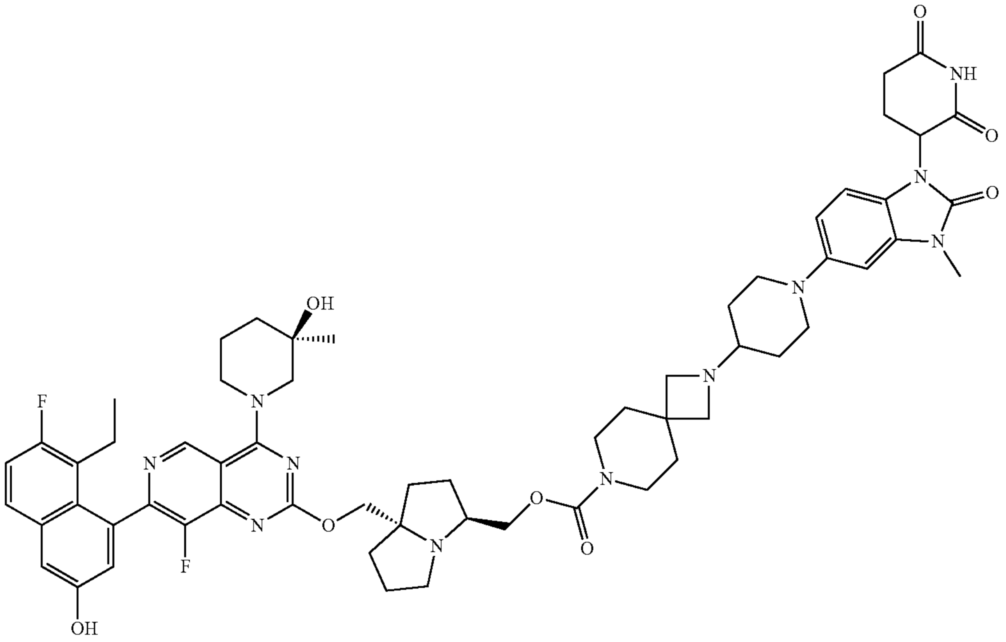 [SMILES: CCc1c(F)ccc2cc(O)cc(-c3ncc4c(N5CCC[C@@](C)(O)C5)nc(OC[C@@]56CCCN5[C@H](COC(=O)N5CCC7(CC5)CN(C5CCN(c8ccc9c(c8)n(C)c(=O)n9C8CCC(=O)NC8=O)CC5)C7)CC6)nc4c3F)c12] |
| 464 | 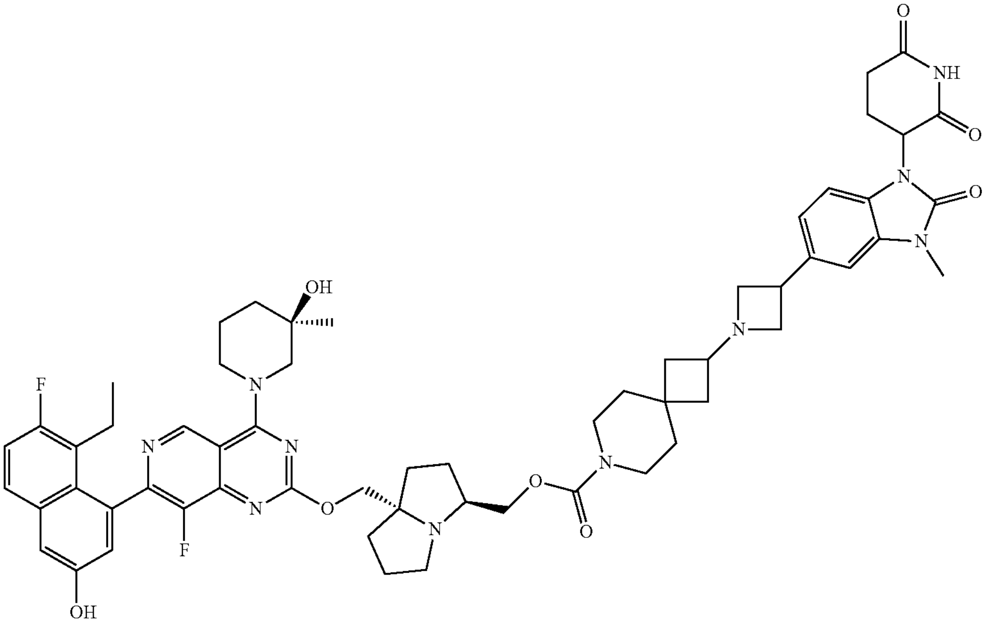 [SMILES: CCc1c(F)ccc2cc(O)cc(-c3ncc4c(N5CCC[C@@](C)(O)C5)nc(OC[C@@]56CCCN5[C@H](COC(=O)N5CCC7(CC5)CC(N5CC(c8ccc9c(c8)n(C)c(=O)n9C8CCC(=O)NC8=O)C5)C7)CC6)nc4c3F)c12] |

TABLE 3-continued
Example Compounds of the Disclosure
| Compound No. | Compound Structure |
|---|---|
| 465 | 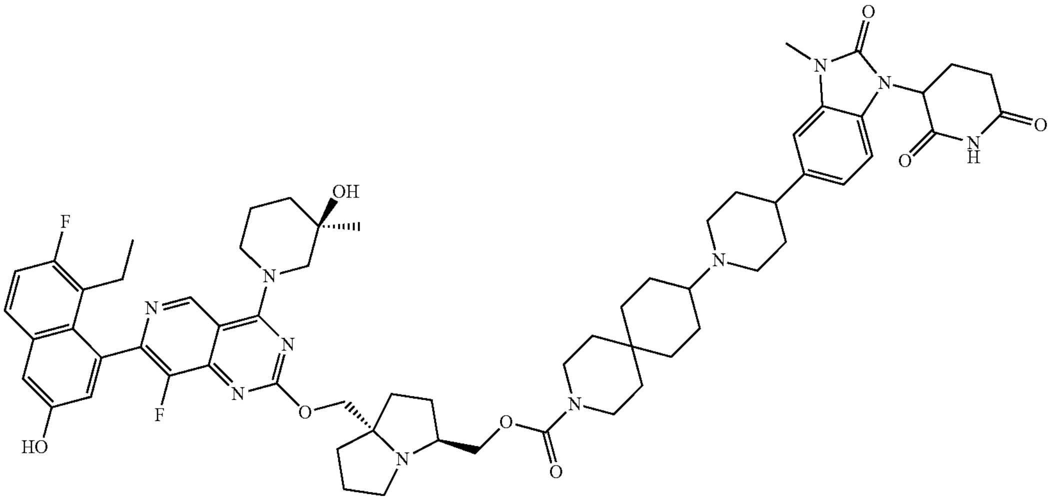 [SMILES: CCc1c(F)ccc2cc(O)cc(-c3ncc4c(N5CCC[C@@](C)(O)C5)nc(OC[C@@]56CCCN5[C@H](COC(=O)N5CCC7(CCC(N8CCC(c9ccc%10c(c9)n(C)c(=O)n%10C9CCC(=O)NC9=O)CC8)CC7)CC5)CC6)nc4c3F)c12] |
| 466 | 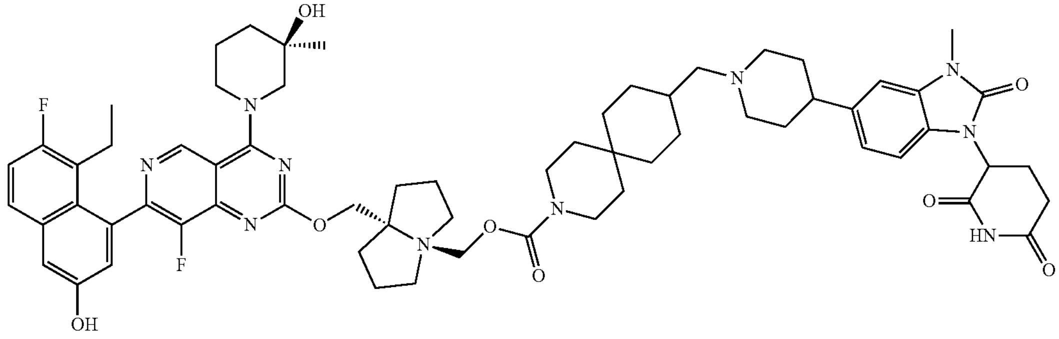 |
| 467 | 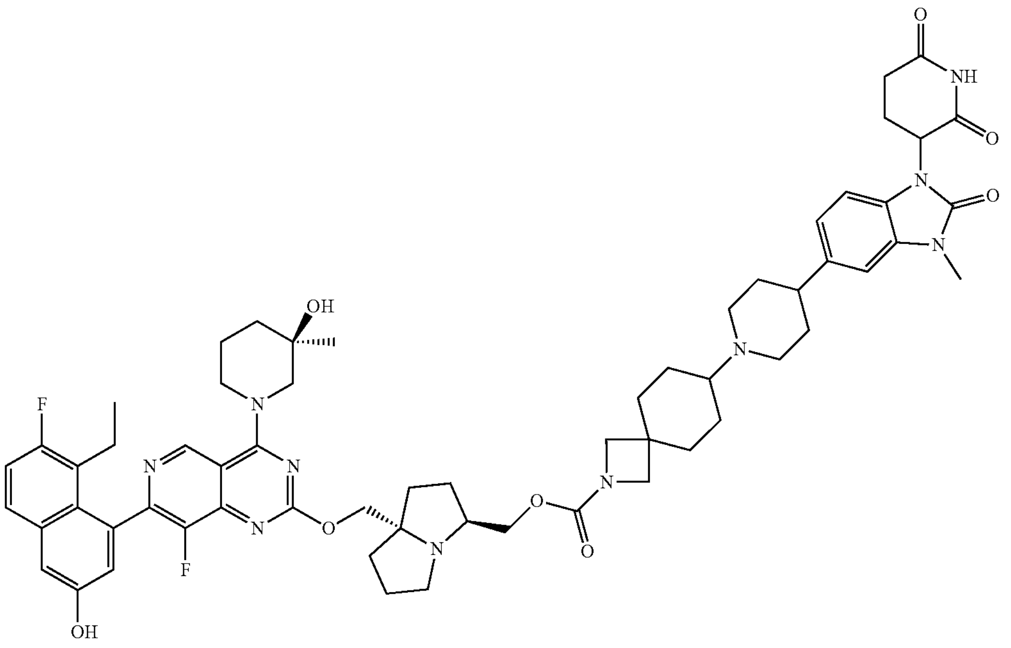 [SMILES: CCc1c(F)ccc2cc(O)cc(-c3ncc4c(N5CCC[C@@](C)(O)C5)nc(OC[C@@]56CCCN5[C@H](COC(=O)N5CC7(CCC(N8CCC(c9ccc%10c(c9)n(C)c(=O)n%10C9CCC(=O)NC9=O)CC8)CC7)C5)CC6)nc4c3F)c12] |

TABLE 3-continued
| Example Compounds of the Disclosure | |
|---|---|
| Compound No. | Compound Structure |
| 468 | 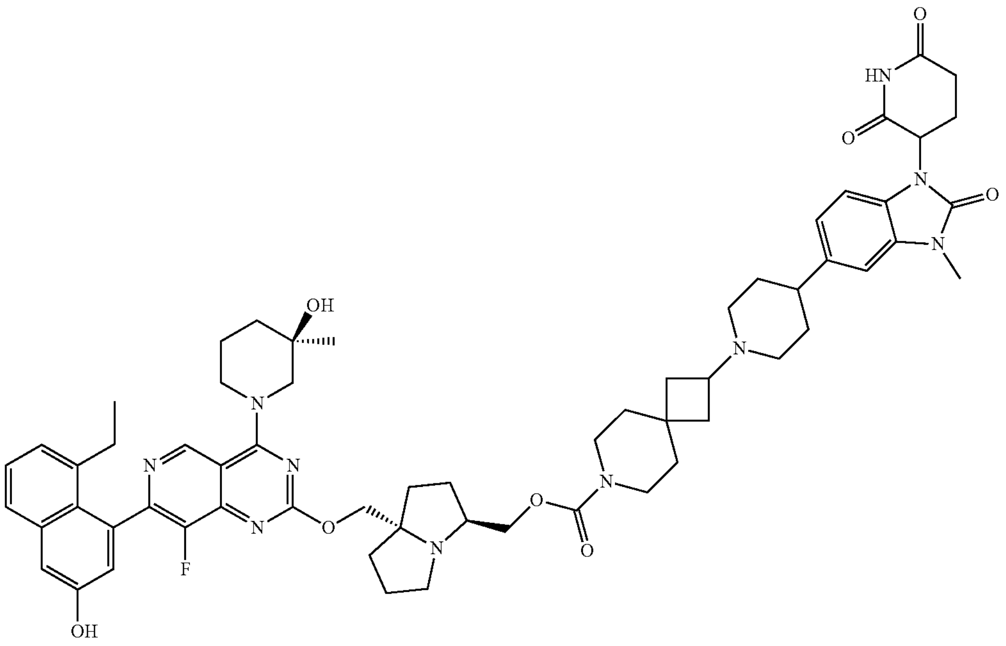 [SMILES: CCc1cccc2cc(O)cc(-c3ncc4c(N5CCC[C@@](C)(O)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 469 | 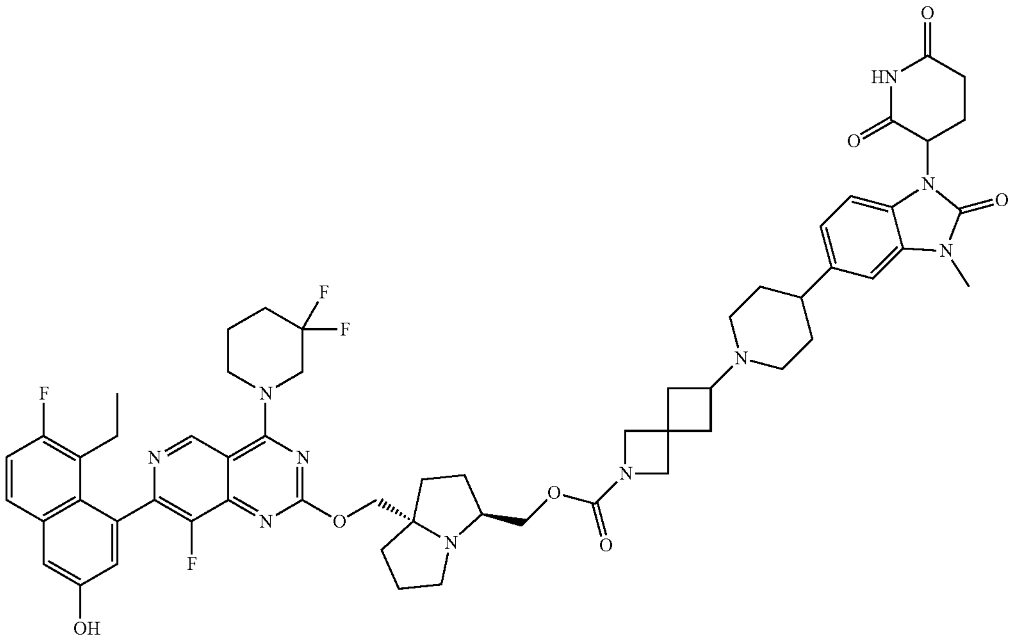 [SMILES: CCc1c(F)ccc2cc(O)cc(-c3ncc4c(N5CCCC(F)(F)C5)nc(OC[C@@]56CCCN5[C@H](COC(=O)N5CC7(CC(N8CCC(c9ccc%10c(c9)n(C)c(=O)n%10C9CCC(=O)NC9=O)CC8)C7)C5)CC6)nc4c3F)c12] |

TABLE 3-continued
| Example Compounds of the Disclosure | |
|---|---|
| Compound No. | Compound Structure |
| 470 | 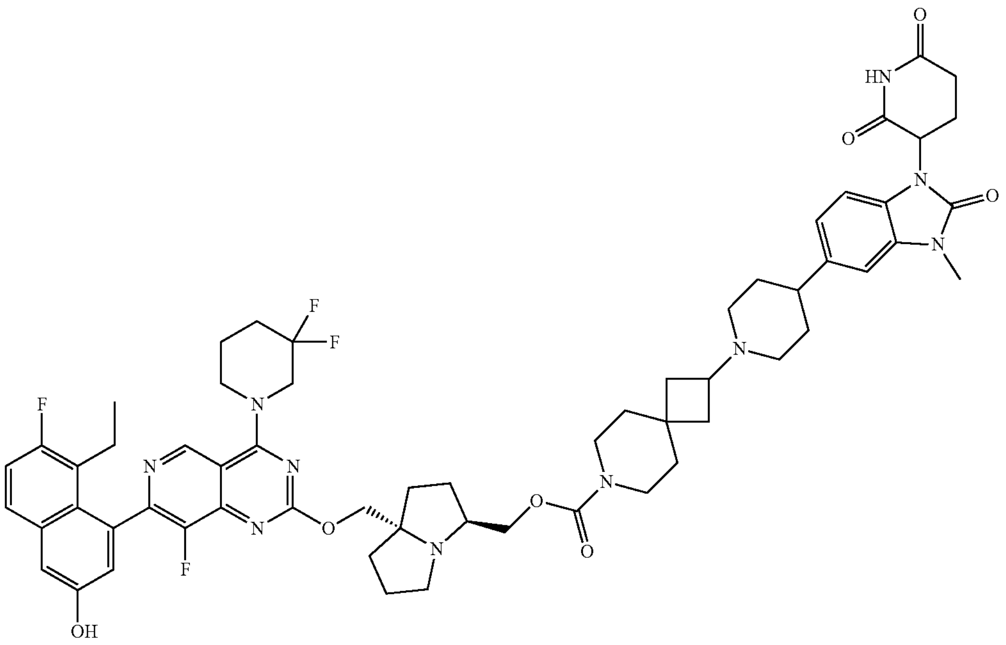 [SMILES: CCc1c(F)ccc2cc(O)cc(-c3ncc4c(N5CCCC(F)(F)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 471 | 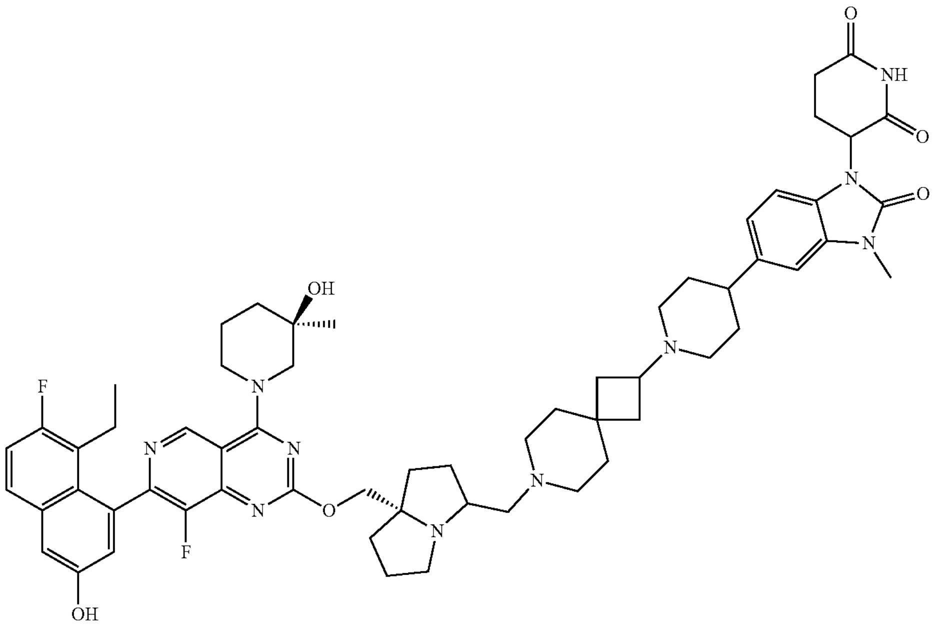 [SMILES: CCc1c(F)ccc2cc(O)cc(-c3ncc4c(N5CCC[C@@](C)(O)C5)nc(OC[C@@]56CCCN5C(CN5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 472 | 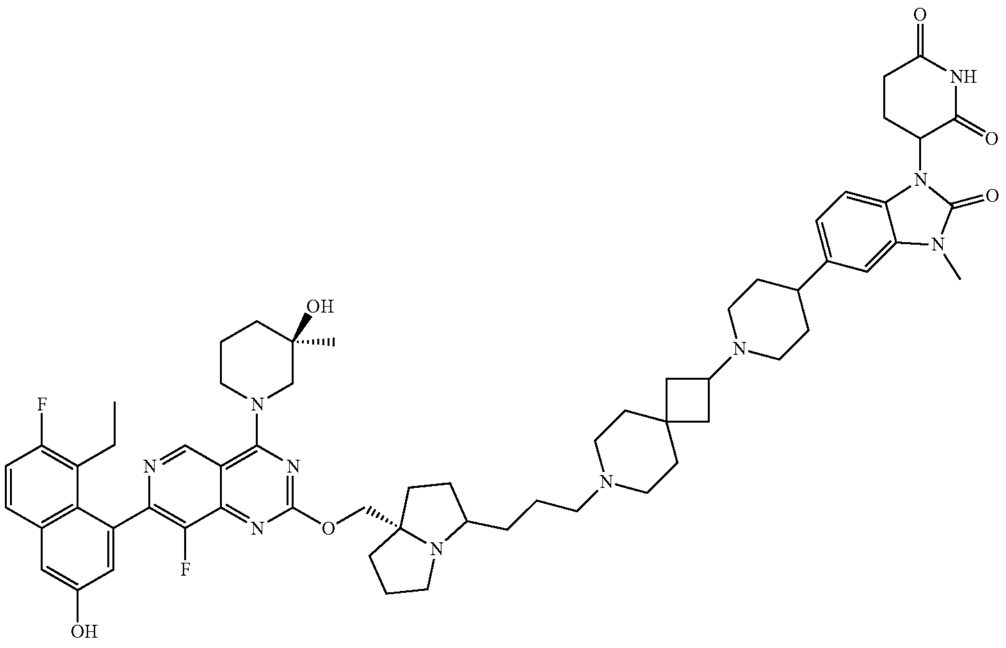 [SMILES: CCc1c(F)ccc2cc(O)cc(-c3ncc4c(N5CCC[C@@](C)(O)C5)nc(OC[C@@]56CCCN5C(CCCN5CCC7(CC5)CC(N5CCC(c8ccc9c(c8)n(C)c(=O)n9C8CCC(=O)NC8=O)CC5)C7)CC6)nc4c3F)c12] |
| 473 | 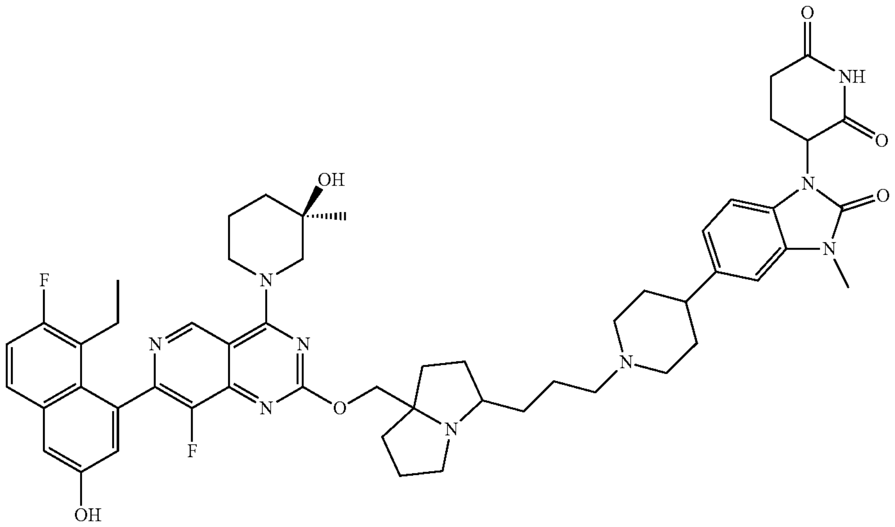 [SMILES: CCc1c(F)ccc2cc(O)cc(-c3ncc4c(N5CCC[C@@](C)(O)C5)nc(OCC56CCCN5C(CCCN5CCC(c7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 474 | 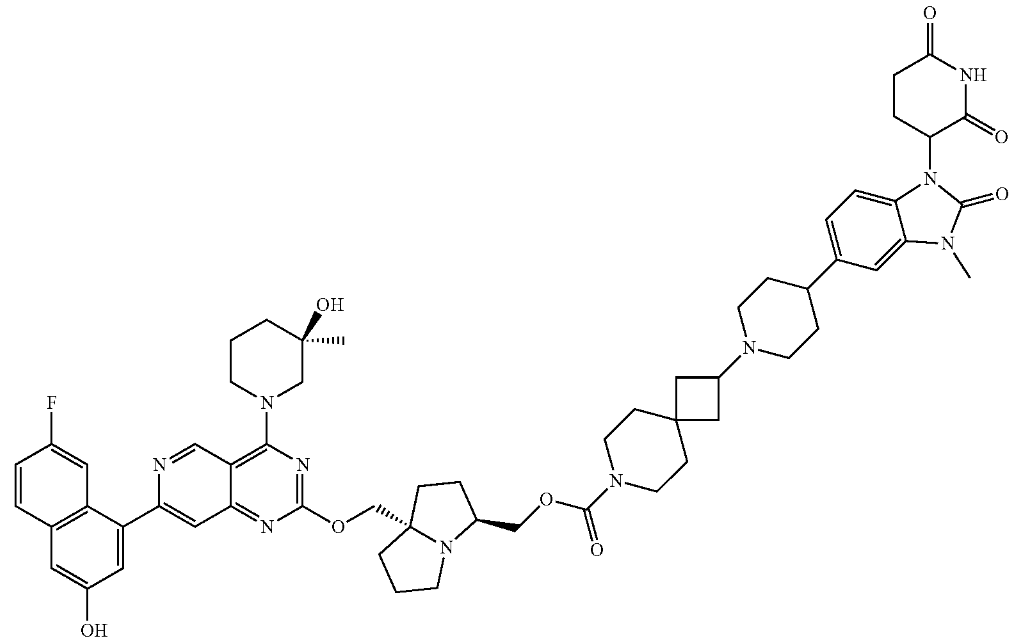 [SMILES: Cn1c(=O)n(C2CCC(=O)NC2=O)c2ccc(C3CCN(C4CC5(CCN(C(=O)OC[C@@H]6CC[C@]7(COc8nc(N9CCC[C@@](C)(O)C9)c9cnc(-c%10cc(O)cc%11ccc(F)cc%10%11)cc9n8)CCCN67)CC5)C4)CC3)cc21] |
| 476 | 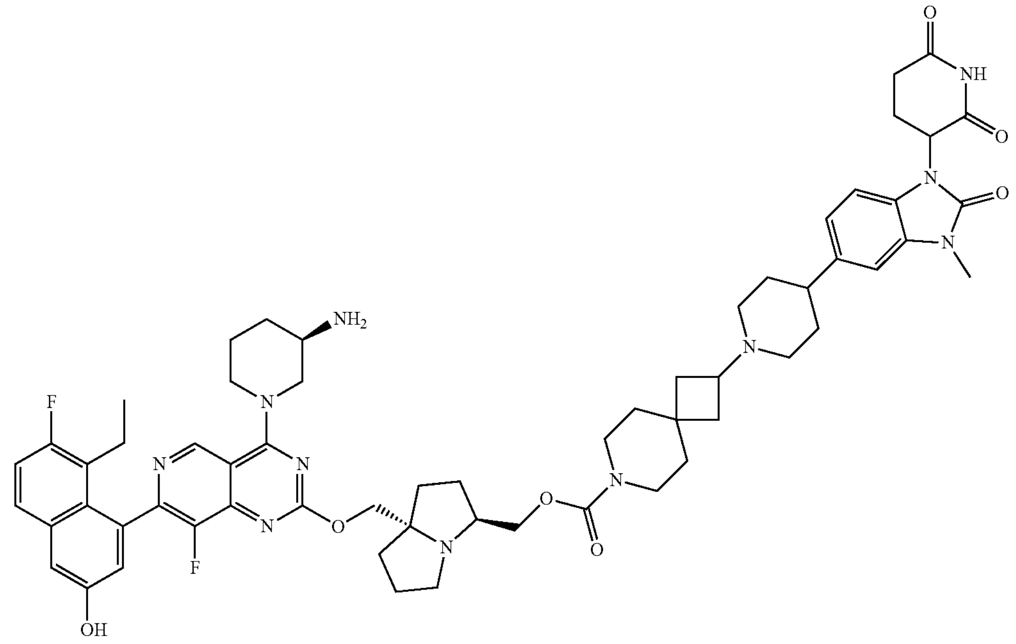 [SMILES: CCc1c(F)ccc2cc(O)cc(-c3ncc4c(N5CCC[C@@H](N)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 477 | 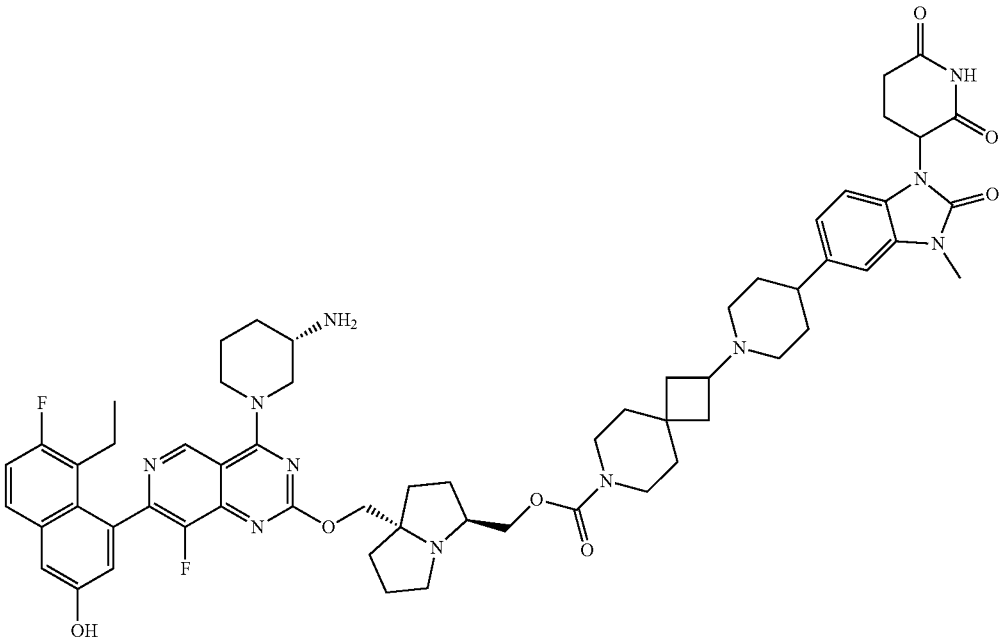 [SMILES: CCc1c(F)ccc2cc(O)cc(-c3ncc4c(N5CCC[C@H](N)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 478 | 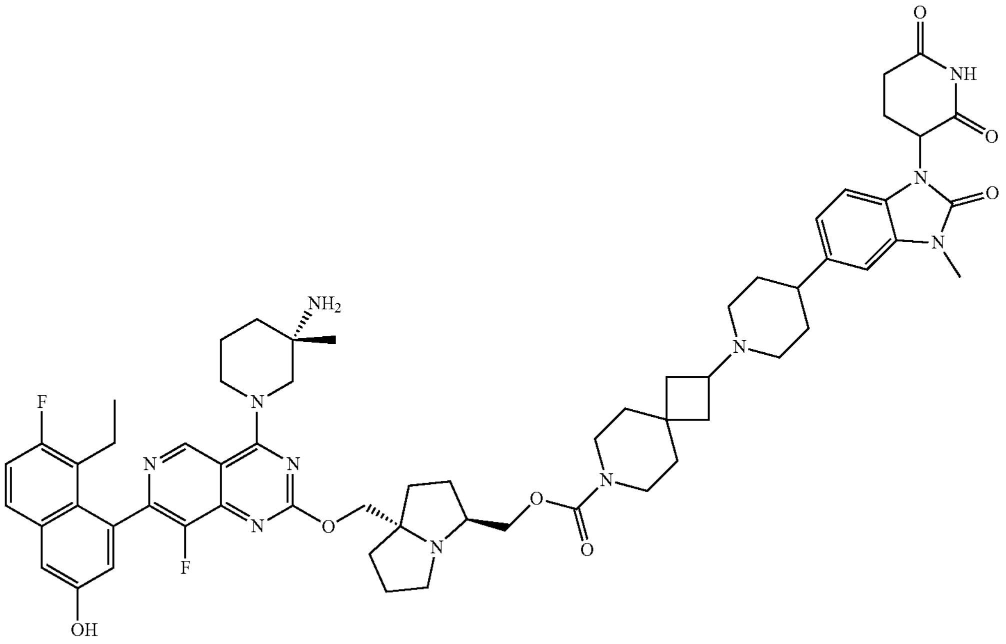 [SMILES: CCc1c(F)ccc2cc(O)cc(-c3ncc4c(N5CCC[C@](C)(N)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |

TABLE 3-continued
| Example Compounds of the Disclosure | |
|---|---|
| Compound No. | Compound Structure |
| 479 | 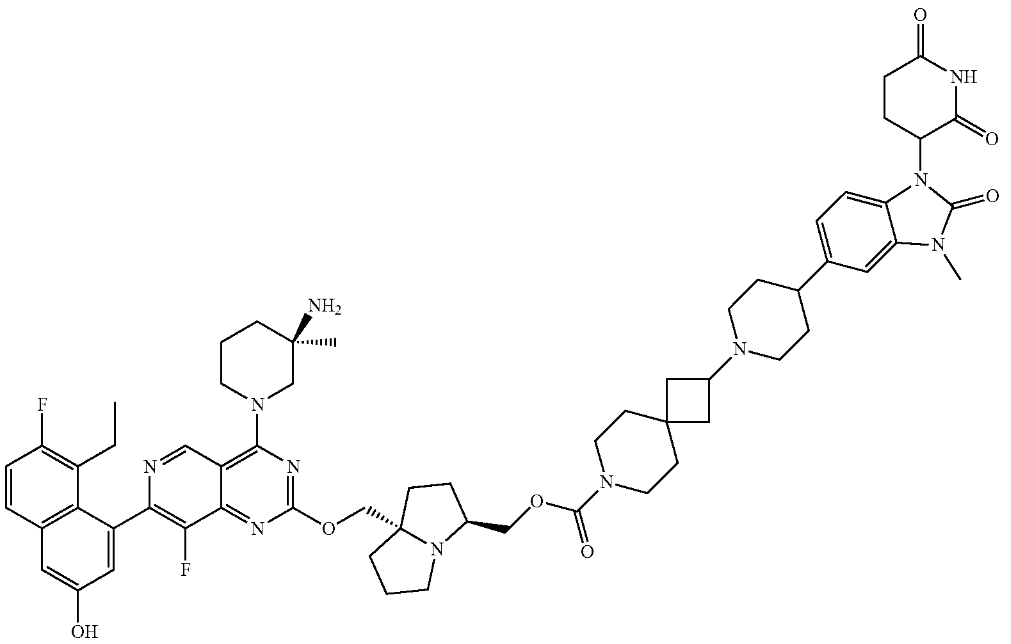 [SMILES: CCc1c(F)ccc2cc(O)cc(-c3ncc4c(N5CCC[C@@](C)(N)C5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 484 | 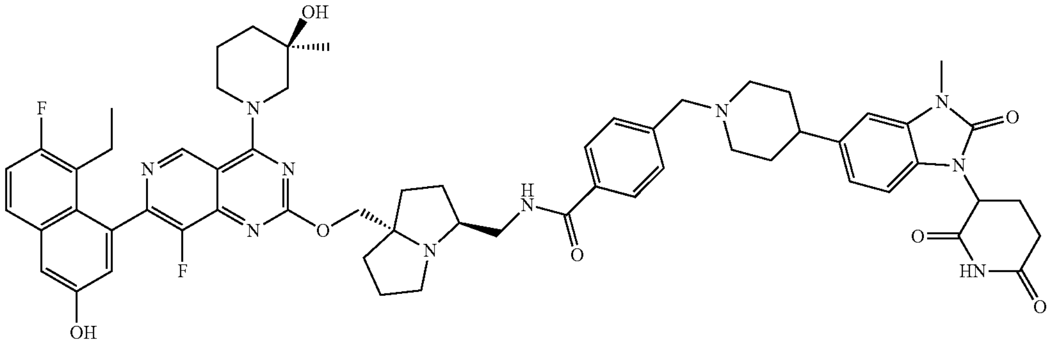 [SMILES: CCc1c(F)ccc2cc(O)cc(-c3ncc4c(N5CCC[C@@](C)(O)C5)nc(OC[C@@]56CCCN5[C@H](CNC(=O)c5ccc(CN7CCC(c8ccc9c(c8)n(C)c(=O)n9C8CCC(=O)NC8=O)CC7)cc5)CC6)nc4c3F)c12] |
| 485 | 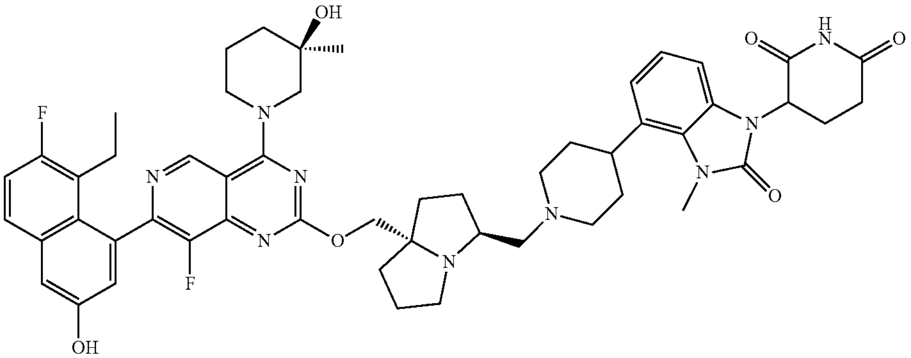 [SMILES: CCc1c(F)ccc2cc(O)cc(-c3ncc4c(N5CCC[C@@](C)(O)C5)nc(OC[C@@]56CCCN5[C@H](CN5CCC(c7cccc8c7n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 486 | 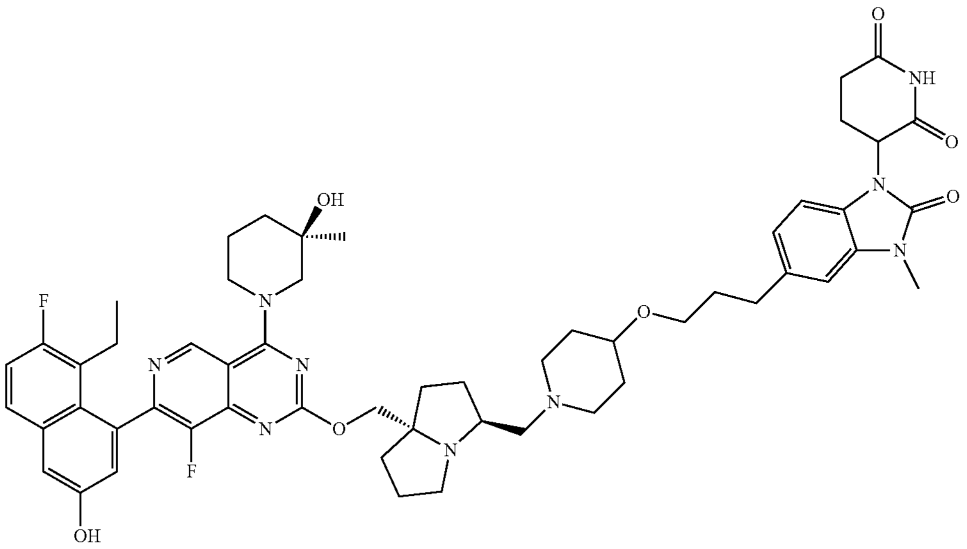 [SMILES: CCc1c(F)ccc2cc(O)cc(-c3ncc4c(N5CCC[C@@](C)(O)C5)nc(OC[C@@]56CCCN5[C@H](CN5CCC(OCCCc7ccc8c(c7)n(C)c(=O)n8C7CCC(=O)NC7=O)CC5)CC6)nc4c3F)c12] |
| 487 | 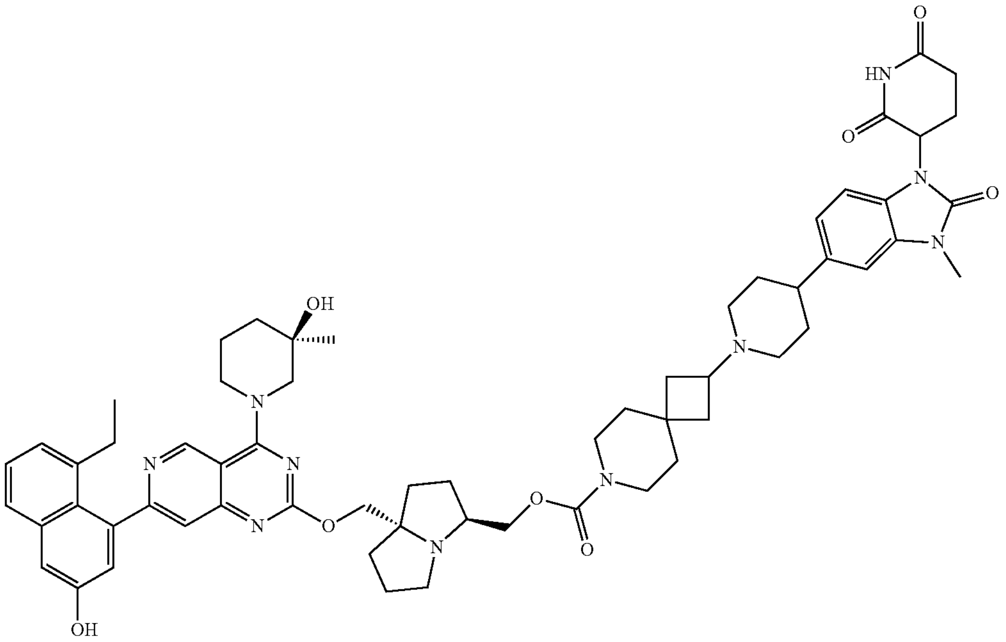 [SMILES: CCc1cccc2cc(O)cc(-c3cc4nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc(N5CCC[C@@](C)(O)C5)c4cn3)c12] |

TABLE 3-continued
| Example Compounds of the Disclosure | |
|---|---|
| Compound No. | Compound Structure |
| 489 | 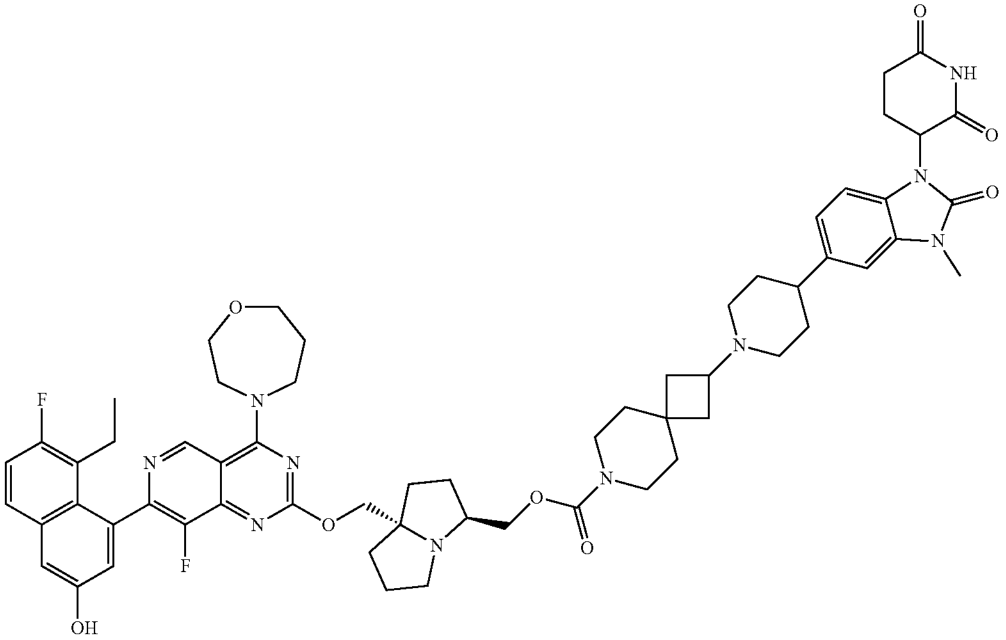 [SMILES: CCc1c(F)ccc2cc(O)cc(-c3ncc4c(N5CCCOCC5)nc(OC[C@@]56CCCN5[C@H](COC(=O)N5CCC7(CC5)CC(N5CCC(c8ccc9c(c8)n(C)c(=O)n9C8CCC(=O)NC8=O)CC5)C7)CC6)nc4c3F)c12] |
| 490 | 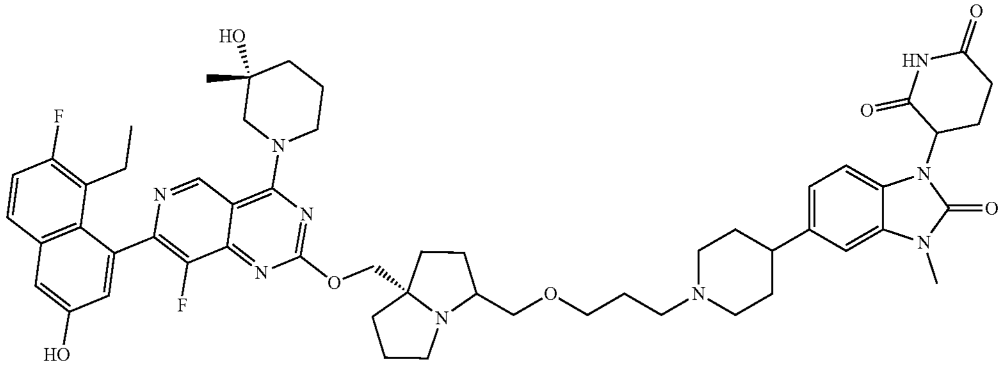 [SMILES: CCc1c(F)ccc2cc(O)cc(-c3ncc4c(N5CCC[C@@](C)(O)C5)nc(OC[C@@]56CCCN5C(COCCCN5CCC(c7ccc8c(c7)n(C)c(=O)n8C7CCC(=O)NC7=O)CC5)CC6)nc4c3F)c12] |

TABLE 3-continued
| Example Compounds of the Disclosure | |
|---|---|
| Compound No. | Compound Structure |
| 491 | 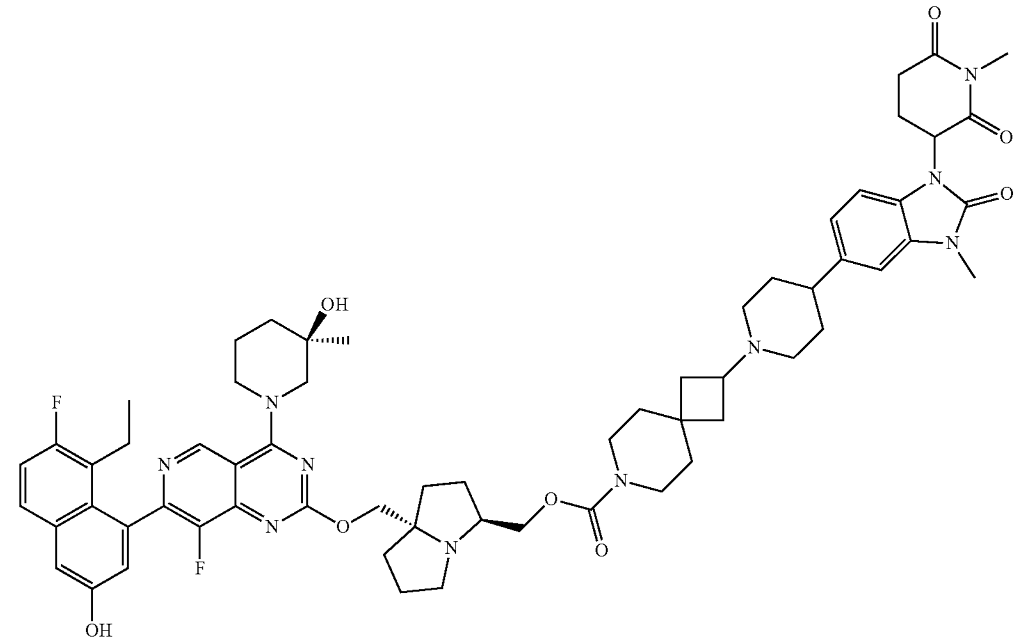 [SMILES: CCc1c(F)ccc2cc(O)cc(-c3ncc4c(N5CCC[C@@](C)(O)C5)nc(OC[C@@]56CCCN5[C@H](COC(=O)N5CCC7(CC5)CC(N5CCC(c8ccc9c(c8)n(C)c(=O)n9C8CCC(=O)N(C)C8=O)CC5)C7)CC6)nc4c3F)c12] |
| 492 | 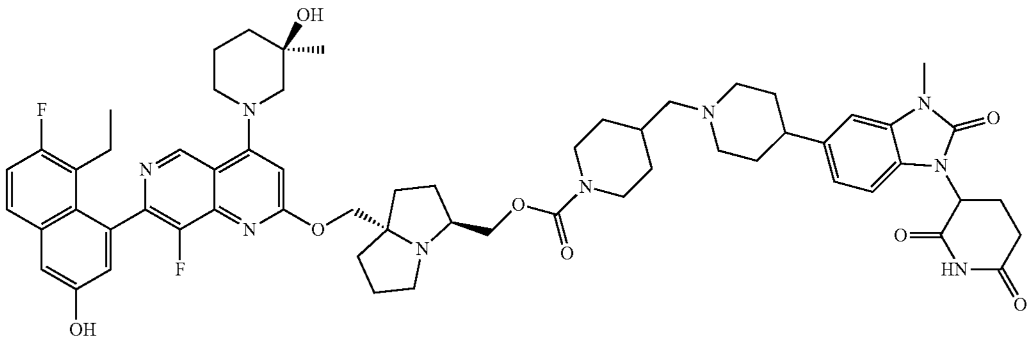 [SMILES: CCc1c(F)ccc2cc(O)cc(-c3ncc4c(N5CCC[C@@](C)(O)C5)cc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12] |
| 493 | 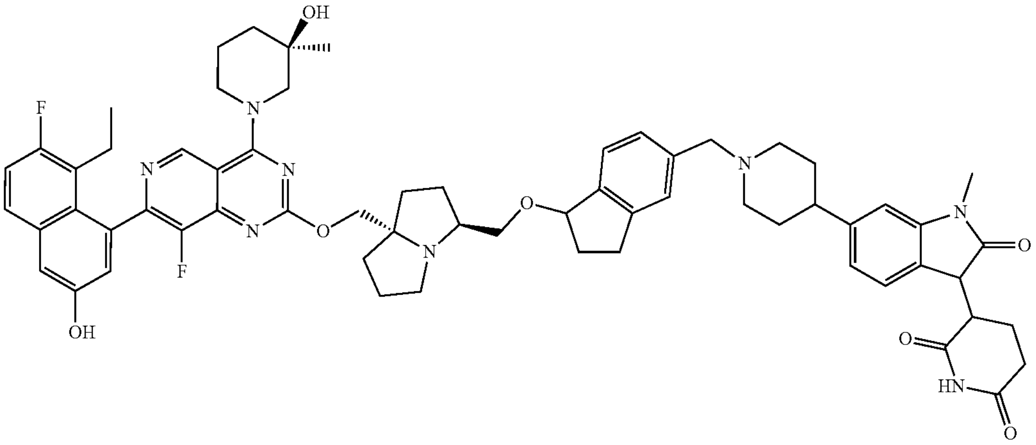 [SMILES: CCc1c(F)ccc2cc(O)cc(-c3ncc4c(N5CCC[C@@](C)(O)C5)nc(OC[C@@]56CCCN5[C@H](COC5CCc7cc(CN8CCC(c9ccc%10c(c9)N(C)C(=O)C%10C9CCC(=O)NC9=O)CC8)ccc75)CC6)nc4c3F)c12] |

TABLE 3-continued
| Compound No. | Compound Structure |
|---|---|
| 494 | 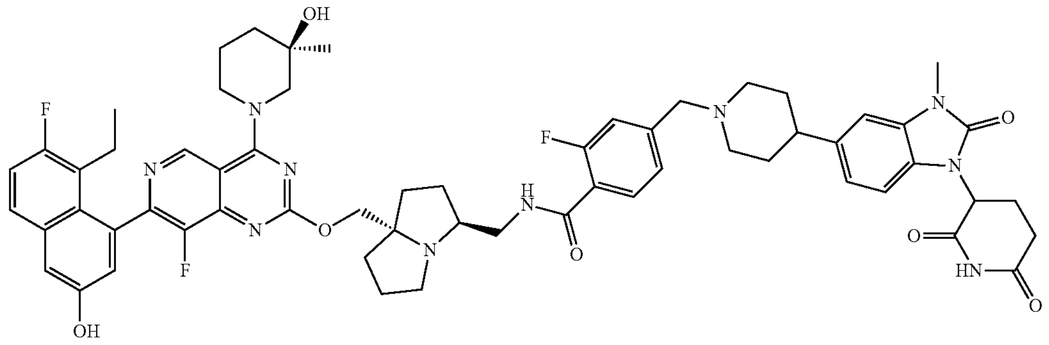 [SMILES: CCc1c(F)ccc2cc(O)cc(-c3ncc4c(N5CCC[C@@](C)(O)C5)nc(OC[C@@]56CCCN5[C@H](CNC(=O)c5ccc(CN7CCC(c8ccc9c(c8)n(C)c(=O)n9C8CCC(=O)NC8=O)CC7)cc5F)CC6)nc4c3F)c12] |
| 495 | 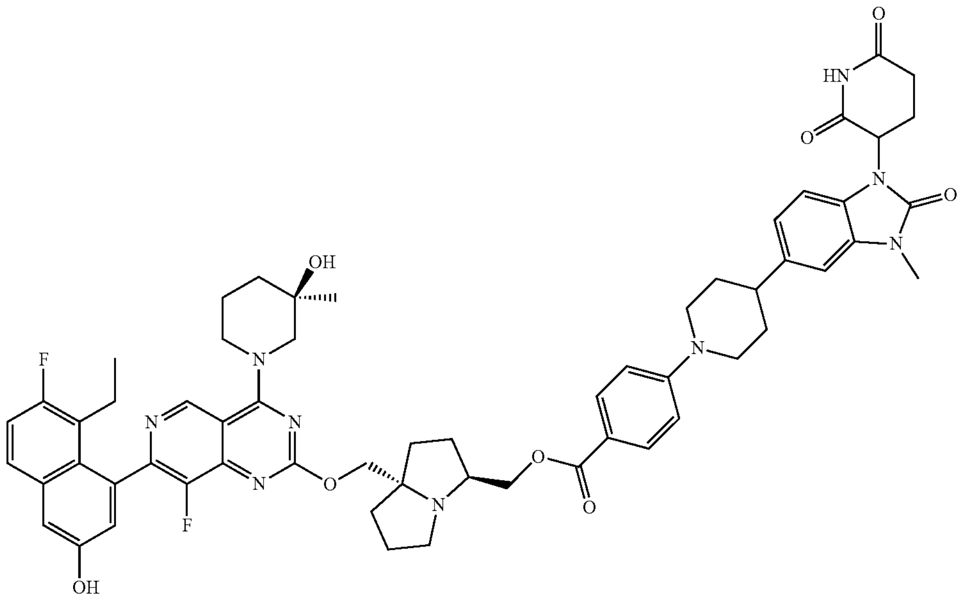 [SMILES: CCc1c(F)ccc2cc(O)cc(-c3ncc4c(N5CCC[C@@](C)(O)C5)nc(OC[C@@]56CCCN5[C@H](COC(=O)c5ccc(N7CCC(c8ccc9c(c8)n(C)c(=O)n9C8CCC(=O)NC8=O)CC7)cc5)CC6)nc4c3F)c12] |
| 496 | 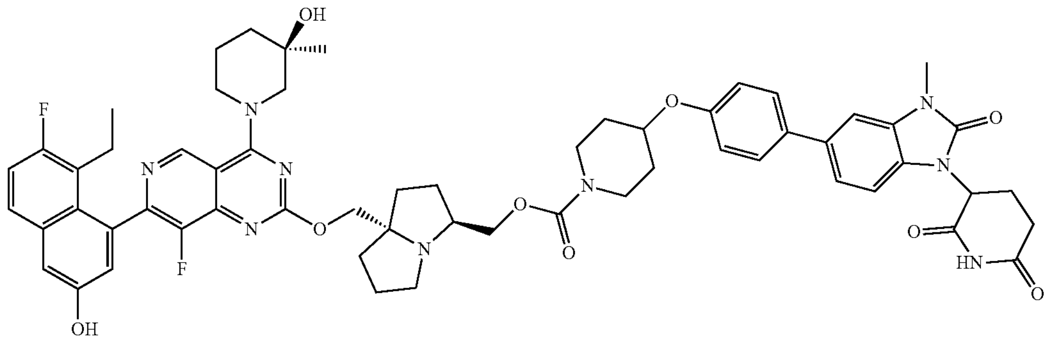 [SMILES: CCc1c(F)ccc2cc(O)cc(-c3ncc4c(N5CCC[C@@](C)(O)C5)nc(OC[C@@]56CCCN5[C@H](COC(=O)N5CCC(Oc7ccc(-c8ccc9c(c8)n(C)c(=O)n9C8CCC(=O)NC8=O)cc7)CC5)CC6)nc4c3F)c12] |
Example Compounds of the Disclosure TABLE 3-continued
| Example Compounds of the Disclosure | |
|---|---|
| Compound No. | Compound Structure |
| 497 | 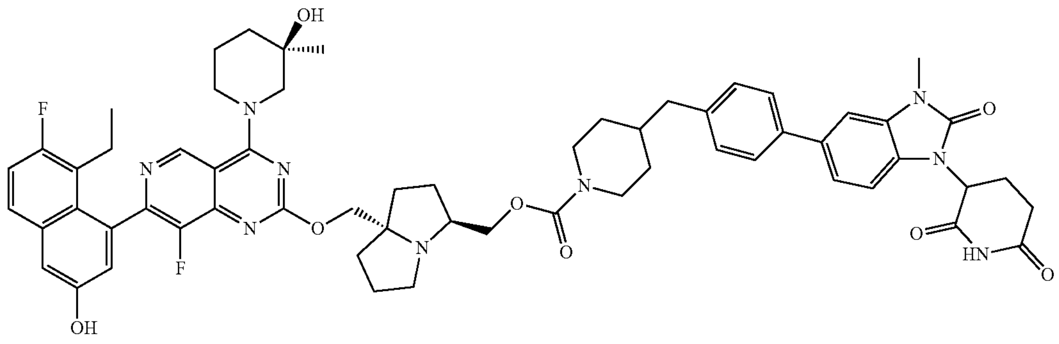 [SMILES: CCc1c(F)ccc2cc(O)cc(-c3ncc4c(N5CCC[C@@](C)(O)C5)nc(OC[C@@]56CCCN5[C@H](COC(=O)N5CCC(Cc7ccc(-c8ccc9c(c8)n(C)c(=O)n9C8CCC(=O)NC8=O)cc7)CC5)CC6)nc4c3F)c12] |
| 499 | 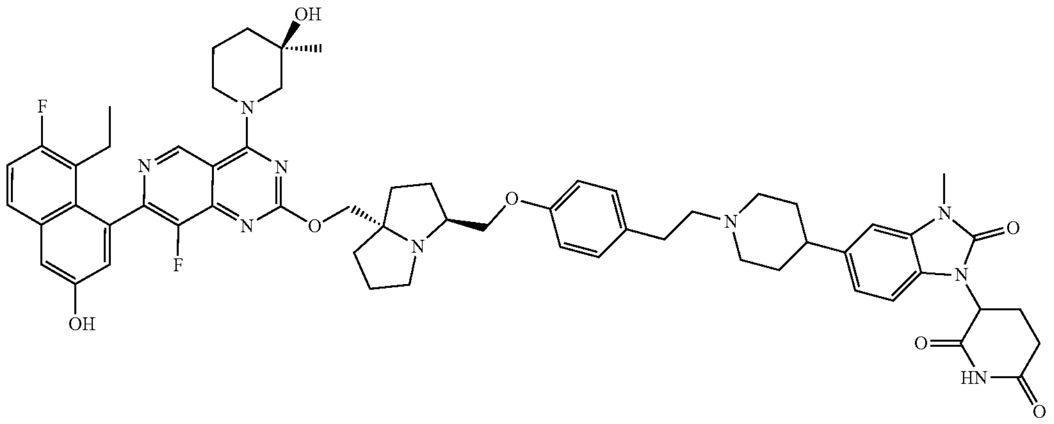 [SMILES: CCc1c(F)ccc2cc(O)cc(-c3ncc4c(N5CCC[C@@](C)(O)C5)nc(OC[C@@]56CCCN5[C@H](COc5ccc(CCN7CCC(c8ccc9c(c8)n(C)c(=O)n9C8CCC(=O)NC8=O)CC7)cc5)CC6)nc4c3F)c12] |
| 500 | 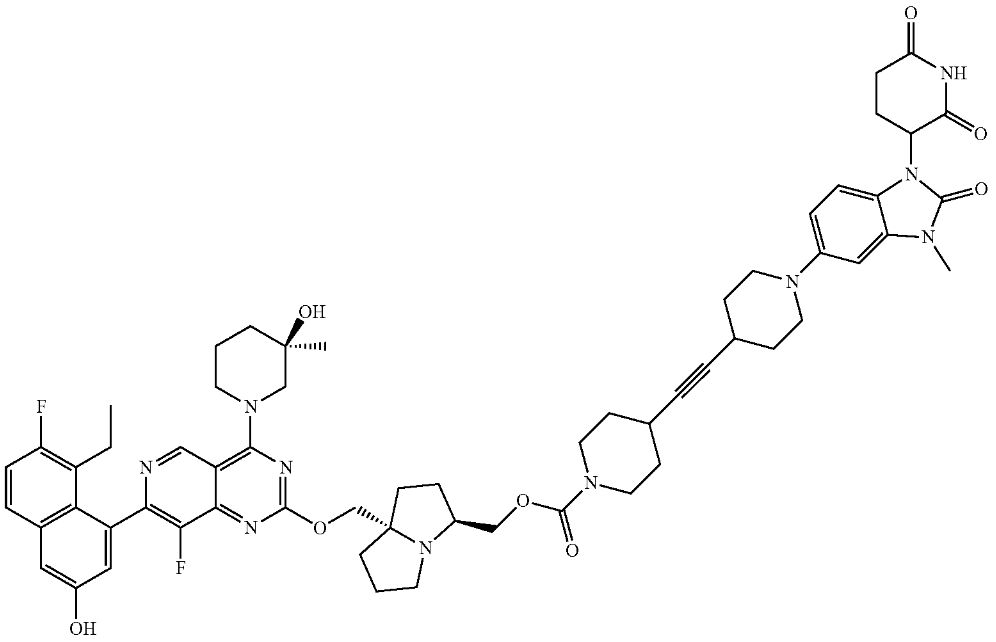 [SMILES: CCc1c(F)ccc2cc(O)cc(-c3ncc4c(N5CCC[C@@](C)(O)C5)nc(OC[C@@]56CCCN5[C@H](COC(=O)N5CCC(C#CC7CCN(c8ccc9c(c8)n(C)c(=O)n9C8CCC(=O)NC8=O)CC7)CC5)CC6)nc4c3F)c12] |

TABLE 3-continued

| Example Compounds of the Disclosure | |
|---|---|
| Compound No. | Compound Structure |
| 501 | 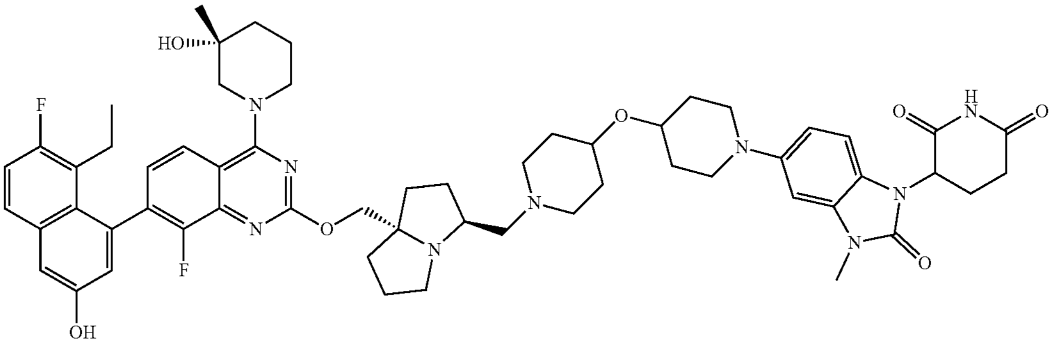 [SMILES: CCc1c(F)ccc2cc(O)cc(-c3ccc4c(N5CCC[C@@](C)(O)C5)nc(OC[C@@]56CCCN5[C@H](CN5CCC(OC7CCN(c8ccc9c(c8)n(C)c(=O)n9C8CCC(=O)NC8=O)CC7)CC5)CC6)nc4c3F)c12] |
| 502 | 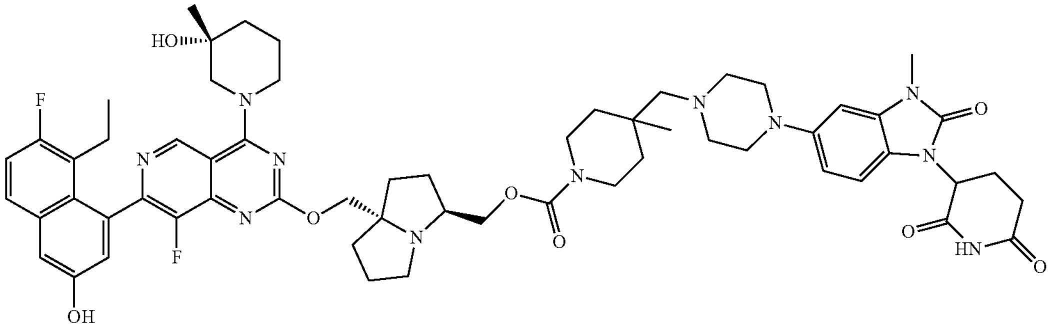 [SMILES: CCc1c(F)ccc2cc(O)cc(-c3ncc4c(N5CCC[C@@](C)(O)C5)nc(OC[C@@]56CCCN5[C@H](COC(=O)N5CCC(C)(CN7CCN(c8ccc9c(c8)n(C)c(=O)n9C8CCC(=O)NC8=O)CC7)CC5)CC6)nc4c3F)c12] |
| 503 | 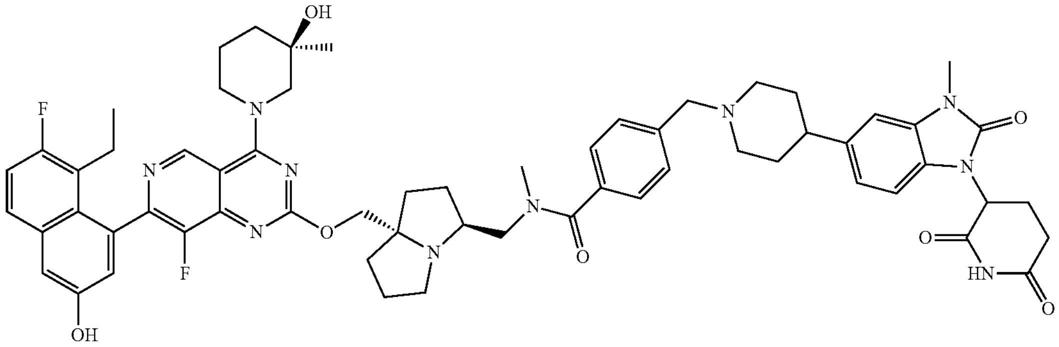 [SMILES: CCc1c(F)ccc2cc(O)cc(-c3ncc4c(N5CCC[C@@](C)(O)C5)nc(OC[C@@]56CCCN5[C@H](CN(C)C(=O)c5ccc(CN7CCC(c8ccc9c(c8)n(C)c(=O)n9C8CCC(=O)NC8=O)CC7)cc5)CC6)nc4c3F)c12] |

Representative methods of making compounds of the disclosure are described in the Exemplification and, for example, in International Application No. PCT/US2023/066709, the entire content of which is incorporated herein by reference.

Compositions, Combinations, Kits

Typically, for administration to a subject, a compound of the disclosure is formulated with one or more pharmaceutically acceptable carriers. The disclosure provides such compositions, including pharmaceutical compositions. Thus, one embodiment is a composition (e.g., pharmaceutical composition) comprising a compound of the disclosure and a pharmaceutically acceptable carrier. The compositions described herein can be used in accordance with the uses and/or methods described herein, e.g., to supply a compound of the disclosure for administration to a subject.

Compositions described herein and, hence, compounds of the disclosure, may be administered orally, parenterally (including subcutaneously, intramuscularly, intravenously and intradermally), by inhalation spray, topically, rectally, nasally, buccally, vaginally or via an implanted reservoir. The terms "parenteral" and "parenterally," as used herein, include subcutaneous, intracutaneous, intravenous, intramuscular, intraocular, intravitreal, intra-articular, intra-arterial, intra-synovial, intrasternal, intrathecal, intralesional, intrahepatic, intraperitoneal, intralesional and intracranial injection or infusion techniques. In some aspects, a composition described herein is administrable intravenously and/or intraperitoneally. In some aspects, a composition described herein is administrable intravenously. In some aspects, a composition described herein is administrable orally. Preferably, a composition described herein is administered orally, subcutaneously, intraperitoneally or intravenously.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some aspects, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Liquid dosage forms for oral administration include pharmaceutically acceptable emulsions, microemulsions, solutions, suspensions, syrups, and elixirs. In addition to the compound of the disclosure, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, or mixtures thereof. Besides inert diluents, the oral compositions can also include adjuvants such as wetting agents, emulsifying and suspending agents, sweetening, flavoring, coloring, perfuming, and preservative agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the disclosure can also be in micro-encapsulated form with one or more excipients, as noted above. In such solid dosage forms, the compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another aspect, a compound of the disclosure can be provided in an extended (or "delayed" or "sustained") release composition. This delayed-release composition comprises the compound of the disclosure and a delayed-release component. Such a composition allows targeted release of the compound, for example, into the lower gastrointestinal tract, for example, into the small intestine, the large intestine, the colon and/or the rectum. In certain aspects, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition can provide controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

Compositions described herein can also be administered subcutaneously, intraperitoneally or intravenously, e.g., in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, dextrose, water, Ringer's solution, lactated Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

Compositions described herein can also be administered in the form of suppositories for rectal administration. These can be prepared by mixing a compound of the disclosure with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topical transdermal patches can also be used.

For other topical applications, the compositions can be formulated in a suitable ointment containing the active component suspended or dissolved in one or more carriers. Carriers for topical administration of a compound described herein include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active compound suspended or dissolved in one or more pharmaceutically acceptable carriers. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. Suitable carriers also include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents. Without wishing to be bound by any particular theory, it is believed that local delivery of a composition described herein, as can be achieved by nasal aerosol or inhalation, for example, can reduce the risk of systemic consequences of the composition, for example, consequences for red blood cells.

Other pharmaceutically acceptable carriers that can be used in the compositions described herein include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

In some aspects, a composition described herein further includes one or more additional therapeutic agents, e.g., for use in combination with a compound of the disclosure.

Some embodiments provide a combination (e.g., pharmaceutical combination) comprising a compound of the disclosure (e.g., a composition described herein comprising a compound of the disclosure) and one or more additional therapeutic agents (e.g., one or more compositions comprising one or more additional therapeutic agents). Such combinations are particularly useful as, for example, when the compound of the disclosure and the one or more additional therapeutic agents are to be administered separately. In a combination provided herein, the compound of the disclosure and the one or more additional therapeutic agents can be administrable by the same route of administration or by different routes of administration.

Some embodiments provide a kit comprising a compound of the disclosure (e.g., a composition described herein comprising a compound of the disclosure) and an additional therapeutic agent(s)(e.g., a composition comprising an additional therapeutic agent(s)). In one embodiment, the kit comprises a therapeutically effective amount of the compound of the disclosure to treat a disease, disorder or condition described herein, and a therapeutically effective amount of the one or more additional therapeutic agents to treat the disease, disorder or condition. In some aspects, the kit further comprises written instructions for administering the compound of the disclosure and/or the additional agent (s) to a subject to treat a disease, disorder or condition described herein.

Additional therapeutic agents for use in the compositions, combinations and/or kits provided herein include any of those discussed herein with respect to combination therapies.

The compositions described herein are, in some aspects, provided in unit dosage form. Thus, some embodiments provide a unit dosage form comprising a compound of the disclosure, e.g., and a pharmaceutically acceptable carrier. The amount of a compound of the disclosure or other therapeutic agent that can be combined with carrier material (s) to produce a composition in a unit dosage form will vary depending, for example, upon the subject treated, the particular mode of administration and the activity of the agent employed. Preferably, compositions and/or unit dosage forms should be formulated so that a compound of the disclosure or other therapeutic agent can be administered to a subject receiving the composition and/or unit dosage form at a dose and/or frequency consistent with those described herein. Typically, a unit dosage form will contain from about 1 mg to about 5,000 mg, from about 10 mg to about 2,500 mg, from about 100 mg to about 1,000 mg, from about 1 mg to about 1000 mg, from about 1 mg to about 500 mg, from about 1 mg to about 250 mg, from about 1 mg to about 150 mg, from about 0.5 mg to about 100 mg, or from about 1 mg to about 50 mg of active ingredient(s).

In some embodiments, the concentration of a therapeutic agent (e.g., a compound of the disclosure) in a composition is less than 100%, 90%, 80%, 70%, 60%, 50%, 40%, 30%, 20%, 15%, 10%, 9%, 8%, 7%, 6%, 5%, 4%, 3%, 2%, 1%, 0.5%, or 0.1% w/w, w/v or v/v; and/or greater than 90%, 80%, 70%, 60%, 50%, 40%, 30%, 20%, 15%, 10%, 9%, 8%, 7%, 6%, 5%, 4%, 3%, 2%, 1%, 0.5%, or 0.1% w/w, w/v, or v/v. In some embodiments, the concentration of a therapeutic agent (e.g., a compound of the disclosure) in a composition is in the range from about 0.001% to about 50%, about 0.001% to about 25%, about 0.01% to about 20%, about 0.05% to about 15%, about 0.1% to about 10%, or about 1% to about 10% w/w, w/v or v/v. In some embodiments, the concentration of a therapeutic agent (e.g., a compound of the disclosure) in a composition is in the range from about 0.001% to about 10%, about 0.01% to about 5%, or about 0.1% to about 1% w/w, w/v or v/v.

Uses

Various compounds of the disclosure have been shown to exhibit effects consistent with degradation of wild-type KRAS or one or more mutants thereof, such as KRAS G12D and KRAS G12V. Accordingly, provided herein in one embodiment is a method of reducing a level or activity of a KRAS (e.g., wild-type KRAS, a KRAS mutant, such as a KRAS mutant identified herein) in a cell (e.g., a cell expressing a KRAS), comprising contacting the cell with (e.g., an effective amount of) a compound of the disclosure or a composition comprising a compound of the disclosure. In some aspects, the method is conducted in vitro. In some aspects, the method is conducted ex vivo. In some aspects, the method is conducted in vivo. In some aspects, the cell is in a subject, such as a subject having a KRAS-associated cancer.

Thus, provided herein in another embodiment is a method of reducing a level or activity of a KRAS (e.g., wild-type KRAS, a KRAS mutant, such as a KRAS mutant identified herein) in a subject in need thereof, comprising administering to the subject an effective amount (e.g., a therapeutically effective amount) of a compound of the disclosure or a composition comprising a compound of the disclosure.

KRAS level or activity can be reduced in accordance with the methods described herein by, e.g., promoting degradation of the KRAS, via the UPP, for example, and/or inhibiting activity of the KRAS. In some aspects, the method of reducing a level or activity of a KRAS is a method of promoting (e.g., inducing) degradation of the KRAS. Additionally or alternatively, in some aspects, the method of reducing a level or activity of a KRAS is a method of inhibiting activity of the KRAS.

Also provided herein in an embodiment is a method for treating a cancer (e.g., a KRAS-associated cancer) in a subject in need thereof, comprising administering to the subject a therapeutically effective amount of a compound of the disclosure or a composition comprising a compound of the disclosure. The cancer can be a solid tumor cancer or a hematological cancer (e.g., a leukemia, a lymphoma or a myeloma). In some aspects, the cancer is a solid tumor cancer. In some aspects, the cancer is a hematologic cancer.

Cancers (e.g., KRAS-associated cancers) that may be treated in accordance with the methods described herein include, but are not limited to, astrocytic, breast, cervical, skin, colorectal, endometrial, esophageal, gastric, head and neck, hepatocellular, laryngeal, lung, oral, ovarian, testicular and prostate cancers, thyroid carcinomas and sarcomas. For example, the following cancers (e.g., KRAS-associated cancers) are treatable in accordance with the methods described herein: cardiac cancers, such as sarcoma (e.g., angiosarcoma, fibrosarcoma, rhabdomyosarcoma, liposarcoma), myxoma, rhabdomyoma, fibroma, lipoma and teratoma; lung cancers, such as bronchogenic carcinoma (e.g., squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; gastrointestinal cancers, such as cancers of the esophagus (e.g., squamous cell carcinoma, adenocarcinoma, leiomyosarcoma, lymphoma), stomach (e.g., carcinoma, lymphoma, leiomyosarcoma), pancreas (e.g., ductal adenocarcinoma, insulinoma, glueagonoma, gastrinoma, carcinoid tumors, vipoma), small bowel (e.g., adenocarcinoma, lymphoma, carcinoid tumors, Kaposi's sarcoma, leiomyoma, hemangioma, lipoma, neurofibroma, fibroma), large bowel (e.g., adenocarcinoma, tubular adenoma, villous adenoma, hamartoma, leiomyoma); genitourinary tract cancers, such as cancers of the kidney (e.g., adenocarcinoma, Wilm's tumor (nephroblastoma), lymphoma, leukemia), bladder and urethra (e.g., squamous cell carcinoma, transitional cell carcinoma, adenocarcinoma), prostate (e.g., adenocarcinoma, sarcoma), testis (e.g., seminoma, teratoma, embryonal carcinoma, teratocarcinoma, choriocarcinoma, sarcoma, interstitial cell carcinoma, fibroma, fibroadenoma, adenomatoid tumors, lipoma); liver cancers, such as hepatoma (e.g., hepatocellular carcinoma), cholangiocarcinoma, hepatoblastoma, angiosarcoma, hepatocellular adenoma, hemangioma; biliary tract cancers, such as gall bladder carcinoma, ampullary carcinoma, cholangiocarcinoma; bone cancers, such as osteogenic sarcoma (e.g., osteosarcoma), fibrosarcoma, malignant fibrous histiocytoma, chondrosarcoma, Ewing's sarcoma, malignant lymphoma (e.g., reticulum cell sarcoma), multiple myeloma, malignant giant cell tumor chordoma, osteochronfroma (e.g., osteocartilaginous exostoses), benign chondroma, chondroblastoma, chondromyxofibroma. osteoid osteoma and giant cell tumors; nervous system cancers, such as cancers of the skull (e.g., osteoma, hemangioma, granuloma, xanthoma, osteitis deformans), meninges (e.g., meningioma, meningiosarcoma, gliomatosis), brain (e.g., astrocytoma, medulloblastoma, glioma, ependymoma, germinoma (e.g., pinealoma), glioblastoma multiform, oligodendroglioma, schwannoma, retinoblastoma, congenital tumors), spinal cord (e.g., neurofibroma, meningioma, glioma, sarcoma); gynecological cancers, such as cancers of the uterus (e.g., endometrial carcinoma), cervix (e.g., cervical carcinoma, pre-tumor cervical dysplasia), ovaries (e.g., ovarian carcinoma (e.g., serous cystadenocarcinoma, mucinous eysiadenocarcinoma, unclassified carcinoma), granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma (e.g., embryonal rhabdomyosarcoma), fallopian tubes (e.g., carcinoma); hematologic cancers, such as cancers of the blood (e.g., myeloid leukemia (e.g., acute, chronic), acute lymphoblastic leukemia, chronic lymphocytic leukemia, myeloproliferative diseases, multiple myeloma, myelodysplastic syndrome), Hodgkin's disease, non-Hodgkin's lymphoma (e.g., malignant lymphoma); skin cancers, such as malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, such as neuroblastoma.

Other examples of cancer treatable according to the methods described herein include Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS- Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sézary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sézary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sèzary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. In some aspects, the cancer is a metastatic cancer.

In some aspects, the cancer is a cardiac cancer, gastrointestinal cancer, genitourinary tract cancer, liver cancer, biliary tract cancer, bone cancer, nervous system cancer, gynecological cancer, hematologic cancer, skin cancer or adrenal gland cancer. In some aspects, the cancer is non-small cell lung cancer, small cell lung cancer, colorectal cancer, rectal cancer or pancreatic cancer.

In some aspects, the method further comprises determining whether the cell and/or subject has a KRAS mutation, such as any of the KRAS mutations identified herein. In some aspects, the method further comprises determining whether the cell and/or subject has a KRAS mutation, and administering to the cell and/or subject having a KRAS mutation (e.g., a therapeutically effective amount of) a compound of the disclosure or a composition comprising a compound of the disclosure. In some aspects, the method comprises determining whether a subject (e.g., a subject in need thereof, such as a subject having cancer) has a KRAS-associated cancer, and administering to a subject having a KRAS-associated cancer a therapeutically effective amount of a compound of the disclosure or a composition comprising a compound of the disclosure. Common KRAS-associated cancers are known in the art. Methods for determining whether a subject has a KRAS mutation or a KRAS-associated cancer, are known in the art and described herein.

A compound of the disclosure can also be administered in combination with one or more other therapies (e.g., radiation therapy, a chemotherapy, such as a chemotherapeutic agent; an immunotherapy, such as an immunotherapeutic agent) to treat a disease, disorder or condition described herein (e.g., cancer, an autoimmune disease). When administered "in combination," the compound of the disclosure can be administered before, after or concurrently with the other therapy(ies)(e.g., radiation therapy, an additional therapeutic agent(s)). When co-administered simultaneously (e.g., concurrently), the compound of the disclosure and another therapeutic agent can be in separate formulations or the same formulation. Alternatively, the compound of the disclosure and another therapeutic agent can be administered sequentially, either at approximately the same time or at different times, as separate compositions. When the compound of the disclosure and the other therapy (e.g., therapeutic agent) are administered as separate formulations or compositions, the compound of the disclosure and the other therapy can be administered by the same route of administration or by different routes of administration. A skilled clinician can determine appropriate timing for administration of each therapy being used in combination (e.g., timing sufficient to allow an overlap of the pharmaceutical effects of the therapies).

In some aspects, a method described herein further comprises administering to the subject (e.g., a therapeutically effective amount of) an additional therapy (ies)(e.g., radiation therapy; additional therapeutic agent(s), such as a chemotherapeutic agent, an immunotherapeutic agent, an antibody, such as a monoclonal antibody; a vaccine), e.g., in combination with the compound of the disclosure. In some aspects, the compound of the disclosure is administered before the additional therapy (ies). In some aspects, the compound of the disclosure is administered after the additional therapy (ies). In some aspects, the compound of the disclosure is administered concurrently with the additional therapy (ies).

In some aspects, a method further comprises administering to the subject radiation therapy (e.g., a therapeutically effective amount of radiation therapy), e.g., proton beam therapy.

In some aspects, a method further comprises administering to the subject hormone therapy (e.g., a therapeutically effective amount of hormone therapy), e.g., anti-estrogen therapy, androgen deprivation therapy (ADT), such as flutamide, nilutamide, bicalutamide, leuprolide or goserelin, a luteinizing hormone-releasing hormone (LHRH) agonist, an aromatase inhibitor (AI), such as anastrozole, exemestane or letrozole, an estrogen receptor modulator, such as tamoxifen, raloxifene or toremifene.

In some aspects, a method further comprises administering to the subject a receptor tyrosine kinase (RTK) inhibitor (e.g., a therapeutically effective amount of an RTK inhibitor). The RTK inhibitor may be, for example, an epidermal growth factor receptor (EGFR) inhibitor, vascular endothelial growth factor receptor (VEGFR) inhibitor, an anaplastic lymphoma kinase (ALK) inhibitor, a RET proto-oncogene inhibitor, a ROS proto-oncogene inhibitor, a fibroblast growth factor receptor (FGFR) inhibitor, neurotrophic tyrosine receptor kinase (NTRK) inhibitor, a Bruton tyrosine kinase (BTK) inhibitor, FMS-like tyrosine kinase 3 (FLT3), or a platelet-derived growth factor receptor (PDGF-R) inhibitor. The RTK inhibitor may be a specific inhibitor, having selectivity for a single receptor tyrosine kinase, or a broad inhibitor, affecting two or more receptor tyrosine kinases. The RTK inhibitor may be a type-I inhibitor, competing with ATP, a type-II inhibitor binding adjacent to the ATP site, a type-III inhibitor binding at an allosteric site, a type-IV inhibitor reversibly binding at the substrate binding site, or a type-V inhibitor covalently binding at the kinase active site. Examples of RTK inhibitors include alectinib, brigatinib, ceritanib, crizotinib, entrectinib, ceritinib, lorlatinib, afatinib, dacomitinib, erlotinib, gefitinib, lapatinib, neratinib, osimertinib, vandetanib, gilteritinib, midostaurin, erdafitinib, larotrectinib, axitinib, cabozantinib, lenvatinib, pazopanib, regorafenib, sorafenib, sunitinib, imatinib, acalabrutinib, ibrutinib, selpercatinib, pralsetinib, and bevacizumab.

In some aspects, a method further comprises administering to the subject an epidermal growth factor receptor (EGFR) inhibitor (e.g., a therapeutically effective amount of an EGFR inhibitor), such as cetuximab. Other examples of EGFR inhibitors include the pan-EGFR inhibitors dacomitinib and mefatinib.

In some aspects, a method further comprises administering to the subject (e.g., a therapeutically effective amount of) a cyclin-dependent kinase (CDK) inhibitor (e.g., a CDK4/6 inhibitor). Examples of CDK inhibitors include abemaciclib, alvocidib, palbociclib, and ribociclib.

In some aspects, a method further comprises administering to the subject (e.g., a therapeutically effective amount of) a son of sevenless (SOS), e.g., SOS1, inhibitor. SOS1 inhibitors are disclosed, for example, in International Publication No. WO 2021/173524.

In some aspects, a method further comprises administering to the subject (e.g., a therapeutically effective amount of) a small heterodimer partner (SHP), e.g., SHP2, inhibitor. Examples of SHP2 inhibitors include SHP-099, RMC-4550, RMC4360 and TNO155.

In some aspects, a method further comprises administering to the subject an immunotherapy (e.g., a therapeutically effective amount of an immunotherapy). Immunotherapy agents include antibodies that inhibit proteins expressed by cancer cells, vaccines and immune cell (e.g., T-cell) infusions. Antibody agents useful for promoting anti-tumor responses include anti-CTLA-4 antibodies (e.g., ipilimumab, tremelimumab), anti-PD-1 antibodies (e.g., pembrolizumab, nivolumab, cemiplimab), anti-PD-L1 antibodies (e.g., atezolizumab, avelumab, durvalumab), anti-PD-L2 antibodies, anti-TIM-3 antibodies, anti-LAG-3 antibodies (e.g., relatlimab), anti-OX40 antibodies and anti-GITR antibodies. In some aspects, the immunotherapy is an immune checkpoint inhibitor (e.g., a therapeutically effective amount of an immune checkpoint inhibitor), e.g., for treating a solid tumor cancer. Examples of immune checkpoint inhibitors include inhibitors of CTLA-4 (e.g., ipilimumab, tremelimumab), PD-1 (e.g., nivolumab, pembrolizumab), PD-L1 (e.g., avelumab), PD-L2, TIM-3, LAG-3 (e.g., relatlimab), OX40 and GITR. In some aspects, the immune checkpoint inhibitor (e.g., for treating a solid tumor cancer) is an inhibitor of CTLA-4, PD-1, PD-L1 or LAG-3. In some aspects, the immune checkpoint inhibitor (e.g., for treating a solid tumor cancer) is an inhibitor of PD-1 or PD-L1. In some aspects, the immune checkpoint inhibitor (e.g., for treating a solid tumor cancer) is an inhibitor of PD-1, such as pembrolizumab.

In some aspects, a method further comprises administering to the subject a chemotherapy (e.g., a therapeutically effective amount of a chemotherapy), e.g., comprising one or more chemotherapeutic agents. Examples of chemotherapeutic agents include, for example, antimetabolites (e.g., folic acid, nucleotide analogs, in particular, purine and pyrimidine derivatives); alkylating agents (e.g., cyclophosphamide, mechlorethamine, chlorambucil, melphalan, dacarbazine, temozolomide, thiotepa); anthracyclines (e.g., daunorubicin, doxorubicin, epirubicin, idarubicin, mitoxantrone, valrubicin); taxanes (e.g., paclitaxel, docetaxel, abraxane, taxotere); epothilones; histone deacetylase inhibitors (e.g., vorinostat, romidepsin); topoisomerase inhibitors (e.g., irinotecan, topotecan, etoposide, teniposide, tafluposide); kinase inhibitors (e.g., bortezomib, erlotinib, gefitinib, imatinib, vemurafenib, vismodegib); nucleotide analogs (e.g., azacitidine, azathioprine, capecitabine, cytarabine, doxifluridine, fluorouracil, gemcitabine, hydroxyurea, mercaptopurine, methotrexate, tioguanine); peptide antibiotics (e.g., bleomycin, actinomycin); platinum-based agents (e.g., carboplatin, cisplatin, oxaliplatin); retinoids (e.g., tretinoin, alitretinoin, bexarotene); and vinca alkaloids (e.g., vinblastine, vincristine, vindesine, vinorelbine), as well as their pharmaceutically acceptable salts. Further examples of chemotherapeutic agents include alkylating agents, such as thiotepa and cyclophosphamide (CYTOXAN™); alkyl sulfonates, such as busulfan, improsulfan and piposulfan; aziridines, such as benzodopa, carboquone, meturedopa, and uredopa; ethylenimines and methylamelamines, such as altretamine, triethylenemelamine, trietylenephosphoramide, triethylenethiophosphaoramide and trimethylolomelamine; acetogenins, such as bullatacin and bullatacinone; camptothecins, including the synthetic analogue topotecan; bryostatin; callystatin; CC-1065, including its adozelesin, carzelesin and bizelesin analogues; cryptophycins, such as cryptophycin 1 and cryptophycin 8; dolastatin; duocarmycin, including the synthetic analogues, KW-2189 and CBI-TMI; eleutherobin; pancratistatin; sarcodictyins; spongistatin; nitrogen mustards, such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosoureas, such as carmustine, chlorozotocin, fotemustine, lomustine, nimustine, and ranimustine; antibiotics, such as the enediyne antibiotics (e.g., calicheamicin, especially calicheamicin gamma 1 and calicheamicin theta I, see, e.g., Angew Chem. Intl. Ed. Engl. 33:183-186 (1994); dynemicin, such as dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, nitomycins, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, methotrexate, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, floxuridine, and 5-FU; androgens, such as calusterone, dromostanolone propionate, epitiostanol, mepitiostane, and testolactone; anti-adrenals, such as aminoglutethimide, mitotane, and trilostane; folic acid replenishers, such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; epothilones; etoglucid; gallium nitrate; hydroxyurea; lentinan; lonidamine; maytansinoids, such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes, such as T-2 toxin, verracurin A, roridin A and anguidine; urethan; vindesine; dacarbazine; mannomustine; mitobronitol; mitolactol; pipobroman; gacytosine; arabinoside ("Ara-C"); cyclophosphamide; thiotepa; taxoids, such as paclitaxel (e.g., TAXOL™, Bristol-Myers Squibb Oncology, Princeton, N.J.; nab-paclitaxel, such as the nanoparticle albumin-bound form of paclitaxel sold as ABRAXANE®) and doxetaxel (TAXOTERE®, Rhone-Poulenc Rorer, Antony, France); chlorambucil; gemcitabine; 6-thioguanine; mercaptopurine; methotrexate; folinic acid; platinum analogs such as cisplatin, oxaliplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitors, such as irinotecan and RFS 2000; difluoromethylomithine (DFMO); retinoic acid; and capecitabine; as well as their pharmaceutically acceptable salts.

Specific examples of chemotherapeutic agents include aclarubicin, actinomycin, alitretinon, altretamine, aminopterin, aminolevulinic acid, amrubicin, amsacrine, anagrelide, arsenic trioxide, asparaginase, atrasentan, belotecan, bexarotene, bendamustine, bleomycin, bortezomib, busulfan, camptothecin, capecitabine, carboplatin, carboquone, carmofur, carmustine, celecoxib, chlorambucil, chlormethine, cisplatin, cladribine, clofarabine, crisantaspase, cyclophosphamide, cytarabine, dacarbazine, dactinomycin, daunorubicin, decitabine, demecolcine, docetaxel, doxorubicin, efaproxiral, elesclomol, elsamitrucin, enocitabine, epirubicin, estramustine, etoglucid, etoposide, floxuridine, fludarabine, fluorouracil (5FU), fotemustine, gemcitabine, gliadel implants, hydroxycarbamide, hydroxyurea, idarubicin, ifosfamide, irinotecan, irofulven, ixabepilone, larotaxel, leucovorin, liposomal doxorubicin, liposomal daunorubicin, lonidamine, lomustine, lucanthone, mannosulfan, masoprocol, melphalan, mercaptopurine, mesna, methotrexate, methyl aminolevulinate, mitobronitol, mitoguazone, mitotane, mitomycin, mitoxantrone, nedaplatin, nimustine, oblimersen, omacetaxine, ortataxel, oxaliplatin, paclitaxel, pegaspargase, pemetrexed, pentostatin, pirarubicin, pixantrone, plicamycin, porfimer sodium, prednimustine, procarbazine, raltitrexed, ranimustine, rubitecan, sapacitabine, semustine, sitimagene ceradenovec, strataplatin, streptozocin, talaporfin, tegafur-uracil, temoporfin, temozolomide, teniposide, tesetaxel, testolactone, tetranitrate, thiotepa, tiazofurine, tioguanine, tipifarnib, topotecan, trabectedin, triaziquone, triethylenemelamine, triplatin, tretinoin, treosulfan, trofosfamide, uramustine, valrubicin, verteporfin, vinblastine, vincristine, vindesine, vinflunine, vinorelbine, vorinostat and zorubicin, or a pharmaceutically acceptable salt of the foregoing.

Numerous other therapies can also be administered during treatment (e.g., cancer treatment, treatment of an autoimmune disease) to mitigate the effects of the disease and/or side effects of the treatment, including therapies to manage pain (e.g., narcotics, acupuncture), gastric discomfort (e.g., antacids), dizziness (e.g., anti-vertigo medications), nausea (e.g., anti-nausea medications), infection (e.g., medications to increase red/white blood cell counts) and the like, all of which are readily appreciated by the person skilled in the art.

A compound of the disclosure or other therapeutic agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. In some aspects, administration (e.g., of a compound of the disclosure) is oral. In some aspects, administration (e.g., of a compound of the disclosure) is intravenous. In some aspects, administration (e.g., of a compound of the disclosure) is by injection or infusion. The preferred mode of administration can vary depending on the particular compound or agent.

Typically, a compound of the disclosure or other therapeutic agent will be administered from about 1 to about 6 (e.g., 1, 2, 3, 4, 5 or 6) times per day, also or alternatively, as an infusion (e.g., a continuous infusion). In some embodiments, a compound of the disclosure or other therapeutic agent is administered once daily (QD) or twice daily (BID). In some embodiments, a compound of the disclosure or other therapeutic agent is administered BID.

A compound of the disclosure or other therapeutic agent can be administered in a dosage ranging from about 0.001 mg/kg to about 100 mg/kg of body weight or, alternatively, in a dosage ranging from about 1 mg/dose to about 5,000 mg/dose, every 4 to 120 hours, or according to the requirements of the particular agent. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages can be from about 1 mg/dose to about 5,000 mg/dose, from about 10 mg/dose to about 2,500 mg/dose or from about 100 mg/dose to about 1,000 mg/dose.

Doses lower or higher than those recited above may be required. Specific dosage and treatment regimens for any particular patient will depend, for example, upon a variety of factors, such as the activity of the specific agent employed, the age, body weight, general health status, sex, diet, time of administration, rate of excretion, drug combination, the severity and course of the disease, condition or symptoms, the subject's disposition to the disease, condition or symptoms, and the judgment of the treating physician. Determining the dosage for a particular agent, subject and disease, disorder or condition is within the abilities of one of skill in the art.

Exemplification

The compounds of the disclosure can be prepared in a number of ways known to one skilled in the art in view of the methods, reaction schemes and examples provided herein. The compounds of the disclosure can be synthesized using the methods described below, together with synthetic methods known in the art of synthetic organic chemistry, or by variations thereon, as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound.

The starting materials are generally available from commercial sources such as Sigma Aldrich or other commercial vendors, or are prepared as described herein, or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), Larock, R. C., *Comprehensive Organic Transformations*, $2^{nd}$ ed., Wiley-VCH Weinheim, Germany (1999), or Beilsteins Handbuch der organischen Chemie, 4, Aufl. ed. Springer-Verlag, Berlin, including supplements (also available via the Beilstein online database).

For illustrative purposes, the reaction schemes depicted below provide potential routes for synthesizing the compounds of the disclosure as well as intermediates. Those skilled in the art will appreciate that other synthetic routes may be used to synthesize the compounds of the present disclosure. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the disclosure, protection of remote functionality of intermediates may be necessary. The need for such protection will vary depending on the nature of the remote functionality and the conditions of the preparation methods. The need for such protection is readily determined by one skilled in the art. For a general description of protecting groups and their use, see Greene, T. W. et al., *Protecting Groups in Organic Synthesis*, 4th Ed., Wiley (2007). Protecting groups incorporated in making of the compounds of the present disclosure, such as the trityl protecting group, may be shown as one regioisomer but may also exist as a mixture of regioisomers.

The following abbreviations when used hereinbelow have the corresponding meanings:

ACN acetonitrile;
Boc tert-butyloxycarbonyl;
C Celsius;
CMBP 2-(tributyl-phosphanylidene) acetonitrile
d doublet;
dd doublet of doublets;
DCM dichloromethane;
DMAP 4-dimethylaminopyridine;
DIEA N,N-diisopropylethylamine;
DMSO dimethylsulfoxide;
Dtbbpy 4,4'-di-tert-butyl-2,2'-dipyridyl;
Dtbpf (di-tert-butylphosphino) ferrocene
DME dimethoxyethane;
EtOAc/EA ethyl acetate;
EtOH ethanol;
FA formic acid;
g gram(s);
h/hr hour(s);
HPLC high pressure liquid chromatography;
HCl hydrochloric acid
L liter;
LC liquid chromatography;
LCMS liquid chromatography and mass spectrometry;
$LiAlH_4$ lithium aluminum hydride;
LiHMDS lithium bis(trimethylsilyl)amine;
MeOH methanol;
MOM methoxymethyl
MS mass spectrometry;
M molar;
m multiplet;
Me methyl;
min/min. minute(s);
mL milliliter(s);
μM micromolar;
m/z mass to charge ratio;
nM nanomolar;
NMP N-methylpyrrolidone;
NMR nuclear magnetic resonance;
NaH sodium hydride;
$NaHCO_3$ sodium bicarbonate;
Pd/C palladium on carbon;
PG protecting group;

PE petroleum ether;
$POCl_3$ phosphoryl chloride;
rt room temperature
S singlet;
sat. saturated;
SFC supercritical fluid chromatography;
t triplet;
t-Bu tert-butyl;
TEA triethylamine;
TBAF Tetra-n-butylammonium fluoride;
TBDPS tert-butyl(diphenyl)silyl
TTMSS tris(trimethylsilyl) silane;
TFA trifluoroacetic acid;
THF tetrahydrofuran;
TLC thin layer chromatography Synthesis of Int.A and Int.B a) Step 1-Synthesis of O1-benzyl O2-methyl 2-but-3-enylpyrrolidine-1,2-dicarboxylate

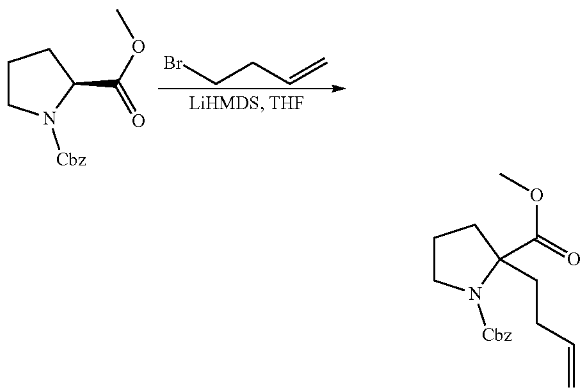

A solution of O1-benzyl O2-methyl (2S)-pyrrolidine-1,2-dicarboxylate (120 g, 455 mmol, CAS #182210-00-0) in THF (200 mL) was added dropwise to a solution of LiHMDS (1 M, 546 mL) at −78° C. for 1 hr. To the mixture was added 4-bromobut-1-ene (123 g, 911 mmol, CAS #5162-44-7) and was stirred at 25° C. for 16 hrs under $N_2$ atmosphere. Upon completion, the reaction mixture was concentrated in vacuo to provide a residue. The residue was purified via column chromatography ($SiO_2$, PE:EA=0:1 to 5:1) to afford the title compound (120 g, 66% yield) as white oil. LC-MS ($ESI^+$) m/z 318.0 $(M+H)^+$.

b) Step 2-Synthesis of O1-benzyl O2-methyl 2-[2-(oxiran-2-yl)ethyl]pyrrolidine-1,2-dicarboxylate

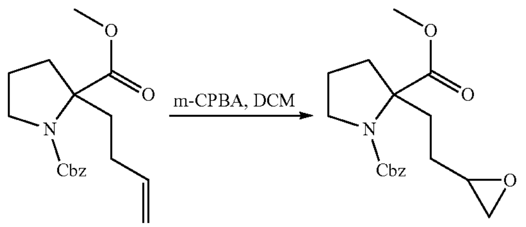 [SMILES: C=CCCC1(C(=O)OC)CCCN1C(=O)OCc1ccccc1 ; COC(=O)C1(CCC2CO2)CCCN1C(=O)OCc1ccccc1]

A solution of O1-benzyl O2-methyl 2-but-3-enylpyrrolidine-1,2-dicarboxylate (146 g, 460 mmol) and m-CPBA (233 g, 1.15 mol, 85% purity) in DCM (1500 mL) was stirred at 20° C. for 16 hrs. Upon completion, the reaction mixture was extracted with EA (3×400 mL). The combined organic layers were washed with brine (300 mL), dried over anhydrous $Na_2SO_4$, filtered and the filtrate was concentrated in vacuo to give a residue. The residue was purified via column chromatography ($SiO_2$, PE:EA=0:1 to 3:1) to afford the title compound (110 g, 45% yield) as white oil. $^1H$ NMR (400 MHz, $CDCl_3$) δ 7.40-7.27 (m, 5H), 5.18-5.07 (m, 2H), 3.78-3.70 (m, 3H), 3.50-3.46 (m, 2H), 2.73-2.71 (m, 2H), 2.43-2.42 (m, 2H), 2.13-1.85 (m, 5H), 1.53-1.45 (m, 2H); LC-MS ($ESI^+$) m/z 334.1 $(M+H)^+$.

c) Step 3-Synthesis of Methyl 3-(hydroxymethyl)-1,2,3,5,6,7-hexahydropyrrolizine-8-carboxylate

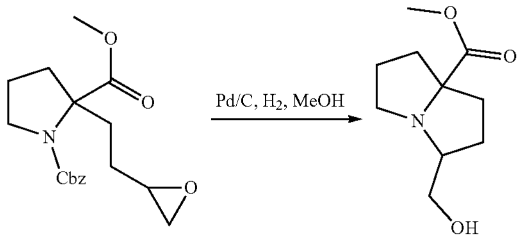

To a solution of O1-benzyl O2-methy 2-[2-(oxiran-2-yl)ethyl]pyrrolidine-1,2-dicarboxylate (110 g, 329 mmol) in MeOH (1000 mL) was added Pd/C (10.0 g, 330 mmol, 10% purity) under $N_2$ atmosphere. The suspension was degassed and purged with hydrogen gas for 3 times. The reaction mixture was stirred under hydrogen (50 psi) at 20° C. for 16 hrs. Upon completion, the reaction mixture was filtered and the filtrate was concentrated in vacuo to afford the title compound (62.0 g, 94% yield) as a yellow oil. LC-MS ($ESI^+$) m/z 200.0 $(M+H)^+$.

d) Step 4-Synthesis of Methyl 3-[[tert-butyl(diphenyl)silyl]oxymethyl]-1,2,3,5,6,7-hexahydropyrrolizine-8-carboxylate

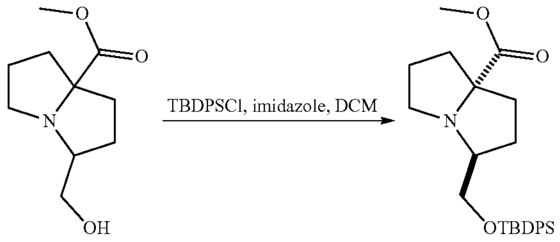

To a solution of methyl 3-(hydroxymethyl)-1,2,3,5,6,7-hexahydropyrrolizine-8-carboxylate (54.0 g, 271 mmol), tert-butyl-chloro-diphenyl-silane (111 g, 406 mmol) and imidazole (55.3 g, 813 mmol) in DCM (500 mL) was stirred at 20° C. for 16 hrs. Upon completion, the mixture was filtered and the filtrate was concentrated in vacuo to afford a residue. The residue was purified by column chromatography ($SiO_2$, PE:EA=0:1 to 3:1) to afford the title compound (trans racemic)(61.0 g, 41% yield) as a yellow oil. LC-MS ($ESI^+$) m/z 438.7 $(M+H)^+$.

e) Step 5-Synthesis of [3-[[Tert-butyl(diphenyl) silyl]oxymethyl]-1,2,3,5,6,7-hexahydropyrrolizin-8-yl]methanol

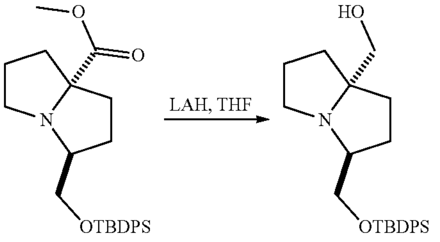

To a solution of methyl 3-[[tert-butyl(diphenyl)silyl] oxymethyl]-1,2,3,5,6,7-hexahydropyrrolizine-8-carboxylate (10.4 g, 23.0 mmol) in THF (100 mL) was added $LiAlH_4$ (1.80 g, 47.0 mmol). The mixture was stirred at −20° C. for 2 hrs. Upon completion, to the mixture was added $H_2O$ (2.2 mL) and 15% NaOH (2.2 mL). The mixture was then dried over anhydrous sodium sulfate, filtered and the filtrate was concentrated in vacuo to give a residue. The residue was purified by reverse phase (0.1% FA condition) to afford the title compound (trans racemic)(7.10 g 73% yield) as white solid. LC-MS ($ESI^+$) m/z 410.3 $(M+H)^+$.

f) Step 6-[(3S,8S)-3-[[tert-butyl(diphenyl)silyl] oxymethyl]-1,2,3,5,6,7-hexahydropyrrolizin-8-yl] methanol (Int.A) and [(3R,8R)-3-[[tert-butyl(diphenyl)silyl]oxymethyl]-1,2,3,5,6,7-hexahydropyrrolizin-8-yl]methanol (Int.B)

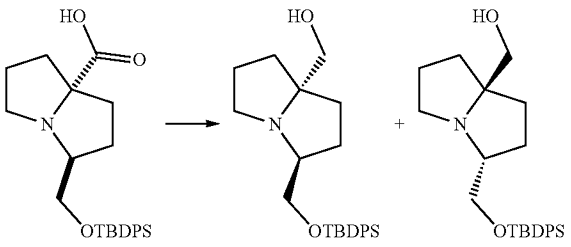

Int. A Int. B

[(3S,8S)-3-[[tert-butyl(diphenyl)silyl]oxymethyl]-1,2,3,5,6,7-hexahydropyrrolizin-8-yl]methanol (trans racemic) (40.0 g, 97.6 mmol) was separated by SFC (column: REGIS (s,s) WHELK-01 (250 mm*50 mm, 10 μm); mobile phase: [0.1% $NH_3$—$H_2O$ EtOH]; B %: 50%-50%, B2.95; 300 min) to afford Int.A (15.0 g, 37% yield)(retention time: 2.088 min) as yellow oil and Int.B (15.0 g, 37% yield)(retention time: 1.823 min) as yellow oil.

Int.A: $^1H$ NMR (400 MHz, $CDCl_3$) δ 8.38 (s, 1H), 7.58-7.53 (m, 4H), 7.41-7.30 (m, 6H), 3.93-3.88 (m, 1H), 3.81 (d, J=13.2 Hz, 1H), 3.76-3.64 (m, 2H), 3.57-3.48 (m, 2H), 3.39 (s, 1H), 3.22-3.12 (m, 1H), 2.32-2.22 (m, 1H), 2.08-1.83 (m, 5H), 1.75-1.61 (m, 2H), 1.00 (s, 9H); LC-MS ($ESI^+$) m/z 410.6 $(M+H)^+$.

Int.B: $^1H$ NMR (400 MHz, $CDCl_3$) δ 7.70-7.65 (m, 4H), 7.46-7.37 (m, 6H), 3.95-3.88 (m, 1H), 3.81-3.75 (m, 1H), 3.48 (s, 1H), 3.31 (s, 2H), 3.26-3.16 (m, 1H), 2.93-2.84 (m, 1H), 2.81-2.68 (m, 1H), 2.02-1.93 (m, 1H), 1.80-1.62 (m, 6H), 1.59-1.51 (m, 1H), 1.07 (s, 9H); LC-MS ($ESI^+$) m/z 410.6 $(M+H)^+$.

X-ray crystallographic analysis revealed that Int. A corresponded to [(3S,8S)-3-[[tert-butyl(diphenyl)silyl]oxymethyl]-1,2,3,5,6,7-hexahydropyrrolizin-8-yl]methanol, and Int.B corresponded to [(3R,8R)-3-[[tert-butyl(diphenyl)silyl]oxymethyl]-1,2,3,5,6,7-hexahydropyrrolizin-8-yl] methanol. Briefly, 10 mg Int.A and 25 μL HCl (1 mol/L) were dissolved in 600 μL heptane and kept in a sealed, 4-mL vial. In a separate sealed, 4-mL vial, 10 mg Int.B and 25 μL HCl (1 mol/L) were dissolved in 600 μL heptane and kept. The solutions were evaporated slowly at room temperature. The resulting crystals were analyzed using a Rigaku Oxford Diffraction XtaLAB Synergy-S four-circle diffractometer equipped with a HyPix-6000HE area detector, and the following equipment:

Cryogenic system: Oxford Cryostream 800

Cu: λ=1.54184 Å, 50W, Micro focus source with multilayer mirror (μ-CMF).

Distance from the crystal to the CCD detector: d=35 mm

Tube Voltage: 50 kV

Tube Current: 1 mA.

The resulting Int.A HCl crystal was a colorless block with the following dimensions: 0.30×0.30×0.20 $mm^3$. The symmetry of the crystal structure was assigned the monoclinic space group P21 with the following parameters: a=10.9303 (10) Å, b=7.80050 (10) Å, c=15.03770 (10) Å, α=90°, β=103.4170 (10)°, γ=90°, V=1247.15 (2) $Å^3$, Z=2, Dc=1.188 g/cm3, F (000)=480.0, μ(Cu Kα)=1.966 $mm^{-1}$, and T=293 (2) K. The resulting Int.B HCl crystal was a colorless block with the following dimensions: 0.30×0.30×0.20 $mm^3$. The symmetry of the crystal structure was assigned the monoclinic space group P21 with the following parameters: a=10.9653 (3) Å, b=7.7994 (2) Å, c=15.0838 (3) Å, α=90°, β=103.489 (2)°, γ=90°, V=1254.42 (5) $Å^3$, Z=2, Dc=1.181 g/cm3, F (000)=480.0, μ (Cu Kα)=1.955 $mm^{-1}$, and T=293 (2) K.

Example 1. Synthesis of Compound 1

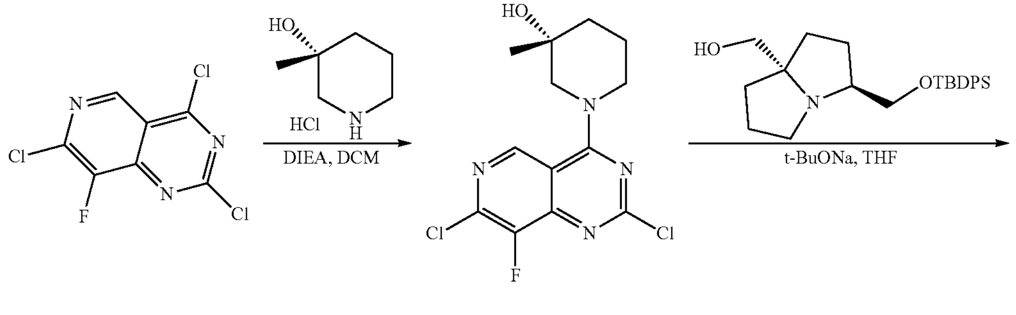

-continued
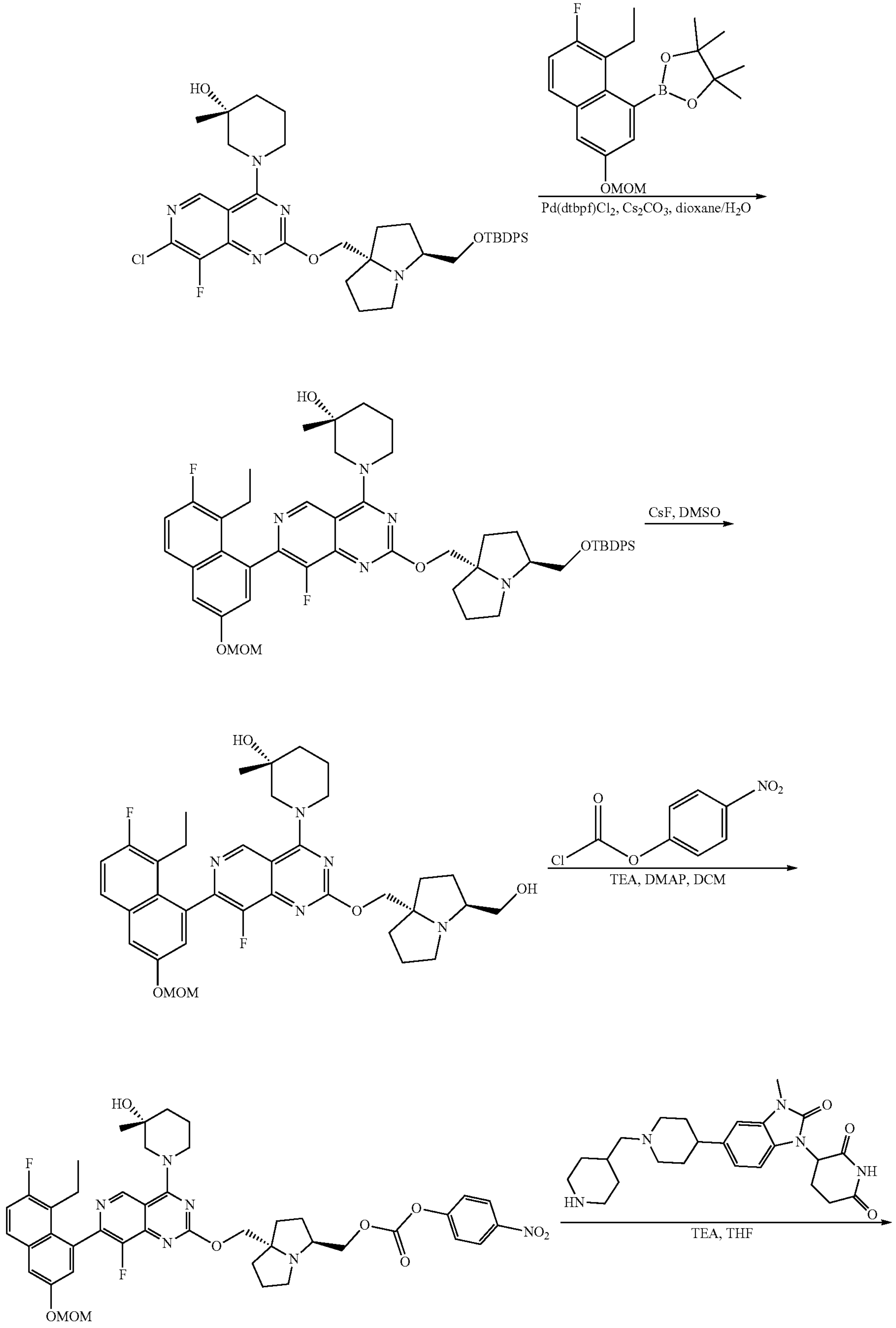

-continued

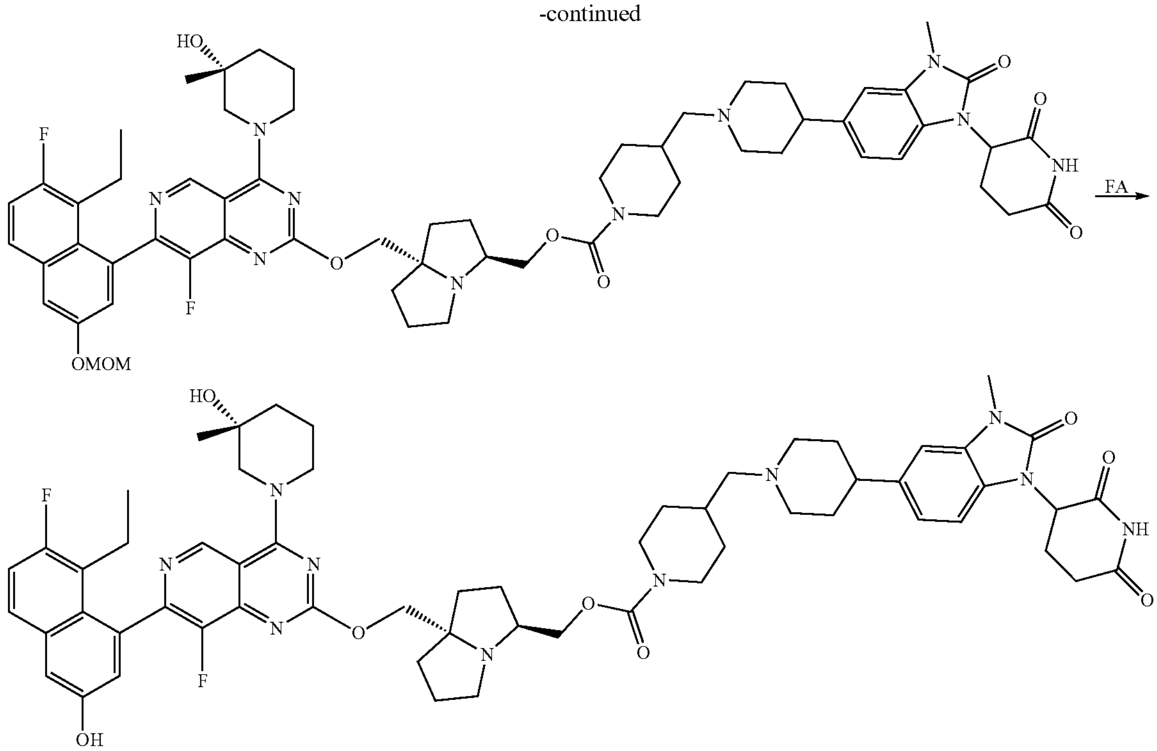

1

(a) Step 1-(3R)-1-(2,7-Dichloro-8-fluoro-pyrido[4,3-d]pyrimidin-4-yl)-3-methyl-piperidin-3-ol To a solution of 2,4,7-trichloro-8-fluoro-pyrido[4,3-d]pyrimidine (5.00 g, 19.8 mmol, CAS #2454396-80-4) and (3R)-3-methylpiperidin-3-ol (3.00 g, 19.8 mmol, HCl, CAS #2305080-34-4) in DCM (100 mL) was added DIEA (7.68 g, 59.4 mmol, 10.3 mL) at 0° C. The reaction mixture was stirred at 25° C. for 1 hr. On completion, the residue was diluted with water (30 mL), then the residue was extracted with EA (3×50 mL). The combined organic layers were dried over $Na_2SO_4$ and filtered, and the filtrate was concentrated in vacuo to give a residue. The reaction mixture was triturated with PE:EA 5:1 and filtered to afford a yellow solid, and the solid was concentrated in vacuo to give the title compound (4.50 g, 68% yield) as yellow solid. $^1$H NMR (400 MHz, DMSO-$d_6$) δ 9.18 (s, 1H), 4.74 (s, 1H), 4.46 (d, J=12.0 Hz, 1H), 4.11 (d, J=13.2 Hz, 1H), 3.57 (d, J=13.2 Hz, 1H), 3.29 (s, 1H), 1.67 (d, J=4.0 Hz, 3H), 1.16 (s, 3H), 0.90-0.76 (m, 1H); LC-MS (ESI) m/z 331.0 $(M+H)^+$.

(b) Step 2-(3R)-1-[2-[[(3S,8S)-3-[[Tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3-methyl-piperidin-3-ol To a solution of [(3S,8S)-3-[[tert-butyl(diphenyl)silyl]oxymethyl]-1,2,3,5,6,7-hexahydropyrrolizin-8-yl]methanol (2.47 g, 6.04 mmol) in toluene (30 mL) was added t-BuONa (1.16 g, 12.0 mmol) at 0° C. for 0.5 hr, then (3R)-1-(2,7-dichloro-8-fluoro-pyrido[4,3-d]pyrimidin-4-yl)-3-methyl-piperidin-3-ol (2.00 g, 6.04 mmol) was added. The reaction mixture was stirred at 25° C. for 0.5 hr. On completion, the residue was diluted with water (30 mL), then the residue was extracted with EA (3×50 mL). The combined organic layers were dried over $Na_2SO_4$, filtered and the filtrate was concentrated in vacuo to give a residue. The residue was purified by reverse phase (0.1% FA condition) to give the title compound (3.00 g, 70% yield) as white solid. LC-MS (ESI) m/z 704.3 $(M+H)^+$.

(c) Step 3-(3R)-1-[2-[[(3S,8S)-3-[[Tert-butyl(diphenyl)silyl]oxymethyl]-1,2,3,5,6,7-hexahydropyrrolizin-8-yl]methoxy]-7-[8-ethyl-7-fluoro-3-(methoxymethoxy)-1-naphthyl]-8-fluoro-pyrido[4,3-d]pyrimidin-4-yl]-3-methyl-piperidin-3-ol To a solution of (3R)-1-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3-methyl-piperidin-3-ol (1.00 g, 1.42 mmol) and 2-[8-ethyl-7-fluoro-3-(methoxymethoxy)-1-naphthyl]-4,4,5,5-tetramethyl-1,3,2-dioxaborolane (664 mg, 1.85 mmol, CAS #2621932-48-5) in dioxane (10 mL) and $H_2O$ (2 mL) was added ditert-butyl(cyclopentyl)phosphane; dichloropalladium; iron (46.2 mg, 70.9 μmol) and $Cs_2CO_3$ (1.39 g, 4.26 mmol), the reaction mixture was stirred at 100° C. for 2 hrs under $N_2$. On completion, the residue was diluted with water (30 mL), then the residue was extracted with EA (3×30 mL). The combined organic layers were dried over $Na_2SO_4$, filtered and the filtrate was concentrated in vacuo to give a residue. The residue was purified by column chromatography ($SiO_2$, DCM:MeOH=50:1 to 10:1) to give the title compound (500 mg, 39% yield) as yellow solid. LC-MS (ESI) m/z 902.4 $(M+H)^+$.

(d) Step 4-(3R)-1-[7-[8-Ethyl-7-fluoro-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol To a solution of (3R)-1-[2-[[(3S,8S)-3-[[tert-butyl(diphenyl)silyl]oxymethyl]-1,2,3,5,6,7-hexahydropyrrolizin-8-yl]methoxy]-7-[8-ethyl-7-fluoro-3-(methoxymethoxy)-1-naphthyl]-8-fluoro-pyrido[4,3-d]pyrimidin-4-yl]-3-methyl-piperidin-3-ol (400 mg, 443 μmol) in DMSO (10 mL) was added CsF (336 mg, 2.22 mmol). The reaction mixture was stirred at 25° C. for 1 hr. On completion, the residue was diluted with water (30 mL), then the residue was extracted with EA (3×30 mL). The combined organic layers were dried over $Na_2SO_4$, filtered and the filtrate concentrated in vacuo. The residue was purified by column chromatography ($SiO_2$, DCM:MeOH=50:1 to 10:1) to give the title compound (150 mg, 50% yield) as yellow solid. $^1H$ NMR (400 MHz, DMSO-$d_6$) δ 9.24 (s, 1H), 7.95 (s, 1H), 7.90 (dd, J=6.4, 8.4 Hz, 1H), 7.69-7.64 (m, 1H), 7.43 (t, J=9.2 Hz, 1H), 5.35-5.33 (m, 2H), 4.76 (d, J=10.0 Hz, 1H), 4.40-4.32 (m, 1H), 4.06 (dd, J=14.0, 19.2 Hz, 1H), 3.68-3.60 (m, 2H), 3.60-3.50 (m, 2H), 3.43 (s, 3H), 2.36 (td, J=6.8, 13.6 Hz, 2H), 2.21-1.96 (m, 4H), 1.87-1.50 (m, 14H), 1.17 (d, J=9.2 Hz, 3H), 0.75 (d, J=7.2 Hz, 3H); LC-MS (ESI) m/z 664.3 $(M+H)^+$.

(e) Step 5-[(3S,8S)-8-[[7-[8-Ethyl-7-fluoro-3-(methoxymethoxy)-1-naphthyl]-8-fluoro-4-[(3R)-3-hydroxyl-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate To a mixture of (3R)-1-[7-[8-ethyl-7-fluoro-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (60.0 mg, 90.4 μmol) in DCM (3 mL) was added TEA (27.4 mg, 271 μmol, 37.7 μL) and DMAP (1.10 mg, 9.04 μmol), then (4-nitrophenyl) carbonochloridate (54.6 mg, 271 μmol, CAS #7693-46-1) was added. The reaction mixture was stirred at 25° C. for 4 hrs. On completion, the residue was diluted with water (30 mL), then the residue was extracted with DCM (3×30 mL). The combined organic layers was dried over $Na_2SO_4$, filtered and the filtrate was concentrated in vacuo to give a residue to give the title compound (74.0 mg, 98% yield) as yellow solid. LC-MS (ESI) m/z 829.3 $(M+H)^+$.

(f) Step 6-[(3S,8S)-8-[[7-[8-Ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl-4-[[4-[1-(2,6-dioxo-3-piperidyl)-3-methyl-2-oxo-benzimidazol-5-yl]-1-piperidyl]methyl]piperidine-1-carboxylate To a solution of [(3S,8S)-8-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate (70 mg, 84.45 μmol) in THF (1 mL) was added TEA (8.55 mg, 84.4 μmol, 11.75 μL), then 3-[3-methyl-2-oxo-5-[1-(4-piperidylmethyl)-4-piperidyl]benzimidazol-1-yl]piperidine-2,6-dione (60.7 mg, 109 μmol) was added, the reaction mixture was stirred at 25° C. for 0.5 hr. On completion, the reaction mixture was concentrated in vacuo. The residue was purified by prep-HPLC (column: Phenomenex luna C18 150*25 mm*10 μm; mobile phase: [water (FA)-ACN]; gradient: 10%-40% B over 15 min) to give the title compound (20.0 mg, 20% yield) as white solid. LC-MS (ESI) m/z 1129.5 $(M+H)^+$.

(g) Step 7-[(3S,8S)-8-[[7-(8-Ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[1-(2,6-dioxo-3-piperidyl)-3-methyl-2-oxo-benzimidazol-5-yl]-1-piperidyl]methyl]piperidine-1-carboxylate (Compound 1)

A solution of [(3S,8S)-8-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[1-(2,6-dioxo-3-piperidyl)-3-methyl-2-oxo-benzimidazol-5-yl]-1-piperidyl]methyl]piperidine-1-carboxylate (20.0 mg, 17.7 μmol) in HCOOH (850 μg, 17.7 μmol) was stirred at 25° C. for 0.2 hr. On completion, the reaction mixture was concentrated in vacuo. The residue was purified by prep-HPLC (column: Phenomenex luna C18 150*25 mm*10 μm; mobile phase: [water (FA)-ACN]; gradient: 15%-60% B over 13 min) to give the title compound (15.5 mg, 74% yield, FA) as white solid. 1H NMR (400 MHz, DMSO-$d_6$) δ 11.08 (s, 1H), 9.22 (d, J=4.0 Hz, 1H), 8.19 (s, 1H), 7.76 (dd, J=6.0, 8.8 Hz, 1H), 7.38-7.30 (m, 2H), 7.08 (s, 1H), 7.03 (d, J=2.0 Hz, 1H), 6.99 (d, J=8.4 Hz, 1H), 6.89 (d, J=8.0 Hz, 1H), 5.33 (dd, J=5.2, 12.4 Hz, 1H), 4.91-4.61 (m, 1H), 4.36-4.28 (m, 1H), 4.24-4.04 (m, 6H), 4.03-3.88 (m, 4H), 3.32 (s, 3H), 2.92 (d, J=8.4 Hz, 2H), 2.81-2.66 (m, 6H), 2.34 (d, J=6.8 Hz, 1H), 2.13 (d, J=6.0 Hz, 3H), 2.07-1.90 (m, 6H), 1.70 (s, 16H), 1.59-1.45 (m, 2H), 1.16 (d, J=8.8 Hz, 3H), 1.00-0.90 (m, 2H), 0.73 (q, J=7.2 Hz, 3H). LC-MS (ESI) m/z 1085.4 $(M+H)^+$.

Example 2. Synthesis of Compound 2

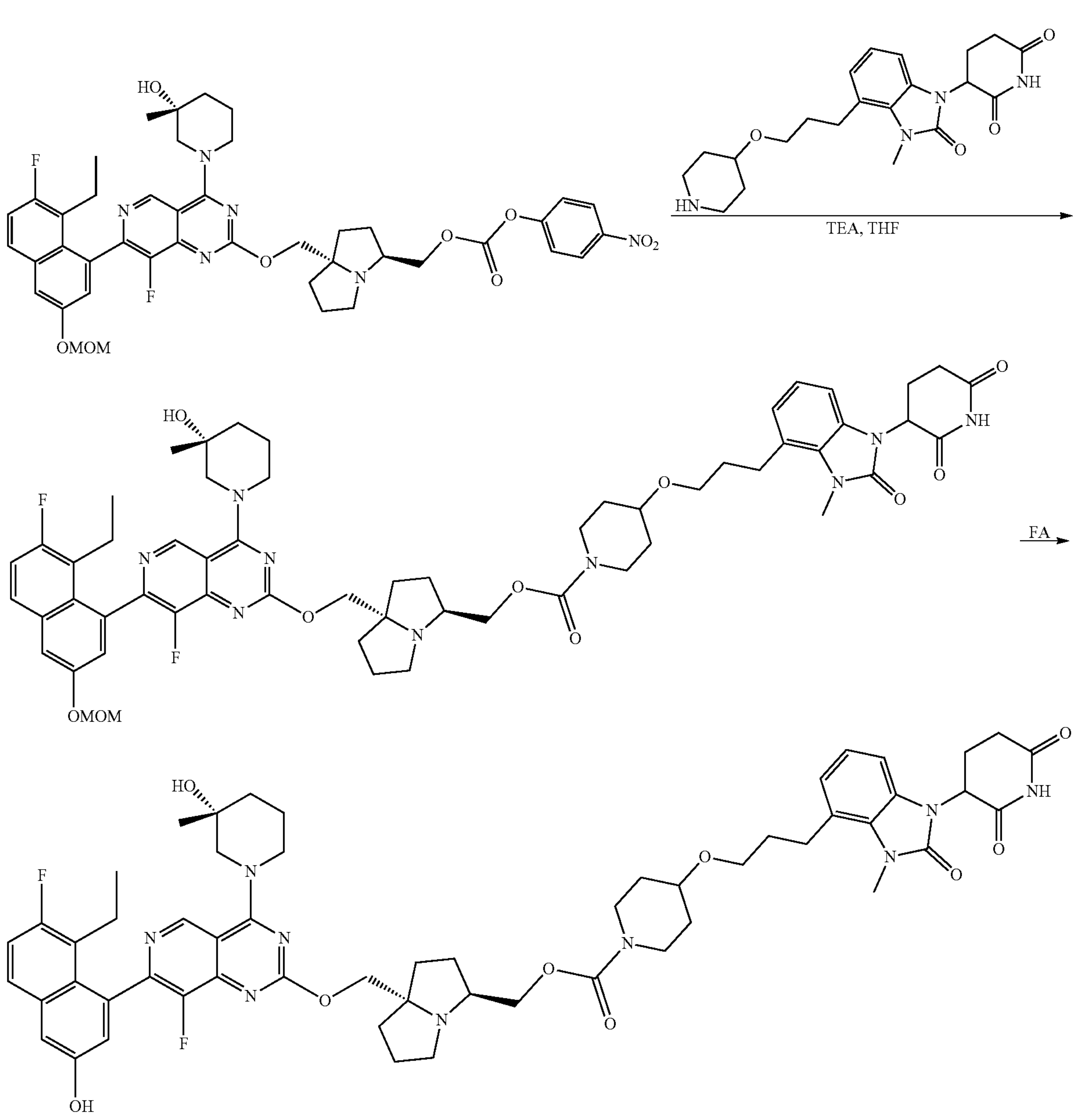

2

Step 1-[(3S,8S)-8-[[7-[8-Ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy]piperidine-1-carboxylate. To a solution of 3-[3-methyl-2-oxo-4-[3-(4-piperidyloxy) propyl]benzimidazol-1-yl]piperidine-2,6-dione (67.6 mg, 168 μmol, HCl salt) in THF (3 mL) was added TEA (59.8 mg, 591 μmol) and [(3S,8S)-8-[[7-[8-ethyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate (70.0 mg, 84.4 μmol). The mixture was stirred at 25° C. for 1 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 20%-50% B over 8 min) to give the title compound (50.0 mg, 54% yield) as yellow solid. LC-MS (ESI) m/z 1090.5 $(M+H)^+$.

Step 2-[(3S,8S)-8-[[7-(8-Ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[3-[1-(2,6-dioxo-3-piperidyl)-3-methyl-2-oxo-benzimidazol-4-yl]propoxy]piperidine-1-carboxylate (Compound 2). A solution of [(3S,8S)-8-[[7-[8-ethyl-7-fluoro-3-(methoxymethoxy)-1- naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[3-[1-(2,6-dioxo-3-piperidyl)-3-methyl-2-oxo-benzimidazol-4-yl]propoxy]piperidine-1-carboxylate (50.0 mg, 45.8 μmol) in HCOOH (22.0 mg, 458 μmol) was stirred at 25° C. for 1 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 22%-52% B over 10 min) to give the title compound (3.41 mg, 7% yield, FA salt) as yellow solid. $^1H$ NMR (400 MHz, DMSO-$d_6$) δ 11.08 (s, 1H), 10.10-9.82 (m, 1H), 9.22 (d, J=2.4 Hz, 1H), 7.84-7.64 (m, 1H), 7.41-7.27 (m, 2H), 7.03 (d, J=2.4 Hz, 1H), 6.98-6.90 (m, 2H), 6.89-6.82 (m, 1H), 5.35 (dd, J=5.2, 12.4 Hz, 1H), 4.75 (d, J=6.8 Hz, 1H), 4.33 (dt, J=2.8, 13.6 Hz, 1H), 4.26-4.17 (m, 1H), 4.17-4.10 (m, 2H), 4.07 (d, J=11.6 Hz, 2H), 3.69-3.59 (m, 3H), 3.55 (s, 3H), 3.46 (d, J=6.4 Hz, 3H), 3.12 (d, J=10.0 Hz, 2H), 3.00-2.89 (m, 3H), 2.79-2.69 (m, 3H), 2.65-2.59 (m, 2H), 2.21-1.93 (m, 5H), 1.87-1.59 (m, 14H), 1.56-1.45 (m, 1H), 1.44-1.30 (m, 2H), 1.22-1.09 (m, 3H), 0.73 (q, J=7.2 Hz, 3H); LC-MS (ESI*) m/z 1047.4 $(M+H)^+$.

Example 3. Synthesis of Compound 3

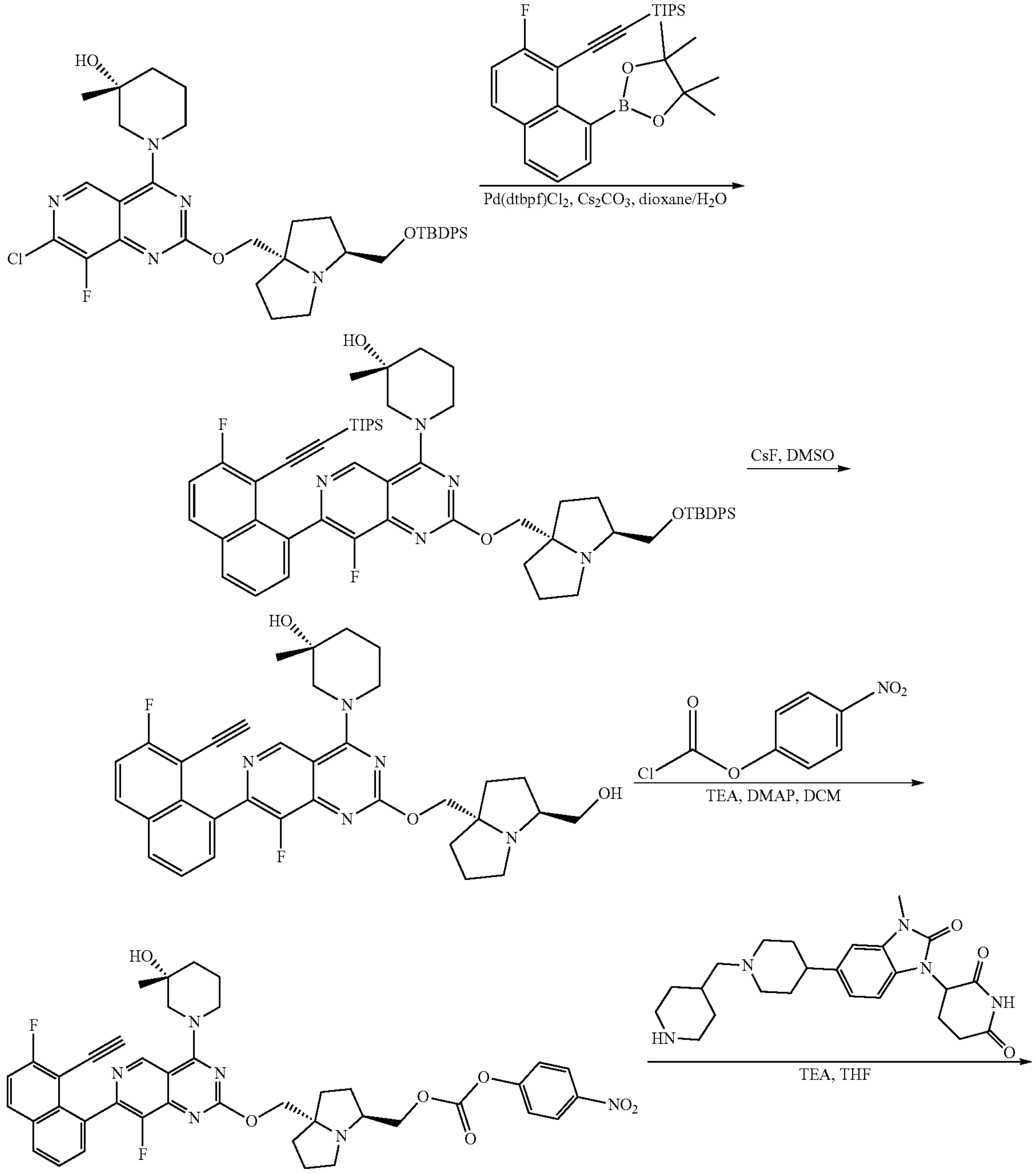

-continued

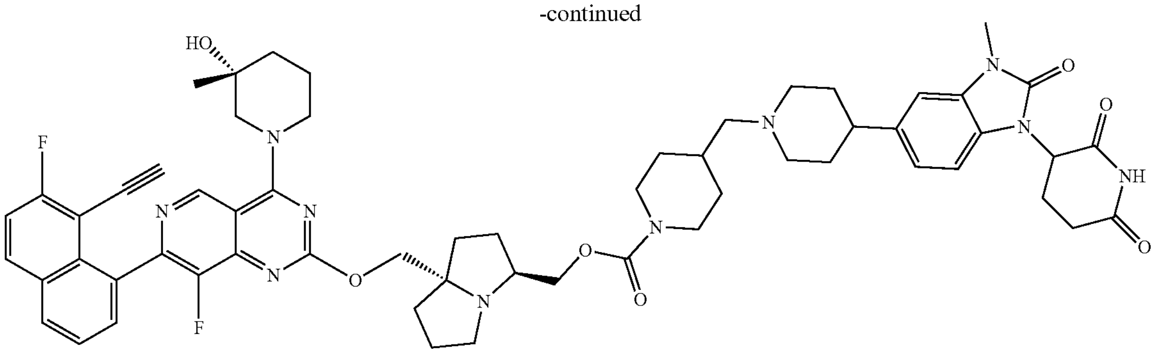

3

Step 1-(3R)-1-[2-[[(3S,8S)-3-[[Tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3-methyl-piperidin-3-ol. A mixture of (3R)-1-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3-methyl-piperidin-3-ol (1.00 g, 1.42 mmol), 2-[2-fluoro-8-(4,4,5,5-tetramethyl-1,3,2-dioxaborolan-2-yl)-1-naphthyl]ethynyl-triisopropyl-silane (835 mg, 1.85 mmol, CAS-2503307-87-5), $Cs_2CO_3$ (1.39 g, 4.26 mmol) and Pd (dtbpf) $Cl_2$ (46.2 mg, 70.9 μmol) in dioxane (5 mL) and $H_2O$ (1 mL) was degassed and purged with $N_2$ for 3 times, and then the mixture was stirred at 100° C. for 1 hr under $N_2$ atmosphere. On completion, the mixture was quenched with water (25 mL) and extracted with EA (3×25 mL), the combined organic phase was dried over anhydrous $Na_2SO_4$, filtered and filtrate was concentrated in vacuo to give a residue. The residue was purified by column chromatography ($SiO_2$, DCM/EA=1/0 to 7/3) to give the title compound (600 mg, 42% yield) as yellow solid. $^1H$ NMR (400 MHz, $CDCl_3$) δ 9.27-9.10 (m, 1H), 7.99-7.86 (m, 2H), 7.76-7.63 (m, 4H), 7.62-7.51 (m, 2H), 7.46-7.31 (m, 7H), 4.43-4.11 (m, 4H), 4.03-3.94 (m, 1H), 3.81 (d, J=4.8 Hz, 1H), 3.57-3.39 (m, 1H), 3.37-3.22 (m, 2H), 2.87-2.77 (m, 2H), 2.28-2.16 (m, 1H), 2.15-2.03 (m, 1H), 2.01-1.67 (m, 10H), 1.59-1.48 (m, 1H), 1.35 (s, 3H), 1.29-1.21 (m, 2H), 1.06 (s, 9H), 0.89 (t, J=6.0 Hz, 18H); LC-MS (ESI) m/z 995.0 $(M+H)^+$.

Step 2-(3R)-1-[7-(8-Ethynyl-7-fluoro-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol. To a solution of (3R)-1-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-8-(2-triisopropylsilylethynyl)-1-naphthyl]pyrido[4,3-d]pyrimidin-4-yl]-3-methyl-piperidin-3-ol (300 mg, 301 μmol) in DMSO (5 mL) was added CsF (137 mg, 905 μmol). The mixture was stirred at 25° C. for 12 hrs. On completion, the mixture was quenched with water (25 mL) and extracted with EA (3×25 mL), the combined organic layers was dried over anhydrous $Na_2SO_4$, filtered and filtrate was concentrated in vacuo to give a residue. The residue was purified by column chromatography ($SiO_2$, DCM/MeOH=1/0 to 9/1) to give the title compound (120 mg, 66% yield) as yellow solid. LC-MS (ESI) m/z 600.3 $(M+H)^+$.

Step 3-[(3S,8S)-8-[[7-(8-Ethynyl-7-fluoro-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate. To a solution of (3R)-1-[7-(8-ethynyl-7-fluoro-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (70.0 mg, 116 μmol) in DCM (5 mL) was added TEA (35.4 mg, 350 μmol), (4-nitrophenyl) carbonochloridate (70.5 mg, 350 μmol, CAS #7693-46-1) and DMAP (1.43 mg, 11.6 μmol). The mixture was stirred at 25° C. for 12 hrs. On completion, the mixture was quenched with water (5 mL) and extracted with DCM (5 mL×3), the combined organic phase was dried over anhydrous $Na_2SO_4$, filtered and filtrate was concentrated in vacuo to give the title compound (85.0 mg, 95% yield) as yellow solid. LC-MS (ESI) m/z 765.3 $(M+H)^+$.

Step 4-[(3S,8S)-8-[[7-(8-Ethynyl-7-fluoro-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[1-(2,6-dioxo-3-piperidyl)-3-methyl-2-oxo-benzimidazol-5-yl]-1-piperidyl]methyl]piperidine-1-carboxylate (Compound 3). To a solution of 3-[3-methyl-2-oxo-5-[1-(4-piperidylmethyl)-4-piperidyl]benzimidazol-1-yl]piperidine-2,6-dione (80.4 mg, 183 μmol, HCl salt) in THF (5 mL) was added TEA (9.26 mg, 91.5 μmol) and [(3S,8S)-8-[[7-(8-ethynyl-7-fluoro-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate (70.0 mg, 91.5 μmol). The mixture was stirred at 25° C. for 1 hr. On completion, the reaction mixture was concentrated in vacuo to give a residue. The residue was purified by prep-HPLC (column: Phenomenex luna C18 150*25 mm*10 μm; mobile phase: [water (HCl)-ACN]; gradient: 15%-45% B over 10 min) to give the title compound (4.46 mg, 8% yield, HCl salt) as yellow solid. $^1H$ NMR (400 MHz, DMSO-$d_6$) δ 11.09 (s, 1H), 10.72-10.53 (m, 1H), 9.85-9.68 (m, 1H), 9.23 (d, J=56.8 Hz, 1H), 8.23 (dt, J=5.6, 9.6 Hz, 2H), 7.78-7.55 (m, 3H), 7.04 (t, J=16.0 Hz, 2H), 6.92 (d, J=7.6 Hz, 1H), 5.36 (dd, J=4.8, 12.4 Hz, 1H), 4.78 (d, J=10.4 Hz, 1H), 4.70-4.52 (m, 2H), 4.50-4.34 (m, 2H), 4.28-4.11 (m, 2H), 4.02 (s, 3H), 3.66-3.55 (m, 2H), 3.15-2.95 (m, 5H), 2.95-2.74 (m, 5H), 2.71-2.61 (m, 2H), 2.35-2.28 (m, 2H), 2.24-1.91 (m, 15H), 1.90-1.78 (m, 3H), 1.77-1.58 (m, 4H), 1.27-1.08 (m, 7H); LC-MS $(ESI^+)$ m/z 1065.4 $(M+H)^+$.

Example 4. Synthesis of Compound 14
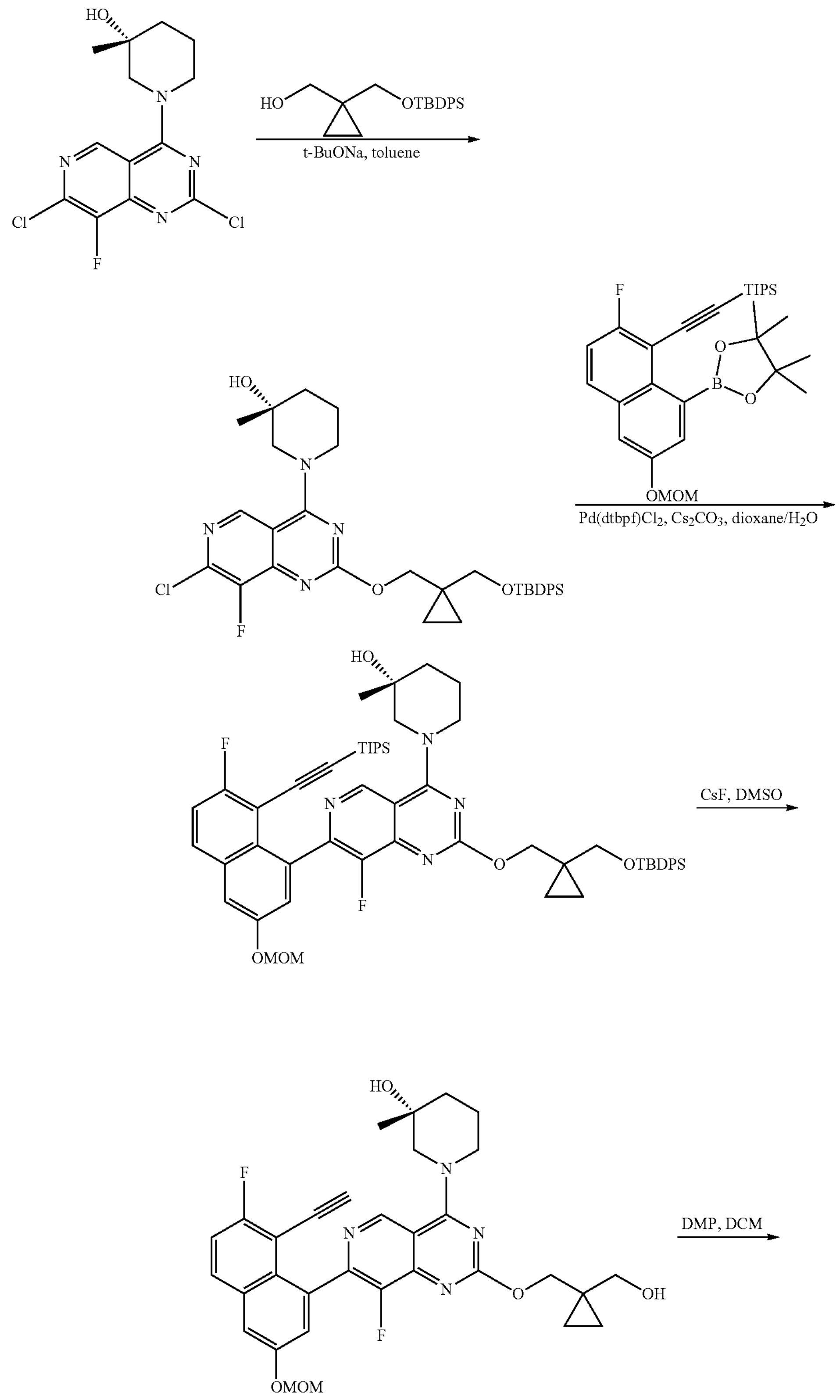

-continued

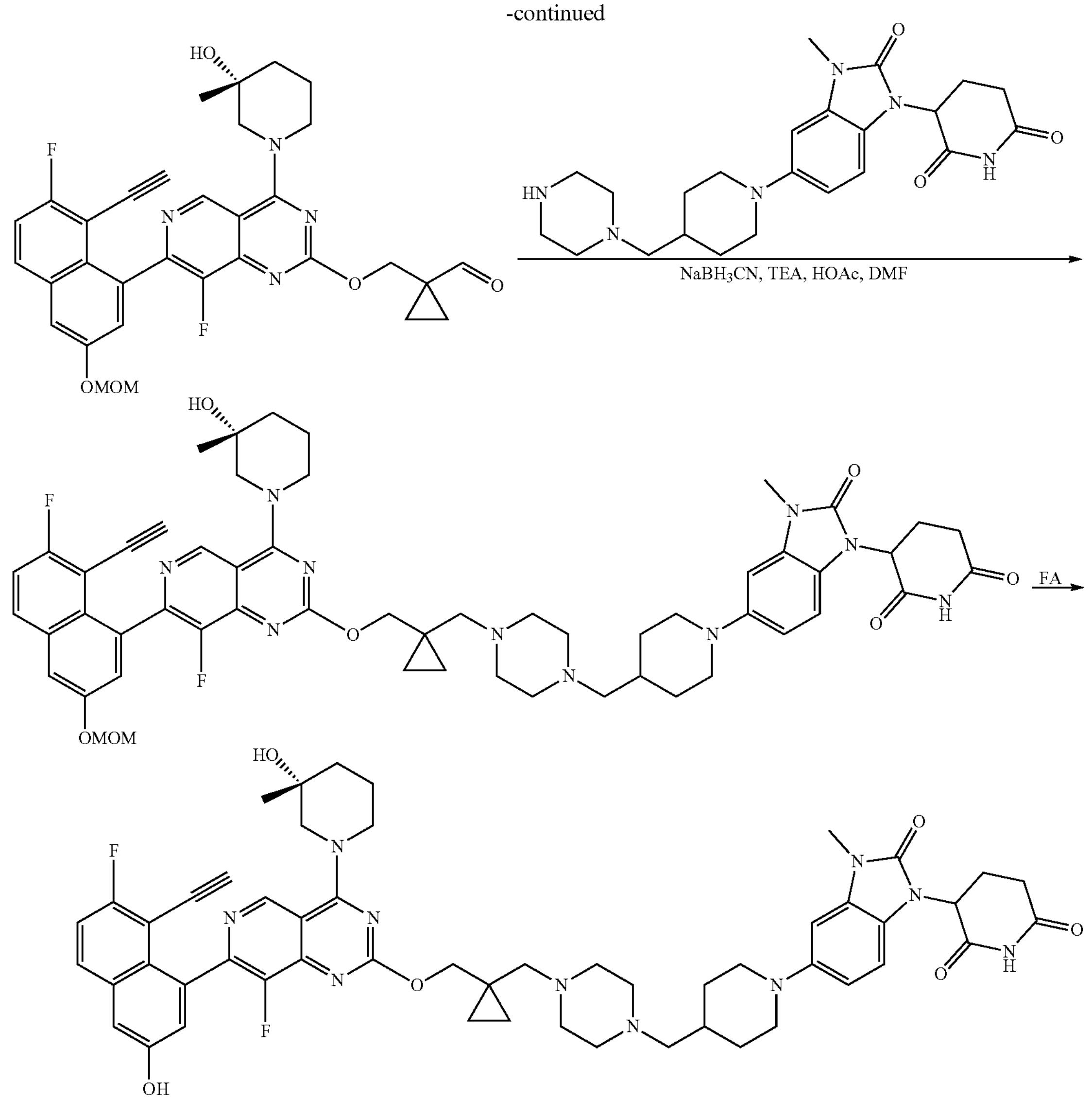

14

Step 1-(3R)-1-[2-[[1-[[Tert-butyl(diphenyl)silyl]oxymethyl]cyclopropyl]methoxy]-7-chloro-8-fluoro-pyrido[4,3-d]pyrimidin-4-yl]-3-methyl-piperidin-3-ol. To a solution of [1-[[tert-butyl(diphenyl)silyl]oxymethyl]cyclopropyl] methanol (2.26 g, 6.64 mmol, CAS #441785-04-2) in toluene (20 mL) was added t-BuONa (1.74 g, 18.1 mmol) at 0° C. for 1 hr, then (3R)-1-(2,7-dichloro-8-fluoro-pyrido[4,3-d]pyrimidin-4-yl)-3-methyl-piperidin-3-ol (2.00 g, 6.04 mmol) was added the mixture. The mixture was stirred at 25° C. for 1 hr under $N_2$ atmosphere. On completion, the reaction was quenched with aq·$NH_4Cl$ (20 mL), diluted with water (50 mL) and the mixture was extracted with DCM (3×50 mL), washed with brine (2×50 mL). The organic layer was dried with $Na_2SO_4$ and concentrated in vacuo to afford a residue. The crude product was purified by reversed-phase (0.1% FA condition) to give the title compound (800 mg, 20% yield) as yellow solid. $^1$H NMR (400 MHz, DMSO-$d_6$) δ 9.03 (s, 1H), 7.55 (d, J=7.2 Hz, 4H), 7.41-7.31 (m, 6H), 4.65 (s, 1H), 4.42-4.31 (m, 3H), 4.06-3.99 (m, 1H), 3.63 (s, 2H), 3.54 (d, J=13.2 Hz, 1H), 3.27-3.22 (m, 1H), 1.95 (s, 1H), 1.72-1.58 (m, 3H), 1.13 (s, 3H), 0.94 (s, 9H), 0.62 (s, 2H), 0.52 (s, 2H).

Step 2-(3R)-1-[2-[[1-[[Tert-butyl(diphenyl)silyl]oxymethyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3-methyl-piperidin-3-ol. To a solution of (3R)-1-[2-[[1-[[tert-butyl(diphenyl)silyl]oxymethyl]cyclopropyl]methoxy]-7-chloro-8-fluoro-pyrido[4,3-d]pyrimidin-4-yl]-3-methyl-piperidin-3-ol (334 mg, 525 μmol) in dioxane (5 mL) was added $Cs_2CO_3$ (513 mg, 1.58 mmol) in $H_2O$ (1 mL) and ditert-butyl(cyclopentyl) phosphane; dichloropalladium; iron (68.5 mg, 105 μmol), 2-[2-fluoro-6-(methoxymethoxy)-8-(4,4,5,5-tetramethyl-1,3,2-dioxaborolan-2-yl)-1-naphthyl]ethynyl-triisopropyl-silane (404 mg, 788 μmol, CAS #2503307-87-5). The mixture was stirred at 100° C. for 2 hrs under $N_2$ atmosphere. On completion, the reaction was diluted with water (50 mL) and the mixture was extracted with EA (3×50 mL), washed with brine (2×50 mL). The organic layer was dried with $Na_2SO_4$, filtered and the filtrate was concentrated in vacuo to afford a residue. The residue was purified by column chromatography ($SiO_2$, Petroleum ether/Ethyl acetate=100/1 to 4/1) to give the title compound (400 mg, 73% yield) as black solid. LC-MS (ESI) m/z 985.3 $(M+H)^+$.

Step 3-(3R)-1-[7-[8-Ethynyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-3-methyl-piperidin-3-ol. To a solution of (3R)-1-[2-[[1-[[tert-butyl(diphenyl)silyl]oxymethyl]cyclopropyl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3-methyl-piperidin-3-ol (285 mg, 289 μmol) in DMSO (10 mL) was added CsF (131 mg, 867 μmol). The mixture was stirred at 40° C. for 16 hrs. On completion, the reaction was diluted with water (50 mL) and the mixture was extracted with EA (3×50 mL), washed with brine (2×50 mL). The organic layer was dried with $Na_2SO_4$, filtered and the filtrate was concentrated in vacuo to afford a residue. The residue was purified by column chromatography ($SiO_2$, DCM/MeOH=100/1 to 10/1) to give the title compound (120 mg, 70% yield) as black solid. $^1H$ NMR (400 MHz, DMSO-$d_6$) δ 9.09-8.99 (m, 1H), 8.17-8.06 (m, 1H), 7.74 (s, 1H), 7.60-7.51 (m, 1H), 7.46-7.37 (m, 1H), 5.38 (s, 2H), 4.74 (d, J=12.4 Hz, 1H), 4.64 (d, J=4.4 Hz, 2H), 4.42-4.31 (m, 2H), 4.28 (s, 2H), 4.04-3.99 (m, 2H), 3.93 (s, 1H), 3.45 (s, 3H), 1.18 (s, 2H), 1.14 (d, J=3.6 Hz, 2H), 1.07 (s, 3H), 0.55 (s, 2H), 0.51 (s, 2H).

Step 4-1-[[7-[8-Ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde. To a solution of (3R)-1-[7-[8-ethynyl-7-fluoro-3-(methoxymethoxy)-1-naphthyl]-8-fluoro-2-[[1-(hydroxymethyl)cyclopropyl]methoxy]pyrido[4,3-d]pyrimidin-4-yl]-3-methyl-piperidin-3-ol (120 mg, 203 μmol) in DCM (5 mL) was added DMP (129 mg, 304 μmol). The mixture was stirred at 25° C. for 1 hr. On completion, the reaction mixture was quenched by saturated $Na_2S_2O_3$ (100 mL) and saturated $NaHCO_3$ (100 mL) at 25° C., then stirred for 30 minutes. The mixture was extracted with DCM (2×150 mL), then the combined organic layers was dried over anhydrous $Na_2SO_4$, filtered and the filtrate was concentrated in vacuo to give the title compound (100 mg, 83% yield) as yellow solid. $^1H$ NMR (400 MHz, DMSO-$d_6$) δ 9.14-9.00 (m, 1H), 8.97-8.88 (m, 1H), 8.15-8.09 (m, 1H), 7.75 (s, 1H), 7.56 (t, J=9.2 Hz, 1H), 7.49-7.37 (m, 1H), 5.39 (s, 2H), 4.75 (d, J=13.2 Hz, 1H), 4.58-4.50 (m, 2H), 4.46-4.31 (m, 2H), 4.06-3.96 (m, 3H), 3.45 (s, 3H), 1.32-1.31 (s, 2H), 1.24 (s, 3H), 1.14 (d, J=2.8 Hz, 2H), 0.91-0.65 (m, 3H), 0.54 (d, J=13.6 Hz, 1H).

Step 5-3-[5-[4-[[4-[[1-[[7-[8-Ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]-1-piperidyl]-3-methyl-2-oxo-benzimidazol-1-yl]piperidine-2,6-dione. To a solution of 3-[3-methyl-2-oxo-5-[4-(piperazin-1-ylmethyl)-1-piperidyl]benzimidazol-1-yl]piperidine-2,6-dione (53.8 mg, 122 μmol) in DMF (5 mL) was added TEA (30.9 mg, 305 μmol, 42.5 μL), HOAc (24.4 mg, 407 μmol, 23.3 μL), 1-[[7-[8-ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropanecarbaldehyde (60.0 mg, 101 μmol) and $NaBH_3CN$ (12.8 mg, 203 μmol). The mixture was stirred at 50° C. for 2 hrs. On completion, the reaction was concentrated in vacuo to afford a residue. The residue was purified by prep-HPLC (column: Phenomenex luna C18 150*25 mm*10 μm; mobile phase: [water (FA)-ACN]; gradient: 13%-43% B over 10 min) to give the title compound (50.0 mg, 43% yield) as white solid. LC-MS (ESI) m/z 1013.2 $(M+H)^+$.

Step 6-3-[5-[4-[[4-[[1-[[7-(8-Ethynyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]-1-piperidyl]-3-methyl-2-oxo-benzimidazol-1-yl]piperidine-2,6-dione (Compound 14). A solution of 3-[5-[4-[[4-[[1-[[7-[8-ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]cyclopropyl]methyl]piperazin-1-yl]methyl]-1-piperidyl]-3-methyl-2-oxo-benzimidazol-1-yl]piperidine-2,6-dione (40.0 mg, 39.4 μmol) in HCOOH (1.90 mg, 39.4 μmol, 3.00 mL) was stirred at 25° C. for 4 hrs. On completion, the reaction was concentrated in vacuo to afford a residue. The residue was purified by prep-HPLC (column: CD07-Daisogel SP-100-8-ODS-PK 150*25*10 μm; mobile phase: [water (NH4HCO3)-ACN]; gradient: 35%-64% B over 10 min) to give the title compound (15.3 mg, 38% yield) as yellow solid. $^1H$ NMR (400 MHz, DMSO-$d_6$) δ 10.88-10.65 (m, 1H), 9.95-9.81 (m, 1H), 9.25-9.04 (m, 1H), 7.94 (dd, J=5.6, 9.2 Hz, 1H), 7.47-7.35 (m, 2H), 7.22 (d, J=9.6 Hz, 1H), 6.90 (d, J=8.4 Hz, 1H), 6.76 (d, J=2.0 Hz, 1H), 6.62 (dd, J=2.0, 8.4 Hz, 1H), 5.22 (dd, J=5.6, 12.4 Hz, 1H), 4.61-4.48 (m, 1H), 4.45-4.22 (m, 3H), 4.11-3.93 (m, 1H), 3.82-3.75 (m, 1H), 3.62 (t, J=12.4 Hz, 1H), 3.54 (d, J=12.0 Hz, 2H), 3.49-3.37 (m, 1H), 3.30 (s, 3H), 2.94-2.83 (m, 1H), 2.73-2.61 (m, 4H), 2.47-2.44 (m, 3H), 2.37-2.33 (m, 5H), 2.15 (d, J=6.8 Hz, 2H), 2.07-1.98 (m, 2H), 1.80-1.69 (m, 4H), 1.65-1.55 (m, 1H), 1.26 (s, 3H), 1.25-1.23 (m, 1H), 1.20 (d, J=9.6 Hz, 3H), 0.69-0.59 (m, 2H), 0.45-0.40 (m, 2H); LC-MS ($ESI^+$) m/z 969.3 $(M+H)^+$.

Example 5. Synthesis of Compound 4

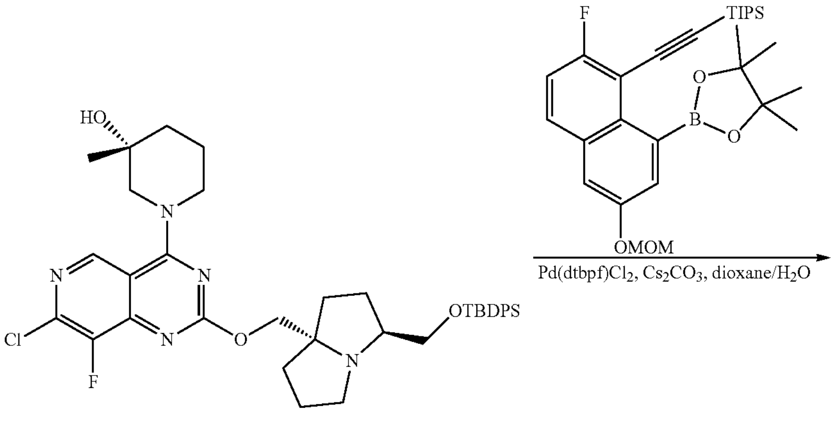

-continued
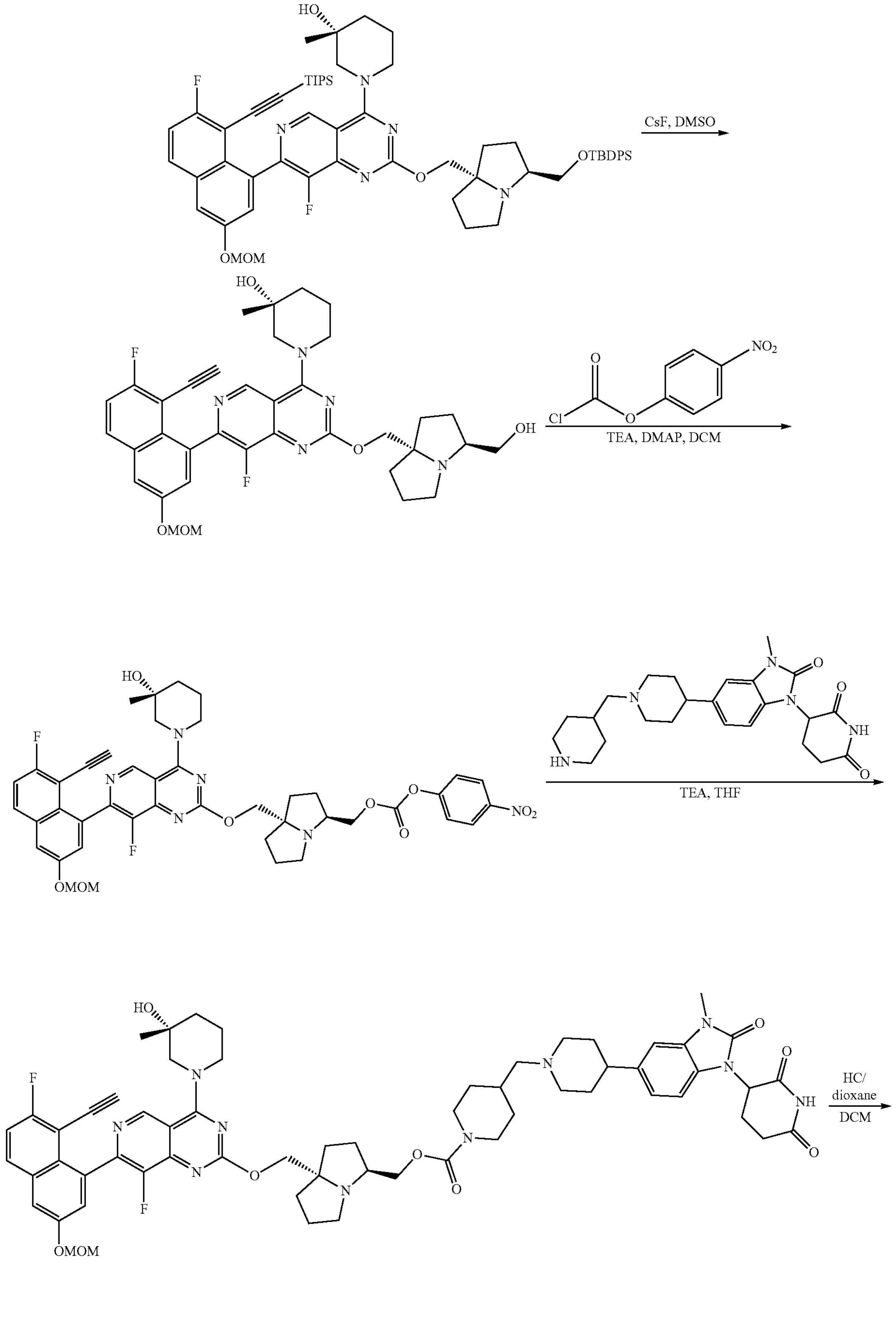

-continued

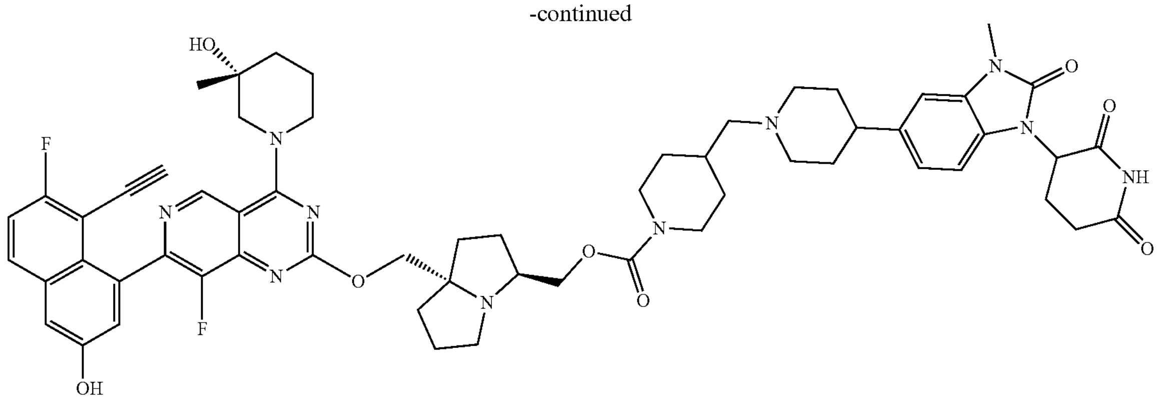

4

Step 1-(3R)-1-[2-[[(3S,8S)-3-[[Tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3-methyl-piperidin-3-ol. A mixture of (3R)-1-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3-methyl-piperidin-3-ol (500 mg, 709 μmol), 2-[2-fluoro-6-(methoxymethoxy)-8-(4,4,5,5-tetramethyl-1,3,2-dioxaborolan-2-yl)-1-naphthyl]ethynyl-triisopropyl-silane (545 mg, 1.06 mmol, CAS #2621932-37-2), $Cs_2CO_3$ (462 mg, 1.42 mmol) and ditert-butyl(cyclopentyl)phosphane; dichloropalladium; iron (23.1 mg, 35.4 μmol) in dioxane (5 mL) and $H_2O$ (1 mL) was degassed and purged with $N_2$ for 3 times, and then the mixture was stirred at 100° C. for 0.5 hrs under $N_2$ atmosphere. On completion, the mixture was concentrated in vacuo. The crude product was purified by reversed-phase HPLC (0.1% FA condition) to give the title compound (720 mg, 48% yield) as brown solid. $^1H$ NMR (400 MHz, DMSO-$d_6$) δ 9.48-9.23 (m, 1H), 8.13-8.08 (m, 1H), 7.77-7.72 (m, 1H), 7.64 (t, J=6.4 Hz, 4H), 7.57 (t, J=8.8 Hz, 1H), 7.53-7.41 (m, 6H), 7.32 (dd, J=2.0, 15.2 Hz, 1H), 5.41-5.33 (m, 2H), 4.95-4.68 (m, 1H), 4.68-4.42 (m, 3H), 4.25-4.10 (m, 1H), 3.98-3.89 (m, 3H), 3.67-3.52 (m, 2H), 3.50-3.45 (m, 2H), 3.44-3.40 (m, 4H), 2.54 (s, 2H), 2.30-2.03 (m, 6H), 1.98-1.91 (m, 2H), 1.80-1.61 (m, 3H), 1.23-1.18 (m, 3H), 1.03 (d, J=6.8 Hz, 9H), 0.86-0.80 (m, 15H), 0.65-0.45 (m, 3H).

Step 2-(3R)-1-[7-[8-Ethynyl-7-fluoro-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol. To a solution of (3R)-1-[2-[[(3S,8S)-3-[[tert-butyl(diphenyl)silyl]oxymethyl]-1,2,3,5,6,7-hexahydropyrrolizin-8-yl]methoxy]-8-fluoro-7-[7-fluoro-3-(methoxymethoxy)-8-(2-triisopropylsilylethynyl)-1-naphthyl]pyrido[4,3-d]pyrimidin-4-yl]-3-methyl-piperidin-3-ol (660 mg, 625 μmol) in DMSO (5 mL) was added CsF (475 mg, 3.13 mmol). The mixture was stirred at 25° C. for 16 hrs. On completion, the reaction mixture was added $H_2O$ (50 mL) and extracted with ethyl acetate (3×40 mL). The combined organic layers were washed with brine (30 mL), dried over anhydrous sodium sulfate, filtered and the filtrate was concentrated in vacuo to give the title compound (420 mg, 98% yield) as brown oil. $^1H$ NMR (400 MHz, DMSO-$d_6$) δ 9.23-8.96 (m, 1H), 8.12-8.00 (m, 1H), 7.70 (s, 1H), 7.50 (t, J=8.8 Hz, 1H), 7.38 (d, J=19.6 Hz, 1H), 5.34 (s, 2H), 4.73 (d, J=18.8 Hz, 1H), 4.60-4.25 (m, 2H), 4.08-3.97 (m, 2H), 3.95 (s, 1H), 3.66-3.55 (m, 2H), 3.49-3.42 (m, 2H), 3.40 (s, 3H), 3.10-3.00 (m, 1H), 2.72-2.59 (m, 2H), 2.08-1.93 (m, 2H), 1.73-1.46 (m, 10H), 1.13 (d, J=15.6 Hz, 3H); LC-MS (ESI) m/z 660.3 $(M+H)^+$.

Step 3-[(3S,8S)-8-[[7-[8-Ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate. To a solution of (3R)-1-[7-[8-ethynyl-7-fluoro-3-(methoxymethoxy)-1-naphthyl]-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (100 mg, 151 μmol) in DCM (3 mL) was added TEA (727 mg, 7.18 mmol) and DMAP (1.85 mg, 15.1 μmol). The mixture of (4-nitrophenyl) carbonochloridate (106 mg, 530 μmol, CAS #7693-46-1) in DCM (3 mL) was added to the reaction. The mixture was stirred at 25° C. for 16 hrs. On completion, the reaction mixture was added $H_2O$ (50 mL) and extracted with DCM (3×30 mL). The combined organic layers were washed with brine (20 mL), dried over anhydrous sodium sulfate, filtered and the filtrate was concentrated in vacuo to give the title compound (100 mg, 79% yield) as brown oil. LC-MS ($ESI^+$) m/z 825.4 $(M+H)^+$.

Step 4-[(3S,8S)-8-[[7-[8-Ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-3-methyl-2-oxo-benzimidazol-5-yl]-1-piperidyl]methyl]piperidine-1-carboxylate. To a solution of 3-[3-methyl-2-oxo-5-[1-(4-piperidylmethyl)-4-piperidyl]benzimidazol-1-yl]piperidine-2,6-dione (74.6 mg, 169 μmol) in THF (0.5 mL) was added TEA (25.7 mg, 254 μmol) and [(3S,8S)-8-[[7-[8-ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate (70.0 mg, 84.8 μmol). The mixture was stirred at 25° C. for 0.5 hrs. On completion, the mixture was concentrated in vacuo. The residue was purified by prep-HPLC (column: Phenomenex luna C18 150*25 mm*10 μm; mobile phase: [water (FA)-ACN]; gradient: 18%-48% B over 10 min) to give the title compound (35.0 mg, 39% yield) as faint yellow solid. LC-MS ($ESI^+$) m/z 563.7 $(1/2M+H)^+$.

Step 5-[(3S,8S)-8-[[7-(8-Ethynyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-3-methyl-2-oxo-benzimidazol-5-yl]-1-piperidyl]methyl]piperidine-1-carboxylate (Compound 4). To a solution of [(3S,8S)-8-[[7-[8-ethynyl-7-fluoro-3-(methoxymethoxy)-1-naphthyl]-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-3-methyl-2-oxo-benzimidazol-5-yl]-1-piperidyl]methyl]piperidine-1-carboxylate (20.0 mg, 17.7 μmol) in DCM (0.5 mL) was added HCl/dioxane (2 M, 0.5 mL). The mixture was stirred at 25° C. for 0.1 hr. On completion, the mixture was concentrated in vacuo. The residue was purified by prep-HPLC (column: Phenomenex luna C18 150*25 mm*10 μm; mobile phase: [water (FA)-ACN]; gradient: 5%-35% B over 8 min) to give the title compound (7.73 mg, 36% yield, FA salt) as yellow solid. $^1H$ NMR (400 MHz, DMSO-$d_6$) δ 11.07 (s, 1H), 9.28-9.01 (m, 1H), 7.97 (dd, J=6.0, 9.2 Hz, 1H), 7.45 (t, J=9.2 Hz, 1H), 7.39 (s, 1H), 7.21 (dd, J=2.0, 17.6 Hz, 1H), 7.08 (s, 1H), 6.99 (d, J=8.0 Hz, 1H), 6.90 (d, J=7.6 Hz, 1H), 5.38-5.28 (m, 1H), 4.78-4.30 (m, 2H), 4.30-4.11 (m, 4H), 4.10-4.01 (m, 2H), 3.98 (s, 1H), 3.94 (s, 3H), 3.64-3.54 (m, 4H), 2.92 (d, J=10.0 Hz, 2H), 2.81-2.72 (m, 4H), 2.71-2.62 (m, 2H), 2.14 (d, J=4.8 Hz, 2H), 2.04-1.94 (m, 4H), 1.90-1.60 (m, 18H), 1.55-1.50 (m, 1H), 1.17 (d, J=16.0 Hz, 3H), 1.02-0.91 (m, 2H); LC-MS ($ESI^+$) m/z 1081.5 $(M+H)^+$.

Example 6. Synthesis of Compound 94

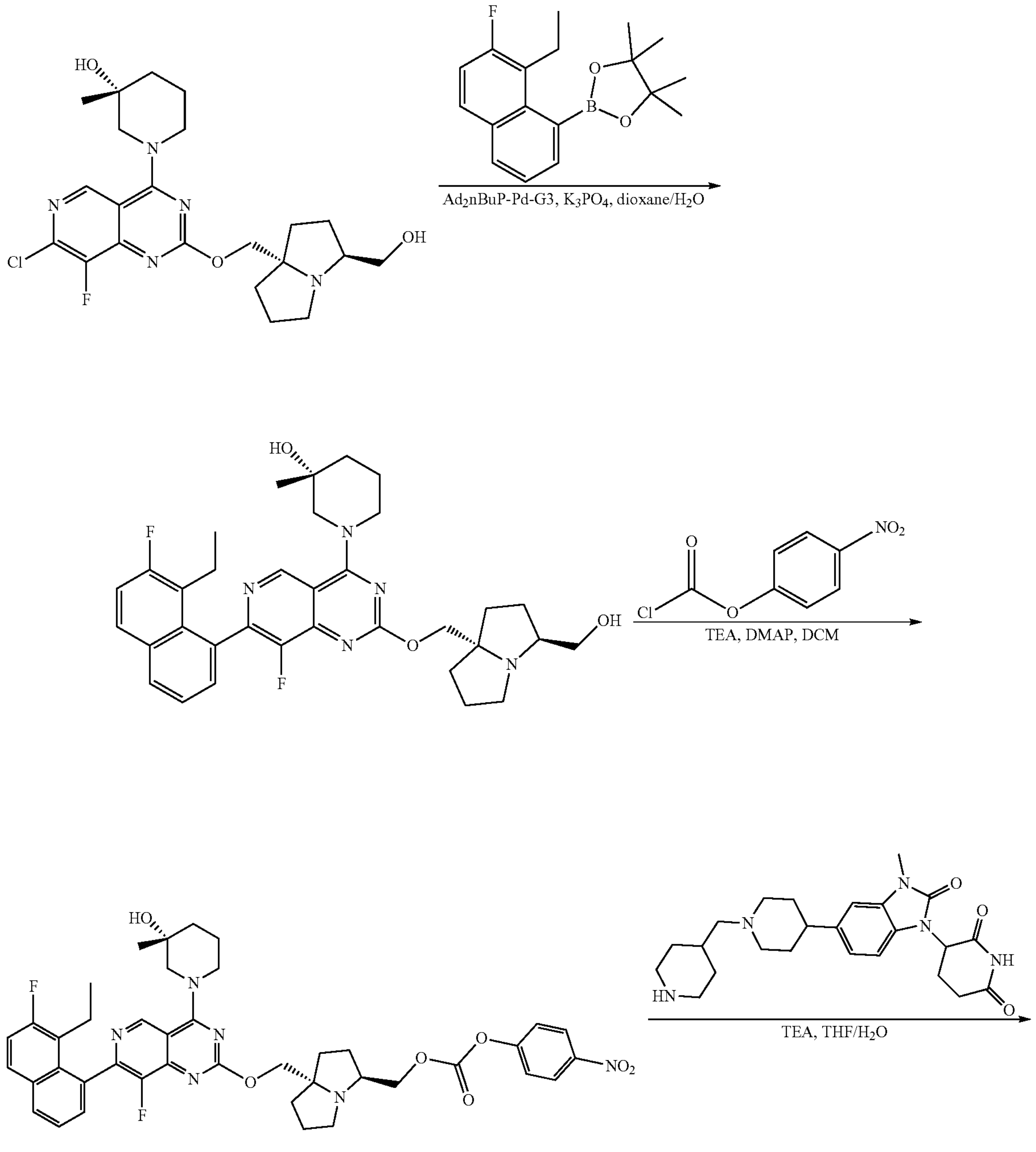

-continued

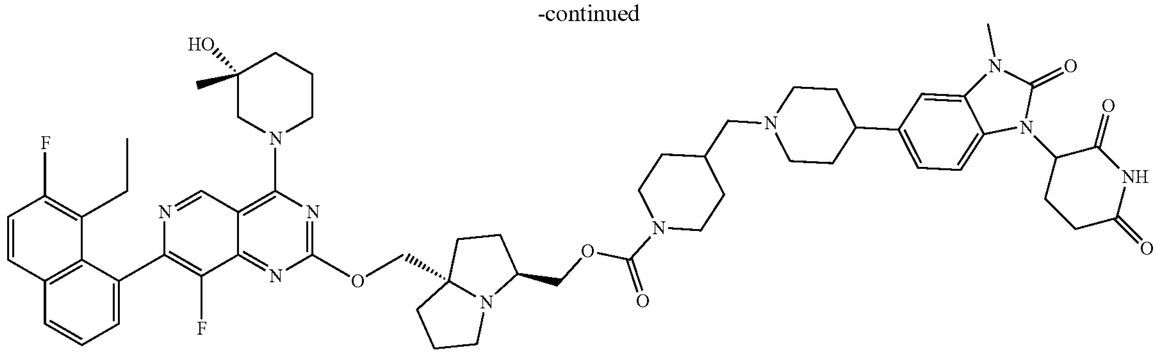

94

Step 1-(3R)-1-[7-(8-Ethyl-7-fluoro-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol. A mixture of 2-(8-ethyl-7-fluoro-1-naphthyl)-4,4,5,5-tetramethyl-1,3,2-dioxaborolane (360 mg, 1.20 mmol, CAS #2848567-14-4), (3R)-1-[7-chloro-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (280 mg, 600 μmol), [2-(2-aminophenyl)phenyl]palladium (1+); bis(1-adamantyl)-butyl-phosphane; methanesulfonate (43.7 mg, 60.0 μmol), $K_3PO_4$ (1.5 M, 1.20 mL) in dioxane (5 mL) and $H_2O$ (0.1 mL) was degassed and purged with $N_2$ for 3 times, and then the mixture was stirred at 80° C. for 1 hr under $N_2$ atmosphere. On completion, the mixture was diluted with $H_2O$ (10 mL), extracted with EA (3×20 mL), the organic layer was washed with brine (3×20 mL), dried with anhydrous $Na_2SO_4$, filtered and the filtrate was concentrated in vacuo. The residue was purified by column chromatography ($SiO_2$, DCM:MeOH=60/40) to give the title compound (300 mg, 82% yield) as yellow solid. $^1H$ NMR (400 MHz, DMSO-$d_6$) δ 9.23 (d, J=5.2 Hz, 1H), 8.12 (d, J=8.0 Hz, 1H), 8.02 (dd, J=6.0, 8.8 Hz, 1H), 7.58 (t, J=7.6 Hz, 1H), 7.53-7.46 (m, 2H), 4.76 (d, J=12.0 Hz, 1H), 4.69-4.52 (m, 1H), 4.34 (t, J=14.4 Hz, 1H), 4.22-4.12 (m, 1H), 4.11-3.98 (m, 2H), 3.70-3.59 (m, 2H), 3.57-3.48 (m, 2H), 3.16-3.03 (m, 1H), 2.86-2.76 (m, 1H), 2.75-2.68 (m, 1H), 2.42 (dd, J=6.6, 15.2 Hz, 1H), 2.28-2.15 (m, 1H), 2.09-1.97 (m, 2H), 1.77-1.51 (m, 10H), 1.17 (d, J=9.6 Hz, 3H), 0.76 (q, J=7.2 Hz, 3H); LC-MS ($ESI^+$) m/z 604.3 $(M+H)^+$ Step 2-(4-Nitrophenyl) [(3S,8S)-8-[[7-(8-ethyl-7-fluoro-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate. To a solution of (3R)-1-[7-(8-ethyl-7-fluoro-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (60.0 mg, 99.3 μmol) and (4-nitrophenyl) carbonochloridate (60.1 mg, 298 μmol, CAS #7693-46-1) in DCM (5 mL) was added TEA (30.1 mg, 298 μmol, 41.5 L) and DMAP (1.21 mg, 9.94 μmol). The mixture was stirred at 25° C. for 12 hrs. On completion, the mixture was concentrated in vacuo, then dissolved in DCM (10 mL), diluted with $H_2O$ (20 mL), extracted with DCM (3×10 mL), the organic layer was washed with brine (3×10 mL), dried with anhydrous $Na_2SO_4$, filtered and the filtrate was concentrated in vacuo to give the title compound (70.0 mg, 91% yield) as yellow solid. LC-MS (ESI) m/z 769.2 $(M+H)^+$.

Step 3-[(3S,8S)-8-[[7-(8-ethyl-7-fluoro-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl-4-[[4-[1-(2,6-dioxo-3-piperidyl)-3-methyl-2-oxo-benzimidazol-5-yl]-1-piperidyl]methyl] piperidine-1-carboxylate (Compound 94). To a solution of (4-nitrophenyl) [(3S,8S)-8-[[7-(8-ethyl-7-fluoro-1-naphthyl)-8-fluoro-4-[(3R)-3-hydroxy-3-methyl-1-piperidyl] pyrido[4,3-d]pyrimidin-2-yl]oxymethyl]-1,2,3,5,6,7-hexahydropyrrolizin-3-yl]methyl carbonate (70.0 mg, 91.0 μmol) and 3-[3-methyl-2-oxo-5-[1-(4-piperidylmethyl)-4-piperidyl]benzimidazol-1-yl]piperidine-2,6-dione (65.0 mg, 136 μmol) in THF (2 mL) and $H_2O$ (0.5 mL) was added TEA (27.6 mg, 273 μmol). The mixture was stirred at 25° C. for 0.5 hr. On completion, the mixture was concentrated in vacuo. The residue was purified by prep-HPLC (column: Phenomenex luna C18 150*25 mm*10 μm; mobile phase: [water (FA)-ACN]; gradient: 5%-35% B over 8 min) to give the title compound (30.4 mg, 29% yield, FA) as yellow solid. $^1H$ NMR (400 MHz, DMSO-$d_6$) δ 11.08 (s, 1H), 9.23 (d, J=7.2 Hz, 1H), 8.11 (d, J=7.6 Hz, 1H), 8.02 (dd, J=6.0, 9.2 Hz, 1H), 7.62-7.55 (m, 1H), 7.53-7.41 (m, 2H), 7.11-7.05 (m, 1H), 6.99 (dd, J=2.0, 8.0 Hz, 1H), 6.94-6.86 (m, 1H), 5.33 (dd, J=5.2, 12.8 Hz, 1H), 4.94-4.55 (m, 1H), 4.33 (t, J=13.6 Hz, 1H), 4.24-4.12 (m, 3H), 4.10 (dd, J=3.2, 10.4 Hz, 1H), 4.06-4.00 (m, 1H), 3.96 (d, J=11.2 Hz, 2H), 3.66-3.60 (m, 2H), 3.56-3.54 (m, 2H), 3.32 (s, 3H), 3.29-3.24 (m, 2H), 2.95-2.84 (m, 3H), 2.81-2.69 (m, 4H), 2.68-2.57 (m, 2H), 2.46-2.38 (m, 1H), 2.25-2.18 (m, 1H), 2.13 (d, J=6.0 Hz, 2H), 2.08-1.91 (m, 5H), 1.78-1.62 (m, 14H), 1.56-1.47 (m, 1H), 1.16 (d, J=9.2 Hz, 3H), 1.03-0.88 (m, 2H), 0.76 (q, J=7.2 Hz, 3H); LC-MS (ESI*) m/z 1069.6 $(M+H)^+$.

Example 7. Synthesis of Compound 96

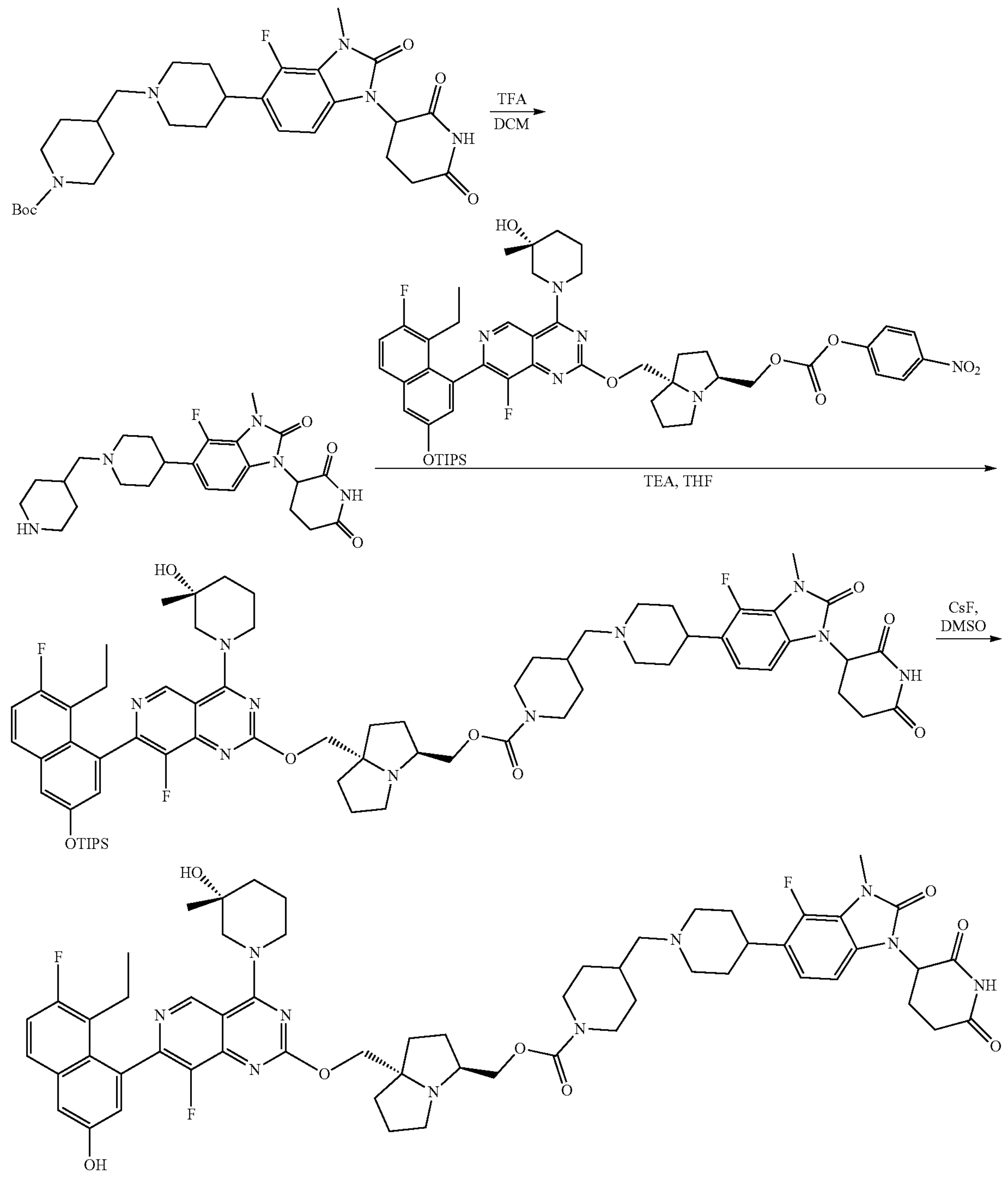

96

Step 1-3-[4-Fluoro-3-methyl-2-oxo-5-[1-(4-piperidylmethyl)-4-piperidyl/benzimidazol-1-yl]piperidine-2,6-dione. To a mixture of tert-butyl 4-[4-[1-(2,6-dioxo-3-piperidyl)-4-fluoro-3-methyl-2-oxo-benzimidazol-5-yl]-1-piperidyl]methyl]piperidine-1-carboxylate (100 mg, 179 μmol) in DCM (1 mL) was added TFA (4.61 g, 40.3 mmol, 3.00 mL). The reaction mixture was stirred at 25° C. for 1 hr. On completion, the reaction mixture was concentrated in vacuo to give the title compound (80.0 mg, 97% yield, TFA salt) as yellow oil. LC-MS (ESI*) m/z 458.2 $(M+H)^+$.

Step 2-[(3S,8S)-8-[[7-(8-Ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[1-(2,6-dioxo-3-piperidyl)-4-fluoro-3-methyl-2-oxo-benzimidazol-5-yl]-1-piperidyl]methyl]piperidine-1-carboxylate. To a mixture of 3-[4-fluoro-3-methyl-2-oxo-5-[1-(4-piperidylmethyl)-4-piperidyl]benzimidazol-1-yl]piperidine-2,6-dione (58.3 mg, 127 μmol, TFA) and (4-nitrophenyl) [(3S,8S)-8-[[7-(8-ethyl-7-fluoro-3-triisopropylsilyloxy-1-naphthyl)-8-fluoro-4-[(3R)-3-hydroxyl-3-methyl-1-piperidyl]pyrido[4,3-d]pyrimidin-2-yl]oxymethyl]-1,2,3,5,6,7-hexahydropyrrolizin-3-yl]methyl carbonate (60.0 mg, 63.7 μmol) in THF (1 mL) was added TEA (6.45 mg, 63.7 μmol, 8.87 μL). The reaction mixture was stirred at 25° C. for 0.5 hr. On completion, the reaction mixture was concentrated in vacuo. The residue was purified by prep-HPLC (column: Phenomenex luna C18 150*25 mm*10 μm; mobile phase: [water (FA)-ACN]; gradient: 28%-58% B over 10 min) to give the title compound (40.0 mg, 49% yield) as white solid. LC-MS (ESI$^+$) m/z 1259.5 (M+H)$^+$.

Step 3-[(3S,8S)-8-[[7-(8-Ethyl-7-fluoro-3-hydroxy-1-naphthyl)-8-fluoro-4-[(3R)-3-hydroxyl-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-4-fluoro-3-methyl-2-oxo-benzimidazol-5-yl]-1-piperidyl]methyl]piperidine-1-carboxylate (Compound 96). To a mixture of [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-4-fluoro-3-methyl-2-oxo-benzimidazol-5-yl]-1-piperidyl]methyl]piperidine-1-carboxylate (30.0 mg, 23.8 μmol) in DMSO (1 mL) was added CsF (7.24 mg, 47.6 μmol). The reaction mixture was stirred at 25° C. for 0.5 hr. On completion, the residue was diluted with water (10 mL) and extracted with EA (2×20 mL). The combined organic layers was dried over $Na_2SO_4$, filtered and the filtrate was concentrated in vacuo to give a residue. The residue was purified by prep-HPLC (column: Phenomenex luna C18 150*25 mm*10 μm; mobile phase: [water (FA)-ACN]; gradient: 5%-35% B over 8 min) to give the title compound (21.9 mg, 78% yield, FA) as white solid. $^1$H NMR (400 MHz, DMSO-$d_6$) δ 11.12 (s, 1H), 10.27-9.63 (m, 1H), 9.23 (d, J=4.4 Hz, 1H), 7.76 (dd, J=6.0, 8.8 Hz, 1H), 7.39-7.29 (m, 2H), 7.03 (d, J=2.4 Hz, 1H), 6.98-6.88 (m, 2H), 5.36 (dd, J=5.2, 12.4 Hz, 1H), 4.83-4.69 (m, 1H), 4.39-4.29 (m, 1H), 4.23-4.08 (m, 4H), 4.01 (s, 1H), 4.00-3.92 (m, 2H), 3.64 (d, J=13.2 Hz, 2H), 3.48 (s, 3H), 2.96-2.89 (m, 3H), 2.82-2.73 (m, 5H), 2.62 (d, J=19.6 Hz, 2H), 2.37 (d, J=6.0 Hz, 1H), 2.14 (d, J=5.6 Hz, 3H), 2.07-1.94 (m, 5H), 1.83-1.61 (m, 17H), 1.56-1.50 (m, 1H), 1.17 (d, J=9.2 Hz, 3H), 1.01-0.90 (m, 2H), 0.74 (q, J=7.6 Hz, 3H); LC-MS (ESI$^+$) m/z 1103.4 (M+H)$^+$.

Example 8. Synthesis of Compound 95

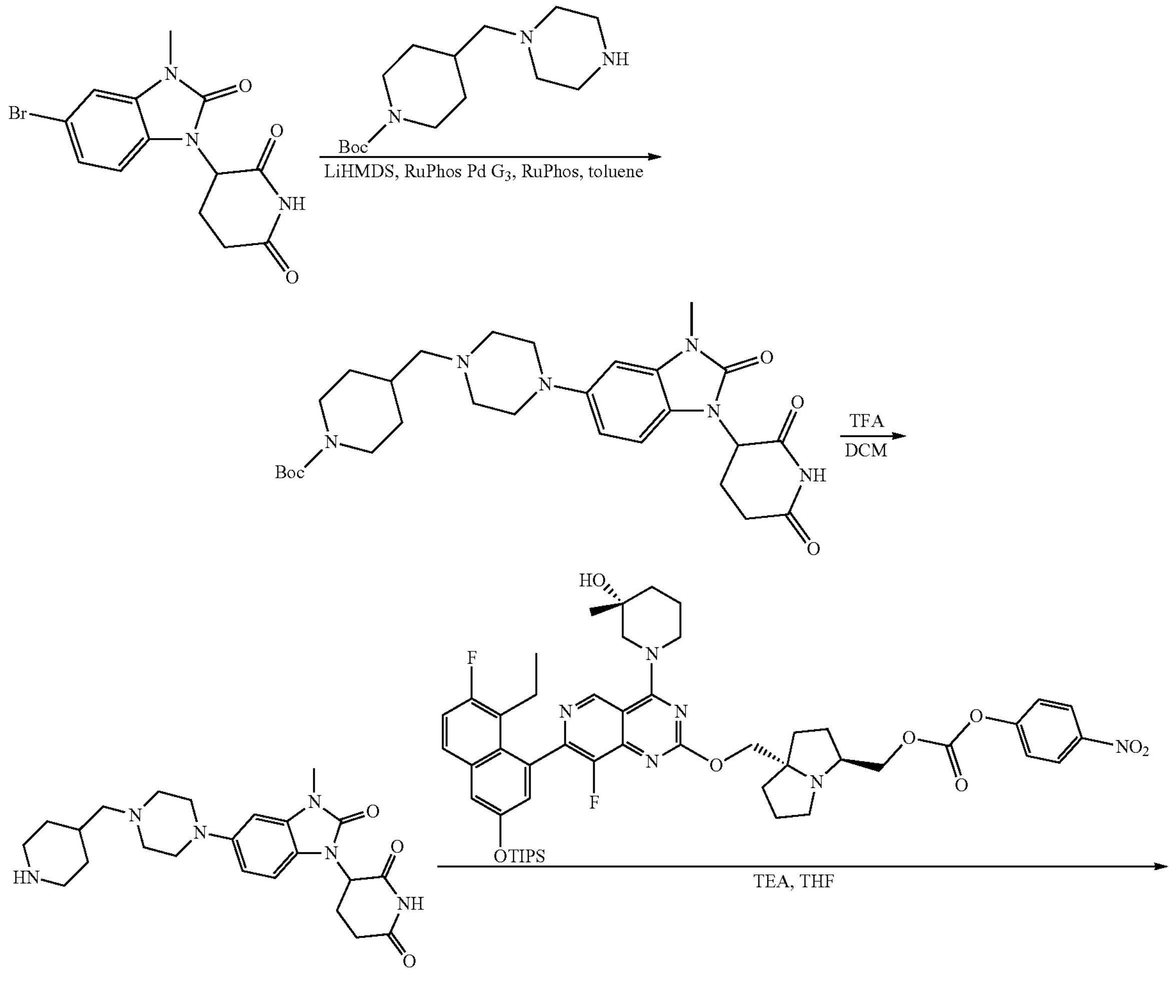

-continued

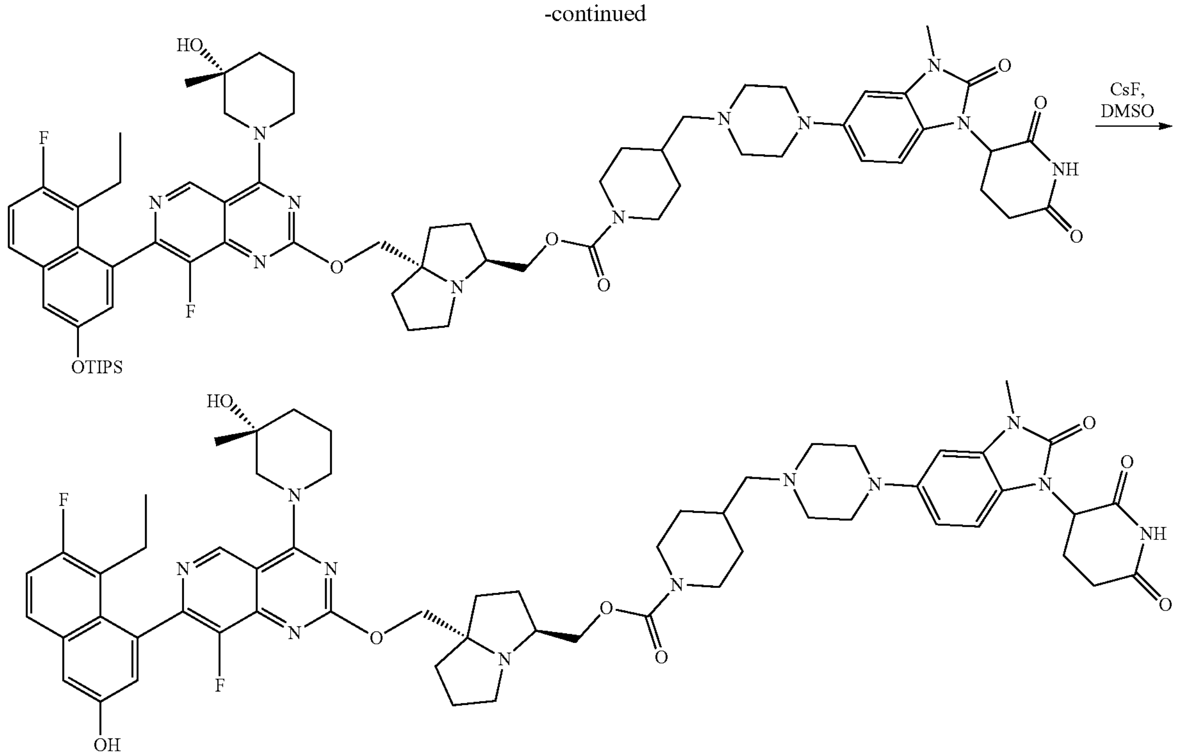

95

Step 1-Tert-butyl 4-[[4-[1-(2,6-dioxo-3-piperidyl)-3-methyl-2-oxo-benzimidazol-5-yl]piperazin-1-yl]methyl]piperidine-1-carboxylate. A mixture of 3-(5-bromo-3-methyl-2-oxo-benzimidazol-1-yl) piperidine-2,6-dione (500 mg, 1.48 mmol, CAS #2300099-98-1), tert-butyl 4-(piperazin-1-ylmethyl) piperidine-1-carboxylate (838 mg, 2.96 mmol, CAS #381722-48-1), RuPhos (69.0 mg, 147 μmol) and RuPhos Pd G3 (123 mg, 147 μmol) in toluene (20 mL) was degassed and purged with $N_2$ for 3 times, and then the mixture of LiHMDS (1 M, 4.44 mL) was added to reaction at 0° C. under $N_2$ atmosphere. Finally, the mixture was stirred at 70° C. for 1 hr. On completion, the mixture was added the $H_2O$ (1 mL) and FA to pH=6, finally, the mixture was concentrated in vacuo. The crude product was purified by reversed-phase HPLC (0.1% FA condition) to give the title compound (1.30 g, 37% yield) as white solid. $^1$H NMR (400 MHz, DMSO-$d_6$) δ 11.06 (s, 1H), 6.93 (d, J=8.5 Hz, 1H), 6.83 (d, J=2.0 Hz, 1H), 6.62 (dd, J=2.0, 8.4 Hz, 1H), 5.28 (dd, J=5.2, 12.8 Hz, 1H), 3.35-3.32 (m, 4H), 3.30 (s, 3H), 3.11-3.06 (m, 4H), 2.98-2.78 (m, 2H), 2.76-2.61 (m, 4H), 2.60-2.54 (m, 2H), 2.24-2.18 (m, 2H), 2.03-1.94 (m, 1H), 1.75-1.65 (m, 3H), 1.46-1.41 (m, 1H), 1.39 (s, 9H); LC-MS (ESI$^+$) m/z 541.3 $(M+H)^+$.

Step 2-3-[3-Methyl-2-oxo-5-[4-(4-piperidylmethyl) piperazin-1-yl]benzimidazol-1-yl]piperidine-2,6-dione. To a solution of tert-butyl 4-[[4-[1-(2,6-dioxo-3-piperidyl)-3-methyl-2-oxo-benzimidazol-5-yl]piperazin-1-yl]methyl]piperidine-1-carboxylate (90.0 mg, 166 μmol) in DCM (1 mL) was added TFA (1.54 g, 13.4 mmol). The mixture was stirred at 25° C. for 0.5 hrs. On completion, the mixture was concentrated in vacuo to give the title compound (80.0 mg, 86% yield, TFA salt) as colorless oil. LC-MS (ESI) m/z 441.3 $(M+H)^+$.

Step 3-[(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-3-methyl-2-oxo-benzimidazol-5-yl]piperazin-1-yl]methyl]piperidine-1-carboxylate. To a solution of 3-[3-methyl-2-oxo-5-[4-(4-piperidylmethyl) piperazin-1-yl] benzimidazol-1-yl]piperidine-2,6-dione (70.7 mg, 127 μmol, TFA salt) in THF (2 mL) was added TEA (19.3 mg, 191 μmol) and (4-nitrophenyl) [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate (60.0 mg, 63.7 μmol). The mixture was stirred at 25° C. for 0.5 hrs. On completion, the mixture was concentrated in vacuo. The residue was purified by prep-HPLC (column: Phenomenex luna C18 150*25 mm*10 μm; mobile phase: [water (FA)-ACN]; gradient: 25%-55% B over 8 min) to give the title compound (42.0 mg, 49% yield) as white solid. LC-MS (ESI) m/z 1243.8 $(M+H)^+$.

Step 4-[(3S,8S)-8-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-3-methyl-2-oxo-benzimidazol-5-yl]piperazin-1-yl]methyl]piperidine-1-carboxylate (Compound 95). To a solution of [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl4-[[4-[1-(2,6-dioxo-3-piperidyl)-3-methyl-2-oxo-benzimidazol-5-yl]piperazin-1-yl]methyl]piperidine-1-carboxylate (35.0 mg, 28.1 μmol) in DMSO (0.5 mL) was added CsF (17.1 mg, 112 μmol). The mixture was stirred at 25° C. for 0.2 hrs. On completion, the reaction was filtered by Syringe-driven Filte to obtain the filtrate. The residue was purified by prep-HPLC (column:

Phenomenex luna C18 150*25 mm*10 μm; mobile phase: [water (FA)-ACN]; gradient: 7%-37% B over 8 min) to give the title compound (29.1 mg, 89% yield, FA salt) as white solid. $^{1}$H NMR (400 MHz, DMSO-$d_6$) δ 11.06 (s, 1H), 9.96 (s, 1H), 9.26 (d, J=4.4 Hz, 1H), 7.76 (dd, J=6.0, 9.2 Hz, 1H), 7.38-7.30 (m, 2H), 7.03 (d, J=2.4 Hz, 1H), 6.93 (d, J=8.4 Hz, 1H), 6.82 (d, J=1.6 Hz, 1H), 6.61 (dd, J=1.6, 8.4 Hz, 1H), 5.29 (dd, J=5.2, 12.8 Hz, 1H), 4.75 (d, J=11.6 Hz, 1H), 4.49-4.23 (m, 4H), 4.22-3.96 (m, 4H), 3.71-3.52 (m, 2H), 3.30 (s, 3H), 3.27-3.22 (m, 1H), 3.20-3.00 (m, 6H), 2.97-2.83 (m, 2H), 2.83-2.61 (m, 4H), 2.60-2.52 (m, 2H), 2.40-2.17 (m, 4H), 2.15-2.10 (m, 1H), 2.09-1.99 (m, 2H), 1.98-1.92 (m, 2H), 1.92-1.60 (m, 12H), 1.17 (d, J=9.2 Hz, 3H), 1.07-0.94 (m, 2H), 0.73 (q, J=7.2 Hz, 3H); LC-MS ($ESI^+$) m/z 1086.4 $(M+H)^+$.
Example 9. Synthesis of Compound 97
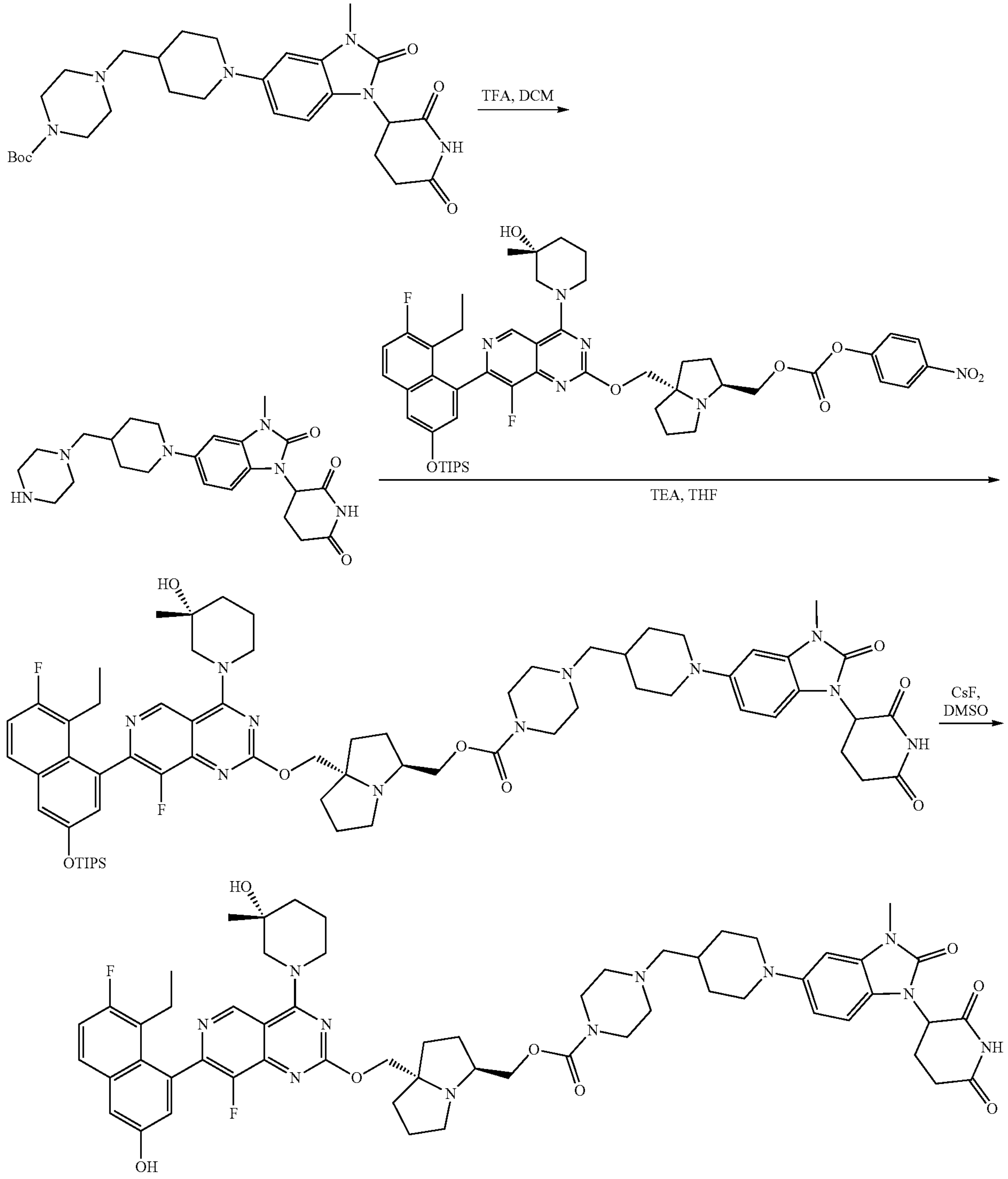
97

Step 1-3-[3-Methyl-2-oxo-5-[4-(piperazin-1-ylmethyl)-1-piperidyl]benzimidazol-1-yl]piperidine-2,6-dione. To a solution of tert-butyl 4-[[1-[1-(2,6-dioxo-3-piperidyl)-3-methyl-2-oxo-benzimidazol-5-yl]-4-piperidyl]methyl]piperazine-1-carboxylate (60.0 mg, 111 μmol) in DCM (1 mL) was added TFA (0.5 mL, 6.73 mmol). The mixture was stirred at 25° C. for 1 hr. On completion, the mixture was concentrated in vacuo to give the title compound (60.0 mg, 97% yield, TFA salt) as yellow oil. LC-MS ($ESI^+$) m z 441.3 $(M+H)^+$.

Step 2-[(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[1-[1-(2,6-dioxo-3-piperidyl)-3-methyl-2-oxo-benzimidazol-5-yl]-4-piperidyl]methyl]piperazine-1-carboxylate. A solution of 3-[3-methyl-2-oxo-5-[4-(piperazin-1-ylmethyl)-1-piperidyl]benzimidazol-1-yl]piperidine-2,6-dione (47.9 mg, 86.3 μmol, TFA salt) in THF (1 mL) and $H_2O$ (0.1 mL) was basified with TEA (84.0 μL, 604 μmol) to pH=8. Then a solution of (4-nitrophenyl) [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate (65.0 mg, 69.1 μmol) in THF (1 mL) was added to the mixture, and then the mixture was stirred at 25° C. for 0.5 hr. On completion, the mixture was concentrated in vacuo to give a residue. The residue was purified by prep-HPLC (column: Phenomenex luna C18 150*25 mm*10 μm; mobile phase: [water (FA)-ACN]; gradient: 20%-50% B over 8 min) to give the title compound (35.0 mg, 30% yield) as yellow solid. LC-MS ($ESI^+$) m/z 1242.8 $(M+H)^+$.

Step 3-[(3S,8S)-8-[[7-(8-ethyl-7-fluoro-3-hydroxy-1-naphthyl)-8-fluoro-4-[(3R)-3-hydro-xy-3-methyl-1-piperidyl]pyrido[4,3-d]pyrimidin-2-yl]oxymethyl]-1,2,3,5,6,7-hexahydropyrrolizin-3-yl]methyl 4-[[1-[1-(2,6-dioxo-3-piperidyl)-3-methyl-2-oxo-benzimidazol-5-yl]-4-piperidyl]methyl]piperazine-1-carboxylate (Compound 97). To a solution of [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[1-[1-(2,6-dioxo-3-piperidyl)-3-methyl-2-oxo-benzimidazol-5-yl]-4-piperidyl]methyl]piperazine-1-carboxylate (30.0 mg, 24.1 μmol) in DMSO (1 mL) was added CsF (11.0 mg, 72.4 μmol). The mixture was stirred at 25° C. for 1 hr. On completion, the mixture was filtered and the filtrate was concentrated in vacuo to give a residue. The residue was purified by prep-HPLC (column: Phenomenex luna C18 150*25 mm*10 μm; mobile phase: [water (FA)-ACN]; gradient: 10%-40% B over 8 min) to give the title compound (11.6 mg, 42% yield, FA salt) as white solid. $^1H$ NMR (400 MHz, DMSO-$d_6$) δ 11.06 (s, 1H), 9.22 (d, J=3.6 Hz, 1H), 7.76 (dd, J=6.0, 9.2 Hz, 1H), 7.37-7.31 (m, 2H), 7.03 (d, J=2.4 Hz, 1H), 6.91 (d, J=8.8 Hz, 1H), 6.80 (s, 1H), 6.61 (d, J=8.8 Hz, 1H), 5.28 (dd, J=5.2, 12.8 Hz, 1H), 4.87-4.62 (m, 1H), 4.32 (t, J=14.8 Hz, 1H), 4.25-4.18 (m, 1H), 4.18-4.11 (m, 2H), 4.09-3.99 (m, 2H), 3.63 (d, J=13.2 Hz, 1H), 3.59-3.50 (m, 4H), 3.29 (s, 3H), 2.90-2.83 (m, 1H), 2.77-2.55 (m, 7H), 2.39-2.24 (m, 6H), 2.16 (d, J=7.2 Hz, 3H), 2.07-1.96 (m, 3H), 1.82-1.58 (m, 14H), 1.54-1.45 (m, 1H), 1.28-1.19 (m, 2H), 1.17 (d, J=9.2 Hz, 3H), 0.73 (q, J=7.2 Hz, 3H); LC-MS ($ESI^+$) m/z 1086.2 $(M+H)^+$.

Example 10. Synthesis of Compound 98

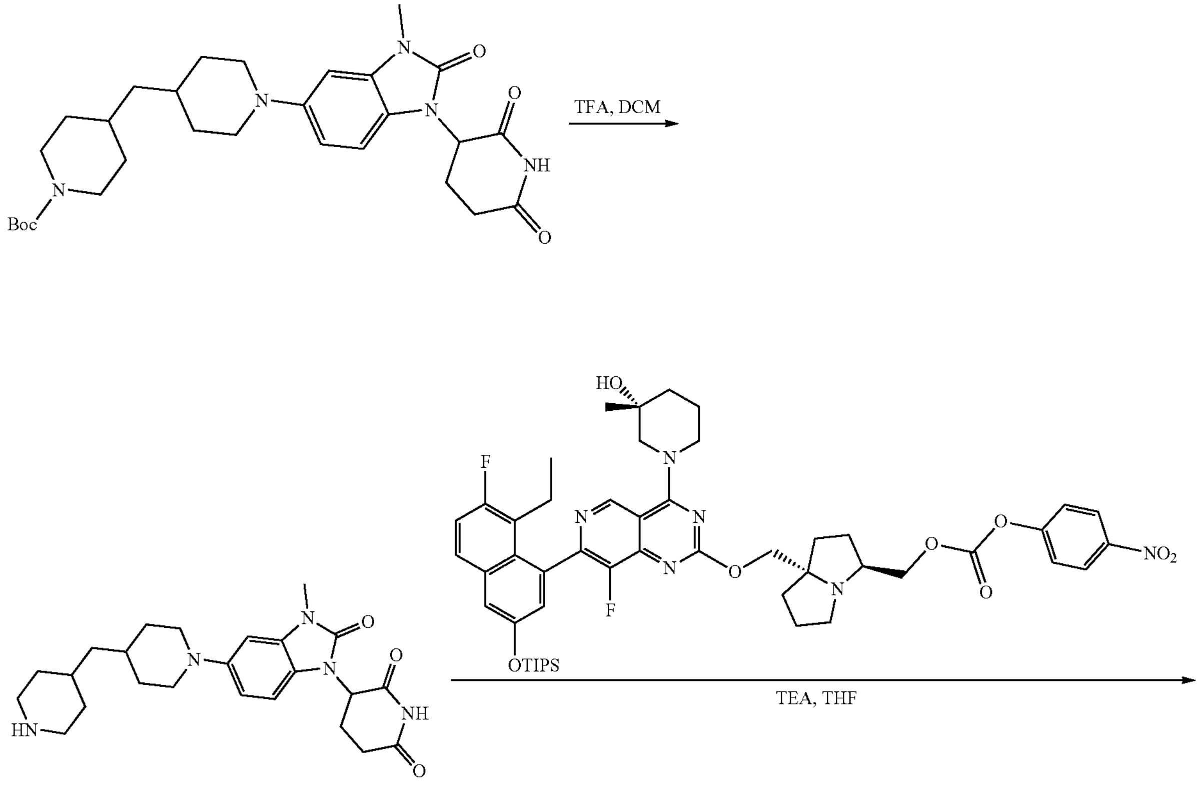

-continued

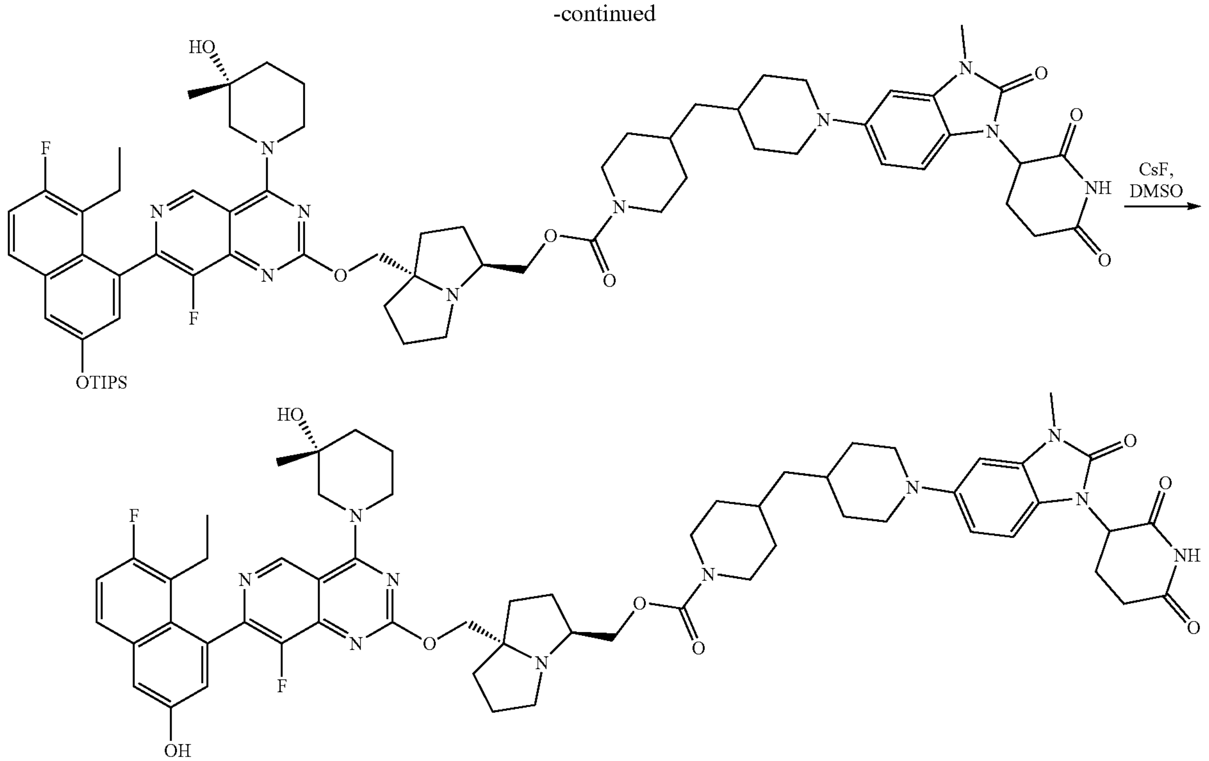

98

Step 1-3-[3-Methyl-2-oxo-5-[4-(4-piperidylmethyl)-1-piperidyl]benzimidazol-1-yl]piperidine-2,6-dione. To a solution of tert-butyl 4-[[1-[1-(2,6-dioxo-3-piperidyl)-3-methyl-2-oxo-benzimidazol-5-yl]-4-piperidyl]methyl]piperidine-1-carboxylate (100 mg, 185 μmol) in DCM (2 mL) was added TFA (767 mg, 6.73 mmol, 0.50 mL). The mixture was stirred at 25° C. for 10 mins. On completion, the reaction mixture was concentrated in vacuo to give the title compound (80.0 mg, 98% yield, TFA salt) as white solid. LC-MS (ESI) m z 440.1 $(M+H)^+$.

Step 2-[(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[1-[1-(2,6-dioxo-3-piperidyl)-3-methyl-2-oxo-benzimidazol-5-yl]-4-piperidyl]methyl]piperidine-1-carboxylate. To a solution of 3-[3-methyl-2-oxo-5-[4-(4-piperidylmethyl)-1-piperidyl]benzimidazol-1-yl]piperidine-2,6-dione (42.0 mg, 95.6 μmol, TFA salt) in THF (5 mL) was added TEA (45.1 mg, 446 μmol, 62.1 μL) and (4-nitrophenyl) [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate (60.0 mg, 63.7 μmol). The mixture was stirred at 25° C. for 10 mins. On completion, the reaction mixture was concentrated in vacuo. The residue was purified by prep-HPLC (column: Phenomenex luna C18 150*25 mm*10 μm; mobile phase: [water (FA)-ACN]; gradient: 35%-65% B over 10 min) to give the title compound (60.0 mg, 72% yield) as white solid. LC-MS (ESI) m/z 1241.6 $(M+H)^+$.

Step 3-[(3S,8S)-8-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[1-[1-(2,6-dioxo-3-piperidyl)-3-methyl-2-oxo-benzimidazol-5-yl]-4-piperidyl]methyl]piperidine-1-carboxylate (Compound 98). To a solution of [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[1-[1-(2,6-dioxo-3-piperidyl)-3-methyl-2-oxo-benzimidazol-5-yl]-4-piperidyl]methyl]piperidine-1-carboxylate (60.0 mg, 48.3 μmol) in DMSO (0.5 mL) was added CsF (22.0 mg, 144 μmol). The mixture was stirred at 25° C. for 20 mins. On completion, The reaction mixture was purified by prep-HPLC (column: CD01-Phenomenex luna C18 150*25*10 μm; mobile phase: [water (FA)-ACN]; gradient: 15%-45% B over 12 min) to give the title compound (30.0 mg, 53% yield, FA salt) as white solid. 1H NMR (400 MHz, DMSO-$d_6$) δ 11.05 (s, 1H), 10.24-9.61 (m, 1H), 9.22 (d, J=3.6 Hz, 1H), 7.77-7.74 (m, 1H), 7.41-7.29 (m, 2H), 7.03 (d, J=2.4 Hz, 1H), 6.97-6.88 (m, 1H), 6.80 (d, J=1.6 Hz, 1H), 6.66-6.55 (m, 1H), 5.30-5.25 (m, 1H), 4.75 (s, 1H), 4.41-4.27 (m, 1H), 4.22-4.08 (m, 4H), 4.06-3.99 (m, 1H), 3.95 (d, J=11.2 Hz, 2H), 3.63 (d, J=13.2 Hz, 1H), 3.56-3.51 (m, 2H), 3.44-3.35 (m, 4H), 3.32 (s, 3H), 2.93-2.85 (m, 1H), 2.82-2.71 (m, 4H), 2.69-2.61 (m, 2H), 2.60-2.53 (m, 2H), 2.39-2.30 (m, 1H), 2.16-1.95 (m, 4H), 1.79-1.62 (m, 12H), 1.58-1.50 (m, 2H), 1.49-1.37 (m, 1H), 1.28-1.20 (m, 2H), 1.17 (d, J=9.2 Hz, 3H), 1.15-1.12 (m, 1H), 1.04-0.88 (m, 2H), 0.73 (q, J=7.2 Hz, 3H); LC-MS $(ESI^+)$ m/z 1085.3 $(M+H)^+$.

Example 11. Synthesis of Compound 99
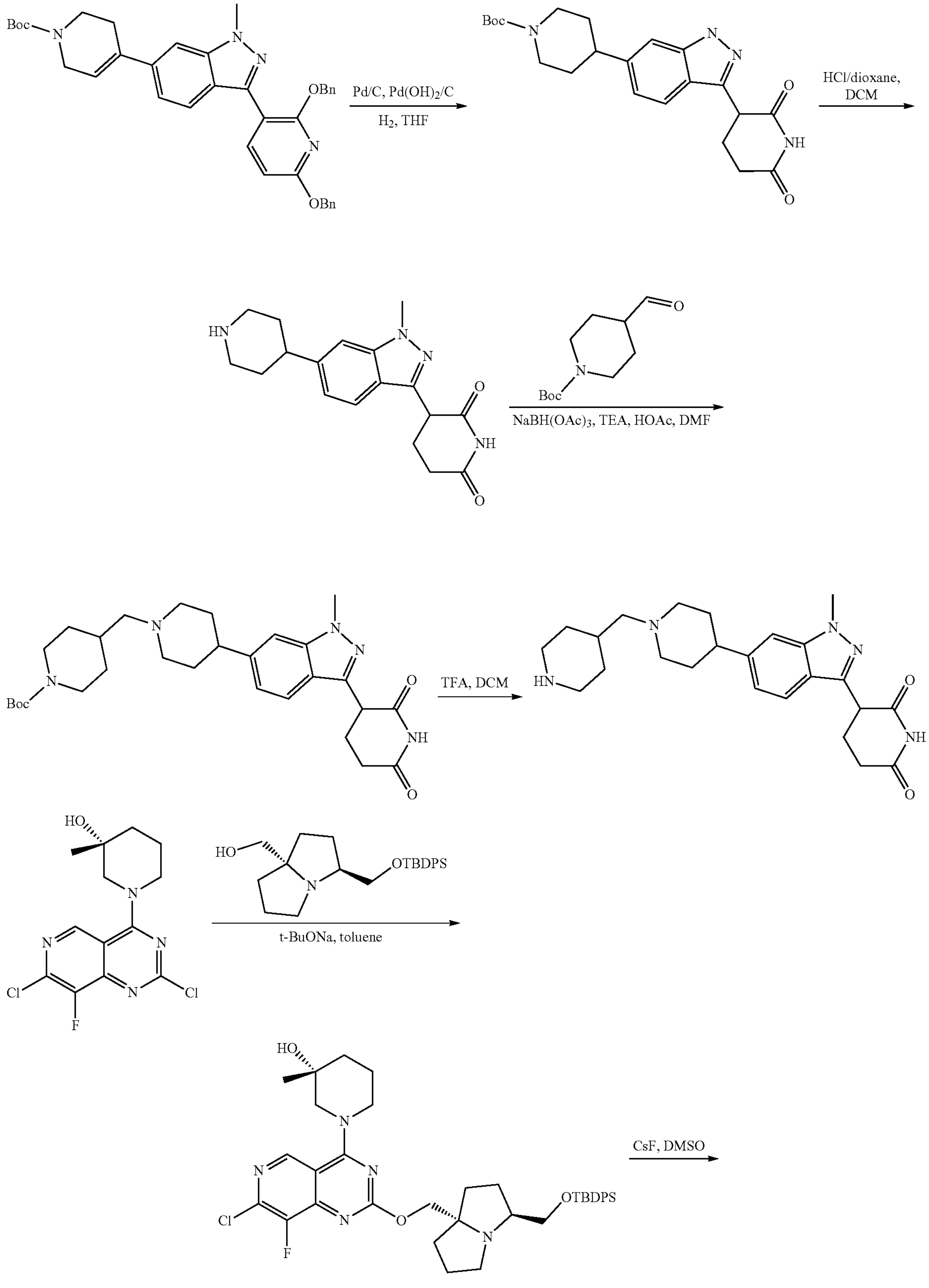

-continued
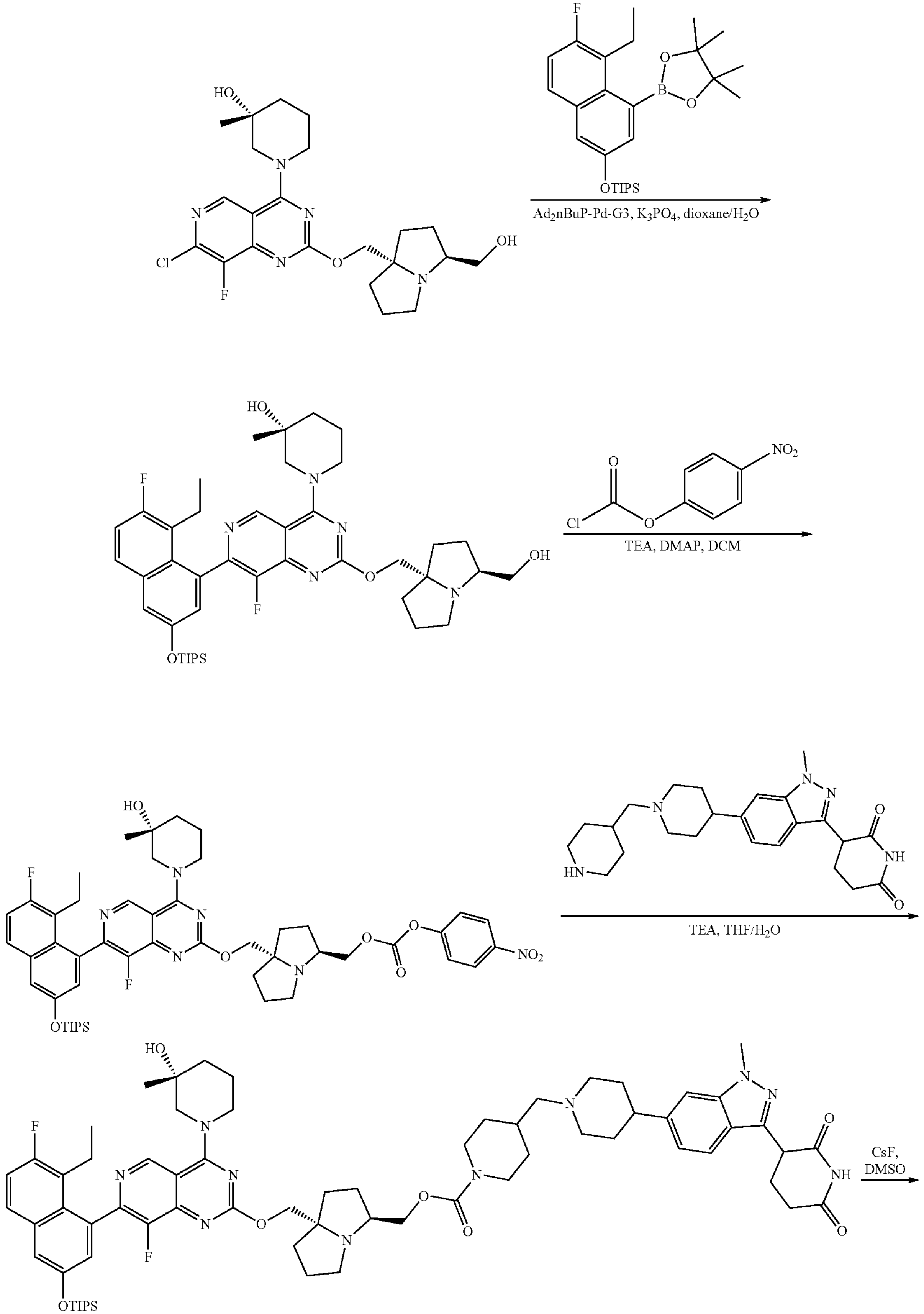

-continued

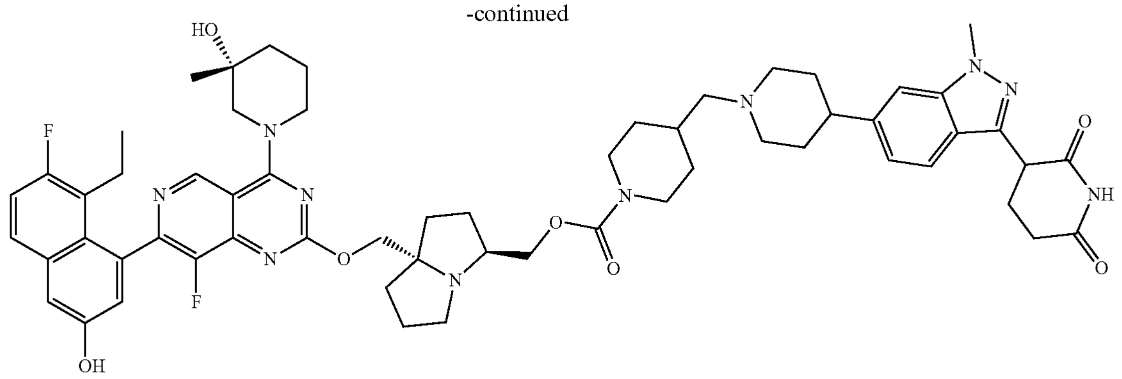

99

Step 1-Tert-butyl 4-[3-(2,6-dioxo-3-piperidyl)-1-methyl-indazol-6-yl]piperidine-1-carboxylate. To a solution of tert-butyl 4-[3-(2,6-dibenzyloxy-3-pyridyl)-1-methyl-indazol-6-yl]-3,6-dihydro-2H-pyridine-1-carboxylate (4.00 g, 6.64 mmol) in THF (40 mL) was added Pd/C (4.00 g, 3.76 mmol, 10% purity) and $Pd(OH)_2/C$ (4.00 g, 5.69 mmol, 20% purity). The suspension was degassed and purged with $H_2$ for 3 times. The mixture was stirred at 25° C. for 3 hrs under $H_2$ (15 Psi). On completion, the reaction mixture was filtered to remove Pd/C and $Pd(OH)_2/C$, concentrated in vacuo to give the title compound (2.47 g, 79% yield) as black solid. $^1H$ NMR (400 MHz, DMSO-$d_6$) δ 10.87 (s, 1H), 7.60 (d, J=8.4 Hz, 1H), 7.44 (s, 1H), 7.03 (dd, J=0.8, 8.4 Hz, 1H), 4.32 (dd, J=5.2, 10.0 Hz, 1H), 4.16-4.06 (m, 2H), 3.96 (s, 3H), 2.86-2.78 (m, 2H), 2.77-2.54 (m, 3H), 2.39-2.29 (m, 1H), 2.15 (qd, J=5.6, 13.2 Hz, 1H), 1.80 (d, J=12.0 Hz, 2H), 1.59 (dq, J=4.4, 12.4 Hz, 2H), 1.42 (s, 9H); LC-MS (ESI) m/z 427.0 $(M+H)^+$.

Step 2-3-[1-Methyl-6-(4-piperidyl) indazol-3-yl]piperidine-2,6-dione. To a solution of tert-butyl 4-[3-(2,6-dioxo-3-piperidyl)-1-methyl-indazol-6-yl]piperidine-1-carboxylate (1.97 g, 4.62 mmol) in DCM (20 mL) was added TFA (6.14 g, 53.8 mmol, 4 mL). The mixture was stirred at 25° C. for 0.5 hr. On completion, the reaction mixture was concentrated in vacuo to give the title compound (2.00 g, 98% yield, TFA salt) as black oil. LC-MS (ESI) m/z 327.0 $(M+H)^+$.

Step 3-Tert-butyl 4-[[4-[3-(2,6-dioxo-3-piperidyl)-1-methyl-indazol-6-yl]-1-piperidyl]methyl]piperidine-1-carboxylate. To a solution of 3-[1-methyl-6-(4-piperidyl) indazol-3-yl]piperidine-2,6-dione (2.00 g, 4.54 mmol, TFA salt) in DMF (20 mL) was basified with TEA (919 mg, 9.08 mmol, 1.26 mL) to pH=7-8. The mixture was acidified with HOAc (818 mg, 13.62 mmol) to pH=6-7. And then tert-butyl 4-formylpiperidine-1-carboxylate (1.45 g, 6.81 mmol, CAS #137076-22-3) was added to the mixture. The mixture was stirred at 25° C. for 0.5 hr. At last $NaBH_3CN$ (342 mg, 5.45 mmol) was added to the mixture and the mixture was stirred at 25° C. for 1 hr. On completion, the reaction mixture was quenched with $H_2O$ (0.5 mL) and then concentrated in vacuo to give a residue. The residue was purified by reverse-phase HPLC (0.1% FA condition) to give the title compound (460 mg, 19% yield) as white solid. $^1H$ NMR (400 MHz, DMSO-$d_6$) δ 10.88 (s, 1H), 7.62 (d, J=7.6 Hz, 1H), 7.43 (s, 1H), 7.03 (d, J=8.0 Hz, 1H), 4.33 (dd, J=4.8, 9.6 Hz, 1H), 3.97 (s, 3H), 3.92 (s, 2H), 3.16 (d, J=1.2 Hz, 2H), 2.78-2.59 (m, 5H), 2.47-2.24 (m, 5H), 2.16 (dd, J=5.2, 12.8 Hz, 1H), 1.85 (s, 5H), 1.71 (d, J=12.4 Hz, 2H), 1.39 (s, 9H), 0.99 (d, J=10.0 Hz, 2H); LC-MS (ESI) m/z 524.2 $(M+H)^+$.

Step 4-3-[1-Methyl-6-[1-(4-piperidylmethyl)-4-piperidyl]indazol-3-yl]piperidine-2,6-dione. To a solution of tert-butyl 4-[[4-[3-(2,6-dioxo-3-piperidyl)-1-methyl-indazol-6-yl]-1-piperidyl]methyl]piperidine-1-carboxylate (60.0 mg, 171 μmol) in DCM (1 mL) was added TFA (219 mg, 1.92 mmol, 0.2 mL). The mixture was stirred at 25° C. for 0.5 hr. On completion, the reaction mixture was concentrated in vacuo to give the title compound (60.0 mg, 97% yield, TFA salt) as yellow oil. LC-MS (ESI) m/z 424.1 $(M+H)^+$.

Step 5-(3R)-1-[2-[[(3S,8S)-3-[[Tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3-methyl-piperidin-3-ol. To a solution of [(3S,8S)-3-[[tert-butyl(diphenyl)silyl]oxymethyl]-1,2,3,5,6,7-hexahydropyrrolizin-8-yl]methanol (618 mg, 1.51 mmol) in toluene (5 mL) was added t-BuONa (290 mg, 3.02 mmol) at 0° C. The mixture was stirred at 25° C. for 0.5 hr under $N_2$ atmosphere. And then (3R)-1-(2,7-dichloro-8-fluoro-pyrido[4,3-d]pyrimidin-4-yl)-3-methyl-piperidin-3-ol (500 mg, 1.51 mmol) was added to the mixture at 0° C. The mixture was stirred at 25° C. for 0.5 hr under $N_2$ atmosphere. On completion, the reaction mixture was diluted with $H_2O$ (30 mL) and extracted with EA (3×50 mL). The combined organic layers were washed with brine (3×50 mL), dried over anhydrous $Na_2SO_4$, filtered and the filtrate was concentrated in vacuo to give a residue. The residue was purified by reverse-phase HPLC (0.1% FA condition) to give the title compound (367 mg, 25% yield) as yellow oil. LC-MS (ESI) m/z 704.2 $(M+H)^+$.

Step 6-(3R)-1-[7-chloro-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol. To a solution of (3R)-1-[7-chloro-8-fluoro-2-[[(3S,8S)-3-[[tert-butyl(diphenyl)silyl]oxymethyl]-1,2,3,5,6,7-hexahydropyrrolizin-8-yl]methoxy]pyrido[4,3-d]pyrimidin-4-yl]-3-methyl-piperidin-3-ol (367 mg, 521 μmol) in DMSO (2 mL) was added CsF (237 mg, 1.56 mmol). The mixture was stirred at 40° C. for 3 hrs. The reaction mixture was diluted with EA (20 mL) and $H_2O$ (10 mL), extracted with EA (2×20 mL). The combined organic layers were washed with brine (3×20 mL), dried over anhydrous $Na_2SO_4$, filtered and the filtrate was concentrated in vacuo to give a residue. The residue was purified by prep-TLC($SiO_2$, DCM: MeOH=10:1) to give the title compound (150 mg, 48% yield) as yellow solid. LC-MS (ESI) m/z 466.1 $(M+H)^+$.

Step 7-(3R)-1-[7-(8-ethyl-7-fluoro-3-triisopropylsilyloxy-1-naphthyl)-8-fluoro-2-[[(3S,8S)-3-(hydroxymethyl)-1,2,3,5,6,7-hexahydropyrrolizin-8-yl]methoxy]pyrido[4,3- d]pyrimidin-4-yl]-3-methyl-piperidin-3-ol. A mixture of (3R)-1-[7-chloro-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (150 mg, 321 μmol), [5-ethyl-6-fluoro-4-(4,4,5,5-tetramethyl-1,3,2-dioxaborolan-2-yl)-2-naphthyl]oxy-triisopropyl-silane (304 mg, 643 μmol), [2-(2-aminophenyl)phenyl]palladium (1+); bis (1-adamantyl)-butyl-phosphane; methanesulfonate (23.4 mg, 32.1 μmol) and $K_3PO_4$ (1.5 M, 643 μL) in dioxane (2 mL) was degassed and purged with $N_2$ for 3 times, and then the mixture was stirred at 80° C. for 0.5 hr under $N_2$ atmosphere. On completion, the reaction mixture was concentrated in vacuo to give a residue. The residue was purified by column chromatography ($SiO_2$, DCM/MeOH=100/1 to 10/1) to give the title compound (120 mg, 48% yield) as yellow solid. LC-MS (ESI) m/z 776.3 $(M+H)^+$.

Step 8-(4-Nitrophenyl) [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate. To a solution of (3R)-1-[7-(8-ethyl-7-fluoro-3-triisopropylsilyloxy-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (60.0 mg, 77.3 μmol), TEA (290 mg, 2.87 mmol) and DMAP (944 μg, 7.73 μmol) in DCM (5 mL) was added (4-nitrophenyl) carbonochloridate (77.9 mg, 386 μmol). The mixture was stirred at 25° C. for 1 hr. On completion, the mixture was diluted with DCM (30 mL), and extracted with $H_2O$ (3×50 mL). The organic layer was washed with brine (2×50 mL), dried over anhydrous $Na_2SO_4$, filtered and the filtrate was concentrated in vacuo to give the title compound (70.0 mg, 96% yield) as yellow solid. LC-MS (ESI) m/z 941.3 $(M+H)^+$.

Step 9-[(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[3-(2,6-dioxo-3-piperidyl)-1-methyl-indazol-6-yl]-1-piperidyl]methyl]piperidine-1-carboxylate. To a solution of 3-[1-methyl-6-[1-(4-piperidylmethyl)-4-piperidyl]indazol-3-yl]piperidine-2,6-dione (49.6 mg, 92.4 μmol, TFA salt) in THF (1 mL) and $H_2O$ (0.5 mL) was added TEA (19.3 mg, 191 μmol) to adjusted pH=7-8. And then a solution of (4-nitrophenyl) [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate (60.0 mg, 63.7 μmol) in THF (3 mL) was added to the mixture. The mixture was stirred at 25° C. for 0.5 hr under $N_2$ atmosphere. On completion, the mixture was concentrated in vacuo to give a residue. The residue was purified by prep-HPLC (column: Phenomenex luna C18 150*25 mm*10 μm; mobile phase: [water (FA)-ACN]; gradient: 28%-58% B over 8 min) to give the title compound (50.0 mg, 55% yield) as yellow solid. LC-MS $(ESI^+)$ m/z 1225.4 (M+H)+

Step 10-[(3S,8S)-8-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[3-(2,6-dioxo-3-piperidyl)-1-methyl-indazol-6-yl]-1-piperidyl]methyl]piperidine-1-carboxylate (Compound 99). To a solution of [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[3-(2,6-dioxo-3-piperidyl)-1-methyl-indazol-6-yl]-1-piperidyl]methyl]piperidine-1-carboxylate (50.0 mg, 40.8 μmol) in DMSO (1 mL) was added CsF (18.6 mg, 122 μmol). The mixture was stirred at 25° C. for 0.5 hr. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 16%-46% B over 10 min) to give the title compound (28.1 mg, 59% yield, FA salt) as white solid. $^1H$ NMR (400 MHz, DMSO-$d_6$) δ 10.88 (s, 1H), 10.43-9.58 (m, 1H), 9.22 (d, J=4.0 Hz, 1H), 7.76 (dd, J=6.0, 9.2 Hz, 1H), 7.59 (d, J=8.4 Hz, 1H), 7.43 (s, 1H), 7.38-7.31 (m, 2H), 7.05-7.00 (m, 2H), 4.85-4.60 (m, 1H), 4.39-4.29 (m, 2H), 4.25-4.12 (m, 3H), 4.11-4.03 (m, 2H), 4.00 (s, 2H), 3.96 (s, 3H), 3.63 (d, J=13.2 Hz, 1H), 3.54 (s, 1H), 2.94 (d, J=10.8 Hz, 2H), 2.81-2.70 (m, 4H), 2.67-2.58 (m, 3H), 2.39-2.30 (m, 2H), 2.20-2.10 (m, 4H), 2.08-1.95 (m, 4H), 1.84-1.60 (m, 17H), 1.55-1.47 (m, 1H), 1.16 (d, J=9.2 Hz, 3H), 1.03-0.92 (m, 2H), 0.73 (q, J=7.2 Hz, 3H); LC-MS $(ESI^+)$ m/z 1069.3 $(M+H)^+$.

Example 12. Synthesis of Compound 100

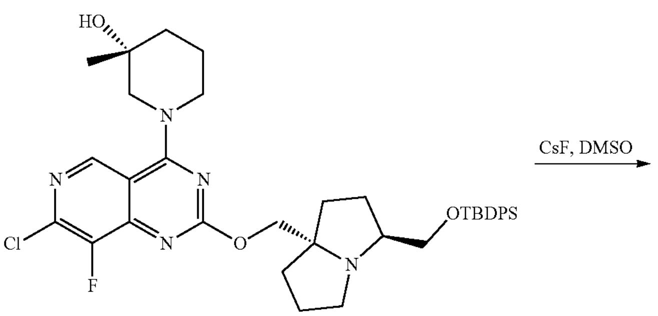

-continued
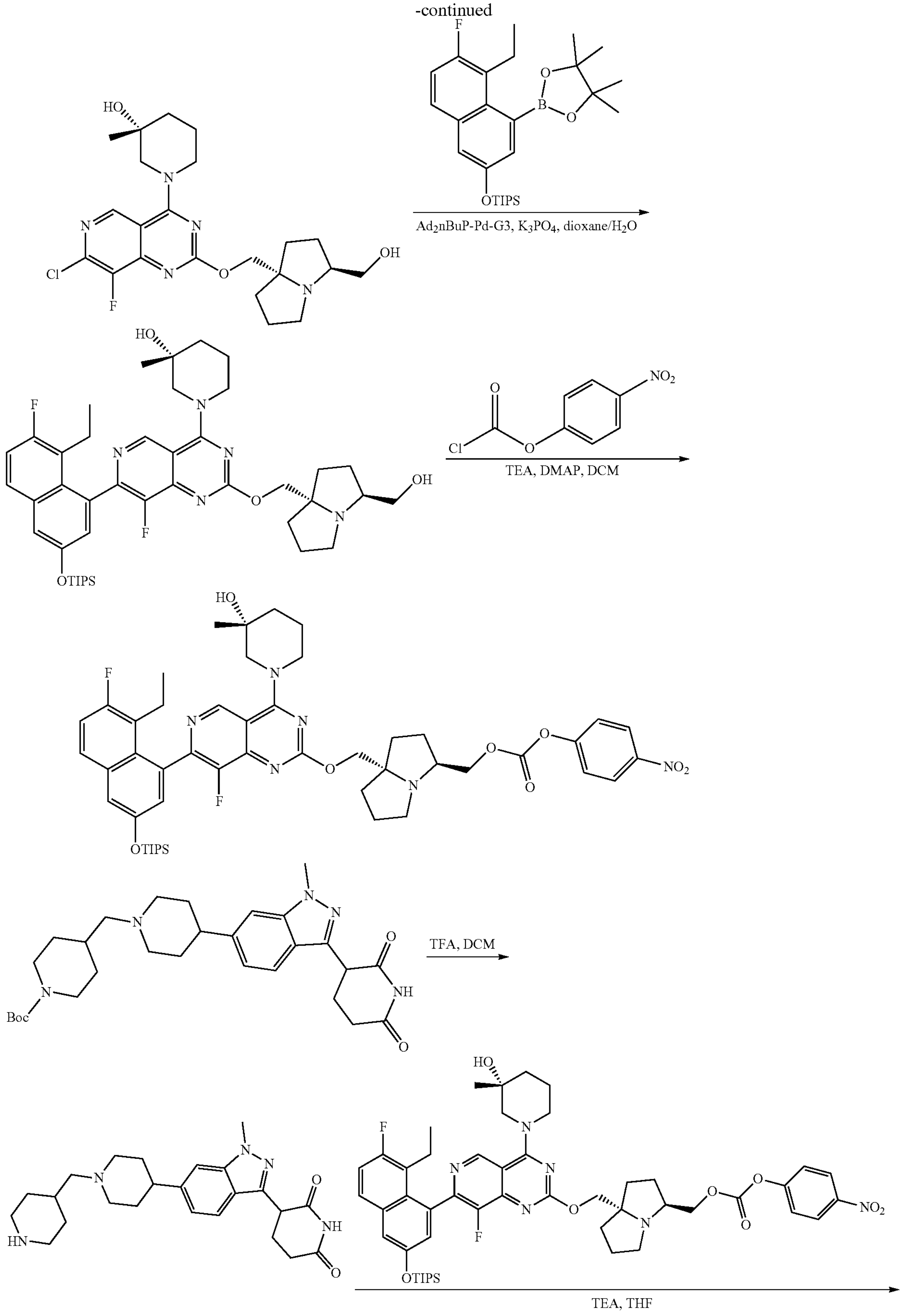

-continued

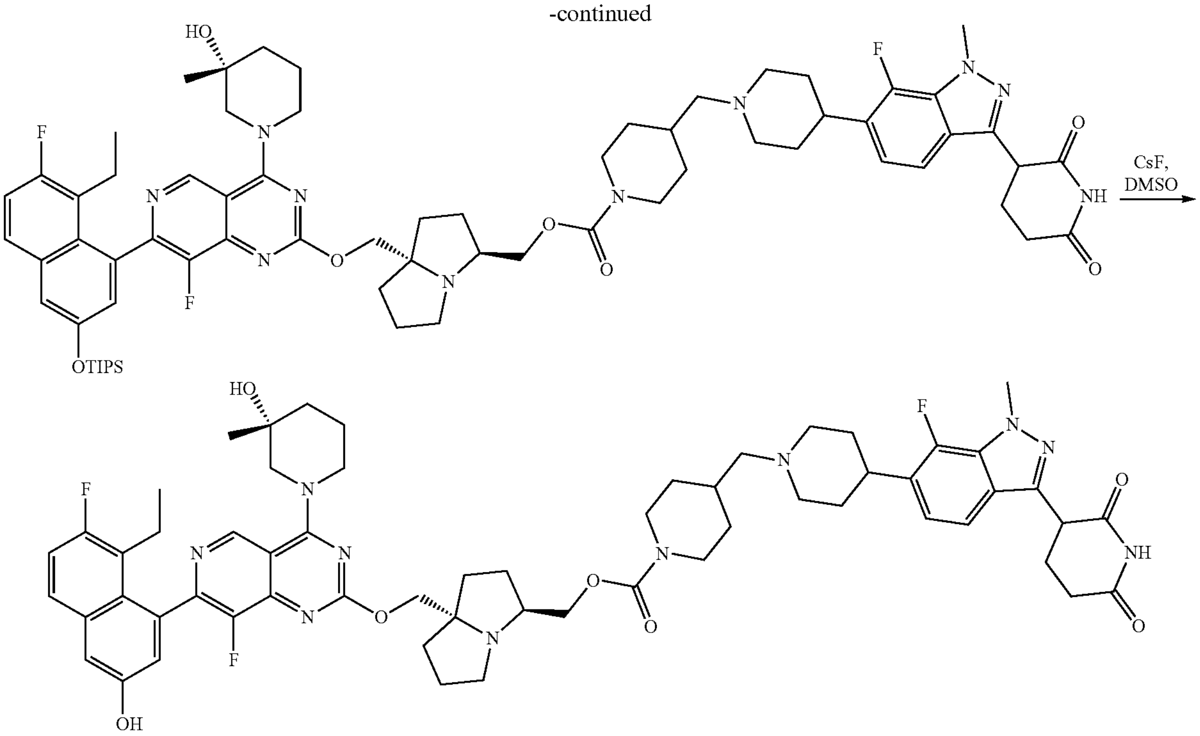

100

Step 1-(3R)-1-[7-Chloro-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol. To a solution of (3R)-1-[2-[[(3S,8S)-3-[[tert-butyl(diphenyl)silyl]oxymethyl]-1,2,3,5,6,7-hexahydropyrrolizin-8-yl]methoxy]-7-chloro-8-fluoro-pyrido[4,3-d]pyrimidin-4-yl]-3-methyl-piperidin-3-ol (2.90 g, 4.12 mmol) in DMSO (10 mL) was added CsF (3.13 g, 20.5 mmol). The mixture was stirred at 50° C. for 1 hr. On completion, the reaction mixture was diluted with $H_2O$ (20 mL) and extracted with EA (3×30 mL). The combined organic layers were dried over anhydrous $Na_2SO_4$, filtered and the filtrate was concentrated in vacuo to give a residue. The residue was purified by reversed-phase HPLC (0.1% FA condition) to give the title compound (1.30 g, 67% yield) as white solid. $^1$H NMR (400 MHz, DMSO-$d_6$) δ 9.01 (s, 1H), 4.74-4.50 (m, 2H), 4.35 (d, J=12.8 Hz, 1H), 4.13-4.08 (m, 1H), 4.04-3.95 (m, 2H), 3.64 (dd, J=6.4, 10.8 Hz, 1H), 3.56-3.45 (m, 2H), 3.25 (t, J=10.8 Hz, 1H), 3.10-3.01 (m, 1H), 2.80-2.73 (m, 1H), 2.67 (dt, J=6.0, 9.2 Hz, 1H), 2.04-1.91 (m, 2H), 1.73-1.42 (m, 10H), 1.14 (s, 3H); LC-MS ($ESI^+$) m/z 466.2 $(M+H)^+$.

Step 2-(3R)-1-[7-(8-Ethyl-7-fluoro-3-triisopropylsilyloxy-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol. A mixture of (3R)-1-[7-chloro-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (100 mg, 214 μmol), [5-ethyl-6-fluoro-4-(4,4,5,5-tetramethyl-1,3,2-dioxaborolan-2-yl)-2-naphthyl]oxy-triisopropyl-silane (152 mg, 321 μmol, CAS #2621932-48-5), $K_3PO_4$ (136 mg, 643 μmol) and [2-(2-aminophenyl)phenyl]palladium (1+); bis(1-adamantyl)-butyl-phosphane; methanesulfonate (15.6 mg, 21.4 μmol) in dioxane (1 mL) and $H_2O$ (0.2 mL) was degassed and purged with $N_2$ for 3 times, and then the mixture was stirred at 100° C. for 10 mins under $N_2$ atmosphere. On completion, the reaction mixture was diluted with $H_2O$ (20 mL) and extracted with EA (3×30 mL). The combined organic layers were washed with brine (2×50 mL), dried over anhydrous $Na_2SO_4$, filtered and the filtrate was concentrated in vacuo to give a residue. The residue was purified by column chromatography ($SiO_2$, PE/EA=15/1 to 10/1) to give the title compound (70.0 mg, 42% yield) as yellow solid; LC-MS (ESI) m/z 776.3 $(M+H)^+$.

Step 3-(4-Nitrophenyl) [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate. To a solution of (3R)-1-[7-(8-ethyl-7-fluoro-3-triisopropylsilyloxy-1-naphthyl)-8-fluoro-2-[[(3S,8S)-3-(hydroxymethyl)-1,2,3,5,6,7-hexahydropyrrolizin-8-yl]methoxy]pyrido[4,3-d]pyrimidin-4-yl]-3-methyl-piperidin-3-ol (60.0 mg, 77.3 μmol) in DCM (5 mL) was added DMAP (944 μg, 7.73 μmol) and TEA (290 mg, 2.87 mmol). Then (4-nitrophenyl) carbonochloridate (77.9 mg, 386 μmol) was added to the mixture was stirred at 25° C. for 2 hrs. On completion, the reaction mixture was diluted with DCM (30 mL) and extracted with $H_2O$ (3×50 mL). The combined organic layers were washed with brine (2×50 mL), dried over anhydrous $Na_2SO_4$, filtered and the filtrate was concentrated in vacuo to give the title compound (70.0 mg, 96% yield) as yellow solid; LC-MS (ESI) m/z 941.3 $(M+H)^+$.

Step 4-3-[7-Fluoro-1-methyl-6-[1-(4-piperidylmethyl)-4-piperidyl]indazol-3-yl]piperidine-2,6-dione. To a solution of tert-butyl 4-[[4-[3-(2,6-dioxo-3-piperidyl)-7-fluoro-1-methyl-indazol-6-yl]-1-piperidyl]methyl]piperidine-1-carboxylate (80.0 mg, 147 μmol) in DCM (5 mL) was added TFA (1.54 g, 13.4 mmol, 1 mL). The mixture was stirred at 25° C. for 0.5 hr. On completion, the mixture was concentrated in vacuo to give the title compound (82.0 mg, 99% yield, TFA salt) as yellow oil; LC-MS (ESI) m/z 442.1 $(M+H)^+$.

Step 5-[(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[3-(2,6-dioxo-3-piperidyl)-7-fluoro-1-methyl-indazol-6-yl]-1-piperidyl]methyl]piperidine-1-carboxylate. To a solution of 3-[7-fluoro-1-methyl-6-[1-(4-piperidylmethyl)-4-piperidyl]indazol-3-yl]piperidine-2,6-dione (81.4 mg, 146 μmol, TFA salt) in THF (2 mL) was added TEA (22.2 mg, 219 μmol) to adjusted pH=10, then a solution of (4-nitrophenyl) [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl carbonate (69.0 mg, 73.3 μmol) in THF (2 mL) was added to the mixture and the mixture was stirred at 25° C. for 1 hr. On completion, the mixture was concentrated in vacuo to give a residue. The residue was purified by prep-HPLC (column: Phenomenex luna C18 150*25 mm*10 μm; mobile phase: [water (FA)-ACN]; gradient: 30%-60% B over 8 min) to give the title compound (63.0 mg, 67% yield) as white solid. LC-MS (ESI) m/z 1243.3 $(M+H)^+$.

Step 6-[(3S,8S)-8-[[7-(8-ethyl-7-fluoro-3-hydroxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[3-(2,6-dioxo-3-piperidyl)-7-fluoro-1-methyl-indazol-6-yl]-1-piperidyl]methyl]piperidine-1-carboxylate (Compound 100). To a solution of [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl 4-[[4-[3-(2,6-dioxo-3-piperidyl)-7-fluoro-1-methyl-indazol-6-yl]-1-piperidyl]methyl]piperidine-1-carboxylate (55.0 mg, 44.2 μmol) in DMSO (0.5 mL) was added CsF (20.1 mg, 132 μmol). The mixture was stirred at 25° C. for 0.5 hr. On completion, the mixture was concentrated in vacuo to give a residue and the residue was purified by prep-HPLC (column: CD01-Phenomenex luna C18 150*25*10 μm; mobile phase: [water (FA)-ACN]; gradient: 14%-44% B over 10 min) to give the title compound (28.8 mg, 55% yield) as white solid. $^1H$ NMR (400 MHz, DMSO-$d_6$) δ 10.91 (s, 1H), 10.18-9.66 (m, 1H), 9.25 (d, J=4.4 Hz, 1H), 7.76 (dd, J=6.0, 9.2 Hz, 1H), 7.44 (dd, J=2.0, 8.4 Hz, 1H), 7.38-7.31 (m, 2H), 7.07-6.99 (m, 2H), 4.84-4.65 (m, 1H), 4.38-4.28 (m, 3H), 4.21 (s, 3H), 4.11 (s, 3H), 4.06 (d, J=6.0 Hz, 1H), 3.98 (d, J=12.4 Hz, 2H), 3.64 (d, J=13.2 Hz, 1H), 3.52 (s, 1H), 3.03-2.89 (m, 6H), 2.83-2.73 (m, 2H), 2.67 (dd, J=5.6, 10.4 Hz, 1H), 2.63-2.55 (m, 1H), 2.39-2.29 (m, 2H), 2.22 (d, J=3.2 Hz, 2H), 2.17-2.09 (m, 4H), 2.04-1.97 (m, 1H), 1.90-1.63 (m, 18H), 1.17 (d, J=9.2 Hz, 3H), 1.06-0.93 (m, 2H), 0.73 (q, J=7.2 Hz, 3H); LC-MS (ESI) m/z 1087.4 $(M+H)^+$.

Example 13. Synthesis of Compound 106

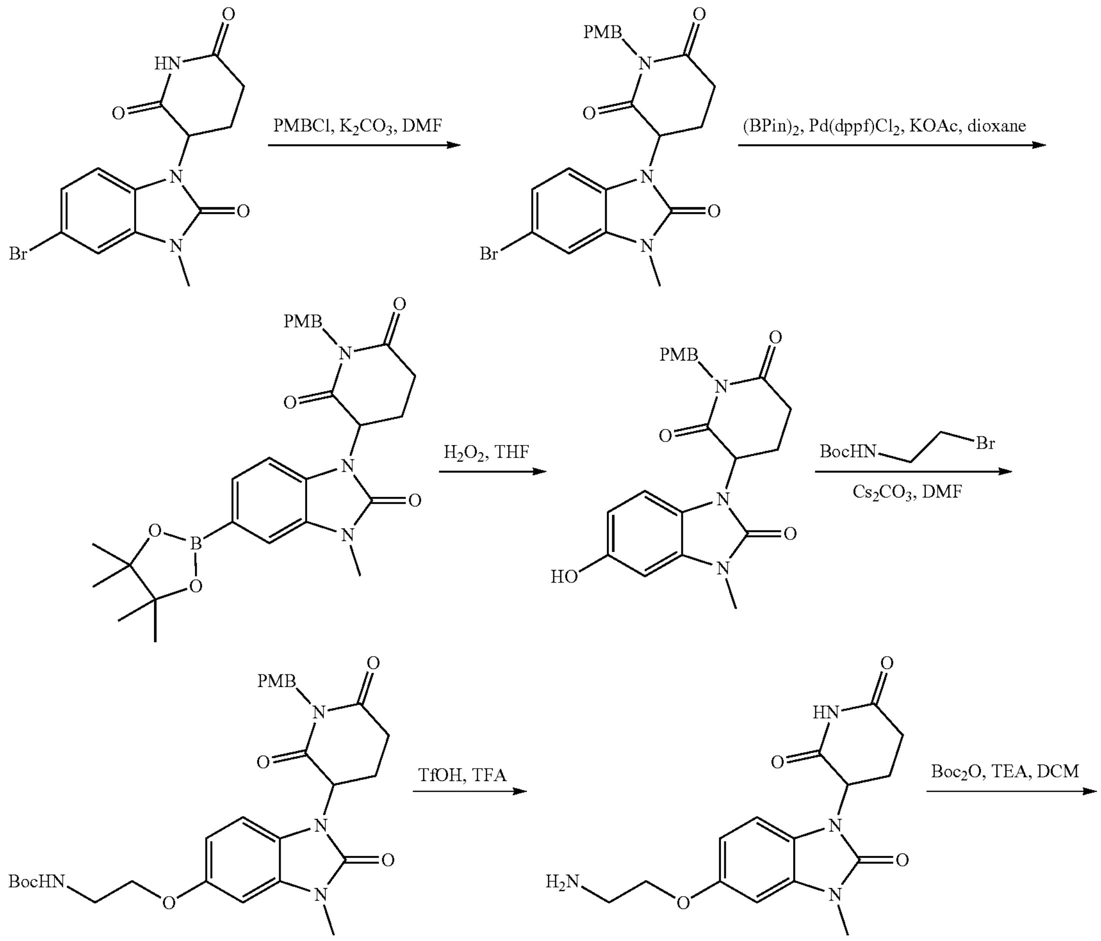

-continued
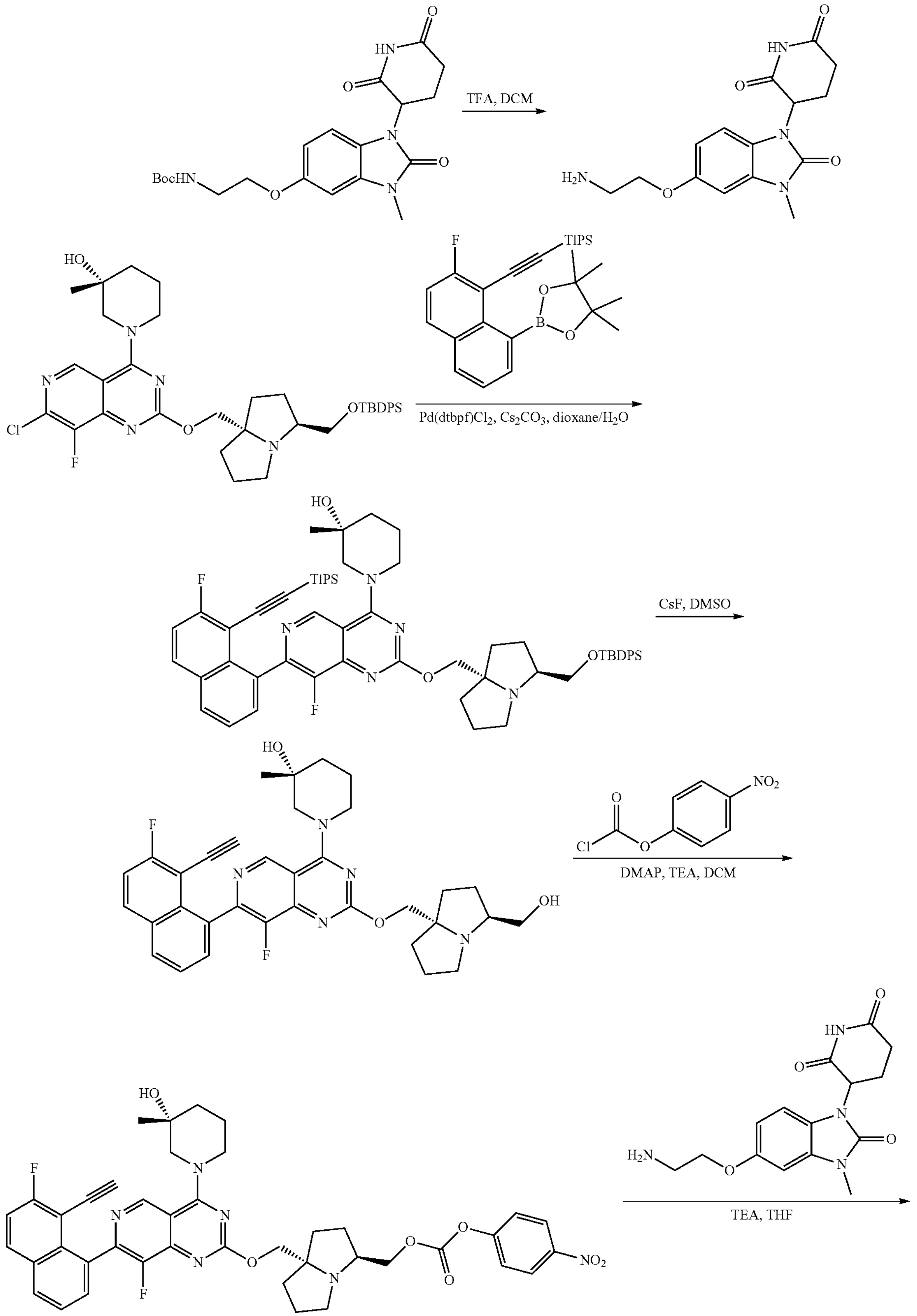

-continued

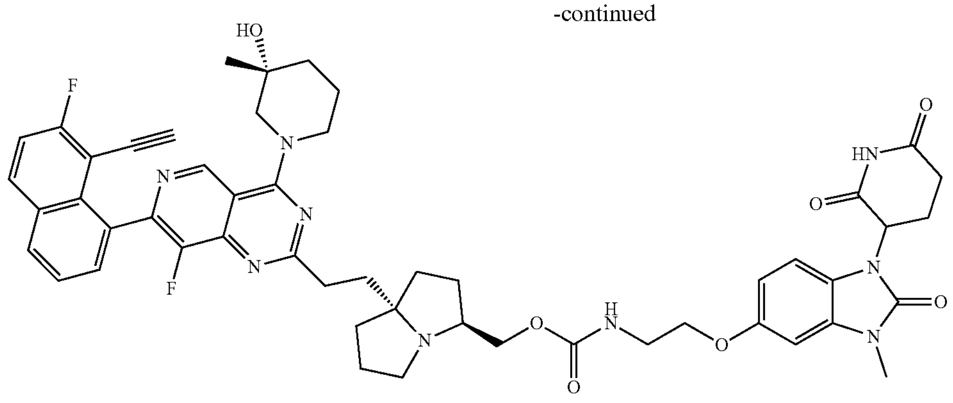

106

Step 1-3-(5-Bromo-3-methyl-2-oxo-benzimidazol-1-yl)-1-[(4-methoxyphenyl)methyl]piperidine-2,6-dione. To a mixture of 3-(5-bromo-3-methyl-2-oxo-benzimidazol-1-yl) piperidine-2,6-dione (9.00 g, 26.6 mmol, CAS #2300099-98-1) in DMF (90 mL) was added PMB-Cl (6.25 g, 39.9 mmol, 5.42 mL) and $K_2CO_3$ (11.0 g, 79.8 mmol), the reaction mixture was stirred at 50° C. for 3 hrs. On completion, the reaction mixture residue was diluted with water (500 mL) and extracted with EA (2×500 mL). The combined organic layers was dried over $Na_2SO_4$, filtered and the filtrate was concentrated in vacuo to give a residue. The residue was triturated with EtOH (30 mL), filtered and the filter cake was dried to give the title compound (11.5 g, 94% yield) as yellow solid. $^1H$ NMR (400 MHz, DMSO-$d_6$) δ 7.47 (d, J=1.6 Hz, 1H), 7.22-7.14 (m, 3H), 7.01 (d, J=8.4 Hz, 1H), 6.85 (d, J=8.8 Hz, 2H), 5.54 (dd, J=5.6, 13.2 Hz, 1H), 4.78 (q, J=14.4 Hz, 2H), 3.72 (s, 3H), 3.34-3.33 (m, 3H), 3.11-2.99 (m, 1H), 2.86-2.77 (m, 1H), 2.77-2.66 (m, 1H), 2.11-2.02 (m, 1H).

Step 2-1-[(4-Methoxyphenyl)methyl]-3-[3-methyl-2-oxo-5-(4,4,5,5-tetramethyl-1,3,2-dioxaborolan-2-yl)benzimidazol-1-yl]piperidine-2,6-dione. To a mixture of 3-(5-bromo-3-methyl-2-oxo-benzimidazol-1-yl)-1-[(4-methoxyphenyl)methyl]piperidine-2,6-dione (10.0 g, 21.8 mmol) in dioxane (100 mL) was added Pd (dppf) $Cl_2$ (1.60 g, 2.18 mmol), KOAc (6.42 g, 65.4 mmol) and $Pin_2B_2$ (11.0 g, 43.6 mmol), the reaction mixture was stirred at 70° C. for 12 hrs under $N_2$ atmosphere. On completion, the reaction mixture was diluted with water (300 mL) and extracted with EA (2×300 mL). The combined organic layers was dried over $Na_2SO_4$, filtered and the filtrate was concentrated in vacuo to give a residue. The residue was purified by column chromatography ($SiO_2$, PE:EA=20:1) to give the title compound (14.7 g, crude) as yellow solid. $^1H$ NMR (400 MHz, DMSO-$d_6$) δ 7.39 (s, 1H), 7.37 (d, J=8.0 Hz, 1H), 7.21 (d, J=8.8 Hz, 2H), 7.03 (d, J=7.2 Hz, 1H), 6.86 (d, J=8.8 Hz, 2H), 5.59-5.52 (m, 1H), 4.86-4.73 (m, 2H), 3.73 (s, 3H), 3.53 (d, J=8.8 Hz, 3H), 3.12-3.00 (m, 1H), 2.87-2.69 (m, 2H), 2.11-2.02 (m, 1H), 1.30 (s, 12H).

Step 3-3-(5-Hydroxy-3-methyl-2-oxo-benzimidazol-1-yl)-1-[(4-methoxyphenyl)methyl]piperidine-2,6-dione. To a mixture of 1-[(4-methoxyphenyl)methyl]-3-[3-methyl-2-oxo-5-(4,4,5,5-tetramethyl-1,3,2-dioxaborolan-2-yl)benzimidazol-1-yl]piperidine-2,6-dione (13.7 g, 27.2 mmol) in THF (150 mL) was added $H_2O_2$ (9.2 g, 81.6 mmol, 7.84 mL, 30% purity) dropwise at 0° C., the reaction mixture was stirred at 25° C. for 12 hrs. On completion, the reaction mixture was quenched with sat. $Na_2S_2O_3$ (200 mL) and sat.$NH_4Cl$ (200 mL) under stirring. And then the residue was diluted with water (500 mL) and extracted with EA (2×500 mL). The combined organic layers was dried over $Na_2SO_4$, filtered and the filtrate was concentrated in vacuo to give a residue. The residue was purified by column chromatography ($SiO_2$, PE:EA=1:4) to give the title compound (6.83 g, 63% yield) as yellow solid. $^1H$ NMR (400 MHz, DMSO-$d_6$) δ 9.16 (s, 1H), 7.20 (d, J=8.8 Hz, 2H), 6.85 (d, J=8.8 Hz, 2H), 6.74 (d, J=8.4 Hz, 1H), 6.58 (d, J=2.0 Hz, 1H), 6.40 (dd, J=2.0, 8.4 Hz, 1H), 5.42 (dd, J=5.2, 13.2 Hz, 1H), 4.85-4.72 (m, 2H), 3.72 (s, 3H), 3.26 (s, 3H), 3.11-2.97 (m, 1H), 2.85-2.74 (m, 1H), 2.68 (dq, J=4.0, 13.2 Hz, 1H), 2.06-1.98 (m, 1H).

Step 4-Tert-butyl N-[2-[1-[1-[(4-methoxyphenyl)methyl]-2,6-dioxo-3-piperidyl]-3-methyl-2-oxo-benzimidazol-5-yl]oxyethyl]carbamate. To a mixture of 3-(5-hydroxy-3-methyl-2-oxo-benzimidazol-1-yl)-1-[(4-methoxyphenyl)methyl]piperidine-2,6-dione (1.60 g, 4.05 mmol), tert-butyl N-(2-bromoethyl) carbamate (1.09 g, 4.86 mmol, CAS #39684-80-5) and $Cs_2CO_3$ (2.64 g, 8.09 mmol) in DMF (15 mL), the reaction mixture was stirred at 70° C. for 2 hrs. On completion, the reaction mixture was filtered and the filtrate was concentrated in vacuo to give a residue. The residue was purified by reverse phase (0.1% FA condition) to give the title compound (1.10 g, 50% yield) as yellow solid. LC-MS (ESI) m/z 561.2 $(M+Na)^+$.

Step 5-3-[5-(2-Aminoethoxy)-3-methyl-2-oxo-benzimidazol-1-yl]piperidine-2,6-dione. To a mixture of tert-butyl N-[2-[1-[1-[(4-methoxyphenyl)methyl]-2,6-dioxo-3-piperidyl]-3-methyl-2-oxo-benzimidazol-5-yl]oxyethyl]carbamate (900 mg, 1.67 mmol) in TFA (9 mL) was added TfOH (5.09 g, 33.9 mmol, 3 mL), the reaction mixture was stirred at 70° C. for 1 hr. On completion, the reaction mixture was concentrated in vacuo to give the title compound (730 mg, crude, TFA) as brown oil. LC-MS (ESI) m/z 319.0 $(M+H)^+$.

Step 6-Tert-butyl N-[2-[1-(2,6-dioxo-3-piperidyl)-3-methyl-2-oxo-benzimidazol-5-yl]oxyethyl]carbamate. To a mixture of 3-[5-(2-aminoethoxy)-3-methyl-2-oxo-benzimidazol-1-yl]piperidine-2,6-dione (730 mg, 1.69 mmol, TFA) in DCM (8 mL) was added TEA (170 mg, 1.69 mmol, 235 μL) and $Boc_2O$ (737 mg, 3.38 mmol, 775 μL), the reaction mixture was stirred at 25° C. for 12 hrs. On completion, the reaction mixture was diluted with water (10 mL) and extracted with DCM (2×15 mL). The combined organic layers was dried over $Na_2SO_4$, filtered and the filtrate was concentrated in vacuo to give a residue. The residue was purified by reverse phase (0.1% FA condition) to give the title compound (450 mg, 63% yield) as brown solid. $^1$H NMR (400 MHz, DMSO-$d_6$) δ 11.07 (s, 1H), 7.00-6.98 (m, 1H), 6.87 (d, J=2.0 Hz, 1H), 6.62 (dd, J=2.4, 8.4 Hz, 1H), 5.31 (dd, J=5.2, 12.8 Hz, 1H), 3.95 (t, J=5.6 Hz, 2H), 3.31 (s, 3H), 3.30-3.25 (m, 2H), 2.93-2.84 (m, 1H), 2.74-2.57 (m, 2H), 1.99 (s, 1H), 1.39 (s, 9H).

Step 7-3-[5-(2-Aminoethoxy)-3-methyl-2-oxo-benzimidazol-1-yl]piperidine-2,6-dione. To a solution of tert-butyl N-[2-[1-(2,6-dioxo-3-piperidyl)-3-methyl-2-oxo-benzimidazol-5-yl]oxyethyl]carbamate (60.0 mg, 143 μmol) in DCM (1 mL) was added TFA (16.3 mg, 143 μmol, 10.6 μL). The mixture was stirred at 25° C. for 0.2 hr. On completion, the reaction mixture was concentrated in vacuo to give the title compound (45.0 mg, 98% yield, TFA) as white solid. LC-MS (ESI) m/z 319.0 (M+H)$^+$.

Step 8-(R)-1-(2-(((3S,7aS)-3-(((tert-butyldiphenylsilyl)oxy)methyl)tetrahydro-1H-pyrrolizin-7a (5H)-yl) methoxy)-8-fluoro-7-(7-fluoro-8-((triisopropylsilyl) ethynyl) naphthalen-1-yl)pyrido[4,3-d]pyrimidin-4-yl)-3-methylpiperidin-3-ol. To a solution of (R)-1-(2-(((3S,7aS)-3-(((tert-butyldiphenylsilyl)oxy)methyl)tetrahydro-1H-pyrrolizin-7a (5H)-yl) methoxy)-7-chloro-8-fluoropyrido[4,3-d]pyrimidin-4-yl)-3-methylpiperidin-3-ol (4.00 g, 5.68 mmol) in dioxane (40 mL) and $H_2O$ (8 mL) was added ditert-butyl(cyclopentyl)phosphane; dichloropalladium; iron (370 mg, 567 μmol) and $Cs_2CO_3$ (5.55 g, 17.0 mmol), 2-[2-fluoro-8-(4,4,5,5-tetramethyl-1,3,2-dioxaborolan-2-yl)-1-naphthyl]ethynyl-triisopropyl-silane (3.85 g, 8.52 mmol, CAS #2503307-87-5). The mixture was stirred at 100° C. for 3 hrs under $N_2$ atmosphere. On completion, the reaction mixture was partitioned between EA (200 mL) and water (100 mL). The organic phase was separated, washed with brine (100 mL), dried over anhydrous sodium sulfate, filtered and the filtrate was concentrated in vacuo. The residue was purified by column chromatography ($SiO_2$, DCM/MeOH=100/1 to 10/1) to give the title compound (4.40 g, 65% yield) as brown solid. $^1$H NMR (400 MHz, DMSO-$d_6$) δ 9.44-9.06 (m, 1H), 8.30-8.13 (m, 2H), 7.68 (d, J=3.6 Hz, 1H), 7.67-7.61 (m, 6H), 7.60 (s, 1H), 7.47-7.44 (m, 4H), 7.44-7.40 (m, 1H), 4.46-4.27 (m, 1H), 4.12-4.05 (m, 1H), 4.05-3.96 (m, 2H), 3.94 (s, 1H), 3.93-3.87 (m, 1H), 3.80-3.71 (m, 1H), 3.69-3.60 (m, 1H), 3.57 (s, 1H), 3.55-3.46 (m, 1H), 3.28-3.15 (m, 2H), 2.78-2.67 (m, 2H), 2.55 (s, 2H), 2.07-2.01 (m, 1H), 1.85-1.59 (m, 9H), 1.55-1.46 (m, 1H), 1.19 (d, J=4.2 Hz, 3H), 1.00 (d, J=4.8 Hz, 9H), 0.88-0.79 (m, 18H).

Step 9-(R)-1-(7-(8-ethynyl-7-fluoronaphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol. To a solution of (R)-1-(2-(((3S,7aS)-3-(((tert-butyldiphenylsilyl)oxy)methyl)tetrahydro-1H-pyrrolizin-7a (5H)-yl) methoxy)-8-fluoro-7-(7-fluoro-8-((triisopropylsilyl) ethynyl) naphthalen-1-yl)pyrido[4,3-d]pyrimidin-4-yl)-3-methylpiperidin-3-ol (4.40 g, 4.42 mmol) in DMSO (50 mL) was added CsF (2.02 g, 13.2 mmol). The mixture was stirred at 50° C. for 3 hrs. On completion, the reaction mixture was partitioned between EA (200 mL) and water (100 mL). The organic phase was separated, washed with brine (100 mL), dried over anhydrous sodium sulfate, filtered and the filtrate was concentrated in vacuo. The residue was purified by column chromatography ($SiO_2$, DCM/MeOH=100/1 to 10/1) to give the title compound (1.40 g, 49% yield) as yellow solid. $^1$H NMR (400 MHz, DMSO-$d_6$) δ 9.29-8.99 (m, 1H), 8.30-8.12 (m, 2H), 7.71-7.67 (m, 1H), 7.64-7.58 (m, 1H), 7.51-7.29 (m, 1H), 4.76 (d, J=17.2 Hz, 1H), 4.68-4.55 (m, 1H), 4.40-4.27 (m, 1H), 4.17-4.11 (m, 1H), 4.08-4.03 (m, 1H), 4.03-3.95 (m, 1H), 3.69-3.56 (m, 2H), 3.50 (dd, J=6.0, 10.8 Hz, 1H), 3.45-3.38 (m, 1H), 3.13-3.07 (m, 1H), 2.85-2.77 (m, 1H), 2.76-2.65 (m, 1H), 2.06-2.02 (m, 1H), 1.75-1.68 (m, 6H), 1.62-1.46 (m, 2H), 1.44-1.34 (m, 1H), 1.33-1.23 (m, 1H), 1.19-1.15 (m, 3H), 1.01 (s, 1H), 0.90-0.82 (m, 1H); LC-MS (ESI) m/z 600.1 (M+H)$^+$.

Step 10-((35,7aS)-7a-(((7-(8-ethynyl-7-fluoronaphthalen-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl)methyl (4-nitrophenyl) carbonate. To a solution of (R)-1-(7-(8-ethynyl-7-fluoronaphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (60.0 mg, 100 μmol) in DCM (6 mL) was added TEA (290 mg, 2.87 mmol, 0.4 mL) and (4-nitrophenyl) carbonochloridate (60.5 mg, 300 μmol, CAS #7693-46-1), DMAP (1.22 mg, 10.0 μmol). The mixture was stirred at 25° C. for 16 hrs. On completion, the reaction mixture was partitioned between DCM (80 mL) and water (30 mL). The organic phase was separated, washed with brine (50 mL), dried over anhydrous sodium sulfate, filtered and the filtrate was concentrated in vacuo to give the title compound (60.0 mg, 78% yield) as white solid. LC-MS (ESI) m z 765.3 (M+H)$^+$.

Step 11-((3S,7aS)-7a-(((7-(8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (2-((1-(2,6-dioxopiperidin-3-yl)-3-methyl-2-oxo-2,3-dihydro-1H-benzo[d]imidazol-5-yl)oxy) ethyl) carbamate (Compound 106). To a solution of 3-[5-(2-aminoethoxy)-3-methyl-2-oxo-benzimidazol-1-yl] piperidine-2,6-dione (37.4 mg, 117 μmol, TFA) in THF (5 mL) was added TEA (55.5 mg, 549 μmol, 76.4 μL) and ((3S,7aS)-7a-(((7-(8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (60.0 mg, 78.4 μmol). The mixture was stirred at 25° C. for 0.5 hr. On completion, the reaction mixture was concentrated in vacuo. The residue was purified by prep-HPLC (column: CD01-Phenomenex luna C18 150*25*10 μm; mobile phase: [water (FA)-ACN]; gradient: 12%-42% B over 10 min) and (column: CD07-Daisogel SP-100-8-ODS-PK 150*25*10 μm; mobile phase: [water ($NH_4HCO_3$)-ACN]; gradient: 30%-60% B over 10 min) to give the title compound (16.8 mg, 22% yield) as white solid. $^1$H NMR (400 MHz, DMSO-$d_6$) δ 11.06 (s, 1H), 9.27-9.01 (m, 1H), 8.26-8.15 (m, 2H), 7.73-7.64 (m, 2H), 7.60 (t, J=8.8 Hz, 1H), 7.49-7.40 (m, 1H), 6.98 (d, J=8.4 Hz, 1H), 6.90-6.80 (m, 1H), 6.61 (dd, J=2.4, 8.4 Hz, 1H), 5.30 (dd, J=5.2, 12.4 Hz, 1H), 4.75 (d, J=17.2 Hz, 1H), 4.41-4.26 (m, 1H), 4.19-4.08 (m, 3H), 4.05-3.95 (m, 4H), 3.58 (t, J=13.8 Hz, 1H), 3.29 (s, 3H), 3.26-3.21 (m, 2H), 2.92-2.83 (m, 1H), 2.76-2.59 (m, 4H), 2.06-1.93 (m, 3H), 1.80-1.57 (m, 10H), 1.55-1.48 (m, 1H), 1.43-1.25 (m, 1H), 1.16 (d, J=14.8 Hz, 3H), 1.02-0.73 (m, 1H); LC-MS (ESI$^+$) m/z 944.2 (M+H)$^+$.

Example 14. Synthesis of Compound 101
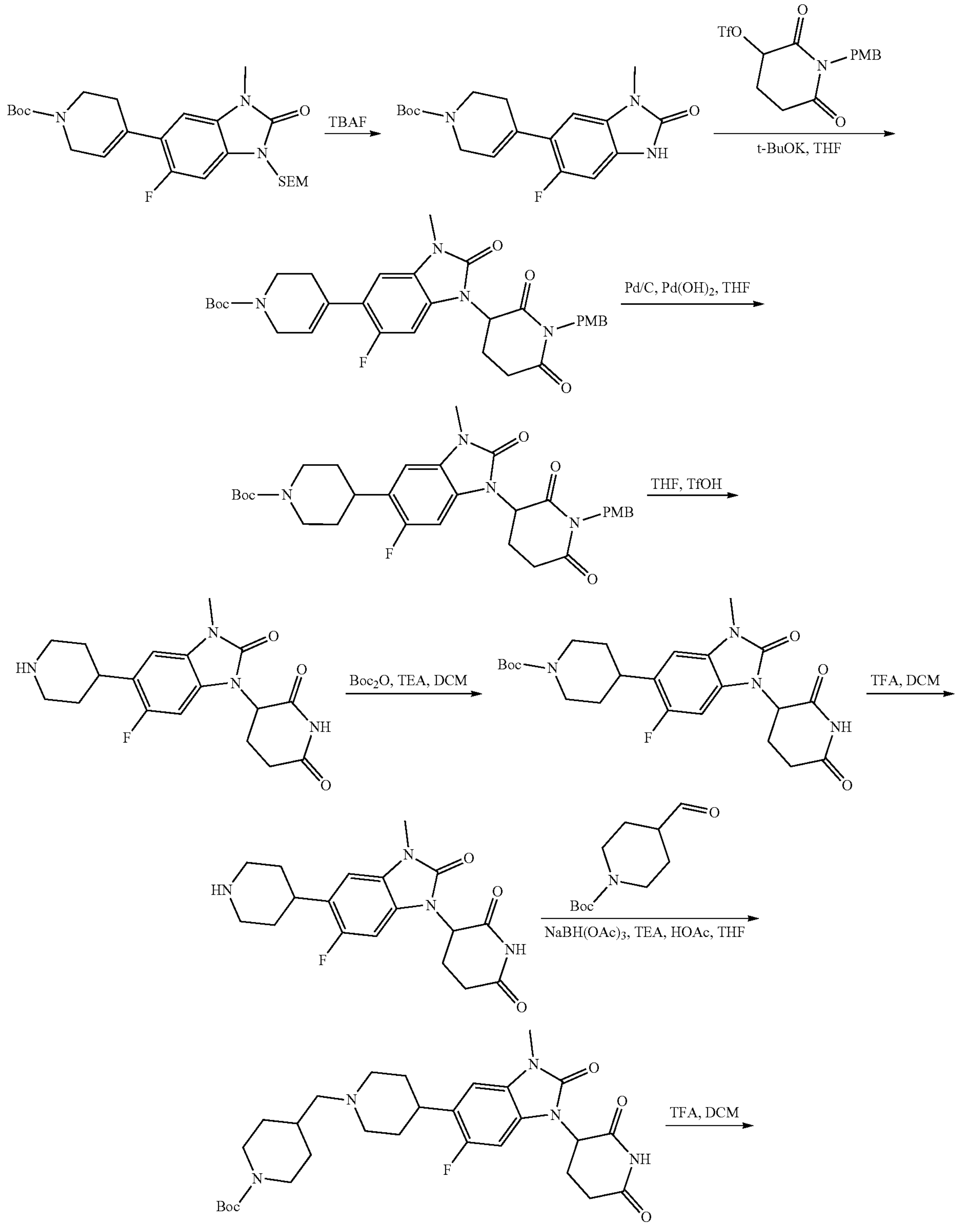

-continued

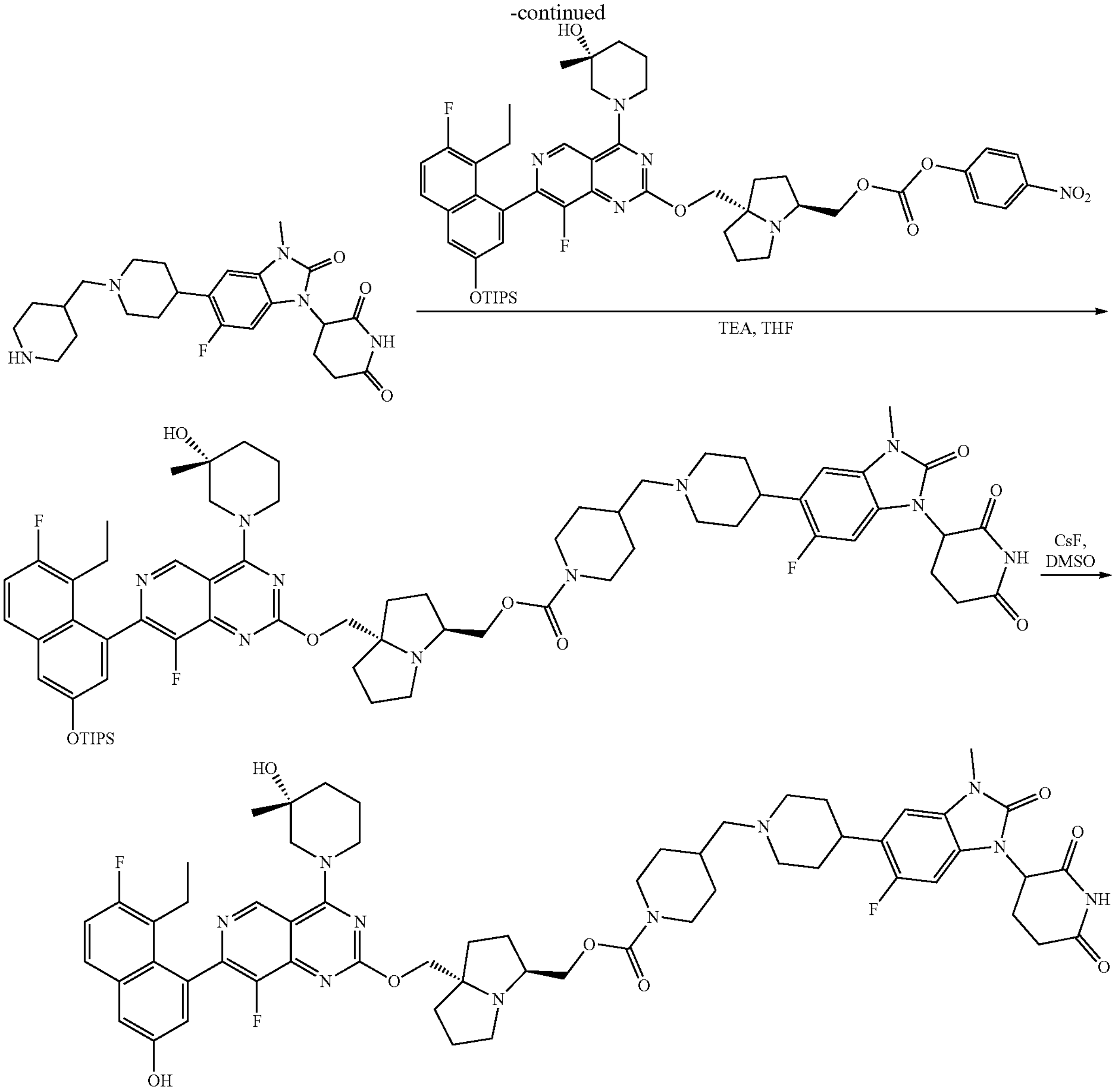

101

Step 1-Tert-butyl 4-(6-fluoro-3-methyl-2-oxo-1H-benzimidazol-5-yl)-3,6-dihydro-2H-pyridine-1-carboxylate. To a solution of tert-butyl 4-[6-fluoro-3-methyl-2-oxo-1-(2-trimethylsilylethoxymethyl)benzimidazol-5-yl]-3,6-dihydro-2H-pyridine-1-carboxylate (4.00 g, 8.37 mmol) in THF (40 mL) was added TBAF (1 M, 83.7 mL). The reaction mixture was stirred at 80° C. for 16 hrs. On completion, the reaction mixture was concentrated in vacuo to give a residue. The residue was diluted with water (100 mL) and extracted with DCM (2×150 mL). The combined organic layers were dried over anhydrous $Na_2SO_4$, filtered and the filtrate was concentrated in vacuo to give a residue. The residue was purified by column chromatography ($SiO_2$, PE:EA=50:1 to PE:EA=0:1) to give the title compound (1.80 g, 62% yield) as yellow solid. $^1H$ NMR (400 MHz, DMSO-$d_6$) δ 10.96 (s, 1H), 7.02 (d, J=6.4 Hz, 1H), 6.82 (d, J=10.8 Hz, 1H), 5.90 (s, 1H), 4.03-3.95 (m, 2H), 3.52 (t, J=5.6 Hz, 2H), 3.26 (s, 3H), 2.43 (s, 2H), 1.43 (s, 9H); LC-MS (ESI) m/z 348.2 $(M+H)^+$.

Step 2-Tert-butyl 4-[6-fluoro-1-[1-[(4-methoxyphenyl)methyl]-2,6-dioxo-3-piperidyl]-3-methyl-2-oxo-benzimidazol-5-yl]-3,6-dihydro-2H-pyridine-1-carboxylate. To a solution of tert-butyl 4-(6-fluoro-3-methyl-2-oxo-1H-benzimidazol-5-yl)-3,6-dihydro-2H-pyridine-1-carboxylate (1.60 g, 4.61 mmol) in THF (35 mL) was added t-BuOK (775 mg, 6.91 mmol) at −20° C. The reaction mixture was stirred at −20° C. for 0.5 hr. [1-[(4-methoxyphenyl)methyl]-2,6-dioxo-3-piperidyl]trifluoromethanesulfonate (2.11 g, 5.53 mmol, CAS #2304754-47-8) was added to the mixture. The reaction mixture was stirred at −20° C. for 0.5 hr. On completion, the reaction mixture was quenched with $NH_4Cl$ solution (10 mL) under stirring. The residue was diluted with water (70 mL) and extracted with EA (100 mL×3). The combined organic layer was dried over anhydrous $Na_2SO_4$, filtered and the filtrate was concentrated in vacuo to give a residue. The residue was purified by column chromatography ($SiO_2$, PE:EA=50:1 to PE:EA=1:1) to give the title compound (2.60 g, 97% yield) as green solid. LC-MS (ESI) m/z 601.1 $(M+Na)^+$.

Step 3-Tert-butyl 4-[6-fluoro-1-[1-[(4-methoxyphenyl)methyl]-2,6-dioxo-3-piperidyl]-3-methyl-2-oxo-benzimidazol-5-yl]piperidine-1-carboxylate. To a solution of tert-butyl 4-[6-fluoro-1-[1-[(4-methoxyphenyl)methyl]-2,6-dioxo-3-piperidyl]-3-methyl-2-oxo-benzimidazol-5-yl]-3,6-dihydro-2H-pyridine-1-carboxylate (2.10 g, 3.63 mmol) in THF (20 mL) was added Pd/C (1.05 g, 986 μmol, 10% purity) and $Pd(OH)_2/C$ (1.05 g, 1.50 mmol, 20% purity) under $N_2$ atmosphere. The suspension was degassed and purged with $H_2$ for 3 times. The mixture was stirred at 25° C. for 2 hrs under $H_2$ (15 psi) atmosphere. On completion, the reaction mixture was filtered and the filtrate was concentrated in vacuo to give the title compound (2.00 g, 95% yield) as white solid. $^1$H NMR (400 MHz, DMSO-$d_6$) δ 7.25-7.13 (m, 3H), 6.99 (d, J=10.4 Hz, 1H), 6.84 (d, J=8.8 Hz, 2H), 5.48 (dd, J=5.2, 13.2 Hz, 1H), 4.87-4.69 (m, 2H), 4.19-4.05 (m, 2H), 3.72 (s, 3H), 3.30 (s, 3H), 3.11-2.94 (m, 2H), 2.90-2.69 (m, 4H), 2.08-1.99 (m, 1H), 1.76-1.55 (m, 4H), 1.42 (s, 9H); LC-MS (ESI) m/z 603.1 $(M+Na)^+$.

Step 4-3-[6-Fluoro-3-methyl-2-oxo-5-(4-piperidyl)benzimidazol-1-yl]piperidine-2,6-dione. A solution of tert-butyl 4-[6-fluoro-1-[1-[(4-methoxyphenyl)methyl]-2,6-dioxo-3-piperidyl]-3-methyl-2-oxo-benzimidazol-5-yl]piperidine-1-carboxylate (1.90 g, 3.27 mmol) in TfOH (4.24 g, 28.2 mmol, 2.50 mL) and TFA (30.7 g, 269 mmol, 20 mL) was stirred at 70° C. for 1 hr. On completion, the reaction mixture was concentrated in vacuo to give the title compound (1.55 g, 100% yield, TFA salt) as brown oil. LC-MS (ESI) m/z 361.0 $(M+H)^+$.

Step 5-Tert-butyl 4-[1-(2,6-dioxo-3-piperidyl)-6-fluoro-3-methyl-2-oxo-benzimidazol-5-yl]piperidine-1-carboxylate. To a solution of 3-[6-fluoro-3-methyl-2-oxo-5-(4-piperidyl)benzimidazol-1-yl]piperidine-2,6-dione (1.50 g, 3.16 mmol, TFA salt) in DCM (15 mL) was added TEA (959 mg, 9.49 mmol, 1.32 mL) and $Boc_2O$ (828 mg, 3.79 mmol) at 0° C. The reaction mixture was stirred at 25° C. for 0.5 hr. On completion, the reaction mixture was concentrated in vacuo to give a residue. The residue was diluted with water (60 mL) and extracted with DCM (2×80 mL). The combined organic layers was dried over anhydrous $Na_2SO_4$, filtered and the filtrate was concentrated in vacuo to give a residue. The residue was purified by reverse phase (0.1% FA condition) to give the title compound (1.40 g, 96% yield) as yellow solid. $^1$H NMR (400 MHz, DMSO-$d_6$) δ 11.08 (s, 1H), 7.20-7.06 (m, 2H), 5.32 (dd, J=5.2, 12.8 Hz, 1H), 4.10 (d, J=9.2 Hz, 2H), 3.33 (s, 3H), 3.04-2.96 (m, 1H), 2.92-2.62 (m, 5H), 2.03-1.93 (m, 1H), 1.74-1.56 (m, 4H), 1.42 (s, 9H); LC-MS (ESI) m/z 483.0 $(M+Na)^+$.

Step 6-3-[6-Fluoro-3-methyl-2-oxo-5-(4-piperidyl)benzimidazol-1-yl]piperidine-2,6-dione. To a solution of tert-butyl 4-[1-(2,6-dioxo-3-piperidyl)-6-fluoro-3-methyl-2-oxo-benzimidazol-5-yl]piperidine-1-carboxylate (500 mg, 1.09 mmol) in DCM (5 mL) was added TFA (1.54 g, 13.4 mmol, 1 mL). The reaction mixture was stirred at 25° C. for 0.5 hr. On completion, the reaction mixture was concentrated in vacuo to give the title compound (515 mg, 99% yield, TFA salt) as yellow oil. LC-MS (ESI) m/z 361.0 $(M+H)^+$.

Step 7-Tert-butyl 4-[[4-[1-(2,6-dioxo-3-piperidyl)-6-fluoro-3-methyl-2-oxo-benzimidazol-5-yl]-1-piperidyl]methyl]piperidine-1-carboxylate. To a solution of 3-[6-fluoro-3-methyl-2-oxo-5-(4-piperidyl)benzimidazol-1-yl]piperidine-2,6-dione (510 mg, 1.08 mmol, TFA salt) in THF (5 mL) was added TEA (326 mg, 3.23 mmol). The reaction mixture was stirred at 25° C. for 0.1 hr. Then tert-butyl 4-formylpiperidine-1-carboxylate (458 mg, 2.15 mmol, CAS #137076-22-3) and AcOH (129 mg, 2.15 mmol) were added to the mixture. The reaction mixture was stirred at 25° C. for 0.4 hr. $NaBH(OAc)_3$ (273 mg, 1.29 mmol) was added to the mixture. The reaction mixture was stirred at 25° C. for 0.5 hr. On completion, the reaction mixture was quenched with water (0.3 mL) and concentrated in vacuo to give a residue. The residue was purified by reverse phase (0.1% FA condition) to give the title compound (570 mg, 95% yield) as white solid. LC-MS (ESI) m/z 558.1 $(M+H)^+$.

Step 8-3-[6-Fluoro-3-methyl-2-oxo-5-[1-(4-piperidylmethyl)-4-piperidyl/benzimidazol-1-yl]piperidine-2,6-dione. To a solution of tert-butyl 4-[4-[1-(2,6-dioxo-3-piperidyl)-6-fluoro-3-methyl-2-oxo-benzimidazol-5-yl]-1-piperidyl]methyl]piperidine-1-carboxylate (100 mg, 179 μmol) in DCM (1 mL) was added TFA (307 mg, 2.69 mmol). The reaction mixture was stirred at 25° C. for 0.5 hr. On completion, the reaction mixture was concentrated in vacuo to give the title compound (102 mg, 99% yield, TFA salt) as yellow oil. LC-MS (ESI) m/z 458.3 $(M+H)^+$.

Step 9-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl) piperidin-1-yl)methyl) piperidine-1-carboxylate. To a solution of 3-[6-fluoro-3-methyl-2-oxo-5-[1-(4-piperidylmethyl)-4-piperidyl]benzimidazol-1-yl]piperidine-2,6-dione (65.5 mg, 114 μmol, TFA salt) in THF (2 mL) and $H_2O$ (0.4 mL) was added TEA (23.2 mg, 229 μmol, 31.9 μL). Then a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (72.0 mg, 76.5 μmol) in THF (2 mL) was added to the mixture. The reaction mixture was stirred at 25° C. for 0.5 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 25%-55% B over 8 min) to give the title compound (60.0 mg, 62% yield) as white solid. LC-MS (ESI) m/z 1260.8 $(M+H)^+$.

Step 10-((35,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl) piperidin-1-yl)methyl) piperidine-1-carboxylate (Compound 101). To a solution of ((3S,7aS)-7a-(((7-(8-ethyl-7-fluoro-3-((triisopropylsilyl) oxy) naphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl) piperidin-1-yl)methyl) piperidine-1-carboxylate (50.0 mg, 39.7 μmol) in DMSO (1 mL) was added CsF (18.0 mg, 119 μmol). The reaction mixture was stirred at 25° C. for 0.5 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 10%-40% B over 8 min) to give the title compound (26.8 mg, 57% yield, FA salt) as white solid. $^1$H NMR (400 MHz, DMSO-$d_6$) δ 11.08 (s, 1H), 10.01-9.83 (m, 1H), 9.23 (d, J=4.0 Hz, 1H), 7.76 (dd, J=6.0, 9.2 Hz, 1H), 7.40-7.26 (m, 2H), 7.20-6.96 (m, 3H), 5.33 (dd, J=5.2, 12.8 Hz, 1H), 4.75 (d, J=9.2 Hz, 1H), 4.40-4.27 (m, 1H), 4.26-4.08 (m, 4H), 4.06-3.90 (m, 3H), 3.66-3.50 (m, 1H), 3.42 (s, 3H), 2.94 (d, J=9.6 Hz, 2H), 2.89-2.61 (m, 8H), 2.44-2.24 (m, 2H), 2.19-1.93 (m, 8H), 1.90-1.41 (m, 18H), 1.17 (d, J=9.2 Hz, 3H), 1.05-0.88 (m, 2H), 0.73 (q, J=7.2 Hz, 3H); LC-MS (ESI) m/z 1103.3 $(M+H)^+$.

Example 15. Synthesis of Compound 102

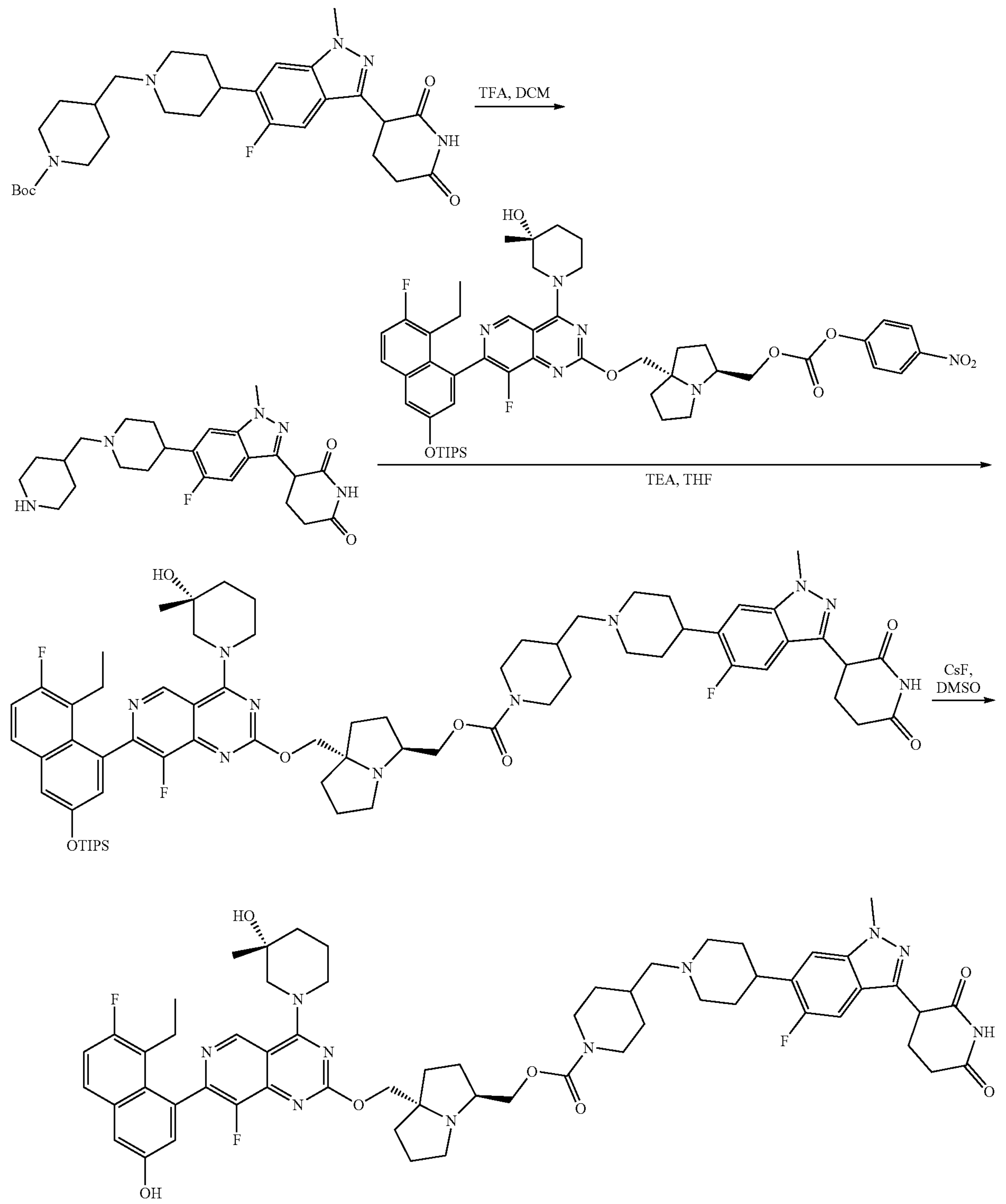

102

Step 1-3-[5-Fluoro-1-methyl-6-[1-(4-piperidylmethyl)-4-piperidyl]indazol-3-yl]piperidine-2,6-dione. To a solution of tert-butyl 4-[[4-[3-(2,6-dioxo-3-piperidyl)-5-fluoro-1-methyl-indazol-6-yl]-1-piperidyl]methyl]piperidine-1-carboxylate (90.0 mg, 166 μmol) in DCM (2 mL) was added TFA (767 mg, 6.73 mmol, 500 μL). The mixture was stirred at 25° C. for 2 hrs. On completion, the mixture was concentrated in vacuo to give the title compound (70 mg, 75% yield, TFA) as yellow oil. LC-MS (ESI$^+$) m/z 442.2 (M+H)$^+$.

Step 2-((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl4-((4-(3-(2,6-dioxopiperidin-3-yl)-5-fluoro-1-methyl-1H-indazol-6-yl) piperidin-1-yl)methyl) piperidine-1-carboxylate. To a solution of 3-[5-fluoro-1-methyl-6-[1-(4-piperidylmethyl)-4-piperidyl]indazol-3-yl]piperidine-2,6-dione (49.2 mg, 111 μmol, TFA) and ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl) oxy)methyl)hexahydro-1H-pyrrolizin-3-yl)methyl (4-nitrophenyl) carbonate (70.0 mg, 74.3 μmol) in THF (1 mL) was added TEA (22.5 mg, 223 μmol). The mixture was stirred at 25° C. for 10 mins. On completion, the mixture was concentrated in vacuo. The residue was purified by prep-HPLC (column: Phenomenex luna C18 150*25 mm*10 μm; mobile phase: [water (FA)-ACN]; gradient: 30%-60% B over 10 min) to give the title compound (40.0 mg, 43% yield) as white solid. LC-MS (ESI) m/z 1244.5 $(M+H)^+$.

Step 3-((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl4-((4-(3-(2,6-dioxopiperidin-3-yl)-5-fluoro-1-methyl-1H-indazol-6-yl) piperidin-1-yl)methyl) piperidine-1-carboxylate (Compound 102). To a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d] pyrimidin-2-yl)oxy)methyl)hexahydro-1H-pyrrolizin-3-yl) methyl4-((4-(3-(2,6-dioxopiperidin-3-yl)-5-fluoro-1-methyl-1H-indazol-6-yl) piperidin-1-yl)methyl) piperidine-1-carboxylate (35.0 mg, 28.1 μmol) in DMSO (1 mL) was added CsF (12.8 mg, 84.4 μmol). The mixture was stirred at 25° C. for 0.5 hr. On completion, the mixture was filtered. The filtrate was purified by prep-HPLC (column: CD01-Phenomenex luna C18 150*25*10 μm; mobile phase: [water (FA)-ACN]; gradient: 15%-45% B over 10 min) and then re-purified by prep-HPLC (column: Phenomenex luna C18 150*25 mm*10 μm; mobile phase: [water (HCl)-ACN]; gradient: 18%-48% B over 10 min) to give the title compound (9.09 mg, 27% yield, HCl) as yellow solid. $^1H$ NMR (400 MHz, DMSO-$d_6$) δ 10.96-10.84 (m, 1H), 10.03 (dd, J=4.4, 7.2 Hz, 1H), 9.30 (s, 1H), 7.83-7.73 (m, 1H), 7.59-7.51 (m, 1H), 7.45 (d, J=6.0 Hz, 1H), 7.39-7.32 (m, 2H), 7.11-7.02 (m, 1H), 4.70-4.58 (m, 2H), 4.49-4.31 (m, 3H), 4.26-4.07 (m, 6H), 4.03-3.98 (m, 5H), 3.45-3.31 (m, 4H), 3.22-3.11 (m, 2H), 2.99 (s, 2H), 2.84 (s, 2H), 2.67-2.60 (m, 1H), 2.41-2.24 (m, 5H), 2.22-1.79 (m, 17H), 1.77-1.62 (m, 3H), 1.23-1.11 (m, 5H), 0.78-0.69 (m, 3H); LC-MS (ESI) m/z 1087.6 $(M+H)^+$.

Example 16. Synthesis of Compound 103

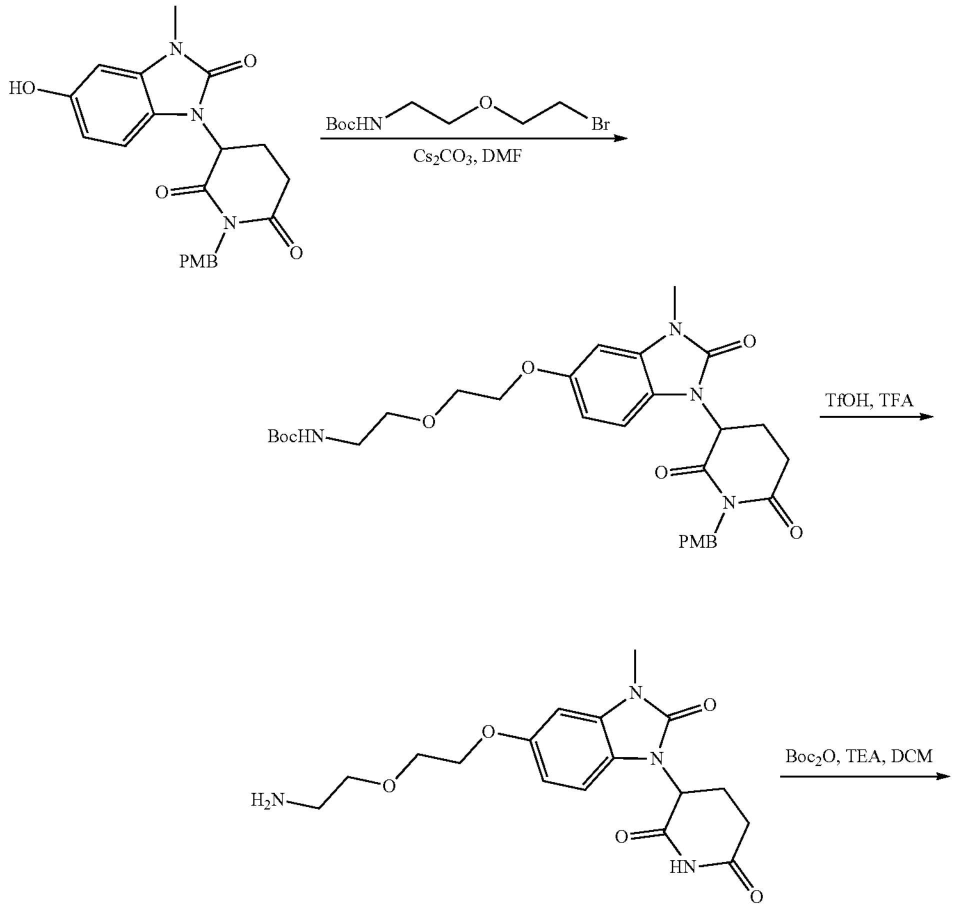

-continued

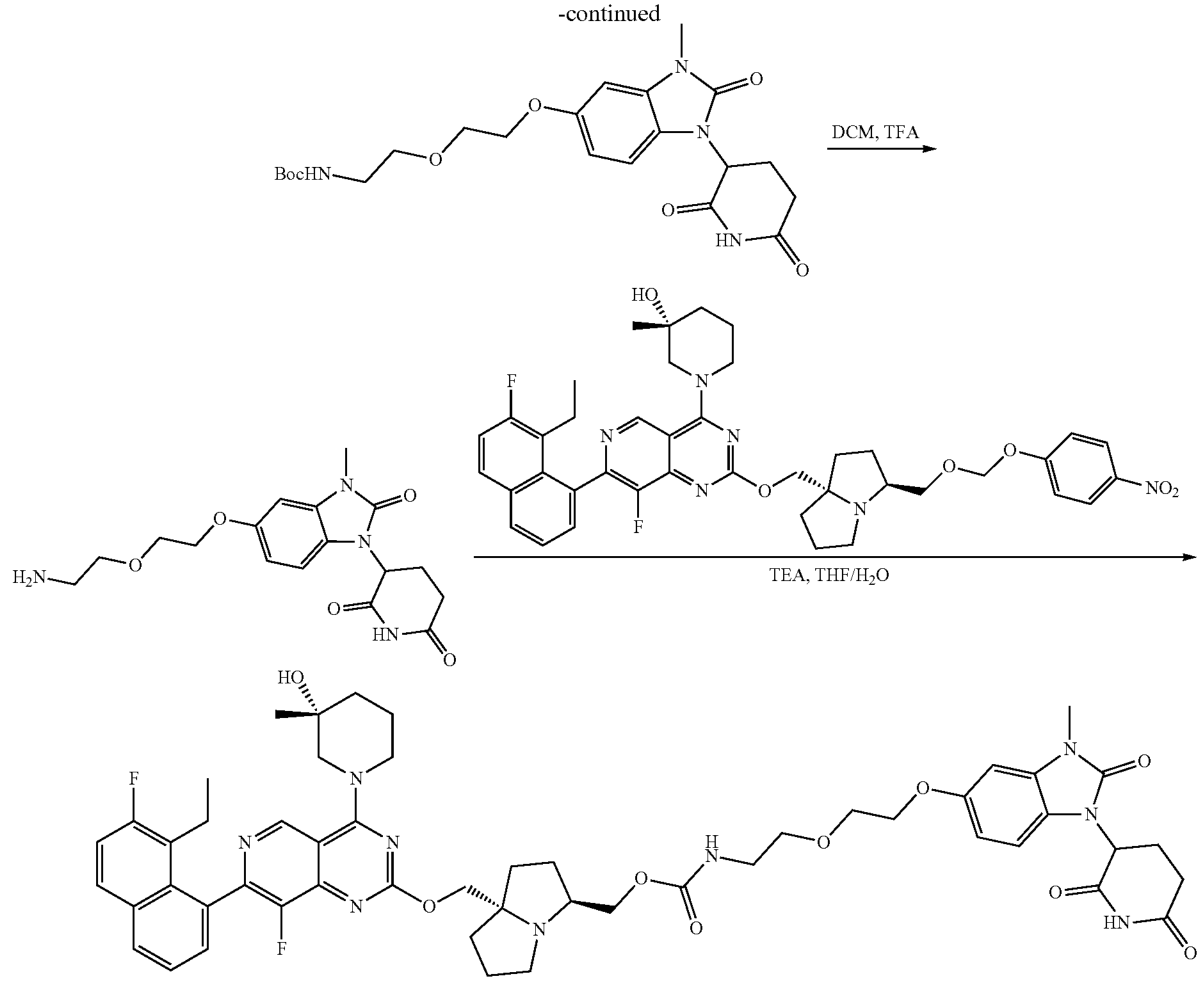

103

Step 1-Tert-butyl(2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy)ethyl) carbamate. To a solution of 3-(5-hydroxy-3-methyl-2-oxo-2,3-dihydro-1H-benzo[d]imidazol-1-yl)-1-(4-methoxybenzyl) piperidine-2,6-dione (500 mg, 1.26 mmol) and tert-butyl(2-(2-bromoethoxy)ethyl) carbamate (406 mg, 1.52 mmol, CAS #164332-88-1) in DMF (5 mL) was added $Cs_2CO_3$ (824 mg, 2.53 mmol). The mixture was stirred at 80° C. for 1 hr. On completion, the reaction mixture was concentrated in vacuo to give a residue. The residue was purified by reversed-phase HPLC (0.1% FA condition) to give the title compound (600 mg, 79% yield) as white solid. $^1H$ NMR (400 MHz, $CDCl_3$) δ 7.37 (d, J=8.8 Hz, 2H), 6.83 (d, J=8.8 Hz, 2H), 6.65 (d, J=2.0 Hz, 1H), 6.54 (dd, J=2.4, 8.8 Hz, 1H), 6.40 (d, J=8.4 Hz, 1H), 5.17 (dd, J=5.6, 13.2 Hz, 1H), 5.04-4.92 (m, 3H), 4.14-4.08 (m, 2H), 3.84-3.81 (m, 2H), 3.80 (s, 3H), 3.63 (t, J=5.2 Hz, 2H), 3.40 (s, 3H), 3.36 (d, J=5.2 Hz, 2H), 3.06-2.96 (m, 1H), 2.91-2.75 (m, 1H), 2.59 (dq, J=4.4, 13.2 Hz, 1H), 2.24-2.12 (m, 1H), 1.45 (s, 9H); LC-MS ($ESI^+$) m/z 483.1 $(M\text{-}Boc+H)^+$.

Step 2-3-(5-(2-(2-Aminoethoxy)ethoxy)-3-methyl-2-oxo-2,3-dihydro-1H-benzo[d]imidazol-1-yl) piperidine-2,6-dione. To a solution of Tert-butyl(2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy)ethyl) carbamate (1.20 g, 2.06 mmol) in TFA (12 mL) was added TfOH (6.78 g, 45.2 mmol, 4 mL). The mixture was stirred at 65° C. for 1.5 hr. On completion, the reaction mixture was concentrated in vacuo to give the title compound (980 mg, 99% yield, TFA salt) was obtained as red oil. LC-MS ($ESI^+$) m/z 363.0 $(M+H)^+$.

Step 3-Tert-butyl(2-(2-((1-(2,6-dioxopiperidin-3-yl)-3-methyl-2-oxo-2,3-dihydro-1H-benzo[d]imidazol-5-yl)oxy) ethoxy)ethyl) carbamate. To a solution of 3-(5-(2-(2-Aminoethoxy)ethoxy)-3-methyl-2-oxo-2,3-dihydro-1H-benzo [d]imidazol-1-yl) piperidine-2,6-dione (980 mg, 2.06 mmol, TFA salt) in DCM (10 mL) was added TEA (2.08 g, 20.5 mmol) and $Boc_2O$ (673 mg, 3.09 mmol). The mixture was stirred at 25° C. for 0.5 hr. On completion, the reaction mixture was concentrated in vacuo to give a residue. The residue was purified by prep-HPLC (0.1% FA condition) to give the title compound (700 mg, 73% yield) as white solid. $^1H$ NMR (400 MHz, DMSO-$d_6$) δ 11.07 (s, 1H), 6.99 (d, J=8.8 Hz, 1H), 6.89 (d, J=2.0 Hz, 1H), 6.84-6.76 (m, 1H), 6.62 (dd, J=2.4, 8.6 Hz, 1H), 5.31 (dd, J=5.2, 12.8 Hz, 1H), 4.08 (t, J=4.4 Hz, 2H), 3.78-3.69 (m, 2H), 3.45 (bt, J=6.0 Hz, 2H), 3.31 (s, 3H), 3.09 (q, J=6.0 Hz, 2H), 2.94-2.82 (m, 1H), 2.75-2.61 (m, 2H), 2.04-1.95 (m, 1H), 1.37 (s, 9H); LC-MS (ESI) m/z 363.0 $(M\text{-}Boc+H)^+$.

Step 4-3-(5-(2-(2-Aminoethoxy)ethoxy)-3-methyl-2-oxo-2,3-dihydro-1H-benzo[d]imidazol-1-yl) piperidine-2,6-dione. To a solution of tert-butyl(2-(2-((1-(2,6-dioxopiperidin-3-yl)-3-methyl-2-oxo-2,3-dihydro-1H-benzo[d]imidazol-5-yl)oxy) ethoxy)ethyl) carbamate (70.0 mg, 151 μmol) in DCM (1 mL) was added TFA (304 mg, 2.67 mmol, 0.2 mL). The mixture was stirred at 25° C. for 0.5 hr. On completion, the reaction mixture was concentrated in vacuo to give the title compound (70.0 mg, 97% yield, TFA salt) as yellow oil. LC-MS (ESI) m/z 363.0 $(M+H)^+$.

Step 5-((3S,7aS)-7a-(((7-(8-ethyl-7-fluoronaphthalen-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl)methyl (2-(2-((1-(2,6-dioxopiperidin-3-yl)-3-methyl-2-oxo-2,3-dihydro-1H-benzo[d]imidazol-5-yl) oxy) ethoxy)ethyl) carbamate (Compound 103). To a solution of 3-(5-(2-(2-aminoethoxy)ethoxy)-3-methyl-2-oxo-2,3-dihydro-1H-benzo[d]imidazol-1-yl) piperidine-2,6-dione (70.0 mg, 146 μmol, TFA salt) in THF (1 mL) and $H_2O$ (0.5 mL) was basified pH=7-8 with TEA (29.7 mg, 293 μmol). And then ((3S,7aS)-7a-(((7-(8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (75.3 mg, 97.9 μmol) in THF (4 mL) was added. The mixture was stirred at 25° C. for 0.5 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 18%-48% B over 10 min) to give the title compound (31.7 mg, 31% yield, FA salt) as yellow solid. $^1H$ NMR (400 MHz, DMSO-$d_6$) δ 11.07 (s, 1H), 9.23 (d, J=5.2 Hz, 1H), 8.14-8.10 (m, 1H), 8.02 (dd, J=6.2, 8.8 Hz, 1H), 7.62-7.56 (m, 1H), 7.52-7.45 (m, 2H), 7.26 (s, 1H), 6.98 (d, J=8.4 Hz, 1H), 6.87 (d, J=2.0 Hz, 1H), 6.61 (dd, J=2.4, 8.4 Hz, 1H), 5.30 (dd, J=5.6, 12.8 Hz, 1H), 4.75 (d, J=12.0 Hz, 1H), 4.40-4.26 (m, 1H), 4.18-3.99 (m, 7H), 3.76-3.69 (m, 2H), 3.66-3.49 (m, 2H), 3.47 (t, J=6.0 Hz, 2H), 3.30 (s, 3H), 3.15 (q, J=5.6 Hz, 2H), 2.93-2.82 (m, 1H), 2.78-2.55 (m, 5H), 2.45-2.37 (m, 1H), 2.28-2.13 (m, 1H), 2.07-1.92 (m, 3H), 1.80-1.59 (m, 9H), 1.54-1.45 (m, 1H), 1.16 (d, J=10.0 Hz, 3H), 0.76 (q, J=7.2 Hz, 3H); LC-MS ($ESI^+$) m/z 922.4 $(M+H)^+$.

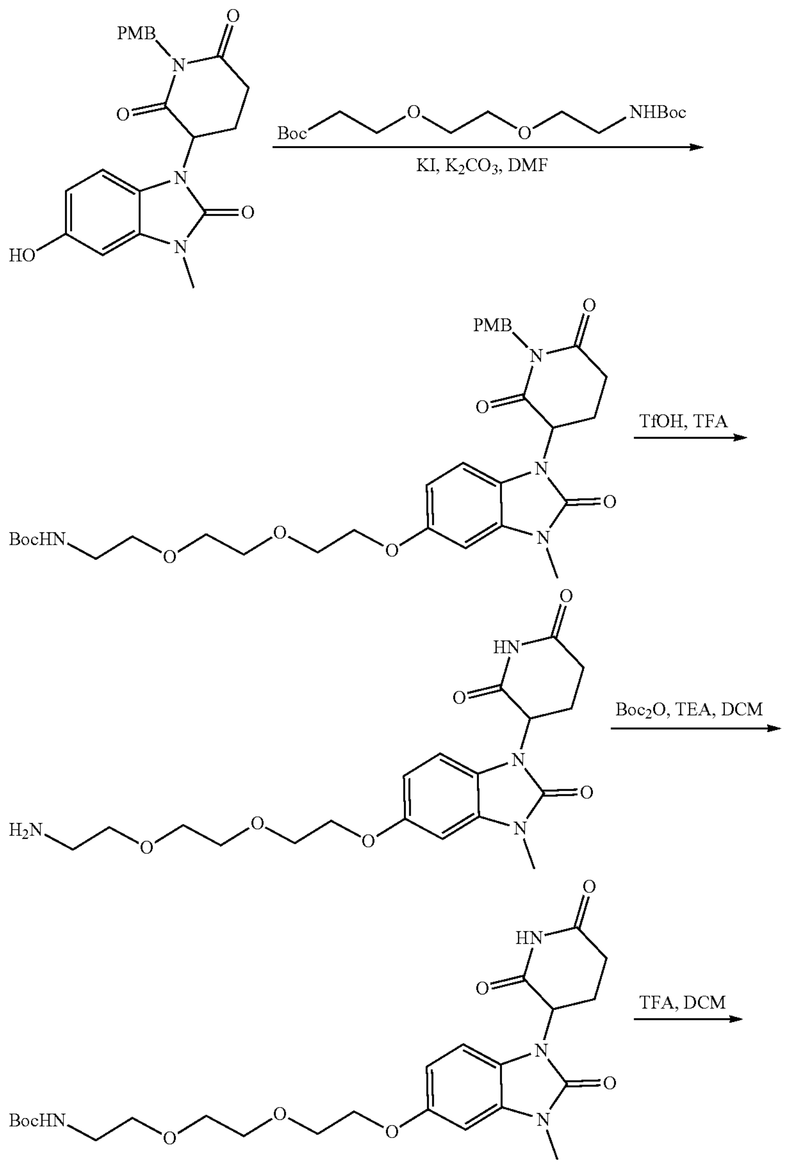

-continued

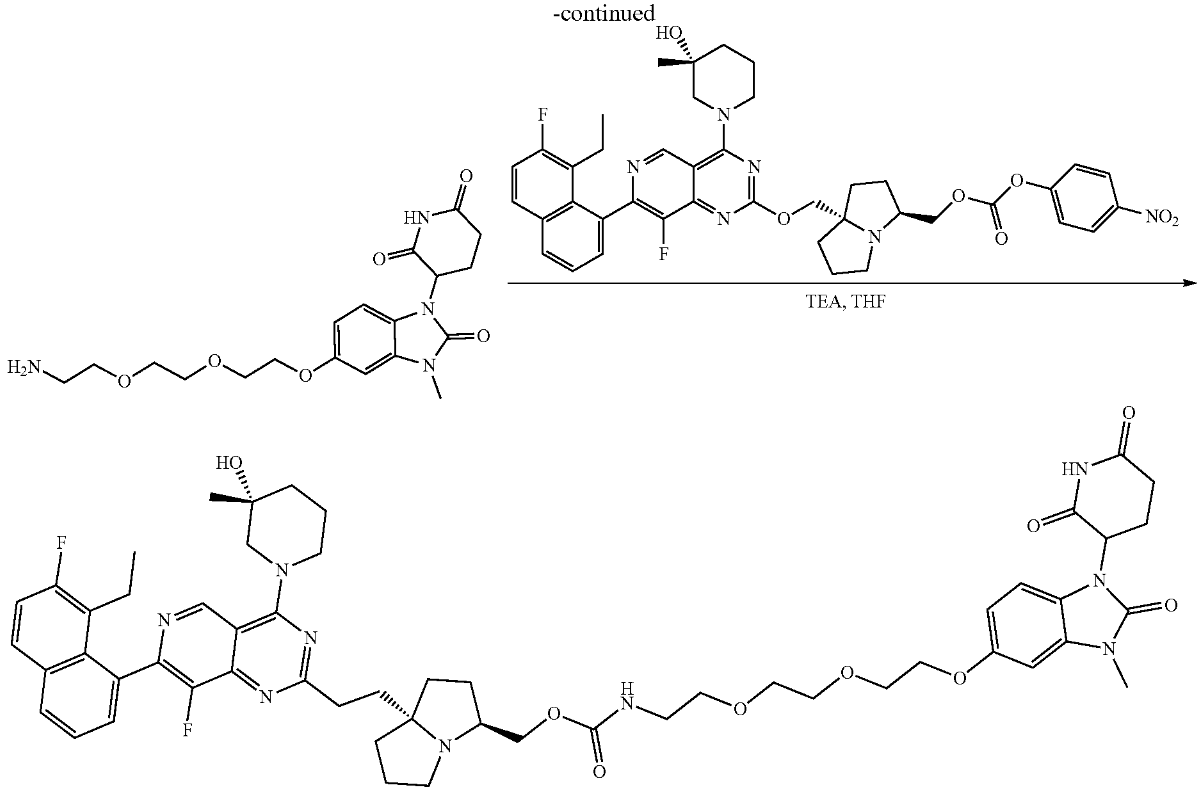

104

Step 1-Tert-butyl N-[2-[2-[2-[1-[1-[(4-methoxyphenyl)methyl]-2,6-dioxo-3-piperidyl]-3-methyl-2-oxo-benzimidazol-5-yl]oxyethoxy]ethoxy]ethyl]carbamate. To a solution of 3-(5-hydroxy-3-methyl-2-oxo-benzimidazol-1-yl)-1-[(4-methoxyphenyl)methyl]piperidine-2,6-dione (1.50 g, 3.79 mmol) in DMF (10 mL) was added KI (1.26 g, 7.59 mmol), tert-butyl N-[2-[2-(2-bromoethoxy)ethoxy]ethyl]carbamate (1.54 g, 4.93 mmol, CAS #165963-71-3) and $Cs_2CO_3$ (2.47 g, 7.59 mmol). The mixture was stirred at 70° C. for 1 hr. On completion, the reaction mixture was quenched by water (25 mL) at 25° C., and then extracted with EA (3x25 mL). The combined organic layers were washed with brine (50 mL), dried over anhydrous $Na_2SO_4$, filtered and the filtrate was concentrated in vacuo to give the residue. The residue was purified by reverse phase (0.1% FA condition) to give the title compound (2.30 g, 96% yield) as yellow oil. $^1H$ NMR (400 MHz, $CDCl_3$) δ 7.35 (d, J=8.8 Hz, 2H), 6.84-6.78 (m, 2H), 6.64 (d, J=1.6 Hz, 1H), 6.55-6.49 (m, 1H), 6.40 (d, J=8.4 Hz, 1H), 5.17 (dd, J=5.2, 13.2 Hz, 1H), 5.03 (s, 1H), 4.94 (d, J=3.6 Hz, 1H), 4.16-4.09 (m, 2H), 3.87-3.83 (m, 2H), 3.77 (s, 3H), 3.74-3.69 (m, 2H), 3.66-3.63 (m, 2H), 3.58-3.51 (m, 3H), 3.37 (s, 3H), 3.31 (d, J=4.8 Hz, 2H), 3.02-2.93 (m, 1H), 2.87-2.76 (m, 1H), 2.58 (m, 1H), 2.21-2.10 (m, 1H), 1.44-1.42 (m, 9H); LC-MS (ESI) m/z 527.3 $(M-Boc+H)^+$.

Step 2-3-[5-[2-[2-(2-Aminoethoxy)ethoxy]ethoxy]-3-methyl-2-oxo-benzimidazol-1-yl]piperidine-2,6-dione. To a solution of tert-butyl N-[2-[2-[2-[1-[1-[(4-methoxyphenyl)methyl]-2,6-dioxo-3-piperidyl]-3-methyl-2-oxo-benzimidazol-5-yl]oxyethoxy]ethoxy]ethyl]carbamate (2.30 g, 3.67 mmol) in TFA (17.6 g, 154 mmol, 11.5 mL) was added TfOH (6.50 g, 43.3 mmol, 3.83 mL). The mixture was stirred at 70° C. for 2 hrs. On completion, the reaction mixture was filtered and the filtrate concentrated in vacuo to give the title compound (1.48 g, 99% yield, TFA salt) as red oil. LC-MS (ESI) m/z 407.0 $(M+H)^+$.

Step 3-Tert-butyl N-[2-[2-[2-[1-(2,6-dioxo-3-piperidyl)-3-methyl-2-oxo-benzimidazol-5-yl]oxyethoxy]ethoxy]ethyl]carbamate. To a solution of 3-[5-[2-[2-(2-aminoethoxy)ethoxy]ethoxy]-3-methyl-2-oxo-benzimidazol-1-yl]piperidine-2,6-dione (1.48 g, 3.64 mmol, TFA salt) in DCM (15 mL) was added $Boc_2O$ (1.19 g, 5.46 mmol) and TEA (1.11 g, 10.9 mmol). The mixture was stirred at 25° C. for 1 hr. On completion, the reaction mixture was quenched by water (25 mL) at 25° C., and then extracted with EA (3x25 mL). The combined organic layers were washed with brine (50 mL), dried over anhydrous $Na_2SO_4$, filtered and the filtrate was concentrated in vacuo to give the residue. The residue was purified by reverse phase (0.1% FA condition) to give the title compound (1.00 g, 54% yield) as white solid. $^1H$ NMR (400 MHz, $CDCl_3$) δ 8.28 (s, 1H), 7.28 (s, 1H), 6.76-6.61 (m, 3H), 5.20 (dd, J=5.2, 12.8 Hz, 1H), 4.21-4.12 (m, 2H), 3.92-3.84 (m, 2H), 3.77-3.70 (m, 2H), 3.70-3.64 (m, 2H), 3.57 (t, J=5.2 Hz, 2H), 3.42 (s, 3H), 3.34 (d, J=4.4 Hz, 2H), 3.00-2.90 (m, 1H), 2.89-2.64 (m, 2H), 2.24 (m, 1H), 1.45 (s, 9H); LC-MS (ESI) m/z 407.1 $(M-Boc+H)^+$.

Step 4-3-[5-[2-[2-(2-Aminoethoxy)ethoxy]ethoxy]-3-methyl-2-oxo-benzimidazol-1-yl]piperidine-2,6-dione. To a solution of tert-butyl N-[2-[2-[2-[1-(2,6-dioxo-3-piperidyl)-3-methyl-2-oxo-benzimidazol-5-yl]oxyethoxy]ethoxy]ethyl]carbamate (100 mg, 197 μmol) in DCM (3 mL) was added TFA (1.54 g, 13.4 mmol). The mixture was stirred at 25° C. for 0.3 hr. On completion, the mixture was concentrated in vacuo to give the title compound (80.0 mg, 99.71% yield, TFA salt) as white solid. LC-MS (ESI) m/z 407.1 $(M+H)^+$.

Step 5-((3S,7aS)-7a-(((7-(8-ethyl-7-fluoronaphthalen-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl)methyl (2-(2-(2-((1-(2,6-dioxopiperidin-3-yl)-3-methyl-2-oxo-2,3-dihydro-1H-benzo[d]imidazol-5-yl) oxy) ethoxy)ethoxy)ethyl) carbamate (Compound 104). To a solution of 3-[5-[2-[2-(2-aminoethoxy)ethoxy]ethoxy]-3-methyl-2-oxo-benzimidazol-1-yl]piperidine-2,6-dione (79.3 mg, 195 μmol) in THF (5 mL) was added TEA (9.87 mg, 97.5 μmol) and ((3S,7aS)-7a-(((7-(8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (75.0 mg, 97.5 μmol). The mixture was stirred at 25° C. for 1 hr. On completion, the mixture was filtered and the filtrate was concentrated in vacuo to give a residue. The residue was purified by prep-HPLC (column: Phenomenex luna C18 150*25 mm*10 μm; mobile phase: [water (FA)-ACN]; gradient: 18%-48% B over 8 min) to give the title compound (39.1 mg, 36% yield, FA salt) as white solid. $^1$H NMR (400 MHz, DMSO-$d_6$) δ 11.08 (s, 1H), 9.25 (d, J=5.6 Hz, 1H), 8.13 (d, J=8.4 Hz, 1H), 8.03 (dd, J=6.0, 8.8 Hz, 1H), 7.59 (t, J=7.2 Hz, 1H), 7.54-7.45 (m, 2H), 7.24 (s, 1H), 6.99 (d, J=8.4 Hz, 1H), 6.88 (d, J=2.0 Hz, 1H), 6.62 (dd, J=2.0, 8.4 Hz, 1H), 5.31 (dd, J=5.2, 12.8 Hz, 1H), 4.76 (d, J=12.8 Hz, 1H), 4.35 (t, J=14.8 Hz, 1H), 4.27-4.00 (m, 7H), 3.78-3.69 (m, 2H), 3.66-3.46 (m, 6H), 3.44-3.40 (m, 3H), 3.30 (s, 3H), 3.14 (q, J=6.0 Hz, 2H), 2.95-2.76 (m, 3H), 2.75-2.65 (m, 1H), 2.64-2.57 (m, 1H), 2.46-2.36 (m, 1H), 2.27-2.15 (m, 1H), 2.13-2.06 (m, 1H), 2.00 (dd, J=4.8, 10.0 Hz, 2H), 1.90-1.51 (m, 10H), 1.17 (d, J=9.6 Hz, 3H), 0.84-0.71 (m, 3H); LC-MS (ESI$^+$) m/z 1036.3 (M+H)$^+$.

Example 18. Synthesis of Compound 105

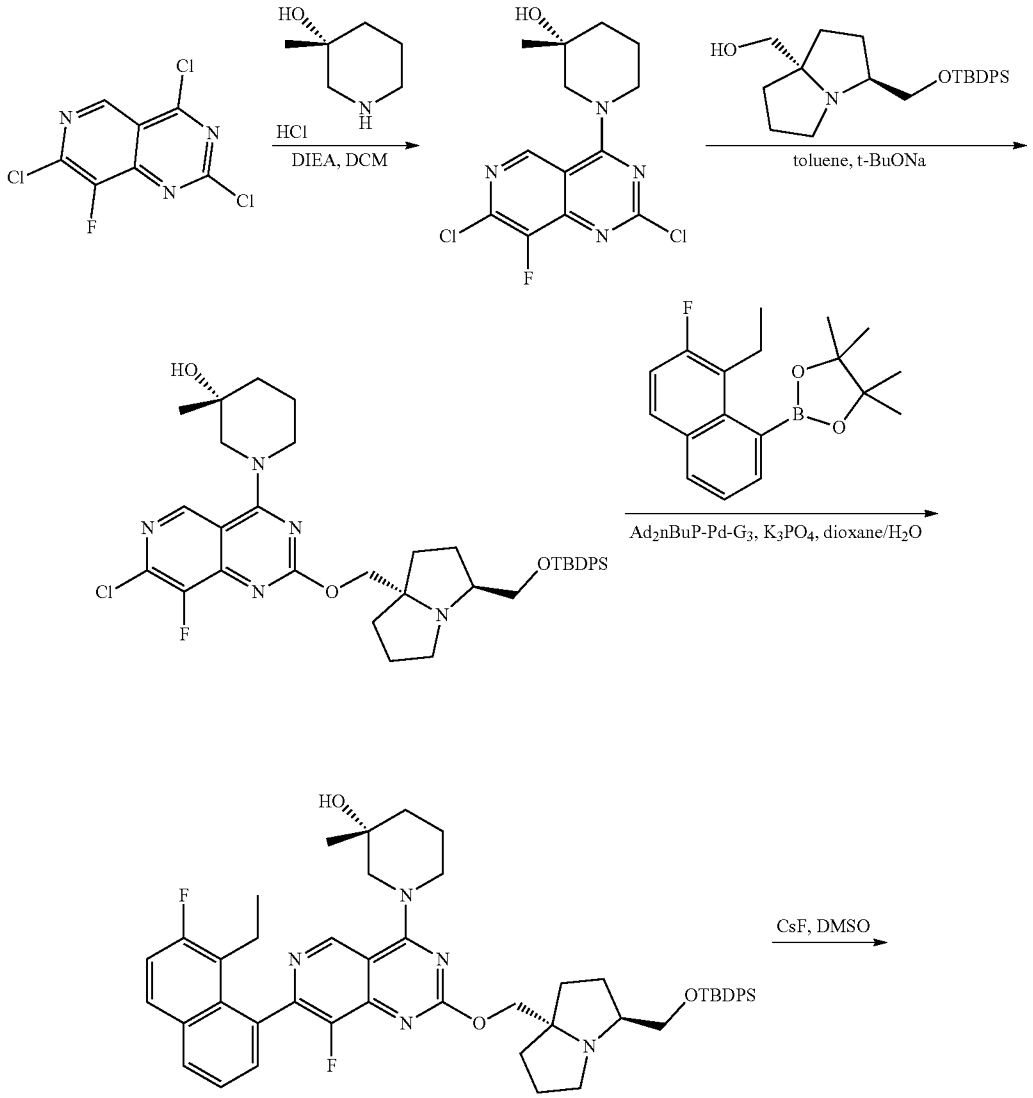

-continued
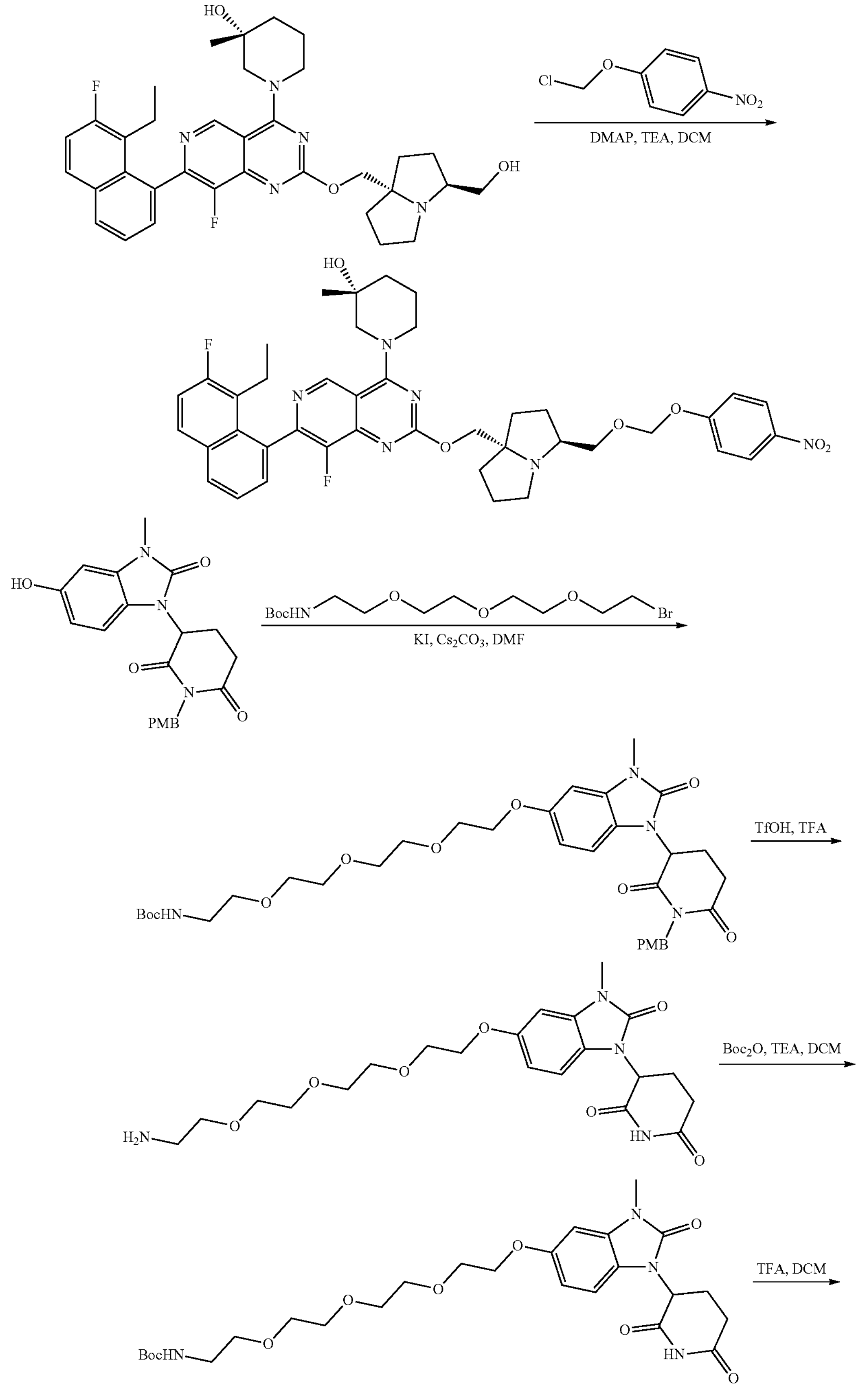

-continued

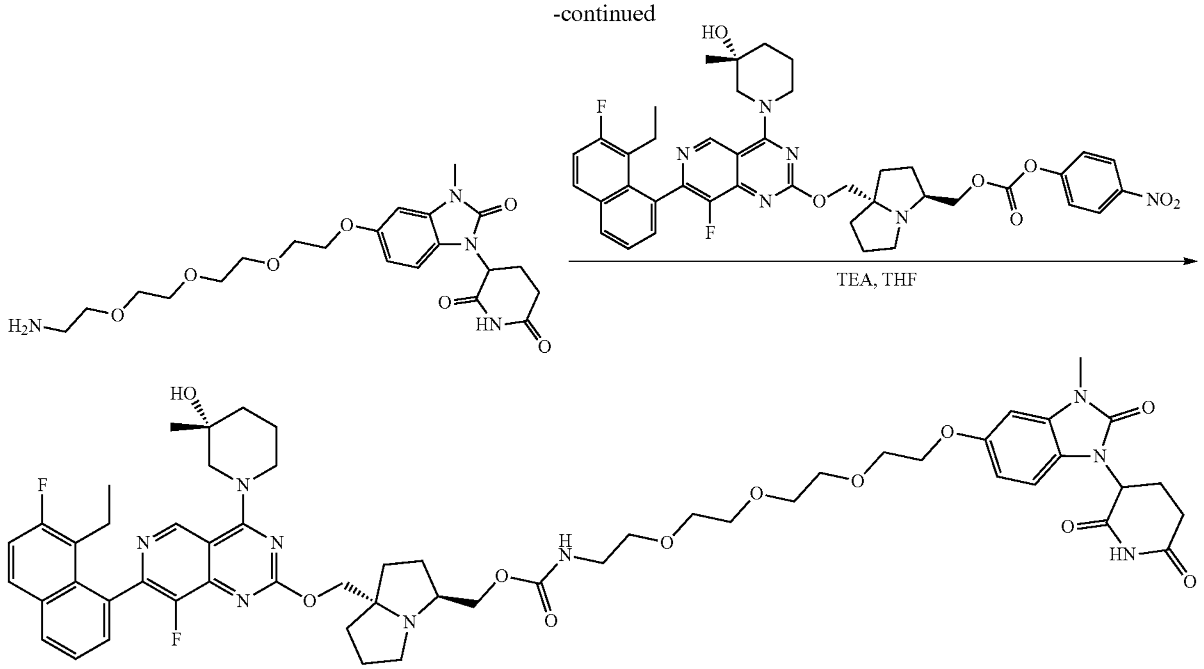

105

Step 1-(R)-1-(2,7-dichloro-8-fluoropyrido[4,3-d]pyrimidin-4-yl)-3-methylpiperidin-3-ol. To a mixture of (R)-3-methylpiperidin-3-ol (10.0 g, 65.9 mmol, HCl, CAS #2305080-34-4) in DCM (200 mL) and 2,4,7-trichloro-8-fluoro-pyrido[4,3-d]pyrimidine (16.6 g, 65.9 mmol, CAS #2454396-80-4) was added DIEA (25.5 g, 197 mmol, 34.4 mL) at 0° C. The reaction mixture was stirred at 0° C. for 0.5 hr. On completion, the residue was diluted with water (100 mL) and extracted with EA (2×100 mL). The combined organic layers was dried over $Na_2SO_4$, filtered and the filtrate was concentrated in vacuo to give a residue. The residue was purified by column chromatography ($SiO_2$, PE:EA=50:1 to 3:1) to give the title compound (15.4 g, 70% yield) as yellow solid. $^1H$ NMR (400 MHz, DMSO-$d_6$) δ 9.18 (s, 1H), 4.73 (s, 1H), 4.46 (d, J=12.4 Hz, 1H), 4.11 (d, J=13.6 Hz, 1H), 3.57 (d, J=13.6 Hz, 1H), 3.31-3.23 (m, 1H), 1.98-1.90 (m, 1H), 1.72-1.61 (m, 3H), 1.18-1.15 (m, 3H); LC-MS (ESI$^+$) m/z 331.0 $(M+H)^+$.

Step 2-(R)-1-(2-(((35,7aS)-3-(((tert-butyldiphenylsilyl)oxy)methyl)tetrahydro-1H-pyrrolizin-7a (5H)-yl)methoxy)-7-chloro-8-fluoropyrido[4,3-d]pyrimidin-4-yl)-3-methylpiperidin-3-ol. To a mixture of ((3S,7aS)-3-(((tert-butyldiphenylsilyl)oxy)methyl)tetrahydro-1H-pyrrolizin-7a (5H)-yl) methanol (6.68 g, 16.3 mmol) in toluene (60 mL) was added t-BuONa (3.13 g, 32.6 mmol) at 0° C. The reaction mixture was stirred at 0° C. for 0.5 hr. (R)-1-(2,7-dichloro-8-fluoropyrido[4,3-d]pyrimidin-4-yl)-3-methylpiperidin-3-ol (5.40 g, 16.3 mmol) was added above solution. The reaction mixture was stirred at 25° C. for 1.5 hrs. On completion, the residue was diluted with water (60 mL) and extracted with EA (2×60 mL). The combined organic layers was dried over $Na_2SO_4$, filtered and the filtrate was concentrated in vacuo to give a residue. The residue was purified by column chromatography ($SiO_2$, DCM:EA=50:1 to 1:1) to give the title compound (7.60 g, 66% yield) as yellow solid. LC-MS (ESI) m/z 704.3 $(M+H)^+$.

Step 3-(R)-1-(2-(((3S,7aS)-3-(((tert-butyldiphenylsilyl)oxy)methyl)tetrahydro-1H-pyrrolizin-7a (5H)-yl)methoxy)-7-(8-ethyl-7-fluoronaphthalen-1-yl)-8-fluoropyrido[4,3-d]pyrimidin-4-yl)-3-methylpiperidin-3-ol. To a mixture of (R)-1-(2-(((3S,7aS)-3-(((tert-butyldiphenylsilyl)oxy)methyl)tetrahydro-1H-pyrrolizin-7a (5H)-yl)methoxy)-7-chloro-8-fluoropyrido[4,3-d]pyrimidin-4-yl)-3-methylpiperidin-3-ol (2.00 g, 2.84 mmol) and 2-(8-ethyl-7-fluoro-1-naphthyl)-4,4,5,5-tetramethyl-1,3,2-dioxaborolane (1.28 g, 4.26 mmol, CAS #2848567-14-4) in dioxane (30 mL) and $H_2O$ (5 mL) was added $K_3PO_4$ (1.5 M, 5.68 mL) and [2-(2-aminophenyl)phenyl]palladium (1+); bis(1-adamantyl)-butyl-phosphane; methanesulfonate (206 mg, 283 μmol). The reaction mixture was stirred at 80° C. for 0.2 hr under $N_2$. On completion, the residue was diluted with water (30 mL) and extracted with EA (2×30 mL). The combined organic layers was dried over $Na_2SO_4$, filtered and the filtrate was concentrated in vacuo to give a residue. The residue was purified by column chromatography ($SiO_2$, DCM:MeOH=100:1 to 15:1) to give the title compound (520 mg, 21% yield) as yellow solid. $^1H$ NMR (400 MHz, DMSO-$d_6$) δ 9.40-9.15 (m, 1H), 8.13 (d, J=8.0 Hz, 1H), 8.04 (dd, J=6.0, 8.8 Hz, 1H), 7.67-7.62 (m, 4H), 7.58 (d, J=4.0, 7.6 Hz, 1H), 7.53-7.49 (m, 2H), 7.48-7.43 (m, 6H), 4.77 (d, J=13.6 Hz, 1H), 4.46-4.30 (m, 1H), 4.18-4.03 (m, 2H), 3.98-3.83 (m, 2H), 3.81-3.72 (m, 1H), 3.68-3.60 (m, 1H), 3.57-3.49 (m, 1H), 3.41 (s, 3H), 2.79-2.69 (m, 1H), 2.46-2.37 (m, 1H), 2.21 (ddd, J=3.2, 6.8, 14.0 Hz, 1H), 2.07-1.98 (m, 2H), 1.82-1.61 (m, 7H), 1.18 (d, J=9.0 Hz, 3H), 1.07 (s, 2H), 1.01 (s, 9H), 0.77 (q, J=7.6 Hz, 3H); LC-MS (ESI) m/z 842.4 $(M+H)^+$.

Step 4-(R)-1-(7-(8-ethyl-7-fluoronaphthalen-1-yl)-8-fluoro-2-(((35,7aS)-3-(hydroxymethyl)tetrahydro-1H-pyrrolizin-7a (5H)-yl) methoxy)pyrido[4,3-d]pyrimidin-4-yl)-3-methylpiperidin-3-ol. To a mixture of (R)-1-(7-(8-ethyl-7-fluoronaphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (520 mg, 617 μmol) in DMSO (5 mL) was added CsF (281 mg, 1.85 mmol). The reaction mixture was stirred at 25° C. for 1.5 hrs. On completion, the residue was diluted with water (30 mL) and extracted with EA (2×20 mL). The combined organic layers was dried over $Na_2SO_4$, filtered and the filtrate was concentrated in vacuo to give a residue. The residue was purified by column chromatography ($SiO_2$, DCM:MeOH=100:1 to 10:1) to give the title compound (270 mg, 72% yield) as yellow solid. LC-MS (ESI) m/z 604.1 $(M+H)^+$.

Step 5-((3S,7aS)-7a-(((7-(8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate. To a mixture of (R)-1-(7-(8-ethyl-7-fluoronaphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (60.0 mg, 99.3 μmol) and (4-nitrophenyl) carbonochloridate (60.1 mg, 298 μmol, CAS #7693-46-1) in DCM (3 mL) was added TEA (30.1 mg, 298 μmol) and DMAP (1.21 mg, 9.94 μmol). The reaction mixture was stirred at 25° C. for 3 hrs. On completion, the residue was diluted with water (20 mL) and extracted with EA (2×20 mL). The combined organic layers was dried over $Na_2SO_4$, filtered and the filtrate was concentrated in vacuo to give the title compound (75.0 mg, 98% yield) as yellow solid. LC-MS (ESI) m/z 769.3 $(M+H)^+$.

Step 6-Tert-butyl N-[2-[2-[2-[2-[1-[1-[(4-methoxyphenyl)methyl]-2,6-dioxo-3-piperidyl]-3-methyl-2-oxo-benzimidazol-5-yl]oxyethoxy]ethoxy]ethoxy]ethyl]carbamate. To a mixture of 3-(5-hydroxy-3-methyl-2-oxo-benzimidazol-1-yl)-1-[(4-methoxyphenyl)methyl]piperidine-2,6-dione (1.50 g, 3.79 mmol) and tert-butyl N-[2-[2-[2-(2-bromoethoxy)ethoxy]ethoxy]ethyl]carbamate (1.76 g, 4.93 mmol, CAS #1076199-21-7) in DMF (15 mL) was added KI (1.26 g, 7.59 mmol) and $Cs_2CO_3$ (2.47 g, 7.59 mmol). The reaction mixture was stirred at 70° C. for 0.7 hr. On completion, the residue was diluted with water (30 mL) and extracted with EA (2×30 mL). The combined organic layers was dried over $Na_2SO_4$, filtered and the filtrate was concentrated in vacuo to give a residue. The residue was purified by reverse phase (0.1% FA condition) to give the title compound (2.30 g, 90% yield) as yellow oil. $^1H$ NMR (400 MHz, DMSO-$d_6$) δ 7.21 (d, J=8.8 Hz, 2H), 6.93-6.83 (m, 4H), 6.79-6.73 (m, 1H), 6.58 (dd, J=2.4, 8.4 Hz, 1H), 5.47 (dd, J=5.2, 13.2 Hz, 1H), 4.79 (q, J=14.4 Hz, 2H), 4.13-4.08 (m, 2H), 3.75 (d, J=4.8 Hz, 2H), 3.73 (s, 3H), 3.61-3.58 (m, 2H), 3.57-3.54 (m, 2H), 3.53-3.50 (m, 4H), 3.37 (s, 2H), 3.32 (s, 3H), 3.06 (q, J=6.0 Hz, 3H), 2.85-2.77 (m, 1H), 2.75-2.67 (m, 1H), 2.08 (s, 1H), 1.38-1.36 (m, 9H); LC-MS (ESI) m/z 671.3 $(M+H)^+$.

Step 7-3-[5-[2-[2-[2-(2-Aminoethoxy)ethoxy]ethoxy]ethoxy]-3-methyl-2-oxo-benzimidazol-1-yl]piperidine-2,6-dione. To a mixture of tert-butyl N-[2-[2-[2-[2-[1-[1-[(4-methoxyphenyl)methyl]-2,6-dioxo-3-piperidyl]-3-methyl-2-oxo-benzimidazol-5-yl]oxyethoxy]ethoxy]ethoxy]ethyl]carbamate (2.20 g, 3.28 mmol) in TFA (20 mL) was added TfOH (6.78 g, 45.2 mmol, 4 mL). The reaction mixture was stirred at 70° C. for 2 hrs. On completion, the reaction mixture was concentrated in vacuo to give the title compound (1.45 g, 98% yield) as brown oil. LC-MS (ESI) m/z 451.1 $(M+H)^+$.

Step 8-Tert-butyl N-[2-[2-[2-[2-[1-(2,6-dioxo-3-piperidyl)-3-methyl-2-oxo-benzimidazol-5-yl]oxyethoxy]ethoxy]ethoxy]ethyl]carbamate. To a mixture of 3-[5-[2-[2-[2-(2-aminoethoxy)ethoxy]ethoxy]ethoxy]-3-methyl-2-oxo-benzimidazol-1-yl]piperidine-2,6-dione (1.45 g, 3.22 mmol) in DCM (15 mL) was added $Boc_2O$ (1.05 g, 4.83 mmol, 1.11 mL) and TEA (977 mg, 9.66 mmol, 1.34 mL). The reaction mixture was stirred at 25° C. for 3 hrs. On completion, the residue was diluted with water (30 mL) and extracted with DCM (2×30 mL). The combined organic layers was dried over $Na_2SO_4$, filtered and the filtrate was concentrated in vacuo to give a residue. The residue was purified by reverse phase (0.1% FA condition) to give the title compound (480 mg, 27% yield) as yellow oil. $^1H$ NMR (400 MHz, DMSO-$d_6$) δ 11.08 (s, 1H), 7.94 (d, J=8.8 Hz, 1H), 7.00 (d, J=8.4 Hz, 1H), 6.89 (d, J=2.0 Hz, 1H), 6.76 (t, J=5.2 Hz, 1H), 6.63 (dd, J=2.0, 8.4 Hz, 1H), 5.31 (dd, J=5.2, 12.4 Hz, 1H), 4.14-4.06 (m, 2H), 3.84 (s, 1H), 3.77-3.72 (m, 2H), 3.61-3.58 (m, 2H), 3.57-3.54 (m, 2H), 3.51 (d, J=3. Hz, 3H), 3.31 (s, 3H), 3.06 (d, J=6.0 Hz, 2H), 2.89 (s, 1H), 2.67 (d, J=4.0 Hz, 2H), 2.08 (s, 1H), 2.04-1.97 (m, 1H), 1.37 (s, 9H); LC-MS (ESI) m/z 573.2 $(M+Na)^+$.

Step 9-3-[5-[2-[2-[2-(2-Aminoethoxy)ethoxy]ethoxy]ethoxy]-3-methyl-2-oxo-benzimidazol-1-yl]piperidine-2,6-dione. To a mixture of tert-butyl N-[2-[2-[2-[2-[1-(2,6-dioxo-3-piperidyl)-3-methyl-2-oxo-benzimidazol-5-yl]oxyethoxy]ethoxy]ethoxy]ethyl]carbamate (100 mg, 181 μmol) in DCM (2 mL) was added TFA (767 mg, 6.73 mmol, 0.5 mL). The reaction mixture was stirred at 25° C. for 0.5 hr. On completion, the reaction mixture was concentrated in vacuo to give the title compound (80.0 mg, 97% yield, TFA salt) as yellow oil. LC-MS $(ESI^+)$ m/z 451.1 $(M+H)^+$.

Step 10-((3S,7aS)-7a-(((7-(8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (2-(2-(2-(2-((1-(2,6-dioxopiperidin-3-yl)-3-methyl-2-oxo-2,3-dihydro-1H-benzo[d]imidazol-5-yl)oxy) ethoxy)ethoxy) ethoxy)ethyl) carbamate (Compound 105). To a mixture of 3-[5-[2-[2-[2-(2-amino-ethoxy)ethoxy]ethoxy]ethoxy]-3-methyl-2-oxo-benzimidazol-1-yl]piperidine-2,6-dione (80.0 mg, 177 μmol, TFA) and ((3S,7aS)-7a-(((7-(8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (70.0 mg, 91.0 μmol) in THF (3 mL) was added TEA (9.21 mg, 91.0 μmol, 12.6 μL). The reaction mixture was stirred at 25° C. for 0.05 hr. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 25%-45% B over 5 min) to give the title compound (20.3 mg, 20% yield) as white solid. $^1H$ NMR (400 MHz, DMSO-$d_6$) δ 11.08 (s, 1H), 9.26 (d, J=4.0 Hz, 1H), 8.13 (d, J=8.8 Hz, 1H), 8.03 (dd, J=6.0, 8.8 Hz, 1H), 7.62-7.56 (m, 1H), 7.54-7.46 (m, 2H), 7.23 (s, 1H), 6.99 (d, J=8.8 Hz, 1H), 6.88 (d, J=2.0 Hz, 1H), 6.62 (dd, J=2.0, 8.4 Hz, 1H), 5.31 (dd, J=5.2, 12.8 Hz, 1H), 4.76 (d, J=13.6 Hz, 1H), 4.47-4.28 (m, 2H), 4.26-4.14 (m, 2H), 4.13-3.96 (m, 4H), 3.77-3.70 (m, 2H), 3.64 (d, J=13.2 Hz, 1H), 3.61-3.45 (m, 10H), 3.40 (s, 2H), 3.31 (s, 3H), 3.16-3.11 (m, 2H), 2.91-2.84 (m, 1H), 2.75-2.61 (m, 3H), 2.59 (s, 1H), 2.44-2.38 (m, 1H), 2.27-2.13 (m, 2H), 2.12-1.93 (m, 4H), 1.91-1.61 (m, 8H), 1.17 (d, J=10.0 Hz, 3H), 0.76 (q, J=7.2 Hz, 3H); LC-MS $(ESI^+)$ m/z 1080.3 $(M+H)^+$.

Example 19. Synthesis of Compound 107

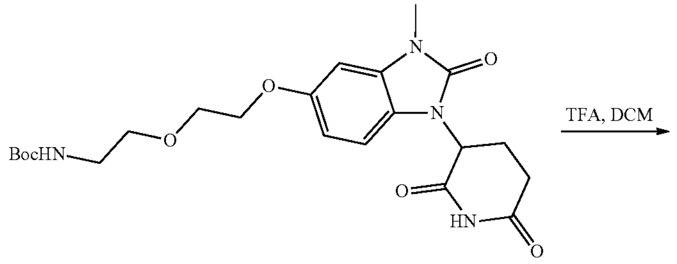

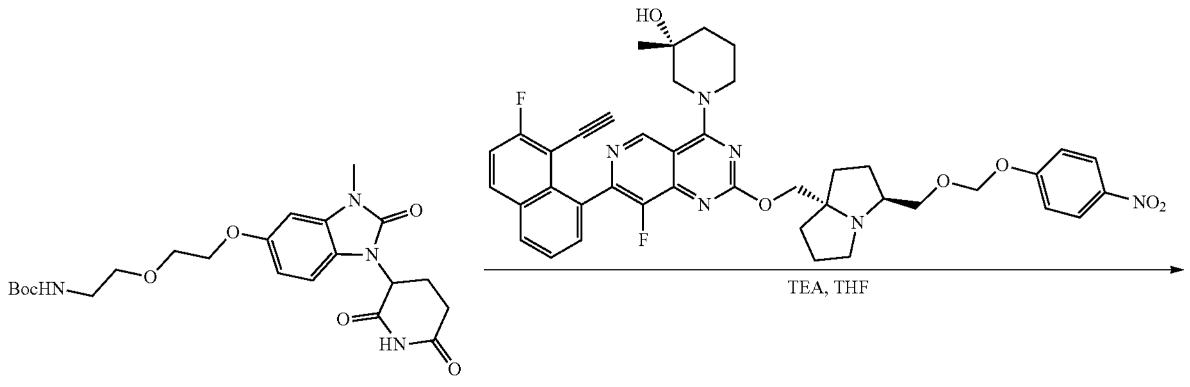

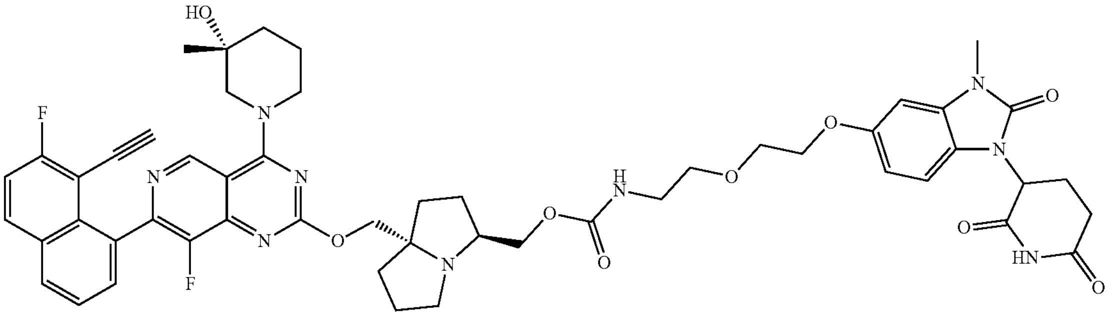

107

Step 1-3-[5-[2-(2-Aminoethoxy)ethoxy]-3-methyl-2-oxo-benzimidazol-1-yl]piperidine-2,6-dione. To a solution tert-butyl N-[2-[2-[1-(2,6-dioxo-3-piperidyl)-3-methyl-2-oxo-benzimidazol-5-yl]oxyet-hoxy]ethyl]carbamate (60.0 mg, 130 μmol) in DCM was added TFA (740 mg, 6.49 mmol, 480 μL), then the reaction mixture was stirred at 25° C. for 0.5 hr. On completion, the mixture was concentrated in vacuo to give the title compound (61.0 mg, 99% yield, TFA salt) as brown oil. LC-MS (ESI) m/z 363.0 $(M+H)^+$.

Step 2-((3S,7aS)-7a-(((7-(8-ethynyl-7-fluoronaphthalen-1-yl)-8-fluoro-4-((R)-3-hydroxy-3-ethylpiperidin-1-yl) pyrido[4,3-d]pyrimidin-2-yl)oxy)methyl)hexahydro-1H-pyrrolizin-3-yl)methyl (2-(2-((1-(2,6-dioxopiperidin-3-yl)-3-methyl-2-oxo-2,3-dihydro-1H-benzo[d]imidazol-5-yl) oxy) ethoxy)ethyl) carbamate (Compound 107). To a suspension of 3-[5-[2-(2-aminoethoxy)ethoxy]-3-methyl-2-oxo-benzi-midazol-1-yl]piperidine-2,6-dione (56.9 mg, 157 μmol, TFA salt) in THF (3 mL) was added TEA (95.3 mg, 940 μmol, 131 μL) until pH=8-9. Then ((3S,7aS)-7a-(((7-(8-ethynyl-7-fluoronaphthalen-1-yl)-8-fluoro-4-((R)-3-ydroxy-3methylpiperidin-1-yl)pyrido[4,3-d]pyrimidin-2-yl) oxy)methyl)hexahydro-1H-pyrrolizin-3-yl)methyl (4-nitrophenyl) carbonate 60.0 mg, 78.5 μmol) in THF (1 mL) was added and stirred at 25° C. for 1 hr. On completion, the mixture was concentrated in vacuo to give residue. The residue was purified by prep-HPLC (column: CD04-Welch Utimate C18 150*25*7 μm; mobile phase: [water (FA)-ACN]; gradient: 17%-47% B over 10 min) to give the title compound (14.3 mg, 18% yield, FA salt) as yellow solid. $^1H$ NMR (400 MHz, DMSO-$d_6$) δ 11.07 (s, 1H), 9.22-9.07 (m, 1H), 8.26-8.21 (m, 1H), 8.20-8.17 (m, 1H), 7.76-7.52 (m, 3H), 7.25 (s, 1H), 6.98 (d, J=8.4 Hz, 1H), 6.87 (d, J=1.2 Hz, 1H), 6.66-6.53 (m, 1H), 5.30 (dd, J=5.6, 12.4 Hz, 1H), 4.86-4.65 (m, 1H), 4.41-4.27 (m, 1H), 4.16-3.94 (m, 8H), 3.73-3.69 (m, 2H), 3.63-3.55 (m, 2H), 3.49-3.46 (m, 3H), 3.29 (s, 3H), 3.19-3.13 (m, 2H), 2.91-2.84 (m, 1H), 2.75-2.65 (m, 3H), 2.63-2.57 (m, 1H), 2.08-1.95 (m, 3H), 1.77-1.58 (m, 9H), 1.55-1.46 (m, 1H), 1.16 (d, J=14.8 Hz, 3H); LC-MS (ESI) m/z 988.3 $(M+H)^+$.

Example 20. Synthesis of Compound 108

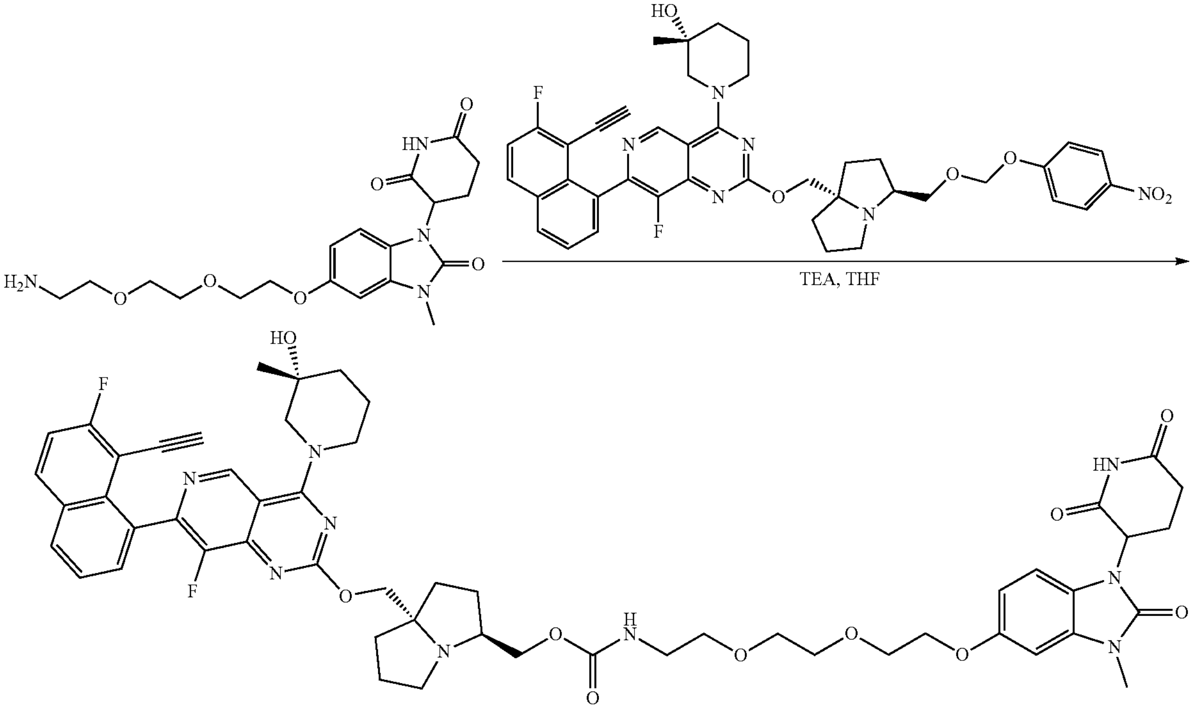

108

Step 1-((3S,7aS)-7a-(((7-(8-ethynyl-7-fluoronaphthalen-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl)methyl (2-(2-(2-((1-(2,6-dioxopiperidin-3-yl)-3-methyl-2-oxo-2,3-dihydro-1H-benzo[d]imidazol-5-yl) oxy) ethoxy)ethoxy)ethyl) carbamate (Compound 108). To a solution of 3-[5-[2-[2-(2-aminoethoxy)ethoxy]ethoxy]-3-methyl-2-oxo-benzimidazol-1-yl]piperidine-2,6-dione (74.4 mg, 183 μmol, TFA salt) in THF (5 mL) was added TEA (27.7 mg, 274 μmol) and ((3S,7aS)-7a-(((7-(8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl (4-nitrophenyl) carbonate (70.0 mg, 91.5 μmol). The mixture was stirred at 25° C. for 0.5 hr. On completion, the mixture was filtered and the filtrate was concentrated in vacuo to give a residue. The residue was purified by prep-HPLC (column: Phenomenex luna C18 150*25 mm*10 μm; mobile phase: [water (FA)-ACN]; gradient: 12%-42% B over 8 min) to give the title compound (33.6 mg, 33% yield, FA salt) as yellow solid. $^1$H NMR (400 MHz, DMSO-$d_6$) δ 11.07 (s, 1H), 9.26-9.03 (m, 1H), 8.27-8.18 (m, 2H), 7.73-7.63 (m, 2H), 7.60 (t, J=9.2 Hz, 1H), 7.22 (s, 1H), 6.98 (d, J=8.4 Hz, 1H), 6.87 (d, J=2.0 Hz, 1H), 6.61 (dd, J=2.0, 8.4 Hz, 1H), 5.30 (dd, J=5.2, 12.8 Hz, 1H), 4.84-4.67 (m, 1H), 4.43-4.26 (m, 1H), 4.18-3.92 (m, 8H), 3.77-3.70 (m, 2H), 3.57 (dd, J=3.6, 6.0 Hz, 3H), 3.54-3.49 (m, 3H), 3.40 (d, J=6.0 Hz, 3H), 3.30 (s, 3H), 3.12 (q, J=6.0 Hz, 2H), 2.93-2.82 (m, 1H), 2.80-2.64 (m, 3H), 2.64-2.56 (m, 1H), 2.11-1.93 (m, 3H), 1.80-1.58 (m, 9H), 1.56-1.46 (m, 1H), 1.16 (d, J=14.8 Hz, 3H); LC-MS (ESI$^+$) m/z 1032.2 (M+H)$^+$.

Example 21. Synthesis of Compound 109

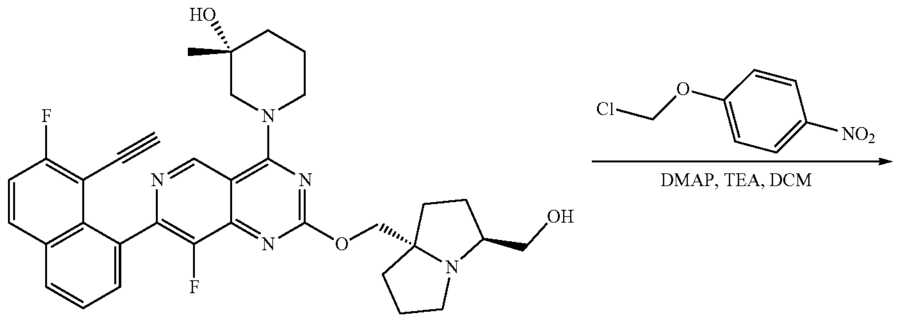

-continued

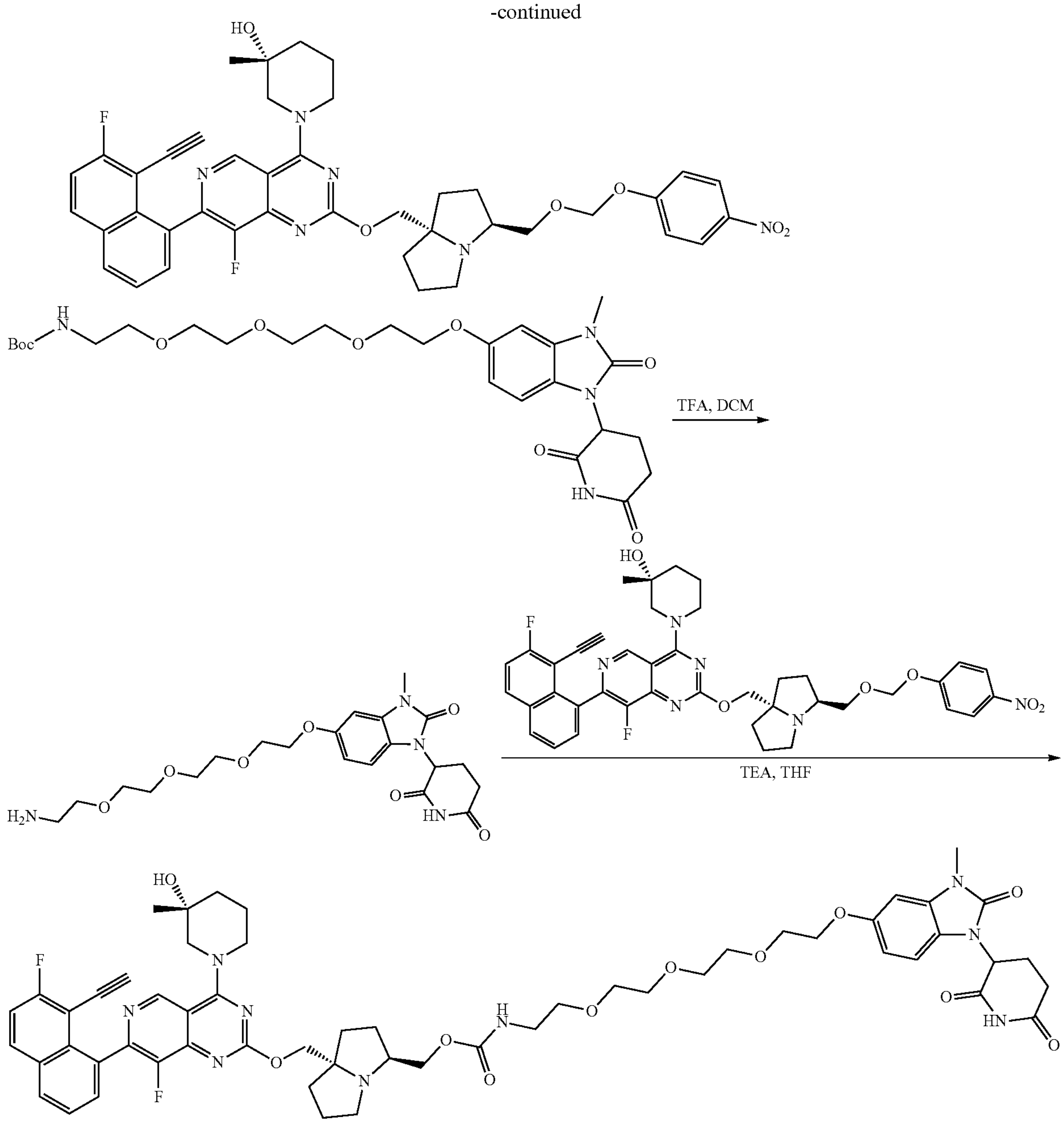

109

Step 1-3-[5-[2-[2-[2-(2-Aminoethoxy)ethoxy]ethoxy]ethoxy]-3-methyl-2-oxo-benzimidazol-1-yl]piperidine-2,6-dione. To a mixture of tert-butyl N-[2-[2-[2-[2-[1-(2,6-dioxo-3-piperidyl)-3-methyl-2-oxo-benzimidazol-5-yl]oxyethoxy]ethoxy]ethoxy]ethyl]carbamate (80.0 mg, 145 μmol) in DCM (1 mL) was added TFA (767 mg, 6.73 mmol, 0.5 mL), the reaction mixture was stirred at 25° C. for 0.5 hr. On completion, the reaction mixture was concentrated in vacuo to give the title compound (75.0 mg, 91% yield, TFA) as yellow oil. LC-MS (ESI) m/z 451.2 $(M+H)^+$.

Step 2-((3S,7aS)-7a-(((7-(8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate. To a mixture of (R)-1-(7-(8-ethynyl-7-fluoronaphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (60.0 mg, 100 μmol) in DCM (3 mL) was added TEA (363 mg, 3.59 mmol, 0.5 mL), DMAP (1.22 mg, 10.0 μmol) and (4-nitrophenyl) carbonochloridate (60.5 mg, 300 μmol, CAS #7693-46-1), the reaction mixture was stirred at 25° C. for 3 hrs. On completion, the reaction mixture was diluted with water (10 mL) and extracted with DCM (2×10 mL). The combined organic layers was dried over $Na_2SO_4$, filtered and the filtrate was concentrated in vacuo to give the title compound (81.0 mg, crude) as yellow oil. LC-MS (ESI) m/z 765.3 $(M+H)^+$.

Step 3-((3S,7aS)-7a-(((7-(8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H- pyrrolizin-3-yl)methyl (2-(2-(2-(2-((1-(2,6-dioxopiperidin-3-yl)-3-methyl-2-oxo-2,3-dihydro-1H-benzo[d]imidazol-5-yl)oxy) ethoxy)ethoxy) ethoxy)ethyl) carbamate (Compound 109). To a mixture of 3-[5-[2-[2-[2-(2-amino-ethoxy)ethoxy]ethoxy]ethoxy]-3-methyl-2-oxo-benzimidazol-1-yl]piperidine-2,6-dione (75.0 mg, 166 μmol, TFA) in THF (1 mL) was added TEA (1.36 g, 13.4 mmol, 1.87 mL) and ((3S,7aS)-7a-(((7-(8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (63.6 mg, 83.2 μmol), the reaction mixture was stirred at 25° C. for 0.5 hr. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 16%-46% B over 10 min) to give the title compound (21.2 mg, 10% yield, FA) as yellow solid. $^1$H NMR (400 MHz, DMSO-$d_6$) δ 11.07 (s, 1H), 9.23-9.05 (m, 1H), 8.26-8.18 (m, 2H), 7.72-7.64 (m, 2H), 7.63-7.56 (m, 1H), 7.24-7.16 (m, 1H), 7.01-6.95 (m, 1H), 6.87 (d, J=2.0 Hz, 1H), 6.61 (dd, J=2.0, 8.4 Hz, 1H), 5.35-5.27 (m, 1H), 4.80-4.71 (m, 1H), 4.41-4.26 (m, 1H), 4.18-4.04 (m, 6H), 4.04-3.94 (m, 2H), 3.75-3.69 (m, 2H), 3.57 (dd, J=3.6, 6.4 Hz, 3H), 3.54-3.47 (m, 6H), 3.41-3.38 (m, 2H), 3.30 (s, 3H), 3.22 (s, 1H), 3.11 (q, J=6.0 Hz, 2H), 2.87 (dd, J=5.2, 16.2 Hz, 1H), 2.76-2.61 (m, 4H), 2.08-1.95 (m, 3H), 1.77-1.61 (m, 9H), 1.56-1.44 (m, 1H), 1.16 (d, J=14.4 Hz, 3H); LC-MS (ESI$^+$) m/z 1076.3 $(M+H)^+$.

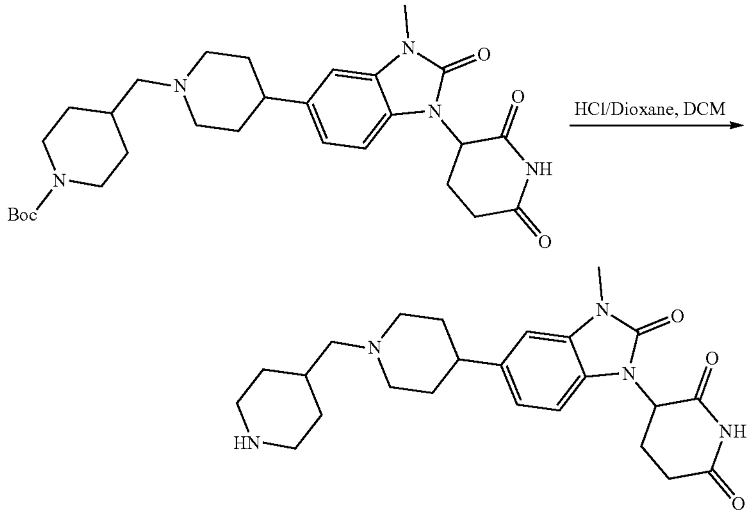 [SMILES: Cn1c(=O)n(C2CCC(=O)NC2=O)c2ccc(C3CCN(CC4CCN(C(=O)OC(C)(C)C)CC4)CC3)cc21 ; Cn1c(=O)n(C2CCC(=O)NC2=O)c2ccc(C3CCN(CC4CCNCC4)CC3)cc21]

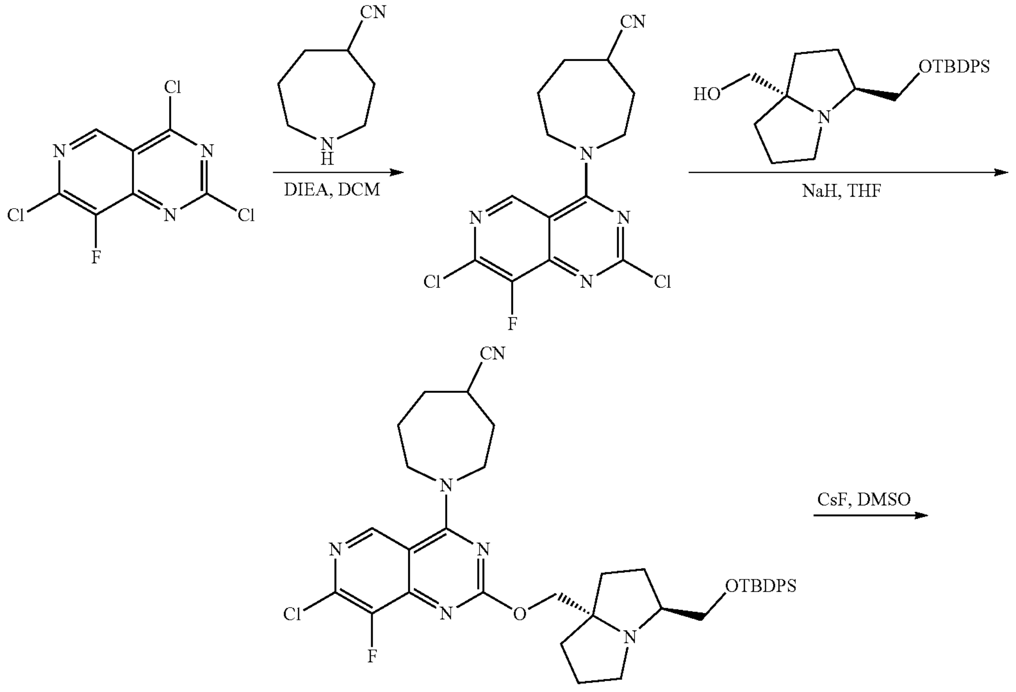

-continued
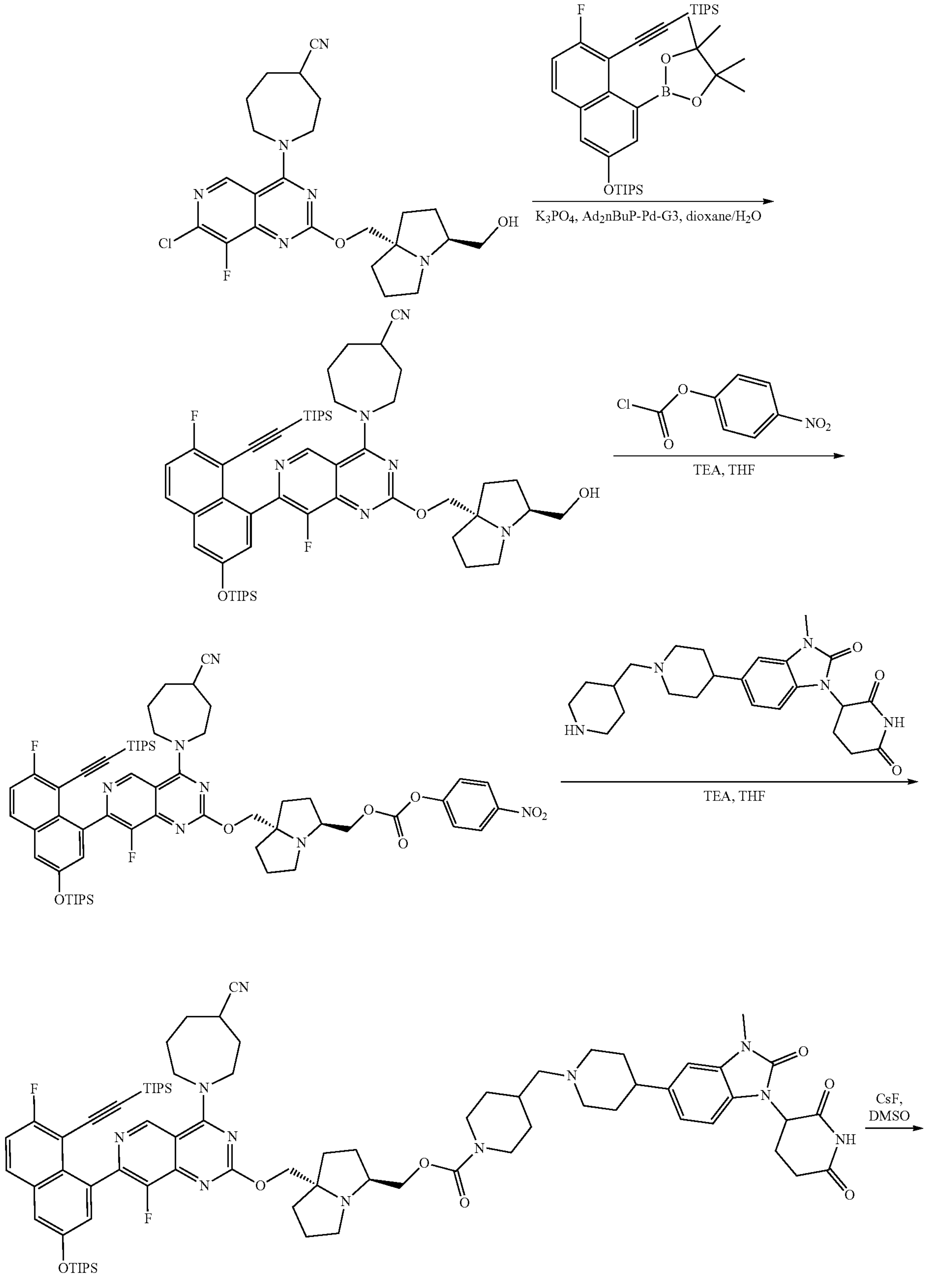

-continued

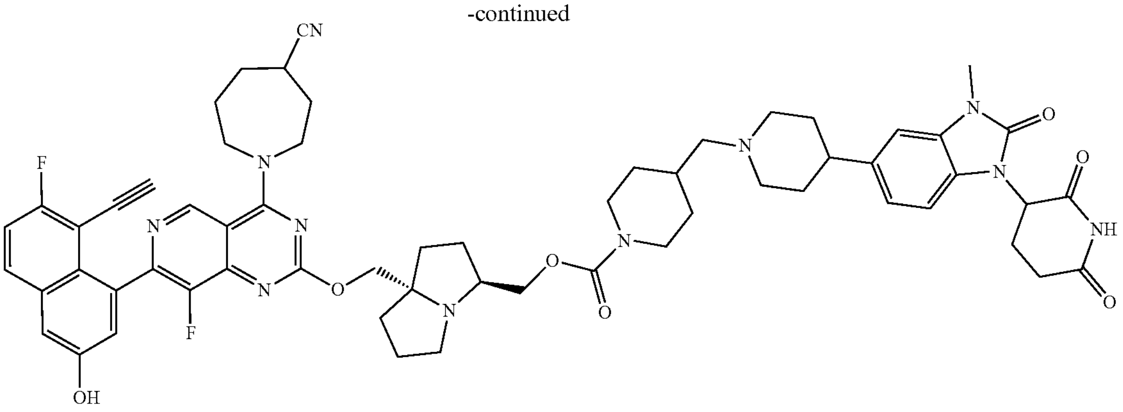

110

Step 1-3-[3-Methyl-2-oxo-5-[1-(4-piperidylmethyl)-4-piperidyl]benzimidazol-1-yl]piperidine-2,6-dione. To a solution of tert-butyl 4-[[4-[1-(2,6-dioxo-3-piperidyl)-3-methyl-2-oxo-benzimidazol-5-yl]-1-piperidyl]methyl]piperidine-1-carboxylate (100 mg, 185 μmol) in DCM (0.5 mL) was added TFA (767 mg, 6.73 mmol, 500 μL). The mixture was stirred at 25° C. for 1 hr. On completion, the reaction mixture was concentrated in vacuo to give the title compound (102 mg, 99% yield, TFA salt) as yellow oil. $^1H$ NMR (400 MHz, DMSO-$d_6$) δ 11.10 (s, 1H), 9.27-9.10 (m, 1H), 8.58 (d, J=9.6 Hz, 1H), 8.41-8.24 (m, 1H), 7.09-7.01 (m, 2H), 6.92 (d, J=8.0 Hz, 1H), 5.36 (dd, J=5.2, 12.8 Hz, 1H), 3.34 (s, 3H), 3.32-3.21 (m, 3H), 3.09-3.02 (m, 4H), 2.93-2.84 (m, 4H), 2.72-2.58 (m, 3H), 2.05-1.99 (m, 4H), 1.94-1.88 (m, 2H), 1.36 (q, J=11.6 Hz, 2H).

Step 2-1-(2,7-Dichloro-8-fluoro-pyrido[4,3-d]pyrimidin-4-yl) azepane-4-carbonitrile. To a solution of 2,4,7-trichloro-8-fluoro-pyrido[4,3-d]pyrimidine (982 mg, 3.89 mmol, CAS #2454396-80-4) and azepane-4-carbonitrile (750 mg, 4.67 mmol, HCl, CAS #1259062-50-4) in DCM (18 mL) was added DIEA (1.51 g, 11.6 mmol, 2.03 mL) at 0° C., The mixture was stirred at 25° C. for 0.5 hr. On completion, the reaction was diluted with water (20 mL), then the residue was extracted with DCM (3×30 mL). The combined organic layers was dried over $Na_2SO_4$, filtered and the filtrate was concentrated in vacuo to give a residue. The crude product was triturated with PE:EA=4:1 (10 mL: 2.5 mL) at 25° C. for 30 mins to give the title compound (890 mg, 67% yield) as white solid. $^1H$ NMR (400 MHz, DMSO-$d_6$) δ 9.07 (s, 1H), 4.11-3.92 (m, 4H), 3.19-3.10 (m, 1H), 2.27-2.13 (m, 2H), 2.08-1.95 (m, 2H), 1.92-1.79 (m, 2H).

Step 3-1-(2-(((3S,7aS)-3-(((Tert-butyldiphenylsilyl)oxy)methyl)tetrahydro-1H-pyrrolizin-7a (5H)-yl) methoxy)-7-chloro-8-fluoropyrido[4,3-d]pyrimidin-4-yl) azepane-4-carbonitrile. To a solution of ((3S,7aS)-3-(((tert-butyldiphenylsilyl)oxy)methyl)tetrahydro-1H-pyrrolizin-7a (5H)-yl) methanol (903 mg, 2.20 mmol) in THF (15 mL) was added NaH (176 mg, 4.41 mmol, 60% purity) at 0° C. for 0.5 hr. the 1-(2,7-dichloro-8-fluoro-pyrido[4,3-d]pyrimidin-4-yl) azepane-4-carbonitrile (750 mg, 2.20 mmol) was added into above solution at 0° C., The mixture was stirred at 25° C. for 5.5 hrs. On completion, the mixture was quenched with $H_2O$ (5 mL), extracted with EA (3×10 mL), the organic layer was washed with brine (3×10 mL), dried with anhydrous $Na_2SO_4$, filtered and the filtrate was concentrated in vacuo. The residue was purified by column chromatography ($SiO_2$, DCM:MeOH=93:7) to give the title compound (1.30 g, 78% yield) as pink oil. $^1H$ NMR (400 MHz, DMSO-$d_6$) δ 8.92 (s, 1H), 7.66-7.60 (m, 4H), 7.48-7.41 (m, 6H), 4.22-4.05 (m, 2H), 4.03-3.92 (m, 4H), 3.87 (dd, J=6.0, 10.4 Hz, 1H), 3.79-3.71 (m, 1H), 3.24-3.12 (m, 2H), 2.79-2.64 (m, 2H), 2.27-2.15 (m, 2H), 2.08-1.96 (m, 3H), 1.90-1.82 (m, 2H), 1.79-1.65 (m, 6H), 1.49 (s, 1H), 0.99 (s, 9H).

Step 4-1-(7-Chloro-8-fluoro-2-(((3S,7aS)-3-(hydroxymethyl)tetrahydro-1H-pyrrolizin-7a (5H)-yl) methoxy)pyrido [4,3-d]pyrimidin-4-yl) azepane-4-carbonitrile. To a solution of 1-(2-(((3S,7aS)-3-(((tert-butyldiphenylsilyl)oxy)methyl) tetrahydro-1H-pyrrolizin-7a (5H)-yl) methoxy)-7-chloro-8-fluoropyrido[4,3-d]pyrimidin-4-yl) azepane-4-carbonitrile (500 mg, 700 μmol) in DMSO (3 mL) was added CsF (319 mg, 2.10 mmol). The mixture was stirred at 40° C. for 3 hrs. On completion, the mixture was diluted with $H_2O$ (20 mL), adjusted pH=4-5 with FA, extracted with EA (3×15 mL), then the $H_2O$ phase was adjusted pH=7-8 with $NH_3{\cdot}H_2O$, extracted with EA (3×15 mL), the organic layer was washed with brine (20 mL), dried with anhydrous $Na_2SO_4$, filtered and the filtrate was concentrated in vacuo to give the title compound (282 mg, 84% yield) as white solid. $^1H$ NMR (400 MHz, DMSO-$d_6$) δ 8.92 (s, 1H), 4.65-4.50 (m, 1H), 4.15-4.09 (m, 1H), 4.08-4.04 (m, 1H), 4.04-3.93 (m, 4H), 3.68-3.61 (m, 1H), 3.52-3.45 (m, 1H), 3.18-3.12 (m, 1H), 3.10-3.02 (m, 1H), 2.79-2.73 (m, 1H), 2.72-2.64 (m, 1H), 2.27-2.15 (m, 2H), 2.07-2.02 (m, 3H), 1.86 (dt, J=3.6, 7.6 Hz, 2H), 1.75-1.64 (m, 5H), 1.61-1.45 (m, 2H).

Step 5-1-(8-Fluoro-7-(7-fluoro-8-((triisopropylsilyl) ethynyl)-3-((triisopropylsilyl)oxy) naphthalen-1-yl)-2-(((3S,7aS)-3-(hydroxymethyl)tetrahydro-1H-pyrrolizin-7a (5H)-yl) methoxy)pyrido[4,3-d]pyrimidin-4-yl) azepane-4-carbonitrile. A mixture of 1-(7-chloro-8-fluoro-2-(((3S,7aS)-3-(hydroxymethyl)tetrahydro-1H-pyrrolizin-7a (5H)-yl) methoxy)pyrido[4,3-d]pyrimidin-4-yl) azepane-4-carbonitrile (280 mg, 589 μmol), [6-fluoro-4-(4,4,5,5-tetramethyl-1,3,2-dioxaborolan-2-yl)-5-(2-triisopropylsilylethynyl)-2-naphthyl]oxy-triisopropyl-silane (552 mg, 884 μmol, CAS #2791277-41-1), $K_3PO_4$ (1.5 M, 1.18 mL), [2-(2-aminophenyl)phenyl]palladium (1+); bis(1-adamantyl)-butyl-phosphane; methanesulfonate (42.9 mg, 58.9 μmol) in dioxane (5 mL) was degassed and purged with $N_2$ for 3 times, and then the mixture was stirred at 80° C. for 1 hr under $N_2$ atmosphere. On completion, the mixture was diluted with $H_2O$ (15 mL), extracted with EA (3×15 mL), the organic layer was washed with brine (10 mL), dried with anhydrous $Na_2SO_4$, filtered and the filtrate was concentrated in vacuo. The residue was purified by column chromatography ($SiO_2$, DCM:MeOH=91:9) to give the title compound (420 mg, 76% yield) as brown solid. $^1H$ NMR (400 MHz, DMSO-$d_6$) δ 9.15 (d, J=6.4 Hz, 1H), 8.12 (dd, J=6.0, 9.2 Hz, 1H), 7.61-7.49 (m, 2H), 7.18 (dd, J=2.0, 8.8 Hz, 1H), 4.78-4.49 (m, 1H), 4.15-3.99 (m, 4H), 3.99-3.86 (m, 2H), 3.70-3.61 (m, 1H), 3.56-3.48 (m, 1H), 3.13-3.05 (m, 1H), 2.91-2.63 (m, 2H), 2.35-2.28 (m, 1H), 2.25-2.10 (m, 2H), 2.08-2.02 (m, 2H), 1.92-1.44 (m, 10H), 1.36-1.29 (m, 3H), 1.08 (d, J=7.6 Hz, 18H), 0.82 (t, J=6.4 Hz, 18H), 0.55-0.44 (m, 3H).

Step 6-((3S,7aS)-7a-(((4-(4-Cyanoazepan-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy) methyl)hexahydro-1H-pyrrolizin-3-yl)methyl (4-nitrophenyl) carbonate. To a solution of 1-(8-fluoro-7-(7-fluoro-8-((triisopropylsilyl) ethynyl)-3-((triisopropylsilyl) oxy) naphthalen-1-yl)-2-(((3S,7aS)-3-(hydroxymethyl)tetrahydro-1H-pyrrolizin-7a (5H)-yl) methoxy)pyrido[4,3-d] pyrimidin-4-yl) azepane-4-carbonitrile (60.0 mg, 64.0 μmol) in THF (5 mL) was added TEA (48.5 mg, 480 μmol, 66.8 μL), the solution of (4-nitrophenyl) carbonochloridate (64.5 mg, 320 μmol, CAS #7693-46-1) in THF (1 mL) was added into above solution. The mixture was stirred at 25° C. for 30 hrs. On completion, the mixture was concentrated in vacuo, then dissolved in DCM (10 mL), diluted with $H_2O$ (20 mL), extracted with DCM (3×10 mL), the organic layer was washed with brine (5×10 mL), dried with anhydrous $Na_2SO_4$, filtered and the filtrate was concentrated in vacuo to give the title compound (65.0 mg, 92% yield) as yellow solid. LC-MS (ESI) m/z 1102.4 $(M+H)^+$.

Step 7-((3S,7aS)-7a-(((4-(4-Cyanoazepan-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy) methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate. To a solution of ((3S,7aS)-7a-(((4-(4-cyanoazepan-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy)methyl) hexahydro-1H-pyrrolizin-3-yl)methyl (4-nitrophenyl) carbonate (65.0 mg, 58.9 μmol) and 3-[3-methyl-2-oxo-5-[1-(4-piperidylmethyl)-4-piperidyl]benzimidazol-1-yl] piperidine-2,6-dione (48.9 mg, 88.4 μmol, TFA) in THF (3 mL) and $H_2O$ (0.5 mL) was added TEA (11.9 mg, 117 μmol). The mixture was stirred at 25° C. for 0.5 hr. On completion, the mixture was concentrated in vacuo. The residue was purified by prep-HPLC (column: Phenomenex luna C18 150*25 mm*10 μm; mobile phase: [water (FA)-ACN]; gradient: 38%-68% B over 8 min) to give the title compound (45.0 mg, 53% yield) as white solid. $^1H$ NMR (400 MHz, DMSO-$d_6$) δ 11.09 (s, 1H), 9.29-9.16 (m, 1H), 8.19-8.09 (m, 1H), 7.64-7.50 (m, 2H), 7.19 (d, J=10.0 Hz, 1H), 7.10-6.98 (m, 2H), 6.96-6.87 (m, 1H), 5.34 (dd, J=5.2, 12.8 Hz, 1H), 4.74-4.38 (m, 2H), 4.36-4.12 (m, 3H), 4.07 (s, 3H), 4.03-3.84 (m, 3H), 3.21-3.02 (m, 6H), 2.96-2.75 (m, 6H), 2.74-2.58 (m, 4H), 2.39-2.26 (m, 3H), 2.22 (s, 2H), 2.15-1.69 (m, 20H), 1.33 (td, J=7.6, 14.8 Hz, 3H), 1.23 (s, 1H), 1.08 (d, J=7.2 Hz, 18H), 0.82 (t, J=8.0 Hz, 18H), 0.58-0.47 (m, 3H); LC-MS (ESI) m/z 1402.6 $(M+H)^+$.

Step 8-((3S,7aS)-7a-(((4-(4-Cyanoazepan-1-yl)-7-(8-ethynyl-7-fluoro-3-hydroxynaphthalen-1-yl)-8-fluoropyrido [4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (Compound 110). To a solution of ((3S,7aS)-7a-(((4-(4-cyanoazepan-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl) methyl) piperidine-1-carboxylate (40.0 mg, 28.5 μmol) in DMSO (1 mL) was added CsF (12.9 mg, 85.5 μmol). The mixture was stirred at 25° C. for 0.5 hr. On completion, the mixture was filtered and the filtrate was purified by prep-HPLC (column: Phenomenex luna C18 150*25 mm*10 μm; mobile phase: [water (FA)-ACN]; gradient: 7%-37% B over 8 min) to give the title compound (23.5 mg, 71% yield, FA salt) as yellow solid. $^1H$ NMR (400 MHz, DMSO-$d_6$) δ 11.08 (s, 1H), 10.23-10.09 (m, 1H), 9.11 (d, J=7.6 Hz, 1H), 7.97 (ddd, J=2.0, 6.4, 8.8 Hz, 1H), 7.46 (t, J=9.2 Hz, 1H), 7.39 (s, 1H), 7.19 (dd, J=2.4, 5.6 Hz, 1H), 7.08 (s, 1H), 7.00 (d, J=8.0 Hz, 1H), 6.90 (d, J=8.4 Hz, 1H), 5.33 (dd, J=5.4, 12.4 Hz, 1H), 4.27-4.15 (m, 4H), 4.14-4.08 (m, 2H), 3.99 (s, 1H), 3.96 (s, 2H), 3.91-3.77 (m, 1H), 3.43-3.36 (m, 2H), 3.31-3.30 (m, 3H), 3.22-3.12 (m, 1H), 2.96 (d, J=9.6 Hz, 2H), 2.92-2.72 (m, 5H), 2.72-2.61 (m, 2H), 2.34-2.25 (m, 2H), 2.19 (d, J=5.2 Hz, 2H), 2.13-2.07 (m, 2H), 2.05-1.94 (m, 4H), 1.93-1.53 (m, 17H), 1.04-0.91 (m, 2H); LC-MS $(ESI^+)$ m z 1090.3 $(M+H)^+$.

Example 23. Synthesis of Compound 111

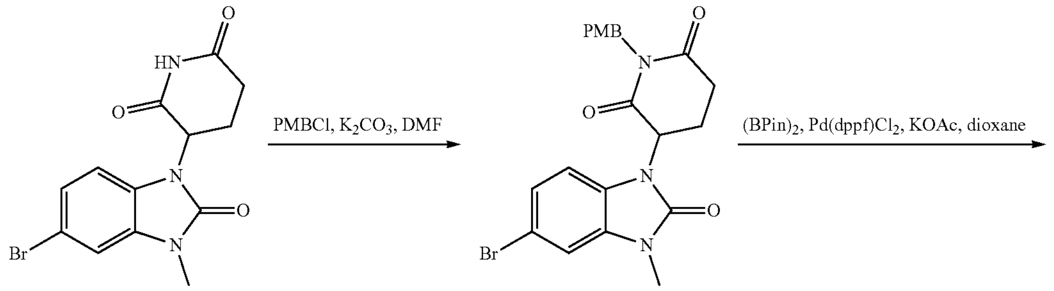

-continued
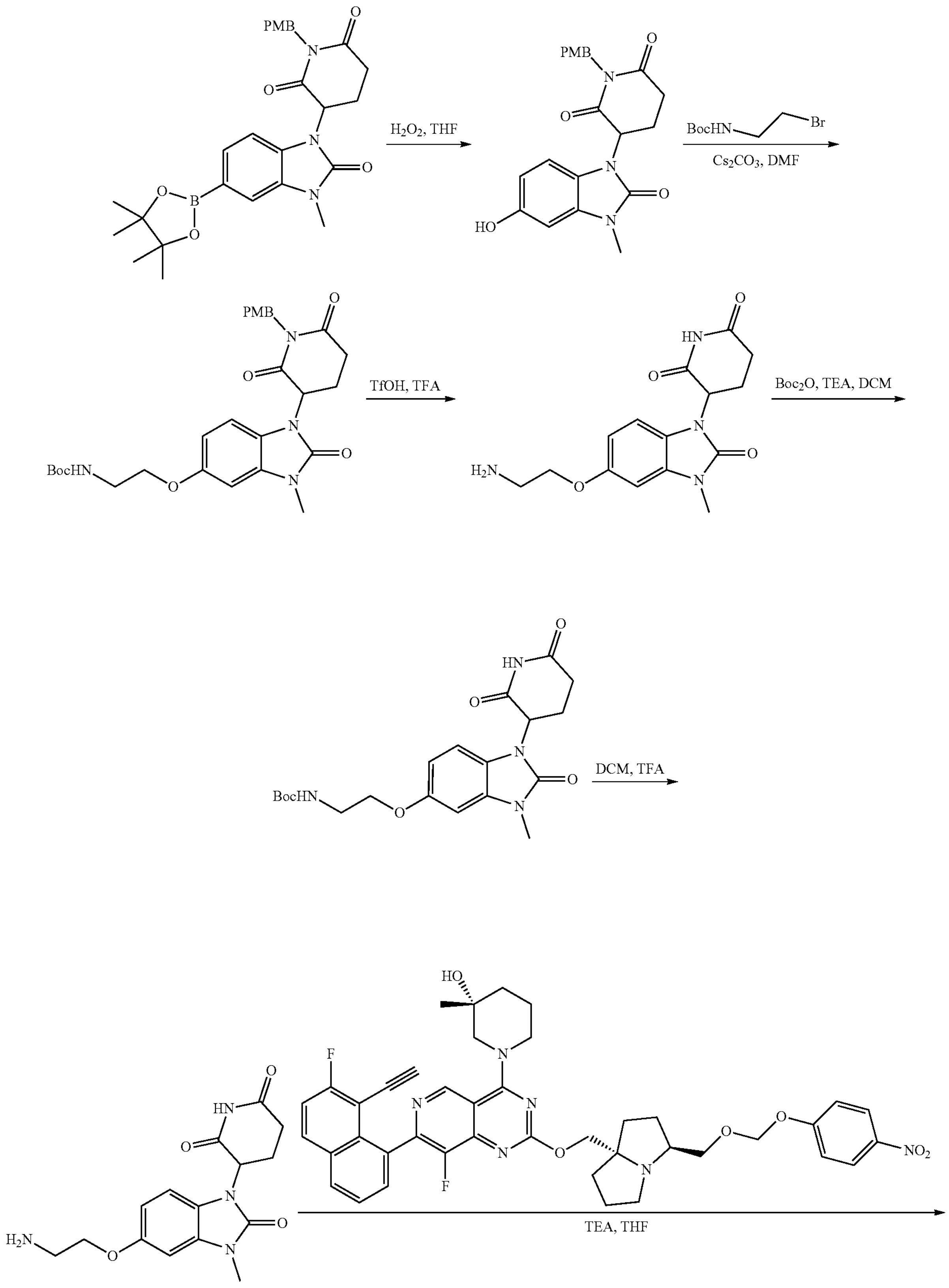

-continued

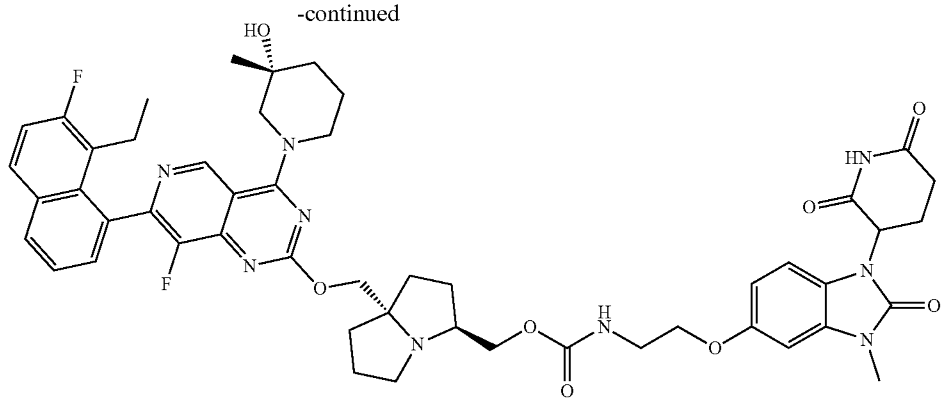

111

Step 1-3-(5-Bromo-3-methyl-2-oxo-benzimidazol-1-yl)-1-[(4-methoxyphenyl)methyl]piperidine-2,6-dione. To a mixture of 3-(5-bromo-3-methyl-2-oxo-benzimidazol-1-yl) piperidine-2,6-dione (9.00 g, 26.6 mmol, CAS #2300099-98-1) in DMF (90 mL) was added PMB-$C_1$ (6.25 g, 39.9 mmol, 5.42 mL) and $K_2CO_3$ (11.0 g, 79.8 mmol), the reaction mixture was stirred at 50° C. for 3 hrs. On completion, the reaction mixture residue was diluted with water (500 mL) and extracted with EA (2×500 mL). The combined organic layers was dried over $Na_2SO_4$, filtered and the filtrate was concentrated in vacuo to give a residue. The residue was triturated with EtOH (30 mL), filtered and the filter cake was dried to give the title compound (11.5 g, 94% yield) as yellow solid. $^1$H NMR (400 MHz, DMSO-$d_6$) δ 7.47 (d, J=1.6 Hz, 1H), 7.22-7.14 (m, 3H), 7.01 (d, J=8.4 Hz, 1H), 6.85 (d, J=8.8 Hz, 2H), 5.54 (dd, J=5.6, 13.2 Hz, 1H), 4.78 (q, J=14.4 Hz, 2H), 3.72 (s, 3H), 3.34-3.33 (m, 3H), 3.11-2.99 (m, 1H), 2.86-2.77 (m, 1H), 2.77-2.66 (m, 1H), 2.11-2.02 (m, 1H).

Step 2-1-[(4-Methoxyphenyl)methyl]-3-[3-methyl-2-oxo-5-(4,4,5,5-tetramethyl-1,3,2-dioxaborolan-2-yl)benzimidazol-1-yl]piperidine-2,6-dione. To a mixture of 3-(5-bromo-3-methyl-2-oxo-benzimidazol-1-yl)-1-[(4-methoxyphenyl)methyl]piperidine-2,6-dione (10.0 g, 21.8 mmol) in dioxane (100 mL) was added Pd (dppf) $Cl_2$ (1.60 g, 2.18 mmol), KOAc (6.42 g, 65.4 mmol) and $Pin_2B_2$ (11.0 g, 43.6 mmol), the reaction mixture was stirred at 70° C. for 12 hrs under $N_2$ atmosphere. On completion, the reaction mixture was diluted with water (300 mL) and extracted with EA (2×300 mL). The combined organic layers was dried over $Na_2SO_4$, filtered and the filtrate was concentrated in vacuo to give a residue. The residue was purified by column chromatography ($SiO_2$, PE:EA=20:1) to give the title compound (14.7 g, crude) as yellow solid. $^1$H NMR (400 MHz, DMSO-$d_6$) δ 7.39 (s, 1H), 7.37 (d, J=8.0 Hz, 1H), 7.21 (d, J=8.8 Hz, 2H), 7.03 (d, J=7.2 Hz, 1H), 6.86 (d, J=8.8 Hz, 2H), 5.59-5.52 (m, 1H), 4.86-4.73 (m, 2H), 3.73 (s, 3H), 3.53 (d, J=8.8 Hz, 3H), 3.12-3.00 (m, 1H), 2.87-2.69 (m, 2H), 2.11-2.02 (m, 1H), 1.30 (s, 12H).

Step 3-3-(5-Hydroxy-3-methyl-2-oxo-benzimidazol-1-yl)-1-[(4-methoxyphenyl)methyl]piperidine-2,6-dione. To a mixture of 1-[(4-methoxyphenyl)methyl]-3-[3-methyl-2-oxo-5-(4,4,5,5-tetramethyl-1,3,2-dioxaborolan-2-yl)benzimidazol-1-yl]piperidine-2,6-dione (13.7 g, 27.2 mmol) in THF (150 mL) was added $H_2O_2$ (9.2 g, 81.6 mmol, 7.84 mL, 30% purity) dropwise at 0° C., the reaction mixture was stirred at 25° C. for 12 hrs. On completion, the reaction mixture was quenched with saturated (sat.) $Na_2S_2O_3$ (200 mL) and sat. $NH_4C_1$ (200 mL) under stirring. And then the residue was diluted with water (500 mL) and extracted with EA (2×500 mL). The combined organic layers were dried over $Na_2SO_4$, filtered and the filtrate was concentrated in vacuo to give a residue. The residue was purified by column chromatography ($SiO_2$, PE:EA=1:4) to give the title compound (6.83 g, 63% yield) as yellow solid. $^1$H NMR (400 MHz, DMSO-$d_6$) δ 9.16 (s, 1H), 7.20 (d, J=8.8 Hz, 2H), 6.85 (d, J=8.8 Hz, 2H), 6.74 (d, J=8.4 Hz, 1H), 6.58 (d, J=2.0 Hz, 1H), 6.40 (dd, J=2.0, 8.4 Hz, 1H), 5.42 (dd, J=5.2, 13.2 Hz, 1H), 4.85-4.72 (m, 2H), 3.72 (s, 3H), 3.26 (s, 3H), 3.11-2.97 (m, 1H), 2.85-2.74 (m, 1H), 2.68 (dq, J=4.0, 13.2 Hz, 1H), 2.06-1.98 (m, 1H).

Step 4-Tert-butyl N-[2-[1-[1-[(4-methoxyphenyl) methyl]-2,6-dioxo-3-piperidyl]-3-methyl-2-oxo-benzimidazol-5-yl]oxyethyl]carbamate. To a mixture of 3-(5-hydroxy-3-methyl-2-oxo-benzimidazol-1-yl)-1-[(4-methoxyphenyl) methyl]piperidine-2,6-dione (1.60 g, 4.05 mmol), tert-butyl N-(2-bromoethyl) carbamate (1.09 g, 4.86 mmol, CAS #39684-80-5) and $Cs_2CO_3$ (2.64 g, 8.09 mmol) in DMF (15 mL), the reaction mixture was stirred at 70° C. for 2 hrs. On completion, the reaction mixture was filtered and the filtrate was concentrated in vacuo to give a residue. The residue was purified by reverse phase (0.1% FA condition) to give the title compound (1.10 g, 50% yield) as yellow solid. LC-MS (ESI) m/z 561.2 $(M+Na)^+$.

Step 5-3-[5-(2-Aminoethoxy)-3-methyl-2-oxo-benzimidazol-1-yl]piperidine-2,6-dione. To a mixture of tert-butyl N-[2-[1-[1-[(4-methoxyphenyl)methyl]-2,6-dioxo-3-piperidyl]-3-methyl-2-oxo-benzimidazol-5-yl]oxyethyl]carbamate (900 mg, 1.67 mmol) in TFA (9 mL) was added TfOH (5.09 g, 33.9 mmol, 3 mL), the reaction mixture was stirred at 70° C. for 1 hr. On completion, the reaction mixture was concentrated in vacuo to give the title compound (730 mg, crude, TFA) as brown oil. LC-MS (ESI) m/z 319.0 $(M+H)^+$.

Step 6-Tert-butyl N-[2-[1-(2,6-dioxo-3-piperidyl)-3-methyl-2-oxo-benzimidazol-5-yl]oxyethyl]carbamate. To a mixture of 3-[5-(2-aminoethoxy)-3-methyl-2-oxo-benzimidazol-1-yl]piperidine-2,6-dione (730 mg, 1.69 mmol, TFA) in DCM (8 mL) was added TEA (170 mg, 1.69 mmol, 235 μL) and $Boc_2O$ (737 mg, 3.38 mmol, 775 μL), the reaction mixture was stirred at 25° C. for 12 hrs. On completion, the reaction mixture was diluted with water (10 mL) and extracted with DCM (2×15 mL). The combined organic layers was dried over $Na_2SO_4$, filtered and the filtrate was concentrated in vacuo to give a residue. The residue was purified by reverse phase (0.1% FA condition) to give the title compound (450 mg, 63% yield) as brown solid. $^1$H NMR (400 MHz, DMSO-$d_6$) δ 11.07 (s, 1H), 7.00-6.98 (m, 1H), 6.87 (d, J=2.0 Hz, 1H), 6.62 (dd, J=2.4, 8.4 Hz, 1H), 5.31 (dd, J=5.2, 12.8 Hz, 1H), 3.95 (t, J=5.6 Hz, 2H), 3.31 (s, 3H), 3.30-3.25 (m, 2H), 2.93-2.84 (m, 1H), 2.74-2.57 (m, 2H), 1.99 (s, 1H), 1.39 (s, 9H).

Step 7-3-[5-(2-Aminoethoxy)-3-methyl-2-oxo-benzimidazol-1-yl]piperidine-2,6-dione. To a mixture of tert-butyl N-[2-[1-(2,6-dioxo-3-piperidyl)-3-methyl-2-oxo-benzimidazol-5-yl]oxyethyl]carbamate (70.0 mg, 167 μmol) in DCM (1 mL) was added TFA (767 mg, 6.73 mmol, 0.5 mL), the reaction mixture was stirred at 25° C. for 0.5 hr. On completion, the reaction mixture was concentrated in vacuo to give the title compound (70.0 mg, 96% yield, TFA) as yellow oil. LC-MS (ESI$^+$) m/z 319.0 (M+H)$^+$.

Step 8-((3S,7aS)-7a-(((7-(8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (2-((1-(2,6-dioxopiperidin-3-yl)-3-methyl-2-oxo-2,3-dihydro-1H-benzo[d]imidazol-5-yl)oxy)ethyl) carbamate (Compound 111). To a mixture of 3-[5-(2-aminoethoxy)-3-methyl-2-oxo-benzimidazol-1-yl]piperidine-2,6-dione (70.0 mg, 161 μmol, TFA) in THF (1 mL) was added TEA (363 mg, 3.59 mmol, 0.5 mL) and ((3S,7aS)-7a-(((7-(8-ethyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (62.2 mg, 80.9 μmol), the reaction mixture was stirred at 25° C. for 0.5 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 15%-45% B over 8 min) to give the title compound (16.9 mg, 10% yield, FA) as white solid. $^1$H NMR (400 MHz, DMSO-$d_6$) δ 11.07 (s, 1H), 9.23 (d, J=5.6 Hz, 1H), 8.12 (d, J=8.4 Hz, 1H), 8.02 (dd, J=6.0, 9.2 Hz, 1H), 7.61-7.55 (m, 1H), 7.52-7.43 (m, 3H), 6.98 (d, J=8.4 Hz, 1H), 6.87 (d, J=1.6 Hz, 1H), 6.64-6.58 (m, 1H), 5.34-5.26 (m, 1H), 4.79-4.70 (m, 1H), 4.39-4.26 (m, 1H), 4.21-4.09 (m, 3H), 4.08 (s, 2H), 3.97 (t, J=5.6 Hz, 2H), 3.65-3.51 (m, 1H), 3.29 (s, 3H), 2.93-2.83 (m, 1H), 2.77-2.55 (m, 5H), 2.47-2.30 (m, 3H), 2.26-2.15 (m, 1H), 2.07-1.95 (m, 3H), 1.79-1.57 (m, 10H), 1.55-1.46 (m, 1H), 1.16 (d, J=9.6 Hz, 3H), 0.76 (q, J=7.2 Hz, 3H); LC-MS (ESI$^+$) m/z 948.2 (M+H)$^+$.

Example 24. Synthesis of Compound 112

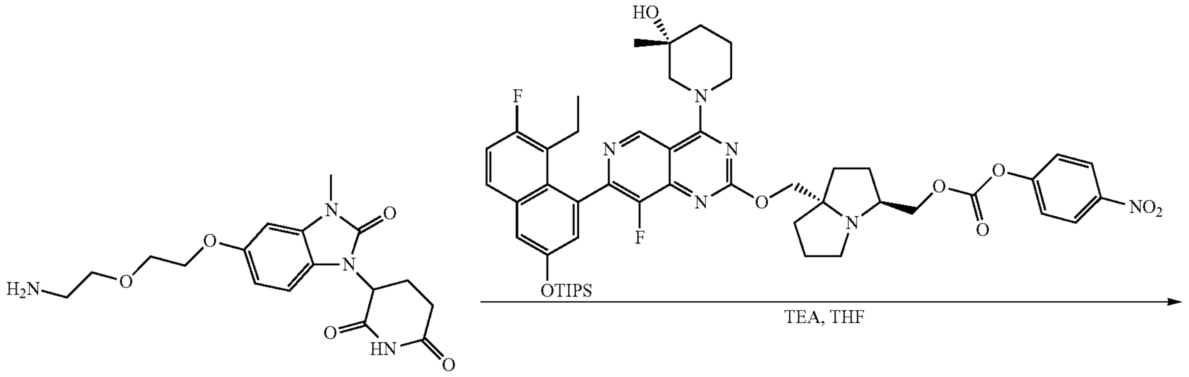

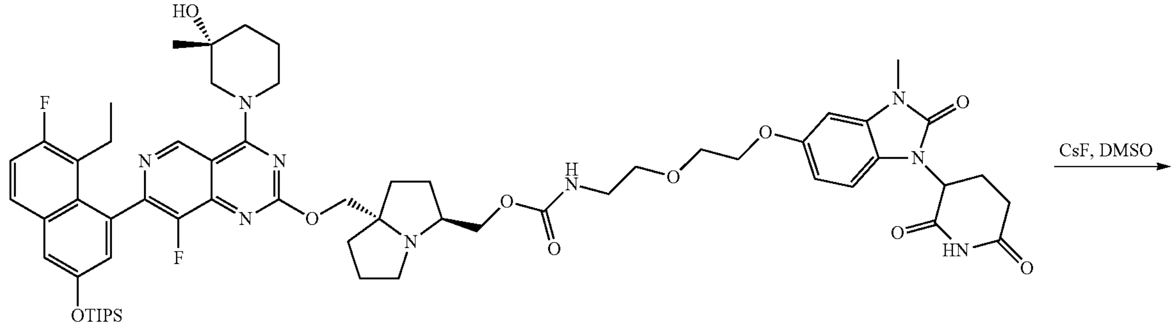

-continued

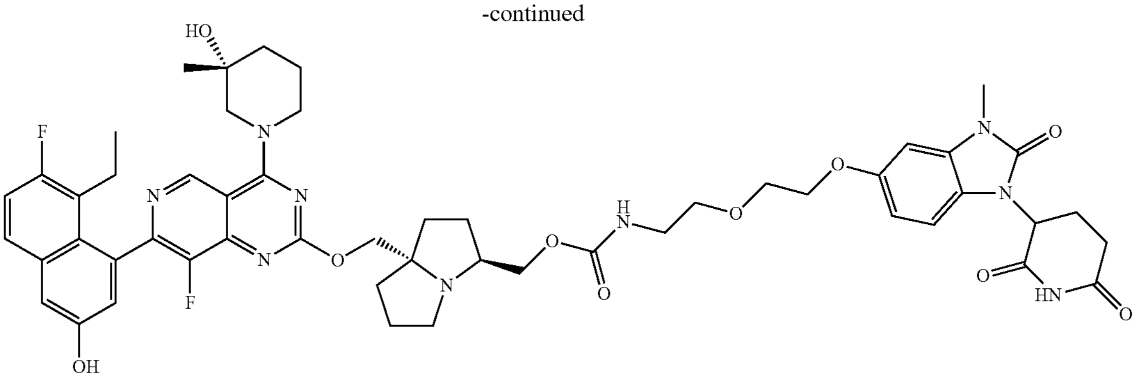

112

Step 1-((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (2-(2-((1-(2,6-dioxopiperidin-3-yl)-3-methyl-2-oxo-2,3-dihydro-1H-benzo[d]imidazol-5-yl)oxy) ethoxy)ethyl) carbamate. To a solution of 3-[5-[2-(2-aminoethoxy)ethoxy]-3-methyl-2-oxo-benzimidazol-1-yl]piperidine-2,6-dione (40.4 mg, 111 μmol) and ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate (70.0 mg, 74.3 μmol) in THF (1 mL) was added TEA (22.5 mg, 223 μmol, 31.0 μL). The mixture was stirred at 25° C. for 0.5 hr. On completion, the mixture was concentrated in vacuo. The residue was purified by prep-HPLC (column: Phenomenex luna C18 150*25 mm*10 μm; mobile phase: [water (FA)-ACN]; gradient: 40%-70% B over 10 min) to give the title compound (60.0 mg, 69% yield) as white solid. LC-MS (ESI) m/z 1164.5 $(M+H)^+$.

Step 2-((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl (2-(2-((1-(2,6-dioxopiperidin-3-yl)-3-methyl-2-oxo-2,3-dihydro-1H-benzo[d]imidazol-5-yl)oxy) ethoxy)ethyl) carbamate (Compound 112). To a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (2-(2-((1-(2,6-dioxopiperidin-3-yl)-3-methyl-2-oxo-2,3-dihydro-1H-benzo[d]imidazol-5-yl)oxy) ethoxy) ethyl) carbamate (50.0 mg, 42.9 μmol) in DMSO (1 mL) was added CsF (19.5 mg, 128 μmol). The mixture was stirred at 25° C. for 0.5 hr. On completion, the mixture was concentrated in vacuo. The residue was purified by prep-HPLC (column: Phenomenex luna C18 150*25 mm*10 μm; mobile phase: [water (FA)-ACN]; gradient: 15%-45% B over 8 min) to give the title compound (19.4 mg, 41% yield, FA) as white solid. $^1H$ NMR (400 MHz, DMSO-$d_6$) δ 11.11 (s, 1H), 10.01-9.87 (m, 1H), 9.22 (d, J=2.0 Hz, 1H), 7.71 (s, 1H), 7.38-7.31 (m, 2H), 7.26 (s, 1H), 7.03 (d, J=2.4 Hz, 1H), 6.98 (d, J=8.4 Hz, 1H), 6.88 (d, J=2.0 Hz, 1H), 6.56 (s, 1H), 5.35-5.26 (m, 1H), 4.74 (d, J=6.8 Hz, 1H), 4.39-4.27 (m, 1H), 4.16-4.03 (m, 6H), 3.75-3.68 (m, 2H), 3.65-3.52 (m, 1H), 3.47 (t, J=6.0 Hz, 2H), 3.30 (s, 3H), 3.18-3.11 (m, 2H), 2.92-2.83 (m, 1H), 2.76 (s, 4H), 2.40-2.27 (m, 2H), 2.19-1.94 (m, 5H), 1.79-1.58 (m, 10H), 1.55-1.46 (m, 1H), 1.16 (d, J=9.6 Hz, 3H), 0.73 (q, J=7.2 Hz, 3H); LC-MS (ESI) m/z 1008.2 $(M+H)^+$.

Example 25. Synthesis of Compound 113

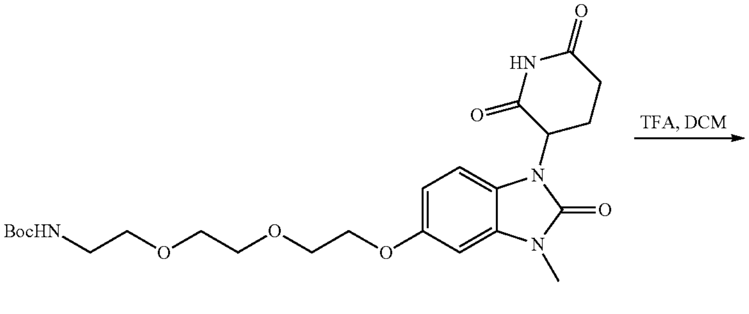

-continued

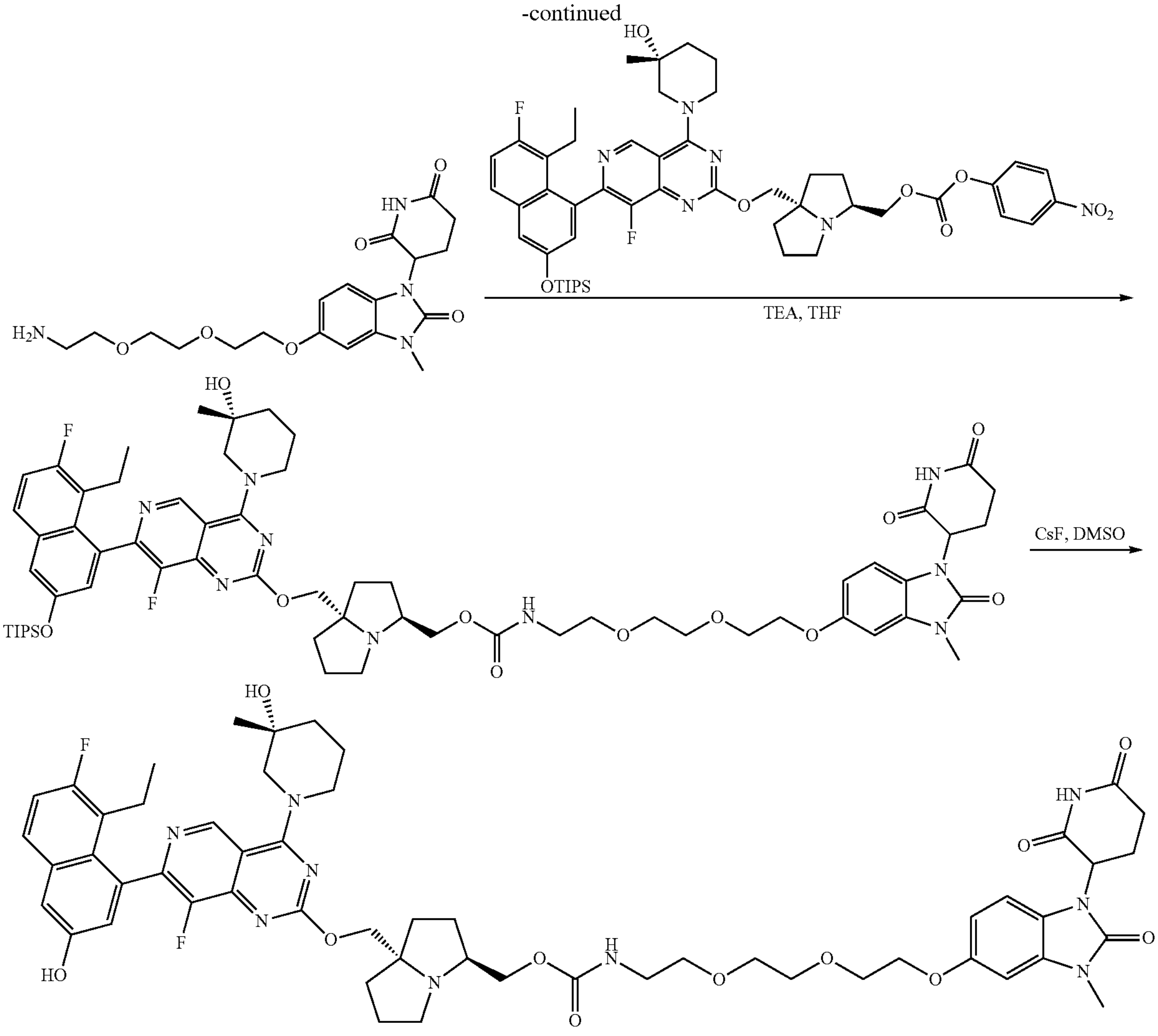

113

Step 1-3-(5-(2-(2-(2-Aminoethoxy)ethoxy) ethoxy)-3-methyl-2-oxo-2,3-dihydro-1H-benzo-[d]imidazol-1-yl) piperidine-2,6-dione. To a solution tert-butyl N-[2-[2-[2-[1-(2,6-dioxo-3-piperidyl)-3-methyl-2-oxo-benzimidazol-5-yl]-oxyethoxy]ethoxy]ethyl]carbamate (70.0 mg, 140 μmol) in DCM (2 mL) was added TFA (790 mg, 6.90 mmol, 510 μL) dropwise at 25° C. The reaction mixture was stirred at 25° C. for 0.5 hr. On completion, the mixture was concentrated in vacuo to give the title compound (71.0 mg, 99% yield, TFA salt) as brown oil. LC-MS ($ESI^+$) m/z 407.0 $(M+H)^+$.

Step 2-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (2-(2-(2-((1-(2,6-dioxopiperidin-3-yl)-3-methyl-2-oxo-2,3-dihydro-1H-benzo-[d]imidazol-5-yl)oxy) ethoxy)ethoxy)ethyl) carbamate. To a suspension of 3-[5-[2-[2-(2-aminoethoxy) ethoxy]ethoxy]-3-methyl-2-oxo-benzimidazol-1-yl]pip-eridine-2,6-dione (66.3 mg, 130 μmol, TFA salt) in THF (3 mL) as added TEA (77.4 mg, 770 μmol, 110 μL) until pH=8-9. Then (4-nitrophenyl) [(3S,8S)-8-[[7-(8-ethyl-7-fluoro-3-tri-isoprop-ylsilyloxy-1-naphthyl)-8-fluoro-4-[(3R)-3-hydroxy-3-methyl-1-piperidyl]pyrido[4,3-d]pyrimidin-2-yl] oxymethyl]-1,2,3,5,6,7-hexahydropyrrolizin-3-yl]methyl carbonate (60.0 mg, 63.8 μmol) in THF (1 mL) was added and stirred at 25° C. for 1 hr. On completion, the mixture was concentrated in vacuo to give residue. The residue was purified by prep-HPLC (column: CD04-Welch Utimate C18 150*25*7 μm; mobile phase: [water (FA)-ACN]; gradient: 44%-74% B over 10 min) to give the title compound (37.0 mg, 48% yield) as white solid. LC-MS ($ESI^+$) m/z 1208.4 $(M+H)^+$.

Step 3-((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl (2-(2-(2-((1-(2,6-dioxopiperidin-3-yl)-3-methyl-2-oxo-2,3-dihydro-1H-benzo[d]imidazol-5-yl)oxy) ethoxy)ethoxy)ethyl) carbamate (Compound 113). To a solution of [(3S,8S)-8-[[7-(8-ethyl-7-fluoro-3-triisopropylsilyloxy-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl N-[2-[2-[2-[1-(2,6-dioxo-3-piperidyl)-3-methyl-2-oxo-benzimidazol-5-yl]-oxyethoxy]ethoxy]ethyl]carbamate (33.0 mg, 27.3 μmol) in DMSO (0.5 mL) was added CsF (12.4 mg, 82.0 μmol). The mixture was stirred at 25° C. for 0.5 hr. On completion, the mixture was concentrated in vacuo to give a residue. The residue was purified by prep-HPLC (column: CD01-Phenomenex luna C18 150*25*10 μm; mobile phase: [water (FA)-ACN]; gradient: 13%-43% B over 10 min) to give the title compound (17.2 mg, 60% yield, FA salt) as white solid. $^1$H NMR (400 MHz, DMSO-$d_6$) δ 11.07 (s, 1H), 9.95 (s, 1H), 9.24 (d, J=2.4 Hz, 1H), 7.77 (dd, J=6.0, 9.2 Hz, 1H), 7.46-7.28 (m, 2H), 7.27-7.18 (m, 1H), 7.08-6.93 (m, 2H), 6.88 (d, J=2.0 Hz, 1H), 6.62 (dd, J=2.0, 8.6 Hz, 1H), 5.31 (dd, J=5.2, 12.8 Hz, 1H), 4.75 (d, J=8.0 Hz, 1H), 4.41-4.30 (m, 1H), 4.27-3.98 (m, 7H), 3.77-3.70 (m, 2H), 3.69-3.47 (m, 6H), 3.44-3.39 (m, 3H), 3.31 (s, 3H), 3.14 (q, J=5.6 Hz, 2H), 3.01-2.76 (m, 3H), 2.74-2.66 (m, 1H), 2.64-2.58 (m, 1H), 2.41-2.40 (m, 1H), 2.19-2.06 (m, 2H), 2.05-1.94 (m, 2H), 1.92-1.50 (m, 10H), 1.17 (d, J=9.6 Hz, 3H), 0.74 (q, J=7.2 Hz, 3H); LC-MS (ESI) m/z 1052.3 (M+H)$^+$.

Example 26. Synthesis of Compound 114

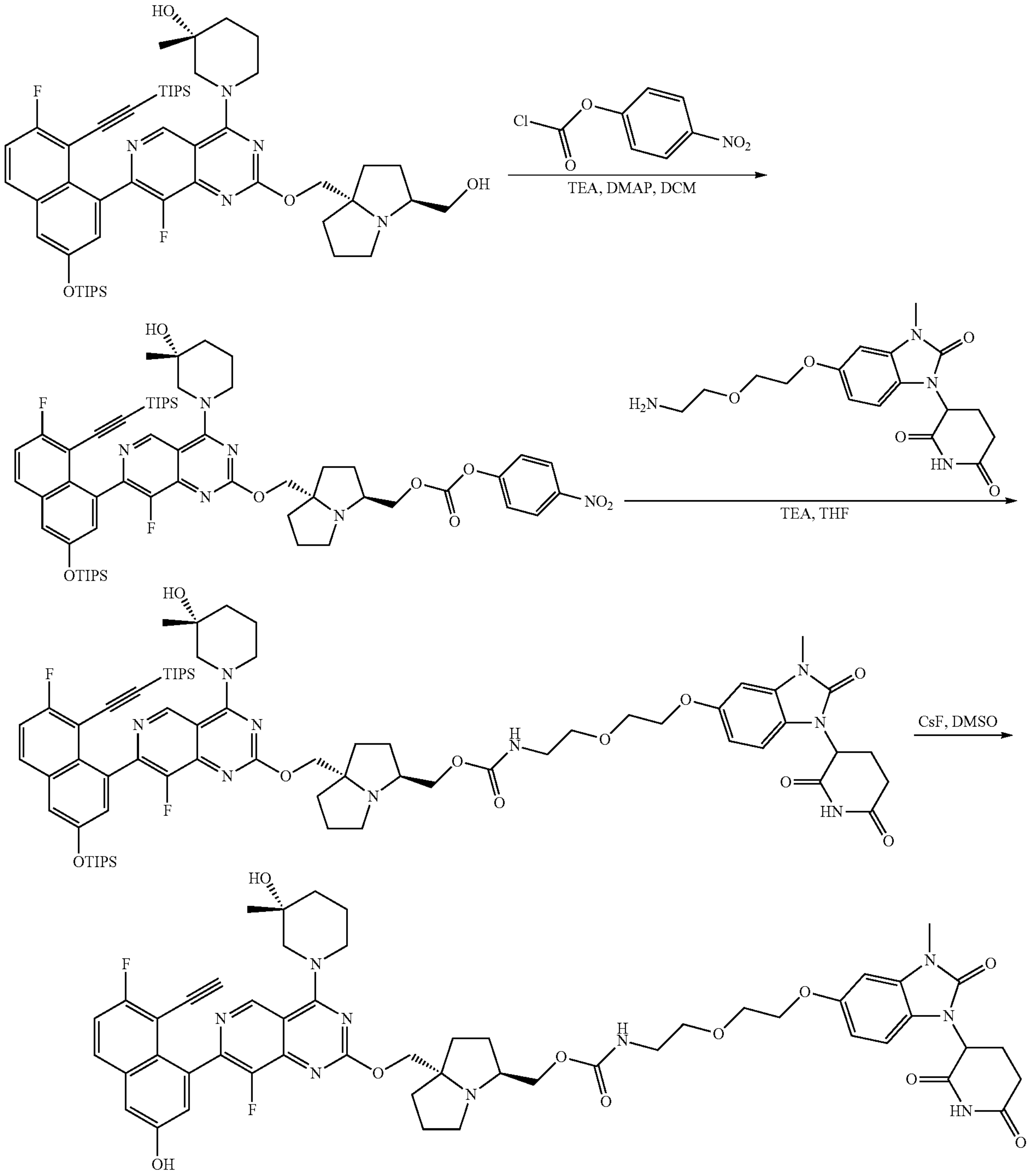

114

Step 1-((3S,7aS)-7a-(((8-Fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate. To a solution of (R)-1-(8-fluoro-7-(7-fluoro-8-((triisopropylsilyl) ethynyl)-3-((triisopropylsilyl)oxy) naphthalen-1-yl)-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (60.0 mg, 64.6 μmol) in DCM (5 mL) was added DMAP (790 μg, 6.46 μmol) and TEA (67 μL, 485 μmol). Then 4-nitrophenyl carbonochloridate (39.1 mg, 194 μmol, CAS #7693-46-1) was added to the mixture and the mixture was stirred at 25° C. for 16 hrs. On completion, the reaction mixture was diluted with DCM (50 mL) and extracted with $H_2O$ (3×50 mL). The combined organic layers were washed with brine (2×50 mL), dried over anhydrous $Na_2SO_4$, filtered and the filtrate was concentrated in vacuo to give the title compound (70 mg, 99% yield) as yellow solid. LC-MS (ESI) m/z 1093.6 $(M+H)^+$.

Step 2-((3S,7aS)-7a-(((8-Fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl (2-(2-((1-(2,6-dioxopiperidin-3-yl)-3-methyl-2-oxo-2,3-dihydro-1H-benzo[d]imidazol-5-yl)oxy) ethoxy) ethyl) carbamate. To a solution of 3-(5-(2-(2-aminoethoxy) ethoxy)-3-methyl-2-oxo-2,3-dihydro-1H-benzo[d]imidazol-1-yl) piperidine-2,6-dione (61.0 mg, 128 μmol, TFA salt) in THF (2 mL) and $H_2O$ (0.2 mL) was added TEA (26.7 μL, 192 μmol) adjust pH=10, then a solution of ((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate (70.0 mg, 64.0 μmol) in THF (2 mL) was added to the mixture and the mixture was stirred at 25° C. for 1 hr. On completion, the mixture was concentrated in vacuo to give a residue. The residue was purified by prep-HPLC (column: Phenomenex luna C18 150*25 mm*10 μm; mobile phase: [water (FA)-ACN]; gradient: 30%-60% B over 8 min) to give the title compound (30.0 mg, 35% yield) as white solid. LC-MS (ESI) m/z 1317.5 $(M+H)^+$.

Step 3-((3S,7aS)-7a-(((7-(8-Ethynyl-7-fluoro-3-hydroxynaphthalen-1-yl)-8-fluoro-4-((R)-3-hydro-xy-3-methylpiperidin-1-yl)pyrido[4,3-d]pyrimidin-2-yl)oxy)methyl) hexahydro-1H-pyrrolizin-3-yl)methyl (2-(2-((1-(2,6-dioxopiperidin-3-yl)-3-methyl-2-oxo-2,3-dihydro-1H-benzo[d]imidazol-5-yl)oxy) ethoxy)ethyl) carbamate (Compound 114). To a solution of ((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl) hexahydro-1H-pyrrolizin-3-yl)methyl (2-(2-((1-(2,6-dioxopiperidin-3-yl)-3-methyl-2-oxo-2,3-dihy-dro-1H-benzo[d]imidazol-5-yl)oxy) ethoxy)ethyl) carbamate (25.0 mg, 19.0 μmol) in DMSO (1 mL) was added CsF (8.65 mg, 57.0 μmol). The mixture was stirred at 25° C. for 9 hrs. On completion, the mixture was concentrated in vacuo to give a residue. The residue was purified by prep-HPLC (column: Phenomenex luna C18 150*25 mm*10 μm; mobile phase: [water (FA)-ACN]; gradient: 10%-40% B over 8 min) to give the title compound (16.9 mg, 87% yield, FA salt) as yellow solid. $^1H$ NMR (400 MHz, DMSO-$d_6$) δ 11.07 (s, 1H), 10.33-10.02 (m, 1H), 9.22-9.03 (m, 1H), 7.97 (dd, J=6.0, 9.2 Hz, 1H), 7.46 (t, J=9.2 Hz, 1H), 7.39 (s, 1H), 7.30-7.24 (m, 1H), 7.21 (dd, J=2.4, 18.4 Hz, 1H), 6.98 (d, J=8.8 Hz, 1H), 6.88 (d, J=2.0 Hz, 1H), 6.61 (dd, J=2.0, 8.4 Hz, 1H), 5.30 (dd, J=5.2, 12.8 Hz, 1H), 4.83-4.69 (m, 1H), 4.40-4.27 (m, 1H), 4.19-4.05 (m, 6H), 4.05-4.00 (m, 1H), 3.94 (s, 1H), 3.73-3.69 (m, 2H), 3.58 (t, J=13.6 Hz, 1H), 3.47 (t, J=6.0 Hz, 2H), 3.30 (s, 3H), 3.17-3.13 (m, 2H), 2.92-2.83 (m, 1H), 2.77-2.72 (m, 1H), 2.68 (dd, J=4.0, 12.4 Hz, 2H), 2.65-2.54 (m, 2H), 2.07-1.96 (m, 3H), 1.78-1.58 (m, 10H), 1.54-1.46 (m, 1H), 1.16 (d, J=16.4 Hz, 3H); LC-MS $(ESI^+)$ m/z 1004.3 $(M+H)^+$.

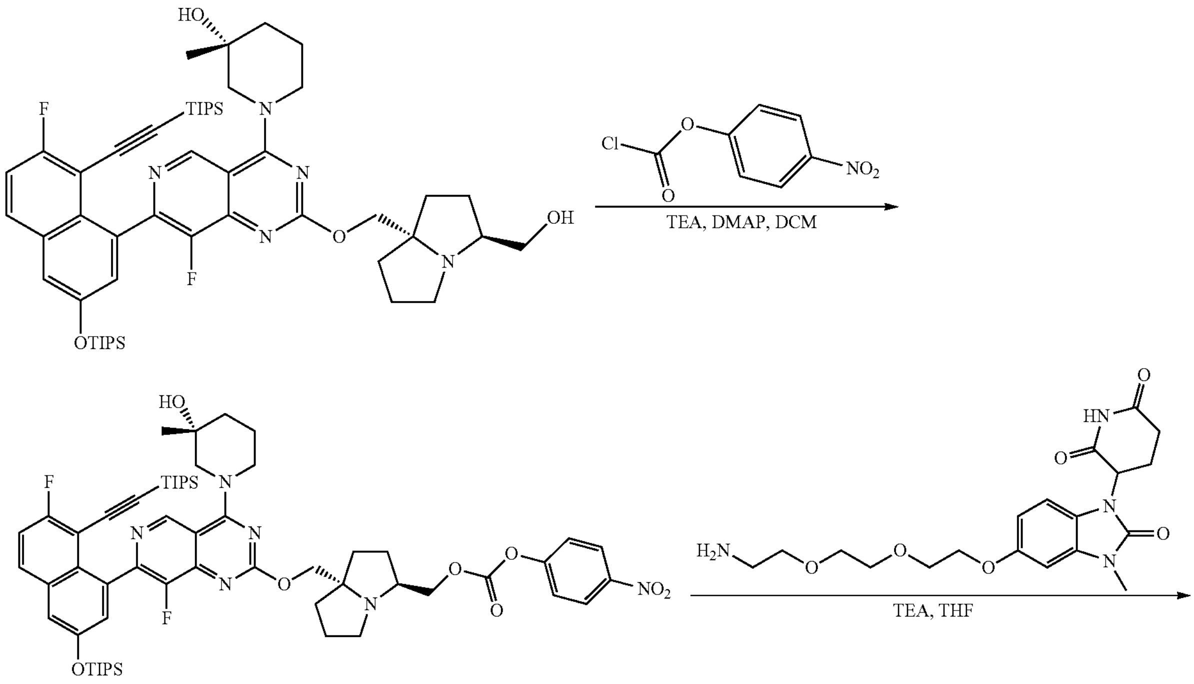

-continued

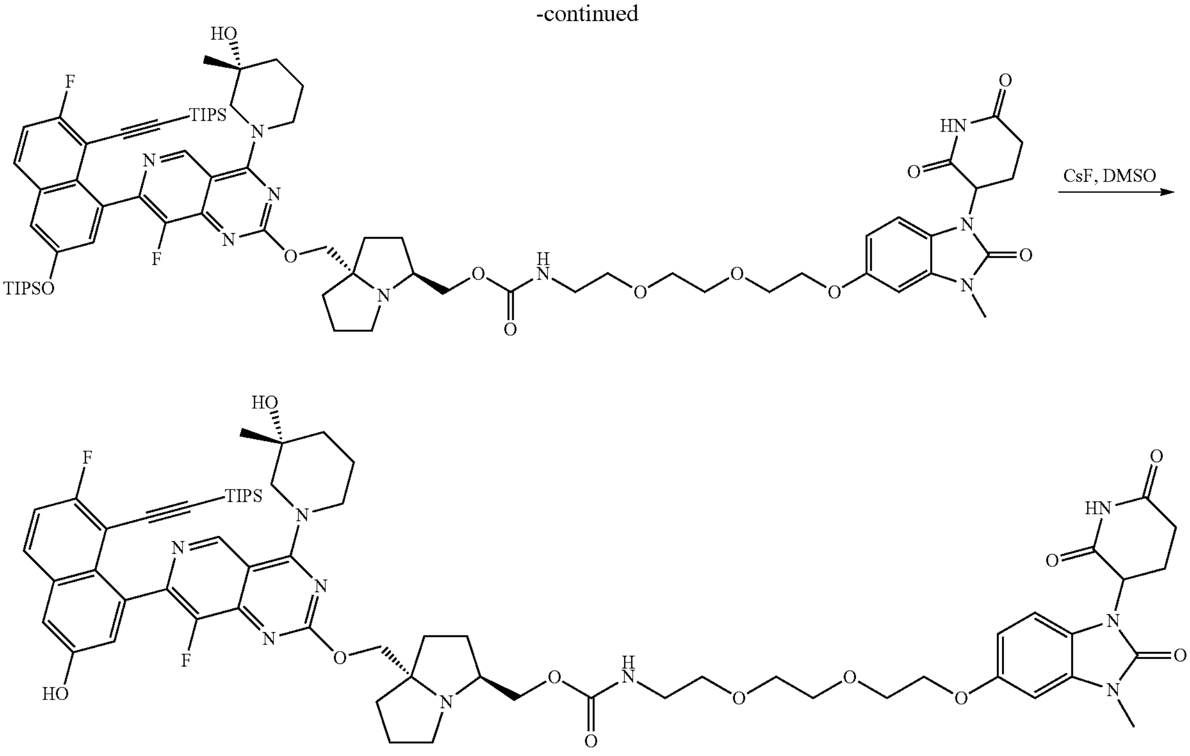

115

Step 1-((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d] pyrimidin-2-yl)oxy)methyl)hexahydro-1H-pyrrolizin-3-yl) methyl (4-nitrophenyl) carbonate. To a solution of (R)-1-(8-fluoro-7-(7-fluoro-8-((triisopropylsilyl) ethynyl)-3-((triisopropylsilyl)oxy) naphthalen-1-yl)-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (60.0 mg, 64.6 μmol) and (4-nitrophenyl) carbonochloridate (39.0 mg, 193 μmol, CAS #7693-46-1) in DCM (2 mL) was added TEA (6.54 mg, 64.6 μmol) and DMAP (789 μg, 6.46 μmol). The mixture was stirred at 25° C. for 16 hrs. On completion, the mixture was diluted with $H_2O$ (10 mL) and extracted with DCM (3×30 mL). The combined organic layers were washed with brine (3×20 mL), dried over anhydrous $Na_2SO_4$, filtered and the filter liquor was concentrated in vacuo to give the title compound (70.0 mg, 99% yield) as brown solid. LC-MS (ESI) m/z 1094.6 $(M+H)^+$.

Step 2-((35,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d] pyrimidin-2-yl)oxy)methyl)hexahydro-1H-pyrrolizin-3-yl) methyl (2-(2-(2-((1-(2,6-dioxopiperidin-3-yl)-3-methyl-2-oxo-2,3-dihydro-1H-benzo[d]imidazol-5-yl)oxy) ethoxy) ethoxy)ethyl) carbamate. To a solution of ((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate (39.0 mg, 96.0 μmol) in THF (1 mL) was added TEA (19.4 mg, 192 μmol). The mixture was stirred at 25° C. for 0.5 hr. On completion, the mixture was concentrated in vacuo. The residue was purified by prep-HPLC (column: Phenomenex luna C18 150*25 mm*10 μm; mobile phase: [water (FA)-ACN]; gradient: 52%-82% B over 8 min) to give the title compound (70.0 mg, 80% yield) as white solid; LC-MS (ESI) m/z 1360.6 $(M+H)^+$.

Step 3 ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl (2-(2-(2-((1-(2,6-dioxopiperidin-3-yl)-3-methyl-2-oxo-2,3-dihydro-1H-benzo[d]imidazol-5-yl)oxy) ethoxy)ethoxy)ethyl) carbamate (Compound 115). To a solution of ((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy) methyl)hexahydro-1H-pyrrolizin-3-yl)methyl-(2-(2-(2-((1-(2,6-dioxopiperidin-3-yl)-3-methyl-2-oxo-2,3-dihydro-1H-benzo[d]imidazol-5-yl)oxy) ethoxy)ethoxy)ethyl) carbamate (60.0 mg, 44.0 μmol) in DMSO (1 mL) was added CsF (20.0 mg, 132 μmol). The mixture was stirred at 25° C. for 0.5 hr. On completion, the mixture was filtered and the filtrate was purified by prep-HPLC (column: Phenomenex luna C18 150*25 mm*10 μm; mobile phase: [water (FA)-ACN]; gradient: 12%-42% B over 10 min) to give the title compound (20.8 mg, 41% yield, FA) as brown solid. 1H NMR (400 MHz, DMSO-$d_6$) δ 11.12-11.04 (m, 1H), 10.17 (d, J=1.6 Hz, 1H), 9.27-8.99 (m, 1H), 8.02-7.94 (m, 1H), 7.50-7.43 (m, 1H), 7.41-7.37 (m, 1H), 7.28-7.18 (m, 2H), 6.99 (d, J=8.4 Hz, 1H), 6.88 (d, J=2.0 Hz, 1H), 6.66-6.60 (m, 1H), 5.36-5.26 (m, 1H), 4.81-4.71 (m, 1H), 4.41-4.27 (m, 1H), 4.18-3.94 (m, 9H), 3.77-3.70 (m, 2H), 3.63-3.50 (m, 6H), 3.41 (t, J=6.0 Hz, 3H), 3.13 (q, J=5.6 Hz, 2H), 2.94-2.83 (m, 1H), 2.75-2.62 (m, 4H), 2.09-1.97 (m, 3H), 1.82-1.44 (m, 12H), 1.17 (d, J=16.0 Hz, 3H); LC-MS $(ESI^+)$ m/z 1048.3 $(M+H)^+$.

Example 28. Synthesis of Compound 118
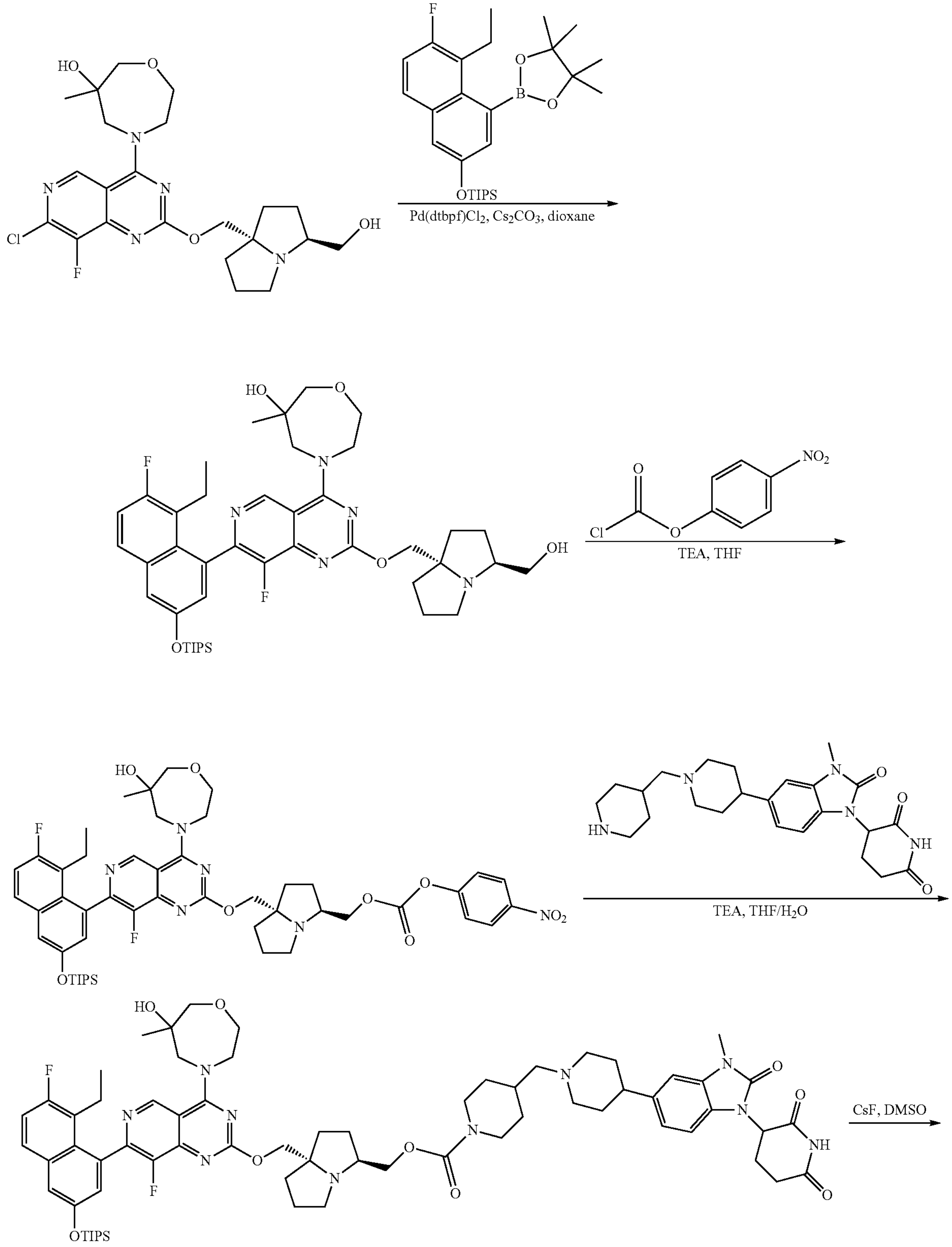

-continued

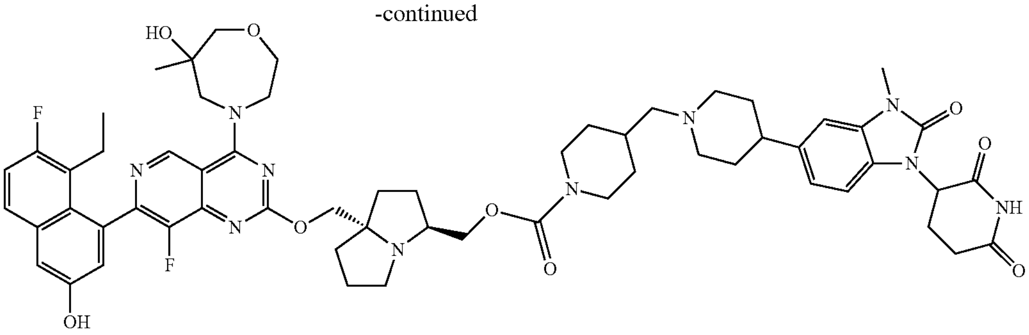

118

Step 1-4-(7-(8-Ethyl-7-fluoro-3-((triisopropylsilyl)oxy) naphthalen-1-yl)-8-fluoro-2-(((3S,7aS)-3-(hydroxymethyl) tetrahydro-1H-pyrrolizin-7a (5H)-yl) methoxy)pyrido[4,3-d]pyrimidin-4-yl)-6-methyl-1,4-oxazepan-6-ol. A mixture of 4-(7-chloro-8-fluoro-2-(((3S,7aS)-3-(hydroxymethyl)tetrahydro-1H-pyrrolizin-7a (5H)-yl) methoxy)pyrido[4,3-d] pyrimidin-4-yl)-6-methyl-1,4-oxazepan-6-ol (320 mg, 663 μmol), ((5-ethyl-6-fluoro-4-(4,4,5,5-tetramethyl-1,3,2-dioxaborolan-2-yl) naphthalen-2-yl)oxy)triisopropylsilane (470 mg, 995 μmol, CAS #2621932-48-5), $Cs_2CO_3$ (1.5 M, 1.33 mL) and ditert-butyl(cyclopentyl)phosphane; dichloropalladium; iron (43.2 mg, 66.4 μmol) in dioxane (6.5 mL) was degassed and purged with $N_2$ for 3 times, and then the mixture was stirred at 100° C. for 15 mins under $N_2$ atmosphere. On completion, the reaction mixture concentrated in vacuo to give the residue. The residue was purified by column chromatography ($SiO_2$, DCM/MeOH=1/0 to 10/1) to give the title compound (190 mg, 36% yield) as yellow solid. $^1H$ NMR (400 MHz, DMSO-$d_6$) δ 9.50 (s, 1H), 7.91 (dd, J=6.0, 9.2 Hz, 1H), 7.50 (t, J=2.0 Hz, 1H), 7.41 (t, J=9.2 Hz, 1H), 7.07 (dd, J=2.4, 12.4 Hz, 1H), 5.17 (dd, J=2.4, 18.0 Hz, 1H), 4.38-4.27 (m, 2H), 4.21-3.85 (m, 7H), 3.71-3.60 (m, 2H), 3.58-3.53 (m, 2H), 3.17 (d, J=5.2 Hz, 1H), 2.38-2.32 (m, 1H), 2.23-2.08 (m, 2H), 1.84-1.67 (m, 4H), 1.36-1.23 (m, 5H), 1.17-1.06 (m, 24H), 0.77-0.71 (m, 3H); LC-MS (ESI$^+$) m/z 792.2 $(M+H)^+$.

Step 2-((3S,7aS)-7a-(((7-(8-Ethyl-7-fluoro-3-((triisopropylsilyl)oxy) naphthalen-1-yl)-8-fluoro-4-(6-hydroxy-6-methyl-1,4-oxazepan-4-yl)pyrido[4,3-d]pyrimidin-2-yl) oxy)methyl)hexahydro-1H-pyrrolizin-3-yl)methyl (4-nitrophenyl) carbonate. To a solution of 4-(7-(8-ethyl-7-fluoro-3-((triisopropylsilyl)oxy) naphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl)-6-methyl-1,4-oxazepan-6-ol (100 mg, 126 μmol) in THF (8 mL) was added TEA (95.8 mg, 946 μmol) and a solution of (4-nitrophenyl) carbonochloridate (50.9 mg, 252 μmol, CAS #7693-46-1) in THF (2 mL). The mixture was stirred at 25° C. for 0.5 hr. On completion, the reaction mixture was concentrated in vacuo to give a residue. The residue was diluted with $H_2O$ (20 mL) and extracted with DCM (2×20 mL). The combined organic layers were washed with brine (5×50 mL), dried over anhydrous $Na_2SO_4$, filtered and the filtrate was concentrated in vacuo to give the title compound (120 mg, 99% yield) as yellow oil. LC-MS (ESI) m/z 957.5 $(M+H)^+$.

Step 3-((3S,7aS)-7a-(((7-(8-Ethyl-7-fluoro-3-((triisopropylsilyl)oxy) naphthalen-1-yl)-8-fluoro-4-(6-hydroxy-6-methyl-1,4-oxazepan-4-yl)pyrido[4,3-d]pyrimidin-2-yl) oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate. To a solution of 3-(3-methyl-2-oxo-5-(1-(piperidin-4-ylmethyl) piperidin-4-yl)-2,3-dihydro-1H-benzo[d]imidazol-1-yl) piperidine-2,6-dione (104 mg, 188 μmol, TFA salt) in THF (2 mL) and $H_2O$ (100 μL) was added TEA (38.0 mg, 376 μmol, 52.3 μL) and ((3S,7aS)-7a-(((7-(8-ethyl-7-fluoro-3-((triisopropylsilyl)oxy) naphthalen-1-yl)-8-fluoro-4-(6-hydroxy-6-methyl-1,4-oxazepan-4-yl) pyrido[4,3-d]pyrimidin-2-yl)oxy)methyl)hexahydro-1H-pyrrolizin-3-yl)methyl (4-nitrophenyl) carbonate (120 mg, 125 μmol). The mixture was stirred at 25° C. for 0.5 hr. On completion, the reaction mixture was concentrated in vacuo give a residue. The residue was purified by prep-HPLC (column: Phenomenex luna C18 150*25 mm*10 μm; mobile phase: [water (FA)-ACN]; gradient: 25%-55% B over 8 min) to give the title compound (80.0 mg, 50% yield) as yellow solid. $^1H$ NMR (400 MHz, DMSO-$d_6$) δ 11.09 (s, 1H), 10.68-10.33 (m, 1H), 9.55 (s, 1H), 8.14-8.09 (m, 1H), 7.92 (dd, J=6.0, 9.2 Hz, 1H), 7.51 (s, 1H), 7.42 (t, J=9.2 Hz, 1H), 7.14-7.01 (m, 3H), 6.96-6.88 (m, 2H), 5.35 (dd, J=5.2, 12.8 Hz, 1H), 5.22-5.11 (m, 1H), 4.70-4.45 (m, 2H), 4.44-4.12 (m, 5H), 4.09-3.82 (m, 7H), 3.61-3.54 (m, 2H), 2.93-2.75 (m, 6H), 2.68-2.61 (m, 2H), 2.41-2.25 (m, 3H), 2.20-1.71 (m, 18H), 1.31 (qd, J=7.2, 14.8 Hz, 4H), 1.17-1.06 (m, 24H), 0.79-0.70 (m, 3H); LC-MS (ESI) m/z 1257.9 $(M+H)^+$.

Step 4-((3S,7aS)-7a-(((7-(8-Ethyl-7-fluoro-3-hydroxynaphthalen-1-yl)-8-fluoro-4-(6-hydroxy-6-methyl-1,4-oxazepan-4-yl)pyrido[4,3-d]pyrimidin-2-yl)oxy)methyl) hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (Compound 118). To a solution of ((3S,7aS)-7a-(((7-(8-ethyl-7-fluoro-3-((triisopropylsilyl)oxy) naphthalen-1-yl)-8-fluoro-4-(6-hydroxy-6-methyl-1,4-oxazepan-4-yl)pyrido[4,3-d]pyrimidin-2-yl)oxy)methyl) hexahydro-1H-pyrrolizin-3-yl)methyl4-((4-(1-(2,6-dioxopiperidin-3-yl)-3-methyl-2-oxo-2,3-dihydro-1H-benzo[d] imidazol-5-yl) piperidin-1-yl)methyl) piperidine-1-carboxylate (80.0 mg, 63.6 μmol) in DMSO (0.5 mL) was added CsF (28.9 mg, 190 μmol). The mixture was stirred at 25° C. for 0.5 hr. On completion, the reaction mixture was filtered and the filtrate was concentrated in vacuo to give a residue. The residue was purified by prep-HPLC (column: Phenomenex luna C18 150*25 mm*10 μm; mobile phase: [water (FA)-ACN]; gradient: 7%-37% B over 8 min) to give the title compound (36.2 mg, 47% yield, FA salt) as white solid. $^1H$ NMR (400 MHz, DMSO-$d_6$) δ 11.09 (s, 1H), 10.15-9.75 (m, 1H), 9.56-9.41 (m, 1H), 7.76 (dd, J=6.0, 8.8 Hz, 1H), 7.38-7.30 (m, 2H), 7.08 (s, 1H), 7.05-6.96 (m, 2H), 6.90 (d, J=8.4 Hz, 1H), 5.33 (dd, J=5.2, 12.4 Hz, 1H), 5.23-5.12 (m, 1H), 4.40-4.10 (m, 7H), 4.07-3.92 (m, 5H), 3.89-3.81 (m, 1H), 3.60-3.54 (m, 2H), 2.92 (d, J=10.8 Hz, 3H), 2.86-2.58 (m, 8H), 2.39-2.32 (m, 1H), 2.18-1.92 (m, 8H), 1.81-1.63 (m, 14H), 1.56-1.49 (m, 1H), 1.15 (d, J=5.2 Hz, 3H), 1.00-0.90 (m, 2H), 0.76-0.70 (m, 3H); LC-MS ($ESI^+$) m/z 1101.4 $(M+H)^+$.
Example 29. Synthesis of Compound 116
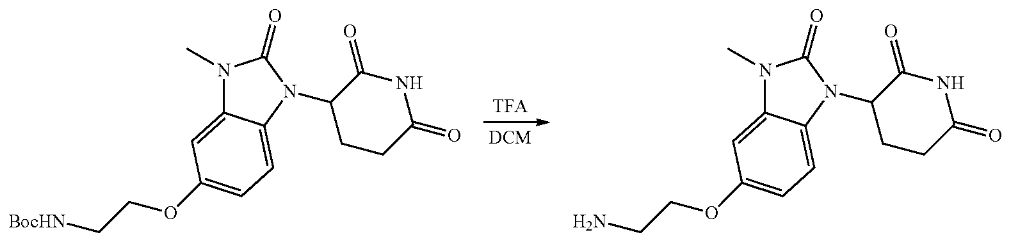
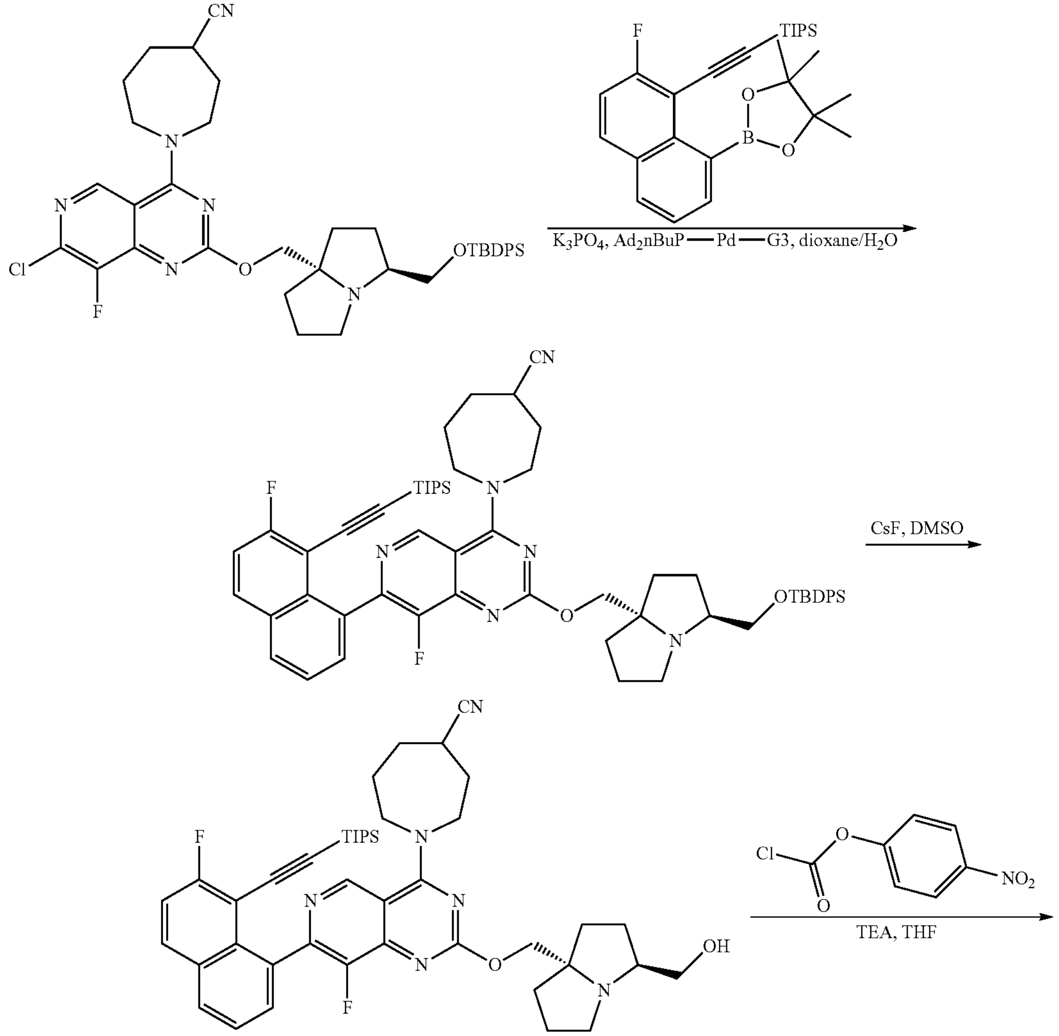

-continued

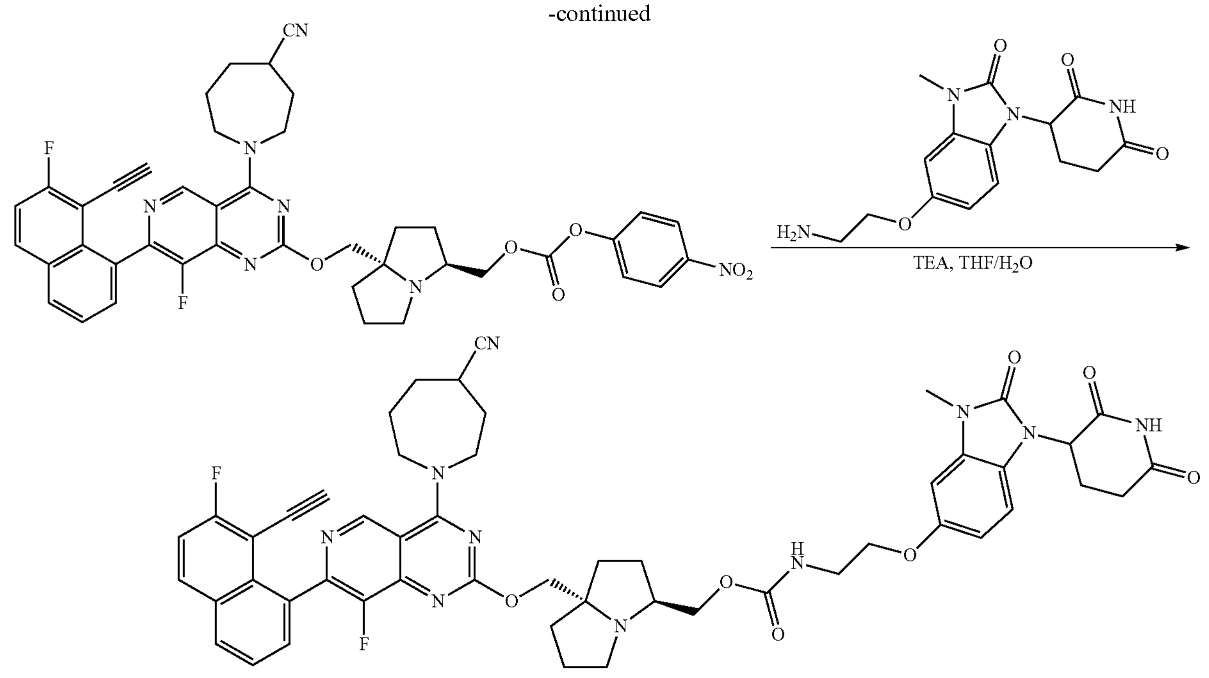

116

Step 1-3-[5-(2-Aminoethoxy)-3-methyl-2-oxo-benzimidazol-1-yl]piperidine-2,6-dione. To a solution of tert-butyl N-[2-[1-(2,6-dioxo-3-piperidyl)-3-methyl-2-oxo-benzimidazol-5-yl]oxyethyl]carbamate (90.0 mg, 215 μmol) in DCM (1 mL) was added TFA (767 mg, 6.73 mmol, 500 μL). The mixture was stirred at 25° C. for 0.2 hr. On completion, the reaction mixture was concentrated in vacuo to give the title compound (92.0 mg, 98% yield, TFA salt) as yellow oil. LC-MS (ESI$^+$) m/z 319.0 $(M+H)^+$.

Step 2-1-(2-(((3S,7aS)-3-(((tert-butyldiphenylsilyl)oxy) methyl)tetrahydro-1H-pyrrolizin-7a (5H)-yl) methoxy)-8-fluoro-7-(7-fluoro-8-((triisopropylsilyl) ethynyl) naphthalen-1-yl)pyrido[4,3-d]pyrimidin-4-yl) azepane-4-carbonitrile. A mixture of 1-(2-(((3S,7aS)-3-(((tert-butyldiphenylsilyl)oxy)methyl)tetrahydro-1H-pyrrolizin-7a (5H)-yl) methoxy)-7-chloro-8-fluoropyrido[4,3-d]pyrimidin-4-yl) azepane-4-carbonitrile (600 mg, 841 μmol), 2-[2-fluoro-8-(4,4,5,5-tetramethyl-1,3,2-dioxaborolan-2-yl)-1-naphthyl]ethynyl-triisopropyl-silane (570 mg, 1.26 mmol, CAS #2503307-87-5), $K_3PO_4/H_2O$ (1.5 M, 1.68 mL), [2-(2-aminophenyl)phenyl]palladium (1+); bis(1-adamantyl)-butyl-phosphane; methanesulfonate (61.2 mg, 84.1 μmol) in dioxane (13 mL) was degassed and purged with $N_2$ for 3 times, and then the mixture was stirred at 80° C. for 1 hr under $N_2$ atmosphere. On completion, the mixture was diluted with $H_2O$ (20 mL), extracted with EA (3×50 mL), the organic layer was washed with brine (20 mL), dried with anhydrous $Na_2SO_4$, filtered and the filtrate was concentrated in vacuo. The residue was purified by column chromatography ($SiO_2$, DCM:MeOH=93:7) to give the title compound (800 mg, 94% yield) as brown oil. $^1H$ NMR (400 MHz, DMSO-$d_6$) δ 9.19-9.12 (m, 1H), 8.26-8.17 (m, 3H), 7.67-7.60 (m, 8H), 7.45 (d, J=1.6 Hz, 4H), 4.09-4.05 (m, 2H), 3.92-3.89 (m, 1H), 3.78-3.74 (m, 1H), 3.22-3.16 (m, 2H), 3.15-3.07 (m, 2H), 2.75-2.69 (m, 2H), 2.31-2.27 (m, 1H), 2.23-2.19 (m, 1H), 2.10-2.02 (m, 4H), 1.92-1.88 (m, 2H), 1.78-1.65 (m, 8H), 1.00 (d, J=4.8 Hz, 9H), 0.91-0.89 (m, 3H), 0.85-0.81 (m, 18H).

Step 3-1-(7-(8-Ethynyl-7-fluoronaphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl) azepane-4-carbonitrile. To a solution of 1-[8-fluoro-7-[7-fluoro-8-(2-triisopropylsilylethynyl)-1-naphthyl]-2-[[(3S, 8S)-3-[[tert-butyl(diphenyl)silyl]oxymethyl]-1,2,3,5,6,7-hexahydropyrrolizin-8-yl]methoxy]pyrido[4,3-d]pyrimidin-4-yl]azepane-4-carbonitrile (1.60 g, 1.59 mmol) in DMSO (5 mL) was added CsF (726 mg, 4.78 mmol). The mixture was stirred at 40° C. for 7 hrs. On completion, the mixture was diluted with $H_2O$ (50 mL), adjusted pH-3-4 with FA, extracted with EA (3×50 mL), then the $H_2O$ phase was adjusted pH=7-8 with $NH_3{\cdot}H_2O$, extracted with EA (3×50 mL), the organic layer was washed with brine (20 mL), dried with anhydrous $Na_2SO_4$, filtered and the filtrate was concentrated in vacuo. The residue was purified by column chromatography ($SiO_2$, DCM:MeOH=92:8) to give the title compound (282 mg, 84% yield) as white solid. $^1H$ NMR (400 MHz, DMSO-$d_6$) δ 9.12 (d, J=6.4 Hz, 1H), 8.28-8.17 (m, 2H), 7.73-7.64 (m, 2H), 7.61 (t, J=9.2 Hz, 1H), 4.96-4.49 (m, 1H), 4.26-4.08 (m, 4H), 4.04 (s, 1H), 4.02-3.94 (m, 1H), 3.91-3.83 (m, 1H), 3.69-3.62 (m, 1H), 3.59-3.49 (m, 1H), 3.29-3.26 (m, 1H), 3.23-3.18 (m, 1H), 2.93-2.89 (m, 1H), 2.72-2.70 (m, 1H), 2.32-2.25 (m, 2H), 2.14-2.02 (m, 3H), 1.97-1.86 (m, 3H), 1.85-1.60 (m, 6H). LC-MS (ESI) m/z 609.1 $(M+H)^+$.

Step 4-((3S,7aS)-7a-(((4-(4-cyanoazepan-1-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl) methyl (4-nitrophenyl) carbonate. To a solution of 1-(7-(8-ethynyl-7-fluoronaphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl) azepane-4-carbonitrile (60.0 mg, 98.5 μmol) in THF (6 mL) was added TEA (74.8 mg, 739 μmol, 102 μL), the solution of (4-nitrophenyl) carbonochloridate (39.7 mg, 197 μmol, CAS #7693-46-1) in THF (1 mL) was added into above solution. The mixture was stirred at 25° C. for 3 hrs. On completion, the mixture was concentrated in vacuo, then dissolved in DCM (10 mL), diluted with $H_2O$ (20 mL), extracted with DCM (3×10 mL), the organic layer was washed with brine (5×10 mL), dried with anhydrous $Na_2SO_4$, filtered and the filtrate was concentrated in vacuo to give the title compound (70.0 mg, 91% yield) as yellow solid. LC-MS (ESI) m/z 774.2 $(M+H)^+$.

Step 5-((3S,7aS)-7a-(((4-(4-cyanoazepan-1-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl) methyl (2-((1-(2,6-dioxopiperidin-3-yl)-3-methyl-2-oxo-2,3-dihydro-1H-benzo[d]imidazol-5-yl)oxy)ethyl) carbamate (Compound 116). To a solution of ((3S,7aS)-7a-(((4-(4-cyanoazepan-1-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl)methyl (4-nitrophenyl) carbonate and 3-[3-methyl-2-oxo-5-[1-(4-piperidylmethyl)-4-piperidyl]benzimidazol-1-yl]piperidine-2,6-dione (70.0 mg, 90.4 μmol) and 3-[5-(2-aminoethoxy)-3-methyl-2-oxo-benzimidazol-1-yl]piperidine-2,6-dione (58.6 mg, 135 μmol, TFA) in THF (2 mL) and $H_2O$ (0.5 mL) was added TEA (27.4 mg, 271 μmol, 37.7 μL). The mixture was stirred at 25° C. for 0.2 hr. On completion, the mixture was concentrated in vacuo. The residue was purified by prep-HPLC (column: Phenomenex luna C18 150*25 mm*10 μm; mobile phase: [water (FA)-ACN]; gradient: 12%-42% B over 8 min) to give the title compound (42.7 mg, 46% yield, FA) as yellow solid. $^1H$ NMR (400 MHz, DMSO-$d_6$) δ 11.09 (s, 1H), 9.13 (d, J=7.2 Hz, 1H), 8.28-8.17 (m, 2H), 7.74-7.57 (m, 3H), 7.48 (s, 1H), 6.98 (d, J=8.4 Hz, 1H), 6.87 (d, J=2.0 Hz, 1H), 6.61 (dd, J=2.0, 8.4 Hz, 1H), 5.31 (dd, J=5.2, 12.4 Hz, 1H), 4.36-4.13 (m, 4H), 4.10 (s, 2H), 4.07-4.03 (m, 1H), 3.98 (t, J=5.6 Hz, 2H), 3.90-3.81 (m, 1H), 3.32-3.26 (m, 5H), 3.21-3.12 (m, 1H), 2.96-2.80 (m, 2H), 2.71-2.55 (m, 3H), 2.32-2.23 (m, 2H), 2.17-2.06 (m, 2H), 2.05-1.40 (m, 13H); LC-MS (ESI) m/z 953.3 $(M+H)^+$.

Example 30. Synthesis of Compound 117

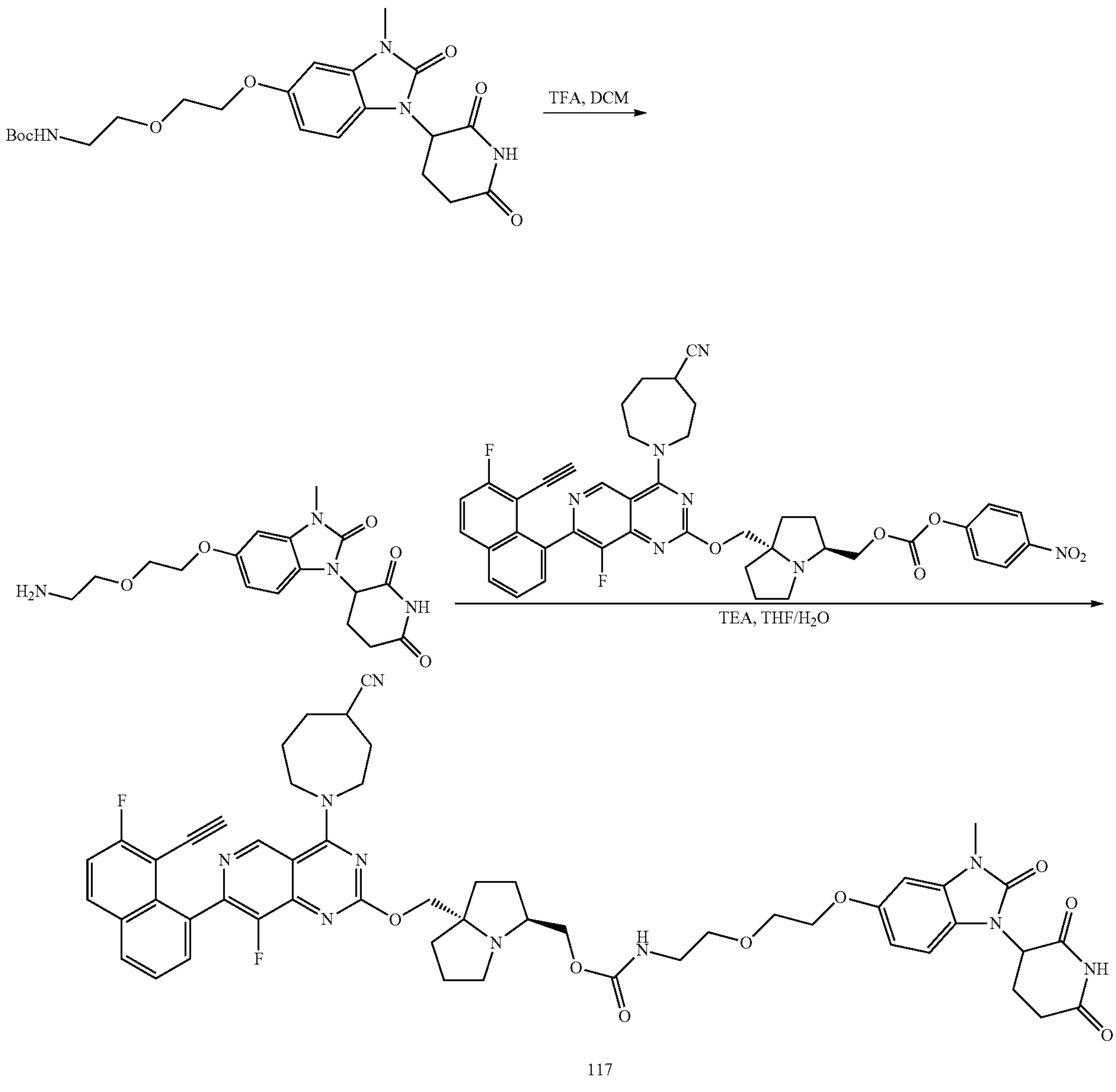

117

Step 1-3-(5-(2-(2-Aminoethoxy)ethoxy)-3-methyl-2-oxo-2,3-dihydro-1H-benzo[d]imidazol-1-yl) piperidine-2,6-dione. To a solution of tert-butyl(2-(2-((1-(2,6-dioxopiperidin-3-yl)-3-methyl-2-oxo-2,3-dihydro-1H-benzo[d]imidazol-5-yl)oxy) ethoxy)ethyl) carbamate (70.0 mg, 151 μmol) in DCM (1 mL) was added TFA (307 mg, 2.69 mmol). The mixture was stirred at 25° C. for 0.5 hr. On completion, the reaction mixture was concentrated in vacuo to give the title compound (70.0 mg, 97% yield, TFA salt) as yellow oil. LC-MS (ESI$^+$) m/z 363.0 (M+H)$^+$.

Step 2-((3S,7aS)-7a-(((4-(4-Cyanoazepan-1-yl)-7-(8-ethynyl-7-fluoronaphthalen-1-yl)-8-fluoropyrido[4,3-d]pyrimidin-2-yl)oxy)methyl)hexahydro-1H-pyrrolizin-3-yl) methyl (2-(2-((1-(2,6-dioxopiperidin-3-yl)-3-methyl-2-oxo-2,3-dihydro-1H-benzo[d]imidazol-5-yl)oxy) ethoxy)ethyl) carbamate (Compound 117). To a solution of 3-(5-(2-(2-aminoethoxy)ethoxy)-3-methyl-2-oxo-2,3-dihydro-1H-benzo[d]imidazol-1-yl) piperidine-2,6-dione (60.0 mg, 126 μmol, TFA salt) in $H_2O$ (0.6 mL) and THF (1 mL) was basified with TEA (25.5 mg, 252 μmol) to pH=7-8. And then a solution of ((3S,7aS)-7a-(((4-(4-cyanoazepan-1-yl)-7-(8-ethynyl-7-fluoronaphthalen-1-yl)-8-fluoropyrido[4,3-d]pyrimidin-2-yl)oxy)methyl)hexahydro-1-pyrrolizin-3-yl) methyl (4-nitrophenyl) carbonate (65.0 mg, 84.0 μmol) in THF (3 mL) was added to the mixture. The mixture was stirred at 25° C. for 0.5 hr $N_2$ atmosphere. On completion, the mixture was filtered and the filtrate was concentrated in vacuo to give a residue. The residue was purified by prep-HPLC (column: CD01-Phenomenex luna C18 150*25*10 μm; mobile phase: [water (FA)-ACN]; gradient: 18%-48% B over 10 min) to give the title compound (21.5 mg, 23% yield, FA salt) as yellow solid. $^1H$ NMR (400 MHz, DMSO-$d_6$) δ 11.08 (s, 1H), 9.10 (d, J=6.4 Hz, 1H), 8.27-8.16 (m, 2H), 7.75-7.53 (m, 3H), 7.27 (s, 1H), 6.98 (d, J=8.4 Hz, 1H), 6.88 (s, 1H), 6.61 (d, J=8.0 Hz, 1H), 5.31 (dd, J=5.2, 12.4 Hz, 1H), 4.18-3.95 (m, 10H), 3.90-3.82 (m, 1H), 3.75-3.68 (m, 2H), 3.47 (t, J=6.0 Hz, 2H), 3.29 (s, 3H), 3.18-3.14 (m, 2H), 2.93-2.83 (m, 1H), 2.77-2.55 (m, 5H), 2.31-2.22 (m, 2H), 2.18-1.82 (m, 7H), 1.77-1.59 (m, 6H), 1.56-1.45 (m, 1H); LC-MS (ESI$^+$) m/z 997.2 (M+H)$^+$.

Example 32. Synthesis of Compound 120

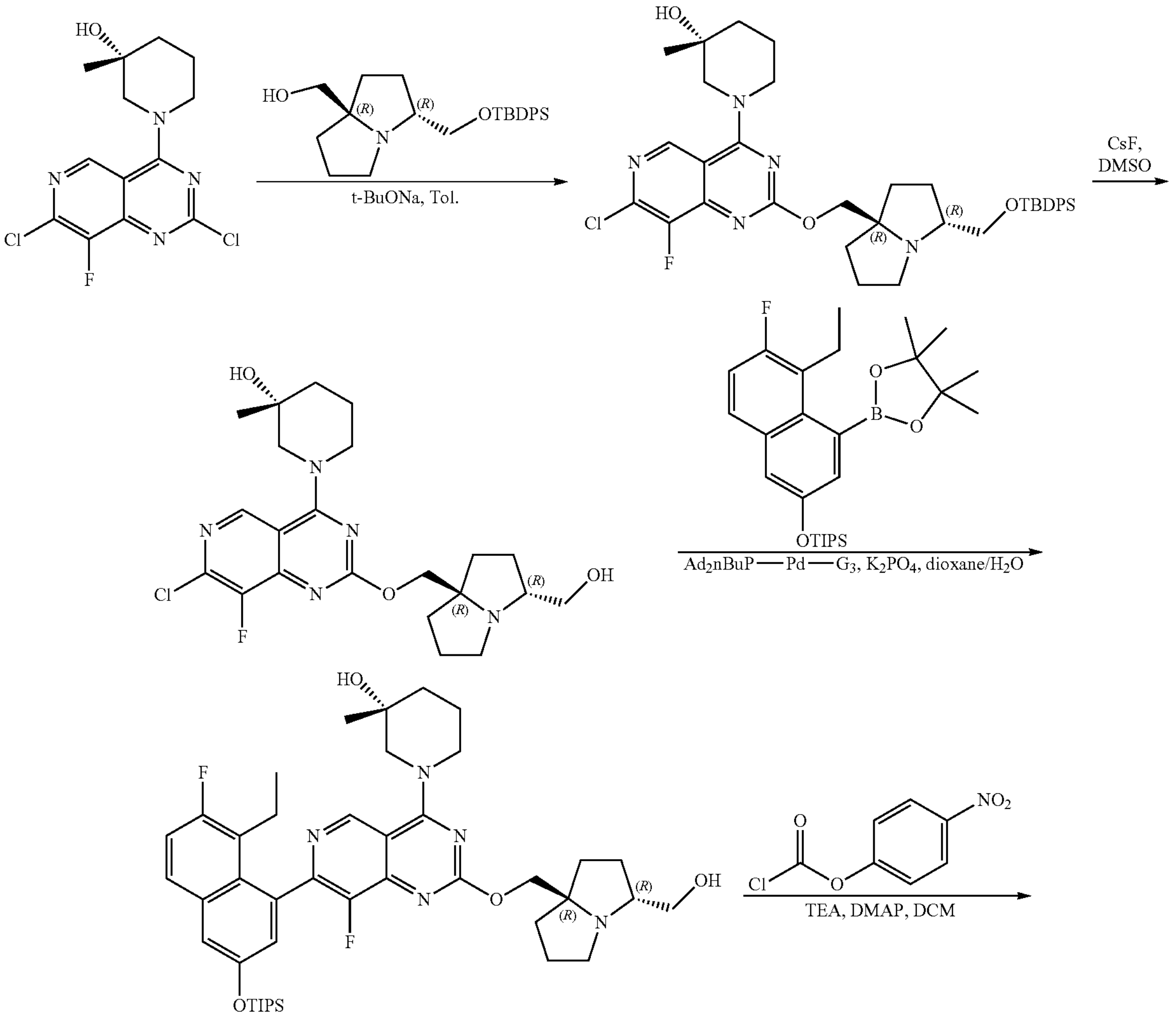

-continued

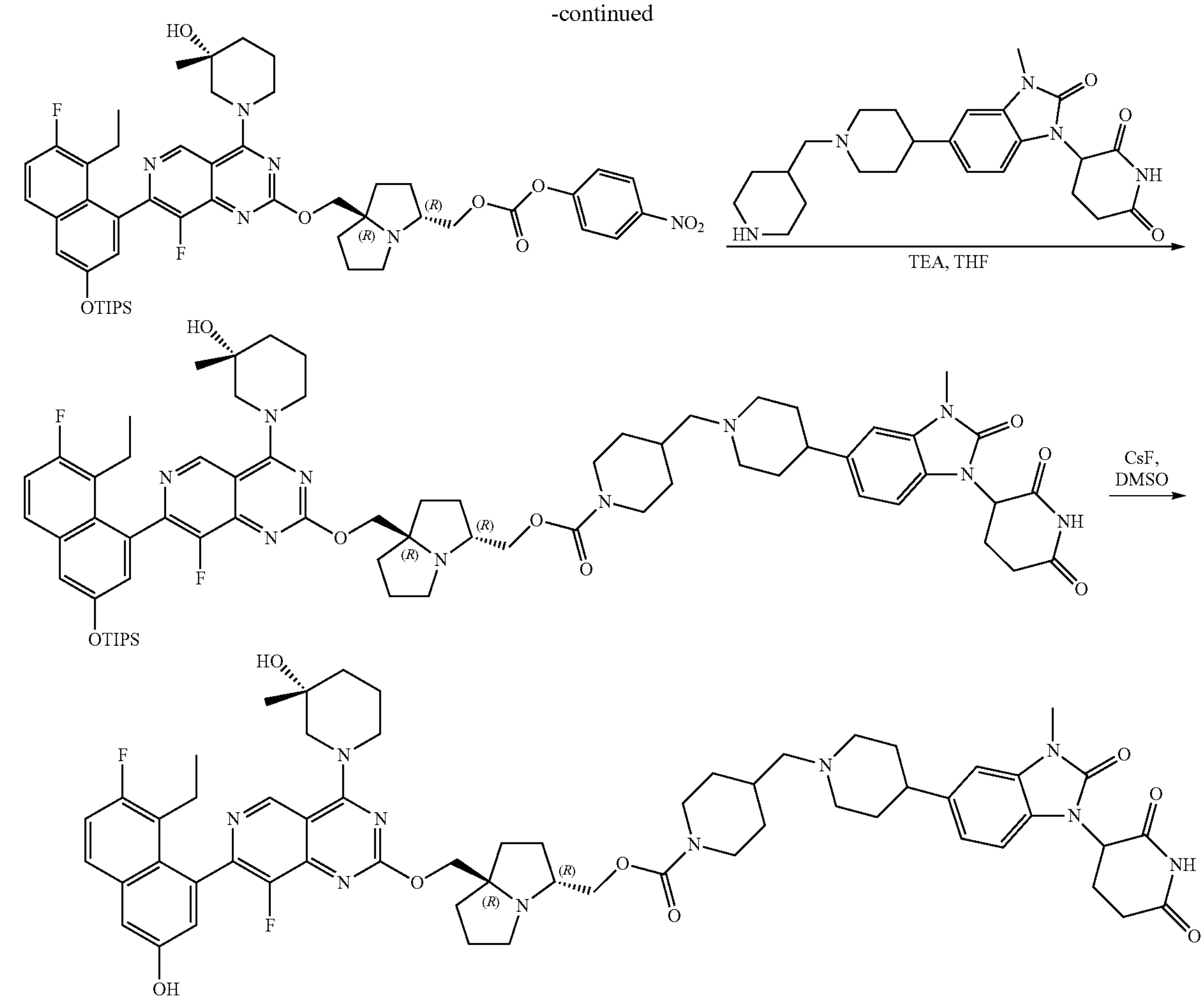

120

Step 1-(R)-1-(2-(((3R,7aR)-3-(((Tert-butyldiphenylsilyl)oxy)methyl)tetrahydro-1H-pyrrolizin-7a (5H)-yl)methoxy)-7-chloro-8-fluoropyrido[4,3-d]pyrimidin-4-yl)-3-methylpiperidin-3-ol. To a solution of ((3R,7aR)-3-(((tert-butyldiphenylsilyl)oxy)methyl)tetrahydro-1H-pyrrolizin-7a (5H)-yl) methanol (1.24 g, 3.02 mmol, CAS #2763159-60-8) in toluene (10 mL) was added t-BuONa (580 mg, 6.04 mmol) stirred at 0° C. for 0.5 hr, then (R)-1-(2,7-dichloro-8-fluoropyrido[4,3-d]pyrimidin-4-yl)-3-methylpiperidin-3-ol (1.00 g, 3.02 mmol) was added, the reaction mixture was stirred at 25° C. for 1 hr. On completion, the residue was diluted with water (30 mL), then the residue was extracted with EA (3×50 mL). The combined organic layers was dried over $Na_2SO_4$, filtered and the filtrate was concentrated in vacuo to give a residue. The residue was purified by reverse phase (0.1% FA condition) to give the title compound (1.60 g, 75% yield) as white solid. $^1$H NMR (400 MHz, DMSO-$d_6$) δ 9.02 (s, 1H), 7.67-7.58 (m, 4H), 7.49-7.41 (m, 6H), 4.87-4.47 (m, 1H), 4.36 (d, J=13.2 Hz, 1H), 4.19-4.07 (m, 2H), 4.00 (d, J=13.6 Hz, 1H), 3.87 (dd, J=6.0, 10.4 Hz, 1H), 3.76 (dd, J=6.0, 10.4 Hz, 1H), 3.51 (s, 1H), 3.26 (d, J=10.4 Hz, 2H), 2.81-2.70 (m, 2H), 2.08-1.93 (m, 2H), 1.84-1.54 (m, 10H), 1.16-1.11 (m, 3H), 1.00 (s, 9H); LC-MS (ESI$^+$) m/z 704.3 (M+H)$^+$.

Step 2-(R)-1-(7-Chloro-8-fluoro-2-(((3R,7aR)-3-(hydroxymethyl)tetrahydro-1H-pyrrolizin-7a (5H)-yl)methoxy)pyrido[4,3-d]pyrimidin-4-yl)-3-methylpiperidin-3-ol. To a solution of (R)-1-(2-(((3R,7aR)-3-(((tert-butyldiphenylsilyl)oxy)methyl)tetrahydro-1H-pyrrolizin-7a (5H)-yl) methoxy)-7-chloro-8-fluoropyrido[4,3-d]pyrimidin-4-yl)-3-methylpiperidin-3-ol (1.50 g, 2.13 mmol) in DMSO (15 mL) was added CsF (970 mg, 6.39 mmol), the reaction mixture was stirred at 50° C. for 1 hr. On completion, the residue was diluted with water (30 mL), then the residue was extracted with EA (30 mL). Then the aqueous phase was added TEA (0.5 mL), then the residue was extracted with EA (2×30 mL), the combined organic layers was dried over $Na_2SO_4$, filtered and the filtrate was concentrated in vacuo to give the title compound (0.70 g, 70% yield) as white solid. $^1$H NMR (400 MHz, DMSO-$d_6$) δ 9.01 (s, 1H), 4.65 (s, 1H), 4.56 (t, J=5.2 Hz, 1H), 4.35 (d, J=12.8 Hz, 1H), 4.12-4.05 (m, 1H), 4.04-3.98 (m, 2H), 3.68-3.61 (m, 1H), 3.57-3.45 (m, 2H), 3.27-3.21 (m, 1H), 3.09-3.00 (m, 1H), 2.78-2.72 (m, 1H), 2.70-2.63 (m, 1H), 2.04-1.99 (m, 1H), 1.75-1.52 (m, 10H), 1.51-1.41 (m, 1H), 1.14 (s, 3H); LC-MS (ESI) m/z 466.1 (M+H)$^+$.

Step 3-(R)-1-(7-(8-Ethyl-7-fluoro-3-((triisopropylsilyl)oxy) naphthalen-1-yl)-8-fluoro-2-(((3R,7aR)-3-(hydroxymethyl)tetrahydro-1H-pyrrolizin-7a (5H)-yl) methoxy)pyrido[4,3-d]pyrimidin-4-yl)-3-methylpiperidin-3-ol. To a mixture of (R)-1-(7-chloro-8-fluoro-2-(((3R,7aR)-3-(hydroxymethyl)tetrahydro-1H-pyrrolizin-7a (5H)-yl) methoxy)pyrido [4,3-d]pyrimidin-4-yl)-3-methylpiperidin-3-ol (0.60 g, 1.29 mmol) in dioxane (10 mL) and $H_2O$ (2 mL) was added [2-(2-aminophenyl)phenyl]palladium (1+); bis(1-adamantyl)-butyl-phosphane; methanesulfonate (93.7 mg, 128 μmol), then [5-ethyl-6-fluoro-4-(4,4,5,5-tetramethyl-1,3,2-dioxaborolan-2-yl)-2-naphthyl]oxy-triisopropyl-silane (730 mg, 1.55 mmol) and $K_3PO_4$ (820 mg, 3.86 mmol) was added, the reaction mixture was stirred at 100° C. for 0.1 hr under $N_2$. On completion, the residue was diluted with water (30 mL), then the residue was extracted with EA (3×50 mL). The combined organic layers was dried over $Na_2SO_4$, filtered and the filtrate was concentrated in vacuo to give a residue. The residue was purified by reverse phase (0.1% FA condition) to give the title compound (170 mg, 17% yield) as brown solid. LC-MS (ESI) m/z 776.5 $(M+H)^+$.

Step 4-((3R,7aR)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate. To a solution of (R)-1-(7-(8-Ethyl-7-fluoro-3-((triisopropylsilyl)oxy) naphthalen-1-yl)-8-fluoro-2-(((3R,7aR)-3-(hydroxymethyl)tetrahydro-1H-pyrrolizin-7a (5H)-yl) methoxy)pyrido[4,3-d]pyrimidin-4-yl)-3-methylpiperidin-3-ol (60.0 mg, 77.3 μmol) in DCM (2 mL) was added TEA (23.4 mg, 231 μmol, 32.2 μL) and DMAP (944 μg, 7.73 μmol) and (4-nitrophenyl) carbonochloridate (46.7 mg, 231 μmol, CAS #7693-46-1). The mixture was stirred at 25° C. for 2 hrs. On completion, the residue was diluted with water (30 mL), then the residue was extracted with DCM (3×30 mL). The combined organic layers was dried over $Na_2SO_4$, filtered and the filtrate was concentrated in vacuo to give the title compound (70.0 mg, 96% yield) as yellow solid. LC-MS (ESI) m/z 941.5 $(M+H)^+$.

Step 5-((3R,7aR)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazole-5-yl) piperidin-1-yl)methyl) piperidine-1-carboxylate. To a solution of 3-[3-methyl-2-oxo-5-[1-(4-piperidylmethyl)-4-piperidyl]benzimidazol-1-yl]piperidine-2,6-dione (61.7 mg, 111 μmol, TFA) in THF (1 mL) was added TEA (22.5 mg, 223 μmol, 31.0 μL) and ((3R,7aR)-7a-(((7-(8-Ethyl-7-fluoro-3-((triisopropylsilyl)oxy) naphthalen-1-yl)-8-fluoro-4-((R)-3-hydroxyl-3-methylpiperidin-1-yl)pyrido[4,3-d]pyrimidin-2-yl)oxy)methyl)hexahydro-1H-pyrrolizin-3-yl)methyl (4-nitrophenyl) carbonate (70.0 mg, 74.3 μmol). The mixture was stirred at 25° C. for 0.1 hr. On completion, the reaction mixture was concentrated in vacuo. The residue was purified by prep-HPLC (column: CD01-Phenomenex luna C18 150*25*10 μm; mobile phase: [water (FA)-ACN]; gradient: 30%-60% B over 10 min) to give the title compound (50.0 mg, 54% yield) as white solid. LC-MS (ESI) m/z 1241.4 $(M+H)^+$.

Step 6-((3R,7aR)-7a-(((7-(8-Ethyl-7-fluoro-3-hydroxynaphthalen-1-yl)-8-fluoro-4-((R)-3-hydroxyl-3-methylpiperidin-1-yl)pyrido[4,3-d]pyrimidin-2-yl)oxy)methyl) hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (Compound 120). To a solution of ((3R,7aR)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d] imidazole-5-yl) piperidin-1-yl)methyl) piperidine-1-carboxylate (30.0 mg, 24.1 μmol) in DMSO (1 mL) was added CsF (11.0 mg, 72.4 μmol). The mixture was stirred at 50° C. for 0.2 hr. On completion, the reaction mixture was concentrated in vacuo. The residue was purified by prep-HPLC (column: CD01-Phenomenex luna C18 150*25*10 μm; mobile phase: [water (FA)-ACN]; gradient: 10%-40% B over 10 min) to give the title compound (15.0 mg, 52% yield, FA) as white solid. $^1H$ NMR (400 MHz, DMSO-$d_6$) δ 11.08 (s, 1H), 9.93 (s, 1H), 9.24 (d, J=4.0 Hz, 1H), 7.76 (dd, J=6.0, 9.2 Hz, 1H), 7.38-7.29 (m, 2H), 7.08 (s, 1H), 7.04-6.97 (m, 2H), 6.90 (d, J=7.6 Hz, 1H), 5.33 (dd, J=5.6, 12.4 Hz, 1H), 4.75 (d, J=10.0 Hz, 1H), 4.42-4.16 (m, 5H), 4.12-4.03 (m, 1H), 4.02-3.95 (m, 2H), 3.66-3.54 (m, 1H), 3.02-2.88 (m, 4H), 2.85-2.57 (m, 6H), 2.40-2.28 (m, 2H), 2.25-1.96 (m, 9H), 1.92-1.46 (m, 20H), 1.17 (d, J=9.6 Hz, 3H), 1.04-0.93 (m, 2H), 0.73 (q, J=7.2 Hz, 3H); LC-MS $(ESI^+)$ m/z 1085.3 $(M+H)^+$.

Example 33. Synthesis of Compound 121

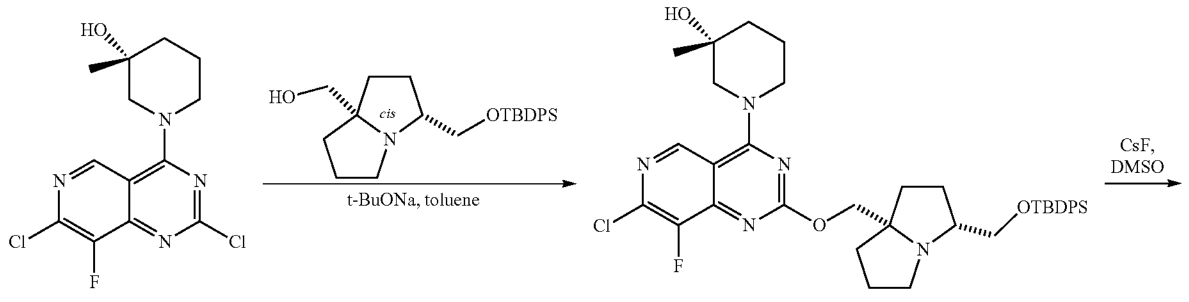

-continued
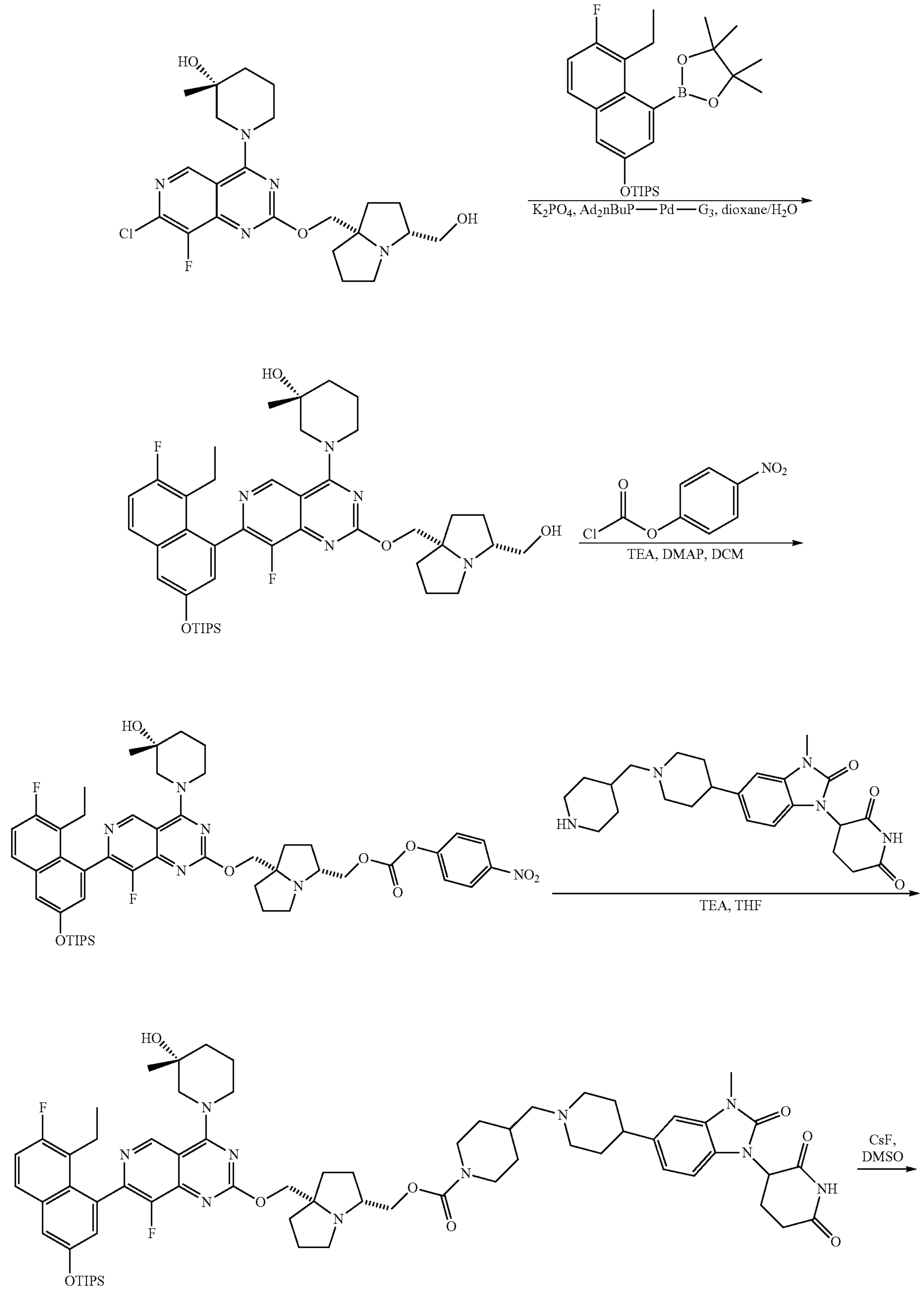

-continued

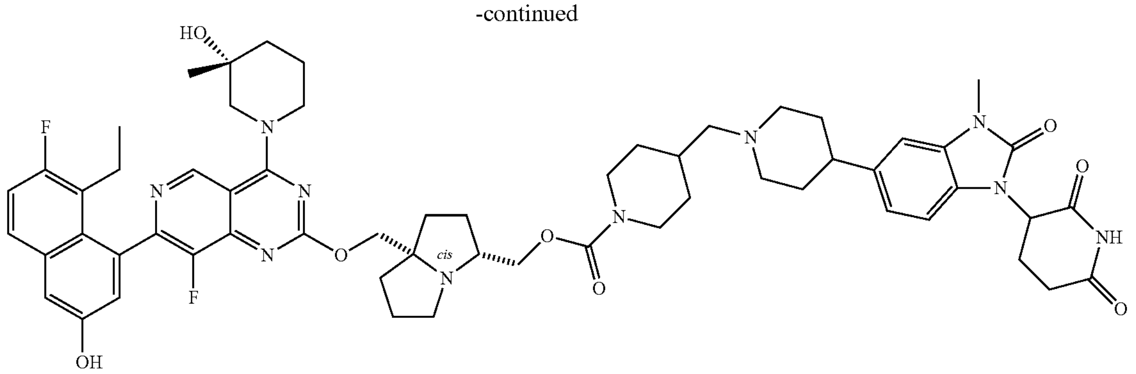

121

Step 1-(R)-1-(2-((cis -3-(((Tert-butyldiphenylsilyl)oxy) methyl)tetrahydro-1H-pyrrolizin-7a (5H)-yl) methoxy)-7-chloro-8-fluoropyrido[4,3-d]pyrimidin-4-yl)-3-methylpiperidin-3-ol. To a mixture of (cis -3-(((tert-butyldiphenylsilyl)oxy)methyl)tetrahydro-1H-pyrrolizin-7a (5H)-yl) methanol (1.61 g, 3.93 mmol) in toluene (15 mL) was added t-BuONa (754 mg, 7.85 mmol) at 0° C. for 0.5 hr, then (R)-1-(2,7-dichloro-8-fluoropyrido[4,3-d]pyrimidin-4-yl)-3-methylpiperidin-3-ol (1.30 g, 3.93 mmol) was added, the reaction mixture was stirred at 25° C. for 12 hrs. On completion, the residue was diluted with water (30 mL) and extracted with EA (2×30 mL). The combined organic layers were dried over $Na_2SO_4$, filtered and the filtrate was concentrated in vacuo to give a residue. The residue was purified by reverse phase (0.1% FA condition) to give the title compound (0.91 g, 32% yield) as yellow solid. $^1$H NMR (400 MHz, DMSO-$d_6$) δ 9.14-8.95 (m, 1H), 7.69 (s, 2H), 7.65 (d, J=6.8 Hz, 2H), 7.47 (d, J=7.2 Hz, 6H), 5.69-5.61 (m, 1H), 4.67-4.63 (m, 1H), 4.60-4.51 (m, 1H), 4.43-4.24 (m, 1H), 2.29-2.03 (m, 6H), 1.95-1.56 (m, 10H), 1.20-1.10 (m, 4H), 1.02 (s, 12H).

Step 2-(R)-1-(7-Chloro-8-fluoro-2-((cis -3-(hydroxymethyl)tetrahydro-1H-pyrrolizin-7a (5H)-yl) methoxy)pyrido [4,3-d]pyrimidin-4-yl)-3-methylpiperidin-3-ol. To a mixture of (R)-1-(2-((cis -3-(((tert-butyldiphenylsilyl)oxy)methyl) tetrahydro-1H-pyrrolizin-7a (5H)-yl) methoxy)-7-chloro-8-fluoropyrido[4,3-d]pyrimidin-4-yl)-3-methylpiperidin-3-ol (0.86 g, 1.22 mmol) in DMSO (10 mL) was added CsF (741 mg, 4.88 mmol), the reaction mixture was stirred at 25° C. for 12 hrs. On completion, the residue was diluted with water (10 mL) and extracted with EA (2×10 mL). The combined organic layers was dried over $Na_2SO_4$, filtered and the filtrate was concentrated in vacuo to give a residue. Then the residue was added TEA (0.2 mL) until pH=8, then the mixture was extracted with EA (2×10 mL) and the combined organic layers was dried over $Na_2SO_4$, filtered and the filtrate was concentrated in vacuo to give the title compound (230 mg, 40% yield) as white solid. $^1$H NMR (400 MHz, DMSO-$d_6$) δ 9.01 (s, 1H), 4.66 (s, 1H), 4.41 (t, J=4.8 Hz, 1H), 4.35 (d, J=12.8 Hz, 1H), 4.06-4.00 (m, 2H), 3.98 (d, J=6.0 Hz, 1H), 3.53 (d, J=13.2 Hz, 1H), 3.34-3.30 (m, 1H), 3.27-3.20 (m, 2H), 2.93-2.85 (m, 1H), 2.68 (dt, J=5.2, 10.8 Hz, 2H), 1.99 (s, 2H), 1.90 (s, 1H), 1.77 (dd, J=5.2, 8.4 Hz, 2H), 1.66-1.46 (m, 6H), 1.17 (t, J=7.2 Hz, 1H), 1.13 (s, 3H).

Step 3-(R)-1-(7-(8-Ethyl-7-fluoro-3-((triisopropylsilyl) oxy) naphthalen-1-yl)-8-fluoro-2-((cis -3-(hydroxymethyl) tetrahydro-1H-pyrrolizin-7a (5H)-yl) methoxy)pyrido[4,3-d]pyrimidin-4-yl)-3-methylpiperidin-3-ol. To a mixture of (R)-1-(7-chloro-8-fluoro-2-((cis -3-(hydroxymethyl)tetrahydro-1H-pyrrolizin-7a (5H)-yl) methoxy)pyrido[4,3-d]pyrimidin-4-yl)-3-methylpiperidin-3-ol (180 mg, 386 μmol) and ((5-ethyl-6-fluoro-4-(4,4,5,5-tetramethyl-1,3,2-dioxaborolan-2-yl) naphthalen-2-yl)oxy)triisopropylsilane (273 mg, 579 μmol, CAS #2621932-48-5) in dioxane (2 mL) and $H_2O$ (0.4 mL) was added $K_3PO_4$ (246 mg, 1.16 mmol) and [2-(2-aminophenyl)phenyl]palladium (1+); bis(1-adamantyl)-butyl-phosphane; methanesulfonate (28.1 mg, 38.6 μmol), the reaction mixture was stirred at 100° C. for 0.1 hr under $N_2$ atmosphere. On completion, the residue was diluted with water (10 mL) and extracted with EA (2×10 mL). The combined organic layers was dried over $Na_2SO_4$, filtered and the filtrate was concentrated in vacuo to give a residue. The residue was purified by reverse phase (0.1% FA condition) to give the title compound (200 mg, 66% yield) as white solid. $^1$H NMR (400 MHz, DMSO-$d_6$) δ 9.22 (s, 1H), 7.91 (dd, J=6.0, 8.8 Hz, 1H), 7.50 (d, J=2.4 Hz, 1H), 7.41 (t, J=9.6 Hz, 1H), 7.09 (d, J=1.6 Hz, 1H), 4.81-4.68 (m, 1H), 4.38-4.26 (m, 1H), 4.12-3.98 (m, 3H), 3.62 (d, J=13.6 Hz, 1H), 3.56-3.49 (m, 1H), 3.44-3.40 (m, 1H), 3.23 (dd, J=6.4, 10.4 Hz, 2H), 2.94-2.86 (m, 1H), 2.73-2.68 (m, 1H), 2.38-2.30 (m, 1H), 2.15 (dd, J=2.0, 6.8 Hz, 1H), 2.05-1.96 (m, 2H), 1.95-1.88 (m, 1H), 1.82-1.49 (m, 10H), 1.37-1.27 (m, 3H), 1.17 (d, J=7.2 Hz, 3H), 1.09 (d, J=7.6 Hz, 18H), 0.74 (q, J=7.2 Hz, 3H).

Step 4-(cis -7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate. To a mixture of (R)-1-(7-(8-ethyl-7-fluoro-3-((triisopropylsilyl)oxy) naphthalen-1-yl)-8-fluoro-2-((cis -3-(hydroxymethyl)tetrahydro-1H-pyrrolizin-7a (5H)-yl) methoxy)pyrido[4,3-d]pyrimidin-4-yl)-3-methylpiperidin-3-ol (60.0 mg, 77.3 μmol) in DCM (3 mL) was added TEA (363 mg, 3.59 mmol, 0.5 mL), DMAP (944 μg, 7.73 μmol) and (4-nitrophenyl) carbonochloridate (46.7 mg, 231 μmol, CAS #7693-46-1), the reaction mixture was stirred at 25° C. for 12 hrs. On completion, the residue was diluted with water (10 mL) and extracted with DCM (2×10 mL). The combined organic layers were dried over $Na_2SO_4$, filtered and the filtrate was concentrated in vacuo to give the title compound (75.0 mg, crude) as yellow oil. LC-MS (ESI) m/z 941.5 $(M+H)^+$.

Step 5-(cis -7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl 4-((4-(1-(2,6-dioxopiperidin-3-yl)-3-methyl-2-oxo-2,3-dihydro-1H- benzo[d]imidazol-5-yl) piperidin-1-yl)methyl) piperidine-1-carboxylate. To a mixture of 3-(3-methyl-2-oxo-5-(1-(piperidin-4-ylmethyl) piperidin-4-yl)-2,3-dihydro-1H-benzo[d]imidazol-1-yl) piperidine-2,6-dione (75.0 mg, 135 μmol) in THF (1 mL) was added TEA (363 mg, 3.59 mmol, 0.5 mL) and (cis -7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate (63.7 mg, 67.7 μmol), the reaction mixture was stirred at 25° C. for 0.5 hr. On completion, the reaction mixture was concentrated in vacuo to give a residue. The residue was purified by prep-HPLC (column: Phenomenex luna C18 150*25 mm*10 μm; mobile phase: [water (FA)-ACN]; gradient: 25%-55% B over 8 min) to give the title compound (30.0 mg, 17% yield) as white solid. LC-MS (ESI) m/z 1242.1 $(M+H)^+$.

Step 6-(cis -7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (Compound 121). To a mixture of (cis -7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (20.0 mg, 16.1 μmol) in DMSO (1 mL) was added CsF (7.34 mg, 48.3 μmol), the reaction mixture was stirred at 50° C. for 0.1 hr. On completion, the reaction mixture was filtered and the filtrate was concentrated in vacuo to give a residue. The residue was purified by prep-HPLC (column: Phenomenex luna C18 150*25 mm*10 μm; mobile phase: [water (FA)-ACN]; gradient: 11%-41% B over 10 min) to give the title compound (8.25 mg, 43% yield) as white solid. $^1H$ NMR (400 MHz, DMSO-$d_6$) δ 11.14-11.03 (m, 1H), 10.15-9.74 (m, 1H), 9.22 (d, J=2.8 Hz, 1H), 7.76 (dd, J=6.0, 8.8 Hz, 1H), 7.38-7.30 (m, 2H), 7.06 (d, J=19.6 Hz, 2H), 6.99 (d, J=8.0 Hz, 1H), 6.92-6.87 (m, 1H), 5.33 (dd, J=5.6, 12.8 Hz, 1H), 4.78-4.70 (m, 1H), 4.38-4.26 (m, 1H), 4.14-4.08 (m, 1H), 4.05-4.01 (m, 1H), 3.97 (d, J=14.4 Hz, 3H), 3.82 (dd, J=5.6, 10.8 Hz, 1H), 3.32-3.31 (m, 3H), 2.97-2.82 (m, 6H), 2.74-2.62 (m, 4H), 2.38-2.31 (m, 1H), 2.20-1.88 (m, 10H), 1.87-1.48 (m, 19H), 1.16 (d, J=8.8 Hz, 3H), 1.01-0.89 (m, 2H), 0.73 (q, J=7.2 Hz, 3H); LC-MS (ESI) m/z 1085.3 $(M+H)^+$.

Example 34. Synthesis of Compound 128

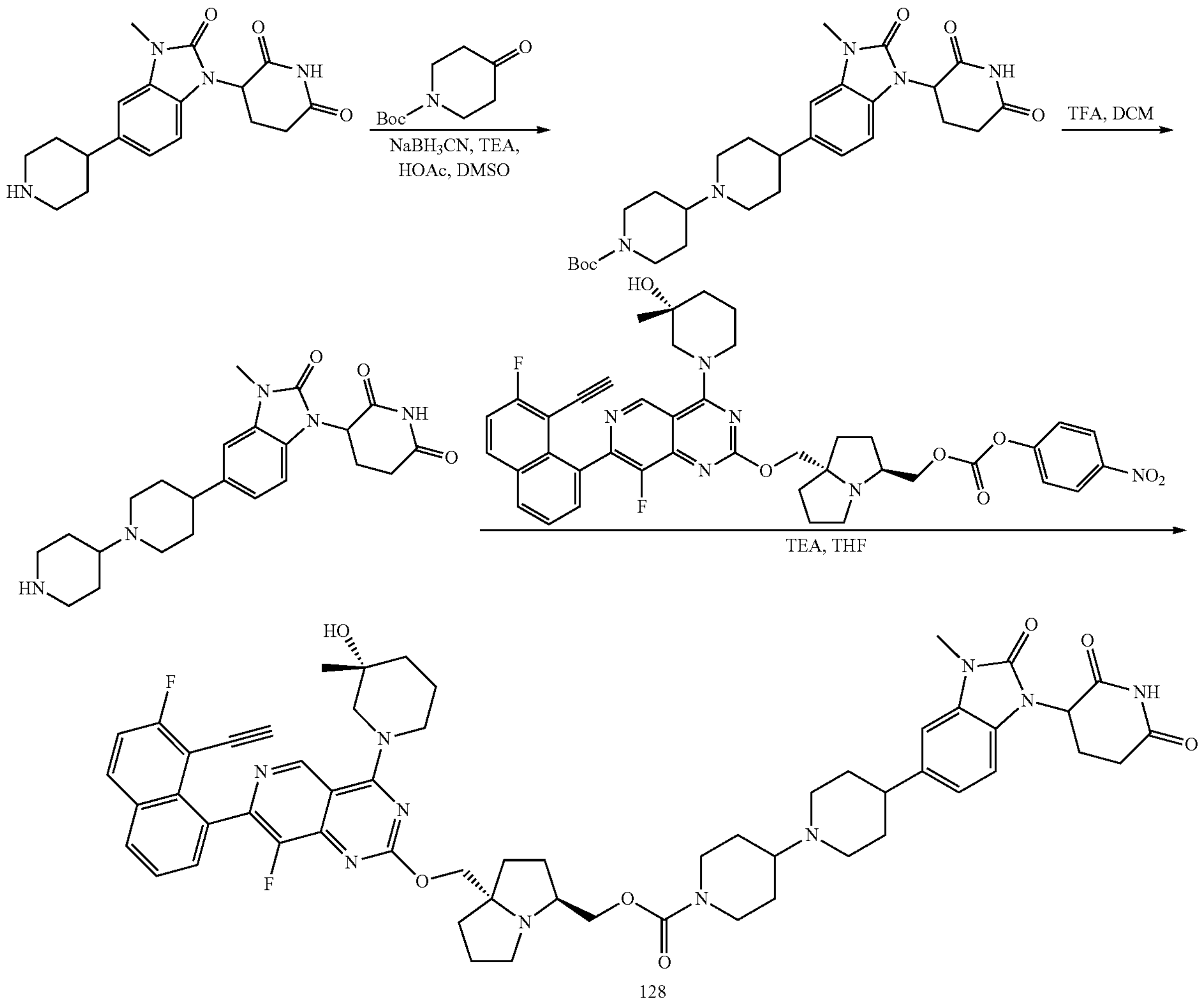

128

Step 1-Tert-butyl 4-[4-[1-(2,6-dioxo-3-piperidyl)-3-methyl-2-oxo-benzimidazol-5-yl]-1-piperidyl]piperidine-1-carboxylate. To a solution of 3-[3-methyl-2-oxo-5-(4-piperidyl)benzimidazol-1-yl]piperidine-2,6-dione (1.80 g, 5.26 mmol) in DMSO (10 mL) was added TEA (585 mg, 5.78 mmol) at 25° C. until pH stabilized at 8. The mixture was stirred at 25° C. for 0.5 hr. Then HOAc (378 mg, 6.31 mmol) was added to the solution at 25° C. until pH stabilized at 5~6. Subsequently, tert-butyl 4-oxopiperidine-1-carboxylate (1.26 g, 6.31 mmol, CAS #79099-07-3) was added and stirred at 60° C. for 3 hrs. After that, $NaBH_3CN$ (660 mg, 10.5 mmol) was added one portion at 25° C. The resulting reaction mixture was stirred at 25° C. for 1.5 hrs. On completion, the mixture was quenched with water (50 mL) and extracted with DCM (3x30 mL), the combined organic phase was dried over anhydrous sodium sulfate, filtered and the filtrate was concentrated in vacuo to give a residue. The residue was purified by reversed-phase HPLC (0.1% TFA condition) to give the title compound (2.20 g, 79% yield) as white solid. $^1H$ NMR (400 MHz, $CDCl_3$) δ 12.06-11.70 (m, 1H), 8.41 (s, 1H), 6.96-6.86 (m, 2H), 6.75 (d, J=8.0 Hz, 1H), 5.22 (dd, J=5.2, 12.8 Hz, 1H), 4.49-4.17 (m, 2H), 3.61 (d, J=11.2 Hz, 2H), 3.41 (s, 3H), 2.91-2.84 (m, 4H), 2.80-2.64 (m, 4H), 2.43-2.28 (m, 2H), 2.27-2.17 (m, 1H), 2.16-1.98 (m, 4H), 1.75-1.62 (m, 2H), 1.47 (s, 9H); LC-MS (ESI) m/z 526.5 $(M+H)^+$.

Step 2-3-[3-Methyl-2-oxo-5-[1-(4-piperidyl)-4-piperidyl]benzimidazol-1-yl]piperidine-2,6-dione. To a solution of tert-butyl 4-[4-[1-(2,6-dioxo-3-piperidyl)-3-methyl-2-oxo-benzimidazol-5-yl]-1-piperidyl]piperidine-1-carboxylate (100 mg, 190 μmol) in DCM (5 mL) was added TFA (21.6 mg, 190 μmol). The mixture was stirred at 25° C. for 1 hr. On completion, the reaction was concentrated in vacuo to give the title compound (80.0 mg, 98% yield, TFA salt) as white oil. LC-MS (ESI) m/z 426.3 $(M+H)^+$.

Step 3-((3S,7aS)-7a-(((7-(8-Ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(1-(2,6-dioxopiperidin-3-yl)-3-methyl-2-oxo-2,3-dihydro-1H-benzo[d]imidazol-5-yl)-[1,4'-bipiperidine]-1'-carboxylate (Compound 128). To a solution of 3-[3-methyl-2-oxo-5-[1-(4-piperidyl)-4-piperidyl]benzimidazol-1-yl]piperidine-2,6-dione (77.9 mg, 183 μmol) in THF (5 mL) was added TEA (64.8 mg, 640 μmol) and [(3S,8S)-8-[[7-(8-ethynyl-7-fluoro-1-naphthyl)-8-fluoro-4-[(3R)-3-hydroxy-3-methyl-1-piperidyl]pyrido[4,3-d]pyrimidin-2-yl]oxymethyl]-1,2,3,5,6,7-hexahydropyrrolizin-3-yl]methyl (4-nitrophenyl) carbonate (70.0 mg, 91.5 μmol). The mixture was stirred at 30° C. for 0.5 hr. On completion, the mixture was concentrated in vacuo to give a residue. The residue was purified by column chromatography (column: CD02-Waters Xbidge BEH C18 150*25*10 μm; mobile phase: [water ($NH_4HCO_3$)-ACN]; gradient: 34%-64% B over 10 min) to give the title compound (36.2 mg, 37% yield) as yellow solid. $^1H$ NMR (400 MHz, DMSO-$d_6$) δ 11.07 (s, 1H), 9.25-9.04 (m, 1H), 8.27-8.14 (m, 2H), 7.74-7.54 (m, 3H), 7.07 (s, 1H), 7.01-6.93 (m, 1H), 6.92-6.83 (m, 1H), 5.33 (dd, J=5.2, 12.8 Hz, 1H), 4.75 (d, J=17.6 Hz, 1H), 4.42-4.27 (m, 1H), 4.26-4.18 (m, 1H), 4.16-4.10 (m, 2H), 4.09-4.04 (m, 1H), 4.02 (s, 2H), 3.99-3.95 (m, 1H), 3.59 (t, J=13.2 Hz, 1H), 3.32 (s, 3H), 2.98-2.84 (m, 3H), 2.80-2.56 (m, 6H), 2.47-2.36 (m, 4H), 2.23 (t, J=10.4 Hz, 2H), 2.08-1.94 (m, 3H), 1.80-1.59 (m, 16H), 1.54-1.46 (m, 1H), 1.37-1.27 (m, 2H), 1.17 (d, J=14.4 Hz, 3H); LC-MS $(ESI^+)$ m/z 1051.4 $(M+H)^+$.

Example 35. Synthesis of Compound 126

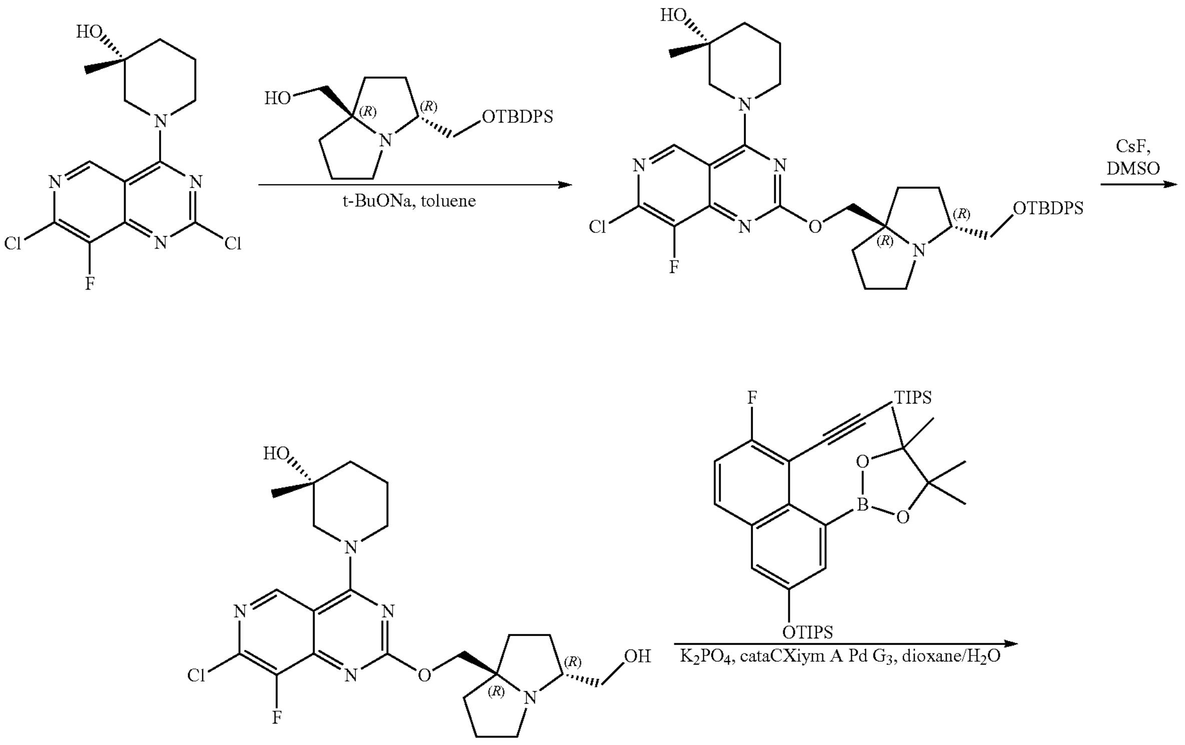

-continued

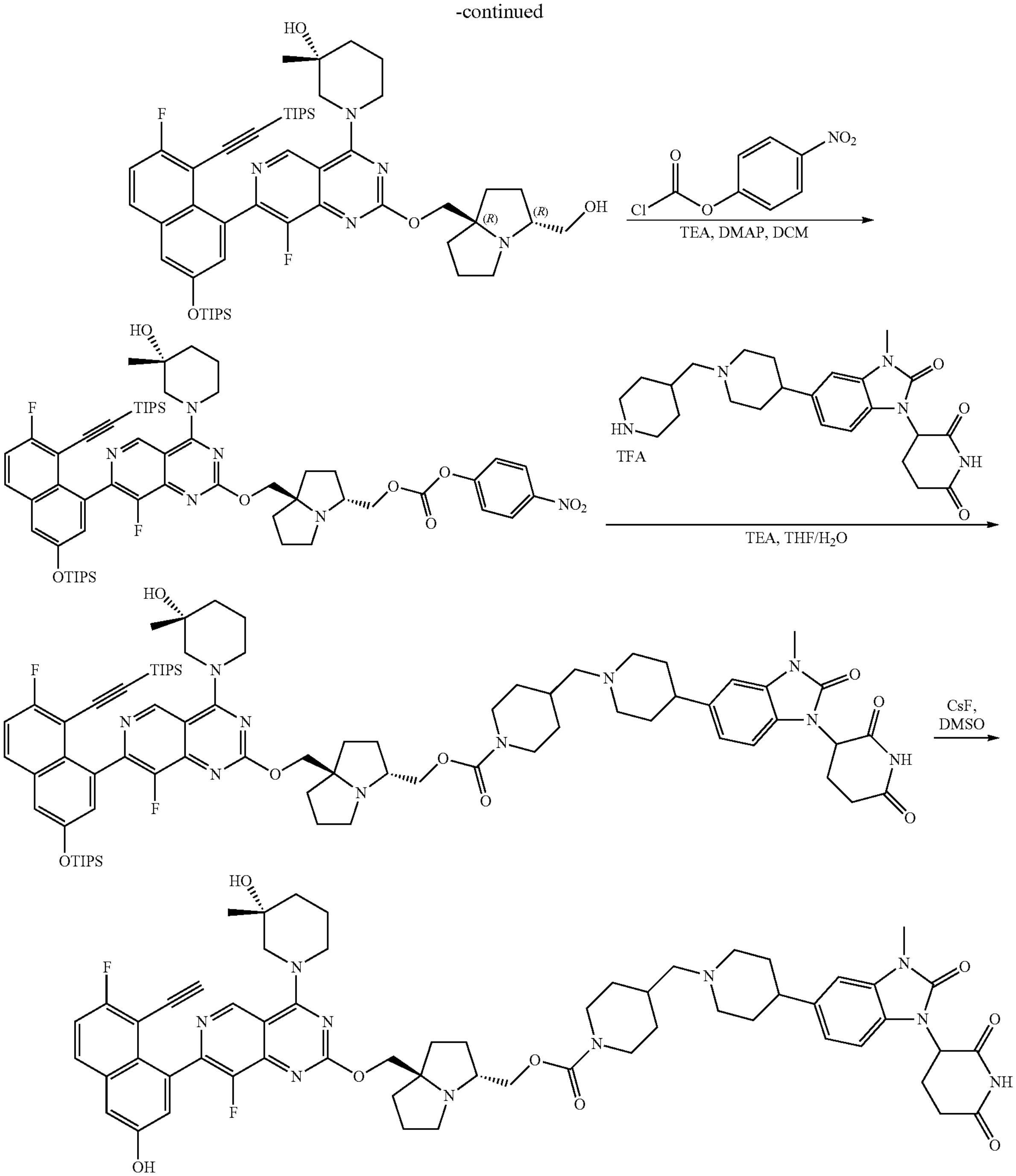

126

Step 1-(R)-1-(2-(((3R,7aR)-3-(((Tert-butyldiphenylsilyl)oxy)methyl)tetrahydro-1H-pyrrolizin-7a (5H)-yl) methoxy)-7-chloro-8-fluoropyrido[4,3-d]pyrimidin-4-yl)-3-methylpiperidin-3-ol. To a solution of ((3R,7aR)-3-(((tert-butyldiphenylsilyl)oxy)methyl)tetrahydro-1H-pyrrolizin-7a (5H)-yl) methanol (2.47 g, 6.04 mmol) in toluene (20 mL) was added t-BuONa (1.16 g, 12.1 mmol) at 0° C. The reaction mixture was stirred at 0° C. for 0.5 hr. Then (R)-1-(2,7-dichloro-8-fluoropyrido[4,3-d]pyrimidin-4-yl)-3-methylpiperidin-3-ol (2.00 g, 6.04 mmol) was added to the mixture and mixture was stirred at 0° C. for 0.5 hr. On completion, the mixture was diluted with $H_2O$ (20 mL), extracted with EA (3×20 mL), and the organic layer was washed with brine (2×100 mL). After dried over anhydrous $Na_2SO_4$, filtered and the filtrate was concentrated in vacuo to give a residue. The residue was purified by prep-HPLC (0.1% TFA condition) to give the title compound (3.37 g, 77% yield) as white solid. $^1H$ NMR (400 MHz, DMSO-$d_6$) δ 10.24 (s, 1H), 7.69-7.62 (m, 4H), 7.53-7.44 (m, 6H), 4.66-4.61 (m, 1H), 4.57-4.51 (m, 1H), 4.45 (d, J=13.2 Hz, 1H), 4.07 (d, J=13.2 Hz, 1H), 3.98-3.90 (m, 3H), 3.56 (d, J=13.2 Hz, 1H), 3.47-3.39 (m, 1H), 3.26 (t, J=11.2 Hz, 1H), 2.34-2.26 (m, 1H), 2.24-1.84 (m, 9H), 1.75-1.59 (m, 3H), 1.15 (s, 3H), 1.04 (s, 9H); LC-MS (ESI) m/z 704.5 $(M+H)^+$.

Step 2-(R)-1-(7-Chloro-8-fluoro-2-(((3R,7aR)-3-(hydroxymethyl)tetrahydro-1H-pyrrolizin-7a (5H)-yl) methoxy)pyrido[4,3-d]pyrimidin-4-yl)-3-methylpiperidin-3-ol. To a solution of (R)-1-(2-(((3R,7aR)-3-(((tert-butyldiphenylsilyl)oxy)methyl)tetrahydro-1H-pyrrolizin-7a (5H)-yl) methoxy)-7-chloro-8-fluoropyrido[4,3-d]pyrimidin-4-yl)-3-methylpiperidin-3-ol (2.00 g, 2.84 mmol) in DMSO (5 mL) was added CsF (1.29 g, 8.52 mmol). The mixture was stirred at 50° C. for 16 hrs. On completion, the mixture was diluted with $H_2O$ (20 mL), extracted with EA (2×50 mL), and then the water phase was basified pH=8 with TEA. The water phase was extracted with EA (2×50 mL), then the organic layer was washed with brine (2×50 mL). After dried over anhydrous $Na_2SO_4$, filtered and the filtrate was concentrated in vacuo to give the title compound (1.14 g, 80% yield) as yellow solid. $^1H$ NMR (400 MHz, DMSO-$d_6$) δ 9.01 (s, 1H), 4.59 (s, 1H), 4.35 (d, J=13.2 Hz, 1H), 4.14-4.08 (m, 1H), 3.69-3.61 (m, 1H), 3.54 (d, J=13.2 Hz, 1H), 3.50-3.46 (m, 1H), 3.29-3.22 (m, 2H), 3.10-3.03 (m, 1H), 2.77 (s, 1H), 2.71-2.64 (m, 1H), 2.06-2.00 (m, 1H), 1.98-1.89 (m, 1H), 1.76-1.42 (m, 12H), 1.14 (s, 3H); LC-MS (ESI) m/z 466.2 $(M+H)^+$.

Step 3-(R)-1-(8-Fluoro-7-(7-fluoro-8-((triisopropylsilyl) ethynyl)-3-((triisopropylsilyl)oxy) naphtha-len-1-yl)-2-(((3R,7aR)-3-(hydroxymethyl)tetrahydro-1H-pyrrolizin-7a (5H)-yl) methoxy)pyrido[4,3-d]pyrimidin-4-yl)-3-methylpiperidin-3-ol. A mixture of (R)-1-(7-chloro-8-fluoro-2-(((3R,7aR)-3-(hydroxymethyl)tetrahydro-1H-pyrrolizin-7a (5H)-yl) methoxy)pyrido[4,3-d]pyrimidin-4-yl)-3-methylpiperidin-3-ol (1.00 g, 2.15 mmol), ((6-fluoro-4-(4,4,5,5-tetramethyl-1,3,2-dioxaborolan-2-yl)-5-((triisopropylsilyl) ethynyl) naphthalen-2-yl)oxy) triisopropylsilane (2.01 g, 3.22 mmol, CAS #2791277-41-1), cataCXium A Pd G3 (156 mg, 215 μmol), $K_3PO_4$ (1.37 g, 6.44 mmol) in dioxane (10 mL) and $H_2O$ (2 mL) was degassed and purged with $N_2$ for 3 times, and then the mixture was stirred at 100° C. for 0.5 hr under $N_2$ atmosphere. On completion, the mixture was concentrated in vacuo to give a residue. The residue was purified by column chromatography ($SiO_2$, DCM/MeOH=100/1 to 10/1) to give the title compound (670 mg, 33% yield) as yellow solid. $^1H$ NMR (400 MHz, DMSO-$d_6$) δ 9.36-9.11 (m, 1H), 8.12 (dd, J=6.4, 8.8 Hz, 1H), 7.59-7.49 (m, 2H), 7.19 (s, 1H), 4.60 (s, 1H), 4.07-4.00 (m, 2H), 3.71-3.60 (m, 2H), 3.57-3.46 (m, 3H), 3.26 (s, 2H), 3.13-3.03 (m, 1H), 2.84-2.76 (m, 1H), 2.67 (d, J=2.0 Hz, 1H), 2.09-1.92 (m, 3H), 1.83-1.44 (m, 12H), 1.33 (td, J=7.6, 14.8 Hz, 3H), 1.19 (s, 3H), 1.09 (d, J=7.2 Hz, 18H), 0.82 (t, J=8.4 Hz, 18H); LC-MS (ESI) m/z 928.9 $(M+H)^+$.

Step 4-((3R,7aR)-7a-(((8-Fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate. To a solution of (R)-1-(8-fluoro-7-(7-fluoro-8-((triisopropylsilyl) ethynyl)-3-((triisopropylsilyl)oxy) naphthalen-1-yl)-2-(((3R,7aR)-3-(hydroxymethyl)tetrahydro-1H-pyrrolizin-7a (5H)-yl) methoxy)pyrido[4,3-d]pyrimidin-4-yl)-3-methylpiperidin-3-ol (100 mg, 108 μmol) in DCM (6 mL) was added DMAP (1.32 mg, 10.8 μmol) and TEA (150 μL, 1.08 mmol). Then a solution of 4-nitrophenyl carbonochloridate (65.1 mg, 323 μmol, CAS #7693-46-1) in DCM (1 mL) was added to the mixture and the mixture was stirred at 25° C. for 16 hrs. On completion, the mixture was diluted with $H_2O$ (15 mL) and DCM (20 mL), extracted with $H_2O$ (2×30 mL). The organic layer was washed with brine (3×20 mL). After dried over anhydrous $Na_2SO_4$, the mixture was concentrated in vacuo to give the title compound (100 mg, 84% yield) as yellow solid. LC-MS (ESI) m/z 1093.8 $(M+H)^+$.

Step 5-((3R,7aR)-7a-(((8-Fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl) methyl) piperidine-1-carboxylate. A solution of 3-(3-methyl-2-oxo-5-(1-(piperidin-4-ylmethyl) piperidin-4-yl)-2,3-dihydro-1H-benzo[d]imidazol-1-yl) piperidine-2,6-dione (90.0 mg, 162 μmol, TFA salt) in THF (1 mL) and $H_2O$ (0.5 mL) was basified pH=8 with TEA (79.0 μL, 569 μmol). Then a solution of ((3R,7aR)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (88.9 mg, 81.3 μmol) in THF (1 mL) was added to the mixture, and then the mixture was stirred at 25° C. for 0.5 hr. On completion, the mixture was concentrated in vacuo to give a residue. The residue was purified by prep-HPLC (column: CD04-Welch Utimate C18 150*25*7 μm; mobile phase: [water (FA)-ACN]; gradient: 35%-65% B over 8 min) to give the title compound (60.0 mg, 52% yield) as white solid. $^1H$ NMR (400 MHz, DMSO-$d_6$) δ 11.09 (s, 1H), 9.43-9.23 (m, 1H), 8.18-8.10 (m, 1H), 7.60-7.50 (m, 2H), 7.19 (s, 1H), 7.09-6.98 (m, 2H), 6.91 (d, J=8.4 Hz, 1H), 5.35 (dd, J=4.8, 12.4 Hz, 1H), 4.94-4.58 (m, 2H), 4.56-3.87 (m, 9H), 3.69-3.55 (m, 2H), 3.54-3.36 (m, 4H), 3.27 (d, J=1.6 Hz, 2H), 3.16-2.77 (m, 8H), 2.77-2.61 (m, 3H), 2.30-2.21 (m, 1H), 2.17-1.85 (m, 14H), 1.85-1.59 (m, 8H), 1.37-1.29 (m, 3H), 1.23 (s, 1H), 1.21 (s, 3H), 1.09 (d, J=7.6 Hz, 18H), 0.83 (dd, J=7.6, 12.4 Hz, 18H); LC-MS $(ESI^+)$ m/z 1393.9 $(M+H)^+$.

Step 6-((3R,7aR)-7a-(((7-(8-Ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (Compound 126). To a solution of ((3R,7aR)-7a-(((8-fluoro-7-(7-fluoro-8-((triisopropylsilyl) ethynyl)-3-((triisopropylsi-lyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (60.0 mg, 43.0 μmol) in DMSO (1 mL) was added CsF (19.6 mg, 129 μmol). The mixture was stirred at 25° C. for 2 hrs. On completion, the mixture was concentrated in vacuo to give a residue. The residue was purified by prep-HPLC (column: CD04-Welch Utimate C18 150*25*7 μm; mobile phase: [water (FA)-ACN]; gradient: 5%-35% B over 8 min) to give the title compound (33.3 mg, 66% yield, FA salt) as yellow solid. $^1H$ NMR (400 MHz, DMSO-$d_6$) δ 11.11 (s, 1H), 10.33-10.03 (m, 1H), 9.24-9.03 (m, 1H), 7.97 (dd, J=6.4, 8.8 Hz, 1H), 7.45 (t, J=9.2 Hz, 1H), 7.39 (s, 1H), 7.21 (dd, J=2.4, 17.6 Hz, 1H), 7.11 (d, J=7.6 Hz, 1H), 7.06-7.01 (m, 1H), 7.01-6.95 (m, 1H), 5.38 (dd, J=5.2, 12.6 Hz, 1H), 4.81-4.70 (m, 1H), 4.40-4.28 (m, 1H), 4.25-4.19 (m, 1H), 4.13 (d, J=10.4 Hz, 2H), 4.09-3.96 (m, 2H), 3.94 (s, 1H), 3.72-3.64 (m, 4H), 3.64 (s, 3H), 3.62 (s, 1H), 3.59-3.51 (m, 4H), 3.10 (d, J=8.4 Hz, 2H), 2.90-2.85 (m, 1H), 2.80-2.67 (m, 6H), 2.67-2.55 (m, 4H), 2.09-1.98 (m, 3H), 1.89-1.57 (m, 13H), 1.54-1.45 (m, 1H), 1.41-1.32 (m, 2H), 1.16 (d, J=16.8 Hz, 3H); LC-MS $(ESI^+)$ m/z 1081.6 $(M+H)^+$.

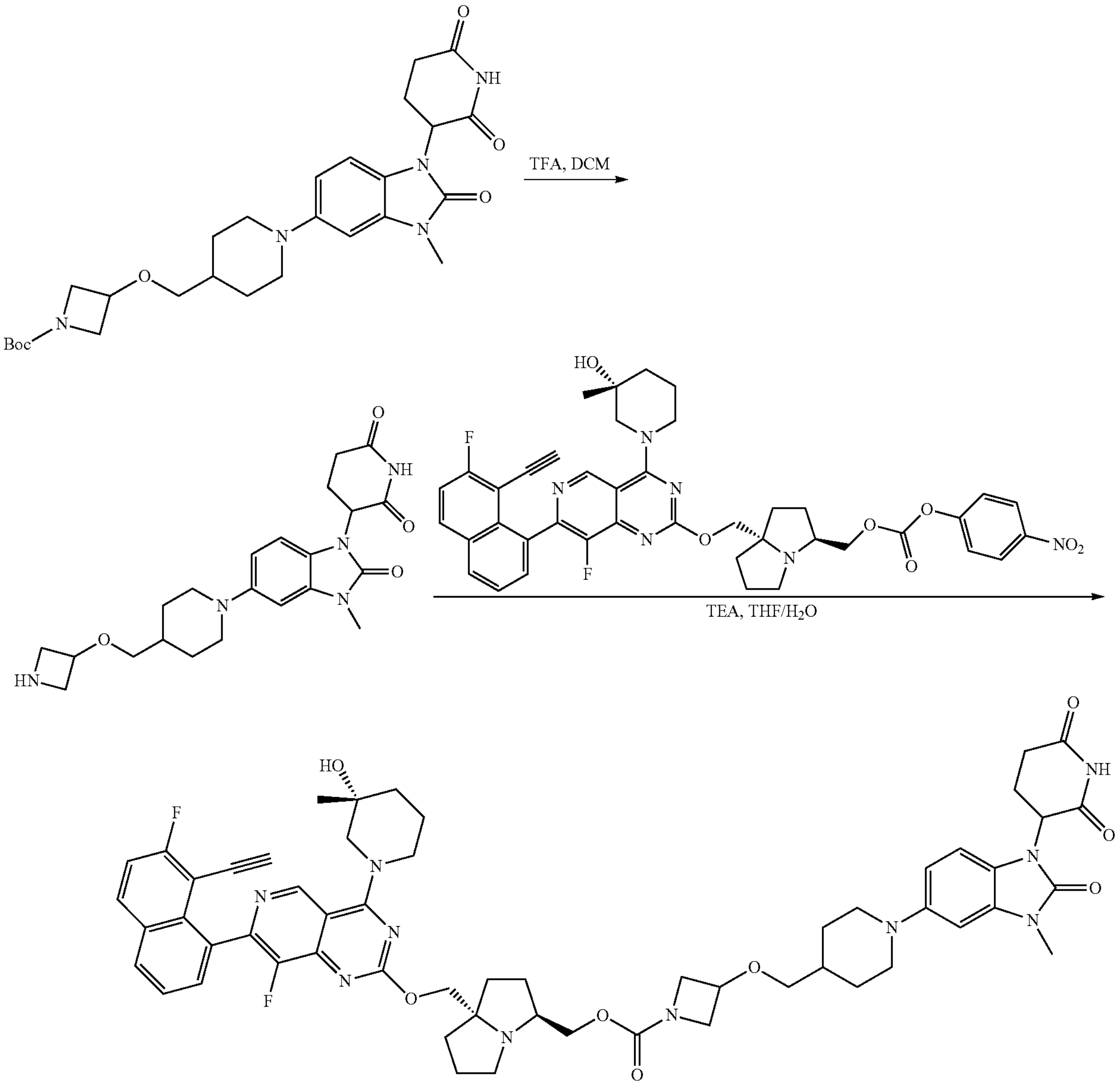

130

Step 1-3-[5-[4-(Azetidin-3-yloxymethyl)-1-piperidyl]-3-methyl-2-oxo-benzimidazol-1-yl]piperidine-2,6-dione. To a solution of tert-butyl 3-[1-[[1-(2,6-dioxo-3-piperidyl)-3-methyl-2-oxo-benzimidazol-5-yl]-4-piperidyl]methoxy]azetidine-1-carboxylate (70.0 mg, 132 μmol) in DCM (1 mL) was added TFA (307 mg, 2.69 mmol). The mixture was stirred at 25° C. for 0.5 hr. On completion, the reaction mixture was concentrated in vacuo to give the title compound (70.0 mg, 97% yield, TFA salt) as black oil; LC-MS ($ESI^+$) m/z 428.1 $(M+H)^+$.

Step 2-((3S,7aS)-7a-(((7-(8-Ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 3-((1-(1-(2,6-dioxopiperidin-3-yl)-3-methyl-2-oxo-2,3-dihydro-1H-benzo[d]imidazol-5-yl)piperidin-4-yl) methoxy) azetidine-1-carboxylate (Compound 130). To a solution of 3-[5-[4-(azetidin-3-yloxymethyl)-1-piperidyl]-3-methyl-2-oxo-benzimidazol-1-yl]piperidine-2,6-dione (63.7 mg, 117 μmol, TFA salt) in THF (1 mL) and $H_2O$ (0.5 mL) was basified pH=7-8 with TEA (23.8 mg, 235 μmol). And then a solution of ((3S,7aS)-7a-(((7-(8-ethynyl-7-fluoronaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (60.0 mg, 78.4 μmol) in THF (3 mL) was added. The mixture was stirred at 25° C. for 0.5 hr. On completion, the mixture was filtered and the filtrate was concentrated in vacuo to give a residue. The residue was purified by prep-HPLC (column: Phenomenex luna C18 150*25 mm*10 μm; mobile phase: [water (FA)-ACN]; gradient: 10%-40% B over 10 min) to give the title compound (27.6 mg, 30% yield, FA salt) yellow solid. $^1H$ NMR (400 MHz, DMSO-$d_6$) δ 11.06 (s, 1H), 9.29-9.01 (m, 1H), 8.25-8.16 (m, 2H), 7.73-7.56 (m, 3H), 6.92 (d, J=8.4 Hz, 1H), 6.81 (d, J=1.6 Hz, 1H), 6.62 (dd, J=1.6, 8.8 Hz, 1H), 5.28 (dd, J=5.6, 12.8 Hz, 1H), 4.75 (d, J=16.4 Hz, 1H), 4.41-4.30 (m, 1H), 4.28-4.17 (m, 2H), 4.15-4.05 (m, 5H), 4.04-3.94 (m, 2H), 3.71 (d, J=2.4 Hz, 2H), 3.57 (d, J=13.2 Hz, 2H), 3.29 (s, 3H), 3.23 (d, J=6.4 Hz, 2H), 2.91-2.83 (m, 1H), 2.80-2.54 (m, 8H), 2.08-1.95 (m, 3H), 1.80-1.60 (m, 13H), 1.54-1.48 (m, 1H), 1.36-1.27 (m, 2H), 1.17 (d, J=14.4 Hz, 3H); LC-MS (ESI) m/z 1053.2 $(M+H)^+$.
Example 37. Synthesis of Compound 127
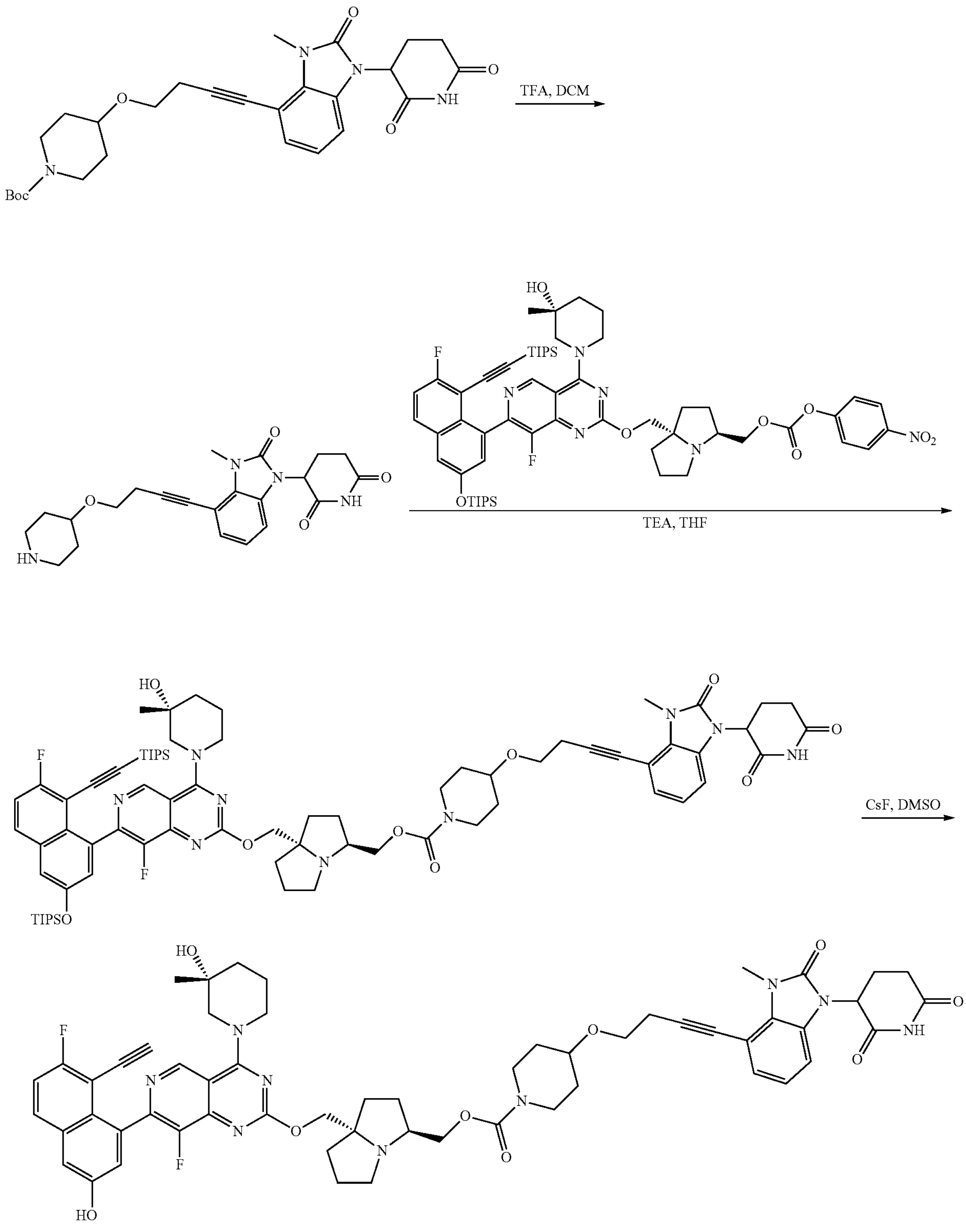
127

Step 1-3-(3-Methyl-2-oxo-4-(4-(piperidin-4-yloxy) but-1-yn-1-yl)-2,3-dihydro-1H-benzo[d]imidazol-1-yl) piperidine-2,6-dione. To a solution of tert-butyl 4-((4-(1-(2,6-dioxopiperidin-3-yl)-3-methyl-2-oxo-2,3-dihydro-1H-benzo[d]imidazol-4-yl) but-3-yn-1-yl)oxy)piperidine-1-carboxylate (70.0 mg, 137 μmol) in DCM (1 mL) was added TFA (0.5 mL, 6.73 mmol). The mixture was stirred at 25° C. for 1 hr. On completion, the mixture was concentrated in vacuo to give the title compound as (70.0 mg, 97% yield, TFA salt) yellow oil. LC-MS (ESI) m/z 411.3 $(M+H)^+$.

Step 2-((3S,7aS)-7a-(((8-Fluoro-7-(7-fluoro-8-((triisopropylsilyl) ethynyl)-3-((triisopropylsily-l)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-di-hydro-1H-benzo[d]imidazol-4-yl) but-3-yn-1-yl) oxy)piperidine-1-carboxylate. A solution of 3-(3-methyl-2-oxo-4-(4-(piperidin-4-yloxy) but-1-yn-1-yl)-2,3-dihydro-1H-benzo[d]imidazol-1-yl) piperidine-2,6-dione (70.0 mg, 133 μmol, TFA salt) in THF (1 mL) was basified to pH 8 with TEA (65 μL, 467 μmol). Then a solution of ((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate (73.0 mg, 66.7 μmol) in THF (1 mL) was added to the mixture, and then the mixture was stirred at 25° C. for 0.5 hr. On completion, the mixture was concentrated in vacuo to give a residue. The residue was purified by prep-HPLC (column: CD04-Welch Utimate C18 150*25*7 μm; mobile phase: [water (FA)-ACN]; gradient: 55%-85% B over 8 min) to give the title compound as (30.0 mg, 32% yield) white solid. $^1H$ NMR (400 MHz, DMSO-$d_6$) δ 11.11 (s, 1H), 9.41-9.10 (m, 1H), 8.16-8.10 (m, 1H), 7.59-7.51 (m, 2H), 7.19 (s, 1H), 7.11 (d, J=7.6 Hz, 1H), 7.06-6.95 (m, 2H), 5.41-5.33 (m, 1H), 4.89-4.49 (m, 2H), 4.44-4.33 (m, 1H), 4.28-4.21 (m, 1H), 4.16-3.88 (m, 3H), 3.74-3.69 (m, 1H), 3.64 (s, 6H), 3.58-3.54 (m, 1H), 3.23 (s, 2H), 3.15-3.06 (m, 2H), 2.91-2.83 (m, 1H), 2.76-2.62 (m, 5H), 2.12-1.59 (m, 16H), 1.45-1.27 (m, 6H), 1.26-1.22 (m, 1H), 1.19 (d, J=4.8 Hz, 3H), 1.09 (d, J=7.6 Hz, 18H), 1.01-0.96 (m, 2H), 0.82 (dd, J=7.6, 11.2 Hz, 18H); LC-MS (ESI) m/z 1365.4 $(M+H)^+$.

Step 3-((3S,7aS)-7a-(((7-(8-Ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((4-(1-(2,6-dioxopiperidin-3-yl)-3-methyl-2-oxo-2,3-dihydro-1H-benzo[d]imidazol-4-yl) but-3-yn-1-yl)oxy)piperidine-1-carboxylate (Compound 127). To a solution of ((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy) methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-4-yl) but-3-yn-1-yl)oxy)piperidine-1-carboxylate (30.0 mg, 22.0 μmol) in DMSO (1 mL) was added CsF (10.0 mg, 66.0 μmol). The mixture was stirred at 25° C. for 2 hrs. On completion, the mixture was concentrated in vacuo to give a residue. The residue was purified by prep-HPLC (column: CD04-Welch Utimate C18 150*25*7 μm; mobile phase: [water (FA)-ACN]; gradient: 15%-45% B over 8 min) to give the title compound (11.8 mg, 46% yield, FA salt) as yellow solid. $^1H$ NMR (400 MHz, DMSO-$d_6$) δ 11.08 (s, 1H), 10.28-10.09 (m, 1H), 9.27-9.06 (m, 1H), 7.98 (dd, J=6.0, 9.2 Hz, 1H), 7.46 (t, J=9.2 Hz, 1H), 7.39 (s, 1H), 7.21 (dd, J=2.4, 16.0 Hz, 1H), 7.07 (s, 1H), 7.00 (d, J=8.0 Hz, 1H), 6.90 (d, J=7.6 Hz, 1H), 5.33 (dd, J=5.2, 12.4 Hz, 1H), 4.81-4.70 (m, 1H), 4.44-4.28 (m, 2H), 4.23 (d, J=1.2 Hz, 2H), 4.12 (d, J=13.6 Hz, 1H), 3.99 (d, J=12.8 Hz, 2H), 3.93 (s, 1H), 3.60 (s, 1H), 3.06-2.93 (m, 4H), 2.90 (d, J=5.2 Hz, 1H), 2.82-2.76 (m, 1H), 2.72 (dd, J=4.0, 13.2 Hz, 1H), 2.68-2.63 (m, 1H), 2.59 (s, 1H), 2.34-2.22 (m, 2H), 2.20-2.07 (m, 3H), 2.04-1.96 (m, 2H), 1.92-1.81 (m, 5H), 1.79-1.59 (m, 12H), 1.17 (d, J=16.8 Hz, 3H), 1.06-0.94 (m, 2H); LC-MS (ESI) m/z 1052.5 $(M+H)^+$.

Example 38. Synthesis of Compound 209

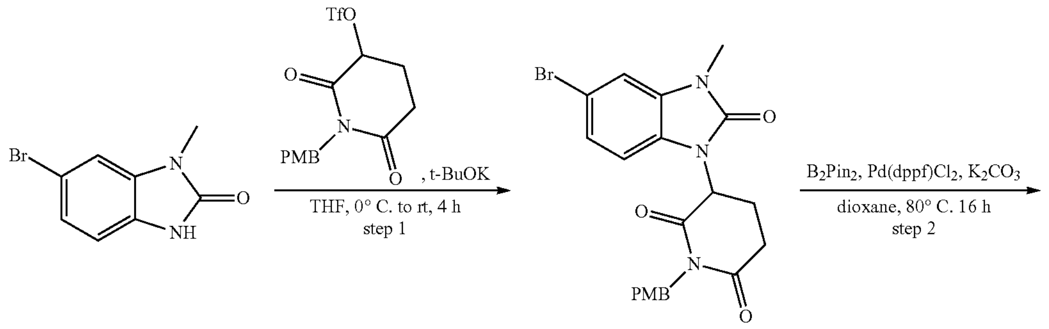

-continued
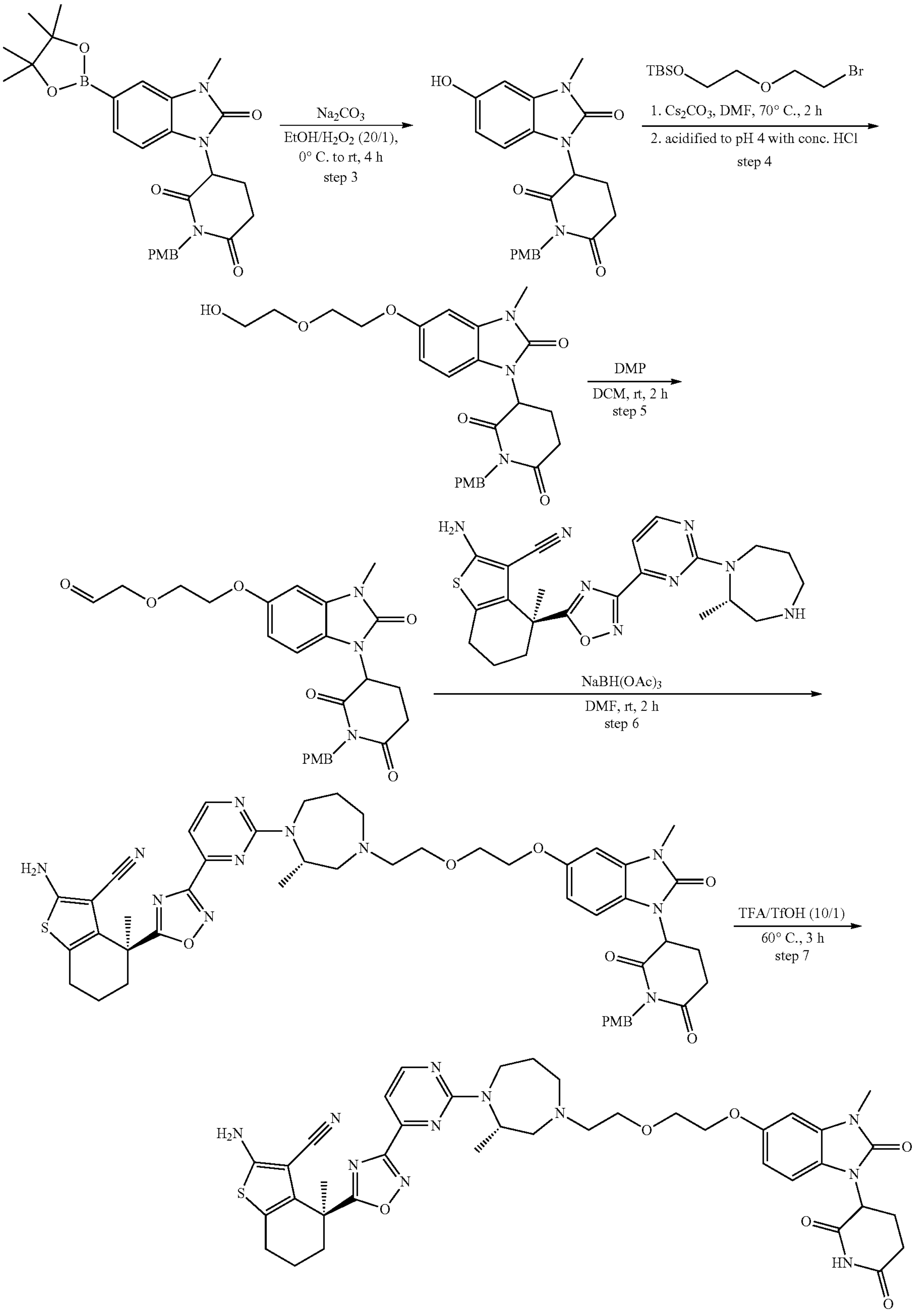

3-(5-bromo-3-methyl-2-oxo-2,3-dihydro-1H-benzo[d]imidazol-1-yl)-1-(4-methoxybenzyl) piperidine-2,6-dione: To a stirred solution of 6-bromo-1-methyl-3H-1,3-benzodiazol-2-one (20 g, 88.082 mmol) in THF (400 mL) was added t-BuOK (14.8 g, 132.123 mmol) at 0° C. under air atmosphere. The resulting mixture was stirred for 1 h at 0° C. under air atmosphere. To the above mixture was added 1-[(4-methoxyphenyl)methyl]-2,6-dioxopiperidin-3-yl trifluoromethanesulfonate (36.9 g, 96.890 mmol) in THF (300 mL) dropwise at 0° C. The resulting mixture was stirred for an additional 4 h at 0° C. Desired product could be detected by LCMS. The resulting mixture was diluted with water (500 mL). The resulting mixture was concentrated under reduced pressure. The residue was purified by trituration with water (400 mL). The precipitated solids were collected by filtration and washed with water (3×100 mL). The precipitated solids were purified by trituration with EtOAc (200 mL). The precipitated solids were collected by filtration and washed with EtOAc (3×50 mL). This resulted in 3-(5-bromo-3-methyl-2-oxo-2,3-dihydro-1H-benzo[d]imidazol-1-yl)-1-(4-methoxybenzyl) piperidine-2,6-dione (30 g, 74%) as a light blue solid. $^1$H NMR (400 MHz, DMSO-$d_6$) δ 7.48 (d, J=2.0 Hz, 1H), 7.26-7.14 (m, 3H), 7.01 (d, J=8.4 Hz, 1H), 6.86 (d, J=8.4 Hz, 2H), 5.64-5.40 (m, 1H), 4.79-4.74 (m, 2H), 3.73 (s, 3H), 3.35 (s, 3H), 3.12-2.96 (m, 1H), 2.89-2.63 (m, 2H), 2.15-1.94 (m, 1H). LC/MS (ESI, m/z): $[(M+1)]^+$=458.05 Chemical Formula: $C_{21}H_{20}BrN_3O_4$, Exact Mass: 457.06.

1-(4-methoxybenzyl)-3-(3-methyl-2-oxo-5-(4,4,5,5-tetramethyl-1,3,2-dioxaborolan-2-yl)-2,3-dihydro-1H-benzo[d]imidazol-1-yl) piperidine-2,6-dione: To a stirred solution of 3-(5-bromo-3-methyl-2-oxo-2,3-dihydro-1H-benzo[d]imidazol-1-yl)-1-(4-methoxybenzyl) piperidine-2,6-dione (30 g, 65.458 mmol) and bis(pinacolato)diboron (33.2 g, 130.916 mmol) in dioxane (600 mL) were added KOAc (12.9 g, 130.916 mmol) and Pd (dppf) $Cl_2$ (4.8 g, 6.546 mmol) at room temperature under air atmosphere. The resulting mixture was stirred for 16 h at 80° C. under nitrogen atmosphere. Desired product could be detected by LCMS. The mixture was allowed to cool down to room temperature. The resulting mixture was concentrated under reduced pressure. The residue was purified by silica gel column chromatography, eluted with $CH_2Cl_2$/MeOH (15:1) to afford 1-(4-methoxybenzyl)-3-(3-methyl-2-oxo-5-(4,4,5,5-tetramethyl-1,3,2-dioxaborolan-2-yl)-2,3-dihydro-1H-benzo[d]imidazol-1-yl) piperidine-2,6-dione (30 g, 90%) as a light brown oil. 1H NMR (400 MHz, Chloroform-d) δ 7.51-7.45 (m, 2H), 7.41-7.34 (m, 2H), 6.88-6.82 (m, 2H), 6.57 (d, J=8.0 Hz, 1H), 5.22 (dd, J=13.6, 8.0 Hz, 1H), 4.98 (q, J=13.6 Hz, 2H), 3.82 (s, 3H), 3.47 (s, 3H), 3.08-2.96 (m, 1H), 2.90-2.75 (m, 1H), 2.70-2.55 (m, 1H), 2.23-2.13 (m, 1H), 1.38 (s, 12H). LC/MS (ESI, m/z): $[(M+1)]^+$=506.35 Chemical Formula: $C_{27}H_{32}BN_3O_6$, Exact Mass: 505.24.

3-(5-Hydroxy-3-methyl-2-oxo-2,3-dihydro-1H-benzo[d]imidazol-1-yl)-1-(4-methoxybenzyl) piperidine-2,6-dione: To a stirred solution of 1-(4-methoxybenzyl)-3-(3-methyl-2-oxo-5-(4,4,5,5-tetramethyl-1,3,2-dioxaborolan-2-yl)-2,3-dihydro-1H-benzo[d]imidazol-1-yl) piperidine-2,6-dione (30 g, 59.361 mmol) and $Na_2CO_3$ (12.6 g, 118.722 mmol) in EtOH (600 mL) was added $H_2O_2$ (30.00 mL, 1287.540 mmol) dropwise at 0° C. under air atmosphere. The resulting mixture was stirred for 4 h at room temperature under air atmosphere. Desired product could be detected by LCMS. The reaction was quenched by the addition of sat. $Na_2S_2O_3$ (aq.)(50 mL) at 0° C. The resulting mixture was concentrated under reduced pressure. The residue was diluted with water (300 mL). The precipitated solids were collected by filtration and washed with water (3×50 mL). The residue was purified by trituration with EtOAc (200 mL). The precipitated solids were collected by filtration and washed with EtOAc (3×50 mL). This resulted in 3-(5-hydroxy-3-methyl-2-oxo-2,3-dihydro-1H-benzo[d]imidazol-1-yl)-1-(4-methoxybenzyl) piperidine-2,6-dione (14 g, 59%) as a white solid. $^1$H NMR (400 MHz, DMSO-$d_6$) δ 9.17 (br s, 1H), 7.25-7.15 (m, 2H), 6.86 (d, J=8.4 Hz, 2H), 6.75 (d, J=8.4 Hz, 1H), 6.59 (d, J=2.4 Hz, 1H), 6.44-6.35 (m, 1H), 5.50-5.30 (m, 1H), 4.88-4.65 (m, 2H), 3.73 (s, 3H), 3.27 (s, 3H), 3.14-2.98 (m, 1H), 2.87-2.60 (m, 2H), 2.09-1.94 (m, 1H). LC/MS (ESI, m/z): $[(M+1)]^+$=396.15 Chemical Formula: $C_{21}H_{21}N_3O_5$, Exact Mass: 395.15.

3-(5-(2-(2-hydroxyethoxy)ethoxy)-3-methyl-2-oxo-2,3-dihydro-1H-benzo[d]imidazol-1-yl)-1-(4-methoxybenzyl) piperidine-2,6-dione: To a stirred solution of 3-(5-hydroxy-3-methyl-2-oxo-2,3-dihydro-1H-benzo[d]imidazol-1-yl)-1-(4-methoxybenzyl) piperidine-2,6-dione (1 g, 2.529 mmol) and [2-(2-bromoethoxy)ethoxy](tert-butyl)dimethylsilane (859.7 mg, 3.035 mmol) in DMF (15 mL) was added $Cs_2CO_3$ (1.7 g, 5.058 mmol) at room temperature under air atmosphere. The resulting mixture was stirred for 2 h at 70° C. under air atmosphere. Desired product could be detected by LCMS. The mixture was allowed to cool down to room temperature. The mixture was acidified to pH 4 with conc. HCl. The mixture was purified by reversed-phase flash chromatography with the following conditions: column, C18 silica gel; mobile phase, MeCN in water (10 mmol/L $NH_4HCO_3$), 30% to 50% gradient in 15 min; detector, UV 254 nm. This resulted in 3-(5-(2-(2-hydroxyethoxy)ethoxy)-3-methyl-2-oxo-2,3-dihydro-1H-benzo[d]imidazol-1-yl)-1-(4-methoxybenzyl) piperidine-2,6-dione (500 mg, 40%) as a white solid. $^1$H NMR (400 MHz, DMSO-$d_6$) δ 7.25-7.14 (m, 2H), 6.94-6.80 (m, 4H), 6.59-6.54 (m, 1H), 5.47-5.42 (m, 1H), 4.79-4.73 (m, 2H), 4.61 (s, 1H), 4.17-4.01 (m, 2H), 3.79-3.64 (m, 5H), 3.57-3.45 (m, 4H), 3.15-2.96 (m, 1H), 2.87-2.63 (m, 2H), 2.11-1.93 (m, 1H). LC/MS (ESI, m/z): [(M+1)]=484.20 Chemical Formula: $C_{25}H_{29}N_3O_7$, Exact Mass: 483.20.

2-(2-((1-(1-(4-methoxybenzyl)-2,6-dioxopiperidin-3-yl)-3-methyl-2-oxo-2,3-dihydro-1H-benzo[d]imidazol-5-yl) oxy) ethoxy) acetaldehyde: To a stirred solution of 3-(5-(2-(2-hydroxyethoxy)ethoxy)-3-methyl-2-oxo-2,3-dihydro-1H-benzo[d]imidazol-1-yl)-1-(4-methoxybenzyl) piperidine-2,6-dione (500 mg, 1.034 mmol) in DCM (10 mL) was added DMP (526.3 mg, 1.241 mmol) at 0° C. under nitrogen atmosphere. The resulting mixture was stirred for 2 h at room temperature under nitrogen atmosphere. Desired product could be detected by LCMS. The resulting mixture was concentrated under reduced pressure. The residue was purified by silica gel column chromatography, eluted with $CH_2C_{12}$/MeOH (10:1) to afford 2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy) acetaldehyde (300 mg, crude) as a light yellow semi-solid. The crude product was used in the next step directly without further purification. LC/MS (ESI, m/z): $[(M+1)]^+$=482.20 Chemical Formula: $C_{25}H_{27}N_3O_7$, Exact Mass: 481.18.

(4S)-2-amino-4-(3-(2-((2S)-4-(2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy)ethyl)-2-methyl-1,4-diazepan-1-yl)pyrimidin-4-yl)-1,2,4-oxadiazol-5-yl)-4-methyl-4,5,6,7-tetrahydrobenzo[b]thiophene-3-carbonitrile: To a stirred solution of (4S)-2-amino-4-methyl-4-(3-{2-[(2S)-2-methyl-1,4-diazepan-1-yl]pyrimidin-4-yl}-1,2,4-oxadiazol-5-yl)-6,7-dihydro-5H-1-benzothiophene-3-carbonitrile (200 mg, 0.444 mmol) and $NaBH(OAc)_3$ (396.2 mg, 1.9 mmol) in DMF (4 mL) was added 2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy) acetaldehyde (300 mg, 0.623 mmol) in DMF (4 mL) dropwise at room temperature under air atmosphere. The resulting mixture was stirred for 2 h at room temperature under air atmosphere. Desired product could be detected by LCMS. The mixture was purified by reversed-phase flash chromatography with the following conditions: column, C18 silica gel; mobile phase, MeCN in water (10 mmol/L $NH_4HCO_3$), 50% to 80% gradient in 15 min; detector, UV 254 nm. This resulted in (45)-2-amino-4-(3-(2-((2S)-4-(2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy)ethyl)-2-methyl-1,4-diazepan-1-yl)pyrimidin-4-yl)-1,2,4-oxadiazol-5-yl)-4-methyl-4,5,6,7-tetrahydrobenzo[b] thiophene-3-carbonitrile (280 mg, 49%) as a light yellow solid. $^1$H NMR (400 MHz, DMSO-$d_6$) δ 8.56 (d, J=4.8 Hz, 1H), 7.21 (d, J=8.4 Hz, 2H), 7.14-7.04 (m, 3H), 6.86 (t, J=4.8 Hz, 4H), 6.57 (d, J=8.4 Hz, 1H), 5.46-5.42 (m, 1H), 4.86-4.68 (m, 3H), 4.30-4.27 (m, 1H), 4.06 (s, 2H), 3.72 (s, 3H), 3.71-3.66 (m, 2H), 3.54 (t, J=6.0 Hz, 2H), 3.23-2.99 (m, 3H), 2.95-2.51 (m, 11H), 2.16-1.50 (m, 11H), 1.01 (d, J=6.0 Hz, 3H). LC/MS (ESI, m/z): $[(M+1)]^+$=916.35 Chemical Formula: $C_{47}H_{53}N_{11}O_7S$, Exact Mass: 915.39.

(4S)-2-amino-4-(3-(2-((2S)-4-(2-(2-((1-(2,6-dioxopiperidin-3-yl)-3-methyl-2-oxo-2,3-dihydro-1H-benzo[d]imidazol-5-yl)oxy) ethoxy)ethyl)-2-methyl-1,4-diazepan-1-yl)pyrimidin-4-yl)-1,2,4-oxadiazol-5-yl)-4-methyl-4,5,6,7-tetrahydrobenzo[b]thiophene-3-carbonitrile (Compound 209) formate: To a stirred solution of (45)-2-amino-4-(3-(2-((25)-4-(2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy)ethyl)-2-methyl-1,4-diazepan-1-yl) pyrimidin-4-yl)-1,2,4-oxadiazol-5-yl)-4-methyl-4,5,6,7-tetrahydrobenzo[b]thiophene-3-carbonitrile (220 mg, 0.240 mmol) in TFA (4.4 mL) was added Trifluoromethanesulfonic acid (0.44 mL) at room temperature under air atmosphere. The resulting mixture was stirred for 3 h at 60° C. under air atmosphere. Desired product could be detected by LCMS. The mixture was allowed to cool down to room temperature. The resulting mixture was concentrated under reduced pressure. The residue was purified by reversed-phase flash chromatography with the following conditions: column, C18 silica gel; mobile phase, MeCN in water (10 mmol/L $NH_4HCO_3$), 40% to 70% gradient in 15 min; detector, UV 254 nm. This resulted in (4S)-2-amino-4-(3-(2-((2S)-4-(2-(2-((1-(2,6-dioxopiperidin-3-yl)-3-methyl-2-oxo-2,3-dihydro-1H-benzo[d]imidazol-5-yl)oxy) ethoxy)ethyl)-2-methyl-1,4-diazepan-1-yl)pyrimidin-4-yl)-1,2,4-oxadiazol-5-yl)-4-methyl-4,5,6,7-tetrahydrobenzo[b]thiophene-3-carbonitrile formate (35.7 mg, 17%) as a white solid. $^1$H NMR (400 MHz, DMSO-$d_6$) δ 11.09 (br s, 1H), 8.56-8.52 (m, 1H), 8.17 (s, 1H), 7.11-7.05 (m, 3H), 6.98-6.95 (m, 1H), 6.90-6.85 (m, 1H), 6.61-6.56 (m, 1H), 5.31-5.28 (m, 1H), 4.80-4.67 (m, 1H), 4.37-4.20 (m, 1H), 4.09-3.98 (m, 2H), 3.73-3.65 (m, 2H), 3.53-3.50 (m, 2H), 3.24-3.05 (m, 3H), 2.95-2.82 (m, 2H), 2.76-2.51 (m, 10H), 2.14-2.04 (m, 1H), 2.02-1.76 (m, 7H), 1.74-1.63 (m, 1H), 1.62-1.49 (m, 1H), 1.05-0.90 (m, 3H). LC/MS (ESI, m/z): $[(M+1)]^+$=796.30.

Example 39. Synthesis of Compound 202

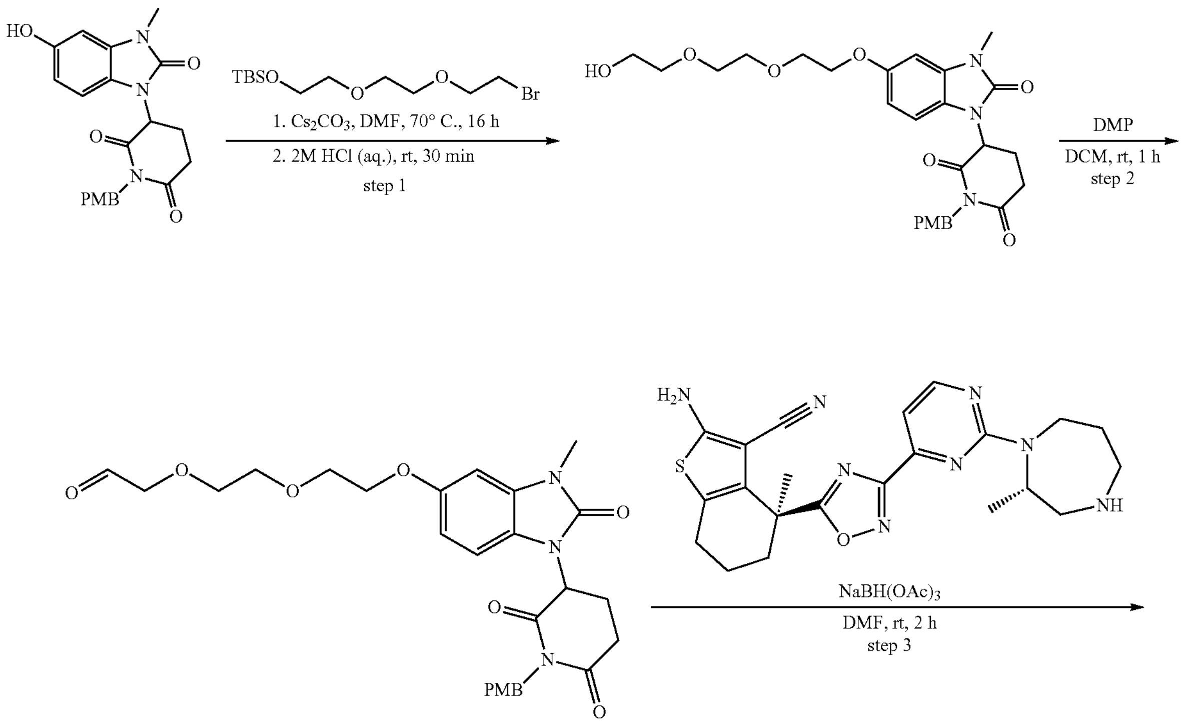

-continued

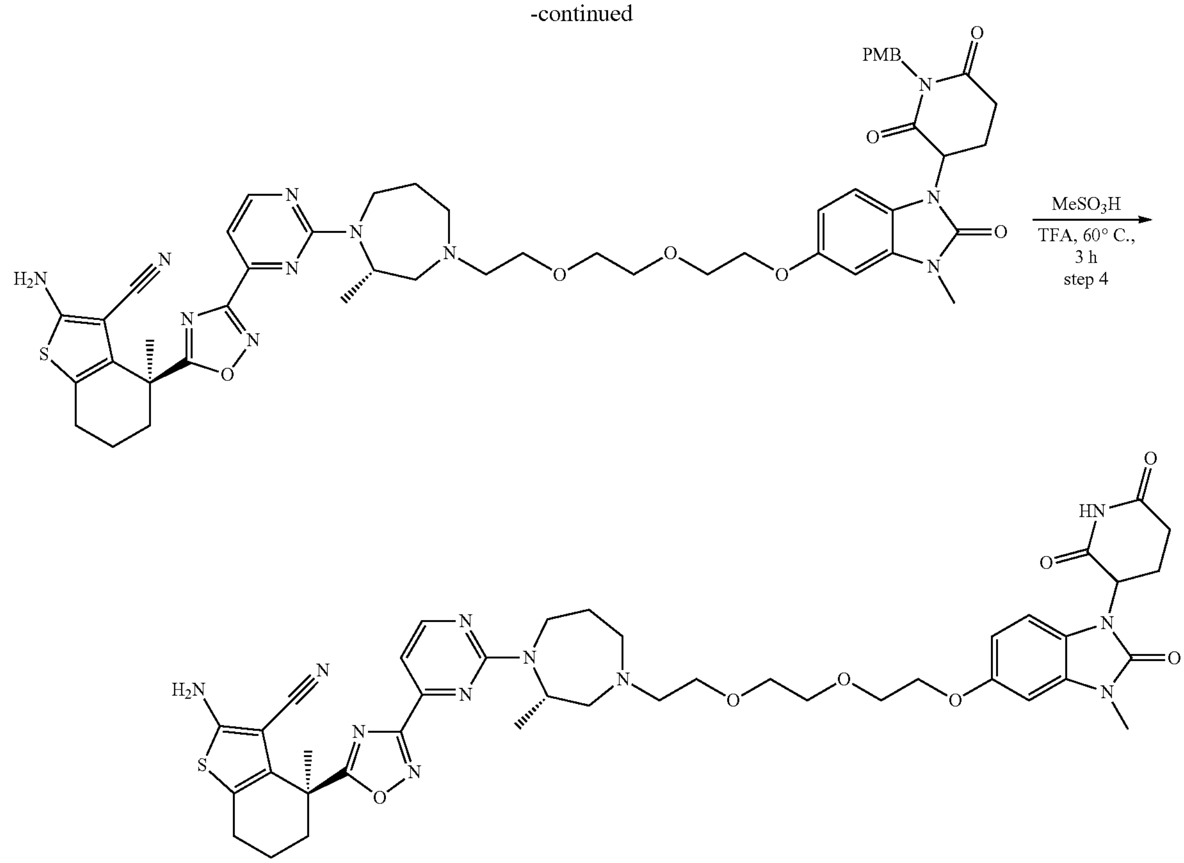

202

3-(5-{2-[2-(2-hydroxyethoxy)ethoxy]ethoxy}-3-methyl-2-oxo-1,3-benzodiazol-1-yl)-1-[(4-methoxyphenyl)methyl]piperidine-2,6-dione: To a stirred solution of 3-(5-hydroxy-3-methyl-2-oxo-1,3-benzodiazol-1-yl)-1-[(4-methoxyphenyl)methyl]piperidine-2,6-dione (1 g, 2.529 mmol) and 12-bromo-2,2,3,3-tetramethyl-4,7,10-trioxa-3-siladodecane (910.61 mg, 2.782 mmol) in DMF (15 mL) was added $Cs_2CO_3$ (1.65 g, 5.058 mmol) in portions at room temperature under nitrogen atmosphere. The resulting mixture was stirred for 2 h at 70° C. under nitrogen atmosphere. Desired product could be detected by LCMS. The mixture was allowed to cool down to room temperature. The mixture/residue was acidified to pH 3 with HCl (aq.). The resulting mixture was concentrated under reduced pressure. The residue was purified by reverse phase flash chromatography with the following conditions: Column: Spherical C18, 20-40 μm, 330 g; Mobile Phase A: Water (plus 10 mM $NH_4HCO_3$); Mobile Phase B: ACN; Flow rate: 80 mL/min; Gradient: 5%-5% B, 10 min, 60% B-955% B gradient in 20 min; Detector: 220 nm. The fractions containing the desired product were collected at 82% B and concentrated under reduced pressure to afford 3-(5-{2-[2-(2-hydroxyethoxy)ethoxy]ethoxy}-3-methyl-2-oxo-1,3-benzodiazol-1-yl)-1-[(4-methoxyphenyl)methyl]piperidine-2,6-dione (530 mg, 39%) as a light yellow solid. $^1H$ NMR (400 MHz, DMSO-$d_6$) chemical shifts 7.21-7.15 (m, 2H), 6.93-6.81 (m, 4H), 6.61-6.53 (m, 1H), 5.51-5.41 (m, 1H), 4.87-4.79 (m, 1H), 4.79-4.72 (m, 1H), 4.57 (t, J=5.6 Hz, 1H), 4.14-4.07 (m, 2H), 3.78-3.69 (m, 2H), 3.73 (s, 3H), 3.64-3.47 (m, 7H), 3.44 (t, J=5.6 Hz, 2H), 3.13-2.99 (m, 1H), 2.87-2.64 (m, 2H), 2.09-2.00 (m, 2H). LC/MS (ESI, m/z): [(M+1)]=528.20 Chemical Formula: $C_{27}H_{33}N_3O_8$, Exact Mass: 527.23.

2-(2-{2-[(1-{1-[(4-methoxyphenyl)methyl]-2,6-dioxopiperidin-3-yl}-3-methyl-2-oxo-1,3-benzodiazol-5-yl)oxy]ethoxy}ethoxy) acetaldehyde: To a stirred solution of 3-(5-{2-[2-(2-hydroxyethoxy)ethoxy]ethoxy}-3-methyl-2-oxo-1,3-benzodiazol-1-yl)-1-[(4-methoxyphenyl)methyl]piperidine-2,6-dione (530 mg, 1.005 mmol) in DCM (10 mL) was added DMP (511.31 mg, 1.206 mmol) in portions at 0° C. under nitrogen atmosphere. The resulting mixture was stirred for 3 h at room temperature under nitrogen atmosphere. Desired product could be detected by LCMS. The resulting mixture was concentrated under reduced pressure. The residue was purified by silica gel column chromatography, eluted with $CH_2Cl_2$/MeOH (10:1) to afford 2-(2-{2-[(1-{1-[(4-methoxyphenyl)methyl]-2,6-dioxopiperidin-3-yl}-3-methyl-2-oxo-1,3-benzodiazol-5-yl)oxy]ethoxy}ethoxy) acetaldehyde (500 mg, 94%) as an off-white solid. LC/MS (ESI, m/z): $[(M+1)]^+$=526.40 Chemical Formula: $C_{27}H_{31}N_3O_8$, Exact Mass: 525.21.

(4S)-2-amino-4-(3-{2-[(2S)-4-[2-(2-{2-[(1-{1-[(4-methoxyphenyl)methyl]-2,6-dioxopiperidin-3-yl}-3-methyl-2-oxo-1,3-benzodiazol-5-yl)oxy]ethoxy}ethoxy)ethyl]-2-methyl-1,4-diazepan-1-yl]pyrimidin-4-yl}-1,2,4-oxadiazol-5-yl)-4-methyl-6,7-dihydro-5H-1-benzothiophene-3-carbonitrile: To a stirred solution of (4S)-2-amino-4-methyl-4-(3-{2-[(25)-2-methyl-1,4-diazepan-1-yl]pyrimidin-4-yl}-1,2,4-oxadiazol-5-yl)-6,7-dihydro-5H-1-benzothiophene-3-carbonitrile (428.66 mg, 0.951 mmol) and $NaBH(OAc)_3$ (403.27 mg, 1.902 mmol) in DMF (10 mL) was added 2-(2-{2-[(1-{1-[(4-methoxyphenyl)methyl]-2,6-dioxopiperidin-3-yl}-3-methyl-2-oxo-1,3-benzodiazol-5-yl)oxy]ethoxy}ethoxy) acetaldehyde (500 mg, 0.951 mmol) in DMF (10 mL) dropwise at room temperature under air atmosphere. The resulting mixture was stirred for 2 h at room temperature under air atmosphere. Desired product could be detected by LCMS. The resulting mixture was concentrated under reduced pressure. The residue was purified by reverse phase flash chromatography with the following conditions: Column: Spherical C18, 20-40 μm, 120 g; Mobile Phase A: Water (plus 10 mM $NH_4HCO_3$); Mobile Phase B: ACN; Flow rate: 60 mL/min; Gradient: 5%-5% B, 10 min, 45% B-70% B gradient in 20 min; Detector: 220 nm. The fractions containing the desired product were collected at 65% B and concentrated under reduced pressure to afford (4S)-2-amino-4-(3-{2-[(25)-4-[2-(2-{2-[(1-{1-[(4-methoxyphenyl)methyl]-2,6-dioxopiperidin-3-yl}-3-methyl-2-oxo-1,3-benzodiazol-5-yl)oxy] ethoxy}ethoxy)ethyl]-2-methyl-1,4-diazepan-1-yl] pyrimidin-4-yl}-1,2,4-oxadiazol-5-yl)-4-methyl-6,7-dihydro-5H-1-benzothiophene-3-carbonitrile (220 mg, 24%) as an off-white solid. $^1$H NMR (400 MHz, DMSO-$d_6$) chemical shifts 8.55-8.52 (m, 1H), 7.26-7.18 (m, 2H), 7.13-7.03 (m, 3H), 6.92-6.82 (m, 4H), 6.57-6.52 (m, 1H), 5.51-5.41 (m, 1H), 4.87-4.67 (m, 3H), 4.37-4.19 (m, 1H), 4.07 (s, 2H), 3.73 (s, 5H), 3.61-3.41 (m, 6H), 3.23-2.98 (m, 3H), 2.91-2.51 (m, 12H), 2.12-1.99 (m, 2H), 1.79 (s, 6H), 1.73-1.50 (m, 2H), 1.01 (s, 3H). LC/MS (ESI, m/z): $[(M+1)]^+$ =960.30 Chemical Formula: $C_{49}H_{57}N_{11}O_8S$, Exact Mass: 959.41.

(4S)-2-amino-4-(3-{2-[(2S)-4-{2-[2-(2-{[1-(2,6-dioxopiperidin-3-yl)-3-methyl-2-oxo-1,3-benzodiazol-5-yl] oxy}ethoxy)ethoxy]ethyl}-2-methyl-1,4-diazepan-1-yl]pyrimidin-4-yl}-1,2,4-oxadiazol-5-yl)-4-methyl-6,7-dihydro-5H-1-benzothiophene-3-carbonitrile: To a stirred solution of (4S)-2-amino-4-(3-{2-[(2S)-4-[2-(2-{2-[(1-{1-[(4-methoxyphenyl)methyl]-2,6-dioxopiperidin-3-yl}-3-methyl-2-oxo-1,3-benzodiazol-5-yl)oxy]ethoxy}ethoxy) ethyl]-2-methyl-1,4-diazepan-1-yl]pyrimidin-4-yl}-1,2,4-oxadiazol-5-yl)-4-methyl-6,7-dihydro-5H-1-benzothiophene-3-carbonitrile (150 mg, 0.156 mmol) in TFA (3 mL) was added $CF_3SO_3H$ (0.3 mL) dropwise at room temperature under nitrogen atmosphere. The resulting mixture was stirred for 3 h at 60° C. under nitrogen atmosphere. Desired product could be detected by LCMS. The resulting mixture was concentrated under reduced pressure. The residue was purified by reverse phase flash chromatography with the following conditions: Column: Spherical C18, 20-40 μm, 330 g; Mobile Phase A: Water (0.1% FA); Mobile Phase B: ACN; Flow rate: 80 mL/min; Gradient: 5%-5% B, 10 min, 33% B-50% B gradient in 20 min; Detector: 220 nm. The fractions containing the desired product were collected at 46% B and concentrated under reduced pressure to afford (45)-2-amino-4-(3-{2-[(25)-4-{2-[2-(2-{[1-(2,6-dioxopiperidin-3-yl)-3-methyl-2-oxo-1,3-benzodiazol-5-yl]oxy}ethoxy)ethoxy]ethyl}-2-methyl-1,4-diazepan-1-yl]pyrimidin-4-yl}-1,2,4-oxadiazol-5-yl)-4-methyl-6,7-dihydro-5H-1-benzothiophene-3-carbonitrile (10 mg, 7%) as an off-white solid. $^1$H NMR (400 MHz, DMSO-$d_6$) chemical shifts δ 11.09 (s, 1H), 8.55 (d, J=2.4 Hz, 1H), 8.34 (s, 1H), 7.11-7.09 (m, 3H), 7.00-6.97 (m, 1H), 6.88-6.87 (m, 1H), 6.62-6.60 (m, 1H), 5.31-5.30 (m, 1H), 4.72-4.70 (m, 1H), 4.37-4.19 (m, 1H), 4.07 (s, 2H), 3.71-3.68 (m, 3H), 3.54-3.44 (m, 7H), 3.30 (s, 3H), 3.18-3.07 (m, 3H), 2.92-2.85 (m, 2H), 2.70-2.33 (m, 4H), 2.08-1.56 (m, 11H), 0.99 (s, 3H). LC/MS (ESI, m/z): $[(M+1)]^+$=840.35.

Example 40. Synthesis of Compound 200

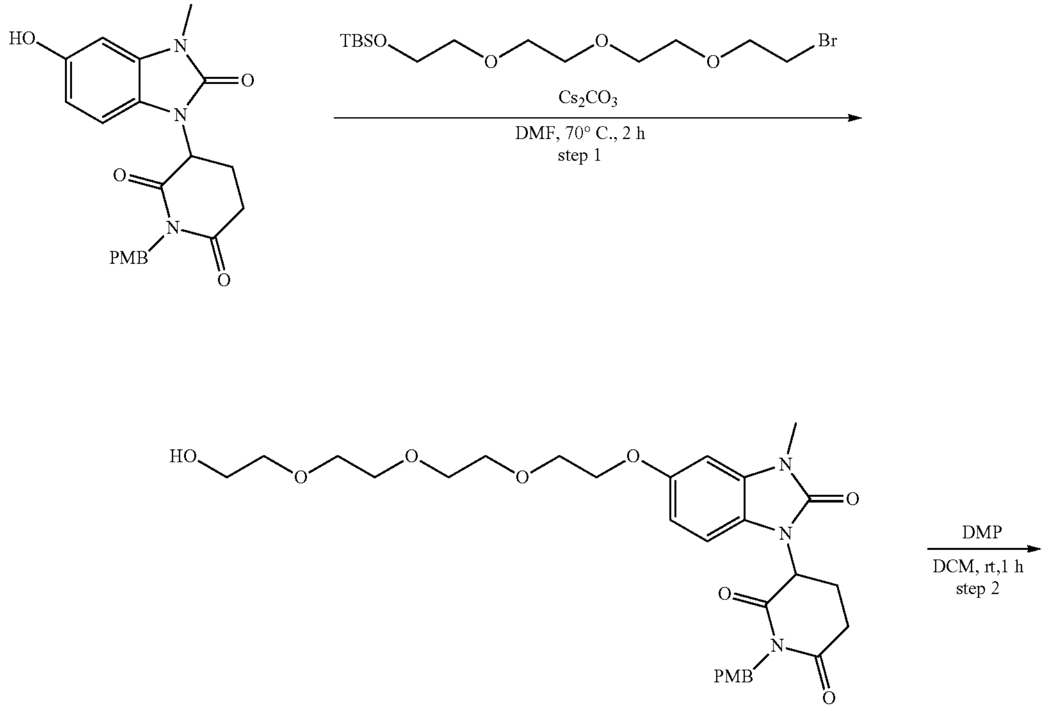

-continued

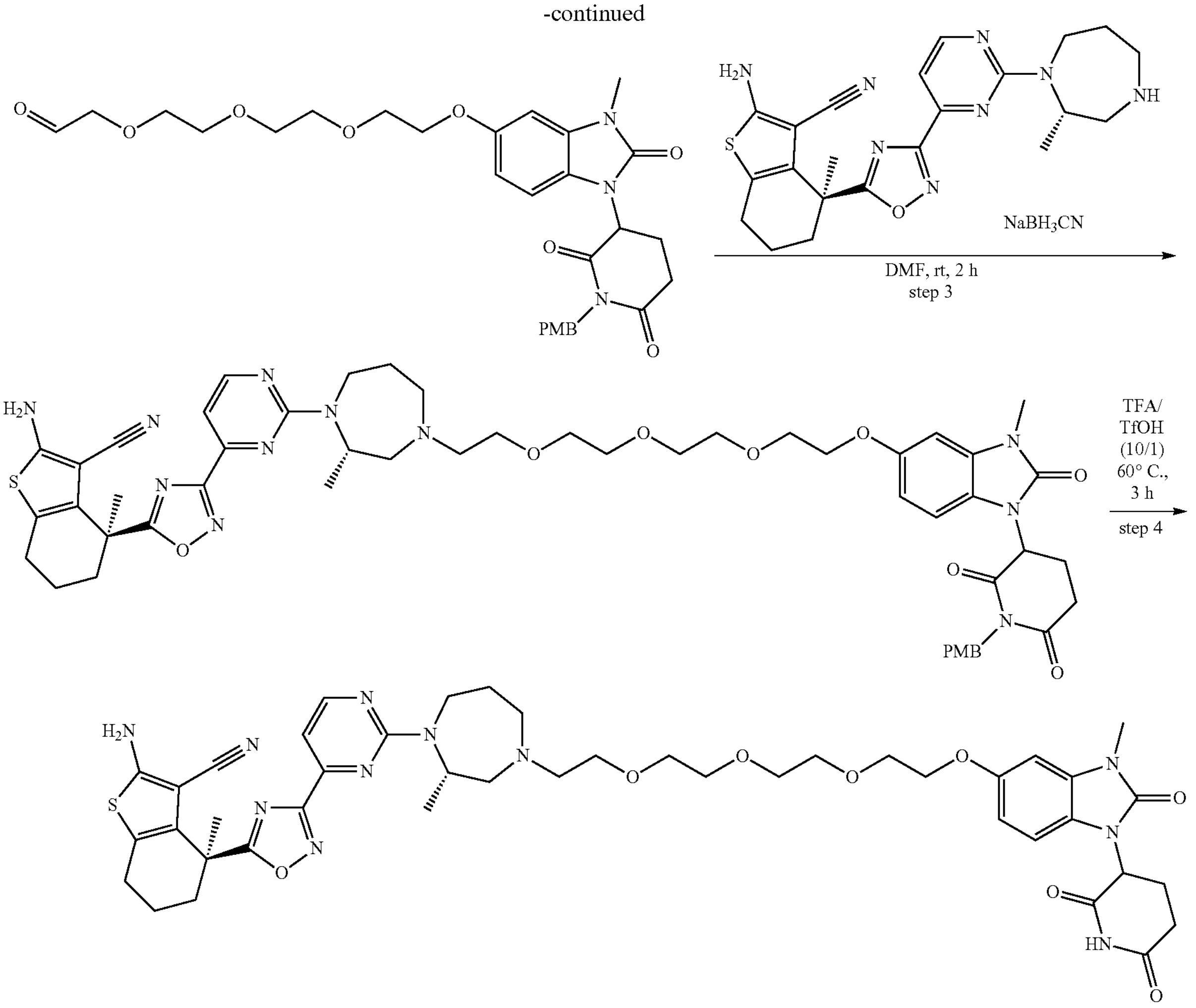

200

3-(5-(2-(2-(2-(2-hydroxyethoxy)ethoxy) ethoxy)ethoxy)-3-methyl-2-oxo-2,3-dihydro-1H-benzo[d]imidazol-1-yl)-1-(4-methoxybenzyl) piperidine-2,6-dione: To a stirred mixture of 3-(5-hydroxy-3-methyl-2-oxo-1,3-benzodiazol-1-yl)-1-[(4-methoxyphenyl)methyl]piperidine-2,6-dione (1 g, 2.529 mmol) and 15-bromo-2,2,3,3-tetramethyl-4,7,10,13-tetraoxa-3-silapentadecane (1.13 g, 3.035 mmol) in DMF (15 mL) was added $Cs_2CO_3$ (1.65 g, 5.058 mmol) at room temperature under air atmosphere. The resulting mixture was stirred at 70° C. under air atmosphere for 2 h. The reaction was monitored by LCMS. The mixture was allowed to cool down to room temperature. The mixture was acidified to pH 3 with conc. HCl. The resulting mixture was stirred for 10 min at room temperature under air atmosphere. The resulting mixture was concentrated under reduced pressure. The residue was purified by reverse phase flash chromatography with the following conditions: Column: Spherical C18, 20-40 μm, 330 g; Mobile Phase A: Water (plus 5 mM $NH_4HCO_3$); Mobile Phase B: ACN; Flow rate: 80 mL/min; Gradient: 5%-5% B, 10 min, 33% B-45% B gradient in 20 min; Detector: 220 nm. The fractions containing the desired product were collected at 40% B and concentrated under reduced pressure to afford 3-(5-(2-(2-(2-(2-hydroxyethoxy)ethoxy) ethoxy)ethoxy)-3-methyl-2-oxo-2,3-dihydro-1H-benzo[d]imidazol-1-yl)-1-(4-methoxybenzyl) piperidine-2,6-dione (458 mg, 32%) as a black oil. 1H NMR (400 MHz, DMSO-$d_6$) δ 7.27-7.17 (m, 2H), 6.97-6.80 (m, 4H), 6.59-6.54 (m, 1H), 5.47-5.43 (m, 1H), 4.91-4.71 (m, 2H), 4.58-4.55 (m, 1H), 4.17-4.05 (m, 2H), 3.81-3.69 (m, 5H), 3.63-3.54 (m, 4H), 3.53-3.50 (m, 4H), 3.51-3.45 (m, 2H), 3.44-3.39 (m, 2H), 3.34 (s, 2H), 2.98-3.12 (m, 1H), 2.87-2.76 (m, 1H), 2.75-2.65 (m, 1H), 2.13-1.96 (m, 1H). LC/MS (ESI, m/z): $[(M-1)]^-$=570.40 Chemical Formula: $C_{29}H_{37}N_3O_9$, Exact Mass: 571.25.

2-(2-(2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy)ethoxy) ethoxy) acetaldehyde: To a stirred mixture of 3-(5-(2-(2-(2-(2-hydroxyethoxy)ethoxy) ethoxy) ethoxy)-3-methyl-2-oxo-2,3-dihydro-1H-benzo[d]imidazol-1-yl)-1-(4-methoxybenzyl) piperidine-2,6-dione (400 mg, 0.700 mmol) in DCM (10 mL) was added DMP (359 mg, 0.847 mmol) at 0° C. under air atmosphere. The resulting mixture was stirred at room temperature under air atmosphere for 1 h. The reaction was monitored by LCMS. The residue was purified by silica gel column chromatography, eluted with $CH_2Cl_2$/MeOH (10:1) to afford the crude product used in the next step directly without further purification.

(4S)-2-amino-4-(3-(2-((2S)-4-(2-(2-(2-(2-((1-(1-(4-methoxybenzyl)-2,6-dioxopiperidin-3-yl)-3-methyl-2-oxo- 2,3-dihydro-1H-benzo[d]imidazol-5-yl)oxy) ethoxy) ethoxy) ethoxy)ethyl)-2-methyl-1,4-diazepan-1-yl) pyrimidin-4-yl)-1,2,4-oxadiazol-5-yl)-4-methyl-4,5,6,7-tetrahydrobenzo[b]thiophene-3-carbonitrile: To a stirred mixture of (4S)-2-amino-4-methyl-4-(3-{2-[(2S)-2-methyl-1,4-diazepan-1-yl]pyrimidin-4-yl}-1,2,4-oxadiazol-5-yl)-6,7-dihydro-5H-1-benzothiophene-3-carbonitrile (200 mg, 0.444 mmol) in DMF (5 mL) was added $NaBH(OAc)_3$ (282 mg, 1.332 mmol) at room temperature under air atmosphere. The resulting mixture was stirred at room temperature under air atmosphere for 30 min. To the above mixture was added 2-[2-(2-{2-[(1-{1-[(4-methoxyphenyl)methyl]-2,6-dioxopiperidin-3-yl}-3-methyl-2-oxo-1,3-benzodiazol-5-yl)oxy]ethoxy}ethoxy)ethoxy]acetaldehyde (252 mg, 0.444 mmol) in DMF (5 mL) at room temperature. The resulting mixture was stirred at room temperature for an additional 2 h. The reaction was monitored by LCMS. The residue was purified by reverse phase flash chromatography with the following conditions: Column: Spherical C18, 20-40 μm, 330 g; Mobile Phase A: Water (plus 5 mM $NH_4HCO_3$); Mobile Phase B: ACN; Flow rate: 80 mL/min; Gradient: 5%-5% B, 10 min, 60% B-80% B gradient in 20 min; Detector: 220 nm. The fractions containing the desired product were collected at 70% B and concentrated under reduced pressure to afford (4S)-2-amino-4-(3-(2-((25)-4-(2-(2-(2-(2-((1-(1-(4-methoxybenzyl)-2,6-dioxopiperidin-3-yl)-3-methyl-2-oxo-2,3-dihydro-1H-benzo[d]imidazol-5-yl)oxy) ethoxy) ethoxy) ethoxy)ethyl)-2-methyl-1,4-diazepan-1-yl) pyrimidin-4-yl)-1,2,4-oxadiazol-5-yl)-4-methyl-4,5,6,7-tetrahydrobenzo[b]thiophene-3-carbonitrile (350 mg, 78%) as a white solid. $^1$H NMR (300 MHz, DMSO-$d_6$) δ 8.56-8.52 (m, 1H), 7.21-7.15 (m, 2H), 7.10 (d, J=8.8 Hz, 3H), 6.93-6.81 (m, 4H), 6.58 (d, J=8.8 Hz, 1H), 5.47-5.42 (m, 1H), 4.88-4.70 (m, 2H), 4.28 (s, 1H), 4.08 (s, 2H), 3.72 (s, 4H), 3.57-3.47 (m, 7H), 3.23-3.09 (m, 2H), 3.06 (s, 1H), 2.84 (s, 1H), 2.06 (s, 2H), 1.79 (s, 8H), 1.58 (s, 2H), 1.24 (s, 1H), 1.01 (s, 3H). LC/MS (ESI, m/z): $[(M+1)]^+$=1004.60 Chemical Formula: $C_{51}$H61N1109S, Exact Mass: 1003.44.

(4S)-2-amino-4-(3-(2-((2S)-4-(2-(2-(2-(2-((1-(2,6-dioxopiperidin-3-yl)-3-methyl-2-oxo-2,3-dihydro-1H-benzo[d]imidazol-5-yl)oxy) ethoxy)ethoxy) ethoxy)ethyl)-2-methyl-1,4-diazepan-1-yl)pyrimidin-4-yl)-1,2,4-oxadiazol-5-yl)-4-methyl-4,5,6,7-tetrahydrobenzo[b]thiophene-3-carbonitrile (Compound 200); formic acid: To a stirred mixture of (4S)-2-amino-4-(3-{2-[(2S)-4-{2-[2-(2-{2-[(1-{1-[(4-methoxyphenyl)methyl]-2,6-dioxopiperidin-3-yl}-3-methyl-2-oxo-1,3-benzodiazol-5-yl)oxy]ethoxy}ethoxy) ethoxy]ethyl}-2-methyl-1,4-diazepan-1-yl]pyrimidin-4-yl}-1,2,4-oxadiazol-5-yl)-4-methyl-6,7-dihydro-5H-1-benzothiophene-3-carbonitrile (250 mg, 0.249 mmol) in TFA (6.00 mL, 80.791 mmol) were added trifluoromethanesulfonic acid (0.6 mL, 0.004 mmol) dropwise at room temperature under air atmosphere. The resulting mixture was stirred at 60° C. under air atmosphere for 2 h. The reaction was monitored by LCMS. The mixture was allowed to cool down to room temperature. The residue was purified by reverse phase flash chromatography with the following conditions: Column: Spherical C18, 20-40 um, 120 g; Mobile Phase A: Water (plus 5 mM $NH_4HCO_3$); Mobile Phase B: ACN; Flow rate: 60 mL/min; Gradient: 5%-5% B, 10 min, 33% B-50% B gradient in 20 min; Detector: 220 nm. The fractions containing the desired product were collected at 45% B and concentrated under reduced pressure to afford (4S)-2-amino-4-(3-(2-((2S)-4-(2-(2-(2-(2-((1-(2,6-dioxopiperidin-3-yl)-3-methyl-2-oxo-2,3-dihydro-1H-benzo[d]imidazol-5-yl)oxy) ethoxy)ethoxy) ethoxy)ethyl)-2-methyl-1,4-diazepan-1-yl)pyrimidin-4-yl)-1,2,4-oxadiazol-5-yl)-4-methyl-4,5,6,7-tetrahydrobenzo[b]thiophene-3-carbonitrile; formic acid (41.8 mg, 18%) as a white solid. $^1$H NMR (400 MHz, DMSO-$d_6$) δ 11.09 (s, 1H), 8.60-8.53 (m, 1H), 7.11-7.05 (m, 2H), 6.99-6.95 (m, 1H), 6.89-8.85 (m, 1H), 6.62-6.58 (m, 1H), 5.32-5.28 (m, 1H), 4.77-4.68 (m, 1H), 4.28-4.22 (m, 1H), 4.08-4.03 (m, 2H), 3.72-3.68 (m, 2H), 3.60-3.42 (m, 9H), 3.34 (s, 3H), 3.14-3.10 (m, 2H), 2.94-2.84 (m, 2H), 2.75-2.51 (m, 10H), 2.13-2.05 (m, 1H), 2.03-1.82 (m, 3H), 1.78 (s, 3H), 1.68-1.65 (m, 1H), 1.56-1.52 (m, 1H), 1.01-0.99 (m, 3H). LC/MS (ESI, m/z): $[(M+1)]^+$=884.40.

Example 41. Synthesis of Compound 210

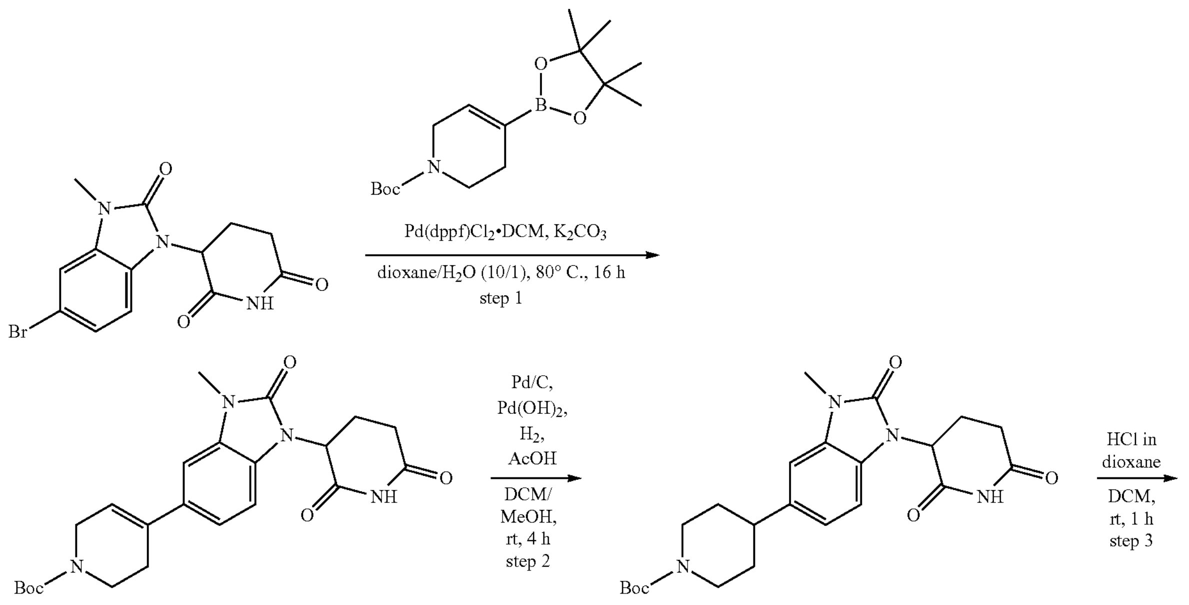

-continued
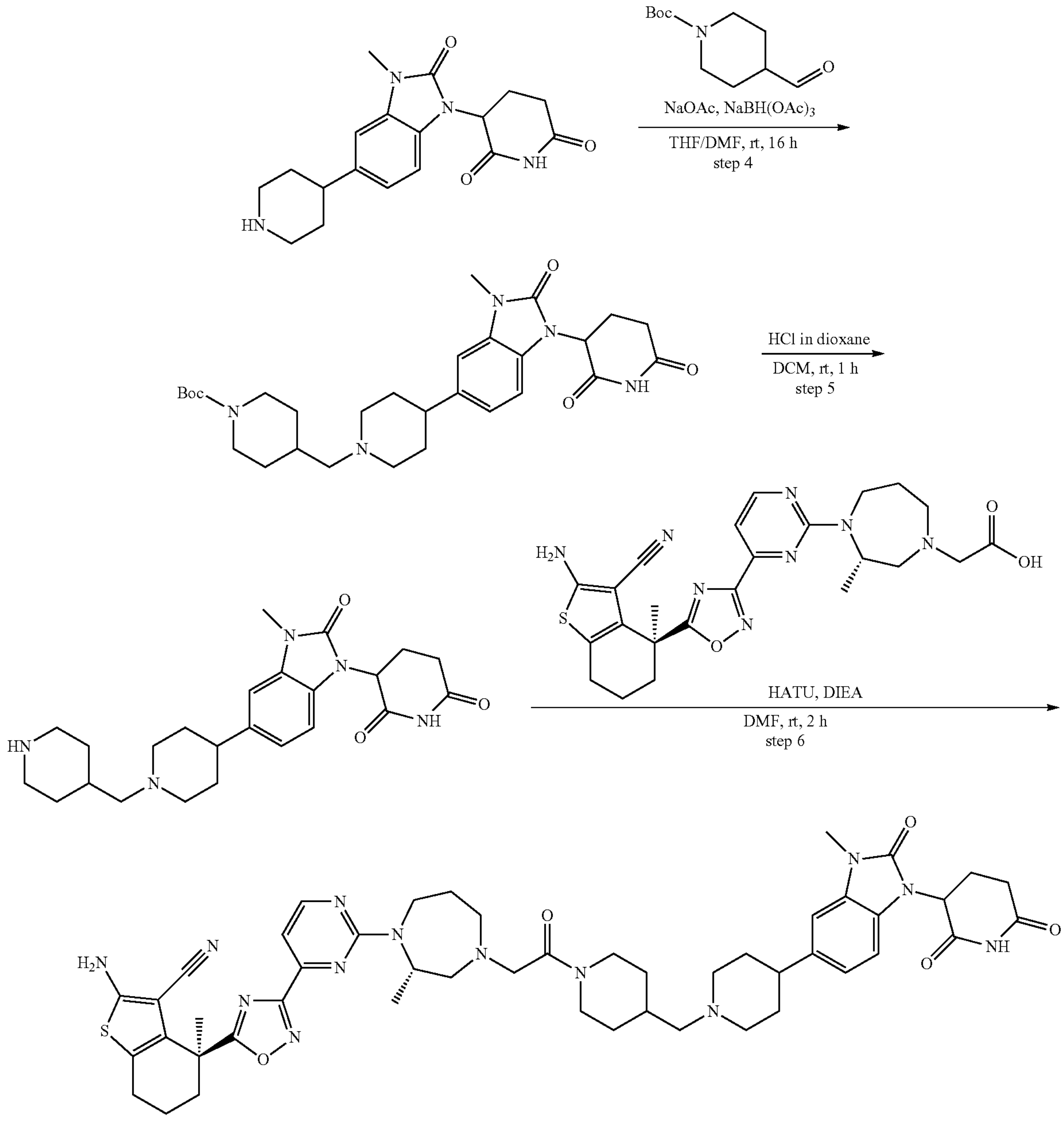
210
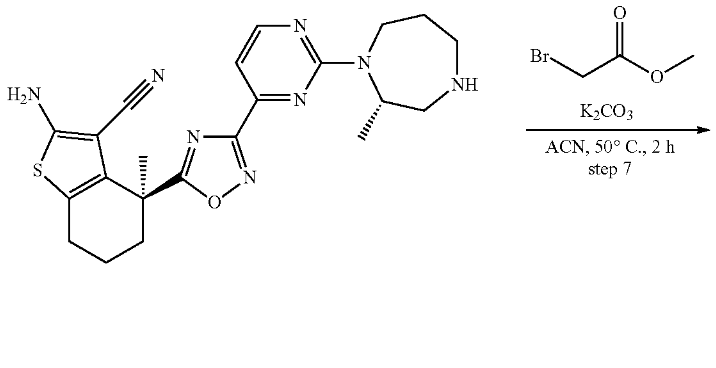

-continued

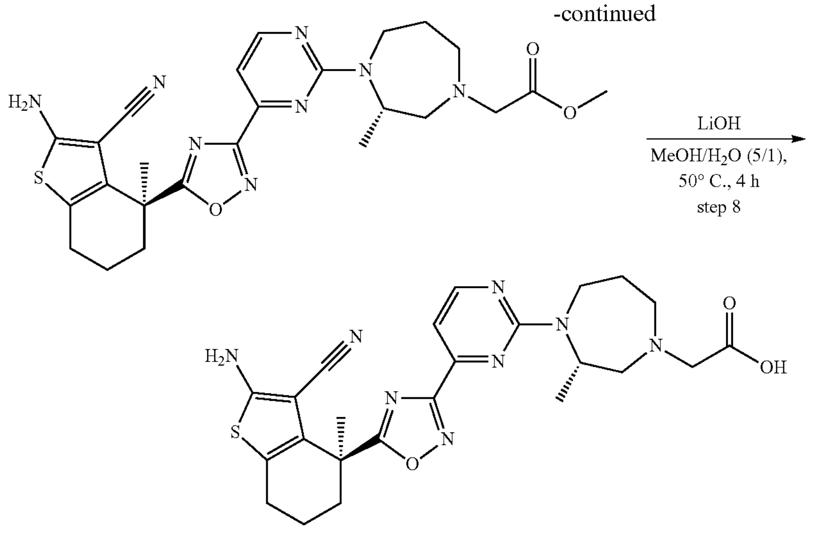

tert-Butyl 4-[1-(2,6-dioxopiperidin-3-yl)-3-methyl-2-oxo-1,3-benzodiazol-5-yl]-3,6-dihydro-2H-pyridine-1-carboxylate: To a stirred solution of 3-(5-bromo-3-methyl-2-oxo-1,3-benzodiazol-1-yl) piperidine-2,6-dione (2 g, 5.914 mmol) and tert-butyl 4-(4,4,5,5-tetramethyl-1,3,2-dioxaborolan-2-yl)-3,6-dihydro-2H-pyridine-1-carboxylate (2.74 g, 8.871 mmol) in 1,4-dioxane (30 mL) and $H_2O$ (3 mL) were added $K_2CO_3$ (1.63 g, 11.828 mmol) and Pd (dppf) $C_{12}$·$CH_2Cl_2$ (481.79 mg, 0.591 mmol) in portions at room temperature under nitrogen atmosphere. The resulting mixture was stirred for 16 h at 80° C. under nitrogen atmosphere. Desired product could be detected by LCMS. The resulting mixture was diluted with water (100 mL). The resulting mixture was extracted with EtOAc (3×100 mL). The combined organic layers were washed with water (100 mL), dried over anhydrous $Na_2SO_4$. After filtration, the filtrate was concentrated under reduced pressure. The residue was purified by silica gel column chromatography, eluted with $CH_2Cl_2$/MeOH (10:1) to afford tert-butyl 4-[1-(2,6-dioxopiperidin-3-yl)-3-methyl-2-oxo-1,3-benzodiazol-5-yl]-3,6-dihydro-2H-pyridine-1-carboxylate (1.1 g, 42%) as an off-white solid. $^1H$ NMR (400 MHz, DMSO-$d_6$) chemical shifts 11.10 (s, 1H), 7.32-7.23 (m, 1H), 7.14-7.02 (m, 2H), 6.12 (s, 1H), 5.41-5.28 (m, 1H), 4.05-3.89 (m, 3H), 3.56-3.52 (m, 2H), 3.36-3.33 (m, 4H), 2.98-2.85 (m, 1H), 2.78-2.56 (m, 2H), 2.06-1.98 (m, 1H), 1.44 (s, 9H). LC/MS (ESI, m/z): [(M+1)]=441.35 Chemical Formula: $C_{23}H_{28}N_4O_5$, Exact Mass: 440.21.

tert-Butyl 4-[1-(2,6-dioxopiperidin-3-yl)-3-methyl-2-oxo-1,3-benzodiazol-5-yl]piperidine-1-carboxylate: To a stirred solution of tert-butyl 4-[1-(2,6-dioxopiperidin-3-yl)-3-methyl-2-oxo-1,3-benzodiazol-5-yl]-3,6-dihydro-2H-pyridine-1-carboxylate (300 mg, 0.681 mmol) in DCM (3 mL) and MeOH (3 mL) were added $Pd(OH)_2/C$ (191.28 mg, 1.362 mmol), Pd/C (144.95 mg, 1.362 mmol) and AcOH (4.09 mg, 0.068 mmol) in portions at room temperature under hydrogen atmosphere. The resulting mixture was stirred for 4 h at room temperature under hydrogen atmosphere. Desired product could be detected by LCMS. The resulting mixture was filtered, the filter cake was washed with MeOH (3×5 mL). The filtrate was concentrated under reduced pressure to afford tert-butyl 4-[1-(2,6-dioxopiperidin-3-yl)-3-methyl-2-oxo-1,3-benzodiazol-5-yl]piperidine-1-carboxylate (110 mg, 36%) as an off-white solid. $^1H$ NMR (400 MHz, DMSO-$d_6$) chemical shifts 11.05 (s, 1H), 7.13-7.09 (m, 1H), 7.02-7.00 (m, 1H), 6.95-6.89 (m, 1H), 5.39-5.29 (m, 1H), 4.16-4.05 (m, 2H), 3.33 (s, 3H), 2.96-2.53 (m, 4H), 2.05-1.95 (m, 1H), 1.88-1.78 (m, 6H), 1.43 (s, 9H). LC/MS (ESI, m/z): $[(M+1)]^+$=443.10. Chemical Formula: $C_{23}H_{30}N_4O_5$, Exact Mass: 442.22.

3-[3-Methyl-2-oxo-5-(piperidin-4-yl)-1,3-benzodiazol-1-yl]piperidine-2,6-dione: To a stirred solution of tert-butyl 4-[1-(2,6-dioxopiperidin-3-yl)-3-methyl-2-oxo-1,3-benzodiazol-5-yl]piperidine-1-carboxylate (110 mg, 0.249 mmol) in DCM (2.5 mL) was added HCl (gas) in 1,4-dioxane (1 mL) dropwise at room temperature under nitrogen atmosphere. The resulting mixture was stirred for 1 h at room temperature under nitrogen atmosphere. Desired product could be detected by LCMS. The resulting mixture was concentrated under reduced pressure to afford crude product. The crude product was used in the next step directly without further purification. LC/MS (ESI, m/z): $[(M+1)]^+$=343.20. Chemical Formula: $C_{18}H_{22}N_4O_3$, Exact Mass: 342.17.

tert-Butyl 4-({4-[1-(2,6-dioxopiperidin-3-yl)-3-methyl-2-oxo-1,3-benzodiazol-5-yl]piperidin-1-yl}methyl) piperidine-1-carboxylate: To a stirred solution of 3-[3-methyl-2-oxo-5-(piperidin-4-yl)-1,3-benzodiazol-1-yl]piperidine-2,6-dione (150 mg, 0.438 mmol) and tert-butyl 4-formylpiperidine-1-carboxylate (112.12 mg, 0.526 mmol) in THF (1.5 mL) and DMF (1.5 mL) was added NaOAc (71.88 mg, 0.876 mmol) in portions at room temperature under nitrogen atmosphere. The resulting mixture was stirred for 1 h at room temperature under nitrogen atmosphere. To the above mixture was added $NaBH(OAc)_3$ (278.54 mg, 1.314 mmol) in portions at room temperature. The resulting mixture was stirred for additional 16 h at room temperature. Desired product could be detected by LCMS. The resulting mixture was concentrated under reduced pressure. The residue was purified by reverse phase flash chromatography with the following conditions: Column: Spherical C18, 20-40 μm, 80 g; Mobile Phase A: Water (plus 10 mM $NH_4HCO_3$); Mobile Phase B: ACN; Flow rate: 60 mL/min; Gradient: 5%-5% B, 10 min, 33% B-55% B gradient in 20 min; Detector: 220 nm. The fractions containing the desired product were collected at 48% B and concentrated under reduced pressure to afford tert-butyl 4-({4-[1-(2,6-dioxopiperidin-3-yl)-3-methyl-2-oxo-1,3-benzodiazol-5-yl]piperidin-1-yl}methyl) piperidine-1-carboxylate (110 mg, 46%) as an off-white solid. $^1$H NMR (400 MHz, DMSO-$d_6$) chemical shifts 11.07 (s, 1H), 7.12-7.05 (m, 1H), 7.01-6.98 (m, 1H), 6.93-6.89 (m, 1H), 5.39-5.27 (m, 1H), 4.02-3.81 (m, 3H), 3.02-2.84 (m, 3H), 2.83-2.57 (m, 5H), 2.17 (d, J=6.8 Hz, 3H), 2.07-1.91 (m, 4H), 1.79-1.60 (m, 8H), 1.40 (s, 11H); LC/MS (ESI, m/z): [(M+1)]$^+$=540.45. Chemical Formula: $C_{29}H_{41}N_5O_5$, Exact Mass: 539.31.

3-{3-Methyl-2-oxo-5-[1-(piperidin-4-ylmethyl) piperidin-4-yl]-1,3-benzodiazol-1-yl}piperidine-2,6-dione: To a stirred solution of tert-butyl 4-({4-[1-(2,6-dioxopiperidin-3-yl)-3-methyl-2-oxo-1,3-benzodiazol-5-yl]piperidin-1-yl}methyl) piperidine-1-carboxylate (70 mg, 0.130 mmol) in DCM (1 mL) was added HCl (gas) in 1,4-dioxane (0.2 mL) dropwise at room temperature under nitrogen atmosphere. The resulting mixture was stirred for 1 h at room temperature under nitrogen atmosphere. Desired product could be detected by LCMS. The resulting mixture was concentrated under reduced pressure to get crude product. The crude product was used in the next step directly without further purification. LC/MS (ESI, m/z): [(M+1)]=440.15. Chemical Formula: $C_{24}H_{33}N_5O_3$, Exact Mass: 439.26.

Methyl 2-[(3S)-4-(4-{5-[(4S)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetate: To a stirred solution of (4S)-2-amino-4-methyl-4-(3-{2-[(2S)-2-methyl-1,4-diazepan-1-yl]pyrimidin-4-yl}-1,2,4-oxadiazol-5-yl)-6,7-dihydro-5H-1-benzothiophene-3-carbonitrile (190 mg, 0.422 mmol) and methyl 2-bromoacetate (70.96 mg, 0.464 mmol) in ACN (4 mL) was added $K_2CO_3$ (174.84 mg, 1.266 mmol) in portions at room temperature under nitrogen atmosphere. The resulting mixture was stirred for 2 h at 50° C. under nitrogen atmosphere. Desired product could be detected by LCMS. The mixture was allowed to cool down to room temperature. The residue was purified by reverse phase flash chromatography with the following conditions: Column: Spherical C18, 20-40 μm, 80 g; Mobile Phase A: Water (plus 10 mM $NH_4HCO_3$); Mobile Phase B: ACN; Flow rate: 60 mL/min; Gradient: 5%-5% B, 10 min, 33% B-60% B gradient in 20 min; Detector: 220 nm. The fractions containing the desired product were collected at 50% B and concentrated under reduced pressure to afford methyl 2-[(3S)-4-(4-{5-[(4S)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetate (140 mg, 63%) as an off-white solid. $^1$H NMR (400 MHz, DMSO-$d_6$) chemical shifts 8.58-8.53 (m, 1H), 7.15-7.06 (m, 3H), 4.77-4.63 (m, 1H), 4.36-4.22 (m, 1H), 3.59 (s, 3H), 3.51-3.40 (m, 1H), 3.25-3.14 (m, 2H), 3.11-3.03 (m, 1H), 2.81-2.70 (m, 1H), 2.76 (s, 2H), 2.60-2.52 (m, 2H), 2.16-2.05 (m, 1H), 2.00-1.89 (m, 1H), 1.86 (s, 2H), 1.80 (s, 3H), 1.68 (s, 1H), 1.60-1.53 (m, 1H), 1.02 (d, J=6.4 Hz, 3H); LC/MS (ESI, m/z): [(M+1)]$^+$=523.20. Chemical Formula: $C_{25}H_{30}N_8O_3S$, Exact Mass: 522.22.

[(3S)-4-(4-{5-[(4S)-2-Amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetic acid: To a stirred solution of methyl 2-[(3S)-4-(4-{5-[(4S)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetate (140 mg, 0.268 mmol) in MeOH (3 mL) and $H_2O$ (0.6 mL) was added LiOH (25.66 mg, 1.072 mmol) in portions at room temperature under nitrogen atmosphere. The resulting mixture was stirred for 4 h at 50° C. under nitrogen atmosphere. Desired product could be detected by LCMS. The mixture was allowed to cool down to room temperature. The resulting mixture was concentrated under reduced pressure. The residue was purified by reverse phase flash chromatography with the following conditions: Column: Spherical C18, 20-40 μm, 330 g; Mobile Phase A: Water (plus 10 mM $NH_4HCO_3$); Mobile Phase B: ACN; Flow rate: 60 mL/min; Gradient: 5%-5% B, 10 min, 33% B-45% B gradient in 20 min; Detector: 220 nm. The fractions containing the desired product were collected at 40% B and concentrated under reduced pressure to afford [(3S)-4-(4-{5-[(45)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetic acid (110 mg, 80%) as an off-white solid. $^1$H NMR (400 MHz, DMSO-$d_6$) chemical shifts 8.58 (d, J=4.8 Hz, 1H), 8.24 (s, 1H), 7.13 (d, J=4.8 Hz, 1H), 7.08 (s, 2H), 4.78-4.65 (m, 1H), 4.38-4.25 (m, 1H), 3.24-3.16 (m, 1H), 3.12 (s, 1H), 2.89-2.71 (m, 3H), 2.59-2.52 (m, 2H), 2.16-2.06 (m, 1H), 2.01 (s, 2H), 2.00-1.91 (m, 1H), 1.91-1.81 (m, 2H), 1.80 (s, 2H), 1.74-1.67 (m, 2H), 1.64-1.56 (m, 1H), 1.03-1.01 (m, 3H); LC/MS (ESI, m/z): [(M+1)]$^+$=509.25. Chemical Formula: $C_{24}H_{28}N_8O_3S$, Exact Mass: 508.20.

(4S)-2-amino-4-(3-{2-[(2S)-4-{2-[4-({4-[1-(2,6-dioxopiperidin-3-yl)-3-methyl-2-oxo-1,3-benzodiazol-5-yl]piperidin-1-yl}methyl) piperidin-1-yl]-2-oxoethyl}-2-methyl-1,4-diazepan-1-yl]pyrimidin-4-yl}-1,2,4-oxadiazol-5-yl)-4-methyl-6,7-dihydro-5H-1-benzothiophene-3-carbonitrile (Compound 210): To a stirred solution of [(3S)-4-(4-{5-[(4S)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetic acid (80 mg, 0.157 mmol) in DMF (2 mL) was added HATU (83.73 mg, 0.220 mmol) in portions at room temperature under nitrogen atmosphere. The resulting mixture was stirred for 5 min at room temperature under nitrogen atmosphere. To the above mixture was added DIEA (60.99 mg, 0.471 mmol) dropwise at room temperature. The resulting mixture was stirred for an additional 5 min at room temperature. To the above mixture was added 3-{3-methyl-2-oxo-5-[1-(piperidin-4-ylmethyl) piperidin-4-yl]-1,3-benzodiazol-1-yl}piperidine-2,6-dione (82.97 mg, 0.188 mmol) in portions at room temperature. The resulting mixture was stirred for an additional 2 h at room temperature. Desired product could be detected by LCMS. The resulting mixture was concentrated under reduced pressure. The residue was purified by reverse phase flash chromatography with the following conditions: Column: Spherical C18, 20-40 μm, 40 g; Mobile Phase A: Water (0.1% FA); Mobile Phase B: ACN; Flow rate: 30 mL/min; Gradient: 5%-5% B, 10 min, 33% B-55% B gradient in 20 min; Detector: 220 nm. The fractions containing the desired product were collected at 47% B and concentrated under reduced pressure to afford the title compound (40.0 mg, 26%) as an off-white solid. $^1$H NMR (400 MHz, DMSO-$d_6$) chemical shifts 11.08 (s, 1H), 8.63-8.53 (m, 1H), 8.20 (s, 2H), 7.14-7.05 (m, 3H), 7.00 (d, J=8.0 Hz, 1H), 6.91 (d, J=8.0 Hz, 1H), 5.40-5.29 (m, 1H), 4.88-4.63 (m, 2H), 4.34-4.09 (m, 4H), 3.95-3.70 (m, 3H), 3.48-3.39 (m, 1H), 3.34 (s, 3H), 3.26-3.10 (m, 2H), 3.07-2.96 (m, 1H), 2.93-2.54 (m, 8H), 2.47 (s, 2H), 2.14-2.05 (m, 1H), 2.04-1.74 (m, 10H), 1.74-1.47 (m, 8H), 1.02-0.99 (m, 3H), 0.90-0.68 (m, 2H); LC/MS (ESI, m/z): [(M+1)]=930.75.

Example 42. Synthesis of Compound 211

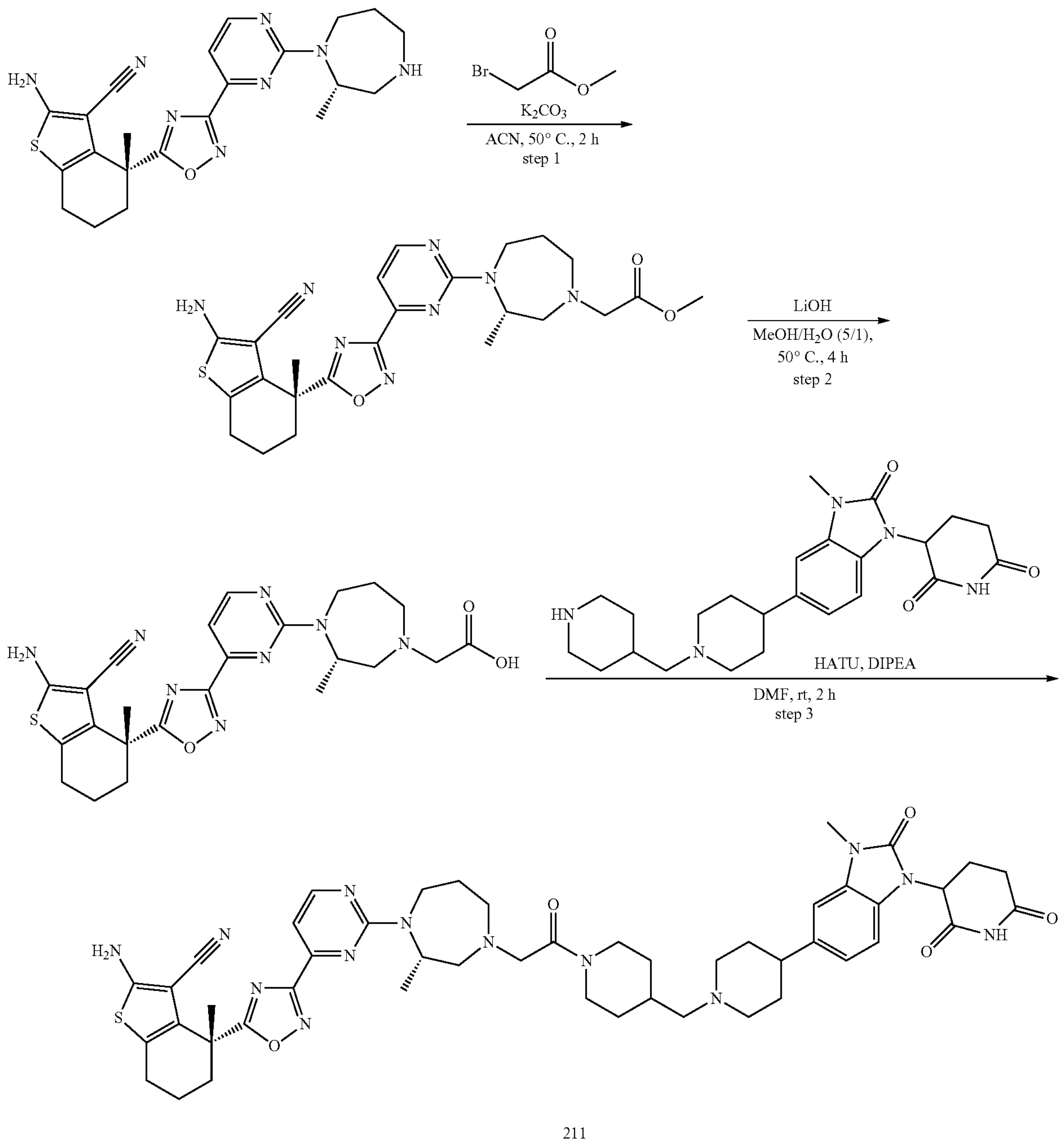

211

Methyl 2-[(3S)-4-(4-{5-[(4R)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetate: To a stirred solution of (4R)-2-amino-4-methyl-4-(3-{2-[(2S)-2-methyl-1,4-diazepan-1-yl]pyrimidin-4-yl}-1,2,4-oxadiazol-5-yl)-6,7-dihydro-5H-1-benzothiophene-3-carbonitrile (200 mg, 0.444 mmol) and methyl 2-bromoacetate (81.48 mg, 0.533 mmol) in ACN (4 mL) was added $K_2CO_3$ (122.69 mg, 0.888 mmol) in portions at room temperature under nitrogen atmosphere. The resulting mixture was stirred for 2 h at 50° C. under nitrogen atmosphere. Desired product could be detected by LCMS. The resulting mixture was concentrated under reduced pressure. The residue was purified by reverse phase flash chromatography with the following conditions: Column: Spherical C18, 20-40 μm, 80 g; Mobile Phase A: Water (plus 10 mM $NH_4HCO_3$); Mobile Phase B: ACN; Flow rate: 60 mL/min; Gradient: 5%-5% B, 10 min, 33% B-65% B gradient in 20 min; Detector: 220 nm. The fractions containing the desired product were collected at 500% B and concentrated under reduced pressure to afford methyl 2-[(3S)-4-(4-{5-[(4R)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetate (180 mg, 77%) as an off-white solid.

$^1H$ NMR (400 MHz, DMSO-$d_6$) chemical shifts 8.58-8.55 (m, 1H), 7.15-7.06 (m, 3H), 4.77-4.63 (m, 1H), 4.36-4.22 (m, 1H), 3.59 (s, 3H), 3.51-3.40 (m, 1H), 3.25-3.14 (m, 2H), 3.11-3.03 (m, 1H), 2.81-2.70 (m, 1H), 2.76 (s, 2H), 2.60-2.52 (m, 2H), 2.16-2.05 (m, 1H), 2.00-1.89 (m, 1H), 1.86 (s, 2H), 1.80 (s, 3H), 1.68 (s, 1H), 1.60-1.53 (m, 1H), 1.02-0.99 (m, 3H); LC/MS (ESI, m/z): [(M+1)]=523.20. Chemical Formula: $C_{25}H_{30}N_8O_3S$, Exact Mass: 522.22.

[(3S)-4-(4-{5-[(4R)-2-Amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetic acid: To a stirred solution of methyl 2-[(3S)-4-(4-{5-[(4R)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetate (180 mg, 0.344 mmol) in MeOH (4 mL) and $H_2O$ (0.8 mL) was added LiOH (49.49 mg, 2.064 mmol) in portions at room temperature under air atmosphere. The resulting mixture was stirred for 4 h at 50° C. under nitrogen atmosphere. Desired product could be detected by LCMS. The resulting mixture was concentrated under reduced pressure. The residue was purified by reverse phase flash chromatography with the following conditions: Column: Spherical C18, 20-40 μm, 80 g; Mobile Phase A: Water (plus 10 mM $NH_4HCO_3$); Mobile Phase B: ACN; Flow rate: 60 mL/min; Gradient: 5%-5% B, 10 min, 33% B-45% B gradient in 20 min; Detector: 220 nm. The fractions containing the desired product were collected at 40% B and concentrated under reduced pressure to afford [(35)-4-(4-{5-[(4R)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetic acid (140 mg, 79%) as an off-white solid. $^1H$ NMR (400 MHz, DMSO-$d_6$) chemical shifts 8.58-8.55 (m, 1H), 7.21-6.99 (m, 3H), 4.80-4.56 (m, 1H), 4.39-4.17 (m, 1H), 3.28-3.07 (m, 3H), 2.92-2.67 (m, 3H), 2.19-2.06 (m, 1H), 2.01-1.48 (m, 9H), 1.24 (s, 1H), 1.10-0.77 (m, 3H); LC/MS (ESI, m/z): $[(M+1)]^+$=509.35. Chemical Formula: $C_{24}H_{28}N_8O_3S$, Exact Mass: 508.20.

(4R)-2-amino-4-(3-{2-[(2S)-4-{2-[4-({4-[1-(2,6-dioxopiperidin-3-yl)-3-methyl-2-oxo-1,3-benzodiazol-5-yl]piperidin-1-yl}methyl) piperidin-1-yl]-2-oxoethyl}-2-methyl-1,4-diazepan-1-yl]pyrimidin-4-yl}-1,2,4-oxadiazol-5-yl)-4-methyl-6,7-dihydro-5H-1-benzothiophene-3-carbonitrile (Compound 211); formic acid: To a stirred solution of [(3S)-4-(4-{5-[(4R)-2-amino-3-cyano-4-methyl-6,7-dihydro-5H-1-benzothiophen-4-yl]-1,2,4-oxadiazol-3-yl}pyrimidin-2-yl)-3-methyl-1,4-diazepan-1-yl]acetic acid (100 mg, 0.197 mmol) in DMF (2 mL) was added HATU (104.67 mg, 0.276 mmol) in portions at room temperature under nitrogen atmosphere. The resulting mixture was stirred for 5 min at room temperature under nitrogen atmosphere. To the above mixture was added DIEA (76.24 mg, 0.591 mmol) in portions at room temperature. The resulting mixture was stirred for an additional 5 min at room temperature. To the above mixture was added 3-{3-methyl-2-oxo-5-[1-(piperidin-4-ylmethyl) piperidin-4-yl]-1,3-benzodiazol-1-yl}piperidine-2,6-dione (103.71 mg, 0.236 mmol) in portions at room temperature. The resulting mixture was stirred for an additional 2 h at room temperature. Desired product could be detected by LCMS. The resulting mixture was concentrated under reduced pressure. The crude product (80 mg) was purified by Prep-HPLC with the following conditions (Column: XBridge Prep OBD C18 Column, 30*150 mm, 5 μm; Mobile Phase A: Water (0.1% FA), Mobile Phase B: ACN; Flow rate: 60 mL/min; Gradient: 45% B to 60% B in 10 min; Wave Length: 254/220 nm; $RT_1$ (min): 6.9) to afford (4R)-2-amino-4-(3-{2-[(2S)-4-{2-[4-({4-[1-(2,6-dioxopiperidin-3- yl)-3-methyl-2-oxo-1,3-benzodiazol-5-yl]piperidin-1-yl}methyl) piperidin-1-yl]-2-oxo-ethyl}-2-methyl-1,4-diazepan-1-yl]pyrimidin-4-yl}-1,2,4-oxadiazol-5-yl)-4-methyl-6,7-dihydro-5H-1-benzothiophene-3-carbonitrile; formic acid (51.6 mg, 26%) as an off-white solid. $^1H$ NMR (400 MHz, DMSO-$d_6$) chemical shifts 11.08 (s, 1H), 8.63-8.53 (m, 1H), 8.20 (s, 2H), 7.14-7.05 (m, 3H), 7.00 (d, J=8.0 Hz, 1H), 6.91 (d, J=8.0 Hz, 1H), 5.40-5.29 (m, 1H), 4.88-4.63 (m, 2H), 4.34-4.09 (m, 4H), 3.95-3.70 (m, 3H), 3.48-3.39 (m, 1H), 3.34 (s, 3H), 3.26-3.10 (m, 2H), 3.07-2.96 (m, 1H), 2.93-2.54 (m, 8H), 2.47 (s, 2H), 2.14-2.05 (m, 1H), 2.04-1.74 (m, 10H), 1.74-1.47 (m, 8H), 1.02 (t, J=5.2 Hz, 3H), 0.90-0.68 (m, 2H).; LC/MS (ESI, m/z): $[(M+1)]^+$=930.75.

Example 43. Synthesis of Compound 122

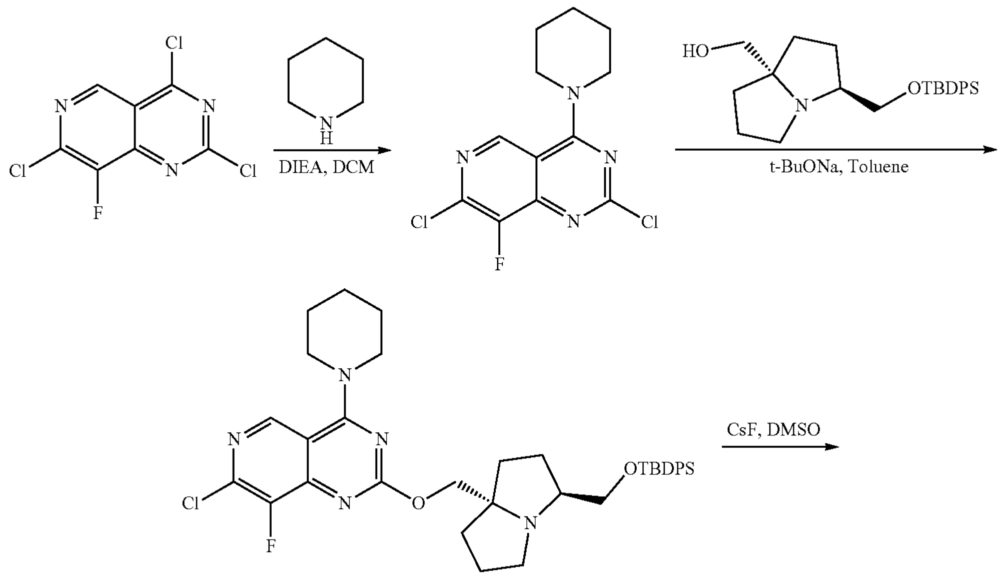

-continued
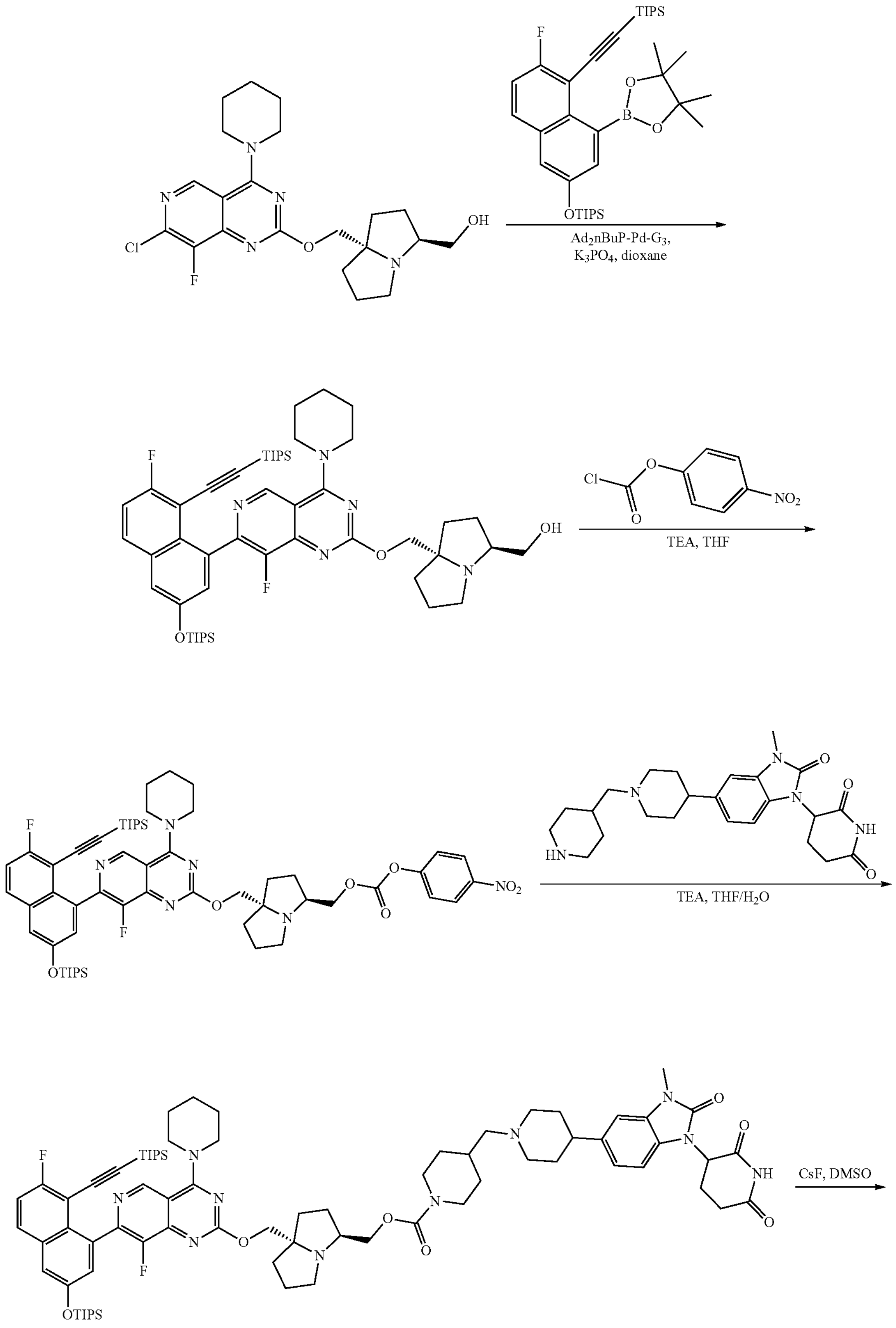

-continued

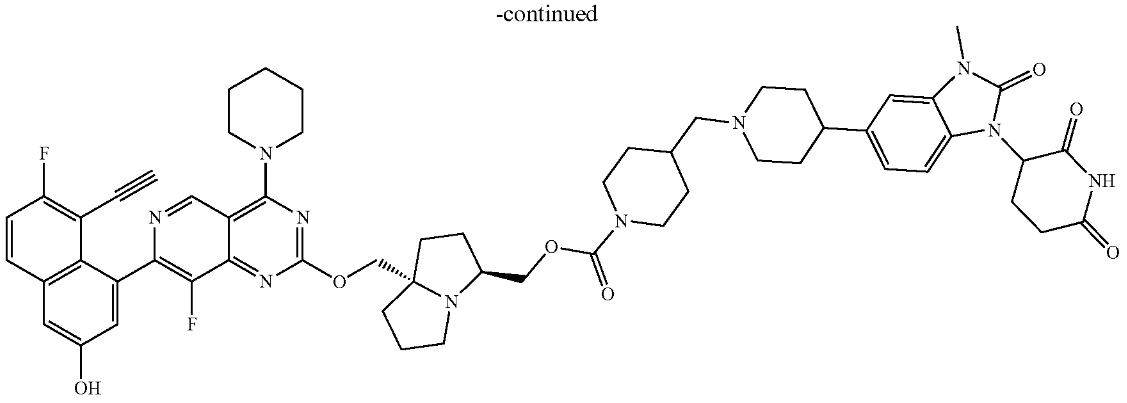

122

Step 1-2,7-Dichloro-8-fluoro-4-(piperidin-1-yl)pyrido[4,3-d]pyrimidine. To a solution of 2,4,7-trichloro-8-fluoro-pyrido[4,3-d]pyrimidine (5.00 g, 19.8 mmol, CAS #2454396-80-4) in DCM (50 mL) was added DIEA (7.68 g, 59.4 mmol, 10.3 mL) and piperidine (1.69 g, 19.8 mmol, 1.96 mL, CAS #110-89-4) at −40° C. The mixture was stirred at −40° C. for 0.5 hr. On completion, the reaction mixture was concentrated in vacuo to give the residue. The residue was purified by column chromatography ($SiO_2$, Petroleum ether/Ethyl acetate=1/0 to 3/1) to give the title compound (4.60 g, 77% yield) as yellow solid. $^1H$ NMR (400 MHz, $CDCl_3$) δ 8.83 (s, 1H), 4.01-3.94 (m, 4H), 1.84 (s, 6H).

Step 2-2-(((35,7aS)-3-(((Tert-butyldiphenylsilyl)oxy)methyl)tetrahydro-1H-pyrrolizin-7a (5H)-yl) methoxy)-7-chloro-8-fluoro-4-(piperidin-1-yl)pyrido[4,3-d]pyrimidine. To a solution of ((3S,7aS)-3-(((tert-butyldiphenylsilyl)oxy)methyl)tetrahydro-1H-pyrrolizin-7a (5H)-yl) methanol (1.22 g, 2.99 mmol) in Toluene (40 mL) was added t-BuONa (638 mg, 6.64 mmol) at 0° C. The mixture was stirred at 0° C. for 0.5 hr under $N_2$ atmosphere. After that, 2,7-dichloro-8-fluoro-4-(1-piperidyl)pyrido[4,3-d]pyrimidine (1.00 g, 3.32 mmol) was added to the mixture and the mixture was stirred at 0° C. for 0.5 hr. On completion, the reaction mixture was filtered and the filtrate was concentrated in vacuo to give a residue. The residue was purified by column chromatography ($SiO_2$, DCM/MeOH=1/0 to 10/1) to give the title compound (1.66 g, 74% yield) as yellow solid. $^1H$ NMR (400 MHz, $CDCl_3$) δ 8.71 (s, 1H), 7.68 (t, J=6.0 Hz, 4H), 7.50-7.33 (m, 6H), 4.33-4.09 (m, 2H), 3.99 (dd, J=4.8, 10.4 Hz, 1H), 3.89 (s, 4H), 3.85-3.76 (m, 1H), 3.31 (s, 1H), 2.96-2.69 (m, 2H), 2.22 (d, J=6.4 Hz, 1H), 1.98-1.77 (m, 13H), 1.06 (s, 9H); LC-MS (ESI) m/z 674.2 $(M+H)^+$.

Step 3-((3S,7aS)-7a-(((7-Chloro-8-fluoro-4-(piperidin-1-yl)pyrido[4,3-d]pyrimidin-2-yl)oxy)methyl)hexahydro-1H-pyrrolizin-3-yl) methanol. To a solution of 2-(((3S,7aS)-3-(((tert-butyldiphenylsilyl)oxy)methyl)tetrahydro-1H-pyrrolizin-7a (5H)-yl) methoxy)-7-chloro-8-fluoro-4-(piperidin-1-yl)pyrido[4,3-d]pyrimidine (700 mg, 1.04 mmol) in DMSO (2.5 mL) was added CsF (473 mg, 3.11 mmol). The mixture was stirred at 25° C. for 2 hrs. On completion, the reaction mixture was quenched by water (20 mL) and extracted with EA (3×20 mL). The combined organic layers were washed with brine (3×40 mL), dried over anhydrous $Na_2SO_4$, filtered and the filtrate was concentrated in vacuo to give a residue. The residue was purified by column chromatography ($SiO_2$, DCM/MeOH=1/0 to 10/1) to give the title compound (380 mg, 83% yield) as white solid. $^1H$ NMR (400 MHz, $CDCl_3$) δ 8.72 (s, 1H), 4.42-4.26 (m, 2H), 3.94-3.83 (m, 6H), 3.60-3.48 (m, 1H), 3.18 (d, J=4.4 Hz, 1H), 2.86-2.75 (m, 1H), 2.33-2.28 (m, 1H), 2.04-1.99 (m, 2H), 1.95-1.86 (m, 4H), 1.81 (s, 6H), 1.71-1.61 (m, 2H); LC-MS (ESI) m/z 436.1 $(M+H)^+$.

Step 4-((3S,7aS)-7a-(((8-Fluoro-7-(7-fluoro-8-((triisopropylsilyl) ethynyl)-3-((triisopropylsilyl)oxy) naphthalen-1-yl)-4-(piperidin-1-yl)pyrido[4,3-d]pyrimidin-2-yl)oxy) methyl)hexahydro-1H-pyrrolizin-3-yl) methanol. A mixture of ((3S,7aS)-7a-(((7-chloro-8-fluoro-4-(piperidin-1-yl) pyrido[4,3-d]pyrimidin-2-yl)oxy)methyl)hexahydro-1H-pyrrolizin-3-yl) methanol (330 mg, 757 μmol), ((6-fluoro-4-(4,4,5,5-tetramethyl-1,3,2-dioxaborolan-2-yl)-5-((triisopropylsilyl) ethynyl) naphthalen-2-yl)oxy) triisopropylsilane (709 mg, 1.14 mmol, CAS #2791277-41-1), $K_3PO_4$ (1.5 M, 1.51 mL) and [2-(2-aminophenyl)phenyl] palladium (1+); bis(1-adamantyl)-butyl-phosphane; methanesulfonate (55.1 mg, 75.7 μmol) in dioxane (7.5 mL) was degassed and purged with $N_2$ for 3 times, and then the mixture was stirred at 80° C. for 0.5 hr under $N_2$ atmosphere. On completion, the reaction mixture was concentrated in vacuo to give a residue. The residue was purified by column chromatography ($SiO_2$, DCM/MeOH=1/0 to 10/1) to give the title compound (600 mg, 88% yield) as yellow solid. $^1H$ NMR (400 MHz, $CDCl_3$) δ 9.04 (s, 1H), 7.72 (dd, J=5.6, 8.8 Hz, 1H), 7.31 (d, J=2.4 Hz, 1H), 7.28 (s, 1H), 7.23 (s, 1H), 4.64-4.45 (m, 2H), 4.00-3.82 (m, 7H), 3.65-3.54 (m, 1H), 3.02-2.96 (m, 1H), 2.41 (dd, J=4.8, 12.8 Hz, 1H), 2.28-2.00 (m, 6H), 1.90-1.76 (m, 8H), 1.35-1.28 (m, 3H), 1.13 (d, J=7.2 Hz, 18H), 0.89 (dd, J=7.6, 11.2 Hz, 18H), 0.63-0.53 (m, 3H).

Step 5-((3S,7aS)-7a-(((8-Fluoro-7-(7-fluoro-8-((triisopropylsilyl) ethynyl)-3-((triisopropylsilyl)oxy) naphthalen-1-yl)-4-(piperidin-1-yl)pyrido[4,3-d]pyrimidin-2-yl)oxy) methyl)hexahydro-1H-pyrrolizin-3-yl)methyl (4-nitrophenyl) carbonate. To a solution of ((3S,7aS)-7a-(((8-fluoro-7-(7-fluoro-8-((triisopropylsilyl) ethynyl)-3-((triisopropylsilyl)oxy) naphthalen-1-yl)-4-(piperidin-1-yl) pyrido[4,3-d]pyrimidin-2-yl)oxy)methyl)hexahydro-1H-pyrrolizin-3-yl) methanol (150 mg, 166 μmol) in THF (12 mL) was added TEA (126 mg, 1.25 mmol, 174 μL) and a solution of (4-nitrophenyl) carbonochloridate (67.3 mg, 333 μmol, CAS #7693-46-1) in THF (3 mL). The mixture was stirred at 25° C. for 0.5 hr. On completion, the reaction mixture was concentrated in vacuo to give a residue. The residue was diluted with DCM (30 mL) and $H_2O$ (30 mL). Then the mixture was extracted with DCM (3×30 mL). The combined organic layers were washed with brine (3×50 mL), dried over anhydrous $Na_2SO_4$, filtered and the filtrate was concentrated in vacuo to give the title compound (177 mg, 99% yield) as yellow oil. LC-MS (ESI) m/z 532.8 (M/2+H).

Step 6-((3S,7aS)-7a-(((8-Fluoro-7-(7-fluoro-8-((triisopropylsilyl) ethynyl)-3-((triisopropylsilyl)oxy) naphthalen-1-yl)-4-(piperidin-1-yl)pyrido[4,3-d]pyrimidin-2-yl)oxy) methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate. To a solution of 3-(3-methyl-2-oxo-5-(1-(piperidin-4-ylmethyl) piperidin-4-yl)-2,3-dihydro-1H-benzo[d]imidazol-1-yl) piperidine-2,6-dione (136 mg, 246 μmol, TFA salt) in THF (6 mL) and $H_2O$ (300 μL) was added TEA (49.9 mg, 493 μmol, 68.7 μL) and ((3S,7aS)-7a-(((8-fluoro-7-(7-fluoro-8-((triisopropylsilyl) ethynyl)-3-((triisopropylsilyl)oxy) naphthalen-1-yl)-4-(piperidin-1-yl)pyrido [4,3-d]pyrimidin-2-yl)oxy)methyl)hexahydro-1H-pyrrolizin-3-yl)methyl (4-nitrophenyl) carbonate (175 mg, 164 μmol). The mixture was stirred at 25° C. for 3 hrs. On completion, the reaction mixture was concentrated in vacuo to give a residue. The residue was purified by prep-HPLC (column: CD04-Welch Utimate C18 150*25*7 μm; mobile phase: [water (FA)-ACN]; gradient: 42%-72% B over 8 min) to give the title compound (160 mg, 71% yield) as yellow solid. $^1$H NMR (400 MHz, $CDCl_3$) δ 9.05 (s, 1H), 8.10 (s, 1H), 7.76-7.69 (m, 1H), 7.31 (d, J=2.4 Hz, 1H), 7.28 (s, 1H), 7.23 (s, 1H), 6.96-6.89 (m, 2H), 6.74 (d, J=8.0 Hz, 1H), 5.22 (dd, J=5.2, 12.8 Hz, 1H), 4.82-4.58 (m, 2H), 4.52-4.43 (m, 1H), 4.40-4.18 (m, 4H), 4.00-3.89 (m, 4H), 3.82-3.69 (m, 3H), 3.43 (s, 3H), 3.10-2.68 (m, 12H), 2.58 (s, 1H), 2.51-2.32 (m, 4H), 2.28-2.06 (m, 6H), 2.00 (dd, J=1.6, 12.4 Hz, 2H), 1.84 (d, J=4.4 Hz, 8H), 1.30 (dd, J=7.6, 14.8 Hz, 5H), 1.12 (d, J=7.2 Hz, 18H), 0.88 (dd, J=7.6, 11.6 Hz, 18H), 0.61-0.52 (m, 3H); LC-MS (ESI) m/z 682.9 (M/2+H).

Step 7-((3S,7aS)-7a-(((7-(8-Ethynyl-7-fluoro-3-hydroxynaphthalen-1-yl)-8-fluoro-4-(piperidin-1-yl)pyrido[4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl) methyl) piperidine-1-carboxylate (Compound 122). To a solution of ((3S,7aS)-7a-(((8-fluoro-7-(7-fluoro-8-((triisopropylsilyl) ethynyl)-3-((triisopropylsilyl)oxy) naphthalen-1-yl)-4-(piperidin-1-yl)pyrido[4,3-d]pyrimidin-2-yl)oxy) methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (160 mg, 117 μmol) in DMSO (2 mL) was added CsF (53.4 mg, 351 μmol). The mixture was stirred at 25° C. for 1 hr. On completion, the reaction mixture was filtered and the filtrate was concentrated in vacuo to give a residue. The residue was purified by prep-HPLC (column: CD04-Welch Utimate C18 150*25*7 μm; mobile phase: [water (FA)-ACN]; gradient: 9%-39% B over 8 min) to give the title compound (78.7 mg, 60% yield, FA salt) as yellow solid. $^1$H NMR (400 MHz, DMSO-$d_6$) δ 11.08 (s, 1H), 10.33-10.01 (m, 1H), 8.98 (s, 1H), 7.97 (dd, J=6.0, 9.2 Hz, 1H), 7.46 (t, J=9.2 Hz, 1H), 7.39 (d, J=2.4 Hz, 1H), 7.19 (d, J=2.4 Hz, 1H), 7.08 (s, 1H), 7.00 (d, J=8.0 Hz, 1H), 6.90 (d, J=7.6 Hz, 1H), 5.33 (dd, J=5.2, 12.8 Hz, 1H), 4.25-4.10 (m, 4H), 4.00-3.89 (m, 7H), 3.48-3.37 (m, 3H), 2.96 (d, J=10.4 Hz, 2H), 2.91 (s, 8H), 2.18 (d, J=4.8 Hz, 2H), 2.11-1.97 (m, 4H), 1.85-1.67 (m, 20H), 1.61-1.53 (m, 1H), 1.03-0.92 (m, 2H); LC-MS (ESI) m/z 1051.5 (M+H)$^+$.

Example 44. Synthesis of Compound 123

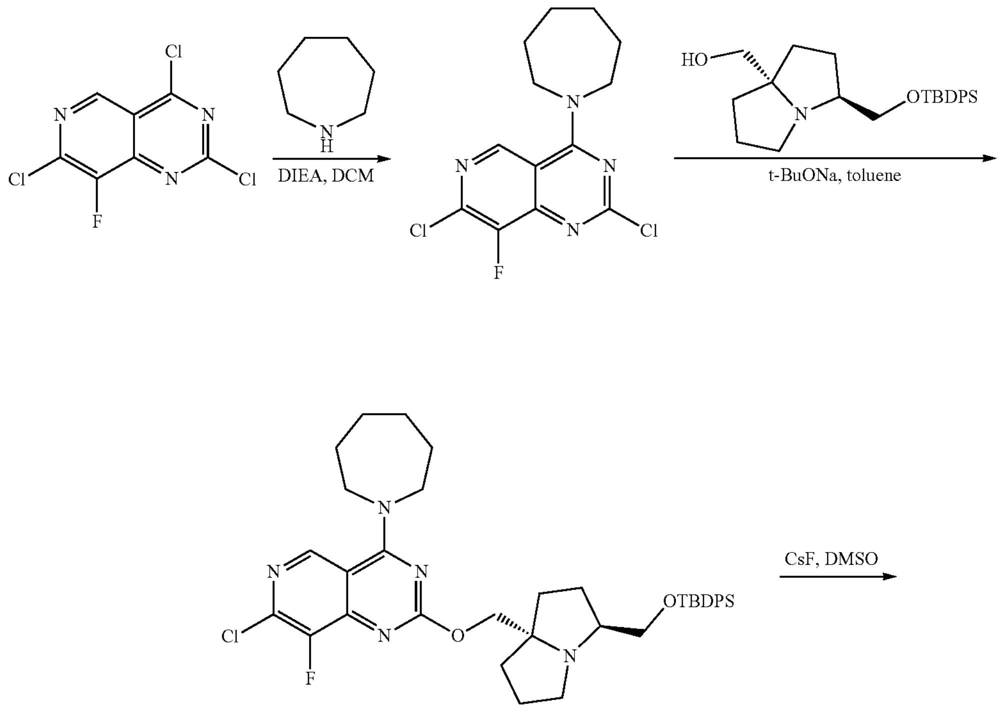

-continued
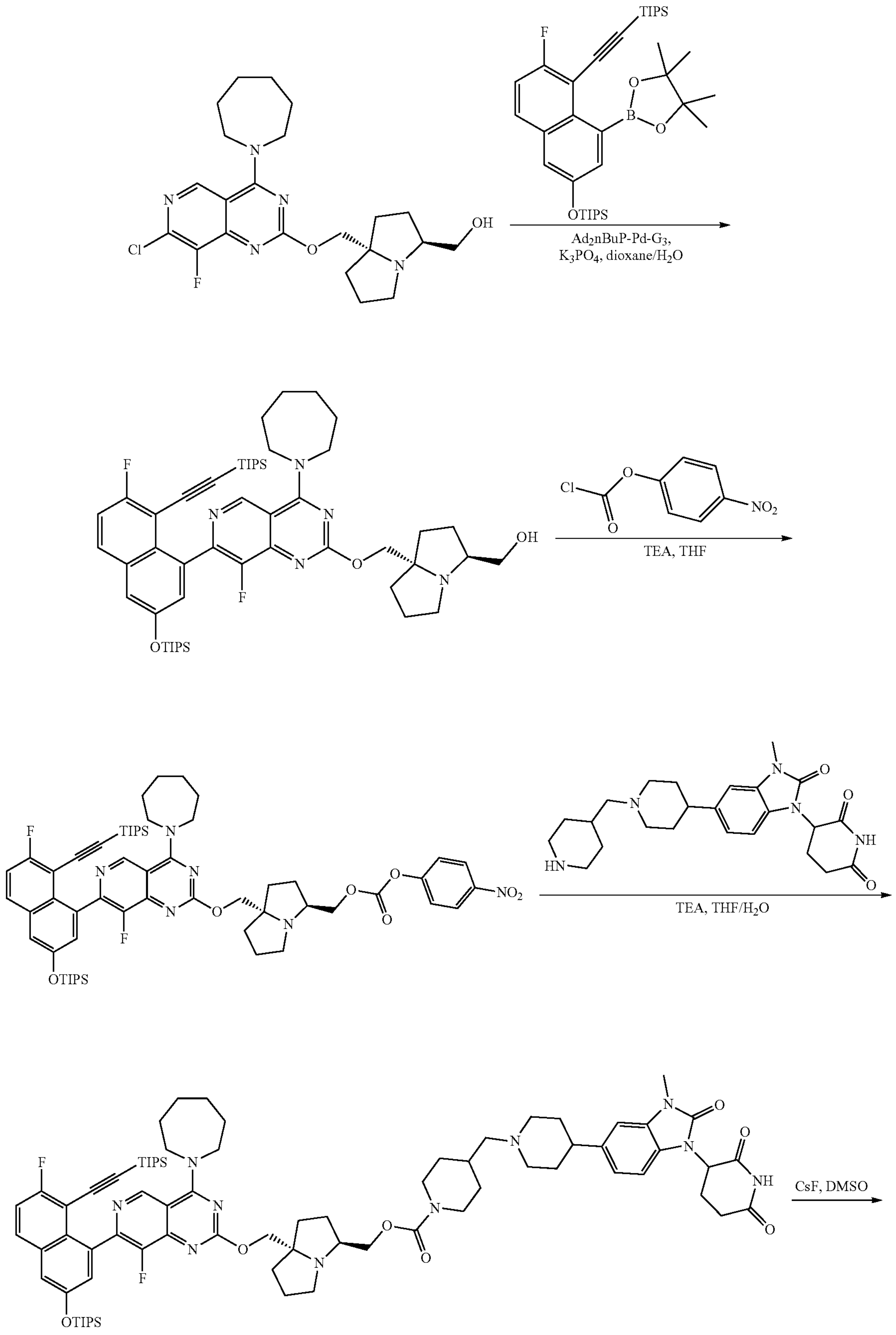

-continued

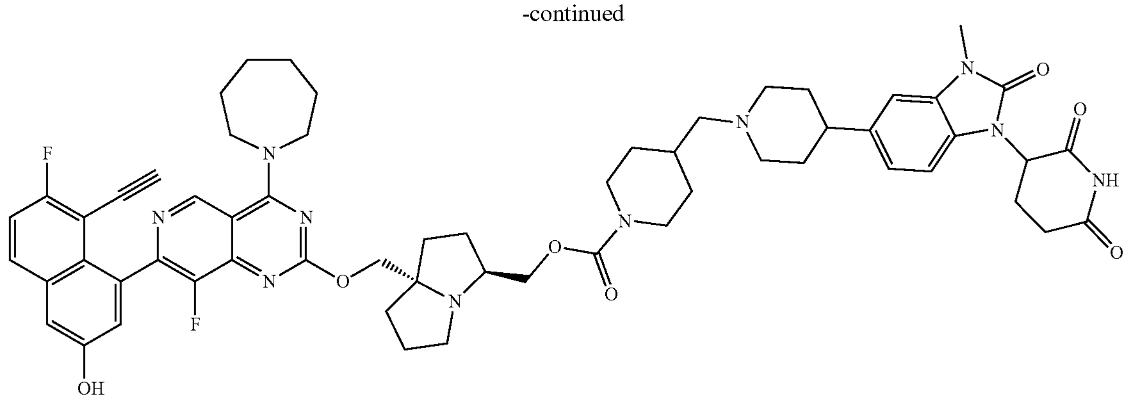

123

Step 1-4-(Azepan-1-yl)-2,7-dichloro-8-fluoropyrido[4,3-d]pyrimidine. To a solution of 2,4,7-trichloro-8-fluoropyrido[4,3-d]pyrimidine (2.00 g, 7.92 mmol, CAS #2454396-80-4) in DCM (20 mL) was added DIEA (3.07 g, 23.7 mmol, 4.14 mL) and azepane (785 mg, 7.92 mmol, 892 μL, CAS #111-49-9) at −40° C. The reaction mixture was stirred at −40° C. for 0.5 hr. On completion, the reaction mixture was quenched by $H_2O$ (1 mL), then diluted with water (50 mL) and extracted with DCM (2×100 mL), the combined organic layers were washed with brine (2×150 mL). The combined organic layers were dried over anhydrous $Na_2SO_4$, filtered and the filtrate was concentrated in vacuo to give a residue. The residue was purified by column chromatography ($SiO_2$, PE:EA=1:0 to PE:EA=2:1) to give the title compound (2.30 g, 92% yield) as yellow solid. $^1H$ NMR (400 MHz, $CDCl_3$) δ 8.94 (s, 1H), 4.05-3.95 (m, 4H), 2.01 (s, 4H), 1.75-1.63 (m, 4H).

Step 2-4-(Azepan-1-yl)-2-(((3S,7aS)-3-(((tert-butyldiphenylsilyl)oxy)methyl)tetrahydro-1H-pyrrolizin-7a (5H)-yl) methoxy)-7-chloro-8-fluoropyrido[4,3-d]pyrimidine. To a solution of ((3S,7aS)-3-(((tert-butyldiphenylsilyl)oxy) methyl)tetrahydro-1H-pyrrolizin-7a (5H)-yl) methanol (2.78 g, 6.78 mmol) in toluene (17 mL) was added t-BuONa (1.09 g, 11.3 mmol) at 0° C. The reaction mixture was stirred at 0° C. for 0.5 hr. Then 4-(azepan-1-yl)-2,7-dichloro-8-fluoropyrido[4,3-d]pyrimidine (1.78 g, 5.65 mmol) was added to the mixture. The reaction mixture was stirred at 0° C. for 1.5 hrs. On completion, the reaction mixture was filtered and the filtrate was concentrated in vacuo to give a residue. The residue was diluted with water (80 mL) and extracted with EA (2×100 mL), the combined organic layers were washed with brine (2×150 mL). The combined organic layers were dried over anhydrous $Na_2SO_4$, filtered and the filtrate was concentrated in vacuo to give a residue. The residue was purified by column chromatography ($SiO_2$, DCM:EA=1:0 to DCM:EA=88:12) to give the title compound (3.58 g, 92% yield) as yellow solid. LC-MS (ESI) m/z 688.4 $(M+H)^+$.

Step 3-((3S,7aS)-7a-(((4-(Azepan-1-yl)-7-chloro-8-fluoropyrido[4,3-d]pyrimidin-2-yl)oxy)methyl)hexahydro-1H-pyrrolizin-3-yl) methanol. To a solution of 4-(azepan-1-yl)-2-(((3S,7aS)-3-(((tert-butyldiphenylsilyl)oxy)methyl) tetrahydro-1H-pyrrolizin-7a (5H)-yl) methoxy)-7-chloro-8-fluoropyrido[4,3-d]pyrimidine (3.08 g, 4.47 mmol) in DMSO (30 mL) was added CsF (2.04 g, 13.4 mmol). The reaction mixture was stirred at 30° C. for 2 hrs. On completion, the reaction mixture was concentrated in vacuo to give a residue. The residue was diluted with water (100 mL) and extracted with EA (2×200 mL). The combined organic layers were washed with brine (2×100 mL). The combined organic layers was dried over anhydrous $Na_2SO_4$, filtered and the filtrate was concentrated in vacuo to give a residue. The residue was purified by column chromatography ($SiO_2$, DCM:MeOH=1:0 to DCM:MeOH=10:1) to give the title compound (1.27 g, 63% yield) as yellow solid. LC-MS (ESI) m/z 450.1 $(M+H)^+$.

Step 4-((3S,7aS)-7a-(((4-(Azepan-1-yl)-8-fluoro-7-(7-fluoro-8-((triisopropylsilyl) ethynyl)-3-((triisopropylsilyl) oxy) naphthalen-1-yl)pyrido[4,3-d]pyrimidin-2-yl)oxy) methyl)hexahydro-1H-pyrrolizin-3-yl) methanol. To a solution of ((3S,7aS)-7a-(((4-(azepan-1-yl)-7-chloro-8-fluoropyrido[4,3-d]pyrimidin-2-yl)oxy)methyl)hexahydro-1H-pyrrolizin-3-yl) methanol (400 mg, 888 μmol) and ((6-fluoro-4-(4,4,5,5-tetramethyl-1,3,2-dioxaborolan-2-yl)-5-((triisopropylsilyl) ethynyl) naphthalen-2-yl)oxy) triisopropylsilane (833 mg, 1.33 mmol, CAS #2791277-41-1) in dioxane (4 mL) was added [2-(2-aminophenyl)phenyl] palladium (1+); bis(1-adamantyl)-butyl-phosphane; methanesulfonate (64.7 mg, 88.9 μmol) and $K_3PO_4$ (1.5 M, 1.78 mL). The reaction mixture was stirred at 80° C. for 0.5 hr under $N_2$ atmosphere. On completion, the reaction mixture was concentrated in vacuo to give a residue. The residue was diluted with water (20 mL) and extracted with EA (2×30 mL). The combined organic layers were washed with brine (2×25 mL). The combined organic layers were dried over anhydrous $Na_2SO_4$, filtered and the filtrate was concentrated in vacuo to give a residue. The residue was purified by column chromatography ($SiO_2$, PE:EA=50:1 to PE:EA=0:1) to give the title compound (570 mg, 70% yield) as brown solid. LC-MS (ESI) m/z 913.7 $(M+H)^+$.

Step 5-((3S,7aS)-7a-(((4-(Azepan-1-yl)-8-fluoro-7-(7-fluoro-8-((triisopropylsilyl) ethynyl)-3-((triisopropylsilyl) oxy) naphthalen-1-yl)pyrido[4,3-d]pyrimidin-2-yl)oxy) methyl)hexahydro-1H-pyrrolizin-3-yl)methyl (4-nitrophenyl) carbonate. To a solution of ((3S,7aS)-7a-(((4-(azepan-1-yl)-8-fluoro-7-(7-fluoro-8-((triisopropylsilyl) ethynyl)-3-((triisopropylsilyl)oxy) naphthalen-1-yl) pyrido[4,3-d]pyrimidin-2-yl)oxy)methyl)hexahydro-1H-pyrrolizin-3-yl) methanol (150 mg, 164 μmol) in THF (15 mL) was added TEA (124 mg, 1.23 mmol) and (4-nitrophenyl) carbonochloridate (66.2 mg, 328 μmol, CAS #7693-46-1). The reaction mixture was stirred at 25° C. for 12 hrs. On completion, the reaction mixture was concentrated in vacuo to give a residue. The residue was diluted with water (50 mL) and extracted with DCM (2×80 mL). The combined organic layers were dried over anhydrous $Na_2SO_4$, filtered and the filtrate was concentrated in vacuo to give the title compound (177 mg, 99% yield) as yellow oil. LC-MS (ESI) m/z 1077.5 $(M+H)^+$.

Step 6-((3S,7aS)-7a-(((4-(Azepan-1-yl)-8-fluoro-7-(7-fluoro-8-((triisopropylsilyl) ethynyl)-3-((triisopropylsilyl) oxy) naphthalen-1-yl)pyrido[4,3-d]pyrimidin-2-yl)oxy) methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate. To a solution of 3-(3-methyl-2-oxo-5-(1-(piperidin-4-ylmethyl) piperidin-4-yl)-2,3-dihydro-1H-benzo[d]imidazol-1-yl) piperidine-2,6-dione (128 mg, 232 μmol, TFA salt) in THF (4 mL) and $H_2O$ (1 mL) was added TEA (47.0 mg, 464 μmol, 64.7 μL) and ((3S,7aS)-7a-(((4-(azepan-1-yl)-8-fluoro-7-(7-fluoro-8-((triisopropylsilyl) ethynyl)-3-((triisopropylsilyl)oxy) naphthalen-1-yl)pyrido [4,3-d]pyrimidin-2-yl)oxy)methyl)hexahydro-1H-pyrrolizin-3-yl)methyl (4-nitrophenyl) carbonate (167 mg, 155 μmol). The reaction mixture was stirred at 25° C. for 0.5 hr. On completion, the reaction mixture was concentrated in vacuo to give a residue. The residue was purified by reverse phase (0.1% FA condition) to give the title compound (155 mg, 72% yield) as yellow solid. LC-MS (ESI) m/z 1378.8 $(M+H)^+$.

Step 7-((3S,7aS)-7a-(((4-(Azepan-1-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl) methyl4-((4-(1-(2,6-dioxopiperidin-3-yl)-3-methyl-2-oxo-2,3-dihydro-1H-benzo[d]imidazol-5-yl) piperidin-1-yl) methyl) piperidine-1-carboxylate (Compound 123). To a solution of ((3S,7aS)-7a-(((4-(azepan-1-yl)-8-fluoro-7-(7-fluoro-8-((triisopropylsilyl) ethynyl)-3-((triisopropylsilyl) oxy) naphthalen-1-yl)pyrido[4,3-d]pyrimidin-2-yl)oxy) methyl) hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (150 mg, 108 μmol) in DMSO (2 mL) was added CsF (49.6 mg, 326 μmol). The reaction mixture was stirred at 35° C. for 1 hr. On completion, the reaction mixture was filtered and the filtrate was concentrated in vacuo to give a residue. The residue was purified by prep-HPLC (column: CD04-Welch Utimate C18 150*25*7 μm; mobile phase: [water (FA)-ACN]; gradient: 9%-39% B over 8 min) to give the title compound (48.6 mg, 38% yield, FA salt) as yellow solid. 1H NMR (400 MHz, DMSO-$d_6$) δ 11.08 (s, 1H), 10.24-10.05 (m, 1H), 9.10 (s, 1H), 7.97 (dd, J=6.0, 9.2 Hz, 1H), 7.46 (t, J=9.2 Hz, 1H), 7.39 (d, J=2.4 Hz, 1H), 7.17 (d, J=2.4 Hz, 1H), 7.08 (s, 1H), 7.00 (d, J=8.0 Hz, 1H), 6.90 (d, J=7.6 Hz, 1H), 5.33 (dd, J=5.2, 12.8 Hz, 1H), 4.32-4.12 (m, 4H), 4.07-3.90 (m, 7H), 3.53-3.39 (m, 2H), 3.32 (s, 3H), 3.03-2.84 (m, 5H), 2.82-2.61 (m, 4H), 2.20 (s, 2H), 2.12-1.91 (m, 8H), 1.88-1.56 (m, 18H), 1.07-0.90 (m, 2H); LC-MS $(ESI^+)$ m/z 1065.6 $(M+H)^+$.

Example 45. Synthesis of Compound 124

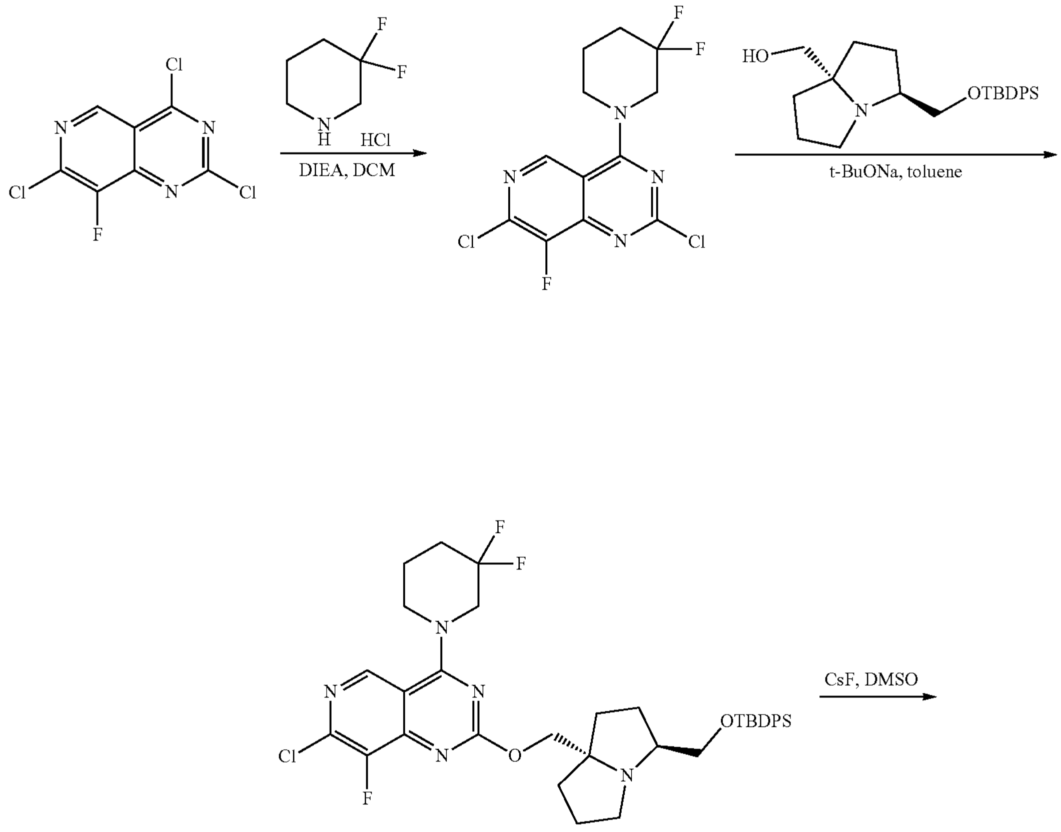

-continued
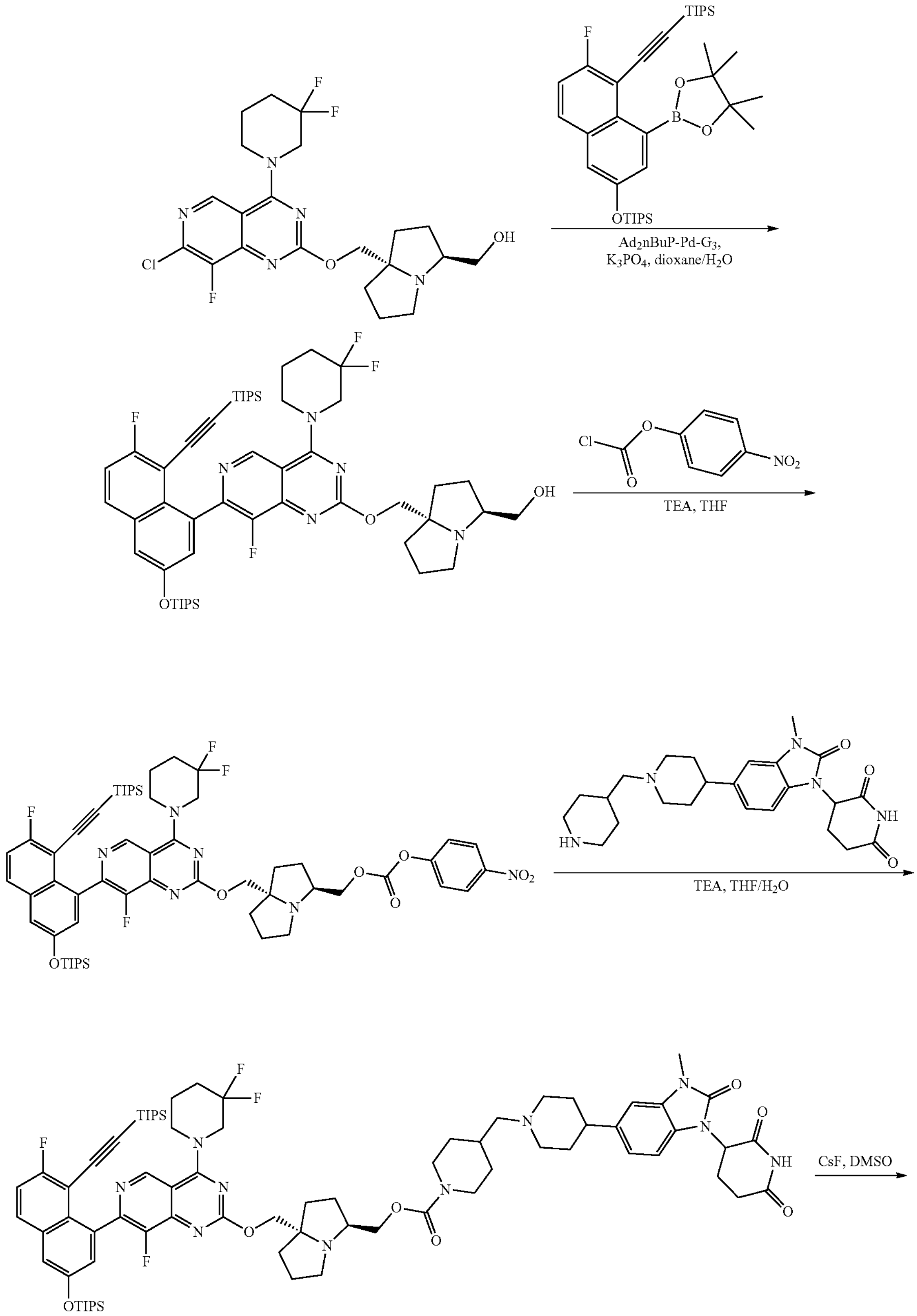

-continued

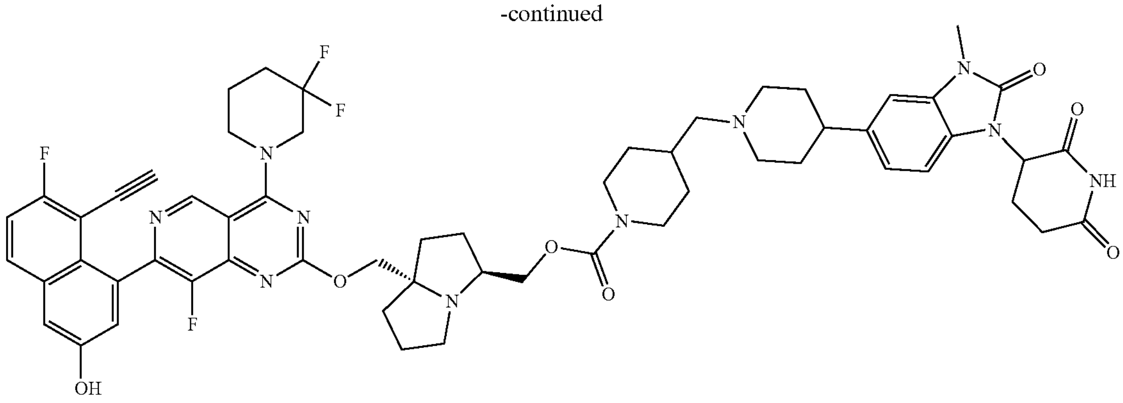

124

Step 1-2,7-Dichloro-4-(3,3-difluoropiperidin-1-yl)-8-fluoropyrido[4,3-d]pyrimidine. To a solution of 2,4,7-trichloro-8-fluoro-pyrido[4,3-d]pyrimidine (2.00 g, 7.92 mmol, CAS #2454396-80-4) and 3,3-difluoropiperidine; hydrochloride (1.37 g, 8.71 mmol, CAS #496807-97-7) in DCM (50 mL) was added DIEA (3.07 g, 23.7 mmol, 4.14 mL) at 0° C., the mixture was stirred at 0° C. for 0.5 hr. On completion, the reaction was diluted with water (20 mL), then the residue was extracted with DCM (3×30 mL). The combined organic layers was dried over $Na_2SO_4$, filtered and the filtrate was concentrated in vacuo to give a residue. The crude product was triturated with PE:EA=5:1 (10 mL: 2 mL) at 25° C. for 30 mins, then the residue was re-purified by column chromatography ($SiO_2$, DCM:EA=1:0) to give the title compound (2.40 g, 89% yield) as yellow solid. $^1H$ NMR (400 MHz, $CDCl_3$) δ 8.92 (s, 1H), 4.17 (t, J=10.8 Hz, 2H), 3.99-3.95 (m, 2H), 2.30-2.20 (m, 2H), 2.12-2.06 (m, 2H).

Step 2-2-(((3S,7aS)-3-(((Tert-butyldiphenylsilyl)oxy)methyl)tetrahydro-1H-pyrrolizin-7a (5H)-yl) methoxy)-7-chloro-4-(3,3-difluoropiperidin-1-yl)-8-fluoropyrido[4,3-d]pyrimidine. To a solution of ((3S,7aS)-3-(((tert-butyldiphenylsilyl)oxy)methyl)tetrahydro-1H-pyrrolizin-7a (5H)-yl) methanol ((3S,7aS)-3-(((tert-butyldiphenylsilyl)oxy)methyl)tetrahydro-1H-pyrrolizin-7a (5H)-yl) methanol (2.43 g, 5.93 mmol) in toluene (40 mL) was added t-BuONa (1.14 g, 11.8 mmol) at 0° C. The mixture was stirred at 0° C. for 0.5 hr, the 2,7-dichloro-4-(3,3-difluoro-1-piperidyl)-8-fluoro-pyrido[4,3-d]pyrimidine (2.00 g, 5.93 mmol) was added into above solution, the mixture was stirred at 0° C. for 1 hr. On completion, the mixture was diluted with $H_2O$ (50 mL), extracted with EA (3×50 mL), the organic layer was washed with brine (50 mL), dried with anhydrous $Na_2SO_4$, filtered and the filtrate was concentrated in vacuo. The residue was purified by column chromatography ($SiO_2$, DCM:MeOH=82:18) to give the title compound (3.10 g, 73% yield) as yellow oil. $^1H$ NMR (400 MHz, $CDCl_3$) δ 8.78 (s, 1H), 7.68 (t, J=5.6 Hz, 4H), 7.47-7.34 (m, 6H), 4.35-4.28 (m, 1H), 4.25 (s, 1H), 4.06 (t, J=11.2 Hz, 2H), 3.99 (dd, J=4.8, 10.4 Hz, 1H), 3.85 (d, J=4.8 Hz, 2H), 3.40-3.20 (m, 1H), 2.87-2.74 (m, 1H), 2.19 (dt, J=6.4, 12.8 Hz, 3H), 2.11-1.98 (m, 3H), 1.97-1.41 (m, 8H), 1.06 (s, 9H).

Step 3-((3S,7aS)-7a-(((7-Chloro-4-(3,3-difluoropiperidin-1-yl)-8-fluoropyrido[4,3-d]pyrimidin-2-yl)oxy)methyl) hexahydro-1H-pyrrolizin-3-yl) methanol. To a solution of 2-(((3S,7aS)-3-(((tert-butyldiphenylsilyl)oxy)methyl)tetrahydro-1H-pyrrolizin-7a (5H)-yl) methoxy)-7-chloro-4-(3,3-difluoropiperidin-1-yl)-8-fluoropyrido[4,3-d]pyrimidine (600 mg, 844 μmol) in DMSO (1 mL) was added CsF (384 mg, 2.53 mmol). The mixture was stirred at 25° C. for 0.5 hr. On completion, the mixture was diluted with $H_2O$ (50 mL), adjusted pH=3-4 with FA, extracted with EA (3×50 mL), then the $H_2O$ phase was adjusted pH=7-8 with $NH_3 \cdot H_2O$, extracted with EA (3×50 mL), the organic layer was washed with brine (20 mL), dried with anhydrous $Na_2SO_4$, filtered and the filtrate was concentrated in vacuo to give the title compound (335 mg, 84% yield) as yellow oil. $^1H$ NMR (400 MHz, DMSO-$d_6$) δ 8.78 (s, 1H), 4.40-4.32 (m, 1H), 4.29-4.22 (m, 1H), 4.07 (t, J=11.2 Hz, 2H), 3.92-3.78 (m, 4H), 3.44-3.35 (m, 1H), 3.07-3.00 (m, 1H), 2.80-2.70 (m, 1H), 2.27-2.15 (m, 4H), 2.11-2.06 (m, 2H), 1.92-1.81 (m, 4H), 1.67-1.56 (m, 2H).

Step 4-((3S,7aS)-7a-(((4-(3,3-Difluoropiperidin-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy)methyl)hexahydro-1H-pyrrolizin-3-yl) methanol. A mixture of ((3S,7aS)-7a-(((7-chloro-4-(3,3-difluoropiperidin-1-yl)-8-fluoropyrido[4,3-d]pyrimidin-2-yl)oxy)methyl) hexahydro-1H-pyrrolizin-3-yl) methanol (280 mg, 593 μmol), [6-fluoro-4-(4,4,5,5-tetramethyl-1,3,2-dioxaborolan-2-yl)-5-(2-triisopropylsilylethynyl)-2-naphthyl]oxy-triisopropyl-silane (556 mg, 890 μmol, CAS #2791277-41-1), [2-(2-aminophenyl)phenyl]palladium (1+); bis(1-adamantyl)-butyl-phosphane; methanesulfonate (43.2 mg, 59.3 μmol), $K_3PO_4/H_2O$ (1.5 M, 395 μL) in dioxane (7 mL) was degassed and purged with $N_2$ for 3 times, and then the mixture was stirred at 80° C. for 3 hrs under $N_2$ atmosphere. On completion, the mixture was diluted with $H_2O$ (20 mL), extracted with EA (3×50 mL), the organic layer was washed with brine (50 mL), dried with anhydrous $Na_2SO_4$, filtered and the filtrate was concentrated in vacuo. The residue was purified by column chromatography ($SiO_2$, DCM: MeOH=75:25) to give the title compound (60 mg, 10% yield) as brown solid. $^1H$ NMR (400 MHz, DMSO-$d_6$) δ 9.14 (s, 1H), 7.78-7.71 (m, 1H), 7.33 (d, J=2.0 Hz, 1H), 7.25-7.21 (m, 2H), 4.41-4.26 (m, 2H), 4.17-4.09 (m, 2H), 4.08-4.03 (m, 1H), 3.97-3.87 (m, 2H), 3.79-3.70 (m, 2H), 3.21-3.08 (m, 1H), 2.52-2.39 (m, 2H), 2.21-2.14 (m, 4H), 1.91-1.82 (m, 8H), 1.36-1.30 (m, 3H), 1.13 (d, J=7.2 Hz, 18H), 0.87 (dd, J=7.6, 14.8 Hz, 18H), 0.59-0.49 (m, 3H).

Step 5-((3S,7aS)-7a-(((4-(3,3-Difluoropiperidin-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy)methyl)hexahydro-1H-pyrrolizin-3-yl)methyl (4-nitrophenyl) carbonate. To a solution of ((3S,7aS)-7a-(((4-(3,3-difluoropiperidin-1-yl)-8-fluoro-7-(7-fluoro-8-

((triisopropylsilyl) ethynyl)-3-((triisopropylsilyl)oxy) naphthalen-1-yl)pyrido[4,3-d]pyrimidin-2-yl)oxy)methyl) hexahydro-1H-pyrrolizin-3-yl) methanol (60.0 mg, 64.2 µmol) and (4-nitrophenyl) carbonochloridate (51.7 mg, 256 µmol, CAS #7693-46-1) in DCM (5 mL) was added DMAP (784 µg, 6.42 µmol) and TEA (363 mg, 3.59 mmol, 500 µL). The mixture was stirred at 25° C. for 16 hrs. On completion, the mixture was diluted with $H_2O$ (20 mL), extracted with DCM (3×10 mL), the organic layer was washed with brine (3×10 mL), dried with anhydrous $Na_2SO_4$, filtered and the filtrate was concentrated in vacuo to give the title compound (60.0 mg, 84% yield) as yellow solid. LC-MS (ESI) m/z 1099.5 $(M+H)^+$.

Step 6-((3S,7aS)-7a-(((4-(3,3-Difluoropiperidin-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate. To a solution of ((3S,7aS)-7a-(((4-(3,3-difluoropiperidin-1-yl)-8-fluoro-7-(7-fluoro-8-((triisopropylsilyl) ethynyl)-3-((triisopropylsilyl)oxy) naphthalen-1-yl)pyrido[4,3-d]pyrimidin-2-yl)oxy)methyl)hexahydro-1H-pyrrolizin-3-yl)methyl (4-nitrophenyl) carbonate (60.0 mg, 54.5 µmol) and 3-[3-methyl-2-oxo-5-[1-(4-piperidylmethyl)-4-piperidyl]benzimidazol-1-yl]piperidine-2,6-dione (45.3 mg, 81.8 µmol, TFA) in THF (4 mL) and $H_2O$ (0.5 mL) was added TEA (16.5 mg, 163 µmol). The mixture was stirred at 25° C. for 3 hrs. On completion, the mixture was concentrated in vacuo. The residue was purified by prep-HPLC (column: CD04-Welch Utimate C18 150*25*7 µm; mobile phase: [water (FA)-ACN]; gradient: 40%-70% B over 8 min) to give the title compound (35.0 mg, 45% yield) as white solid. LC-MS (ESI) m z 1400.8 $(M+H)^+$.

Step 7-((35,7aS)-7a-(((4-(3,3-Difluoropiperidin-1-yl)-7-(8-ethynyl-7-fluoro-3-hydroxynaphthalen-1-yl)-8-fluoro-pyrido[4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (Compound 124). To a solution of ((3S,7aS)-7a-(((4-(3,3-difluoropiperidin-1-yl)-8-fluoro-7-(7-fluoro-8-((triisopropylsilyl) ethynyl)-3-((triisopropylsilyl)oxy) naphthalen-1-yl)pyrido [4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (30.0 mg, 21.4 µmol) in DMSO (1 mL) was added CsF (9.77 mg, 64.2 µmol). The mixture was stirred at 25° C. for 1 hr. On completion, the mixture was filtered and the filtrate was purified by prep-HPLC (column: CD04-Welch Utimate C18 150*25*7 µm; mobile phase: [water (FA)-ACN]; gradient: 9%-39% B over 8 min) to give the title compound (22.7 mg, 92% yield, FA salt) as yellow solid. $^1H$ NMR (400 MHz, DMSO-$d_6$) δ 11.08 (s, 1H), 10.19 (s, 1H), 9.08 (s, 1H), 8.03-7.93 (m, 1H), 7.47 (t, J=9.2 Hz, 1H), 7.41 (d, J=2.4 Hz, 1H), 7.21 (d, J=2.0 Hz, 1H), 7.07 (s, 1H), 7.01 (d, J=8.1 Hz, 1H), 6.90 (d, J=7.6 Hz, 1H), 5.34 (dd, J=5.2, 12.4 Hz, 1H), 4.53-4.13 (m, 6H), 4.06-3.93 (m, 4H), 3.91 (s, 1H), 3.33 (s, 5H), 3.21-2.97 (m, 3H), 2.97-2.73 (m, 4H), 2.72-2.58 (m, 3H), 2.31-2.10 (m, 5H), 2.07-1.97 (m, 4H), 1.95-1.48 (m, 14H), 1.10-0.93 (m, 2H); LC-MS ($ESI^+$) m/z 1087.4 $(M+H)^+$.

Example 46. Synthesis of Compound 125

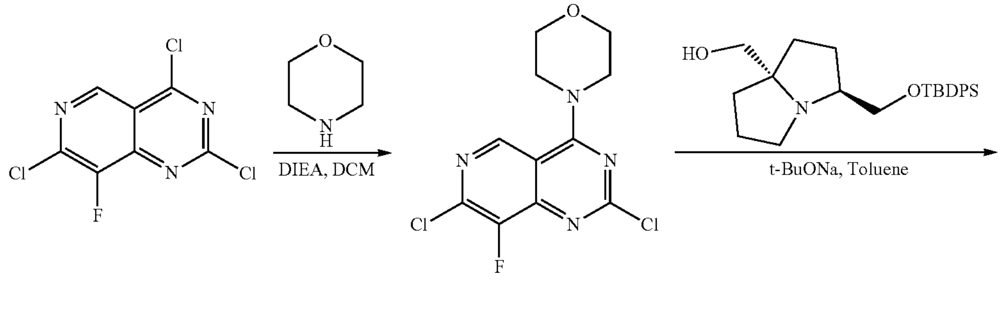

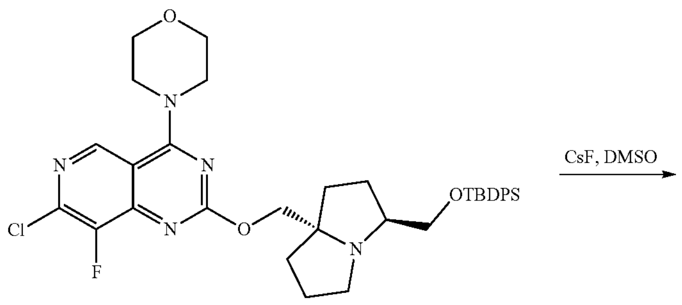

-continued
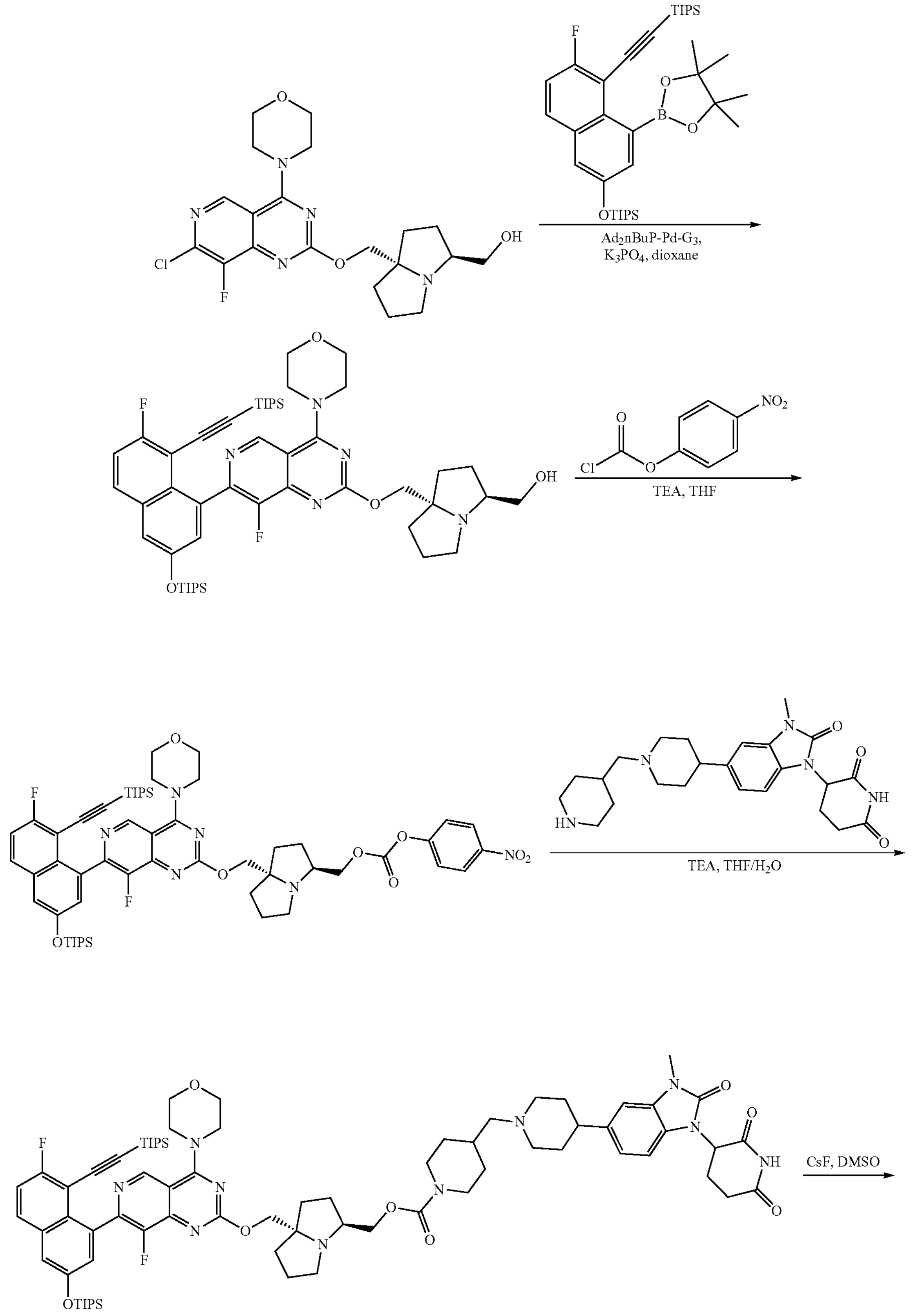

-continued

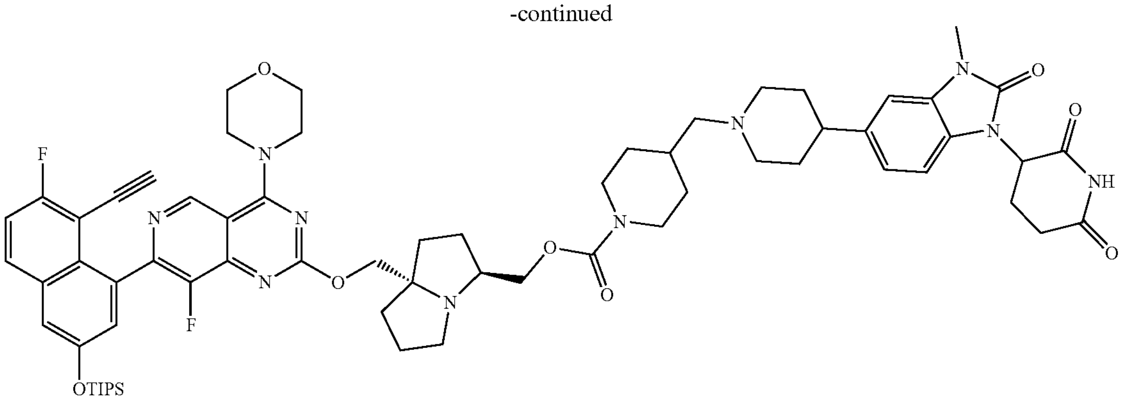

125

Step 1-4-(2,7-Dichloro-8-fluoro-pyrido[4,3-d]pyrimidin-4-yl) morpholine. To a solution of 2,4,7-trichloro-8-fluoro-pyrido[4,3-d]pyrimidine (5.00 g, 19.8 mmol, CAS #2454396-80-4) in DCM (50 mL) was added DIEA (17.9 g, 138 mmol, 24.1 mL) and morpholine (1.73 g, 19.8 mmol, 1.7 mL, CAS #110-91-8). The mixture was stirred at 25° C. for 0.5 hr. On completion, the reaction mixture was concentrated in vacuo to give a residue. The crude product was triturated with PE:EA=7:1 at 25° C. for 15 mins to give the title compound (5.70 g, 94% yield) as yellow solid. 1H NMR (400 MHz, $CDCl_3$) δ 8.87 (s, 1H), 4.13-4.08 (m, 4H), 3.91-3.87 (m, 4H).

Step 2-4-(2-(((35,7aS)-3-(((Tert-butyldiphenylsilyl)oxy) methyl)tetrahydro-1H-pyrrolizin-7a (5H)-yl) methoxy)-7-chloro-8-fluoropyrido[4,3-d]pyrimidin-4-yl) morpholine. To a solution of ((3S,7aS)-3-(((tert-butyldiphenylsilyl)oxy) methyl)tetrahydro-1H-pyrrolizin-7a (5H)-yl) methanol (1.00 g, 2.44 mmol) in Tol. (10 mL) was added t-BuONa (703 mg, 7.32 mmol) and 4-(2,7-dichloro-8-fluoro-pyrido [4,3-d]pyrimidin-4-yl) morpholine (961 mg, 3.17 mmol). The mixture was stirred at 0° C. for 1 hr. On completion, the reaction mixture was quenched by $H_2O$ (100 mL), and then extracted with EA (3×100 mL), the combined organic layers were washed with brine (3×100 mL), dried over anhydrous sodium sulfate, filtered and the filtrate was concentrated in vacuo to give a residue. The residue was purified by column chromatography ($SiO_2$, Petroleum ether/Ethyl acetate=100/1 to 5/1) to give the title compound (800 mg, 48% yield) as a white solid. $^1H$ NMR (400 MHz, $CDCl_3$) δ 8.74 (s, 1H), 7.70-7.65 (m, 4H), 7.43-7.38 (m, 6H), 4.33-4.16 (m, 2H), 4.00-3.95 (m, 4H), 3.88-3.84 (m, 4H), 3.82-3.76 (m, 1H), 3.35-3.10 (m, 1H), 2.82 (d, J=4.0 Hz, 2H), 2.21-2.17 (m, 1H), 1.99-1.74 (m, 8H), 1.06 (s, 9H).

Step 3-((3S,7aS)-7A-(((7-Chloro-8-fluoro-4-morpholino-pyrido[4,3-d]pyrimidin-2-yl)oxy)methyl)hexahydro-1H-pyrrolizin-3-yl) methanol. To a solution of 4-(2-(((3S,7aS)-3-(((tert-butyldiphenylsilyl)oxy)methyl)tetrahydro-1H-pyrrolizin-7a (5H)-yl) methoxy)-7-chloro-8-fluoropyrido[4,3-d]pyrimidin-4-yl) morpholine (618 mg, 913 μmol) in THF (5 mL) was added TBAF (1 M, 2.74 mL). The mixture was stirred at 25° C. for 1 hr. On completion, the reaction mixture was quenched by $H_2O$ (100 mL), and then extracted with DCM (3×100 mL), the combined organic layers were washed with brine (3×100 mL), dried over anhydrous sodium sulfate, filtered and the filtrate was concentrated in vacuo to give a residue. The residue was purified by column chromatography ($SiO_2$, Petroleum ether/Ethyl acetate=100/1 to 0/1) to give the title compound (350 mg, 87% yield) as white solid. $^1H$ NMR (400 MHz, $CDCl_3$) δ 8.74 (s, 1H), 4.41-4.31 (m, 1H), 4.31-4.20 (m, 1H), 4.06-3.98 (m, 4H), 3.92-3.82 (m, 6H), 3.46-3.41 (m, 1H), 3.14-3.03 (m, 1H), 2.83-2.72 (m, 1H), 2.29-2.24 (m, 1H), 2.00-1.78 (m, 6H), 1.71-1.58 (m, 2H).

Step 4-((3S,7aS)-7A-(((8-Fluoro-7-(7-fluoro-8-((triisopropylsilyl) ethynyl)-3-((triisopropylsilyl)oxy) naphthalen-1-yl)-4-morpholinopyrido[4,3-d]pyrimidin-2-yl)oxy) methyl)hexahydro-1H-pyrrolizin-3-yl) methanol. To a solution of ((3S,7aS)-7a-(((7-chloro-8-fluoro-4-morpholinopyrido[4,3-d]pyrimidin-2-yl)oxy)methyl)hexahydro-1H-pyrrolizin-3-yl) methanol (230 mg, 525 μmol) in dioxane (5 mL) and $H_2O$ (1 mL) was added $Ad_2nBuP$ Pd G3 (38.2 mg, 52.5 μmol) and $K_3PO_4$ (334 mg, 1.58 mmol), [6-fluoro-4-(4,4,5,5-tetramethyl-1,3,2-dioxaborolan-2-yl)-5-(2-triisopropylsilylethynyl)-2-naphthyl]oxy-triisopropyl-silane (492 mg, 787 μmol, CAS #2791277-41-1). The mixture was stirred at 100° C. for 1 hr under $N_2$ atmosphere. On completion, the reaction mixture was quenched by $H_2O$ (100 mL), and then extracted with EA (3×100 mL), the combined organic layers were washed with brine (3×100 mL), dried over anhydrous sodium sulfate, filtered and the filtrate was concentrated in vacuo to give a residue. The residue was purified by column chromatography ($SiO_2$, Petroleum ether/Ethyl acetate=100/1 to 0/1) to give the title compound (350 mg, 74% yield) as white solid. $^1H$ NMR (400 MHz, $CDCl_3$) δ 9.05 (s, 1H), 7.73 (dd, J=5.6, 9.2 Hz, 1H), 7.32-7.29 (m, 1H), 7.26-7.22 (m, 1H), 4.44-4.30 (m, 2H), 4.17-4.09 (m, 2H), 3.96-3.84 (m, 8H), 3.60-3.47 (m, 1H), 3.18 (s, 1H), 2.88-2.75 (m, 1H), 2.40-2.24 (m, 2H), 1.95-1.82 (m, 4H), 1.74-1.61 (m, 2H), 1.37-1.23 (m, 4H), 1.13 (d, J=7.2 Hz, 18H), 0.89 (dd, J=7.6, 10.4 Hz, 19H), 0.58-0.51 (m, 3H).

Step 5-((3S,7aS)-7A-(((8-Fluoro-7-(7-fluoro-8-((triisopropylsilyl) ethynyl)-3-((triisopropylsilyl)oxy) naphthalen-1-yl)-4-morpholinopyrido[4,3-d]pyrimidin-2-yl)oxy) methyl)hexahydro-1H-pyrrolizin-3-yl)methyl (4-nitrophenyl) carbonate. To a solution of ((3S,7aS)-7a-(((8-fluoro-7-(7-fluoro-8-((triisopropylsilyl) ethynyl)-3-((triisopropylsilyl)oxy) naphthalen-1-yl)-4-morpholino-pyrido[4,3-d]pyrimidin-2-yl)oxy)methyl)hexahydro-1H-pyrrolizin-3-yl) methanol (60.0 mg, 66.6 μmol) in THF (5 mL) was added TEA (50.5 mg, 499 μmol, 69.5 μL) and (4-nitrophenyl) carbonochloridate (26.8 mg, 133 μmol, CAS #7693-46-1). The mixture was stirred at 25° C. for 1 hr. On completion, the reaction mixture was quenched by $H_2O$ (100 mL), and then extracted with DCM (3×80 mL), the combined organic layers were washed with brine (3×50 mL), dried over anhydrous sodium sulfate, filtered and the filtrate was concentrated in vacuo to give the title compound (71.0 mg, 100% yield) as yellow solid. LC-MS (ESI) m/z 1065.5 $(M+H)^+$.

Step 6-((3S,7aS)-7A-(((8-Fluoro-7-(7-fluoro-8-((triisopropylsilyl) ethynyl)-3-((triisopropylsilyl)oxy) naphthalen-1-yl)-4-morpholinopyrido[4,3-d]pyrimidin-2-yl)oxy) methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazole-5-yl) piperidin-1-yl)methyl) piperidine-1-carboxylate. To a solution of 3-[3-methyl-2-oxo-5-[1-(4-piperidylmethyl)-4-piperidyl]benzimidazol-1-yl]piperidine-2,6-dione (37.1 mg, 84.4 μmol) in THF (5 mL) was added TEA (39.8 mg, 394 μmol, 54.8 μL) and ((3S,7aS)-7a-(((8-fluoro-7-(7-fluoro-8-((triisopropylsilyl) ethynyl)-3-((triisopropylsilyl)oxy) naphthalen-1-yl)-4-morpholinopyrido[4,3-d]pyrimidin-2-yl)oxy)methyl)hexahydro-1H-pyrrolizin-3-yl)methyl (4-nitrophenyl) carbonate (60.0 mg, 56.3 μmol). The mixture was stirred at 25° C. for 0.5 hr. On completion, the reaction mixture was concentrated in vacuo. The crude product was purified by reversed-phase HPLC (0.1% FA condition) to give the title compound (50.0 mg, 65% yield) as white solid. $^1H$ NMR (400 MHz, DMSO-$d_6$) δ 11.08 (s, 1H), 9.19 (s, 1H), 8.18-8.08 (m, 1H), 7.59 (d, J=2.4 Hz, 1H), 7.55 (t, J=8.8 Hz, 1H), 7.20 (d, J=2.4 Hz, 1H), 7.08-6.99 (m, 2H), 6.90 (d, J=8.0 Hz, 1H), 5.34 (dd, J=5.2, 12.4 Hz, 1H), 4.44-4.17 (m, 3H), 4.11-3.98 (m, 4H), 3.95-3.69 (m, 7H), 3.33 (s, 3H), 2.93-2.81 (m, 3H), 2.78-2.61 (m, 4H), 2.61-2.51 (m, 4H), 2.23-2.09 (m, 2H), 2.08-1.64 (m, 16H), 1.37-1.28 (m, 3H), 1.09 (dd, J=1.2, 7.6 Hz, 19H), 1.01 (s, 2H), 0.83 (dd, J=7.6, 11.6 Hz, 19H), 0.59-0.42 (m, 3H).

Step 7-((3S,7aS)-7A-(((7-(8-Ethynyl-7-fluoro-3-hydroxynaphthalen-1-yl)-8-fluoro-4-morpholinopyrido[4,3-d]pyrimidin-2-yl)oxy)methyl)hexahydro-1H-pyrrolizin-3-yl) methyl 4-((4-(1-(2,6-dioxopiperidin-3-yl)-3-methyl-2-oxo-2,3-dihydro-1H-benzo[d]imidazol-5-yl) piperidin-1-yl) methyl) piperidine-1-carboxylate (Compound 18). To a solution of ((3S,7aS)-7a-(((8-fluoro-7-(7-fluoro-8-((triisopropylsilyl) ethynyl)-3-((triisopropylsilyl)oxy) naphthalen-1-yl)-4-morpholinopyrido[4,3-d]pyrimidin-2-yl)oxy) methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazole-5-yl) piperidin-1-yl)methyl) piperidine-1-carboxylate (35.0 mg, 25.6 μmol) in DMSO (3 mL) was added CsF (11.6 mg, 76.8 μmol). The mixture was stirred at 25° C. for 0.5 hr. On completion, the reaction mixture was filtered and the filtrate was purified by reversed-phase HPLC (0.1% FA condition) to give the title compound (16.3 mg, 57% yield, FA salt) as yellow solid. $^1H$ NMR (400 MHz, DMSO-$d_6$) δ 11.08 (s, 1H), 10.03 (s, 1H), 9.08 (s, 1H), 7.97 (dd, J=5.6, 9.2 Hz, 1H), 7.46 (t, J=8.8 Hz, 1H), 7.39 (d, J=2.4 Hz, 1H), 7.19 (d, J=2.4 Hz, 1H), 7.08 (s, 1H), 6.99 (d, J=8.0 Hz, 1H), 6.90 (d, J=8.4 Hz, 1H), 5.33 (dd, J=5.2, 12.8 Hz, 1H), 4.25-4.10 (m, 3H), 4.10-4.04 (m, 1H), 4.02-3.97 (m, 3H), 3.94 (t, J=4.4 Hz, 2H), 3.90 (d, J=4.4 Hz, 1H), 3.87-3.77 (m, 4H), 3.35-3.34 (m, 3H), 2.97-2.87 (m, 3H), 2.82-2.70 (m, 4H), 2.68-2.57 (m, 2H), 2.54 (s, 2H), 2.14 (d, J=5.6 Hz, 2H), 2.08-1.90 (m, 4H), 1.81-1.60 (m, 13H), 1.57-1.46 (m, 1H), 1.23 (s, 1H), 1.04-0.88 (m, 2H); LC-MS ($ESI^+$) m/z 1053.4 $(M+H)^+$.

Example 47. Synthesis of Compound 15

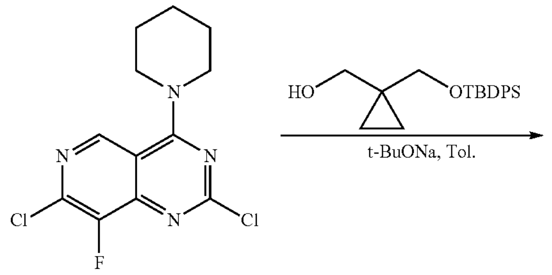

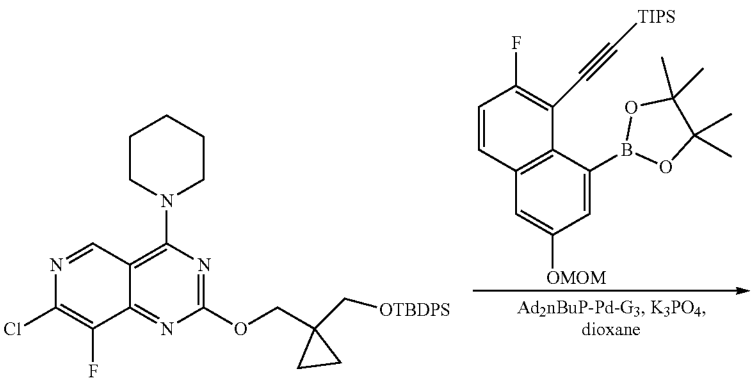

-continued
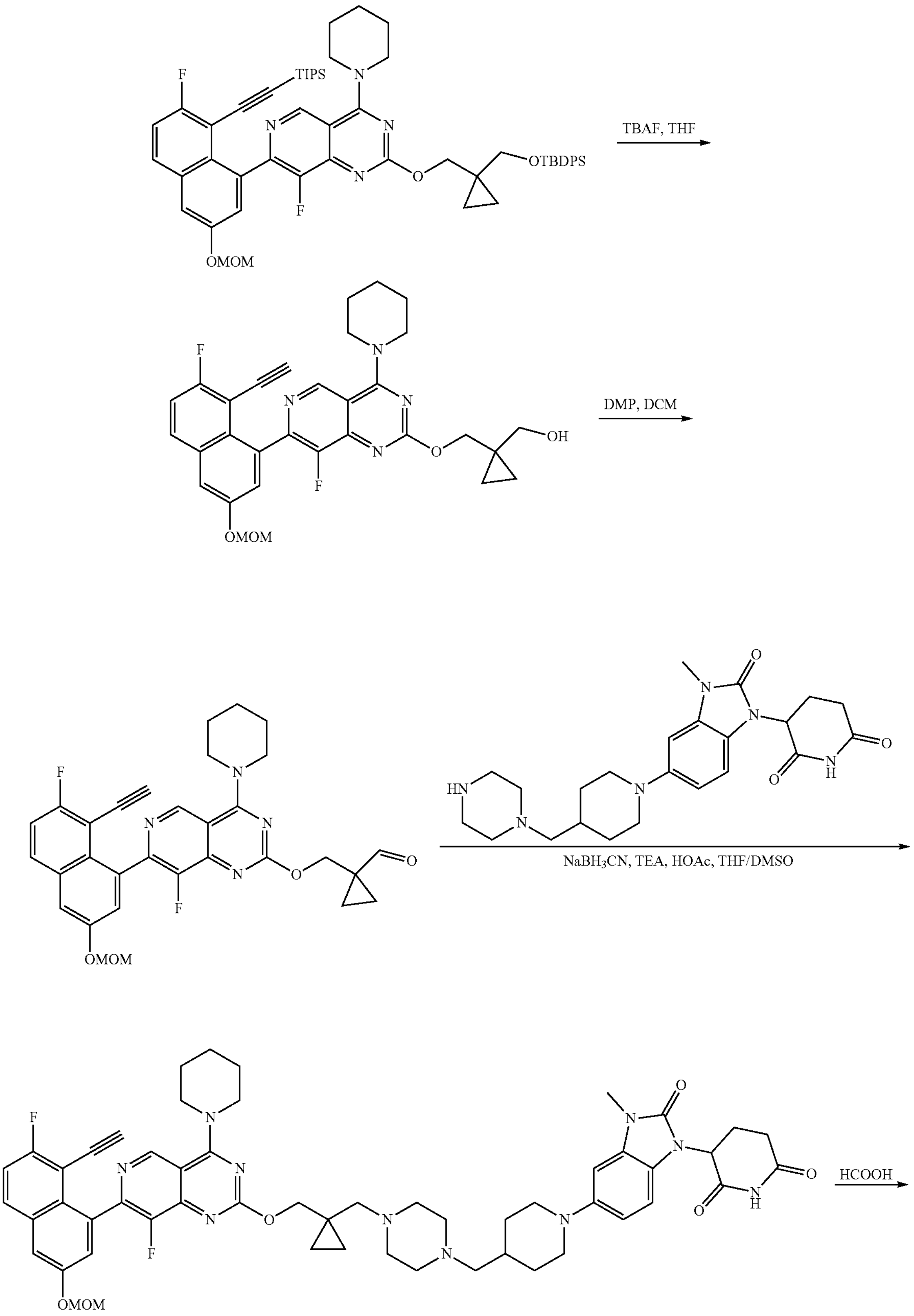

-continued

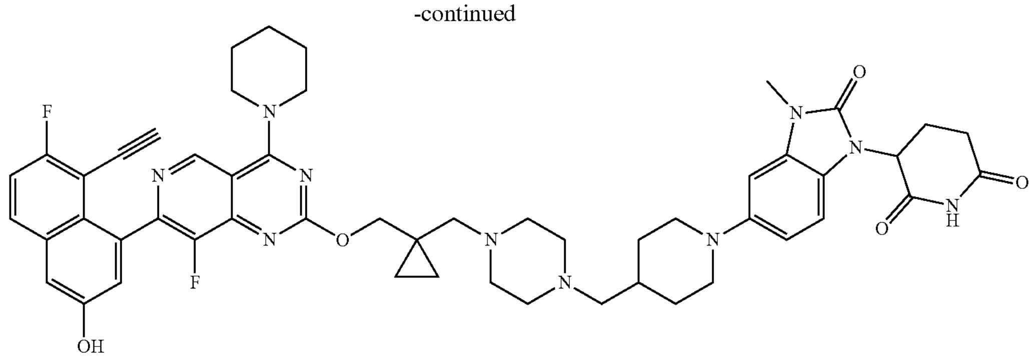

15

Step 1-2-((1-(Tert-butyldiphenylsilyl)oxy) methyl)cyclopropyl) methoxy)-7-chloro-8-fluoro-4-(piperidin-1-yl) pyrido[4,3-d]pyrimidine. To a solution of (1-(((tert-butyldiphenylsilyl)oxy) methyl)cyclopropyl) methanol (2.26 g, 6.64 mmol, CAS #441785-04-2) in toluene (40 mL) was added t-BuONa (1.28 g, 13.2 mmol) at 0° C. The mixture was stirred at 0° C. for 0.5 hr under N2 atmosphere. After that, 2,7-dichloro-8-fluoro-4-(piperidin-1-yl)pyrido[4,3-d] pyrimidine (2.00 g, 6.64 mmol) was added to the reaction and the mixture was stirred at 0° C. for 0.5 hr. On completion, the reaction mixture was quenched by water (50 mL), and then extracted with EA (3×50 mL). The combined organic layers were washed with brine (3×50 mL), dried over anhydrous $Na_2SO_4$, filtered and the filtrate was concentrated in vacuo to give a residue. The residue was purified by column chromatography ($SiO_2$, Petroleum ether/Ethyl acetate=I/O to 10/1) to give the title compound (3.00 g, 74% yield) as yellow solid. $^1$H NMR (400 MHz, $CDCl_3$) δ 8.72 (s, 1H), 7.67-7.61 (m, 4H), 7.39-7.35 (m, 2H), 7.34-7.28 (m, 4H), 4.50-4.45 (m, 2H), 3.89-3.84 (m, 4H), 3.73 (s, 2H), 1.80 (s, 6H), 1.03 (s, 9H), 0.67-0.61 (m, 2H), 0.58-0.53 (m, 2H); LC-MS (ESI*) m/z 605.4 $(M+H)^+$.

Step 2-2-((1-(((Tert-butyldiphenylsilyl)oxy) methyl)cyclopropyl) methoxy)-8-fluoro-7-(7-fluoro-3-(methoxymethoxy)-8-((triisopropylsilyl) ethynyl) naphthalen-1-yl)-4-(piperidin-1-yl)pyrido[4,3-d]pyrimidine. A mixture of 2-((1-(((tert-butyldiphenylsilyl)oxy)methyl)cyclopropyl)methoxy)-7-chloro-8-fluoro-4-(piperidin-1-yl) pyrido[4,3-d]pyrimidine (1.00 g, 1.65 mmol), ((2-fluoro-6-(methoxymethoxy)-8-(4,4,5,5-tetramethyl-1,3,2-dioxaborolan-2-yl) naphthalen-1-yl) ethynyl) triisopropylsilane (1.27 g, 2.48 mmol, CAS #2621932-37-2), $K_3PO_4$ (1.5 M, 3.30 mL) and [2-(2-aminophenyl)phenyl] palladium (1+); bis(1-adamantyl)-butyl-phosphane; methanesulfonate (120 mg, 165 μmol) in dioxane (15 mL) was degassed and purged with $N_2$ for 3 times, and then the mixture was stirred at 80° C. for 0.5 hr under $N_2$ atmosphere. On completion, the reaction mixture was concentrated in vacuo to give a residue. The residue was purified by column chromatography ($SiO_2$, Petroleum ether/Ethyl acetate=1/0 to 3/1) to give the title compound (1.30 g, 82% yield) as yellow solid. $^1$H NMR (400 MHz, $CDCl_3$) δ 9.03 (s, 1H), 7.79 (dd, J=5.6, 9.2 Hz, 1H), 7.70-7.63 (m, 4H), 7.51 (d, J=2.4 Hz, 1H), 7.43-7.29 (m, 8H), 5.33-5.29 (m, 2H), 4.58-4.39 (m, 2H), 3.95-3.87 (m, 4H), 3.82-3.74 (m, 2H), 3.51 (s, 3H), 1.89-1.77 (m, 6H), 1.05 (s, 9H), 0.87 (dd, J=7.6, 12.4 Hz, 18H), 0.64-0.51 (m, 7H); LC-MS (ESI) m/z 955.6 $(M+H)^+$.

Step 3-(1-(((7-(8-Ethynyl-7-fluoro-3-(methoxymethoxy) naphthalen-1-yl)-8-fluoro-4-(piperidin-1-yl)pyrido[4,3-d] pyrimidin-2-yl)oxy)methyl)cyclopropyl) methanol. To a solution of 2-((1-(((tert-butyldiphenylsilyl)oxy)methyl)cyclopropyl) methoxy)-8-fluoro-7-(7-fluoro-3-(methoxymethoxy)-8-((triisopropylsilyl) ethynyl) naphthalen-1-yl)-4-(piperidin-1-yl)pyrido[4,3-d]pyrimidine (1.00 g, 1.05 mmol) in THF (10 mL) was added TBAF (1 M, 3.14 mL). The mixture was stirred at 40° C. for 1 hr. On completion, the reaction mixture was quenched by water (50 mL), and then extracted with EA (3×50 mL). The combined organic layers were washed with brine (3×50 mL), dried over anhydrous $Na_2SO_4$, filtered and the filtrate was concentrated in vacuo to give a residue. The residue was purified by column chromatography ($SiO_2$, Petroleum ether/Ethyl acetate=1/0 to 1/2) to give the title compound (450 mg, 76% yield) as white solid. $^1$H NMR (400 MHz, $CDCl_3$) δ 9.00 (s, 1H), 7.83 (dd, J=6.0, 9.2 Hz, 1H), 7.54 (d, J=2.4 Hz, 1H), 7.40 (d, J=2.4 Hz, 1H), 7.33-7.28 (m, 1H), 5.34-5.30 (m, 2H), 4.70 (d, J=12.0 Hz, 1H), 4.30 (d, J=12.0 Hz, 1H), 3.97 (s, 4H), 3.57-3.51 (m, 4H), 3.33 (d, J=12.0 Hz, 1H), 2.85 (s, 1H), 2.01 (s, 1H), 1.85 (s, 6H), 0.72-0.56 (m, 4H).

Step 4-1-(((7-(8-Ethynyl-7-fluoro-3-(methoxymethoxy) naphthalen-1-yl)-8-fluoro-4-(piperidin-1-yl)pyrido[4,3-d] pyrimidin-2-yl)oxy)methyl)cyclopropane-1-carbaldehyde. To a solution of (1-(((7-(8-ethynyl-7-fluoro-3-(methoxymethoxy) naphthalen-1-yl)-8-fluoro-4-(piperidin-1-yl)pyrido[4,3-d]pyrimidin-2-yl)oxy)methyl)cyclopropyl) methanol (400 mg, 713 μmol) in DCM (8 mL) was added DMP (453 mg, 1.07 mmol, 331 μL) at 0° C. The mixture was stirred at 25° C. for 1 hr. On completion, the reaction mixture was quenched by addition $Na_2S_2O_3$ (20 mL) and $NaHCO_3$ (20 mL), and then extracted with DCM (3×40 mL). The combined organic layers were washed with brine (3×40 mL), dried over anhydrous $Na_2SO_4$, filtered and the filtrate was concentrated in vacuo to give the title compound (398 mg, 99% yield) as yellow solid. 1H NMR (400 MHz, $CDCl_3$) δ 9.26 (s, 1H), 9.00 (s, 1H), 7.84 (dd, J=6.0, 8.8 Hz, 1H), 7.55 (d, J=2.0 Hz, 1H), 7.40 (d, J=2.0 Hz, 1H), 7.33-7.28 (m, 1H), 5.35-5.26 (m, 2H), 4.89-4.60 (m, 2H), 3.95 (s, 4H), 3.53 (s, 3H), 1.84 (s, 6H), 1.40-1.31 (m, 4H), 1.31-1.26 (m, 1H); LC-MS (ESI) m/z 559.3 $(M+H)^+$.

Step 5-3-(5-(4-((4-((1-(((7-(8-Ethynyl-7-fluoro-3-(methoxymethoxy) naphthalen-1-yl)-8-fluoro-4-(piperidin-1-yl)pyrido[4,3-d]pyrimidin-2-yl)oxy)methyl)cyclopropyl) methyl) piperazin-1-yl)methyl) piperidin-1-yl)-3-methyl-2-oxo-2,3-dihydro-1H-benzo[d]imidazol-1-yl) piperidine-2,6-dione. To a solution of 3-(3-methyl-2-oxo-5-(4-(piperazin-1-ylmethyl) piperidin-1-yl)-2,3-dihydro-1H-benzo[d]

imidazol-1-yl) piperidine-2,6-dione (170 mg, 356.4 μmol, HCl salt) in THF (4 mL) and DMSO (0.5 mL) was added TEA (72.1 mg, 712 μmol, 99.2 μL) to pH=10. The mixture was stirred at 25° C. for 10 mins, and then acidified with HOAc (64.2 mg, 1.07 mmol, 61.2 μL) to pH=6. Then 1-(((7-(8-ethynyl-7-fluoro-3-(methoxymethoxy) naphthalen-1-yl)-8-fluoro-4-(piperidin-1-yl)pyrido[4,3-d]pyrimidin-2-yl)oxy)methyl)cyclopropane-1-carbaldehyde (199 mg, 356 μmol) was added to the mixture and the mixture was stirred at 25° C. for 20 mins. Then $NaBH_3CN$ (33.5 mg, 534 μmol) was added. The reaction mixture was stirred at 25° C. for 0.5 hr. On completion, the reaction mixture was concentrated in vacuo to give a residue. The residue was purified by reverse-phase (water/ACN) to give the title compound (100 mg, 28% yield) as yellow oil. $^1H$ NMR (400 MHz, $CDCl_3$) δ 9.02 (s, 1H), 8.18 (s, 1H), 7.85 (dd, J=6.4, 8.4 Hz, 1H), 7.63-7.51 (m, 1H), 7.43 (d, J=2.0 Hz, 1H), 7.34-7.27 (m, 1H), 6.88-6.66 (m, 3H), 5.33 (q, J=6.8 Hz, 2H), 5.20 (dd, J=5.6, 12.8 Hz, 1H), 4.78-4.49 (m, 1H), 4.02 (d, J=0.8 Hz, 4H), 3.78-3.68 (m, 1H), 3.54 (s, 4H), 3.42 (s, 3H), 2.86-2.61 (m, 7H), 2.28-2.19 (m, 2H), 1.91-1.58 (m, 20H), 1.49-1.43 (m, 2H), 0.97-0.82 (m, 4H); LC-MS (ESI) m/z 983.3 $(M+H)^+$.

Step 6-3-(5-(4-((4-(1-(((7-(8-Ethynyl-7-fluoro-3-hydroxynaphthalen-1-yl)-8-fluoro-4-(piperidin-1-yl)pyrido[4,3-d]pyrimidin-2-yl)oxy)methyl)cyclopropyl)methyl) piperazin-1-yl)methyl) piperidin-1-yl)-3-methyl-2-oxo-2,3-dihydro-1H-benzo[d]imidazol-1-yl) piperidine-2,6-dione (Compound 15). A solution of 3-(5-(4-((4-((1-(((7-(8-ethynyl-7-fluoro-3-(methoxymethoxy) naphthalen-1-yl)-8-fluoro-4-(piperidin-1-yl)pyrido[4,3-d]pyrimidin-2-yl)oxy) methyl)cyclopropyl)methyl) piperazin-1-yl)methyl) piperidin-1-yl)-3-methyl-2-oxo-2,3-dihydro-1H-benzo[d]imidazol-1-yl) piperidine-2,6-dione (90.0 mg, 91.5 μmol) in FA (2 mL) was stirred at 25° C. for 1 hr. On completion, the reaction mixture was concentrated in vacuo to give a residue. The residue was purified by prep-HPLC (column: CD04-Welch Utimate C18 150*25*7 μm; mobile phase: [water (FA)-ACN]; gradient: 10%-40% B over 8 min) to give the title compound (49.1 mg, 53% yield, FA salt) as yellow solid. $^1H$ NMR (400 MHz, DMSO-$d_6$) δ 11.05 (s, 1H), 10.36-9.94 (m, 1H), 8.96 (s, 1H), 8.03-7.86 (m, 1H), 7.46 (t, J=8.8 Hz, 1H), 7.39 (d, J=2.0 Hz, 1H), 7.19 (d, J=2.0 Hz, 1H), 6.91 (d, J=8.8 Hz, 1H), 6.80 (s, 1H), 6.61 (d, J=9.2 Hz, 1H), 5.27 (dd, J=5.2, 12.4 Hz, 1H), 4.27 (s, 2H), 3.99 (s, 1H), 3.90 (s, 4H), 3.57-3.53 (m, 2H), 3.29 (s, 3H), 2.93-2.87 (m, 1H), 2.73-2.56 (m, 6H), 2.43-2.27 (m, 8H), 2.12 (d, J=7.2 Hz, 2H), 2.00-1.95 (m, 1H), 1.76 (s, 8H), 1.62-1.55 (m, 1H), 1.26-1.18 (m, 2H), 0.63 (s, 2H), 0.41 (s, 2H); LC-MS ($ESI^+$) m/z 939.2 $(M+H)^+$.

Example 48. Synthesis of Compound 16

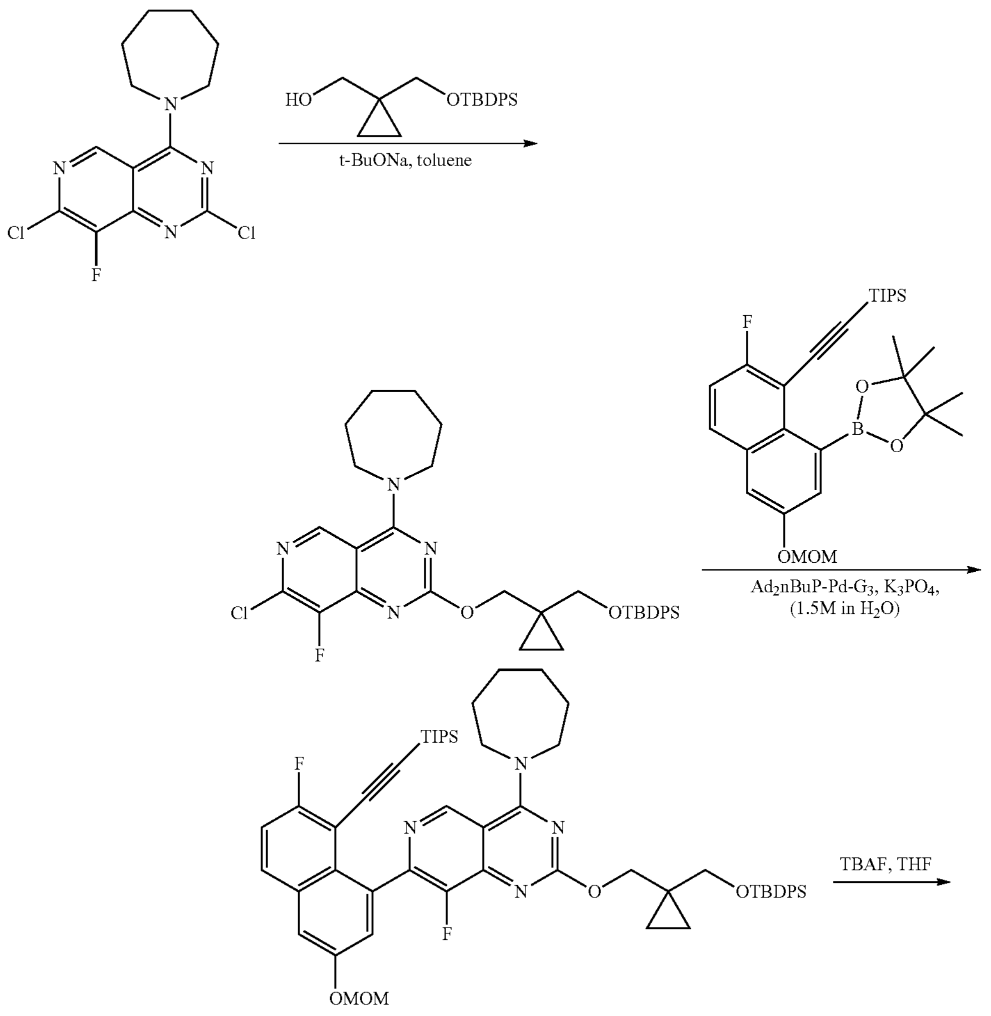

-continued

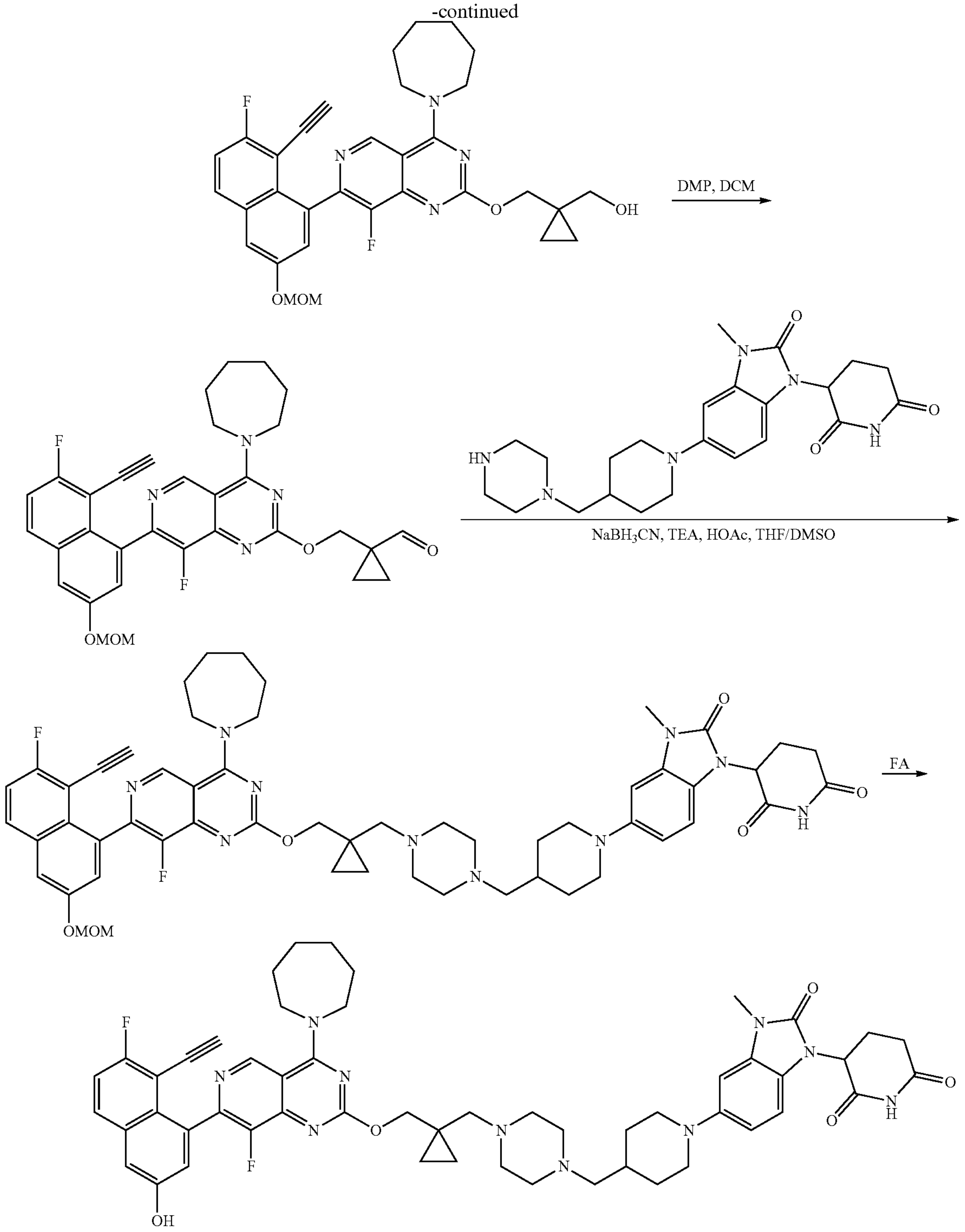

16

Step 1-4-(Azepan-1-yl)-2-((1-(((tert-butyldiphenylsilyl) oxy) methyl)cyclopropyl) methoxy)-7-chloro-8-fluoro-pyrido[4,3-d]pyrimidine. To a solution of (1-(((tert-butyldi-phenylsilyl)oxy) methyl)cyclopropyl) methanol (1.08 g, 3.17 mmol, CAS #441785-04-2) in toluene (10 mL) was added 1-BuONa (609 mg, 6.35 mmol) at 0° C. The reaction mixture was stirred at 0° C. for 0.5 hr. Then 4-(azepan-1-yl)-2,7-dichloro-8-fluoropyrido[4,3-d]pyrimidine (1.00 g, 3.17 mmol) was added to the mixture. The reaction mixture was stirred at 0° C. for 11.5 hrs. On completion, the reaction mixture was filtered and the filtrate was concentrated in vacuo to give a residue. The residue was diluted with water (40 mL) and extracted with EA (2×50 mL). Then the combined organic layers were washed with brine (2×30 mL). The combined organic layers were dried over anhydrous $Na_2SO_4$, filtered and the filtrate was concentrated in vacuo to give a residue. The residue was purified by column chromatography ($SiO_2$, PE:EA=50:1 to PE:EA=3:2) to give the title compound (1.70 g, 86% yield) as yellow solid. $^1H$ NMR (400 MHz, $CDCl_3$) δ 8.84 (s, 1H), 7.68-7.59 (m, 4H), 7.40-7.28 (m, 6H), 4.45 (s, 2H), 3.99-3.90 (m, 4H), 3.74 (s, 2H), 1.98 (s, 4H), 1.66 (s, 4H), 1.03 (s, 9H), 0.66-0.59 (m, 2H), 0.54 (t, J=5.2 Hz, 2H).

Step 2-4-(Azepan-1-yl)-2-((1-(((tert-butyldiphenylsilyl) oxy)methyl)cyclopropyl) methoxy)-8-fluoro-7-(7-fluoro-3-(methoxymethoxy)-8-((triisopropylsilyl) ethynyl) naphthalen-1-yl)pyrido[4,3-d]pyrimidine. To a solution of 4-(azepan-1-yl)-2-((1-(((tert-butyldiphenylsilyl)oxy) methyl)cyclopropyl) methoxy)-7-chloro-8-fluoropyrido[4, 3-d]pyrimidine (1.40 g, 2.26 mmol) and ((2-fluoro-6-(methoxymethoxy)-8-(4,4,5,5-tetramethyl-1,3,2-dioxaborolan-2-yl) naphthalen-1-yl) ethynyl) triisopropylsilane (1.74 g, 3.39 mmol, CAS #2621932-37-2) in dioxane (14 mL) was added [2-(2-aminophenyl)phenyl] palladium (1+); bis(1-adamantyl)-butyl-phosphane; methanesulfonate (164 mg, 226 μmol) and $K_3PO_4$ (1.50 M, 4.52 mL). The reaction mixture was stirred at 80° C. for 0.5 hr under $N_2$ atmosphere. On completion, the reaction mixture was concentrated in vacuo to give a residue. The residue was diluted with water (50 mL) and extracted with EA (2×100 mL). The combined organic layers were washed with brine (2×80 mL). The combined organic layers was dried over anhydrous $Na_2SO_4$, filtered and the filtrate was concentrated in vacuo to give a residue. The residue was purified by column chromatography ($SiO_2$, PE:EA=50:1 to PE:EA=78:22) to give the title compound (1.87 g, 85% yield) as brown oil. LC-MS (ESI) m/z 969.5 $(M+H)^+$.

Step 3-(1-(((4-(Azepan-1-yl)-7-(8-ethynyl-7-fluoro-3-(methoxymethoxy) naphthalen-1-yl)-8-fluoropyrido[4,3-d] pyrimidin-2-yl)oxy)methyl)cyclopropyl) methanol. To a solution of 4-(azepan-1-yl)-2-((1-(((tert-butyldiphenylsilyl) oxy)methyl)cyclopropyl) methoxy)-8-fluoro-7-(7-fluoro-3-(methoxymethoxy)-8-((triisopropylsilyl) ethynyl) naphthalen-1-yl)pyrido[4,3-d]pyrimidine (1.87 g, 1.93 mmol) in THF (18 mL) was added TBAF (1.00 M, 9.65 mL). The reaction mixture was stirred at 40° C. for 2 hrs. On completion, the reaction mixture was concentrated in vacuo to give a residue. The residue was purified by column chromatography ($SiO_2$, DCM:MeOH=1:0 to DCM:MeOH=98:2) to give the title compound (1.10 g, 99% yield) as brown oil. LC-MS (ESI) m/z 575.3 $(M+H)^+$.

Step 4-1-(((4-(Azepan-1-yl)-7-(8-ethynyl-7-fluoro-3-(methoxymethoxy) naphthalen-1-yl)-8-fluoropyrido[4,3-d] pyrimidin-2-yl)oxy)methyl)cyclopropane-1-carbaldehyde. To a solution of (1-(((4-(azepan-1-yl)-7-(8-ethynyl-7-fluoro-3-(methoxymethoxy) naphthalen-1-yl)-8-fluoropyrido[4,3-d]pyrimidin-2-yl)oxy)methyl)cyclopropyl) methanol (900 mg, 1.57 mmol) in DCM (9 mL) was added DMP (797 mg, 1.88 mmol). The reaction mixture was stirred at 25° C. for 0.5 hr. On completion, the reaction mixture was quenched by saturated $Na_2S_2O_3$ (8 mL) and saturated $NaHCO_3$ (8 mL) at 25° C., and then stirred for 30 minutes. The mixture was diluted with water (20 mL) and extracted with DCM (2×30 mL), then the organic layers were separated and concentrated in vacuo to give a residue. The residue was purified by column chromatography ($SiO_2$, PE:EA=50:1 to PE:EA=1:1) to give the title compound (456 mg, 51% yield) as yellow solid. $^1H$ NMR (400 MHz, DMSO-$d_6$) δ 9.10 (s, 1H), 8.92 (s, 1H), 8.10 (dd, J=6.0, 8.8 Hz, 1H), 7.74 (s, 1H), 7.55 (t, J=8.8 Hz, 1H), 7.38 (s, 1H), 5.37 (s, 2H), 4.60-4.46 (m, 2H), 4.06 (s, 1H), 3.99 (t, J=4.8 Hz, 4H), 3.44 (s, 3H), 2.01-1.90 (m, 4H), 1.62 (s, 4H), 1.32 (d, J=19.2 Hz, 4H).

Step 5-3-(5-(4-((4-((1-(((4-(Azepan-1-yl)-7-(8-ethynyl-7-fluoro-3-(methoxymethoxy) naphthalene-1-yl)-8-fluoro-pyrido[4,3-d]pyrimidin-2-yl)oxy)methyl)cyclopropyl) methyl) piperazin-1-yl)methyl) piperidin-1-yl)-3-methyl-2-oxo-2,3-dihydro-1H-benzo[d]imidazol-1-yl) piperidine-2,6-dione. To a solution of 3-(3-methyl-2-oxo-5-(4-(piperazin-1-ylmethyl) piperidin-1-yl)-2,3-dihydro-1H-benzo[d] imidazol-1-yl) piperidine-2,6-dione (244 mg, 511 μmol, HCl salt) in THF (4 mL) and DMSO (4 mL) was added TEA (129 mg, 1.28 mmol). The reaction mixture was stirred at 30° C. for 0.2 hr. Then 1-(((4-(azepan-1-yl)-7-(8-ethynyl-7-fluoro-3-(methoxymethoxy) naphthalen-1-yl)-8-fluoropyrido[4,3-d]pyrimidin-2-yl)oxy)methyl)cyclopropane-1-carbaldehyde (244 mg, 426 μmol) and HOAc (51.2 mg, 852 μmol) were added to the mixture. The reaction mixture was stirred at 30° C. for 0.3 hr. Then $NaBH_3CN$ (32.1 mg, 511 μmol) was added to the mixture. The reaction mixture was stirred at 30° C. for 2.5 hrs. On completion, the reaction mixture was quenched by water (0.05 mL) and concentrated in vacuo to give a residue. The residue was purified by reverse phase (0.1% FA condition), the reaction mixture was concentrated in vacuo to give a residue. The residue was diluted with water (20 mL) and extracted with EA (2×30 mL). The combined organic layers were washed with brine (2×50 mL). The combined organic layers was dried over anhydrous $Na_2SO_4$, filtered and the filtrate was concentrated in vacuo to give the title compound (140 mg, 33% yield) as yellow solid. LC-MS ($ESI^+$) m z 997.6 $(M+H)^+$.

Step 6-3-(5-(4-((1-(1-(Azepan-1-yl)-7-(8-ethynyl-7-fluoro-3-hydroxynaphthalen-1-yl)-8-fluoropyrido[4,3-d]pyrimidin-2-yl)oxy)methyl)cyclopropyl)methyl) piperazin-1-yl)methyl) piperidin-1-yl)-3-methyl-2-oxo-2,3-dihydro-1H-benzo[d]imidazol-1-yl) piperidine-2,6-dione (Compound 16). A solution of 3-(5-(4-((4-((1-(((4-(azepan-1-yl)-7-(8-ethynyl-7-fluoro-3-(methoxymethoxy) naphthalen-1-yl)-8-fluoropyrido[4,3-d]pyrimidin-2-yl)oxy)methyl)cyclopropyl)methyl) piperazin-1-yl)methyl) piperidin-1-yl)-3-methyl-2-oxo-2,3-dihydro-1H-benzo[d]imidazol-1-yl) piperidine-2,6-dione (130 mg, 130 μmol) in FA (6.26 mg, 130 μmol, 1 mL) was stirred at 30° C. for 1 hr. On completion, the reaction mixture was concentrated in vacuo to give a residue. The residue was purified by prep-HPLC (column: CD04-Welch Utimate C18 150*25*7 μm; mobile phase: [water (FA)-ACN]; gradient: 10%-40% B over 8 min) to give the title compound (36.8 mg, 27% yield, FA salt) as yellow solid. $^1H$ NMR (400 MHz, DMSO-$d_6$) δ 11.05 (s, 1H), 10.75-9.80 (m, 1H), 9.07 (s, 1H), 7.97 (dd, J=6.0, 9.2 Hz, 1H), 7.46 (t, J=9.2 Hz, 1H), 7.38 (d, J=2.4 Hz, 1H), 7.17 (d, J=2.4 Hz, 1H), 6.91 (d, J=8.4 Hz, 1H), 6.80 (d, J=1.6 Hz, 1H), 6.61 (dd, J=2.0, 8.4 Hz, 1H), 5.28 (dd, J=5.2, 12.8 Hz, 1H), 4.34-4.21 (m, 2H), 4.08-3.90 (m, 5H), 3.55 (d, J=11.6 Hz, 2H), 3.29 (s, 3H), 2.94-2.83 (m, 1H), 2.73-2.65 (m, 1H), 2.64-2.54 (m, 4H), 2.45-2.23 (m, 8H), 2.11 (d, J=6.8 Hz, 2H), 2.02-1.89 (m, 5H), 1.88-1.47 (m, 8H), 1.28-1.14 (m, 2H), 0.63 (s, 2H), 0.40 (s, 2H); LC-MS ($ESI^+$) m/z 953.3 $(M+H)^+$.

Example 49. Synthesis of Compound 17
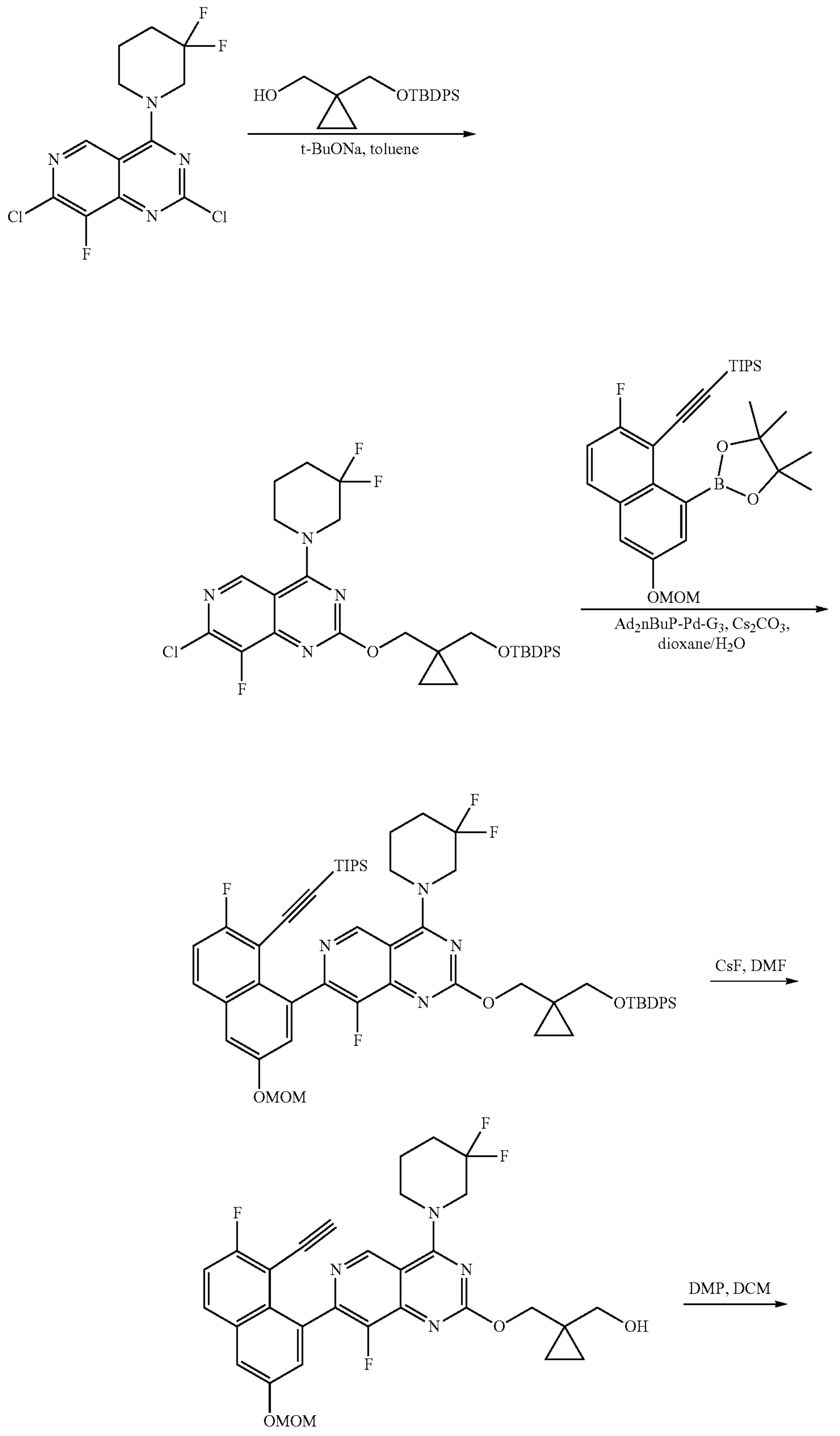

-continued

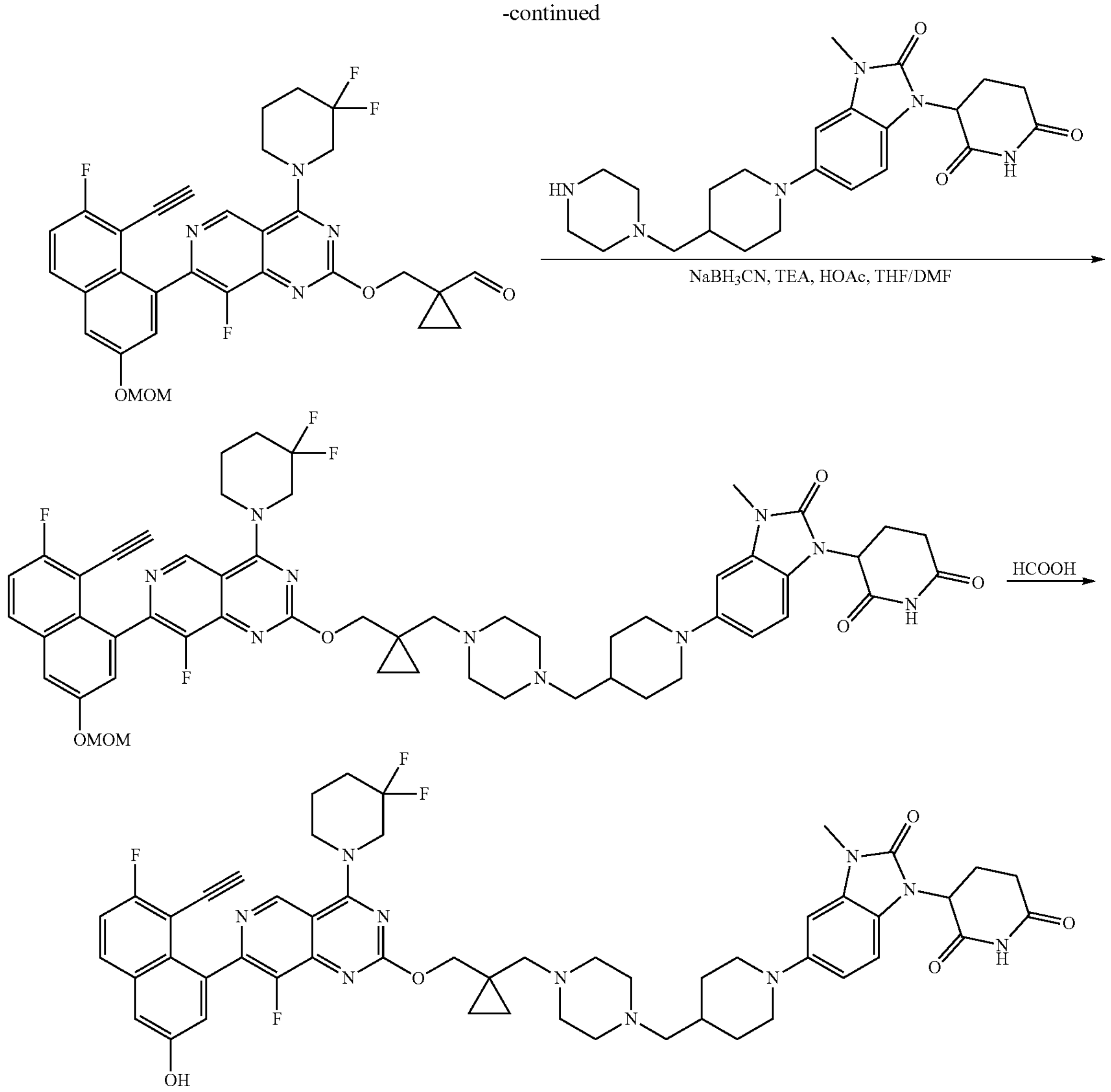

17

Step 1-2-((1-((Tert-butyldiphenylsilyl)oxy) methyl)cyclopropyl) methoxy)-7-chloro-4-(3,3-difluoropiperidin-1-yl)-8-fluoropyrido[4,3-d]pyrimidine. To a solution of [1-[[tert-butyl (diphenyl) silyl]oxymethyl]cyclopropyl]methanol (2.02 g, 5.93 mmol, CAS #441785-04-2) in toluene (20 mL) was added t-BuONa (1.14 g, 11.8 mmol) at 0° C. The mixture was stirred at 0° C. for 0.5 hr, the 2,7-dichloro-4-(3,3-difluoro-1-piperidyl)-8-fluoro-pyrido[4,3-d]pyrimidine (2.00 g, 5.93 mmol) was added into above solution, the mixture was stirred at 0° C. for 2 hrs. On completion, the mixture was diluted with $H_2O$ (50 mL), extracted with EA (3×50 mL), the organic layer was washed with brine (50 mL), dried with anhydrous $Na_2SO_4$, filtered and the filtrate was concentrated in vacuo. The residue was purified by column chromatography ($SiO_2$, PE:EA=4:1) to give the title compound (3.70 g, 97% yield) as yellow oil. $^1H$ NMR (400 MHz, $CDCl_3$) δ 8.79 (s, 1H), 7.67-7.60 (m, 4H), 7.39-7.34 (m, 2H), 7.33-7.28 (m, 4H), 4.49 (s, 2H), 4.04 (t, J=11.2 Hz, 2H), 3.87-3.80 (m, 2H), 3.73 (s, 2H), 2.27-2.14 (m, 2H), 2.10-2.05 (m, 2H), 1.03 (s, 9H), 0.67-0.62 (m, 2H), 0.59-0.54 (m, 2H).

Step 2-2-((1-(((Tert-butyldiphenylsilyl)oxy) methyl)cyclopropyl) methoxy)-4-(3,3-difluoropiperidin-1-yl)-8-fluoro-7-(7-fluoro-3-(methoxymethoxy)-8-((triisopropylsilyl) ethynyl) naphthalen-1-yl)pyrido[4,3-d]pyrimidine. A mixture of tert-butyl-[[1-[[7-chloro-4-(3,3-difluoro-1-piperidyl)-8-fluoro-pyrido[4,3-d]pyrimidin-2-yl]oxymethyl] cyclopropyl]methoxy]-diphenyl-silane (2.00 g, 3.12 mmol), 2-[2-fluoro-6-(methoxymethoxy)-8-(4,4,5,5-tetramethyl-1,3,2-dioxaborolan-2-yl)-1-naphthyl]ethynyl-triisopropyl-silane (2.40 g, 4.68 mmol, CAS #2621932-37-2), $Cs_2CO_3$ (3.05 g, 9.36 mmol), [2-(2-aminophenyl)phenyl]palladium (1+); bis(1-adamantyl)-butyl-phosphane; methanesulfonate (227 mg, 311 μmol) in dioxane (10 mL) and $H_2O$ (1 mL) was degassed and purged with $N_2$ for 3 times, and then the mixture was stirred at 80° C. for 0.5 hr under $N_2$ atmosphere. On completion, the mixture was diluted with $H_2O$ (50 mL), extracted with EA (3×50 mL), the organic layer was washed with brine (50 mL), dried with anhydrous $Na_2SO_4$, filtered and the filtrate was concentrated in vacuo. The residue was purified by column chromatography ($SiO_2$, PE:EA=4:1) to give the title compound (2.40 g, 77% yield) as brown solid. $^1$H NMR (400 MHz, $CDCl_3$) δ 9.09 (s, 1H), 7.80 (dd, J=5.6, 9.2 Hz, 1H), 7.70-7.62 (m, 4H), 7.52 (d, J=2.4 Hz, 1H), 7.43-7.28 (m, 8H), 5.34-5.26 (m, 2H), 4.60 (d, J=11.2 Hz, 1H), 4.41 (d, J=11.2 Hz, 1H), 4.29-4.17 (m, 1H), 4.09-4.00 (m, 1H), 3.98-3.89 (m, 1H), 3.83-3.73 (m, 2H), 3.71-3.64 (m, 1H), 3.52 (s, 3H), 2.37-2.23 (m, 1H), 2.22-2.08 (m, 2H), 2.05-1.97 (m, 1H), 1.29-1.18 (m, 3H), 1.05 (s, 9H), 0.85 (dd, J=7.6, 13.2 Hz, 18H), 0.66-0.61 (m, 2H), 0.58-0.55 (m, 2H).

Step 3—(1-(((4-(3,3-Difluoropiperidin-1-yl)-7-(8-ethynyl-7-fluoro-3-(methoxymethoxy) naphthalen-1-yl)-8-fluoropyrido[4,3-d]pyrimidin-2-yl)oxy)methyl)cyclopropyl) methanol. To a solution of tert-butyl-[[1-[[4-(3,3-difluoro-1-piperidyl)-8-fluoro-7-[7-fluoro-3-(methoxymethoxy)-8-(2-triisopropylsilylethynyl)-1-naphthyl]pyrido[4,3-d]pyrimidin-2-yl]oxymethyl]cyclopropyl]methoxy]-diphenyl-silane (800 mg, 807 μmol) in DMF (8 mL) was added CsF (367 mg, 2.42 mmol). The mixture was stirred at 40° C. for 8 hrs. On completion, the mixture was diluted with $H_2O$ (20 mL), extracted with EA (3×20 mL), the organic layer was washed with brine (20 mL), dried with anhydrous $Na_2SO_4$, filtered and the filtrate was concentrated in vacuo. The residue was purified by column chromatography ($SiO_2$, PE:EA-68:32) to give the title compound (485 mg, crude) as brown solid. LC-MS (ESI) m/z 597.1 $(M+H)^+$.

Step 4-1-(((4-(3,3-Difluoropiperidin-1-yl)-7-(8-ethynyl-7-fluoro-3-(methoxymethoxy) naphthalen-1-yl)-8-fluoro-pyrido[4,3-d]pyrimidin-2-yl)oxy)methyl)cyclopropane-1-carbaldehyde. To a solution of [1-[[4-(3,3-difluoro-1-piperidyl)-7-[8-ethynyl-7-fluoro-3-(methoxymethoxy)-1-naphthyl]-8-fluoro-pyrido[4,3-d]pyrimidin-2-yl]oxymethyl] cyclopropyl]methanol (383 mg, 642 μmol) in DCM (4 mL) was added DMP (408 mg, 963 μmol). The mixture was stirred at 25° C. for 2 hrs. On completion, the mixture was quenched with Na2S2O3 solution (20 mL), diluted with $H_2O$ (15 mL), extracted with DCM (3×20 mL), the organic layer was washed with $NaHCO_3$ solution (20 mL), brine (20 mL), dried with anhydrous $Na_2SO_4$, filtered and filtrate was concentrated in vacuo. The mixture was purified by reversed phase (0.1% FA condition) to give the title compound (243 mg, 63% yield) as brown oil. $^1$H NMR (400 MHz, $CDCl_3$) δ 9.19 (s, 1H), 9.09 (s, 1H), 7.85 (dd, J=5.6, 9.2 Hz, 1H), 7.57 (d, J=2.4 Hz, 1H), 7.41 (d, J=2.4 Hz, 1H), 7.31 (t, J=8.8 Hz, 1H), 5.37-5.29 (m, 2H), 4.83-4.70 (m, 2H), 4.27 (dt, J=7.6, 13.6 Hz, 1H), 4.10-4.05 (m, 1H), 3.85-3.76 (m, 1H), 3.54 (s, 3H), 2.36-2.06 (m, 6H), 1.42-1.38 (m, 2H), 1.36-1.32 (m, 2H).

Step 5-3-(5-(4-((4-((1-(((4-(3,3-Difluoropiperidin-1-yl)-7-(8-ethynyl-7-fluoro-3-(methoxymethoxy) naphthalen-1-yl)-8-fluoropyrido[4,3-d]pyrimidin-2-yl)oxy)methyl)cyclopropyl)methyl) piperazin-1-yl)methyl) piperidin-1-yl)-3-methyl-2-oxo-2,3-dihydro-1H-benzo[d]imidazol-1-yl) piperidine-2,6-dione. To a solution of 1-[[4-(3,3-difluoro-1-piperidyl)-7-[8-ethynyl-7-fluoro-3-(methoxymethoxy)-1-naphthyl]-8-fluoro-pyrido[4,3-d]pyrimidin-2-yl]oxymethyl] cyclopropanecarbaldehyde (155 mg, 262 μmol) and 3-[3-methyl-2-oxo-5-[4-(piperazin-1-ylmethyl)-1-piperidyl] benzimidazol-1-yl]piperidine-2,6-dione (150 mg, 314 μmol, HCl) in THF (2 mL) and DMSO (2 mL) was added TEA (39.7 mg, 393 μmol, 54.7 μL), the mixture was stirred at 25° C. for 10 mins. AcOH (31.4 mg, 524 μmol, 30.0 μL) was added into above solution, the mixture was stirred at 25° C. for 20 mins, then $NaBH_3CN$ (24.7 mg, 393 μmol) was added into above solution, the mixture was stirred at 25° C. for 15.5 hrs. On completion, the mixture was quenched with $H_2O$ (1 mL). The residue was purified by reversed phase (0.1% FA) to give the title compound (145 mg, 54% yield) as yellow solid. $^1$H NMR (400 MHz, $CDCl_3$) δ 9.04 (s, 1H), 8.31 (s, 1H), 7.83 (dd, J=6.0, 7.6 Hz, 1H), 7.58-7.52 (m, 1H), 7.41 (d, J=2.4 Hz, 1H), 7.31-7.27 (m, 1H), 6.73-6.57 (m, 3H), 5.35-5.29 (m, 2H), 5.19 (dd, J=5.2, 12.4 Hz, 1H), 4.57-4.48 (m, 1H), 4.42 (d, J=10.8 Hz, 1H), 4.34-4.21 (m, 1H), 4.10-4.01 (m, 2H), 3.53 (s, 3H), 3.50-3.43 (m, 2H), 3.39 (s, 3H), 2.92 (dd, J=7.2, 14.4 Hz, 4H), 2.76-2.48 (m, 8H), 2.30-2.16 (m, 4H), 2.14-2.07 (m, 2H), 1.98-1.91 (m, 2H), 1.53-1.38 (m, 5H), 1.17-1.05 (m, 4H), 0.89-0.85 (m, 4H); LC-MS (ESI) m/z 1019.5 $(M+H)^+$.

Step 6-3-(5-(4-((4-((1-(((4-(3,3-Difluoropiperidin-1-yl)-7-(8-ethynyl-7-fluoro-3-hydroxynaphthalen-1-yl)-8-fluoro-pyrido[4,3-d]pyrimidin-2-yl)oxy)methyl)cyclopropyl) methyl) piperazin-1-yl)methyl) piperidin-1-yl)-3-methyl-2-oxo-2,3-dihydro-1H-benzo[d]imidazol-1-yl) piperidine-2,6-dione (Compound 17). A solution of 3-(5-(4-((4-((1-(((4-(3,3-difluoropiperidin-1-yl)-7-(8-ethynyl-7-fluoro-3-(methoxymethoxy) naphthalen-1-yl)-8-fluoropyrido[4,3-d] pyrimidin-2-yl)oxy) methyl)cyclopropyl)methyl) piperazin-1-yl)methyl) piperidin-1-yl)-3-methyl-2-oxo-2,3-dihydro-1H-benzo[d]imidazol-1-yl) piperidine-2,6-dione (140 mg, 137 μmol) in HCOOH (3 mL) was stirred at 25° C. for 2 hrs. On completion, the mixture was concentrated in vacuo. The crude product was purified by prep-HPLC (column: CD01-Phenomenex luna C18 150*25*10 μm; mobile phase: [water (FA)-ACN]; gradient: 12%-42% B over 11 min) to give the title compound (46.2 mg, 32% yield, FA salt) as yellow solid. $^1$H NMR (400 MHz, DMSO-$d_6$) δ 11.05 (s, 1H), 10.16 (s, 1H), 9.04 (s, 1H), 7.98 (dd, J=6.0, 9.2 Hz, 1H), 7.47 (t, J=9.2 Hz, 1H), 7.40 (d, J=2.4 Hz, 1H), 7.21 (d, J=2.4 Hz, 1H), 6.91 (d, J=8.8 Hz, 1H), 6.80 (d, J=1.6 Hz, 1H), 6.61 (dd, J=2.0, 8.8 Hz, 1H), 5.28 (dd, J=5.2, 12.8 Hz, 1H), 4.31 (s, 2H), 4.29-4.21 (m, 1H), 4.15 (q, J=12.8 Hz, 1H), 4.00-3.91 (m, 1H), 3.93 (s, 1H), 3.92-3.85 (m, 1H), 3.55 (d, J=11.6 Hz, 2H), 3.29 (s, 3H), 2.95-2.82 (m, 1H), 2.73-2.65 (m, 1H), 2.65-2.54 (m, 4H), 2.44-2.17 (m, 11H), 2.11 (d, J=7.2 Hz, 2H), 2.04-1.95 (m, 3H), 1.75 (d, J=12.0 Hz, 2H), 1.64-1.52 (m, 1H), 1.28-1.15 (m, 2H), 0.65 (s, 2H), 0.42 (s, 2H); LC-MS $(ESI^+)$ m/z 975.2 $(M+H)^+$.

Example 50. Synthesis of Compound 18

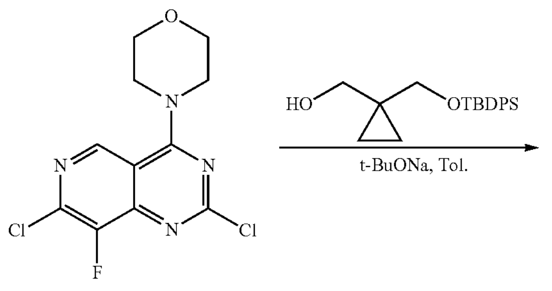

-continued
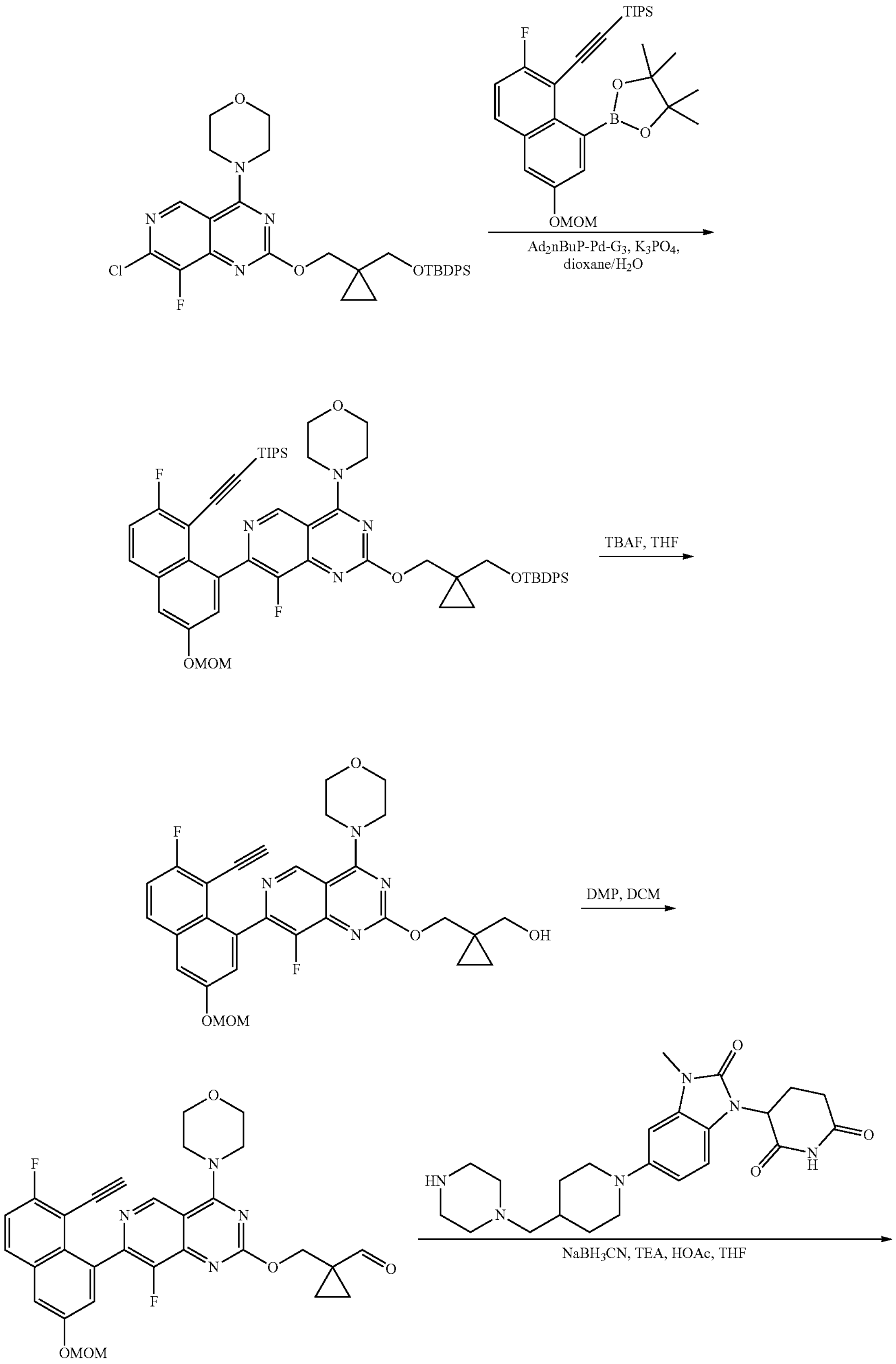

-continued

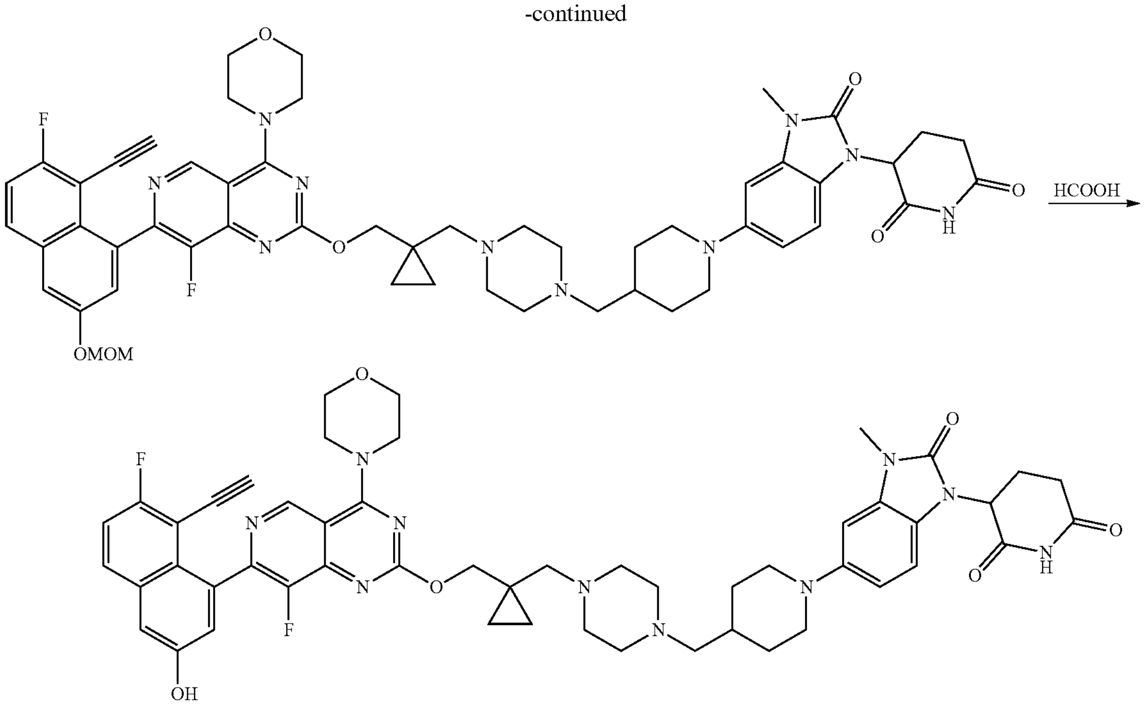

18

Step 1-4-(2-((1-(((Tert-butyldiphenylsilyl)oxy) methyl) cyclopropyl) methoxy)-7-chloro-8-fluoropyrido[4,3-d]pyrimidin-4-yl) morpholine. To a solution of 4-(2,7-dichloro-8-fluoro-pyrido[4,3-d]pyrimidin-4-yl) morpholine (1.78 g, 5.87 mmol, CAS #441785 Apr. 2) in Tol. (30 mL) was added t-BuONa (1.69 g, 17.62 mmol) and [1-[[tert-butyl(diphenyl) silyl]oxymethyl]cyclopropyl]methanol (2.00 g, 5.87 mmol). The mixture was stirred at 0° C. for 1 hr. On completion, the reaction mixture was quenched by saturated $NH_4Cl$ solution (100 mL), and then extracted with DCM (3×100 mL), the combined organic layers were washed with brine (3×100 mL), dried over anhydrous sodium sulfate, filtered and the filtrate was concentrated in vacuo to give a residue. The crude product was purified by reversed-phase HPLC (0.1% FA condition) to give the title compound (2.20 g, 61% yield) as white solid. $^1H$ NMR (400 MHz, DMSO-$d_6$) δ 8.97 (s, 1H), 7.61-7.53 (m, 4H), 7.45-7.39 (m, 2H), 7.39-7.30 (m, 4H), 4.42 (s, 2H), 4.08-3.90 (m, 4H), 3.82-3.72 (m, 4H), 3.66 (s, 2H), 0.97 (s, 9H), 0.70-0.62 (m, 2H), 0.59-0.51 (m, 2H).

Step 2-4-(2-((1-(((Tert-butyldiphenylsilyl)oxy)methyl) cyclopropyl) methoxy)-8-fluoro-7-(7-fluoro-3-(methoxymethoxy)-8-((triisopropylsilyl) ethynyl) naphthalen-1-yl)pyrido[4,3-d]pyrimidin-4-yl) morpholine. To a solution of 4-(2-((1-(((Tert-butyldiphenylsilyl)oxy)methyl) cyclopropyl) methoxy)-7-chloro-8-fluoropyrido[4,3-d]pyrimidin-4-yl) morpholine (1.00 g, 1.65 mmol) in dioxane (10 mL) and $H_2O$ (2 mL) was added [2-(2-aminophenyl)phenyl] palladium (1+); bis(1-adamantyl)-butyl-phosphane; methanesulfonate (119 mg, 164 μmol) and $K_3PO_4$ (1.05 g, 4.94 mmol), 2-[2-fluoro-6-(methoxymethoxy)-8-(4,4,5,5-tetramethyl-1,3,2-dioxaborolan-2-yl)-1-naphthyl]ethynyl-triisopropyl-silane (1.27 g, 2.47 mmol, CAS #2621932-37-2). The mixture was stirred at 90° C. for 1 hr under $N_2$ atmosphere. On completion, the reaction mixture was quenched by $H_2O$ (100 mL), and then extracted with EA (3×100 mL), the combined organic layers were washed with brine (3×100 mL), dried over anhydrous sodium sulfate, filtered and the filtrate was concentrated in vacuo to give a residue. The residue was purified by column chromatography ($SiO_2$, Petroleum ether/Ethyl acetate=100/1 to 3/1) to give the title compound (700 mg, 44% yield) as yellow solid. $^1H$ NMR (400 MHz, $CDCl_3$) δ 9.05 (s, 1H), 7.80 (dd, J=5.6, 9.0 Hz, 1H), 7.71-7.62 (m, 4H), 7.52 (d, J=2.4 Hz, 1H), 7.44-7.29 (m, 8H), 5.44-5.23 (m, 2H), 4.60 (d, J=11.2 Hz, 1H), 4.40 (d, J=11.2 Hz, 1H), 4.12-4.00 (m, 2H), 3.97-3.84 (m, 6H), 3.83-3.72 (m, 2H), 3.51 (s, 3H), 1.93 (s, 1H), 1.60 (s, 2H), 1.05 (s, 9H), 0.86 (dd, J=7.6, 12.4 Hz, 18H), 0.58-0.53 (m, 4H).

Step 3 [1-[[7-[8-Ethynyl-7-fluoro-3-(methoxymethoxy)-1-naphthyl]-8-fluoro-4-morpholino-pyrido[4,3-d]pyrimidin-2-yl]oxymethyl]cyclopropyl]methanol. To a solution of 4-(2-((1-(((tert-butyldiphenylsilyl)oxy)methyl)cyclopropyl) methoxy)-8-fluoro-7-(7-fluoro-3-(methoxymethoxy)-8-((triisopropylsilyl) ethynyl) naphthalen-1-yl)pyrido[4,3-d] pyrimidin-4-yl) morpholine (1.40 g, 1.46 mmol) in THF (10 mL) was added TBAF (1 M, 4.39 mL). The mixture was stirred at 25° C. for 16 hrs. On completion, the reaction mixture was concentrated under reduced pressure to remove THF and extracted with EA (3×100 mL), the combined organic layers were washed with brine (3×100 mL), dried over anhydrous sodium sulfate, filtered and the filtrate was concentrated in vacuo to give a residue. The residue was purified by column chromatography ($SiO_2$, Petroleum ether/Ethyl acetate=100/1 to 0/1) to give the title compound (700 mg, 85% yield) as white solid. $^1H$ NMR (400 MHz, DMSO-$d_6$) δ 9.08 (s, 1H), 8.10 (dd, J=5.6, 9.2 Hz, 1H), 7.74 (d, J=2.4 Hz, 1H), 7.55 (t, J=9.2 Hz, 1H), 7.40 (d, J=2.4 Hz, 1H), 5.37 (s, 2H), 4.63 (t, J=5.6 Hz, 1H), 4.30 (s, 2H), 4.06-3.98 (m, 3H), 3.96-3.88 (m, 2H), 3.86-3.77 (m, 4H), 3.44 (s, 3H), 3.39 (dd, J=6.0, 7.6 Hz, 2H), 0.53 (d, J=13.6 Hz, 4H).

Step 4-1-[[7-[8-Ethynyl-7-fluoro-3-(methoxymethoxy)-1-naphthyl]-8-fluoro-4-morpholino-pyrido[4,3-d]pyrimidin-2-yl]oxymethyl]cyclopropanecarbaldehyde. To a solution of [1-[[7-[8-ethynyl-7-fluoro-3-(methoxymethoxy)-1-naphthyl]-8-fluoro-4-morpholino-pyrido[4,3-d]pyrimidin-2-yl]oxymethyl]cyclopropyl]methanol (325 mg, 577 μmol) in DCM (10 mL) was added DMP (367 mg, 866 μmol). The mixture was stirred at 25° C. for 1 hr. On completion, the reaction mixture was quenched by saturated $Na_2S_2O_3$ (100 mL) and saturated $NaHCO_3$ solution (100 mL) at 25° C., and then stirred for 30 minutes. The mixture was extracted with DCM (2×150 mL). Then the combined organic layers was dried over anhydrous $Na_2SO_4$, filtered and filtrate was concentrated in vacuo to give the title compound (323 mg, 99% yield) as yellow solid. $^1$H NMR (400 MHz, DMSO-$d_6$) δ 9.09 (s, 1H), 8.92 (s, 1H), 8.10 (dd, J=6.0, 9.2 Hz, 1H), 7.75 (d, J=2.4 Hz, 1H), 7.55 (t, J=9.2 Hz, 1H), 7.40 (d, J=2.4 Hz, 1H), 5.37 (s, 2H), 4.55 (s, 2H), 4.06-3.97 (m, 3H), 3.96-3.87 (m, 2H), 3.87-3.77 (m, 4H), 3.44 (s, 3H), 1.39-1.28 (m, 4H).

Step 5-3-[5-[4-[[4-[[1-[[7-[8-Ethynyl-7-fluoro-3-(methoxymethoxy)-1-naphthyl]-8-fluoro-4-morpholino-pyrido[4,3-d]pyrimidin-2-yl]oxymethyl]cyclopropyl]methyl]piperazin-1-yl]methyl]-1-piperidyl]-3-methyl-2-oxo-benzimidazol-1-yl]piperidine-2,6-dione. To a solution of 3-[3-methyl-2-oxo-5-[4-(piperazin-1-ylmethyl)-1-piperidyl]benzimidazol-1-yl]piperidine-2,6-dione (253 mg, 576 μmol) in THF (10 mL) was added TEA (174 mg, 1.73 mmol, 240 μL), AcOH (138 mg, 2.30 mmol, 131 μL), 1-[[7-[8-ethynyl-7-fluoro-3-(methoxymethoxy)-1-naphthyl]-8-fluoro-4-morpholino-pyrido[4,3-d]pyrimidin-2-yl]oxymethyl]cyclopropanecarbaldehyde (323 mg, 576 μmol) and $NaBH_3CN$ (54.3 mg, 864 μmol). The mixture was stirred at 25° C. for 1 hr. On completion, the reaction mixture was concentrated was concentrated in vacuo. The crude product was purified by reversed-phase HPLC (neutral condition) to give the title compound (100 mg, 15% yield) as white solid. LC-MS (ESI$^+$) m/z 985.2 (M+H)$^+$.

Step 6-3-[5-[4-[[4-[[1-[[7-(8-Ethynyl-7-fluoro-3-hydroxy-1-naphthyl)-8-fluoro-4-morpholino-pyrido[4,3-d]pyrimidin-2-yl]oxymethyl]cyclopropyl]methyl]piperazin-1-yl]methyl]-1-piperidyl]-3-methyl-2-oxo-benzimidazol-1-yl]piperidine-2,6-dione (Compound 18). A solution of 3-[5-[4-[[4-[[1-[[7-[8-ethynyl-7-fluoro-3-(methoxymethoxy)-1-naphthyl]-8-fluoro-4-morpholino-pyrido[4,3-d]pyrimidin-2-yl]oxymethyl]cyclopropyl]methyl]piperazin-1-yl]methyl]-1-piperidyl]-3-methyl-2-oxo-benzimidazol-1-yl]piperidine-2,6-dione (90.0 mg, 91.3 μmol) in HCOOH (0.5 mL) was stirred at 25° C. for 1 hr. On completion, the reaction mixture was concentrated was concentrated in vacuo. The residue was purified by prep-HPLC (column: CD04-Welch Utimate C18 150*25*7 μm; mobile phase: [water (FA)-ACN]; gradient: 8%-38% B over 15 min) to give the title compound (29.7 mg, 31% yield, FA salt) as yellow solid. $^1$H NMR (400 MHz, DMSO-$d_6$) δ 11.05 (s, 1H), 10.58-9.78 (m, 1H), 9.07 (s, 1H), 7.97 (dd, J=6.0, 9.2 Hz, 1H), 7.46 (t, J=9.2 Hz, 1H), 7.39 (d, J=2.4 Hz, 1H), 7.19 (d, J=2.4 Hz, 1H), 6.91 (d, J=8.4 Hz, 1H), 6.80 (d, J=2.0 Hz, 1H), 6.61 (dd, J=1.6, 8.4 Hz, 1H), 5.28 (dd, J=5.2, 12.8 Hz, 1H), 4.28 (s, 2H), 4.08-3.96 (m, 3H), 3.95-3.87 (m, 2H), 3.86-3.78 (m, 4H), 3.55 (d, J=11.6 Hz, 2H), 3.29 (s, 3H), 2.95-2.85 (m, 1H), 2.73-2.54 (m, 5H), 2.48-2.21 (m, 9H), 2.13 (d, J=7.2 Hz, 2H), 2.04-1.89 (m, 1H), 1.75 (d, J=11.2 Hz, 2H), 1.65-1.49 (m, 1H), 1.28-1.12 (m, 2H), 0.64 (s, 2H), 0.42 (s, 2H); LC-MS (ESI$^+$) m/z 941.2 (M+H)$^+$.

Example 51. Synthesis of Compound 154

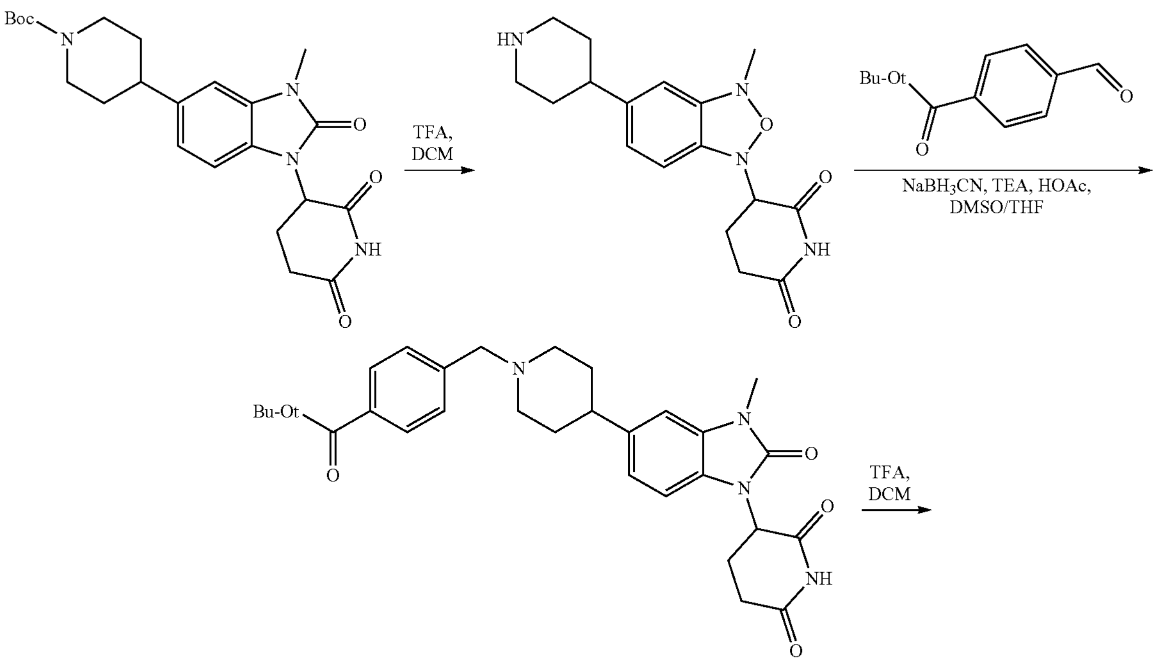

-continued

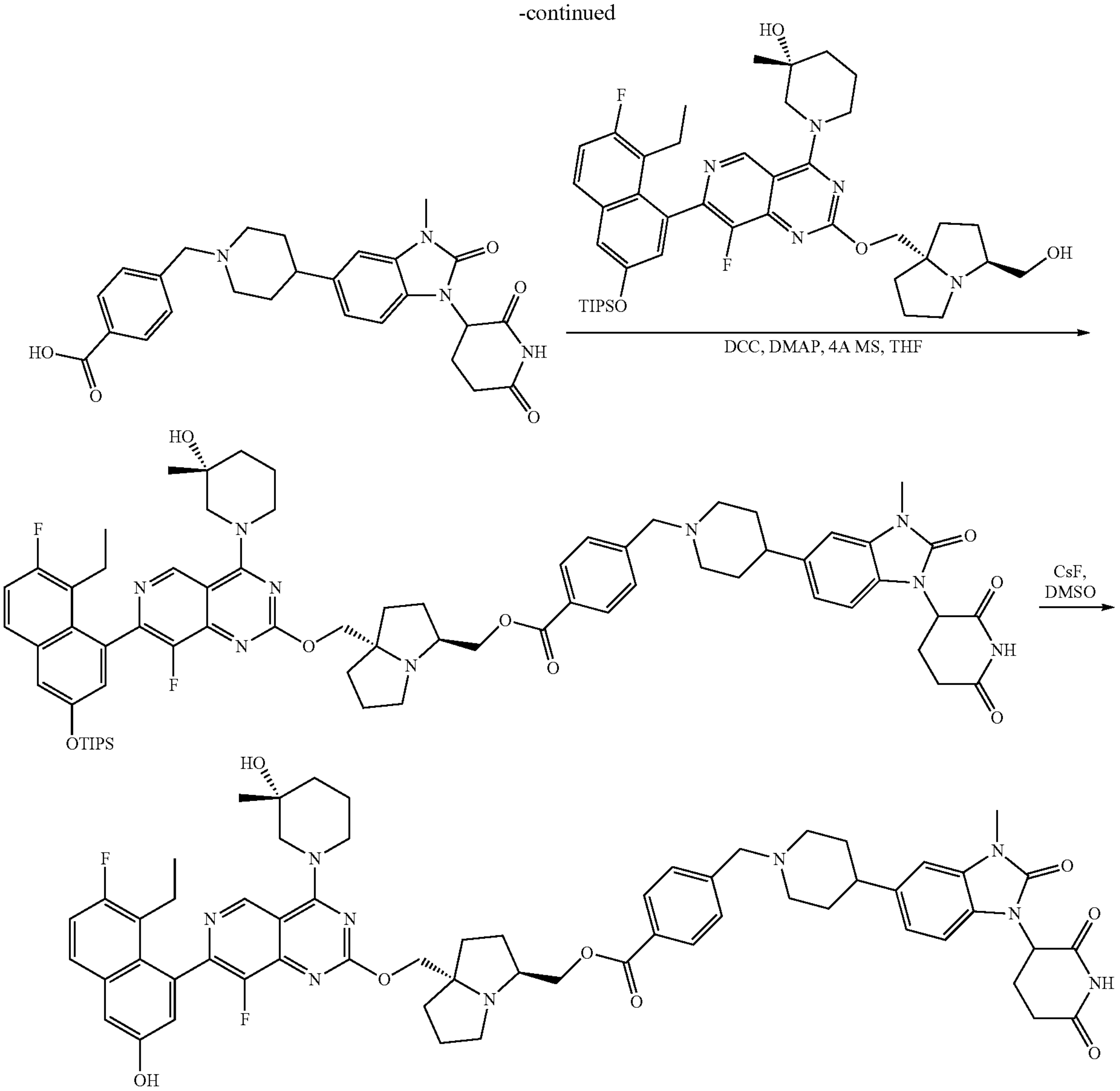

Compound 154

Step 1-3-(3-Methyl-2-oxo-5-(piperidin-4-yl)-2,3-dihydro-1H-benzo[d]imidazol-1-yl) piperidine-2,6-dione. To a solution of tert-butyl 4-[1-(2,6-dioxo-3-piperidyl)-3-methyl-2-oxo-benzimidazol-5-yl]piperidine-1-carboxylate (500 mg, 1.13 mmol, from Example 55) in DCM (6 mL) was added TFA (3.07 g, 26.9 mmol, 2 mL). The mixture was stirred at 25° C. for 0.5 hr. On completion, the reaction mixture was concentrated in vacuo to give the title compound (500 mg, 96% yield, TFA salt) as yellow oil. LC-MS ($ESI^+$) m/z 343.1 $(M+H)^+$.

Step 2-Tert-butyl 4-((4-(1-(2,6-Dioxopiperidin-3-yl)-3-methyl-2-oxo-2,3-dihydro-1H-benzo[d]imidazol-5-yl) piperidin-1-yl)methyl)benzoate. To a solution of 3-[3-methyl-2-oxo-5-(4-piperidyl)benzimidazol-1-yl]piperidine-2,6-dione (500 mg, 1.10 mmol, TFA salt) in THF (4 mL) and DMSO (1 mL) was added TEA (221 mg, 2.19 mmol, 304 μL) until pH-8-9, then stirred for 0.5 hr, HOAc (197 mg, 3.29 mmol, 188 μL) was added until pH=5-6. Then tert-butyl 4-formylbenzoate (271 mg, 1.31 mmol, CAS #65874-27-3) was added and stirred at 25° C. for 0.5 hr. Finally, $NaBH_3CN$ (103 mg, 1.64 mmol) was added and stirred at 25° C. for another 11 hrs. On completion, the reaction mixture was quenched with water (2 mL). The mixture was purified by reverse phase HPLC (0.1% TFA condition) to give the title compound (490 mg, 83% yield) as white solid. LC-MS ($ESI^+$) m/z 533.2 $(M+H)^+$.

Step 3-4-((4-(1-(2,6-Dioxopiperidin-3-yl)-3-methyl-2-oxo-2,3-dihydro-1H-benzo[d]imidazol-5-yl) piperidin-1-yl) methyl)benzoic acid. To a solution of tert-butyl 4-((4-(1-(2,6-dioxopiperidin-3-yl)-3-methyl-2-oxo-2,3-dihydro-1H-benzo[d]imidazol-5-yl) piperidin-1-yl)methyl)benzoate (170 mg, 319 μmol) in DCM (5 mL) was added TFA (1.54 g, 13.4 mmol, 1 mL). The mixture was stirred at 25° C. for 0.5 hr. On completion, the reaction mixture was concentrated in vacuo to give a residue, the residue was diluted with DCM (1 mL), adjusted pH=8 with TEA. Then the mixture was concentrated in vacuo to give the title compound (150 mg, 98% yield) as yellow oil. LC-MS ($ESI^+$) m/z 477.2 $(M+H)^+$.

Step 4-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-5-yl) piperidin-1-yl)methyl)benzoate. To a solution of 4-((4-(1-(2,6-dioxopiperidin-3-yl)-3-methyl-2-oxo-2,3-dihydro-1H-benzo[d]imidazol-5-yl) piperidin-1-yl) methyl)benzoic acid (138 mg, 289 μmol) in THF (4 mL) was added DCC (119 mg, 579 μmol, 117 μL) and DMAP (23.6 mg, 193 μmol), 4A MS (150 mg). The mixture was stirred at 25° C. for 0.5 hr. After that, (R)-1-(7-(8-ethyl-7-fluoro-3-((triisopropylsilyl)oxy) naphthalen-1-yl)-8-fluoro-2-(((3S, 7aS)-3-(hydroxymethyl)hexahydro-1H-pyrrolizin-7a-yl) methoxy)pyrido[4,3-d]pyrimidin-4-yl)-3-methylpiperidin-3-ol (150 mg, 193 μmol) was added to the reaction. The mixture was stirred at 60° C. for 11.5 hrs. On completion, the reaction mixture was concentrated in vacuo to give a residue. The residue was purified by reverse phase HPLC (0.1% TFA condition) to give the title compound (60.0 mg, 25% yield) as yellow solid. LC-MS ($ESI^+$) m/z 1234.4 $(M+H)^+$.

Step 5-((3S,7aS)-7a-(((7-(8-Ethyl-7-fluoro-3-hydroxynaphthalen-1-yl)-8-fluoro-4-((S)-1-oxa-6-azaspiro [3.5]nonan-6-yl)pyrido[4,3-d]pyrimidin-2-yl)oxy)methyl) hexahydro-1H-pyrrolizin-3-yl)methyl-4-(3-(1-(2,6-dioxopiperidin-3-yl)-3-methyl-2-oxo-2,3-dihydro-1H-benzo[d]imidazol-5-yl) prop-2-yn-1-yl) piperidine-1-carboxylate (Compound 154). To a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d] imidazol-5-yl) piperidin-1-yl)methyl)benzoate (55.0 mg, 44.5 μmol) in DMSO (0.50 mL) was added CsF (13.5 mg, 89.1 μmol). The mixture was stirred at 25° C. for 0.5 hr. On completion, the reaction mixture was filtered to give a residue. The residue was purified by prep-HPLC (column: CD01-Phenomenex luna C18 150*25*10 μm; mobile phase: [water (FA)-ACN]; gradient: 7%-37% B over 8 min) to give the title compound (35.6 mg, 70% yield, FA salt) as yellow solid. 1H NMR (400 MHz, DMSO-$d_6$) δ 11.07 (s, 1H), 9.93 (s, 1H), 9.24 (d, J=3.6 Hz, 1H), 7.98 (d, J=7.6 Hz, 2H), 7.76 (dd, J=6.0, 8.8 Hz, 1H), 7.50 (d, J=8.0 Hz, 2H), 7.38-7.30 (m, 2H), 7.08 (s, 1H), 7.04-6.96 (m, 2H), 6.90 (d, J=8.0 Hz, 1H), 5.33 (dd, J=5.6, 12.8 Hz, 1H), 4.74 (d, J=11.6 Hz, 1H), 4.60-4.48 (m, 2H), 4.44-4.20 (m, 3H), 4.11-4.01 (m, 1H), 3.69-3.48 (m, 4H), 3.42-3.37 (m, 2H), 3.30-3.28 (m, 3H), 3.16-3.07 (m, 1H), 2.94-2.85 (m, 3H), 2.76-2.63 (m, 2H), 2.36-2.30 (m, 1H), 2.25-1.82 (m, 13H), 1.78-1.62 (m, 8H), 1.16 (d, J=6.8 Hz, 3H), 0.72 (q, J=7.2 Hz, 3H); LC-MS ($ESI^+$) m/z 1078.3 $(M+H)^+$.

Example 52. Synthesis of Compound 155

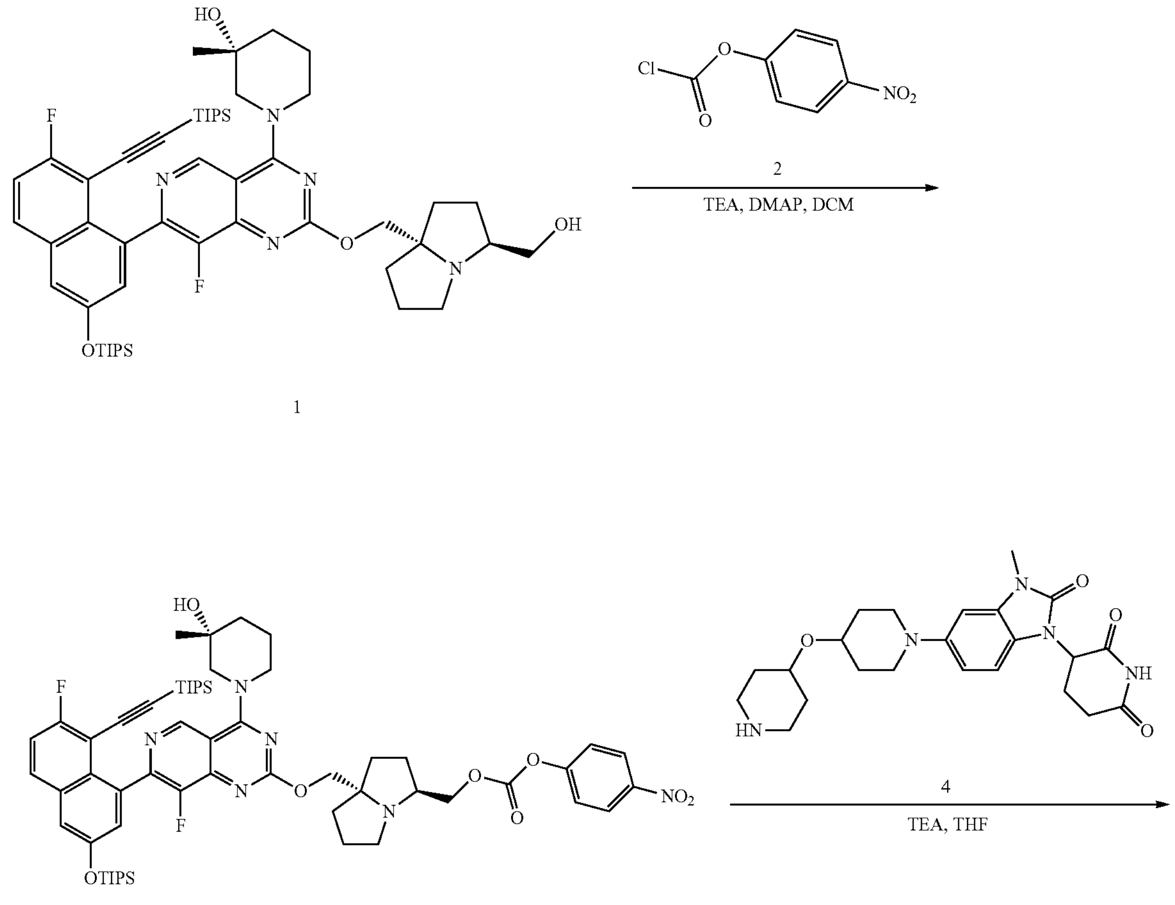

-continued

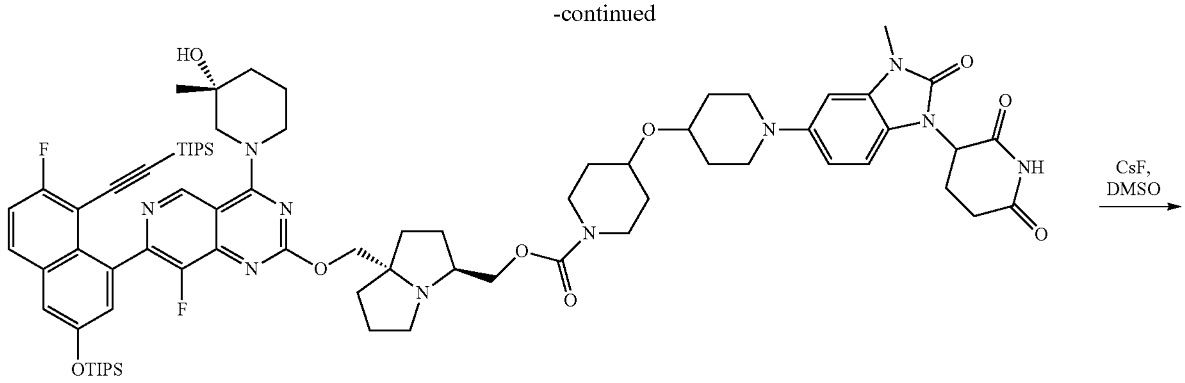

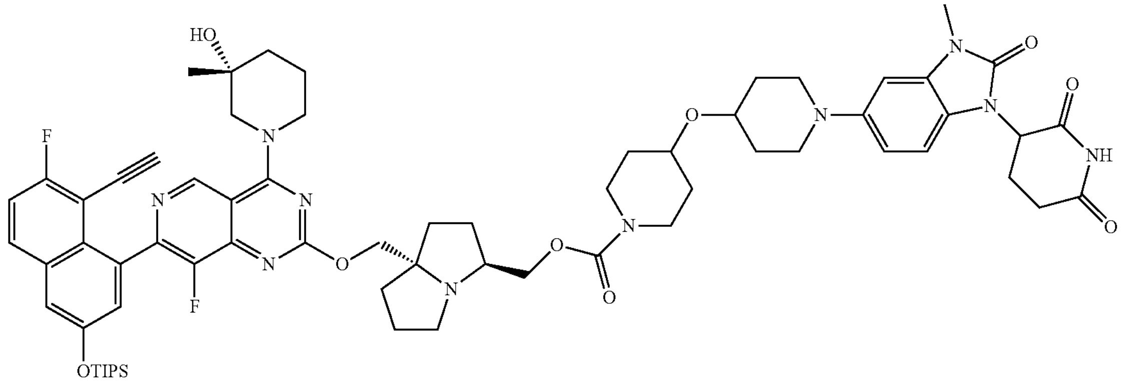

Step 1-((3S,7aS)-7a-(((8-Fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate. To a mixture of (R)-1-(8-fluoro-7-(7-fluoro-8-((triisopropylsilyl) ethynyl)-3-((triisopropylsilyl)oxy) naphthalen-1-yl)-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (100 mg, 107 μmol) in DCM (5 mL) was added TEA (363 mg, 3.59 mmol, 0.5 mL), DMAP (1.32 mg, 10.7 μmol) and 4-nitrophenyl carbonochloridate (65.1 mg, 323 μmol, CAS #7693-46-1), the reaction mixture was stirred at 25° C. for 12 hrs. On completion, the reaction mixture diluted with water (10 mL) and extracted with DCM (2x10 mL). The combined organic layers were dried over $Na_2SO_4$, filtered and the filtrate was concentrated in vacuo to give the title compound (120 mg, crude) as yellow oil. LC-MS ($ESI^+$) m/z 1093.3 $(M+H)^+$.

Step 2-((3S,7aS)-7a-(((8-Fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(1-(2,6-dioxopiperidin-3-yl)-3-methyl-2-oxo-2,3-dihydro-1H-benzo[d]imidazol-5-yl) piperidin-4-yl) oxy)piperidine-1-carboxylate. To a mixture of 3-(3-methyl-2-oxo-5-(4-(piperidin-4-yloxy)piperidin-1-yl)-2,3-dihydro-1H-benzo[d]imidazol-1-yl) piperidine-2,6-dione (110 mg, 198 μmol, TFA) in THF (2 mL) was added TEA (363 mg, 3.59 mmol, 0.5 mL) and ((3S,7aS)-7a-(((8-fluoro-7-(7-fluoro-8-((triisopropylsilyl) ethynyl)-3-((triisopropylsilyl) oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (108 mg, 99.0 μmol), the reaction mixture was stirred at 25° C. for 0.5 hr. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 45%-75% B over 8 min) to give the title compound (100 mg, 36% yield) as yellow solid. LC-MS (ESI) m/z 1395.4 $(M+H)^+$.

Step 3-((3S,7aS)-7a-(((7-(8-Ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((1-(1-(2,6-dioxopiperidin-3-yl)-3-methyl-2-oxo-2,3-dihydro-1H-benzo[d]imidazol-5-yl) piperidin-4-yl)oxy)piperidine-1-carboxylate (Compound 155). To a mixture of ((3S,7aS)-7a-(((8-fluoro-7-(7-fluoro-8-((triisopropylsilyl) ethynyl)-3-((triisopropylsilyl)oxy) naphthalen-1-yl)-4-((R)-3-hydroxy-3-methylpiperidin-1-yl)pyrido[4,3-d]pyrimidin-2-yl)oxy) methyl)hexahydro-1H-pyrrolizin-3-yl)methyl 4-((1-(1-(2,6-dioxopiperidin-3-yl)-3-methyl-2-oxo-2,3-dihydro-1H-benzo[d]imidazol-5-yl) piperidin-4-yl)oxy)piperidine-1-carboxylate (90.0 mg, 64.4 μmol) in DMSO (2 mL) was added CsF (29.3 mg, 193 μmol), the reaction mixture was stirred at 40° C. for 0.5 hr. On completion, the reaction mixture was filtered to afford the filtrate. The residue was purified by prep-HPLC (column: CD01-Phenomenex luna C18 150*25*10 μm; mobile phase: [water (FA)-ACN]; gradient: 5%-35% B over 8 min) to give the title compound (41.2 mg, 56% yield, FA) as yellow solid. $^1H$ NMR (400 MHz, DMSO-$d_6$) δ 11.06 (s, 1H), 9.24-9.03 (m, 1H), 7.97 (dd, J=6.0, 8.8 Hz, 1H), 7.46 (t, J=9.2 Hz, 1H), 7.39 (s, 1H), 7.25-7.16 (m, 1H), 6.91 (d, J=8.8 Hz, 1H), 6.82 (s, 1H), 6.61 (d, J=8.8 Hz, 1H), 5.28 (dd, J=5.2, 12.4 Hz, 1H), 4.90-4.58 (m, 1H), 4.43-4.24 (m, 2H), 4.22-4.06 (m, 5H), 3.95 (s, 1H), 3.67 (d, J=14.0 Hz, 3H), 3.58 (s, 2H), 3.39 (m, 2H), 3.29 (s, 3H), 3.10 (s, 2H), 2.93-2.83 (m, 2H), 2.81-2.74 (m, 3H), 2.68-2.57 (m, 3H), 2.09-2.01 (m, 2H), 1.99-1.95 (m, 1H), 1.89 (d, J=9.2 Hz, 2H), 1.82-1.63 (m, 12H), 1.54 (d, J=7.6 Hz, 3H), 1.34 (d, J=8.8 Hz, 2H), 1.16 (d, J=16.4 Hz, 3H); LC-MS (ESI) m/z 1083.2 $(M+H)^+$.
Example 53. Synthesis of Compound 156
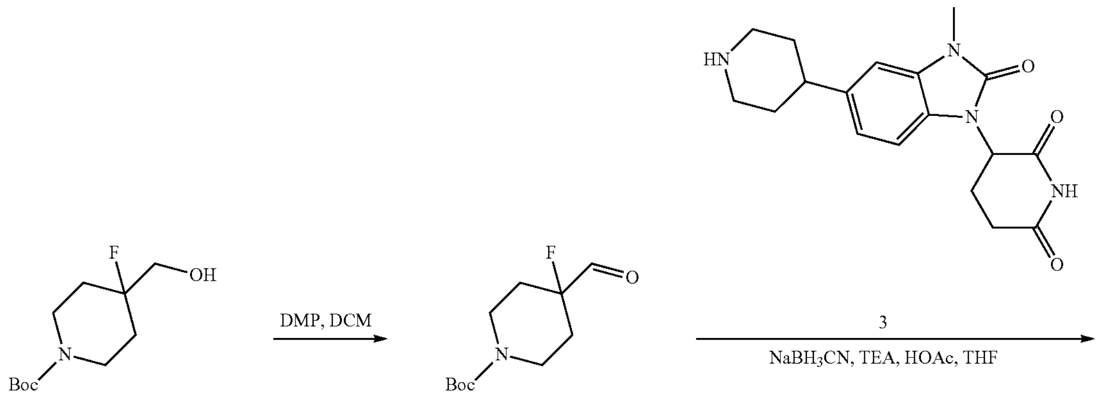
1
2
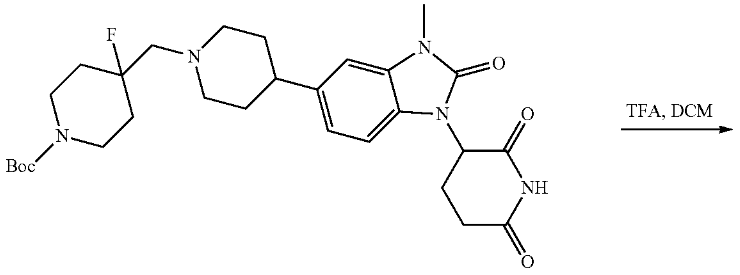
4
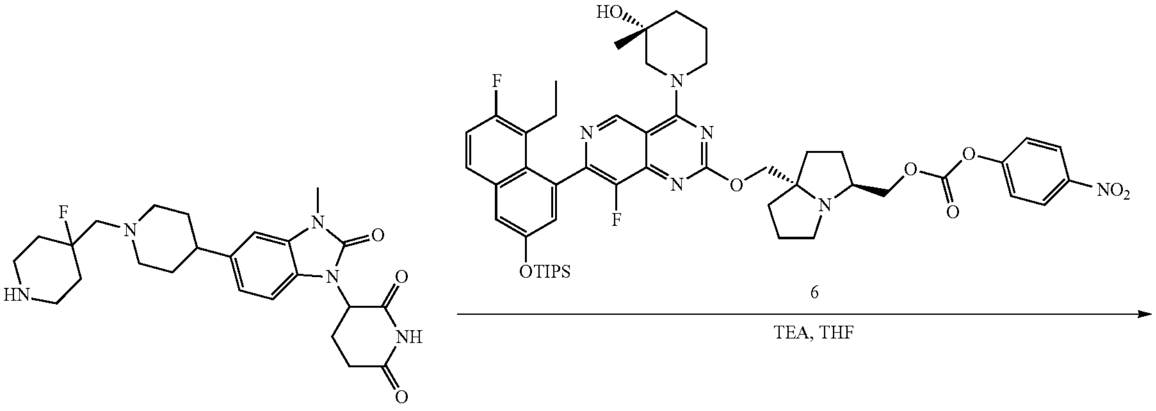
5

-continued

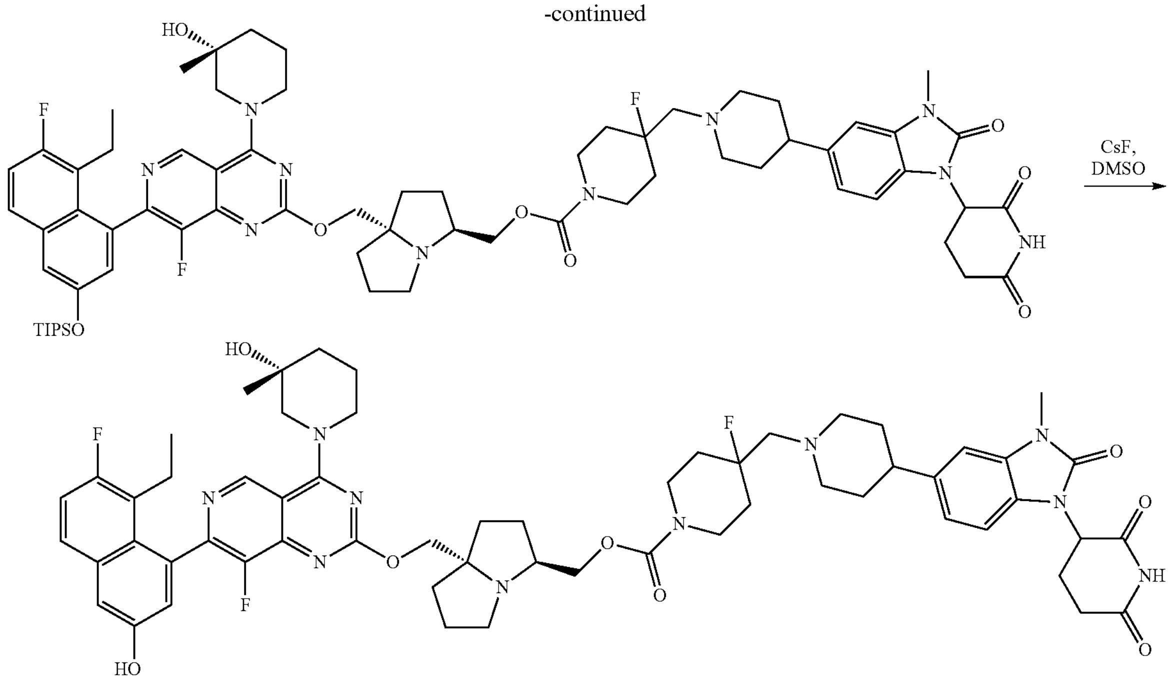

Step 1-Tert-butyl 4-fluoro-4-formylpiperidine-1-carboxylate. To a solution of tert-butyl 4-fluoro-4-(hydroxymethyl) piperidine-1-carboxylate (1.90 g, 8.14 mmol, CAS #614730-97-1) in DCM (5 mL) was added DMP (5.18 g, 12.2 mmol, 3.79 mL). The mixture was stirred at 25° C. for 1 hr. On completion, the reaction mixture was quenched by saturated $Na_2S_2O_3$ (100 mL) and saturated $NaHCO_3$ solution (100 mL) at 25° C., and then stirred for 30 minutes. The mixture was extracted with DCM (2×150 mL). Then the combined organic layers was dried over anhydrous $Na_2SO_4$, filtered and filtrate was concentrated in vacuo to give the title compound (1.80 g, 95% yield) as yellow solid. 1H NMR (400 MHz, DMSO-$d_6$) δ 9.65 (d, J=6.4 Hz, 1H), 3.05-2.98 (m, 2H), 2.92-2.85 (m, 2H), 1.80-1.77 (m, 2H), 1.74-1.70 (m, 2H), 1.41 (s, 9H).

Step 2-Tert-butyl 4-((4-(1-(2,6-dioxopiperidin-3-yl)-3-methyl-2-oxo-2,3-dihydro-1H-benzo[d]imidazole-5-yl) piperidin-1-yl)methyl)-4-fluoropiperidine-1-carboxylate. To a solution of 3-(3-methyl-2-oxo-5-(piperidin-4-yl)-2,3-dihydro-1H-benzo[d]imidazol-1-yl) piperidine-2,6-dione (309 mg, 902 μmol) in THF (5 mL) was added TEA (273 mg, 2.71 mmol, 376 μL), HOAc (216 mg, 3.61 mmol, 206 μL) tert-butyl 4-fluoro-4-formylpiperidine-1-carboxylate (626 mg, 2.71 mmol) and $NaBH_3CN$ (85.0 mg, 1.35 mmol). The mixture was stirred at 50° C. for 16 hrs. On completion, the reaction mixture was concentrated in vacuo. The crude product was purified by reversed-phase HPLC (0.1% FA condition) to give the title compound (300 mg, 59% yield) as white solid. $^1$H NMR (400 MHz, DMSO-$d_6$) δ 11.07 (s, 1H), 7.08 (s, 1H), 7.00 (d, J=8.0 Hz, 1H), 6.90 (d, J=8.0 Hz, 1H), 5.33 (dd, J=5.2, 12.8 Hz, 1H), 3.73 (d, J=13.2 Hz, 2H), 3.33 (s, 3H), 3.10-2.96 (m, 4H), 2.94-2.86 (m, 1H), 2.75-2.67 (m, 1H), 2.65-2.56 (m, 2H), 2.23 (s, 2H), 2.03-1.96 (m, 1H), 1.89-1.74 (m, 3H), 1.74-1.51 (m, 6H), 1.42-1.38 (m, 9H), 1.17 (t, J=7.2 Hz, 1H)

Step 3-3-(5-(1-((4-Fluoropiperidin-4-yl)methyl) piperidin-4-yl)-3-methyl-2-oxo-2,3-dihydro-1H-benzo[d]imidazol-1-yl) piperidine-2,6-dione. To a solution of tert-butyl 4-((4-(1-(2,6-dioxopiperidin-3-yl)-3-methyl-2-oxo-2,3-dihydro-1H-benzo[d]imidazol-5-yl) piperidin-1-yl)methyl)-4-fluoropiperidine-1-carboxylate (150 mg, 268 μmol) in DCM (1 mL) was added TFA (1.54 g, 13.4 mmol, 1.00 mL). The mixture was stirred at 25° C. for 0.5 hr. On completion, the reaction mixture was concentrated in vacuo to give the title compound (123 mg, 99% yield, TFA salt) as white solid. LC-MS (ESI) m/z 458.2 (M+H)$^+$.

Step 4-((3S,7AS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl)-4-fluoropiperidine-1-carboxylate. To a solution of 3-(5-(1-((4-fluoropiperidin-4-yl)methyl) piperidin-4-yl)-3-methyl-2-oxo-2,3-dihydro-1H-benzo[d]imidazol-1-yl) piperidine-2,6-dione (106 mg, 233 μmol) in THF (3 mL) was added TEA (82.7 mg, 818 μmol, 113 μL) and ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (110 mg, 116 μmol). The mixture was stirred at 25° C. for 1 hr. On completion, the reaction mixture was concentrated in vacuo. The crude product was purified by reversed-phase HPLC (0.1% FA condition) to give the title compound (110 mg, 73% yield) as white solid. LC-MS (ESI) m z 1259.3 (M+H)$^+$.

Step 5-((3S,7AS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl)-4-fluoropiperidine-1-carboxylate (Compound 156). To a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)

oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl)-4-fluoropiperidine-1-carboxylate (100 mg, 79.3 μmol) in DMSO (2 mL) was added CsF (36.1 mg, 238 μmol). The mixture was stirred at 30° C. for 2 hrs. On completion, the residue was purified by prep-HPLC (column: CD01-Phenomenex luna C18 150*25*10 μm; mobile phase: [water (FA)-ACN]; gradient: 13%-43% B over 10 min) to give the title compound (39.6 mg, 42% yield, FA salt) as white solid. 1H NMR (400 MHz, DMSO-$d_6$) δ 11.08 (s, 1H), 9.94 (d, J=1.2 Hz, 1H), 9.26 (d, J=4.4 Hz, 1H), 7.76 (dd, J=6.0, 8.8 Hz, 1H), 7.38-7.29 (m, 2H), 7.09-6.96 (m, 3H), 6.89 (d, J=8.4 Hz, 1H), 5.33 (dd, J=5.2, 12.8 Hz, 1H), 4.75 (d, J=11.6 Hz, 1H), 4.50-4.19 (m, 5H), 4.08 (dd, J=13.6, 19.4 Hz, 1H), 3.81 (d, J=12.4 Hz, 2H), 3.71-3.48 (m, 2H), 3.32 (s, 3H), 3.18-3.02 (m, 4H), 3.01-2.84 (m, 4H), 2.76-2.54 (m, 4H), 2.37-2.32 (m, 1H), 2.25-2.13 (m, 4H), 2.04-1.80 (m, 11H), 1.70 (s, 10H), 1.17 (d, J=8.8 Hz, 3H), 0.77-0.68 (m, 3H); LC-MS ($ESI^+$) m/z 1103.2 $(M+H)^+$.

Example 54. Synthesis of Compound 157

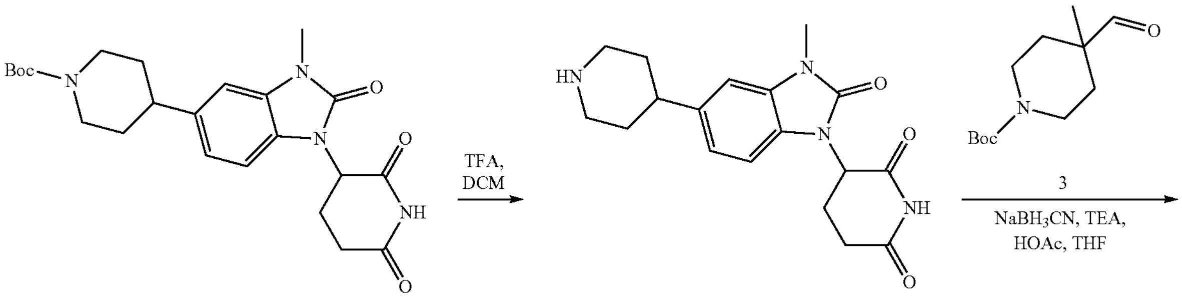

1

5

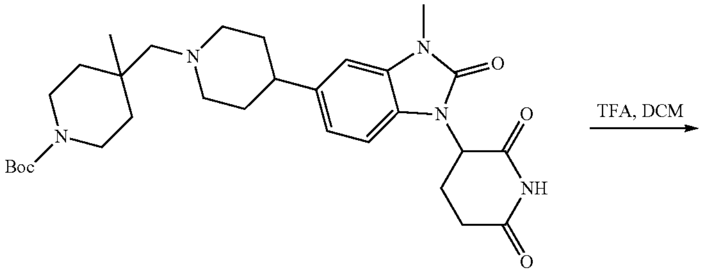

4

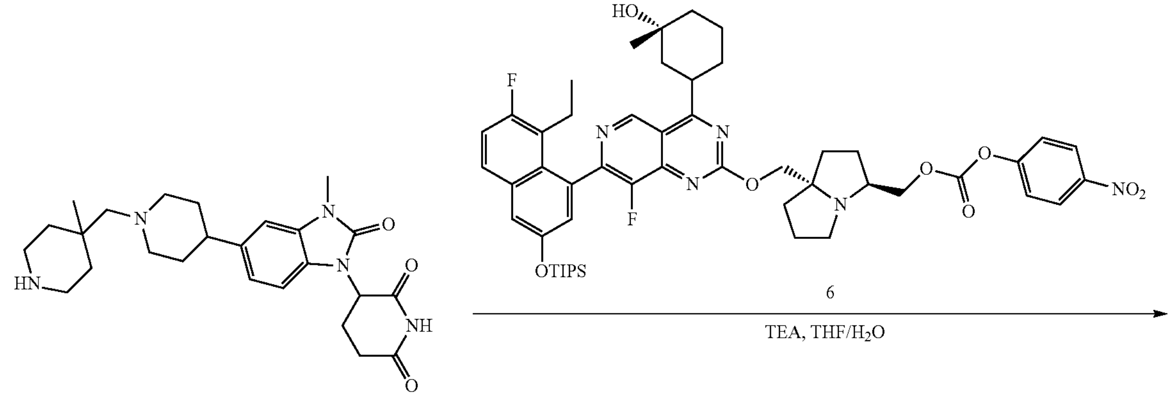

5

-continued

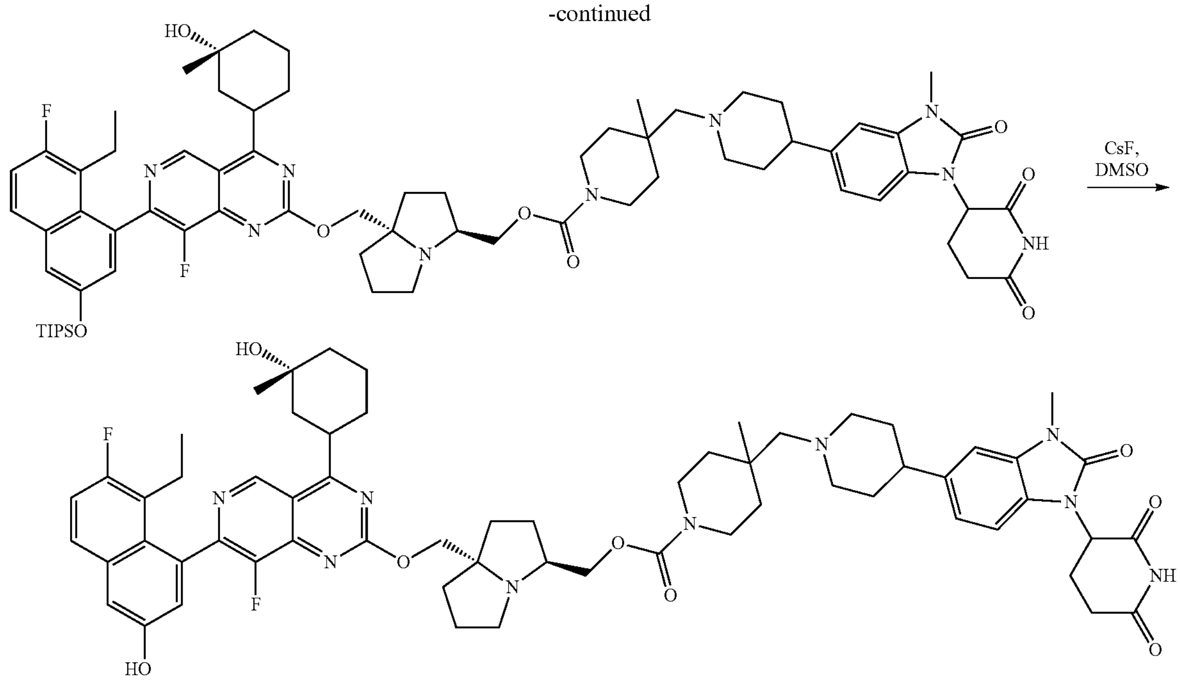

Step 1-3-(3-Methyl-2-oxo-5-(piperidin-4-yl)-2,3-dihydro-1H-benzo[d]imidazol-1-yl) piperidine-2,6-dione. To a solution of tert-butyl 4-(1-(2,6-dioxopiperidin-3-yl)-3-methyl-2-oxo-2,3-dihydro-1H-benzo[d]imidazol-5-yl) piperidine-1-carboxylate (450 mg, 1.02 mmol) in DCM (5 mL) was added TFA (3.84 g, 33.6 mmol, 2.5 mL). The mixture was stirred at 25° C. for 0.5 hr. On completion, the mixture was filtered and the filtrate was concentrated in vacuo to give the title compound (450 mg, 96% yield, TFA salt) as yellow oil. LC-MS ($ESI^+$) m/z 343.0 $(M+H)^+$.

Step 2-Tert-butyl 4-((4-(1-(2,6-dioxopiperidin-3-yl)-3-methyl-2-oxo-2,3-dihydro-1H-benzo[d]imidazol-5-yl) piperidin-1-yl)methyl)-4-methylpiperidine-1-carboxylate. To a solution of 3-[3-methyl-2-oxo-5-(4-piperidyl)benzimidazol-1-yl]piperidine-2,6-dione (450 mg, 985 μmol, TFA salt) in THF (10 mL) was basified with TEA (199 mg, 1.97 mmol) to pH=7-8. The mixture was acidified with HOAc (177 mg, 2.96 mmol) to pH=6-7. And then tert-butyl 4-formyl-4-methyl-piperidine-1-carboxylate (448 mg, 1.97 mmol, CAS #189442-92-0) was added. The mixture was stirred at 30° C. for 0.5 hr. At last $NaBH_3CN$ (92.9 mg, 1.48 mmol) was added, the mixture was stirred at 30° C. for 11.5 hrs. On completion, the reaction mixture was concentrated in vacuo to give a residue. The residue was purified by reversed-phase HPLC (0.1% TFA condition) to give the title compound (200 mg, 34% yield) as white solid. $^1H$ NMR (400 MHz, DMSO-$d_6$) δ 11.11 (s, 1H), 7.16-6.91 (m, 3H), 5.37 (dd, J=5.2, 12.8 Hz, 1H), 3.60 (br d, J=10.4 Hz, 7H), 3.37-3.33 (m, 3H), 3.27-3.20 (m, 2H), 3.13 (d, J=3.2 Hz, 2H), 2.92 (dd, J=8.4, 13.6 Hz, 1H), 2.74-2.67 (m, 1H), 2.63 (d, J=17.2 Hz, 1H), 2.21-2.09 (m, 2H), 2.06-1.97 (m, 1H), 1.93 (d, J=13.2 Hz, 2H), 1.54-1.43 (m, 4H), 1.41 (s, 9H), 1.19-1.14 (m, 3H); LC-MS (ESI) m/z 454.1 $(M+H)^+$. LC-MS (ESI) m/z 554.2 $(M+H)^+$.

Step 3-3-(3-Methyl-5-(1-((4-methylpiperidin-4-yl) methyl) piperidin-4-yl)-2-oxo-2,3-dihydro-1H-benzo[d]imidazol-1-yl) piperidine-2,6-dione. To a solution of tert-butyl 4-((4-(1-(2,6-dioxopiperidin-3-yl)-3-methyl-2-oxo-2,3-dihydro-1H-benzo[d]imidazol-5-yl) piperidin-1-yl)methyl)-4-methylpiperidine-1-carboxylate (80.0 mg, 144 μmol) in DCM (1 mL) was added TFA (767 mg, 6.73 mmol, 0.5 mL). The mixture was stirred at 25° C. for 0.5 hr. On completion, the reaction mixture was concentrated in vacuo to give the title compound (80.0 mg, 97% yield, TFA salt) as yellow oil. LC-MS (ESI) m/z 454.1 $(M+H)^+$.

Step 4-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl)-4-methylpiperidine-1-carboxylate. To a solution of 3-(3-methyl-5-(1-((4-methylpiperidin-4-yl)methyl) piperidin-4-yl)-2-oxo-2,3-dihydro-1H-benzo[d]imidazol-1-yl) piperidine-2,6-dione (80.0 mg, 140 μmol, TFA salt) in $H_2O$ (0.5 mL) and THF (1 mL) was basified with TEA (28.5 mg, 281 μmol) to pH=7-8. And then ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (88.4 mg, 93.9 μmol) in THF (2 mL) was added. The mixture was stirred at 25° C. for 0.5 hr. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 28%-58% B over 10 min) to give the title compound (80.0 mg, 66% yield) as white solid. LC-MS (ESI) m/z 1255.9 $(M+H)^+$.

Step 5-((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl)-4-methylpiperidine-1-carboxylate (Compound 157). To a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(piperidin-1-ylmethyl) piperidine-1-carboxylate (80.0 mg, 63.7 μmol) in DMSO (1 mL) was added CsF (29.0 mg, 191 μmol). The mixture was stirred at 30° C. for 0.5 hr. On completion, the reaction mixture was concentrated in vacuo to give a residue. The residue was purified by prep-HPLC (column: C18 150×40 mm; mobile phase: [water (FA)-ACN]; gradient: 12%-42% B over 10 min) to give the title compound (35.2 mg, 48% yield, FA salt) as white solid. $^1$H NMR (400 MHz, DMSO-$d_6$) δ 11.08 (s, 1H), 9.22 (d, J=3.6 Hz, 1H), 7.76 (dd, J=6.0, 9.2 Hz, 1H), 7.38-7.30 (m, 2H), 7.07 (s, 1H), 7.03 (d, J=2.4 Hz, 1H), 6.99 (d, J=8.0 Hz, 1H), 6.89 (d, J=8.4 Hz, 1H), 5.33 (dd, J=5.6, 12.8 Hz, 1H), 4.88-4.66 (m, 1H), 4.37-4.28 (m, 1H), 4.21-3.99 (m, 5H), 3.61 (dd, J=9.2, 13.2 Hz, 2H), 3.52 (d, J=13.2 Hz, 1H), 3.36 (d, J=2.0 Hz, 1H), 3.32 (s, 3H), 3.29-3.27 (m, 1H), 3.16-3.08 (m, 2H), 2.94-2.88 (m, 1H), 2.85-2.70 (m, 5H), 2.61 (d, J=18.4 Hz, 2H), 2.44 (dd, J=6.8, 10.4 Hz, 1H), 2.37-2.28 (m, 3H), 2.15 (s, 3H), 2.07-1.95 (m, 3H), 1.83-1.61 (m, 14H), 1.56-1.48 (m, 1H), 1.44-1.36 (m, 2H), 1.22 (s, 2H), 1.16 (d, J=9.2 Hz, 2H), 0.91 (s, 3H), 0.73 (q, J=7.2 Hz, 3H); LC-MS (ESI$^+$) m/z 1099.2 (M+H)$^+$.

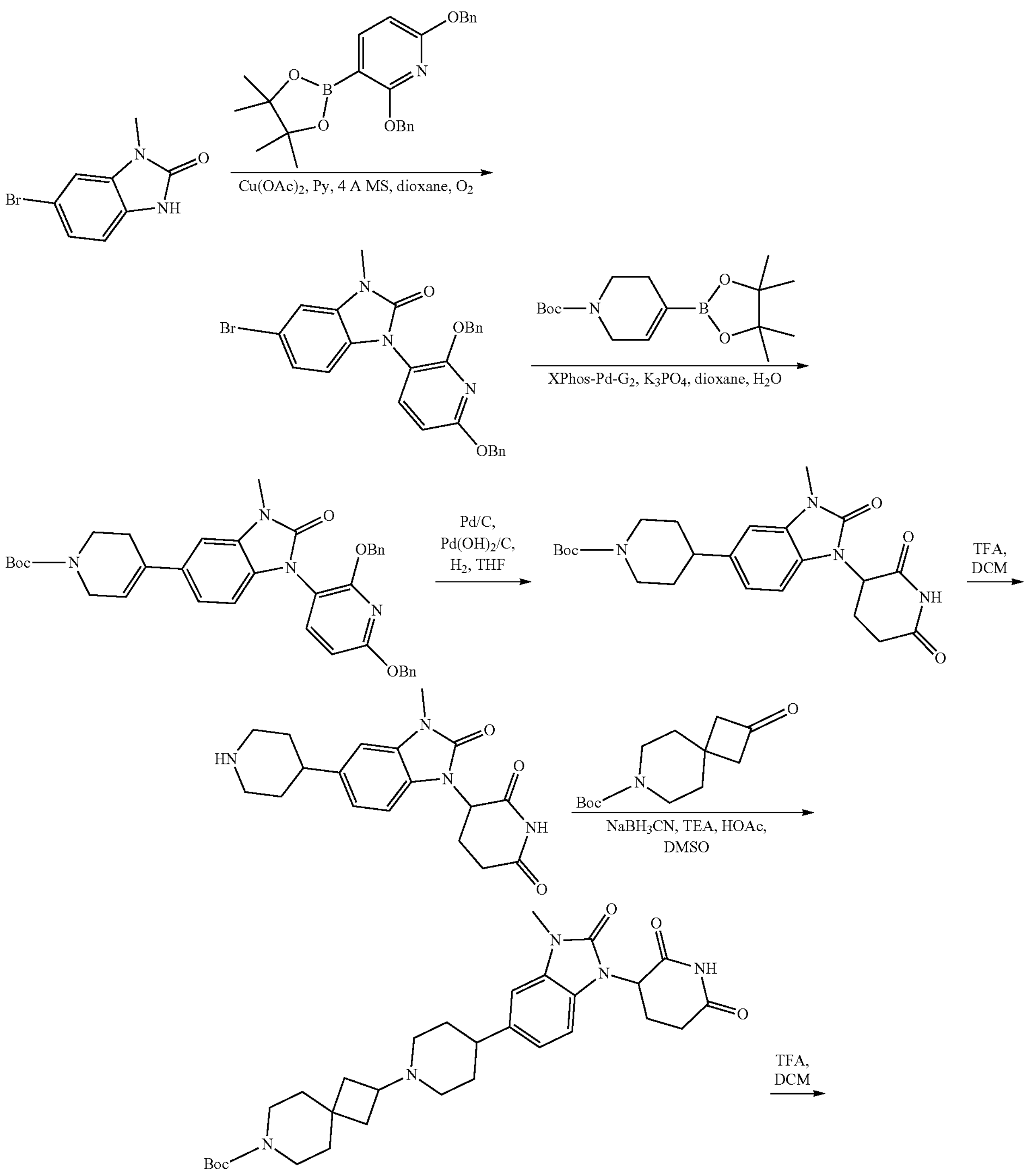

-continued

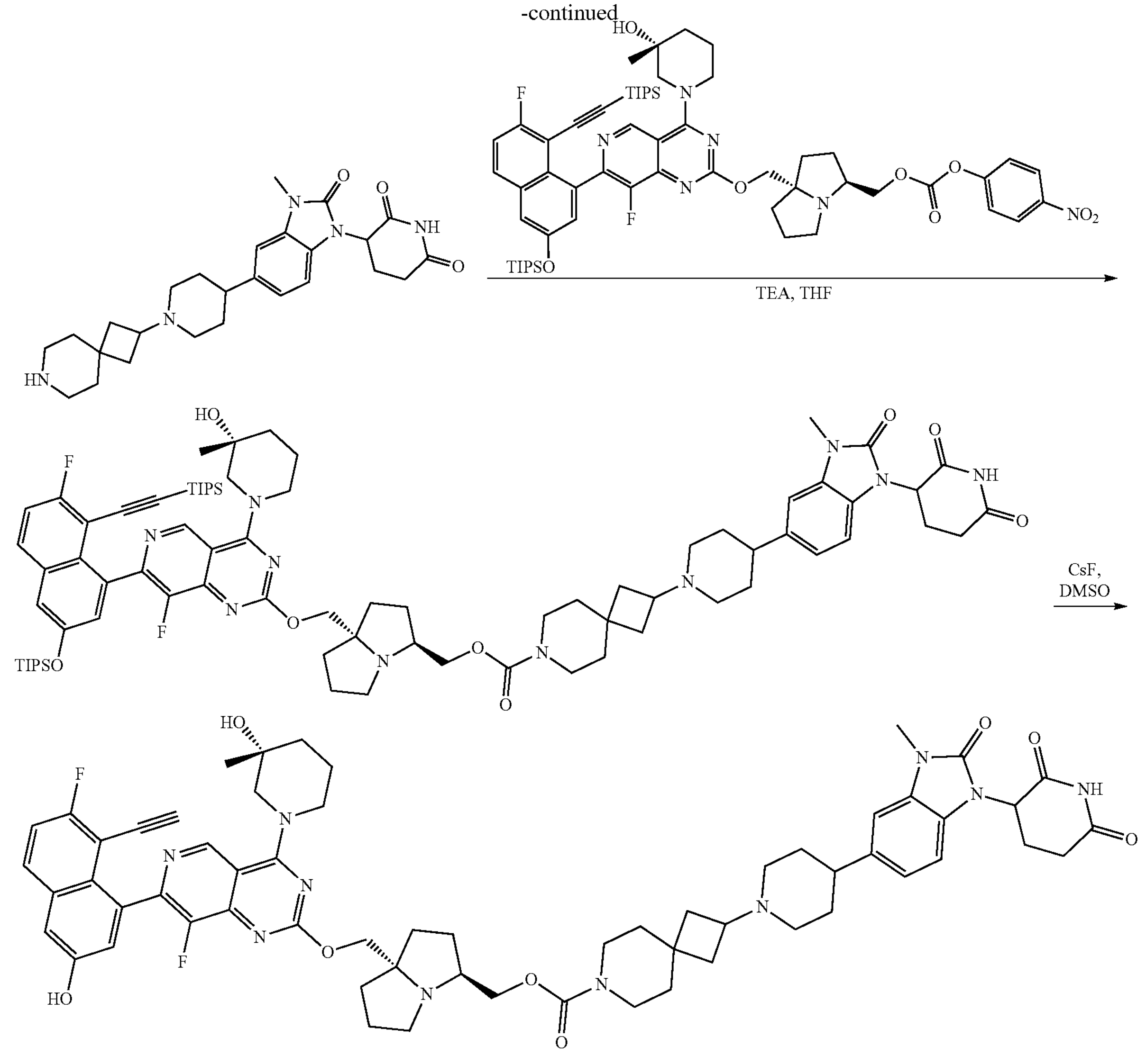

Compound 158

Step 1-1-(2,6-Bis(benzyloxy)pyridin-3-yl)-5-bromo-3-methyl-1H-benzo[d]imidazol-2 (3H)-one. To a suspention of 5-bromo-3-methyl-1H-benzimidazol-2-one (5.00 g, 22.0 mmol, from Example 58) and 2,6-dibenzyloxy-3-(4,4,5,5-tetramethyl-1,3,2-dioxaborolan-2-yl)-pyridine (11.0 g, 26.4 mmol, CAS #2152673-80-6) in dioxane (80 mL) was added 4A MS (5.00 g), diacetoxycopper (4.00 g, 22.0 mmol) and pyridine (5.23 g, 66.0 mmol), the mixture was stirred at 80° C. for 16 hrs under 02 atmosphere. On completion, the mixture was filtered and combined organic phase. Afterward, the organic phase was filtered and the filtrate was concentrated in vacuo to give a residue. The crude product was purified by column chromatography ($SiO_2$, PE:EA=2:1) to give the title compound (10.9 g, 95% yield) as brown solid. $^1H$ NMR (400 MHz, DMSO-$d_6$) δ 7.81 (d, J=8.4 Hz, 1H), 7.53-7.32 (m, 6H), 7.31-7.22 (m, 5H), 7.15 (dd, J=1.6, 8.4 Hz, 1H), 6.63 (dd, J=8.4, 11.6 Hz, 2H), 5.48-5.32 (m, 4H), 3.38 (s, 3H).

Step 2-Tert-butyl 4-(1-(2,6-bis(benzyloxy)pyridin-3-yl)-3-methyl-2-oxo-2,3-dihydro-1H-benzo[d]imidazol-5-yl)-5,6-dihydropyridine-1 (2H)-carboxylate. To a solution of 5-bromo-1-(2,6-dibenzyloxy-3-pyridyl)-3-methyl-benzimidazol-2-one (9.00 g, 17.4 mmol) in dioxane (100 mL) and $H_2O$ (10 mL) was added tert-butyl 4-(4,4,5,5-tetramethyl-1,3,2-dioxaborolan-2-yl)-3,6-dihydro-2H-pyridine-1-carboxylate (7.01 g, 22.6 mmol, CAS #286961-14-6), [2-(2-aminophenyl)-phenyl]-chloro-palladium; dicyclohexyl-[3-(2,4,6-triisopropylphenyl)phenyl]-phosphane (685 mg, 871 μmol) and $K_3PO_4$ (11.1 g, 52.2 mmol). The mixture was stirred under $N_2$ at 80° C. for 3 hrs. On completion, the reaction mixture was quenched a solution of sat. NaCl (100 mL), extracted with EA (3×100 mL), dried over anhydrous $Na_2SO_4$, filtered and the filtrate was concentrated in vacuo to give a residue. The crude product was purified by column chromatography ($SiO_2$, PE:EA=2:1) to give the title compound (10.5 g, 97% yield) as brown solid. $^1H$ NMR (400 MHz, DMSO-$d_6$) δ 7.79 (d, J=8.4 Hz, 1H), 7.54-7.21 (m, 11H), 7.07 (d, J=8.0 Hz, 1H), 6.62 (dd, J=8.4, 14.4 Hz, 2H), 6.19-6.16 (m, 1H), 5.48-5.30 (m, 4H), 4.01 (d, J=6.8 Hz, 2H), 3.55 (t, J=5.6 Hz, 2H), 3.40 (s, 3H), 2.50 (s, 2H), 1.43 (s, 9H).

Step 3-Tert-butyl 4-(1-(2,6-dioxopiperidin-3-yl)-3-methyl-2-oxo-2,3-dihydro-1H-benzo-[d]imidazol-5-yl) piperidine-1-carboxylate. To a solution of tert-butyl 4-[1-(2,6-dibenzyloxy-3-pyridyl)-3-methyl-2-oxo-benzimidazol-5-yl]-3,6-dihydro-2H-pyridine-1-carboxylate (10.5 g, 16.9 mmol) in THF (100 mL) was added Pd/C (9.50 g, 8.93 mmol, 10% purity) and dihydroxypalladium (9.50 g, 13.5 mmol, 20% purity) under Ar atmosphere. The suspension was degassed under vacuo and purged with $H_2$ several times. The mixture was stirred under $H_2$ (15 psi) at 25° C. for 6 hrs. On completion, the mixture was filtered and the filtrate was concentrated in vacuo to give the title compound (6.90 g, 91% yield) as white solid. $^1$H NMR (400 MHz, DMSO-$d_6$) δ 8.67 (s, 1H), 6.91 (d, J=8.0 Hz, 1H), 6.86 (s, 1H), 6.74 (d, J=8.0 Hz, 1H), 5.22 (dd, J=5.2, 12.8 Hz, 1H), 4.25 (d, J=12.4 Hz, 2H), 3.42 (s, 3H), 2.94-2.87 (m, 1H), 2.84-2.78 (m, 2H), 2.73-2.63 (m, 2H), 2.22-2.16 (m, 2H), 1.82 (d, J=12.4 Hz, 2H), 1.67-1.56 (m, 2H), 1.49 (s, 9H).

Step 4-3-(3-Methyl-2-oxo-5-(piperidin-4-yl)-2,3-dihydro-1H-benzo[d]imidazol-1-yl) piperidine-2,6-dione. To a solution of tert-butyl 4-[1-(2,6-dioxo-3-piperidyl)-3-methyl-2-oxo-benzimidazol-5-yl]-piperidine-1-carboxylate (1.60 g, 3.62 mmol) in DCM (40 mL) was added TFA (20.6 g, 180 mmol) dropwise at 30° C., then the mixture was stirred at 30° C. for 1 hr. On completion, the mixture was concentrated in vacuo to give the title compound (1.60 g, 96% yield, TFA salt) as brown oil. LC-MS (ESI$^+$) m/z 343.0 (M+H)$^+$.

Step 5-Tert-butyl 2-(4-(1-(2,6-dioxopiperidin-3-yl)-3-methyl-2-oxo-2,3-dihydro-1H-benzo[d]imidazol-5-yl) piperidin-1-yl)-7-azaspirSo[3.5]nonane-7-carboxylate. To a solution of 3-[3-methyl-2-oxo-5-(4-piperidyl)benzimidazol-1-yl]piperidine-2,6-dione (1.60 g, 4.67 mmol, TFA salt) in DMSO (16 mL) was added TEA (472 mg, 4.67 mmol) until pH=8-9, then stirred at 30° C. for 10 mins, HOAc (280 mg, 4.67 mmol) was added until pH=5-6. Then tert-butyl 2-oxo-7-azaspiro[3.5]nonane-7-carboxylate (1.34 g, 5.61 mmol, CAS #203661-69-2) was added and stirred at 30° C. for 0.5 hr. Finally, $NaBH_3CN$ (587 mg, 9.35 mmol) was added and stirred at 60° C. for another 11 hr. On completion, the mixture was concentrated in vacuo to give a residue. The crude product was purified by reverse phase (0.1% FA condition) to give the title compound (1.00 g, 37% yield) as white solid. $^1$H NMR (400 MHz, DMSO-$d_6$) δ 8.61 (s, 1H), 7.01-6.82 (m, 2H), 6.75 (d, J=8.8 Hz, 1H), 5.21 (dd, J=5.6, 12.8 Hz, 1H), 4.07-3.97 (m, 2H), 3.66 (d, J=11.2 Hz, 2H), 3.41-3.34 (m, 5H), 3.32-3.28 (m, 2H), 2.95-2.79 (m, 2H), 2.77-2.64 (m, 2H), 2.61-2.51 (m, 2H), 2.46-2.36 (m, 2H), 2.35-2.25 (m, 2H), 2.24-2.19 (m, 2H), 2.02 (d, J=14.0 Hz, 2H), 1.63-1.55 (m, 4H), 1.47-1.43 (m, 9H); LC-MS (ESI$^+$) m/z 566.3 (M+H)$^+$.

Step 6-3-(5-(1-(7-Azaspiro[3.5]nonan-2-yl) piperidin-4-yl)-3-methyl-2-oxo-2,3-dihydro-1H-benzo[d]imidazol-1-yl) piperidine-2,6-dione. To a solution of tert-butyl 2-[4-[1-(2,6-dioxo-3-piperidyl)-3-methyl-2-oxo-benzimidazol-5-yl]-1-piperidyl]-7-azaspiro[3.5]nonane-7-carboxylate (200 mg, 353 μmol) in DCM (3 mL) was added TFA (2.02 g, 17.6 mmol) dropwise at 25° C., then the mixture was stirred at 25° C. for 0.5 hr. On completion, the mixture was concentrated in vacuo to give the title compound (160 mg, 97% yield, TFA salt) as brown oil; LC-MS (ESI$^+$) m/z 466.1 (M+H)$^+$.

Step 7-((3S,7aS)-7a-(((8-Fluoro-7-(7-fluoro-8-((triisopropylsilyl) ethynyl)-3-((triisopropylsil-yl)oxy) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl-2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5]nonane-7-carboxylate. To a suspension of 3-[5-[1-(7-azaspiro[3.5]nonan-2-yl)-4-piperidyl]-3-methyl-2-oxo-benzimidazol-1-yl]piperidine-2,6-dione (160 mg, 343 μmol, TFA salt) in THF (6 mL) was added TEA (255 mg, 2.52 mmol) until pH=8-9. Then [(3S,8S)-8-[[8-fluoro-7-[7-fluoro-8-(2-triisopropylsilylethynyl)-3-triisopropylsilyloxy-1-naphthyl]-4-[(3R)-3-hydroxy-3-methyl-1-piperidyl] pyrido[4,3-d]pyrimidin-2-yl]oxymethyl]-1,2,3,5,6,7-hexahydropyrrolizin-3-yl]methyl (4-nitrophenyl) carbonate (230 mg, 210 μmol) in THF (1 mL) was added and stirred at 30° C. for 12 hr. The resulting solution was concentrated in vacuo to give a residue. The residue was purified by Prep-HPLC (column: CD01-Phenomenex luna C18 150*25*10 μm; mobile phase: [water (FA)-ACN]; gradient: 42%-72% B over 10 min) to give the title compound (175 mg, 58% yield) as white solid. LC-MS (ESI$^+$) m/z 1420.7 (M+H)$^+$.

Step 8-((3S,7aS)-7a-(((7-(8-Ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl-2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5] nonane-7-carboxylate (Compound 158). To a solution of [(3S,8S)-8-[[8-fluoro-7-[7-fluoro-8-(2-triisopropylsilylethynyl)-3-triisopropylsilyloxy-1-naphthyl]-4-[(3R)-3-hydroxy-3-methyl-1-piperidyl]pyrido[4,3-d]pyrimidin-2-yl] oxymethyl]-1,2,3,5,6,7-hexahydropyrrolizin-3-yl]methyl-2-[4-[1-(2,6-dioxo-3-piperidyl)-3-methyl-2-oxo-benzimidazol-5-yl]-1-piperidyl]-7-azaspiro[3.5]nonane-7-carboxylate (90.0 mg, 63.3 μmol) in DMSO (0.5 mL) was added CsF (28.8 mg, 190 μmol). The mixture was stirred at 30° C. for 20 min. The mixture was concentrated in vacuo to give a residue. The residue was purified by prep-HPLC (column: Phenomenex luna C18 150*25 mm*10 μm; mobile phase: [water (FA)-ACN]; gradient: 5%-35% B over 10 min) to give the title compound (46.8 mg, 66% yield, FA salt) as yellow solid. $^1$H NMR (400 MHz, DMSO-$d_6$) δ 11.08 (s, 1H), 10.31-10.01 (m, 1H), 9.30-8.99 (m, 1H), 7.98 (dd, J=6.0, 9.2 Hz, 1H), 7.46 (t, J=9.2 Hz, 1H), 7.39 (s, 1H), 7.21 (dd, J=2.4, 17.6 Hz, 1H), 7.08 (s, 1H), 7.02 (d, J=8.0 Hz, 1H), 6.91 (d, J=8.0 Hz, 1H), 5.34 (dd, J=5.2, 12.8 Hz, 1H), 4.85-4.67 (m, 1H), 4.43-4.18 (m, 5H), 4.13-3.93 (m, 2H), 3.63-3.57 (m, 1H), 3.33 (s, 3H), 3.29 (m, 5H), 3.11-2.87 (m, 7H), 2.72-2.59 (m, 3H), 2.16-1.97 (m, 7H), 1.90-1.77 (m, 8H), 1.75-1.62 (m, 8H), 1.55-1.42 (m, 4H), 1.17 (d, J=15.8 Hz, 3H); LC-MS (ESI$^+$) m/z 1107.2 (M+H)$^+$.

Example 56. Synthesis of Compound 159
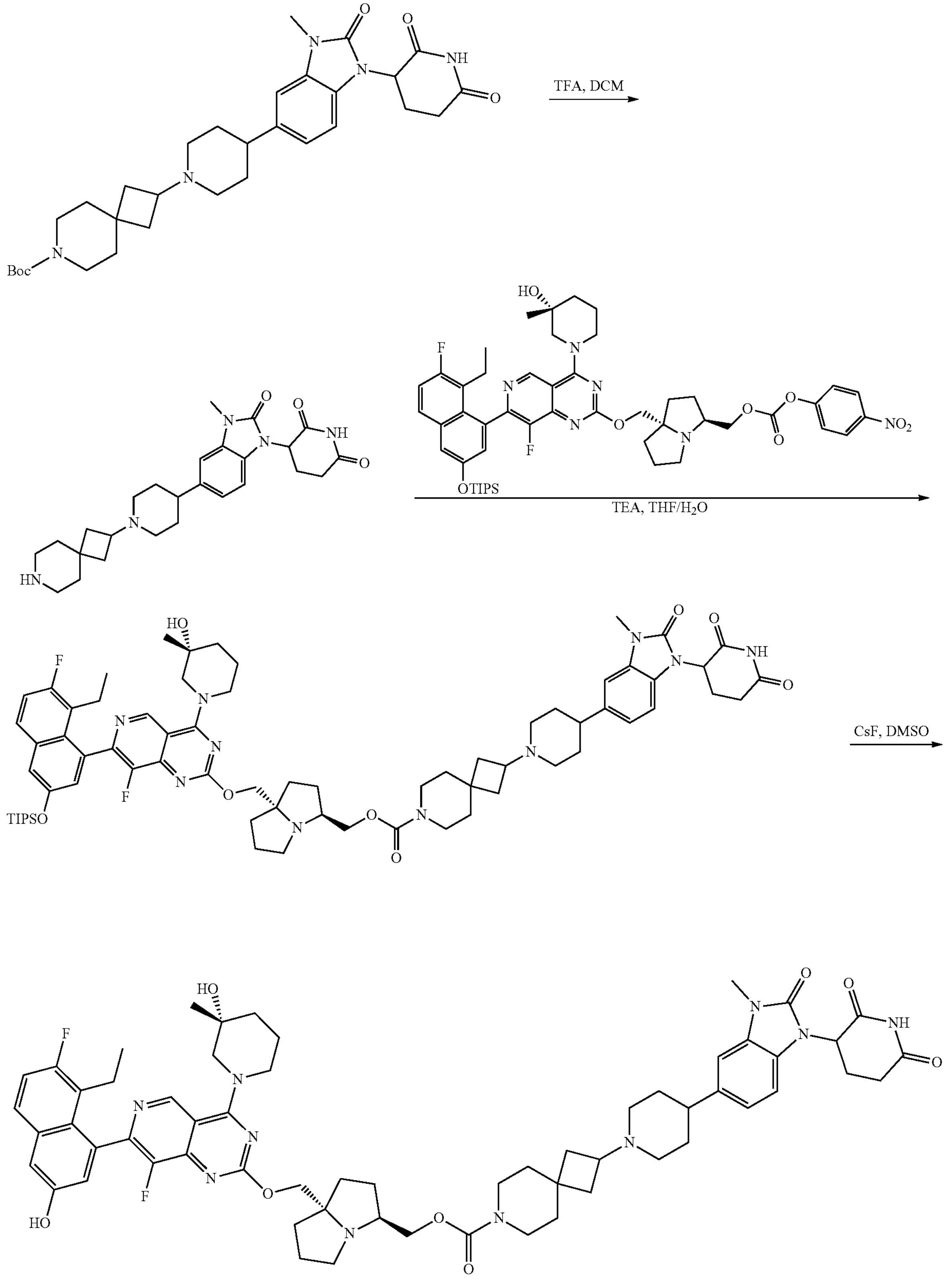
Compound 159

Step 1-3-(5-(1-(7-Azaspiro[3.5]nonan-2-yl) piperidin-4-yl)-3-methyl-2-oxo-2,3-dihydro-1H-benzo[d]imidazol-1-yl) piperidine-2,6-dione. To a solution of tert-butyl 2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5] nonane-7-carboxylate (120 mg, 212 μmol, from Example 55) in DCM (3 mL) was added TFA (1.54 g, 13.4 mmol, 1 mL). The mixture was stirred at 25° C. for 0.5 hr. On completion, the reaction mixture was concentrated in vacuo to give the title compound (122 mg, 99% yield, TFA salt) as yellow oil. LC-MS (ESI) m/z 466.2 $(M+H)^+$.

Step 2-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5] nonane-7-carboxylate. To a solution of 3-(5-(1-(7-azaspiro [3.5]nonan-2-yl) piperidin-4-yl)-3-methyl-2-oxo-2,3-dihydro-1H-benzo[d]imidazol-1-yl) piperidine-2,6-dione (110 mg, 191 μmol, TFA salt) in THF (4 mL) and $H_2O$ (400 μL) was added TEA (38.7 mg, 382 μmol, 53.2 μL) and ((3S,7aS)-7a-(((7-(8-ethyl-7-fluoro-3-((triisopropylsilyl) oxy) naphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl (4-nitrophenyl) carbonate (120 mg, 127 μmol). The mixture was stirred at 25° C. for 3 hrs. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 26%-56% B over 8 min) to give the title compound (100 mg, 61% yield) as yellow solid. LC-MS (ESI) m/z 1267.7 $(M+H)^+$.

Step 3-((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5] nonane-7-carboxylate (Compound 159). To a solution of ((3S,7aS)-7a-(((7-(8-ethyl-7-fluoro-3-((triisopropylsilyl) oxy) naphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5] nonane-7-carboxylate (100 mg, 78.8 μmol) in DMSO (1 mL) was added CsF (35.9 mg, 236 μmol). The mixture was stirred at 25° C. for 0.5 hr. On completion, the reaction mixture was filtered to give a residue. The residue was purified by prep-HPLC (column: CD01-Phenomenex luna C18 150*25*10 μm; mobile phase: [water (FA)-ACN]; gradient: 10%-40% B over 8 min) to give the title compound (52.3 mg, 56% yield, FA salt) as white solid. $^1H$ NMR (400 MHz, DMSO-$d_6$) δ 11.09 (s, 1H), 10.33-9.66 (m, 1H), 9.23 (d, J=3.6 Hz, 1H), 7.76 (dd, J=6.0, 9.2 Hz, 1H), 7.41-7.29 (m, 2H), 7.10 (s, 1H), 7.05-6.96 (m, 2H), 6.90 (d, J=8.0 Hz, 1H), 5.33 (dd, J=5.2, 12.8 Hz, 1H), 4.92-4.62 (m, 1H), 4.38-4.28 (m, 1H), 4.21-4.00 (m, 5H), 3.63 (d, J=13.2 Hz, 1H), 3.53 (d, J=13.2 Hz, 1H), 3.42-3.36 (m, 5H), 3.25 (s, 3H), 2.94-2.86 (m, 3H), 2.81-2.58 (m, 6H), 2.38-2.31 (m, 1H), 2.16-1.95 (m, 6H), 1.80-1.62 (m, 15H), 1.56-1.46 (m, 5H), 1.39 (s, 2H), 1.17 (d, J=9.2 Hz, 3H), 0.73 (q, J=7.2 Hz, 3H); LC-MS ($ESI^+$) m/z 1111.2 $(M+H)^+$.

Example 57. Synthesis of Compound 160

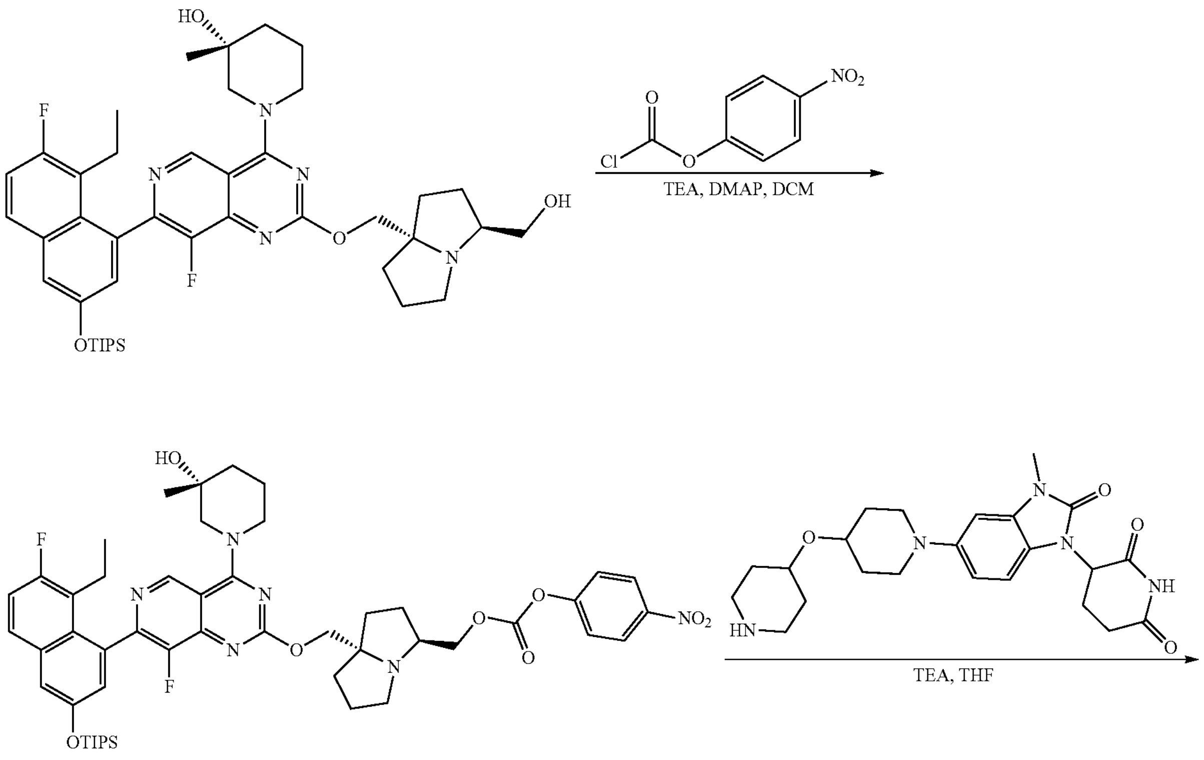

-continued

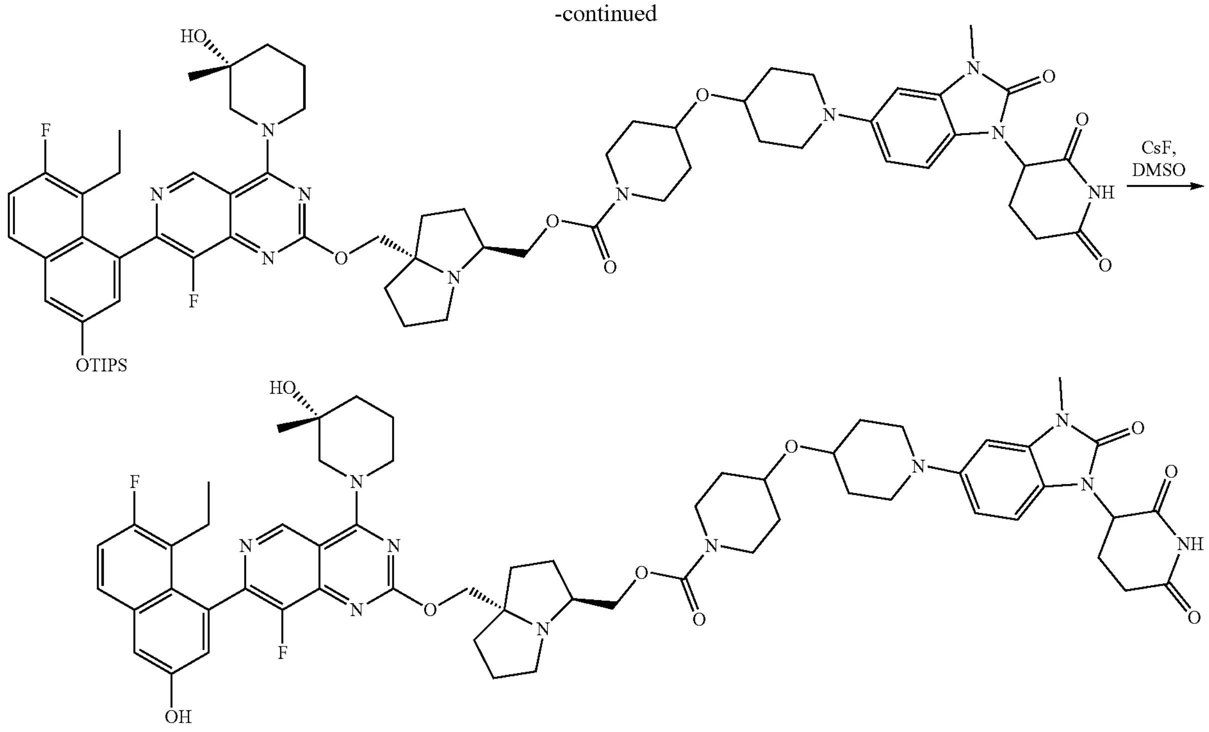

Compound 160

Step 1-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate. To a solution of (R)-1-(7-(8-ethyl-7-fluoro-3-((triisopropylsilyl)oxy) naphthalen-1-yl)-8-fluoro-2-(((3S,7aS)-3-(hydroxymethyl)tetrahydro-1H-pyrrolizin-7a (5H)-yl) methoxy)pyrido[4,3-d]pyrimidin-4-yl)-3-methylpiperidin-3-ol (100 mg, 128 μmol) in DCM (3 mL) was added TEA (13.0 mg, 128 μmol, 17.9 μL) and DMAP (1.57 mg, 12.8 μmol), (4-nitrophenyl) carbonochloridate (77.9 mg, 386 μmol, CAS #7693-46-1). The mixture was stirred at 25° C. for 12 hrs. On completion, the residue was diluted with water (30 mL), and then the residue was extracted with DCM (3×30 mL). The combined organic layers was dried over $Na_2SO_4$, filtered and the filtrate was concentrated in vacuo to give the title compound (120 mg, 98% yield) as yellow solid. LC-MS (ESI) m/z 941.4 $(M+H)^+$.

Step 2-((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((1-(1-(2,6-dioxopiperidin-3-yl)-3-methyl-2-oxo-2,3-dihydro-1H-benzo[d]imidazol-5-yl) piperidin-4-yl)oxy)piperidine-1-carboxylate. To a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d] pyrimidin-2-yl)oxy)methyl)hexahydro-1H-pyrrolizin-3-yl) methyl (4-nitrophenyl) carbonate (100 mg, 106 μmol) in THF (1 mL) was added TEA (10.7 mg, 106 μmol, 14.7 μL), 3-(3-methyl-2-oxo-5-(4-(piperidin-4-yloxy)piperidin-1-yl)-2,3-dihydro-1H-benzo[d]imidazol-1-yl) piperidine-2,6-dione (59.0 mg, 106 μmol, TFA). The mixture was stirred at 25° C. for 0.1 hr. On completion, the reaction mixture was concentrated in vacuo. The residue was purified by prep-HPLC (column: CD01-Phenomenex luna C18 150*25*10 μm; mobile phase: [water (FA)-ACN]; gradient: 33%-63% B over 10 min) to give the title compound (60.0 mg, 45% yield) as yellow solid. LC-MS (ESI) m/z 1243.3 $(M+H)^+$.

Step 3-((3S,7aS)-7a-(((7-(8-Ethyl-7-fluoro-3-hydroxynaphthalen-1-yl)-8-fluoro-4-((R)-3-hydroxyl-3-methylpiperidin-1-yl)pyrido[4,3-d]pyrimidin-2-yl)oxy)methyl) hexahydro-1H-pyrrolizin-3-yl)methyl 4-((1-(1-(2,6-dioxopiperidin-3-yl)-3-methyl-2-oxo-2,3-dihydro-1H-benzo[d]imidazol-5-yl) piperidin-4-yl)oxy)piperidine-1-carboxylate (Compound 160). To a solution of ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(1-(2,6-dioxopiperidin-3-yl)-3-methyl-2-oxo-2,3-dihydro-1H-benzo[d]imidazole-5-yl) piperidin-4-yl)oxy)piperidine-1-carboxylate (50.0 mg, 40.2 μmol) in DMSO (2 mL) was added CsF (18.3 mg, 120 μmol). The mixture was stirred at 50° C. for 0.5 hr. On completion, the reaction mixture was filtered. The filtrate was purified by prep-HPLC (column: CD01-Phenomenex luna C18 150*25*10 μm; mobile phase: [water (FA)-ACN]; gradient: 10%-40% B over 11 min) to give the title compound (26.1 mg, 56% yield, FA) as white solid. $^1H$ NMR (400 MHz, DMSO-$d_6$) δ 11.06 (s, 1H), 9.95 (s, 1H), 9.22 (d, J=2.4 Hz, 1H), 7.76 (dd, J=6.0, 9.2 Hz, 1H), 7.38-7.26 (m, 2H), 7.03 (d, J=2.4 Hz, 1H), 6.91 (d, J=8.4 Hz, 1H), 6.82 (d, J=2.0 Hz, 1H), 6.62 (dd, J=2.0, 8.8 Hz, 1H), 5.28 (dd, J=5.2, 12.8 Hz, 1H), 4.82-4.65 (m, 1H), 4.40-4.28 (m, 1H), 4.25-4.13 (m, 3H), 4.11-4.00 (m, 2H), 3.70-3.61 (m, 4H), 3.58-3.51 (m, 2H), 3.29 (s, 3H), 3.16-3.04 (m, 3H), 2.94-2.87 (m, 1H), 2.86-2.71 (m, 5H), 2.69-2.58 (m, 2H), 2.36-2.28 (m, 1H), 2.15-1.96 (m, 4H), 1.92-1.86 (m, 2H), 1.83-1.61 (m, 12H), 1.58-1.49 (m, 3H), 1.37-1.28 (m, 2H), 1.16 (d, J=9.2 Hz, 3H), 0.73 (q, J=7.2 Hz, 3H); LC-MS (ESI) m/z 1087.3 $(M+H)^+$.

Example 58. Synthesis of Compound 370

Step 1-Tert-butyl 4-((4-(1-(2,6-dioxopiperidin-3-yl)-3-methyl-2-oxo-2,3-dihydro-1H-benzo[d]imidazol-4-yl) but-3-yn-1-yl)oxy)piperidine-1-carboxylate. A mixture of 3-(4-bromo-3-methyl-2-oxo-benzimidazol-1-yl) piperidine-2,6-dione (250 mg, 739 μmol), tert-butyl 4-but-3-ynoxypiperidine-1-carboxylate (561 mg, 2.22 mmol), $Pd(PPh_3)_2Cl_2$ (51.8 mg, 73.9 μmol), CuI (14.0 mg, 73.9 μmol), $Cs_2CO_3$ (722 mg, 2.22 mmol) and 4A MS (200 mg) in DMF (5 mL) was degassed and purged with $N_2$ for 3 times, and then the mixture was stirred at 80° C. for 6 hrs under $N_2$ atmosphere. On completion, the mixture was filtered and the filtrate was concentrated in vacuo. The residue was purified by reverse phase (0.1% FA condition), then the crude product was triturated with EA (5 mL) at 25° C. for 30 mins (three times) to give the title compound (150 mg, 39% yield) as white solid. $^1H$ NMR (400 MHz, DMSO-$d_6$) δ 11.11 (s, 1H), 7.11 (d, J=7.6 Hz, 1H), 7.06-7.03 (m, 1H), 7.01-6.96 (m, 1H), 5.38 (dd, J=5.2, 12.8 Hz, 1H), 3.69-3.60 (m, 7H), 3.57-3.50 (m, 1H), 3.05-2.96 (m, 2H), 2.93-2.83 (m, 1H), 2.72 (t, J=6.4 Hz, 2H), 2.69-2.58 (m, 2H), 2.05-1.99 (m, 1H), 1.86-1.76 (m, 2H), 1.38 (s, 9H), 1.36-1.28 (m, 2H).

Step 2-3-(3-Methyl-2-oxo-4-(4-(piperidin-4-yloxy) but-1-yn-1-yl)-2,3-dihydro-1H-benzo[d]imidazole-1-yl) piperidine-2,6-dione. To a solution of tert-butyl 4-[4-[1-(2,6-dioxo-3-piperidyl)-3-methyl-2-oxo-benzimidazol-4-yl]but-3-ynoxy]piperidine-1-carboxylate (130 mg, 254 μmol) in DCM (1 mL) was added TFA (498 mg, 4.38 mmol, 325 μL). The mixture was stirred at 25° C. for 0.5 hr. On completion, the mixture was concentrated in vacuo to give the title compound (133 mg, 99% yield, TFA) as yellow oil. LC-MS (ESI) m z 411.0 $(M+H)^+$.

Step 3-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-4-yl) but-3-yn-1-yl)oxy)piperidine-1-carboxylate. To a solution of 3-[3-methyl-2-oxo-4-[4-(4-piperidyloxy) but-1-ynyl]benzimidazol-1-yl]piperidine-2,6-dione (66.8 mg, 127 μmol, TFA) and ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (80.0 mg, 85.0 μmol) in THF (3 mL) and $H_2O$ (0.5 mL) was added TEA (17.2 mg, 170 μmol, 23.6 μL). The mixture was stirred at 25° C. for 0.5 hr. On completion, the mixture was concentrated in vacuo. The residue was purified by prep-HPLC (column: CD01-Phenomenex luna C18 150*25*10 μm; mobile phase: [water (FA)-ACN]; gradient: 42%-72% B over 8 min) to give the title compound (95.0 mg, 92% yield) as white solid. LC-MS (ESI) m/z 1212.7 $(M+H)^+$.

Step 4-((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl4-((4-(1-(2,6-dioxopiperidin-3-yl)-3-methyl-2-oxo-2,3-dihydro-1H-benzo[d]imidazol-4-yl) but-3-yn-1-yl)oxy)piperidine-1-carboxylate (Compound 370). To a solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl4-((4-(1-(2,6-dioxopiperidin-3-yl)-3-methyl-2-oxo-2,3-dihydro-1H-benzo[d]imidazol-4-yl) but-3-yn-1-yl)oxy)piperidine-1-carboxylate (90.0 mg, 74.2 μmol) in DMSO (1 mL) was added CsF (33.8 mg, 222 μmol). The mixture was stirred at 30° C. for 0.5 hr. On completion, the mixture was filtered and the filtrate was purified by prep-HPLC (column: CD01-Phenomenex luna C18 150*25*10 μm; mobile phase: [water (FA)-ACN]; gradient: 20%-50% B over 8 min) to give the title compound (27.9 mg, 33% yield, FA) as white solid. $^1H$ NMR (400 MHz, DMSO-$d_6$) δ 11.11 (s, 1H), 9.95 (s, 1H), 9.22 (d, J=2.4 Hz, 1H), 7.82-7.72 (m, 1H), 7.39-7.31 (m, 2H), 7.11 (d, J=7.6 Hz, 1H), 7.07-6.95 (m, 3H), 5.44-5.33 (m, 1H), 4.80-4.69 (m, 1H), 4.40-4.27 (m, 1H), 4.24-4.00 (m, 5H), 3.72-3.65 (m, 3H), 3.64 (s, 3H), 3.62-3.60 (m, 1H), 3.59-3.49 (m, 2H), 3.44-3.36 (m, 2H), 3.16-3.03 (m, 2H), 2.92-2.82 (m, 1H), 2.78-2.75 (m, 1H), 2.74-2.59 (m, 5H), 2.38-2.29 (m, 1H), 2.18-2.10 (m, 1H), 2.08-1.97 (m, 3H), 1.84-1.64 (m, 11H), 1.55-1.46 (m, 1H), 1.42-1.30 (m, 2H), 1.16 (d, J=9.2 Hz, 3H), 0.73 (q, J=7.2 Hz, 3H); LC-MS (ESI) m/z 1056.2 $(M+H)^+$.

Example 59. Synthesis of Compound 384

Step 1-1-Benzyl 2-methyl 2-(but-3-en-1-yl)pyrrolidine-1,2-dicarboxylate. To a mixture of(S)-1-benzyl 2-methyl pyrrolidine-1,2-dicarboxylate (200 g, 759 mmol) and 4-bromobut-1-ene (205 g, 1.52 mol, 154 mL) in THF (2000 mL) was added LiHMDS (1 M, 911 mL) at 0° C. The reaction mixture was stirred at 25° C. for 5 hrs. On completion, the reaction mixture was quenched with $NH_4Cl$ (1000 mL). The residue was diluted with water (500 mL) and extracted with EA (2×1000 mL). The combined organic layers was dried over $Na_2SO_4$, filtered and the filtrate was concentrated in vacuo to give a residue. The residue was purified by column chromatography ($SiO_2$, PE:EA=50:1 to 5:1) to give the compound (197 g, 81% yield) as yellow oil. $^1H$ NMR (400 MHz, $CDCl_3$) δ 7.39-7.27 (m, 5H), 5.88-5.66 (m, 1H), 5.18-5.07 (m, 2H), 5.06-4.98 (m, 1H), 4.97-4.91 (m, 1H), 3.84-3.65 (m, 3H), 3.51-3.46 (m, 2H), 2.48-2.22 (m, 1H), 2.15-2.06 (m, 3H), 2.01 (dd, J=2.8, 9.2 Hz, 1H), 1.99-1.90 (m, 2H), 1.90-1.83 (m, 1H).

Step 2-1-Benzyl 2-methyl 2-(2-(oxiran-2-yl)ethyl)pyrrolidine-1,2-dicarboxylate. To a mixture of 1-benzyl 2-methyl 2-(but-3-en-1-yl)pyrrolidine-1,2-dicarboxylate (193 g, 608 mmol) in DCM (2000 mL) was added m-CPBA (262 g, 1.29 mol, 85% purity) at 0° C. The reaction mixture was stirred at 25° C. for 12 hrs. On completion, the reaction mixture was quenched with $Na_2SO_3$ (400 mL). The residue was diluted with water (500 mL) and extracted with DCM (2×800 mL). The combined organic layers was dried over $Na_2SO_4$, filtered and the filtrate was concentrated in vacuo to give a residue. The residue was purified by column chromatography ($SiO_2$, PE:EA=100:1 to 6:1) to give the title compound (136 g, 67% yield) as yellow oil. $^1H$ NMR (400 MHz, DMSO-$d_6$) δ 7.50-7.18 (m, 5H), 5.13-4.99 (m, 2H), 3.68-3.54 (m, 3H), 3.49 (d, J=6.0 Hz, 1H), 3.45-3.31 (m, 1H), 2.90-2.74 (m, 1H), 2.67-2.58 (m, 1H), 2.44-2.32 (m, 1H), 2.31-2.18 (m, 1H), 2.13-1.92 (m, 3H), 1.89-1.75 (m, 2H), 1.63-1.45 (m, 1H), 1.28 (ddd, J=5.6, 12.4, 18.4 Hz, 1H).

Step 3-Methyl 3-(hydroxymethyl)-1,2,3,5,6,7-hexahydropyrrolizine-8-carboxylate. The Pd/C (13.6 g, 12.7 mmol, 10% purity) was added O1-benzyl O2-methyl 2-[2-(oxiran-2-yl)ethyl]pyrrolidine-1,2-dicarboxylate (136 g, 406 mmol) in MeOH (2600 mL) at Ar. The reaction mixture was stirred at 25° C. for 5 hrs under $H_2$ under 50 psi. On completion, the reaction mixture was filtered and the filtrate was concentrated in vacuo to give the title compound (81 g, 99% yield) as brown oil. $^1$H NMR (400 MHz, $CDCl_3$) δ 3.69 (d, J=6.4 Hz, 3H), 3.14-2.88 (m, 2H), 2.76-2.48 (m, 2H), 2.35-2.13 (m, 2H), 1.89-1.50 (m, 8H).

Step 4-(3R,7aS)-Methyl 3-(((tert-butyldimethylsilyl)oxy)methyl)hexahydro-1H-pyrrolizine-7a-carboxylate & (3S,7aS)-methyl 3-(((tert-butyldimethylsilyl)oxy)methyl)hexahydro-1H-pyrrolizine-7a-carboxylate. To a mixture of methyl 3-(hydroxymethyl)-1,2,3,5,6,7-hexahydropyrrolizine-8-carboxylate (78.0 g, 391 mmol) in DCM (800 mL) was added IMIDAZOLE (53.3 g, 782 mmol) and TBSCI (88.5 g, 587 mmol, 72.2 mL). The reaction mixture was stirred at 25° C. for 4 hrs. On completion, the residue was diluted with water (500 mL) and extracted with EA (2×500 mL). The combined organic layers was dried over $Na_2SO_4$, filtered and the filtrate was concentrated in vacuo to give a residue. The residue was purified by column chromatography ($SiO_2$, PE:EA=50:1 to 10:1) to give the filtrate compound (6a)(44 g, 35% yield) as yellow oil. $^1$H NMR (400 MHz, $CDCl_3$) δ 3.74-3.71 (m, 1H), 3.69 (s, 3H), 3.49-3.42 (m, 1H), 3.08 (d, J=6.4, 10.8 Hz, 1H), 2.86-2.72 (m, 2H), 2.42-2.35 (m, 1H), 2.24-2.15 (m, 1H), 2.05-1.97 (m, 1H), 1.88-1.78 (m, 2H), 1.78-1.65 (m, 1H), 1.64-1.51 (m, 2H), 0.90-0.87 (m, 9H), 0.05 (s, 6H). Compound (6b)(12.3 g, 10% yield) as yellow oil. $^1$H NMR (400 MHz, $CDCl_3$) δ 3.91-3.85 (m, 1H), 3.76 (dd, J=6.0, 10.4 Hz, 1H), 3.69 (s, 3H), 3.34-3.22 (m, 1H), 2.98-2.88 (m, 1H), 2.81 (q, J=8.4 Hz, 1H), 2.48-2.40 (m, 1H), 2.20-2.10 (m, 1H), 1.91-1.83 (m, 1H), 1.82-1.75 (m, 3H), 1.74-1.68 (m, 1H), 1.63-1.55 (m, 1H), 0.88 (s, 9H), 0.04 (s, 6H)

Step 5-((3S,7aS)-3-(((Tert-butyldimethylsilyl)oxy)methyl)hexahydro-1H-pyrrolizin-7a-yl) methanol. To a mixture of (3S,7aS)-methyl 3-(((tert-butyldimethylsilyl)oxy)methyl)hexahydro-1H-pyrrolizine-7a-carboxylate (12.0 g, 38.2 mmol) in THF (120 mL) was added $LiAlH_4$ (2.5 M, 16.8 mL). The reaction mixture was stirred at 0° C. for 1 hr. On completion, the reaction mixture was quenched with water (1.6 mL) and NaOH (15%)(4.8 ml) and $H_2O$ (1.6 ml). The reaction mixture was filtered and the filtrate was concentrated in vacuo to give the title compound (9.50 g, 86% yield) as yellow oil. $^1$H NMR (400 MHz, DMSO-$d_6$) δ 4.36 (s, 1H), 3.78 (dd, J=5.6, 10.4 Hz, 1H), 3.69-3.59 (m, 1H), 3.14-3.09 (m, 1H), 3.07-2.94 (m, 2H), 2.70-2.62 (m, 2H), 1.90 (ddd, J=2.4, 7.2, 12.0 Hz, 1H), 1.70-1.46 (m, 6H), 1.37-1.25 (m, 1H), 0.86 (s, 9H), 0.04 (s, 6H).

Step 6-(3S,7aS)-3-(((Tert-butyldimethylsilyl)oxy)methyl)-7a-(((tert-butyldiphenylsilyl)oxy)methyl)hexahydro-1H-pyrrolizine. To a mixture of ((3S,7aS)-3-(((tert-butyldimethylsilyl)oxy)methyl)hexahydro-1H-pyrrolizin-7a-yl) methanol (9.50 g, 33.2 mmol) in DCM (100 mL) was added imidazole (4.53 g, 66.5 mmol), TBDPSCl (11.8 g, 43.2 mmol, 11.0 mL). The reaction mixture was stirred at 25° C. for 2 hrs. On completion, the residue was diluted with water (80 mL) and extracted with EA (2×100 mL). The combined organic layers was dried over $Na_2SO_4$, filtered and concentrated in vacuo to give a residue. The residue was purified by reverse phase (0.1% FA condition) to give the title compound (17.0 g, 97% yield) as yellow oil. $^1$H NMR (400 MHz, $CDCl_3$) δ 7.71-7.66 (m, 4H), 7.42-7.36 (m, 6H), 3.86 (dd, J=4.8, 10.0 Hz, 1H), 3.70 (dd, J=6.8, 10.0 Hz, 1H), 3.51-3.35 (m, 2H), 3.08 (d, J=6.0 Hz, 1H), 2.82-2.67 (m, 2H), 2.11 (d, J=5.6, 7.2 Hz, 1H), 1.89-1.76 (m, 2H), 1.75-1.59 (m, 4H), 1.46-1.37 (m, 1H), 1.09-1.07 (m, 9H), 0.90 (s, 9H), 0.05 (s, 6H).

Step 7-((3S,7aS)-7a-(((Tert-butyldiphenylsilyl)oxy)methyl)hexahydro-1H-pyrrolizin-3-yl) methanol. To a mixture of (3S,7aS)-3-(((tert-butyldimethylsilyl)oxy)methyl)-7a-(((tert-butyldiphenylsilyl)oxy)methyl)hexahydro-1H-pyrrolizine (17.0 g, 32.4 mmol) in DCM (50 mL) was added HCl/dioxane (2 M, 40 mL). The reaction mixture was stirred at 25° C. for 12 hrs. On completion, the residue was acidified basified with $NaHCO_3$ till pH=7. The residue was diluted with water (80 mL) and extracted with EA (2×100 mL). The combined organic layers was dried over $Na_2SO_4$, filtered and the filtrate was concentrated in vacuo to give a residue. The residue was purified by reverse phase (0.1% FA condition) to give the title compound (9.20 g, 69% yield) as yellow solid. $^1$H NMR (400 MHz, $CDCl_3$) δ 11.28 (s, 1H), 7.73 (ddd, J=1.6, 7.6, 18.0 Hz, 4H), 7.49-7.37 (m, 6H), 4.13-3.76 (m, 6H), 3.22-3.05 (m, 1H), 2.18-2.01 (m, 5H), 1.91-1.66 (m, 3H), 1.12 (s, 9H). LC-MS (ESI) m/z 410.2 $(M+H)^+$.

Step 8-(3S,7aS)-7a-(((tert-butyldiphenylsilyl)oxy)methyl)hexahydro-1H-pyrrolizine-3-carbaldehyde. To a mixture of $(COCl)_2$ (340 mg, 2.69 mmol, 235 μL) in DCM (6 mL) was added DMSO (286 mg, 3.66 mmol, 286 μL) stirred at −78° C. for 10 min under $N_2$. Then the ((3S,7aS)-7a-(((tert-butyldiphenylsilyl)oxy)methyl)hexahydro-1H-pyrrolizin-3-yl) methanol (500 mg, 1.22 mmol) in DCM (3 mL) was added the mixture dropwise for 20 mins −78° C. and stirred at −78° C. for 10 min. The TEA (1.36 g, 13.4 mmol, 1.87 mL) in DCM (1 mL) was added the mixture for 30 mins at −78° C. On completion, the residue was diluted with $NaHCO_3$ (20 mL) and extracted with DCM (2×20 mL). The combined organic layers was dried over $Na_2SO_4$, filtered and the filtrate was concentrated in vacuo (15° C.) to give the title compound (490 mg, 98% yield) as yellow oil. LC-MS (ESI) m/z 426.2 $(M+H_2O)^+$.

Step 9-3-(5-(3-((1-(((35,7aS)-7a-(((Tert-butyldiphenylsilyl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione To a mixture of (3S,7aS)-7a-(((tert-butyldiphenylsilyl)oxy)methyl)hexahydro-1H-pyrrolizine-3-carbaldehyde (442 mg, 1.10 mmol) and 3-(3-methyl-2-oxo-5-(3-(piperidin-4-yloxy) propyl)-2,3-dihydro-1H-benzo[d]imidazol-1-yl) piperidine-2,6-dione (300 mg, 735 μmol), HOAc (66.2 mg, 1.10 mmol, 63.2 μL) in THF (4 mL) and MeOH (2 mL) was added HOAc (66.2 mg, 1.10 mmol, 63.2 μL). The reaction mixture was stirred at −10° C. for 2 hrs. Then the pyridin-1-ium-1-ylboranuide (136 mg, 1.47 mmol, 147 μL) was added to the mixture. The reaction mixture was stirred at −10° C. for 10 hrs. On completion, the reaction mixture was quenched with water (0.05 mL) and concentrated in vacuo. The residue was purified by reverse phase (0.1% FA condition) to give the title compound (300 mg, 51% yield) as yellow oil. $^1$H NMR (400 MHz, DMSO-$d_6$) δ 11.09 (s, 1H), 7.68-7.63 (m, 4H), 7.53-7.46 (m, 6H), 7.06-6.97 (m, 2H), 6.91-6.85 (m, 1H), 5.38-5.31 (m, 1H), 3.48-3.43 (m, 4H), 3.33 (s, 3H), 3.18-3.11 (m, 2H), 2.97-2.86 (m, 2H), 2.72-2.66 (m, 4H), 2.29-2.19 (m, 2H), 2.12-1.97 (m, 10H), 1.92-1.77 (m, 8H), 1.71-1.51 (m, 2H), 1.06 (s, 9H). LC-MS (ESI) m/z 792.3 $(M+H)^+$.

Step 10-3-(5-(3-((1-(((35,7aS)-7a-(((Tert-butyldiphenylsilyl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione. To a mixture of 3-(5-(3-((1-(((3S,7aS)-7a-(((tert-butyldiphenylsilyl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione (280 mg, 353 μmol) in DMSO (3 mL) was added CsF (161 mg, 1.06 mmol). The reaction mixture was stirred at 40° C. for 1 hr. On completion, the reaction mixture was filtered to give the filtrate. The residue was purified by reverse phase (0.1% FA condition) to give the title compound (120 mg, 61% yield) as white solid. LC-MS (ESI) m/z 554.3 $(M+H)^+$.

Step 11-3-(5-(3-((1-(((3S,7aS)-7a-(((7-(8-Ethyl-7-fluoro-3-(methoxymethoxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione. To a mixture of 3-(5-(3-((1-(((3S,7aS)-7a-(((tert-butyldiphenylsilyl) oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione (100 mg, 180 μmol) in THF (2 mL) was added NaH (10.8 mg, 270 μmol, 60% purity) and 4A MS (100 mg, 180 μmo). The reaction mixture was stirred at 0° C. for 0.5 hr. Then the (R)-1-(7-(8-ethyl-7-fluoro-3-(methoxymethoxy) naphthalen-1-yl)-8-fluoro-2-(methylsulfonyl)pyrido[4,3-d]pyrimidin-4-yl)-3-methylpiperidin-3-ol (155 mg, 270 μmol) was added to the mixture. The reaction mixture was stirred at 0° C. for 0.5 hr. On completion, the reaction mixture was quenched with HCl/EA (1 mL). The reaction mixture was concentrated in vacuo to give the title compound (90.0 mg, 47% yield) as yellow solid. LC-MS (ESI) m/z 524.0 (M/2+H).

Step 12-3-(5-(3-((1-(((35,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl) piperidin-4-yl)oxy) propyl)-3-methyl-2-oxo-2,3-dihydro-1H-benzo[d] imidazol-1-yl) piperidine-2,6-dione (Compound 384). A mixture of (R)-1-(7-(8-ethyl-7-fluoro-3-(methoxymethoxy) naphthalen-1-yl)-8-fluoro-2-(methylsulfonyl)pyrido[4,3-d] pyrimidin-4-yl)-3-methylpiperidin-3-ol (90.0 mg, 86.0 μmol) in HCl/dioxane (1.5 M, 57.3 μL) was stirred at 25° C. for 0.2 hr. On completion the reaction mixture was concentrated in vacuo. The residue was purified by prep-HPLC (column: CD01-Phenomenex luna C18 150*25*10 μm; mobile phase: [water (FA)-ACN]; gradient: 10%-40% B over 8 min) to give the title compound (29.4 mg, 31% yield, FA) as white solid. $^1$H NMR (400 MHz, DMSO-$d_6$) δ 11.09 (s, 1H), 10.04-9.88 (m, 1H), 9.23 (s, 1H), 7.81-7.72 (m, 1H), 7.39-7.30 (m, 2H), 7.05-6.96 (m, 3H), 6.85 (d, J=8.0 Hz, 1H), 5.36-5.29 (m, 1H), 4.81-4.68 (m, 1H), 4.41-4.18 (m, 3H), 4.10-4.00 (m, 1H), 3.66-3.61 (m, 1H), 3.54 (s, 1H), 3.31 (s, 3H), 2.96-2.84 (m, 3H), 2.79-2.69 (m, 4H), 2.67-2.61 (m, 4H), 2.43-2.35 (m, 2H), 2.11 (s, 5H), 2.02-1.95 (m, 2H), 1.84-1.50 (m, 16H), 1.44-1.36 (m, 2H), 1.16 (d, J=9.6 Hz, 3H), 0.76-0.69 (m, 3H). LC-MS (ESI) m/z 1002.3 $(M+H)^+$.

Example 60. Synthesis of Compound 399

Step 1-Tert-butyl 4-(1-(4-(1-(2,6-dioxopiperidin-3-yl)-3-methyl-2-oxo-2,3-dihydro-1H-benzo[d]imidazol-5-yl) piperidin-1-yl)cyclopropyl) piperidine-1-carboxylate. To a solution of 3-[3-methyl-2-oxo-5-(4-piperidyl)benzimidazol-1-yl]piperidine-2,6-dione (800 mg, 1.75 mmol, TFA salt) and tert-butyl 4-(1-methylsulfonyloxycyclopropyl) piperidine-1-carboxylate (559 mg, 1.75 mmol) in ACN (14 mL) was added $K_2CO_3$ (484 mg, 3.51 mmol) and NaI (262 mg, 1.75 mmol). The mixture was stirred under 50 Psi at 90° C. for 96 hrs in a 30 mL of sealed tube. On completion, the mixture was filtered and the filtrate was concentrated in vacuo to give a residue. The residue was purified by reversed-phase HPLC (10 mmol/L $NH_4HCO_3$) to give the title compound (25.0 mg, 2.50% yield) as purple solid. LC-MS (ESI) m/z 566.2 $(M+H)^+$.

Step 2-3-(3-Methyl-2-oxo-5-(1-(1-(piperidin-4-yl)cyclopropyl) piperidin-4-yl)-2,3-dihydro-1H-benzo[d]imidazol-1-yl) piperidine-2,6-dione. To a solution of tert-butyl 4-(1-(4-(1-(2,6-dioxopiperidin-3-yl)-3-methyl-2-oxo-2,3-dihydro-1H-benzo[d]imidazol-5-yl) piperidin-1-yl) cyclopropyl) piperidine-1-carboxylate (24.0 mg, 42.4 μmol) in DCM (1 mL) was added TFA (307 mg, 2.69 mmol, 0.2 mL). The mixture was stirred at 25° C. for 0.5 hr. On completion, the mixture was concentrated in vacuo to give the title compound (24.0 mg, 97% yield, TFA salt) as yellow oil. LC-MS (ESI) m/z 466.1 $(M+H)^+$.

Step 3-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl 4-(1-(4-(1-(2,6-dioxopiperidin-3-yl)-3-methyl-2-oxo-2,3-dihydro-1H-benzo[d]imidazol-5-yl) piperidin-1-yl)cyclopropyl) piperidine-1-carboxylate. To a solution of 3-[3-methyl-2-oxo-5-[1-[1-(4-piperidyl)cyclopropyl]-4-piperidyl]benzimidazol-1-yl]piperidine-2,6-dione (19.0 mg, 32.7 μmol, TFA salt) in THF (1 mL) and $H_2O$ (0.5 mL) was basified with TEA (9.95 mg, 98.3 μmol) to pH=7-8. And then ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate (30.8 mg, 32.7 μmol) in THF (1 mL) was added. The mixture was stirred at 25° C. for 0.5 hr. On completion, the mixture was filtered and the filtrate was concentrated in vacuo to give a residue. The residue was purified by prep-HPLC (0.1% TFA condition) to give the title compound (40.0 mg, 96% yield) as white solid. LC-MS (ESI) m z 1267.5 $(M+H)^+$.

Step 4-((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-(1-(4-(1-(2,6-dioxopiperidin-3-yl)-3-methyl-2-oxo-2,3-dihydro-1H-benzo[d]imidazol-5-yl) piperidin-1-yl)cyclopropyl) piperidine-1-carboxylate (Compound 399). To a solution of ((3S,7aS)-7a-(((7-(8-ethyl-7-fluoro-3-((triisopropylsilyl) oxy) naphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-(1-(4-(1-(2,6-dioxopiperidin-3-yl)-3-methyl-2-oxo-2,3-dihydro-1H-benzo[d]imidazol-5-yl) piperidin-1-yl)cyclopropyl) piperidine-1-carboxylate (40.0 mg, 31.5 μmol) in DMSO (1 mL) was added CsF (14.3 mg, 94.6 μmol). The mixture was stirred at 30° C. for 0.5 hr. On completion, the reaction mixture was filtered and the filtrate was concentrated in vacuo to give a residue. The residue was purified by prep-HPLC (column: CD01-Phenomenex luna C18 150*25*10 μm; mobile phase: [water (FA)-ACN]; gradient: 8%-38% B over 10 min) to give the title compound (17.8 mg, 46% yield, FA salt) as white solid. $^1$H NMR (400 MHz, DMSO-$d_6$) δ 11.09 (s, 1H), 10.04-9.80 (m, 1H), 9.24 (d, J=3.6 Hz, 1H), 7.77 (dd, J=6.0, 9.2 Hz, 1H), 7.40-7.32 (m, 2H), 7.09 (s, 1H), 7.03 (d, J=2.4 Hz, 1H), 7.00 (d, J=8.4 Hz, 1H), 6.94-6.89 (m, 1H), 5.34 (dd, J=5.6, 12.8 Hz, 1H), 5.00-4.84 (m, 2H), 4.76 (d, J=10.4 Hz, 1H), 4.41-4.16 (m, 5H), 4.12-4.02 (m, 3H), 3.63-3.54 (m, 1H), 3.33 (s, 3H), 2.98-2.88 (m, 6H), 2.86-2.72 (m, 4H), 2.62 (d, J=17.6 Hz, 2H), 2.25-2.06 (m, 4H), 2.06-1.90 (m, 5H), 1.89-1.56 (m, 17H), 1.32-1.22 (m, 2H), 1.17 (d, J=9.2 Hz, 3H), 0.74 (q, J=7.2 Hz, 3H); LC-MS (ESI) m/z 1111.3 $(M+H)^+$.

Example 61. Synthesis of Compound 402

3-[3-Methyl-2-oxo-5-(4-piperidyl)benzimidazol-1-yl]piperidine-2,6-dione. To a solution of tert-butyl 4-[1-(2,6-dioxo-3-piperidyl)-3-methyl-2-oxo-benzimidazol-5-yl]piperidine-1-carboxylate (300 mg, 677 μmol) in DCM (3 mL) was added TFA (2.30 g, 20.1 mmol, 1.50 mL) and the mixture was stirred at 25° C. for 0.5 hr. On completion, the mixture was concentrated in vacuo to give the title compound (300 mg, 96% yield, TFA salt) as yellow oil. LC-MS (ESI) m/z 343.0 $(M+H)^+$.

Step 1-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl 4-methylbenzenesulfonate. To a solution of (R)-1-(7-(8-ethyl-7-fluoro-3-((triisopropylsilyl)oxy) naphthalen-1-yl)-8-fluoro-2-(((3S,7aS)-3-(hydroxymethyl)hexahydro-1H-pyrrolizin-7a-yl) methoxy)pyrido[4,3-d]pyrimidin-4-yl)-3-methylpiperidin-3-ol (400 mg, 515 μmol) in DCM (6 mL) was added TEA (260 mg, 2.58 mmol), DMAP (6.30 mg, 51.5 μmol) and TosCl (294 mg, 1.55 mmol) at 0° C. Then the mixture was stirred at 30° C. for 16 hrs. On completion, the reaction was diluted with DCM (20 mL), quenched with $H_2O$ (30 mL) and extracted with DCM (3×50 mL). The organic layer was washed with brine (2×50 mL), dried over anhydrous $Na_2SO_4$, filtered and the filtrate was concentrated in vacuo to afford a residue. The residue was purified by column chromatography ($SiO_2$, DCM/MeOH=50/1 to 10/1) to give the title compound (400 mg, 75% yield) as yellow solid. $^1H$ NMR (400 MHz, $CDCl_3$) δ 9.15 (d, J=6.0 Hz, 1H), 7.81 (d, J=8.0 Hz, 2H), 7.65-7.57 (m, 1H), 7.36 (d, J=8.0 Hz, 2H), 7.31 (d, J=2.8 Hz, 1H), 7.23 (t, J=9.2 Hz, 1H), 7.14-7.08 (m, 1H), 4.49-4.36 (m, 2H), 4.33-4.16 (m, 3H), 3.52-3.26 (m, 3H), 2.86-2.76 (m, 1H), 2.68-2.56 (m, 1H), 2.54-2.48 (m, 1H), 2.45 (s, 3H), 2.25-2.13 (m, 2H), 2.11-2.06 (m, 1H), 1.95-1.75 (m, 6H), 1.74-1.63 (m, 5H), 1.56-1.47 (m, 1H), 1.35 (s, 3H), 1.33-1.26 (m, 3H), 1.12 (d, J=7.2 Hz, 18H), 0.88-0.80 (m, 3H); LC-MS (ESI) m/z 930.3 $(M+H)^+$.

Step 2-(R)-1-(2-(((35,7aS)-3-((4-(Dimethoxymethyl) piperidin-1-yl)methyl)hexahydro-1H-pyrrolizin-7a-yl) methoxy)-7-(8-ethyl-7-fluoro-3-((triisopropylsilyl)oxy) naphthalen-1-yl)-8-fluoropyrido[4,3-d]pyrimidin-4-yl)-3-methylpiperidin-3-ol. A solution of 4-(dimethoxymethyl) piperidine (228 mg, 1.44 mmol) in ACN (13 mL) was added KI (79.4 mg, 478 μmol), $K_2CO_3$ (264 mg, 1.91 mmol) and ((3S,7aS)-7a-(((7-(8-ethyl-7-fluoro-3-((triisopropylsilyl) oxy) naphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl4-methylbenzenesulfonate (445 mg, 478 μmol). Then the mixture was stirred at 85° C. for 3 hrs under $N_2$atmosphere. On completion, the mixture was quenched with aq. $NH_4Cl$ (30 mL), extracted with EA (3×40 mL), dried over anhydrous $Na_2SO_4$, filtered and the filtrate was concentrated in vacuo to give a residue. The residue was purified by column chromatography ($SiO_2$, DCM/EA=10/1 to 1/1) to give the title compound (85.0 mg, 19% yield) as yellow solid. $^1H$ NMR (400 MHz, $CDCl_3$) δ 9.13 (d, J=6.4 Hz, 1H), 7.65-7.56 (m, 1H), 7.31 (d, J=2.4 Hz, 1H), 7.25-7.19 (m, 1H), 7.15-7.05 (m, 1H), 4.44-4.37 (m, 2H), 4.05-3.96 (m, 1H), 3.58-3.48 (m, 1H), 3.33 (s, 6H), 3.05-2.94 (m, 2H), 2.78-2.61 (m, 2H), 2.56-2.43 (m, 2H), 2.34-2.25 (m, 1H), 2.22-2.17 (m, 1H), 2.02-1.83 (m, 14H), 1.77-1.54 (m, 8H), 1.36 (s, 3H), 1.33-1.25 (m, 5H), 1.12 (d, J=7.2 Hz, 18H), 0.89-0.82 (m, 3H); LC-MS (ESI) m/z 917.5 $(M+H)^+$.

Step 3-(R)-1-(2-(((3S,7aS)-3-((4-(Dimethoxymethyl) piperidin-1-yl)methyl)hexahydro-1H-pyrrolizin-7a-yl) methoxy)-7-(8-ethyl-7-fluoro-3-hydroxynaphthalen-1-yl)-8-fluoropyrido[4,3-d]pyrimidin-4-yl)-3-methylpiperidin-3-ol. To a solution of (R)-1-(2-(((3S,7aS)-3-((4-(dimethoxymethyl) piperidin-1-yl)methyl)hexahydro-1H-pyrrolizin-7a-yl) methoxy)-7-(8-ethyl-7-fluoro-3-((triisopropylsilyl)oxy) naphthalen-1-yl)-8-fluoropyrido[4,3-d]pyrimidin-4-yl)-3-methylpiperidin-3-ol (70.0 mg, 76.3 μmol) in DMSO (1.5 mL) was added CsF (23.1 mg, 152 μmol). Then the mixture was stirred at 30° C. for 0.5 hr. On completion, the mixture was quenched with aq. $NH_4Cl$ (30 mL), extracted with EA (3×30 mL), dried over anhydrous $Na_2SO_4$, filtered and the filtrate was concentrated in vacuo to give the title compound (55.0 mg, 94% yield) as yellow oil. LC-MS (ESI) m z 761.4 $(M+H)^+$.

Step 4-1-(((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl) piperidine-4-carbaldehyde. A solution of (R)-1-(2-(((3S,7aS)-3-((4-(dimethoxymethyl) piperidin-1-yl)methyl)hexahydro-1H-pyrrolizin-7a-yl) methoxy)-7-(8-ethyl-7-fluoro-3-hydroxynaphthalen-1-yl)-8-fluoropyrido[4,3-d]pyrimidin-4-yl)-3-methylpiperidin-3-ol (55.0 mg, 72.2 μmol) in FA (1.22 g, 26.50 mmol, 1 mL) was stirred at 60° C. for 0.5 hr. On completion, the mixture was concentrated in vacuo to give the title compound (50.0 mg, 96% yield) as yellow oil. LC-MS (ESI) m/z 715.4 $(M+H)^+$.

Step 5-3-(5-(1-((1-(((35,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl) piperidin-4-yl)methyl) piperidin-4-yl)-3-methyl-2-oxo-2,3-dihydro-1H-benzo[d]imidazol-1-yl) piperidine-2,6-dione (Compound 402). To a solution of 3-[3-methyl-2-oxo-5-(4-piperidyl) benzimidazol-1-yl]piperidine-2,6-dione (63.8 mg, 139 μmol, TFA salt) in THF (2 mL) and DMSO (1 mL) was added TEA (21.2 mg, 209 μmol, 29.2 μL), HOAc (16.8 mg, 279 μmol, 16.0 μL) and 1-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl) oxy)methyl)hexahydro-1H-pyrrolizin-3-yl)methyl) piperidine-4-carbaldehyde (50.0 mg, 69.9 μmol). The mixture was stirred at 25° C. for 1 hr. Then $NaBH(OAc)_3$ (22.2 mg, 104 μmol) was added to the mixture and the mixture was stirred at 25° C. for 1 hr. On completion, the reaction was quenched with $H_2O$ (0.2 mL) and mixture was concentrated in vacuo to give a residue. The residue was purified by prep-HPLC (column: CD01-Phenomenex luna C18 150*25*10 μm; mobile phase: [water (AA)-ACN]; gradient: 16%-46% B over 10 min) to give the title compound (26.7 mg, 35% yield, FA salt) as white solid. $^1H$ NMR (400 MHz, DMSO-$d_6$) δ 11.08 (s, 1H), 9.27 (d, J=4.4 Hz, 1H), 7.80-7.70 (m, 1H), 7.38-7.28 (m, 2H), 7.07 (s, 1H), 7.04-7.01 (m, 1H), 7.00-6.94 (m, 1H), 6.92-6.84 (m, 1H), 5.39-5.28 (m, 1H), 4.44-4.29 (m, 3H), 4.12-4.02 (m, 1H), 3.67-3.50 (m, 3H), 3.44-3.33 (m, 2H), 3.31 (d, J=4.8 Hz, 3H), 3.14-3.07 (m, 1H), 2.99-2.85 (m, 6H), 2.72-2.59 (m, 3H), 2.40-2.34 (m, 1H), 2.20-2.11 (m, 4H), 2.07-1.94 (m, 7H), 1.93-1.79 (m, 5H), 1.78-1.61 (m, 12H), 1.54-1.48 (m, 1H), 1.17 (d, J=6.0 Hz, 3H), 1.14-1.07 (m, 2H), 0.78-0.71 (m, 3H); LC-MS (ESI) m/z 1041.3 $(M+H)^+$.

Example 62. Synthesis of Compound 405

Step 1-(R)-1-(7-Chloro-8-fluoro-2-(((3S,7aS)-3-(hydroxymethyl)hexahydro-1H-pyrrolizin-7a-yl) methoxy) pyrido[4,3-d]pyrimidin-4-yl)-3-methylpiperidin-3-ol. To a solution of (R)-1-(2-(((3S,7aS)-3-(((tert-butyldiphenylsilyl) oxy)methyl)hexahydro-1H-pyrrolizin-7a-yl) methoxy)-7-chloro-8-fluoropyrido[4,3-d]pyrimidin-4-yl)-3-methylpiperidin-3-ol (600 mg, 851 μmol) in DMSO (6 mL) was added CsF (388 mg, 2.56 mmol). The mixture was stirred at 40° C. for 1 hr. On completion, the residue was diluted with water (30 mL). then the residue was extracted with EA (3×80 mL). The combined organic layers was dried over $Na_2SO_4$, filtered and the filtrate was concentrated in vacuo to give the title compound (390 mg. 98% yield) as yellow solid. LC-MS (ESI) m/z 466.1 $(M+H)^+$.

Step 2-6-Fluoro-8-((triisopropylsilyl) ethynyl) naphthalen-1-ol. A mixture of 6-fluoronaphthalen-1-ol (5.50 g, 33.9 mmol), (bromoethynyl)triisopropylsilane (9.30 g, 35.6 mmol), KOAc (6.66 g, 67.8 mmol), dichlororuthenium; 1-isopropyl-4-methyl-benzene (2.08 g, 3.39 mmol) in dioxane (60 mL) was degassed and purged with $N_2$ for 3 times, and then the mixture was stirred at 100° C. for 2 hrs under $N_2$ atmosphere. On completion, the residue was diluted with water (50 mL), then the residue was extracted with EA (3×100 mL). The combined organic layers was dried over $Na_2SO_4$, filtered and the filtrate was concentrated in vacuo to give a residue. The residue was purified by column chromatography ($SiO_2$, PE:EA=50:1 to 5:1) to give the title compound (10.0 g, 86% yield) as yellow solid. LC-MS (ESI) m/z 343.1 $(M+H)^+$.

Step 3-6-Fluoro-8-((triisopropylsilyl) ethynyl) naphthalen-1-yl pivalate. To a solution of 6-fluoro-8-(2-triisopropylsilylethynyl) naphthalen-1-ol (10.0 g, 29.2 mmol) in DCM (100 mL) was added DIEA (7.55 g, 58.3 mmol, 10.1 mL) and 2,2-dimethylpropanoyl chloride (10.5 g, 87.5 mmol, 10.7 mL) at 0° C. The mixture was stirred at 25° C. for 3 hrs. On completion, the residue was diluted with water (50 mL), then the residue was extracted with DCM (3×100 mL). The combined organic layers was dried over $Na_2SO_4$, filtered and the filtrate was concentrated in vacuo to give a residue. The residue was purified by column chromatography ($SiO_2$, PE:EA=10:1) to give the title compound (12.0 g, 96% yield) as yellow solid. $^1H$ NMR (400 MHz, DMSO-$d_6$) δ 7.94 (dd, J=2.8, 9.6 Hz, 1H), 7.90 (d, J=8.4 Hz, 1H), 7.62 (t, J=8.0 Hz, 1H), 7.56 (dd, J=2.8, 8.8 Hz, 1H), 7.16 (d, J=7.6 Hz, 1H), 1.40 (s, 9H), 1.18-1.14 (m, 3H), 1.11 (s, 18H); LC-MS (ESI) m/z 427.2 $(M+H)^+$.

Step 4-6-Fluoro-3-(4,4,5,5-tetramethyl-1,3,2-dioxaborolan-2-yl)-8-((triisopropylsilyl) ethynyl) naphthalen-1-yl pivalate. To a solution of 6-fluoro-8-((triisopropylsilyl) ethynyl) naphthalen-1-yl pivalate (10.0 g, 23.4 mmol) in Hexane (100 mL) was added 4-tert-butyl-2-(4-tert-butyl-2-pyridyl) pyridine (943 mg, 3.52 mmol), (1Z,5Z)-cycloocta-1,5-diene (methoxy) iridium (I) dimer (1.55 g, 2.34 mmol), 4,4,5,5-tetramethyl-1,3,2-dioxaborolane (9.00 g, 70.3 mmol, 10.2 mL) at 25° C. The mixture was stirred at 60° C. for 2 hrs under $N_2$ atmosphere. On completion, the residue was diluted with water (30 mL), then the residue was extracted with EA (3×100 mL). The combined organic layers was dried over $Na_2SO_4$, filtered and the filtrate was concentrated in vacuo to give a residue. The residue was purified by column chromatography ($SiO_2$, PE:EA=10:1) to give the title compound (12.0 g, 92% yield) as yellow solid. LC-MS (ESI) m/z 553.3 $(M+H)^+$.

Step 5-6-Fluoro-3-hydroxy-8-((triisopropylsilyl) ethynyl) naphthalen-1-yl pivalate. To a solution of 6-fluoro-3-(4,4,5,5-tetramethyl-1,3,2-dioxaborolan-2-yl)-8-((triisopropylsilyl) ethynyl) naphthalen-1-yl pivalate (8.00 g, 14.48 mmol) in THF (100 mL) was added $H_2O_2$ (6.38 g, 56.2 mmol, 5.41 mL, 30% purity) at 0° C., the reaction mixture was stirred at 25° C. for 2 hrs. On completion, the reaction mixture was quenched by saturated $Na_2S_2O_3$ (50 mL) and saturated $NaHCO_3$ (50 mL) at 25° C., and then stirred for 30 minutes. The mixture was extracted with EA (2×80 mL) then the combined organic layers was dried over $Na_2SO_4$, filtered and concentrated in vacuo to give a residue. The residue was purified by column chromatography ($SiO_2$, PE:EA=10:1) to give the title compound (4.7 g, 73% yield) as white solid. $^1H$ NMR (400 MHz, DMSO-$d_6$) δ 10.31 (s, 1H), 7.69 (dd, J=2.4, 10.0 Hz, 1H), 7.29 (dd, J=2.6-8, 8.8 Hz, 1H), 7.12 (d, J=2.4 Hz, 1H), 6.70 (d, J=2.4 Hz, 1H), 1.38 (s, 9H), 1.18-1.13 (m, 3H), 1.13-1.09 (m, 18H); LC-MS (ESI) m/z 443.2 $(M+H)^+$.

Step 6-6-Fluoro-3-(methoxymethoxy)-8-((triisopropylsilyl) ethynyl) naphthalen-1-yl pivalate. To a solution of 6-fluoro-3-hydroxy-8-((triisopropylsilyl) ethynyl) naphthalen-1-yl pivalate (4.70 g, 10.6 mmol) in DCM (50 mL) was added DIEA (5.49 g, 42.4 mmol, 7.40 mL), MOMCl (4.68 g, 58.1 mmol, 4.42 mL) at 0° C., the reaction mixture was stirred at 25° C. for 2 hrs. On completion, the residue was diluted with water (60 mL), then the residue was extracted with EA (3×100 mL). The combined organic layers was dried over $Na_2SO_4$, filtered and the filtrate was concentrated in vacuo to give the title compound (5.00 g, 96% yield) as yellow solid. 1H NMR (400 MHz, DMSO-$d_6$) δ 7.81 (dd, J=2.8, 9.6 Hz, 1H), 7.46 (d, J=2.4 Hz, 1H), 7.40 (dd, J=2.8, 8.8 Hz, 1H), 6.91 (d, J=2.4 Hz, 1H), 5.33 (s, 2H), 3.42 (s, 3H), 1.39 (s, 9H), 1.19-1.14 (m, 3H), 1.13-1.10 (m, 18H); LC-MS (ESI) m/z 487.2 $(M+H)^+$.

Step 7-6-Fluoro-3-(methoxymethoxy)-8-((triisopropylsilyl) ethynyl) naphthalen-1-ol. To a solution of 6-fluoro-3-(methoxymethoxy)-8-((triisopropylsilyl) ethynyl) naphthalen-1-yl pivalate (4.50 g, 9.25 mmol) in MeOH (50 mL) was added $CH_3ONa$ (1.50 g, 27.7 mmol). The mixture was stirred at 25° C. for 1 hr. On completion, the residue was diluted with water (30 mL), then the residue was extracted with EA (3×50 mL). The combined organic layers was dried over $Na_2SO_4$, filtered and the filtrate was concentrated in vacuo to give a residue. The residue was purified by column chromatography ($SiO_2$, PE:EA=10:1) to give the title compound (2.50 g, 67% yield) as yellow oil. $^1H$ NMR (400 MHz, DMSO-$d_6$) δ 10.36 (s, 1H), 7.52 (dd, J=2.4, 10.0 Hz, 1H), 7.22 (dd, J=2.4, 9.2 Hz, 1H), 6.90 (d, J=2.4 Hz, 1H), 6.61 (d, J=2.4 Hz, 1H), 5.23 (s, 2H), 3.40 (s, 3H), 1.13 (s, 21H); LC-MS (ESI) m/z 403.1 $(M+H)^+$.

Step 8-6-Fluoro-3-(methoxymethoxy)-8-((triisopropylsilyl) ethynyl) naphthalen-1-yl trifluoromethanesulfonate. To a solution of 6-fluoro-3-(methoxymethoxy)-8-((triisopropylsilyl) ethynyl) naphthalen-1-ol (2.00 g, 4.97 mmol) in DCM (20 mL) was added DIEA (1.93 g, 14.9 mmol, 2.60 mL) and $Tf_2O$ (2.10 g, 7.45 mmol, 1.23 mL). The mixture was stirred at 0° C. for 1 hr. On completion, the residue was diluted with water (30 mL), then the residue was extracted with DCM (3×500 mL). The combined organic layers was dried over $Na_2SO_4$, filtered and the filtrate was concentrated in vacuo to give the title compound (2.50 g. 94% yield) as yellow oil. $^1H$ NMR (400 MHz, DMSO-$d_6$) δ 7.90 (dd, J=2.4, 9.6 Hz, 1H). 7.69 (d. J=2.4 Hz, 1H). 7.59 (dd. J=2.4, 8.8 Hz, 1H). 7.41 (d. J=2.0 Hz, 1H). 5.37 (s, 2H). 3.43 (s, 3H), 1.19-1.16 (m. 3H). 1.14-1.10 (m. 18H).

Step 9-((3-Fluoro-6-(methoxymethoxy)-8-(4,4,5,5-tetramethyl-1,3,2-dioxaborolan-2-yl) naphthalene-1-yl) ethynyl)triisopropylsilane. To a solution of 6-fluoro-3-(methoxymethoxy)-8-((triisopropylsilyl) ethynyl) naphthalen-1-yl trifluoromethanesulfonate (2.50 g, 4.68 mmol) 4,4,5,5-tetramethyl-2-(4,4,5,5-tetramethyl-1,3,2-dioxaborolan-2-yl)-1,3,2-dioxaborolane (2.37 g, 9.35 mmol) in dioxane (25 mL) was added KOAc (1.38 g, 14.0 mmol) and Pd (dppf) $Cl_2$ (342 mg, 467 μmol). The mixture was stirred at 80° C. for 2 hrs under $N_2$. On completion, the residue was diluted with water (30 mL), then the residue was extracted with EA (3×30 mL). The combined organic layers was dried over $Na_2SO_4$, filtered and the filtrate was concentrated in vacuo to give a residue. The residue was purified by column chromatography ($SiO_2$, PE:EA=10:1) to give the title compound (1.0 g, 41% yield) as yellow solid. $^1$H NMR (400 MHz, DMSO-$d_6$) δ 7.73 (dd, J=2.4, 10.0 Hz, 1H), 7.51 (d, J=2.6 Hz, 1H), 7.42 (dd, J=2.8, 8.8 Hz, 1H), 7.30 (d, J=2.4 Hz, 1H), 5.32 (s, 2H), 3.41 (s, 3H), 1.34 (s, 12H), 1.13 (d, J=4.8 Hz, 3H), 1.12-1.08 (m, 18H).

Step 10-(R)-1-(8-Fluoro-7-(6-fluoro-3-(methoxymethoxy)-8-((triisopropylsilyl) ethynyl) naphthalen-1-yl)-2-(((3S,7aS)-3-(hydroxymethyl)hexahydro-1H-pyrrolizin-7a-yl) methoxy)pyrido[4,3-d]pyrimidin-4-yl)-3-methylpiperidin-3-ol. A mixture of ((3-fluoro-6-(methoxymethoxy)-8-(4,4,5,5-tetramethyl-1,3,2-dioxaborolan-2-yl) naphthalen-1-yl) ethynyl) triisopropylsilane (428 mg, 837 μmol), (R)-1-(7-chloro-8-fluoro-2-(((3S,7aS)-3-(hydroxymethyl)hexahydro-1H-pyrrolizin-7a-yl) methoxy)pyrido[4,3-d]pyrimidin-4-yl)-3-methylpiperidin-3-ol (300 mg, 643 μmol), [2-(2-aminophenyl)phenyl]palladium (1+); bis(1-adamantyl)-butyl-phosphane; methanesulfonate (46.8 mg, 64.3 μmol), $Cs_2CO_3$ (629 mg, 1.93 mmol) in dioxane (5 mL) and $H_2O$ (1 mL) was degassed and purged with $N_2$ for 3 times, and then the mixture was stirred at 60° C. for 2 hrs under $N_2$ atmosphere. On completion, the residue was diluted with water (30 mL), then the residue was extracted with EA (3×30 mL). The combined organic layers was dried over $Na_2SO_4$, filtered and the filtrate was concentrated in vacuo to give a residue. The residue was purified by column chromatography ($SiO_2$. PE:EA=10:1) to give the title compound (160 mg. 30% yield) was obtained as yellow solid. LC-MS (ESI) m/z 816.4 $(M+H)^+$.

Step 11-((3S,7aS)-7a-(((8-Fluoro-7-(6-fluoro-3-(methoxymethoxy)-8-((triisopropylsilyl) ethynyl) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl (4-nitrophenyl) carbonate. To a solution of (R)-1-(8-fluoro-7-(6-fluoro-3-(methoxymethoxy)-8-((triisopropylsilyl) ethynyl) naphthalene-1-yl)-2-(((3S,7aS)-3-(hydroxymethyl)hexahydro-1H-pyrrolizin-7a-yl) methoxy)pyrido[4,3-d]pyrimidin-4-yl)-3-methylpiperidin-3-ol (150 mg, 183 μmol) in DCM (5 mL) was added DMAP (2.25 mg, 18.3 μmol) and TEA (55.8 mg, 551 μmol, 76.7 μL), then (4-nitrophenyl) carbonochloridate (111 mg, 551 μmol) was added, the reaction mixture was stirred at 25° C. for 2 hrs. On completion, the residue was diluted with water (30 mL), then the residue was extracted with DCM (3×50 mL). The combined organic layers was dried over $Na_2SO_4$, filtered and the filtrate was concentrated in vacuo to give the title compound (180 mg, 99% yield) as yellow solid. LC-MS (ESI) m/z 491.4 $(M/2+H)^+$.

Step 12-((3S,7aS)-7a-(((8-Fluoro-7-(6-fluoro-3-(methoxymethoxy)-8-((triisopropylsilyl) ethynyl) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate. To a solution of 3-(3-methyl-2-oxo-5-(1-(piperidin-4-ylmethyl) piperidin-4-yl)-2,3-dihydro-1H-benzo[d]imidazol-1-yl) piperidine-2,6-dione (12.0 mg, 229 mol, TFA) in THF (2 mL) was added TEA (15.4 mg, 152 μmol, 21.2 μL) and ((3S,7aS)-7a-(((8-fluoro-7-(6-fluoro-3-(methoxymethoxy)-8-((triisopropylsilyl) ethynyl) naphthalen-1-yl)-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate (150 mg, 152 μmol). The mixture was stirred at 25° C. for 0.2 hr. On completion, the reaction mixture was concentrated in vacuo. The residue was purified by reverse phase (0.1% TFA condition) to give the title compound (100 mg, 51% yield) as yellow solid. $^1$H NMR (400 MHz, DMSO-$d_6$) δ 11.09 (s, 1H), 10.52-10.36 (m, 1H), 9.47-9.22 (m, 1H), 9.16-8.98 (m, 1H), 7.93-7.85 (m, 1H), 7.69 (t, J=2.0 Hz, 1H), 7.46-7.38 (m, 1H), 7.25 (dd, J=2.8, 4.4 Hz, 1H), 7.10-6.99 (m, 2H), 6.91 (d, J=8.8 Hz, 1H), 5.34 (d, J=5.2 Hz, 1H), 4.67-4.42 (m, 4H), 4.36-4.21 (m, 2H), 4.13-3.93 (m, 6H), 3.52 (d, J=9.4 Hz, 2H), 3.43 (s, 3H), 3.34 (s, 3H), 3.03 (s, 3H), 2.95-2.81 (m, 4H), 2.73-2.63 (m, 2H), 2.31-2.23 (m, 1H), 2.15-1.88 (m, 16H), 1.83-1.58 (m, 6H), 1.21 (d, J=7.2 Hz, 3H), 1.17-1.10 (m, 2H), 0.86-0.80 (m, 18H), 0.55 (q, J=7.6 Hz, 3H); LC-MS (ESI) m/z 1281.4 $(M+H)^+$.

Step 13-((35,7aS)-7a-(((7-(8-Ethynyl-6-fluoro-3-(methoxymethoxy) naphthalen-1-yl)-8-fluoro-4-((R)-3-hydroxy-3-methylpiperidin-1-yl)pyrido[4,3-d]pyrimidin-2-yl) oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazole-5-yl) piperidin-1-yl)methyl) piperidine-1-carboxylate. To a solution of ((3S,7aS)-7a-(((8-fluoro-7-(6-fluoro-3-(methoxymethoxy)-8-((triisopropylsilyl) ethynyl) naphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (80.0 mg, 62.4 μmol) in DMSO (1 mL) was added CsF (28.4 mg, 187 μmol). The mixture was stirred at 25° C. for 1 hr. On completion, the residue was diluted with water (30 mL), then the residue was extracted with DCM (3×30 mL). The combined organic layers was dried over $Na_2SO_4$, filtered and the filtrate was concentrated in vacuo to give the title compound (70.0 mg, 99% yield) as yellow solid. LC-MS (ESI) m/z 1125.6 $(M+H)^+$.

Step 14-((3S,7aS)-7a-(((7-(8-Ethynyl-6-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 4-((4-(1-(2,6-dioxopiperidin-3-yl)-3-methyl-2-oxo-2,3-dihydro-1H-benzo[d]imidazole-5-yl) piperidin-1-yl)methyl) piperidine-1-carboxylate (Compound 405). A solution of ((3S,7aS)-7a-(((7-(8-ethynyl-6-fluoro-3-(methoxymethoxy) naphthalen-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl) piperidin-1-yl)methyl) piperidine-1-carboxylate (60.0 mg, 53.3 μmol) in HCOOH (2.56 mg, 53.3 μmol) was stirred at 25° C. for 1 hr. On completion, the reaction mixture was concentrated in vacuo. The residue was purified by prep-HPLC (column: CD01-Phenomenex luna C18 150*25*10 μm; mobile phase: [water (FA)-ACN]; gradient: 5%-35% B over 8 min) to give the title compound (11.4 mg, 18% yield, FA) as yellow solid. $^1$H NMR (400 MHz, DMSO-$d_6$) δ 11.08 (s, 1H), 10.53-10.19 (m, 1H), 9.25-9.00 (m, 1H), 7.74 (dd, J=2.4, 10.0 Hz, 1H), 7.37-7.30 (m, 2H), 7.15-7.06 (m, 2H), 7.01-6.96 (m, 1H), 6.90 (d, J=8.4 Hz, 1H), 5.33 (dd, J=5.2, 12.8 Hz, 1H), 4.81-4.66 (m, 1H), 4.40-4.27 (m, 1H), 4.25-4.18 (m, 1H), 4.16-4.01 (m, 4H), 3.96 (d, J=12.4 Hz, 2H), 3.76 (d, J=2.0 Hz, 1H), 3.58 (t, J=12.8 Hz, 1H), 3.32 (s, 3H), 2.92 (d, J=8.4 Hz, 3H), 2.79-2.60 (m, 6H), 2.13 (d, J=5.6 Hz, 2H), 2.09-1.88 (m, 6H), 1.83-1.58 (m, 18H), 1.54-1.46 (m, 1H), 1.16 (d, J=17.2 Hz, 3H), 1.02-0.91 (m, 2H). LC-MS (ESI) m/z 1081.3 (M+H)$^+$.

Example 63. Synthesis of Compound 406

Step 1-N-(2-Chloro-3-fluoro-5-iodopyridin-4-yl) acetamide. To a solution of 2-chloro-3-fluoro-5-iodopyridin-4-amine (20.0 g, 73.4 mmol) in $Ac_2O$ (100 mL) was added DMAP (1.79 g, 14.6 mmol). The mixture was stirred at 80° C. for 36 hrs. On completion, the reaction mixture was quenched by water (200 mL) and extracted with EA (2×100 mL). The combined organic layers were washed with water (3×100 mL), dried over anhydrous $Na_2SO_4$, filtered and the filtrate was concentrated in vacuo to give a residue. The residue was purified by column chromatography ($SiO_2$, Petroleum ether/Ethyl acetate=1/0 to 5/1) to give the title compound (22.0 g, 95% yield) as white solid. $^1$H NMR (400 MHz, $CDCl_3$) δ 8.66 (s, 1H), 2.34 (s, 3H); LC-MS (ESI) m/z 314.8 (M+H)$^+$.

Step 2-Ethyl 4-acetamido-6-chloro-5-fluoronicotinate. A mixture of N-(2-chloro-3-fluoro-5-iodopyridin-4-yl) acetamide (20.0 g, 63.6 mmol), TEA (25.7 g, 254 mmol, 35.4 mL) and $Pd(PPh_3)_2Cl_2$ (4.46 g, 6.36 mmol) in EtOH (200 mL) was degassed and purged with CO for 3 times, and then the mixture was stirred at 80° C. for 12 hrs under CO (15 Psi) atmosphere. On completion, the reaction mixture was concentrated in vacuo to give a residue. The residue was purified by column chromatography ($SiO_2$, Petroleum ether/Ethyl acetate=1/0 to 3/1) to give the title compound (11.4 g, 68% yield) as yellow solid. $^1$H NMR (400 MHz, $CDCl_3$) δ 9.60 (s, 1H), 8.72 (s, 1H), 4.44 (q, J=7.2 Hz, 2H), 2.29 (s, 3H), 1.44 (t, J=7.2 Hz, 3H); LC-MS (ESI) m/z 260.8 (M+H)$^+$.

Step 3-Ethyl 4-(N-benzylacetamido)-6-chloro-5-fluoronicotinate. To a solution of ethyl 4-acetamido-6-chloro-5-fluoronicotinate (10.0 g, 38.3 mmol) in DMF (100 mL) was added KOH (2.37 g, 42.2 mmol) and a solution of bromomethylbenzene (7.22 g, 42.2 mmol, 5.01 mL) in DMF (60 mL) at 0° C. The mixture was stirred at 25° C. for 12 hrs. On completion, the reaction was poured into ice-water (200 mL), and then extracted with EA (2×150 mL). The combined organic layers were washed with brine (3×150 mL), dried over anhydrous $Na_2SO_4$, filtered and the filtrate was concentrated in vacuo to give a residue. The residue was purified by column chromatography ($SiO_2$, Petroleum ether/Ethyl acetate=1/0 to 4/1) to give the title compound (10.0 g, 74% yield) as yellow oil. $^1$H NMR (400 MHz, $CDCl_3$) δ 8.74-8.64 (m, 1H), 7.25-7.21 (m, 3H), 7.12 (dd, J=2.4, 6.8 Hz, 2H), 4.87-4.76 (m, 2H), 4.23-4.13 (m, 2H), 1.92 (s, 3H), 1.31 (t, J=7.2 Hz, 3H); LC-MS (ESI) m/z 350.9 (M+H)$^+$.

Step 4-1-Benzyl-7-chloro-8-fluoro-4-hydroxy-1,6-naphthyridin-2 (1H)-one. To a solution of ethyl 4-(N-benzylacetamido)-6-chloro-5-fluoronicotinate (5.00 g, 14.2 mmol) in THF (50 mL) was added LiHMDS (1 M, 17.1 mL) at 0° C. The mixture was stirred at 25° C. for 12 hrs. On completion, the reaction mixture was quenched by ice water (50 mL), and then diluted with water (50 mL), then adjust pH to 4-5 with 1N HCl, and extracted with EA (2×100 mL). The combined organic layers were washed with brine (100 mL), dried over anhydrous $Na_2SO_4$, filtered and the filtrate was concentrated in vacuo to give a residue. The residue was triturated with (Ethyl acetate/Petroleum ether=5/1, 60 mL) to give the title compound (3.55 g, 81% yield) as yellow solid. $^1$H NMR (400 MHz, DMSO-$d_6$) δ 12.34 (d, J=5.2 Hz, 1H), 8.69 (s, 1H), 7.34-7.28 (m, 2H), 7.26-7.19 (m, 1H), 7.10 (d, J=7.2 Hz, 2H), 6.04 (s, 1H), 5.50 (s, 2H); LC-MS (ESI) m/z 305.1 (M+H)$^+$.

Step 5-1-Benzyl-4,7-dichloro-8-fluoro-1,6-naphthyridin-2 (1H)-one. To a solution of 1-benzyl-7-chloro-8-fluoro-4-hydroxy-1,6-naphthyridin-2 (1H)-one (3.55 g, 11.6 mmol) in Tol. (35 mL) was added $POCl_3$ (8.93 g, 58.2 mmol, 5.43 mL) and DIEA (4.52 g, 34.9 mmol, 6.09 mL) at 0° C. The mixture was stirred at 110° C. for 12 hrs. On completion, the reaction mixture was slowly dropwise into ice-water (100 mL), and then extracted with EA (3×80 mL). The combined organic layers were washed with brine (2×50 mL), dried over anhydrous $Na_2SO_4$, filtered and the filtrate was concentrated in vacuo to give a residue. The residue was purified by column chromatography ($SiO_2$, Petroleum ether/Ethyl acetate=1/0 to 10/1) to give the title compound (1.65 g, 43% yield) as yellow solid. $^1$H NMR (400 MHz, $CDCl_3$) δ 8.82 (s, 1H), 7.35-7.28 (m, 3H), 7.19 (d, J=7.2 Hz, 2H), 7.02 (s, 1H), 5.67 (s, 2H).

Step 6-(R)-1-Benzyl-7-chloro-8-fluoro-4-(3-hydroxy-3-methylpiperidin-1-yl)-1,6-naphthyridin-2 (1H)-one. To a solution of 1-benzyl-4,7-dichloro-8-fluoro-1,6-naphthyridin-2 (1H)-one (1.65 g, 5.11 mmol) and (R)-3-methylpiperidin-3-ol (851 mg, 5.62 mmol, HCl salt) in DMSO (15 mL) was added CsF (1.78 g, 11.7 mmol). The mixture was stirred at 60° C. for 12 hrs. On completion, the reaction mixture was quenched by water (50 mL), and then extracted with EA (3×40 mL). The combined organic layers were washed with brine (50 mL), dried over anhydrous $Na_2SO_4$, filtered and the filtrate was concentrated in vacuo to give a residue. The residue was purified by column chromatography ($SiO_2$, Petroleum ether/Ethyl acetate=1/0 to 1/1) to give the title compound (1.45 g, 70% yield) as yellow solid. LC-MS (ESI) m/z 402.0 (M+H)$^+$.

Step 7-(R)-1-Benzyl-7-(8-ethyl-7-fluoro-3-(methoxymethoxy) naphthalen-1-yl)-8-fluoro-4-(3-hydroxy-3-methylpiperidin-1-yl)-1,6-naphthyridin-2 (1H)-one. A mixture of (R)-1-benzyl-7-chloro-8-fluoro-4-(3-hydroxy-3-methylpiperidin-1-yl)-1,6-naphthyridin-2 (1H)-one (1.20 g, 2.99 mmol), 2-(8-ethyl-7-fluoro-3-(methoxymethoxy) naphthalen-1-yl)-4,4,5,5-tetramethyl-1,3,2-dioxaborolane (1.61 g, 4.48 mmol), $K_3PO_4$ (1.90 g, 8.96 mmol) and [2-(2-aminophenyl)phenyl]palladium (1+); bis (1-adamantyl)-butyl-phosphane; methanesulfonate (217 mg, 298 μmol) in dioxane (15 mL) and $H_2O$ (3 mL) was degassed and purged with $N_2$ for 3 times, and then the mixture was stirred at 100° C. for 0.5 hr under $N_2$ atmosphere. On completion, the reaction mixture was concentrated in vacuo to give a residue. The residue was purified by column chromatography ($SiO_2$, Petroleum ether/Ethyl acetate=1/0 to 1/1) to give the title compound (1.70 g, 94% yield) as white solid. $^1$H NMR (400 MHz, $CDCl_3$) δ 9.12-8.89 (m, 1H), 7.65 (dd, J=5.6, 9.2 Hz, 1H), 7.49 (d, J=2.4 Hz, 1H), 7.26-7.16 (m, 4H), 7.13 (d, J=7.2 Hz, 2H), 7.07 (s, 1H), 6.35 (s, 1H), 5.91-5.72 (m, 1H), 5.64-5.40 (m, 1H), 5.32-5.23 (m, 2H), 3.59-3.42 (m, 4H), 3.39-3.23 (m, 1H), 2.97-2.78 (m, 2H), 2.32-2.22 (m, 1H), 2.13-2.05 (m, 2H), 1.92-1.78 (m, 2H), 1.64 (d, J=2.0 Hz, 2H), 1.35 (d, J=8.4 Hz, 3H), 0.69-0.44 (m, 3H); LC-MS (ESI) m/z 600.2 $(M+H)^+$.

Step 8-(R)-7-(8-Ethyl-7-fluoro-3-(methoxymethoxy) naphthalen-1-yl)-8-fluoro-4-(3-hydroxy-3-methylpiperidin-1-yl)-1,6-naphthyridin-2 (1H)-one. To a mixture of Pd/C (1.10 g, 1.03 mmol, 10% purity) in THF (10 mL) and MeOH (20 mL) was added (R)-1-benzyl-7-(8-ethyl-7-fluoro-3-(methoxymethoxy) naphthalen-1-yl)-8-fluoro-4-(3-hydroxy-3-methylpiperidin-1-yl)-1,6-naphthyridin-2 (1H)-one (1.10 g, 1.83 mmol) under Ar atmosphere. The suspension was degassed and purged with $H_2$ for 3 times. The mixture was stirred under $H_2$ (15 Psi) at 25° C. for 12 hrs. On completion, the reaction mixture was filtered, the filter cake was washed with THF (3×100 mL). The filtrate was filtered and the filtrate was concentrated in vacuo to give a residue. The residue was purified by reverse phase (0.1% TFA condition) to give the title compound (600 mg, 64% yield) as white solid. $^1$H NMR (400 MHz, $CDCl_3$) δ 9.18 (d, J=16.4 Hz, 1H), 7.70 (dd, J=6.0, 9.2 Hz, 1H), 7.55 (d, J=2.4 Hz, 1H), 7.31-7.28 (m, 1H), 7.20 (d, J=2.4 Hz, 1H), 6.18 (d, J=2.0 Hz, 1H), 5.30 (d, J=1.2 Hz, 2H), 3.52 (s, 3H), 3.06-2.78 (m, 4H), 2.38-2.10 (m, 4H), 1.94-1.79 (m, 3H), 1.36 (d, J=5.2 Hz, 4H), 0.88-0.81 (m, 3H); LC-MS (ESI) m/z 510.2 $(M+H)^+$.

Step 9-(R)-1-(2-(((3S,7aS)-3-(((Tert-butyldiphenylsilyl) oxy)methyl)hexahydro-1H-pyrrolizin-7a-yl) methoxy)-7-(8-ethyl-7-fluoro-3-(methoxymethoxy) naphthalen-1-yl)-8-fluoro-1,6-naphthyridin-4-yl)-3-methylpiperidin-3-ol and 1-(((3S,7aS)-3-(((tert-butyldiphenylsilyl)oxy)methyl)hexahydro-1H-pyrrolizin-7a-yl)methyl)-7-(8-ethyl-7-fluoro-3-(methoxymethoxy) naphthalen-1-yl)-8-fluoro-4-((R)-3-hydroxy-3-methylpiperidin-1-yl)-1,6-naphthyridin-2 (1H)-one. A mixture of (R)-7-(8-ethyl-7-fluoro-3-(methoxymethoxy) naphthalen-1-yl)-8-fluoro-4-(3-hydroxy-3-methylpiperidin-1-yl)-1,6-naphthyridin-2 (1H)-one (600 mg, 1.18 mmol), ((3S,7aS)-3-(((tert-butyldiphenylsilyl)oxy)methyl)hexahydro-1H-pyrrolizin-7a-yl) methanol (723 mg, 1.77 mmol) and 2-(tributylphosphanylidene) acetonitrile (1.71 g, 7.07 mmol) in Tol. (12 mL) was degassed and purged with $N_2$ for 3 times, and then the mixture was stirred at 100° C. for 1 hr under $N_2$ atmosphere. On completion, the reaction mixture was concentrated in vacuo to give a residue. The residue was purified by column chromatography ($SiO_2$, Dichloromethane/Methanol=1/0 to 10/1) to give the title compound (700 mg, 65% yield, mixture of 13+13a) as yellow solid. LC-MS (ESI) m/z 901.3 $(M+H)^+$.

Step 10-(R)-1-(7-(8-Ethyl-7-fluoro-3-(methoxymethoxy) naphthalen-1-yl)-8-fluoro-2-(((3S,7aS)-3-(hydroxymethyl) hexahydro-1H-pyrrolizin-7a-yl) methoxy)-1,6-naphthyridin-4-yl)-3-methylpiperidin-3-ol and 7-(8-ethyl-7-fluoro-3-(methoxymethoxy) naphthalen-1-yl)-8-fluoro-4-((R)-3-hydroxy-3-methylpiperidin-1-yl)-1-(((3S,7aS)-3-(hydroxymethyl)hexahydro-1H-pyrrolizin-7a-yl)methyl)-1,6-naphthyridin-2 (1H)-one. To a solution of (R)-1-(2-(((3S,7aS)-3-(((tert-butyldiphenylsilyl)oxy)methyl)hexahydro-1H-pyrrolizin-7a-yl) methoxy)-7-(8-ethyl-7-fluoro-3-(methoxymethoxy) naphthalen-1-yl)-8-fluoro-1,6-naphthyridin-4-yl)-3-methylpiperidin-3-ol and 1-(((3S,7aS)-3-(((tert-butyldiphenylsilyl)oxy)methyl)hexahydro-1H-pyrrolizin-7a-yl)methyl)-7-(8-ethyl-7-fluoro-3-(methoxymethoxy) naphthalen-1-yl)-8-fluoro-4-((R)-3-hydroxy-3-methylpiperidin-1-yl)-1,6-naphthyridin-2 (1H)-one (580 mg, 643 μmol) in DMSO (3 mL) was added CsF (293 mg, 1.93 mmol). The mixture was stirred at 25° C. for 1 hr. On completion, the reaction mixture was quenched by water (20 mL), and then extracted with EA (3×20 mL), dried over anhydrous $Na_2SO_4$, filtered and the filtrate was concentrated in vacuo to give a residue. The residue was purified by reverse phase (0.1% TFA condition) to give (R)-1-(7-(8-ethyl-7-fluoro-3-(methoxymethoxy) naphthalen-1-yl)-8-fluoro-2-(((3S,7aS)-3-(hydroxymethyl)hexahydro-1H-pyrrolizin-7a-yl) methoxy)-1,6-naphthyridin-4-yl)-3-methylpiperidin-3-ol (150 mg, 35% yield) and 7-(8-ethyl-7-fluoro-3-(methoxymethoxy) naphthalen-1-yl)-8-fluoro-4-((R)-3-hydroxy-3-methylpiperidin-1-yl)-1-(((3S,7aS)-3-(hydroxymethyl)hexahydro-1H-pyrrolizin-7a-yl)methyl)-1,6-naphthyridin-2 (1H)-one as yellow solid (100 mg, 23% yield) were as yellow solid. 14: $^1$H NMR (400 MHz, $CDCl_3$) δ 12.55-12.10 (m, 1H), 9.63-9.25 (m, 1H), 7.71 (t, J=7.2 Hz, 1H), 7.60-7.53 (m, 1H), 7.31 (d, J=3.2 Hz, 1H), 6.87-6.51 (m, 1H), 5.43-5.25 (m, 2H), 4.91-4.67 (m, 2H), 4.56-4.22 (m, 2H), 4.18-4.04 (m, 1H), 3.97-3.72 (m, 1H), 3.69-3.46 (m, 6H), 3.19-3.00 (m, 4H), 2.51-1.75 (m, 13H), 1.58 (t, J=12.4 Hz, 1H), 1.39-1.28 (m, 3H), 0.82 (td, J=7.2, 12.0 Hz, 3H); LC-MS (ESI) m/z 663.2 $(M+H)^+$. 14a: $^1$H NMR (400 MHz, $CDCl_3$) δ 11.00-10.55 (m, 1H), 9.16 (d, J=16.0 Hz, 1H), 7.71 (dd, J=6.0, 8.4 Hz, 1H), 7.56 (d, J=2.4 Hz, 1H), 7.36-7.28 (m, 1H), 7.16 (s, 1H), 6.32 (d, J=5.6 Hz, 1H), 5.40-5.25 (m, 2H), 4.86-4.65 (m, 2H), 4.20 (d, J=0.8 Hz, 1H), 4.13-4.01 (m, 1H), 3.89-3.71 (m, 2H), 3.60-3.42 (m, 5H), 3.35 (s, 1H), 3.01 (s, 2H), 2.41-1.92 (m, 11H), 1.87-1.61 (m, 4H), 1.32 (d, J=1.6 Hz, 3H), 0.93-0.80 (m, 3H); LC-MS (ESI) m/z 663.4 $(M+H)^+$.

Step 11-((35,7aS)-7a-(((7-(8-Ethyl-7-fluoro-3-(methoxymethoxy) naphthalen-1-yl)-8-fluoro-4-((R)-3-hydroxy-3-methylpiperidin-1-yl)-1,6-naphthyridin-2-yl)oxy) methyl)hexahydro-1H-pyrrolizin-3-yl)methyl (4-nitrophenyl) carbonate. To a solution of (R)-1-(7-(8-ethyl-7-fluoro-3-(methoxymethoxy) naphthalen-1-yl)-8-fluoro-2-(((3S,7aS)-3-(hydroxymethyl)hexahydro-1H-pyrrolizin-7a-yl) methoxy)-1,6-naphthyridin-4-yl)-3-methylpiperidin-3-ol (60.0 mg, 90.5 μmol) and $Na_2CO_3$ (23.9 mg, 226 μmol) in THF (0.6 mL) was added a solution of bis(4-nitrophenyl) carbonate (35.8 mg, 117 μmol) in THF (0.2 mL). The mixture was stirred at 25° C. for 12 hrs. On completion, the reaction mixture was filtered, IPA (0.6 mL) and TEA (63.0 μL) were added to the filtrate, and then stirred at 25° C. for 0.5 hr to give the title compound (74.0 mg, 98% yield) as yellow liquid. LC-MS (ESI) m/z 828.2 $(M+H)^+$.

Step 12-((35,7aS)-7a-(((7-(8-Ethyl-7-fluoro-3-(methoxymethoxy) naphthalen-1-yl)-8-fluoro-4-((R)-3-hydroxy-3-methylpiperidin-1-yl)-1,6-naphthyridin-2-yl)oxy) methyl)hexahydro-1H-pyrrolizin-3-yl)methyl2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5] nonane-7-carboxylate. To a solution of 3-(5-(1-(7-azaspiro[3.5]nonan-2-yl) piperidin-4-yl)-3-methyl-2-oxo-2,3-dihydro-1H-benzo[d]imidazol-1-yl) piperidine-2,6-dione (51.8 mg, 89.3 μmol, TFA salt) in DMA (0.60 mL) was added TEA (27.1 mg, 268 μmol, 37.3 μL) and ((3S,7aS)-7a-(((7-(8-ethyl-7-fluoro-3-(methoxymethoxy) naphthalen-1-yl)-8-fluoro-4-((R)-3-hydroxy-3-methylpiperidin-1-yl)-1,6-naphthyridin-2-yl)oxy)methyl)hexahydro-1H-pyrrolizin-3-yl)methyl (4-nitrophenyl) carbonate (74.0 mg, 89.3 μmol). The mixture was stirred at 25° C. for 12 hrs. On completion, the reaction mixture was poured into ice water (10 mL), and then diluted with brine (10 mL) and extracted with EA (3×10 mL). The combined organic layers were washed with $K_2CO_3$ (3×10 mL) and brine (3×10 mL), dried over anhydrous $Na_2SO_4$, filtered and the filtrate was concentrated in vacuo to give a residue. The residue was purified by reverse phase (0.1% TFA condition) to give the title compound (80.0 mg, 77% yield) as yellow solid. LC-MS (ESI) m/z 1154.4 $(M+H)^+$.

Step 13-((3S,7aS)-7a-(((7-(8-Ethyl-7-fluoro-3-hydroxynaphthalen-1-yl)-8-fluoro-4-((R)-3-hydroxy-3-methylpiperidin-1-yl)-1,6-naphthyridin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5] nonane-7-carboxylate (Compound 406). A solution of ((3S,7aS)-7a-(((7-(8-ethyl-7-fluoro-3-(methoxymethoxy) naphthalen-1-yl)-8-fluoro-4-((R)-3-hydroxy-3-methylpiperidin-1-yl)-1,6-naphthyridin-2-yl)oxy)methyl)hexahydro-1H-pyrrolizin-3-yl)methyl2-(4-(1-(2,6-dioxopiperidin-3-yl)-3-methyl-2-oxo-2,3-dihydro-1H-benzo[d]imidazol-5-yl) piperidin-1-yl)-7-azaspiro[3.5]nonane-7-carboxylate (75.0 mg, 64.9 μmol) in HCOOH (2 mL) was stirred at 25° C. for 0.5 hr. On completion, the reaction mixture was concentrated in vacuo give a residue. The residue was purified by prep-HPLC (column: CD04-Welch Utimate C18 150*25*7 μm; mobile phase: [water (FA)-ACN]; gradient: 10%-40% B over 8 min) to give the title compound (29.9 mg, 39% yield, FA salt) as white solid. 1H NMR (400 MHz, DMSO-$d_6$) δ 11.07 (s, 1H), 10.02-9.80 (m, 1H), 9.22 (d, J=13.6 Hz, 1H), 7.76 (dd, J=6.0, 8.8 Hz, 1H), 7.39-7.29 (m, 2H), 7.10 (s, 1H), 7.05-6.95 (m, 2H), 6.90 (d, J=8.0 Hz, 1H), 6.49 (d, J=1.6 Hz, 1H), 5.33 (dd, J=5.6, 12.4 Hz, 1H), 4.83-4.66 (m, 1H), 4.24-4.10 (m, 4H), 3.32 (s, 3H), 3.23 (d, J=1.2 Hz, 3H), 3.15-2.97 (m, 3H), 2.88 (d, J=9.6 Hz, 3H), 2.80-2.61 (m, 6H), 2.34-2.31 (m, 1H), 2.15-1.88 (m, 7H), 1.81-1.45 (m, 22H), 1.38 (s, 2H), 1.23 (s, 3H), 0.73-0.66 (m, 3H); LC-MS (ESI) m/z 1110.3 $(M+H)^+$.

Example 64. Synthesis of Compound 441

Step 1-(R)-1-(7-(8-Ethyl-7-fluoro-3-((triisopropylsilyl) oxy) naphthalen-1-yl)-8-fluoro-2-(((3S,7aS)-3-((((4-(hydroxymethyl)cyclohexyl)methyl)amino)methyl)hexahydro-1H-pyrrolizin-7a-yl) methoxy)pyrido[4,3-d]pyrimidin-4-yl)-3-methylpiperidin-3-ol. A solution of ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl)methyl 4-methylbenzenesulfonate (200 mg, 215 μmol) and [4-(aminomethyl)cyclohexyl]methanol (615 mg, 4.30 mmol) in ACN (20 mL) was added into KI (3.5 mg, 21.5 μmol), the mixture was stirred at 85° C. for 2 hrs. On completion, the mixture was concentrated in vacuo, then dissolved with EA (10 mL), diluted with $H_2O$ (20 mL), extracted with EA (3×20 mL), the organic layer was washed with brine (20 mL), dried with anhydrous $Na_2SO_4$, filtered and the filtrate was concentrated in vacuo. The residue was purified by column chromatography ($SiO_2$, DCM: MeOH=87:13, 0.1% $NH_3 \cdot H_2O$) to give the title compound (85 mg, 43% yield) as yellow oil. LC-MS (ESI) m/z 901.3 $(M+H)^+$.

Step 2-Tert-butyl(((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)((4-(hydroxymethyl)cyclohexyl)methyl) carbamate. To a solution of (R)-1-(7-(8-ethyl-7-fluoro-3-((triisopropylsilyl) oxy) naphthalen-1-yl)-8-fluoro-2-(((3S,7aS)-3-((((4-(hydroxymethyl)cyclohexyl)methyl)amino)methyl)hexahydro-1H-pyrrolizin-7a-yl) methoxy)pyrido[4,3-d]pyrimidin-4-yl)-3-methylpiperidin-3-ol (85.0 mg, 58.4 μmol) in DCM (4 mL) was added TEA (11.8 mg, 116 μmol) and $Boc_2O$ (14.0 mg, 64.3 μmol). The mixture was stirred at 25° C. for 16 hrs. On completion, the mixture was diluted with $H_2O$ (20 mL), extracted with DCM (3×20 mL), the organic layer was washed with brine (5×10 mL), dried with anhydrous $Na_2SO_4$, filtered and the filtrate was concentrated in vacuo. The crude product was purified by reversed-phase (neutral condition) to give the title compound (30 mg, 51% yield) as yellow solid. LC-MS (ESI) m/z 1001.4 $(M+H)^+$.

Step 3-Tert-butyl(((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)((4-formylcyclohexyl)methyl) carbamate To a solution of tert-butyl(((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)((4-(hydroxymethyl)cyclohexyl)methyl) carbamate (20.0 mg, 19.9 μmol) in DCM (1 mL) was added DMP (12.7 mg, 29.9 μmol). The mixture was stirred at 25° C. for 8 hrs. On completion, the mixture was quenched with $Na_2$S2O3 solution (10 mL), diluted with $H_2O$ (10 mL), extracted with DCM (3×10 mL), the organic layer was washed with $NaHCO_3$ solution (5×10 mL), brine (10 mL), dried with anhydrous $Na_2SO_4$, filtered and filtrate was concentrated in vacuo to give the title compound (18.0 mg, 90% yield) as yellow solid. LC-MS (ESI) m/z 999.4 $(M+H)^+$.

Step 4-Tert-butyl(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl)((4-formylcyclohexyl)methyl) carbamate. To a solution of tert-butyl(((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)((4-formylcyclohexyl)methyl) carbamate (18.0 mg, 18.0 μmol) in DMSO (0.5 mL) was added CsF (8.21 mg, 54.0 μmol). The mixture was stirred at 25° C. for 1 hr. On completion, the mixture was diluted with $H_2O$ (10 mL), extracted with EA (3×10 mL), the organic layer was washed with brine (10 mL), dried with anhydrous $Na_2SO_4$, filtered and the filtrate was concentrated in vacuo to give the title compound (15.0 mg, 98% yield) as yellow solid. LC-MS (ESI) m/z 843.3 $(M+H)^+$.

Step 5-Tert-butyl((4-((4-(1-(2,6-dioxopiperidin-3-yl)-3-methyl-2-oxo-2,3-dihydro-1H-benzo[d]imidazol-5-yl) piperidin-1-yl)methyl)cyclohexyl)methyl)(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d] pyrimidin-2-yl)oxy)methyl)hexahydro-1H-pyrrolizin-3-yl) methyl) carbamate. To a solution of tert-butyl(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d] pyrimidin-2-yl)oxy)methyl)hexahydro-1H-pyrrolizin-3-yl) methyl)((4-formylcyclohexyl)methyl) carbamate (15.0 mg, 17.7 μmol) and 3-[3-methyl-2-oxo-5-(4-piperidyl)benzimidazol-1-yl]piperidine-2,6-dione (16.2 mg, 35.5 μmol, TFA) in THF (0.5 mL) was added TEA (3.60 mg, 35.5 μmol), the mixture was stirred at 25° C. for 5 mins, AcOH (1.60 mg, 26.6 μmol) as added into above solution, the mixture was stirred at 25° C. for 25 mins, then $NaBH(OAc)_3$ (5.66 mg, 26.6 μmol) was added into above solution, the mixture was stirred at 25° C. for 2 hrs. On completion, the mixture was quenched with $H_2O$ (5 mL), then diluted with EA (5 mL), adjusted pH=8-9 with TEA, extracted with EA (3×5 mL), the organic layer was washed with brine (2×10 mL), dried with anhydrous $Na_2SO_4$, filtered and the filtrate was concentrated in vacuo to give the title compound (15 mg, 72% yield) as yellow solid. LC-MS (ESI) m/z 1169.4 $(M+H)^+$.

Step 6-3-(5-(1-((4-(((((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl)amino) methyl)cyclohexyl)methyl) piperidin-4-yl)-3-methyl-2-oxo-2,3-dihydro-1H-benzo[d]imidazol-1-yl) piperidine-2,6-dione (Compound 441). To a solution of tert-butyl((4-((4-(1-(2,6-dioxopiperidin-3-yl)-3-methyl-2-oxo-2,3-dihydro-1H-benzo[d]imidazol-5-yl) piperidin-1-yl)methyl) cyclohexyl)methyl)(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl) carbamate (15.0 mg, 12.8 μmol) in DCM (1 mL) was added TFA (76.7 mg, 673 μmol, 50 μL). The mixture was stirred at 25° C. for 1 hr. On completion, the mixture was concentrated in vacuo. The residue was purified by prep-HPLC (column: CD18-Welch Utimate C18 150*40*7 μm; mobile phase: [water (FA)-ACN]; B %: %, isocratic elution mode) to give the title compound (9.30 mg, 64% yield, FA) as white solid. $^1H$ NMR (400 MHz, DMSO-$d_6$) δ 11.06 (s, 1H), 9.23 (s, 1H), 7.76 (dd, J=6.0, 8.8 Hz, 1H), 7.38-7.28 (m, 2H), 7.09 (s, 1H), 7.03 (d, J=2.4 Hz, 1H), 6.99 (d, J=8.0 Hz, 1H), 6.90 (d, J=8.0 Hz, 1H), 5.33 (dd, J=5.6, 12.8 Hz, 1H), 4.96-4.50 (m, 1H), 4.42-4.27 (m, 2H), 4.19 (t, J=11.6 Hz, 1H), 4.15-4.09 (m, 1H), 4.08-4.00 (m, 1H), 3.66-3.60 (m, 2H), 3.55-3.51 (m, 2H), 3.38 (d, J=10.4 Hz, 2H), 3.33 (s, 3H), 3.23-3.16 (m, 2H), 2.96-2.84 (m, 6H), 2.79-2.69 (m, 2H), 2.68-2.62 (m, 2H), 2.60-2.54 (m, 2H), 2.21-2.14 (m, 1H), 2.12-2.07 (m, 2H), 2.01-1.93 (m, 3H), 1.85-1.62 (m, 17H), 1.50-1.41 (m, 2H), 1.17 (d, J=9.2 Hz, 3H), 0.91-0.79 (m, 3H), 0.73 (q, J=6.8 Hz, 3H); LC-MS (ESI) m/z 1069.4 $(M+H)^+$.

Example 65. Synthesis of Compound 444

Step 1-((3S,7aR)-3-(((Tert-butyldimethylsilyl)oxy) methyl)hexahydro-1H-pyrrolizin-7a-yl) methanol. To a solution of methyl (3R,8S)-3-[[tert-butyl(dimethyl)silyl] oxymethyl]-1,2,3,5,6,7-hexahydropyrrolizine-8-carboxylate (39 g, 12.4 mmol) in THF (180 mL) was added LAH (2.5 M, 18.6 mL). The mixture was stirred at 0° C. for 1 hr with fluid. On completion, the reaction mixture was quenched by (2.8 mL) $H_2O$, (2.8 mL) 15% NaOH, (8.4 mL) $H_2O$. The whole process under $N_2$ atmosphere. The mixture was concentrated to give the title compound (34 g, 87% yield) as a yellow oil. LC-MS (ESI) m z 286.2 $(M+H)^+$.

Step 2-(3S,7aR)-3-(((Tert-butyldimethylsilyl)oxy) methyl)-7a-(((tert-butyldiphenylsilyl)oxy)methyl)hexahydro-1H-pyrrolizine. To a solution of ((3S,7aR)-3-(((tert-butyldimethylsilyl)oxy)methyl)hexahydro-1H-pyrrolizin-7a-yl) methanol (34.0 g, 119 mmol) in DCM (400 mL) was added TBDPSCl (42.5 g, 154 mmol) and imidazole (16.2 g, 238 mmol) at 0° C. The mixture was stirred at 25° C. for 2 hrs. On completion, the mixture was diluted with DCM (300 mL) and extracted with $H_2O$ (3×100 mL), the combined organic phase was dried over anhydrous sodium sulfate, filtered and the filtrate was concentrated to give a residue. The residue was purified by column chromatography ($SiO_2$, Petroleum ether/Ethyl acetate=20/1 to 5/1) to give the title compound (60.0 g, 76% yield) as a yellow oil. LC-MS (ESI) m/z 524.3 $(M+H)^+$.

Step 3-((3S,7aR)-7a-(((Tert-butyldiphenylsilyl)oxy) methyl)hexahydro-1H-pyrrolizin-3-yl) methanol. The (3S, 7aR)-3-(((tert-butyldimethylsilyl)oxy)methyl)-7a-(((tert-butyldiphenylsilyl)oxy)methyl)hexahydro-1H-pyrrolizine (45.0 g, 85.9 mmol) in HCl/dioxane (2 M, 450.00 mL) was stirred at 25° C. for 16 hrs. On completion, the reaction mixture was concentrated in vacuo to give a residue. The residue was purified by prep-HPLC (0.1% FA condition) to give the title compound (30.0 g, 85% yield) as a yellow oil. LC-MS (ESI) m/z 410.5 $(M+H)^+$.

Step 4-(35,7aR)-7a-(((Tert-butyldiphenylsilyl)oxy) methyl)hexahydro-1H-pyrrolizine-3-carbaldehyde. To a solution of $(COCl)_2$ (2.32 g, 18.3 mmol, 1.60 mL) in DCM (50 mL) was added DMSO (2.86 g, 36.6 mmol, 2.86 mL) at −78° C. and the mixture was stirred at −78° C. for 1 hr under nitrogen atmosphere. Then a solution of ((3S,7aR)-7a-(((tert-butyldiphenylsilyl)oxy)methyl)hexahydro-1H-pyrrolizin-3-yl) methanol (5.00 g, 12.2 mmol) in DCM (20 mL) was added to the mixture at −78° C. under nitrogen atmosphere and the mixture was stirred at −78° C. for 1 hr. TEA (7.41 g, 73.2 mmol) was added to the mixture at −78° C. and the mixture was stirred at −78° C. for 0.5 h under nitrogen atmosphere. Warmed to 25° C. and stirred for 1 hr. On completion, the reaction mixture was diluted with $H_2O$ (50 mL) and extracted with DCM (3×60 mL). The combined organic layers were washed with brine (2×50 mL), dried over anhydrous $Na_2SO_4$, filtered and the filtrate was concentrated in vacuo to give the title compound (5.30 g, crude) as a yellow oil. LC-MS (ESI) m/z 426.2 $(M+H_2O)^+$.

Step 5-3-(5-(3-((1-(((35,7aR)-7a-(((Tert-butyldiphenylsilyl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione. To a solution of 3-(3-methyl-2-oxo-5-(3-(piperidin-4-yloxy) propyl)-2,3-dihydro-1H-benzo[d]imidazol-1-yl) piperidine-2,6-dione (500 mg, 1.25 mmol) in THF (10 mL) was added TEA (379 mg, 3.75 mmol) adjust pH=10. HOAc (149 mg, 2.50 mmol) was added the mixture to adjust pH=6 and (3S,7aR)-7a-(((tert-butyldiphenylsilyl)oxy)methyl)hexahydro-1H-pyrrolizine-3-carbaldehyde (508 mg, 1.25 mmol) was added and stirred 0.5 hr. Then $NaBH_3CN$ (156 mg, 2.50 mmol) was added to the mixture and stirred at 25° C. for 0.5 hr. On completion, the reaction mixture was concentrated in vacuo to give a residue. The residue was purified by prep-HPLC (0.1% TFA condition) to give the title compound (302 mg, 29% yield) as a white solid. $^1H$ NMR (400 MHz, DMSO-$d_6$) δ 11.08 (s, 1H), 7.65-7.60 (m, 4H), 7.54-7.43 (m, 6H), 7.06-6.96 (m, 2H), 6.87 (d, J=7.2 Hz, 1H), 5.34 (dd, J=5.2, 12.8 Hz, 1H), 3.73 (s, 2H), 3.43 (t, J=6.0 Hz, 2H), 3.32 (s, 3H), 2.98-2.82 (m, 2H), 2.76-2.60 (m, 4H), 2.50 (s, 9H), 2.32 (d, J=1.6 Hz, 1H), 2.21-1.74 (m, 14H), 1.05 (s, 9H); LC-MS (ESI) m/z 792.5 $(M+H)^+$.

Step 6-3-(5-(3-((1-(((35,7aR)-7a-(((Tert-butyldiphenylsilyl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione. To a solution of 3-(5-(3-((1-(((3S,7aR)-7a-(((tert-butyldiphenylsilyl)oxy) methyl)hexahydro-1H-pyrrolizin-3-yl)methyl) piperidin-4-yl)oxy) propyl)-3-methyl-2-oxo-2,3-dihydro-1H-benzo[d] imidazol-1-yl) piperidine-2,6-dione (300 mg, 378 μmol) in DMSO (2 mL) was added CsF (172 mg, 1.14 mmol). The mixture was stirred at 25° C. for 1 hr. On completion, the reaction mixture was added ACN (1 mL). The residue was purified by prep-HPLC (0.1% TFA condition) to give the title compound (200 mg, 94% yield) as a white solid. LC-MS (ESI) m/z 554.4 $(M+H)^+$.

Step 7-(R)-1-(7-Chloro-8-fluoro-2-(methylthio)pyrido[4,3-d]pyrimidin-4-yl)-3-methylpiperidin-3-ol. To a solution of 7-chloro-8-fluoro-2-(methylthio)pyrido[4,3-d]pyrimidin-4-ol (972 mg, 3.96 mmol) and (R)-3-methylpiperidin-3-ol (1.20 g, 7.91 mmol, HCl salt) in DMF (20 mL) was added DIEA (1.53 g, 11.8 mmol) adjust pH=10. Then PYBOP (6.18 g, 11.8 mmol) was added to the mixture and stirred at 25° C. for 16 hrs. On completion, the reaction mixture was diluted with $H_2O$ (50 mL) and extracted with EA (3×50 mL). The combined organic layers were washed with brine (2×100 mL), dried over anhydrous $Na_2SO_4$, filtered and the filtrate was concentrated in vacuo to give the mixture. The residue was purified by column chromatography ($SiO_2$, PE/EA=4/1 to 3/1) to give the title compound (877 mg, 63% yield) as a yellow solid. LC-MS (ESI) m/z 342.9 $(M+H)^+$.

Step 8-(R)-1-(7-(8-Ethyl-7-fluoro-3-(methoxymethoxy) naphthalen-1-yl)-8-fluoro-2-(methylthio)pyrido[4,3-d]pyrimidin-4-yl)-3-methylpiperidin-3-ol. A mixture of (R)-1-(7-chloro-8-fluoro-2-(methylthio)pyrido[4,3-d]pyrimidin-4-yl)-3-methylpiperidin-3-ol (870 mg, 2.54 mmol), 2-(8-ethyl-7-fluoro-3-(methoxymethoxy) naphthalen-1-yl)-4,4,5,5-tetramethyl-1,3,2-dioxaborolane (1.37 g, 3.81 mmol), AdanBuP-Pd-G3 (184 mg, 253 μmol), $K_3PO_4$ (1.62 g, 7.61 mmol) in dioxane (12 mL) and $H_2O$ (2 mL) was degassed and purged with $N_2$ for 3 times, and then the mixture was stirred at 100° C. for 30 min under $N_2$ atmosphere. On completion, the reaction mixture was diluted with $H_2O$ (50 mL) and extracted with EA (2×50 mL). The combined organic layers were washed with brine (2×50 mL), dried over anhydrous $Na_2SO_4$, filtered and the filtrate was concentrated in vacuo to give the mixture. The residue was purified by column chromatography ($SiO_2$, PE/EA=1/1 to 1/1) to give the title compound (1.30 g, 89% yield) as a yellow solid. $^1H$ NMR (400 MHz, $CDCl_3$) δ 9.09 (d, J=2.0 Hz, 1H), 7.61 (dd, J=6.0, 8.8 Hz, 1H), 7.44 (d, J=2.4 Hz, 1H), 7.25-7.09 (m, 2H), 5.28-5.17 (m, 2H), 4.43-4.23 (m, 2H), 3.44 (s, 3H), 3.41-3.30 (m, 1H), 3.23 (dd, J=13.6, 18.0 Hz, 1H), 2.85 (d, J=13.2 Hz, 1H), 2.57 (d, J=1.2 Hz, 3H), 2.50-2.35 (m, 1H), 2.19-2.11 (m, 1H), 2.05-1.92 (m, 1H), 1.76 (d, J=12.8 Hz, 1H), 1.69-1.58 (m, 2H), 1.25 (s, 3H), 0.77 (q, J=7.2 Hz, 3H); LC-MS (ESI) m/z 541.1 $(M+H)^+$.

Step 9-(R)-1-(7-(8-Ethyl-7-fluoro-3-(methoxymethoxy) naphthalen-1-yl)-8-fluoro-2-(methylsulfonyl)pyrido[4,3-d] pyrimidin-4-yl)-3-methylpiperidin-3-ol. To a solution of (R)-1-(7-(8-ethyl-7-fluoro-3-(methoxymethoxy) naphthalen-1-yl)-8-fluoro-2-(methylthio)pyrido[4,3-d]pyrimidin-4-yl)-3-methylpiperidin-3-ol (1.00 g, 1.85 mmol) in DCM (12 mL) was added m-CPBA (1.13 g, 5.55 mmol, 85% purity) at 0° C. The mixture was stirred at 25° C. for 2 hrs. On completion, the reaction mixture was quenched by addition $Na_2SO_3$ (100 mL) at 0° C., extracted with DCM (2×50 mL). The combined organic layers were washed with brine (2×50 mL), dried over anhydrous $Na_2SO_4$, filtered and the filtrate was concentrated in vacuo to give the title compound (500 mg, 46% yield) as a yellow solid. LC-MS (ESI) m/z 573.0 $(M+H)^+$.

Step 10-3-(5-(3-((1-(((3S,7aR)-7a-(((7-(8-Ethyl-7-fluoro-3-(methoxymethoxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione. A mixture of 3-(5-(3-((1-(((3S,7aR)-7a-(hydroxymethyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione (150 mg, 270 μmol) in THF (2 mL) was added NaH (21.6 mg, 541 μmol, 60% purity) at 0° C. for 0.5 hr. Then (R)-1-(7-(8-ethyl-7-fluoro-3-(methoxymethoxy) naphthalen-1-yl)-8-fluoro-2-(methylsulfonyl)pyrido[4,3-d] pyrimidin-4-yl)-3-methylpiperidin-3-ol (155 mg, 270 μmol) was added to the mixture and stirred at 25° C. for 1 hr under $N_2$ atmosphere. On completion, the reaction mixture was quenched by addition HCl/EA (1 mL) at 0° C. The mixture was filtered and the filter cake was concentrated in vacuo to give the title compound (155 mg, crude) as yellow solid. LC-MS (ESI) m/z 1046.4 $(M+H)^+$.

Step 11-3-(5-(3-((1-(((3S,7aR)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl) piperidin-4-yl)oxy) propyl)-3-methyl-2-oxo-2,3-dihydro-1H-benzo[d] imidazol-1-yl) piperidine-2,6-dione (Compound 444). To a solution of 3-(5-(3-((1-(((3S,7aR)-7a-(((7-(8-ethyl-7-fluoro-3-(methoxymethoxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl) piperidin-4-yl)oxy) propyl)-3-methyl-2-oxo-2,3-dihydro-1H-benzo[d]imidazol-1-yl) piperidine-2,6-dione (150 mg, 143 μmol) in DCM (2 mL) was added HCl/dioxane (2 M, 1 mL). The mixture was stirred at 25° C. for 1 hr. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 12%-42% B over 2 min) to give the title compound (23.3 mg, 14% yield, FA salt) as white solid. $^1H$ NMR (400 MHz, DMSO-$d_6$) δ 11.08 (s, 1H), 9.22 (d, J=2.8 Hz, 1H), 7.76 (dd, J=6.0, 9.2 Hz, 1H), 7.39-7.29 (m, 2H), 7.05-6.95 (m, 3H), 6.85 (d, J=8.0 Hz, 1H), 5.33 (dd, J=5.2, 12.8 Hz, 1H), 4.92-4.55 (m, 1H), 4.39-4.28 (m, 1H), 4.10 (d, J=8.0 Hz, 1H), 4.07-3.99 (m, 2H), 3.61 (s, 1H), 3.51 (s, 1H), 3.38 (d, J=6.4 Hz, 2H), 3.31 (s, 3H), 3.22 (d, J=9.2 Hz, 2H), 2.95-2.84 (m, 3H), 2.79-2.56 (m, 8H), 2.37-2.28 (m, 2H), 2.26-2.20 (m, 1H), 2.13-2.06 (m, 2H), 2.03-1.92 (m, 4H), 1.83-1.74 (m, 7H), 1.73-1.53 (m, 6H), 1.41 (d, J=9.2 Hz, 2H), 1.16 (d, J=9.2 Hz, 3H), 0.73 (q, J=7.2 Hz, 3H); LC-MS (ESI) m/z 1002.3 $(M+H)^+$.

Example 66. Synthesis of Compound 453

Step 1-Tert-butyl 7-prop-2-ynyl-2,7-diazaspiro[3.5] nonane-2-carboxylate. To a solution of tert-butyl 2,7-diazaspiro[3.5]nonane-2-carboxylate (1.00 g, 4.42 mmol) in THF (25 mL) was added $K_2CO_3$ (1.22 g, 8.84 mmol) and 3-bromoprop-1-yne (985 mg, 6.63 mmol). The mixture was stirred at 25° C. for 1 hr. On completion, the reaction mixture was diluted with water (30 mL) and extracted with EA (2×25 mL). The combined organic layers were washed with brine (2×50 mL). The combined organic layers was dried over anhydrous $Na_2SO_4$, filtered and the filtrate was concentrated in vacuo to give the title compound (800 mg, 68% yield) as white solid. LC-MS (ESI) m/z 265.2 $(M+H)^+$.

Step 2-Tert-butyl 7-[3-[1-(2,6-dioxo-3-piperidyl)-3-methyl-2-oxo-benzimidazol-5-yl]prop-2-ynyl]-2,7-diazaspiro[3.5]nonane-2-carboxylate. A mixture of tert-butyl 7-prop-2-ynyl-2,7-diazaspiro[3.5]nonane-2-carboxylate (600 mg, 2.27 mmol), 3-(5-bromo-3-methyl-2-oxo-benzimidazol-1-yl) piperidine-2,6-dione (767 mg, 2.27 mmol), $Pd(PPh_3)_2Cl_2$ (159 mg, 226 μmol), CuI (43.2 mg, 226 μmol) and $Cs_2CO_3$ (2.22 g, 6.81 mmol) in DMF (5 mL) was degassed and purged with $N_2$ for 3 times, and then the mixture was stirred at 80° C. for 2 hrs under $N_2$ atmosphere. On completion, the reaction mixture was diluted with water (50 mL) and extracted with EA (2×50 mL). The combined organic layers were washed with brine (2×50 mL). The combined organic layers was dried over anhydrous $Na_2SO_4$, filtered and the filtrate was concentrated in vacuo to give a residue. The residue was purified by reversed-phase HPLC (0.1% TFA condition) to give the title compound (370 mg, 31% yield) as white solid. LC-MS (ESI) m/z 522.2 $(M+H)^+$.

Step 3-3-[5-[3-(2,7-Diazaspiro[3.5]nonan-7-yl) prop-1-ynyl]-3-methyl-2-oxo-benzimidazol-1-yl]piperidine-2,6-dione. To a solution of tert-butyl 7-[3-[1-(2,6-dioxo-3-piperidyl)-3-methyl-2-oxo-benzimidazol-5-yl]prop-2-ynyl]-2,7-diazaspiro[3.5]nonane-2-carboxylate (200 mg, 383 μmol) in DCM (3 mL) was added TFA (1.54 g, 13.4 mmol). The mixture was stirred at 25° C. for 1 hr. On completion, the reaction mixture was concentrated in vacuo to give the title compound (161 mg, 99% yield TFA salt) as white oil. LC-MS (ESI) m/z 422.2 $(M+H)^+$.

Step 4-((3S,7aS)-7a-(((7-(8-Ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl 7-(3-(1-(2,6-dioxopiperidin-3-yl)-3-methyl-2-oxo-2,3-dihydro-1H-benzo[d]imidazole-5-yl) prop-2-yn-1-yl)-2,7-diazaspiro[3.5]nonane-2-carboxylate. To a solution of 3-[5-[3-(2,7-diazaspiro[3.5]nonan-7-yl) prop-1-ynyl]-3-methyl-2-oxo-benzimidazol-1-yl]piperidine-2,6-dione (125 mg, 297 μmol, TFA salt) in THF (5 mL) was added TEA (15.0 mg, 148 μmol) and ((3S,7aS)-7a-(((7-(8-ethyl-7-fluoro-3-((triisopropylsilyl)oxy) naphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl (4-nitrophenyl) carbonate (140 mg, 148 μmol). The mixture was stirred at 25° C. for 1 hr. On completion, the reaction mixture was filtered and the filtrate was concentrated in vacuo to give a residue. The residue was purified by reversed-phase HPLC (0.1% TFA condition) to give the title compound (110 mg, 65% yield) as white solid. LC-MS (ESI) m/z 1223.4 $(M+H)^+$.

Step 5-((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 7-(3-(1-(2,6-dioxopiperidin-3-yl)-3-methyl-2-oxo-2,3-dihydro-1H-benzo[d]imidazol-5-yl) prop-2-yn-1-yl)-2,7-diazaspiro[3.5] nonane-2-carboxylate (Compound 453). To a solution of ((3S,7aS)-7a-(((7-(8-ethyl-7-fluoro-3-((triisopropylsilyl) oxy) naphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl)methyl 7-(3-(1-(2,6-dioxopiperidin-3-yl)-3-methyl-2-oxo-2,3-dihydro-1H-benzo[d]imidazol-5-yl) prop-2-yn-1-yl)-2,7-diazaspiro[3.5] nonane-2-carboxylate (100 mg, 81.7 μmol) in DMSO (1 mL) was added CsF (37.2 mg, 245 μmol). The mixture was stirred at 25° C. for 1 hr. On completion, the reaction mixture was filtered and the filtrate was concentrated in vacuo to give a residue. The residue was purified by prep-HPLC (column: Phenomenex luna C18 150*25 mm*10 μm; mobile phase: [water (FA)-ACN]; gradient: 7%-37% B over 10 min) to give the title compound (10.7 mg, 11% yield, FA salt) as white solid. $^1$H NMR (400 MHz, DMSO-$d_6$) δ 11.11 (s, 1H), 9.94 (d, J=2.0 Hz, 1H), 9.24 (d, J=3.6 Hz, 1H), 7.76 (dd, J=6.0, 9.2 Hz, 1H), 7.39-7.31 (m, 2H), 7.27 (s, 1H), 7.15-7.08 (m, 2H), 7.03 (d, J=2.4 Hz, 1H), 5.38 (dd, J=5.2, 12.8 Hz, 1H), 4.74 (d, J=10.0 Hz, 1H), 4.43-4.26 (m, 2H), 4.25-4.13 (m, 3H), 4.06 (dd, J=13.2, 19.6 Hz, 1H), 3.68-3.50 (m, 6H), 3.43 (s, 3H), 3.05-2.80 (m, 3H), 2.79-2.52 (m, 4H), 2.43 (s, 3H), 2.37-2.28 (m, 2H), 2.20-2.07 (m, 2H), 2.06-1.96 (m, 2H), 1.93-1.76 (m, 6H), 1.76-1.61 (m, 9H), 1.17 (d, J=9.2 Hz, 3H), 0.73 (q, J=7.2 Hz, 3H); LC-MS (ESI) m/z 1067.2 $(M+H)^+$.

Example 67. Synthesis of Compound 471

Step 1-3-(5-(1-(7-(((3S,7aS)-7a-(((Tert-butyldiphenylsilyl)oxy)methyl)hexahydro-1H-pyrrolizin-3-yl)methyl)-7-azaspiro[3.5]nonan-2-yl) piperidin-4-yl)-3-methyl-2-oxo-2,3-dihydro-1H-benzo[d]imidazol-1-yl) piperidine-2,6-dione. To a mixture of 3-(5-(1-(7-azaspiro[3.5]nonan-2-yl) piperidin-4-yl)-3-methyl-2-oxo-2,3-dihydro-1H-benzo[d]imidazol-1-yl) piperidine-2,6-dione (350 mg, 751 μmol) and (3S,7aS)-7a-(((tert-butyldiphenylsilyl)oxy)methyl)hexahydro-1H-pyrrolizine-3-carbaldehyde (398 mg, 977 μmol) in THF (4 mL) and MeOH (2 mL) was added HOAc (45.1 mg, 751 μmol, 43.0 μL). The reaction mixture was stirred at 0° C. for 0.5 hr. Then the pyridin-1-ium-1-ylboranuide (139 mg, 1.50 mmol, 150 μL) was added to the mixture. The reaction mixture was stirred at 25° C. for 11.5 hrs. On completion, the reaction mixture was concentrated in vacuo. The residue was purified by reverse phase (0.1% FA condition) to give the title compound (300 mg, 46% yield) as yellow solid. $^1$H NMR (400 MHz, DMSO-$d_6$) δ 11.10 (s, 1H), 7.70-7.61 (m, 4H), 7.55-7.42 (m, 6H), 7.11-7.03 (m, 2H), 6.92 (d, J=7.6 Hz, 1H), 5.36 (dd, J=5.2, 12.8 Hz, 1H), 3.81-3.71 (m, 4H), 3.62-3.55 (m, 1H), 3.49-3.42 (m, 3H), 3.39-3.31 (m, 5H), 3.20-3.11 (m, 1H), 2.98-2.82 (m, 5H), 2.77-2.64 (m, 2H), 2.38-2.20 (m, 3H), 2.15 (s, 2H), 2.08 (s, 6H), 2.05-1.98 (m, 4H), 1.94-1.79 (m, 8H), 1.05 (s, 9H).

Step 2-3-(5-(1-(7-(((3S,7aS)-7a-(Hydroxymethyl)hexahydro-1H-pyrrolizin-3-yl)methyl)-7-azaspiro[3.5]nonan-2-yl) piperidin-4-yl)-3-methyl-2-oxo-2,3-dihydro-1H-benzo [d]imidazol-1-yl) piperidine-2,6-dione. To a mixture of 3-(5-(1-(7-(((3S,7aS)-7a-(((tert-butyldiphenylsilyl)oxy)methyl) hexahydro-1H-pyrrolizin-3-yl)methyl)-7-azaspiro[3.5] nonan-2-yl) piperidin-4-yl)-3-methyl-2-oxo-2,3-dihydro-1H-benzo[d]imidazol-1-yl) piperidine-2,6-dione (300 mg, 349 μmol) in DMSO (2 mL) was added CsF (159 mg, 1.05 mmol). The reaction mixture was stirred at 25° C. for 3 hrs. On completion, the reaction mixture was filtered to give the filtrate. The residue was purified by reverse phase (0.1% FA condition) to give the title compound (123 mg, 56% yield) as white solid. $^1$H NMR (400 MHz, DMSO-$d_6$) δ 11.11 (s, 1H), 7.11-7.03 (m, 2H), 6.95-6.90 (m, 1H), 5.41-5.32 (m, 1H), 3.78-3.65 (m, 4H), 3.35 (s, 3H), 3.20-3.07 (m, 2H), 2.94-2.85 (m, 4H), 2.73-2.59 (m, 4H), 2.46-2.36 (m, 4H), 2.23-1.96 (m, 12H), 1.94-1.56 (m, 12H)

Step 3-3-(5-(1-(7-(((3S,7aS)-7a-(((7-(8-Ethyl-7-fluoro-3-(methoxymethoxy) naphthalen-1-yl)-8-fluoro-4-((R)-3-hydroxy-3-methylpiperidin-1-yl)pyrido[4,3-d]pyrimidin-2-yl) oxy)methyl)hexahydro-1H-pyrrolizin-3-yl)methyl)-7-azaspiro[3.5]nonan-2-yl) piperidin-4-yl)-3-methyl-2-oxo-2,3-dihydro-1H-benzo[d]imidazol-1-yl) piperidine-2,6-dione. To a mixture of 3-(5-(1-(7-(((3S,7aS)-7a-(hydroxymethyl) hexahydro-1H-pyrrolizin-3-yl)methyl)-7-azaspiro[3.5] nonan-2-yl) piperidin-4-yl)-3-methyl-2-oxo-2,3-dihydro-1H-benzo[d]imidazol-1-yl) piperidine-2,6-dione (100 mg, 161 μmol) in THF (2 mL) was added NaH (9.70 mg, 242 μmol, 60% purity) at 0° C. The reaction mixture was stirred at 0° C. for 0.5 hr. Then the (R)-1-(7-(8-ethyl-7-fluoro-3-(methoxymethoxy) naphthalen-1-yl)-8-fluoro-2-(methylsulfonyl)pyrido[4,3-d]pyrimidin-4-yl)-3-methylpiperidin-3-ol (101 mg, 177 μmol) was added to the mixture. The reaction mixture was stirred at 25° C. for 1 hr. On completion, the reaction mixture was quenched with HCl/dioxane (5 mL). The reaction mixture was filtered and concentrated in vacuo to give the title compound (150 mg, 83% yield) as yellow solid. LC-MS (ESI) m/z 1111.5 $(M+H)^+$.

Step 4-3-(5-(1-(7-(((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl)methyl)-7-azaspiro [3.5]nonan-2-yl) piperidin-4-yl)-3-methyl-2-oxo-2,3-dihydro-1H-benzo[d]imidazol-1-yl) piperidine-2,6-dione (Compound 471). A mixture of 3-(5-(1-(7-(((3S,7aS)-7a-(((7-(8-ethyl-7-fluoro-3-(methoxymethoxy) naphthalene-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl)methyl)-7-azaspiro[3.5]nonan-2-yl) piperidin-4-yl)-3-methyl-2-oxo-2,3-dihydro-1H-benzo[d] imidazol-1-yl) piperidine-2,6-dione (150 mg, 134 μmol) in HCl/dioxane (1.5 M, 4 mL) was stirred at 25° C. for 0.2 hr. On completion, the reaction mixture was concentrated in vacuo. The residue was purified by prep-HPLC (column: CD01-Phenomenex luna C18 150*25*10 μm; mobile phase: [water (FA)-ACN]; gradient: 5%-35% B over 8 min) to give the title compound (41.7 mg, 27% yield, FA) as white solid. $^1$H NMR (400 MHz, DMSO-$d_6$) δ 11.08 (s, 1H), 9.23 (d, J=2.8 Hz, 1H), 7.77 (dd, J=6.0, 9.2 Hz, 1H), 7.40-7.31 (m, 2H), 7.10 (s, 1H), 7.05-6.98 (m, 2H), 6.91 (d, J=8.0 Hz, 1H), 5.34 (dd, J=5.2, 12.8 Hz, 1H), 4.83-4.66 (m, 1H), 4.41-4.29 (m, 1H), 4.15-4.03 (m, 3H), 3.66 (s, 2H), 3.33 (s, 3H), 2.98-2.85 (m, 6H), 2.78-2.66 (m, 4H), 2.62 (d, J=17.6 Hz, 2H), 2.42-2.25 (m, 6H), 2.19-2.12 (m, 1H), 2.06-1.90 (m, 6H), 1.88-1.62 (m, 14H), 1.61-1.42 (m, 7H), 1.18 (d, J=9.4 Hz, 3H), 0.74 (q, J=7.2 Hz, 3H). LC-MS (ESI) m/z 1067.4 $(M+H)^+$.

Example 68. Synthesis of Compound 472

Step 1-(E)-Ethyl 3-((3S,7aS)-7a-(((tert-butyldiphenylsilyl)oxy)methyl)hexahydro-1H-pyrrolizin-3-yl) acrylate. To a mixture of ethyl 2-diethoxyphosphorylacetate (1.32 g, 5.89 mmol, 1.17 mL) in THF (20 mL) was added t-BuOK (550 mg, 4.91 mmol) at 0° C. The reaction mixture was stirred at 1 hr at 0° C. Then the (3S,7aS)-7a-(((tert-butyldiphenylsilyl) oxy)methyl)hexahydro-1H-pyrrolizine-3-carbaldehyde (2.00 g, 4.91 mmol) was added to the mixture. The reaction mixture was stirred at 25° C. for 1 hr. On completion, the residue was diluted with water (30 mL) and extracted with EA (2×30 mL). The combined organic layers was dried over $Na_2SO_4$, filtered and the filtrate was concentrated in vacuo to give a residue. The residue was purified by column chromatography ($SiO_2$, PE:EA=50:1 to 3:1) to give the title compound (1.30 g, 55% yield) as yellow oil. LC-MS (ESI) m/z 479.2 $(M+H)^+$.

Step 2-Ethyl 3-((3S,7aS)-7a-(((tert-butyldiphenylsilyl) oxy)methyl)hexahydro-1H-pyrrolizin-3-yl) propanoate. The Pd/C (650 mg, 610 μmol, 10% purity) was added to ethyl (E)-ethyl 3-((3S,7aS)-7a-(((tert-butyldiphenylsilyl)oxy) methyl)hexahydro-1H-pyrrolizin-3-yl) acrylate (1.30 g, 2.72 mmol) in THF (10 mL) under Ar. The reaction mixture was stirred at 25° C. for 1 hr under $H_2$ (15 Psi). On completion, the reaction mixture was filtered and concentrated in vacuo to give the title compound (1.20 g, 91% yield) as yellow oil. LC-MS (ESI) m/z 480.9 $(M+H)^+$.

Step 3-3-((3S,7aS)-7a-(((Tert-butyldiphenylsilyl)oxy) methyl)hexahydro-1H-pyrrolizin-3-yl) propan-1-ol. To a mixture of ethyl 3-((3S,7aS)-7a-(((tert-butyldiphenylsilyl) oxy)methyl)hexahydro-1H-pyrrolizin-3-yl) propanoate (1.10 g, 2.29 mmol) in THF (20 mL) was added $LiAlH_4$ (1.5 M, 2.29 mL) at 0° C. The reaction mixture was stirred at 0° C. for 1 hr. On completion, the reaction mixture was quenched with water (0.13 mL), 15% NaOH solution (0.42 mL), water (0.13 mL). The combined organic layers was dried over $Na_2SO_4$, filtered and the filtrate was concentrated in vacuo to give a residue. The residue was purified by reverse phase (0.1% FA condition) to give the title compound (533 mg, 53% yield) as yellow oil. $^1$H NMR (400 MHz, DMSO-$d_6$) δ 7.71-7.64 (m, 4H), 7.49-7.42 (m, 6H), 3.48 (s, 2H), 3.41 (d, J=5.2 Hz, 2H), 3.37 (s, 1H), 3.07-3.02 (m, 1H), 2.96-2.89 (m, 1H), 2.78-2.70 (m, 1H), 2.03 (dd, J=6.6, 12.0 Hz, 1H), 1.76-1.48 (m, 10H), 1.21 (d, J=3.2 Hz, 1H), 1.04-0.99 (m, 9H). LC-MS (ESI) m/z 438.5 $(M+H)^+$.

Step 4-3-((3S,7aS)-7a-(((Tert-butyldiphenylsilyl)oxy) methyl)hexahydro-1H-pyrrolizin-3-yl) propanal. To a mixture of $(COCl)_2$ (255 mg, 2.01 mmol, 176 μL) in DCM (6 mL) was added DMSO (214 mg, 2.74 mmol, 214 μL) in DCM (3 mL) at −75° C. dropwise. The reaction mixture was stirred at 0.4 hr. Then the 3-((3S,7aS)-7a-(((tert-butyldiphenylsilyl)oxy)methyl)hexahydro-1H-pyrrolizin-3-yl) propan-1-ol (400 mg, 913 μmol) in DCM (1 mL) was added to the mixture at −75° C. dropwise. The reaction mixture was stirred at −75° C. for 0.2 hr. Then the TEA (2.77 g, 27.4 mmol, 3.82 mL) was added to the mixture at −75° C. dropwise. Then mixture was stirred at −75° C. for 0.5 hr. On completion, the residue was diluted with $NaHCO_3$ (30 mL) and extracted with DCM (2×20 mL). The combined organic layers was dried over $Na_2SO_4$, filtered and the filtrate was concentrated in vacuo to give the title compound (398 mg, 99% yield) as yellow solid. LC-MS (ESI) m z 436.2 $(M+H)^+$.

Step 5-3-(5-(1-(7-(3-((3R,7aS)-7a-(((Tert-butyldiphenylsilyl)oxy)methyl)hexahydro-1H-pyrrolizin-3-yl) propyl)-7-azaspiro[3.5]nonan-2-yl) piperidin-4-yl)-3-methyl-2-oxo-2,3-dihydro-1H-benzo[d]imidazol-1-yl) piperidine-2,6-dione. To a mixture of 3-[5-[1-(7-azaspiro[3.5]nonan-2-yl)-4-piperidyl]-3-methyl-2-oxo-benzimidazol-1-yl]piperidine-2,6-dione (500 mg, 862 μmol, TFA) in THF (4 mL) and MeOH (2 mL) was added TEA (90.5 mg, 895 μmol, 124 μL), 3-((3S,7aS)-7a-(((tert-butyldiphenylsilyl)oxy)methyl)hexahydro-1H-pyrrolizin-3-yl) propanal (390 mg, 895 μmol) and HOAc (53.7 mg, 895 μmol, 51.2 μL). The reaction mixture was stirred at 25° C. for 0.5 hr. Then the pyridin-1-ium-1-ylboranuide (166 mg, 1.79 mmol, 179 μL) was added to the mixture. The reaction mixture was stirred at 25° C. for 11.5 hrs. On completion, the reaction mixture was concentrated in vacuo. The residue was purified by reverse phase (0.1% FA condition) compound (200 mg, 25% yield) as white solid. LC-MS (ESI) m/z 885.9 $(M+H)^+$.

Step 6-3-(5-(1-(7-(3-((3R,7aS)-7a-(Hydroxymethyl) hexahydro-1H-pyrrolizin-3-yl) propyl)-7-azaspiro[3.5] nonan-2-yl) piperidin-4-yl)-3-methyl-2-oxo-2,3-dihydro-1H-benzo[d]imidazol-1-yl) piperidine-2,6-dione. To a mixture of 3-(5-(1-(7-(3-((3R,7aS)-7a-(((tert-butyldiphenylsilyl)oxy)methyl)hexahydro-1H-pyrrolizin-3-yl) propyl)-7-azaspiro[3.5]nonan-2-yl) piperidin-4-yl)-3-methyl-2-oxo-2,3-dihydro-1H-benzo[d]imidazol-1-yl) piperidine-2,6-dione (170 mg, 192 μmol) in DMSO (2 mL) was added CsF (87.5 mg, 576 μmol). The reaction mixture was stirred at 25° C. for 1 hr. On completion, the reaction mixture was filtered to give the filtrate. The residue was purified by reverse phase (0.1% FA condition) to give the title compound (100 mg, 80% yield) as white solid. LC-MS (ESI) m z 647.5 $(M+H)^+$.

Step 7-3-(5-(1-(7-(3-((3R,7aS)-7a-(((7-(8-Ethyl-7-fluoro-3-(methoxymethoxy) naphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl) propyl)-7-azaspiro[3.5]nonan-2-yl) piperidin-4-yl)-3-methyl-2-oxo-2,3-dihydro-1H-benzo[d]imidazol-1-yl) piperidine-2,6-dione. To a mixture of 3-(5-(1-(7-(3-((3R,7aS)-7a-(hydroxymethyl)hexahydro-1H-pyrrolizin-3-yl) propyl)-7-azaspiro[3.5]nonan-2-yl) piperidin-4-yl)-3-methyl-2-oxo-2,3-dihydro-1H-benzo[d]imidazol-1-yl) piperidine-2,6-dione (90.0 mg, 139 μmol) in THF (2 mL) was added NaH (8.35 mg, 208 μmol, 60% purity) at 0° C. The reaction mixture was stirred at 0° C. for 0.5 hr. Then the (R)-1-(7-(8-ethyl-7-fluoro-3-(methoxymethoxy) naphthalen-1-yl)-8-fluoro-2-

(methylsulfonyl)pyrido[4,3-d]pyrimidin-4-yl)-3-methylpiperidin-3-ol (79.6 mg, 139 μmol) was added to the mixture. The reaction mixture was stirred at 25° C. for 0.5 hr. On completion, the reaction mixture was quenched with HCl/EA (2 mL). The reaction mixture was filtered and the filtrate was concentrated in vacuo to give the title compound (90.0 mg, 56% yield) as yellow solid.

Step 8-3-(5-(1-(7-(3-((3R,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl) propyl)-7-azaspiro [3.5]nonan-2-yl) piperidin-4-yl)-3-methyl-2-oxo-2,3-dihydro-1H-benzo[d]imidazol-1-yl) piperidine-2,6-dione (Compound 472). A mixture of 3-(5-(1-(7-(3-((3R,7aS)-7a-(((7-(8-ethyl-7-fluoro-3-(methoxymethoxy) naphthalen-1-yl)-8-fluoro-4-((R)-3-hydroxy-3-methylpiperidin-1-yl) pyrido[4,3-d]pyrimidin-2-yl)oxy)methyl)hexahydro-1H-pyrrolizin-3-yl) propyl)-7-azaspiro[3.5]nonan-2-yl) piperidin-4-yl)-3-methyl-2-oxo-2,3-dihydro-1H-benzo[d] imidazol-1-yl) piperidine-2,6-dione (90.0 mg, 78.9 μmol) in HCl/EtOAc (1.5 M, 2 mL) was stirred at 25° C. for 0.5 hr. On completion, the reaction mixture was concentrated in vacuo. The residue was purified by reverse phase (0.1% FA condition) to give the title Compound (10.7 mg, 11% yield, FA) as white solid. $^1$H NMR (400 MHz, DMSO-$d_6$) δ 11.08 (s, 1H), 10.15-9.79 (m, 1H), 9.23 (d, J=3.2 Hz, 1H), 7.77 (dd, J=5.6, 8.8 Hz, 1H), 7.39-7.31 (m, 2H), 7.11 (s, 1H), 7.06-6.97 (m, 2H), 6.94-6.88 (m, 1H), 5.38-5.30 (m, 1H), 4.81-4.71 (m, 1H), 4.39-4.30 (m, 1H), 4.29-4.22 (m, 1H), 4.19-4.12 (m, 1H), 4.10-4.00 (m, 1H), 3.70-3.62 (m, 1H), 3.57-3.52 (m, 1H), 3.33 (s, 3H), 3.08-3.04 (m, 1H), 2.94-2.82 (m, 4H), 2.73-2.62 (m, 4H), 2.40-2.25 (m, 8H), 2.17-2.10 (m, 2H), 2.04-1.97 (m, 2H), 1.93-1.87 (m, 2H), 1.81-1.67 (m, 14H), 1.58-1.42 (m, 12H), 1.18 (d, J=9.2 Hz, 3H), 0.78-0.70 (m, 3H). LC-MS (ESI) m/z 1095.4 (M+H)$^+$.

Example 69. Synthesis of Compound 473

Step 1-(E)-Ethyl 3-((3S,7aR)-7a-(((tert-butyldiphenylsilyl)oxy)methyl)hexahydro-1H-pyrrolizin-3-yl) acrylate. To a solution of ethyl 2-(diethoxyphosphoryl)acetate (2.40 g, 10.7 mmol) in THF (40 mL) was added t-BuOK (1.64 g, 14.6 mmol) at 0° C. and stirred at 0.5 hr. Then (3S,7aR)-7a-(((tert-butyldiphenylsilyl)oxy)methyl)hexahydro-1H-pyrrolizine-3-carbaldehyde (3.97 g, 9.73 mmol) was added to the mixture and stirred at 25° C. for 1.5 hrs. On completion, the reaction mixture was quenched with $H_2O$ (30 mL) at 0° C., and then extracted with EA (3×50 mL). The combined organic layers were washed with brine (2×50 mL), dried over anhydrous $Na_2SO_4$, filtered and the filtrate was concentrated in vacuo to give a residue. The residue was purified by column chromatography ($SiO_2$, Petroleum ether/Ethyl acetate=4/1 to 3/1) to give the title compound (2.60 g, 52% yield) as yellow oil. $^1$H NMR (400 MHz, DMSO-$d_6$) δ 7.70 (ddd, J=1.2, 4.8, 6.4 Hz, 4H), 7.44-7.37 (m, 6H), 6.84 (dd, J=6.4, 15.6 Hz, 1H), 5.95 (d, J=15.6 Hz, 1H), 4.18 (q, J=7.2 Hz, 2H), 3.42-3.31 (m, 2H), 3.28-3.18 (m, 1H), 2.84 (td, J=6.4, 10.8 Hz, 1H), 2.54 (td, J=5.6, 11.2 Hz, 1H), 2.17 (dd, J=6.4, 12.4 Hz, 1H), 1.99-1.88 (m, 2H), 1.83-1.69 (m, 2H), 1.67-1.55 (m, 2H), 1.53-1.45 (m, 1H), 1.28 (t, J=7.2 Hz, 3H), 1.07 (s, 9H); LC-MS (ESI) m/z 478.4 (M+H)$^+$.

Step 2-Ethyl 3-((3S,7aR)-7a-(((tert-butyldiphenylsilyl) oxy)methyl)hexahydro-1H-pyrrolizin-3-yl) propanoate. A mixture of (E)-ethyl 3-((3S,7aR)-7a-(((tert-butyldiphenylsilyl)oxy)methyl)hexahydro-1H-pyrrolizin-3-yl) acrylate (2.60 g, 5.44 mmol), Pd/C (1.30 g, 1.22 mmol, 10% purity) in THF (30 mL) was degassed and purged with $H_2$ for 3 times, and then the mixture was stirred at 25° C. for 4 hrs under $H_2$ atmosphere (15 psi). On completion, the reaction mixture was filtered and the filtrate was concentrated in vacuo to give the title compound (2.40 g, 91% yield) as yellow oil. LC-MS (ESI) m/z 480.3 (M+H)$^+$.

Step 3-3-((3S,7aR)-7a-(((Tert-butyldiphenylsilyl)oxy) methyl)hexahydro-1H-pyrrolizin-3-yl) propan-1-ol. To a solution of ethyl 3-((3S,7aR)-7a-(((tert-butyldiphenylsilyl) oxy)methyl)hexahydro-1H-pyrrolizin-3-yl) propanoate (1.50 g, 3.13 mmol) in THF (20 mL) was added LAH (2.5 M, 1.88 mL) at 0° C. . . . The mixture was stirred at 0° C. for 20 mins. On completion, the reaction mixture was quenched with $H_2O$ (2.5 mL) at 0° C., NaOH (2.5 mL, 15%) and $H_2O$ (7.5 mL) were added to the mixture. Then the mixture was dried over anhydrous $Na_2SO_4$, filtered and the filtrate was concentrated in vacuo to give the title compound (1.30 g, 94% yield) as yellow oil. LC-MS (ESI) m/z 438.3 (M+H)$^+$.

Step 4-3-((3S,7aR)-7a-(((Tert-butyldiphenylsilyl)oxy) methyl)hexahydro-1H-pyrrolizin-3-yl) propanal. To a solution of $(COCl)_2$ (87.0 mg, 685 μmol) in DCM (3 mL) was added DMSO (80.3 mg, 1.03 mmol) at −78° C. and the mixture was stirred at −78° C. for 1 hr under $N_2$ atmosphere. Then a solution of 3-((3S,7aR)-7a-(((tert-butyldiphenylsilyl) oxy)methyl)hexahydro-1H-pyrrolizin-3-yl) propan-1-ol (150 mg, 342 μmol) in DCM (2 mL) was added to the mixture at −78° C. and the mixture was stirred at −78° C. for 1 hr. TEA (1.04 g, 10.28 mmol) was added to the mixture at −78° C. and the mixture was stirred at −78° C. for 1 hr. Warmed to 25° C. and stirred for 0.5 hr. On completion, the reaction mixture was quenched by addition $H_2O$ (20 mL) at 0° C., and then extracted with DCM (3×30 mL). The combined organic layers were washed with brine (2×50 mL), dried over anhydrous $Na_2SO_4$, filtered and the filtrate was concentrated in vacuo to give the title compound (145 mg, crude) as yellow oil. LC-MS (ESI) m/z 436.2 (M+H)$^+$.

Step 5-3-(5-(1-(3-((3R,7aR)-7a-(((Tert-butyldiphenylsilyl)oxy)methyl)hexahydro-1H-pyrrolizin-3-yl) propyl) piperidin-4-yl)-3-methyl-2-oxo-2,3-dihydro-1H-benzo[d]imidazol-1-yl) piperidine-2,6-dione. To a solution of 3-(3-methyl-2-oxo-5-(piperidin-4-yl)-2,3-dihydro-1H-benzo[d] imidazol-1-yl) piperidine-2,6-dione (100 mg, 219 μmol, TFA salt) in THF (2 mL) was added TEA (44.3 mg, 438 μmol) to adjust pH=10, then AcOH (39.47 mg, 657 μmol) was added to the mixture adjust pH=5. 3-((3S,7aR)-7a-(((Tert-butyldiphenylsilyl)oxy)methyl)hexahydro-1H-pyrrolizin-3-yl) propanal (95.4 mg, 219 μmol) was added and stirred at 25° C. for 30 mins. Finally, the $NaBH_3CN$ (27.5 mg, 438 μmol) was added and stirred at 25° C. for 30 mins. On completion, the reaction mixture was quenched with $H_2O$ (1 mL) and concentrated in vacuo to give a residue. The residue was purified by prep-HPLC (0.1% TFA condition) to give the title compound (80.0 mg, 34% yield) as white solid. LC-MS (ESI) m/z 762.3 (M+H)$^+$.

Step 6-3-(5-(1-(3-((3R,7aR)-7a-(Hydroxymethyl)hexahydro-1H-pyrrolizin-3-yl) propyl) piperidin-4-yl)-3-methyl-2-oxo-2,3-dihydro-1H-benzo[d]imidazol-1-yl) piperidine-2,6-dione. To a solution of 3-(5-(1-(3-((3R,7aR)-7a-(((tert-butyldiphenylsilyl)oxy)methyl)hexahydro-1H-pyrrolizin-3-yl) propyl) piperidin-4-yl)-3-methyl-2-oxo-2,3-dihydro-1H-benzo[d]imidazol-1-yl) piperidine-2,6-dione (80.0 mg, 104 μmol) in DMSO (1 mL) was added CsF (47.8 mg, 314 μmol). The mixture was stirred at 25° C. for 1 hr. On completion, the reaction mixture was added ACN (1 mL). The residue was purified by prep-HPLC (0.1% TFA condition) to give the title compound (40.0 mg, 72% yield) as white solid; LC-MS (ESI) m/z 524.3 (M+H)$^+$.

Step 7-3-(5-(1-(3-((3R,7aR)-7a-(((7-(8-Ethyl-7-fluoro-3-(methoxymethoxy) naphthalen-1-yl)-8-fluoro-4-((R)-3-hydroxy-3-methylpiperidin-1-yl)pyrido[4,3-d]pyrimidin-2-yl) oxy)methyl)hexahydro-1H-pyrrolizin-3-yl) propyl) piperidin-4-yl)-3-methyl-2-oxo-2,3-dihydro-1H-benzo[d] imidazol-1-yl) piperidine-2,6-dione. To a solution of 3-(5-(1-(3-((3R,7aR)-7a-(Hydroxymethyl)hexahydro-1H-pyrrolizin-3-yl) propyl) piperidin-4-yl)-3-methyl-2-oxo-2,3-dihydro-1H-benzo[d]imidazol-1-yl) piperidine-2,6-dione (30.0 mg, 57.2 μmol) in THF (2 mL) and DMF (0.5 mL) was added NaH (4.58 mg, 114 μmol, 60% purity) at 0° C. and stirred for 0.5 hr. Then (R)-1-(7-(8-ethyl-7-fluoro-3-(methoxymethoxy) naphthalen-1-yl)-8-fluoro-2-(methylsulfonyl)pyrido[4,3-d]pyrimidin-4-yl)-3-methylpiperidin-3-ol (39.3 mg, 68.7 μmol) was added to the mixture and the mixture was stirred at 25° C. for 1.5 hrs under $N_2$ atmosphere. On completion, the reaction mixture was quenched with HCl/dioxane (1 mL) at 0° C., concentrated in vacuo to give the title compound (63.0 mg, crude) as yellow solid. LC-MS (ESI) m/z 1016.4 $(M+H)^+$.

Step 8-3-(5-(1-(3-((3R,7aR)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl) propyl) piperidin-4-yl)-3-methyl-2-oxo-2,3-dihydro-1H-benzo[d]imidazol-1-yl) piperidine-2,6-dione (Compound 473). A mixture of 3-(5-(1-(3-((3R,7aR)-7a-(((7-(8-Ethyl-7-fluoro-3-(methoxymethoxy) naphthalen-1-yl)-8-fluoro-4-((R)-3-hydroxy-3-methylpiperidin-1-yl)pyrido[4,3-d]pyrimidin-2-yl) oxy)methyl)hexahydro-1H-pyrrolizin-3-yl) propyl) piperidin-4-yl)-3-methyl-2-oxo-2,3-dihydro-1H-benzo[d] imidazol-1-yl) piperidine-2,6-dione (60.0 mg, crude) in DCM (2 mL) was added HCl/dioxane (2 M, 1 mL), and then the mixture was stirred at 25° C. for 0.5 hr. On completion, the reaction mixture was concentrated in vacuo to give a residue. The residue was purified by prep-HPLC (column: CD01-Phenomenex luna C18 150*25*10 μm; mobile phase: [water (FA)-ACN]; gradient: 7%-37% B over 8 min) to give the title compound (6.77 mg, 11% yield, FA salt) as white solid. $^1$H NMR (400 MHz, DMSO-$d_6$) δ 11.08 (s, 1H), 9.27-9.18 (m, 1H), 7.76 (dd, J=6.0, 8.8 Hz, 1H), 7.07 (s, 1H), 7.03 (d, J=1.6 Hz, 1H), 6.99 (d, J=8.0 Hz, 1H), 6.89 (d, J=8.4 Hz, 1H), 5.33 (dd, J=5.2, 12.4 Hz, 1H), 4.86-4.63 (m, 1H), 4.39-4.27 (m, 1H), 4.19-4.11 (m, 1H), 4.05 (dd, J=5.2, 10.4 Hz, 2H), 3.63 (dd, J=3.6, 13.2 Hz, 1H), 3.54 (s, 1H), 3.31 (s, 3H), 3.02 (d, J=6.4 Hz, 2H), 2.93-2.84 (m, 2H), 2.75-2.58 (m, 5H), 2.43-2.28 (m, 4H), 2.15-1.91 (m, 8H), 1.82 (s, 3H), 1.77-1.58 (m, 9H), 1.55 (d, J=6.0 Hz, 2H), 1.48 (s, 3H), 1.36-1.23 (m, 1H), 1.16 (d, J=9.2 Hz, 3H), 0.73 (q, J=7.2 Hz, 3H); LC-MS (ESI) m/z 972.3 $(M+H)^+$.

Example 70. Synthesis of Compound 499

Step 1-(R)-1-(2-(((3S,7aS)-3-((4-Bromophenoxy)methyl) hexahydro-1H-pyrrolizin-7a-yl) methoxy)-7-(8-ethyl-7-fluoro-3-((triisopropylsilyl)oxy) naphthalen-1-yl)-8-fluoropyrido[4,3-d]pyrimidin-4-yl)-3-methylpiperidin-3-ol. To a solution of 4-bromophenol (80.2 mg, 463 μmol), (R)-1-(7-(8-ethyl-7-fluoro-3-((triisopropylsilyl)oxy) naphthalen-1-yl)-8-fluoro-2-(((3S,7aS)-3-(hydroxymethyl)hexahydro-1H-pyrrolizin-7a-yl) methoxy)pyrido[4,3-d]pyrimidin-4-yl)-3-methylpiperidin-3-ol (300 mg, 386 μmol) in Tol. (5 mL) was added $PPh_3$ (202 mg, 773 μmol) and DIAD (156 mg, 773 μmol, 149 μL). The mixture was stirred at 110° C. for 16 hrs. On completion, the reaction mixture was diluted with brine (20 mL) and extracted with EA (3×30 mL). The combined organic layers were washed with brine (3×30 mL), dried over anhydrous $Na_2SO_4$, filtered and the filtrate was concentrated in vacuo to give a residue. The crude product was purified by reversed-phase HPLC (0.1% FA condition) to give the title compound (120 mg, 24% yield) as white solid. $^1$H NMR (400 MHz, DMSO-$d_6$) δ 9.23 (s, 1H), 7.91 (dd, J=6.0, 8.8 Hz, 1H), 7.50 (s, 1H), 7.46-7.40 (m, 2H), 7.39-7.22 (m, 1H), 7.08 (d, J=2.4 Hz, 1H), 7.01-6.84 (m, 2H), 4.76 (s, 1H), 4.41-4.26 (m, 1H), 4.26-4.13 (m, 2H), 4.12-3.97 (m, 3H), 3.66-3.53 (m, 1H), 2.74 (d, J=3.2 Hz, 2H), 2.40-2.35 (m, 1H), 2.22-2.10 (m, 1H), 2.09-1.97 (m, 2H), 1.84-1.65 (m, 8H), 1.64-1.47 (m, 3H), 1.34-1.29 (m, 2H), 1.17 (d, J=6.8 Hz, 3H), 1.08 (d, J=7.6 Hz, 18H), 0.90 (d, J=6.8 Hz, 2H), 0.77-0.71 (m, 3H).

Step 2-(R)-1-(2-(((3S,7aS)-3-((4-((E)-2-Ethoxyvinyl) phenoxy)methyl)hexahydro-1H-pyrrolizin-7a-yl) methoxy)-7-(8-ethyl-7-fluoro-3-hydroxynaphthalen-1-yl)-8-fluoropyrido[4,3-d]pyrimidin-4-yl)-3-methylpiperidin-3-ol. To a solution of (R)-1-(2-(((3S,7aS)-3-((4-bromophenoxy)methyl)hexahydro-1H-pyrrolizin-7a-yl) methoxy)-7-(8-ethyl-7-fluoro-3-((triisopropylsilyl)oxy) naphthalen-1-yl)-8-fluoropyrido[4,3-d]pyrimidin-4-yl)-3-methylpiperidin-3-ol (100 mg, 107 μmol) and 2-[(E)-2-ethoxyvinyl]-4,4,5,5-tetramethyl-1,3,2-dioxaborolane (27.6 mg, 139 μmol) in dioxane (2 mL) and $H_2O$ (0.4 mL) was added XPhos Pd G3 (9.09 mg, 10.7 μmol) and $K_3PO_4$ (68.4 mg, 322 μmol). The mixture was stirred at 80° C. for 2 hrs under $N_2$ atmosphere. On completion, the reaction mixture was diluted with brine (20 mL) and extracted with EA (3×30 mL). The combined organic layers were washed with brine (3×30 mL), dried over anhydrous $Na_2SO_4$, filtered and the filtrate was concentrated in vacuo to give a residue. The crude product was purified by reversed-phase HPLC (0.1% TFA condition) to give the title compound (100 mg, 64% yield) as white solid. LC-MS (ESI) m/z 922.4 $(M+H)^+$.

Step 4-(R)-1-(2-(((3S,7aS)-3-((4-((E)-2-Ethoxyvinyl) phenoxy)methyl)hexahydro-1H-pyrrolizin-7a-yl) methoxy)-7-(8-ethyl-7-fluoro-3-hydroxynaphthalen-1-yl)-8-fluoropyrido[4,3-d]pyrimidin-4-yl)-3-methylpiperidin-3-ol. To a solution of (R)-1-(2-(((3S,7aS)-3-((4-((E)-2-ethoxyvinyl)phenoxy)methyl)hexahydro-1H-pyrrolizin-7a-yl) methoxy)-7-(8-ethyl-7-fluoro-3-hydroxynaphthalen-1-yl)-8-fluoropyrido[4,3-d]pyrimidin-4-yl)-3-methylpiperidin-3-ol (100 mg, 108 μmol) in THF (2 mL) was added CsF (49.4 mg, 325 μmol). The mixture was stirred at 25° C. for 1 hr. On completion, the crude product was purified by reversed-phase HPLC (0.1% FA condition) to give the title compound (20.0 mg, 21% yield) as white solid. 1H NMR (400 MHz, DMSO-$d_6$) δ 9.94 (s, 1H), 9.22 (d, J=2.4 Hz, 1H), 7.76 (dd, J=6.0, 9.2 Hz, 1H), 7.39-7.29 (m, 2H), 7.18 (d, J=8.8 Hz, 2H), 7.10-7.01 (m, 2H), 6.88-6.78 (m, 2H), 5.77 (d, J=12.8 Hz, 1H), 4.76 (d, J=6.4 Hz, 1H), 4.41-4.30 (m, 1H), 4.20-3.98 (m, 5H), 3.84 (q, J=7.2 Hz, 2H), 3.65-3.54 (m, 1H), 2.77 (d, J=5.2 Hz, 2H), 2.16-1.91 (m, 4H), 1.85-1.48 (m, 12H), 1.23 (t, J=7.2 Hz, 3H), 1.17 (d, J=9.2 Hz, 3H), 0.73 (q, J=7.6 Hz, 3H).

Step 5-2-(4-(((35,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl) hexahydro-1H-pyrrolizin-3-yl) methoxy)phenyl) acetaldehyde. To a solution of (R)-1-(2-(((3S,7aS)-3-((4-((E)-2-ethoxyvinyl)phenoxy)methyl)hexahydro-1H-pyrrolizin-7a-yl) methoxy)-7-(8-ethyl-7-fluoro-3-hydroxynaphthalen-1-yl)-8-fluoropyrido[4,3-d]pyrimidin-4-yl)-3-methylpiperidin-3-ol (17.0 mg, 22.2 μmol) in DCM (0.50 mL) and $H_2O$ (0.10 mL) was added trichloroacetic acid (18.1 mg, 110 μmol). The mixture was stirred at 25° C. for 0.5 hr. On completion, the reaction mixture was diluted with $NaHCO_3$ (20 mL) and extracted with DCM (3×30 mL). The combined organic layers were washed with brine (3×30 mL), dried over anhydrous $Na_2SO_4$, filtered and the filtrate was concentrated in vacuo to give the title compound (16.0 mg, 97% yield) as white solid. LC-MS (ESI) m/z 738.2 $(M+H)^+$.

Step 6-3-(5-(1-(4-(((3S,7aS)-7a-(((7-(8-Ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy) methyl)hexahydro-1H-pyrrolizin-3-yl) methoxy) phenethyl) piperidin-4-yl)-3-methyl-2-oxo-2,3-dihydro-1H-benzo[d] imidazol-1-yl) piperidine-2,6-dione (Compound 499). To a solution of 3-[3-methyl-2-oxo-5-(4-piperidyl)benzimidazol-1-yl]piperidine-2,6-dione (7.42 mg, 21.6 μmol) in THF (2 mL) was added HOAc (5.21 mg, 86.7 μmol, 4.97 μL), 2-(4-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl) methoxy)phenyl) acetaldehyde (16.0 mg, 21.6 μmol) and $NaBH_3CN$ (2.04 mg, 32.5 μmol). The mixture was stirred at 25° C. for 1 hr. On completion, the reaction mixture was concentrated in vacuo to give a residue. The residue was purified by prep-HPLC (column: CD04-Welch Utimate C18 150*25*7 μm; mobile phase: [$H_2O$ (0.225% FA)-ACN]; gradient: 14%-44% B over 15.0 min) to give the title compound (4.09 mg, 16% yield, FA salt) as white solid. $^1H$ NMR (400 MHz, DMSO-$d_6$) δ 11.08 (s, 1H), 10.01-9.88 (m, 1H), 9.22 (d, J=2.4 Hz, 1H), 7.80-7.72 (m, 1H), 7.39-7.29 (m, 2H), 7.16-7.07 (m, 3H), 7.05-6.97 (m, 2H), 6.93-6.87 (m, 2H), 5.33 (dd, J=5.2, 12.4 Hz, 1H), 4.76 (d, J=6.8 Hz, 1H), 4.41-4.27 (m, 1H), 4.22-3.96 (m, 5H), 3.65-3.55 (m, 2H), 3.28-3.26 (m, 3H), 3.09-3.02 (m, 3H), 2.94-2.85 (m, 2H), 2.77 (d, J=0.8 Hz, 2H), 2.71-2.67 (m, 3H), 2.33 (s, 2H), 2.10-1.95 (m, 6H), 1.88-1.63 (m, 15H), 1.60-1.49 (m, 2H), 1.17 (d, J=9.2 Hz, 3H), 0.73 (q, J=7.6 Hz, 3H); LC-MS (ESI) m/z 1064.4 $(M+H)^+$.

Example 71. Synthesis of Compound 500

Step 1-benzyl 4-{2-[1-(tert-butoxycarbonyl) piperidin-4-yl]ethynyl}piperidine-1-carboxylate. To a stirred solution of tert-butyl 4-ethynylpiperidine-1-carboxylate (6 g, 28.668 mmol) and benzyl 4-iodopiperidine-1-carboxylate (14.84 g, 43.002 mmol) in DMF (20 mL) and Diethyl ether (40 mL) were added CuI (2.73 g, 14.334 mmol), 1,3-bis(1-adamantyl) imidazolium tetrafluoroborate (6.08 g, 14.334 mmol), $Cs_2CO_3$ (13.08 g, 40.135 mmol) and $[PdCl(allyl)]_2$ (2.62 g, 7.167 mmol) in portions at room temperature under air atmosphere. The resulting mixture was stirred at 40° C. for 16 h under air atmosphere. Desired product could be detected by LCMS. The mixture was allowed to cool down to room temperature. The resulting mixture was diluted with water (50 mL). The resulting mixture was extracted with EtOAc (3×50 mL). The combined organic layers were washed with brine (50 mL), dried over anhydrous $Na_2SO_4$. After filtration, the filtrate was concentrated under reduced pressure. The residue was purified by reverse phase flash chromatography with the following conditions: Column: Spherical C18, 20-40 μm, 330 g; Mobile Phase A: Water (plus 10 mM $NH_4HCO_3$); Mobile Phase B: ACN; Flow rate: 80 mL/min; Gradient: 5%-5% B, 10 min, 33% B-95% B gradient in 20 min; Detector: 220 nm. The fractions containing the desired product were collected at 90% B and concentrated under reduced pressure to afford benzyl 4-{2-[1-(tert-butoxycarbonyl) piperidin-4-yl]ethynyl}piperidine-1-carboxylate (600 mg, 4%) as a Brown yellow solid. LC/MS (ESI, m/z): $[(M+1)]^+$=327.20 Chemical Formula: $C_{25}H_{34}N_2O_4$, Exact Mass: 426.25.

Step 2-benzyl 4-[2-(piperidin-4-yl) ethynyl]piperidine-1-carboxylate. To a stirred solution of tert-butyl 4-(2-{1-[(benzyloxy) carbonyl]piperidin-4-yl}ethynyl) piperidine-1-carboxylate (600 mg, 1.407 mmol, 1 equiv) in DCM (10 mL) was added HCl in 1,4-dioxane (4.0 M)(10 mL) dropwise at room temperature under air atmosphere. The resulting mixture was stirred at room temperature for 1 h under air atmosphere. Desired product could be detected by LCMS. The resulting mixture was concentrated under reduced pressure to afford crude product. The crude product was used in the next step directly without further purification. LC/MS (ESI, m/z): $[(M+1)]^+$=327.20 Chemical Formula: $C_{20}H_{26}N_2O_2$, Exact Mass: 326.20.

Step 3-benzyl 4-{2-[1-(1-{1-[(4-methoxyphenyl)methyl]-2,6-dioxopiperidin-3-yl}-3-methyl-2-oxo-1,3-benzodiazol-5-yl) piperidin-4-yl]ethynyl}piperidine-1-carboxylate. To a stirred solution of benzyl 4-[2-(piperidin-4-yl) ethynyl]piperidine-1-carboxylate (450 mg, 1.379 mmol) and 3-(5-bromo-3-methyl-2-oxo-1,3-benzodiazol-1-yl)-1-[(4-methoxyphenyl)methyl]piperidine-2,6-dione (758.14 mg, 1.655 mmol) in 1,4-dioxane (9 mL) were added $Cs_2CO_3$ (2.25 g, 6.895 mmol), XPhos (131.43 mg, 0.276 mmol) and $Pd(OAc)_2$ (30.95 mg, 0.138 mmol) in portions at room temperature under air atmosphere. The resulting mixture was stirred at 90° C. for 16 h under air atmosphere. Desired product could be detected by LCMS. The mixture was allowed to cool down to room temperature. The resulting mixture was concentrated under reduced pressure. The residue was purified by reverse phase flash chromatography with the following conditions: Column: Spherical C18, 20-40 μm, 330 g; Mobile Phase A: Water (plus 10 mM $NH_4HCO_3$); Mobile Phase B: ACN; Flow rate: 60 mL/min; Gradient: 5%-5% B, 10 min, 33% B-70% B gradient in 20 min; Detector: 220 nm. The fractions containing the desired product were collected at 68% B and concentrated under reduced pressure to afford benzyl 4-{2-[1-(1-{1-[(4-methoxyphenyl)methyl]-2,6-dioxopiperidin-3-yl}-3-methyl-2-oxo-1,3-benzodiazol-5-yl) piperidin-4-yl] ethynyl}piperidine-1-carboxylate (140 mg, 14%) as a light yellow oil. LC/MS (ESI, m/z): [(M+1)]=704.35 Chemical Formula: $C_{41}H_{45}N_5O_6$, Exact Mass: 703.34.

Step 4-3-(3-methyl-2-oxo-5-{4-[2-(piperidin-4-yl) ethynyl]piperidin-1-yl}-1,3-benzodiazol-1-yl) piperidine-2,6-dione: To a stirred solution of benzyl 4-{2-[1-(1-{1-[(4-methoxyphenyl)methyl]-2,6-dioxopiperidin-3-yl}-3-methyl-2-oxo-1,3-benzodiazol-5-yl) piperidin-4-yl] ethynyl}piperidine-1-carboxylate (140 mg, 0.199 mmol) in trifluoroacetic acid (3 mL) was added trifluoromethanesulfonic acid (0.6 mL) dropwise at room temperature under air atmosphere. The resulting mixture was stirred at 60° C. for 2 h under air atmosphere. Desired product could be detected by LCMS. The mixture was allowed to cool down to room temperature. The resulting mixture was concentrated under reduced pressure. The residue was purified by reverse phase flash chromatography with the following conditions: Column: Spherical C18, 20-40 μm, 120 g; Mobile Phase A: Water (plus 10 mM $NH_4HCO_3$); Mobile Phase B: ACN; Flow rate: 60 mL/min; Gradient: 5%-5% B, 10 min, 33% B-45% B gradient in 20 min; Detector: 220 nm. The fractions containing the desired product were collected at 40% B and concentrated under reduced pressure to afford 3-(3-methyl-2-oxo-5-{4-[2-(piperidin-4-yl) ethynyl]piperidin-1-yl}-1,3-benzodiazol-1-yl) piperidine-2,6-dione (30 mg, 33%) as an off-white solid. LC/MS (ESI, m/z): [(M+1)]$^+$=450.25 Chemical Formula: $C_{25}H_{31}N_5O_3$, Exact Mass: 449.24.

Step 5-[(3S,7aS)-7a-[({7-[8-ethyl-7-fluoro-3-(methoxymethoxy)naphthalen-1-yl]-8-fluoro-4-[(3R)-3-methyl-3-(oxan-2-yloxy)piperidin-1-yl]pyrido[4,3-d]pyrimidin-2-yl}oxy)methyl]-hexahydropyrrolizin-3-yl]methyl 4-(2-{1-[1-(2,6-dioxopiperidin-3-yl)-3-methyl-2-oxo-1,3-benzodiazol-5-yl]piperidin-4-yl}ethynyl) piperidine-1-carboxylate: To a stirred solution of [(35,7aS)-7a-[({7-[8-ethyl-7-fluoro-3-(methoxymethoxy) naphthalen-1-yl]-8-fluoro-4-[(3R)-3-methyl-3-(oxan-2-yloxy)piperidin-1-yl]pyrido[4,3-d]pyrimidin-2-yl}oxy)methyl]-hexahydropyrrolizin-3-yl] methyl 4-nitrophenyl carbonate (40.62 mg, 0.044 mmol) and $Et_3N$ (45.02 mg, 0.440 mmol) in THF (1.5 mL) and $H_2O$ (0.7 mL) was added 3-(3-methyl-2-oxo-5-{4-[2-(piperidin-4-yl) ethynyl]piperidin-1-yl}-1,3-benzodiazol-1-yl) piperidine-2,6-dione (30.00 mg, 0.066 mmol) in portions at room temperature under air atmosphere. The resulting mixture was stirred at room temperature for 1 h under air atmosphere. Desired product could be detected by LCMS. The resulting mixture was concentrated under reduced pressure. The residue was purified by reverse phase flash chromatography with the following conditions: Column: Spherical C18, 20-40 μm, 80 g; Mobile Phase A: Water (plus 10 mM $NH_4HCO_3$); Mobile Phase B: ACN; Flow rate: 50 mL/min; Gradient: 5%-5% B, 10 min, 33% B-95% B gradient in 20 min; Detector: 220 nm. The fractions containing the desired product were collected at 95% B and concentrated under reduced pressure to afford [(35,7aS)-7a-[({7-[8-ethyl-7-fluoro-3-(methoxymethoxy) naphthalen-1-yl]-8-fluoro-4-[(3R)-3-methyl-3-(oxan-2-yloxy)piperidin-1-yl]pyrido[4,3-d]pyrimidin-2-yl}oxy)methyl]-hexahydropyrrolizin-3-yl] methyl 4-(2-{1-[1-(2,6-dioxopiperidin-3-yl)-3-methyl-2-oxo-1,3-benzodiazol-5-yl]piperidin-4-yl}ethynyl) piperidine-1-carboxylate (40 mg, 73%) as a light yellow solid. LC/MS (ESI, m/z): [(M+1)]=1223.65 Chemical Formula: $C_{67}H_{80}F_2N_{10}O_{10}$, Exact Mass: 1222.60.

Step 6-[(3S,7aS)-7a-({[7-(8-ethyl-7-fluoro-3-hydroxynaphthalen-1-yl)-8-fluoro-4-[(3R)-3-hydroxy-3-methylpiperidin-1-yl]pyrido[4,3-d]pyrimidin-2-yl]oxy}methyl)-hexahydropyrrolizin-3-yl]methyl 4-(2-{1-[1-(2,6-dioxopiperidin-3-yl)-3-methyl-2-oxo-1,3-benzodiazol-5-yl]piperidin-4-yl}ethynyl) piperidine-1-carboxylate (Compound 500). To a stirred solution of [(3S,7aS)-7a-[({7-[8-ethyl-7-fluoro-3-(methoxymethoxy) naphthalen-1-yl]-8-fluoro-4-[(3R)-3-methyl-3-(oxan-2-yloxy)piperidin-1-yl]pyrido[4,3-d]pyrimidin-2-yl}oxy)methyl]-hexahydropyrrolizin-3-yl]methyl 4-(2-{1-[1-(2,6-dioxopiperidin-3-yl)-3-methyl-2-oxo-1,3-benzodiazol-5-yl]piperidin-4-yl}ethynyl) piperidine-1-carboxylate (40 mg, 0.033 mmol) in DCM (1 mL) was added HCl in 1,4-dioxane (4.0 M)(0.2 mL) dropwise at room temperature under air atmosphere. The resulting mixture was stirred at room temperature for 1 h under air atmosphere. Desired product could be detected by LCMS. The resulting mixture was concentrated under reduced pressure. The crude product (30 mg) was purified by Prep-HPLC with the following conditions (Column: XBridge Prep OBD C18 Column, 50×250 mm, 10 μm; Mobile Phase A: Water (10 mmol/L $NH_4HCO_3$), Mobile Phase B: ACN; Flow rate: 80 mL/min; Gradient: 49% B to 59% B in 10 min; Wave Length: 254/220 nm; RT1 (min): 15) to afford [(35,7aS)-7a-({[7-(8-ethyl-7-fluoro-3-hydroxynaphthalen-1-yl)-8-fluoro-4-[(3R)-3-hydroxy-3-methylpiperidin-1-yl]pyrido[4,3-d]pyrimidin-2-yl]oxy}methyl)-hexahydropyrrolizin-3-yl]methyl 4-(2-{1-[1-(2,6-dioxopiperidin-3-yl)-3-methyl-2-oxo-1,3-benzodiazol-5-yl]piperidin-4-yl}ethynyl) piperidine-1-carboxylate (5.2 mg, 14%) as an off-white solid. $^1$H NMR (400 MHz, DMSO-$d_6$) chemical shifts 9.22 (d, J=3.2 Hz, 1H), 7.80-7.72 (m, 1H), 7.39-7.30 (m, 2H), 7.04 (d, J=2.8 Hz, 1H), 6.93 (d, J=8.4 Hz, 1H), 6.82 (d, J=2.4 Hz, 1H), 6.65-6.58 (m, 1H), 5.33-5.24 (m, 1H), 4.75 (d, J=8.0 Hz, 1H), 4.39-4.27 (m, 1H), 4.24-4.16 (m, 1H), 4.14 (s, 2H), 4.11-4.07 (m, 1H), 4.07-3.98 (m, 1H), 3.67-3.52 (m, 3H), 3.18 (s, OH), 2.92-2.83 (m, 3H), 2.73 (s, 5H), 2.65-2.57 (m, 1H), 2.36 (d, J=9.6 Hz, 1H), 2.30 (d, J=2.0 Hz, 1H), 2.15 (s, 1H), 2.01 (d, J=8.8 Hz, 5H), 1.91-1.83 (m, 2H), 1.76 (s, 2H), 1.72 (s, 13H), 1.63 (t, J=8.4 Hz, 1H), 1.41 (s, 1H), 1.24 (s, 4H), 1.17 (d, J=9.2 Hz, 3H), 0.86 (t, J=6.4 Hz, 1H), 0.79-0.69 (m, 3H). 19F NMR (377 MHz, DMSO) chemical shifts-119.631 (1F), -139.581 (1F). LC/MS (ESI, m/z): [(M+1)]$^+$=1095.60 Chemical Formula: $C_{60}H_{68}F_2N_{10}O_8$, Exact Mass: 1094.52.

The compounds in the following table were made according to methods analogous to those described herein.

| Compound No. | Compound Name<br>$^1$H NMR Peaks |
|---|---|
| 300 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(2-((1-(2,6-dioxopiperidin-3-yl)-3-methyl-2-oxo-2,3-dihydro-1H-benzo[d]imidazol-5-yl)oxy)ethyl)piperidine-1-carboxylate<br>$^1$H NMR (400 MHz, DMSO-$d_6$) δ 11.06 (s, 1H), 9.95 (s, 1H), 9.22 (d, J = 2.0 Hz, 1H), 7.81-7.70 (m, 1H), 7.40-7.27 (m, 2H), 7.04 (d, J = 2.8 Hz, 1H), 6.97 (d, J = 8.4 Hz, 1H), 6.85 (d, J = 2.4 Hz, 1H), 6.64-6.54 (m, 1H), 5.37-5.26 (m, 1H), 4.74 (d, J = 7.2 Hz, 1H), 4.40-4.06 (m, 2H), 4.06-3.78 (m, 7H), 3.66-3.44 (m, 1H), 3.43-3.35 (m, 1H), 3.31 (s, 2H), 2.99-2.84 (m, 3H), 2.83-2.53 (m, 7H), 2.43-2.27 (m, 2H), 2.26-1.75 (m, 8H), 1.74-1.53 (m, 10H), 1.17 (d, J = 9.0 Hz, 3H), 1.11-0.98 (m, 2H), 0.80-0.65 (m, 3H). $^{19}$F NMR (377 MHz, DMSO) chemical shifts −119.691(1F), −139.579(1F). LC/MS (ESI, m/z): [(M + 1)]$^+$ = 1032.55 Chemical Formula: $C_{55}H_{63}F_2N_9O_9$, Exact Mass: 1031.47. |
| 301 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(((1-(2,6-dioxopiperidin-3-yl)-3-methyl-2-oxo-2,3-dihydro-1H-benzo[d]imidazol-5-yl)oxy)methyl)piperidine-1-carboxylate<br>$^1$H NMR (400 MHz, DMSO-$d_6$) δ 11.06 (s, 1H), 9.21 (s, 1H), 7.79-7.72 (m, 1H), 7.37-7.30 (m, 1H), 7.03 (t, J = 4.0 Hz, 1H), 6.99-6.94 (m, 1H), 6.84 (d, J = 2.0 Hz, 1H), 6.61-6.54 (m, 1H), 5.34-5.26 (m, 1H), 4.32 (t, J = 16.0 Hz, 1H), 4.12 (t, J = 8.0 Hz, 1H), 4.04 (t, J = 14.0 Hz, 3H), 3.91 (d, J = 6.0 Hz, 1H), 3.88-3.76 (m, 2H), 3.62 (d, J = 14.0 Hz, 1H), 3.52 (d, J = 14.0 Hz, 1H), 2.90 (d, J = 12.0 Hz, 4H), 2.72-2.56 (m, 2H), 2.31 (s, 1H), 2.13 (d, J = 6.0 Hz, 1H), 2.09-1.88 (m, 4H), 1.86-1.57 (m, 8H), 1.16 (d, J = 8.0 Hz, 4H), 0.75- |

-continued

| Compound No. | Compound Name <br> $^1$H NMR Peaks |
|---|---|
| | 0.72 (m, 2H). LC/MS (ESI, m/z): $[(M+1)]^+$ = 1018.60, Chemical Formula: $C_{54}H_{61}F_2N_9O_9$. Exact Mass: 1017.46. |
| 302 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(3-((1-(2,6-dioxopiperidin-3-yl)-3-methyl-2-oxo-2,3-dihydro-1H-benzo[d]imidazol-5-yl)oxy)propyl)piperidine-1-carboxylate |
| | $^1$H NMR (400 MHz, DMSO-$d_6$) δ 11.07 (s, 1H), 9.93 (s, 1H), 9.22 (s, 1H), 7.76 (dd, J = 9.2, 6.0 Hz, 1H), 7.40-7.29 (m, 2H), 7.05-7.03 (m, 1H), 7.00-6.96 (m, 1H), 6.85-6.83 (m, 1H), 6.61-6.57 (m, 1H), 5.36-5.28 (m, 1H), 4.74 (d, J = 7.2 Hz, 1H), 4.39-4.27 (m, 1H), 4.19-3.74 (m, 8H), 3.71-3.38 (m, 2H), 3.32-3.29 (m, 2H), 2.98-2.84 (m, 3H), 2.82-2.56 (m, 5H), 2.43-2.30 (m, 1H), 2.23-2.10 (m, 1H), 2.10-1.88 (m, 5H), 1.87-1.80 (m, 3H), 1.76-1.50 (m, 10H), 1.36-1.28 (m, 3H), 1.19-1.15 (m, 3H), 1.06-0.90 (m, 2H), 0.77-0.71 (m, 3H). LC/MS (ESI, m/z): $[(M+1)]^+$ = 1046.55 Chemical Formula: $C_{56}H_{65}F_2N_9O_9$, Exact Mass: 1045.49. |
| 303 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(4-((1-(2,6-dioxopiperidin-3-yl)-3-methyl-2-oxo-2,3-dihydro-1H-benzo[d]imidazol-5-yl)oxy)butyl)piperidine-1-carboxylate |
| | $^1$H NMR (400 MHz, DMSO-$d_6$) δ 11.06 (s, 1H), 10.00 (s, 1H), 9.22 (d, J = 2.0 Hz, 1H), 7.80-7.73 (m, 1H), 7.40-7.29 (m, 2H), 7.04 (t, J = 4.0 Hz, 1H), 6.98 (d, J = 8.0 Hz, 1H), 6.84 (s, 1H), 6.60 (d, J = 8.0 Hz, 1H), 5.36-5.26 (m, 1H), 4.74 (d, J = 8.0 Hz, 1H), 4.33 (t, J = 16.0 Hz, 1H), 4.17-4.07 (m, 1H), 4.07-3.97 (m, 3H), 3.93 (t, J = 6.0 Hz, 3H), 3.87-3.80 (m, 1H), 3.63 (d, J = 14.0 Hz, 1H), 3.53 (d, J = 14.0 Hz, 1H), 2.97-2.84 (m, 3H), 2.75-2.62 (m, 5H), 2.55 (s, 2H), 2.35 (d, J = 14.0 Hz, 1H), 2.15 (s, 1H), 2.10-1.88 (m, 5H), 1.83-1.79 (m, 3H), 1.67-1.64 (m, 10H), 1.38-1.33 (m, 3H), 1.23 (d, J = 10.0 Hz, 2H), 1.17 (d, J = 10.0 Hz, 3H), 0.96 (d, J = 12.0 Hz, 2H), 0.77-0.73 (m, 3H). LC/MS (ESI, m/z): $[(M+1)]^+$ = 1016.50, Chemical Formula: $C_{54}H_{61}F_2N_9O_9$. Exact Mass: 1017.46. |
| 304 | (7a-(((7-(8-ethyl-7-fluoro-3-hydroxynaphthalen-1-yl)-8-fluoro-4-((R)-3-hydroxy-3-methylpiperidin-1-yl)quinazolin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate |
| | $^1$H NMR (400 MHz, DMSO-$d_6$) δ 11.08 (br s, 1H), 8.18 (s, 2H), 7.97-7.86 (m, 1H), 7.81-7.70 (m, 1H), 7.39-7.24 (m, 3H), 7.12-6.83 (m, 4H), 5.43-5.26 (m, 1H), 4.15-3.67 (m, 9H), 3.57-3.36 (m, 3H), 3.00-2.56 (m, 10H), 2.47-2.25 (m, 5H), 2.19-1.30 (m, 24H), 1.22-1.08 (m, 3H), 1.00-0.85 (m, 2H), 0.79-0.52 (m, 3H). $^{19}$F NMR (377 MHz, DMSO) δ −119.48 (1F), −128.45 (1F). LC/MS (ESI, m/z): $[(M+1)]^+$ = 1084.65 Chemical Formula: $C_{61}H_{73}F_2N_9O_{10}$, Exact Mass: 1129.54. |
| 306 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(2,6-dioxopiperidin-3-yl)-3-methyl-2-oxo-2,3-dihydro-1H-benzo[d]imidazol-4-yl)oxy)piperidine-1-carboxylate |
| | $^1$H NMR (400 MHz, DMSO-$d_6$) δ 11.10 (br s, 1H), 9.97-9.88 (m, 1H), 9.26-9.15 (m, 1H), 7.81-7.69 (m, 1H), 7.40-7.24 (m, 2H), 7.07-6.99 (m, 1H), 6.98-6.84 (m, 1H), 6.83-6.67 (m, 2H), 5.40-5.27 (m, 1H), 4.79-4.61 (m, 2H), 4.40-4.25 (m, 1H), 4.16-3.79 (m, 5H), 3.68-3.56 (m, 2H), 3.50 (s, 3H), 3.43-3.34 (m, 3H), 3.02-2.80 (m, 3H), 2.77-2.54 (m, 3H), 2.39-2.27 (m, 1H), 2.12-1.48 (m, 19H), 1.16 (d, J = 8.8 Hz, 3H), 0.79-0.64 (m, 3H). $^{19}$F NMR (376 MHz, DMSO) δ −119.58 (1F), −139.55 (1F). LC/MS (ESI, m/z): [(M + 1)]+ = 1004.55 Chemical Formula: C53H59F2N9O9, Exact Mass: 1003.44. |
| 307 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(1-(2,6-dioxopiperidin-3-yl)-3-methyl-2-oxo-2,3-dihydro-1H-benzo[d]imidazol-5-yl)piperidine-1-carboxylate |
| | $^1$H NMR (400 MHz, DMSO-$d_6$) chemical shifts 11.08 (s, 1H), 9.92 (d, J = 2.4 Hz, 1H), 9.22 (s, 1H), 7.80-7.72 (m, 1H), 7.39-7.30 (m, 2H), 7.08 (d, J = 2.0 Hz, 1H), 7.05-7.01 (m, 1H), 7.00-6.94 (m, 1H), 6.86 (t, J = 8.8 Hz, 1H), 5.38-5.28 (m, 1H), 4.74 (d, J = 6.8 Hz, 1H), 4.40-4.26 (m, 1H), 4.19-4.10 (m, 3H), 4.09-3.82 (m, 4H), 3.68-3.48 (m, 1H), 3.47-3.35 (m, 1H), 2.02-2.78 (m, 5H), 2.77-2.56 (m, 5H), 2.40-2.27 (m, 1H), 2.20-1.91 (m, 6H), 1.88-1.49 (m, 14H), 1.17 (d, J = 8.4 Hz, 3H), 0.79-0.68 (m, 3H). $^{19}$F NMR (377 MHz, DMSO) chemical shifts −119.537(1F), −139.458(1F). LC/MS (ESI, m/z): $[(M+1)]^+$ = 988.50 Chemical Formula: $C_{53}H_{59}F_2N_9O_8$, Exact Mass: 987.44. |
| 308 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1-(1-(2,6-dioxopiperidin-3-yl)-3-methyl-2-oxo-2,3-dihydro-1H-benzo[d]imidazol-5-yl)piperidin-4-yl)carbamate |
| | $^1$H NMR (400 MHz, DMSO-$d_6$) δ 11.06 (s, 1H), 9.92 (d, J = 2.8 Hz, 1H), 9.23 (d, J = 2.0 Hz, 1H), 7.80-7.74 (m, 1H), 7.41-7.28 (m, 2H), 7.13 (d, J = 7.6 Hz, 1H), 7.05-7.02 (m, 1H), 6.92 (d, J = 8.8 Hz, 1H), 6.87-6.75 (m, 1H), 6.62 (d, J = 8.8 Hz, 1H), 5.32-5.26 (m, 1H), 4.75 (d, J = 6.4 Hz, 1H), 4.38-4.30 (m, 1H), 4.21-3.96 (m, 3H), 3.88-3.80 (m, 2H), 3.65-3.61 (m, 1H), 3.56-3.52 (m, 2H), 3.48-3.36 (m, 2H), 3.30 (s, 3H), 2.98-2.84 (m, |

-continued

| Compound No. | Compound Name<br>$^1$H NMR Peaks |
| --- | --- |
| | 3H), 2.79-2.55 (m, 4H), 2.42-2.27 (m, 1H), 2.19-2.11 (m, 1H), 2.08 (s, 4H), 1.89-1.45 (m, 11H), 1.17 (d, J = 9.2 Hz, 3H), 0.78-0.70 (m, 3H). LC/MS (ESI, m/z): $[(M + 1)]^+$ = 1003.60 Chemical Formula: $C_{53}H_{60}F_2N_{10}O_8$, Exact Mass: 1002.46. |
| 309 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1-(1-(2,6-dioxopiperidin-3-yl)-3-methyl-2-oxo-2,3-dihydro-1H-benzo[d]imidazol-5-yl)piperidin-3-yl)carbamate<br>$^1$H NMR (400 MHz, DMSO-$d_6$) δ 11.06 (s, 1H), 9.92 (d, J = 2.8 Hz, 1H), 9.23 (d, J = 1.6 Hz, 1H), 7.80-7.75 (m, 1H), 7.41-7.28 (m, 2H), 7.16 (d, J = 7.6 Hz, 1H), 7.06-7.02 (m, 1H), 6.93 (d, J = 8.4 Hz, 1H), 6.81 (s, 1H), 6.62 (d, J = 8.4 Hz, 1H), 5.32-5.26 (m, 1H), 4.78-4.72 (m, 1H), 4.38-4.29 (m, 1H), 4.17-3.99 (m, 3H), 3.97-3.76 (m, 2H), 3.67-3.60 (m, 1H), 3.57-3.49 (m, 2H), 3.48-3.35 (m, 2H), 3.30 (s, 3H), 3.02-2.81 (m, 3H), 2.76-2.54 (m, 4H), 2.47-2.27 (m, 2H), 2.23-1.91 (m, 5H), 1.89-1.51 (m, 11H), 1.40-1.23 (m, 1H), 1.17 (d, J = 8.8 Hz, 3H), 0.79-0.69 (m, 3H). LC/MS (ESI, m/z): $[(M + 1)]^+$ = 1003.60 Chemical Formula: $C_{53}H_{60}F_2N_{10}O_8$, Exact Mass: 1002.46. |
| 310 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(1-(2,6-dioxopiperidin-3-yl)-3-methyl-2-oxo-2,3-dihydro-1H-benzo[d]imidazol-4-yl)piperidine-1-carboxylate<br>$^1$H NMR (400 MHz, DMSO-$d_6$) chemical shifts 11.09 (s, 1H), 9.91 (d, J = 4.4 Hz, 1H), 9.22 (s, 1H), 7.76 (t, J = 7.6 Hz, 1H), 7.38-7.27 (m, 2H), 7.06-7.00 (m, 1H), 6.96 (s, 3H), 5.43-5.31 (m, 1H), 4.74 (d, J = 7.2 Hz, 1H), 4.41-4.24 (m, 1H), 4.16-3.89 (m, 6H), 3.66-3.38 (m, 6H), 3.05-2.81 (m, 5H), 2.77-2.56 (m, 5H), 2.32 (s, 1H), 2.12-1.91 (m, 5H), 1.87-1.79 (m, 4H), 1.73-1.49 (m, 8H), 1.17 (d, J = 8.8 Hz, 3H), 0.79-0.65 (m, 3H). $^{19}$F NMR (377 MHz, DMSO) chemical shifts −119.580(1F), −139.524(1F). LC/MS (ESI, m/z): $[(M + 1)]^+$ = 988.50 Chemical Formula: $C_{53}H_{59}F_2N_9O_8$, Exact Mass: 987.44. |
| 311 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1-(1-(2,6-dioxopiperidin-3-yl)-3-methyl-2-oxo-2,3-dihydro-1H-benzo[d]imidazol-4-yl)piperidin-4-yl)carbamate<br>$^1$H NMR (400 MHz, DMSO-$d_6$) δ 11.09 (s, 1H), 9.94 (s, 1H), 9.22 (s, 1H), 7.81-7.70 (m, 1H), 7.47-7.27 (m, 2H), 7.23-7.10 (m, 1H), 7.09-6.54 (m, 4H), 5.40-5.30 (m, 1H), 4.80-4.70 (m, 1H), 4.38-4.28 (m, 1H), 4.20-3.92 (m, 3H), 3.88-3.80 (m, 2H), 3.61 (s, 4H), 3.41-3.33 (m, 1H), 3.13-3.00 (m, 2H), 3.00-2.80 (m, 3H), 2.80-2.51 (m, 5H), 2.44-2.24 (m, 1H), 2.24-1.89 (m, 5H), 2.04-1.40 (m, 15H), 1.21-1.14 (m, 3H), 0.76-0.69 (m, 3H). $^{19}$F NMR (377 MHz, DMSO) δ −119.58(1F), −139.52(1F). LC/MS (ESI, m/z): $[(M + 1)]^+$ = 1003.55 Chemical Formula: $C_{53}H_{60}F_2N_{10}O_8$, Exact Mass: 1002.46. |
| 312 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1-(1-(2,6-dioxopiperidin-3-yl)-3-methyl-2-oxo-2,3-dihydro-1H-benzo[d]imidazol-4-yl)piperidin-3-yl)carbamate<br>$^1$H NMR (400 MHz, DMSO-$d_6$) chemical shifts 11.08 (s, 1H), 9.92 (d, J = 2.8 Hz, 1H), 9.22 (d, J = 2.0 Hz, 1H), 7.80-7.74 (m, 1H), 7.39-7.29 (m, 2H), 7.18 (d, J = 7.6 Hz, 1H), 7.04 (t, J = 2.4 Hz, 1H), 6.94 (d, J = 8.4 Hz, 1H), 6.90-6.81 (m, 2H), 5.42-5.25 (m, 1H), 4.74 (d, J = 6.0 Hz, 1H), 4.40-4.25 (m, 1H), 4.17-3.95 (m, 3H), 3.84 (s, 2H), 3.68-3.45 (m, 5H), 3.43-3.34 (m, 1H), 3.21 (s, 1H), 3.02 (s, 1H), 2.96-2.82 (m, 3H), 2.73-2.56 (m, 4H), 2.41-2.24 (m, 2H), 2.21-2.09 (m, 1H), 2.07-1.86 (m, 5H), 1.86-1.49 (m, 11H), 1.17 (d, J = 8.8 Hz, 4H), 0.81-1.68 (m, 3H). $^{19}$F NMR (377 MHz, DMSO) chemical shifts −119.271(1F), −139.619 (1F). LC/MS (ESI, m/z): $[(M + 1)]^+$ = 1003.55 Chemical Formula: $C_{53}H_{60}F_2N_{10}O_8$, Exact Mass: 1002.4 |
| 313 | ((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(2,6-dioxopiperidin-3-yl)-3-methyl-2-oxo-2,3-dihydro-1H-benzo[d]imidazol-4-yl)oxy)piperidine-1-carboxylate<br>$^1$H NMR (400 MHz, DMSO-$d_6$) δ 11.10 (br s, 1H), 9.97-9.88 (m, 1H), 9.26-9.15 (m, 1H), 7.81-7.69 (m, 1H), 7.40-7.24 (m, 2H), 7.07-6.99 (m, 1H), 6.98-6.84 (m, 1H), 6.83-6.67 (m, 2H), 5.40-5.27 (m, 1H), 4.79-4.61 (m, 2H), 4.40-4.25 (m, 1H), 4.16-3.79 (m, 5H), 3.68-3.56 (m, 2H), 3.50 (s, 3H), 3.43-3.34 (m, 3H), 3.02-2.80 (m, 3H), 2.77-2.54 (m, 3H), 2.39-2.27 (m, 1H), 2.12-1.48 (m, 19H), 1.16 (d, J = 8.8 Hz, 3H), 0.79-0.64 (m, 3H). $^{19}$F NMR (376 MHz, DMSO) δ −119.58 (1F), −139.56 (1F). LC/MS (ESI, m/z): $[(M + 1)]^+$ = 1004.55 Chemical Formula: $C_{53}H_{59}F_2N_9O_9$, Exact Mass: 1003.44. |
| 314 | ((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(((1-(2,6-dioxopiperidin-3-yl)-3-methyl-2-oxo-2,3-dihydro-1H-benzo[d]imidazol-5-yl)oxy)methyl)piperidine-1-carboxylate<br>$^1$H NMR (400 MHz, DMSO-$d_6$) δ 11.08 (s, 1H), 9.22 (d, J = 2.0 Hz, 1H), 8.15 (s, 1H), 7.80-7.72 (m, 1H), 7.38-7.30 (m, 2H), 7.04 (d, J = 4.0 Hz, 1H), 7.00-6.95 (m, 1H), 6.84 (d, J = 2.0 Hz, 1H), 6.62-6.56 (m, 1H), 5.35-5.27 (m, 1H), 4.75 (s, 1H), 4.33 (t, J = 16.0 Hz, 1H), 4.17-3.99 (m, 4H), 3.97-3.90 (m, 1H), 3.89-3.78 (m, 3H), 3.62 (d, J = 14.0 Hz, 1H), 3.56-3.49 (m, 2H), 2.99-2.80 (m, 4H), 2.74-2.57 (m, 3H), 2.41-2.31 (m, 1H), |

-continued

| Compound No. | Compound Name / $^1$H NMR Peaks |
|---|---|
| | 2.20-1.89 (m, 5H), 1.87-1.52 (m, 10H), 1.25-1.12 (m, 4H), 0.76-0.72 (m, 2H). LC/MS (ESI, m/z): $[(M+1)]^+$ = 1018.60, Chemical Formula: $C_{55}H_{63}F_2N_9O_{11}$. Exact Mass: 1017.46. |
| 315 | ((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(2-((1-(2,6-dioxopiperidin-3-yl)-3-methyl-2-oxo-2,3-dihydro-1H-benzo[d]imidazol-5-yl)oxy)ethyl)piperidine-1-carboxylate |
| | $^1$H NMR (400 MHz, DMSO-$d_6$) chemical shifts 11.06 (s, 1H), 9.95 (s, 1H), 9.22 (d, J = 2.0 Hz, 1H), 7.81-7.70 (m, 1H), 7.40-7.27 (m, 2H), 7.04 (d, J = 2.8 Hz, 1H), 6.97 (d, J = 8.4 Hz, 1H), 6.85 (d, J = 2.4 Hz, 1H), 6.64-6.54 (m, 1H), 5.37-5.26 (m, 1H), 4.74 (d, J = 7.2 Hz, 1H), 4.40-4.06 (m, 2H), 4.06-3.78 (m, 7H), 3.66-3.44 (m, 1H), 3.43-3.35 (m, 1H), 3.31 (s, 2H), 2.99-2.84 (m, 3H), 2.83-2.53 (m, 7H), 2.43-2.27 (m, 2H), 2.26-1.75 (m, 8H), 1.74-1.53 (m, 10H), 1.17 (d, J = 8.0 Hz, 3H), 1.11-0.98 (m, 2H), 0.80-0.65 (m, 3H). $^{19}$F NMR (377 MHz, DMSO) chemical shifts −119.691(1F), −139.579(1F). LC/MS (ESI, m/z): $[(M+1)]^+$ = 1032.60 Chemical Formula: $C_{55}H_{63}F_2N_9O_9$, Exact Mass: 1031.47. |
| 316 | ((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(3-((1-(2,6-dioxopiperidin-3-yl)-3-methyl-2-oxo-2,3-dihydro-1H-benzo[d]imidazol-5-yl)oxy)propyl)piperidine-1-carboxylate |
| | $^1$H NMR (400 MHz, DMSO-$d_6$) δ 11.07 (s, 1H), 9.93 (s, 1H), 9.22 (d, J = 2.0 Hz, 1H), 7.78-7.74 (m, 1H), 7.40-7.27 (m, 2H), 7.06-7.03 (m, 1H), 6.98 (d, J = 8.4 Hz, 1H), 6.85-6.83 (m, 1H), 6.62-6.57 (m, 1H), 5.34-5.28 (m, 1H), 4.74 (d, J = 6.8 Hz, 1H), 4.38-4.28 (m, 1H), 4.18-3.78 (m, 9H), 3.66-3.49 (m, 1H), 3.45-3.35 (m, 1H), 3.31 (s, 2H), 2.98-2.84 (m, 3H), 2.83-2.58 (m, 5H), 2.41-2.28 (m, 1H), 2.21-2.10 (m, 1H), 2.10-1.90 (m, 5H), 1.87-1.78 (m, 3H), 1.76-1.48 (m, 10H), 1.48-1.36 (m, 1H), 1.35-1.28 (m, 2H), 1.17 (d, J = 9.2 Hz, 3H), 1.05-0.92 (m, 2H), 0.77-0.71 (m, 3H). LC/MS (ESI, m/z): $[(M+1)]^+$ = 318.05 Chemical Formula: $C_{56}H_{65}F_2N_9O_9$, Exact Mass: 1045.49. |
| 317 | ((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(4-((1-(2,6-dioxopiperidin-3-yl)-3-methyl-2-oxo-2,3-dihydro-1H-benzo[d]imidazol-5-yl)oxy)butyl)piperidine-1-carboxylate |
| | $^1$H NMR (400 MHz, DMSO-$d_6$) δ 11.08 (s, 1H), 9.22 (d, J = 4.0 Hz, 1H), 7.79-7.73 (m, 1H), 7.39-7.30 (m, 2H), 7.04 (t, J = 4.0 Hz, 1H), 6.98 (d, J = 8.0 Hz, 1H), 6.84 (d, J = 4.0 Hz, 1H), 6.62-6.55 (m, 1H), 5.36-5.27 (m, 1H), 4.75 (s, 1H), 4.33 (t, J = 16.0 Hz, 1H), 4.11 (t, J = 10.0 Hz, 1H), 4.07-3.88 (m, 6H), 3.87-3.79 (m, 1H), 3.72 (s, 1H), 3.62 (d, J = 14.0 Hz, 1H), 3.52 (d, J = 14.0 Hz, 1H), 2.97-2.84 (m, 3H), 2.81-2.57 (m, 5H), 2.37-2.32 (m, 1H), 2.20-1.88 (m, 4H), 1.85-1.76 (m, 3H), 1.74-1.49 (m, 9H), 1.42-1.38 (m, 3H), 1.26-1.13 (m, 4H), 1.03-0.88 (m, 2H), 0.78-0.73 (m, 3H). LC/MS (ESI, m/z): $[(M+1)]^+$ = 1065.65, Chemical Formula: $C_{55}H_{63}F_2N_9O_{11}$. Exact Mass: 1063.46. |
| 318 | ((3S,7aR)-7a-(((7-(8-ethyl-7-fluoro-3-hydroxynaphthalen-1-yl)-8-fluoro-4-((R)-3-hydroxy-3-methylpiperidin-1-yl)quinazolin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate |
| | $^1$H NMR (400 MHz, DMSO-$d_6$) δ 11.08 (br s, 1H), 9.90 (br s, 1H), 7.99-7.85 (m, 1H), 7.80-7.67 (m, 1H), 7.39-7.18 (m, 3H), 7.11-6.76 (m, 4H), 5.39-5.24 (m, 1H), 4.72-4.62 (m, 1H), 4.29-3.62 (m, 8H), 3.56-3.37 (m, 3H), 2.97-2.63 (m, 9H), 2.37 (s, 2H), 2.20-1.29 (m, 28H), 1.22-1.09 (m, 3H), 1.01-0.90 (m, 2H), 0.76-0.67 (m, 3H). $^{19}$F NMR (376 MHz, DMSO) δ −119.48 (1F), −128.34 (1F). LC/MS (ESI, m/z): $[(M+1)]^+$ = 1084.55 Chemical Formula: $C_{60}H_{71}F_2N_9O_8$, Exact Mass: 1083.54. |
| 319 | ((3R,7aS)-7a-(((7-(8-ethyl-7-fluoro-3-hydroxynaphthalen-1-yl)-8-fluoro-4-((R)-3-hydroxy-3-methylpiperidin-1-yl)quinazolin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate |
| | $^1$H NMR (400 MHz, DMSO-$d_6$) δ 11.08 (br s, 1H), 9.91 (br s, 1H), 7.98-7.88 (m, 1H), 7.81-7.68 (m, 1H), 7.42-7.22 (m, 3H), 7.12-6.81 (m, 4H), 5.41-5.26 (m, 1H), 4.72-4.63 (m, 1H), 4.14-3.80 (m, 8H), 3.55-3.43 (m, 2H), 3.01-2.63 (m, 10H), 2.40-2.30 (m, 2H), 2.28-1.34 (m, 26H), 1.27-1.11 (m, 4H), 1.01-0.88(m, 2H), 0.85-0.63 (m, 4H).$^{19}$F NMR (376 MHz, DMSO) δ −119.49 (1F), −128.33 (1F). LC/MS (ESI, m/z): [(M + 1)]+ = 1084.60 Chemical Formula: $C_{60}H_{71}F_2N_9O_8$, Exact Mass:1083.54. |
| 320 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 1-(1-(1-(2,6-dioxopiperidin-3-yl)-3-methyl-2-oxo-2,3-dihydro-1H-benzo[d]imidazol-5-yl)piperidin-4-yl)-1,7-diazaspiro[3.5]nonane-7-carboxylate |
| | $^1$H NMR (400 MHz, DMSO-$d_6$) δ 11.05 (s, 1H), 10.17 (s, 1H), 9.26-8.99 (m, 1H), 7.99-7.96 (m, 1H), 7.49-7.43 (m, 1H), 7.42-7.36 (m, 1H), 7.25-7.17 (m, 1H), 6.96-6.86 (m, 1H), 6.80-6.75 (m, 1H), 6.64-6.51 (m, 1H), 5.32-5.28 (m, 1H), 4.79-4.70 (m, 1H), 4.47-4.20 (m, 1H), 4.20-4.03 (m, 2H), 4.03-3.86 (m, 2H), 3.63-3.57 (m, 1H), 3.46-3.38 (m, 2H), 3.28 (s, 5H), 3.10 (s, 2H), 2.96-2.82 (m, 1H), 2.83-2.55 (m, 7H), 2.13-1.92 (m, 2H), 2.08-1.54 (m, 15H), 1.56-1.48 (m, 2H), 1.39-1.22 (m, 2H), 1.21-1.13 (m, 2H). $^{19}$F NMR (377 MHz, DMSO) δ −110.59 (1F), −140.50 (1F). LC/MS (ESI, m/z): $[(M+1)]^+$ = 1108.60 Chemical Formula: $C_{60}H_{67}F_2N_{11}O_8$, Exact Mass: 1107.51. |

-continued

| Compound No. | Compound Name / $^1$H NMR Peaks |
|---|---|
| 321 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 9-((4-(1-(2,6-dioxopiperidin-3-yl)-3-methyl-2-oxo-2,3-dihydro-1H-benzo[d]imidazol-5-yl)piperidin-1-yl)methyl)-3-azaspiro[5.5]undecane-3-carboxylate |
| | $^1$H NMR (400 MHz, DMSO-$d_6$) chemical shifts 11.09 (s, 1H), 10.18 (s, 1H), 9.14 (d, J = 61.6 Hz, 1H), 7.93-8.03 (m, 1H), 7.47 (t, J = 9.2 Hz, 1H), 7.40 (s, 1H), 7.22 (d, J = 16.4 Hz, 1H), 7.09 (s, 1H), 7.00 (d, J = 8.0 Hz, 1H), 6.91 (d, J = 8.4 Hz, 1H), 5.27-5.43 (m, 1H), 4.76 (d, J = 23.2 Hz, 1H), 4.27-4.43 (m, 1H), 4.25-4.02 (m, 4H), 3.95 (d, J = 3.2 Hz, 1H), 3.60 (t, J = 12.0 Hz, 2H), 2.93 (d, J = 12.0 Hz, 3H), 2.80-2.59 (m, 5H), 2.32 (s, 1H), 2.23-1.90 (m, 5H), 0.85 (d, 8H), 1.88-1.30 (m, 22H), 1.28-1.12 (m, 7H), 1.05 (d, J = 10.4 Hz, 5h), 0.85 (J = 9.2 Hz, 2H). LC/MS (ESI, m/z): $[(M + 1)]^+$ = 1149.60 Chemical Formula: $C_{64}H_{74}F_2N_{10}O_8$, Exact Mass: 1148.57. |
| 322 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 3-(4-(1-(2,6-dioxopiperidin-3-yl)-3-methyl-2-oxo-2,3-dihydro-1H-benzo[d]imidazol-5-yl)-[1,4'-bipiperidin]-1'-yl)azetidine-1-carboxylate |
| | $^1$H NMR (300 MHz, Methanol-$d_4$) δ 9.20 (d, J = 32.0 Hz, 1H), 7.93-7.83 (m, 1H), 7.41-7.24 (m, 3H), 7.12-6.99 (m, 3H), 5.38-5.29 (m, 1H), 4.76-4.51 (m, 4H), 4.49-4.29 (m, 3H), 4.06 (s, 3H), 3.87 (s, 2H), 3.76-3.55 (m, 3H), 3.44 (d, J = 6.0 Hz, 10H), 3.15 (s, 2H), 3.04-2.73 (m, 10H), 2.46-1.63 (m, 25H), 1.34-1.30 (m, 4H). LC/MS (ESI, m/z): $[(M + 1)]^+$ = 1122.65, Chemical Formula: $C_{61}H_{71}F_2N_{11}O_8$. Exact Mass: 1121.53. |
| 323 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-((4-(1-(2,6-dioxopiperidin-3-yl)-3-methyl-2-oxo-2,3-dihydro-1H-benzo[d]imidazol-5-yl)piperidin-1-yl)methyl)-7-azaspiro[3.5]nonane-7-carboxylate |
| | $^1$H NMR (300 MHz, Methanol-$d_4$) δ 9.20 (d, J = 32.0 Hz, 1H), 7.88 (t, J = 8.0 Hz, 1H), 7.41-7.20 (m, 2H), 7.14-6.97 (m, 2H), 5.40-5.29 (m, 1H), 4.76-4.51 (m, 3H), 4.49-4.28 (m, 2H), 4.08 (s, 1H), 3.67 (d, J = 12.0 Hz, 1H), 3.58 (s, 1H), 3.41 (d, J = 18.0 Hz, 10H), 3.07 (d, J = 6.0 Hz, 2H), 2.88-2.83 (m, 6H), 2.43-1.74 (m, 21H), 1.65 (s, 4H), 1.52 (s, 2H), 1.30 (d, J = 14.0 Hz, 4H). LC/MS (ESI, m/z): $[(M + 1)]^+$ = 1121.65, Chemical Formula: $C_{62}H_{72}F_2N_{10}O_8$. Exact Mass: 1120.53. |
| 324 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1'-(1-(2,6-dioxopiperidin-3-yl)-3-methyl-2-oxo-2,3-dihydro-1H-benzo[d]imidazol-5-yl)-[1,4'-bipiperidin]-4-yl)carbamate |
| | $^1$H NMR (400 MHz, DMSO-$d_6$) δ 11.06 (s, 1H), 10.17 (s, 1H), 9.22-9.05 (m, 1H), 7.82-7.76 (m, 1H), 7.53-7.42 (m, 1H), 7.42-7.35 (m, 1H), 7.28-7.13 (m, 2H), 6.92 (d, J = 8.8 Hz, 1H), 6.82 (d, J = 2.4 Hz, 1H), 6.62 (dd, J = 8.8, 2.4 Hz, 1H), 5.31-2.27 (m, 1H), 4.79-4.71 (m, 1H), 4.43-4.29 (m, 1H), 4.19-3.86 (m, 5H), 3.64-3.51 (m, 3H), 3.30 (s, 3H), 3.29-3.18 (m, 2H), 2.97-2.79 (m, 3H), 2.79-2.54 (m, 6H), 2.37-2.27 (m, 1H), 2.23-1.92 (m, 5H), 1.90-1.38 (m, 15H), 1.38-1.30 (m, 2H), 1.21-1.14 (m, 3H). $^{19}$F NMR (377 MHz, DMSO) δ −110.58(1F), −140.66(1F). LC/MS (ESI, m/z): $[(M + 1)]^+$ = 1082.65 Chemical Formula: $C_{58}H_{65}F_2N_{11}O_8$, Exact Mass:1081.50. |
| 325 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1-(1-(1-(2,6-dioxopiperidin-3-yl)-3-methyl-2-oxo-2,3-dihydro-1H-benzo[d]imidazol-5-yl)piperidin-4-yl)azetidin-3-yl)carbamate |
| | $^1$H NMR (400 MHz, DMSO-$d_6$) δ 11.06 (br s, 1H), 10.17 (br s, 1H), 9.29-8.96 (m, 1H), 8.03-7.92 (m, 1H), 7.79-7.64 (m, 1H), 7.52-7.35 (m, 2H), 7.28-7.14 (m, 1H), 6.95-6.75 (m, 2H), 6.67-6.54 (m, 1H), 5.35-5.21 (m, 1H), 4.80-4.64 (m, 1H), 4.39-3.93 (m, 8H), 3.63-3.40 (m, 5H), 3.30-3.19 (m, 5H), 2.93-2.60 (m, 9H), 2.16-1.90 (m, 4H), 1.77-1.45 (m, 12H), 1.30-1.13 (m, 5H). $^{19}$F NMR (376 MHz, DMSO) δ −110.57 (1F), −141.27 (1F). LC/MS (ESI, m/z): [(M + 1)]+ = 1054.45 Chemical Formula: $C_{56}H_{61}F_2N_{11}O_8$, Exact Mass: 1053.47. |
| 326 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 7-(1-(1-(2,6-dioxopiperidin-3-yl)-3-methyl-2-oxo-2,3-dihydro-1H-benzo[d]imidazol-5-yl)piperidin-4-yl)-1,7-diazaspiro[3.5]nonane-1-carboxylate |
| | $^1$H NMR (400 MHz, DMSO-$d_6$) chemical shifts 11.06 (s, 1H), 10.17 (s, 1H), 8.99-9.25 (m, 1H), 7.97 (d, J = 8.4 Hz, 1H), 7.36-7.50 (m, 2H), 7.17-7.26 (m, 1H), 7.01-6.77 (m, 2H), 6.70-6.50 (m, 1H), 5.23-5.34 (m, 1H), 4.75 (d, J = 24.4 Hz, 1H), 4.57-4.02 (m, 6H), 4.00-3.92 (m, 1H), 3.86-3.46 (m, 5H), 2.96-2.56 (m, 9H), 2.30 (s, 1H), 2.19-1.88 (m, 9H), 1.82-1.62 (m, 12H), 1.53 (s, 3H), 1.30-1.10 (m, 5H), 0.84 (t, J = 8.8 Hz, 1H). LC/MS (ESI, m/z): $[(M + 1)]^+$ = 1108.50 Chemical Formula: $C_{60}H_{67}F_2N_{11}O_8$, Exact Mass: 1107.51. |
| 327 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 1-((4-(1-(2,6-dioxopiperidin-3-yl)-3-methyl-2-oxo-2,3-dihydro-1H-benzo[d]imidazol-5-yl)piperidin-1-yl)methyl)-7-azaspiro[3.5]nonane-7-carboxylate |

-continued

| Compound No. | Compound Name / $^1H$ NMR Peaks |
|---|---|
| | $^1H$ NMR (400 MHz, DMSO-$d_6$) δ 11.07 (s, 1H), 9.16-9.10 (m, 1H), 8.01-7.93 (m, 1H), 7.46 (t, J = 8.0 Hz, 1H), 7.40 (d, J = 2.8 Hz, 1H), 7.26-7.17 (m, 1H), 7.06 (s, 1H), 6.99 (d, J = 8.0 Hz, 1H), 6.89 (d, J = 8.0 Hz, 1H), 5.38-5.28 (m, 1H), 4.75 (d, J = 24.0 Hz, 1H), 4.44-4.02 (m, 5H), 4.02-3.91 (m, 2H), 3.81-3.52 (m, 5H), 3.05-2.83 (m, 6H), 2.80-2.59 (m, 7H), 2.27-2.15 (m, 2H), 2.10-1.86 (m, 7H), 1.84-1.42 (m, 23H), 1.20-1.15(m, 3H). LC/MS (ESI, m/z): $[(M + 1)]^+$ = 1121.60, Chemical Formula: $C_{62}H_{70}F_2N_{10}O_8$. Exact Mass: 1120.53. |
| 328 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(1-(1-(2,6-dioxopiperidin-3-yl)-3-methyl-2-oxo-2,3-dihydro-1H-benzo[d]imidazol-5-yl)piperidin-4-yl)-2,6-diazaspiro[3.5]nonane-6-carboxylate |
| | $^1H$ NMR (400 MHz, DMSO-$d_6$) δ 11.05 (s, 1H), 9.13 (d, J = 66.0 Hz, 1H), 8.01-7.94 (m, 1H), 7.46 (t, J = 8.0 Hz, 1H), 7.39 (t, J = 2.0 Hz, 1H), 7.26-7.17 (m, 1H), 6.90 (d, J = 8.0 Hz, 1H), 6.79 (s, 1H), 6.59 (s, 1H), 5.33-5.23 (m, 1H), 4.76 (d, J = 30.0 Hz, 1H), 4.43-4.04 (m, 5H), 4.01-3.92 (m, 1H), 3.57 (d, J = 12.0 Hz, 1H), 3.46 (d, J = 16.0 Hz, 4H), 3.38-3.35 (m, 1H), 3.00 (d, J = 6.0 Hz, 2H), 2.94-2.57 (m, 9H), 2.15 (s, 1H), 2.10-1.94 (m, 3H), 1.83-1.59 (m, 12H), 1.51 (q, J = 10.0, 9.0 Hz, 1H), 1.41 (d, J = 12.0 Hz, 2H), 1.33-1.21 (m, 3H), 1.17 (d, J = 18.0 Hz, 3H). LC/MS (ESI, m/z): $[(M + 1)]^+$ = 1108.65, Chemical Formula: $C_{60}H_{67}F_2N_{11}O_8$. Exact Mass: 1107.51. |
| 329 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-((1-(1-(2,6-dioxopiperidin-3-yl)-3-methyl-2-oxo-2,3-dihydro-1H-benzo[d]imidazol-5-yl)piperidin-4-yl)methyl)-2,6-diazaspiro[3.5]nonane-6-carboxylate |
| | $^1H$ NMR (400 MHz, DMSO-$d_6$) chemical shifts 11.04 (s, 1H), 9.26-8.99 (m, 1H), 8.24 (s, 2H), 7.96 (t, J = 7.6 Hz, 1H), 7.51-7.36 (m, 2H), 7.29-7.15 (m, 1H), 6.86 (d, J = 8.4 Hz, 1H), 6.40-6.07 (m, 2H), 5.31-5.17 (m, 1H), 4.41-4.12 (m, 6H), 4.11-4.04 (m, 2H), 3.99-3.91 (m, 2H), 3.63-3.43 (m, 5H), 3.06 (s, 3H), 2.95-2.71 (m, 8H), 2.68-2.58 (m, 3H), 2.35-2.16 (m, 2H), 2.11-1.90 (m, 5H), 1.80-1.71 (m, 6H), 1.71-1.56 (m, 7H), 1.54-1.35 (m, 6H), 1.22-1.12 (m, 3H). $^{19}F$. NMR (377 MHz, DMSO) chemical shifts −110.683 (1F), −140.841(1F). LC/MS (ESI, m/z): $[(M + 1)]^+$ = 1122.75 Chemical Formula: $C_{61}H_{69}F_2N_{11}O_8$, Exact Mass: 1167.54. |
| 330 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(2,6-dioxopiperidin-3-yl)-3-methyl-2-oxo-2,3-dihydro-1H-benzo[d]imidazol-5-yl)oxy)piperidine-1-carboxylate |
| | $^1H$ NMR (400 MHz, DMSO-$d_6$) chemical shifts 11.07 (s, 1H), 9.93 (s, 1H), 9.22 (d, J = 2.8 Hz, 1H), 7.80-7.72 (m, 1H), 7.39-7.29 (m, 2H), 7.04 (t, J = 3.2 Hz, 1H), 6.97 (d, J = 8.4 Hz, 1H), 6.90 (s, 1H), 6.70-6.60 (m, 1H), 5.36-5.27 (m, 1H), 4.74 (d, J = 6.8 Hz, 1H), 4.51 (s, 1H), 4.39-4.26 (m, 1H), 4.17-3.99 (m, 3H), 3.98-3.81 (m, 2H), 3.74-3.49 (m, 4H), 3.45-3.34 (m, 2H), 2.98-2.84 (m, 3H), 2.74-2.57 (m, 4H), 2.40-2.27 (m, 2H), 2.12-1.81 (m, 10H), 1.73-1.49 (m, 9H), 1.17 (d, J = 8.8 Hz, 3H), 0.78-0.68 (m, 3H). $^{19}F$ NMR (377 MHz, DMSO) chemical shifts −119.597 (1F), −139.616 (1F). LC/MS (ESI, m/z): $[(M + 1)]^+$ = 1004.50 Chemical Formula: $C_{53}H_{59}F_2N_9O_9$, Exact Mass: 1003.44. |
| 337 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(3-(1-(2,6-dioxopiperidin-3-yl)-3-methyl-2-oxo-2,3-dihydro-1H-benzo[d]imidazol-5-yl)pyrrolidin-1-yl)piperidine-1-carboxylate |
| | $^1H$ NMR (400 MHz, DMSO-$d_6$) chemical shifts 11.08 (s, 1H), 9.21 (s, 1H), 7.82-7.69 (m, 1H), 7.41-7.24 (m, 2H), 7.12-7.01 (m, 2H), 7.02-6.90 (m, 2H), 5.41-5.25 (m, 1H), 4.75 (s, 1H), 4.40-4.25 (m, 1H), 4.17-3.98 (m, 3H), 3.97-3.79 (m, 4H), 3.66-3.34 (m, 9H), 2.98-2.84 (m, 5H), 2.75-2.58 (m, 5H), 2.38-2.10 (m, 4H), 2.07-1.88 (m, 4H), 1.86-1.75 (m, 5H), 1.73-1.46 (m, 5H), 1.38-1.26 (m, 2H), 1.16 (d, J = 8.8 Hz, 3H), 0.82-0.66 (m, 3H). $^{19}F$ NMR (377 MHz, DMSO) chemical shifts −119.617 (1F), −139.571(1F). LC/MS (ESI, m/z): $[(M + 1)]^+$ = 1057.65 Chemical Formula: $C_{57}H_{66}F_2N_{10}O_8$•$CH_2O_2$, Exact Mass: 1056.51. |
| 338 | ((3S,7aS)-7a-(((7-(8-chloro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate |
| | $^1H$ NMR (400 MHz, DMSO-$d_6$) δ 11.08 (s, 1H), 9.26-9.15 (m, 1H), 7.89-7.81 (m, 1H), 7.46-7.36 (m, 3H), 7.19-7.08 (m, 2H), 7.06-6.86 (m, 2H), 5.36-5.30 (m, 1H), 4.75 (s, 1H), 4.30 (s, 1H), 4.23-4.03 (m, 6H), 3.63 (s, 1H), 2.95-2.87 (m, 3H), 2.78-2.64 (m, 5H), 2.07-1.95 (m, 5H), 1.75-1.68 (m, 16H), 1.55-1.47 (m, 8H), 1.25-1.15 (m, 7H), 0.92-0.71 (m, 2H). $^{19}F$ NMR (377 MHz, DMSO) δ −140.23(1F). LC/MS (ESI, m/z): $[(M + 1)]^+$ = 1099.50 Chemical Formula: $C_{59}H_{68}ClFN_{10}O_8$, Exact Mass: 1098.49. |
| 339 | ((3S,7aS)-7a-(((7-(8-ethyl-7-fluoro-3-hydroxynaphthalen-1-yl)-8-fluoro-4-((S)-3-(hydroxymethyl)piperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate |
| | $^1H$ NMR (400 MHz, DMSO-$d_6$) δ 11.08 (s, 1H), 9.93 (s, 1H), 9.13-9.05 (m, 1H), 7.80- |

-continued

| Compound No. | Compound Name<br>$^1$H NMR Peaks |
|---|---|
| | 7.72 (m, 1H), 7.43-7.29 (m, 1H), 7.17-6.95 (m, 2H), 6.95-6.88 (m, 1H), 5.39-5.29 (m, 1H), 4.76-4.66 (m, 1H), 4.57-4.50 (m, 2H), 4.27-4.05 (m, 3H), 3.96 (s, 2H), 3.54-3.46 (m, 2H), 3.32-3.15 (m, 4H), 2.99-2.85 (m, 2H), 2.82-2.55 (m, 6H), 2.39-2.30 (m, 1H), 2.21-2.10 (m, 2H), 2.09-1.80 (m, 6H), 1.82-1.57 (m, 11H), 1.58-1.49 (m, 1H), 1.43-1.15 (m, 1H), 1.08-0.81 (m, 2H), 0.79-0.69 (m, 2H). $^{19}$F NMR (377 MHz, DMSO) δ −119.60(1F), −139.26(1F). LC/MS (ESI, m/z): $[(M + 1)]^+$ = 1085.60 Chemical Formula: $C_{59}H_{70}F_2N_{10}O_8$, Exact Mass: 1084.53. |
| 340 | ((3S,7aS)-7a-(((7-(8-ethyl-7-fluoro-3-hydroxynaphthalen-1-yl)-8-fluoro-4-((R)-3-(hydroxymethyl)piperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) chemical shifts 11.08 (s, 1H), 9.09 (d, J = 2.8 Hz, 1H), 7.71-7.80 (m, 1H), 7.39-7.31 (m, 2H), 7.09 (s, 1H), 7.06-6.96 (m, 2H), 6.86-6.93 (m, 1H), 5.29-5.38 (m, 1H), 4.61-4.39 (m, 2H), 4.07-4.30 (m, 5H), 3.96 (d, J = 12.8 Hz, 2H), 3.38-3.50 (m, 4H), 2.85-2.98 (m, 4H), 2.81-2.58 (m, 7H), 2.37 (d, J = 9.2 Hz, 2H), 2.18-1.91 (m, 8H), 1.72 (d, J = 7.6 Hz, 15H), 1.57-1.33 (m, 3H), 0.97 (d, J = 12.4 Hz, 2H), 0.85 (d, J = 7.6 Hz, 1H), 0.69-0.77 (m, 3H). LC/MS (ESI, m/z): $[(M + 1)]^+$ = 1085.63 Chemical Formula: : $C_{59}H_{70}F_2N_{10}O_8$•$CH_2O_2$, Exact Mass: 1084.53. |
| 341 | ((3S,7aS)-7a-(((7-(8-ethyl-7-fluoro-3-hydroxynaphthalen-1-yl)-8-fluoro-4-(3-(hydroxymethyl)-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.07 (br s, 1H), 9.98-9.87 (m, 1H), 9.17-9.11 (m, 1H), 7.81-7.69 (m, 1H), 7.39-7.29 (m, 2H), 7.11-6.86 (m, 4H), 5.38-5.24 (m, 1H), 4.79-4.61 (m, 1H), 4.23-3.58 (m, 10H), 3.27-3.11 (m, 2H), 2.98-2.54 (m, 10H), 2.37-2.28 (m, 1H), 2.16-1.43 (m, 27H), 1.23 (s, 1H), 1.05-0.58 (m, 9H). $^{19}$F NMR (377 MHz, DMSO) δ −119.60 (1F), −139.32 (1F). LC/MS (ESI, m/z): $[(M + 1)]^+$ = 1099.65, Chemical Formula: $C_{60}H_{72}F_2N_{10}O_8$. Exact Mass: 1098.55. |
| 344 | ((3S,7aS)-7a-(((4-(azepan-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) chemical shifts 11.08 (s, 1H), 9.93 (s, 1H), 9.15 (d, J = 1.6 Hz, 1H), 7.83-7.71 (m, 1H), 7.40-7.28 (m, 2H), 7.11 (s, 1H), 7.03-6.87 (m, 3H), 5.41-5.26 (m, 1H), 4.24-3.92 (m, 7H), 3.28-3.17 (m, 4H), 2.88 (t, J = 8.4 Hz, 3H), 2.78-2.56 (m, 5H), 2.41-2.10 (m, 4H), 2.08-1.87 (m, 8H), 1.80-1.64 (m, 12H), 1.63-1.20 (m, 15H), 0.74 (t, J = 7.6 Hz, 3H). $^{19}$F NMR (377 MHz, DMSO) chemical shifts −119.685 (1F), −138.962 (1F). LC/MS (ESI, m/z): $[(M + 1)]^+$ = 1095.50 Chemical Formula: $C_{61}H_{72}F_2N_{10}O_7$, Exact Mass: 1094.56. |
| 345 | ((3S,7aS)-7a-(((7-(8-ethyl-7-fluoro-3-hydroxynaphthalen-1-yl)-8-fluoro-4-(hexahydropyrrolo[1,2-a]pyrazin-2(1H)-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.08 (br s, 1H), 9.94 (br s, 1H), 9.13 (s, 1H), 7.83-7.69 (m, 1H), 7.40-7.28 (m, 2H), 7.17-6.81 (m, 4H), 5.40-5.24 (m, 1H), 4.74-4.48 (m, 2H), 4.28-4.02 (m, 4H), 3.60-3.41 (m, 2H), 3.28-2.59 (m, 16H), 2.42-1.32 (m, 35H), 0.84-0.64 (m, 3H). $^{19}$F NMR (376 MHz, DMSO) δ −119.62 (1F), −139.22 (1F). LC/MS (ESI, m/z): $[(M + 1)]^+$ = 1122.65 Chemical Formula: $C_{62}H_{73}F_2N_{11}O_7$, Exact Mass:1121.57. |
| 346 | ((3S,7aS)-7a-(((4-(3-azabicyclo[3.1.0]hexan-3-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.08 (s, 1H), 9.26 (s, 1H), 7.79-7.72 (m, 1H), 7.38-7.31 (m, 2H), 7.10 (d, J = 1.6 Hz, 1H), 7.02-6.97 (m, 1H), 6.94-6.88 (m, 1H), 5.36-5.28 (m, 1H), 4.28-4.01 (m, 6H), 3.33 (s, 8H), 2.90 (d, J = 9.6 Hz, 3H), 2.80-2.58 (m, 4H), 2.34 (d, J = 17.6 Hz, 1H), 2.19-2.09 (m, 1H), 2.09-1.90 (m, 4H), 1.87-1.61 (m, 12H), 1.51 (q, J = 10.2, 9.6 Hz, 4H), 1.39 (s, 2H), 0.88-0.81 (m, 1H), 0.73 (t, J = 7.6 Hz, 2H). LC/MS (ESI, m/z): $[(M + 1)]^+$ = 1079.55, Chemical Formula: $C_{60}H_{68}F_2N_{10}O_7$. Exact Mass: 1078.52. |
| 347 | ((3S,7aS)-7a-(((7-(8-ethyl-7-fluoro-3-hydroxynaphthalen-1-yl)-8-fluoro-4-(2-azaspiro[3.3]heptan-2-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.08 (s, 1H), 8.93 (s, 1H), 7.80-7.74 (m, 1H), 7.52-7.28 (m, 3H), 7.10 (s, 1H), 7.02-6.96 (m, 2H), 6.91 (d, J = 8.4 Hz, 1H), 5.37-5.30 (m, 1H), 4.83 (s, 2H), 4.34 (s, 3H), 4.23-4.10 (m, 4H), 4.05 (d, J = 10.4 Hz, 2H), 3.25 (s, 4H), 2.89 (s, 3H), 2.79-2.58 (m, 6H), 2.28 (t, J = 7.6 Hz, 5H), 2.14-1.90 (m, 6H), 1.85 (p, J = 7.6 Hz, 2H), 1.80-1.60 (m, 13H), 1.50 (s, 5H), 1.40 (s, 2H), 0.97 (s, 1H), 0.72 (t, J = 7.2 Hz, 3H). LC/MS (ESI, m/z): $[(M + 1)]^+$ = 1093.60, Chemical Formula: $C_{61}H_{70}F_2N_{10}O_7$. Exact Mass: 1092.54. |

-continued

| Compound No. | Compound Name<br>$^1H$ NMR Peaks |
|---|---|
| 348 | ((3S,7aS)-7a-(((7-(8-ethyl-7-fluoro-3-hydroxynaphthalen-1-yl)-8-fluoro-4-(pyrrolidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1H$ NMR (400 MHz, DMSO-$d_6$) δ 11.08 (br s, 1H), 9.93 (br s, 1H), 9.29 (s, 1H), 7.81-7.69(m, 1H), 7.39-7.27 (m, 2H), 7.16-6.83 (m, 4H), 5.43-5.26 (m, 1H), 4.35-3.71 (m, 8H), 3.28-3.18 (m, 3H), 2.98-2.61 (m, 8H), 2.50-2.27 (m, 7H), 2.08-1.36 (m, 28H), 0.73 (t, J = 7.2 Hz, 3H). $^{19}F$ NMR (376 MHz, DMSO) δ −119.70 (1F), −139.07 (1F). LC/MS (ESI, m/z): $[(M + 1)]^+$ = 1067.60 Chemical Formula: $C_{59}H_{68}F_2N_{10}O_7$, Exact Mass: 1066.52. |
| 349 | ((3S,7aS)-7a-(((7-(8-ethyl-7-fluoro-3-hydroxynaphthalen-1-yl)-8-fluoro-4-((S)-3-hydroxypyrrolidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1H$ NMR (400 MHz, DMSO-$d_6$) δ 11.08 (s, 1H), 9.93 (s, 1H), 9.29 (s, 1H), 7.80-7.73 (m, 1H), 7.39-7.31 (m, 2H), 7.11 (d, J = 1.6 Hz, 1H), 7.05-6.97 (m, 2H), 6.93-6.89 (m, 1H), 5.38-5.29 (m, 1H), 5.16 (s, 1H), 4.48 (s, 1H), 4.25-4.05 (m, 5H), 3.88 (d, J = 44.8 Hz, 2H), 3.25 (d, J = 5.6 Hz, 3H), 2.98-2.85 (m, 3H), 2.79-2.58 (m, 6H), 2.37 (d, J = 7.6 Hz, 2H), 2.21-1.90 (m, 8H), 1.83-1.59 (m, 14H), 1.57-1.34 (m, 8H), 0.74 (q, J = 7.2 Hz, 3H). LC/MS (ESI, m/z): $[(M + 1)]^+$ = 1083.55, Chemical Formula: $C_{62}H_{72}F_2N_{10}O_8$. Exact Mass: 1082.52. |
| 350 | ((3S,7aS)-7a-(((7-(8-ethyl-7-fluoro-3-hydroxynaphthalen-1-yl)-8-fluoro-4-((R)-3-hydroxypyrrolidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1H$ NMR (400 MHz, DMSO-$d_6$) chemical shifts 11.08 (s, 1H), 9.93 (s, 1H), 9.29 (s, 1H), 7.81-7.73 (m, 1H), 7.40-7.29 (m, 2H), 7.15-6.97 (m, 3H), 6.91 (d, J = 8.0 Hz, 1H), 5.39-5.28 (m, 1H), 5.16 (s, 1H), 4.48 (s, 1H), 4.27-4.05 (m, 6H), 3.83 (s, 1H), 2.94-2.85 (m, 4H), 2.78-2.58 (m, 11H), 2.39-2.31 (m, 1H), 2.19-1.89 (m, 8H), 1.81-1.62 (m, 12H), 1.57-1.36 (m, 7H), 1.24 (s, 1H), 0.85 (d, J = 7.6 Hz, 1H), 0.78-0.69 (m, 3H). $^{19}F$ NMR (377 MHz, DMSO) chemical shifts −119.686 (1F), −139.504 (1F). LC/MS (ESI, m/z): $[(M + 1)]^+$ = 1083.60 Chemical Formula: $C_{59}H_{68}F_2N_{10}O_8$, Exact Mass: 1082.52. |
| 351 | ((3S,7aS)-7a-(((7-(8-ethyl-7-fluoro-3-hydroxynaphthalen-1-yl)-8-fluoro-4-((S)-2-(hydroxymethyl)pyrrolidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1H$ NMR (400 MHz, DMSO-$d_6$) δ 11.08 (br s, 1H), 10.01-9.81 (m, 1H), 9.26 (s, 1H), 7.84-7.67 (m, 1H), 7.40-7.25 (m, 2H), 7.16-6.78 (m, 4H), 5.44-5.25 (m, 1H), 5.05-4.60 (m, 2H), 4.26-3.93 (m, 6H), 3.70 (s, 2H), 3.24 (s, 3H), 2.98-2.55 (m, 9H), 2.49-2.28 (m, 3H), 2.22-1.88 (m, 10H), 1.82-1.14 (m, 21H), 0.83-0.61 (m, 3H). $^{19}F$ NMR (376 MHz, DMSO) δ −119.74 (1F), −139.22 (1F). LC/MS (ESI, m/z): $[(M + 1)]^+$ = 1097.55 Chemical Formula: $C_{60}H_{70}F_2N_{10}O_8$, Exact Mass: 1096.53. |
| 352 | ((3S,7aS)-7a-(((7-(8-ethyl-7-fluoro-3-hydroxynaphthalen-1-yl)-8-fluoro-4-((R)-2-(hydroxymethyl)pyrrolidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1H$ NMR (400 MHz, DMSO-$d_6$) δ 11.08 (s, 1H), 9.93 (s, 1H), 9.29-9.23 (m, 1H), 7.85-7.70 (m, 1H), 7.41-7.28 (m, 2H), 7.13-7.09 (m, 1H), 7.06-6.95 (m, 2H), 6.94-6.88 (m, 1H), 5.35-5.30 (m, 1H), (s, 5H), 3.25 4.91 (s, 1H), 4.70 (s, 1H), 4.40-3.96 (m, 6H), 3.71 (s, 2H), 3.32 1.91 (m, 9H), (s, 4H), 2.98-2.83 (m, 3H), 2.78-2.61 (m, 5H), 2.45-2.30 (m, 1H), 2.23- $^{19}F$ NMR (377 1.85-1097.55 1.60 (m, 12H), 1.57-1.44 (m, 5H), 1.40 (s, 2H), 0.80-0.70 (m, 3H). MHz, DMSO) δ −119.73(1F), −139.19(1F). LC/MS (ESI, m/z): $[(M + 1)]^+$ = Chemical Formula: $C_{60}H_{70}F_2N_{10}O_8$, Exact Mass: 1096.53. |
| 354 | ((3S,7aS)-7a-(((7-(8-ethyl-7-fluoro-3-hydroxynaphthalen-1-yl)-8-fluoro-4-((S)-3-hydroxypiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1H$ NMR (400 MHz, DMSO-$d_6$) chemical shifts 11.08 (s, 1H), 9.93 (s, 1H), 9.19-9.12 (m, 1H), 7.81-7.71 (m, 1H), 7.40-7.29 (m, 2H), 7.11 (s, 1H), 7.06-6.97 (m, 2H), 6.91 (d, J = 8.0 Hz, 1H), 5.38-5.28 (m, 1H), 5.15-5.07 (m, 1H), 4.26-3.90 (m, 7H), 3.85-3.53 (m, 4H), 3.23 (s, 3H), 2.94-2.84 (m, 3H), 2.76-2.57 (m, 7H), 2.43-2.26 (m, 2H), 2.18-1.89 (m, 8H), 1.79-1.59 (m, 14H), 1.57-1.35 (m, 7H), 0.74 (t, J = 7.2 Hz, 3H). $^{19}F$ NMR (377 MHz, DMSO) chemical shifts −119.638 (1F), −139.342 (1F). LC/MS (ESI, m/z): $[(M + 1)]^+$ = 1097.50 Chemical Formula: $C_{60}H_{70}F_2N_{10}O_8$, Exact Mass: 1096.54. |
| 355 | ((3S,7aS)-7a-(((7-(8-ethyl-7-fluoro-3-hydroxynaphthalen-1-yl)-8-fluoro-4-((R)-3-hydroxy-3-methylpiperidin-1-yl)quinazolin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1H$ NMR (400 MHz, DMSO-$d_6$) chemical shifts 11.08 (s, 1H), 9.96 (s, 1H), 7.92 (t, J = 8.4 |

-continued

| Compound No. | Compound Name<br>$^1$H NMR Peaks |
|---|---|
| | Hz, 1H), 7.79-7.71 (m, 1H), 7.37-7.26 (m, 3H), 7.10 (d, J = 1.6 Hz, 1H), 7.01-6.88 (m, 3H), 5.39-5.27 (m, 1H), 4.68 (s, 1H), 4.25-4.00 (m, 5H), 3.92-3.78 (m, 1H), 3.55-3.35 (m, 7H), 3.25 (s, 5H), 2.97-2.83 (m, 3H), 2.82-2.57 (m, 5H), 2.41-2.29 (m, 2H), 2.10-1.90 (m, 5H), 1.84-1.60 (m, 14H), 1.58-1.45 (m, 5H), 1.39 (t, J = 5.6 Hz, 2H), 1.20-1.11 (m, 3H), 0.77-0.65 (m, 3H). $^{19}$F NMR (377 MHz, DMSO) chemical shifts −119.502 (1F), −128.357 (1F). LC/MS (ESI, m/z): [(M + 1)]$^+$ = 1110.60 Chemical Formula: $C_{62}H_{73}F_2N_9O_8$•$CH_2O_2$, Exact Mass: 1155.56. |
| 357 | ((3S,7aS)-7a-(((4-(4,4-difluoropiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) chemical shifts 11.08 (s, 1H), 9.95 (s, 1H), 9.15 (s, 1H), 7.73-7.82 (m, 1H), 7.38-7.28 (m, 2H), 7.11 (s, 1H), 7.05-6.96 (m, 2H), 6.93-6.87 (m, 1H), 5.34 (m, 1H), 4.41-3.80 (m, 9H), 2.89 (d, J = 10.4 Hz, 3H), 2.56-2.80 (m, 5H), 2.30 (t, J = 7.6 Hz, 6H), 2.18-1.90 (m, 5H), 1.81-1.58 (m, 13H), 1.32-1.56 (m, 8H), 1.24 (s, 1H), 0.73 (t, J = 7.6 Hz, 3H). LC/MS (ESI, m/z): [(M + 1)]$^+$ = 1117.65 Chemical Formula: : $C_{60}H_{68}F_4N_{10}O_7$, Exact Mass: 1116.52. |
| 358 | ((3S,7aS)-7a-(((7-(8-ethyl-7-fluoro-3-hydroxynaphthalen-1-yl)-8-fluoro-4-(4-hydroxypiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) chemical shifts 11.08 (s, 1H), 9.93 (s, 1H), 9.07 (s, 1H), 7.70-7.83 (m, 1H), 7.39-7.30 (m, 2H), 7.11 (d, J = 1.6 Hz, 1H), 7.04-6.97 (m, 2H), 6.88-6.94 (m, 1H), 5.28-5.39 (m, 1H), 4.89 (d, J = 4.0 Hz, 1H), 4.28-4.05 (m, 6H), 3.90 (d, J = 3.6 Hz, 1H), 3.63-6.79 (m, 2H), 2.89 (d, J = 10.0 Hz, 3H), 2.77-2.59 (m, 5H), 2.43-2.27 (m, 2H), 2.20-1.88 (m, 8H), 1.79-1.58 (m, 15H), 1.55-1.46 (m, 5H), 1.39 (s, 2H), 1.24 (s, 1H), 0.89-0.62 (m, 5H). LC/MS (ESI, m/z): [(M + 1)]$^+$ = 1097.55 Chemical Formula: : $C_{60}H_{70}F_2N_{10}O_8$, Exact Mass: 1096.53. |
| 362 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(7-(1-(2,6-dioxopiperidin-3-yl)-3-methyl-2-oxo-2,3-dihydro-1H-benzo[d]imidazol-5-yl)-2,7-diazaspiro[3.5]nonan-2-yl)piperidine-1-carboxylate<br>$^1$H NMR (400 MHz, DMSO-$d_6$) δ 11.05 (s, 1H), 9.93 (s, 1H), 9.23 (d, J = 2.4 Hz, 1H), 7.80-7.74 (m, 1H), 7.39-7.30 (m, 2H), 7.04 (d, J = 2.8 Hz, 1H), 6.92 (d, J = 8.4 Hz, 1H), 6.82 (d, J = 2.4 Hz, 1H), 6.64-6.59 (m, 1H), 5.33-5.25 (m, 1H), 4.75 (d, J = 7.6 Hz, 1H), 4.33 (t, J = 14.4 Hz, 1H), 4.26-3.98 (m, 5H), 3.75 (d, J = 12.4 Hz, 2H), 3.64 (d, J = 13.2 Hz, 1H), 3.54 (d, J = 13.2 Hz, 1H), 2.97 (d, J = 29.6 Hz, 11H), 2.80-2.57 (m, 6H), 2.37 (d, J = 8.0 Hz, 1H), 2.28-2.10 (m, 2H), 2.09-1.95 (m, 3H), 1.91 (s, 1H), 1.86-1.45 (m, 17H), 1.24 (s, 1H), 1.17 (d, J = 9.2 Hz, 3H), 1.05 (d, J = 9.6 Hz, 2H), 0.74 (q, J = 7.2 Hz, 3H). LC/MS (ESI, m/z): [(M + 1)]$^+$ = 1112.65, Chemical Formula: $C_{60}H_{71}F_2N_{11}O_8$. Exact Mass: 1111.56. |
| 363 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(7-(1-(2,6-dioxopiperidin-3-yl)-3-methyl-2-oxo-2,3-dihydro-1H-benzo[d]imidazol-5-yl)-2-azaspiro[3.5]nonan-2-yl)piperidine-1-carboxylate<br>$^1$H NMR (400 MHz, DMSO-$d_6$) δ 11.08 (s, 1H), 9.94 (s, 1H), 9.25-9.20 (m, 1H), 7.82-7.72 (m, 1H), 7.41-7.28 (m, 2H), 7.07-7.01 (m, 2H), 7.03-6.93 (m, 1H), 6.90-6.82 (m, 1H), 5.38-5.27 (m, 1H), 4.79-4.71 (m, 1H), 4.43-3.98 (m, 6H), 3.79-3.70 (m, 2H), 3.63-3.55 (m, 1H), 3.47-3.37 (m, 2H), 3.10-2.79 (m, 7H), 2.79-2.58 (m, 5H), 2.43-2.14 (m, 3H), 2.11-1.89 (m, 5H), 1.83-1.52 (m, 14H), 1.53-1.45 (m, 5H), 1.20-1.13 (m, 3H), 1.10-1.00 (m, 2H), 0.80-0.70 (m, 3H). $^{19}$F NMR (377 MHz, DMSO) δ −119.64(1F), −139.49(1F). LC/MS (ESI, m/z): [(M + 1)]$^+$ = 331.05 Chemical Formula: $C_{61}H_{72}F_2N_{10}O_8$, Exact Mass: 1110.55. |
| 364 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((7-(1-(2,6-dioxopiperidin-3-yl)-3-methyl-2-oxo-2,3-dihydro-1H-benzo[d]imidazol-5-yl)-2-azaspiro[3.5]nonan-2-yl)methyl)piperidine-1-carboxylate<br>$^1$H NMR (400 MHz, DMSO-$d_6$) chemical shifts 11.08 (s, 1H), 9.96 (s, 1H), 9.23 (d, J = 3.2 Hz, 1H), 7.82-7.71 (m, 1H), 7.40-7.30 (m, 2H), 7.09-6.94 (m, 3H), 6.86 (d, J = 8.2 Hz, 1H), 5.39-5.25 (m, 1H), 4.75 (d, J = 8.0 Hz, 1H), 4.38-4.26 (m, 1H), 4.22-3.89 (m, 7H), 3.68-3.49 (m, 2H), 3.27 (s, 2H), 2.99-2.82 (m, 5H), 2.78-2.57 (m, 7H), 2.46 (s, 1H), 2.40-2.21 (m, 3H), 2.20-1.88 (m, 7H), 1.78-1.61 (m, 12H), 1.55-1.37 (m, 6H), 1.17 (d, J = 9.2 Hz, 3H), 1.04-0.90 (m, 2H), 0.88-0.69 (m, 4H). $^{19}$F NMR (377 MHz, DMSO) chemical shifts −119.618 (1F), −139.551(1F). LC/MS (ESI, m/z): [(M + 1)]$^+$ = 1125.60 Chemical Formula: $C_{62}H_{74}F_2N_{10}O_8$, Exact Mass: 1124.57. |
| 365 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(6-(1-(2,6-dioxopiperidin-3-yl)-3-methyl-2-oxo-2,3-dihydro-1H-benzo[d]imidazol-5-yl)-2-azaspiro[3.3]heptan-2-yl)piperidine-1-carboxylate<br>$^1$H NMR (400 MHz, DMSO-$d_6$) δ 11.08 (br s, 1H), 9.93 (br s, 1H), 9.29-9.10 (m, 1H), |

-continued

| Compound No. | Compound Name<br>$^1$H NMR Peaks |
|---|---|
| | 7.86-7.68 (m, 1H), 7.40-7.25 (m, 2H), 7.07-6.73 (m, 4H), 5.41-5.22(m, 1H), 4.83-4.65 (m, 1H), 4.41-3.93 (m, 6H), 3.81-3.38 (m, 4H), 3.27-3.15 (m, 3H), 3.08-2.55 (m, 10H), 2.45-2.27 (m, 4H), 2.21-1.41 (m, 21H), 1.20-0.94 (m, 5H), 0.80-0.63 (m, 3H). $^{19}$F NMR (376 MHz, DMSO) δ −119.63 (1F), −139.51 (1F). LC/MS (ESI, m/z): $[(M + 1)]^+$ = 1083.55 Chemical Formula: $C_{59}H_{68}F_2N_{10}O_8$, Exact Mass: 1082.52. |
| 366 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((6-(1-(2,6-dioxopiperidin-3-yl)-3-methyl-2-oxo-2,3-dihydro-1H-benzo[d]imidazol-5-yl)-2-azaspiro[3.3]heptan-2-yl)methyl)piperidine-1-carboxylate<br>$^1$H NMR (400 MHz, DMSO-$d_6$) δ 11.08 (s, 1H), 9.22 (d, J = 3.2 Hz, 1H), 7.79-7.73 (m, 1H), 7.38-7.31 (m, 2H), 7.06-6.97 (m, 3H), 6.86 (d, J = 8.0 Hz, 1H), 5.37-5.29 (m, 1H), 4.76 (s, 1H), 4.33 (t, J = 13.2 Hz, 1H), 4.25-4.00 (m, 5H), 3.93 (d, J = 12.8 Hz, 2H), 3.64 (d, J = 13.2 Hz, 1H), 3.53 (d, J = 13.2 Hz, 1H), 3.01 (s, 2H), 2.96-2.84 (m, 1H), 2.80-2.58 (m, 6H), 2.47-2.29 (m, 4H), 2.23-2.10 (m, 5H), 2.09-1.95 (m, 3H), 1.83-1.58 (m, 13H), 1.55-1.47 (m, 1H), 1.42-1.37 (m, 1H), 1.24 (s, 1H), 1.17 (d, J = 9.2 Hz, 3H), 0.95 (d, J = 12.8 Hz, 2H), 0.74 (q, J = 7.2 Hz, 3H). LC/MS (ESI, m/z): $[(M + 1)]^+$ = 1097.65, Chemical Formula: $C_{60}H_{70}F_2N_{10}O_8$. Exact Mass: 1096.53. |
| 367 | ((3S,7aS)-7a-(((7-(8-ethyl-7-fluoro-3-hydroxynaphthalen-1-yl)-8-fluoro-4-(piperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 9.05 (s, 1H), 7.96-7.82 (m, 1H), 7.71-7.58 (m, 5H), 7.49-7.38 (m, 7H), 7.27-7.18 (m, 1H), 5.43-5.23 (m, 2H), 4.20-3.72 (m, 9H), 3.49-3.36 (m, 3H), 3.27-3.12 (m, 1H), 2.77-2.62 (m, 2H), 2.41-1.94 (m, 3H), 1.83-1.48 (m, 12H), 1.08 (s, 9H), 0.80-0.68 (m, 3H). $^{19}$F NMR (376 MHz, DMSO) δ −117.84 (1F), −139.12 (1F). LC/MS (ESI, m/z): $[(M + 1)]^+$ = 1081.60 Chemical Formula: $C_{60}H_{70}F_2N_{10}O_7$, Exact Mass: 1080.54. |
| 369 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)but-3-yn-1-yl)oxy)piperidine-1-carboxylate<br>$^1$H NMR (400 MHz, DMSO-$d_6$) δ 11.11 (s, 1H), 10.31-10.06 (m, 1H), 9.28-8.95 (m, 1H), 7.97 (dd, J = 6.0, 9.2 Hz, 1H), 7.46 (t, J = 9.2 Hz, 1H), 7.39 (d, J = 2.4 Hz, 1H), 7.25-7.17 (m, 2H), 7.12-7.05 (m, 2H), 5.37 (dd, J = 5.6, 12.8 Hz, 1H), 4.82-4.66 (m, 1H), 4.40-4.28 (m, 1H), 4.26-4.19 (m, 1H), 4.15-3.94 (m, 5H), 3.68-3.55 (m, 6H), 3.32 (s, 3H), 3.25 (d, J = 4.4 Hz, 1H), 3.15-3.08 (m, 2H), 2.92-2.83 (m, 1H), 2.76-2.70 (m, 2H), 2.67-2.65 (m, 1H), 2.64-2.61 (m, 2H), 2.08-1.98 (m, 3H), 1.87-1.59 (m, 13H), 1.54-1.47 (m, 1H), 1.44-1.35 (m, 2H), 1.16 (d, J = 16.4 Hz, 3H); LC-MS ($ESI^+$) m/z 1052.1 $(M + H)^+$. |
| 371 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)but-3-yn-1-yl)oxy)piperidine-1-carboxylate<br>$^1$H NMR (400 MHz, DMSO-$d_6$) δ 11.11 (s, 1H), 9.92 (s, 1H), 9.23 (d, J = 2.4 Hz, 1H), 7.76 (dd, J = 6.0, 9.2 Hz, 1H), 7.39-7.31 (m, 2H), 7.22 (s, 1H), 7.12-7.05 (m, 2H), 7.03 (d, J = 2.4 Hz, 1H), 5.37 (dd, J = 5.6, 12.8 Hz, 1H), 4.74 (d, J = 8.4 Hz, 1H), 4.41-4.28 (m, 1H), 4.25-3.99 (m, 5H), 3.68-3.51 (m, 6H), 3.40-3.36 (m, 1H), 3.32 (s, 3H), 3.16-3.08 (m, 2H), 2.92-2.85 (m, 1H), 2.83-2.78 (m, 1H), 2.75-2.69 (m, 1H), 2.68-2.64 (m, 2H), 2.64-2.60 (m, 2H), 2.35 (d, J = 6.8 Hz, 1H), 2.16-1.98 (m, 4H), 1.88-1.60 (m, 12H), 1.58-1.49 (m, 1H), 1.45-1.34 (m, 2H), 1.16 (d, J = 9.2 Hz, 3H), 0.73 (q, J = 7.2 Hz, 3H); LC-MS ($ESI^+$) m/z 1056.2 $(M + H)^+$. |
| 372 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((3-(1-(2,6-dioxopiperidin-3-yl)-3-methyl-2-oxo-2,3-dihydro-1H-benzo[d]imidazol-4-yl)prop-2-yn-1-yl)oxy)piperidine-1-carboxylate<br>$^1$H NMR (400 MHz, DMSO-$d_6$) δ 11.12 (s, 1H), 10.57-9.90 (m, 1H), 9.27-9.03 (m, 1H), 7.97 (dd, J = 6.0, 9.2 Hz, 1H), 7.46 (t, J = 9.2 Hz, 1H), 7.42-7.35 (m, 1H), 7.26-7.14 (m, 2H), 7.11 (d, J = 7.2 Hz, 1H), 7.06-6.98 (m, 1H), 5.40 (dd, J = 5.2, 12.8 Hz, 1H), 4.84-4.68 (m, 1H), 4.49 (s, 2H), 4.41-4.28 (m, 1H), 4.27-4.19 (m, 1H), 4.19-4.10 (m, 2H), 4.09-4.03 (m, 1H), 3.97-3.92 (m, 1H), 3.75 (dd, J = 4.0, 8.0 Hz, 1H), 3.71-3.65 (m, 2H), 3.63 (s, 3H), 3.57 (d, J = 13.6 Hz, 1H), 3.32 (s, 1H), 3.16-3.07 (m, 2H), 2.94-2.83 (m, 1H), 2.83-2.70 (m, 3H), 2.70-2.63 (m, 1H), 2.60 (s, 1H), 2.54 (s, 1H), 2.10-1.96 (m, 3H), 1.90-1.82 (m, 2H), 1.81-1.60 (m, 9H), 1.57-1.47 (m, 1H), 1.46-1.35 (m, 2H), 1.16 (d, J = 16.8 Hz, 3H); LC-MS (ESI+) m/z 1038.1 $(M + H)^+$. |
| 373 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((3-(1-(2,6-dioxopiperidin-3-yl)-3-methyl-2-oxo-2,3-dihydro-1H-benzo[d]imidazol-5-yl)prop-2-yn-1-yl)oxy)piperidine-1-carboxylate<br>$^1$H NMR (400 MHz, DMSO-$d_6$) δ 11.05 (s, 1H), 10.37-10.00 (m, 1H), 9.08 (s, 1H), 7.98 (dd, J = 6.0, 9.2 Hz, 1H), 7.46 (t, J = 9.2 Hz, 1H), 7.40 (d, J = 2.4 Hz, 1H), 7.19 (d, J = 2.4 |

-continued

| Compound No. | Compound Name<br>$^1$H NMR Peaks |
|---|---|
| | Hz, 1H), 6.93 (d, J = 8.4 Hz, 1H), 6.82 (d, J = 1.6 Hz, 1H), 6.61 (dd, J = 2.0, 8.8 Hz, 1H), 5.28 (dd, J = 5.2, 12.8 Hz, 1H), 4.29 (s, 2H), 4.05-3.97 (m, 3H), 3.94-3.88 (m, 2H), 3.83 (d, J = 4.4 Hz, 4H), 3.30 (s, 3H), 3.10-2.98 (m, 6H), 2.92-2.85 (m, 1H), 2.74-2.59 (m, 4H), 2.47 (d, J = 3.6 Hz, 2H), 2.42-2.32 (m, 2H), 2.14 (d, J = 6.8 Hz, 2H), 2.05-1.90 (m, 3H), 1.73-1.62 (m, 2H), 1.56-1.46 (m, 1H), 1.16-1.03 (m, 2H), 0.66 (s, 2H), 0.44 (s, 2H); LC-MS (ESI$^+$) m/z 941.3 (M + H)$^+$. |
| 374 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(3-(1-(2,6-dioxopiperidin-3-yl)-3-methyl-2-oxo-2,3-dihydro-1H-benzo[d]imidazol-4-yl)prop-2-yn-1-yl)piperidine-1-carboxylate<br>$^1$H NMR (400 MHz, DMSO-d6) δ 11.11 (s, 1H), 10.25-10.07 (m, 1H), 9.26-9.03 (m, 1H), 7.97 (dd, J = 6.0, 9.2 Hz, 1H), 7.46 (t, J = 9.2 Hz, 1H), 7.39 (s, 1H), 7.21 (dd, J = 2.4, 18.0 Hz, 1H), 7.13-6.94 (m, 3H), 5.38 (dd, J = 5.2, 12.8 Hz, 1H), 4.80-4.70 (m, 1H), 4.41-4.29 (m, 1H), 4.25-3.93 (m, 8H), 3.64-3.54 (m, 4H), 2.91-2.74 (m, 5H), 2.72-2.59 (m, 3H), 2.47 (d, J = 6.4 Hz, 2H), 2.09-1.98 (m, 3H), 1.83-1.60 (m, 13H), 1.56-1.47 (m, 1H), 1.22 (dd, J = 2.0, 4.4 Hz, 2H), 1.16 (d, J = 16.8 Hz, 3H); LC-MS (ESI+) m/z 1022.2 (M + H)$^+$ |
| 375 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(3-(1-(2,6-dioxopiperidin-3-yl)-3-methyl-2-oxo-2,3-dihydro-1H-benzo[d]imidazol-5-yl)prop-2-yn-1-yl)piperidine-1-carboxylate<br>$^1$H NMR (400 MHz, DMSO-d6) δ 11.08 (s, 1H), 9.33 (s, 1H), 7.72 (dd, J = 6.0, 8.8 Hz, 1H), 7.47 (s, 1H), 7.39-7.22 (m, 2H), 7.08 (s, 1H), 7.04-6.94 (m, 2H), 6.89 (d, J = 8.0 Hz, 1H), 5.33 (dd, J = 5.2, 12.8 Hz, 1H), 4.83-4.60 (m, 1H), 4.35-4.19 (m, 2H), 4.18-4.11 (m, 2H), 4.07 (d, J = 10.4 Hz, 1H), 3.96 (d, J = 11.2 Hz, 3H), 3.61-3.49 (m, 2H), 3.32 (s, 3H), 2.97-2.84 (m, 4H), 2.82-2.69 (m, 5H), 2.68-2.58 (m, 2H), 2.28 (d, J = 6.4 Hz, 1H), 2.14 (d, J = 6.0 Hz, 2H), 2.09-1.92 (m, 6H), 1.84-1.61 (m, 17H), 1.56-1.46 (m, 1H), 1.16 (s, 3H), 0.97 (d, J = 11.2 Hz, 2H), 0.77 (t, J = 6.8 Hz, 3H); LC-MS (ESI+) m/z 1067.2 (M + H)+. |
| 376 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(4-((1-(2,6-dioxopiperidin-3-yl)-3-methyl-2-oxo-2,3-dihydro-1H-benzo[d]imidazol-4-yl)oxy)but-2-yn-1-yl)piperazine-1-carboxylate<br>$^1$H NMR (400 MHz, DMSO-$d_6$) δ 11.10 (d, J = 3.2 Hz, 1H), 9.23-9.04 (m, 1H), 7.97 (dd, J = 6.0, 9.2 Hz, 1H), 7.46 (t, J = 9.2 Hz, 1H), 7.39 (s, 1H), 7.21 (dd, J = 2.4, 17.6 Hz, 1H), 6.98-6.92 (m, 1H), 6.84 (d, J = 8.4 Hz, 1H), 6.79 (d, J = 8.0 Hz, 1H), 5.33 (dd, J = 5.2 12.4 Hz, 1H), 4.93 (s, 2H), 4.87-4.66 (m, 1H), 4.41-4.29 (m, 1H), 4.28-4.21 (m, 1H), 4.20-4.02 (m, 4H), 3.95 (s, 1H), 3.62-3.53 (m, 2H), 3.50 (s, 3H), 3.32-3.24 (m, 5H), 2.92-2.83 (m, 1H), 2.83-2.57 (m, 5H), 2.37 (d, J = 4.4 Hz, 4H), 2.08-1.96 (m, 3H), 1.83-1.58 (m, 10H), 1.57-1.45 (m, 1H), 1.16 (d, J = 16.4 Hz, 3H); LC-MS (ESI$^+$) m/z 1053.1 (M + H)$^+$. |
| 377 | ((3S,7aS)-7a-(((7-(8-ethyl-7-fluoro-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.08 (s, 1H), 9.33 (s, 1H), 7.72 (dd, J = 6.0, 8.8 Hz, 1H), 7.47 (s, 1H), 7.39-7.22 (m, 2H), 7.08 (s, 1H), 7.04-6.94 (m, 2H), 6.89 (d, J = 8.0 Hz, 1H), 5.33 (dd, J = 5.2, 12.8 Hz, 1H), 4.83-4.60 (m, 1H), 4.35-4.19 (m, 2H), 4.18-4.11 (m, 2H), 4.07 (d, J = 10.4 Hz, 1H), 3.96 (d, J = 11.2 Hz, 3H), 3.61-3.49 (m, 2H), 3.32 (s, 3H), 2.97-2.84 (m, 4H), 2.82-2.69 (m, 5H), 2.68-2.58 (m, 2H), 2.28 (d, J = 6.4 Hz, 1H), 2.14 (d, J = 6.0 Hz, 2H), 2.09-1.92 (m, 6H), 1.84-1.61 (m, 17H), 1.56-1.46 (m, 1H), 1.16 (s, 3H), 0.97 (d, J = 11.2 Hz, 2H), 0.77 (t, J = 6.8 Hz, 3H); LC-MS (ESI$^+$) m/z 1067.2 (M + H)$^+$. |
| 378 | ((3S,7aS)-7a-(((7-(8-ethyl-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.09 (s, 1H), 10.12-9.60 (m, 1H), 9.31 (s, 1H), 7.63 (d, J = 8.4 Hz, 1H), 7.44 (s, 1H), 7.35 (t, J = 7.6 Hz, 1H), 7.22 (d, J = 2.4 Hz, 1H), 7.13-7.07 (m, 2H), 6.99 (d, J = 8.0 Hz, 1H), 6.94 (d, J = 2.4 Hz, 1H), 6.89 (d, J = 8.0 Hz, 1H), 5.38-5.28 (m, 1H), 4.79-4.69 (m, 1H), 4.30-4.18 (m, 2H), 4.17-4.09 (m, 2H), 4.04 (d, J = 10.4 Hz, 1H), 4.01-3.88 (m, 3H), 3.65-3.57 (m, 1H), 3.54-3.43 (m, 3H), 3.32 (s, 5H), 2.96-2.87 (m, 3H), 2.79-2.69 (m, 4H), 2.68-2.66 (m, 1H), 2.64-2.61 (m, 1H), 2.59-2.57 (m, 1H), 2.35-2.31 (m, 1H), 2.28-2.21 (m, 1H), 2.13 (d, J = 6.0 Hz, 2H), 2.04-1.93 (m, 4H), 1.76-1.65 (m, 14H), 1.54-1.48 (m, 1H), 1.20-1.11 (m, 3H), 1.03-0.90 (m, 2H), 0.82 (t, J = 7.2 Hz, 3H); LC-MS (ESI$^+$) m/z 1049.3 (M + H)$^+$. |
| 379 | 3-(5-(1-((1-(((3S,7aS)-7a-(((7-(8-ethyl-7-fluoro-3-hydroxynaphthalen-1-yl)-8-fluoro-4-(piperidin-1-yl)pyrido[4,3-d]pyrimidin-2-yl)oxy)methyl)hexahydro-1H-pyrrolizin-3-yl)methyl)piperidin-4-yl)methyl)piperidin-4-yl)-3-methyl-2-oxo-2,3-dihydro-1H-benzo[d]imidazol-1-yl)piperidine-2,6-dione |

-continued

| Compound No. | Compound Name <br> $^1$H NMR Peaks |
|---|---|
| | $^1$H NMR (400 MHz, DMSO-$d_6$) δ 11.08 (s, 1H), 9.30 (s, 1H), 7.90 (dd, J = 6.0, 9.2 Hz, 1H), 7.41-7.28 (m, 4H), 7.08 (s, 1H), 6.99 (d, J = 8.0 Hz, 1H), 6.89 (d, J = 7.6 Hz, 1H), 5.33 (dd, J = 5.2, 12.8 Hz, 1H), 4.80-4.63 (m, 1H), 4.36 (d, J = 13.6 Hz, 1H), 4.24-4.17 (m, 2H), 4.17-4.13 (m, 1H), 4.12-4.04 (m, 2H), 3.96 (d, J = 10.4 Hz, 2H), 3.60 (d, J = 13.2 Hz, 1H), 3.37 (d, J = 10.0 Hz, 2H), 3.32 (s, 3H), 2.92 (d, J = 9.2 Hz, 2H), 2.87-2.66 (m, 6H), 2.64-2.59 (m, 1H), 2.13 (d, J = 6.0 Hz, 2H), 2.09-1.92 (m, 5H), 1.83-1.60 (m, 17H), 1.57-1.48 (m, 1H), 1.18 (s, 3H), 1.02-0.90 (m, 2H); LC-MS (ESI$^+$) m/z 1057.2 $(M + H)^+$. |
| 383 | 3-(5-((1-(((7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)piperidin-4-yl)methyl)-3-methyl-2-oxo-2,3-dihydro-1H-benzo[d]imidazol-1-yl)piperidine-2,6-dione <br> $^1$H NMR (400 MHz, DMSO-$d_6$) δ 11.08 (s, 1H), 9.22 (s, 1H), 7.77 (dd, J = 6.0, 8.8 Hz, 1H), 7.37-7.31 (m, 2H), 7.05-6.95 (m, 3H), 6.86-6.79 (m, 1H), 5.33 (dd, J = 5.2, 12.8 Hz, 1H), 4.79-4.67 (m, 1H), 4.36-4.28 (m, 1H), 4.15-3.99 (m, 4H), 3.65-3.61 (m, 1H), 3.55-3.53 (m, 1H), 3.31 (s, 3H), 3.24 (s, 1H), 2.93-2.82 (m, 6H), 2.69-2.62 (m, 3H), 2.30-2.09 (m, 4H), 2.00 (dd, J = 3.6, 6.3 Hz, 4H), 1.92-1.88 (m, 1H), 1.85-1.78 (m, 4H), 1.71-1.47 (m, 10H), 1.17 (d, J = 9.6 Hz, 3H), 0.74 (q, J = 7.2 Hz, 3H). LC-MS (ESI$^+$) m/z 958.2 $(M + H)^+$. |
| 387 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-4-yl)piperidin-1-yl)-7-azaspiro[3.5]nonane-7-carboxylate <br> $^1$H NMR (400 MHz, DMSO-$d_6$) δ 11.10 (s, 1H), 10.17 (d, J = 8.0 Hz, 1H), 9.26-9.04 (m, 1H), 8.02-7.92 (m, 1H), 7.46 (t, J = 9.2 Hz, 1H), 7.39 (d, J = 2.0 Hz, 1H), 7.21 (dd, J = 2.4, 18.0 Hz, 1H), 7.04-6.94 (m, 3H), 5.37 (dd, J = 5.2, 12.4 Hz, 1H), 4.83-4.69 (m, 1H), 4.42-4.30 (m, 1H), 4.29-4.02 (m, 5H), 3.95 (s, 1H), 3.63-3.58 (m, 1H), 3.57 (s, 3H), 3.26 (s, 6H), 2.98 (d, J = 8.8 Hz, 2H), 2.92-2.76 (m, 4H), 2.72-2.59 (m, 2H), 2.13-1.95 (m, 7H), 1.87-1.56 (m, 17H), 1.51 (s, 2H), 1.42 (s, 2H), 1.17 (d, J = 16.0 Hz, 3H); LC-MS (ESI$^+$) m/z 1107.2 $(M + H)^+$. |
| 389 | ((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate <br> $^1$H NMR (400 MHz, DMSO-$d_6$) δ 11.08 (s, 1H), 9.93 (d, J = 5.2 Hz, 1H), 9.22 (s, 1H), 7.76 (dd, J = 6.0, 8.4 Hz, 1H), 7.40-7.27 (m, 2H), 7.09-6.97 (m, 3H), 6.90 (d, J = 8.8 Hz, 1H), 5.34 (dd, J = 5.6, 12.8 Hz, 1H), 4.74 (d, J = 7.6 Hz, 1H), 4.40-4.26 (m, 1H), 4.17-3.90 (m, 6H), 3.89-3.77 (m, 1H), 3.67-3.49 (m, 1H), 3.43-3.38 (m, 1H), 3.33 (s, 3H), 2.99-2.85 (m, 4H), 2.84-2.55 (m, 8H), 2.41-2.31 (m, 2H), 2.16-1.90 (m, 7H), 1.86-1.55 (m, 16H), 1.17 (d, J = 9.2 Hz, 3H), 1.08-0.95 (m, 2H), 0.73 (q, J = 7.6 Hz, 3H); LC-MS (ESI$^+$) m/z 1085.2 $(M + H)^+$. |
| 390 | ((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate <br> $^1$H NMR (400 MHz, DMSO-$d_6$) δ 11.08 (s, 1H), 10.07-9.82 (m, 1H), 9.22 (d, J = 3.2 Hz, 1H), 7.76 (dd, J = 6.0, 9.2 Hz, 1H), 7.39-7.28 (m, 2H), 7.08 (s, 1H), 7.03 (t, J = 2.4 Hz, 1H), 7.00 (d, J = 8.0 Hz, 1H), 6.90 (d, J = 8.0 Hz, 1H), 5.33 (dd, J = 5.2, 12.8 Hz, 1H), 4.75 (d, J = 8.4 Hz, 1H), 4.37-4.27 (m, 1H), 4.12 (dd, J = 4.8, 10.4 Hz, 1H), 4.05-3.92 (m, 5H), 3.82 (dd, J = 6.0, 10.4 Hz, 1H), 3.62 (d, J = 12.4 Hz, 1H), 3.53 (d, J = 13.2 Hz, 1H), 2.97-2.83 (m, 6H), 2.74-2.56 (m, 6H), 2.36-2.28 (m, 1H), 2.15 (d, J = 8.8 Hz, 2H), 2.06-1.91 (m, 6H), 1.82 (s, 4H), 1.75-1.62 (m, 12H), 1.55 (s, 1H), 1.22-1.14 (m, 5H), 1.01-0.91 (m, 2H), 0.78-0.69 (m, 3H); LC-MS (ESI$^+$) m/z 1085.2 $(M + H)^+$. |
| 391 | ((3R,7aR)-7a-(((7-(8-ethyl-7-fluoro-3-hydroxynaphthalen-1-yl)-8-fluoro-4-((S)-3-hydroxy-3-methylpiperidin-1-yl)pyrido[4,3-d]pyrimidin-2-yl)oxy)methyl)hexahydro-1H-pyrrolizin-3-yl)methyl 8-((4-(1-(2,6-dioxopiperidin-3-yl)-3-methyl-2-oxo-2,3-dihydro-1H-benzo[d]imidazol-5-yl)piperidin-1-yl)methyl)-3-azabicyclo[3.2.1]octane-3-carboxylate <br> $^1$H NMR (400 MHz, DMSO-$d_6$) δ 11.10 (s, 1H), 10.02-9.89 (m, 1H), 9.32-9.19 (m, 1H), 7.77 (dd, J = 6.0, 9.2 Hz, 1H), 7.42-7.26 (m, 2H), 7.12-6.85 (m, 4H), 5.42-5.27 (m, 1H), 4.83-4.70 (m, 1H), 4.47-4.00 (m, 6H), 3.82-3.73 (m, 2H), 3.64 (d, J = 12.8 Hz, 1H), 3.56-3.37 (m, 4H), 3.33 (s, 3H), 3.21-3.07 (m, 2H), 3.00-2.83 (m, 4H), 2.75-2.59 (m, 4H), 2.39-2.27 (m, 3H), 2.20-2.10 (m, 3H), 2.07-1.60 (m, 20H), 1.48-1.30 (m, 2H), 1.17 (d, J = 9.2 Hz, 3H), 0.73 (q, J = 7.2 Hz, 3H); LC-MS (ESI$^+$) m/z 1111.3 $(M + H)^+$. |
| 392 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 3-((4-(1-(2,6-dioxopiperidin-3-yl)-3-methyl-2-oxo-2,3-dihydro-1H-benzo[d]imidazol-5-yl)piperidin-1-yl)methyl)-8-azabicyclo[3.2.1 ]octane-8-carboxylate <br> $^1$H NMR (400 MHz, DMSO-$d_6$) δ 11.08 (s, 1H), 9.94 (d, J = 1.6 Hz, 1H), 9.26 (d, J = 4.2 Hz, 1H), 7.76 (dd, J = 6.0, 9.0 Hz, 1H), 7.40-7.28 (m, 2H), 7.08-6.98 (m, 3H), 6.89 (d, J = 8.4 Hz, 1H), 5.34 (dd, J = 5.2, 12.8 Hz, 1H), 4.75 (d, J = 10.2 Hz, 1H), 4.45-4.01 (m, 9H), 3.69-3.53 (m, 2H), 3.10 (dd, J = 2.0, 4.4 Hz, 3H), 2.95-2.86 (m, 1H), 2.78-2.55 |

-continued

| Compound No. | Compound Name <br> $^1$H NMR Peaks |
| --- | --- |
| | (m, 4H), 2.33 (s, 1H), 2.28-2.10 (m, 6H), 2.05-1.83 (m, 11H), 1.80-1.53 (m, 15H), 1.24 (d, J = 3.2 Hz, 2H), 1.17 (d, J = 9.2 Hz, 3H), 0.73 (q, J = 7.2 Hz, 3H); LC-MS (ESI$^+$) m/z 1111.2 (M + H)$^+$. |
| 393 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((3-(1-(2,6-dioxopiperidin-3-yl)-3-methyl-2-oxo-2,3-dihydro-1H-benzo[d]imidazol-5-yl)-8-azabicyclo[3.2.1]octan-8-yl)methyl)piperidine-1-carboxylate <br> $^1$H NMR (400 MHz, DMSO-d$_6$) δ 11.08 (s, 1H), 10.05-9.80 (m, 1H), 9.22 (d, J = 4.0 Hz, 1H), 7.76 (dd, J = 6.0, 8.8 Hz, 1H), 7.39-7.30 (m, 2H), 7.06-7.01 (m, 2H), 6.99 (d, J = 7.6 Hz, 1H), 6.94-6.89 (m, 1H), 5.33 (dd, J = 5.2, 12.8 Hz, 1H), 4.74 (d, J = 8.0 Hz, 1H), 4.39-4.28 (m, 1H), 4.23-4.03 (m, 5H), 4.01-3.95 (m, 2H), 3.65-3.54 (m, 1H), 3.32 (s, 3H), 2.94-2.85 (m, 2H), 2.81-2.62 (m, 6H), 2.38-2.28 (m, 4H), 2.20-1.92 (m, 7H), 1.87-1.47 (m, 21H), 1.16 (d, J = 9.2 Hz, 3H), 1.07-0.97 (m, 2H), 0.73 (q, J = 7.2 Hz, 3H); LC-MS (ESI$^+$) m/z 1111.2 (M + H)$^+$. |
| 394 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 3-((4-(1-(2,6-dioxopiperidin-3-yl)-3-methyl-2-oxo-2,3-dihydro-1H-benzo[d]imidazol-5-yl)piperidin-1-yl)methyl)azetidine-1-carboxylate <br> $^1$H NMR (400 MHz, DMSO-d$_6$) δ 11.09 (s, 1H), 10.30-9.63 (m, 1H), 9.22 (d, J = 3.2 Hz, 1H), 7.76 (dd, J = 6.0, 8.8 Hz, 1H), 7.38-7.30 (m, 2H), 7.09 (s, 1H), 7.03 (d, J = 2.4 Hz, 1H), 6.98 (d, J = 8.0 Hz, 1H), 6.89 (d, J = 8.0 Hz, 1H), 5.33 (dd, J = 5.2, 12.8 Hz, 1H), 4.86-4.64 (m, 1H), 4.38-4.29 (m, 1H), 4.20-4.13 (m, 2H), 4.11-4.04 (m, 3H), 4.01-3.93 (m, 2H), 3.63 (d, J = 13.2 Hz, 1H), 3.54 (s, 2H), 3.31 (s, 3H), 2.93-2.86 (m, 3H), 2.79-2.67 (m, 4H), 2.64-2.56 (m, 2H), 2.54 (s, 1H), 2.38-2.31 (m, 1H), 2.18-2.10 (m, 1H), 2.10-1.91 (m, 6H), 1.84-1.57 (m, 15H), 1.55-1.46 (m, 1H), 1.16 (d, J = 9.2 Hz, 3H), 0.73 (q, J = 7.2 Hz, 3H); LC-MS (ESI$^+$) m/z 1057.3 (M + H)$^+$. |
| 395 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((3-(1-(2,6-dioxopiperidin-3-yl)-3-methyl-2-oxo-2,3-dihydro-1H-benzo[d]imidazol-5-yl)azetidin-1-yl)methyl)piperidine-1-carboxylate <br> $^1$H NMR (400 MHz, DMSO-d$_6$) δ 11.10 (s, 1H), 10.06-9.84 (m, 1H), 9.25 (d, J = 3.6 Hz, 1H), 7.77 (dd, J = 6.0, 9.2 Hz, 1H), 7.42-7.28 (m, 2H), 7.20 (s, 1H), 7.10-6.95 (m, 3H), 5.35 (dd, J = 5.2, 12.8 Hz, 1H), 4.76 (d, J = 10.0 Hz, 1H), 4.43-4.16 (m, 5H), 4.12-3.95 (m, 3H), 3.92-3.70 (m, 3H), 3.64 (d, J = 13.2 Hz, 1H), 3.53 (d, J = 12.8 Hz, 4H), 3.34 (s, 3H), 3.05-2.84 (m, 3H), 2.83-2.59 (m, 6H), 2.40-2.26 (m, 1H), 2.20-2.08 (m, 2H), 2.07-1.94 (m, 2H), 1.94-1.49 (m, 13H), 1.17 (d, J = 9.2 Hz, 3H), 1.10-0.93 (m, 2H), 0.73 (q, J = 7.2 Hz, 3H); LC-MS (ESI$^+$) m/z 1057.3 (M + H)$^+$. |
| 396 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 6-((4-(1-(2,6-dioxopiperidin-3-yl)-3-methyl-2-oxo-2,3-dihydro-1H-benzo[d]imidazol-5-yl)piperidin-1-yl)methyl)-2-azaspiro[3.3]heptane-2-carboxylate <br> $^1$H NMR (400 MHz, DMSO-d$_6$) δ 11.07 (s, 1H), 10.08-9.79 (m, 1H), 9.22 (d, J = 2.8 Hz, 1H), 7.76 (dd, J = 6.0, 8.8 Hz, 1H), 7.38-7.30 (m, 2H), 7.08 (s, 1H), 7.03 (d, J = 2.4 Hz, 1H), 6.99 (d, J = 8.0 Hz, 1H), 6.89 (d, J = 8.4 Hz, 1H), 5.33 (dd, J = 5.6, 12.8 Hz, 1H), 4.75 (d, J = 2.8 Hz, 1H), 4.39-4.28 (m, 1H), 4.20-4.13 (m, 2H), 4.09-4.00 (m, 3H), 3.92 (s, 2H), 3.78 (s, 2H), 3.63 (d, J = 13.6 Hz, 1H), 3.53 (d, J = 12.8 Hz, 1H), 3.41-3.39 (m, 1H), 3.32 (s, 3H), 2.93-2.85 (m, 3H), 2.78-2.58 (m, 5H), 2.33 (s, 2H), 2.26-2.20 (m, 2H), 2.17-2.10 (m, 1H), 2.00 (dd, J = 6.8, 11.2 Hz, 5H), 1.84-1.60 (m, 17H), 1.50 (d, J = 11.6 Hz, 1H), 1.17 (d, J = 9.2 Hz, 3H), 0.73 (q, J = 7.2 Hz, 3H); LC-MS (ESI$^+$) m/z 1097.2 (M + H)$^+$. |
| 397 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)-3,3-difluoropiperidine-1-carboxylate <br> $^1$H NMR (400 MHz, DMSO-d$_6$) 11.07 (s, 1H), 9.23 (d, J = 4.0 Hz, 1H), 7.76 (dd, J = 6.0, 8.8 Hz, 1H), 7.38-7.29 (m, 2H), 7.11-7.01 (m, 2H), 7.01-6.87 (m, 2H), 5.33 (dd, J = 5.6, 12.8 Hz, 1H), 4.96-4.56 (m, 1H), 4.35-4.00 (m, 8H), 3.99-3.90 (m, 1H), 3.63 (d, J = 13.2 Hz, 1H), 3.53 (d, J = 13.2 Hz, 1H), 3.44-3.36 (m, 2H), 3.32 (s, 3H), 3.00 (d, J = 9.6 Hz, 2H), 2.92-2.73 (m, 5H), 2.72-2.57 (m, 3H), 2.39-2.29 (m, 3H), 2.20-2.03 (m, 4H), 2.03-1.92 (m, 3H), 1.85-1.66 (m, 13H), 1.59-1.51 (m, 1H), 1.31 (d, J = 10.4 Hz, 1H), 1.17 (d, J = 9.2 Hz, 3H), 0.73 (q, J = 7.2 Hz, 3H); LC-MS (ESI$^+$) m/z 1121.2 (M + H)$^+$. |
| 398 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)-3,3-difluoropiperidin-1-yl)methyl)piperidine-1-carboxylate <br> $^1$H NMR (400 MHz, DMSO-d$_6$) δ 11.09 (s, 1H), 10.07-9.78 (m, 1H), 9.22 (d, J = 3.2 Hz, 1H), 7.76 (dd, J = 6.0, 9.2 Hz, 1H), 7.38-7.30 (m, 2H), 7.13 (s, 1H), 7.07-7.01 (m, 2H), 6.97 (d, J = 8.0 Hz, 1H), 5.36 (dd, J = 5.2, 12.8 Hz, 1H), 4.78-4.70 (m, 1H), 4.38-4.28 (m, 1H), 4.24-4.04 (m, 5H), 4.01-3.94 (m, 2H), 3.65-3.51 (m, 1H), 3.33 (s, 3H), 3.13 (d, J = 6.4 Hz, 2H), 3.09-3.00 (m, 1H), 2.96-2.86 (m, 2H), 2.80-2.60 (m, 6H), 2.34 (d, |

-continued

| Compound No. | Compound Name<br>$^1$H NMR Peaks |
|---|---|
| | J = 10.4 Hz, 2H), 2.28-2.23 (m, 2H), 2.18-2.10 (m, 3H), 2.06-1.96 (m, 3H), 1.81-1.63 (m, 14H), 1.56-1.48 (m, 1H), 1.17 (d, J = 9.2 Hz, 3H), 1.03-0.92 (m, 2H), 0.73 (q, J = 7.2 Hz, 3H); LC-MS (ESI$^+$) m/z 1121.2 (M + H)$^+$. |
| 400 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 6-((4-(1-(2,6-dioxopiperidin-3-yl)-3-methyl-2-oxo-2,3-dihydro-1H-benzo[d]imidazol-5-yl)piperidin-1-yl)methyl)-3-azabicyclo[3.1.1]heptane-3-carboxylate<br>$^1$H NMR (400 MHz, DMSO-d$_6$) δ 11.09 (s, 1H), 9.95 (s, 1H), 9.23 (d, J = 4.4 Hz, 1H), 7.76 (dd, J = 6.4, 8.8 Hz, 1H), 7.39-7.29 (m, 2H), 7.10-7.05 (m, 1H), 7.04-6.96 (m, 2H), 6.90 (d, J = 8.0 Hz, 1H), 5.34 (dd, J = 5.2, 12.8 Hz, 1H), 4.75 (d, J = 10.8 Hz, 1H), 4.38-4.13 (m, 5H), 4.09-3.97 (m, 1H), 3.65-3.45 (m, 6H), 3.32 (s, 3H), 3.11-3.01 (m, 2H), 2.96-2.82 (m, 3H), 2.78-2.60 (m, 4H), 2.43-2.30 (m, 3H), 2.27-2.06 (m, 6H), 2.02-1.95 (m, 2H), 1.92-1.56 (m, 16H), 1.27 (dd, J = 4.8, 9.6 Hz, 1H), 1.16 (d, J = 8.8 Hz, 3H), 0.72 (q, J = 7.2 Hz, 3H); LC-MS (ESI$^+$) m/z 1097.2 (M + H)$^+$. |
| 401 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 6-((4-(1-(2,6-dioxopiperidin-3-yl)-3-methyl-2-oxo-2,3-dihydro-1H-benzo[d]imidazol-5-yl)piperidin-1-yl)methyl)-3-azabicyclo[3.1.0]hexane-3-carboxylate<br>H NMR (400 MHz, DMSO-d$_6$) δ 11.08 (s, 1H), 10.38-9.47 (m, 1H), 9.22 (d, J = 1.6 Hz, 1H), 7.76 (dd, J = 6.0, 8.8 Hz, 1H), 7.40-7.26 (m, 2H), 7.11-7.05 (m, 1H), 7.04-6.95 (m, 2H), 6.93-6.84 (m, 1H), 5.33 (dd, J = 5.2, 12.8 Hz, 1H), 4.87-4.60 (m, 1H), 4.39-4.26 (m, 1H), 4.19 (dd, J = 6.4, 10.0 Hz, 2H), 4.10 (d, J = 11.2 Hz, 2H), 4.06-3.98 (m, 1H), 3.62 (d, J = 13.2 Hz, 1H), 3.49 (d, J = 11.2 Hz, 3H), 3.32 (s, 3H), 3.16-3.03 (m, 3H), 2.94-2.85 (m, 1H), 2.83-2.57 (m, 5H), 2.41-2.30 (m, 3H), 2.23-1.93 (m, 7H), 1.84-1.60 (m, 14H), 1.58-1.49 (m, 1H), 1.43 (s, 2H), 1.16 (d, J = 9.2 Hz, 3H), 0.73 (q, J = 7.2 Hz, 3H), 0.64 (s, 1H); LC-MS (ESI$^+$) m/z 1083.2 (M + H)$^+$. |
| 403 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(2,6-dioxopiperidin-3-yl)-3-methyl-2-oxo-2,3-dihydro-1H-benzo[d]imidazol-4-yl)ethynyl)piperidine-1-carboxylate<br>$^1$H NMR (400 MHz, DMSO-d$_6$) δ 11.11 (s, 1H), 10.02-9.82 (m, 1H), 9.22 (d, J = 2.0 Hz, 1H), 7.76 (dd, J = 6.0, 9.2 Hz, 1H), 7.41-7.28 (m, 2H), 7.16-6.92 (m, 4H), 5.46-5.26 (m, 1H), 4.74 (d, J = 8.0 Hz, 1H), 4.40-4.28 (m, 1H), 4.27-3.98 (m, 5H), 3.73 (d, J = 13.6 Hz, 2H), 3.66-3.59 (m, 3H), 3.54-3.40 (m, 1H), 3.16 (s, 2H), 2.97-2.83 (m, 2H), 2.81-2.60 (m, 4H), 2.39-2.24 (m, 2H), 2.19-1.97 (m, 4H), 1.92-1.83 (m, 2H), 1.82-1.72 (m, 5H), 1.71-1.63 (m, 4H), 1.62-1.43 (m, 4H), 1.16 (d, J = 8.8 Hz, 3H), 0.73 (q, J = 7.2 Hz, 3H); LC-MS (ESI$^+$) m/z 1012.2 (M + H)$^+$. |
| 404 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(2,6-dioxopiperidin-3-yl)-3-methyl-2-oxo-2,3-dihydro-1H-benzo[d]imidazol-5-yl)ethynyl)piperidine-1-carboxylate<br>$^1$H NMR (400 MHz, DMSO-d$_6$) δ 11.11 (s, 1H), 10.08-9.84 (m, 1H), 9.22 (d, J = 2.4 Hz, 1H), 7.76 (dd, J = 6.0, 9.2 Hz, 1H), 7.37-7.29 (m, 2H), 7.25 (s, 1H), 7.09 (s, 2H), 7.03 (d, J = 2.4 Hz, 1H), 5.37 (dd, J = 5.6, 12.8 Hz, 1H), 4.74 (d, J = 8.0 Hz, 1H), 4.38-4.27 (m, 1H), 4.26-4.19 (m, 1H), 4.19-4.11 (m, 2H), 4.11-3.99 (m, 2H), 3.73-3.66 (m, 2H), 3.64-3.49 (m, 1H), 3.44-3.38 (m, 1H), 3.35-3.33 (m, 3H), 3.25-3.12 (m, 3H), 2.90-2.81 (m, 2H), 2.78-2.70 (m, 2H), 2.68-2.58 (m, 2H), 2.37-2.30 (m, 1H), 2.15-1.97 (m, 4H), 1.87-1.61 (m, 11H), 1.57-1.47 (m, 3H), 1.16 (d, J = 8.8 Hz, 3H), 0.73 (q, J = 7.2 Hz, 3H); LC-MS (ESI$^+$) m/z 1012.1 (M + H)$^+$. |
| 407 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-d$_6$) δ 11.08 (s, 1H), 10.35-9.86 (m, 1H), 9.28-9.03 (m, 1H), 8.02-7.92 (m, 1H), 7.45 (t, J = 9.2 Hz, 1H), 7.39 (s, 1H), 7.21 (dd, J = 2.4, 18.0 Hz, 1H), 7.14 (d, J = 6.4 Hz, 1H), 7.09 (d, J = 10.4 Hz, 1H), 5.33 (dd, J = 5.2, 12.8 Hz, 1H), 4.81-4.69 (m, 1H), 4.41-4.30 (m, 1H), 4.21-4.08 (m, 4H), 4.03-3.90 (m, 4H), 3.59 (t, J = 13.2 Hz, 1H), 3.28-3.24 (m, 3H), 2.95 (d, J = 8.8 Hz, 2H), 2.87-2.73 (m, 7H), 2.58 (s, 1H), 2.16 (d, J = 4.8 Hz, 2H), 2.10-1.95 (m, 6H), 1.82-1.64 (m, 17H), 1.57-1.51 (m, 1H), 1.17 (d, J = 16.0 Hz, 3H), 1.01-0.92 (m, 2H); LC-MS (ESI$^+$) m/z 1099.2 (M + H)$^+$. |
| 409 | ((3S,7aS)-7a-(((7-(8-chloro-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-d$_6$) δ 11.08 (s, 1H), 10.42-10.19 (m, 1H), 9.25-9.16 (m, 1H), 7.94 (dd, J = 5.6, 10.0 Hz, 1H), 7.61-7.51 (m, 1H), 7.42 (d, J = 2.0 Hz, 1H), 7.21 (d, J = 2.0 Hz, 1H), 7.08 (s, 1H), 7.01-6.97 (m, 1H), 6.91 (s, 1H), 5.37-5.29 (m, 1H), 4.79-4.71 (m, 1H), 4.38-4.26 (m, 1H), 4.23-4.11 (m, 3H), 4.09-4.02 (m, 2H), 4.00-3.91 (m, 2H), 3.61 (d, J = 12.4 Hz, 1H), 3.56-3.52 (m, 1H), 3.39-3.38 (m, 3H), 2.93-2.89 (m, 2H), 2.76-2.70 (m, 4H), 2.64-2.60 (m, 3H), 2.12 (dd, J = 2.0, 3.2 Hz, 2H), 2.07-1.90 |

-continued

| Compound No. | Compound Name<br>$^1$H NMR Peaks |
|---|---|
| | (m, 6H), 1.83-1.60 (m, 17H), 1.55-1.48 (m, 1H), 1.17 (d, J = 8.8 Hz, 3H), 1.00-0.95 (m, 2H); LC-MS (ESI$^+$) m/z 1091.3 (M + H)$^+$. |
| 410 | ((3S,7aS)-7a-(((7-(7,8-difluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.10 (s, 1H), 9.24 (s, 1H), 7.78-7.71 (m, 1H), 7.62-7.53 (m, 1H), 7.39 (s, 1H), 7.26 (d, J = 3.8 Hz, 1H), 7.09 (s, 1H), 7.00 (d, J = 8.4 Hz, 1H), 6.90 (d, J = 8.0 Hz, 1H), (m, 1H), 5.34 (dd, J = 5.2, 12.8 Hz, 1H), 4.90-4.63 (m, 1H), 4.39-4.31 (m, 1H), 4.24-4.13 (m, 3H), 4.11-4.04 (m, 2H), 3.97 (dd, J = 1.4, 11.4 Hz, 2H), 3.60 (s, 2H), 3.33 (s, 3H), 2.92 (d, J = 8.8 Hz, 3H), 2.83-2.69 (m, 5H), 2.69-2.61 (m, 2H), 2.14 (d, J = 6.4 Hz, 2H), 2.10-1.86 (m, 6H), 1.81-1.63 (m, 16H), 1.57-1.49 (m, 1H), 1.18 (d, J = 4.4 Hz, 3H), 1.02-0.90 (m, 2H). LC-MS (ESI$^+$) m/z 1075.2 (M + H)$^+$. |
| 413 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 9-(4-(1-(2,6-dioxopiperidin-3-yl)-3-methyl-2-oxo-2,3-dihydro-1H-benzo[d]imidazol-5-yl)piperidin-1-yl)-3-azaspiro[5.5]undecane-3-carboxylate<br>$^1$H NMR (400 MHz, DMSO-$d_6$) δ 11.10 (s, 1H), 10.31-10.02 (m, 1H), 9.28-9.00 (m, 1H), 7.98 (dd, J = 6.0, 9.6 Hz, 1H), 7.50-7.43 (m, 1H), 7.39 (s, 1H), 7.21 (dd, J = 2.4, 17.6 Hz, 1H), 7.10-6.99 (m, 2H), 6.93-6.85 (m, 1H), 5.35 (dd, J = 5.6, 13.2 Hz, 1H), 4.84-4.67 (m, 1H), 4.40-4.29 (m, 1H), 4.26-3.89 (m, 7H), 3.59 (t, J = 12.8 Hz, 1H), 3.33 (s, 3H), 3.29-3.17 (m, 3H), 2.97-2.89 (m, 1H), 2.87-2.68 (m, 5H), 2.64-2.58 (m, 4H), 2.15-1.94 (m, 4H), 1.88-1.64 (m, 18H), 1.59-1.34 (m, 6H), 1.24 (s, 2H), 1.17 (d, J = 16.0 Hz, 3H), 1.14-1.05 (m, 2H); LC-MS (ESI$^+$) m/z 1135.2 (M + H)$^+$. |
| 414 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(3-(4-(1-(2,6-dioxopiperidin-3-yl)-3-methyl-2-oxo-2,3-dihydro-1H-benzo[d]imidazol-5-yl)piperidin-1-yl)azetidin-1-yl)piperidine-1-carboxylate<br>$^1$H NMR (400 MHz, DMSO-$d_6$) δ 11.08 (s, 1H), 9.28-8.97 (m, 1H), 7.97 (dd, J = 6.0, 9.2 Hz, 1H), 7.46 (t, J = 9.2 Hz, 1H), 7.39 (s, 1H), 7.21 (dd, J = 2.4, 17.6 Hz, 1H), 7.10 (s, 1H), 7.02-6.95 (m, 1H), 6.90 (d, J = 7.6 Hz, 1H), 5.33 (dd, J = 5.2, 12.8 Hz, 1H), 4.39-4.29 (m, 1H), 4.25-4.01 (m, 6H), 4.00-3.90 (m, 2H), 3.74-3.68 (m, 3H), 3.61-3.59 (m, 1H), 3.32 (s, 3H), 3.02-2.93 (m, 3H), 2.82-2.73 (m, 7H), 2.72-2.59 (m, 3H), 2.36-2.28 (m, 1H), 2.19 (s, 1H), 2.08-1.96 (m, 3H), 1.84-1.54 (m, 19H), 1.17 (d, J = 16.0 Hz, 3H), 1.11-1.04 (m, 2H); LC-MS (ESI$^+$) m/z 1122.2 (M + H)$^+$. |
| 415 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 1-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.09 (s, 1H), 10.17 (d, J = 4.4 Hz, 1H), 9.29-8.99 (m, 1H), 7.98 (dd, J = 6.0, 9.2 Hz, 1H), 7.46 (t, J = 8.8 Hz, 1H), 7.39 (s, 1H), 7.20 (d, J = 17.2 Hz, 1H), 7.08-7.04 (m, 1H), 6.98 (d, J = 8.4 Hz, 1H), 6.91-6.84 (m, 1H), 5.33 (dd, J = 5.2, 12.8 Hz, 1H), 4.81-4.68 (m, 1H), 4.42-4.30 (m, 1H), 4.26-4.07 (m, 4H), 4.00-3.93 (m, 2H), 3.88-3.80 (m, 1H), 3.62-3.53 (m, 1H), 3.31 (s, 3H), 3.29-3.24 (m, 1H), 2.98-2.75 (m, 6H), 2.74-2.69 (m, 1H), 2.63 (s, 1H), 2.60-2.54 (m, 4H), 2.13-1.93 (m, 4H), 1.92-1.60 (m, 20H), 1.56-1.36 (m, 4H), 1.16 (d, J = 16.4 Hz, 3H); LC-MS (ESI$^+$) m/z 1107.8 (M + H)$^+$. |
| 416 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 6-(4-(1-(2,6-dioxopiperidin-3-yl)-3-methyl-2-oxo-2,3-dihydro-1H-benzo[d]imidazol-5-yl)piperidin-1-yl)-2-azaspiro[3.3]heptane-2-carboxylate<br>$^1$H NMR (400 MHz, DMSO-$d_6$) δ 11.10 (s, 1H), 10.00-9.93 (m, 1H), 9.26 (d, J = 4.4 Hz, 1H), 7.77 (dd, J = 6.0, 9.2 Hz, 1H), 7.39-7.32 (m, 2H), 7.08-6.99 (m, 3H), 6.89 (d, J = 8.0 Hz, 1H), 5.34 (dd, J = 5.2, 12.4 Hz, 1H), 4.76 (d, J = 12.4 Hz, 1H), 4.45-4.32 (m, 2H), 4.22 (dd, J = 2.0, 5.2 Hz, 2H), 4.12-4.04 (m, 1H), 4.01-3.92 (m, 2H), 3.86 (dd, J = 3.6, 5.6 Hz, 2H), 3.67-3.61 (m, 1H), 3.54 (d, J = 13.2 Hz, 1H), 3.41 (s, 1H), 3.33 (s, 3H), 3.03-2.85 (m, 4H), 2.75-2.59 (m, 4H), 2.37-2.31 (m, 3H), 2.18-2.10 (m, 2H), 2.09-1.62 (m, 22H), 1.18 (d, J = 9.6 Hz, 3H), 0.73 (q, J = 7.2 Hz, 3H); LC-MS (ESI$^+$) m/z 1083.2 (M + H)$^+$. |
| 417 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-((4-(1-(2,6-dioxopiperidin-3-yl)-3-methyl-2-oxo-2,3-dihydro-1H-benzo[d]imidazol-5-yl)piperidin-1-yl)methyl)-7-azaspiro[3.5]nonane-7-carboxylate<br>$^1$H NMR (400 MHz, DMSO-$d_6$) δ 11.07 (s, 1H), 9.22 (s, 1H), 7.76 (dd, J = 6.0, 9.2 Hz, 1H), 7.39-7.28 (m, 2H), 7.07 (s, 1H), 7.05-6.96 (m, 2H), 6.89 (d, J = 8.4 Hz, 1H), 5.33 (dd, J = 5.2, 12.8 Hz, 1H), 4.93-4.59 (m, 1H), 4.33 (t, J = 15.2 Hz, 1H), 4.24-4.16 (m, 2H), 4.14 (d, J = 5.6 Hz, 1H), 4.12-3.98 (m, 3H), 3.61 (s, 2H), 3.32 (s, 3H), 3.22 (s, 3H), 2.99-2.84 (m, 4H), 2.81-2.69 (m, 3H), 2.68-2.58 (m, 2H), 2.44 (s, 3H), 2.39-2.32 (m, 1H), 2.15-1.96 (m, 6H), 1.95-1.86 (m, 2H), 1.81-1.62 (m, 13H), 1.50 (s, 3H), 1.39 (d, J = 5.6 Hz, 4H), 1.17 (d, J = 9.2 Hz, 3H), 0.73 (q, J = 7.2 Hz, 3H); LC-MS (ESI$^+$) m/z |

-continued

| Compound No. | Compound Name<br>$^1$H NMR Peaks |
|---|---|
| | 1125.3 (M + H)$^+$. |
| 418 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 6-((4-(1-(2,6-dioxopiperidin-3-yl)-3-methyl-2-oxo-2,3-dihydro-1H-benzo[d]imidazol-5-yl)piperidin-1-yl)methyl)-2-azaspiro[3.3]heptane-2-carboxylate<br>$^1$H NMR (400 MHz, DMSO-$d_6$) δ 11.09 (s, 1H), 10.18 (s, 1H), 9.25-9.05 (m, 1H), 7.98 (dd, J = 6.0, 9.2 Hz, 1H), 7.46 (t, J = 8.8 Hz, 1H), 7.39 (s, 1H), 7.21 (dd, J = 2.4, 18.4 Hz, 1H), 7.07 (s, 1H), 7.01 (d, J = 8.0 Hz, 1H), 6.89 (d, J = 8.0 Hz, 1H), 5.34 (dd, J = 5.2, 12.8 Hz, 1H), 4.80-4.70 (m, 1H), 4.42-4.30 (m, 1H), 4.26-4.06 (m, 5H), 4.00 (d, J = 0.8 Hz, 1H), 3.94 (s, 2H), 3.85-3.75 (m, 2H), 3.63-3.56 (m, 1H), 3.33 (s, 3H), 3.27 (s, 1H), 3.06-2.97 (m, 2H), 2.94-2.78 (m, 3H), 2.73-2.58 (m, 4H), 2.41-2.36 (m, 1H), 2.31-2.14 (m, 4H), 2.14-1.92 (m, 4H), 1.89-1.57 (m, 17H), 1.17 (d, J = 16.0 Hz, 3H); LC-MS (ESI$^+$) m/z 1093.2 (M + H)$^+$. |
| 419 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 6-(4-(1-(2,6-dioxopiperidin-3-yl)-3-methyl-2-oxo-2,3-dihydro-1H-benzo[d]imidazol-5-yl)piperidin-1-yl)-2-azaspiro[3.3]heptane-2-carboxylate<br>$^1$H NMR (400 MHz, DMSO-$d_6$) δ 11.09 (s, 1H), 10.19 (s, 1H), 9.26-9.05 (m, 1H), 7.98 (dd, J = 6.0, 9.2 Hz, 1H), 7.47 (t, J = 9.2 Hz, 1H), 7.40 (s, 1H), 7.21 (dd, J = 2.4, 19.2 Hz, 1H), 7.07 (s, 1H), 7.00 (d, J = 8.0 Hz, 1H), 6.89 (d, J = 7.6 Hz, 1H), 5.34 (dd, J = 5.6, 12.8 Hz, 1H), 4.81-4.72 (m, 1H), 4.45-4.36 (m, 1H), 4.34-4.26 (m, 1H), 4.25-4.08 (m, 4H), 3.98 (s, 1H), 3.95 (s, 2H), 3.84 (d, J = 1.2 Hz, 2H), 3.60 (t, J = 12.4 Hz, 1H), 3.32 (s, 3H), 3.00-2.84 (m, 5H), 2.73-2.59 (m, 4H), 2.34-2.29 (m, 2H), 2.16-2.10 (m, 1H), 2.04-1.95 (m, 5H), 1.92-1.60 (m, 17H), 1.17 (d, J = 16.4 Hz, 3H); LC-MS (ESI$^+$) m/z 1079.2 (M + H)$^+$. |
| 420 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 7-(4-(1-(2,6-dioxopiperidin-3-yl)-3-methyl-2-oxo-2,3-dihydro-1H-benzo[d]imidazol-5-yl)piperidin-1-yl)-2-azaspiro[3.5]nonane-2-carboxylate<br>$^1$H NMR (400 MHz, DMSO-$d_6$) δ 11.08 (s, 1H), 9.30-9.00 (m, 1H), 7.97 (dd, J = 6.0, 9.2 Hz, 1H), 7.45 (t, J = 9.2 Hz, 1H), 7.39 (s, 1H), 7.21 (dd, J = 2.4, 18.0 Hz, 1H), 7.07 (s, 1H), 6.99 (d, J = 8.0 Hz, 1H), 6.89 (d, J = 7.6 Hz, 1H), 5.39-5.29 (m, 1H), 4.87-4.57 (m, 1H), 4.40-4.29 (m, 1H), 4.22-3.98 (m, 6H), 3.94 (s, 1H), 3.32 (s, 3H), 3.27 (d, J = 4.4 Hz, 2H), 3.00-2.83 (m, 5H), 2.79-2.69 (m, 3H), 2.68-2.61 (m, 2H), 2.60-2.57 (m, 1H), 2.38-2.24 (m, 4H), 2.09-1.97 (m, 3H), 1.88 (d, J = 12.0 Hz, 2H), 1.82-1.61 (m, 15H), 1.56-1.48 (m, 1H), 1.46-1.37 (m, 2H), 1.33-1.22 (m, 2H), 1.17 (d, J = 16.0 Hz, 3H); LC-MS (ESI$^+$) m/z 1107.2 (M + H)$^+$. |
| 421 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 7-((4-(1-(2,6-dioxopiperidin-3-yl)-3-methyl-2-oxo-2,3-dihydro-1H-benzo[d]imidazol-5-yl)piperidin-1-yl)methyl)-2-azaspiro[3.5]nonane-2-carboxylate<br>$^1$H NMR (400 MHz, DMSO-$d_6$) δ 11.09 (s, 1H), 10.65-9.86 (m, 1H), 9.26-9.02 (m, 1H), 7.97 (dd, J = 6.0, 9.2 Hz, 1H), 7.46 (t, J = 9.2 Hz, 1H), 7.39 (s, 1H), 7.21 (dd, J = 2.4, 18.4 Hz, 1H), 7.09 (s, 1H), 7.02-6.97 (m, 1H), 6.93-6.88 (m, 1H), 5.33 (dd, J = 5.2, 12.8 Hz, 1H), 4.83-4.69 (m, 1H), 4.44-4.26 (m, 1H), 4.23-4.01 (m, 5H), 3.99-3.92 (m, 1H), 3.66-3.51 (m, 5H), 3.32 (s, 3H), 2.99-2.82 (m, 4H), 2.79-2.57 (m, 9H), 2.16-1.90 (m, 8H), 1.85-1.74 (m, 6H), 1.73-1.61 (m, 7H), 1.55-1.31 (m, 4H), 1.17 (d, J = 16.4 Hz, 3H), 0.92-0.78 (m, 2H); LC-MS (ESI$^+$) m/z 1121.3 (M + H)$^+$. |
| 422 | ((3S,7aS)-7a-(((7-(8-ethyl-7-fluoro-3-hydroxynaphthalen-1-yl)-8-fluoro-4-(1,4-oxazepan-4-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.08 (s, 1H), 9.94 (s, 1H), 9.20 (s, 1H), 7.77 (dd, J = 6.0, 9.2 Hz, 1H), 7.40-7.29 (m, 2H), 7.07 (s, 1H), 7.03-6.94 (m, 2H), 6.90 (d, J = 8.0 Hz, 1H), 5.34 (dd, J = 5.2, 12.8 Hz, 1H), 4.47-4.14 (m, 8H), 4.01 (s, 1H), 3.99-3.92 (m, 3H), 3.75 (t, J = 4.8 Hz, 2H), 3.32 (s, 3H), 3.10-2.98 (m, 3H), 2.95-2.86 (m, 1H), 2.82-2.54 (m, 6H), 2.42-2.22 (m, 4H), 2.21-2.05 (m, 6H), 2.04-1.82 (m, 7H), 1.79-1.65 (m, 8H), 1.07-0.95 (m, 2H), 0.73 (t, J = 7.2 Hz, 3H); LC-MS (ESI$^+$) m/z 1071.2 (M + H)$^+$. |
| 423 | ((3S,7aR)-7a-(((7-(8-ethyl-7-fluoro-3-hydroxynaphthalen-1-yl)-8-fluoro-4-(1,4-oxazepan-4-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.09 (s, 1H), 9.95 (s, 1H), 9.18 (s, 1H), 7.79-7.73 (m, 1H), 7.38-7.29 (m, 2H), 7.09-6.99 (m, 3H), 6.91 (d, J = 8.0 Hz, 1H), 5.35 (dd, J = 5.2, 12.8 Hz, 1H), 4.22-4.12 (m, 5H), 4.08-3.81 (m, 7H), 3.77-3.72 (m, 2H), 3.34 (s, 3H), 2.97-2.86 (m, 3H), 2.81-2.67 (m, 5H), 2.66-2.52 (m, 4H), 2.46-2.28 (m, 2H), 2.23-2.04 (m, 5H), 2.03-1.97 (m, 2H), 1.95-1.80 (m, 8H), 1.79-1.42 (m, 6H), 1.12-0.99 (m, 2H), 0.73 (t, J = 7.6 Hz, 3H); LC-MS (ESI$^+$) m/z 1071.3 (M + H)$^+$. |
| 424 | ((3S,7aS)-7a-(((7-(8-ethyl-7-fluoro-3-hydroxynaphthalen-1-yl)-8-fluoro-4-((R)-3-hydroxy-3-methylpiperidin-1-yl)quinazolin-2- |

-continued

| Compound No. | Compound Name<br>$^1$H NMR Peaks |
|---|---|
| | yl)oxy)methyl)hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.22-10.98 (m, 1H), 10.17-9.69 (m, 1H), 7.93 (t, J = 8.0 Hz, 1H), 7.76 (dd, J = 6.0, 8.8 Hz, 1H), 7.40-7.26 (m, 3H), 7.18-7.06 (m, 2H), 6.94 (s, 1H), 5.44-5.24 (m, 1H), 4.68 (d, J = 3.2 Hz, 1H), 4.25-4.12 (m, 3H), 4.11-4.02 (m, 2H), 3.97 (dd, J = 2.0, 10.8 Hz, 2H), 3.89-3.82 (m, 1H), 3.54 (s, 1H), 3.33 (s, 3H), 2.94 (d, J = 10.6 Hz, 2H), 2.89-2.71 (m, 7H), 2.69-2.59 (m, 2H), 2.42-2.34 (m, 2H), 2.15 (d, J = 5.6 Hz, 2H), 2.12-1.89 (m, 6H), 1.83-1.63 (m, 16H), 1.58-1.50 (m, 1H), 1.16 (d, J = 14.0 Hz, 3H), 1.04-0.91 (m, 2H), 0.72 (q, J = 7.2 Hz, 3H). LC-MS (ESI$^+$) m/z 1102.2 (M + H)$^+$. |
| 425 | ((3R,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.09 (s, 1H), 9.95 (d, J = 3.2 Hz, 1H), 9.25 (d, J = 4.0 Hz, 1H), 7.76 (dd, J = 6.4, 8.8 Hz, 1H), 7.41-7.26 (m, 2H), 7.18-7.06 (m, 2H), 7.02 (s, 1H), 5.33 (dd, J = 5.2, 12.8 Hz, 1H), 4.76 (d, J = 10.4 Hz, 1H), 4.44-4.18 (m, 4H), 4.15-3.89 (m, 4H), 3.66-3.52 (m, 1H), 3.45-3.37 (m, 2H), 3.04-2.56 (m, 12H), 2.38-2.29 (m, 2H), 2.06 (s, 9H), 1.91-1.57 (m, 16H), 1.17 (d, J = 9.6 Hz, 3H), 1.06-0.91 (m, 2H), 0.73 (q, J = 7.2 Hz, 3H). LC-MS (ESI$^+$) m/z 1103.2 (M + H)$^+$. |
| 426 | ((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) 11.10 (s, 1H), 9.95 (d, J = 3.2 Hz, 1H), 9.24 (s, 1H), 7.81-7.72 (m, 1H), 7.39-7.30 (m, 2H), 7.14 (d, J = 10.4 Hz, 1H), 7.03 (s, 2H), 5.35 (dd, J = 5.2, 12.4 Hz, 1H), 4.75 (d, J = 8.0 Hz, 1H), 4.39-4.25 (m, 1H), 4.19-3.91 (m, 6H), 3.91-3.77 (m, 1H), 3.68-3.54 (m, 1H), 3.33-3.33 (m, 3H), 3.06-2.59 (m, 12H), 2.54 (s, 2H), 2.39-2.29 (m, 2H), 2.18-2.08 (m, 2H), 2.06-1.77 (m, 11H), 1.76-1.45 (m, 9H), 1.17 (d, J = 9.2 Hz, 3H), 1.11-0.97 (m, 2H), 0.73 (q, J = 7.2 Hz, 3H); LC-MS (ESI$^+$) m/z 1103.2 (M + H)$^+$. |
| 427 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1'-(1-(2,6-dioxopiperidin-3-yl)-3-methyl-2-oxo-2,3-dihydro-1H-benzo[d]imidazol-5-yl)-[1,4'-bipiperidin]-4-yl)carbamate<br>$^1$H NMR (400 MHz, DMSO-$d_6$) δ 11.07 (s, 1H), 9.24 (d, J = 3.2 Hz, 1H), 7.77 (dd, J = 6.0, 9.2 Hz, 1H), 7.40-7.30 (m, 3H), 7.03 (d, J = 2.4 Hz, 1H), 6.93 (d, J = 8.4 Hz, 1H), 6.83 (s, 1H), 6.63 (d, J = 7.6 Hz, 1H), 5.29 (dd, J = 5.2, 12.8 Hz, 1H), 4.89-4.59 (m, 1H), 4.42-4.28 (m, 1H), 4.24-4.11 (m, 4H), 4.09-3.99 (m, 1H), 3.71-3.61 (m, 3H), 3.53 (d, J = 13.2 Hz, 1H), 3.44-3.33 (m, 4H), 3.30 (s, 3H), 3.04 (d, J = 8.0 Hz, 2H), 2.92-2.84 (m, 2H), 2.80 (d, J = 4.4 Hz, 1H), 2.70-2.58 (m, 5H), 2.38-2.28 (m, 1H), 2.17-2.06 (m, 2H), 2.05-1.94 (m, 2H), 1.92-1.57 (m, 17H), 1.54-1.42 (m, 2H), 1.17 (d, J = 9.6 Hz, 3H), 0.73 (q, J = 7.2 Hz, 3H); LC-MS (ESI$^+$) m/z 1086.3 (M + H)$^+$. |
| 428 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (1-((1-(1-(2,6-dioxopiperidin-3-yl)-3-methyl-2-oxo-2,3-dihydro-1H-benzo[d]imidazol-5-yl)piperidin-4-yl)methyl)piperidin-4-yl)carbamate<br>$^1$H NMR (400 MHz, DMSO-$d_6$) δ 11.09 (s, 1H), 9.95 (d, J = 2.4 Hz, 1H), 9.31-9.20 (m, 1H), 7.81-7.74 (m, 1H), 7.40-7.32 (m, 2H), 7.03 (d, J = 2.6 Hz, 1H), 7.01-6.95 (m, 1H), 6.88 (t, J = 7.2 Hz, 2H), 5.39-5.31 (m, 1H), 4.76 (d, J = 10.0 Hz, 1H), 4.46-4.13 (m, 5H), 4.12-4.02 (m, 1H), 3.62 (s, 3H), 3.55 (d, J = 13.6 Hz, 1H), 3.14-3.09 (m, 2H), 3.03-2.84 (m, 4H), 2.74-2.59 (m, 6H), 2.53-2.52 (m, 2H), 2.38-2.32 (m, 2H), 2.20 (s, 3H), 2.06-1.97 (m, 3H), 1.96-1.61 (m, 16H), 1.57-1.28 (m, 5H), 1.18 (d, J = 9.6 Hz, 3H), 0.74 (q, J = 7.2 Hz, 3H). LC-MS (ESI$^+$) m/z 1100.4 (M + H)$^+$. |
| 429 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-((1-(2,6-dioxopiperidin-3-yl)-3-methyl-2-oxo-2,3-dihydro-1H-benzo[d]imidazol-5-yl)methyl)piperidin-1-yl)methyl)piperidine-1-carboxylate<br>$^1$H NMR (400 MHz, DMSO-$d_6$) δ 11.09 (s, 1H), 9.96 (d, J = 2.8 Hz, 1H), 9.28 (d, J = 3.6 Hz, 1H), 7.77 (dd, J = 6.0, 9.2 Hz, 1H), 7.40-7.31 (m, 2H), 7.04-6.98 (m, 3H), 6.83 (d, J = 8.0 Hz, 1H), 5.34 (dd, J = 5.6, 13.2 Hz, 1H), 4.75 (d, J = 12.4 Hz, 1H), 4.59-4.19 (m, 5H), 4.14-3.89 (m, 4H), 3.67-3.53 (m, 1H), 3.46-3.35 (m, 4H), 3.32 (s, 3H), 2.91-2.86 (m, 1H), 2.83-2.68 (m, 4H), 2.62-2.55 (m, 4H), 2.26-1.53 (m, 24H), 1.42-1.25 (m, 2H), 1.18 (d, J = 9.6 Hz, 3H), 1.07-0.94 (m, 2H), 0.73 (q, J = 7.2 Hz, 3H); LC-MS (ESI$^+$) m/z 1099.4 (M + H)$^+$. |
| 430 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(2,6-dioxopiperidin-3-yl)-3-methyl-2-oxo-2,3-dihydro-1H-benzo[d]imidazol-5-yl)methyl)-[1,4'-bipiperidine]-1'-carboxylate |

-continued

| Compound No. | Compound Name / $^1$H NMR Peaks |
|---|---|
| | $^1$H NMR (400 MHz, DMSO-$d_6$) δ 11.08 (s, 1H), 10.06-9.79 (m, 1H), 9.24 (d, J = 2.8 Hz, 1H), 7.77 (dd, J = 6.0, 9.2 Hz, 1H), 7.41-7.27 (m, 2H), 7.05-6.95 (m, 3H), 6.82 (dd, J = 1.2, 8.0 Hz, 1H), 5.33 (dd, J = 5.2, 12.8 Hz, 1H), 4.74 (d, J = 9.2 Hz, 1H), 4.42-4.28 (m, 2H), 4.21 (s, 3H), 4.12-3.98 (m, 3H), 3.64 (d, J = 13.2 Hz, 1H), 3.54 (d, J = 13.2 Hz, 1H), 3.44-3.38 (m, 4H), 3.31 (s, 3H), 3.04 (d, J = 8.8 Hz, 2H), 2.97-2.85 (m, 3H), 2.81-2.73 (m, 2H), 2.72-2.57 (m, 3H), 2.56-2.52 (m, 2H), 2.37-2.30 (m, 1H), 2.18-2.09 (m, 2H), 2.05-1.95 (m, 2H), 1.91-1.76 (m, 7H), 1.73-1.54 (m, 7H), 1.44-1.32 (m, 2H), 1.31-1.21 (m, 2H), 1.17 (d, J = 9.2 Hz, 3H), 0.73 (q, J = 7.2 Hz, 3H); LC-MS (ESI$^+$) m/z 1085.3 (M + H)$^+$. |
| 431 | ((3S,7aR)-7a-(((4-(3,3-difluoropiperidin-1-yl)-7-(8-ethynyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate |
| | $^1$H NMR (400 MHz, DMSO-$d_6$) δ 11.08 (s, 1H), 10.37-9.89 (m, 1H), 9.05 (d, J = 2.0 Hz, 1H), 7.98 (dd, J = 6.0, 9.2 Hz, 1H), 7.47 (t, J = 8.8 Hz, 1H), 7.40 (s, 1H), 7.22 (t, J = 2.8 Hz, 1H), 7.06 (s, 1H), 7.01 (d, J = 8.0 Hz, 1H), 6.90 (d, J = 8.0 Hz, 1H), 5.34 (dd, J = 5.2, 12.8 Hz, 1H), 4.26 (d, J = 11.6 Hz, 1H), 4.18-4.09 (m, 2H), 4.05 (d, J = 10.8 Hz, 1H), 4.00-3.94 (m, 4H), 3.93 (s, 2H), 3.88-3.81 (m, 1H), 3.33 (s, 3H), 3.10-3.01 (m, 2H), 2.99-2.85 (m, 4H), 2.75-2.58 (m, 6H), 2.37-2.20 (m, 5H), 2.07 (dd, J = 5.6, 12.0 Hz, 1H), 2.03-1.97 (m, 3H), 1.93 (dd, J = 5.6, 12.0 Hz, 1H), 1.83 (s, 3H), 1.79-1.65 (m, 9H), 1.63-1.55 (m, 1H), 0.99 (q, J = 10.4 Hz, 2H); LC-MS (ESI$^+$) m/z 1087.2 (M + H)$^+$. |
| 433 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 3-((4-(1-(2,6-dioxopiperidin-3-yl)-3-methyl-2-oxo-2,3-dihydro-1H-benzo[d]imidazol-5-yl)piperidin-1-yl)methyl)pyrrolidine-1-carboxylate |
| | $^1$H NMR (400 MHz, DMSO-$d_6$) δ 11.07 (s, 1H), 10.14-9.72 (m, 1H), 9.21 (d, J = 2.8 Hz, 1H), 7.76 (dd, J = 6.0, 8.8 Hz, 1H), 7.40-7.26 (m, 2H), 7.10 (d, J = 5.4 Hz, 1H), 7.02 (d, J = 2.6 Hz, 1H), 6.99 (d, J = 7.6 Hz, 1H), 6.94-6.85 (m, 1H), 5.32 (dd, J = 6.0, 12.4 Hz, 1H), 4.81-4.65 (m, 1H), 4.37-4.28 (m, 1H), 4.21-4.01 (m, 6H), 3.66-3.56 (m, 4H), 3.03-2.87 (m, 7H), 2.80-2.61 (m, 8H), 2.36-2.26 (m, 4H), 2.16-2.10 (m, 1H), 2.06-1.93 (m, 6H), 1.77-1.66 (m, 11H), 1.58-1.49 (m, 2H), 1.16 (dd, J = 3.4, 9.2 Hz, 3H), 0.73 (q, J = 7.2 Hz, 3H); LC-MS (ESI$^+$) m/z 1071.3 (M + H)$^+$. |
| 434 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-((4-(1-(2,6-dioxopiperidin-3-yl)-3-methyl-2-oxo-2,3-dihydro-1H-benzo[d]imidazol-5-yl)piperidin-1-yl)methyl)pyrrolidine-1-carboxylate |
| | $^1$H NMR (400 MHz, DMSO-$d_6$) δ 11.08 (s, 1H), 9.21 (d, J = 6.4 Hz, 1H), 7.75 (dd, J = 6.4, 8.8 Hz, 1H), 7.40-7.28 (m, 2H), 7.13-6.75 (m, 4H), 5.37-5.27 (m, 1H), 4.32 (d, J = 4.8 Hz, 1H), 4.21 (d, J = 10.0 Hz, 2H), 4.18-4.06 (m, 3H), 4.05-3.97 (m, 1H), 3.88 (s, 2H), 3.65-3.41 (m, 3H), 3.30 (d, J = 16.8 Hz, 6H), 3.08 (d, J = 9.2 Hz, 1H), 2.89-2.82 (m, 2H), 2.77 (d, J = 2.5 Hz, 1H), 2.61 (d, J = 17.6 Hz, 2H), 2.42 (s, 2H), 2.33 (s, 1H), 2.27-2.11 (m, 3H), 2.09-1.95 (m, 4H), 1.86 (s, 1H), 1.80-1.59 (m, 14H), 1.59-1.46 (m, 2H), 1.15 (s, 3H), 0.72 (s, 3H); LC-MS (ESI$^+$) m/z 1071.3 (M + H)$^+$. |
| 435 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((3-(1-(2,6-dioxopiperidin-3-yl)-3-methyl-2-oxo-2,3-dihydro-1H-benzo[d]imidazol-5-yl)pyrrolidin-1-yl)methyl)piperidine-1-carboxylate |
| | $^1$H NMR (400 MHz, DMSO-$d_6$) δ 11.08 (s, 1H), 9.94 (s, 1H), 9.26 (d, J = 3.8 Hz, 1H), 7.77 (dd, J = 6.0, 8.8 Hz, 1H), 7.38-7.31 (m, 2H), 7.14 (s, 1H), 7.07-6.93 (m, 3H), 5.34 (dd, J = 5.2, 12.8 Hz, 1H), 4.74 (d, J = 10.8 Hz, 1H), 4.48-4.35 (m, 2H), 4.25 (s, 2H), 4.13-4.06 (m, 1H), 4.01 (d, J = 13.2 Hz, 2H), 3.69-3.52 (m, 2H), 3.48-3.37 (m, 4H), 3.33 (s, 3H), 2.96-2.87 (m, 2H), 2.86-2.82 (m, 1H), 2.82-2.75 (m, 2H), 2.74-2.70 (m, 1H), 2.69-2.55 (m, 4H), 2.39-2.29 (m, 2H), 2.24-2.01 (m, 3H), 2.00-1.58 (m, 16H), 1.18 (d, J = 9.2 Hz, 3H), 1.08-1.03 (m, 1H), 0.73 (q, J = 7.2 Hz, 3H); LC-MS (ESI$^+$) m/z 1072.4 (M + H)$^+$ |
| 436 | 3-(5-((1-((1-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)piperidin-4-yl)methyl)piperidin-4-yl)methyl)-3-methyl-2-oxo-2,3-dihydro-1H-benzo[d]imidazol-1-yl)piperidine-2,6-dione |
| | $^1$H NMR (400 MHz, DMSO-$d_6$) δ 11.08 (s, 1H), 9.23 (d, J = 2.0 Hz, 1H), 7.82-7.70 (m, 1H), 7.44-7.27 (m, 2H), 7.05-7.01 (m, 1H), 7.00-6.92 (m, 2H), 6.84-6.75 (m, 1H), 5.36-5.29 (m, 1H), 4.37-4.24 (m, 2H), 4.22-4.16 (m, 1H), 4.09-4.01 (m, 1H), 3.66-3.61 (m, 1H), 3.55-3.51 (m, 1H), 3.37-3.34 (m, 1H), 3.31 (s, 3H), 2.93-2.84 (m, 4H), 2.80-2.69 (m, 4H), 2.67-2.58 (m, 3H), 2.42-2.35 (m, 2H), 2.19-1.96 (m, 7H), 1.93-1.85 (m, 2H), 1.81-1.64 (m, 10H), 1.61-1.49 (m, 6H), 1.46-1.34 (m, 2H), 1.22-1.12 (m, 5H), 1.07-0.98 (m, 2H), 0.77-0.70 (m, 3H); LC-MS (ESI$^+$) m/z 1055.3 (M + H)$^+$. |
| 437 | ((3S,7aS)-7a-(((4-(3,3-difluoropiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate |

-continued

| Compound No. | Compound Name<br>$^1$H NMR Peaks |
|---|---|
| | $^1$H NMR (400 MHz, DMSO-$d_6$) δ 11.07 (s, 1H), 9.13 (s, 1H), 7.76 (dd, J = 6.0, 9.2 Hz, 1H), 7.38-7.30 (m, 2H), 7.11-7.03 (m, 2H), 7.01-6.95 (m, 1H), 6.89 (d, J = 7.6 Hz, 1H), 5.33 (dd, J = 5.2, 12.8 Hz, 1H), 4.32-4.17 (m, 4H), 4.16-4.10 (m, 2H), 3.97 (d, J = 4.4 Hz, 4H), 3.32 (d, J = 1.2 Hz, 5H), 3.29-3.27 (m, 2H), 2.97-2.84 (m, 4H), 2.79-2.70 (m, 4H), 2.68-2.58 (m, 2H), 2.28-2.19 (m, 2H), 2.13 (d, J = 6.4 Hz, 2H), 2.01-1.94 (m, 4H), 1.82-1.60 (m, 14H), 1.55-1.47 (m, 1H), 1.01-0.88 (m, 2H), 0.72 (t, J = 7.2 Hz, 3H); LC-MS (ESI$^+$) m/z 1091.3 (M + H)$^+$. |
| 438 | ((3S,7aS)-7a-(((8-fluoro-7-(7-fluoro-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.07 (s, 1H), 10.34-9.72 (m, 1H), 9.30 (s, 1H), 7.90 (dd, J = 5.6, 8.8 Hz, 1H), 7.43-7.27 (m, 4H), 7.10 (s, 1H), 7.02-6.85 (m, 2H), 5.33 (dd, J = 5.2, 12.8 Hz, 1H), 4.79-4.63 (m, 1H), 4.35 (d, J = 12.0 Hz, 1H), 4.26-4.02 (m, 6H), 3.60 (d, J = 13.6 Hz, 2H), 3.32 (s, 3H), 2.95-2.84 (m, 4H), 2.78-2.70 (m, 3H), 2.69-2.60 (m, 4H), 2.12-1.87 (m, 6H), 1.87-1.59 (m, 16H), 1.50 (d, J = 9.6 Hz, 5H), 1.39 (s, 2H), 1.18 (s, 3H); LC-MS (ESI$^+$) m/z 1083.4 (M + H)$^+$. |
| 439 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(2,6-dioxopiperidin-3-yl)-3-methyl-2-oxo-2,3-dihydro-1H-benzo[d]imidazol-5-yl)oxy)-[1,4'-bipiperidine]-1'-carboxylate<br>$^1$H NMR (400 MHz, DMSO-$d_6$) δ 11.07 (s, 1H), 10.07-9.89 (m, 1H), 9.23 (d, J = 2.8 Hz, 1H), 7.76 (dd, J = 6.0, 9.2 Hz, 1H), 7.39-7.29 (m, 2H), 7.02 (d, J = 2.4 Hz, 1H), 6.96 (d, J = 8.8 Hz, 1H), 6.87 (d, J = 2.0 Hz, 1H), 6.62 (dd, J = 2.0, 8.4 Hz, 1H), 5.30 (dd, J = 5.6, 12.8 Hz, 1H), 4.83-4.67 (m, 1H), 4.41-4.15 (m, 7H), 4.11-3.96 (m, 4H), 3.65 (s, 1H), 3.29 (s, 3H), 2.93-2.88 (m, 2H), 2.82-2.75 (m, 4H), 2.70-2.60 (m, 4H), 2.44 (d, J = 8.8 Hz, 1H), 2.16-2.08 (m, 2H), 2.04-1.57 (m, 20H), 1.38-1.28 (m, 2H), 1.16 (d, J = 9.2 Hz, 3H), 0.73 (q, J = 7.2 Hz, 3H); LC-MS (ESI$^+$) m/z 1087.3 (M + H)$^+$. |
| 440 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-4-yl)piperidin-1-yl)methyl)piperidine-1-carboxylate<br>$^1$H NMR (400 MHz, DMSO-$d_6$) δ 11.09 (s, 1H), 9.23 (d, J = 4.0 Hz, 1H), 7.76 (dd, J = 6.0, 9.2 Hz, 1H), 7.38-7.31 (m, 2H), 7.04 (d, J = 2.0 Hz, 1H), 7.02-6.94 (m, 3H), 5.42-5.32 (m, 1H), 4.82-4.69 (m, 1H), 4.39-4.28 (m, 1H), 4.25-4.06 (m, 5H), 4.00-3.92 (m, 2H), 3.64 (d, J = 13.6 Hz, 1H), 3.57 (s, 3H), 2.94 (d, J = 9.6 Hz, 3H), 2.80-2.67 (m, 6H), 2.64 (d, J = 3.6 Hz, 1H), 2.36 (s, 1H), 2.15 (d, J = 6.8 Hz, 3H), 2.10-1.95 (m, 6H), 1.83-1.61 (m, 18H), 1.56-1.49 (m, 1H), 1.17 (d, J = 8.8 Hz, 3H), 1.02-0.93 (m, 2H), 0.74 (q, J = 7.2 Hz, 3H). LC-MS (ESI$^+$) m/z 1085.3 (M + H)$^+$. |
| 442 | 3-(5-(1-((1-(((3S,7aR)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)piperidin-4-yl)methyl)piperidin-4-yl)-3-methyl-2-oxo-2,3-dihydro-1H-benzo[d]imidazol-1-yl)piperidine-2,6-dione<br>$^1$H NMR (400 MHz, DMSO-$d_6$) δ 11.07 (s, 1H), 9.21 (d, J = 3.2 Hz, 1H), 7.76 (dd, J = 6.4, 8.8 Hz, 1H), 7.39-7.30 (m, 2H), 7.08 (s, 1H), 7.03 (d, J = 2.4 Hz, 1H), 6.99 (d, J = 8.0 Hz, 1H), 6.94-6.86 (m, 1H), 5.40-5.26 (m, 1H), 4.82-4.68 (m, 1H), 4.36-4.27 (m, 1H), 4.14-4.09 (m, 1H), 4.06-3.98 (m, 2H), 3.65 (s, 1H), 3.54 (d, J = 4.4 Hz, 1H), 3.32-3.32 (m, 3H), 2.95-2.83 (m, 8H), 2.67 (s, 2H), 2.63-2.58 (m, 2H), 2.14-2.07 (m, 3H), 2.03-1.86 (m, 8H), 1.85-1.54 (m, 16H), 1.53-1.41 (m, 2H), 1.17 (d, J = 9.6 Hz, 3H), 1.13-1.03 (m, 2H), 0.74 (q, J = 7.2 Hz, 3H); LC-MS (ESI$^+$) m/z 1041.4 (M + H)$^+$. |
| 443 | 3-(5-(1-((1-(((3R,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)piperidin-4-yl)methyl)piperidin-4-yl)-3-methyl-2-oxo-2,3-dihydro-1H-benzo[d]imidazol-1-yl)piperidine-2,6-dione<br>$^1$H NMR (400 MHz, DMSO-$d_6$) δ 11.07 (s, 1H), 9.92 (dd, J = 5.6, 7.2 Hz, 1H), 9.23 (d, J = 2.4 Hz, 1H), 7.83-7.72 (m, 1H), 7.40-7.30 (m, 2H), 7.11-7.07 (m, 1H), 7.06-6.97 (m, 2H), 6.94-6.88 (m, 1H), 5.39-5.28 (m, 1H), 4.80-4.71 (m, 1H), 4.41-4.27 (m, 1H), 4.15-4.00 (m, 3H), 3.64 (d, J = 13.2 Hz, 1H), 3.55 (s, 1H), 3.37-3.37 (m, 3H), 2.96-2.85 (m, 8H), 2.65-2.61 (m, 4H), 2.16-2.10 (m, 3H), 2.04-1.90 (m, 8H), 1.85-1.58 (m, 16H), 1.51 (d, J = 8.0 Hz, 2H), 1.18 (d, J = 8.8 Hz, 3H), 1.04-0.98 (m, 2H), 0.79-0.71 (m, 3H); LC-MS (ESI$^+$) m/z 1041.4 (M + H)$^+$. |
| 445 | ((3S,7aS)-7a-(((8-fluoro-7-(7-fluoro-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((1-(1-(2,6-dioxopiperidin-3-yl)-3-methyl-2-oxo-2,3-dihydro-1H-benzo[d]imidazol-5-yl)piperidin-4-yl)methyl)piperazine-1-carboxylate<br>$^1$H NMR (400 MHz, DMSO-$d_6$) δ 11.05 (s, 1H), 9.29 (s, 1H), 7.90 (dd, J = 6.0, 9.2 Hz, 1H), 7.40-7.34 (m, 2H), 7.33-7.29 (m, 2H), 6.91 (d, J = 8.8 Hz, 1H), 6.79 (d, J = 2.0 Hz, 1H), 6.61 (dd, J = 2.0, 8.8 Hz, 1H), 5.28 (dd, J = 5.6, 12.8 Hz, 1H), 4.86-4.52 (m, 1H), 4.35 (d, J = 12.8 Hz, 1H), 4.25-4.12 (m, 3H), 4.11-4.03 (m, 2H), 3.61 (s, 1H), 3.57 (d, J = 8.8 Hz, 2H), 3.53 (s, 1H), 3.35 (s, 6H), 3.29 (s, 3H), 2.93-2.84 (m, 1H), 2.79-2.65 (m, |

-continued

| Compound No. | Compound Name<br>$^1$H NMR Peaks |
|---|---|
| | 3H), 2.63-2.60 (m, 1H), 2.60-2.55 (m, 2H), 2.34-2.26 (m, 4H), 2.15 (d, J = 7.2 Hz, 2H), 2.08-1.96 (m, 3H), 1.83-1.62 (m, 12H), 1.57-1.49 (m, 1H), 1.27-1.19 (m, 2H), 1.18 (s, 3H); LC-MS (ESI$^+$) m/z 1058.3 (M + H)$^+$. |
| 446 | ((3S,7aS)-7a-(((8-fluoro-7-(7-fluoro-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)-4-fluoropiperidine-1-carboxylate<br>$^1$H NMR (400 MHz, DMSO-$d_6$) δ 11.07 (s, 1H), 10.25-9.77 (m, 1H), 9.30 (s, 1H), 7.90 (dd, J = 6.0, 9.2 Hz, 1H), 7.41-7.27 (m, 4H), 7.07 (s, 1H), 6.99 (d, J = 8.0 Hz, 1H), 6.89 (d, J = 8.0 Hz, 1H), 5.33 (dd, J = 5.2, 12.8 Hz, 1H), 4.70 (s, 1H), 4.35 (d, J = 12.8 Hz, 1H), 4.27-4.13 (m, 3H), 4.12-4.04 (m, 2H), 3.82-3.71 (m, 2H), 3.60 (d, J = 13.2 Hz, 1H), 3.39-3.36 (m, 2H), 3.32 (s, 3H), 3.12-3.05 (m, 2H), 2.97 (d, J = 11.2 Hz, 2H), 2.92-2.85 (m, 1H), 2.81-2.59 (m, 5H), 2.54-2.53 (m, 1H), 2.18 (s, 2H), 2.09-1.97 (m, 3H), 1.86-1.62 (m, 17H), 1.58-1.48 (m, 2H), 1.18 (s, 3H); LC-MS (ESI$^+$) m/z 1075.3 (M + H)$^+$. |
| 447 | ((3S,7aS)-7a-(((8-fluoro-7-(7-fluoro-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-6-fluoro-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.07 (s, 1H), 9.30 (s, 1H), 7.89 (dd, J = 6.0, 8.8 Hz, 1H), 7.40-7.28 (m, 4H), 7.17-7.05 (m, 2H), 5.32 (dd, J = 5.2, 12.8 Hz, 1H), 4.80-4.60 (m, 1H), 4.40-4.30 (m, 1H), 4.24-4.16 (m, 2H), 4.12-4.04 (m, 2H), 4.00-3.90 (m, 2H), 3.60 (d, J = 13.2 Hz, 2H), 3.47-3.42 (m, 2H), 3.32 (s, 3H), 3.27-3.26 (m, 1H), 2.95-2.90 (m, 2H), 2.88-2.83 (m, 1H), 2.80-2.73 (m, 4H), 2.18-2.02 (m, 4H), 2.02-1.87 (m, 4H), 1.79-1.63 (m, 16H), 1.57-1.49 (m, 1H), 1.18 (s, 3H), 1.04-0.91 (m, 2H); LC-MS (ESI$^+$) m/z 1075.3 (M + H)$^+$ |
| 448 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 7-((4-(1-(2,6-dioxopiperidin-3-yl)-3-methyl-2-oxo-2,3-dihydro-1H-benzo[d]imidazol-5-yl)piperidin-1-yl)methyl)-2-azaspiro[3.5]nonane-2-carboxylate<br>$^1$H NMR (400 MHz, DMSO-$d_6$) δ 11.08 (s, 1H), 9.95 (s, 1H), 9.26 (d, J = 4.0 Hz, 1H), 7.77 (dd, J = 6.0, 9.2 Hz, 1H), 7.38-7.30 (m, 2H), 7.06 (s, 1H), 7.05-6.99 (m, 2H), 6.91 (d, J = 8.4 Hz, 1H), 5.34 (dd, J = 5.2, 12.8 Hz, 1H), 4.75 (d, J = 11.2 Hz, 1H), 4.45-4.32 (m, 2H), 4.26-4.17 (m, 2H), 4.08 (dd, J = 12.8, 18.8 Hz, 1H), 3.69-3.51 (m, 6H), 3.42 (s, 2H), 3.33 (s, 3H), 3.21-3.15 (m, 2H), 2.94-2.86 (m, 1H), 2.74-2.57 (m, 4H), 2.47-2.43 (m, 2H), 2.42-2.28 (m, 3H), 2.21-2.10 (m, 2H), 2.05-1.93 (m, 4H), 1.93-1.77 (m, 10H), 1.77-1.50 (m, 8H), 1.47-1.35 (m, 2H), 1.18 (d, J = 9.2 Hz, 3H), 0.99-0.83 (m, 2H), 0.73 (q, J = 7.2 Hz, 3H); LC-MS (ESI$^+$) m/z 1125.4 (M + H)$^+$. |
| 449 | 3-(5-(1-(3-((7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methoxy)propyl)piperidin-4-yl)-3-methyl-2-oxo-2,3-dihydro-1H-benzo[d]imidazol-1-yl)piperidine-2,6-dione<br>$^1$H NMR (400 MHz, DMSO-$d_6$) δ 11.08 (s, 1H), 10.29-9.67 (m, 1H), 9.22 (d, J = 2.4 Hz, 1H), 7.76 (dd, J = 6.0, 8.8 Hz, 1H), 7.39-7.30 (m, 2H), 7.07 (s, 1H), 7.05-6.96 (m, 2H), 6.89 (d, J = 8.4 Hz, 1H), 5.41-5.26 (m, 1H), 4.83-4.64 (m, 1H), 4.40-4.24 (m, 1H), 4.18-3.97 (m, 3H), 3.61 (s, 1H), 3.39 (d, J = 6.4 Hz, 2H), 3.32 (s, 3H), 3.27 (d, J = 6.0 Hz, 4H), 2.98 (d, J = 10.0 Hz, 2H), 2.93-2.80 (m, 3H), 2.74-2.60 (m, 4H), 2.39 (t, J = 6.8 Hz, 2H), 2.19-2.08 (m, 1H), 2.07-1.89 (m, 6H), 1.85-1.77 (m, 3H), 1.76-1.44 (m, 12H), 1.16 (d, J = 9.2 Hz, 3H), 0.73 (q, J = 7.2 Hz, 3H); LC-MS (ESI$^+$) m/z 1002.5 (M + H)$^+$. |
| 450 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-((4-(1-(2,6-dioxopiperidin-3-yl)-3-methyl-2-oxo-2,3-dihydro-1H-benzo[d]imidazol-5-yl)piperidin-1-yl)methyl)phenyl)carbamate<br>$^1$H NMR (400 MHz, DMSO-$d_6$) δ 11.06 (s, 1H), 10.01-9.84 (m, 1H), 9.70 (s, 1H), 9.21 (d, J = 3.2 Hz, 1H), 7.76 (dd, J = 6.0, 9.2 Hz, 1H), 7.42 (d, J = 8.4 Hz, 2H), 7.37-7.31 (m, 2H), 7.21 (d, J = 8.4 Hz, 2H), 7.09 (s, 1H), 7.03 (d, J = 2.4 Hz, 1H), 6.99 (d, J = 8.0 Hz, 1H), 6.90 (d, J = 8.4 Hz, 1H), 5.32 (dd, J = 5.2, 12.8 Hz, 1H), 4.74 (d, J = 5.6 Hz, 1H), 4.39-4.30 (m, 1H), 4.29-4.23 (m, 2H), 4.20-4.13 (m, 1H), 4.11-3.98 (m, 2H), 3.68-3.49 (m, 2H), 3.43 (s, 3H), 2.91 (d, J = 11.2 Hz, 3H), 2.86-2.70 (m, 3H), 2.70-2.61 (m, 2H), 2.60-2.56 (m, 1H), 2.42-2.26 (m, 2H), 2.17-1.97 (m, 6H), 1.82-1.63 (m, 14H), 1.59-1.51 (m, 1H), 1.16 (d, J = 9.6 Hz, 3H), 0.73 (q, J = 7.6 Hz, 3H); LC-MS (ESI$^+$) m/z 1093.3 (M + H)$^+$. |
| 451 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl (4-(4-(1-(2,6-dioxopiperidin-3-yl)-3-methyl-2-oxo-2,3-dihydro-1H-benzo[d]imidazol-5-yl)piperidin-1-yl)phenyl)carbamate<br>$^1$H NMR (400 MHz, DMSO-$d_6$) δ 11.08 (s, 1H), 10.13-9.81 (m, 1H), 9.45 (s, 1H), 9.22 (d, J = 3.2 Hz, 1H), 7.76 (dd, J = 6.0, 9.2 Hz, 1H), 7.39-7.28 (m, 4H), 7.13 (s, 1H), 7.06-6.99 (m, 2H), 6.98-6.87 (m, 3H), 5.34 (dd, J = 5.6, 12.8 Hz, 1H), 4.81-4.65 (m, 1H), 4.39-4.22 (m, 3H), 4.19-4.14 (m, 1H), 4.11-3.99 (m, 2H), 3.69 (d, J = 12.0 Hz, 2H), 3.66-3.55 (m, 1H), 3.33 (s, 3H), 2.94-2.81 (m, 2H), 2.75-2.66 (m, 5H), 2.40-2.33 (m, |

-continued

| Compound No. | Compound Name<br>$^1$H NMR Peaks |
|---|---|
| | 1H), 2.23-1.96 (m, 5H), 1.92-1.61 (m, 15H), 1.59-1.50 (m, 1H), 1.17 (d, J = 9.6 Hz, 3H), 0.73 (q, J = 7.6 Hz, 3H); LC-MS (ESI$^+$) m/z 1079.4 (M + H)$^+$. |
| 452 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 7-((1-(1-(2,6-dioxopiperidin-3-yl)-3-methyl-2-oxo-2,3-dihydro-1H-benzo[d]imidazol-5-yl)piperidin-4-yl)methyl)-2,7-diazaspiro[3.5]nonane-2-carboxylate<br>$^1$H NMR (400 MHz, DMSO-d$_6$) δ 11.05 (s, 1H), 9.94 (s, 1H), 9.27 (d, J = 4.0 Hz, 1H), 7.77 (dd, J = 6.0, 9.2 Hz, 1H), 7.39-7.30 (m, 2H), 7.03 (d, J = 2.4 Hz, 1H), 6.92 (d, J = 8.8 Hz, 1H), 6.81 (d, J = 2.0 Hz, 1H), 6.62 (dd, J = 2.0, 8.8 Hz, 1H), 5.28 (dd, J = 5.2, 12.8 Hz, 1H), 4.75 (d, J = 11.2 Hz, 1H), 4.46-4.35 (m, 2H), 4.28-4.20 (m, 2H), 4.08 (dd, J = 13.2, 19.2 Hz, 1H), 3.77-3.58 (m, 6H), 3.58-3.36 (m, 6H), 3.30 (s, 3H), 2.93-2.85 (m, 1H), 2.73-2.55 (m, 6H), 2.55-2.51 (m, 2H), 2.44-2.25 (m, 4H), 2.24-2.13 (m, 2H), 2.06-1.84 (m, 8H), 1.78-1.63 (m, 10H), 1.25 (d, J = 10.8 Hz, 1H), 1.18 (d, J = 9.2 Hz, 3H), 0.74 (q, J = 7.2 Hz, 3H); LC-MS (ESI$^+$) m/z 1127.4 (M + H)$^+$ |
| 454 | ((3S,7aS)-7a-(((7-(8-ethynyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 8-((4-(1-(2,6-dioxopiperidin-3-yl)-3-methyl-2-oxo-2,3-dihydro-1H-benzo[d]imidazol-5-yl)piperidin-1-yl)methyl)-2-azaspiro[4.5]decane-2-carboxylate<br>$^1$H NMR (400 MHz, DMSO-d$_6$) δ 11.17-11.01 (m, 1H), 10.73-9.73 (m, 1H), 9.25-9.02 (m, 1H), 7.98 (dd, J = 6.0, 8.8 Hz, 1H), 7.46 (t, J = 8.8 Hz, 1H), 7.39 (s, 1H), 7.21 (dd, J = 2.4, 17.6 Hz, 1H), 7.13-7.06 (m, 1H), 7.00 (d, J = 8.0 Hz, 1H), 6.91 (d, J = 8.0 Hz, 1H), 5.34 (dd, J = 5.2, 12.8 Hz, 1H), 4.86-4.63 (m, 1H), 4.44-4.28 (m, 1H), 4.25-4.17 (m, 1H), 4.17-3.97 (m, 4H), 3.95 (s, 1H), 3.64-3.55 (m, 2H), 3.33 (s, 3H), 3.30 (s, 2H), 3.04 (d, J = 6.4 Hz, 2H), 2.97-2.84 (m, 4H), 2.82-2.70 (m, 3H), 2.68-2.59 (m, 2H), 2.15 (d, J = 6.8 Hz, 2H), 2.08-1.90 (m, 5H), 1.80-1.61 (m, 17H), 1.58-1.47 (m, 4H), 1.36-1.24 (m, 2H), 1.17 (d, J = 15.9 Hz, 3H), 1.08-0.94 (m, 2H); LC-MS (ESI$^+$) m/z 1135.5 (M + H)$^+$. |
| 455 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-8-azaspiro[4.5]decane-8-carboxylate<br>$^1$H NMR (400 MHz, DMSO-d$_6$) δ 11.08 (s, 1H), 9.95 (d, J = 2.4 Hz, 1H), 9.26 (d, J = 3.6 Hz, 1H), 7.77 (dd, J = 6.0, 9.2 Hz, 1H), 7.43-7.28 (m, 2H), 7.09-6.98 (m, 3H), 6.91 (d, J = 8.0 Hz, 1H), 5.35 (dd, J = 5.2, 12.8 Hz, 1H), 4.75 (d, J = 10.0 Hz, 1H), 4.47-4.20 (m, 5H), 4.07 (dd, J = 13.2, 20.0 Hz, 1H), 3.69-3.52 (m, 2H), 3.43-3.35 (m, 8H), 3.34 (s, 3H), 3.05-2.84 (m, 3H), 2.78-2.58 (m, 5H), 2.39-2.32 (m, 1H), 2.20-2.10 (m, 2H), 2.04-1.78 (m, 14H), 1.74-1.57 (m, 6H), 1.52-1.35 (m, 6H), 1.18 (d, J = 9.2 Hz, 3H), 0.73 (q, J = 7.2 Hz, 3H); LC-MS (ESI$^+$) m/z 1125.3 (M + H)$^+$. |
| 456 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(1-(1-(2,6-dioxopiperidin-3-yl)-3-methyl-2-oxo-2,3-dihydro-1H-benzo[d]imidazol-5-yl)piperidin-4-yl)-2,8-diazaspiro[4.5]decane-8-carboxylate<br>$^1$H NMR (400 MHz, DMSO-d$_6$) δ 11.06 (s, 1H), 9.22 (d, J = 3.2 Hz, 1H), 7.76 (dd, J = 6.0, 9.2 Hz, 1H), 7.39-7.29 (m, 2H), 7.03 (d, J = 2.4 Hz, 1H), 6.92 (d, J = 8.4 Hz, 1H), 6.82 (d, J = 1.6 Hz, 1H), 6.68-6.55 (m, 1H), 5.28 (dd, J = 5.2, 12.8 Hz, 1H), 4.87-4.63 (m, 1H), 4.41-4.22 (m, 2H), 4.25-3.93 (m, 6H), 3.63 (d, J = 13.2 Hz, 2H), 3.55-3.52 (m, 4H), 3.51-3.50 (m, 2H), 3.30 (s, 3H), 2.94-2.88 (m, 1H), 2.80-2.73 (m, 2H), 2.71-2.68 (m, 2H), 2.66-2.60 (m, 2H), 2.60-2.56 (m, 1H), 2.40-2.27 (m, 2H), 2.26-2.13 (m, 2H), 2.12-1.88 (m, 6H), 1.85-1.71 (m, 6H), 1.70-1.66 (m, 2H), 1.62-1.53 (m, 4H), 1.53-1.38 (m, 6H), 1.16 (d, J = 9.2 Hz, 3H), 0.73 (q, J = 7.2 Hz, 3H); LC-MS (ESI$^+$) m/z 1126.3 (M + H)$^+$. |
| 457 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 8-((4-(1-(2,6-dioxopiperidin-3-yl)-3-methyl-2-oxo-2,3-dihydro-1H-benzo[d]imidazol-5-yl)piperidin-1-yl)methyl)-2-azaspiro[4.5]decane-2-carboxylate<br>$^1$H NMR (400 MHz, DMSO-d$_6$) δ 11.07 (s, 1H), 10.40-9.50 (m, 1H), 9.22 (d, J = 2.8 Hz, 1H), 7.80-7.71 (m, 1H), 7.39-7.30 (m, 2H), 7.12-7.06 (m, 1H), 7.06-6.95 (m, 2H), 6.90 (d, J = 8.4 Hz, 1H), 5.33 (dd, J = 5.2, 12.8 Hz, 1H), 4.86-4.62 (m, 1H), 4.40-4.26 (m, 1H), 4.25-4.14 (m, 2H), 4.14-3.98 (m, 3H), 3.63 (d, J = 13.2 Hz, 1H), 3.51 (s, 1H), 3.37 (s, 1H), 3.33 (s, 3H), 3.03 (d, J = 4.4 Hz, 2H), 2.97-2.83 (m, 4H), 2.82-2.56 (m, 6H), 2.41-2.31 (m, 1H), 2.15 (d, J = 6.4 Hz, 2H), 2.06-1.92 (m, 5H), 1.69 (d, J = 9.2 Hz, 18H), 1.56-1.46 (m, 4H), 1.29 (d, J = 2.0 Hz, 2H), 1.17 (d, J = 9.2 Hz, 3H), 1.00 (q, J = 11.6 Hz, 2H), 0.73 (q, J = 7.2 Hz, 3H); LC-MS (ESI+) m/z 1139.3 (M $^+$ H)$^+$. |
| 458 | 3-(5-(1-(4-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methoxy)benzyl)piperidin-4-yl)-3-methyl-2-oxo-2,3-dihydro-1H-benzo[d]imidazol-1-yl)piperidine-2,6-dione<br>$^1$H NMR (400 MHz, DMSO-d$_6$) δ 11.08 (s, 1H), 10.04-9.91 (m, 1H), 9.23 (s, 1H), 7.80-7.73 (m, 1H), 7.39-7.31 (m, 2H), 7.20 (d, J = 8.0 Hz, 2H), 7.10 (s, 1H), 7.03 (d, J = 2.0 Hz, 1H), 6.99 (d, J = 8.4 Hz, 1H), 6.95-6.84 (m, 3H), 5.37-5.28 (m, 1H), 4.79-4.73 (m, |

-continued

| Compound No. | Compound Name<br>$^1$H NMR Peaks |
|---|---|
| | 1H), 4.55-4.48 (m, 1H), 4.47-4.43 (m, 1H), 4.40-4.30 (m, 1H), 4.25-4.15 (m, 1H), 4.12-4.01 (m, 1H), 3.65-3.60 (m, 1H), 3.54-3.50 (m, 1H), 3.40 (s, 3H), 3.21-3.18 (m, 1H), 3.10-2.96 (m, 3H), 2.94-2.84 (m, 4H), 2.73-2.65 (m, 2H), 2.64-2.56 (m, 2H), 2.37-2.31 (m, 2H), 2.19-2.11 (m, 1H), 2.05-1.89 (m, 6H), 1.81-1.59 (m, 12H), 1.17 (d, J = 9.2 Hz, 3H), 0.73 (q, J = 6.8 Hz, 3H); LC-MS (ESI$^+$) m/z 1050.3 (M + H)$^+$. |
| 461 | ((3S,7aS)-7a-(((7-(8-ethyl-7-fluoro-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.08 (s, 1H), 9.33 (s, 1H), 7.73 (dd, J = 6.0, 9.2 Hz, 1H), 7.47 (s, 1H), 7.32 (t, J = 9.2 Hz, 1H), 7.26 (d, J = 2.8 Hz, 1H), 7.10 (s, 1H), 7.02-6.95 (m, 2H), 6.90 (d, J = 7.6 Hz, 1H), 5.33 (dd, J = 5.2, 12.4 Hz, 1H), 4.89-4.66 (m, 1H), 4.29-4.11 (m, 4H), 4.09-3.97 (m, 2H), 3.62-3.46 (m, 4H), 3.32 (s, 3H), 3.25 (d, J = 2.0 Hz, 3H), 2.90 (dd, J = 2.8, 6.0 Hz, 2H), 2.79-2.59 (m, 6H), 2.34-2.25 (m, 1H), 2.08-1.91 (m, 6H), 1.81-1.61 (m, 16H), 1.58-1.48 (m, 5H), 1.40 (s, 2H), 1.16 (s, 3H), 0.77 (t, J = 7.2 Hz, 3H); LC-MS (ESI$^+$) m/z 1093.3 (M + H)$^+$. |
| 462 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 6-((1-(1-(2,6-dioxopiperidin-3-yl)-3-methyl-2-oxo-2,3-dihydro-1H-benzo[d]imidazol-5-yl)piperidin-4-yl)methyl)-2,6-diazaspiro[3.3]heptane-2-carboxylate<br>$^1$H NMR (400 MHz, DMSO-$d_6$) δ 11.05 (s, 1H), 9.23 (d, J = 2.4 Hz, 1H), 7.76 (dd, J = 6.0, 9.2 Hz, 1H), 7.39-7.29 (m, 2H), 7.03 (d, J = 2.4 Hz, 1H), 6.91 (d, J = 8.8 Hz, 1H), 6.80 (d, J = 2.0 Hz, 1H), 6.60 (dd, J = 2.0, 8.8 Hz, 1H), 5.28 (dd, J = 5.6, 12.8 Hz, 1H), 4.95-4.56 (m, 1H), 4.33 (t, J = 14.4 Hz, 1H), 4.23-4.15 (m, 2H), 4.12-4.03 (m, 3H), 3.96 (s, 4H), 3.63 (d, J = 13.2 Hz, 1H), 3.53 (d, J = 12.8 Hz, 4H), 3.43-3.34 (m, 2H), 3.29 (s, 3H), 2.96-2.82 (m, 2H), 2.80-2.61 (m, 4H), 2.60-2.52 (m, 3H), 2.37-2.27 (m, 3H), 2.18-2.10 (m, 1H), 2.08-1.94 (m, 3H), 1.84-1.59 (m, 12H), 1.57-1.48 (m, 1H), 1.39-1.30 (m, 1H), 1.28-1.20 (m, 2H), 1.17 (d, J = 9.2 Hz, 3H), 0.73 (q, J = 7.2 Hz, 3H); LC-MS (ESI$^+$) m/z 1098.4 (M + H)$^+$. |
| 463 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(1-(1-(2,6-dioxopiperidin-3-yl)-3-methyl-2-oxo-2,3-dihydro-1H-benzo[d]imidazol-5-yl)piperidin-4-yl)-2,7-diazaspiro[3.5]nonane-7-carboxylate<br>$^1$H NMR (400 MHz, DMSO-$d_6$) δ 11.06 (s, 1H), 10.09-9.86 (m, 1H), 9.26 (d, J = 3.6 Hz, 1H), 7.77 (dd, J = 6.0, 8.8 Hz, 1H), 7.39-7.27 (m, 2H), 7.03 (d, J = 2.4 Hz, 1H), 6.93 (d, J = 8.4 Hz, 1H), 6.85 (d, J = 1.6 Hz, 1H), 6.64 (dd, J = 1.6, 8.4 Hz, 1H), 5.29 (dd, J = 5.2, 12.8 Hz, 1H), 4.75 (d, J = 9.2 Hz, 1H), 4.46-4.17 (m, 5H), 4.13-4.03 (m, 1H), 3.74-3.51 (m, 8H), 3.45-3.38 (m, 3H), 3.30 (s, 3H), 3.17-2.97 (m, 3H), 2.96-2.81 (m, 2H), 2.72-2.53 (m, 5H), 2.41-2.32 (m, 1H), 2.22-2.09 (m, 2H), 2.06-1.80 (m, 10H), 1.69 (s, 8H), 1.44-1.32 (m, 2H), 1.18 (d, J = 9.6 Hz, 3H), 0.73 (q, J = 7.2 Hz, 3H); LC-MS (ESI$^+$) m/z 1112.4 (M + H)$^+$. |
| 464 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(3-(1-(2,6-dioxopiperidin-3-yl)-3-methyl-2-oxo-2,3-dihydro-1H-benzo[d]imidazol-5-yl)azetidin-1-yl)-7-azaspiro[3.5]nonane-7-carboxylate<br>$^1$H NMR (400 MHz, DMSO-$d_6$) δ 11.08 (s, 1H), 9.22 (d, J = 3.2 Hz, 1H), 7.76 (dd, J = 6.0, 9.2 Hz, 1H), 7.41-7.29 (m, 2H), 7.12 (s, 1H), 7.07-6.94 (m, 3H), 5.34 (dd, J = 5.6, 12.8 Hz, 1H), 4.83-4.63 (m, 1H), 4.39-4.27 (m, 1H), 4.25-3.97 (m, 6H), 3.62-3.56 (m, 4H), 3.33 (s, 3H), 3.05 (s, 2H), 2.94-2.83 (m, 2H), 2.78-2.63 (m, 5H), 2.37-2.29 (m, 2H), 2.21-1.94 (m, 5H), 1.88-1.61 (m, 12H), 1.60-1.38 (m, 8H), 1.17 (d, J = 9.2 Hz, 3H), 0.73 (q, J = 7.2 Hz, 3H); LC-MS (ESI$^+$) m/z 1083.3 (M + H)$^+$. |
| 465 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 9-(4-(1-(2,6-dioxopiperidin-3-yl)-3-methyl-2-oxo-2,3-dihydro-1H-benzo[d]imidazol-5-yl)piperidin-1-yl)-3-azaspiro[5.5]undecane-3-carboxylate<br>$^1$H NMR (400 MHz, DMSO-$d_6$) δ 11.08 (s, 1H), 9.22 (d, J = 4.8 Hz, 1H), 7.82-7.71 (m, 1H), 7.42-7.28 (m, 2H), 7.10-7.02 (m, 2H), 7.01-6.88 (m, 2H), 5.33 (dd, J = 4.8, 13.2 Hz, 1H), 4.80-4.70 (m, 1H), 4.39-3.94 (m, 7H), 3.63 (d, J = 13.6 Hz, 1H), 3.52 (d, J = 12.8 Hz, 1H), 3.32 (s, 3H), 3.03-2.84 (m, 4H), 2.81-2.68 (m, 3H), 2.65-2.58 (m, 1H), 2.54 (s, 2H), 2.31-2.21 (m, 3H), 2.17-1.97 (m, 5H), 1.80-1.49 (m, 20H), 1.45-1.36 (m, 4H), 1.24-1.20 (m, 2H), 1.17 (d, J = 9.2 Hz, 3H), 1.10-1.02 (m, 2H), 0.73 (q, J = 7.6 Hz, 3H); LC-MS (ESI$^+$) m/z 1139.4 (M + H)$^+$. |
| 466 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 9-((4-(1-(2,6-dioxopiperidin-3-yl)-3-methyl-2-oxo-2,3-dihydro-1H-benzo[d]imidazol-5-yl)piperidin-1-yl)methyl)-3-azaspiro[5.5]undecane-3-carboxylate<br>$^1$H NMR (400 MHz, DMSO-$d_6$) δ 11.08 (s, 1H), 10.20-9.69 (m, 1H), 9.24 (d, J = 4.4 Hz, 1H), 7.76 (dd, J = 6.0, 9.2 Hz, 1H), 7.43-7.25 (m, 2H), 7.08 (s, 1H), 7.05-6.97 (m, 2H), 6.90 (d, J = 8.0 Hz, 1H), 5.33 (dd, J = 5.2, 12.8 Hz, 1H), 4.85-4.60 (m, 1H), 4.41-4.24 (m, 2H), 4.23-4.13 (m, 3H), 4.12-3.99 (m, 1H), 3.64 (d, J = 13.2 Hz, 1H), 3.53 (d, J = |

-continued

| Compound No. | Compound Name / $^1$H NMR Peaks |
|---|---|
| | 13.2 Hz, 1H), 3.39 (s, 3H), 3.33 (s, 3H), 3.03 (d, J = 9.6 Hz, 2H), 2.96-2.83 (m, 3H), 2.76-2.62 (m, 2H), 2.61-2.52 (m, 2H), 2.40-2.24 (m, 3H), 2.23-2.07 (m, 4H), 2.06-1.95 (m, 2H), 1.90-1.48 (m, 20H), 1.40 (s, 2H), 1.24 (s, 2H), 1.17 (d, J = 9.2 Hz, 3H), 1.05 (d, J = 9.6 Hz, 4H), 0.73 (q, J = 7.2 Hz, 3H); LC-MS (ESI$^+$) m/z 1153.3 (M + H)$^+$. |
| 467 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 7-(4-(1-(2,6-dioxopiperidin-3-yl)-3-methyl-2-oxo-2,3-dihydro-1H-benzo[d]imidazol-5-yl)piperidin-1-yl)-2-azaspiro[3.5]nonane-2-carboxylate<br>$^1$H NMR (400 MHz, DMSO-$d_6$) δ 11.15-10.99 (m, 1H), 10.01-9.82 (m, 1H), 9.22 (d, J = 2.4 Hz, 1H), 7.76 (dd, J = 6.0, 9.2 Hz, 1H), 7.39-7.29 (m, 2H), 7.07 (s, 1H), 7.05-6.94 (m, 2H), 6.89 (d, J = 8.4 Hz, 1H), 5.33 (dd, J = 4.8, 13.2 Hz, 1H), 4.81-4.68 (m, 1H), 4.39-4.26 (m, 1H), 4.22-3.99 (m, 5H), 3.67-3.49 (m, 6H), 2.98-2.84 (m, 4H), 2.78-2.68 (m, 3H), 2.63 (d, J = 5.6 Hz, 1H), 2.32-2.20 (m, 4H), 2.18-1.95 (m, 5H), 1.92-1.83 (m, 2H), 1.80-1.60 (m, 16H), 1.56-1.21 (m, 7H), 1.17 (d, J = 9.2 Hz, 3H), 0.73 (q, J = 7.6 Hz, 3H); LC-MS (ESI$^+$) m/z 1111.3 (M + H)$^+$. |
| 468 | ((3S,7aS)-7a-(((7-(8-ethyl-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.07 (s, 1H), 10.52-9.51 (m, 1H), 9.21 (d, J = 9.2 Hz, 1H), 7.66 (d, J = 8.4 Hz, 1H), 7.36 (t, J = 7.6 Hz, 1H), 7.28 (d, J = 2.4 Hz, 1H), 7.15-7.08 (m, 2H), 7.03-6.95 (m, 2H), 6.90 (d, J = 8.4 Hz, 1H), 5.33 (dd, J = 5.2, 12.4 Hz, 1H), 4.83-4.63 (m, 1H), 4.37-4.26 (m, 1H), 4.25-4.00 (m, 5H), 3.62-3.53 (m, 1H), 3.44-3.40 (m, 2H), 3.32 (s, 3H), 3.25 (s, 3H), 2.92-2.87 (m, 2H), 2.80-2.59 (m, 6H), 2.30-2.16 (m, 2H), 2.11-1.87 (m, 6H), 1.82-1.61 (m, 16H), 1.57-1.47 (m, 5H), 1.39 (s, 2H), 1.17 (d, J = 10.4 Hz, 3H), 0.87-0.78 (m, 3H); LC-MS (ESI$^+$) m/z 1093.2 (M + H)$^+$. |
| 469 | ((3S,7aS)-7a-(((4-(3,3-difluoropiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 6-(4-(1-(2,6-dioxopiperidin-3-yl)-3-methyl-2-oxo-2,3-dihydro-1H-benzo[d]imidazol-5-yl)piperidin-1-yl)-2-azaspiro[3.3]heptane-2-carboxylate<br>$^1$H NMR (400 MHz, DMSO-$d_6$) δ 11.07 (s, 1H), 10.53-9.37 (m, 1H), 9.13 (s, 1H), 7.77 (dd, J = 6.0, 9.2 Hz, 1H), 7.41-7.28 (m, 2H), 7.06 (d, J = 10.0 Hz, 2H), 6.99 (d, J = 8.0 Hz, 1H), 6.89 (d, J = 7.6 Hz, 1H), 5.33 (dd, J = 5.2, 12.8 Hz, 1H), 4.32-4.20 (m, 3H), 4.19-4.13 (m, 2H), 4.09 (dd, J = 5.6, 11.2 Hz, 1H), 4.00-3.94 (m, 2H), 3.92 (s, 2H), 3.80 (s, 3H), 3.32 (s, 3H), 2.88 (d, J = 10.8 Hz, 3H), 2.82-2.73 (m, 2H), 2.69 (dd, J = 4.0, 13.2 Hz, 1H), 2.65-2.57 (m, 2H), 2.40-2.17 (m, 6H), 2.16-2.04 (m, 2H), 2.02-1.91 (m, 5H), 1.86-1.72 (m, 9H), 1.69-1.50 (m, 4H), 0.72 (t, J = 7.2 Hz, 3H); LC-MS (ESI$^+$) m/z 1089.2 (M + H)$^+$. |
| 470 | ((3S,7aS)-7a-(((4-(3,3-difluoropiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.08 (s, 1H), 9.95 (s, 1H), 9.14 (s, 1H), 7.77 (dd, J = 6.0, 9.2 Hz, 1H), 7.40-7.32 (m, 2H), 7.10 (s, 1H), 7.05 (d, J = 2.4 Hz, 1H), 7.00 (d, J = 8.0 Hz, 1H), 6.91 (d, J = 8.0 Hz, 1H), 5.34 (dd, J = 5.6, 12.4 Hz, 1H), 4.34-4.05 (m, 6H), 4.04-3.91 (m, 2H), 3.25 (s, 3H), 2.98-2.83 (m, 3H), 2.77-2.70 (m, 2H), 2.69-2.62 (m, 2H), 2.60 (s, 1H), 2.41-2.34 (m, 1H), 2.29-2.20 (m, 2H), 2.16-2.11 (m, 1H), 2.07-1.91 (m, 7H), 1.84-1.61 (m, 12H), 1.56-1.45 (m, 5H), 1.44-1.36 (m, 2H), 1.32-1.20 (m, 4H), 0.92-0.79 (m, 1H), 0.73 (t, J = 7.2 Hz, 3H); LC-MS (ESI$^+$) m/z 1117.3 (M + H)$^+$. |
| 474 | ((3S,7aS)-7a-(((7-(7-fluoro-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.08 (s, 1H), 9.46 (s, 1H), 7.88 (dd, J = 6.0, 9.2 Hz, 1H), 7.78 (dd, J = 2.4, 12.0 Hz, 1H), 7.55 (s, 1H), 7.40-7.29 (m, 3H), 7.09 (s, 1H), 6.99 (d, J = 8.0 Hz, 1H), 6.90 (d, J = 7.6 Hz, 1H), 5.33 (dd, J = 5.2, 12.8 Hz, 1H), 4.86-4.53 (m, 1H), 4.31 (d, J = 12.4 Hz, 1H), 4.25-4.01 (m, 6H), 3.59 (d, J = 13.2 Hz, 2H), 3.40-3.34 (m, 2H), 3.32 (s, 3H), 3.24 (s, 2H), 2.91 (d, J = 11.2 Hz, 3H), 2.86-2.69 (m, 4H), 2.68-2.58 (m, 2H), 2.09-1.93 (m, 5H), 1.85-1.61 (m, 16H), 1.59-1.52 (m, 3H), 1.48 (s, 2H), 1.40 (s, 2H), 1.18 (s, 3H); LC-MS (ESI$^+$) m/z 1065.3 (M + H)$^+$. |
| 476 | ((3S,7aS)-7a-(((4-((R)-3-aminopiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>1H NMR (400 MHz, DMSO-d6) δ 11.20-10.90 (m, 1H), 9.11 (s, 1H), 7.83-7.72 (m, 1H), 7.41-7.30 (m, 2H), 7.10 (s, 1H), 7.05-6.96 (m, 2H), 6.90 (d, J = 7.6 Hz, 1H), 5.41-5.24 (m, 1H), 4.42-4.34 (m, 1H), 4.30-4.04 (m, 5H), 3.32 (s, 3H), 3.26 (d, J = 3.2 Hz, 8H), 3.18-3.13 (m, 2H), 2.93-2.85 (m, 3H), 2.77-2.63 (m, 6H), 2.20-1.88 (m, 8H), 1.82-1.60 (m, 14H), 1.59-1.46 (m, 6H), 1.39 (s, 2H), 0.73 (t, J = 7.2 Hz, 3H); LC-MS (ESI+) m/z 1096.4 (M + H)+. |

-continued

| Compound No. | Compound Name <br> $^1$H NMR Peaks |
|---|---|
| 477 | ((3S,7aS)-7a-(((4-((S)-3-aminopiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate <br> 1H NMR (400 MHz, DMSO-d6) δ 11.28-10.87 (m, 1H), 9.11 (s, 1H), 7.76 (dd, J = 6.0, 8.8 Hz, 1H), 7.40-7.27 (m, 2H), 7.10 (s, 1H), 7.03-6.87 (m, 3H), 5.33 (dd, J = 5.6, 12.8 Hz, 1H), 4.42-4.36 (m, 1H), 4.28-4.05 (m, 7H), 3.32 (s, 3H), 3.24 (d, J = 4.0 Hz, 4H), 2.93-2.85 (m, 4H), 2.77-2.68 (m, 4H), 2.61 (d, J = 18.4 Hz, 2H), 2.40-2.35 (m, 1H), 2.16-2.09 (m, 1H), 2.08-1.92 (m, 7H), 1.80-1.63 (m, 14H), 1.58-1.47 (m, 6H), 1.39 (s, 2H), 0.73 (t, J = 7.6 Hz, 3H); LC-MS (ESI+) m/z 1096.4 (M + H)+. |
| 478 | ((3S,7aS)-7a-(((4-((S)-3-amino-3-methylpiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate <br> 1H NMR (400 MHz, DMSO-d6) δ 11.24-10.89 (m, 1H), 9.18 (s, 1H), 7.81-7.71 (m, 1H), 7.39-7.29 (m, 2H), 7.10 (s, 1H), 7.06-6.96 (m, 2H), 6.90 (d, J = 8.0 Hz, 1H), 5.33 (dd, J = 5.2, 12.4 Hz, 1H), 4.08 (s, 10H), 3.83-3.65 (m, 4H), 3.32 (s, 3H), 3.24 (s, 2H), 2.95-2.87 (m, 3H), 2.82-2.65 (m, 5H), 2.61 (d, J = 17.6 Hz, 2H), 2.41-2.32 (m, 1H), 2.14-1.93 (m, 6H), 1.86-1.62 (m, 15H), 1.59-1.47 (m, 5H), 1.40 (s, 2H), 1.27 (d, J = 10.4 Hz, 2H), 0.75-0.71 (m, 2H); LC-MS (ESI+) m/z 1110.4 (M + H)+. |
| 479 | ((3S,7aS)-7a-(((4-((R)-3-amino-3-methylpiperidin-1-yl)-7-(8-ethyl-7-fluoro-3-hydroxynaphthalen-1-yl)-8-fluoropyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate <br> 1H NMR (400 MHz, DMSO-d6) δ 11.25-10.86 (m, 1H), 9.19 (d, J = 2.4 Hz, 1H), 8.25 (s, 2H), 7.76 (dd, J = 6.0, 9.2 Hz, 1H), 7.38-7.30 (m, 2H), 7.10 (s, 1H), 7.03 (d, J = 2.0 Hz, 1H), 7.01-6.96 (m, 1H), 6.90 (d, J = 7.6 Hz, 1H), 5.33 (dd, J = 5.6, 12.8 Hz, 1H), 4.23-4.08 (m, 4H), 4.03 (d, J = 13.6 Hz, 1H), 3.94 (d, J = 13.6 Hz, 1H), 3.80-3.71 (m, 1H), 3.69-3.61 (m, 1H), 3.32 (s, 5H), 3.27-3.22 (m, 2H), 2.94-2.84 (m, 3H), 2.80-2.66 (m, 4H), 2.64-2.57 (m, 1H), 2.42-2.35 (m, 1H), 2.18-2.09 (m, 1H), 2.06-1.92 (m, 5H), 1.85-1.62 (m, 16H), 1.59-1.44 (m, 6H), 1.43-1.36 (m, 2H), 1.24 (d, J = 11.2 Hz, 3H), 0.73 (dt, J = 4.4, 7.2 Hz, 3H); LC-MS (ESI+) m/z 1110.4 (M + H)+. |
| 484 | 4-((4-(1-(2,6-dioxopiperidin-3-yl)-3-methyl-2-oxo-2,3-dihydro-1H-benzo[d]imidazol-5-yl)piperidin-1-yl)methyl)-N-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)benzamide <br> $^1$H NMR (400 MHz, DMSO-$d_6$) δ 11.07 (s, 1H), 10.45-9.45 (m, 1H), 9.22 (d, J = 2.8 Hz, 1H), 8.49 (d, J = 4.4 Hz, 1H), 7.81 (d, J = 7.6 Hz, 2H), 7.76 (dd, J = 6.0, 9.2 Hz, 1H), 7.41 (d, J = 8.0 Hz, 2H), 7.38-7.29 (m, 2H), 7.09 (s, 1H), 7.04-6.96 (m, 2H), 6.91 (d, J = 8.8 Hz, 1H), 5.38-5.26 (m, 1H), 4.83-4.65 (m, 1H), 4.40-4.28 (m, 1H), 4.26-4.19 (m, 1H), 4.18-4.11 (m, 1H), 4.10-3.99 (m, 1H), 3.66-3.57 (m, 2H), 3.54 (s, 2H), 3.50-3.43 (m, 2H), 3.32 (s, 3H), 3.03-2.07 (m, 1H), 2.93-2.80 (m, 4H), 2.74-2.54 (m, 3H), 2.37-2.30 (m, 1H), 2.15-2.03 (m, 4H), 2.02-1.94 (m, 2H), 1.88-1.56 (m, 15H), 1.16 (d, J = 8.8 Hz, 3H), 0.72 (q, J = 7.2 Hz, 3H); LC-MS ($ESI^+$) m/z 1077.3 $(M + H)^+$. |
| 485 | 3-(5-((1-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)piperidin-4-yl)methyl)-3-methyl-2-oxo-2,3-dihydro-1H-benzo[d]imidazol-1-yl)piperidine-2,6-dione <br> $^1$H NMR (400 MHz, DMSO-$d_6$) δ 11.07 (s, 1H), 9.21 (d, J = 2.4 Hz, 1H), 7.76 (dd, J = 6.4, 8.0 Hz, 1H), 7.38-7.29 (m, 2H), 7.02 (s, 1H), 7.00-6.95 (m, 2H), 6.80 (d, J = 8.0 Hz, 1H), 5.32 (dd, J = 5.2, 12.8 Hz, 1H), 4.83-4.64 (m, 1H), 4.37-4.25 (m, 1H), 4.12-3.98 (m, 3H), 3.62 (d, J = 13.2 Hz, 1H), 3.30 (s, 3H), 2.96-2.81 (m, 6H), 2.74-2.57 (m, 4H), 2.39-2.09 (m, 5H), 2.00 (d, J = 6.0 Hz, 3H), 1.91-1.75 (m, 6H), 1.72-1.47 (m, 9H), 1.16 (d, J = 9.6 Hz, 5H), 0.77-0.67 (m, 3H); LC-MS ($ESI^+$) m/z 958.3 $(M + H)^+$. |
| 486 | 3-(5-(3-((1-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)piperidin-4-yl)oxy)propyl)-3-methyl-2-oxo-2,3-dihydro-1H-benzo[d]imidazol-1-yl)piperidine-2,6-dione <br> $^1$H NMR (400 MHz, DMSO-$d_6$) δ 11.07 (s, 1H), 9.22 (d, J = 2.0 Hz, 1H), 7.76 (dd, J = 6.0, 8.8 Hz, 1H), 7.39-7.29 (m, 2H), 7.06-6.96 (m, 3H), 6.85 (d, J = 8.0 Hz, 1H), 5.33 (dd, J = 5.2, 12.8 Hz, 1H), 4.85-4.61 (m, 1H), 4.40-4.25 (m, 1H), 4.13-3.99 (m, 3H), 3.62 (d, J = 13.2 Hz, 1H), 3.38-3.37 (m, 2H), 3.31 (s, 3H), 2.95-2.79 (m, 4H), 2.74-2.61 (m, 7H), 2.39-2.11 (m, 5H), 2.08-1.96 (m, 5H), 1.95-1.89 (m, 1H), 1.82-1.73 (m, 7H), 1.72-1.50 (m, 6H), 1.45-1.34 (m, 2H), 1.16 (d, J = 9.0 Hz, 3H), 0.79-0.69 (m, 3H); LC-MS ($ESI^+$) m/z 1002.3 $(M + H)^+$. |
| 487 | ((3S,7aS)-7a-(((7-(8-ethyl-3-hydroxynaphthalen-1-yl)-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate <br> $^1$H NMR (400 MHz, DMSO-$d_6$) δ 11.09 (s, 1H), 9.32 (s, 1H), 7.63 (d, J = 8.0 Hz, 1H), |

-continued

| Compound No. | Compound Name<br>$^1$H NMR Peaks |
| --- | --- |
| | 7.44 (s, 1H), 7.35 (t, J = 7.6 Hz, 1H), 7.22 (d, J = 2.4 Hz, 1H), 7.13-7.08 (m, 2H), 7.01-6.97 (m, 1H), 6.95 (d, J = 2.8 Hz, 1H), 6.90 (d, J = 7.6 Hz, 1H), 5.33 (dd, J = 5.2, 12.8 Hz, 1H), 4.24-4.11 (m, 4H), 4.07 (d, J = 10.4 Hz, 1H), 3.98 (d, J = 14.0 Hz, 1H), 3.65-3.59 (m, 1H), 3.53-3.47 (m, 1H), 3.39 (s, 2H), 3.32 (s, 3H), 3.25 (s, 2H), 2.91 (d, J = 11.2 Hz, 3H), 2.83-2.69 (m, 4H), 2.68-2.57 (m, 2H), 2.28-2.14 (m, 2H), 2.09-1.94 (m, 5H), 1.84-1.63 (m, 16H), 1.58-1.47 (m, 5H), 1.40 (s, 2H), 1.16 (d, J = 6.0 Hz, 3H), 0.82 (t, J = 7.2 Hz, 3H); LC-MS (ESI$^+$) m/z 1075.4 (M + H)$^+$. |
| 489 | ((3S,7aS)-7a-(((7-(8-ethyl-7-fluoro-3-hydroxynaphthalen-1-yl)-8-fluoro-4-(1,4-oxazepan-4-yl)pyrido[4,3-d]pyrimidin-2-yl)oxy)methyl)hexahydro-1H-pyrrolizin-3-yl)methyl 2-(4-(1-(2,6-dioxopiperidin-3-yl)-3-methyl-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 11.09 (s, 1H), 10.69-10.06 (m, 1H), 9.96 (s, 1H), 9.21 (s, 1H), 7.77 (dd, J = 6.0, 9.2 Hz, 1H), 7.43-7.29 (m, 2H), 7.10-6.99 (m, 3H), 6.91 (d, J = 8.4 Hz, 1H), 5.35 (dd, J = 5.6, 12.8 Hz, 1H), 4.64-4.32 (m, 2H), 4.28-4.12 (m, 6H), 3.96 (d, J = 4.4 Hz, 2H), 3.76 (t, J = 4.8 Hz, 2H), 3.34 (s, 3H), 3.31-3.29 (m, 4H), 2.99-2.82 (m, 2H), 2.80-2.57 (m, 5H), 2.54 (s, 2H), 2.42-2.31 (m, 2H), 2.10 (d, J = 3.6 Hz, 7H), 2.03-1.66 (m, 14H), 1.56-1.42 (m, 4H), 0.73 (t, J = 7.2 Hz, 3H). LC-MS (ESI$^+$) m/z 1097.5 (M + H)$^+$. |
| 490 | 3-(5-(1-(3-(((7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methoxy)propyl)piperidin-4-yl)-3-methyl-2-oxo-2,3-dihydro-1H-benzo[d]imidazol-1-yl)piperidine-2,6-dione<br>$^1$H NMR (400 MHz, DMSO-$d_6$) δ 11.07 (s, 1H), 10.05-9.84 (m, 1H), 9.22 (d, J = 2.0 Hz, 1H), 7.76 (dd, J = 6.0, 9.2 Hz, 1H), 7.39-7.29 (m, 2H), 7.08 (s, 1H), 7.04-6.95 (m, 2H), 6.93-6.85 (m, 1H), 5.38-5.27 (m, 1H), 4.80-4.67 (m, 1H), 4.40-4.25 (m, 1H), 4.21-4.12 (m, 1H), 4.11-3.97 (m, 2H), 3.66-3.54 (m, 3H), 3.52-3.47 (m, 3H), 3.44 (s, 3H), 2.99-2.84 (m, 4H), 2.80-2.69 (m, 3H), 2.65-2.58 (m, 2H), 2.36 (d, J = 6.8 Hz, 2H), 2.20-1.94 (m, 7H), 1.80-1.61 (m, 15H), 1.56-1.46 (m, 1H), 1.17 (d, J = 9.2 Hz, 3H), 0.73 (q, J = 7.2 Hz, 3H); LC-MS (ESI$^+$) m/z 1002.3 (M + H)$^+$. |
| 491 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 2-(4-(3-methyl-1-(1-methyl-2,6-dioxopiperidin-3-yl)-2-oxo-2,3-dihydro-1H-benzo[d]imidazol-5-yl)piperidin-1-yl)-7-azaspiro[3.5]nonane-7-carboxylate<br>$^1$H NMR (400 MHz, DMSO-$d_6$) δ 9.23 (d, J = 3.2 Hz, 1H), 7.76 (dd, J = 6.0, 9.2 Hz, 1H), 7.39-7.29 (m, 2H), 7.10 (s, 1H), 7.05-6.97 (m, 2H), 6.89 (d, J = 8.0 Hz, 1H), 5.40 (dd, J = 5.6, 13.2 Hz, 1H), 4.34 (dd, J = 13.2, 16.4 Hz, 2H), 4.23-4.15 (m, 3H), 4.14-4.04 (m, 3H), 3.65-3.50 (m, 1H), 3.43-3.36 (m, 2H), 3.33 (s, 3H), 3.25 (s, 2H), 3.03 (s, 3H), 2.99-2.92 (m, 3H), 2.82-2.73 (m, 4H), 2.72-2.66 (m, 1H), 2.57-2.53 (m, 1H), 2.38-2.30 (m, 1H), 2.15-1.95 (m, 6H), 1.90-1.63 (m, 16H), 1.61-1.53 (m, 3H), 1.51-1.46 (m, 2H), 1.43-1.37 (m, 2H), 1.17 (d, J = 9.2 Hz, 3H), 0.73 (q, J = 7.2 Hz, 3H); LC-MS (ESI$^+$) m/z 1125.4 (M + H)$^+$. |
| 492 | ((3S,7aS)-7a-(((7-(8-ethyl-7-fluoro-3-hydroxynaphthalen-1-yl)-8-fluoro-4-((R)-3-hydroxy-3-methylpiperidin-1-yl)-1,6-naphthyridin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperidin-1-yl)methyl)piperidine-1-carboxylate<br>$^1$H NMR (400 MHz, DMSO-$d_6$) δ 11.08 (s, 1H), 10.06-9.69 (m, 1H), 9.22 (d, J = 13.2 Hz, 1H), 7.76 (dd, J = 6.0, 8.8 Hz, 1H), 7.39-7.28 (m, 2H), 7.08 (s, 1H), 7.02 (s, 1H), 6.99 (d, J = 7.6 Hz, 1H), 6.89 (d, J = 8.0 Hz, 1H), 6.49 (s, 1H), 5.33 (dd, J = 5.2, 12.4 Hz, 1H), 4.80-4.69 (m, 1H), 4.22-4.10 (m, 4H), 3.98-3.90 (m, 2H), 3.32 (s, 3H), 3.13-3.04 (m, 2H), 2.98 (d, J = 12.0 Hz, 1H), 2.93-2.85 (m, 3H), 2.78-2.70 (m, 4H), 2.67 (d, J = 3.6 Hz, 1H), 2.59 (d, J = 2.4 Hz, 2H), 2.32-2.25 (m, 1H), 2.12-1.90 (m, 9H), 1.78-1.64 (m, 16H), 1.59-1.50 (m, 2H), 1.22 (s, 3H), 0.99-0.89 (m, 2H), 0.73-0.65 (m, 3H); LC-MS (ESI$^+$) m/z 1084.4 (M + H)$^+$. |
| 493 | 3-(5-(1-((1-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methoxy)-2,3-dihydro-1H-inden-5-yl)methyl)piperidin-4-yl)-3-methyl-2-oxo-2,3-dihydro-1H-benzo[d]imidazol-1-yl)piperidine-2,6-dione<br>$^1$H NMR (400 MHz, DMSO-d6) δ 11.08 (s, 1H), 10.11-9.78 (m, 1H), 9.30-9.13 (m, 1H), 7.76 (dd, J = 6.0, 9.2 Hz, 1H), 7.38-7.28 (m, 3H), 7.22 (s, 1H), 7.17-7.12 (m, 1H), 7.11-7.08 (m, 1H), 7.03-6.96 (m, 2H), 6.90 (d, J = 8.0 Hz, 1H), 5.33 (dd, J = 5.6, 12.4 Hz, 1H), 4.91-4.83 (m, 1H), 4.74 (d, J = 7.6 Hz, 1H), 4.38-4.25 (m, 1H), 4.18-4.11 (m, 1H), 4.08-3.96 (m, 2H), 3.74-3.68 (m, 1H), 3.65-3.57 (m, 2H), 3.56-3.49 (m, 2H), 3.47 (s, 3H), 2.99-2.84 (m, 5H), 2.79-2.69 (m, 4H), 2.64-2.58 (m, 2H), 2.29 (d, J = 6.8 Hz, 1H), 2.17-1.95 (m, 8H), 1.78-1.57 (m, 14H), 1.52-1.45 (m, 1H), 1.15 (d, J = 8.8 Hz, 3H), 0.72 (q, J = 7.3 Hz, 3H); LC-MS (ESI+) m/z 1090.5 (M + H)+ |
| 494 | 4-((4-(1-(2,6-dioxopiperidin-3-yl)-3-methyl-2-oxo-2,3-dihydro-1H-benzo[d]imidazol-5-yl)piperidin-1-yl)methyl)-N-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)-2-fluorobenzamide<br>$^1$H NMR (400 MHz, DMSO-$d_6$) δ 11.08 (s, 1H), 9.95 (s, 1H), 9.21 (s, 1H), 8.25 (dd, J = |

-continued

| Compound No. | Compound Name<br>$^1$H NMR Peaks |
|---|---|
| | 5.6, 7.2 Hz, 1H), 7.75 (dd, J = 5.6, 8.8 Hz, 1H), 7.60-7.52 (m, 1H), 7.38-7.29 (m, 2H), 7.25-7.16 (m, 2H), 7.10 (s, 1H), 7.04-6.95 (m, 2H), 6.94-6.89 (m, 1H), 5.33 (dd, J = 5.2, 12.8 Hz, 1H), 4.79-4.69 (m, 1H), 4.38-4.26 (m, 1H), 4.16 (dd, J = 1.6, 10.4 Hz, 1H), 4.11-3.98 (m, 2H), 3.66-3.56 (m, 2H), 3.54 (s, 3H), 3.45-3.43 (m, 2H), 3.21-3.17 (m, 2H), 2.95-2.80 (m, 5H), 2.75-2.58 (m, 4H), 2.35-2.31 (m, 1H), 2.14-2.03 (m, 4H), 2.02-1.95 (m, 2H), 1.78-1.53 (m, 14H), 1.16 (d, J = 8.4 Hz, 3H), 0.78-0.68 (m, 3H); LC-MS (ESI$^+$) m/z 1095.3 (M + H)$^+$. |
| 495 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(4-(1-(2,6-dioxopiperidin-3-yl)-3-methyl-2-oxo-2,3-dihydro-1H-benzo[d]imidazol-5-yl)piperidin-1-yl)benzoate |
| | $^1$H NMR (400 MHz, DMSO-d$_6$) δ 11.08 (s, 1H), 9.22 (d, J = 3.2 Hz, 1H), 7.82-7.72 (m, 3H), 7.38-7.31 (m, 2H), 7.10 (s, 1H), 7.01 (d, J = 9.2 Hz, 4H), 6.92 (d, J = 8.0 Hz, 1H), 5.33 (dd, J = 5.2, 12.4 Hz, 1H), 4.85-4.68 (m, 1H), 4.48-4.40 (m, 1H), 4.39-4.28 (m, 2H), 4.21 (dd, J = 4.4, 10.4 Hz, 1H), 4.15-3.99 (m, 4H), 3.63-3.54 (m, 1H), 3.34 (s, 2H), 3.32 (s, 3H), 2.99-2.88 (m, 3H), 2.87-2.78 (m, 3H), 2.71-2.58 (m, 2H), 2.38-2.29 (m, 1H), 2.17-1.96 (m, 4H), 1.89-1.64 (m, 13H), 1.60-1.50 (m, 1H), 1.16 (d, J = 7.6 Hz, 3H), 0.73 (q, J = 7.2 Hz, 3H); LC-MS (ESI$^+$) m/z 1064.3 (M + H)$^+$. |
| 496 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(4-(1-(2,6-dioxopiperidin-3-yl)-3-methyl-2-oxo-2,3-dihydro-1H-benzo[d]imidazol-5-yl)phenoxy)piperidine-1-carboxylate |
| | $^1$H NMR (400 MHz, DMSO-d$_6$) δ 11.11 (s, 1H), 10.11-9.74 (m, 1H), 9.22 (d, J = 3.2 Hz, 1H), 7.76 (dd, J = 6.4, 8.4 Hz, 1H), 7.59 (d, J = 8.4 Hz, 2H), 7.43 (s, 1H), 7.38-7.30 (m, 2H), 7.30-7.25 (m, 1H), 7.15 (d, J = 8.4 Hz, 1H), 7.08-7.01 (m, 3H), 5.39 (dd, J = 5.2, 12.8 Hz, 1H), 4.81-4.56 (m, 2H), 4.38-4.22 (m, 2H), 4.21-4.14 (m, 2H), 4.12-4.00 (m, 2H), 3.73-3.67 (m, 2H), 3.62 (d, J = 13.2 Hz, 1H), 3.52 (d, J = 13.2 Hz, 1H), 3.39 (s, 3H), 2.95-2.87 (m, 1H), 2.82-2.60 (m, 5H), 2.37 (s, 1H), 2.18-1.89 (m, 7H), 1.83-1.48 (m, 13H), 1.16 (d, J = 9.2 Hz, 3H), 0.73 (q, J = 7.1 Hz, 3H); LC-MS (ESI$^+$) m/z 1080.3 (M + H)$^+$. |
| 497 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-(4-(1-(2,6-dioxopiperidin-3-yl)-3-methyl-2-oxo-2,3-dihydro-1H-benzo[d]imidazol-5-yl)phenoxy)piperidine-1-carboxylate |
| | $^1$H NMR (400 MHz, DMSO-d$_6$) δ 11.12 (s, 1H), 9.94 (s, 1H), 9.23 (d, J = 3.6 Hz, 1H), 7.76 (dd, J = 6.0, 9.2 Hz, 1H), 7.59 (d, J = 8.0 Hz, 2H), 7.46 (s, 1H), 7.39-7.30 (m, 3H), 7.24 (d, J = 8.0 Hz, 2H), 7.17 (d, J = 8.4 Hz, 1H), 5.40 (dd, J = 5.2, 12.8 Hz, 1H), 4.74 (d, J = 9.2 Hz, 1H), 4.41-4.31 (m, 1H), 4.29-4.12 (m, 4H), 4.05 (dd, J = 13.6, 19.6 Hz, 1H), 4.00-3.93 (m, 2H), 3.68-3.47 (m, 2H), 3.40 (s, 3H), 2.96-2.82 (m, 3H), 2.79 (s, 4H), 2.64-2.59 (m, 1H), 2.54 (s, 2H), 2.37-2.29 (m, 1H), 2.23-1.91 (m, 5H), 1.88-1.65 (m, 10H), 1.59 (d, J = 11.2 Hz, 3H), 1.16 (d, J = 9.6 Hz, 3H), 1.12-1.01 (m, 2H), 0.73 (q, J = 7.2 Hz, 3H); LC-MS (ESI$^+$) m/z 1078.3 (M + H)$^+$. |
| 501 | 3-(5-(4-((1-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl)piperidin-4-yl)oxy)piperidin-1-yl)-3-methyl-2-oxo-2,3-dihydro-1H-benzo[d]imidazol-1-yl)piperidine-2,6-dione |
| | $^1$H NMR (400 MHz, DMSO-d6) δ 11.06 (s, 1H), 9.23 (d, J = 2.4 Hz, 1H), 7.76 (dd, J = 6.0, 8.8 Hz, 1H), 7.39-7.29 (m, 2H), 7.03 (d, J = 2.4 Hz, 1H), 6.91 (dd, J = 3.2, 8.8 Hz, 1H), 6.84-6.75 (m, 1H), 6.65-6.56 (m, 1H), 5.28 (dd, J = 5.2, 12.4 Hz, 1H), 4.94-4.57 (m, 1H), 4.37-4.28 (m, 1H), 4.24 (dd, J = 5.2, 10.4 Hz, 1H), 4.15 (d, J = 10.0 Hz, 1H), 4.09-4.00 (m, 1H), 3.63 (d, J = 13.2 Hz, 1H), 3.53 (s, 1H), 3.29 (d, J = 2.4 Hz, 5H), 2.92-2.62 (m, 10H), 2.57 (s, 1H), 2.42-2.28 (m, 3H), 2.17-1.93 (m, 7H), 1.91-1.84 (m, 2H), 1.79-1.64 (m, 10H), 1.59-1.48 (m, 4H), 1.38 (dd, J = 2.8, 5.6 Hz, 2H), 1.16 (d, J = 8.8 Hz, 3H), 0.74 (dt, J = 3.2, 7.2 Hz, 3H); LC-MS (ESI+) m/z 1043.4 (M + H)+. |
| 502 | ((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro-1H-pyrrolizin-3-yl)methyl 4-((4-(1-(2,6-dioxopiperidin-3-yl)-3-methyl-2-oxo-2,3-dihydro-1H-benzo[d]imidazol-5-yl)piperazin-1-yl)methyl)-4-methylpiperidine-1-carboxylate |
| | $^1$H NMR (400 MHz, DMSO-d6) δ 11.06 (s, 1H), 9.93 (s, 1H), 9.24 (d, J = 3.6 Hz, 1H), 8.14 (s, 1H), 7.76 (dd, J = 6.0, 8.8 Hz, 1H), 7.40-7.28 (m, 2H), 7.02 (d, J = 2.4 Hz, 1H), 6.92 (d, J = 8.4 Hz, 1H), 6.81 (s, 1H), 6.59 (d, J = 8.4 Hz, 1H), 5.28 (dd, J = 5.2, 12.8 Hz, 1H), 4.74 (d, J = 10.4 Hz, 1H), 4.43-4.26 (m, 2H), 4.25-4.15 (m, 3H), 4.06 (dd, J = 13.2, 19.6 Hz, 1H), 3.68-3.56 (m, 3H), 3.53 (d, J = 13.2 Hz, 1H), 3.29 (s, 3H), 3.21-3.10 (m, 3H), 3.04 (s, 4H), 2.97-2.83 (m, 3H), 2.73-2.60 (m, 6H), 2.37-2.31 (m, 1H), 2.19 (s, 2H), 2.16-2.07 (m, 2H), 2.02-1.93 (m, 2H), 1.87-1.75 (m, 5H), 1.72-1.60 (m, 4H), 1.40 (t, J = 9.6 Hz, 2H), 1.27-1.12 (m, 5H), 0.93 (s, 3H), 0.73 (q, J = 7.2 Hz, 3H); LC-MS (ESI+) m/z 1100.3 (M + H)+. |
| 503 | 4-((4-(1-(2,6-dioxopiperidin-3-yl)-3-methyl-2-oxo-2,3-dihydro-1H-benzo[d]imidazol-5-yl)piperidin-1-yl)methyl)-N-(((3S,7aS)-7a-(((7-(8-ethyl-7-fluoro-3-hydroxynaphthalen-1-yl)-8-fluoro-4-((R)-3-hydroxy-3-methylpiperidin-1-yl)pyrido[4,3-d]pyrimidin-2-yl)oxy)methyl)hexahydro- |

-continued

| Compound No. | Compound Name<br>$^1$H NMR Peaks |
|---|---|
| | 1H-pyrrolizin-3-yl)methyl)-N-methylbenzamide<br>$^1$H NMR (400 MHz, DMSO-d6) δ 11.24-10.92 (m, 1H), 9.23 (d, J = 5.6 Hz, 1H), 8.11 (d, J = 8.0 Hz, 1H), 8.02 (dd, J = 6.4, 8.8 Hz, 1H), 7.58 (t, J = 7.6 Hz, 1H), 7.53-7.43 (m, 2H), 7.03 (s, 1H), 6.98 (d, J = 8.0 Hz, 1H), 6.86 (d, J = 8.0 Hz, 1H), 5.32 (dd, J = 5.6, 12.8 Hz, 1H), 4.38-4.29 (m, 1H), 4.22-4.08 (m, 4H), 4.06-4.00 (m, 1H), 3.81 (d, J = 12.8 Hz, 2H), 3.65 (s, 1H), 3.34 (s, 3H), 3.31 (s, 3H), 3.15 (s, 2H), 3.01 (s, 2H), 2.93-2.87 (m, 2H), 2.81-2.72 (m, 2H), 2.68 (dd, J = 4.4, 12.8 Hz, 1H), 2.59 (d, J = 1.6 Hz, 1H), 2.43 (dd, J = 6.8, 8.8 Hz, 1H), 2.26-2.17 (m, 1H), 2.09-1.91 (m, 5H), 1.81-1.62 (m, 12H), 1.58-1.40 (m, 5H), 1.16 (d, J = 9.6 Hz, 3H), 1.13-1.01 (m, 2H), 0.76 (q, J = 7.2 Hz, 3H); LC-MS (ESI+) m/z 1091.3 (M + H)+. |

Assay Example 1. KRAS G12D HiBit Assay Protocol

Day 1. Prepared the culture medium for AsPc-1-KRAS (G12D)-HiBit-KI cell (Pharmaron) using RPMI 1640 medium (Gibco, 11875093) with 10% FBS (Gibco, 10099141C) and 1% Penicillin-Streptomycin Liquid (Solarbio, P1400). Cultivated cells in T-75 flasks in a cell culture incubator (Thermo, Model: 371) at 37° C., 5% $CO_2$. Allowed cells to reach approximately 80% confluence before splitting. Rinsed cultivated cells in T-75 flasks with 5 mL PBS (Solarbio, P1020-500). Aspirated off PBS, added 1.5 mL trypsin (Invitrogen, #25300), and incubated at 37° C. for approximately 5 minutes or until the cells detached. Inactivated trypsin by adding excessive serum containing medium. Harvested the cells from flask into cell culture medium and counted the cell number. Seeded AsPc-1-KRAS (G12D)-HiBit-KI cell into 384-well plate (Corning, 3570) (cell density: $5\times10^3$ cells/well in 50 µL medium) in RPMI 1640 medium and incubated overnight at 37° C. and 5% $CO_2$.

Day 2. Test compounds were dissolved at 0.3 mM in DMSO (Solarbio, D8371) as stock solution. Transferred 45 µL of stock solution to a 384-well plate (Labcyte, 001-14555). Performed 3-fold, 10-points dilution via transferring 15 µL compound into 30 µL DMSO by using TECAN liquid handler (TECAN, Freedom EVO200). The compound plates were spin at room temperature at 1,000 RPM for 1 minute (Eppendorf, 5810R). Transferred 50 nL of diluted compounds from compound source plate into the cell plate by Echo (Labcyte, 550) to achieve final concentrations of 300 nM, 100 nM, 33.3 nM, 11.1 nM, 3.7 nM, 1.23 nM, 0.41 nM, 0.14 nM, 0.046 nM and 0.015 nM, then mixed the cell plate on a plate shaker (Yoning, WZ-4) for 15 seconds at 900 rpm.

Day 3. After compound treatment for 24 hours, removed the plate from incubators and equilibrated at room temperature for 15 minutes. Prepared the HiBit reagent (Promega, N3040) by mixing 10 mL of Nano-Glo®-HiBiT Lytic Buffer with 200 µL of Nano-Glo®-HiBiT Lytic Substrate and 100 µL of LgBiT Protein. Added 20 µL of HiBit reagent into each well of the cell plate and spun the plates at room temperature at 1,000 RPM for 1 minute. Then shook the plates at 600 RPM at room temperature for 20 minutes using a plate shaker (Yoning, WZ-4), and read the luminescence by En Vision (PerkinElmer, 2105-0020).

The inhibition activity was calculated using the following formula:

$$HiBit-G12D \text{ level } (\%) = 100\% \times [\text{Luminescence (Sample)/Mean of Luminescence } (HC)]$$

where HC (high control) is obtained from cells treated with 0.1% DMSO only.

Absolute $DC_{50}$ was calculated by fitting the curve using GraphPad Prism v8.0.2 (analysis 263):

$$Y = \text{Bottom} + (100-\text{Bottom})/(1+10\hat{}((\text{LogAbsolute } IC_{50}-X)*\text{HillSlope}+\log((100-\text{Bottom})/(50-\text{Bottom})-1)))$$

The data are reported in Table 4, wherein "+++"=$DC_{50}$ less than 100 nM, "++"=$DC_{50}$ greater than or equal to 100 nM and less than 300 nM; "+"=$DC_{50}$ greater than or equal to 300 nM; "A"=$D_{max}$ greater than 50%; "B"=$D_{max}$ greater than or equal to 15% and less than or equal to 50%; "C"=$D_{max}$ less than 15%.

TABLE 4

KRAS G12D HiBit Assay Data

| Compound No. | Average DC50 | Average Dmax | Compound No. | Average DC50 | Average Dmax |
|---|---|---|---|---|---|
| 1 | +++ | A | 103 | + | B |
| 2 | +++ | A | 104 | + | B |
| 3 | +++ | A | 105 | + | B |
| 4 | +++ | A | 106 | + | C |
| 5 | +++ | A | 107 | + | B |
| 14 | +++ | A | 108 | + | B |
| 15 | ++ | A | 109 | + | B |
| 16 | +++ | A | 110 | +++ | A |
| 17 | +++ | A | 122 | +++ | A |
| 18 | + | B | 123 | +++ | A |
| 94 | +++ | A | 124 | +++ | A |
| 95 | +++ | A | 125 | +++ | A |
| 96 | +++ | A | 209 | + | B |
| 97 | +++ | A | 210 | + | B |
| 98 | +++ | A | 211 | + | C |
| 99 | +++ | A | 12 | +++ | |
| 100 | +++ | A | 24 | + | |
| 101 | +++ | A | 26 | + | |
| 102 | +++ | A | 28 | +++ | |
| 11 | + | | 30 | +++ | |
| 13 | +++ | | 32 | >100 | |
| 25 | +++ | | 34 | +++ | |
| 27 | + | | 36 | + | |
| 29 | + | | 38 | >100 | |
| 31 | + | | 40 | + | |
| 33 | + | | 42 | + | |
| 35 | + | | 44 | >100 | |
| 37 | + | | 46 | +++ | |
| 39 | + | | 41 | + | |
| 45 | +++ | | 49 | >160 | |
| 47 | +++ | | 51 | +++ | |
| 48 | + | | 53 | + | |
| 50 | +++ | | 55 | +++ | |

TABLE 4-continued

KRAS G12D HiBit Assay Data

| Compound No. | Average DC50 | Average Dmax | Compound No. | Average DC50 | Average Dmax |
|---|---|---|---|---|---|
| 52 | +++ | | 57 | +++ | |
| 54 | +++ | | 59 | +++ | |
| 56 | +++ | | 61 | + | |
| 58 | +++ | | 64 | +++ | |
| 60 | +++ | | 66 | + | |
| 63 | + | | 69 | +++ | |
| 65 | +++ | | 71 | +++ | |
| 67 | +++ | | 73 | + | |
| 70 | + | | 77 | +++ | |
| 72 | +++ | | 87 | >100 | |
| 74 | + | | 112 | + | |
| 78 | + | | 114 | + | |
| 85 | +++ | | 116 | + | |
| 111 | + | | 118 | +++ | |
| 113 | + | | 120 | +++ | |
| 115 | + | | 122 | +++ | |
| 117 | + | | 124 | +++ | |
| 119 | + | | 126 | >38.3 | |
| 121 | +++ | | 128 | + | |
| 123 | +++ | | 130 | + | |
| 125 | +++ | | 132 | +++ | |
| 127 | +++ | | 134 | +++ | |
| 129 | + | | 136 | + | |
| 131 | + | | 138 | >100 | |
| 133 | +++ | | 141 | >100 | |
| 135 | + | | 144 | +++ | |
| 137 | ++ | | 146 | +++ | |
| 140 | +++ | | 152 | >100 | |
| 142 | +++ | | 154 | +++ | |
| 145 | +++ | | 156 | +++ | |
| 147 | >100 | | 158 | +++ | |
| 153 | >100 | | 160 | +++ | |
| 155 | +++ | | 223 | >231 | |
| 157 | >100 | | 405 | +++ | |
| 159 | +++ | | 407 | +++ | |
| 222 | + | | 409 | +++ | |
| 224 | + | | 410 | +++ | |
| 300 | +++ | | 413 | +++ | |
| 301 | +++ | | 414 | +++ | |
| 302 | >100 | | 415 | +++ | |
| 303 | +++ | | 416 | +++ | |
| 304 | >100 | | 417 | +++ | |
| 306 | >100 | | 418 | +++ | |
| 307 | +++ | | 419 | +++ | |
| 308 | >100 | | 420 | +++ | |
| 309 | >100 | | 421 | +++ | |
| 310 | >100 | | 422 | +++ | |
| 311 | +++ | | 423 | +++ | |
| 312 | >100 | | 424 | +++ | |
| 313 | >100 | | 425 | +++ | |
| 314 | >100 | | 426 | +++ | |
| 315 | >100 | | 427 | +++ | |
| 316 | >100 | | 428 | +++ | |
| 317 | +++ | | 429 | +++ | |
| 318 | >100 | | 430 | +++ | |
| 319 | >100 | | 431 | >100 | |
| 320 | >100 | | 433 | +++ | |
| 321 | +++ | | 434 | +++ | |
| 322 | >100 | | 435 | +++ | |
| 323 | +++ | | 436 | +++ | |
| 324 | >100 | | 437 | +++ | |
| 325 | >100 | | 438 | +++ | |
| 326 | >100 | | 439 | +++ | |
| 327 | +++ | | 440 | +++ | |
| 328 | >100 | | 441 | +++ | |
| 329 | >100 | | 442 | +++ | |
| 330 | >100 | | 443 | +++ | |
| 337 | +++ | | 444 | +++ | |
| 338 | +++ | | 445 | +++ | |
| 339 | >100 | | 446 | +++ | |
| 340 | +++ | | 447 | +++ | |
| 341 | >100 | | 448 | +++ | |
| 344 | >100 | | 449 | >100 | |
| 345 | >100 | | 450 | +++ | |
| 346 | +++ | | 451 | +++ | |

TABLE 4-continued

KRAS G12D HiBit Assay Data

| Compound No. | Average DC50 | Average Dmax | Compound No. | Average DC50 | Average Dmax |
|---|---|---|---|---|---|
| 347 | >100 | | 452 | +++ | |
| 348 | >100 | | 453 | +++ | |
| 349 | >100 | | 454 | +++ | |
| 350 | +++ | | 455 | +++ | |
| 351 | +++ | | 456 | +++ | |
| 352 | +++ | | 457 | +++ | |
| 354 | +++ | | 458 | +++ | |
| 355 | +++ | | 461 | +++ | |
| 357 | >100 | | 462 | +++ | |
| 358 | +++ | | 463 | +++ | |
| 362 | +++ | | 464 | +++ | |
| 363 | +++ | | 465 | +++ | |
| 364 | +++ | | 466 | +++ | |
| 365 | +++ | | 467 | +++ | |
| 366 | +++ | | 468 | +++ | |
| 367 | +++ | | 469 | +++ | |
| 369 | +++ | | 470 | +++ | |
| 370 | +++ | | 471 | +++ | |
| 371 | +++ | | 472 | +++ | |
| 372 | +++ | | 473 | +++ | |
| 373 | +++ | | 474 | +++ | |
| 374 | ++ | | 476 | +++ | |
| 375 | +++ | | 477 | >100 | |
| 376 | >100 | | 478 | +++ | |
| 377 | +++ | | 479 | >100 | |
| 378 | +++ | | 484 | +++ | |
| 379 | +++ | | 485 | >100 | |
| 383 | +++ | | 486 | >100 | |
| 384 | +++ | | 487 | +++ | |
| 387 | +++ | | 489 | +++ | |
| 389 | +++ | | 490 | >100 | |
| 390 | +++ | | 492 | +++ | |
| 391 | +++ | | 493 | +++ | |
| 392 | +++ | | 494 | +++ | |
| 393 | +++ | | 495 | +++ | |
| 394 | >100 | | 496 | >100 | |
| 395 | +++ | | 497 | +++ | |
| 396 | +++ | | 499 | +++ | |
| 397 | +++ | | 500 | +++ | |
| 398 | +++ | | 501 | +++ | |
| 399 | +++ | | 502 | +++ | |
| 400 | +++ | | 503 | +++ | |
| 401 | +++ | | 403 | >100 | |
| 402 | +++ | | 404 | >100 | |

Assay Example 2. KRAS G12V HiBit Assay Protocol

Day 1. Prepared the culture medium for SW620-KRAS (G12V)-HiBit-KI cell (Pharmaron) using L15 medium (Gibco, 11415064) with 10% FBS (Gibco, 10099141C) and 1% Penicillin-Streptomycin Liquid (Solarbio, P1400). Cultivated cells in T-75 flasks in a cell culture incubator (Thermo, Model: 371) at 37° C., 5% $CO_2$, and allowed to reach approximately 80% confluence before splitting. Rinsed cultivated cells in T-75 flasks with 5 mL PBS (Solarbio, P1020-500). Aspirated off PBS, added 1.5 mL trypsin (Invitrogen, #25300), and incubated at 37° C. for approximately 5 minutes or until the cells detached. Inactivated trypsin by adding excessive serum containing medium. Harvested the cells from flask into cell culture medium and counted the cell number. Seeded SW620-KRAS (G12V)-HiBit-KI cells into 384-well plate (Corning, 3570)(cell density: $1\times10^4$ cells/well in 50 μL medium) in L15 medium, and incubated overnight at 37° C. and 5% $CO_2$.

Day 2. Test compounds were dissolved at 0.3 mM in DMSO (Solarbio, D8371) as stock solution. Transferred 45

μL of stock solution to a 384-well plate (Labcyte, 001-14555). Performed 3-fold, 10-points dilution via transferring 15 μL compound into 30 μL DMSO by using TECAN liquid handler (TECAN, Freedom EVO200). The compound plates were spun at room temperature at 1,000 RPM for 1 minute (Eppendorf, 5810R). Transferred 50 nL of diluted compounds from compound source plate into the cell plate by Echo (Labcyte, 550) to achieve final concentrations of 300 nM, 100 nM, 33.3 nM, 11.1 nM, 3.7 nM, 1.23 nM, 0.41 nM, 0.14 nM, 0.046 nM and 0.015 nM, then mixed the cell plate on a plate shaker (Yoning, WZ-4) for 15 seconds at 900 rpm. After compound treatment for 24 hours, the plate was removed from incubators and equilibrated at room temperature for 15 minutes. Prepare the HiBit reagent (Promega, N3040) by mixing 10 mL of Nano-Glo®-HiBiT Lytic Buffer with 200 μL of Nano-Glo®-HiBiT Lytic Substrate and 100 μL of LgBiT Protein. Added 20 μL of HiBit reagent into each well of the cell plate and spun the plates at room temperature at 1,000 RPM for 1 minute. Then shook the plates at 600 RPM at room temperature for 20 minutes using a plate shaker (Yoning, WZ-4), and read the luminescence by EnVision (PerkinElmer, 2105-0020).

The degradation activity was calculated using the following formula:

$$HiBit-G12V\text{ level (\%)} = 100\% \times [\text{Luminescence (Sample)/Mean of Luminescence }(HC)]$$

where HC (high control) is obtained from cells treated with 0.1% DMSO only.

Absolute $DC_{50}$ was calculated by fitting the curve using GraphPad Prism v8.0.2 (analysis 263):

$$Y = \text{Bottom} + (100-\text{Bottom})/(1+10^{\wedge}((\text{LogAbsolute }IC_{50}-X)*\text{HillSlope} + \log((100-\text{Bottom})/(50-\text{Bottom})-1)))$$

The data are reported in Table 5.

TABLE 5

KRAS G12V HiBit Assay ("+++" = $DC_{50}$ less than 10 nM, "++" = $DC_{50}$ greater than or equal to 10 nM and less than 100 nM; "+" = $DC_{50}$ greater than or equal to 100 nM)

| Compound No. | Average DC50 | Compound No. | Average DC50 | Compound No. | Average DC50 |
|---|---|---|---|---|---|
| 1 | +++ | 2 | +++ | 3 | + |
| 4 | +++ | 5 | +++ | 11 | +++ |
| 12 | + | 13 | +++ | 14 | +++ |
| 15 | + | 16 | + | 17 | + |
| 18 | + | 25 | +++ | 28 | + |
| 31 | + | 33 | + | 34 | +++ |
| 40 | + | 42 | + | 51 | + |
| 47 | + | 50 | +++ | 55 | + |
| 49 | + | 53 | + | 58 | +++ |
| 52 | +++ | 57 | + | 65 | + |
| 56 | +++ | 64 | +++ | 94 | + |
| 60 | + | 67 | +++ | 71 | +++ |
| 63 | + | 70 | + | 74 | + |
| 69 | +++ | 73 | + | 97 | +++ |
| 72 | +++ | 78 | + | 100 | +++ |
| 77 | +++ | 96 | +++ | 103 | + |
| 95 | +++ | 99 | +++ | 106 | + |
| 98 | +++ | 102 | +++ | 116 | + |
| 101 | +++ | 105 | + | 119 | + |
| 104 | + | 111 | + | 122 | +++ |
| 110 | +++ | 118 | +++ | 125 | +++ |
| 117 | + | 121 | +++ | 128 | + |
| 120 | +++ | 124 | +++ | 131 | + |
| 123 | +++ | 127 | ++ | 134 | +++ |
| 126 | +++ | 130 | + | 138 | + |
| 129 | + | 133 | ++ | 142 | +++ |
| 132 | +++ | 137 | >75.7 | 146 | +++ |
| 135 | + | 141 | >79.2 | 152 | + |
| 140 | >38.9 | 145 | +++ | 155 | +++ |
| 144 | +++ | 148 | + | 158 | +++ |
| 147 | + | 154 | +++ | 209 | + |
| 153 | + | 157 | +++ | 216 | + |
| 156 | +++ | 160 | +++ | 220 | + |
| 159 | +++ | 202 | + | 223 | + |
| 200 | + | 211 | + | 437 | +++ |
| 210 | + | 219 | + | 438 | +++ |
| 217 | + | 222 | + | 439 | +++ |
| 221 | + | 371 | +++ | 301 | +++ |
| 224 | + | 372 | ++ | 302 | +++ |
| 300 | +++ | 373 | +++ | 440 | +++ |
| 303 | +++ | 374 | ++ | 441 | ++ |
| 304 | + | 375 | +++ | 442 | ++ |
| 306 | ++ | 376 | + | 443 | ++ |
| 307 | + | 377 | +++ | 444 | >78.5 |
| 308 | ++ | 378 | +++ | 445 | +++ |
| 309 | ++ | 379 | +++ | 446 | +++ |

TABLE 5-continued

KRAS G12V HiBit Assay ("+++" = $DC_{50}$ less than 10 nM, "++" = $DC_{50}$ greater than or equal to 10 nM and less than 100 nM; "+" = $DC_{50}$ greater than or equal to 100 nM)

| Compound No. | Average DC50 | Compound No. | Average DC50 | Compound No. | Average DC50 |
|---|---|---|---|---|---|
| 310 | + | 383 | >91.5 | 447 | +++ |
| 311 | + | 384 | ++ | 448 | +++ |
| 312 | ++ | 387 | +++ | 449 | ++ |
| 313 | + | 389 | >70.5 | 450 | +++ |
| 314 | + | 390 | +++ | 451 | +++ |
| 315 | + | 391 | +++ | 452 | +++ |
| 316 | + | 392 | +++ | 453 | +++ |
| 317 | + | 393 | ++ | 454 | +++ |
| 318 | + | 394 | +++ | 455 | +++ |
| 319 | + | 395 | ++ | 456 | +++ |
| 320 | + | 396 | +++ | 457 | +++ |
| 321 | +++ | 397 | +++ | 458 | ++ |
| 322 | + | 398 | +++ | 461 | +++ |
| 323 | +++ | 399 | +++ | 462 | +++ |
| 324 | + | 400 | +++ | 463 | +++ |
| 325 | + | 401 | ++ | 464 | +++ |
| 326 | + | 402 | ++ | 465 | +++ |
| 327 | + | 403 | + | 466 | +++ |
| 328 | + | 404 | +++ | 467 | +++ |
| 329 | + | 405 | ++ | 468 | +++ |
| 330 | + | 407 | +++ | 469 | +++ |
| 337 | ++ | 409 | +++ | 470 | +++ |
| 338 | +++ | 410 | +++ | 471 | + |
| 339 | + | 413 | +++ | 472 | ++ |
| 340 | +++ | 414 | ++ | 473 | ++ |
| 341 | + | 415 | + | 474 | +++ |
| 344 | + | 416 | +++ | 476 | +++ |
| 345 | + | 417 | +++ | 477 | + |
| 346 | ++ | 418 | +++ | 478 | +++ |
| 347 | + | 419 | +++ | 479 | + |
| 348 | + | 420 | ++ | 484 | ++ |
| 349 | ++ | 421 | +++ | 485 | + |
| 350 | +++ | 422 | +++ | 486 | + |
| 351 | +++ | 423 | +++ | 487 | +++ |
| 352 | +++ | 424 | +++ | 489 | +++ |
| 354 | +++ | 425 | +++ | 490 | + |
| 355 | +++ | 426 | ++ | 491 | + |
| 357 | + | 427 | ++ | 492 | + |
| 358 | +++ | 428 | ++ | 493 | +++ |
| 362 | +++ | 429 | +++ | 494 | ++ |
| 363 | +++ | 430 | ++ | 495 | ++ |
| 364 | +++ | 431 | +++ | 496 | + |
| 365 | +++ | 433 | +++ | 497 | ++ |
| 366 | ++ | 434 | ++ | 499 | ++ |
| 367 | +++ | 435 | ++ | 500 | +++ |
| 369 | +++ | 436 | ++ | 501 | ++ |
| 370 | +++ | | | 502 | +++ |
| | | | | 503 | +++ |

Assay Example 3. KRASamp MSD Protocol

KE39 (KRAS amplified) cells were cultured in RPMI 1640 medium (Gibco, 11875093), seeded into 96 well plate and treated with test compounds for 24 hr. The cells were washed with PBS and lysed in plate for 1 hr at 4° C. with agitation in RIPA buffer (Cat No. BP-115D) supplemented with protease and phosphatase inhibitor cocktail. The lysates were loaded into MSD plate coated with KRAS capture antibody (LSBio, C175665, 1:1000) for 1 h at RT with agitation. The plate was then washed three times with TBST and incubated with KRAS detection antibody (Abcam, Ab275876. 1:2000) for 1 h at RT. After washing three times with TBST, the plate was incubated with secondary detection antibody GAR (1:500) for 1 hr at RT followed with 3×TBST washing. 2×MSD reading buffer was added into individual wells and the plate was finally read by MSD reader (MSD, SQ 120 MM). The recombinant WT KRAS protein was used for standard curve generation and protein quantification. The degradation activity was calculated using the following formula:

$$KRAS \text{ level } (\%) = 100\% \times [(\text{Sample reading} - \text{blank})/(DMSO \text{ reading} - \text{blank})]$$

$DC_{50}$ was calculated by fitting the curve using GraphPad Prism v8.0.2 (analysis 263):

$$Y = \text{Bottom} + (100 - \text{Bottom})/(1 + 10^\wedge((\text{LogAbsolute } IC_{50} - X) * \text{HillSlope} + \log((100 - \text{Bottom})/(50 - \text{Bottom}) - 1)))$$

The data are reported in Table 6.

TABLE 6

| KRASamp MSD Assay | | | | | |
|---|---|---|---|---|---|
| Compound No. | Average DC50 | Compound No. | Average DC50 | Compound No. | Average DC50 |
| 1 | +++ | 2 | +++ | 4 | +++ |
| 5 | +++ | 11 | ++ | 13 | +++ |
| 14 | +++ | 15 | + | 31 | + |
| 32 | ++ | 34 | +++ | 95 | +++ |
| 96 | +++ | 98 | +++ | 99 | +++ |
| 97 | +++ | 101 | +++ | 102 | +++ |
| 100 | +++ | 118 | +++ | 119 | + |
| 110 | ++ | 121 | ++ | 122 | +++ |
| 120 | +++ | 124 | +++ | 125 | +++ |
| 123 | +++ | 132 | ++ | 134 | +++ |
| 126 | +++ | 140 | +++ | 141 | +++ |
| 137 | ++ | 145 | ++ | 154 | +++ |
| 142 | ++ | 156 | +++ | 157 | +++ |
| 155 | +++ | 159 | +++ | 160 | +++ |
| 158 | +++ | 67 | ++ | 64 | +++ |
| 52 | + | 71 | +++ | 69 | +++ |
| 56 | +++ | 40 | + | 58 | + |
| 77 | ++ | 373 | ++ | 50 | ++ |
| 55 | + | 374 | ++ | 433 | ++ |
| 300 | +++ | 375 | ++ | 434 | ++ |
| 301 | +++ | 377 | +++ | 435 | ++ |
| 302 | +++ | 378 | +++ | 436 | ++ |
| 303 | ++ | 379 | +++ | 437 | +++ |
| 307 | ++ | 383 | + | 438 | +++ |
| 308 | +++ | 384 | ++ | 440 | ++ |
| 309 | ++ | 387 | + | 441 | ++ |
| 310 | ++ | 389 | ++ | 442 | ++ |
| 311 | + | 390 | ++ | 443 | ++ |
| 312 | + | 391 | +++ | 444 | ++ |
| 314 | + | 392 | +++ | 445 | +++ |
| 315 | + | 394 | ++ | 446 | +++ |
| 316 | + | 396 | +++ | 447 | +++ |
| 317 | + | 397 | +++ | 448 | +++ |
| 320 | + | 398 | +++ | 450 | +++ |
| 321 | ++ | 399 | +++ | 451 | +++ |
| 322 | + | 402 | ++ | 452 | +++ |
| 323 | ++ | 404 | ++ | 453 | +++ |
| 324 | + | 405 | ++ | 454 | +++ |
| 325 | + | 407 | +++ | 455 | +++ |
| 326 | + | 409 | +++ | 456 | ++ |
| 327 | + | 410 | +++ | 457 | +++ |
| 328 | + | 413 | +++ | 458 | +++ |
| 329 | + | 414 | + | 461 | +++ |
| 330 | ++ | 415 | + | 462 | ++ |
| 337 | ++ | 416 | +++ | 464 | ++ |
| 339 | ++ | 417 | +++ | 465 | +++ |
| 340 | +++ | 418 | ++ | 466 | +++ |
| 341 | + | 419 | +++ | 467 | +++ |
| 344 | ++ | 420 | ++ | 468 | +++ |
| 345 | ++ | 421 | +++ | 469 | +++ |
| 346 | ++ | 422 | +++ | 470 | +++ |
| 347 | + | 423 | +++ | 471 | ++ |
| 348 | + | 424 | +++ | 473 | ++ |
| 349 | ++ | 425 | +++ | 474 | +++ |
| 350 | ++ | 426 | +++ | 476 | ++ |
| 355 | +++ | 427 | + | 477 | + |
| 357 | ++ | 428 | ++ | 478 | +++ |
| 367 | +++ | 429 | +++ | 479 | + |
| 369 | ++ | 430 | ++ | 484 | + |
| 370 | ++ | 431 | ++ | 489 | +++ |
| 371 | ++ | 372 | ++ | 500 | +++ |

("+++" = $DC_{50}$ less than 1 nM, "++" = $DC_{50}$ greater than or equal to 1 nM and less than 10 nM; "+" = $DC_{50}$ greater than or equal to 10 nM)

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A compound of the following formula:

(II)

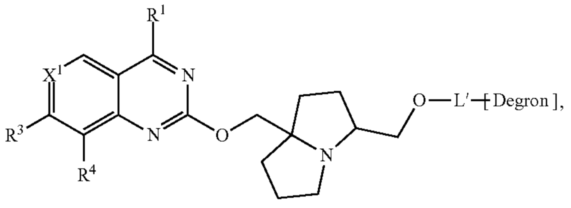

or a pharmaceutically acceptable salt thereof, wherein:

$R^1$ is

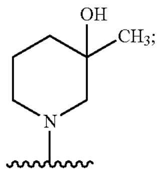 [SMILES: *N1CCCC(C)(O)C1]

$X^1$ is N or $C(R^{10})$;

$R^{10}$ is hydrogen, halogen, $(C_1\text{-}C_6)$alkyl, $(C_1\text{-}C_6)$haloalkyl, $(C_1\text{-}C_6)$haloalkoxy, (C2-C6)alkenyl, (C2-C6) alkynyl, —CN, $(C_1\text{-}C_6)$alkoxy, —S—$(C_1\text{-}C_6)$alkyl or —S—$(C_1\text{-}C_6)$haloalkyl;

$R^3$ is

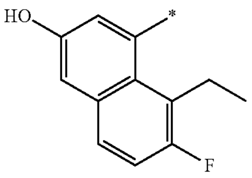

or

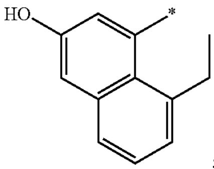

;

$R^4$ is hydrogen or fluoro;

L' is

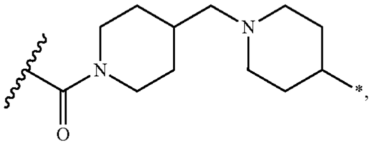

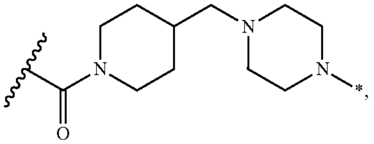

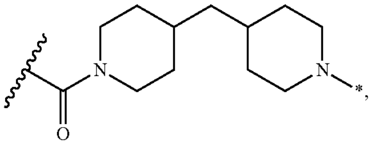

-continued

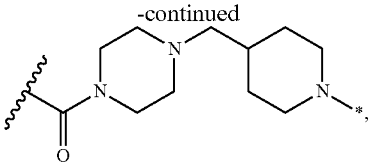

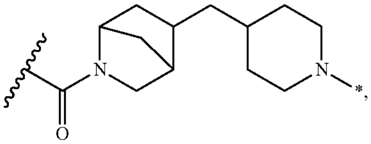

, or

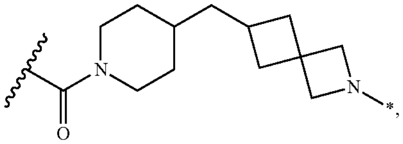

wherein * indicates point of attachment of L' to Degron;

and

Degron is

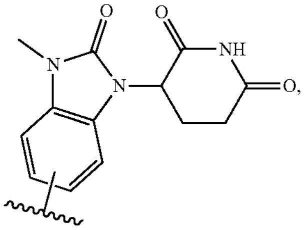

wherein one or more of the hydrogen atoms on the benzene ring of the Degron is optionally replaced with a fluorine atom, provided the compound is not

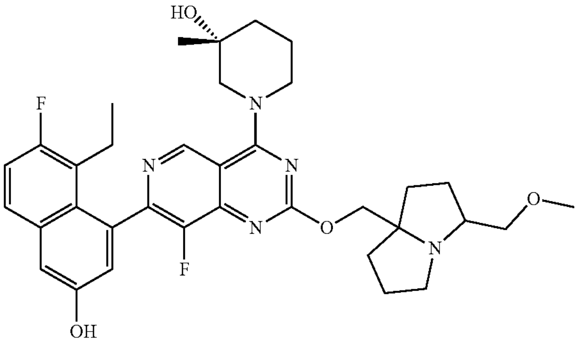

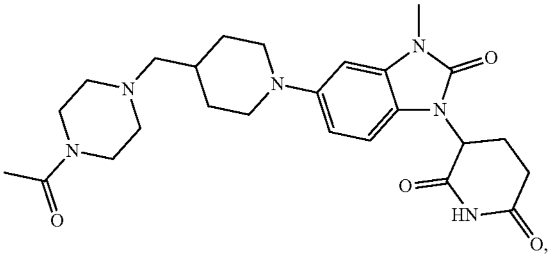

or a salt thereof.

2. The compound of claim 1, wherein $X^1$ is N.

3. The compound of claim 1, wherein $X^1$ is $C(R^{10})$, and $R^{10}$ is hydrogen, fluoro, chloro, methyl, $—CF_3$, $—OCF_3$, —CN, $—OCH_3$, $—SCH_3$, or $—SCF_3$.

4. The compound of claim 1, wherein $R^4$ is fluoro.

5. The compound of claim 1, wherein Degron is

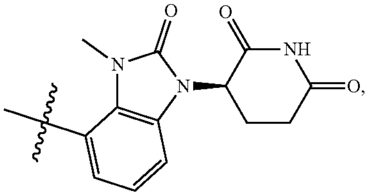

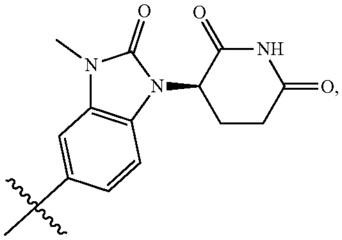

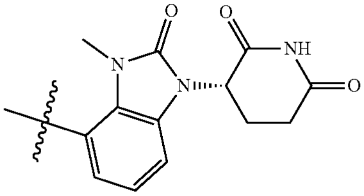

or

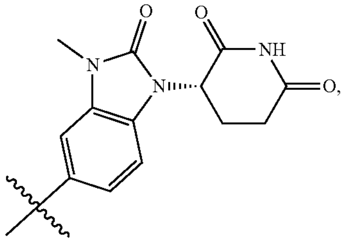

wherein one or more of the hydrogen atoms on the benzene ring of the Degron is optionally replaced with a fluorine atom.

6. A compound of the following structure:
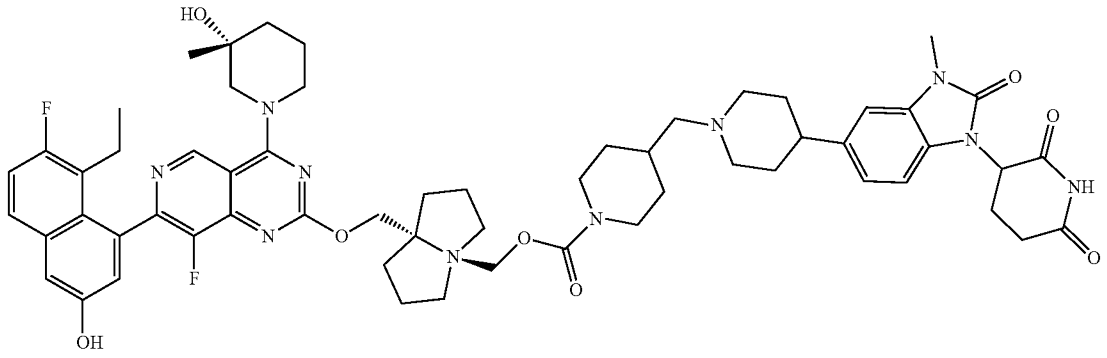
or a pharmaceutically acceptable salt thereof.
7. A compound selected from:
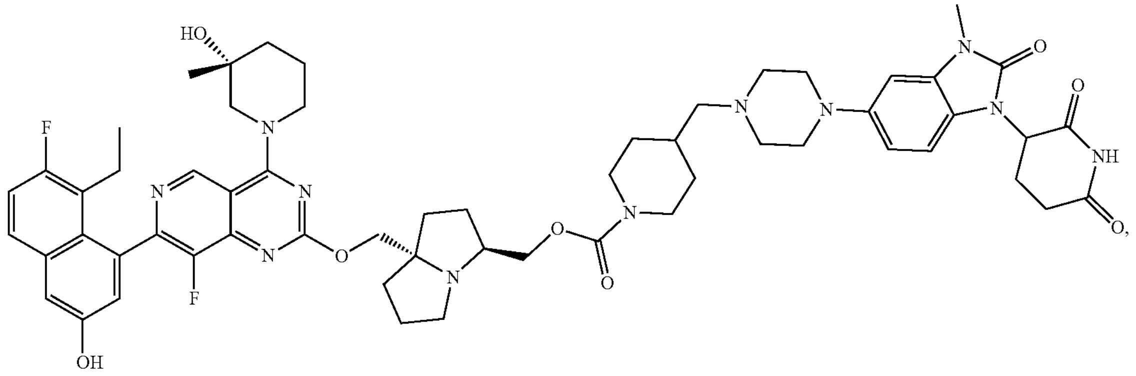
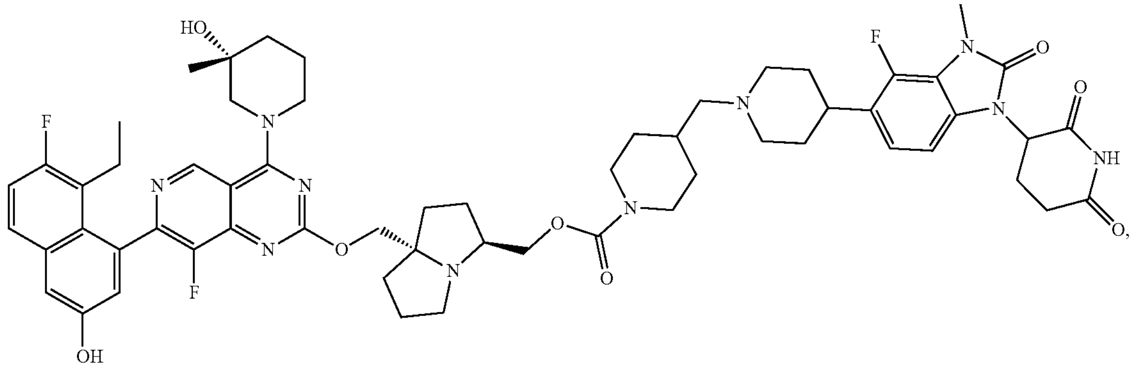
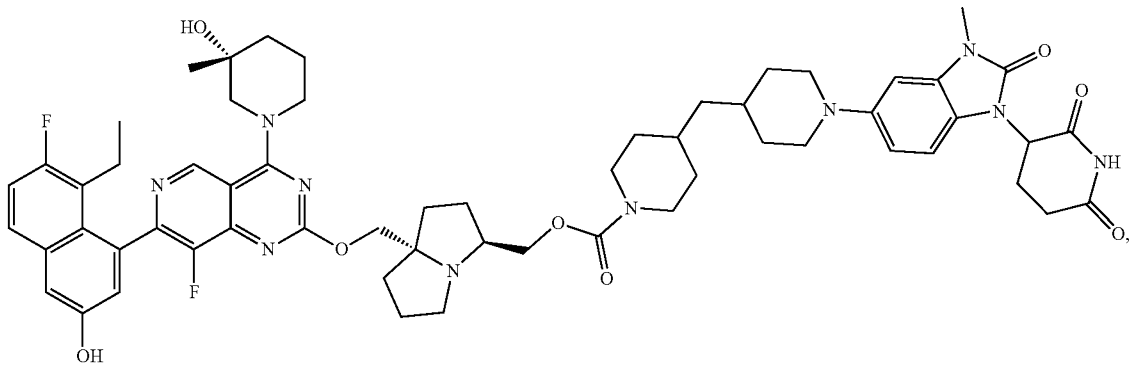

-continued
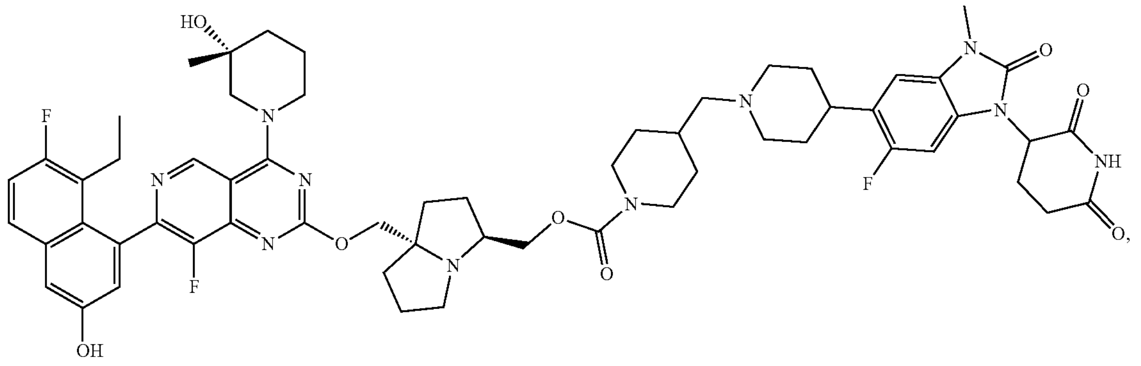
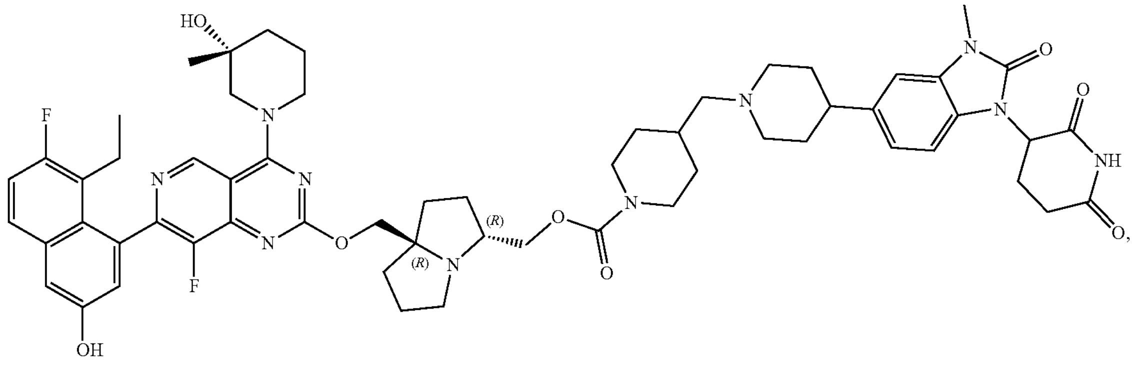
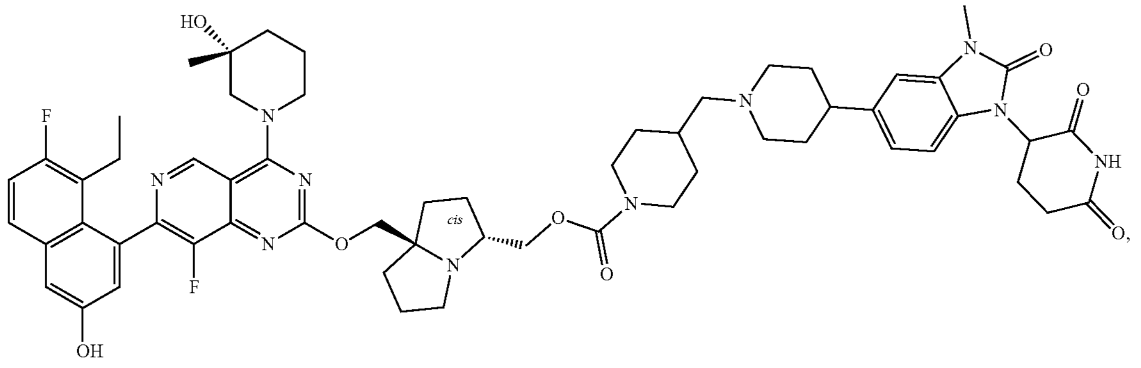
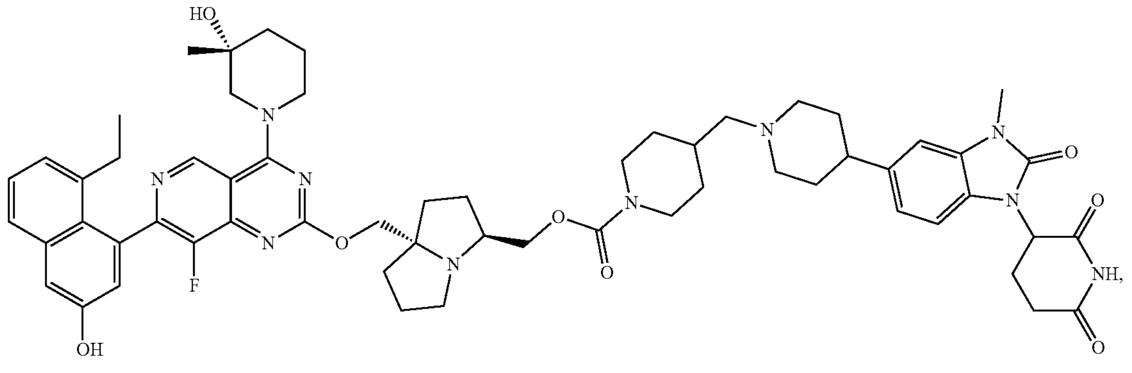

-continued
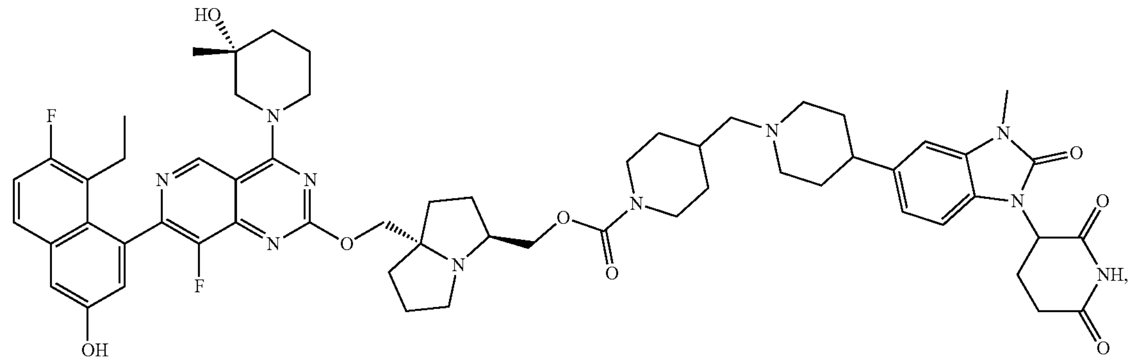
,
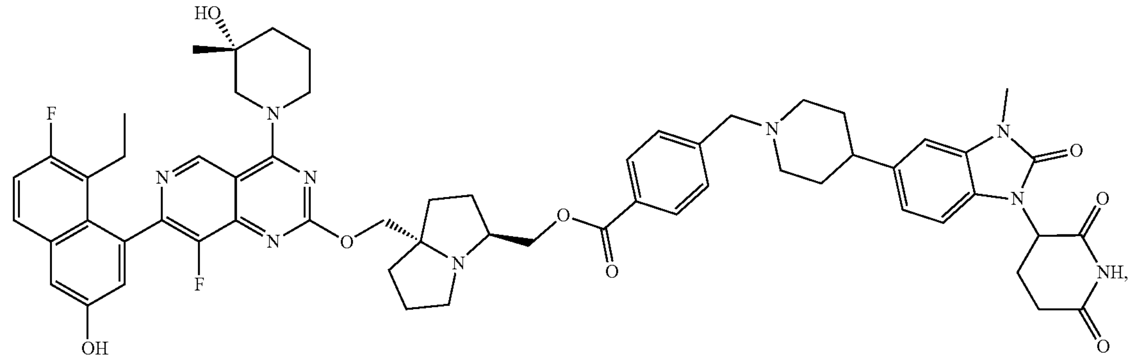
,
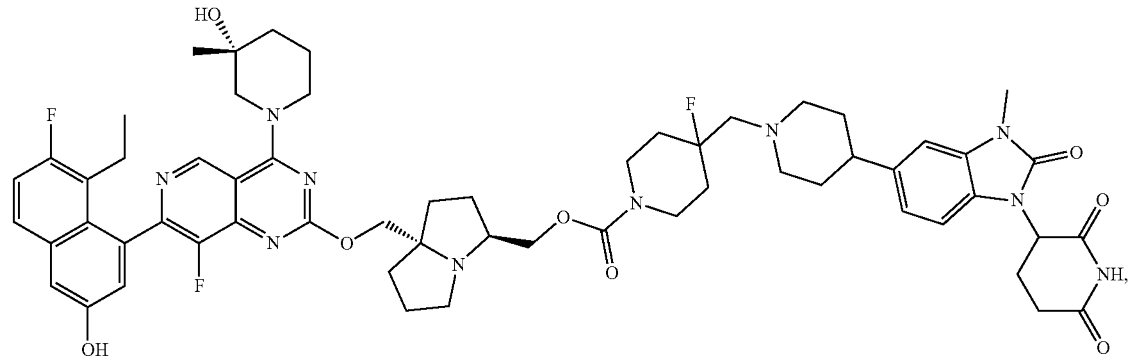
,
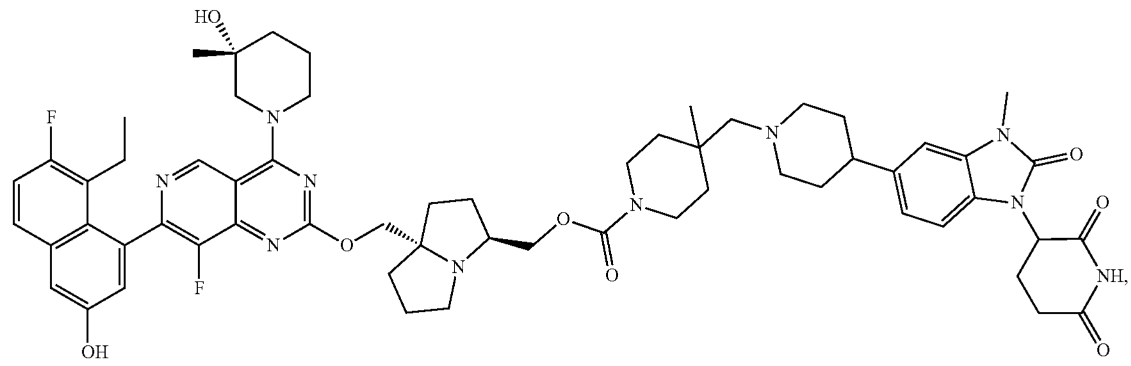
,

-continued
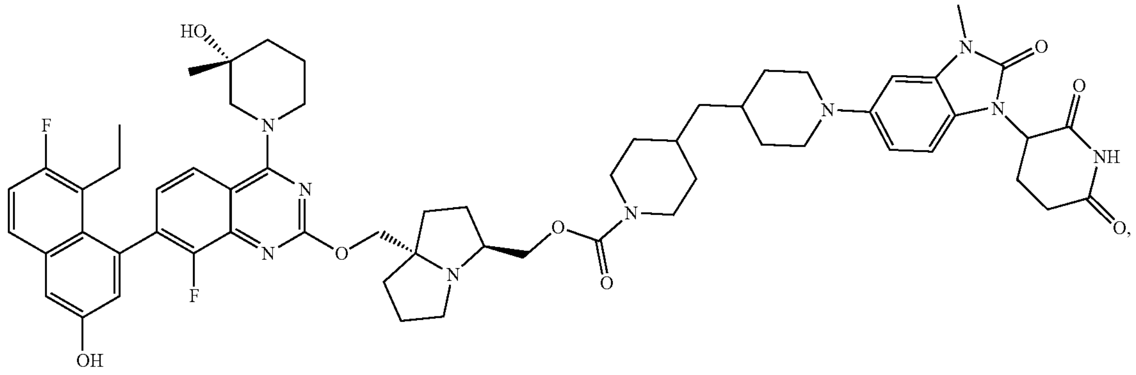
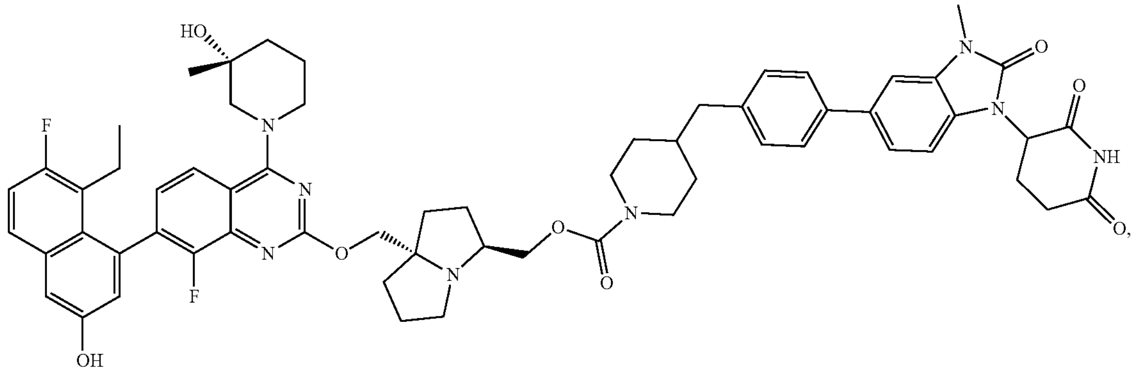
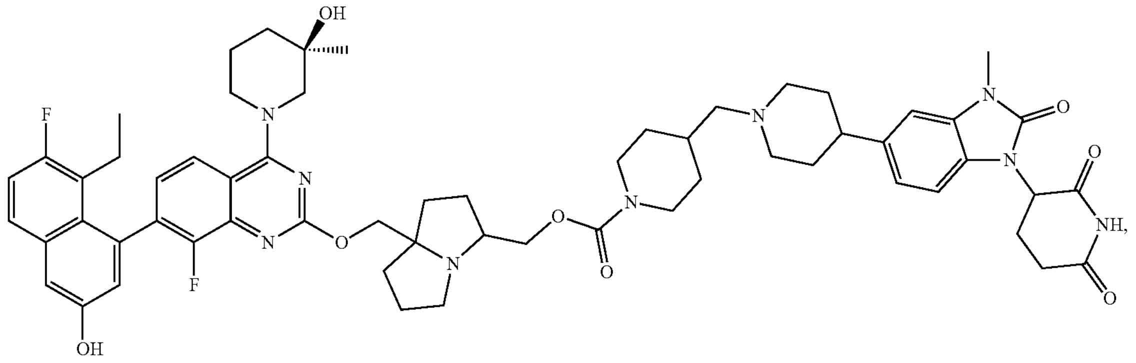
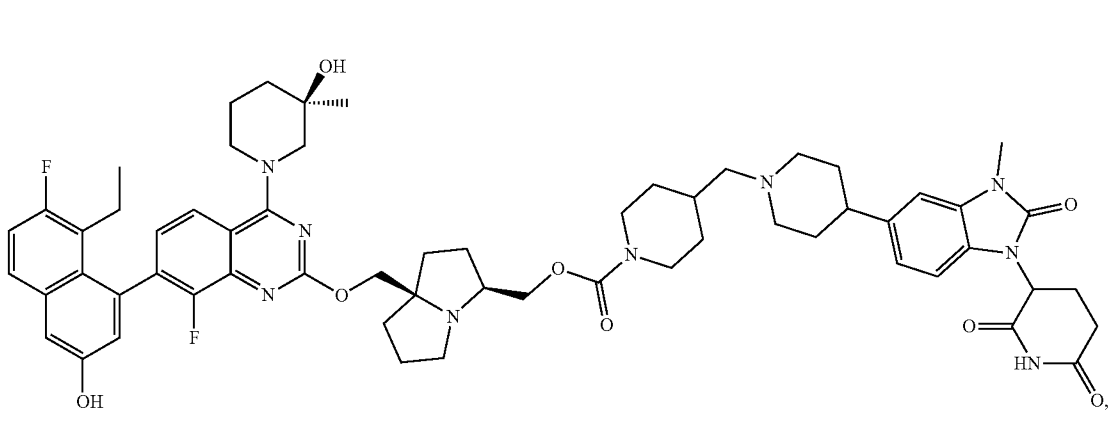

-continued
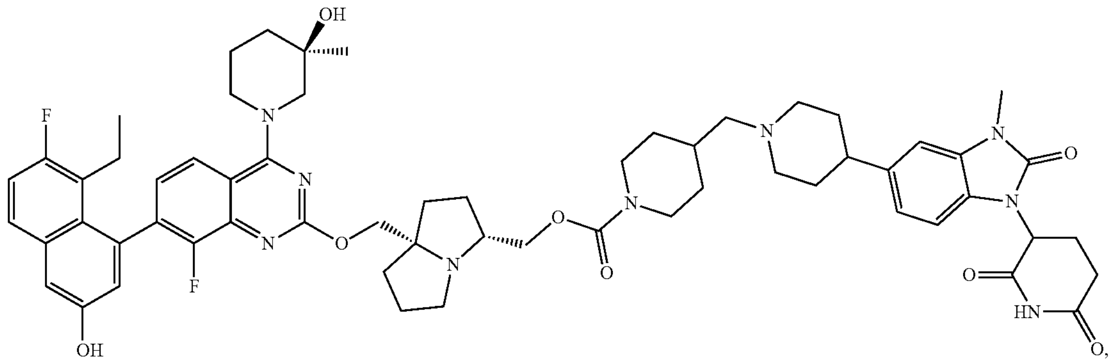
,
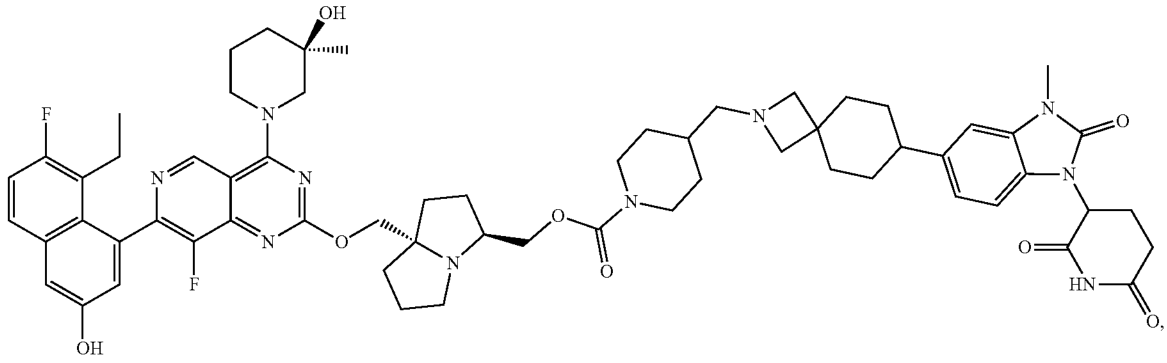
,
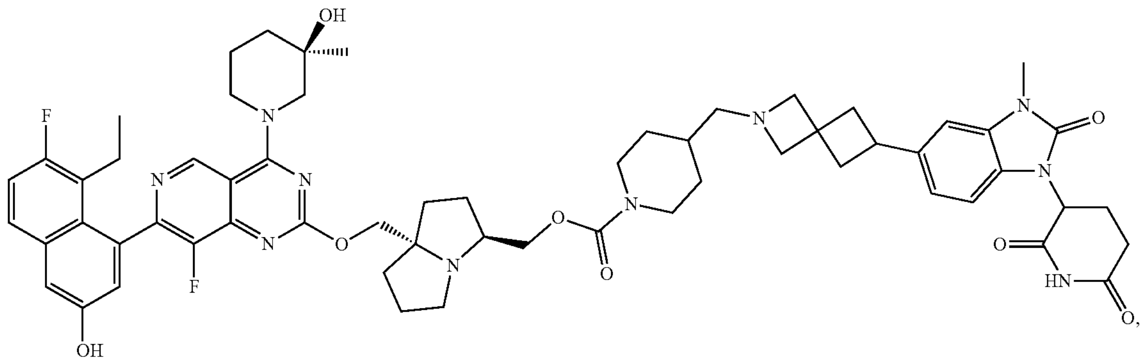
,
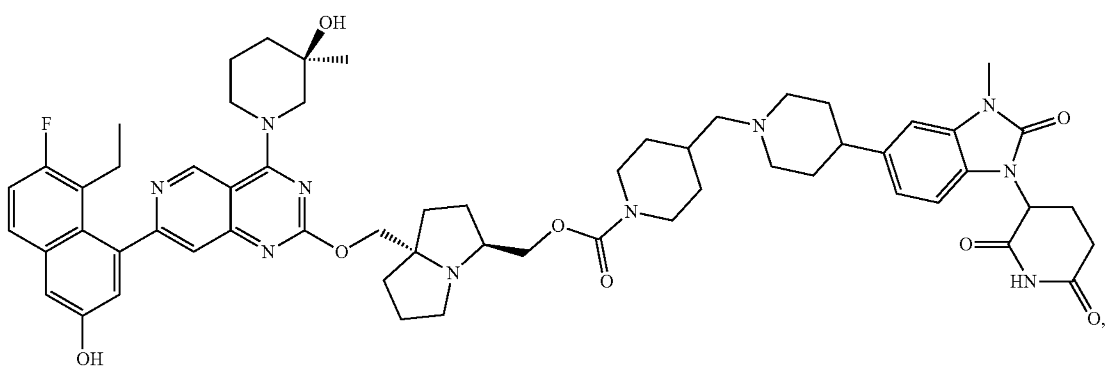
,

-continued
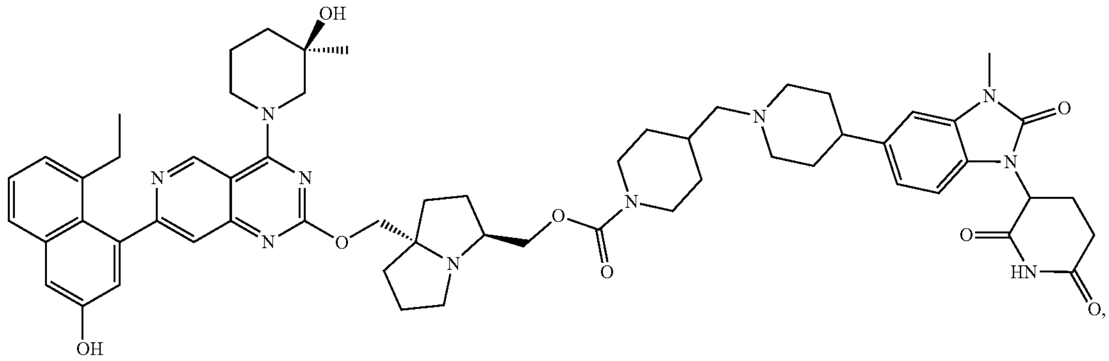
,
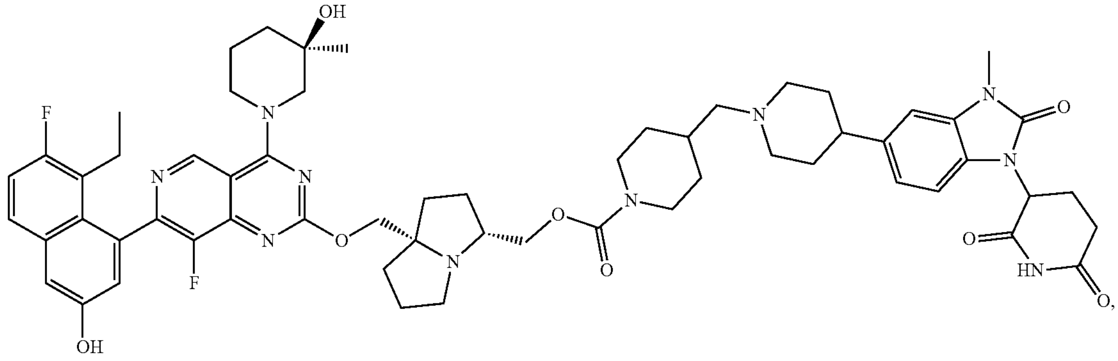
,
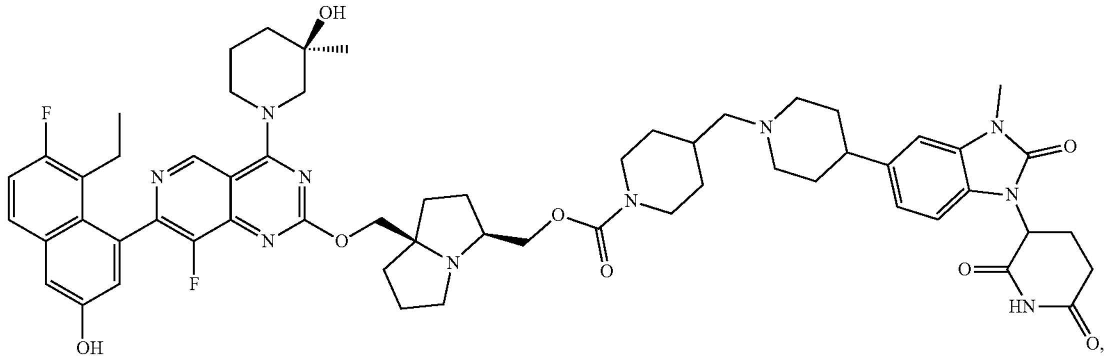
,
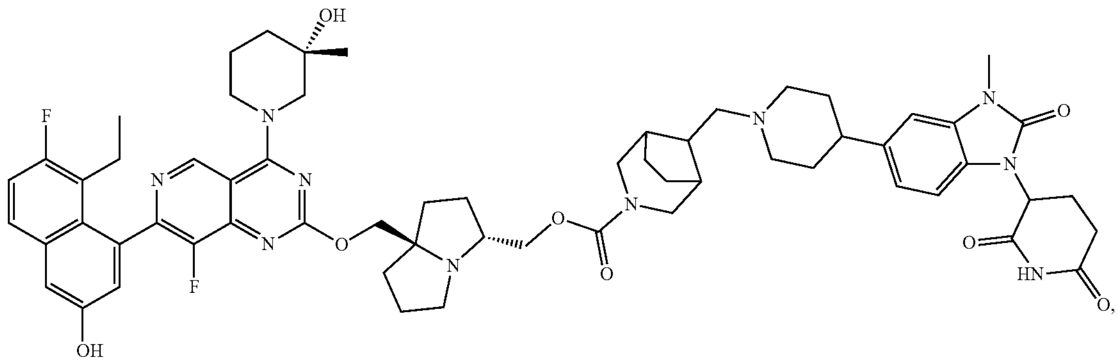
,

-continued
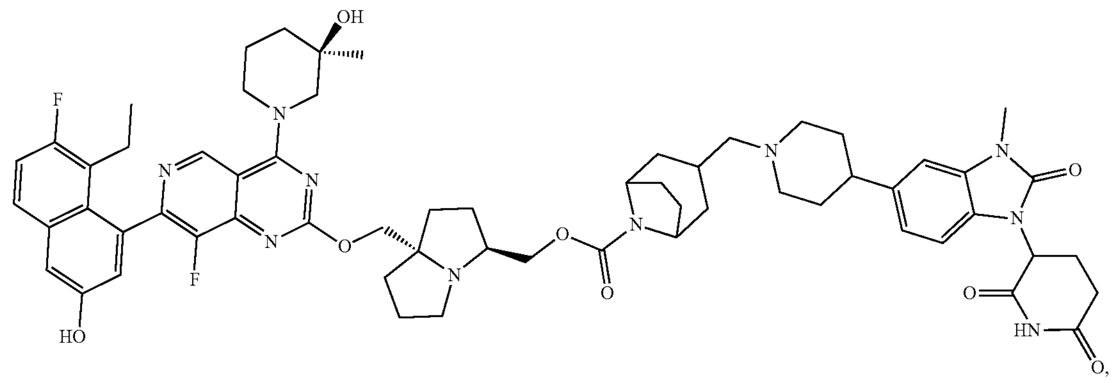
,
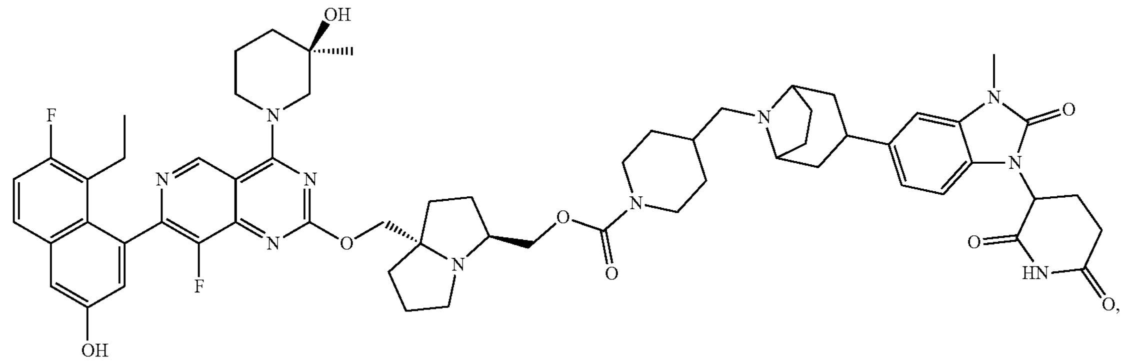
,
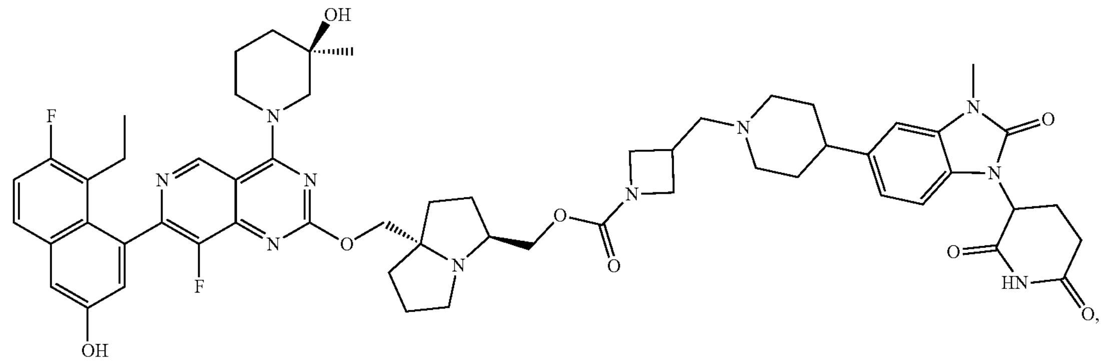
,
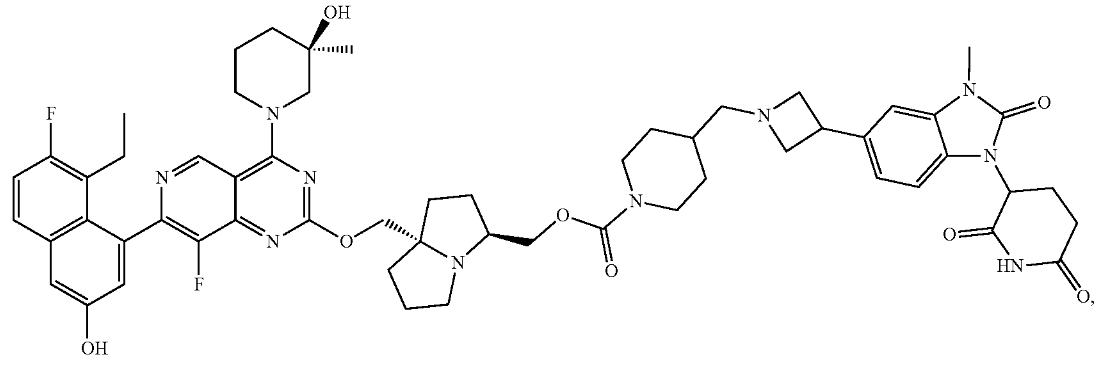
,

-continued
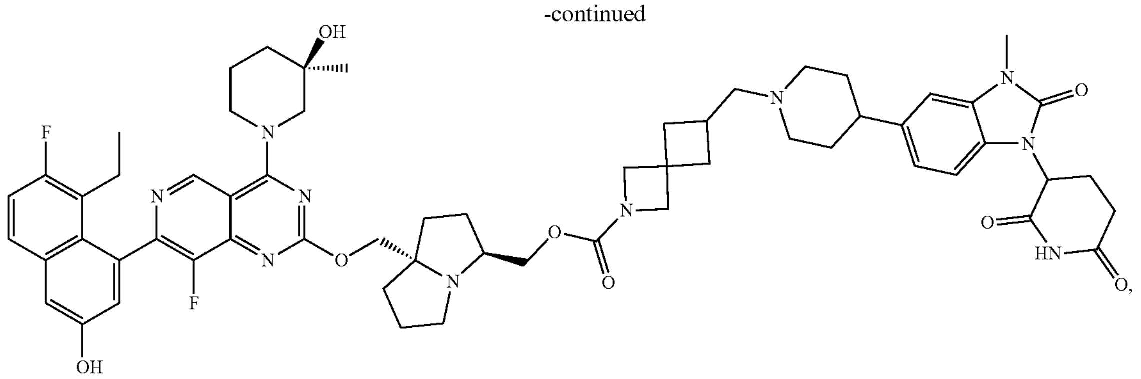
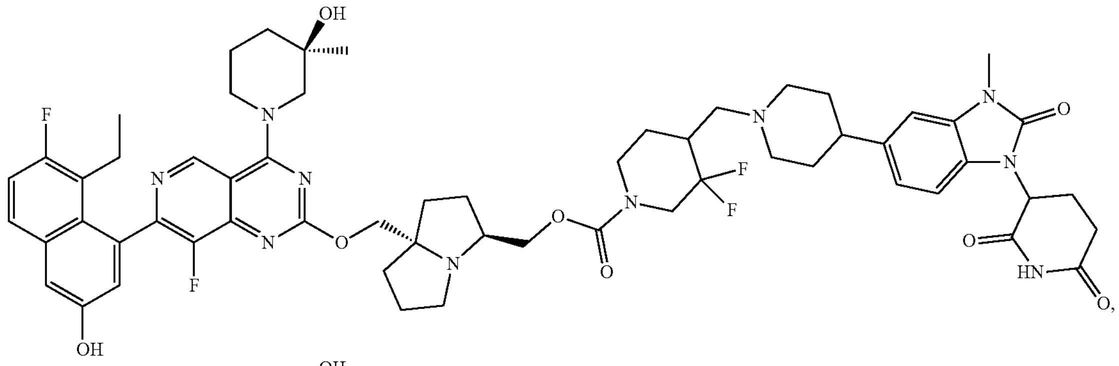
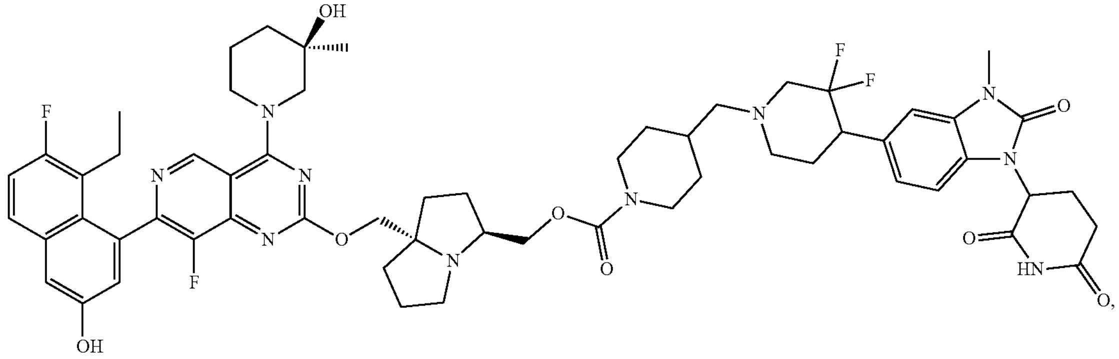
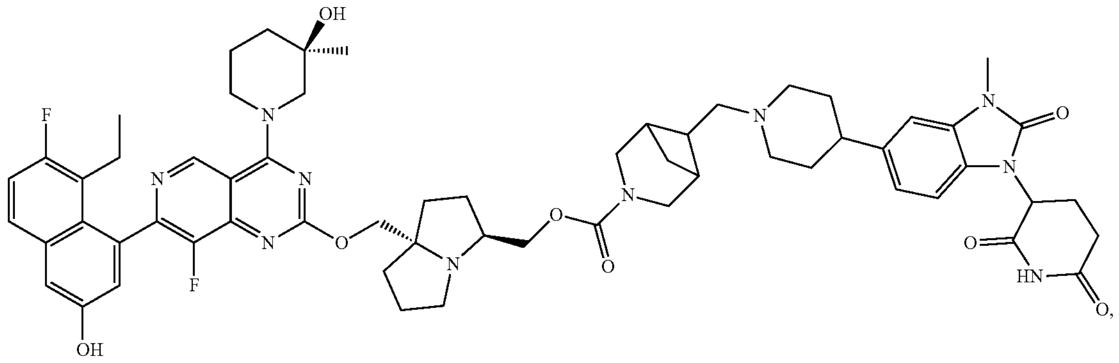

-continued
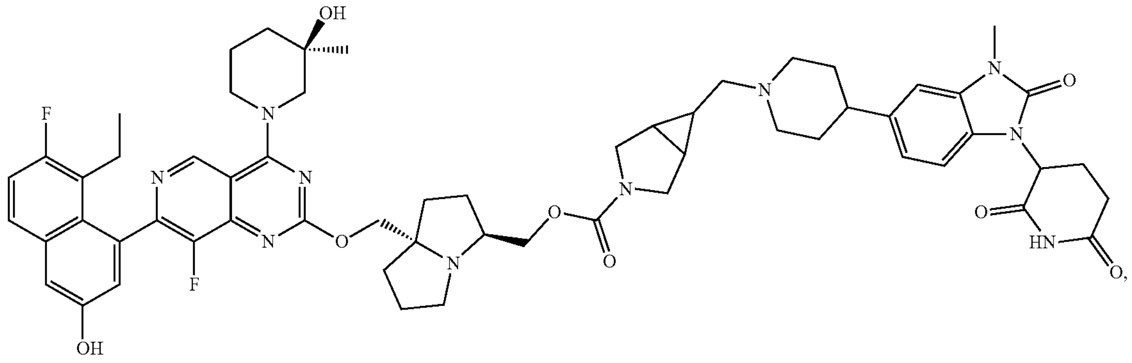
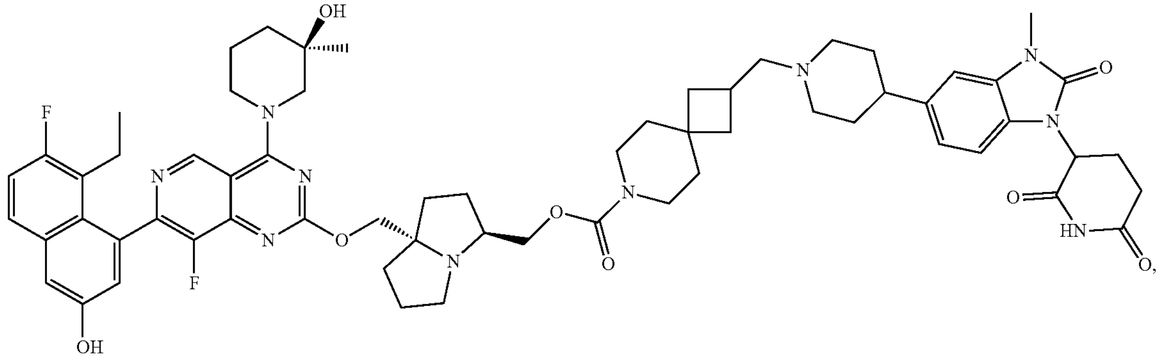
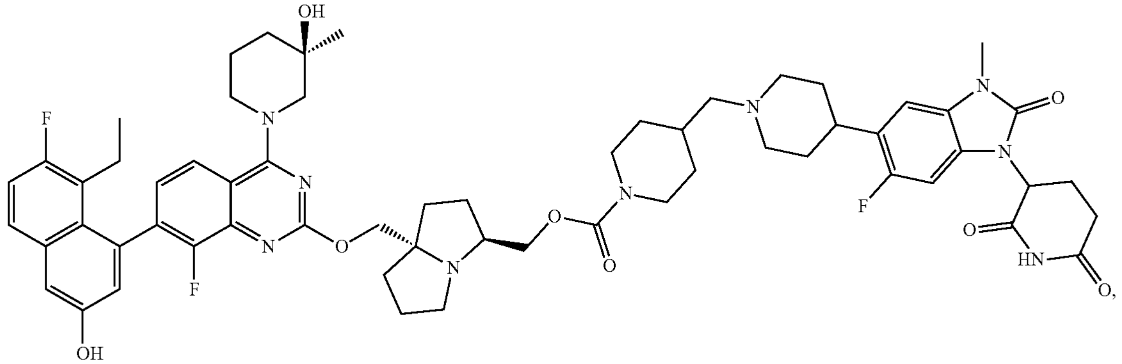
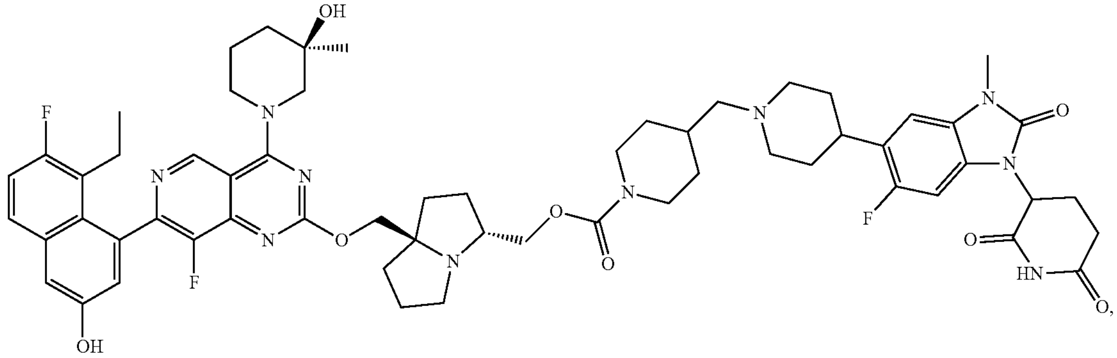

-continued
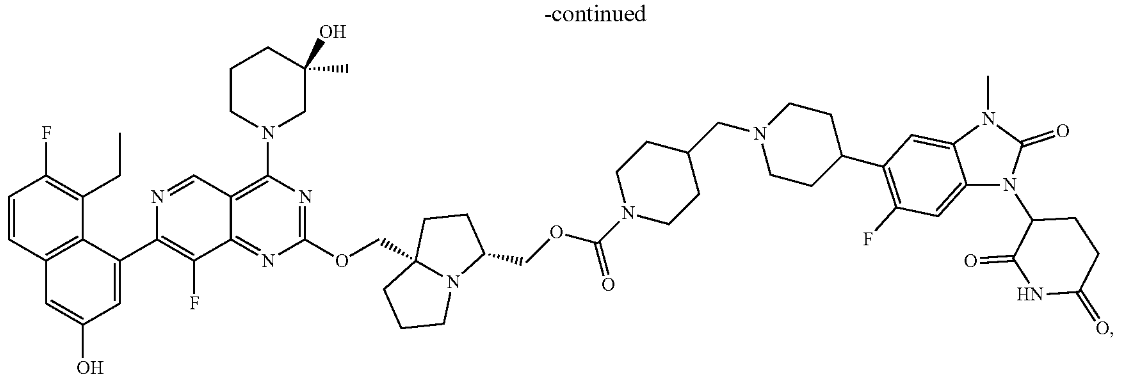
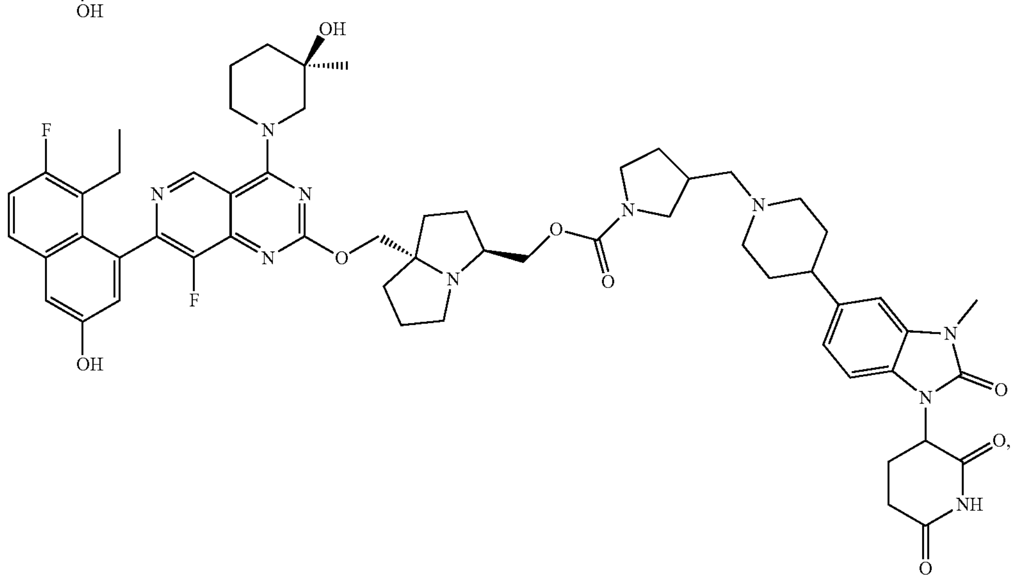
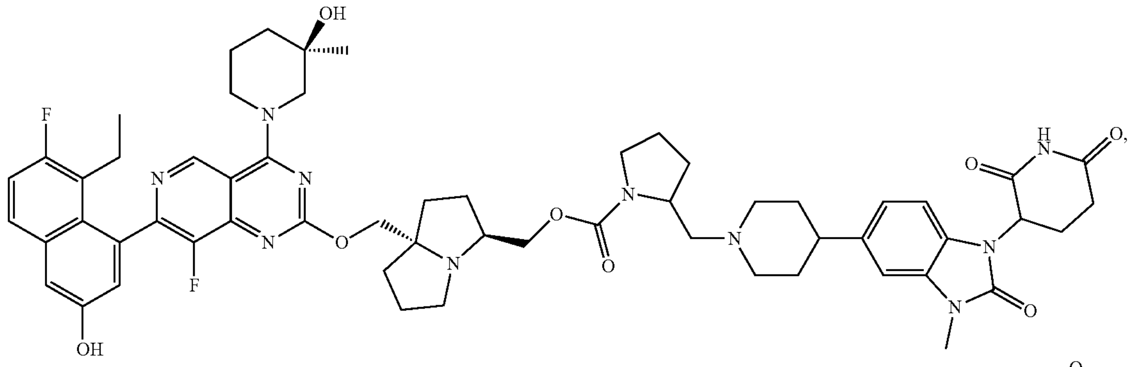
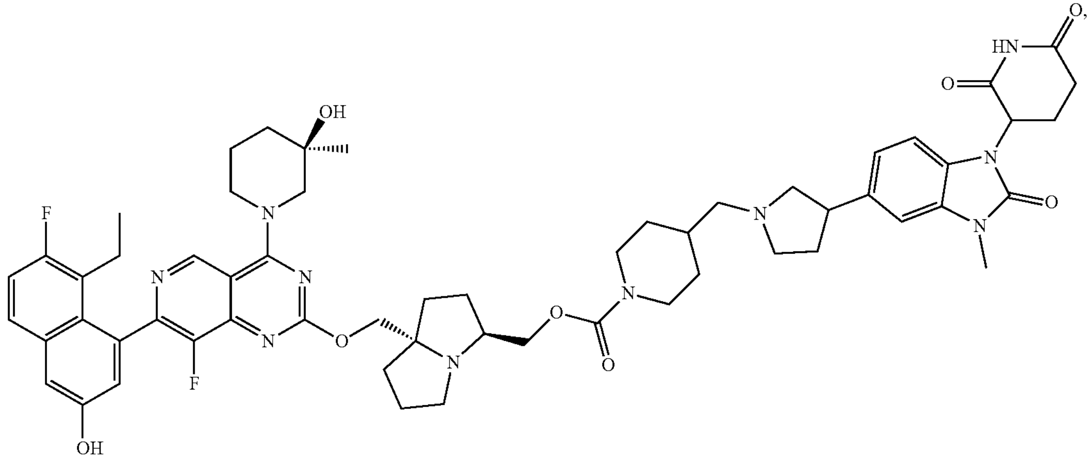

-continued
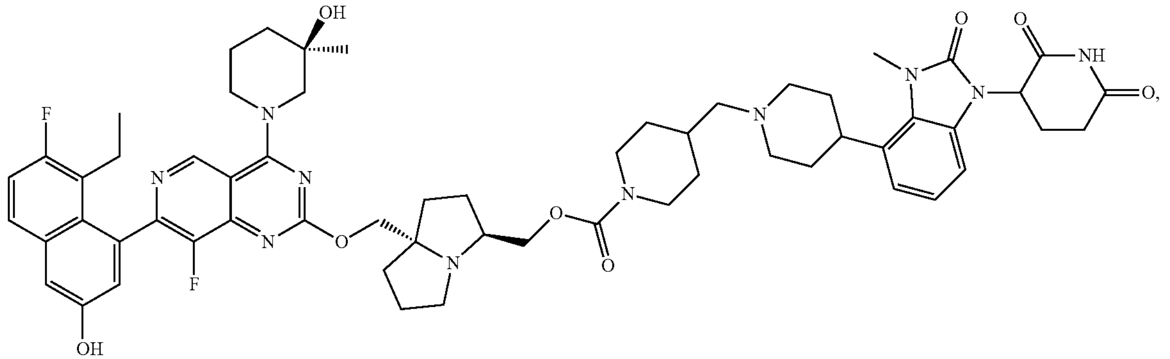
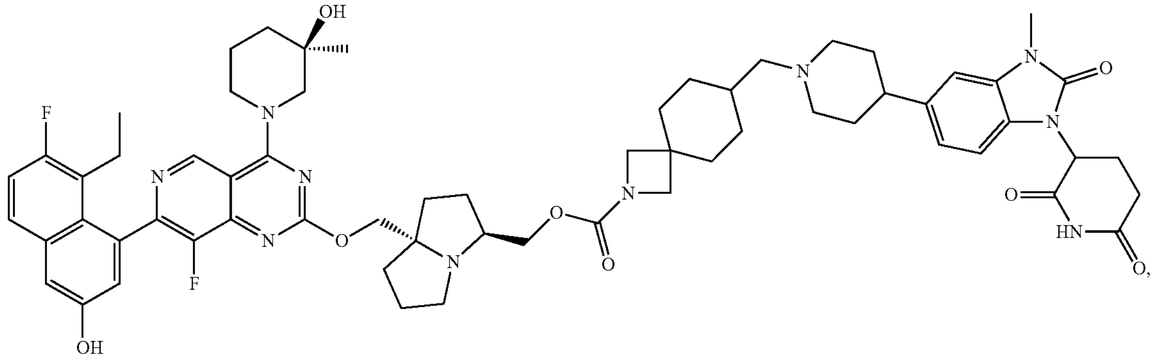
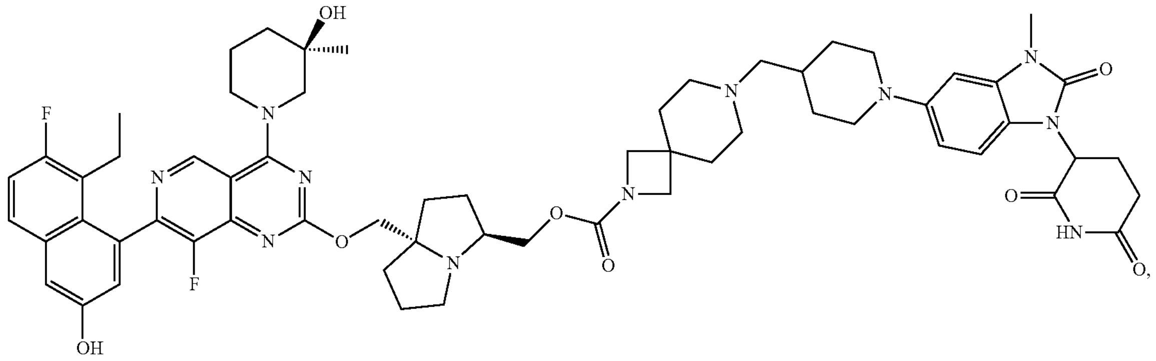
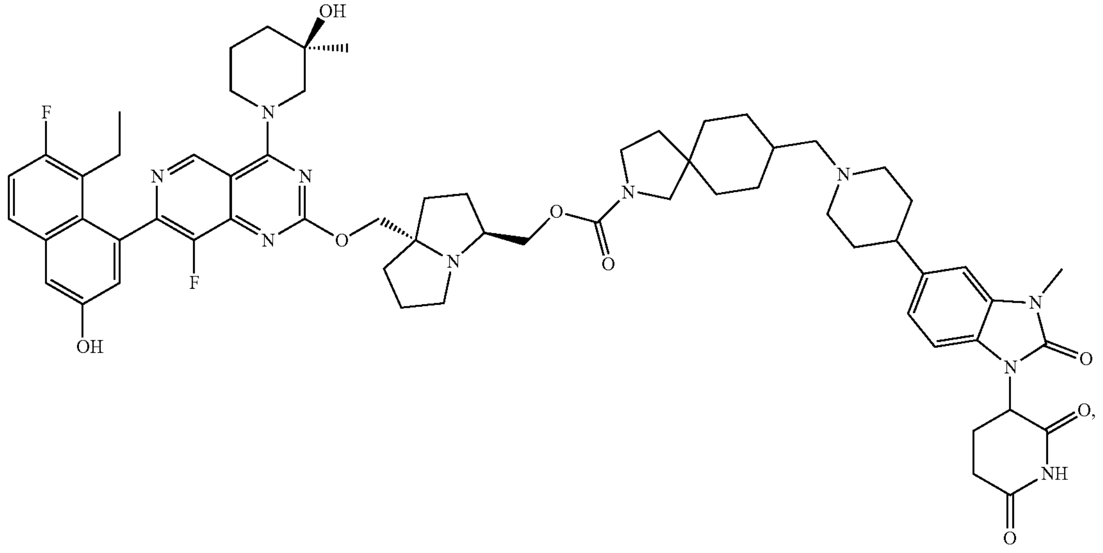

-continued
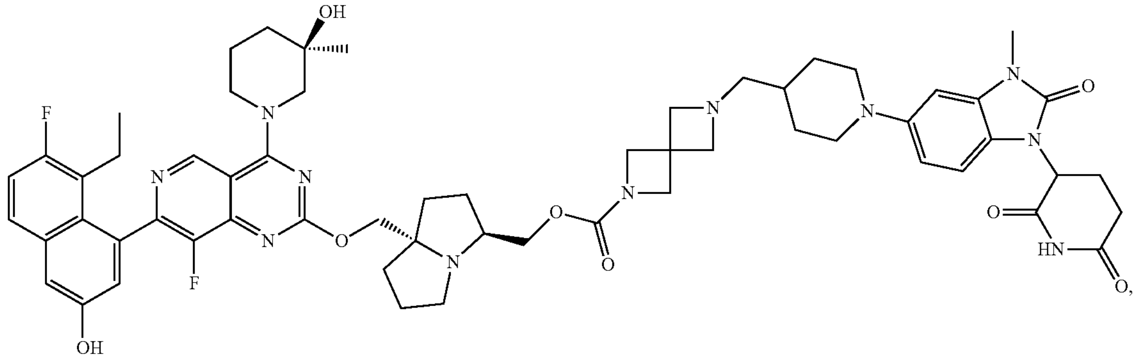
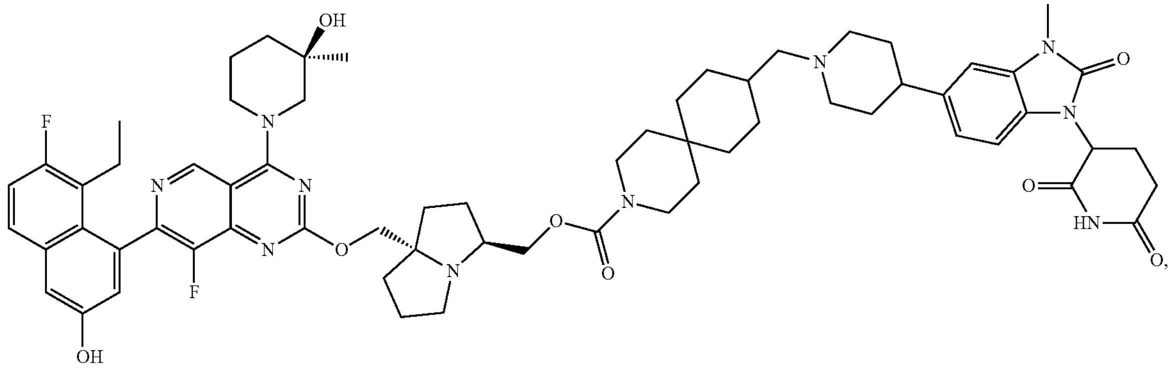
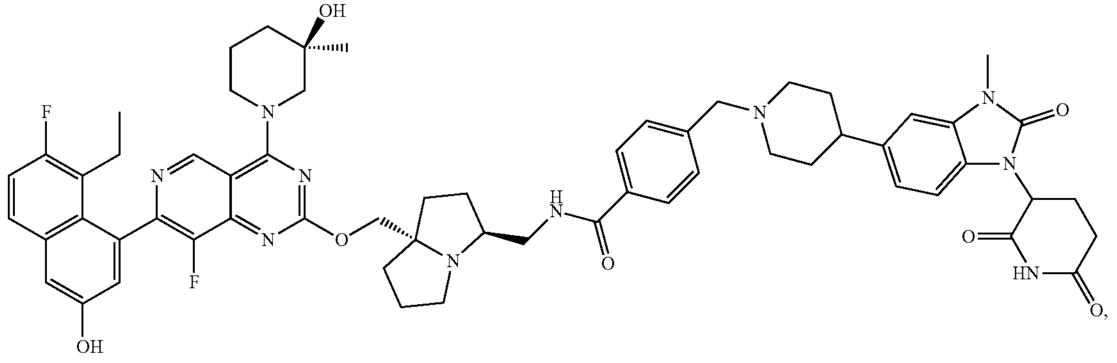
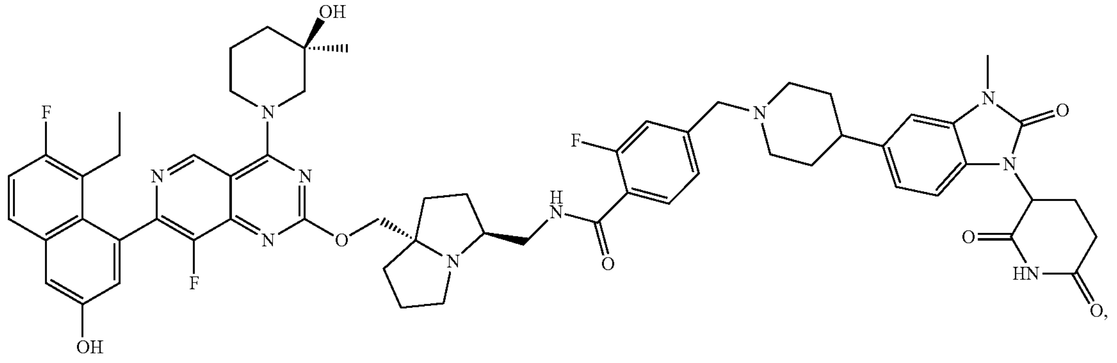

-continued

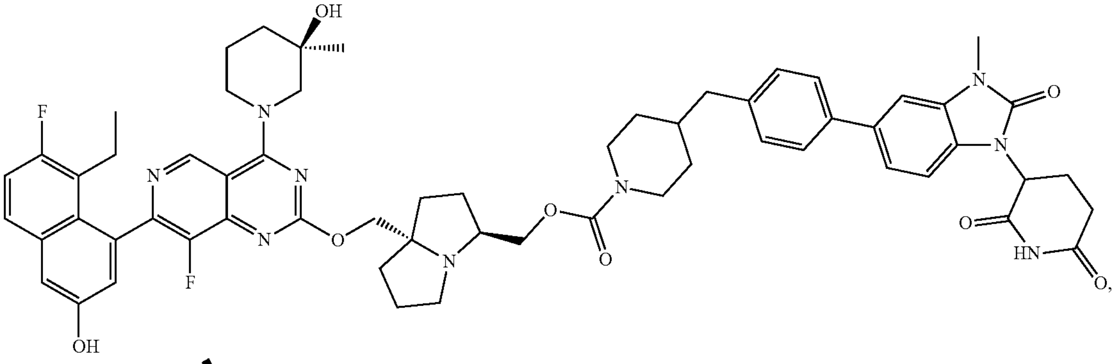

,

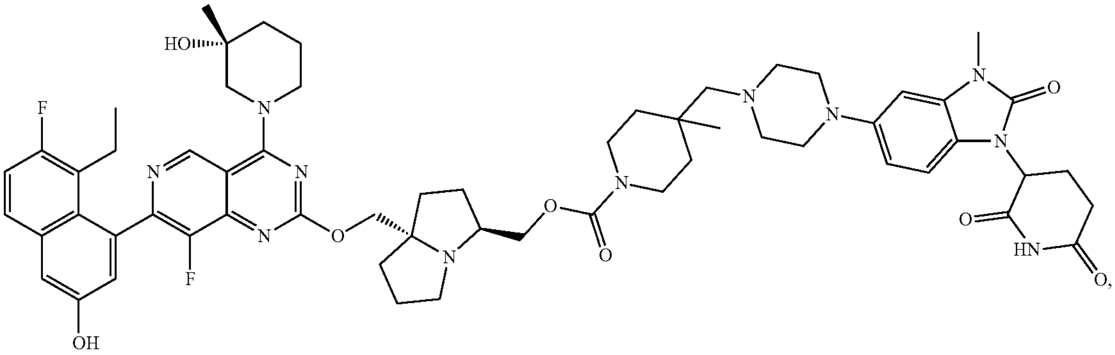

, or

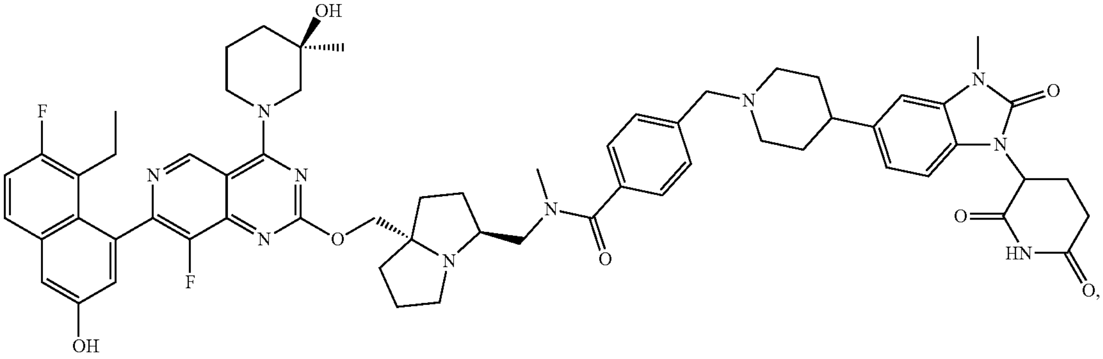

, or a pharmaceutically acceptable salt thereof.

8. A pharmaceutical composition comprising a compound of claim 1, or a pharmaceutically acceptable salt thereof, and a pharmaceutically acceptable carrier.

9. A pharmaceutical composition comprising a compound of claim 6, or a pharmaceutically acceptable salt thereof, and a pharmaceutically acceptable carrier.

10. A pharmaceutical composition comprising a compound of claim 7, or a pharmaceutically acceptable salt thereof, and a pharmaceutically acceptable carrier.

11. The compound of claim 1, of the following formula:

(II')

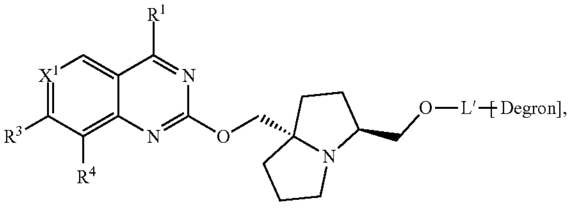

, or a pharmaceutically acceptable salt thereof.

12. The compound of claim 1, wherein $R^3$ is

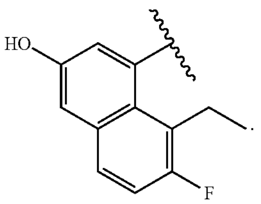 [SMILES: *c1cc(O)cc2ccc(F)c(CC)c12]

.

13. The compound of claim 1, wherein $R^3$ is

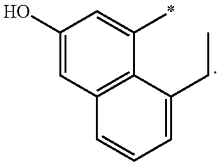 [SMILES: *c1cc(O)cc2cccc(CC)c12]

.

14. The compound of claim 5, wherein Degron is

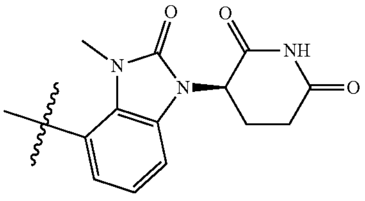

or

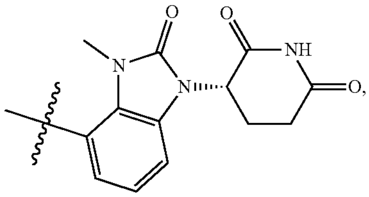

, wherein one or more of the hydrogen atoms on the benzene ring of the Degron is optionally replaced with a fluorine atom.

15. The compound of claim 5, wherein Degron is

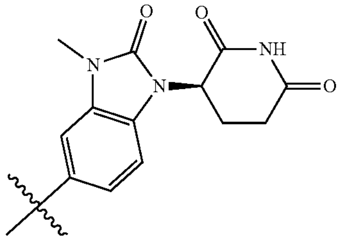

or

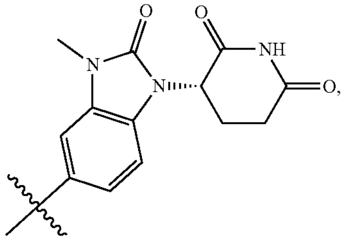

, wherein one or more of the hydrogen atoms on the benzene ring of the Degron is optionally replaced with a fluorine atom.

16. The compound of claim 7, of the following structure:

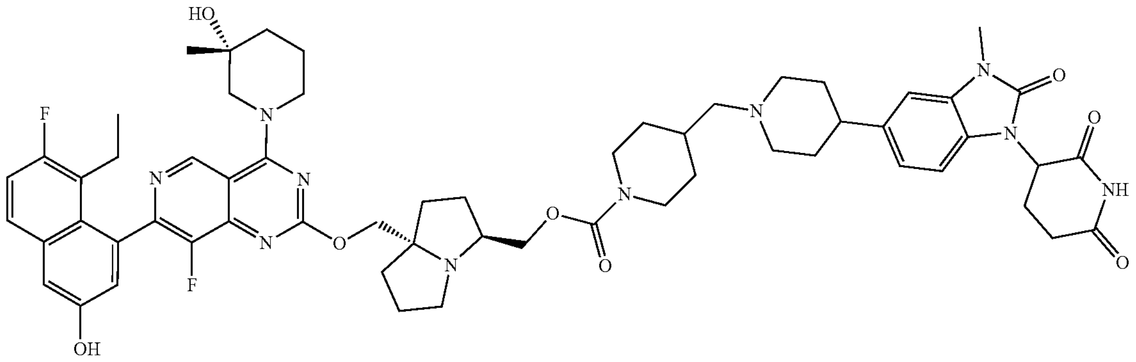

or a pharmaceutically acceptable salt thereof.

17. The compound of claim 7, of the following structure:

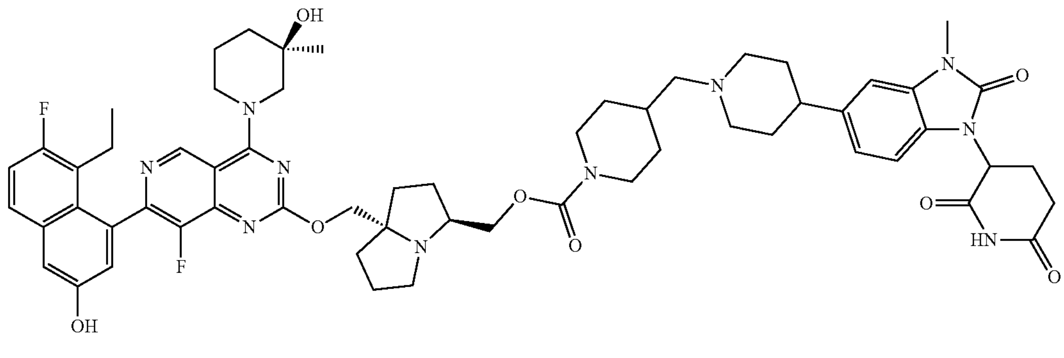 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc4c3F)c12]

or a pharmaceutically acceptable salt thereof.

18. The compound of claim 7, of the following structure:
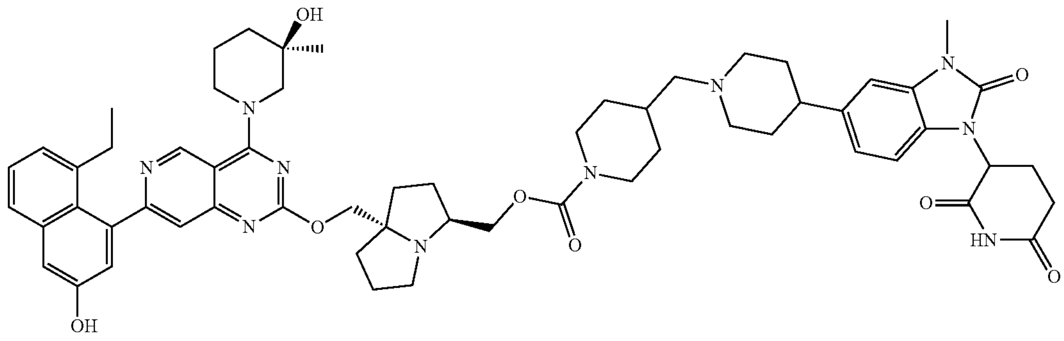 [SMILES: CCc1cccc2cc(O)cc(-c3cc4nc(OC[C@@]56CCCN5[C@H](COC(=O)N5CCC(CN7CCC(c8ccc9c(c8)n(C)c(=O)n9C8CCC(=O)NC8=O)CC7)CC5)CC6)nc(N5CCC[C@@](C)(O)C5)c4cn3)c12]
or a pharmaceutically acceptable salt thereof.
19. The compound of claim 7, of the following structure:
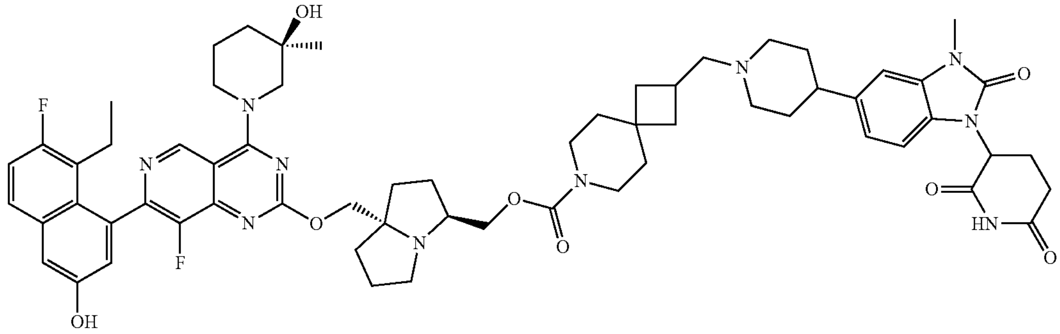 [SMILES: CCc1c(F)ccc2cc(O)cc(-c3ncc4c(N5CCC[C@@](C)(O)C5)nc(OC[C@@]56CCCN5[C@H](COC(=O)N5CCC7(CC5)CC(CN5CCC(c8ccc9c(c8)n(C)c(=O)n9C8CCC(=O)NC8=O)CC5)C7)CC6)nc4c3F)c12]
or a pharmaceutically acceptable salt thereof.
20. The compound of claim 7, of the following structure:
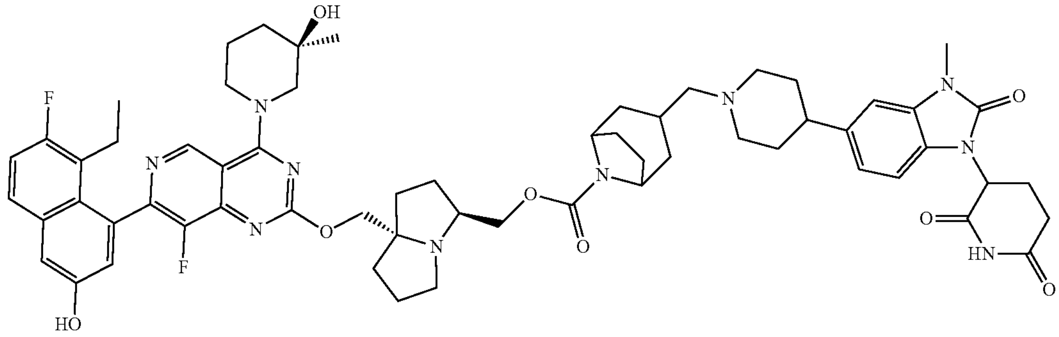 [SMILES: CCc1c(F)ccc2cc(O)cc(-c3ncc4c(N5CCC[C@@](C)(O)C5)nc(OC[C@@]56CCCN5[C@H](COC(=O)N5C7CCC5CC(CN5CCC(c8ccc9c(c8)n(C)c(=O)n9C8CCC(=O)NC8=O)CC5)C7)CC6)nc4c3F)c12]
or a pharmaceutically acceptable salt thereof.

21. The compound of claim 7, of the following structure:
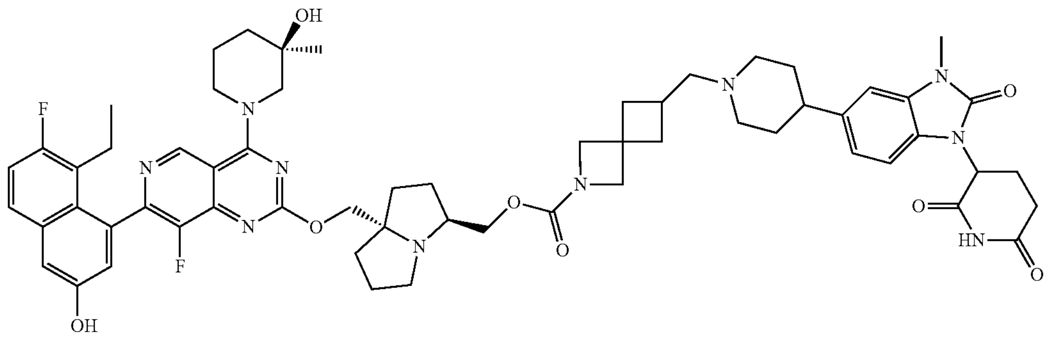 [SMILES: CCc1c(F)ccc2cc(O)cc(-c3ncc4c(N5CCC[C@@](C)(O)C5)nc(OC[C@@]56CCCN5[C@H](COC(=O)N5CC7(CC(CN8CCC(c9ccc%10c(c9)n(C)c(=O)n%10C9CCC(=O)NC9=O)CC8)C7)C5)CC6)nc4c3F)c12]
or a pharmaceutically acceptable salt thereof.
22. The compound of claim 7, of the following structure:
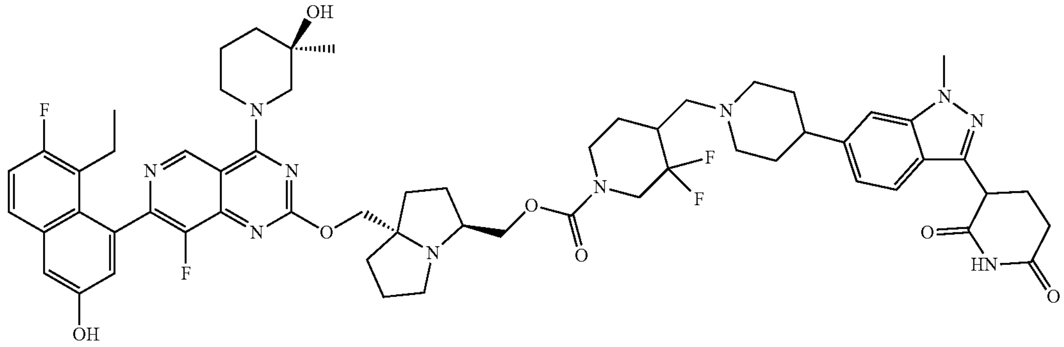 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(C%10CCC(=O)NC%10=O)nn(C)c9c8)CC7)C(F)(F)C5)CC6)nc4c3F)c12]
or a pharmaceutically acceptable salt thereof.
23. The compound of claim 7, of the following structure:
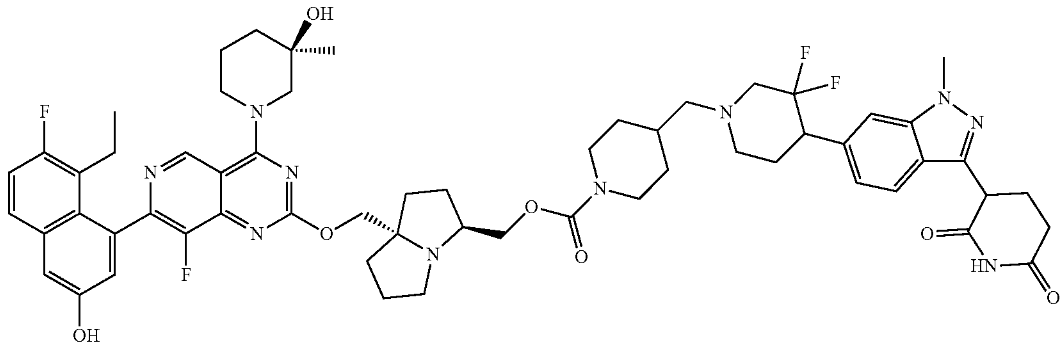 [SMILES: CCc1c(F)ccc2cc(O)cc(-c3ncc4c(N5CCC[C@@](C)(O)C5)nc(OC[C@@]56CCCN5[C@H](COC(=O)N5CCC(CN7CCC(c8ccc9c(C%10CCC(=O)NC%10=O)nn(C)c9c8)C(F)(F)C7)CC5)CC6)nc4c3F)c12]
or a pharmaceutically acceptable salt thereof.

24. The compound of claim 7, of the following structure:
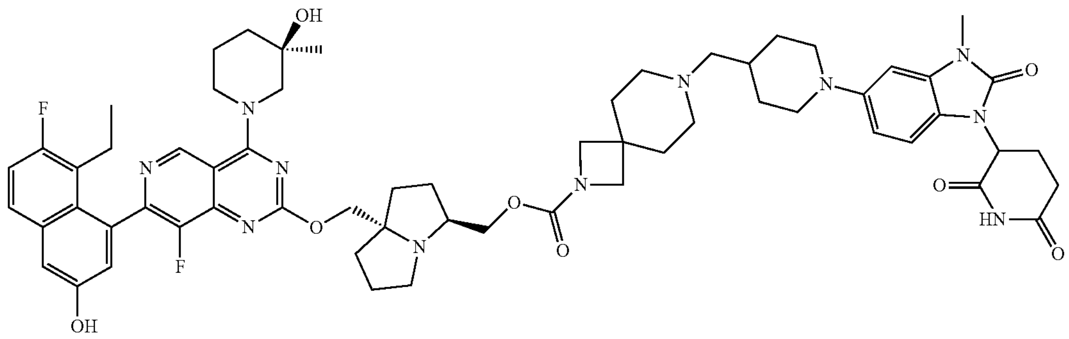 [SMILES: CCc1c(F)ccc2cc(O)cc(-c3ncc4c(N5CCC[C@@](C)(O)C5)nc(OC[C@@]56CCCN5[C@H](COC(=O)N5CC7(CCN(CC8CCN(c9ccc%10c(c9)n(C)c(=O)n%10C9CCC(=O)NC9=O)CC8)CC7)C5)CC6)nc4c3F)c12]
or a pharmaceutically acceptable salt thereof.
25. The compound of claim 7, of the following structure:
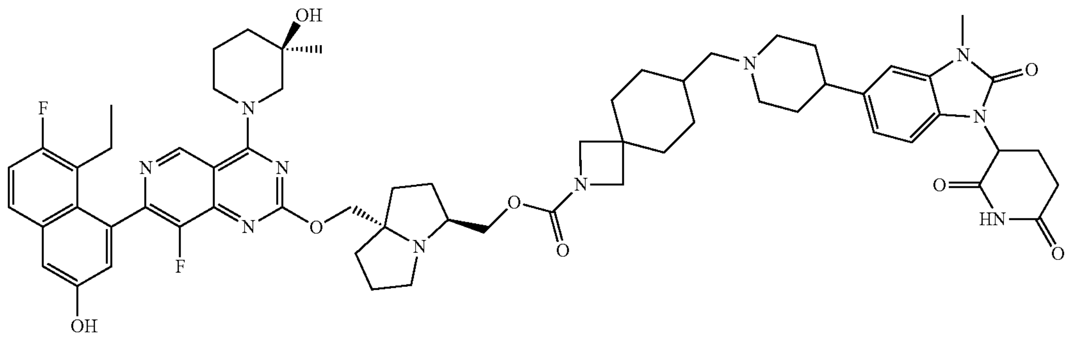 [SMILES: CCc1c(F)ccc2cc(O)cc(-c3ncc4c(N5CCC[C@@](C)(O)C5)nc(OC[C@@]56CCCN5[C@H](COC(=O)N5CC7(CCC(CN8CCC(c9ccc%10c(c9)n(C)c(=O)n%10C9CCC(=O)NC9=O)CC8)CC7)C5)CC6)nc4c3F)c12]
or a pharmaceutically acceptable salt thereof.
* * * * *